(12) United States Patent
Lee et al.

(10) Patent No.: US 10,538,498 B2
(45) Date of Patent: Jan. 21, 2020

(54) 1,3,4-OXADIAZOLE SULFONAMIDE DERIVATIVE COMPOUNDS AS HISTONE DEACETYLASE 6 INHIBITOR, AND THE PHARMACEUTICAL COMPOSITION COMPRISING THE SAME

(71) Applicant: Chong Kun Dang Pharmaceutical Corp., Seoul (KR)

(72) Inventors: Jaekwang Lee, Gyeonggi-do (KR); Younghue Han, Gyeonggi-do (KR); Yuntae Kim, Gyeonggi-do (KR); Daekyu Choi, Gyeonggi-do (KR); Jaeki Min, Gyeonggi-do (KR); Miseon Bae, Gyeonggi-do (KR); Hyunmo Yang, Gyeonggi-do (KR); Dohoon Kim, Gyeonggi-do (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 15/747,952

(22) PCT Filed: Jul. 27, 2016

(86) PCT No.: PCT/KR2016/008214
§ 371 (c)(1),
(2) Date: Jan. 26, 2018

(87) PCT Pub. No.: WO2017/018803
PCT Pub. Date: Feb. 2, 2017

(65) Prior Publication Data
US 2018/0251437 A1    Sep. 6, 2018

(30) Foreign Application Priority Data
Jul. 27, 2015  (KR) .................. 10-2015-0105976

(51) Int. Cl.
| *C07D 271/10* | (2006.01) |
| *C07D 413/12* | (2006.01) |
| *C07D 413/14* | (2006.01) |
| *C07D 413/04* | (2006.01) |
| *C07D 417/12* | (2006.01) |
| *C07D 513/04* | (2006.01) |
| *A61P 25/00* | (2006.01) |
| *A61P 35/00* | (2006.01) |
| *A61P 37/00* | (2006.01) |

(52) U.S. Cl.
CPC ............ *C07D 271/10* (2013.01); *A61P 25/00* (2018.01); *A61P 35/00* (2018.01); *A61P 37/00* (2018.01); *C07D 413/04* (2013.01); *C07D 413/12* (2013.01); *C07D 413/14* (2013.01); *C07D 417/12* (2013.01); *C07D 513/04* (2013.01)

(58) Field of Classification Search
CPC ... C07D 217/10; C07D 413/12; C07D 417/12
See application file for complete search history.

(56) References Cited

U.S. PATENT DOCUMENTS

| 4,871,753 | A  | 10/1989 | Rorh |
| 8,981,084 | B2 | 3/2015  | Baloglu et al. |
| 9,670,193 | B2 | 6/2017  | Hebach et al. |
| 2005/0288282 | A1 | 12/2005 | Delorme et al. |
| 2006/0058298 | A1 | 3/2006  | Delorme et al. |
| 2007/0293530 | A1 | 12/2007 | Smil et al. |
| 2012/0027874 | A1 | 2/2012  | Charrier et al. |
| 2012/0289495 | A1 | 11/2012 | Baloglu et al. |
| 2013/0059883 | A1 | 3/2013  | Baloglu et al. |
| 2014/0005133 | A1 | 1/2014  | Trivedi et al. |
| 2014/0142105 | A1 | 5/2014  | Hebach et al. |
| 2014/0329825 | A1 | 11/2014 | Hebach et al. |
| 2017/0015809 | A1 | 1/2017  | Hawkins et al. |

(Continued)

FOREIGN PATENT DOCUMENTS

| CN | 104744446 | 7/2015 |
| JP | 2005513123 | 5/2005 |

(Continued)

OTHER PUBLICATIONS

Cancer and Metastasis Reviews (1998), 17(1), 91-106.*

(Continued)

*Primary Examiner* — Shawquia Jackson
(74) *Attorney, Agent, or Firm* — Fish & Richardson P.C.

(57) ABSTRACT

The present invention relates to novel compounds represented by the formula I having histone deacetylase 6 (HDAC6) inhibitory activity, stereoisomers thereof or pharmaceutically acceptable salts thereof, the use thereof for the preparation of therapeutic medicaments, pharmaceutical compositions containing the same, a method for treating diseases using the composition, and methods for preparing the novel compounds. (I) The novel compounds, stereoisomers thereof or pharmaceutically acceptable salts thereof according to the present invention have histone deacetylase (HDAC) inhibitory activity and are effective for the prevention or treatment of HDAC6-mediated diseases.

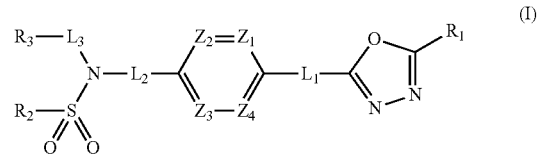

8 Claims, No Drawings

(56) References Cited

U.S. PATENT DOCUMENTS

| | | |
|---|---|---|
| 2018/0230114 A1 | 8/2018 | Lee et al. |
| 2018/0251437 A1 | 9/2018 | Lee et al. |

FOREIGN PATENT DOCUMENTS

| | | |
|---|---|---|
| JP | 2009542752 | 12/2009 |
| JP | 2011008205 | 1/2011 |
| JP | 2011502133 | 1/2011 |
| JP | 2012211149 | 11/2012 |
| JP | 2013517278 | 5/2013 |
| JP | 2013517281 | 5/2013 |
| JP | 2014520794 | 8/2014 |
| JP | 2014524922 | 9/2014 |
| JP | 2014533721 | 12/2014 |
| JP | 2014533734 | 12/2014 |
| KR | 100265385 | 11/2000 |
| KR | 100903743 | 6/2009 |
| KR | 20147017436 | 11/2012 |
| KR | 101262870 | 5/2013 |
| KR | 101320198 | 10/2013 |
| KR | 20130112911 | 10/2013 |
| KR | 20140097459 | 8/2014 |
| KR | 101561860 | 10/2015 |
| RU | 2515611 | 8/2012 |
| WO | WO 2003/028729 | 4/2003 |
| WO | WO2007011626 | 1/2007 |
| WO | WO 2007/032445 | 3/2007 |
| WO | WO 2007/107758 | 9/2007 |
| WO | 2009/010479 | 1/2009 |
| WO | 2010/123933 | 10/2010 |
| WO | 2010/126002 | 11/2010 |
| WO | WO 2011/088181 | 7/2011 |
| WO | WO 2011/088192 | 7/2011 |
| WO | WO 2011/104680 | 9/2011 |
| WO | WO 2011/133888 | 10/2011 |
| WO | 2012/013716 | 2/2012 |
| WO | WO 2013/066833 | 5/2013 |
| WO | WO 2013/066835 | 5/2013 |
| WO | WO 2013/066839 | 5/2013 |
| WO | WO 2013/080120 | 6/2013 |
| WO | WO 2015/033301 | 3/2015 |
| WO | WO 2015/087151 | 6/2015 |
| WO | WO2016082930 | 6/2016 |
| WO | WO 2017/018803 | 2/2017 |
| WO | WO 2017/018804 | 2/2017 |
| WO | WO 2017/018805 | 2/2017 |
| WO | WO 2017/023133 | 2/2017 |
| WO | WO 2017/065473 | 4/2017 |

OTHER PUBLICATIONS

Science (1999), vol. 286, 531-537.*
Cancer [online], [retrieved on Jul. 6, 2007]. Retrieved from the internet, URL http://www.nlm.nih.gov/medlineplus/cancer.html>.*
Bolden et al., Nat. Rev. Drug Discov. 5(9), 769-784 (2006).
Chen, J.J. et al., "discovery of 2-methylpyridine-based biaryl amides as y-secretase modulators for the treatment of Alzheimer's disease," Bioorganic & Medicinal Chemistry letters, 2013, 23(23):6447-6454.
Hassig et al., Curr. Opin. Chem. Biol. 1, 300-308 (1997).
Hu et al., J. Neurol. Sci., 304, 1-8 (2011).
International Search Report of ISA/KR for PCT/KR2016/008214 (dated Nov. 24, 2016).
Li and Woster, Royal Society of Chemistry—Med ChemCommun, Issue 4, pp. 613-618 (2013).
Matthias et al., Mol. Cell. Biol. 28, 1688-1701 (2008).
Methot et al., Biiorg. Med. Chem. Lett. 28:973-978 (2008).
Piekarz et al., Pharmaceuticals 3, 2751-2767 (2010).
Santo et al., Blood 119, 2579-2589 (2012).
Vishwakarma et al., International Immunopharmacology, 16, 72-78 (2013).
Warrell et al., J. Natl. Cancer Inst. 90, 1621-1625 (1998).
Wiest et al., J. Org. Chem. 78, 5051-5055 (2013).
Witt et al., Cancer Letters, 277, 8-21 (2009).
Yao et al., Mol. Cell, 18, 601-607 (2005).
AU Office Action for AU App No. 2016299484, dated Dec. 18, 2018 (3 pages).
AU Office Action for AU App No. 2016299485, dated Sep. 13, 2018 (7 pages).
CA Office Action for CA App No. 2987570, dated Oct. 18, 2018 (5 pages).
EP Extended Search Report for EP App No. 16830836.9, dated Dec. 19, 2018 (7 pages).
EP Extended Search Report for EP App No. 16830837.7, dated Dec. 17, 2018 (9 pages).
EP Extended Search Report for EP App No. 16830838.5, dated Nov. 19, 2018 (7 pages).
JP Office Action for App No. JP 2018-503804, dated Dec. 18, 2018 (with English Translation) (4 pages).
JP Office Action for JP App No. 2018-504096, dated Dec. 18, 2018 (with English Translation) (5 pages).
Rossi et al., 4-N-Hydroxy-4-[ 1-( sulfonyl )piperidin-4-yl ]-butyramides as HDAC inhibitors, Bioorganic & Medicinal Chemistry Letters, 21:6767-6769 (2011).
RU Office Action for App. No. RU2018106877, dated Oct. 18, 2018 (with English translation) (16 pages).
RU Office Action for RU App. No. 2018106904, dated Sep. 20, 2018 (with English translation) (14 pages).
CA Office Action for CA App No. 2993918, dated Dec. 4, 2018 (5 pages).
CAS Registry No. 904529-79-9 (Aug. 25, 2006).
CAS Registry No. 904541-56-6 (Aug. 25, 2006).
CAS Registry No. 904541-91-9 (Aug. 25, 2006).
CAS Registry No. 904548-90-9 (Aug. 25, 2006).
CAS Registry No. 904549-01-5 (Aug. 25, 2006).
CAS Registry No. 904549-10-3 (Aug. 25, 2006).
CAS Registry No. 904556-59-8 (Aug. 25, 2006).
CAS Registry No. 904568-68-9 (Aug. 25, 2006).
CAS Registry No. 904568-84-9 (Aug. 25, 2006).
CAS Registry No. 904569-62-6 (Aug. 25, 2006).
CAS Registry No. 904635-15-0 (Aug. 25, 2006).
CAS Registry No. 904635-23-0 (Aug. 25, 2006).
CAS Registry No. 904635-49-0 (Aug. 25, 2006).
CAS Registry No. 904635-57-0 (Aug. 25, 2006).
CAS Registry No. 904635-61-6 (Aug. 25, 2006).
CAS Registry No. 904635-67-2 (Aug. 25, 2006).
CAS Registry No. 904644-90-2 (Aug. 25, 2006).
CAS Registry No. 904644-93-5 (Aug. 25, 2006).
CAS Registry No. 904645-01-8 (Aug. 25, 2006).
CAS Registry No. 904645-03-0 (Aug. 25, 2006).
CAS Registry No. 904645-27-8 (Aug. 25, 2006).
Cas Registry No. 904645-29-0 (25 Aug. 2006).
CAS Registry No. 904645-35-2 (Aug. 25, 2006).
CAS Registry No. 904645-35-8 (Aug. 25, 2006).
CAS Registry No. 904645-37-0 (Aug. 25, 2006).
CAS Registry No. 904645-47-2 (Aug. 25, 2006).
CAS Registry No. 904652-55-1 (Aug. 25, 2006).
CAS Registry No. 904652-68-2 (Aug. 25, 2006).
CAS Registry No. 904653-05-0 (Aug. 25, 2006).
CAS Registry No. 904653-11-8 (Aug. 25, 2006).
CAS Registry No. 904653-15-2 (Aug. 25, 2006).
CAS Registry No. 904653-17-4 (Aug. 25, 2006).
CAS Registry No. 904653-21-0 (Aug. 25, 2006).
CAS Registry No. 904653-22-1 (Aug. 25, 2006).
JP Office Action for App No. JP 2018-504720, dated Jan. 8, 2019 (English Translation) (4 pages).
NZ Office Action for App No. NZ739211, dated Jun. 14, 2019 (3 pages).
RU Office Action for RU App. No. 2018106914, dated Nov. 15, 2018 (with English translation) (14 pages).
U.S. Appl. No. 15/747,952, filed Jan. 26, 2018, Lee et al.
U.S. Appl. No. 15/747,850, filed Jan. 26, 2018, Lee at al.
U.S. Appl. No. 15/748,081, filed Jan. 26, 2018, Lee et al.
U.S. Appl. No. 15/750,067, filed Feb. 2, 2018, Lee et al.
U.S. Appl. No. 15/763,972, filed Mar. 28, 2018, Kim et al.

(56) References Cited

OTHER PUBLICATIONS

AU Office Action for AU App No. 2016299484, dated Aug. 28, 2018 (6 pages).
AU Office Action for AU App No. 2016299486, dated Jul. 31, 2018 (5 pages).
International Preliminary Report on Patentability and Written Opinion for Intl. App. No. PCT/KR2016/008214 dated Jan. 30, 2018 (8 pages).
International Preliminary Report on Patentability and Written Opinion for Intl. App. No. PCT/KR2016/008216 dated Jan. 30, 2018 (9 pages).
International Preliminary Report on Patentability and Written Opinion for Intl. App. No. PCT/KR2016/008218 dated Jan. 30, 2018 (8 pages).
International Preliminary Report on Patentability and Written Opinion for Intl. App. No. PCT/KR2016/008622 dated Feb. 6, 2018 (8 pages).
International Preliminary Report on Patentability and Written Opinion for Intl. App. No. PCT/KR2016/011355 dated Apr. 17, 2018 (6 pages).
International Search Report for Int. App. No. PCT /KR2016/011355, dated Jan. 26, 2017 (5 pages).
International Search Report of ISA/KR for PCT/KR2016/008216, dated Nov. 21, 2016 (4 pages).
International Search Report of ISA/KR for PCT/KR2016/008218, dated Nov. 21, 2016 (5 pages).
International Search Report of ISA/KR for PCT/KR2016/008622, datedFeb. 17, 2017 (5 pages).
Japan Office Action for JP App No. 2018-505725 dated Sep. 12, 2018 (3 pages).
Korea Office Action for KR Application No. 10-2016-0095332, dated Sep. 5, 2017 (15 pages).
Korea Office Action for KR Application No. 10-2016-0095334, dated Sep. 5, 2017 (17 pages).
Korea Office Action for KR Application No. 10-2016-0099508, dated Sep. 5, 2017 (20 pages).
Korea Office Action for KR Application No. 10-2016-0131245, dated Sep. 5, 2017 (7 pages).
Manku, et al., Synthesis and evaluation of lysine derived sulfamides as histone deacetylase inhibitors, Bioorganic & Medicinal Chemistry Letters 19, 1866-1870 (2009).
Pal et al., Hydroxamic acid—A novel molecule for anticancer therapy, Journal of Advanced Pharmaceutical Technology & Research, 3(2), 92-99 (Apr.-Jun. 2012).
Rajack et al., 2,5-Disubstituted-1,3,4-oxadiazoles/thiadiazole as surface recognition moiety: Design and synthesis of novel hydroxamic acid based histone deacetylase inhibitors, Bioorganic & Medical Chemistry Letters, 21:5735-5738 (2011).
STN Express; Chemical Abstract compound RN: 1355844-43-7 (Feb. 8, 2012).
STN Express; Chemical Abstract compound RN: 1708354-35-1 (May 20, 2015).
STN Express; Chemical Abstract compound RN: 1790675-44-3 (Jun. 29, 2015).
STN Express; Chemical Abstract compound RN: 1798074-73-3 (Jul. 9, 2015).
STN Express; Chemical Abstract compound RN: 904653-20-9 (Aug. 25, 2006).
Taiwan Office Action for TW App No. 105132939 dated Nov. 2, 2017 (with English translation) (8 pages).
CAS Registry No. 904548-10-3 (Aug. 25, 2006).
AU Office Action for App No. AU 2016303891, dated Nov. 16, 2018 (7 pages).
CA Office Action for App No. CA 2993929, dated Dec. 4, 2018 (4 pages).
CAS Registry No. 904645-39-2 Database Registry [Online] retrieved from STN, searched on Nov. 14, 2018.
CAS Registry No. 904652-59-1 Database Registry [Online] retrieved from STN, searched on Nov. 14, 2018.
CAS Registry No. 1384673-31-7 [Entered STN: Jul. 27, 2012] (Year: 2012).
CAS Registry No. 1436149-02-8 [Entered STN: Jun. 9, 2013] (Year: 2013).
CAS Registry No. 904635-69-4 (Aug. 25, 2006).
CAS Registry No. 904652-71-7 (Aug. 25, 2006).
CAS Registry No. 904653-13-0 (Aug. 25, 2006).
EP Suppl Search Report for App No. EP 16833369, dated Apr. 1, 2019 (6 pages).
Gamal Ei-Din. et, al, *Synthesis and* in vitro *antiproliferative activity of new 1,3,4-oxadiazole derivatives possessing sulfonamide moiety*, European Journal of Medicinal Chemistry, 90:45-52, (Jan. 27, 2015).
IN Office Action for App No. 201727037873, dated May 21, 2019 (7 pages).
IN Office Action for App No. 201817006324, dated Jun. 27, 2019 (6 pages).
Othman et al., *1,3,4-Oxadiazole, 1,3,4-thiadiazole and 1,2,4-triazole derivatives as potential antibacterial agents*, Arabian Journal of Chemistry (2014) https://doi.org/10.1016/j.arabjc.2014.09.003 (16 pages).

* cited by examiner

1,3,4-OXADIAZOLE SULFONAMIDE DERIVATIVE COMPOUNDS AS HISTONE DEACETYLASE 6 INHIBITOR, AND THE PHARMACEUTICAL COMPOSITION COMPRISING THE SAME

TECHNICAL FIELD

The present invention relates to 1,3,4-oxadiazole sulfonamide derivative compounds having histone deacetylase 6 (HDAC6) inhibitory activity, stereoisomers thereof, or pharmaceutically acceptable salts thereof; uses thereof for the preparation of therapeutic medicaments; methods of treating diseases using the same; pharmaceutical compositions comprising the same; and methods for preparing the same.

BACKGROUND ART

Post-translational modifications such as acetylation are very crucial regulatory modules at the heart of biological processes in the cells and are tightly regulated by a multitude of enzymes. Histones are the chief protein components of chromatin and act as spools around which DNA strands. Also, the balance of histone acetylation and deacetylation is a critical role in the regulation of gene expression.

Histone deacetylases (HDACs) are enzymes that remove acetyl groups from lysine residues on histone proteins of chromatin, and are known to be associated with gene silencing and induce cell cycle arrest, angiogenic inhibition, immune regulation, cell death, etc. (Hassig et al., Curr. Opin. Chem. Biol. 1997, 1, 300-308). In addition, it was reported that the inhibition of enzymatic function of HDACs induces the apoptosis of cancer cells in vivo by reducing the activity of cancer cell survival-associated factors and activating cancer cell apoptosis-associated factors (Warrell et al, J. Natl. Cancer Inst. 1998, 90, 1621-1625).

In humans, 18 HDACs have been identified and are subdivided into four classes based on their homology to yeast HDACs. Among them, 11 HDACs use zinc as a cofactor and can be divided into three groups: Class I (HDAC1, 2, 3 and 8), Class II (IIa: HDAC4, 5, 7 and 9; IIb: HDAC6 and 10), Class IV (HDAC 11). Additionally, 7 HDACs of Class III (SIRT 1-7) require NAD$^+$ instead of zinc as a cofactor (Bolden et al., Nat. Rev. Drug Discov. 2006, 5(9), 769-784).

Various HDAC inhibitors are in preclinical or clinical development, but to date, only non-selective HDAC inhibitors have been identified as anticancer agents, and only vorinostat (SAHA) and romidepsin (FK228) have been approved for the treatment of cutaneous T-cell lymphoma. However, non-selective HDAC inhibitors are known to cause side effects such as fatigue and nausea, generally at high doses (Piekarz et al., Pharmaceuticals 2010, 3, 2751-2767). Such side effects have been reported to be due to the inhibition of class I HDACs. Due to such side effects, the use of non-selective HDAC inhibitors in the development of drugs other than anticancer drugs has been limited (Witt et al., Cancer Letters, 2009, 277, 8-21).

Meanwhile, it was reported that the selective inhibition of class II HDACs would not show toxicity shown in the inhibition of class I HDACs. Also, when selective HDAC inhibitors are developed, side effects such as toxicity, which are caused by the non-selective HDAC inhibition, can be overcome. Thus, selective HDAC inhibitors have potential to be developed as therapeutic agents effective for the treatment of various diseases (Matthias et al., Mol. Cell. Biol. 2008, 28, 1688-1701).

It is known that HDAC6, a member of Class IIb HDACs, is present mainly in the cytoplasm and is involved in the deacetylation of a number of non-histone substrates (HSP90, cortactin, etc.), including tubulin, (Yao et al., Mol. Cell 2005, 18, 601-607). HDAC6 has two catalytic domains, and the zinc finger domain of C-terminal can bind to ubiquitinated proteins. It is known that HDAC6 has a number of non-histone proteins as substrates, and thus plays an important role in various diseases, including cancer, inflammatory diseases, autoimmune diseases, neurological diseases and neurodegenerative disorders (Santo et al., Blood 2012 119: 2579-258; Vishwakarma et al., International Immunopharmacology 2013, 16, 72-78; Hu et al., J. Neurol. Sci. 2011, 304, 1-8).

The common structural characteristic of various HDAC inhibitors is a structure consisting of a cap group, a linker and a zinc-binding group (ZBG), as shown in the following Vorinostat structure. Many researchers have conducted studies on enzyme inhibitory activity and selectivity by structurally modifying the cap group and the linker Among these groups, the zinc-binding group is known to play a more important role in enzyme inhibitory activity and selectivity (Wiest et al., J. Org. Chem. 2013 78: 5051-5065; Methot et al., Bioorg. Med. Chem. Lett. 2008, 18, 973-978).

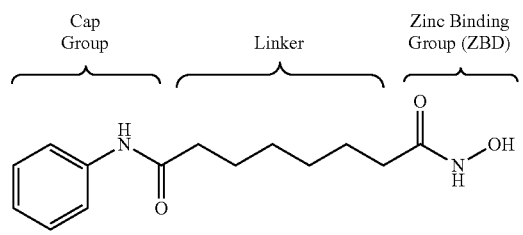 [SMILES: O=C(CCCCCCC(=O)Nc1ccccc1)NO]

The zinc-binding group is generally a hydroxamic acid or benzamide derivative. Herein, the hydroxamic acid derivative exhibits a potent HDAC inhibitory effect, but has problems of low bioavailability and severe off-target activity. In addition, the benzamide derivative has a problem in that it can produce toxic metabolites in vivo, because it contains aniline (Woster et al., Med. Chem. Commun. 2015, online publication).

Accordingly, there is a need for the development of selective HDAC 6 inhibitors for treatment of diseases such as cancer, inflammatory diseases, autoimmune diseases, neurological diseases and neurodegenerative disorders, which have a zinc-binding group with improved bioavailability and, at the same time, cause no side effects, unlike non-selective inhibitors that cause side effects.

DISCLOSURE OF INVENTION

Technical Problem

It is an object of the present invention to provide 1,3,4-oxadiazole sulfonamide derivative compounds having selective HDAC6 inhibitory activity, stereoisomers thereof, or pharmaceutically acceptable salts thereof.

Another object of the present invention is to provide pharmaceutical compositions containing 1,3,4-oxadiazole sulfonamide derivative compounds having selective HDAC6 inhibitory activity, stereoisomers thereof, or pharmaceutically acceptable salts thereof.

Still another object of the present invention is to provide methods for preparing the novel compounds.

Still another object of the present invention is to provide pharmaceutical compositions for prevention or treatment of HDAC6 activity-associated diseases, including infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities, which contain the above compound.

Still another object of the present invention is to provide the use of the compounds for the preparation of therapeutic medicaments against HDAC6 activity-associated diseases.

Yet another object of the present invention is to provide methods for treating HDAC6 activity-associated diseases, which comprise administering a therapeutically effective amount of the pharmaceutical compositions containing the compounds.

Solution to Problem

The present inventors have discovered 1,3,4-oxadiazole sulfonamide derivative compounds, which have histone deacetylase 6 (HDAC6) inhibitory activity, and have found that these compounds can be used for the inhibition or treatment of histone deacetylase 6 (HDAC6) activity-associated diseases, thereby completing the present invention.

1,3,4-Oxadiazole Sulfonamide Derivative Compounds

To achieve the above objects, the present invention provides an 1,3,4-oxadiazole sulfonamide derivative compound represented by the following formula I, a stereoisomer thereof, or a pharmaceutically acceptable salt thereof:

[Formula I]

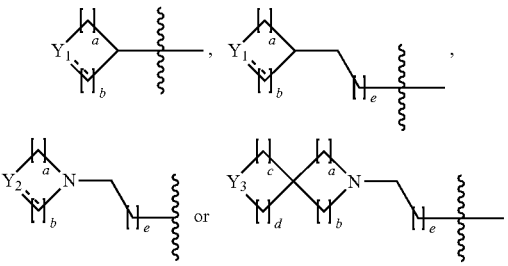

wherein $R_1$ is —$CX_2H$ or —$CX_3$;

$R_2$ is —($C_1$-$C_4$ alkyl), —($C_1$-$C_4$ alkyl)-O($C_1$-$C_4$ alkyl), —($C_1$-$C_4$)—C(=O)—O($C_1$-$C_4$ alkyl), —($C_1$-$C_4$ alkyl)-O—C(=O)—($C_1$-$C_4$ alkyl), —($C_1$-$C_4$ alkyl)-$NR^AR^B$, —($C_1$-$C_4$ alkyl)-aryl, —($C_1$-$C_4$ alkyl)-heteroaryl, -aryl, -heteroaryl,

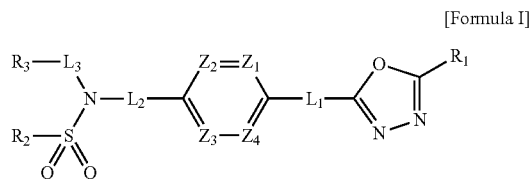

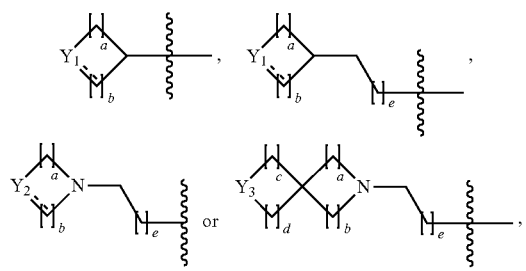

wherein at least one H of the —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_1$-$C_4$ alkyl)-O—C(=O)—($C_1$-$C_4$ alkyl) or —($C_1$-$C_4$ alkyl)-$NR^AR^B$ may be substituted with —X or —OH, at least one H of the —($C_1$-$C_4$ alkyl)-aryl, —($C_1$-$C_4$ alkyl)heteroaryl, -aryl or -heteroaryl may be substituted with —X, —OH, —O($C_1$-$C_4$ alkyl), —($C_1$-$C_4$ alkyl), —$CF_3$, —$CF_2H$, —($C_1$-$C_4$ alkyl)-OH, —C(=O)—($C_1$-$C_4$ alkyl), —C(=O)—O($C_1$-$C_4$ alkyl), —($C_1$-$C_4$ alkyl)-C(=O)—($C_1$-$C_4$ alkyl), —C(=O)—$CF_3$ or —C(=O)—$CF_2H$, and at least one H of

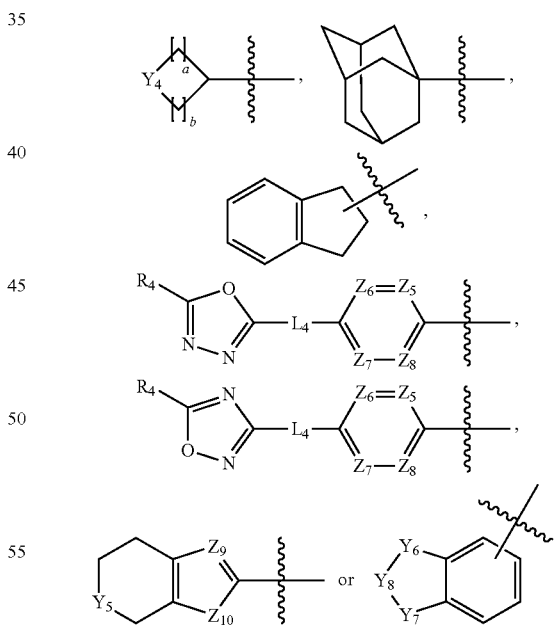

may be substituted with —X, —OH, —O($C_1$-$C_4$ alkyl), —$NR^AR^B$, —CN, —($C_1$-$C_4$ alkyl), —$CF_3$, —$CF_2H$, —($C_1$-$C_4$ alkyl)-OH, —($C_1$-$C_4$ alkyl)-$NR^AR^B$, —C(=O)—($C_1$-$C_4$ alkyl), —C(=O)—$CF_3$, —C(=O)—$CF_2H$, —C(=O)—$NR^AR^B$, —C(=O)—O($C_1$-$C_4$ alkyl), —($C_1$-$C_4$ alkyl)-C(=O)—($C_1$-$C_4$ alkyl), —($C_1$-$C_4$ alkyl)-OC(=O)—$CF_2H$, —($C_3$-$C_6$ heterocycloalkyl), —($C_1$-$C_4$ alkyl)-aryl, aryl or heteroaryl, wherein at least one H of the —($C_1$-$C_4$ alkyl)-aryl, aryl or heteroaryl may be substituted with —X, —OH, —O($C_1$-$C_4$ alkyl) or —($C_1$-$C_4$ alkyl);

$R_3$ is —H, —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), -aryl, -heteroaryl, wherein at least one H of the —($C_1$-$C_4$ alkyl), —($C_1$-$C_4$ alkyl)-O($C_1$-$C_4$ alkyl) or —($C_1$-$C_4$ alkyl)-C(=O)—O($C_1$-$C_4$ alkyl) may be substituted with —X or —OH, at least one H of the -aryl or -heteroaryl may be substituted with —X, —OH, —O($C_1$-$C_4$ alkyl), —($C_1$-$C_4$ alkyl), —$CF_3$, —$CF_2H$, —($C_1$-$C_4$ alkyl)-OH, —C(=O)—($C_1$-$C_4$ alkyl), —C(=O)—O($C_1$-$C_4$ alkyl), —($C_1$-$C_4$ alkyl)-C(=O)—($C_1$-$C_4$ alkyl), —C(=O)—CF3, —C(=O)—$CF_2H$,

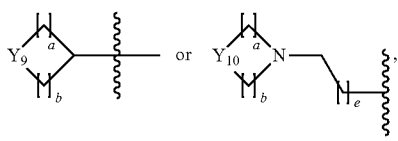

at least one H of

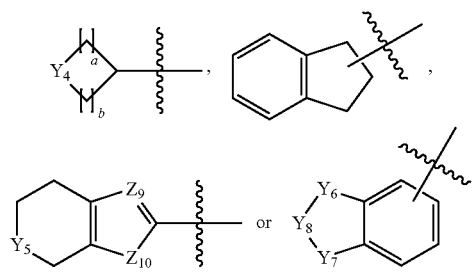

may be substituted with —X, —OH, —O($C_1$-$C_4$ alkyl), —($C_1$-$C_4$ alkyl), —C(=O)—($C_1$-$C_4$ alkyl), —C(=O)—O ($C_1$-$C_4$ alkyl) or —($C_3$-$C_6$ heterocycloalkyl);

$R_4$ is —$CX_2H$ or —$CX_3$;

$L_1$ to $L_4$ are each independently —($C_0$-$C_2$ alkyl)-;

$Z_1$ to $Z_8$ are each independently N or $CR^Z$, wherein at least three of $Z_1$ to $Z_4$ or $Z_5$ to $Z_8$ may not be simultaneously N, and $R^Z$ is —H, —X or —O($C_1$-$C_4$ alkyl);

$Z_9$ and $Z_{10}$ are each independently N or S;

$Y_1$ to $Y_3$ are each independently —$CH_2$—, —$NR^C$—, —O— or —S(=O)$_2$—;

$Y_4$ to $Y_7$ are each independently —$CH_2$—, —$NR^D$— or —O—;

$Y_8$ is —C(=O), —$CH_2$— or —$NR^E$—;

$Y_9$ and $Y_{10}$ are each independently —$NR^F$— or —S(=O)$_2$—;

$R_A$ and $R_B$ are each independently —H, —($C_1$-$C_4$ alkyl), —($C_1$-$C_4$ alkyl)-aryl, —C(=O)—$CF_2H$ or —C(=O)—O ($C_1$-$C_4$ alkyl);

$R^C$ to $R^E$ are each independently —H, —($C_1$-$C_4$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —C(=O)—($C_3$-$C_7$ cycloalkyl), —($C_1$-$C_4$ alkyl)-C(=O)—($C_2$-$C_6$ heterocycloalkyl), —S(=O)$_2$—($C_1$-$C_4$ alkyl), —($C_1$-$C_4$ alkyl) aryl, —($C_2$-$C_4$ alkenyl)-aryl, —($C_1$-$C_4$ alkyl)-heteroaryl, -aryl, -heteroaryl,

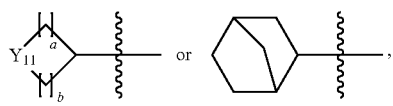

wherein at least one H of the —($C_1$-$C_4$ alkyl)-aryl, —($C_2$-$C_4$ alkenyl)-aryl, —($C_1$-$C_4$ alkyl)-heteroaryl, -aryl, -heteroaryl,

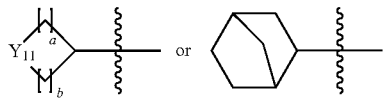

may be substituted with —X, —OH, —O($C_1$-$C_4$ alkyl), —($C_1$-$C_4$ alkyl) or —$CF_3$;

$Y_{11}$ is —$CH_2$—, —$NR^F$— or —O—;

$R^F$ is —($C_1$-$C_4$ alkyl), —C(=O)—($C_1$-$C_4$ alkyl), —C(=O)—($C_1$-$C_4$ alkyl)-OH, —C(=O)—($C_3$-$C_7$ cycloalkyl) or —S(=O)$_2$—($C_1$-$C_4$ alkyl);

≡≡≡≡ is a single bond or a double bond, provided that ≡≡≡≡ is a double bond, $Y_1$ or $Y_2$ is —CH—;

a to e are each independently an integer of 0, 1, 2 or 3, provided that a and b may not be simultaneously 0, and c and d may not be simultaneously 0; and X is F, Cl, Br or I.

According to preferable embodiment of the present invention, $R_1$ is —$CX_2H$ or —$CX_3$;

$R_2$ is —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_1$-$C_4$ alkyl)-O—C(=O)—($C_1$-$C_4$ alkyl), —($C_1$-$C_4$ alkyl)-$NR^AR^B$, —($C_1$-$C_4$ alkyl)-heteroaryl, -aryl, -heteroaryl,

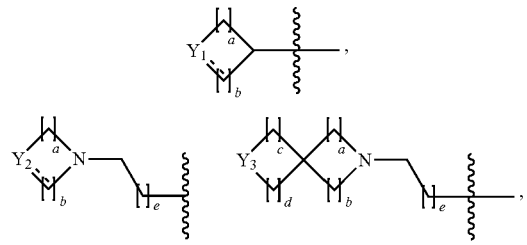

wherein at least one H of the —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_1$-$C_4$ alkyl)-O—C(=O)—($C_1$-$C_4$ alkyl) or —($C_1$-$C_4$ alkyl)-$NR^AR^B$ may be substituted with —X or —OH, at least one H of the —($C_1$-$C_4$ alkyl)-heteroaryl, -aryl or -heteroaryl may be substituted with —O($C_1$-$C_4$ alkyl), —($C_1$-$C_4$ alkyl) or —($C_1$-$C_4$ alkyl)-OH, and at least one H of

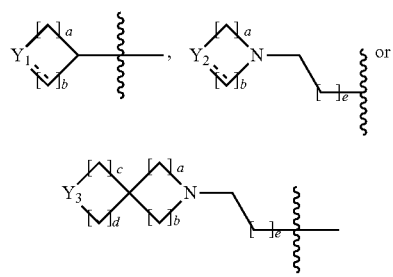

may be substituted with —X, —OH, —$NR^AR^B$, —CN, —($C_1$-$C_4$ alkyl), —($C_1$-$C_4$ alkyl)-OH, —($C_1$-$C_4$ alkyl)-$NR^AR^B$, —C(=O)—$NR^AR^B$, —C(=O)—O($C_1$-$C_4$ alkyl), —($C_1$-$C_4$ alkyl)-C(=O)—($C_1$-$C_4$ alkyl), —($C_1$-$C_4$ alkyl)-OC(=O)—$CF_2H$, —($C_3$-$C_6$ heterocycloalkyl), —($C_1$-$C_4$ alkyl)-aryl, -aryl or -heteroaryl, wherein at least one H of the —(C$_1$-C$_4$ alkyl)-aryl, -aryl or -heteroaryl may be substituted with —X, —OH, —O(C$_1$-C$_4$ alkyl) or —(C$_1$-C$_4$ alkyl);

R$_3$ is —H, —(C$_1$-C$_4$ alkyl), -aryl, -heteroaryl,

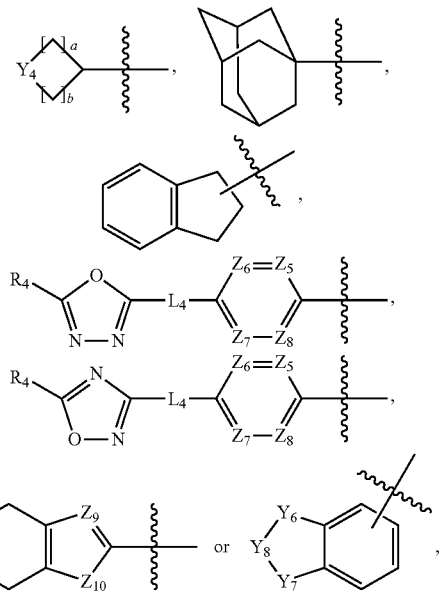

wherein at least one H of the —(C$_1$-C$_4$ alkyl) may be substituted with —X or —OH, at least one H of the -aryl or -heteroaryl may be substituted with —X, —O(C$_1$-C$_4$ alkyl), —(C$_1$-C$_4$ alkyl), —CF$_3$, —C(=O)—(C$_1$-C$_4$ alkyl),

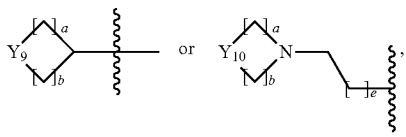

and
at least and H of

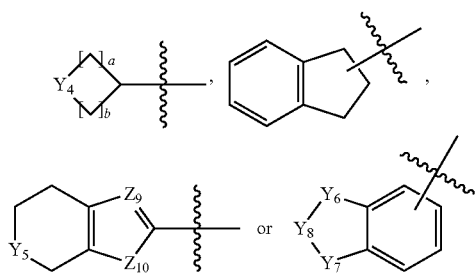

may be substituted with —(C$_1$-C$_4$ alkyl), —C(=O)—(C$_1$-C$_4$ alkyl), —C(=O)—O(C$_1$-C$_4$ alkyl) or —(C$_3$-C$_6$ heterocycloalkyl);

R$_4$ is —CX$_2$H or —CX$_3$;

L$_1$ to L$_4$ are each independently —(C$_0$-C$_2$ alkyl)—;

Z$_1$ to Z$_8$ are each independently N or CR$^Z$, wherein at least three of Z$_1$ to Z$_4$ or Z$_5$ to Z$_8$ may not be simultaneously N, and R$^Z$ is —H, —X or —O(C$_1$-C$_4$ alkyl);

Z$_9$ and Z$_{10}$ are each independently N or S;

Y$_1$ to Y$_3$ are each independently —CH$_2$—, —NR$^C$—, —O— or —S(=O)$_2$—;

Y$_4$ to Y$_7$ are each independently —CH$_2$—, —NR$^D$— or —O—;

Y$_8$ is —C(=O), —CH$_2$— or —NR$^E$—;

Y$_9$ and Y$_{10}$ are each independently —NR$^F$— or —S(=O)$_2$—;

R$^A$ and R$^B$ are each independently —H, —(C$_1$-C$_4$ alkyl), —(C$_1$-C$_4$ alkyl)-aryl, —C(=O)—CF$_2$H or —C(=O)—O(C$_1$-C$_4$ alkyl);

R$^C$ to R$^E$ are each independently —H, —(C$_1$-C$_4$ alkyl), —(C$_1$-C$_4$ alkyl)-OH, —(C$_1$-C$_4$ alkyl)-O—(C$_1$-C$_4$ alkyl), —C(=O)—(C$_1$-C$_4$ alkyl), —C(=O)—O(C$_1$-C$_4$ alkyl), —C(=O)—(C$_3$-C$_7$ cycloalkyl), —(C$_1$-C$_4$ alkyl)-C(=O)—(C$_2$-C$_6$ heterocycloalkyl), —S(=O)$_2$-(C$_1$-C$_4$ alkyl), —(C$_1$-C$_4$ alkyl)-aryl, —(C$_2$-C$_4$ alkenyl)-aryl, —(C$_1$-C$_4$ alkyl)–

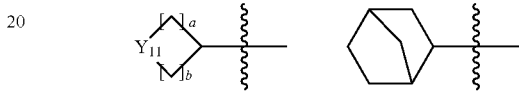

heteroaryl, -aryl, -heteroaryl, wherein at least one H of the —(C$_1$-C$_4$ alkyl)-aryl, —(C$_2$-C$_4$ alkenyl)-aryl, —(C$_1$-C$_4$ alkyl)-heteroaryl, -aryl, -heteroaryl,

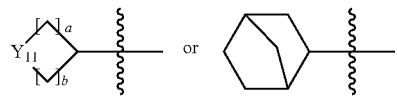

may be substituted with —X, —OH, —O(C$_1$-C$_4$ alkyl), —(C$_1$-C$_4$ alkyl) or —CF$_3$;

Y$_{11}$ is —CH$_2$—, —NR$^F$— or —O—;

R$^F$ is —(C$_1$-C$_4$ alkyl), —C(=O)—(C$_1$-C$_4$ alkyl), —C(=O)—(C$_1$-C$_4$ alkyl)-OH, —C(=O)—(C$_3$-C$_7$ cycloalkyl) or —S(=O)$_2$—(C$_1$-C$_4$ alkyl);

≡≡≡≡ is a single bond or a double bond, provided that

≡≡≡≡ is a double bond, Y$_1$ or Y$_2$ is —CH—;

a to e are each independently an integer of 0, 1, 2 or 3, provided that a and b may not be simultaneously 0, and c and d may not be simultaneously 0; and X is F, C$_l$, Br or I.

According to more preferable embodiment of the present invention,

R$_1$ is —CX$_2$H;

R$_2$ is —(C$_1$-C$_4$ alkyl), —(C$_1$-C$_4$ alkyl)-C(=O)—O(C$_1$-C$_4$ alkyl), —(C$_1$-C$_4$ alkyl)-NR$^A$R$^B$, -heteroaryl,

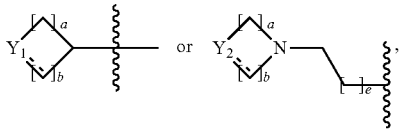

wherein at least one H of the —(C$_1$-C$_4$ alkyl), —(C$_1$-C$_4$ alkyl)-C(=O)—O(C$_1$-C$_4$ alkyl) or —(C$_1$-C$_4$ alkyl)-NR$^A$R$^B$ may be substituted with —X or —OH, at least one H of the -heteroaryl may be substituted with —O(C$_1$-C$_4$ alkyl), —(C$_1$-C$_4$ alkyl) or —(C$_1$-C$_4$ alkyl)-OH, and at least one H of

[structure] or [structure]

may be substituted with —(C$_1$-C$_4$ alkyl) or —(C$_1$-C$_4$ alkyl)-OH;

R$_3$ is -aryl, -heteroaryl or

[structure]

wherein at least one H of the -aryl or -heteroaryl may be substituted with —X, —O(C$_1$-C$_4$ alkyl), —(C$_1$-C$_4$ alkyl), —CF$_3$ or —C(=O)—(C$_1$-C$_4$ alkyl), and
at least one H of

[structure]

may be substituted with —(C$_1$-C$_4$ alkyl);
L$_1$ and L$_3$ are each independently —(C$_0$ alkyl)-;
L$_2$ is —(C$_1$ alkyl)-;
Z$_1$ to Z$_4$ are each independently N or CR$^Z$, wherein at least two of Z$_1$ to Z$_4$ may not be simultaneously N, and R$^Z$ is —H or X;
Y$_1$ is —NR$^C$—, —O— or —S(=O)$_2$—;
Y$_2$ is —CH$_2$— or —NR$^C$—;
Y$_6$ and Y$_7$ are each independently —O—;
Y$_8$ is —CH$_2$—;
R$^A$ and R$^B$ are each independently —(C$_1$-C$_4$ alkyl);
R$^C$ is —(C$_1$-C$_4$ alkyl), —(C$_1$-C$_4$ alkyl)-OH, —C(=O)—(C$_1$-C$_4$ alkyl), —S(=O)$_2$—(C$_1$-C$_4$ alkyl) or

[structure]

wherein at least one H of

[structure]

may be substituted with —(C$_1$-C$_4$ alkyl);
Y$_{11}$ is —NR$^F$— or —O—;
R$^F$ is —(C$_1$-C$_4$ alkyl), —C(=O)—(C$_1$-C$_4$ alkyl), —C(=O)—(C$_1$-C$_4$ alkyl)-OH or —S(=O)$_2$—(C$_1$-C$_4$ alkyl);

===== is a single bond;
a, b and e are each independently an integer of 0, 1 or 2, provided that a and b may not be simultaneously 0; and
X is F, Cl, Br or I.

According to particularly preferable embodiment of the present invention,
R$_1$ is —CF$_2$H;
R$_2$ is —(C$_1$-C$_4$ alkyl), —(C$_1$-C$_4$ alkyl)-NR$^A$R$^B$,

[structure] or [structure];

wherein at least one H of the —(C$_1$-C$_4$ alkyl) or —(C$_1$-C$_4$ alkyl)-NR$^A$R$^B$ may be substituted with —X or OH, and
at least one H of

[structure] or [structure]

may be substituted with —(C$_1$-C$_4$ alkyl);
R$_3$ is -aryl or -heteroaryl,
wherein at least one H of the -aryl or -heteroaryl may be substituted with —X or —(C$_1$-C$_4$ alkyl);
L$_1$ and L$_3$ are each independently —(C$_0$ alkyl)-;
L$_2$ is —(C$_1$ alkyl)-;
Z$_1$ to Z$_4$ are each independently N or CR$^Z$, wherein at least two of Z$_1$ to Z$_4$ may not be simultaneously N, and R$^Z$ is H or X;
Y$_1$ is —NR$^C$—, —O— or —S(=O)$_2$—;
Y$_2$ is —NR$^C$—;
R$^A$ and R$^B$ are each independently —(C$_1$-C$_4$ alkyl);
R$^C$ is —(C$_1$-C$_4$ alkyl), —C(=O)—(C$_1$-C$_4$ alkyl), —S(=O)$_2$—(C$_1$-C$_4$ alkyl) or

[structure]

wherein at least one H of

[structure]

may be substituted with —(C$_1$-C$_4$ alkyl);
Y$_{11}$ is —NR$^F$— or —O—;
R$^F$ is —(C$_1$-C$_4$ alkyl), —C(=O)—(C$_1$-C$_4$ alkyl), —C(=O)—(C$_1$-C$_4$ alkyl)-OH or —S(=O)$_2$—(C$_1$-C$_4$ alkyl);

===== is a single bond;
a, b and e are each independently an integer of 0, 1 or 2, provided that a and b may not be simultaneously 0; and
X is F, Cl or Br.

The specific compounds represented by formula I are shown in Table 1 below:

TABLE 1

| Ex. | Comp. | Structure |
|---|---|---|
| 1 | 11044 | *N-((2-fluoro-4-(5-(trifluoromethyl)-1,3,4-oxadiazol-2-yl)benzyl)-N-(pyridin-2-ylmethyl)methanesulfonamide* |
| 2 | 11045 | *N-(4-(5-(trifluoromethyl)-1,3,4-oxadiazol-2-yl)benzyl)-N-(pyridin-2-ylmethyl)methanesulfonamide* |
| 3 | 11078 | *4-methoxy-N-(4-(5-(trifluoromethyl)-1,3,4-oxadiazol-2-yl)benzyl)benzenesulfonamide* |
| 4 | 11088 | *N-(pyridin-3-yl)-N-(4-(5-(trifluoromethyl)-1,3,4-oxadiazol-2-yl)benzyl)methanesulfonamide* |
| 5 | 1089 | *N-(2-fluoro-4-(5-(trifluoromethyl)-1,3,4-oxadiazol-2-yl)benzyl)-N-(pyridin-3-yl)methanesulfonamide* |
| 6 | 11120 | *N-(4-(5-(difluoromethyl)-1,3,4-oxadiazol-2-yl)-2-fluorobenzyl)-N-(pyridin-3-yl)methanesulfonamide* |

TABLE 1-continued

| Ex. | Comp. | Structure |
|---|---|---|
| 7 | 11121 | methanesulfonamide-CH2-phenyl-oxadiazole-CF3 |
| 8 | 11128 | pyridin-2-yl-CH2-N(SO2Me)-CH2-pyridinyl-oxadiazole-CF3 |
| 9 | 11129 | pyridin-3-yl-N(SO2Me)-CH2-(methoxy)phenyl-oxadiazole-CF3 |
| 10 | 11133 | pyridin-3-yl-N(SO2Me)-CH2-(fluoro)phenyl-oxadiazole-CF3 |
| 11 | 11151 | phenyl-N(SO2-pyridin-3-yl)-CH2-phenyl-oxadiazole-CF3 |
| 12 | 11152 | phenyl-N(SO2-pyridin-3-yl)-CH2-phenyl-oxadiazole-CF2H |

TABLE 1-continued
| Ex. | Comp. | Structure |
|---|---|---|
| 13 | 11153 | 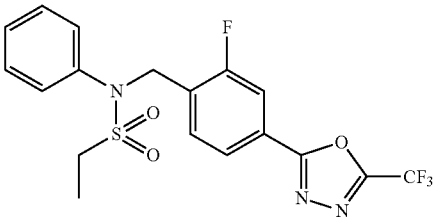 [SMILES: CCS(=O)(=O)N(Cc1ccc(-c2nnc(C(F)(F)F)o2)cc1F)c1ccccc1] |
| 14 | 11154 | 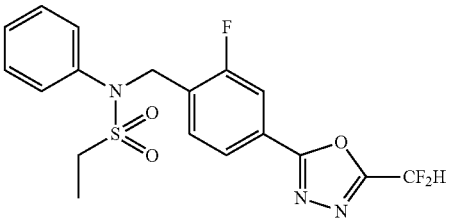 [SMILES: CCS(=O)(=O)N(Cc1ccc(-c2nnc(C(F)F)o2)cc1F)c1ccccc1] |
| 15 | 11155 | 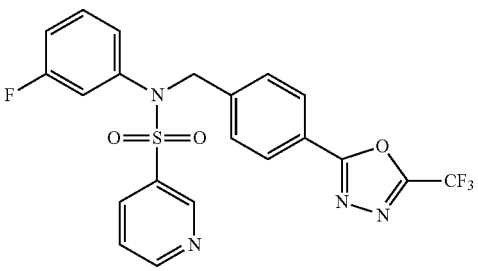 [SMILES: O=S(=O)(c1cccnc1)N(Cc1ccc(-c2nnc(C(F)(F)F)o2)cc1)c1cccc(F)c1] |
| 16 | 11156 | 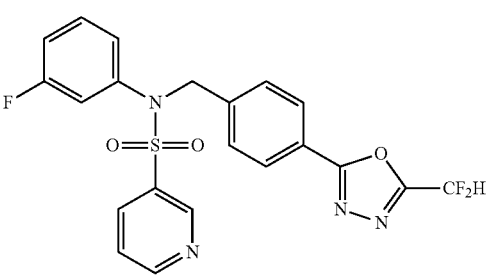 [SMILES: O=S(=O)(c1cccnc1)N(Cc1ccc(-c2nnc(C(F)F)o2)cc1)c1cccc(F)c1] |
| 17 | 11167 | 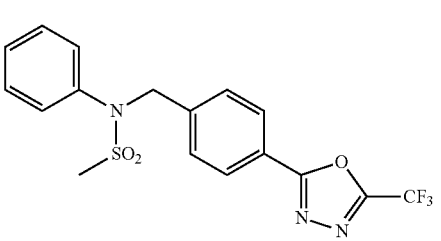 [SMILES: CS(=O)(=O)N(Cc1ccc(-c2nnc(C(F)(F)F)o2)cc1)c1ccccc1] |
| 18 | 11168 | 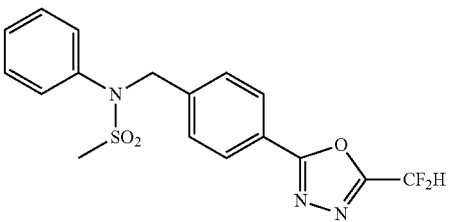 [SMILES: CS(=O)(=O)N(Cc1ccc(-c2nnc(C(F)F)o2)cc1)c1ccccc1] |

TABLE 1-continued

| Ex. | Comp. | Structure |
|---|---|---|
| 19 | 11169 | 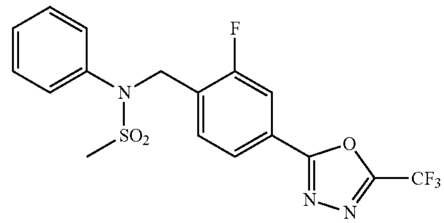 [SMILES: CS(=O)(=O)N(Cc1ccc(-c2nnc(C(F)(F)F)o2)cc1F)c1ccccc1] |
| 20 | 11170 | 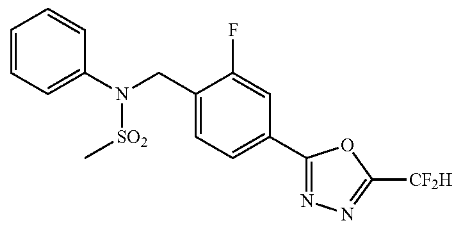 [SMILES: CS(=O)(=O)N(Cc1ccc(-c2nnc(C(F)F)o2)cc1F)c1ccccc1] |
| 21 | 11171 | 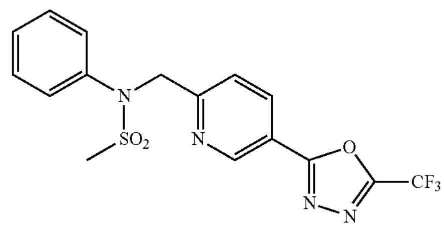 [SMILES: CS(=O)(=O)N(Cc1ccc(-c2nnc(C(F)(F)F)o2)cn1)c1ccccc1] |
| 22 | 11172 | 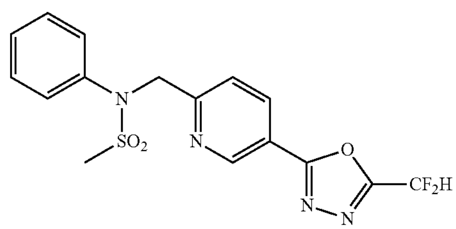 [SMILES: CS(=O)(=O)N(Cc1ccc(-c2nnc(C(F)F)o2)cn1)c1ccccc1] |
| 23 | 11173 | 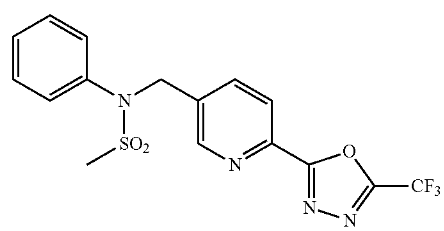 [SMILES: CS(=O)(=O)N(Cc1ccc(-c2nnc(C(F)(F)F)o2)nc1)c1ccccc1] |
| 24 | 11174 | 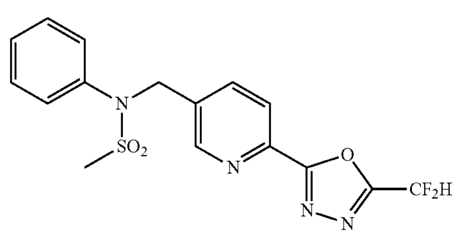 [SMILES: CS(=O)(=O)N(Cc1ccc(-c2nnc(C(F)F)o2)nc1)c1ccccc1] |
| 25 | 11175 | 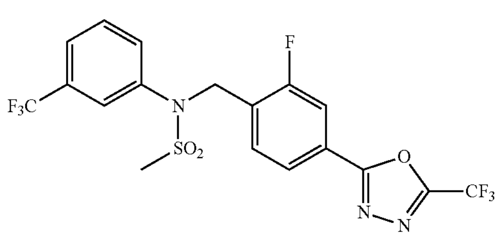 [SMILES: CS(=O)(=O)N(Cc1ccc(-c2nnc(C(F)(F)F)o2)cc1F)c1cccc(C(F)(F)F)c1] |

TABLE 1-continued

| Ex. | Comp. | Structure |
|---|---|---|
| 26 | 11176 | 3-(trifluoromethyl)phenyl-N-methylsulfonyl-N-[[2-fluoro-4-[5-(difluoromethyl)-1,3,4-oxadiazol-2-yl]phenyl]methyl]amine |
| 27 | 11177 | 3-methylphenyl-N-methylsulfonyl-N-[[2-fluoro-4-[5-(trifluoromethyl)-1,3,4-oxadiazol-2-yl]phenyl]methyl]amine |
| 28 | 11178 | 3-methylphenyl-N-methylsulfonyl-N-[[2-fluoro-4-[5-(difluoromethyl)-1,3,4-oxadiazol-2-yl]phenyl]methyl]amine |
| 29 | 11179 | 3-methoxyphenyl-N-methylsulfonyl-N-[[2-fluoro-4-[5-(trifluoromethyl)-1,3,4-oxadiazol-2-yl]phenyl]methyl]amine |
| 30 | 11180 | 3-methoxyphenyl-N-methylsulfonyl-N-[[2-fluoro-4-[5-(difluoromethyl)-1,3,4-oxadiazol-2-yl]phenyl]methyl]amine |
| 31 | 11181 | 3-fluorophenyl-N-methylsulfonyl-N-[[2-fluoro-4-[5-(trifluoromethyl)-1,3,4-oxadiazol-2-yl]phenyl]methyl]amine |

TABLE 1-continued

| Ex. | Comp. | Structure |
|---|---|---|
| 32 | 11182 | 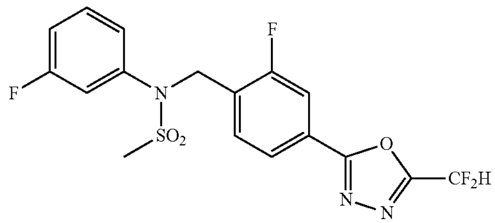 [SMILES: CS(=O)(=O)N(Cc1ccc(-c2nnc(C(F)F)o2)cc1F)c1cccc(F)c1] |
| 33 | 11183 | 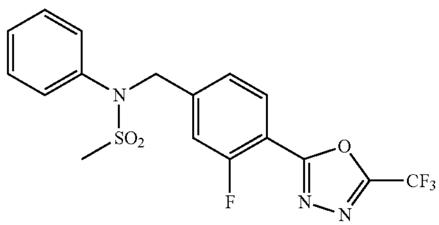 [SMILES: CS(=O)(=O)N(Cc1ccc(-c2nnc(C(F)(F)F)o2)c(F)c1)c1ccccc1] |
| 34 | 11184 | 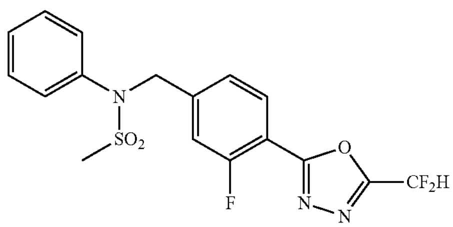 [SMILES: CS(=O)(=O)N(Cc1ccc(-c2nnc(C(F)F)o2)c(F)c1)c1ccccc1] |
| 35 | 11186 | 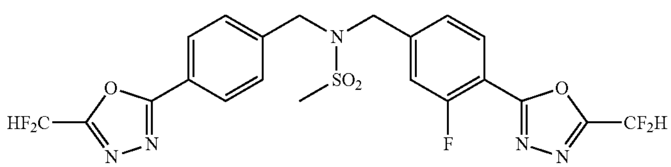 |
| 36 | 11190 | 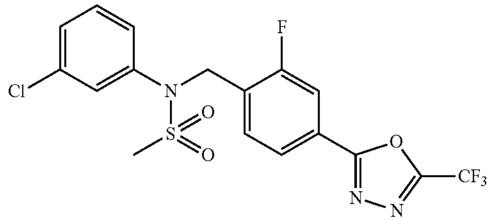 [SMILES: CS(=O)(=O)N(Cc1ccc(-c2nnc(C(F)(F)F)o2)cc1F)c1cccc(Cl)c1] |
| 37 | 11191 | 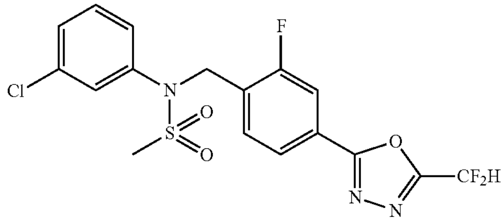 [SMILES: CS(=O)(=O)N(Cc1ccc(-c2nnc(C(F)F)o2)cc1F)c1cccc(Cl)c1] |
| 38 | 11192 | 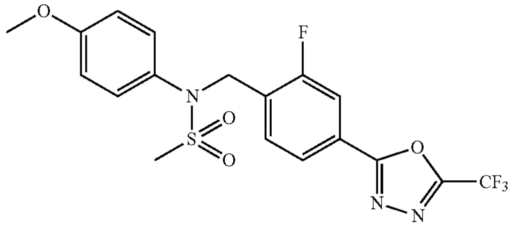 [SMILES: COc1ccc(N(Cc2ccc(-c3nnc(C(F)(F)F)o3)cc2F)S(C)(=O)=O)cc1] |

TABLE 1-continued
| Ex. | Comp. | Structure |
|---|---|---|
| 39 | 11193 | 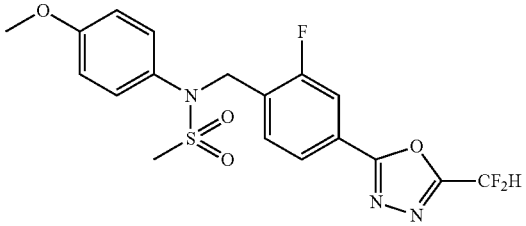 [SMILES: COc1ccc(N(Cc2ccc(-c3nnc(C(F)F)o3)cc2F)S(C)(=O)=O)cc1] |
| 40 | 11194 | 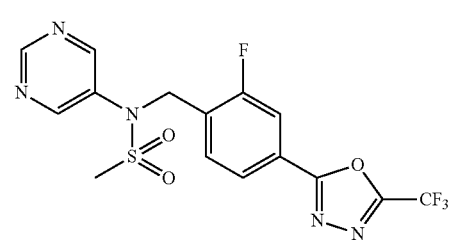 [SMILES: CS(=O)(=O)N(Cc1ccc(-c2nnc(C(F)(F)F)o2)cc1F)c1cncnc1] |
| 41 | 11195 | 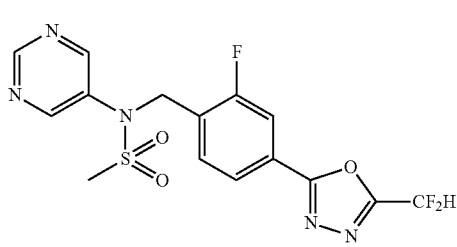 [SMILES: CS(=O)(=O)N(Cc1ccc(-c2nnc(C(F)F)o2)cc1F)c1cncnc1] |
| 42 | 11196 | 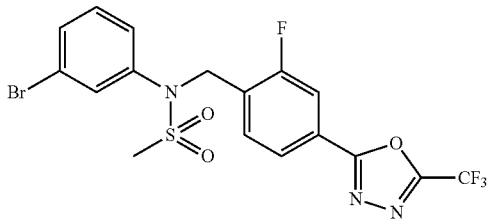 |
| 43 | 11197 | 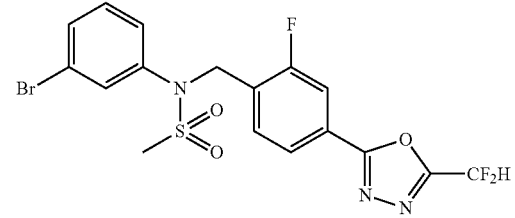 |
| 44 | 11216 | 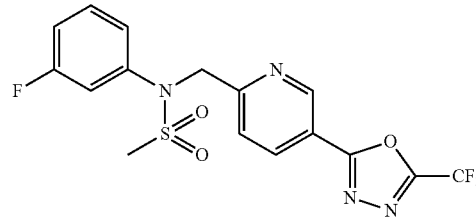 |

TABLE 1-continued

| Ex. | Comp. | Structure |
|-----|-------|-----------|
| 45 | 11217 | 3-fluorophenyl-N(SO2Me)-CH2-(pyridin-2-yl, 5-substituted with 1,3,4-oxadiazol-2-yl-CF2H) |
| 46 | 11218 | 2-(CF3)phenyl-N(SO2Me)-CH2-(2-fluoro-4-(5-CF3-1,3,4-oxadiazol-2-yl)phenyl) |
| 47 | 11219 | 2-(CF3)phenyl-N(SO2Me)-CH2-(2-fluoro-4-(5-CF2H-1,3,4-oxadiazol-2-yl)phenyl) |
| 48 | 11220 | 4-(CF3)phenyl-N(SO2Me)-CH2-(2-fluoro-4-(5-CF3-1,3,4-oxadiazol-2-yl)phenyl) |
| 49 | 11221 | 4-(CF3)phenyl-N(SO2Me)-CH2-(2-fluoro-4-(5-CF2H-1,3,4-oxadiazol-2-yl)phenyl) |
| 50 | 11222 | n-butyl-N(SO2Me)-CH2-(4-(5-CF3-1,3,4-oxadiazol-2-yl)phenyl) |

TABLE 1-continued

| Ex. | Comp. | Structure |
|---|---|---|
| 51 | 11225 | 3-fluorophenyl-N-(pyridin-3-ylsulfonyl)-N-[[2-fluoro-4-[5-(difluoromethyl)-1,3,4-oxadiazol-2-yl]phenyl]methyl]amine |
| 52 | 11226 | benzo[1,3]dioxol-5-yl-N-(methylsulfonyl)-N-[[2-fluoro-4-[5-(trifluoromethyl)-1,3,4-oxadiazol-2-yl]phenyl]methyl]amine |
| 53 | 11227 | benzo[1,3]dioxol-5-yl-N-(methylsulfonyl)-N-[[2-fluoro-4-[5-(difluoromethyl)-1,3,4-oxadiazol-2-yl]phenyl]methyl]amine |
| 54 | 11229 | phenyl-N-(cyclohexylsulfonyl)-N-[[2-fluoro-4-[5-(difluoromethyl)-1,3,4-oxadiazol-2-yl]phenyl]methyl]amine |
| 55 | 11230 | phenyl-N-(sec-butylsulfonyl)-N-[[2-fluoro-4-[5-(difluoromethyl)-1,3,4-oxadiazol-2-yl]phenyl]methyl]amine |
| 56 | 11231 | phenyl-N-(methoxycarbonylmethylsulfonyl)-N-[[2-fluoro-4-[5-(difluoromethyl)-1,3,4-oxadiazol-2-yl]phenyl]methyl]amine |

TABLE 1-continued

| Ex. | Comp. | Structure |
|-----|-------|-----------|
| 57 | 11248 | 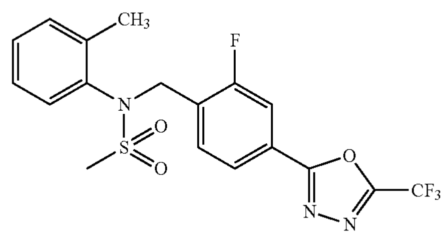 [SMILES: CS(=O)(=O)N(Cc1ccc(-c2nnc(C(F)(F)F)o2)cc1F)c1ccccc1C(F)(F)F] |
| 58 | 11249 | 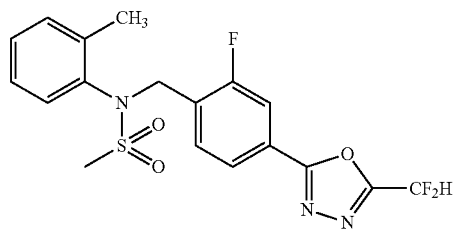 [SMILES: Cc1ccccc1N(Cc1ccc(-c2nnc(C(F)F)o2)cc1F)S(C)(=O)=O] |
| 59 | 11250 | 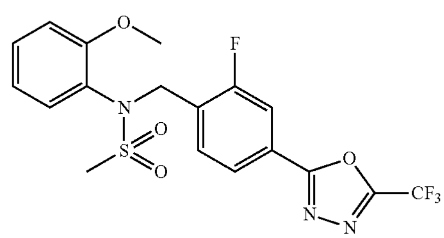 [SMILES: COc1ccccc1N(Cc1ccc(-c2nnc(C(F)(F)F)o2)cc1F)S(C)(=O)=O] |
| 60 | 11251 | 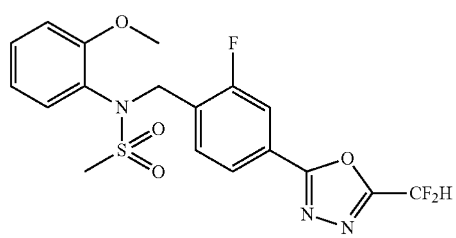 [SMILES: COc1ccccc1N(Cc1ccc(-c2nnc(C(F)F)o2)cc1F)S(C)(=O)=O] |
| 61 | 11252 | 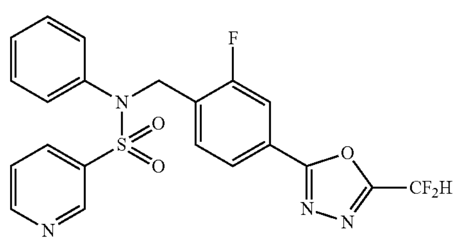 [SMILES: O=S(=O)(c1cccnc1)N(Cc1ccc(-c2nnc(C(F)F)o2)cc1F)c1ccccc1] |
| 62 | 11253 | 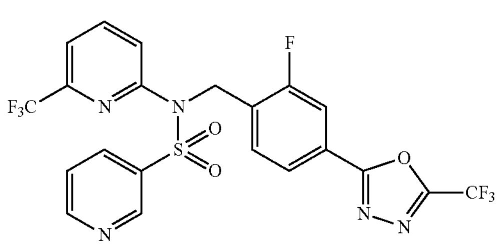 [SMILES: O=S(=O)(c1cccnc1)N(Cc1ccc(-c2nnc(C(F)(F)F)o2)cc1F)c1cccc(C(F)(F)F)n1] |

TABLE 1-continued
| Ex. | Comp. | Structure |
|---|---|---|
| 63 | 11254 | 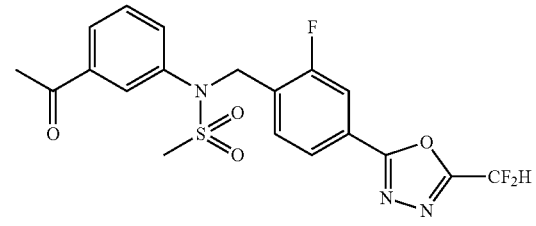 [SMILES: CC(=O)c1cccc(N(Cc2ccc(-c3nnc(C(F)F)o3)cc2F)S(C)(=O)=O)c1] |
| 64 | 11255 | 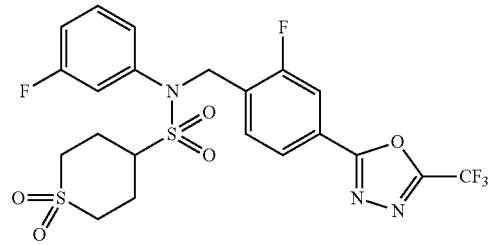 [SMILES: O=S1(=O)CCC(S(=O)(=O)N(Cc2ccc(-c3nnc(C(F)(F)F)o3)cc2F)c2cccc(F)c2)CC1] |
| 65 | 11256 | 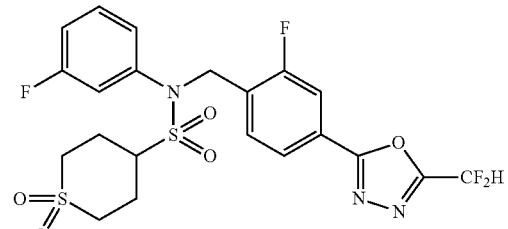 |
| 66 | 11271 | 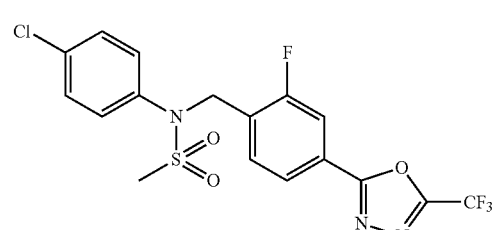 |
| 67 | 11272 | 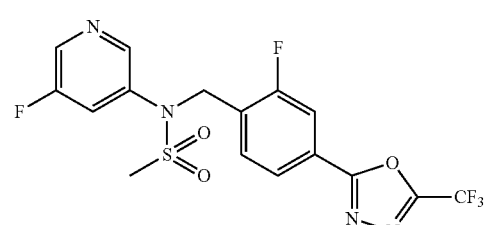 |
| 68 | 11273 | 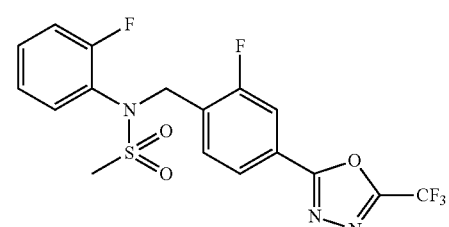 |

TABLE 1-continued

| Ex. | Comp. | Structure |
|---|---|---|
| 69 | 11274 | 2-fluorophenyl-N-methylsulfonyl-N-[[2-fluoro-4-(5-(difluoromethyl)-1,3,4-oxadiazol-2-yl)phenyl]methyl]amine |
| 70 | 11275 | 4-fluorophenyl-N-methylsulfonyl-N-[[2-fluoro-4-(5-(trifluoromethyl)-1,3,4-oxadiazol-2-yl)phenyl]methyl]amine |
| 71 | 11276 | 4-fluorophenyl-N-methylsulfonyl-N-[[2-fluoro-4-(5-(difluoromethyl)-1,3,4-oxadiazol-2-yl)phenyl]methyl]amine |
| 72 | 11277 | 4-bromophenyl-N-methylsulfonyl-N-[[2-fluoro-4-(5-(trifluoromethyl)-1,3,4-oxadiazol-2-yl)phenyl]methyl]amine |
| 73 | 11278 | 4-bromophenyl-N-methylsulfonyl-N-[[2-fluoro-4-(5-(difluoromethyl)-1,3,4-oxadiazol-2-yl)phenyl]methyl]amine |
| 74 | 11279 | 2-chlorophenyl-N-methylsulfonyl-N-[[2-fluoro-4-(5-(trifluoromethyl)-1,3,4-oxadiazol-2-yl)phenyl]methyl]amine |

TABLE 1-continued

| Ex. | Comp. | Structure |
|---|---|---|
| 75 | 11280 | 2-chlorophenyl-N-methylsulfonyl-N-[[2-fluoro-4-[5-(difluoromethyl)-1,3,4-oxadiazol-2-yl]phenyl]methyl]amine |
| 76 | 11281 | 4-chlorophenyl-N-methylsulfonyl-N-[[2-fluoro-4-[5-(difluoromethyl)-1,3,4-oxadiazol-2-yl]phenyl]methyl]amine |
| 77 | 11282 | 4-methylphenyl-N-methylsulfonyl-N-[[2-fluoro-4-[5-(trifluoromethyl)-1,3,4-oxadiazol-2-yl]phenyl]methyl]amine |
| 78 | 11283 | 4-methylphenyl-N-methylsulfonyl-N-[[2-fluoro-4-[5-(difluoromethyl)-1,3,4-oxadiazol-2-yl]phenyl]methyl]amine |
| 79 | 11284 | 5-fluoropyridin-3-yl-N-methylsulfonyl-N-[[2-fluoro-4-[5-(difluoromethyl)-1,3,4-oxadiazol-2-yl]phenyl]methyl]amine |
| 80 | 11287 | phenyl-N-(3-methoxy-3-oxopropylsulfonyl)-N-[[2-fluoro-4-[5-(difluoromethyl)-1,3,4-oxadiazol-2-yl]phenyl]methyl]amine |

TABLE 1-continued
| Ex. | Comp. | Structure |
|---|---|---|
| 81 | 11288 | 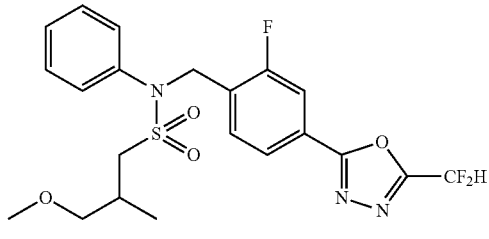 [SMILES: COCC(C)CS(=O)(=O)N(Cc1ccc(-c2nnc(C(F)F)o2)cc1F)c1ccccc1] |
| 82 | 11289 | 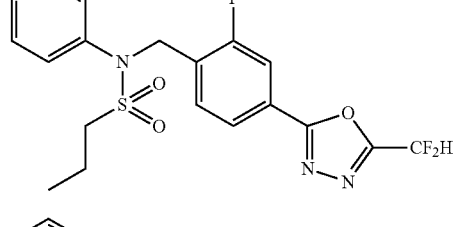 |
| 83 | 11290 | 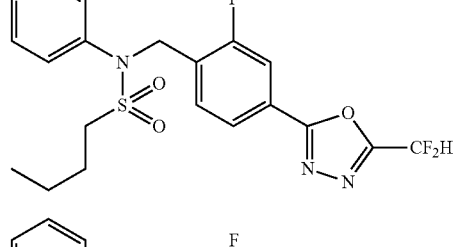 |
| 84 | 11291 | 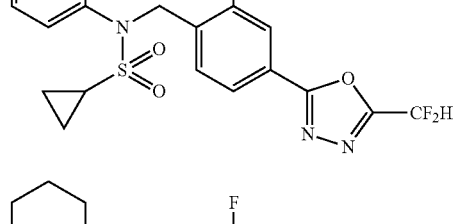 |
| 85 | 11292 | 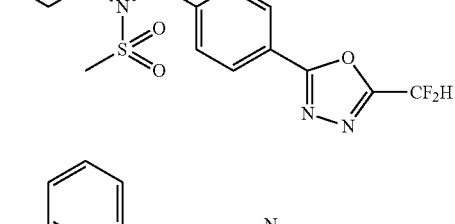 |
| 86 | 11323 | 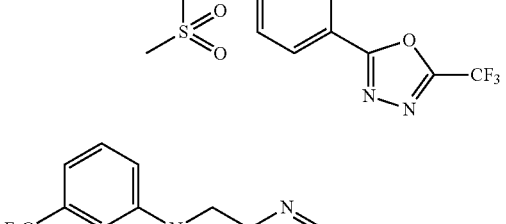 |
| 87 | 11324 | 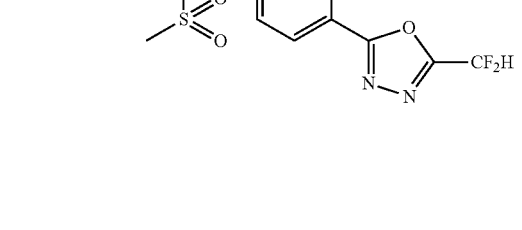 |

TABLE 1-continued

| Ex. | Comp. | Structure |
|---|---|---|
| 88 | 11338 | *tert-butyl 4-(N-(2-fluoro-4-(5-(difluoromethyl)-1,3,4-oxadiazol-2-yl)benzyl)methylsulfonamido)piperidine-1-carboxylate* |
| 89 | 11345 | *N-(benzo[d][1,3]dioxol-5-yl)-N-((5-(5-(difluoromethyl)-1,3,4-oxadiazol-2-yl)pyridin-2-yl)methyl)methanesulfonamide* |
| 90 | 11346 | *N-((5-(5-(difluoromethyl)-1,3,4-oxadiazol-2-yl)pyridin-2-yl)methyl)-N-(4-methoxyphenyl)methanesulfonamide* |
| 91 | 11347 | *N-(5-bromopyridin-2-yl)-N-(4-(5-(difluoromethyl)-1,3,4-oxadiazol-2-yl)benzyl)methanesulfonamide* |
| 92 | 11348 | *N-(5-chloropyridin-2-yl)-N-(4-(5-(difluoromethyl)-1,3,4-oxadiazol-2-yl)benzyl)methanesulfonamide* |
| 93 | 11350 | *N-((5-(5-(difluoromethyl)-1,3,4-oxadiazol-2-yl)pyridin-2-yl)methyl)-N-phenyl-1,1-dioxo-tetrahydro-2H-thiopyran-4-sulfonamide* |

TABLE 1-continued

| Ex. | Comp. | Structure |
|---|---|---|
| 94 | 11351 | Cyclohexyl-N(SO2Me)-CH2-(pyridin-2-yl)-5-(1,3,4-oxadiazol-2-yl)-CF2H |
| 95 | 11352 | (3-Cl-phenyl)-N(SO2Me)-CH2-(pyridin-2-yl)-5-(1,3,4-oxadiazol-2-yl)-CF2H |
| 96 | 11353 | (pyridin-3-yl)-N(SO2Me)-CH2-(pyridin-2-yl)-5-(1,3,4-oxadiazol-2-yl)-CF2H |
| 97 | 11354 | (3-Br-phenyl)-N(SO2Me)-CH2-(pyridin-2-yl)-5-(1,3,4-oxadiazol-2-yl)-CF2H |
| 98 | 11355 | (3-Me-phenyl)-N(SO2Me)-CH2-(pyridin-2-yl)-5-(1,3,4-oxadiazol-2-yl)-CF2H |
| 99 | 11366 | (3-Br-phenyl)-N(SO2Et)-CH2-(pyridin-2-yl)-5-(1,3,4-oxadiazol-2-yl)-CF2H |
| 100 | 11367 | phenyl-N(SO2-(1-methylpiperidin-4-yl))-CH2-(pyridin-2-yl)-5-(1,3,4-oxadiazol-2-yl)-CF2H |

TABLE 1-continued

| Ex. | Comp. | Structure |
|---|---|---|
| 101 | 11368 | 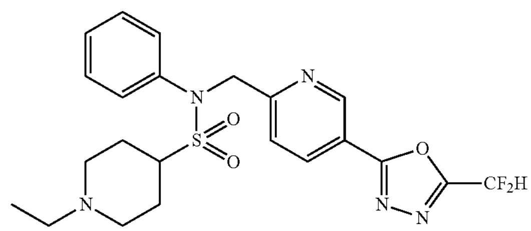 [SMILES: CCN1CCC(S(=O)(=O)N(Cc2ccc(-c3nnc(C(F)F)o3)cn2)c2ccccc2)CC1] |
| 102 | 11372 | 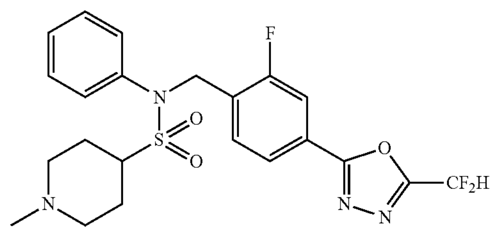 [SMILES: CN1CCC(S(=O)(=O)N(Cc2ccc(-c3nnc(C(F)F)o3)cc2F)c2ccccc2)CC1] |
| 103 | 11373 | 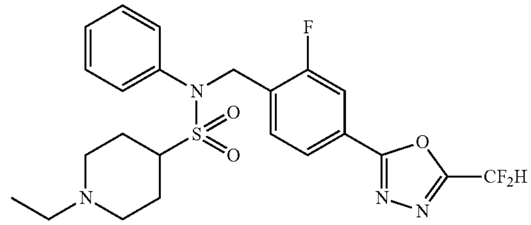 [SMILES: CCN1CCC(S(=O)(=O)N(Cc2ccc(-c3nnc(C(F)F)o3)cc2F)c2ccccc2)CC1] |
| 104 | 11377 | 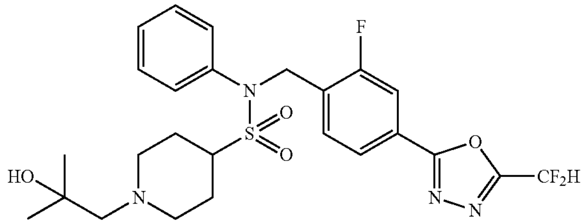 [SMILES: CC(C)(O)CN1CCC(S(=O)(=O)N(Cc2ccc(-c3nnc(C(F)F)o3)cc2F)c2ccccc2)CC1] |
| 105 | 11386 | 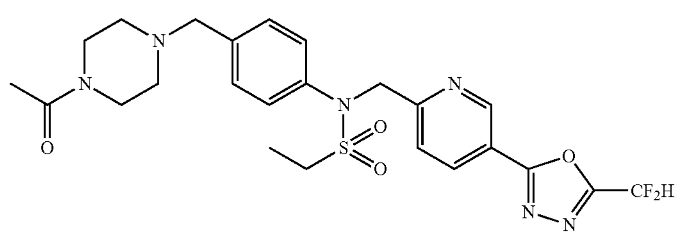 [SMILES: CCS(=O)(=O)N(Cc1ccc(-c2nnc(C(F)F)o2)cn1)c1ccc(CN2CCN(C(C)=O)CC2)cc1] |
| 106 | 11387 | 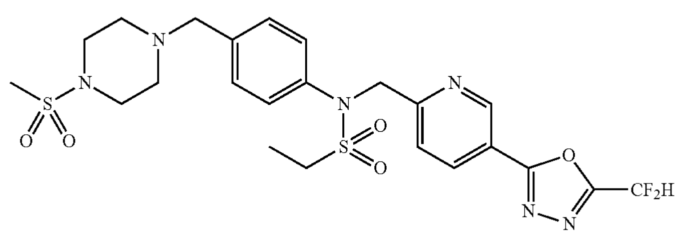 [SMILES: CCS(=O)(=O)N(Cc1ccc(-c2nnc(C(F)F)o2)cn1)c1ccc(CN2CCN(S(C)(=O)=O)CC2)cc1] |

TABLE 1-continued

| Ex. | Comp. | Structure |
|---|---|---|
| 107 | 11388 | 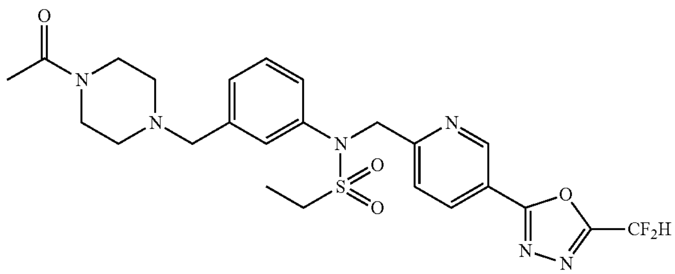 [SMILES: CCS(=O)(=O)N(Cc1ccc(-c2nnc(C(F)F)o2)cn1)c1cccc(CN2CCN(C(C)=O)CC2)c1] |
| 108 | 11389 | 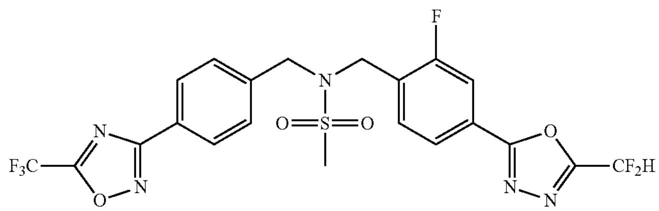 [SMILES: CS(=O)(=O)N(Cc1ccc(-c2noc(C(F)(F)F)n2)cc1)Cc1ccc(-c2nnc(C(F)F)o2)cc1F] |
| 109 | 11390 | 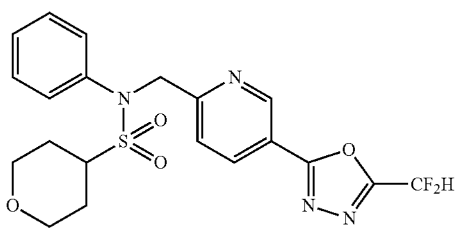 [SMILES: O=S(=O)(C1CCOCC1)N(Cc1ccc(-c2nnc(C(F)F)o2)cn1)c1ccccc1] |
| 110 | 11392 | 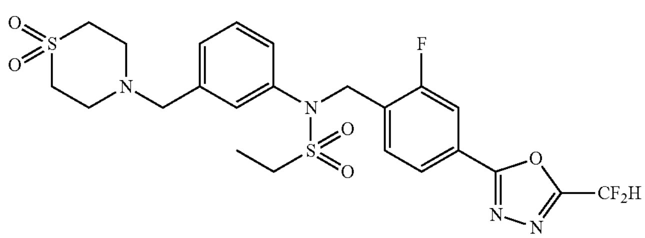 [SMILES: CCS(=O)(=O)N(Cc1ccc(-c2nnc(C(F)F)o2)cc1F)c1cccc(CN2CCS(=O)(=O)CC2)c1] |
| 111 | 11402 | 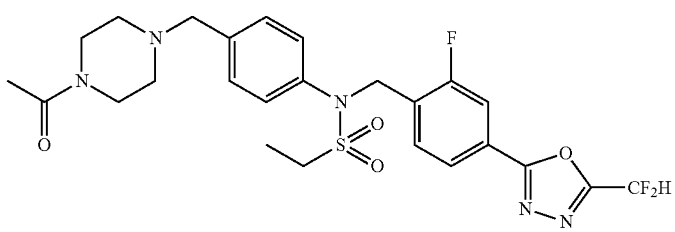 [SMILES: CCS(=O)(=O)N(Cc1ccc(-c2nnc(C(F)F)o2)cc1F)c1ccc(CN2CCN(C(C)=O)CC2)cc1] |
| 112 | 11403 | 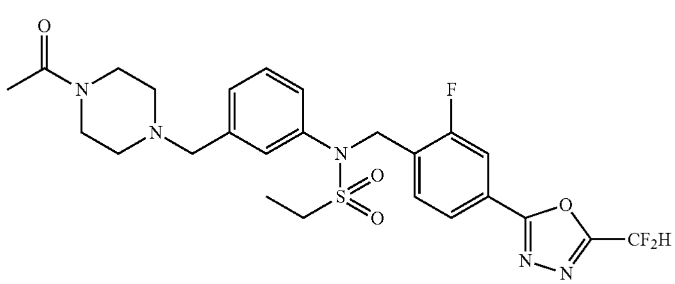 [SMILES: CCS(=O)(=O)N(Cc1ccc(-c2nnc(C(F)F)o2)cc1F)c1cccc(CN2CCN(C(C)=O)CC2)c1] |

TABLE 1-continued

| Ex. | Comp. | Structure |
|---|---|---|
| 113 | 11404 | 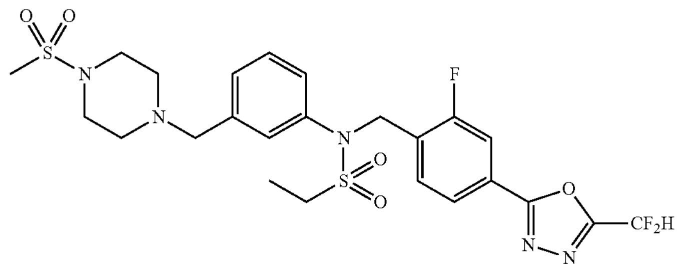 [SMILES: CCS(=O)(=O)N(Cc1ccc(-c2nnc(C(F)F)o2)cc1F)c1cccc(CN2CCN(S(C)(=O)=O)CC2)c1] |
| 114 | 11405 | 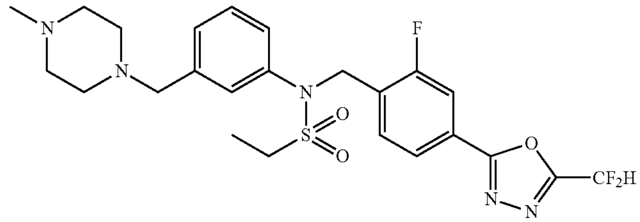 [SMILES: CCS(=O)(=O)N(Cc1ccc(-c2nnc(C(F)F)o2)cc1F)c1cccc(CN2CCN(C)CC2)c1] |
| 115 | 11406 | 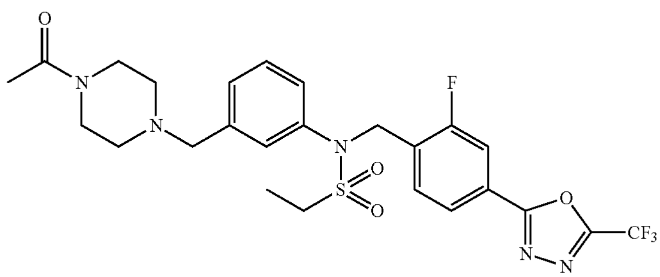 [SMILES: CCS(=O)(=O)N(Cc1ccc(-c2nnc(C(F)(F)F)o2)cc1F)c1cccc(CN2CCN(C(C)=O)CC2)c1] |
| 116 | 11411 | 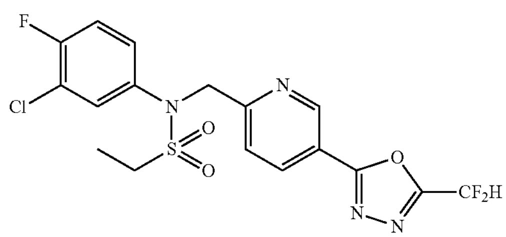 |
| 117 | 11412 | 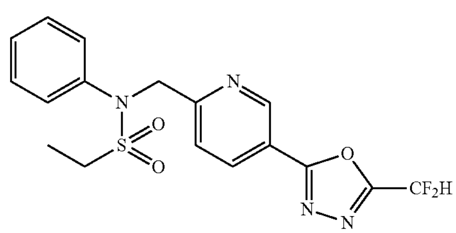 [SMILES: CCS(=O)(=O)N(Cc1ccc(-c2nnc(C(F)F)o2)cn1)c1ccccc1] |
| 118 | 11426 | 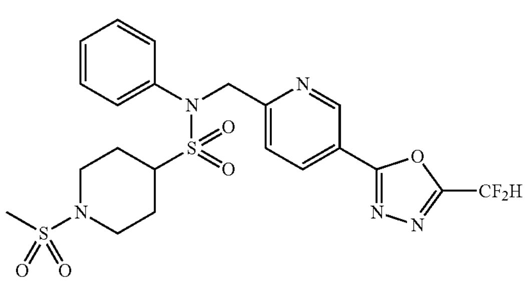 [SMILES: CS(=O)(=O)N1CCC(S(=O)(=O)N(Cc2ccc(-c3nnc(C(F)F)o3)cn2)c2ccccc2)CC1] |

TABLE 1-continued
| Ex. | Comp. | Structure |
|---|---|---|
| 119 | 11427 | 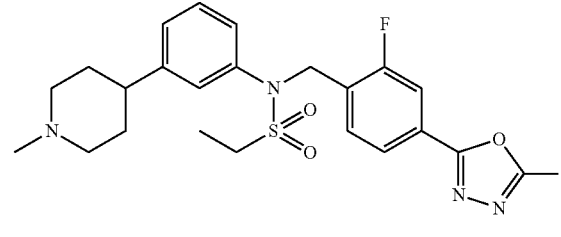 |
| 120 | 11428 | 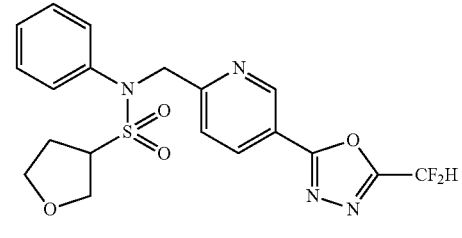 [SMILES: O=S(=O)(C1CCOC1)N(Cc1ccc(-c2nnc(C(F)F)o2)cn1)c1ccccc1] |
| 121 | 11429 | 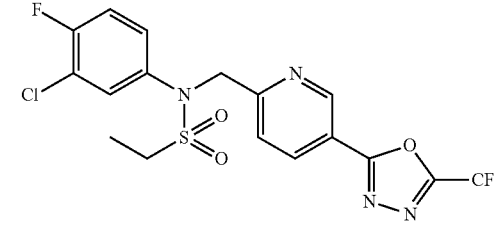 |
| 122 | 11430 | 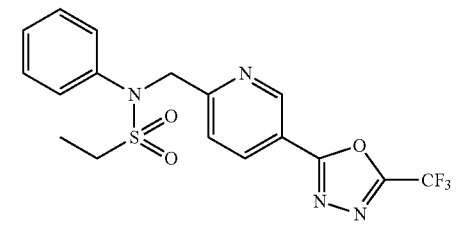 [SMILES: CCS(=O)(=O)N(Cc1ccc(-c2nnc(C(F)(F)F)o2)cn1)c1ccccc1] |
| 123 | 11431 | 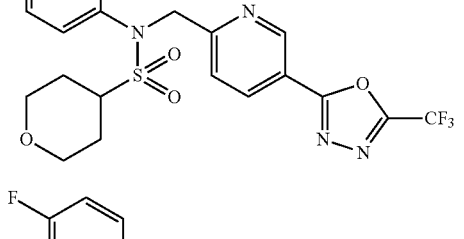 |
| 124 | 11432 | 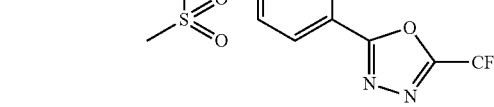 |

TABLE 1-continued

| Ex. | Comp. | Structure |
|---|---|---|
| 125 | 11433 | 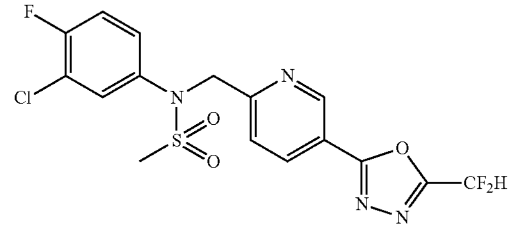 [SMILES: CS(=O)(=O)N(Cc1ccc(-c2nnc(C(F)F)o2)cn1)c1ccc(F)c(Cl)c1] |
| 126 | 11447 | 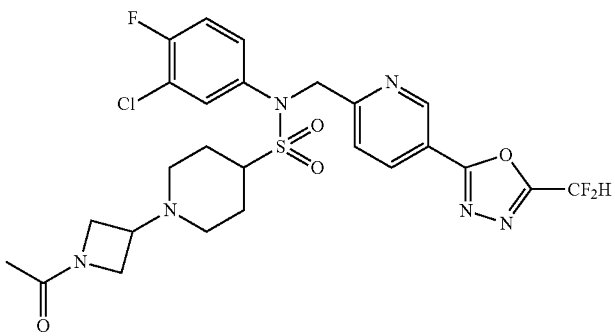 [SMILES: CC(=O)N1CC(N2CCC(S(=O)(=O)N(Cc3ccc(-c4nnc(C(F)F)o4)cn3)c3ccc(F)c(Cl)c3)CC2)C1] |
| 127 | 11448 | 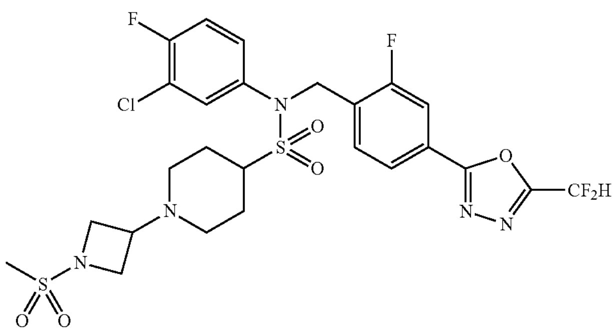 |
| 128 | 11451 | 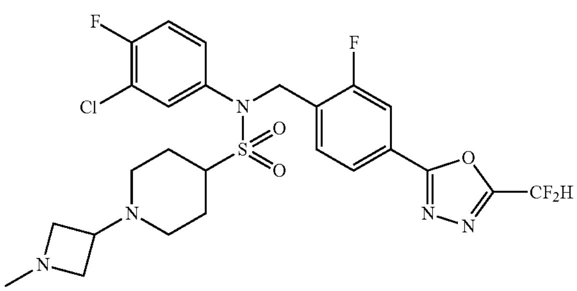 [SMILES: CN1CC(N2CCC(S(=O)(=O)N(Cc3ccc(-c4nnc(C(F)F)o4)cc3F)c3ccc(F)c(Cl)c3)CC2)C1] |
| 129 | 11452 | 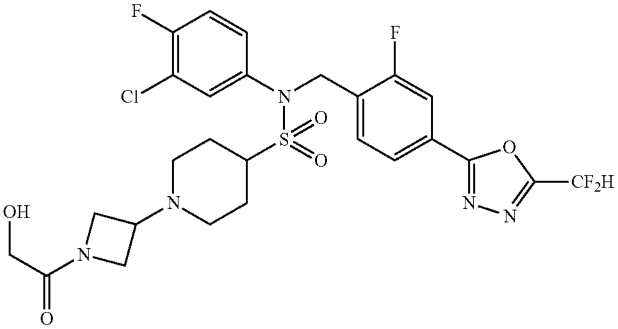 [SMILES: O=C(CO)N1CC(N2CCC(S(=O)(=O)N(Cc3ccc(-c4nnc(C(F)F)o4)cc3F)c3ccc(F)c(Cl)c3)CC2)C1] |

TABLE 1-continued

| Ex. | Comp. | Structure |
|---|---|---|
| 130 | 11460 | 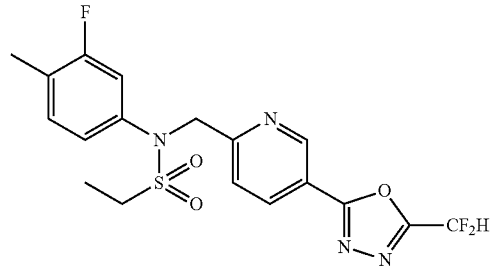 [SMILES: CCS(=O)(=O)N(Cc1ccc(-c2nnc(C(F)F)o2)cn1)c1ccc(C)c(F)c1] |
| 131 | 11461 | 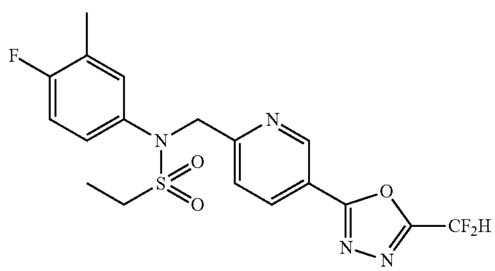 [SMILES: CCS(=O)(=O)N(Cc1ccc(-c2nnc(C(F)F)o2)cn1)c1ccc(F)c(C)c1] |
| 132 | 11462 | 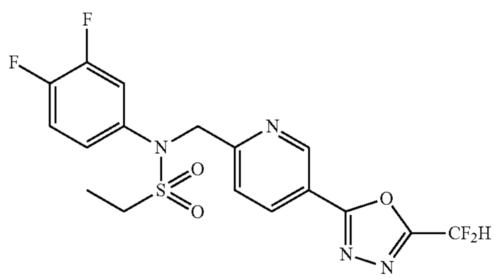 [SMILES: CCS(=O)(=O)N(Cc1ccc(-c2nnc(C(F)F)o2)cn1)c1ccc(F)c(F)c1] |
| 133 | 11463 | 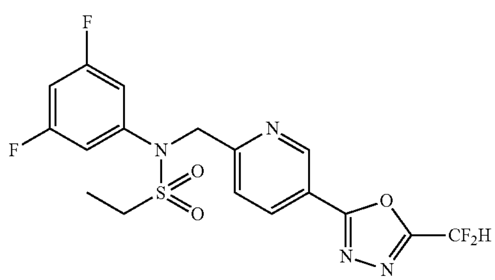 [SMILES: CCS(=O)(=O)N(Cc1ccc(-c2nnc(C(F)F)o2)cn1)c1cc(F)cc(F)c1] |
| 134 | 11497 | 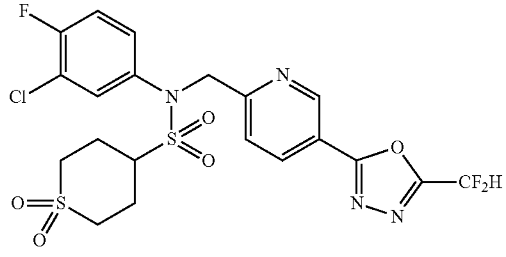 [SMILES: O=S1(=O)CCC(S(=O)(=O)N(Cc2ccc(-c3nnc(C(F)F)o3)cn2)c2ccc(F)c(Cl)c2)CC1] |

TABLE 1-continued
| Ex. | Comp. | Structure |
|-----|-------|-----------|
| 135 | 11501 | 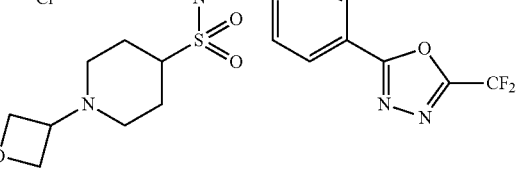 |
| 136 | 11502 | 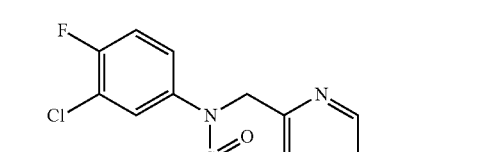 |
| 137 | 11503 | 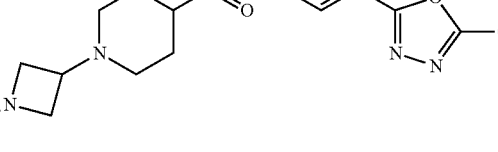 |
| 138 | 11504 | 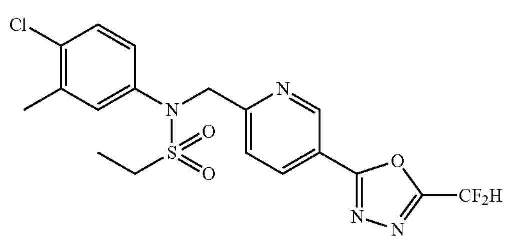 |
| 139 | 11505 | 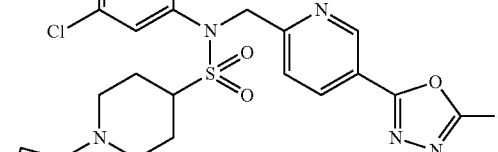 |

TABLE 1-continued

| Ex. | Comp. | Structure |
|---|---|---|
| 140 | 11506 | 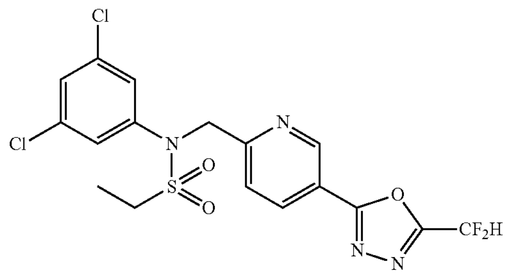 [SMILES: CCS(=O)(=O)N(Cc1ccc(-c2nnc(C(F)F)o2)cn1)c1cc(Cl)cc(Cl)c1] |
| 141 | 11507 | 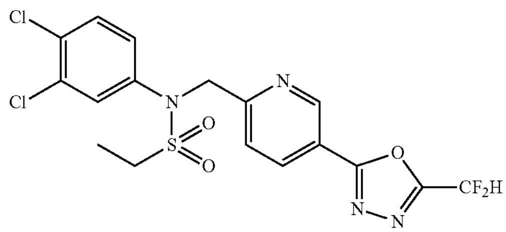 |
| 142 | 11508 | 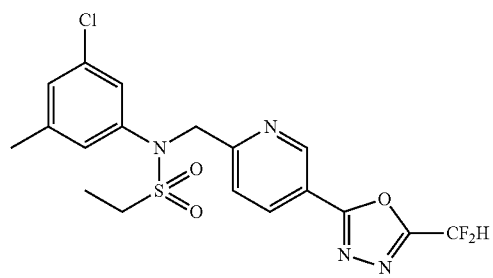 [SMILES: CCS(=O)(=O)N(Cc1ccc(-c2nnc(C(F)F)o2)cn1)c1cc(C)cc(Cl)c1] |
| 143 | 11514 | 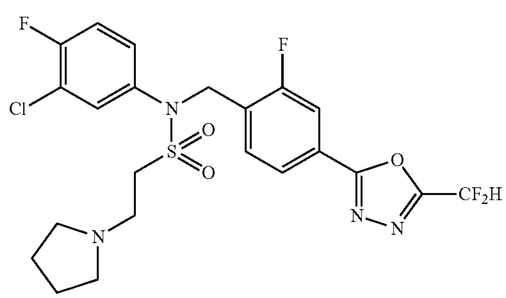 [SMILES: O=S(=O)(CCN1CCCC1)N(Cc1ccc(-c2nnc(C(F)F)o2)cc1F)c1ccc(F)c(Cl)c1] |
| 144 | 11518 | 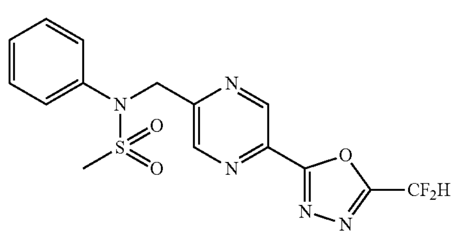 [SMILES: CS(=O)(=O)N(Cc1cnc(-c2nnc(C(F)F)o2)cn1)c1ccccc1] |

TABLE 1-continued

| Ex. | Comp. | Structure |
|---|---|---|
| 145 | 11520 | 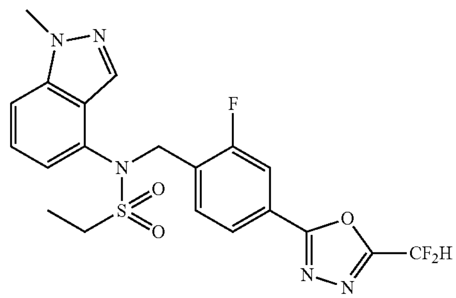 [SMILES: CCS(=O)(=O)N(Cc1ccc(-c2nnc(C(F)F)o2)cc1F)c1cccc2c1cnn2C] |
| 146 | 11521 | 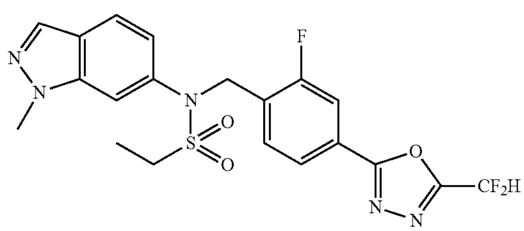 [SMILES: CCS(=O)(=O)N(Cc1ccc(-c2nnc(C(F)F)o2)cc1F)c1ccc2cnn(C)c2c1] |
| 147 | 11522 | 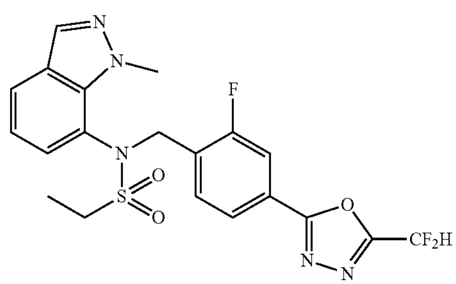 [SMILES: CCS(=O)(=O)N(Cc1ccc(-c2nnc(C(F)F)o2)cc1F)c1cccc2cnn(C)c12] |
| 148 | 11539 | 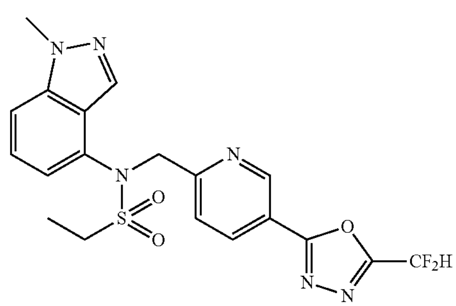 [SMILES: CCS(=O)(=O)N(Cc1ccc(-c2nnc(C(F)F)o2)cn1)c1cccc2c1cnn2C] |
| 149 | 11540 | 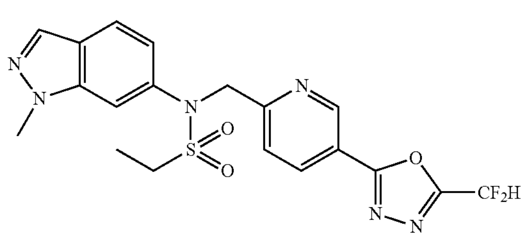 [SMILES: CCS(=O)(=O)N(Cc1ccc(-c2nnc(C(F)F)o2)cn1)c1ccc2cnn(C)c2c1] |

TABLE 1-continued

| Ex. | Comp. | Structure |
|---|---|---|
| 150 | 11541 | 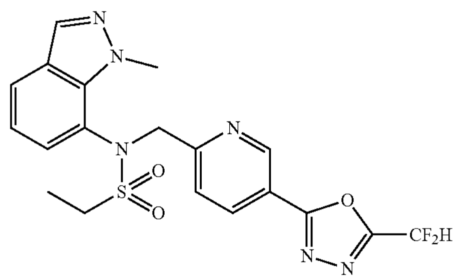 [SMILES: CCS(=O)(=O)N(Cc1ccc(-c2nnc(C(F)F)o2)cn1)c1cccc2cnn(C)c12] |
| 151 | 11552 | 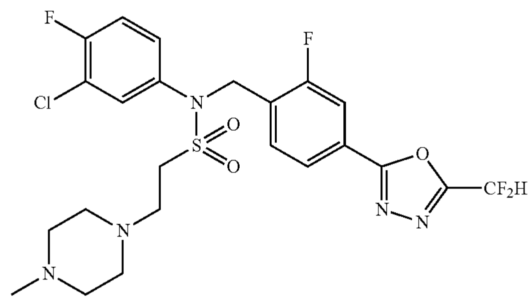 [SMILES: CN1CCN(CCS(=O)(=O)N(Cc2ccc(-c3nnc(C(F)F)o3)cc2F)c2ccc(F)c(Cl)c2)CC1] |
| 152 | 11553 | 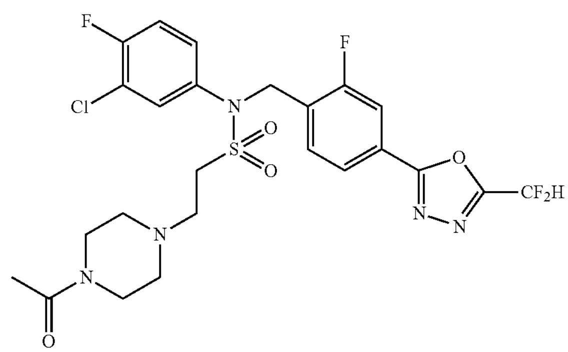 [SMILES: CC(=O)N1CCN(CCS(=O)(=O)N(Cc2ccc(-c3nnc(C(F)F)o3)cc2F)c2ccc(F)c(Cl)c2)CC1] |
| 153 | 11554 | 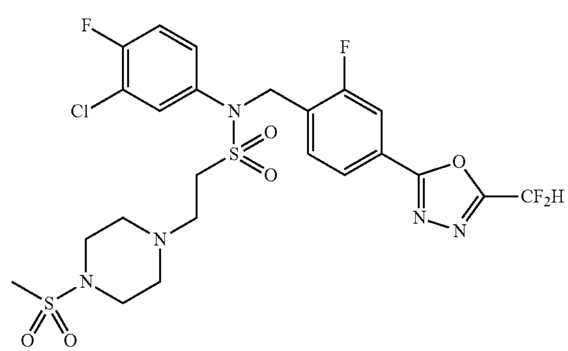 [SMILES: CS(=O)(=O)N1CCN(CCS(=O)(=O)N(Cc2ccc(-c3nnc(C(F)F)o3)cc2F)c2ccc(F)c(Cl)c2)CC1] |
| 154 | 11564 | 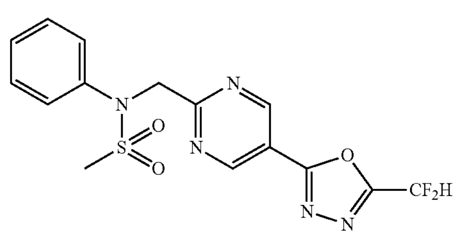 [SMILES: CS(=O)(=O)N(Cc1ncc(-c2nnc(C(F)F)o2)cn1)c1ccccc1] |

TABLE 1-continued
| Ex. | Comp. | Structure |
|---|---|---|
| 155 | 11565 | 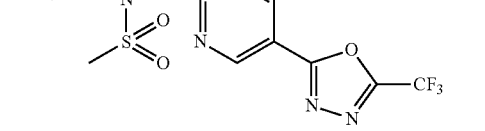 |
| 156 | 11566 | 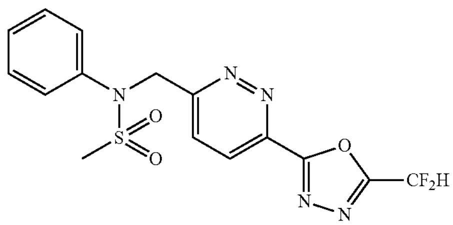 [SMILES: CS(=O)(=O)N(Cc1ccc(-c2nnc(C(F)F)o2)nn1)c1ccccc1] |
| 157 | 11567 | 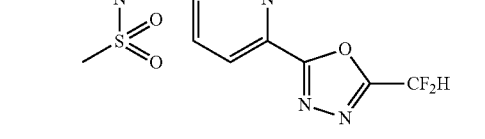 |
| 158 | 11573 | 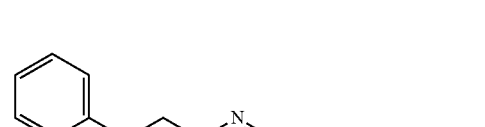 |
| 159 | 11582 | 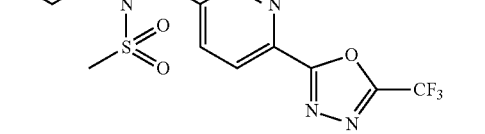 |

TABLE 1-continued
| Ex. | Comp. | Structure |
|---|---|---|
| 160 | 11583 | 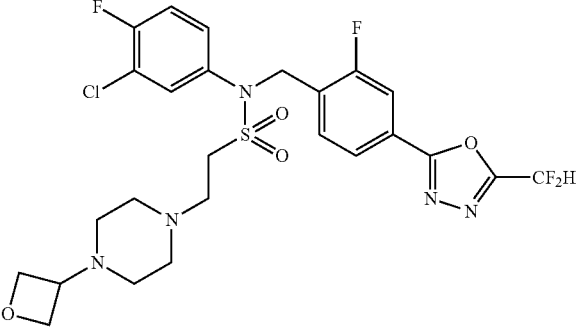 [SMILES: O=S(=O)(CCN1CCN(C2COC2)CC1)N(Cc1ccc(-c2nnc(C(F)F)o2)cc1F)c1ccc(F)c(Cl)c1] |
| 161 | 11588 | 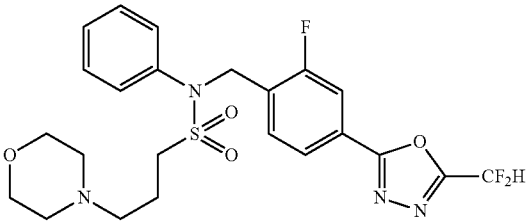 [SMILES: O=S(=O)(CCCN1CCOCC1)N(Cc1ccc(-c2nnc(C(F)F)o2)cc1F)c1ccccc1] |
| 162 | 11589 | 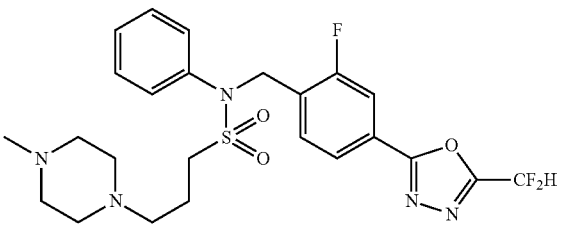 [SMILES: CN1CCN(CCCS(=O)(=O)N(Cc2ccc(-c3nnc(C(F)F)o3)cc2F)c2ccccc2)CC1] |
| 163 | 11605 | 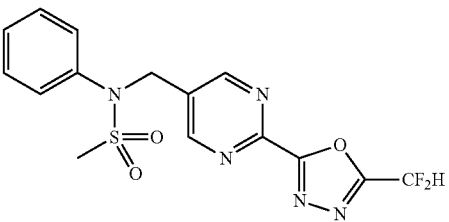 [SMILES: CS(=O)(=O)N(Cc1cnc(-c2nnc(C(F)F)o2)nc1)c1ccccc1] |
| 164 | 11606 | 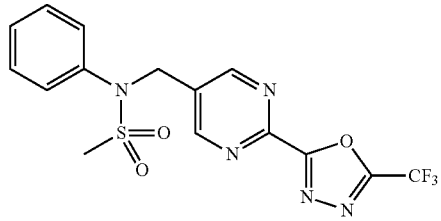 [SMILES: CS(=O)(=O)N(Cc1cnc(-c2nnc(C(F)(F)F)o2)nc1)c1ccccc1] |
| 165 | 11625 | 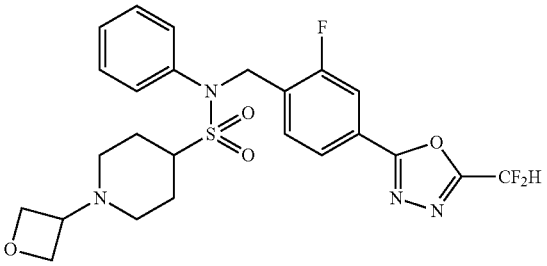 [SMILES: O=S(=O)(C1CCN(C2COC2)CC1)N(Cc1ccc(-c2nnc(C(F)F)o2)cc1F)c1ccccc1] |

TABLE 1-continued

| Ex. | Comp. | Structure |
|---|---|---|
| 166 | 11628 | *N-(pyridin-3-yl)-N-(4-(5-(difluoromethyl)-1,3,4-oxadiazol-2-yl)benzyl)methanesulfonamide* |
| 167 | 11629 | *N-phenyl-N-(4-(5-(difluoromethyl)-1,3,4-oxadiazol-2-yl)benzyl)-2-(piperidin-1-yl)ethanesulfonamide* |
| 168 | 11630 | *N-phenyl-N-(4-(5-(difluoromethyl)-1,3,4-oxadiazol-2-yl)benzyl)-2-(4-methylpiperazin-1-yl)ethanesulfonamide* |
| 169 | 11631 | *N-phenyl-N-(4-(5-(difluoromethyl)-1,3,4-oxadiazol-2-yl)benzyl)-2-(4-Boc-piperazin-1-yl)ethanesulfonamide* |
| 170 | 11632 | *N-phenyl-N-(4-(5-(difluoromethyl)-1,3,4-oxadiazol-2-yl)benzyl)-2-((3,5-dimethylpiperazin-1-yl))ethanesulfonamide* |

TABLE 1-continued

| Ex. | Comp. | Structure |
|---|---|---|
| 171 | 11633 | 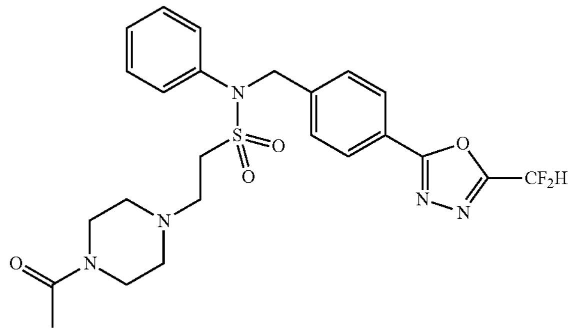 [SMILES: CC(=O)N1CCN(CCS(=O)(=O)N(Cc2ccc(-c3nnc(C(F)F)o3)cc2)c2ccccc2)CC1] |
| 172 | 11634 | 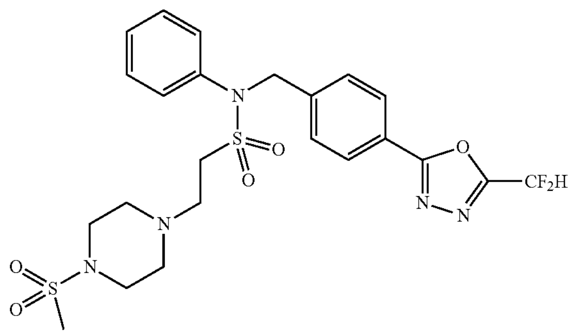 [SMILES: CS(=O)(=O)N1CCN(CCS(=O)(=O)N(Cc2ccc(-c3nnc(C(F)F)o3)cc2)c2ccccc2)CC1] |
| 173 | 11636 | 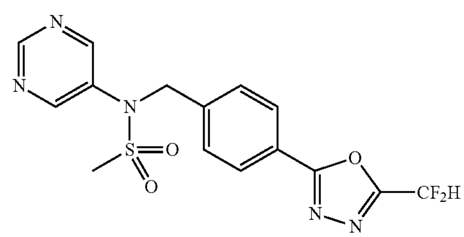 [SMILES: CS(=O)(=O)N(Cc1ccc(-c2nnc(C(F)F)o2)cc1)c1cncnc1] |
| 174 | 11637 | 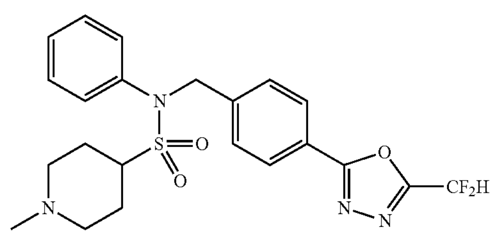 [SMILES: CN1CCC(S(=O)(=O)N(Cc2ccc(-c3nnc(C(F)F)o3)cc2)c2ccccc2)CC1] |
| 175 | 11638 | 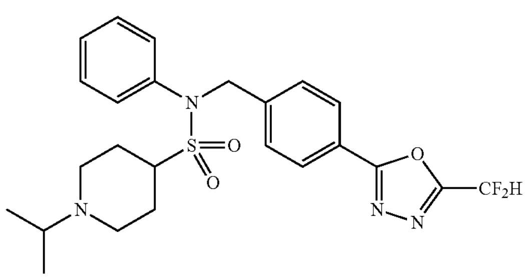 [SMILES: CC(C)N1CCC(S(=O)(=O)N(Cc2ccc(-c3nnc(C(F)F)o3)cc2)c2ccccc2)CC1] |

TABLE 1-continued
| Ex. | Comp. | Structure |
|---|---|---|
| 176 | 11639 | 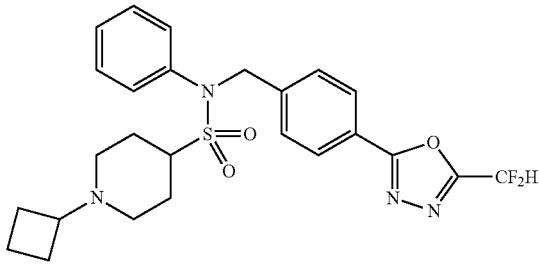 [SMILES: O=S(=O)(C1CCN(C2CCC2)CC1)N(Cc1ccc(-c2nnc(C(F)F)o2)cc1)c1ccccc1] |
| 177 | 11645 | 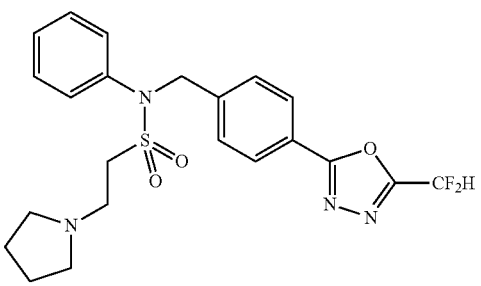 [SMILES: O=S(=O)(CCN1CCCC1)N(Cc1ccc(-c2nnc(C(F)F)o2)cc1)c1ccccc1] |
| 178 | 11646 | 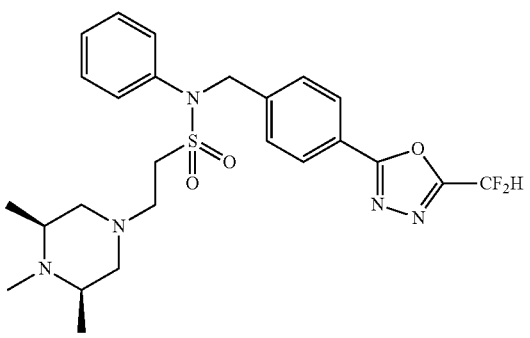 [SMILES: C[C@@H]1CN(CCS(=O)(=O)N(Cc2ccc(-c3nnc(C(F)F)o3)cc2)c2ccccc2)C[C@H](C)N1C] |
| 179 | 11647 | 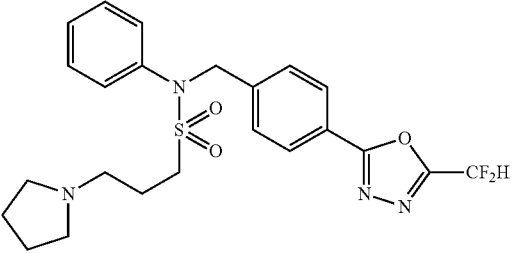 [SMILES: O=S(=O)(CCCN1CCCC1)N(Cc1ccc(-c2nnc(C(F)F)o2)cc1)c1ccccc1] |
| 180 | 11648 | 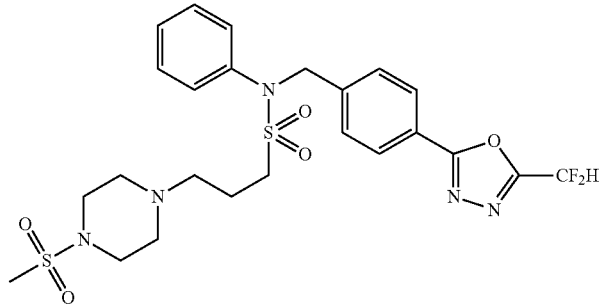 [SMILES: CS(=O)(=O)N1CCN(CCCS(=O)(=O)N(Cc2ccc(-c3nnc(C(F)F)o3)cc2)c2ccccc2)CC1] |

TABLE 1-continued

| Ex. | Comp. | Structure |
|---|---|---|
| 181 | 11655 | 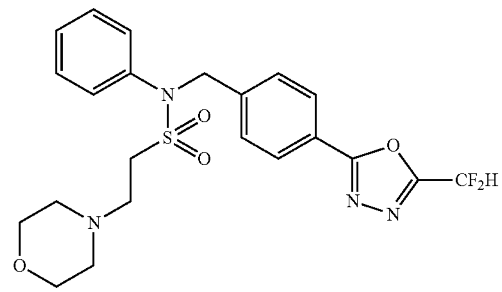 [SMILES: O=S(=O)(CCN1CCOCC1)N(Cc1ccc(-c2nnc(C(F)F)o2)cc1)c1ccccc1] |
| 182 | 11656 | 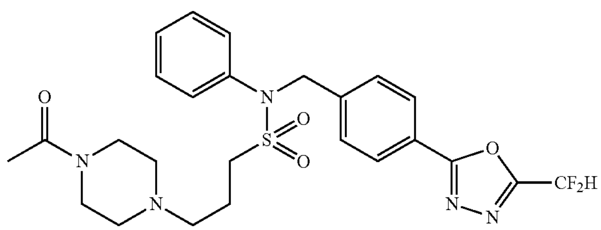 [SMILES: CC(=O)N1CCN(CCCS(=O)(=O)N(Cc2ccc(-c3nnc(C(F)F)o3)cc2)c2ccccc2)CC1] |
| 183 | 11657 | 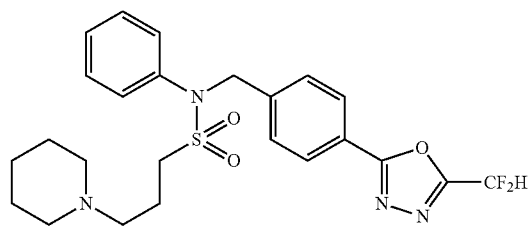 [SMILES: O=S(=O)(CCCN1CCCCC1)N(Cc1ccc(-c2nnc(C(F)F)o2)cc1)c1ccccc1] |
| 184 | 11658 | 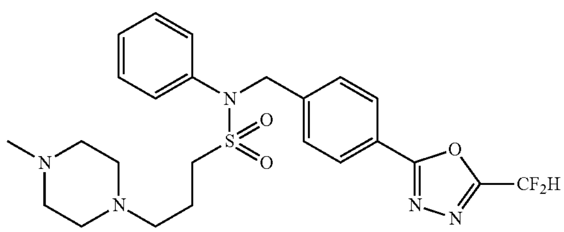 [SMILES: CN1CCN(CCCS(=O)(=O)N(Cc2ccc(-c3nnc(C(F)F)o3)cc2)c2ccccc2)CC1] |
| 185 | 11663 | 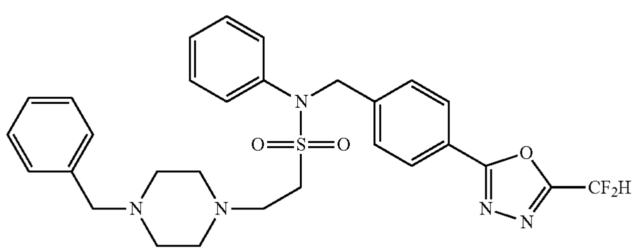 [SMILES: O=S(=O)(CCN1CCN(Cc2ccccc2)CC1)N(Cc1ccc(-c2nnc(C(F)F)o2)cc1)c1ccccc1] |
| 186 | 11665 | 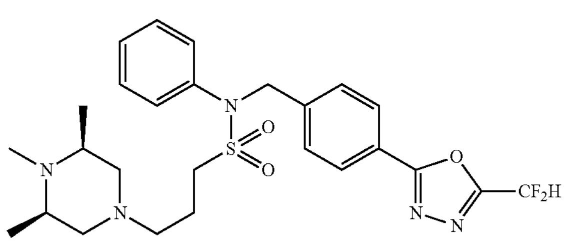 [SMILES: C[C@@H]1CN(CCCS(=O)(=O)N(Cc2ccc(-c3nnc(C(F)F)o3)cc2)c2ccccc2)C[C@H](C)N1C] |

TABLE 1-continued

| Ex. | Comp. | Structure |
|---|---|---|
| 187 | 11668 | 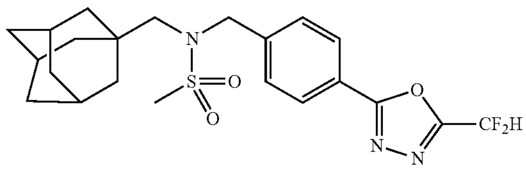 [SMILES: CS(=O)(=O)N(Cc1ccc(-c2nnc(C(F)F)o2)cc1)CC12CC3CC(CC(C3)C1)C2] |
| 188 | 11669 | 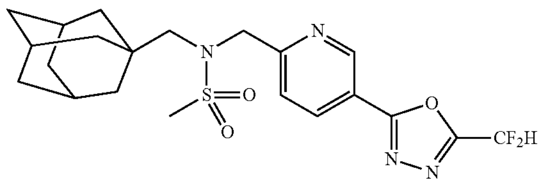 [SMILES: CS(=O)(=O)N(Cc1ccc(-c2nnc(C(F)F)o2)cn1)CC12CC3CC(CC(C3)C1)C2] |
| 189 | 11675 | 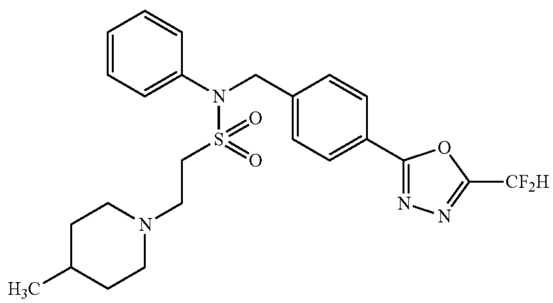 [SMILES: CC1CCN(CCS(=O)(=O)N(Cc2ccc(-c3nnc(C(F)F)o3)cc2)c2ccccc2)CC1] |
| 190 | 11676 | 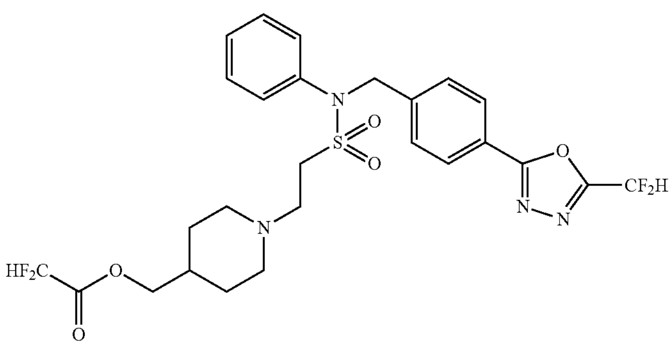 |
| 191 | 11677 | 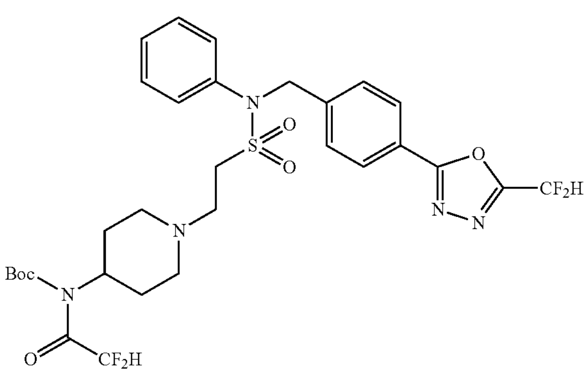 [SMILES: CC(C)(C)OC(=O)N(C(=O)C(F)F)C1CCN(CCS(=O)(=O)N(Cc2ccc(-c3nnc(C(F)F)o3)cc2)c2ccccc2)CC1] |

TABLE 1-continued

| Ex. | Comp. | Structure |
|---|---|---|
| 192 | 11678 | 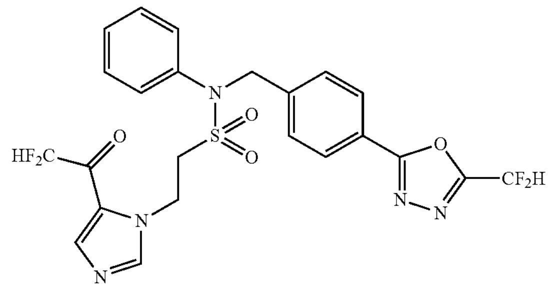 |
| 193 | 11679 | 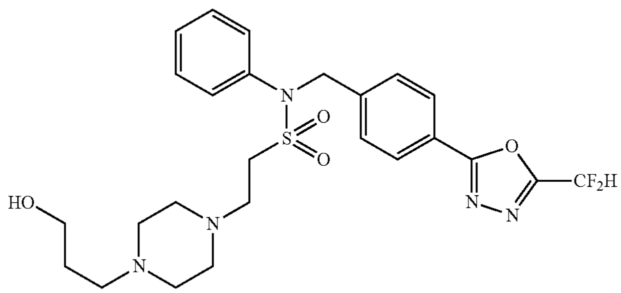 [SMILES: O=S(=O)(CCN1CCN(CCCO)CC1)N(Cc1ccc(-c2nnc(C(F)F)o2)cc1)c1ccccc1] |
| 194 | 11680 | 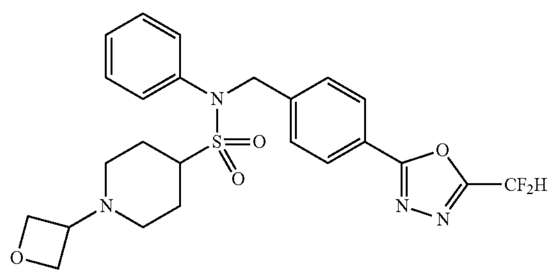 |
| 195 | 11681 | 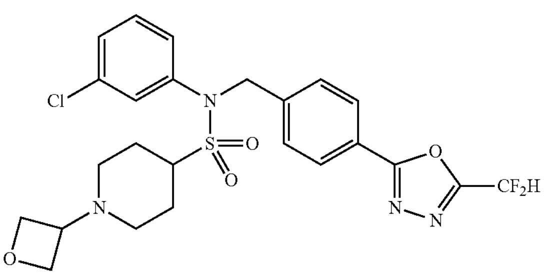 |
| 196 | 11682 | 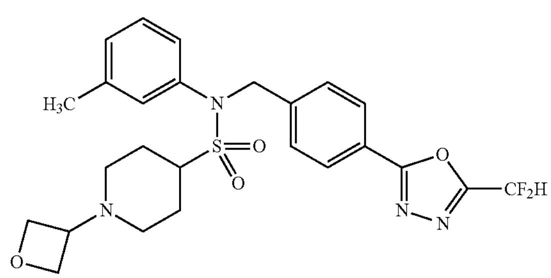 |

TABLE 1-continued

| Ex. | Comp. | Structure |
|---|---|---|
| 197 | 11683 | 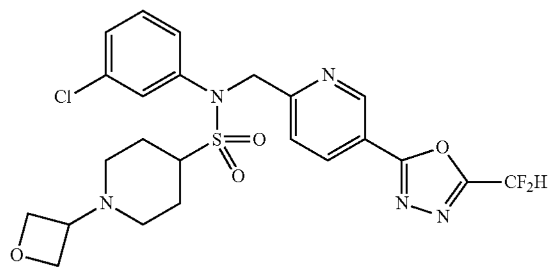 |
| 198 | 11684 | 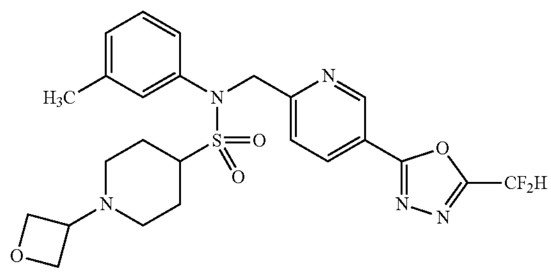 |
| 199 | 11685 | 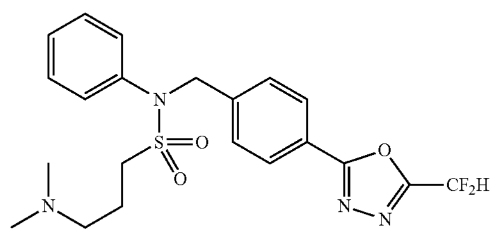 [SMILES: CN(C)CCCS(=O)(=O)N(Cc1ccc(-c2nnc(C(F)F)o2)cc1)c1ccccc1] |
| 200 | 11686 | 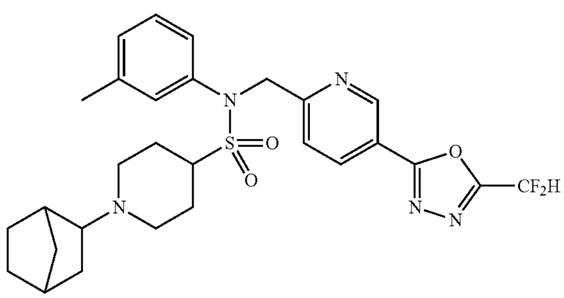 [SMILES: Cc1cccc(N(Cc2ccc(-c3nnc(C(F)F)o3)cn2)S(=O)(=O)C2CCN(C3CC4CCC3C4)CC2)c1] |
| 201 | 11687 | 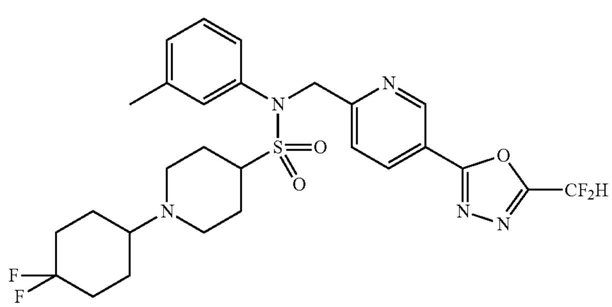 [SMILES: Cc1cccc(N(Cc2ccc(-c3nnc(C(F)F)o3)cn2)S(=O)(=O)C2CCN(C3CCC(F)(F)CC3)CC2)c1] |

TABLE 1-continued

| Ex. | Comp. | Structure |
|---|---|---|
| 202 | 11688 | 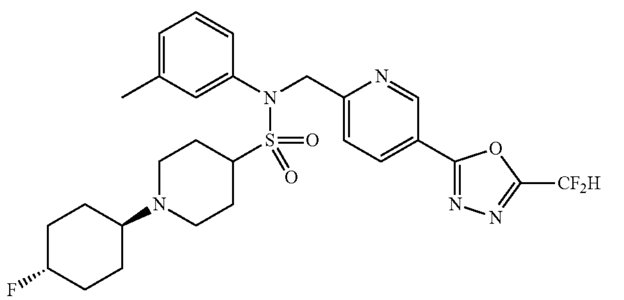 [SMILES: Cc1cccc(N(Cc2ccc(-c3nnc(C(F)F)o3)cn2)S(=O)(=O)C2CCN([C@H]3CC[C@H](F)CC3)CC2)c1] |
| 203 | 11689 | 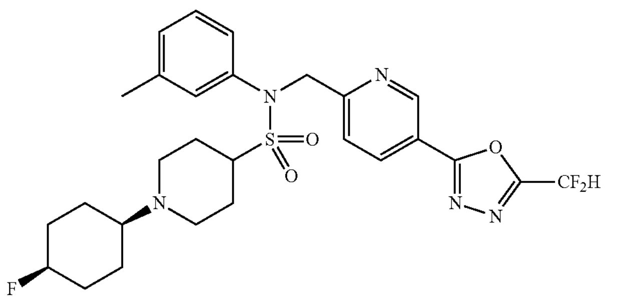 [SMILES: Cc1cccc(N(Cc2ccc(-c3nnc(C(F)F)o3)cn2)S(=O)(=O)C2CCN([C@H]3CC[C@@H](F)CC3)CC2)c1] |
| 204 | 11690 | 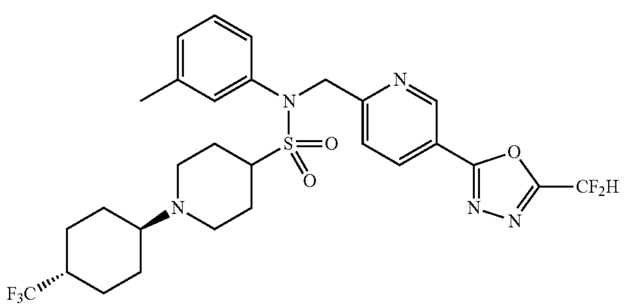 |
| 205 | 11691 | 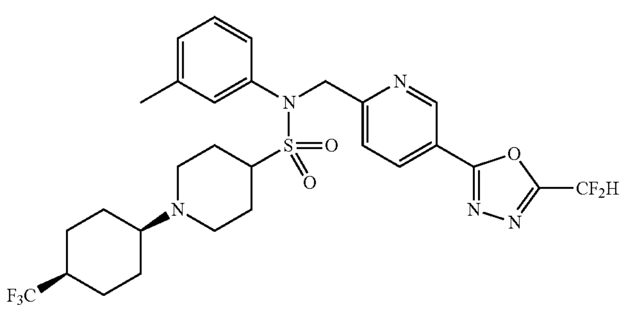 [SMILES: Cc1cccc(N(Cc2ccc(-c3nnc(C(F)F)o3)cn2)S(=O)(=O)C2CCN([C@H]3CC[C@@H](C(F)(F)F)CC3)CC2)c1] |
| 206 | 11692 | 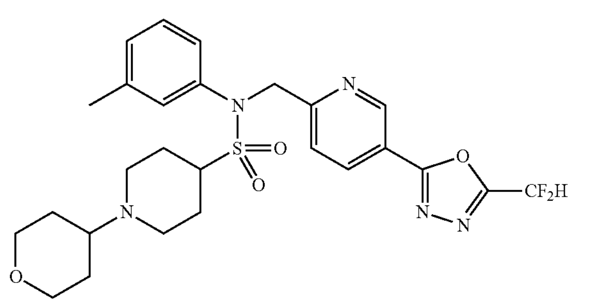 [SMILES: Cc1cccc(N(Cc2ccc(-c3nnc(C(F)F)o3)cn2)S(=O)(=O)C2CCN(C3CCOCC3)CC2)c1] |

TABLE 1-continued

| Ex. | Comp. | Structure |
|---|---|---|
| 207 | 11693 | *(structure)* |
| 208 | 11694 | *(structure)* |
| 209 | 11695 | *(structure)* |
| 210 | 11696 | *(structure)* |
| 211 | 11697 | *(structure)* |

TABLE 1-continued

| Ex. | Comp. | Structure |
|---|---|---|
| 212 | 11698 | 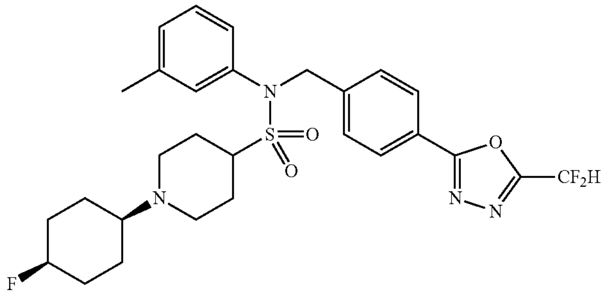 |
| 213 | 11699 | 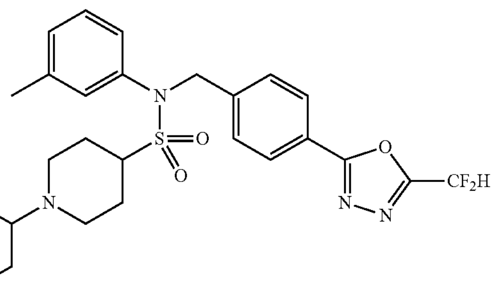 |
| 214 | 11700 | 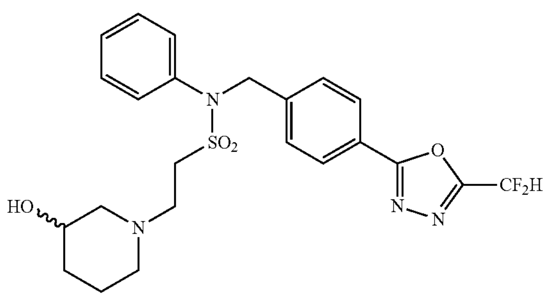 [SMILES: O=S(=O)(CCN1CCCC(O)C1)N(Cc1ccc(-c2nnc(C(F)F)o2)cc1)c1ccccc1] |
| 215 | 11705 | 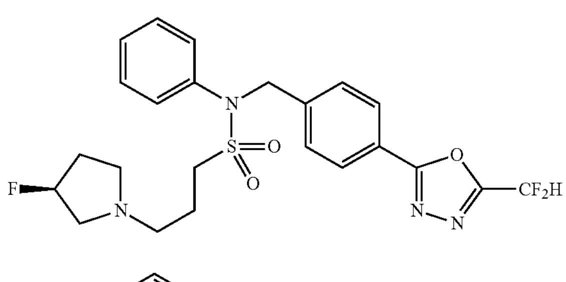 |
| 216 | 11706 | 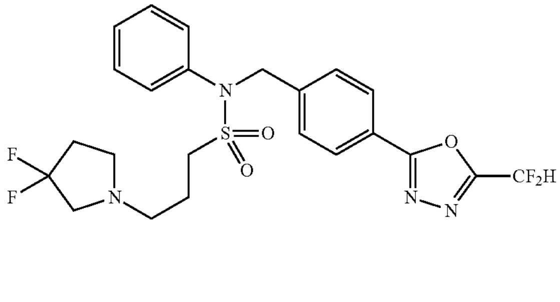 [SMILES: O=S(=O)(CCCN1CCC(F)(F)C1)N(Cc1ccc(-c2nnc(C(F)F)o2)cc1)c1ccccc1] |

TABLE 1-continued

| Ex. | Comp. | Structure |
|---|---|---|
| 217 | 11707 | 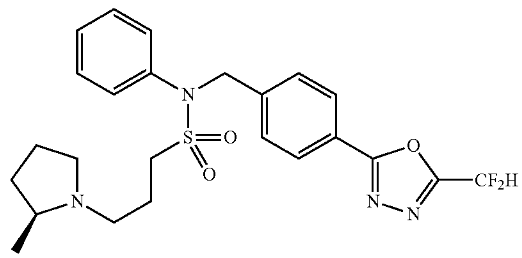 [SMILES: C[C@H]1CCCN1CCCS(=O)(=O)N(Cc1ccc(-c2nnc(C(F)F)o2)cc1)c1ccccc1] |
| 218 | 11708 | 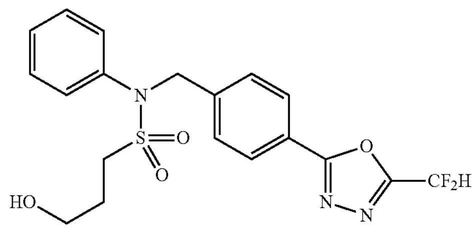 [SMILES: O=S(=O)(CCCO)N(Cc1ccc(-c2nnc(C(F)F)o2)cc1)c1ccccc1] |
| 219 | 11709 | 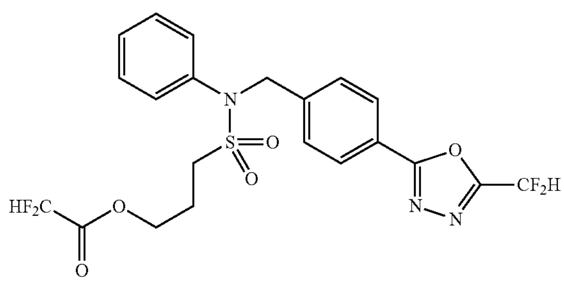 |
| 220 | 11710 | 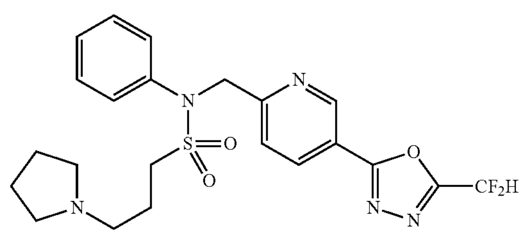 [SMILES: O=S(=O)(CCCN1CCCC1)N(Cc1ccc(-c2nnc(C(F)F)o2)cn1)c1ccccc1] |
| 221 | 11711 | 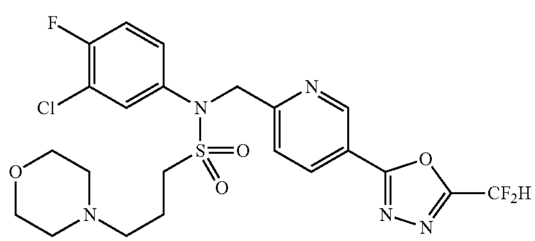 [SMILES: O=S(=O)(CCCN1CCOCC1)N(Cc1ccc(-c2nnc(C(F)F)o2)cn1)c1ccc(F)c(Cl)c1] |
| 222 | 11712 | 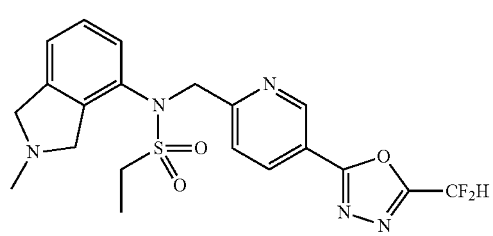 [SMILES: CCS(=O)(=O)N(Cc1ccc(-c2nnc(C(F)F)o2)cn1)c1cccc2c1CN(C)C2] |

TABLE 1-continued

| Ex. | Comp. | Structure |
|---|---|---|
| 223 | 11717 | 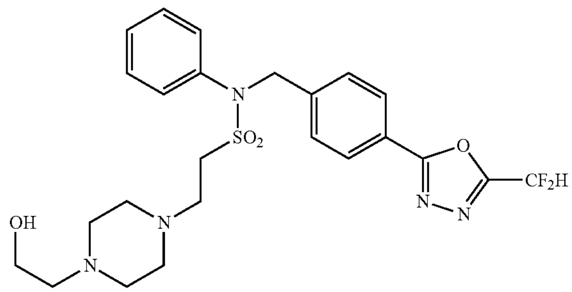 [SMILES: O=S(=O)(CCN1CCN(CCO)CC1)N(Cc1ccc(-c2nnc(C(F)F)o2)cc1)c1ccccc1] |
| 224 | 11718 | 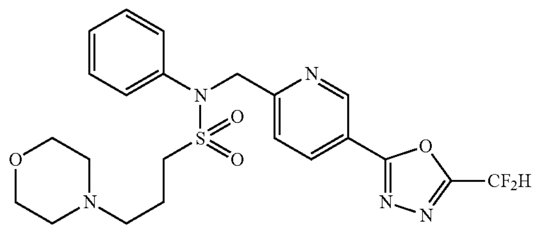 [SMILES: O=S(=O)(CCCN1CCOCC1)N(Cc1ccc(-c2nnc(C(F)F)o2)cn1)c1ccccc1] |
| 225 | 11719 | 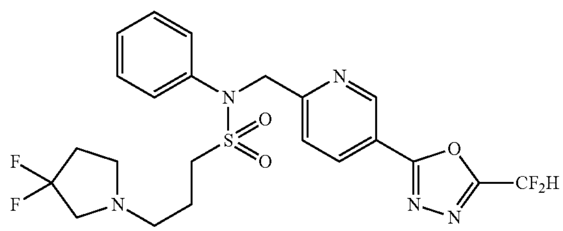 [SMILES: O=S(=O)(CCCN1CCC(F)(F)C1)N(Cc1ccc(-c2nnc(C(F)F)o2)cn1)c1ccccc1] |
| 226 | 11721 | 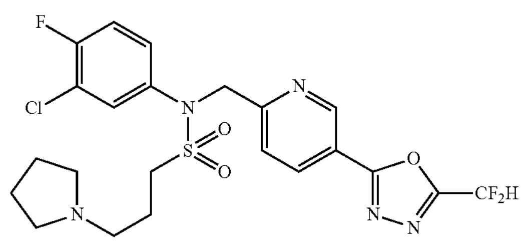 [SMILES: O=S(=O)(CCCN1CCCC1)N(Cc1ccc(-c2nnc(C(F)F)o2)cn1)c1ccc(F)c(Cl)c1] |
| 227 | 11722 | 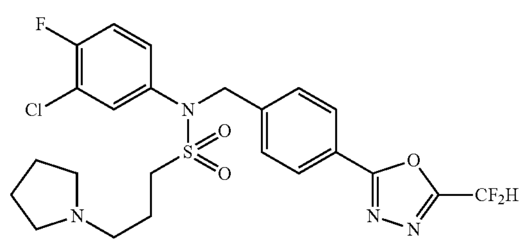 |
| 228 | 11723 | 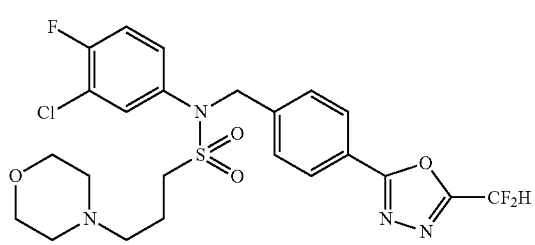 [SMILES: O=S(=O)(CCCN1CCOCC1)N(Cc1ccc(-c2nnc(C(F)F)o2)cc1)c1ccc(F)c(Cl)c1] |

TABLE 1-continued

| Ex. | Comp. | Structure |
|---|---|---|
| 229 | 11724 | 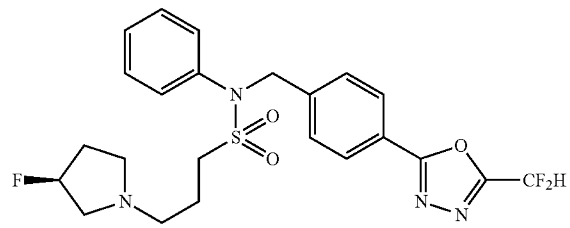 [SMILES: O=S(=O)(CCCN1CC[C@H](F)C1)N(Cc1ccc(-c2nnc(C(F)F)o2)cc1)c1ccccc1] |
| 230 | 11725 | 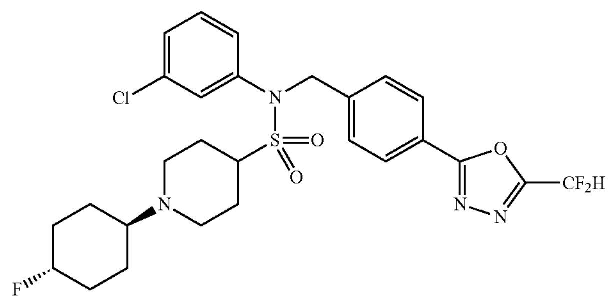 [SMILES: O=S(=O)(C1CCN([C@H]2CC[C@H](F)CC2)CC1)N(Cc1ccc(-c2nnc(C(F)F)o2)cc1)c1cccc(Cl)c1] |
| 231 | 11726 | 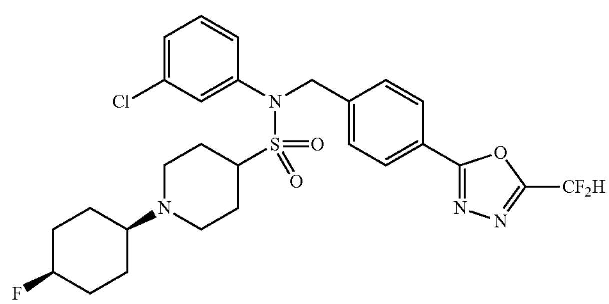 [SMILES: O=S(=O)(C1CCN([C@H]2CC[C@@H](F)CC2)CC1)N(Cc1ccc(-c2nnc(C(F)F)o2)cc1)c1cccc(Cl)c1] |
| 232 | 11727 | 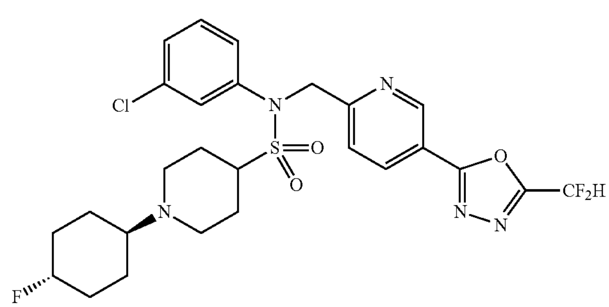 [SMILES: O=S(=O)(C1CCN([C@H]2CC[C@H](F)CC2)CC1)N(Cc1ccc(-c2nnc(C(F)F)o2)cn1)c1cccc(Cl)c1] |
| 233 | 11728 | 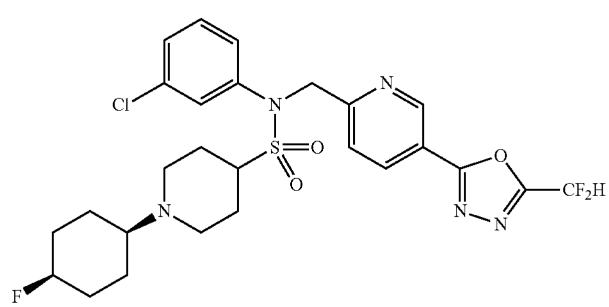 |

TABLE 1-continued

| Ex. | Comp. | Structure |
|---|---|---|
| 234 | 11729 | 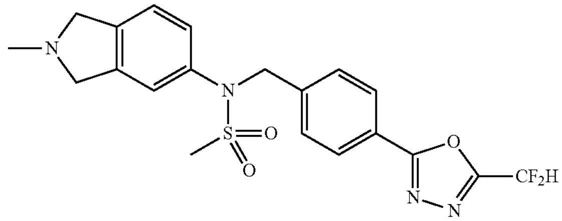 [SMILES: CN1Cc2ccc(N(Cc3ccc(-c4nnc(C(F)F)o4)cc3)S(C)(=O)=O)cc2C1] |
| 235 | 11730 | 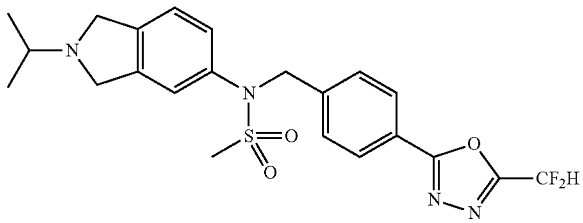 [SMILES: CC(C)N1Cc2ccc(N(Cc3ccc(-c4nnc(C(F)F)o4)cc3)S(C)(=O)=O)cc2C1] |
| 236 | 11731 | 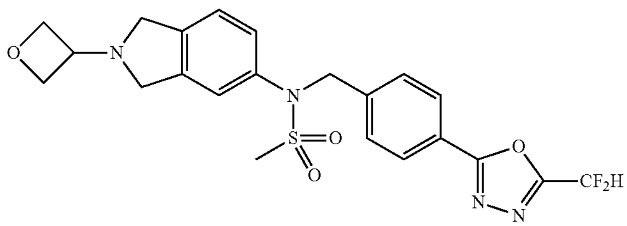 [SMILES: CS(=O)(=O)N(Cc1ccc(-c2nnc(C(F)F)o2)cc1)c1ccc2c(c1)CN(C1COC1)C2] |
| 237 | 11732 | 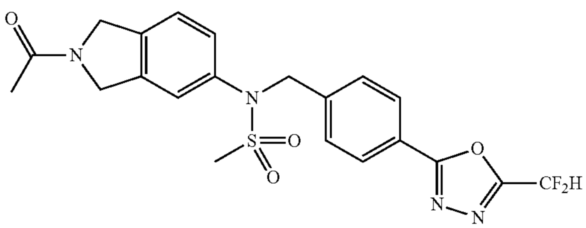 |
| 238 | 11733 | 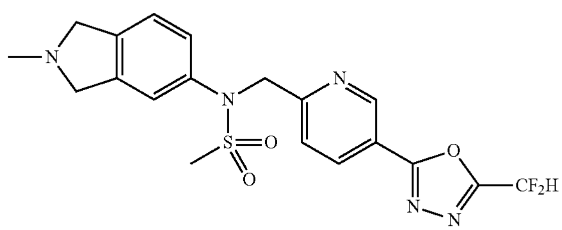 [SMILES: CN1Cc2ccc(N(Cc3ccc(-c4nnc(C(F)F)o4)cn3)S(C)(=O)=O)cc2C1] |
| 239 | 11734 | 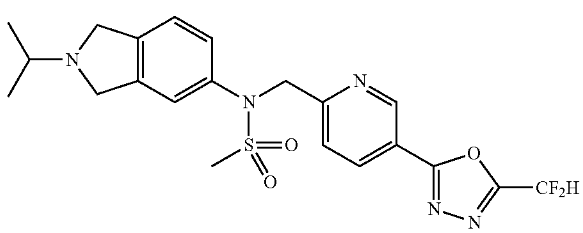 |
| 240 | 11735 | 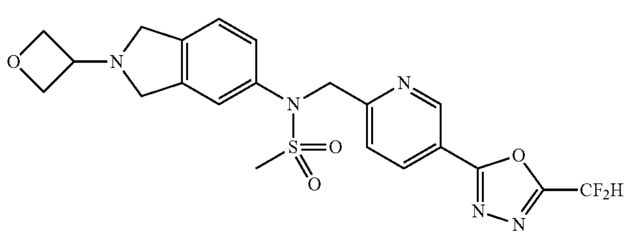 [SMILES: CS(=O)(=O)N(Cc1ccc(-c2nnc(C(F)F)o2)cn1)c1ccc2c(c1)CN(C1COC1)C2] |

TABLE 1-continued
| Ex. | Comp. | Structure |
|---|---|---|
| 241 | 11736 | 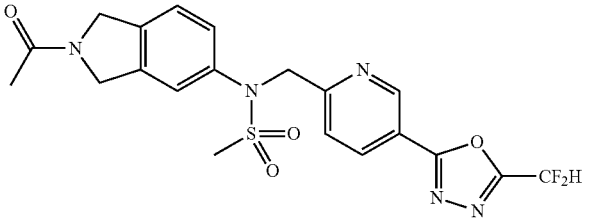 [SMILES: CC(=O)N1Cc2ccc(N(Cc3ccc(-c4nnc(C(F)F)o4)cn3)S(C)(=O)=O)cc2C1] |
| 242 | 11737 | 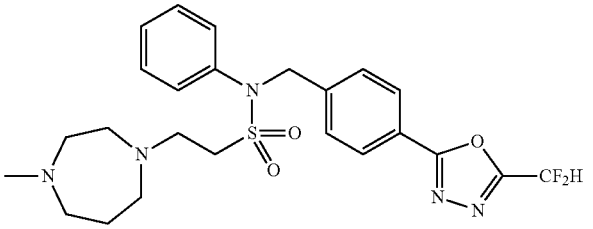 [SMILES: CN1CCCN(CCS(=O)(=O)N(Cc2ccc(-c3nnc(C(F)F)o3)cc2)c2ccccc2)CC1] |
| 243 | 11738 | 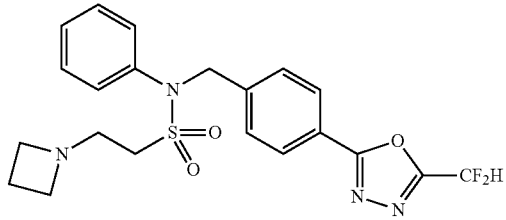 [SMILES: O=S(=O)(CCN1CCC1)N(Cc1ccc(-c2nnc(C(F)F)o2)cc1)c1ccccc1] |
| 244 | 11739 | 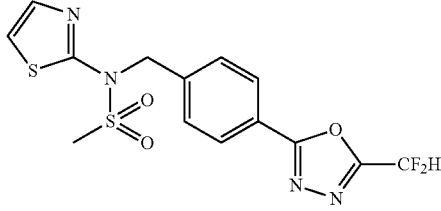 [SMILES: CS(=O)(=O)N(Cc1ccc(-c2nnc(C(F)F)o2)cc1)c1nccs1] |
| 245 | 11740 | 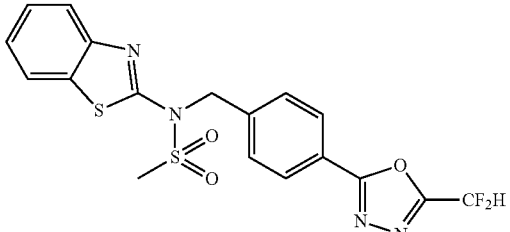 |
| 246 | 11741 | 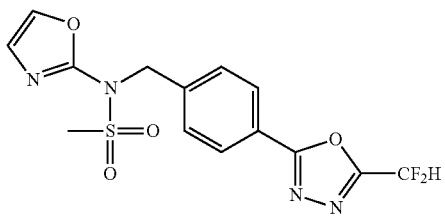 [SMILES: CS(=O)(=O)N(Cc1ccc(-c2nnc(C(F)F)o2)cc1)c1ncco1] |

TABLE 1-continued

| Ex. | Comp. | Structure |
|---|---|---|
| 247 | 11742 | 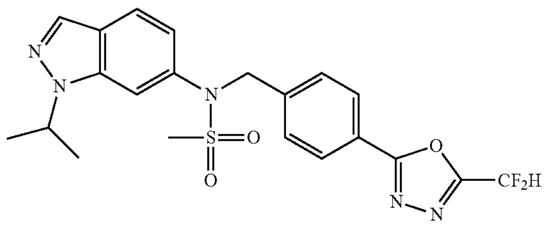 [SMILES: CC(C)n1ncc2ccc(N(Cc3ccc(-c4nnc(C(F)F)o4)cc3)S(C)(=O)=O)cc21] |
| 248 | 11743 | 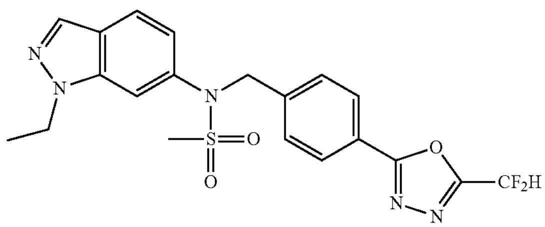 [SMILES: CCn1ncc2ccc(N(Cc3ccc(-c4nnc(C(F)F)o4)cc3)S(C)(=O)=O)cc21] |
| 249 | 11744 | 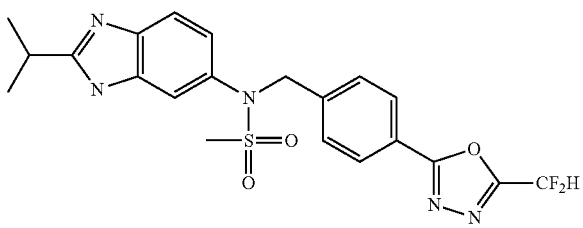 [SMILES: CC(C)c1nc2ccc(N(Cc3ccc(-c4nnc(C(F)F)o4)cc3)S(C)(=O)=O)cc2[nH]1] |
| 250 | 11745 | 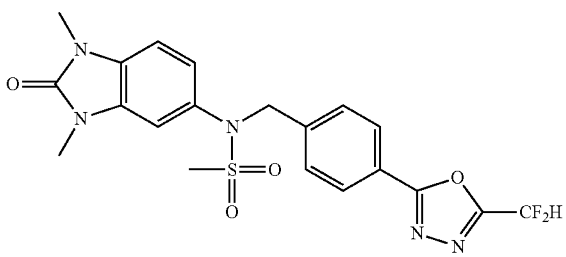 [SMILES: Cn1c(=O)n(C)c2cc(N(Cc3ccc(-c4nnc(C(F)F)o4)cc3)S(C)(=O)=O)ccc21] |
| 251 | 11746 | 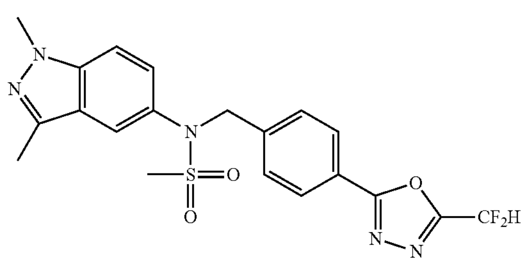 [SMILES: Cc1nn(C)c2ccc(N(Cc3ccc(-c4nnc(C(F)F)o4)cc3)S(C)(=O)=O)cc12] |
| 252 | 11747 | 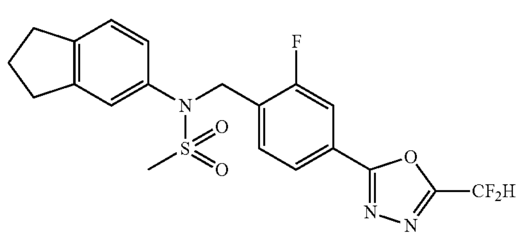 [SMILES: CS(=O)(=O)N(Cc1ccc(-c2nnc(C(F)F)o2)cc1F)c1ccc2c(c1)CCC2] |

TABLE 1-continued

| Ex. | Comp. | Structure |
|---|---|---|
| 253 | 11748 | 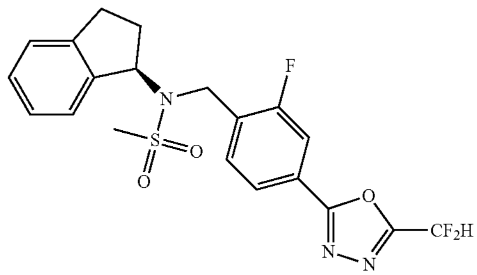 [SMILES: CS(=O)(=O)N(Cc1ccc(-c2nnc(C(F)F)o2)cc1F)[C@@H]1CCc2ccccc21] |
| 254 | 11749 | 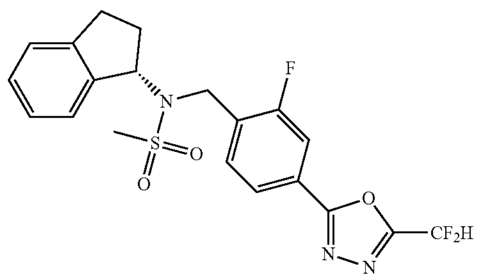 [SMILES: CS(=O)(=O)N(Cc1ccc(-c2nnc(C(F)F)o2)cc1F)[C@H]1CCc2ccccc21] |
| 255 | 11750 | 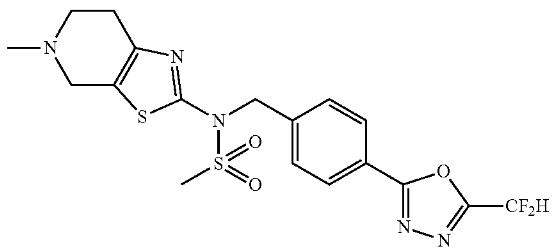 [SMILES: CN1CCc2nc(N(Cc3ccc(-c4nnc(C(F)F)o4)cc3)S(C)(=O)=O)sc2C1] |
| 256 | 11751 | 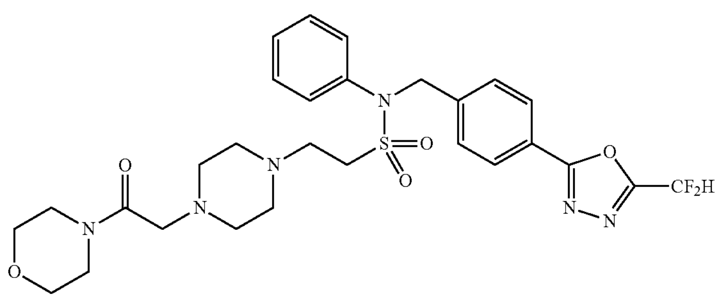 [SMILES: O=C(CN1CCN(CCS(=O)(=O)N(Cc2ccc(-c3nnc(C(F)F)o3)cc2)c2ccccc2)CC1)N1CCOCC1] |
| 257 | 11752 | 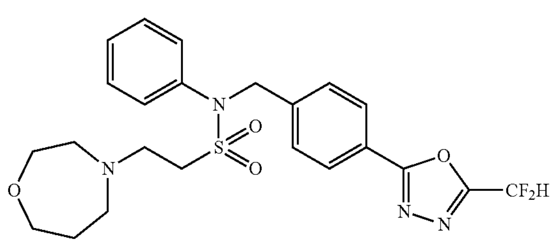 [SMILES: O=S(=O)(CCN1CCCOCC1)N(Cc1ccc(-c2nnc(C(F)F)o2)cc1)c1ccccc1] |
| 258 | 11753 | 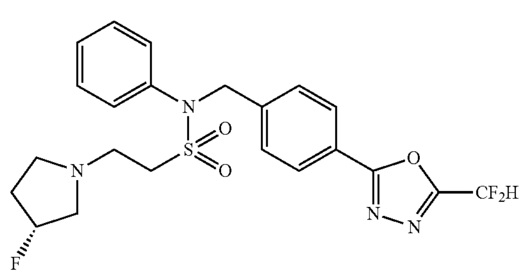 [SMILES: O=S(=O)(CCN1CC[C@@H](F)C1)N(Cc1ccc(-c2nnc(C(F)F)o2)cc1)c1ccccc1] |

TABLE 1-continued

| Ex. | Comp. | Structure |
|---|---|---|
| 259 | 11754 | 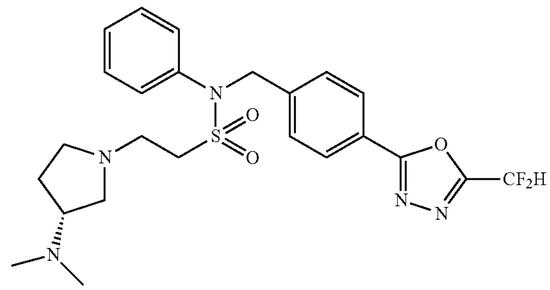 [SMILES: CN(C)[C@@H]1CCN(CCS(=O)(=O)N(Cc2ccc(-c3nnc(C(F)F)o3)cc2)c2ccccc2)C1] |
| 260 | 11755 | 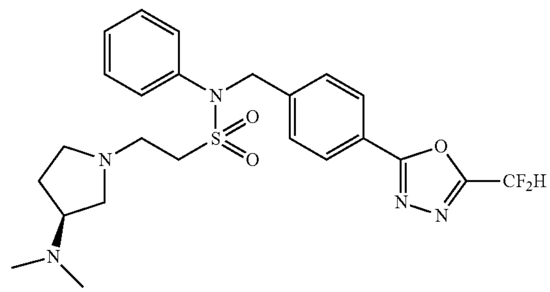 [SMILES: CN(C)[C@H]1CCN(CCS(=O)(=O)N(Cc2ccc(-c3nnc(C(F)F)o3)cc2)c2ccccc2)C1] |
| 261 | 11756 | 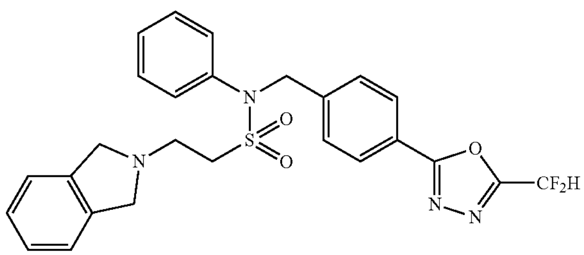 [SMILES: O=S(=O)(CCN1Cc2ccccc2C1)N(Cc1ccc(-c2nnc(C(F)F)o2)cc1)c1ccccc1] |
| 262 | 11757 | 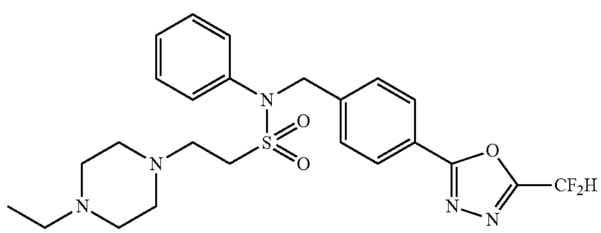 [SMILES: CCN1CCN(CCS(=O)(=O)N(Cc2ccc(-c3nnc(C(F)F)o3)cc2)c2ccccc2)CC1] |
| 263 | 11758 | 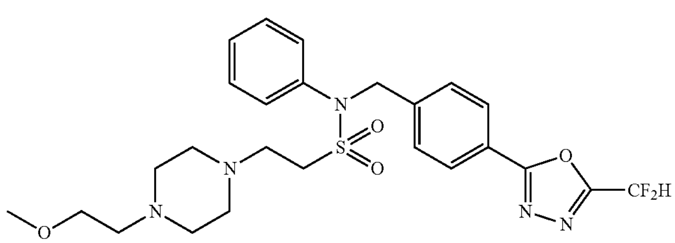 [SMILES: COCCN1CCN(CCS(=O)(=O)N(Cc2ccc(-c3nnc(C(F)F)o3)cc2)c2ccccc2)CC1] |
| 264 | 11759 | 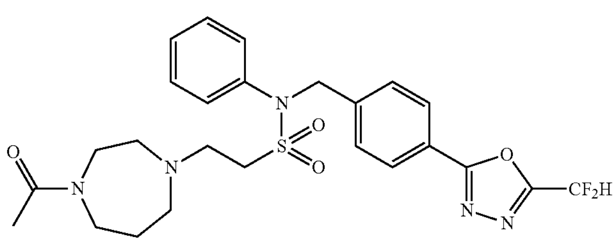 [SMILES: CC(=O)N1CCCN(CCS(=O)(=O)N(Cc2ccc(-c3nnc(C(F)F)o3)cc2)c2ccccc2)CC1] |

TABLE 1-continued
| Ex. | Comp. | Structure |
|---|---|---|
| 265 | 11760 | 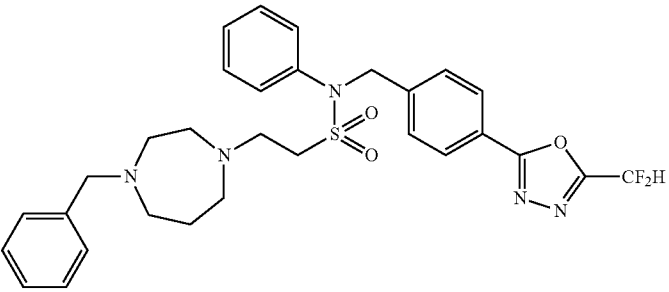 [SMILES: O=S(=O)(CCN1CCCN(Cc2ccccc2)CC1)N(Cc1ccc(-c2nnc(C(F)F)o2)cc1)c1ccccc1] |
| 266 | 11761 | 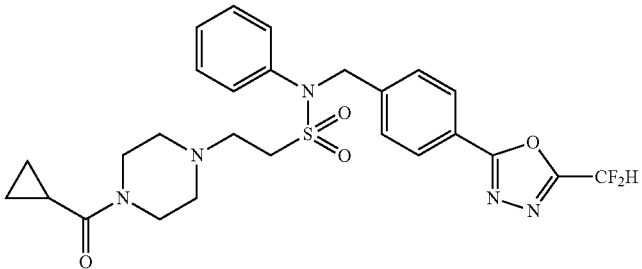 [SMILES: O=C(C1CC1)N1CCN(CCS(=O)(=O)N(Cc2ccc(-c3nnc(C(F)F)o3)cc2)c2ccccc2)CC1] |
| 267 | 11762 | 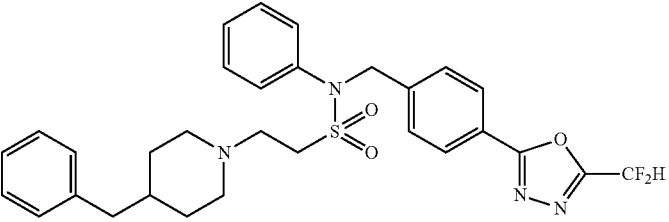 [SMILES: O=S(=O)(CCN1CCC(Cc2ccccc2)CC1)N(Cc1ccc(-c2nnc(C(F)F)o2)cc1)c1ccccc1] |
| 268 | 11763 | 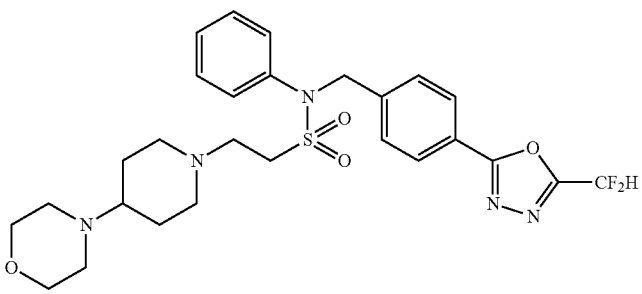 [SMILES: O=S(=O)(CCN1CCC(N2CCOCC2)CC1)N(Cc1ccc(-c2nnc(C(F)F)o2)cc1)c1ccccc1] |
| 269 | 11764 | 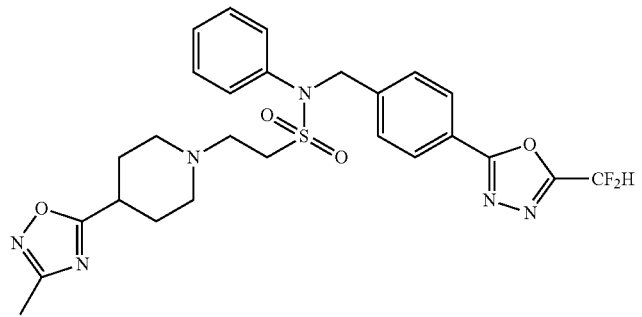 [SMILES: Cc1noc(C2CCN(CCS(=O)(=O)N(Cc3ccc(-c4nnc(C(F)F)o4)cc3)c3ccccc3)CC2)n1] |

TABLE 1-continued
| Ex. | Comp. | Structure |
|---|---|---|
| 270 | 11765 | 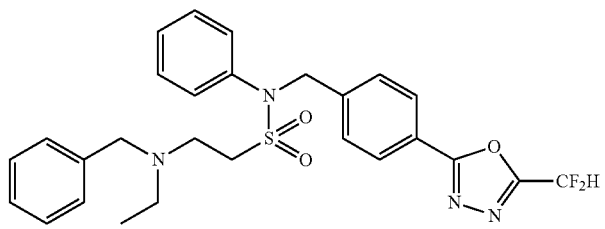 [SMILES: CCN(CCS(=O)(=O)N(Cc1ccc(-c2nnc(C(F)F)o2)cc1)c1ccccc1)Cc1ccccc1] |
| 271 | 11766 | 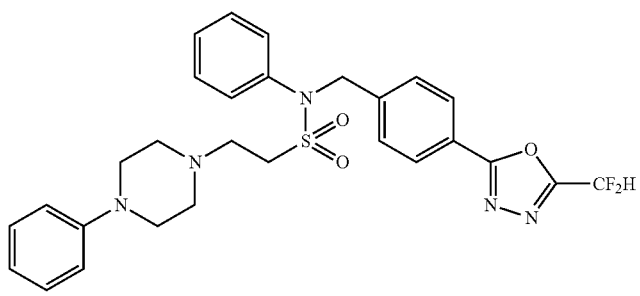 [SMILES: O=S(=O)(CCN1CCN(c2ccccc2)CC1)N(Cc1ccc(-c2nnc(C(F)F)o2)cc1)c1ccccc1] |
| 272 | 11767 | 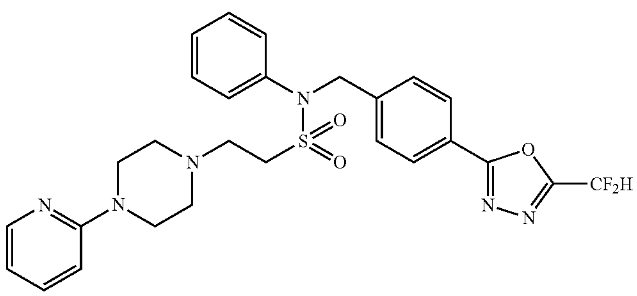 [SMILES: O=S(=O)(CCN1CCN(c2ccccn2)CC1)N(Cc1ccc(-c2nnc(C(F)F)o2)cc1)c1ccccc1] |
| 273 | 11768 | 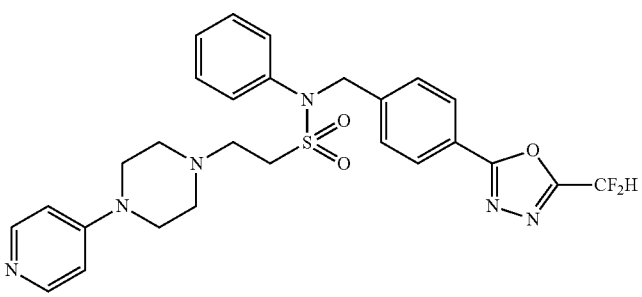 [SMILES: O=S(=O)(CCN1CCN(c2ccncc2)CC1)N(Cc1ccc(-c2nnc(C(F)F)o2)cc1)c1ccccc1] |
| 274 | 11769 | 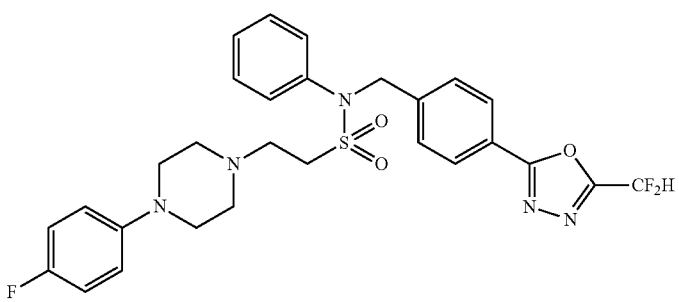 [SMILES: O=S(=O)(CCN1CCN(c2ccc(F)cc2)CC1)N(Cc1ccc(-c2nnc(C(F)F)o2)cc1)c1ccccc1] |

TABLE 1-continued

| Ex. | Comp. | Structure |
|---|---|---|
| 275 | 11770 | 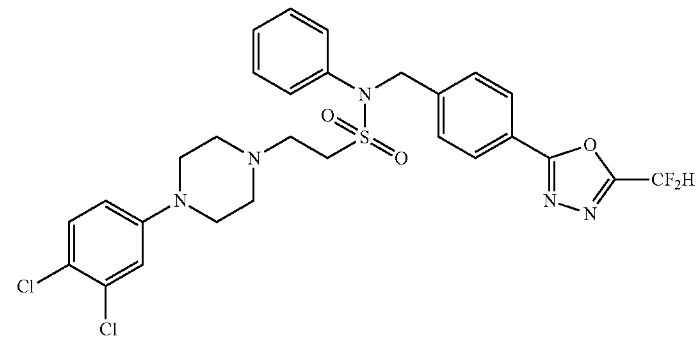 [SMILES: O=S(=O)(CCN1CCN(c2ccc(Cl)c(Cl)c2)CC1)N(Cc1ccc(-c2nnc(C(F)F)o2)cc1)c1ccccc1] |
| 276 | 11771 | 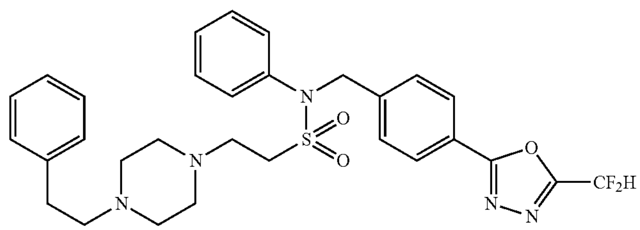 [SMILES: O=S(=O)(CCN1CCN(CCc2ccccc2)CC1)N(Cc1ccc(-c2nnc(C(F)F)o2)cc1)c1ccccc1] |
| 277 | 11772 | 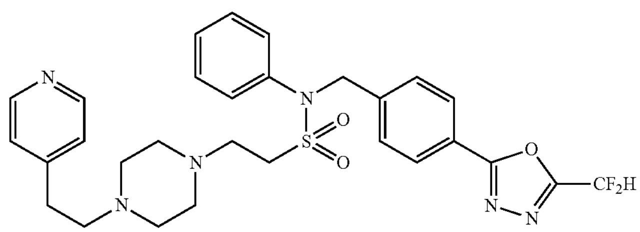 |
| 278 | 11773 | 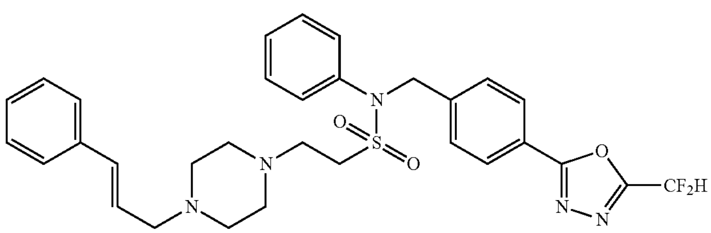 [SMILES: O=S(=O)(CCN1CCN(C/C=C/c2ccccc2)CC1)N(Cc1ccc(-c2nnc(C(F)F)o2)cc1)c1ccccc1] |
| 279 | 11774 | 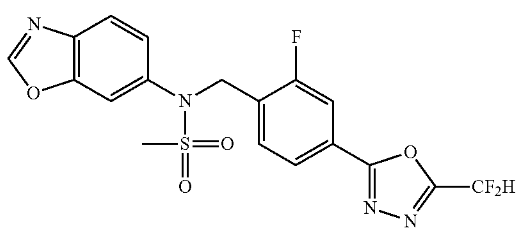 [SMILES: CS(=O)(=O)N(Cc1ccc(-c2nnc(C(F)F)o2)cc1F)c1ccc2ncoc2c1] |
| 280 | 11775 | 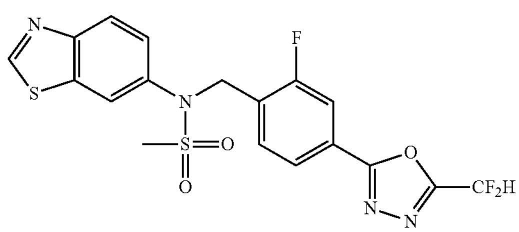 |

TABLE 1-continued
| Ex. | Comp. | Structure |
|---|---|---|
| 281 | 11776 | 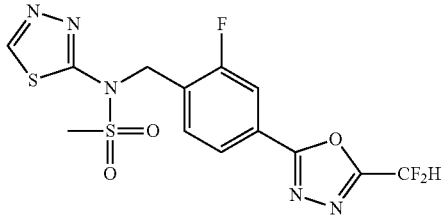 [SMILES: CS(=O)(=O)N(Cc1ccc(-c2nnc(C(F)F)o2)cc1F)c1nncs1] |
| 282 | 11777 | 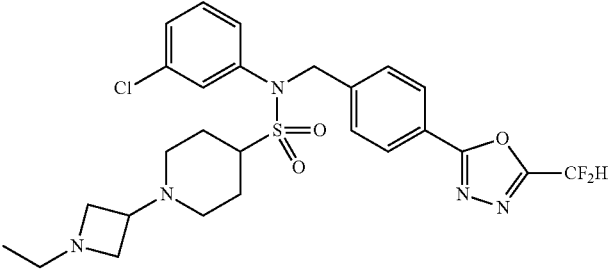 [SMILES: CCN1CC(N2CCC(S(=O)(=O)N(Cc3ccc(-c4nnc(C(F)F)o4)cc3)c3cccc(Cl)c3)CC2)C1] |
| 283 | 11778 | 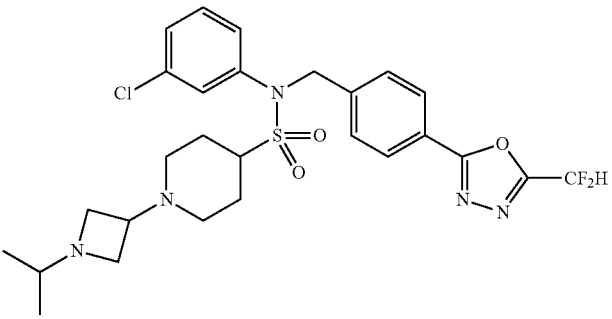 [SMILES: CC(C)N1CC(N2CCC(S(=O)(=O)N(Cc3ccc(-c4nnc(C(F)F)o4)cc3)c3cccc(Cl)c3)CC2)C1] |
| 284 | 11779 | 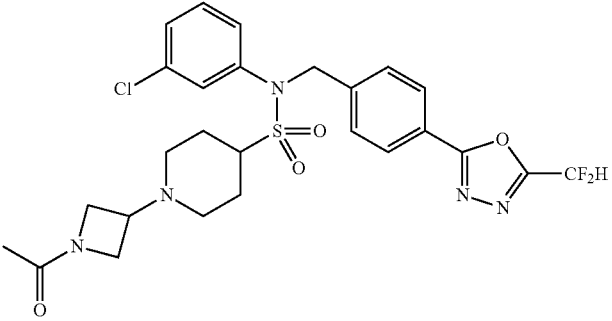 [SMILES: CC(=O)N1CC(N2CCC(S(=O)(=O)N(Cc3ccc(-c4nnc(C(F)F)o4)cc3)c3cccc(Cl)c3)CC2)C1] |
| 285 | 11780 | 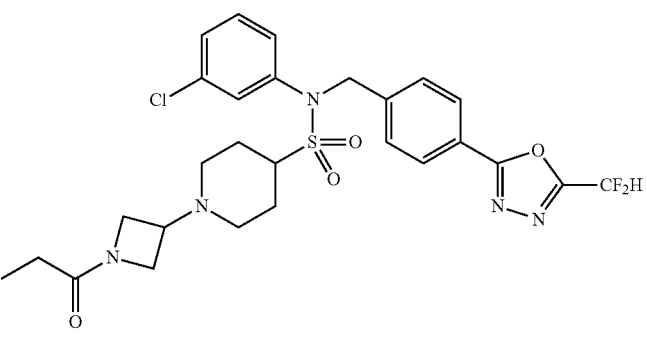 [SMILES: CCC(=O)N1CC(N2CCC(S(=O)(=O)N(Cc3ccc(-c4nnc(C(F)F)o4)cc3)c3cccc(Cl)c3)CC2)C1] |

TABLE 1-continued

| Ex. | Comp. | Structure |
|---|---|---|
| 286 | 11781 | 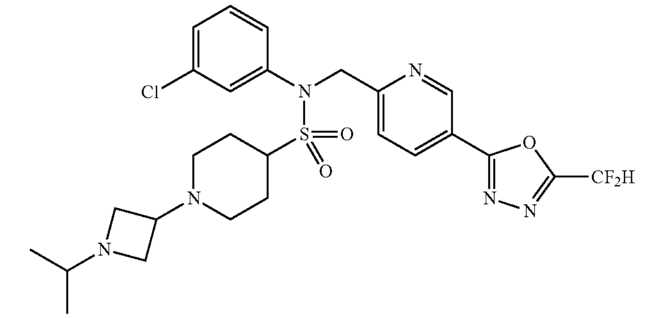 [SMILES: CC(C)N1CC(N2CCC(S(=O)(=O)N(Cc3ccc(-c4nnc(C(F)F)o4)cn3)c3cccc(Cl)c3)CC2)C1] |
| 287 | 11782 | 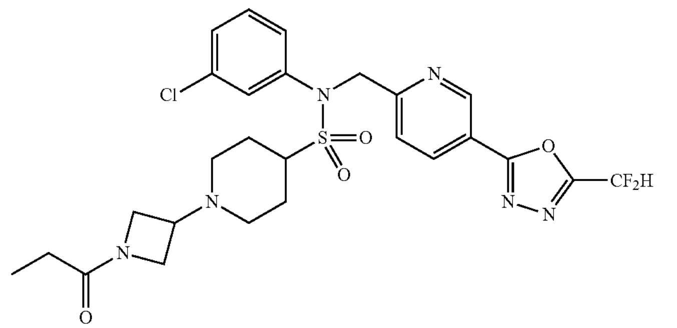 [SMILES: CCC(=O)N1CC(N2CCC(S(=O)(=O)N(Cc3ccc(-c4nnc(C(F)F)o4)cn3)c3cccc(Cl)c3)CC2)C1] |
| 288 | 11783 | 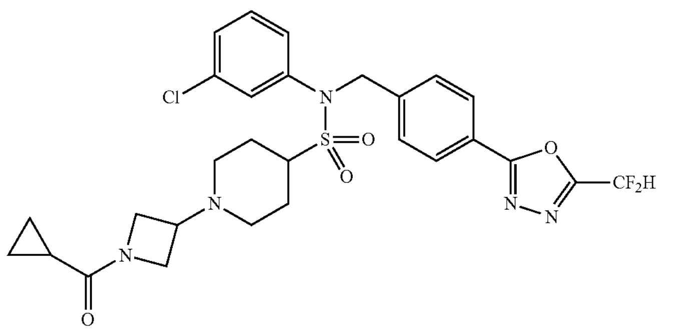 [SMILES: O=C(C1CC1)N1CC(N2CCC(S(=O)(=O)N(Cc3ccc(-c4nnc(C(F)F)o4)cc3)c3cccc(Cl)c3)CC2)C1] |
| 289 | 11784 | 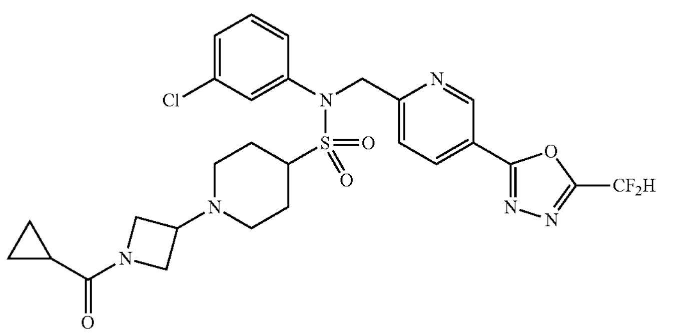 [SMILES: O=C(C1CC1)N1CC(N2CCC(S(=O)(=O)N(Cc3ccc(-c4nnc(C(F)F)o4)cn3)c3cccc(Cl)c3)CC2)C1] |
| 290 | 11785 | 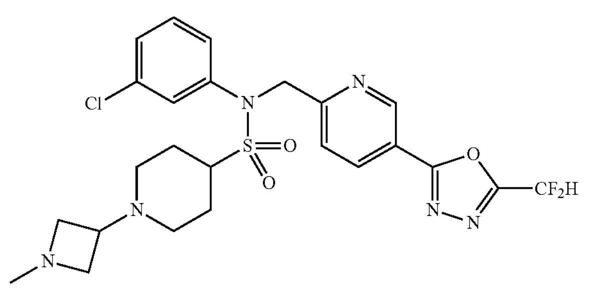 [SMILES: CN1CC(N2CCC(S(=O)(=O)N(Cc3ccc(-c4nnc(C(F)F)o4)cn3)c3cccc(Cl)c3)CC2)C1] |

TABLE 1-continued
| Ex. | Comp. | Structure |
|---|---|---|
| 291 | 11786 | 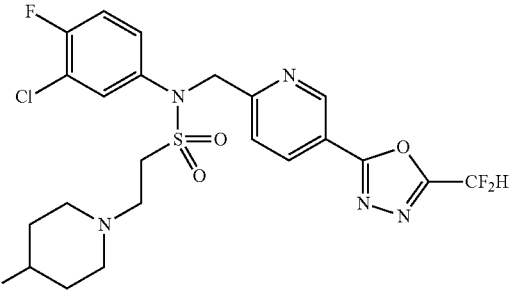 |
| 292 | 11790 | 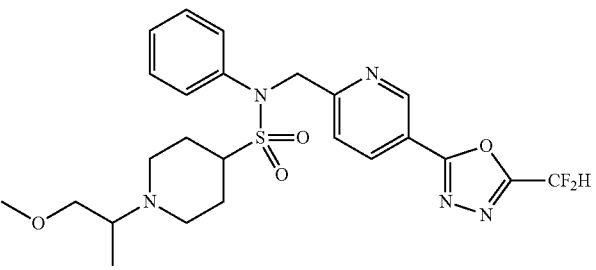 [SMILES: COCC(C)N1CCC(S(=O)(=O)N(Cc2ccc(-c3nnc(C(F)F)o3)cn2)c2ccccc2)CC1] |
| 293 | 11791 | 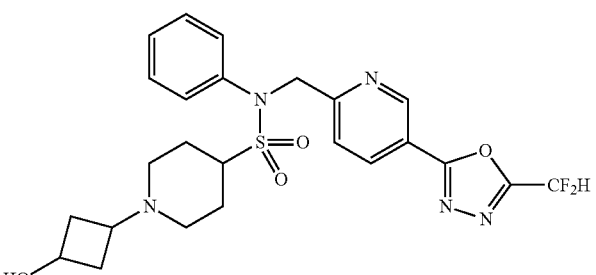 |
| 294 | 11792 | 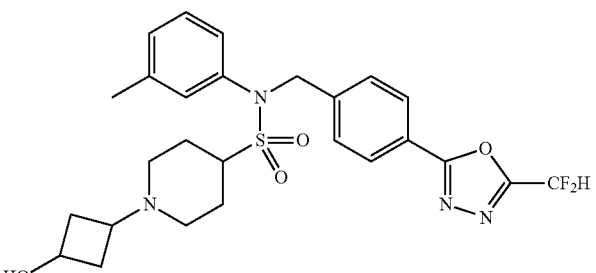 |
| 295 | 11793 | 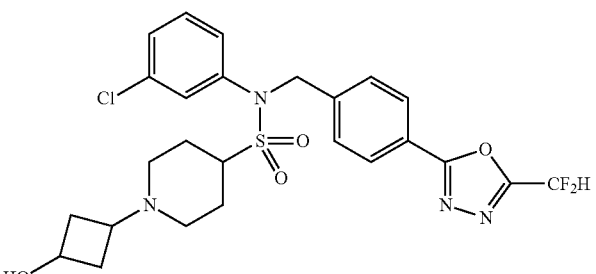 |

TABLE 1-continued
| Ex. | Comp. | Structure |
|---|---|---|
| 296 | 11794 | 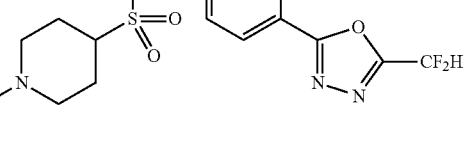 |
| 297 | 11795 | 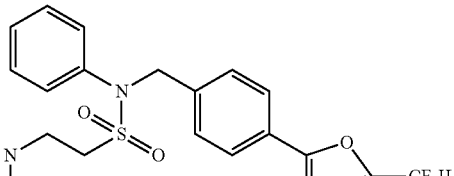 |
| 298 | 11796 | 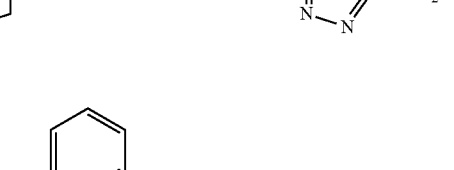 |
| 299 | 11797 | 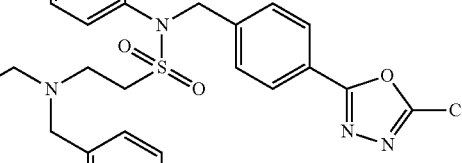 |
| 300 | 11798 | 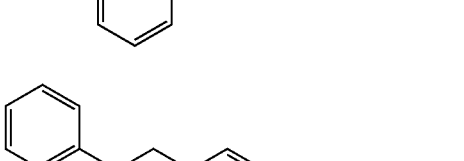 |
| 301 | 11799 | 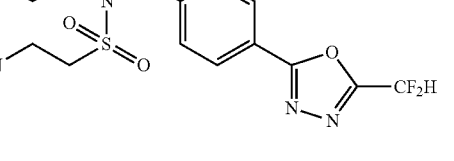 |

TABLE 1-continued

| Ex. | Comp. | Structure |
|---|---|---|
| 302 | 11800 | 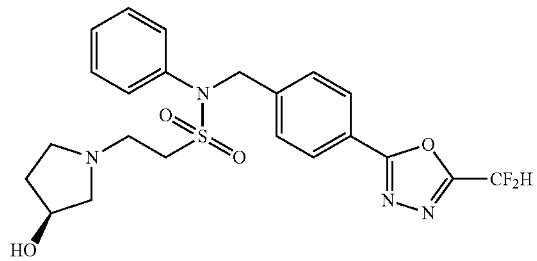 [SMILES: O=S(=O)(CCN1CC[C@H](O)C1)N(Cc1ccc(-c2nnc(C(F)F)o2)cc1)c1ccccc1] |
| 303 | 11801 | 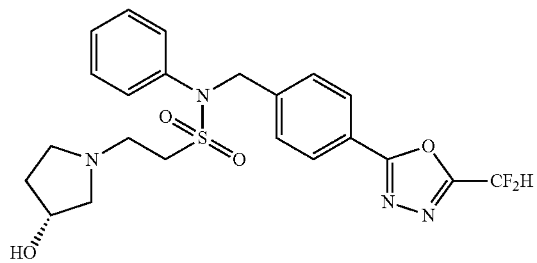 [SMILES: O=S(=O)(CCN1CC[C@@H](O)C1)N(Cc1ccc(-c2nnc(C(F)F)o2)cc1)c1ccccc1] |
| 304 | 11802 | 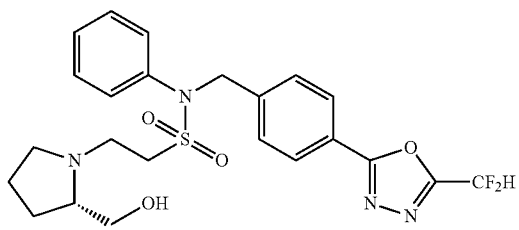 [SMILES: O=S(=O)(CCN1CCC[C@H]1CO)N(Cc1ccc(-c2nnc(C(F)F)o2)cc1)c1ccccc1] |
| 305 | 11803 | 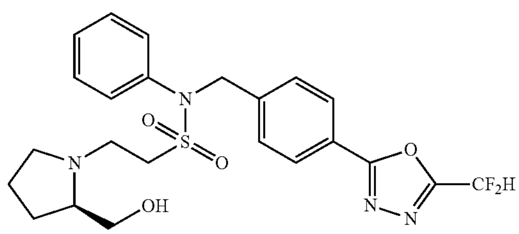 [SMILES: O=S(=O)(CCN1CCC[C@@H]1CO)N(Cc1ccc(-c2nnc(C(F)F)o2)cc1)c1ccccc1] |
| 306 | 11804 | 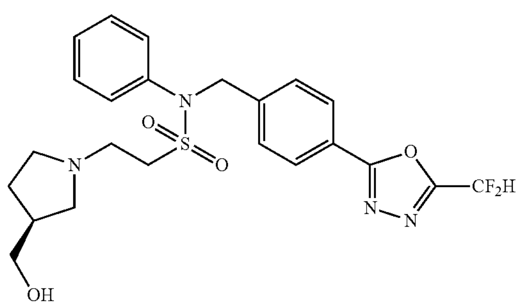 [SMILES: O=S(=O)(CCN1CC[C@H](CO)C1)N(Cc1ccc(-c2nnc(C(F)F)o2)cc1)c1ccccc1] |
| 307 | 11805 | 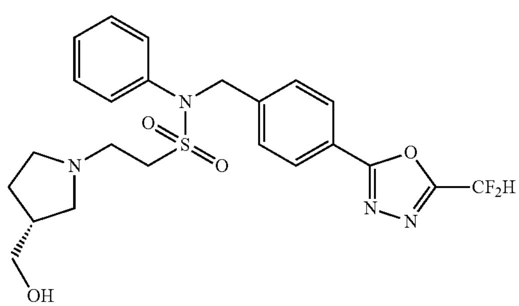 [SMILES: O=S(=O)(CCN1CC[C@@H](CO)C1)N(Cc1ccc(-c2nnc(C(F)F)o2)cc1)c1ccccc1] |

TABLE 1-continued

| Ex. | Comp. | Structure |
|---|---|---|
| 308 | 11806 | 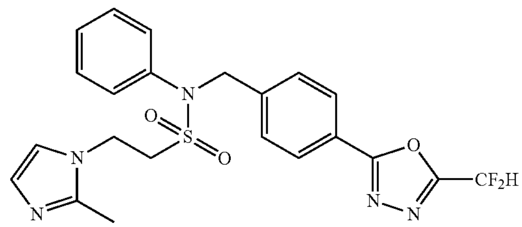 [SMILES: Cc1nccn1CCS(=O)(=O)N(Cc1ccc(-c2nnc(C(F)F)o2)cc1)c1ccccc1] |
| 309 | 11807 | 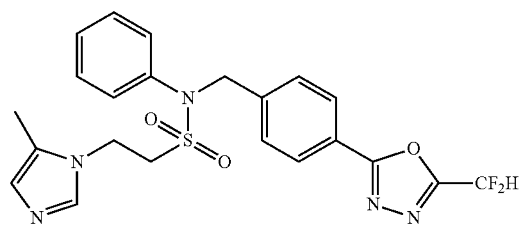 [SMILES: Cc1cncn1CCS(=O)(=O)N(Cc1ccc(-c2nnc(C(F)F)o2)cc1)c1ccccc1] |
| 310 | 11808 | 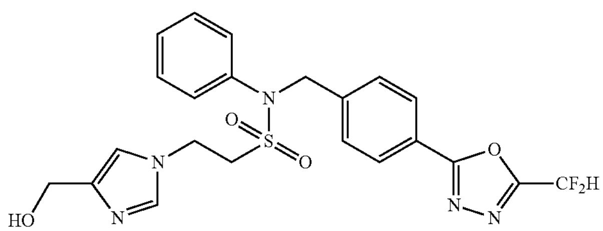 [SMILES: O=S(=O)(CCn1cnc(CO)c1)N(Cc1ccc(-c2nnc(C(F)F)o2)cc1)c1ccccc1] |
| 311 | 11809 | 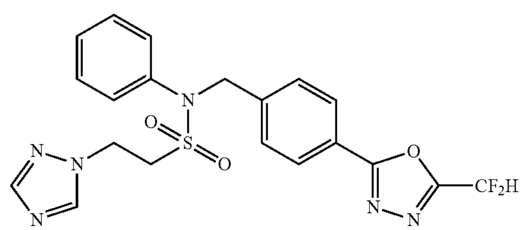 |
| 312 | 11810 | 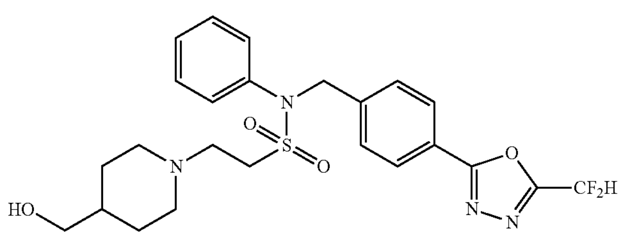 [SMILES: O=S(=O)(CCN1CCC(CO)CC1)N(Cc1ccc(-c2nnc(C(F)F)o2)cc1)c1ccccc1] |
| 313 | 11811 | 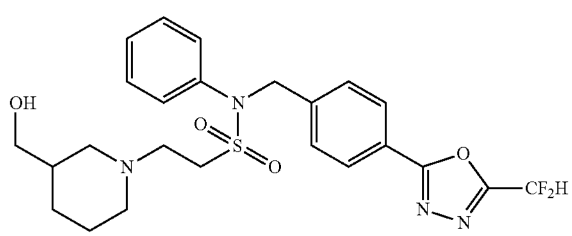 [SMILES: O=S(=O)(CCN1CCCC(CO)C1)N(Cc1ccc(-c2nnc(C(F)F)o2)cc1)c1ccccc1] |

TABLE 1-continued
| Ex. | Comp. | Structure |
|---|---|---|
| 314 | 11812 | 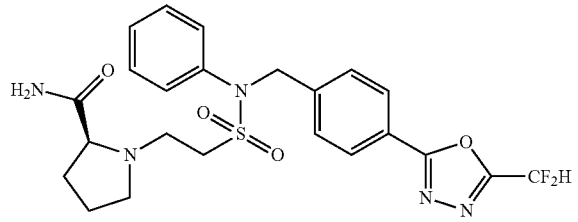 [SMILES: NC(=O)[C@@H]1CCCN1CCS(=O)(=O)N(Cc1ccc(-c2nnc(C(F)F)o2)cc1)c1ccccc1] |
| 315 | 11813 | 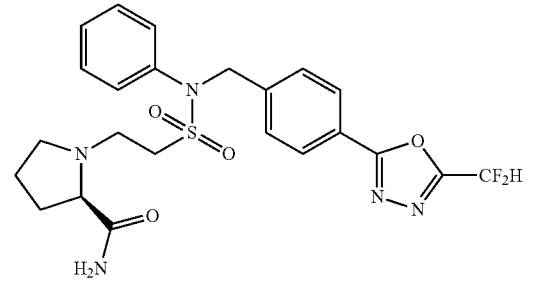 [SMILES: NC(=O)[C@H]1CCCN1CCS(=O)(=O)N(Cc1ccc(-c2nnc(C(F)F)o2)cc1)c1ccccc1] |
| 316 | 11814 | 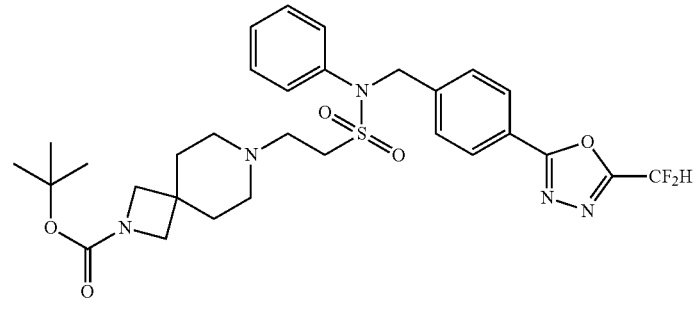 [SMILES: CC(C)(C)OC(=O)N1CC2(CCN(CCS(=O)(=O)N(Cc3ccc(-c4nnc(C(F)F)o4)cc3)c3ccccc3)CC2)C1] |
| 317 | 11815 | 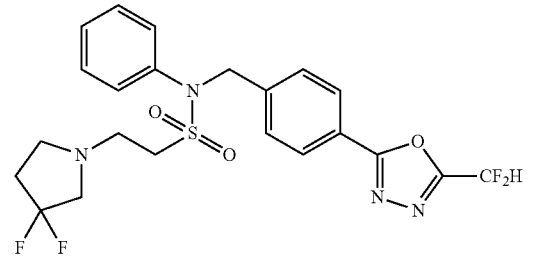 [SMILES: O=S(=O)(CCN1CCC(F)(F)C1)N(Cc1ccc(-c2nnc(C(F)F)o2)cc1)c1ccccc1] |
| 318 | 11816 | 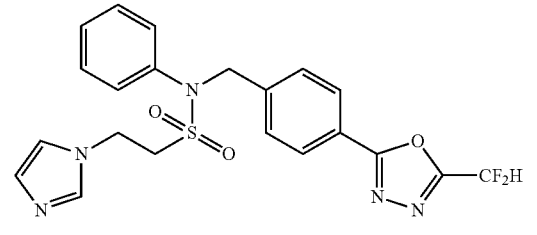 |
| 319 | 11817 | 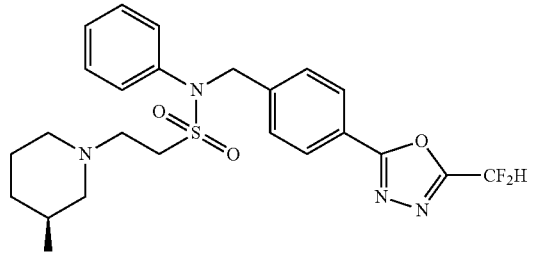 |

TABLE 1-continued

| Ex. | Comp. | Structure |
|---|---|---|
| 320 | 11818 | 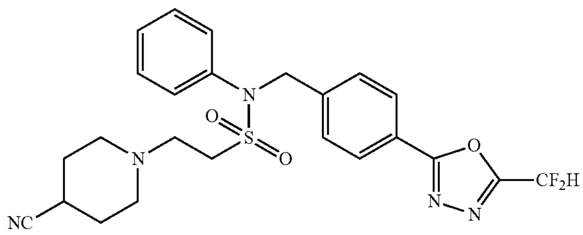 [SMILES: N#CC1CCN(CCS(=O)(=O)N(Cc2ccc(-c3nnc(C(F)F)o3)cc2)c2ccccc2)CC1] |
| 321 | 11819 | 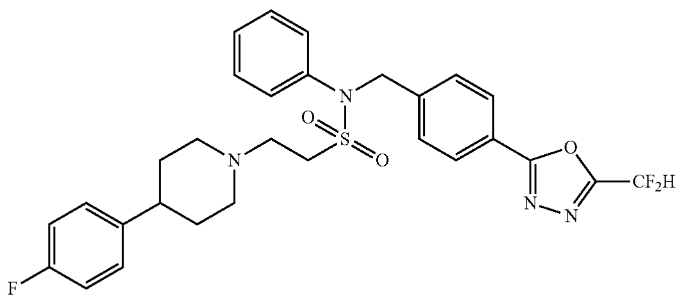 [SMILES: O=S(=O)(CCN1CCC(c2ccc(F)cc2)CC1)N(Cc1ccc(-c2nnc(C(F)F)o2)cc1)c1ccccc1] |
| 322 | 11820 | 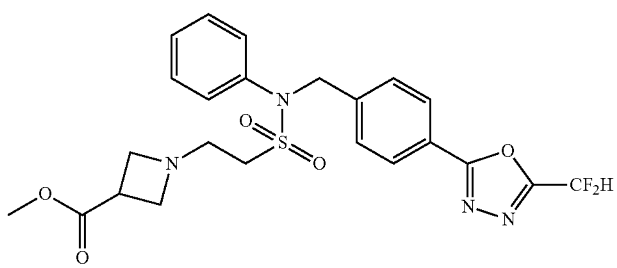 [SMILES: COC(=O)C1CN(CCS(=O)(=O)N(Cc2ccc(-c3nnc(C(F)F)o3)cc2)c2ccccc2)C1] |
| 323 | 11821 | 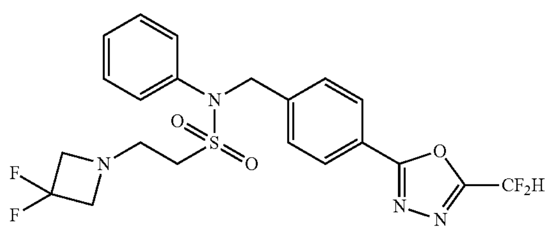 [SMILES: O=S(=O)(CCN1CC(F)(F)C1)N(Cc1ccc(-c2nnc(C(F)F)o2)cc1)c1ccccc1] |
| 324 | 11822 | 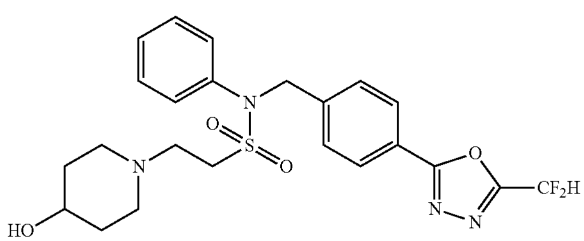 |
| 325 | 11836 | 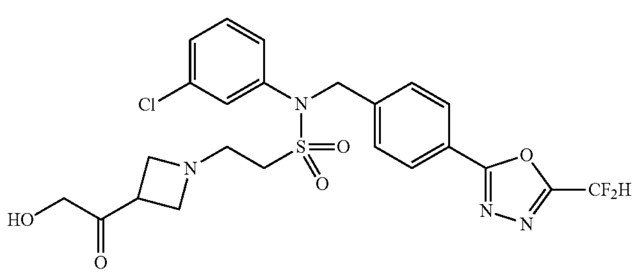 [SMILES: O=C(CO)C1CN(CCS(=O)(=O)N(Cc2ccc(-c3nnc(C(F)F)o3)cc2)c2cccc(Cl)c2)C1] |

TABLE 1-continued

| Ex. | Comp. | Structure |
|---|---|---|
| 326 | 11837 | 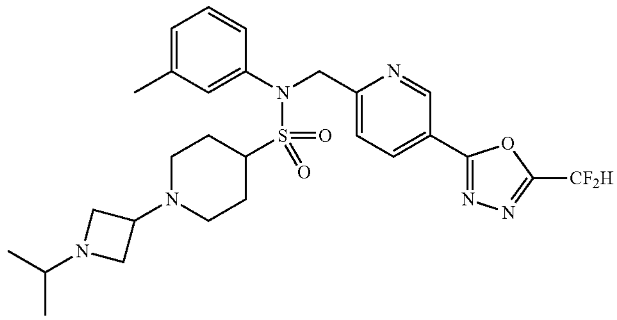 [SMILES: Cc1cccc(N(Cc2ccc(-c3nnc(C(F)F)o3)cn2)S(=O)(=O)C2CCN(C3CN(C(C)C)C3)CC2)c1] |
| 327 | 11838 | 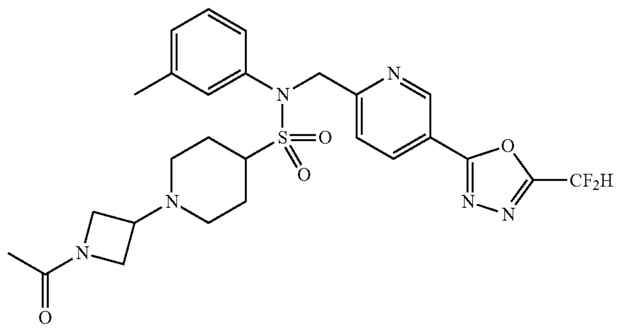 [SMILES: CC(=O)N1CC(N2CCC(S(=O)(=O)N(Cc3ccc(-c4nnc(C(F)F)o4)cn3)c3cccc(C)c3)CC2)C1] |
| 328 | 11839 | 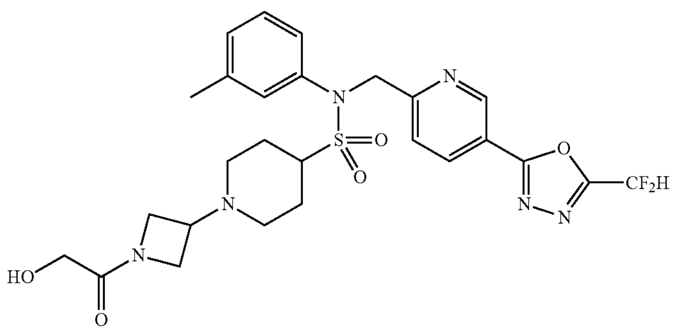 [SMILES: Cc1cccc(N(Cc2ccc(-c3nnc(C(F)F)o3)cn2)S(=O)(=O)C2CCN(C3CN(C(=O)CO)C3)CC2)c1] |
| 329 | 11840 | 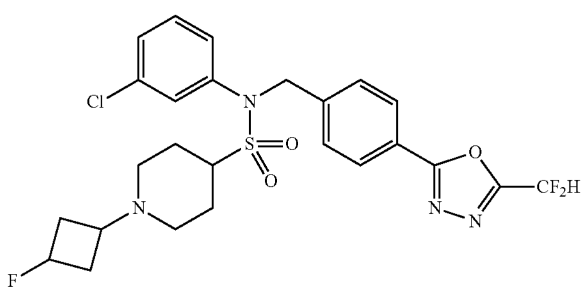 [SMILES: O=S(=O)(C1CCN(C2CC(F)C2)CC1)N(Cc1ccc(-c2nnc(C(F)F)o2)cc1)c1cccc(Cl)c1] |
| 330 | 11841 | 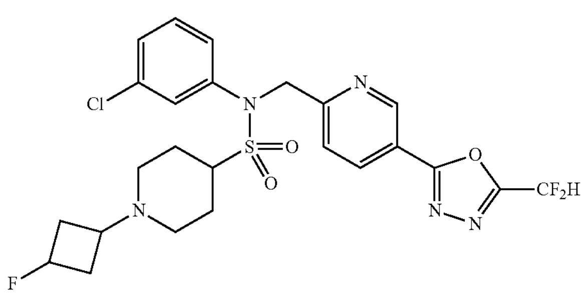 [SMILES: O=S(=O)(C1CCN(C2CC(F)C2)CC1)N(Cc1ccc(-c2nnc(C(F)F)o2)cn1)c1cccc(Cl)c1] |

TABLE 1-continued

| Ex. | Comp. | Structure |
|---|---|---|
| 331 | 11842 | 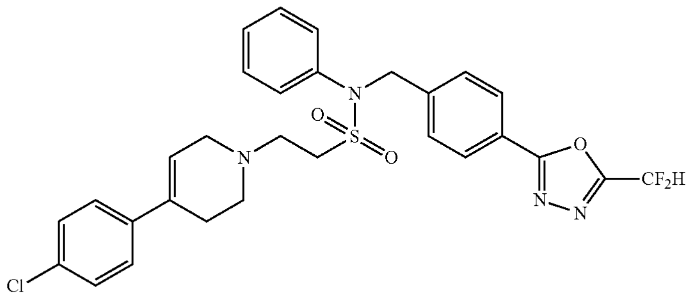 [SMILES: O=S(=O)(CCN1CC=C(c2ccc(Cl)cc2)CC1)N(Cc1ccc(-c2nnc(C(F)F)o2)cc1)c1ccccc1] |
| 332 | 11843 | 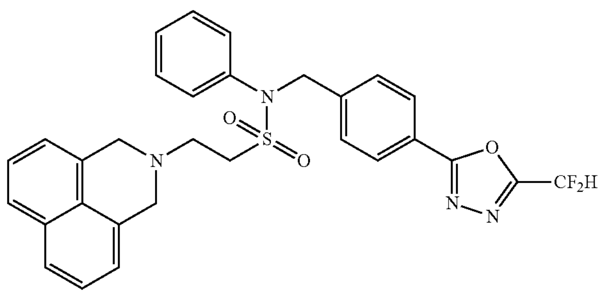 [SMILES: O=S(=O)(CCN1Cc2cccc3cccc(c23)C1)N(Cc1ccc(-c2nnc(C(F)F)o2)cc1)c1ccccc1] |
| 333 | 11844 | 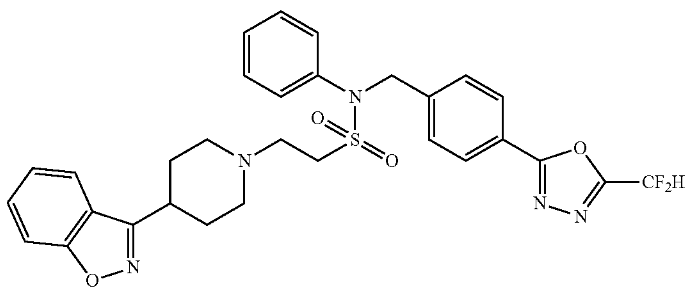 [SMILES: O=S(=O)(CCN1CCC(c2noc3ccccc23)CC1)N(Cc1ccc(-c2nnc(C(F)F)o2)cc1)c1ccccc1] |
| 334 | 11845 | 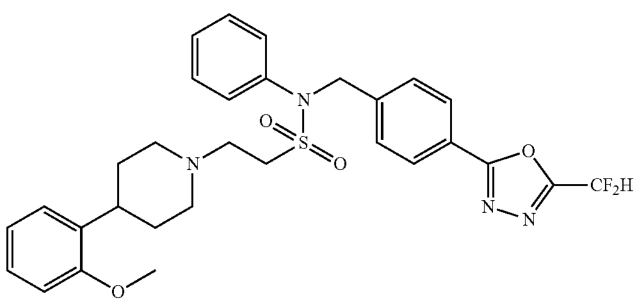 [SMILES: COc1ccccc1C1CCN(CCS(=O)(=O)N(Cc2ccc(-c3nnc(C(F)F)o3)cc2)c2ccccc2)CC1] |
| 335 | 11847 | 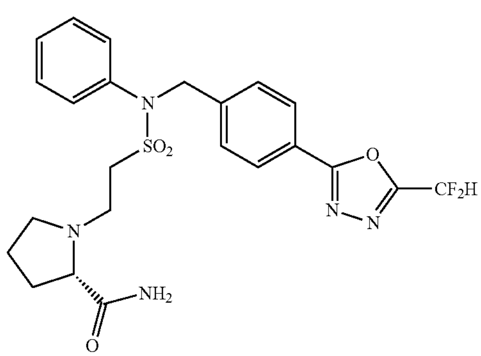 [SMILES: NC(=O)[C@@H]1CCCN1CCS(=O)(=O)N(Cc1ccc(-c2nnc(C(F)F)o2)cc1)c1ccccc1] |

TABLE 1-continued

| Ex. | Comp. | Structure |
|---|---|---|
| 336 | 11848 | 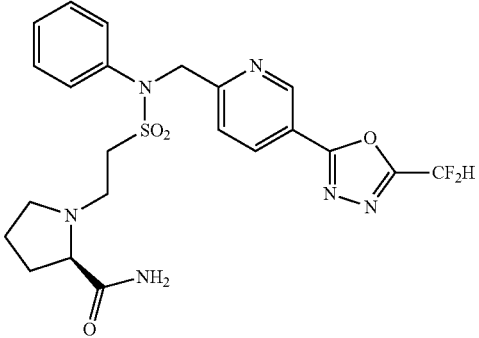 [SMILES: NC(=O)[C@H]1CCCN1CCS(=O)(=O)N(Cc1ccc(-c2nnc(C(F)F)o2)cn1)c1ccccc1] |
| 337 | 11849 | 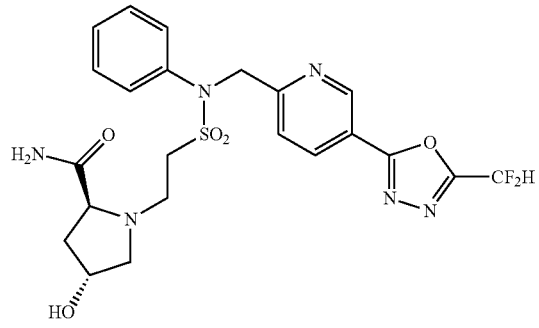 [SMILES: NC(=O)[C@@H]1C[C@@H](O)CN1CCS(=O)(=O)N(Cc1ccc(-c2nnc(C(F)F)o2)cn1)c1ccccc1] |

Preferably, the compounds represented by formula I, stereoisomers thereof or pharmaceutically acceptable salts thereof may be selected from the group consisting of compounds 11154, 11156, 11168, 11170, 11171, 11172, 11176, 11178, 11182, 11191, 11193, 11197, 11217, 11225, 11227, 11231, 11254, 11256, 11276, 11284, 11287, 11289, 11324, 11345, 11346, 11350, 11352, 11353, 11354, 11355, 11366, 11367, 11368, 11372, 11373, 11377, 11390, 11411, 11412, 11426, 11428, 11433, 11447, 11448, 11451, 11452, 11460, 11461, 11462, 11463, 11497, 11501, 11502, 11503, 11504, 11505, 11506, 11507, 11508, 11521, 11522, 11539, 11540, 11541, 11552, 11553, 11554, 11564, 11582, 11583, 11637, 11638, 11646, 11647, 11665, 11679, 11680, 11681, 11682, 11683, 11684, 11685, 11721, 11777, 11781, 11782, 11803, 11806, 11809 and 11837. More preferably, the compounds represented by formula I, stereoisomers thereof or pharmaceutically acceptable salts thereof may be selected from the group consisting of compounds 11154, 11170, 11172, 11178, 11182, 11191, 11197, 11217, 11256, 11350, 11352, 11354, 11355, 11366, 11367, 11368, 11372, 11373, 11390, 11411, 11412, 11426, 11428, 11433, 11447, 11451, 11452, 11460, 11461, 11462, 11463, 11497, 11501, 11502, 11503, 11504, 11505, 11506, 11507, 11521, 11540, 11541, 11552, 11553, 11637, 11646, 11665, 11681, 11683, 11684, 11685 and 11781.

As used herein, the term "pharmaceutically acceptable salt" means any salt that is generally used in the pharmaceutical field. Examples of the pharmaceutically acceptable salt include, but are not limited to, salts with inorganic ions such as calcium, potassium, sodium or magnesium ions, salts with inorganic acids such as hydrochloric acid, nitric acid, phosphoric acid, bromic acid, iodic acid, perchloric acid or sulfuric acid, salts with organic acids such as acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid or the like, salts with sulfonic acids such as methanesulfonic acid, ethanesulfonic acid, benzenesulfonic acid, p-toluenesulfonic acid or naphthalenesulfonic acid, salts with amino acids such as glycine, arginine or lysine, and salts with amines such as trimethylamine, triethylamine, ammonia, pyridine or picoline.

In the present invention, preferred salts include salts with hydrochloric acid, phosphoric acid, sulfuric acid, trifluoroacetic acid, citric acid, bromic acid, maleic acid, tartaric acid or the like, and preferred examples of such compounds include compounds 11172 as disclosed herein.

The compounds represented by formula I may contain one or more asymmetrical carbon atoms, and thus may exist in the form of racemates, racemic mixtures, single enantiomers, diastereomeric mixtures, and individual diastereomers. The compounds of formula I can be separated into such isomers by methods known in the art, for example, column chromatography or HPLC. Alternatively, stereoisomers of the compounds of formula I may be synthesized by stereospecific synthesis using optically pure starting materials and/or reagents of known configuration.

Methods for Preparation of 1,3,4-Oxadiazole Sulfonamide Derivative Compounds

The present invention provides methods for the preparation of the 1,3,4-oxadiazole sulfonamide derivative compounds presented by formula I, stereoisomers thereof, or pharmaceutically acceptable salts thereof.

Preferred methods for the preparation of the 1,3,4-oxadiazole sulfonamide derivative compounds presented by formula I, stereoisomers thereof, or pharmaceutically acceptable salts thereof are as shown in reaction schemes 1 to 25 below, and also include modifications obvious to those skilled in the art.

[Reaction Scheme 1]

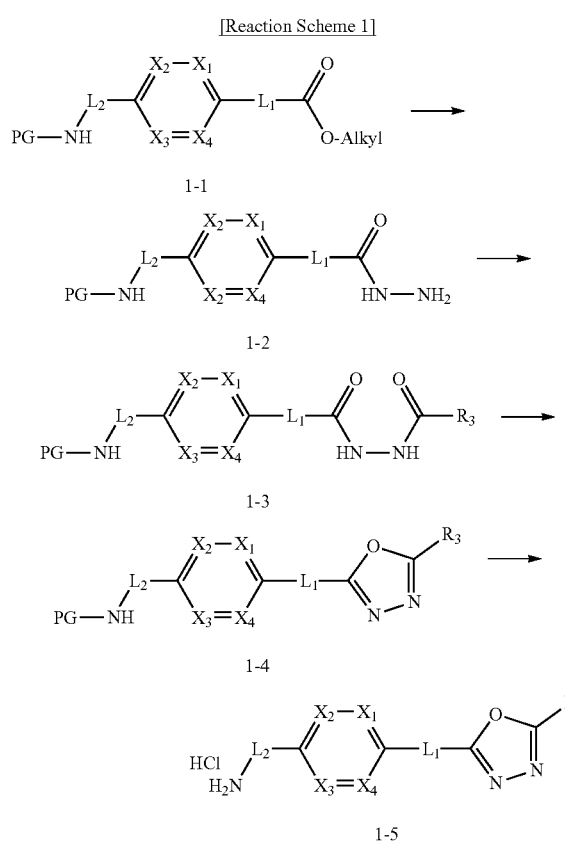

As shown in reaction scheme 1 above, the ester moiety of a compound of formula 1-1 is substituted with hydrazine to prepare a compound of formula 1-2, which is then reacted with trifluoroacetic anhydride or difluoroacetic anhydride to prepare a compound of formula 1-3. Then, the prepared compound of formula 1-3 is reacted with 1-methoxy-N-triethylammoniosulfonyl-methaneimidate (Burgess reagent) to yield a compound of formula 1-4 which has an oxadiazole structure. Then, the compound of formula 1-4 is deprotected, thereby preparing an intermediate of formula 1-5.

[Reaction Scheme 2]

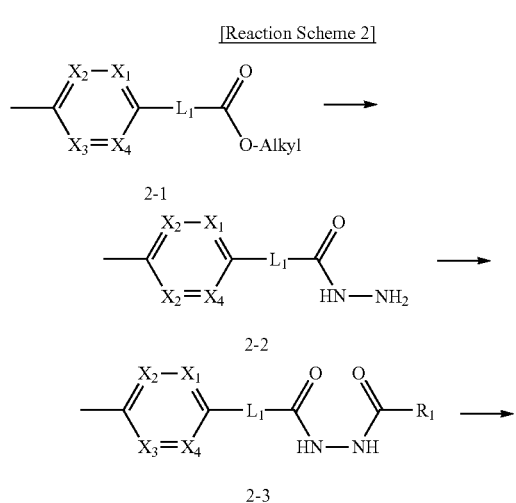

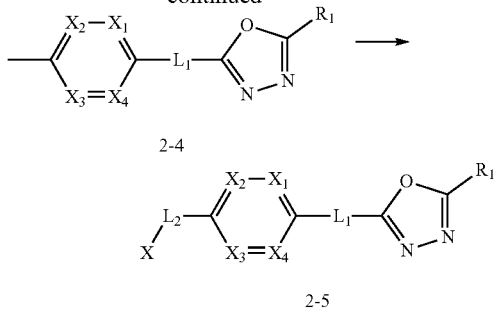

As shown in reaction scheme 2 above, the ester moiety of a compound of formula 2-1 is substituted with hydrazine to prepare a compound of formula 2-2, which is then reacted with trifluoroacetic anhydride or difluoroacetic anhydride to prepare a compound of formula 2-3. Next, the compound of formula 2-3 is reacted with 1-methoxy-N-triethylammoniosulfonyl-methaneimidate (Burgess reagent) to yield a compound of formula 2-4 which has an oxadiazole structure. Then, the methyl group of the compound of formula 2-4 is halogenated, thereby preparing an intermediate of formula 2-5.

[Reaction Scheme 3]

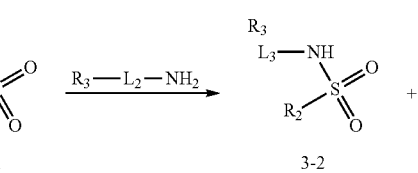

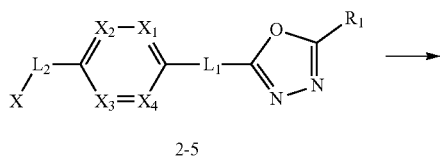

Reaction scheme 3 above shows a general method for synthesis of compounds having a sulfonamide structure. As shown therein, a compound of formula 3-1 is reacted with an amine to yield a compound of formula 3-2, which is then reacted with a compound of formula 2-5 under a basic condition, thereby preparing a compound of formula 3-3.

Compounds that are prepared according to reaction scheme 3 are compounds 11229, 11230, 11231, 11252, 11253, 11254, 11287, 11288, 11289, 11290, 11291, 11292, 11747, 11748, 11749, 11774, 11775 and 11776.

[Reaction Scheme 4]

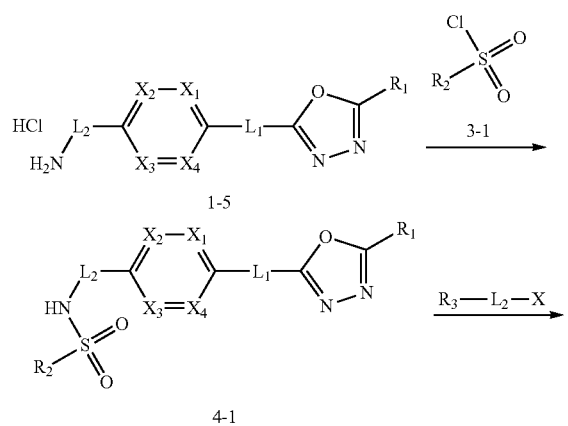

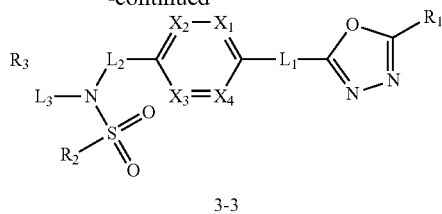

Reaction scheme 4 above shows a general method for synthesis of compounds having a sulfonamide structure. As shown therein, a compound of formula 1-5 is reacted with any of various sulfonyl chloride compounds (formula 3-1) to yield a compound of formula 4-1, which is then subjected to a substitution reaction with $R_3$-$L_2$-X, thereby preparing a compound of formula 3-3.

Compounds that are prepared according to reaction scheme 4 are compounds 11078, 11121 and 11222.

[Reaction Scheme 5]

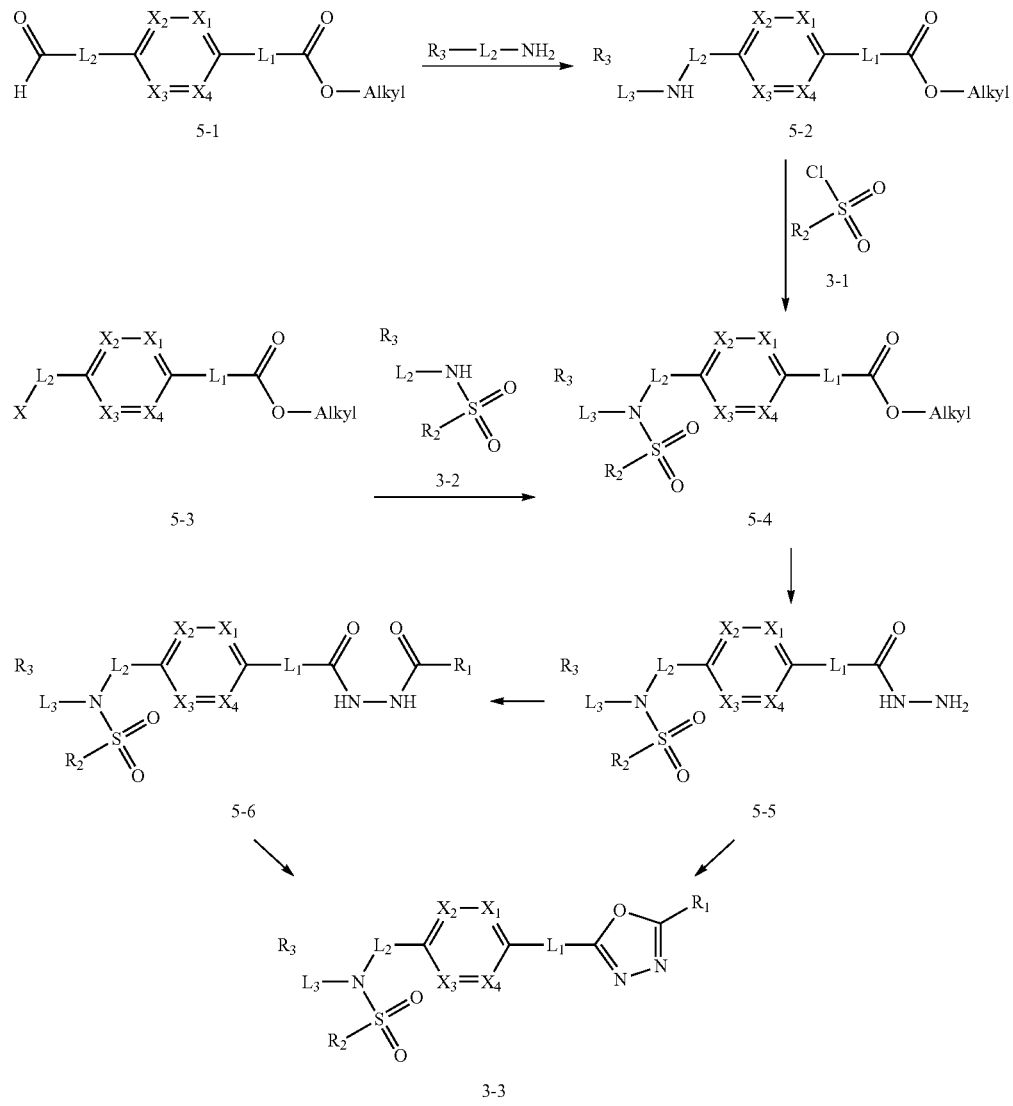

Reaction scheme 5 above shows a general method for synthesis of compounds having a sulfonamide structure. As shown therein, a compound of formula 5-1 is subjected to a reductive amination reaction with an amine compound to yield a compound of formula 5-2, which is then reacted with any of various sulfonyl chloride compounds (formula 3-1) to yield a compound of formula 5-4. Alternatively, a compound of formula 3-2 is subjected to a substitution reaction with a compound of formula 5-3 under a basic condition to yield the compound of formula 5-4. Then, the compound of formula 5-4 is reacted with hydrazine to yield a compound of formula 5-5. Next, the compound of formula 5-5 is reacted with trifluoroacetic anhydride or difluoroacetic anhydride, thereby preparing a compound of formula 3-3 which has an oxadiazole structure. Compounds that are prepared according to reaction scheme 5 above are compounds 11120, 11151, 11152, 11153, 11154, 11155, 11167, 11168, 11173, 11174, 11196, 11197, 11216, 11217, 11218, 11225, 11226, 11227, 11255, 11256, 11271, 11272, 11323, 11324, 11338, 11345, 11346, 11347, 11348, 11350, 11351, 11354, 11355, 11366, 11390, 11411, 11412, 11428, 11429, 11430, 11431, 11432, 11433, 11504, 11505, 11506, 11520, 11521, 11522, 11539, 11540, 11541, 11628, 11636, 11668, 11669, 11739, 11740, 11741, 11742, 11743, 11744, 11745, 11746 and 11750.

In addition, a compound of formula 5-6, which has no oxadiazole structure, is reacted with 1-methoxy-N-triethyl-ammoniosulfonyl-methaneimidate (Burgess reagent) to yield a compound of formula 3-3, which has an oxadiazole structure. Compounds that are prepared according to this reaction scheme are compounds 11044, 11045, 11088, 11089, 11128, 11129, 11133, 11156, 11169, 11170, 11171, 11172, 11175, 11176, 11177, 11178, 11179, 11180, 11181, 11182, 11183, 11184, 11190, 11191, 11192, 11193, 11194, 11195, 11219, 11220, 11221, 11248, 11249, 11250, 11251, 11273, 11274, 11275, 11276, 11277, 11278, 11279, 11280, 11281, 11282, 11283, 11284, 11352, 11353, 11460, 11461, 11462, 11463, 11497, 11507 and 11508.

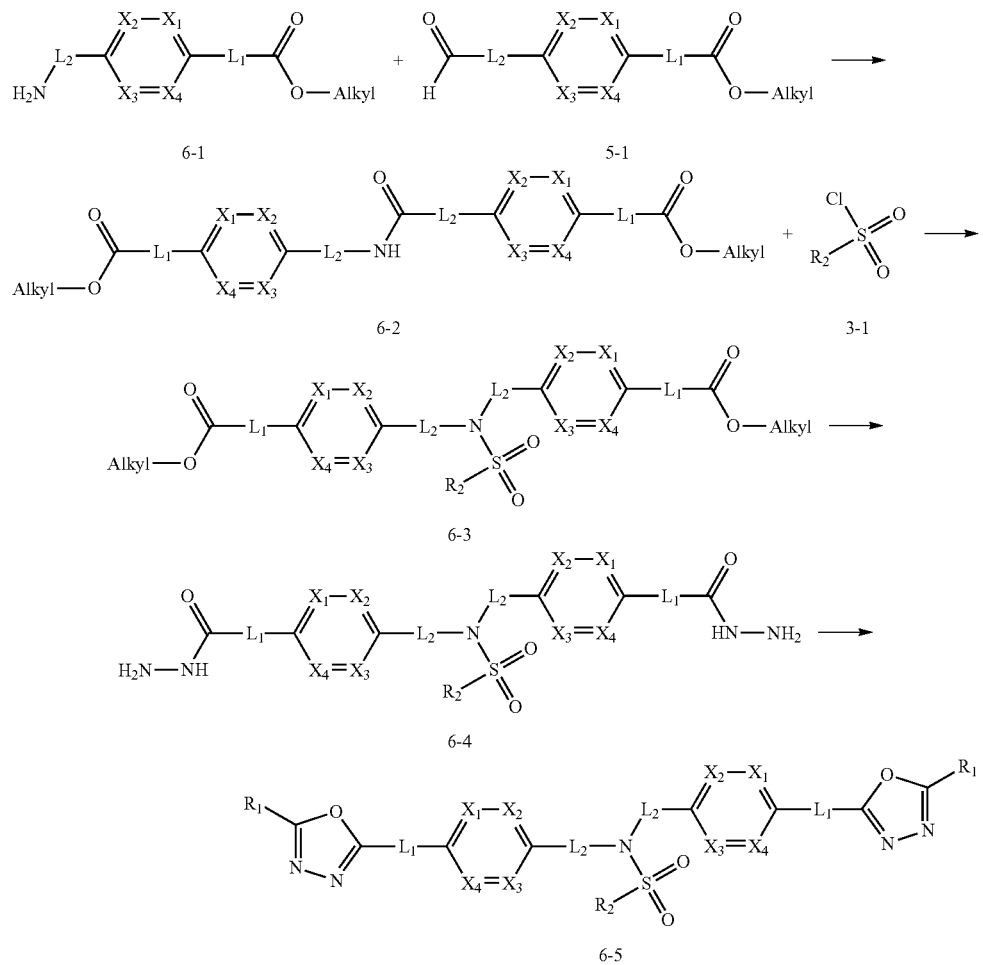

[Reaction Scheme 6]

Reaction scheme 6 above shows a general method for synthesis of compounds having a sulfonamide structure. As shown therein, a compound of formula 6-1 is subjected to a reductive amination reaction with a compound of formula 5-1 to yield a compound of formula 6-2, which is then reacted with any of various sulfonyl chloride compounds (formula 3-1), thereby preparing a compound of formula 6-3. The compound of formula 6-3 is reacted with hydrazine to yield a compound of formula 6-4, which is then reacted with trifluoroacetic anhydride or difluoroacetic anhydride to yield a compound of formula 6-5, which has an oxadiazole structure.

A compound that is prepared according to reaction scheme 6 above is compound 11186.

[Reaction Scheme 7]

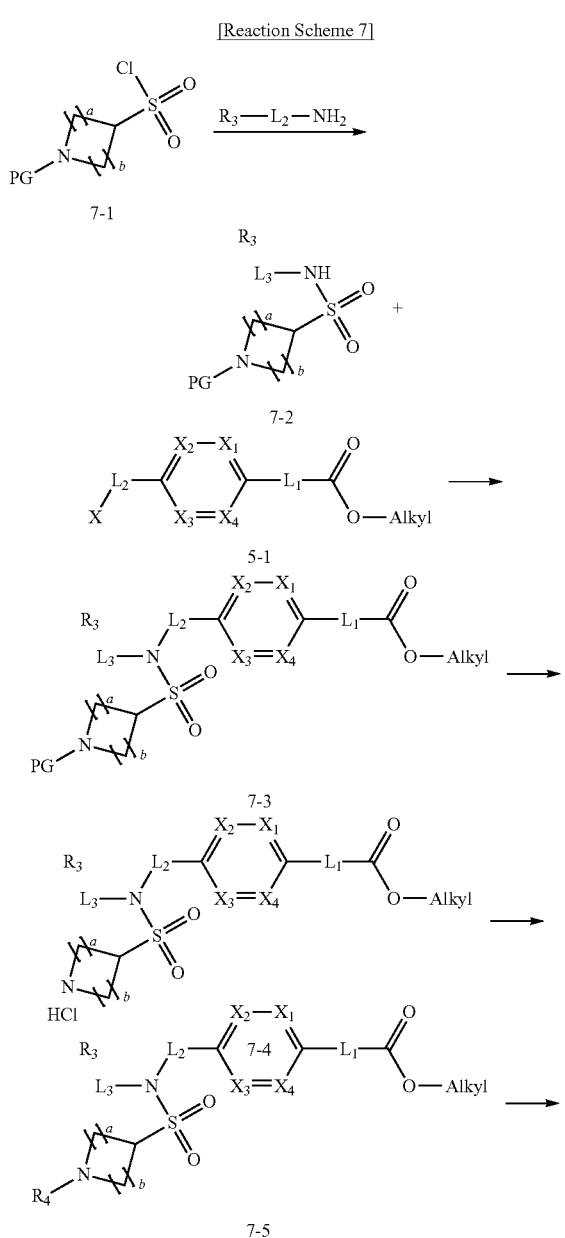

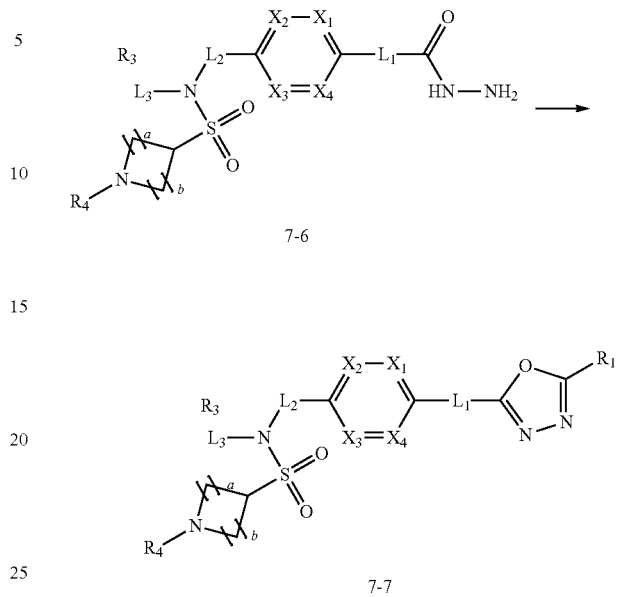

Reaction scheme 7 above shows a general method for synthesis of compounds having a sulfonamide structure. As shown therein, a compound of formula 7-1 is reacted with any of various amine compounds to yield a compound of formula 7-2, which is then subjected to a substitution reaction with a compound of formula 5-1, thereby preparing a compound of formula 7-3. The protecting group of the compound of formula 7-3 is removed, thereby preparing a compound of formula 7-4. The compound of formula 7-4 is subjected to a reductive amination reaction or a substitution reaction, thereby preparing a compound of formula 7-5. The compound of formula 7-5 is reacted with hydrazine to yield a compound of formula 7-6, which is then reacted with trifluoroacetic anhydride or difluoroacetic anhydride, thereby preparing a compound of formula 7-7, which has an oxadiazole structure.

Compounds that are prepared according to reaction scheme 7 above are compounds 11367, 11368, 11372, 11373, 11377, 11426, 11501, 11625, 11637, 11638, 11639 and 11794.

[Reaction Scheme 8]

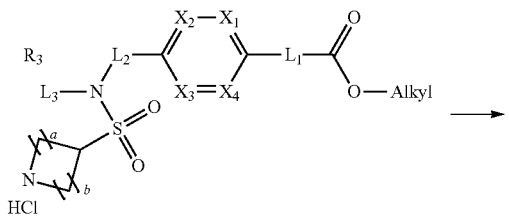

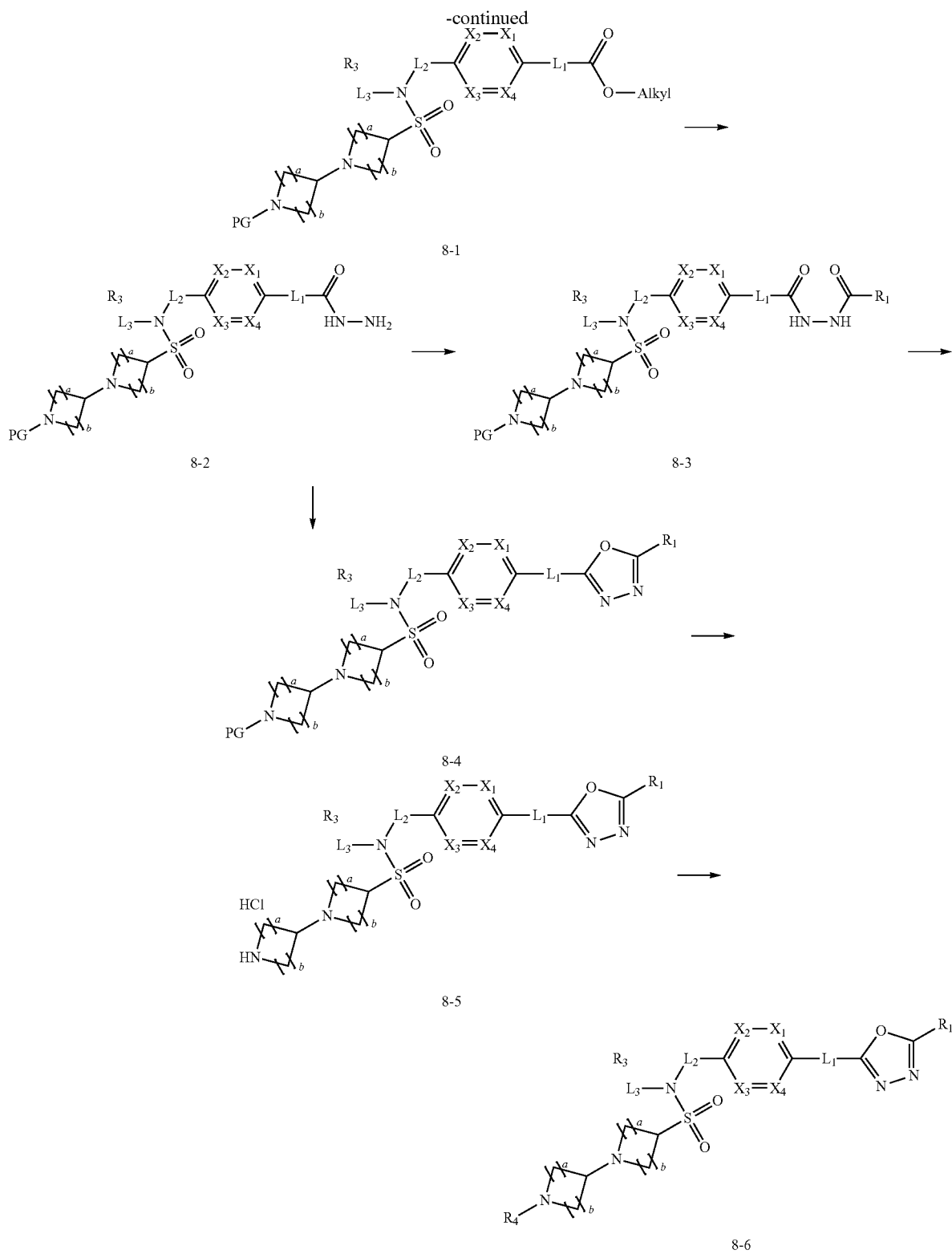

Reaction scheme 8 above shows a general method for synthesis of compounds having a sulfonamide structure. As shown therein, a compound of formula 7-4 is subjected to a reductive amination reaction, a substitution reaction or an amide coupling reaction to yield a compound of formula 8-1, which is then reacted with hydrazine, thereby preparing a compound of formula 8-2. Then, the compound of formula 8-2 is reacted with trifluoroacetic anhydride or difluoroacetic anhydride to yield a compound of formula 8-3 or formula 8-4. Next, the compound of formula 8-3 is subjected to a cyclization reaction using a base and a good leaving group, thereby preparing the compound of formula 8-4. The prepared compound of formula 8-4 is deprotected to yield a compound of formula 8-5, which is then subjected to a reductive amination reaction or a substitution reaction, thereby preparing a compound of formula 8-6.

Compounds that are prepared according to reaction scheme 8 above are compounds 1 1447, 11448, 11451, 11452, 11837, 11838 and 11839.

a substitution reaction, thereby preparing a compound of formula 9-2. Next, the compound of formula 9-2 is reacted with hydrazine to yield a compound of formula 9-3, which is then subjected to a cyclization reaction with trifluoroacetic anhydride or difluoroacetic anhydride, thereby preparing a compound of formula 8-6.

Compounds that are prepared according to reaction scheme 9 above are compounds 11502 and 11503.

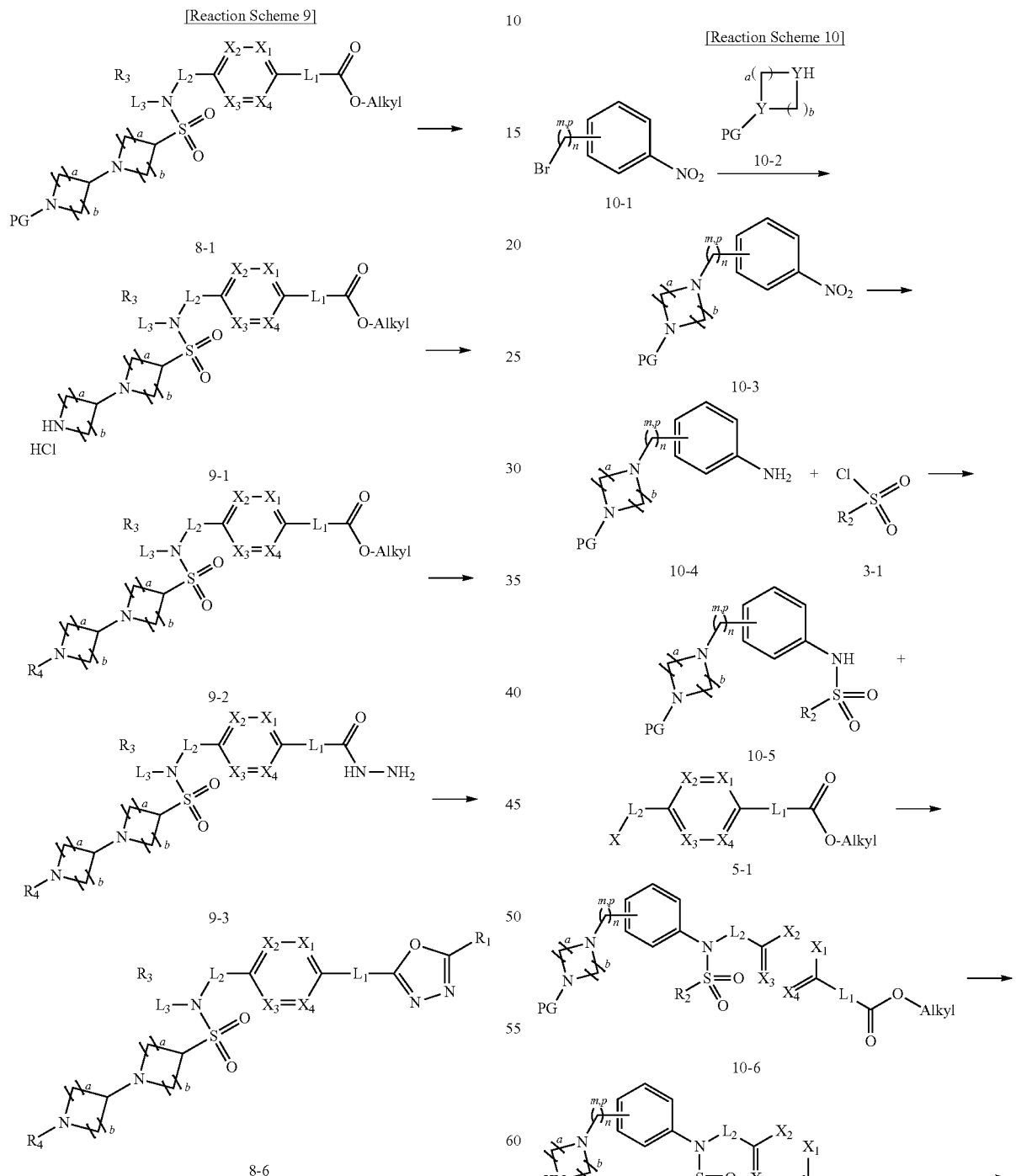

Reaction scheme 9 above shows a general method for synthesis of compounds having a sulfonamide structure. As shown therein, a compound of formula 8-1 is deprotected to yield a compound of formula 9-1, which is then subjected to

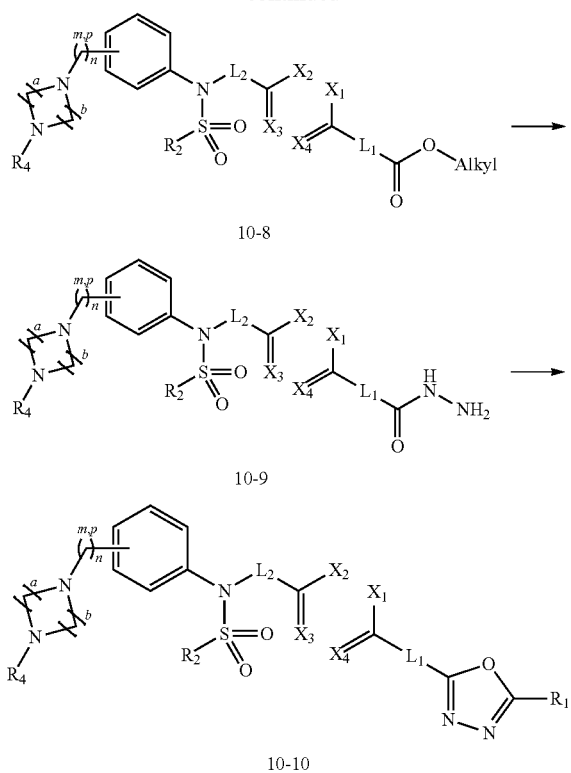

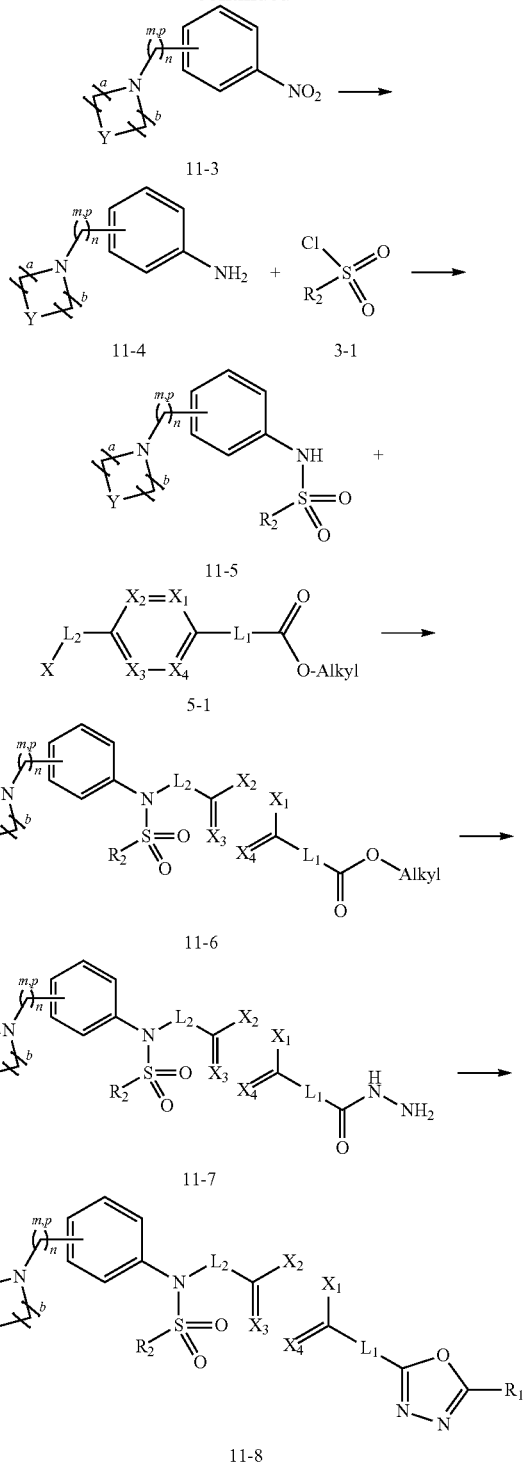

Reaction scheme 10 above shows a general method for synthesis of compounds having a sulfonamide structure. As shown therein, a compound of formula 10-1 is subjected to a substitution reaction with a compound of formula 10-2 to yield a compound of formula 10-3, and the nitro group of the compound of formula 10-3 is reduced with zinc, thereby preparing a compound of formula 10-4. Next, the compound of formula 10-4 is reacted with any of various sulfonyl chloride compounds (formula 3-1) to obtain a compound of formula 10-5, which is then subjected to a substitution reaction with a compound of formula 5-1, thereby preparing a compound of formula 10-7. Next, the compound of formula 10-7 is deprotected and subjected to a reductive amination reaction, a substitution reaction or an amide coupling reaction to yield a compound of formula 10-8, which is then reacted with hydrazine to yield a compound of formula 10-9. Next, the compound of formula 10-9 is subjected to a cyclization reaction with trifluoroacetic anhydride or difluoroacetic anhydride, thereby preparing a compound of formula 10-10.

Compounds that are prepared according to reaction scheme 10 above are compounds 11386, 11387, 11388, 11402, 11403, 11404, 11405 and 11406.

[Reaction Scheme 11]

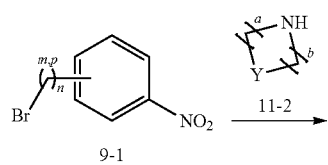

Reaction scheme 11 above shows a general method for synthesis of compounds having a sulfonamide structure. As shown therein, a compound of formula 9-1 is subjected to a substitution reaction with a compound of formula 11-2 to yield a compound of formula 11-3, and the nitro group of the compound of formula 11-3 is reduced with zinc to yield a compound of formula 11-4. Next, the compound of formula 11-4 is reacted with any of various sulfonyl chloride compounds (formula 3-1) to yield a compound of formula 11-5, which is then subjected to a substitution reaction with a compound of formula 5-1, thereby preparing a compound of formula 11-6. The compound of formula 11-6 is reacted with hydrazine to yield a compound of formula 11-7, which is then subjected to a cyclization reaction with trifluoroacetic anhydride or difluoroacetic acid, thereby preparing a compound of formula 11-8.

A compound that is prepared according to reaction scheme 11 above is compound 11392.

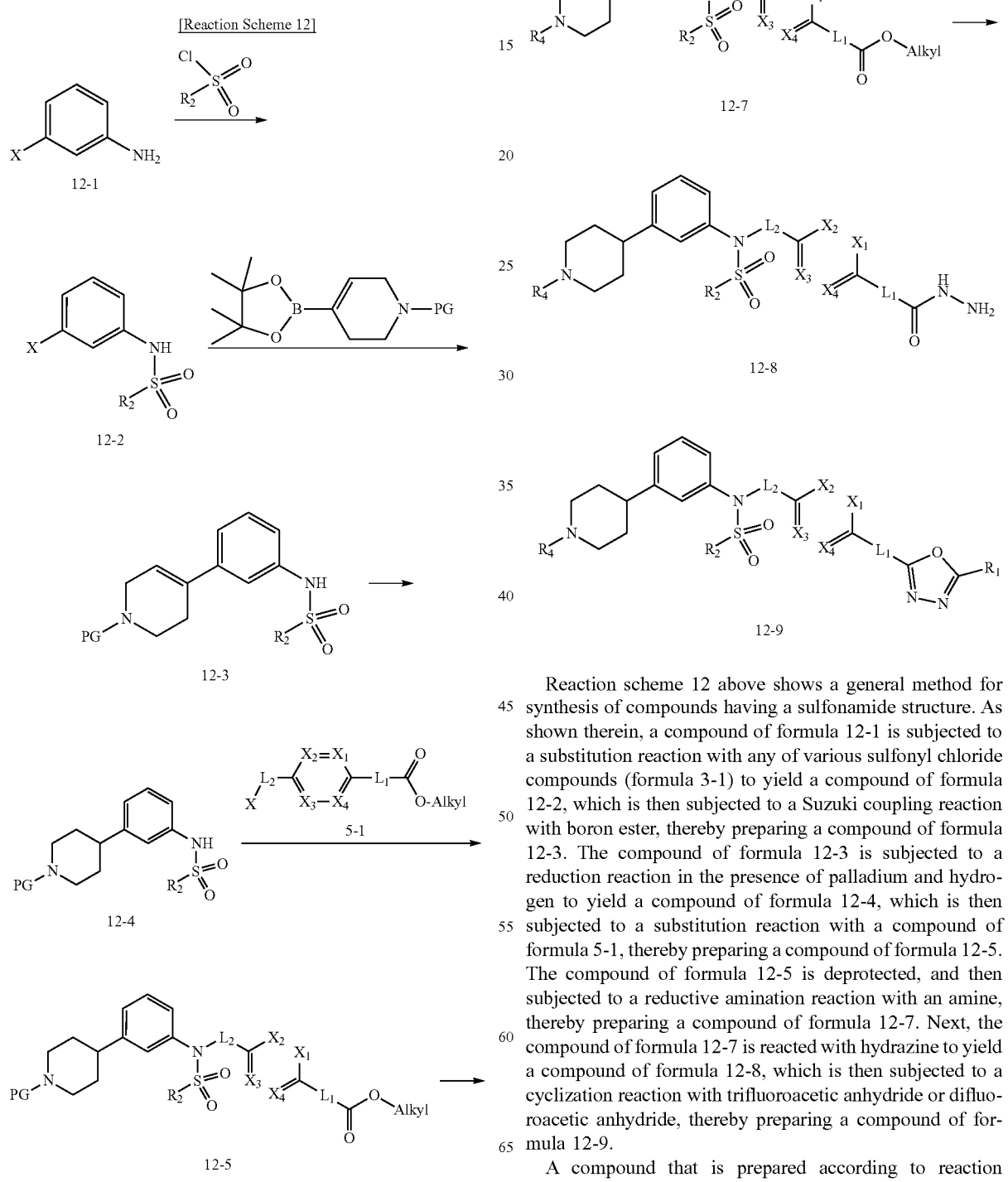

Reaction scheme 12 above shows a general method for synthesis of compounds having a sulfonamide structure. As shown therein, a compound of formula 12-1 is subjected to a substitution reaction with any of various sulfonyl chloride compounds (formula 3-1) to yield a compound of formula 12-2, which is then subjected to a Suzuki coupling reaction with boron ester, thereby preparing a compound of formula 12-3. The compound of formula 12-3 is subjected to a reduction reaction in the presence of palladium and hydrogen to yield a compound of formula 12-4, which is then subjected to a substitution reaction with a compound of formula 5-1, thereby preparing a compound of formula 12-5. The compound of formula 12-5 is deprotected, and then subjected to a reductive amination reaction with an amine, thereby preparing a compound of formula 12-7. Next, the compound of formula 12-7 is reacted with hydrazine to yield a compound of formula 12-8, which is then subjected to a cyclization reaction with trifluoroacetic anhydride or difluoroacetic anhydride, thereby preparing a compound of formula 12-9.

A compound that is prepared according to reaction scheme 12 above is compound 11427.

[Reaction Scheme 13]

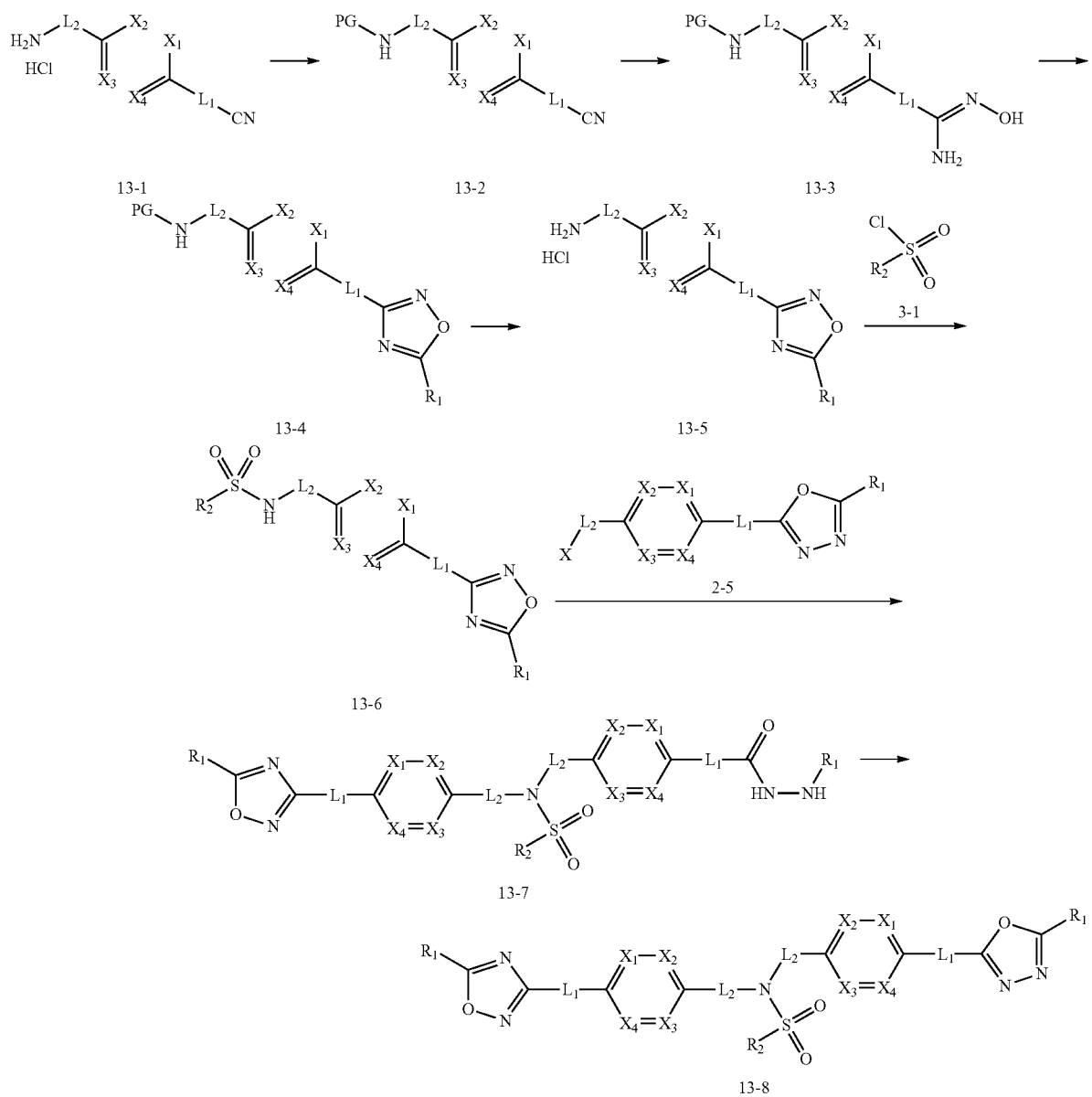

Reaction scheme 13 above shows a general method for synthesis of compounds having a sulfonamide structure. As shown therein, a protecting group is introduced into a compound of formula 13-1 to yield a compound of formula 13-2, and the benzonitrile group of the compound of formula 13-2 is substituted with hydroxybenzimide in the presence of hydroxylamine and a base to yield a compound of formula 13-3. Then, the prepared compound of formula 13-3 is subjected to a cyclization reaction with trifluoroacetic anhydride or difluoroacetic anhydride to yield a compound of formula 13-4. Next, the compound of formula 13-4 is deprotected to yield a compound of formula 13-5, which is then subjected to a substitution reaction with any of various sulfonyl chloride compounds (formula 3-1), thereby preparing a compound of formula 13-6. The compound of formula 13-6 is subjected to a substitution reaction with a compound of formula 2-5 under a basic condition to yield a compound of formula 13-7. When the oxadiazole ring is open, the compound of formula 13-7 is subjected to a cyclization reaction using a good leaving group under a basic condition, thereby preparing a compound of formula 13-8.

A compound that is prepared according to reaction scheme 13 above is compound 11389.

[Reaction Scheme 14]

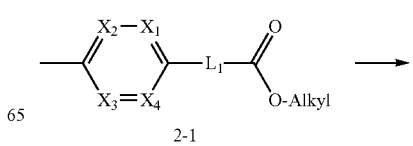

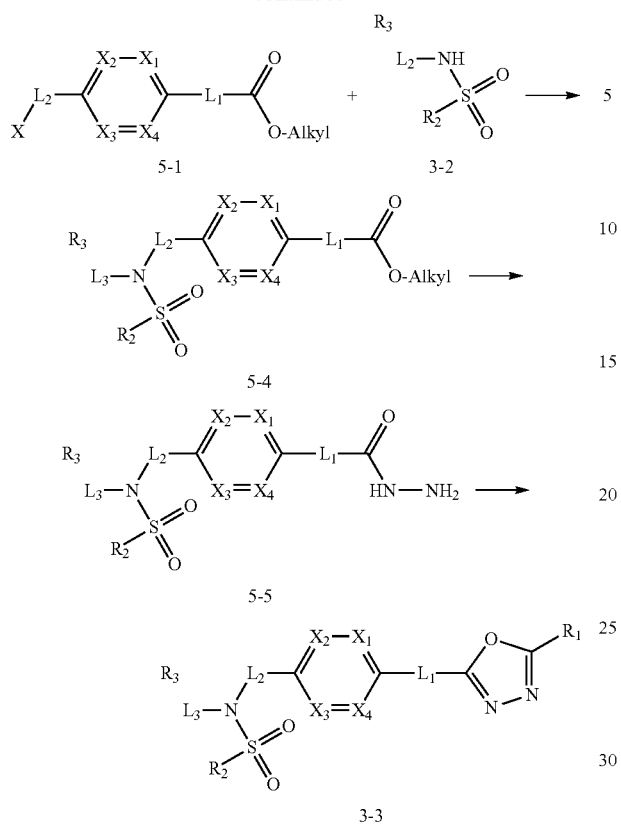
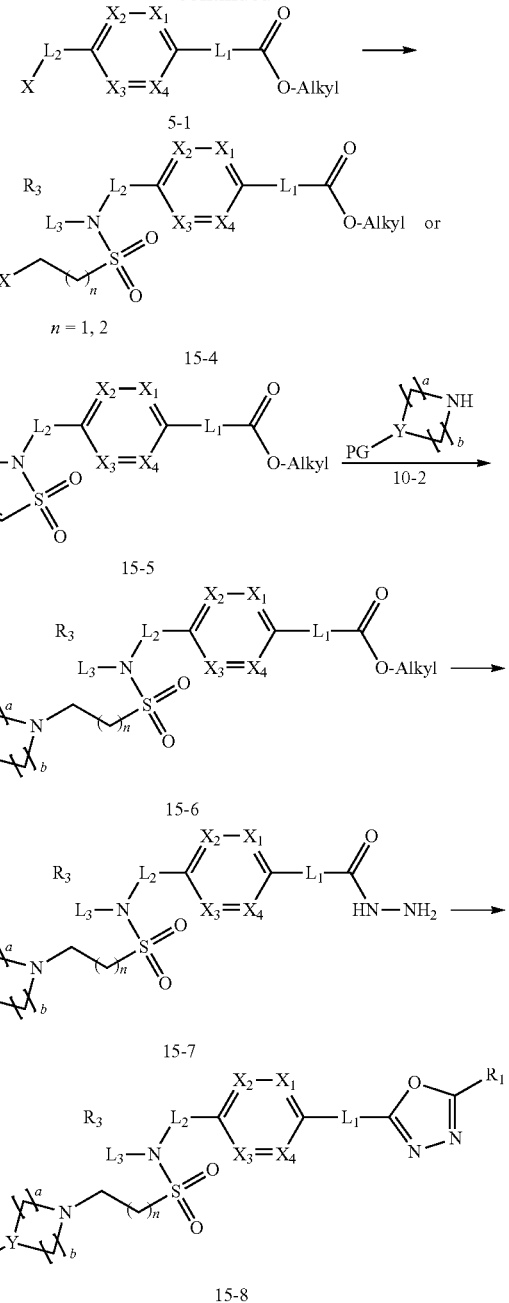

Reaction scheme 14 above shows a general method for synthesis of compounds having a sulfonamide structure. As shown therein, the methyl group of a compound of formula 2-1 is halogenated to yield a compound of formula 5-1, which is then subjected to a substitution reaction with any of various sulfonamide compounds (formula 3-2), thereby preparing a compound of formula 5-4. Next, the compound of formula 5-4 is reacted with hydrazine to yield a compound of formula 5-5, which is then subjected to a cyclization reaction with trifluoroacetic anhydride or difluoroacetic acid, thereby preparing a compound of formula 3-3.

Compounds that are prepared according to reaction scheme 14 above are compounds 11518, 11564, 11565, 11566, 11567, 11573, 11605 and 11606.

[Reaction Scheme 15]

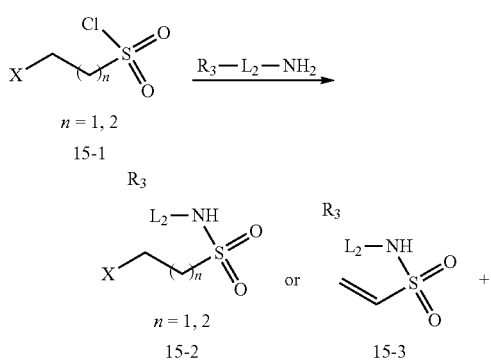

Reaction scheme 15 above shows a general method for synthesis of compounds having a sulfonamide structure. As shown therein, a compound of formula 15-1 is subjected to a substitution reaction any of various primary amine compounds to yield a compound of formula 15-2 or formula 15-3, which is then subjected to a substitution reaction with a compound of formula 5-1, thereby preparing a compound of formula 15-4 or 15-5. The prepared compound is reacted with an amine compound (formula 10-2) to yield a compound of formula 15-6, which is then reacted with hydrazine, thereby preparing a compound of formula 15-7. Next, the prepared compound is subjected to a cyclization reaction with trifluoroacetic anhydride or difluoroacetic anhydride, thereby preparing a compound of formula 15-8.

Compounds that are prepared according to reaction scheme 15 above are compounds 11514, 11588, 11589, 11629, 11630, 11631. 11632, 11645, 11647, 11655, 11657, 11658, 11663, 11675, 11676, 11677, 11678, 11679, 11685, 11700, 11705, 11706, 11707, 11708, 11709, 11710, 11711, 11717, 11718, 11719, 11721, 11722, 11723, 11724 and 11786.

Compounds that are prepared according to reaction scheme 16 above are compounds 11552, 11553, 11554, 11583, 11648 and 11656.

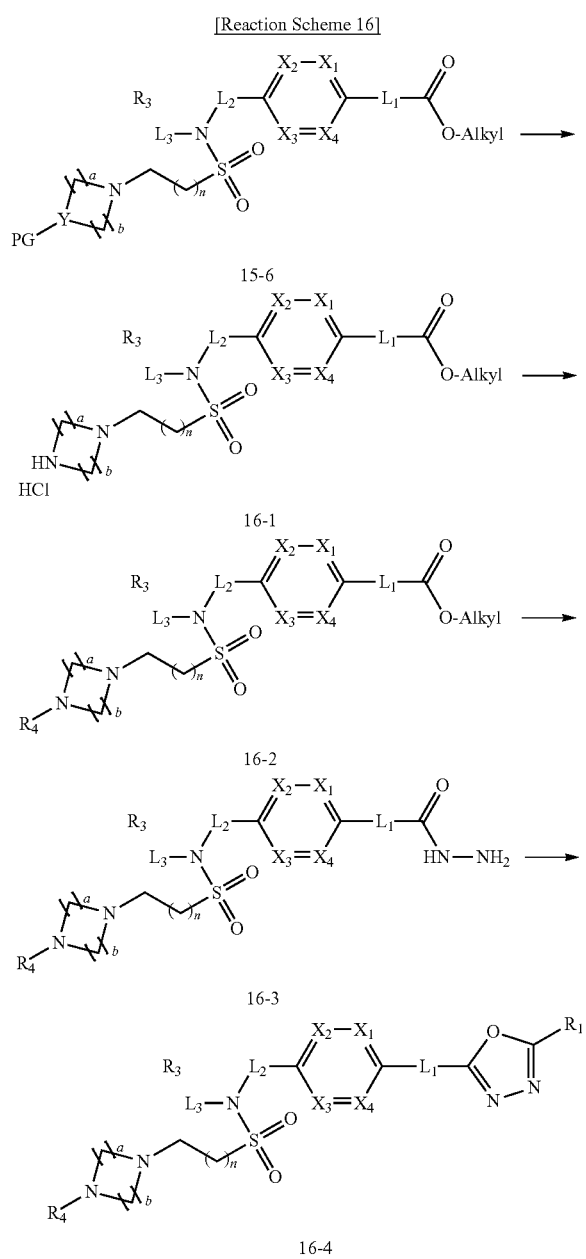

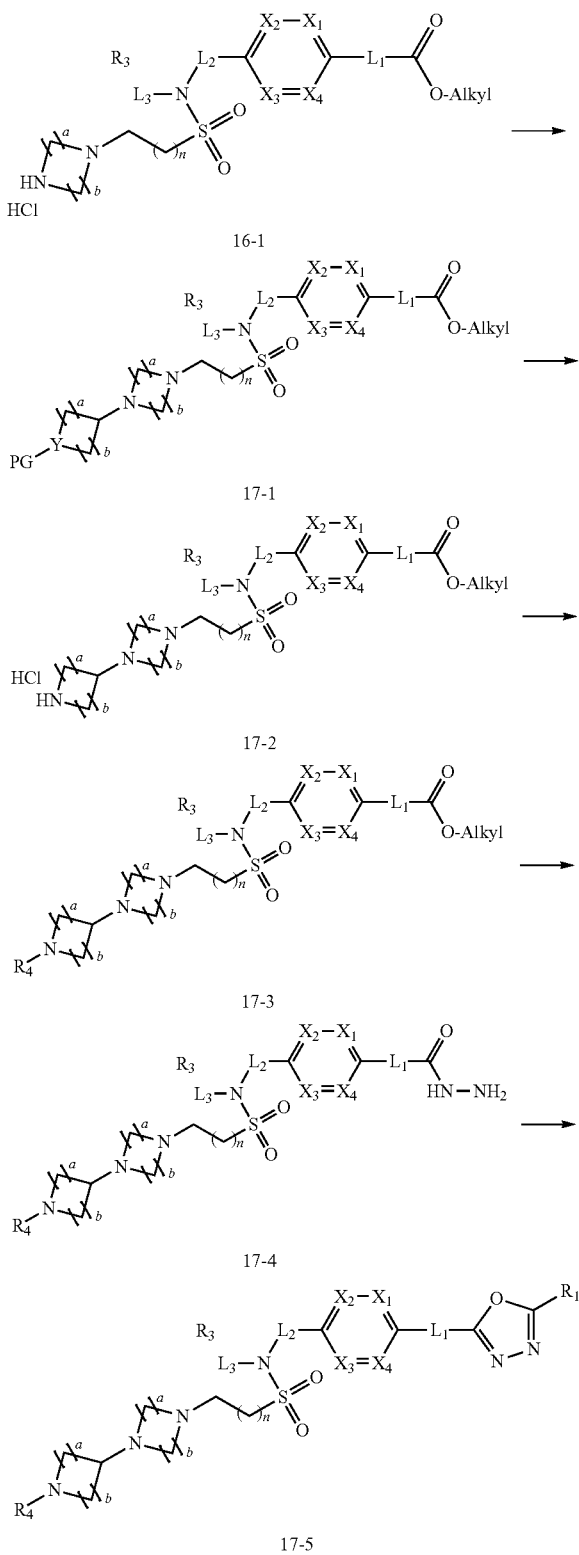

Reaction scheme 16 above shows a general method for synthesis of compounds having a sulfonamide structure. As shown therein, a compound of formula 15-6 is deprotected to yield a compound of formula 16-1, which is then subjected to a reductive amination reaction or a substitution reaction, thereby preparing a compound of formula 16-2. Next, the prepared compound is reacted with hydrazine to yield a compound of formula 16-3, which is then subjected to a cyclization reaction with trifluoroacetic anhydride or difluoroacetic anhydride, thereby preparing a compound of formula 16-4.

Reaction scheme 17 above shows a general method for synthesis of compounds having a sulfonamide structure. As shown therein, a compound of formula 16-1 is subjected to a reductive amination reaction with a ketone compound to yield a compound of formula 17-1 which is then deprotected to yield a compound of formula 17-2. Then, the prepared compound is subjected to a substitution reaction to yield a compound of formula 17-3. The compound of formula 17-3 is reacted with hydrazine to yield a compound of formula 17-4, which is then subjected to a cyclization reaction with trifluoroacetic anhydride or difluoroacetic anhydride, thereby preparing a compound of formula 17-5.

A compound that is prepared according to reaction scheme 17 above is compound 11582.

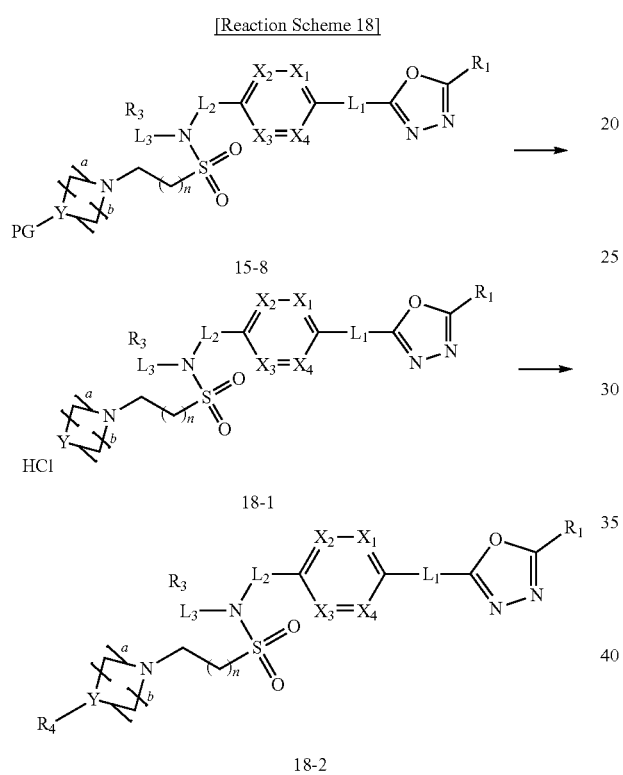

Reaction scheme 18 above shows a general method for synthesis of compounds having a sulfonamide structure. As shown therein, a compound of formula 15-8 is deprotected to yield a compound of formula 18-1, which is then subjected to a substitution reaction, thereby synthesizing a compound of formula 18-2.

Compounds that are prepared according to reaction scheme 18 above are compounds 11633 and 11634.

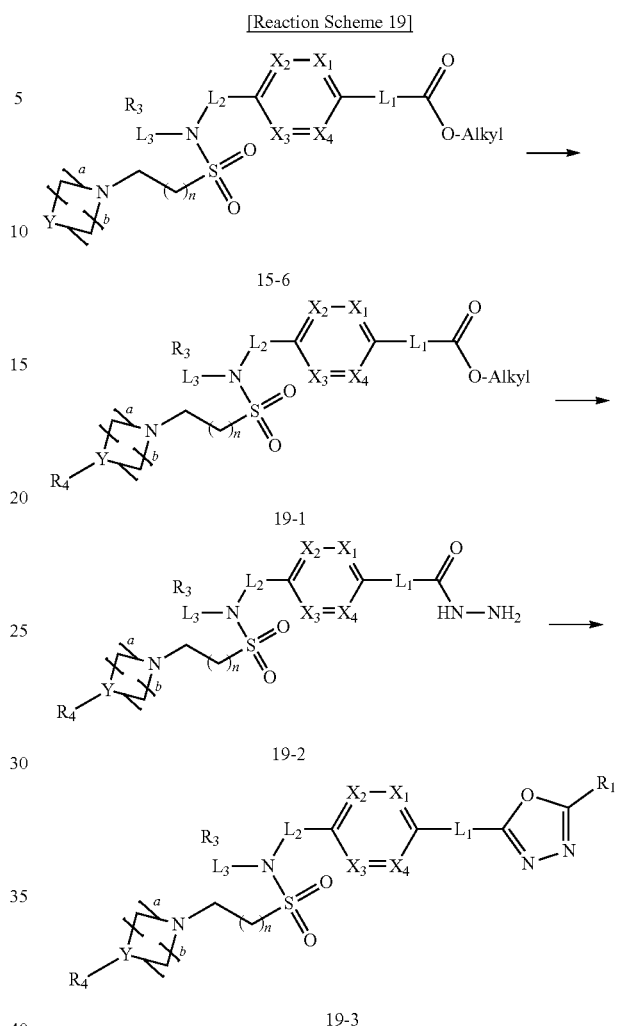

Reaction scheme 19 above shows a general method for synthesis of compounds having a sulfonamide structure. As shown therein, a compound of formula 15-6 is subjected to a reductive amination reaction with aldehyde to yield a compound of formula 19-1. The prepared compound of formula 19-1 is reacted with hydrazine to yield a compound of formula 19-2, which is then subjected to a cyclization reaction with trifluoroacetic anhydride or difluoroacetic anhydride, thereby preparing a compound of formula 19-3.

Compounds that are prepared according to reaction scheme 19 above are compounds 11646 and 11665.

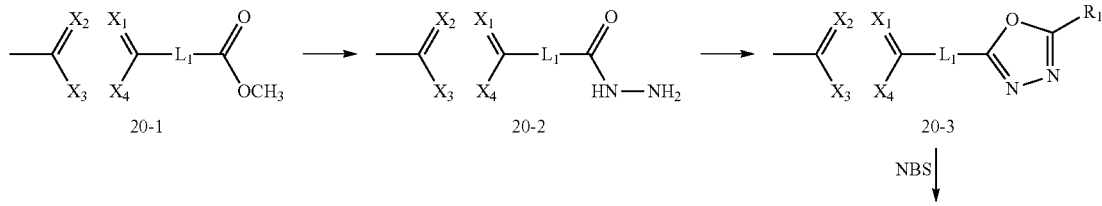

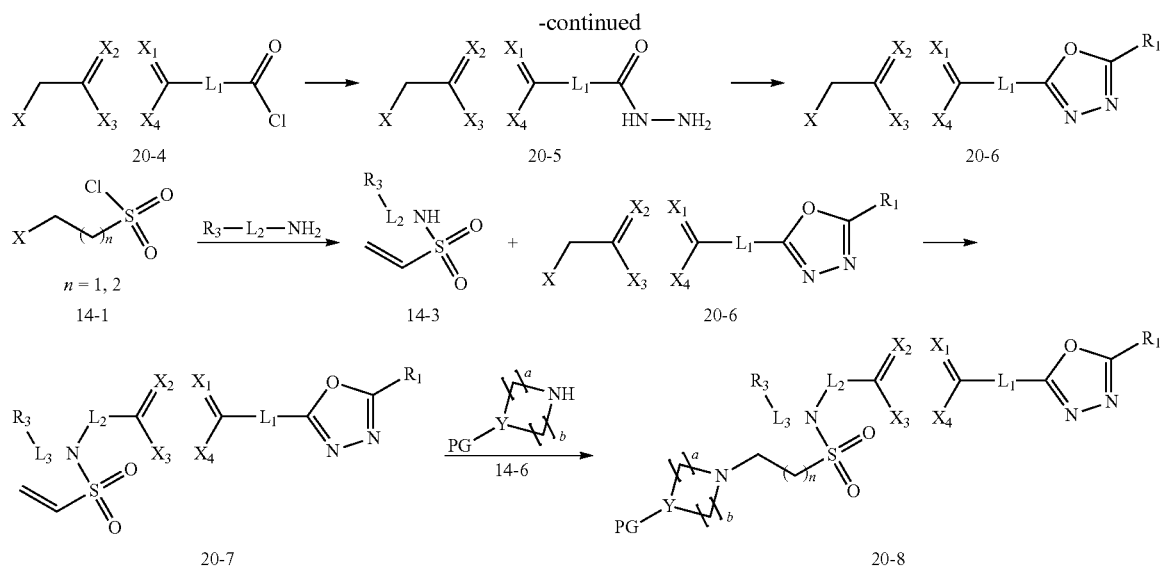

Reaction scheme 20 above shows a general method for synthesis of compounds having a sulfonamide structure. As shown therein, a compound of formula 20-1 is reacted with hydrazine to yield a compound of formula 20-5, which is then subjected to a cyclization reaction to yield a compound of formula 20-3. The prepared compound of formula 20-3 is brominated to yield a compound of formula 20-6. Alternatively, acyl chloride of formula 20-4 is used to yield the compound of formula 20-6. Meanwhile, a compound of formula 14-1 is subjected to a substitution reaction with any of various primary amine compounds to yield a compound of formula 14-3, which is then subjected to a substitution reaction with the compound of formula 20-6 to yield a compound of formula 20-7. Then, the prepared compound is reacted with an amine compound (formula 14-6), thereby preparing a compound of formula 20-8.

Compounds that are prepared according to reaction scheme 20 above are compounds 11737, 11738, 11751, 11752, 11753, 11754, 11755, 11756, 11757, 11758, 11759, 11760, 11761, 11762, 11763, 11764, 11765, 11766, 11767, 11768, 11769, 11770, 11771, 11772, 11773, 11795, 11796, 11797, 11798, 11799, 11800, 11801, 11802, 11803, 11804, 11805, 11806, 11807, 11808, 11809, 11810, 11811, 11812, 11813, 11814, 11815, 11816, 11817, 11818, 11819, 11820, 11821, 11822, 11842, 11843, 11844, 11845, 11847, 11848 and 11849.

[Reaction Scheme 21]

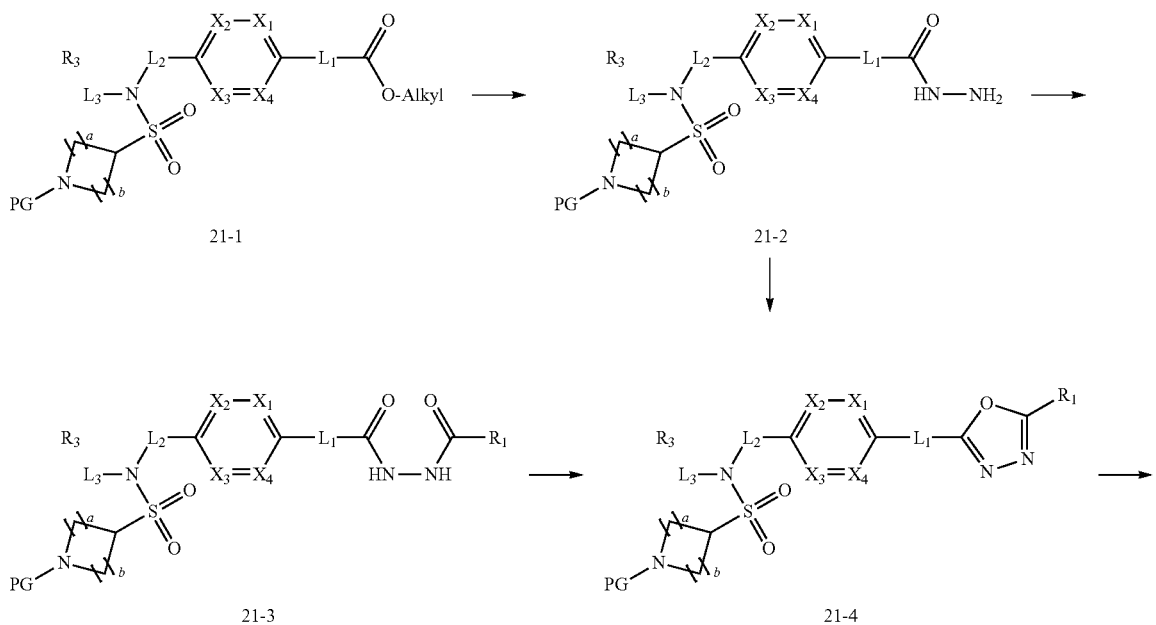

-continued

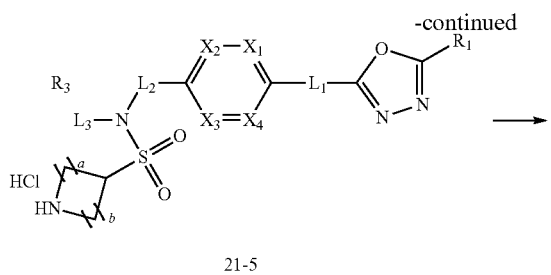

21-5

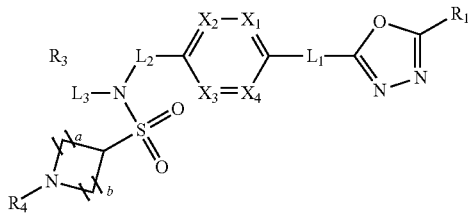

21-6

Reaction scheme 21 above shows a general method for synthesis of compounds having a sulfonamide structure. As shown therein, a compound of formula 21-1 is reacted with hydrazine to yield a compound of formula 21-2, which is then subjected to a cyclization reaction with trifluoroacetic anhydride or difluoroacetic anhydride, thereby preparing a compound of formula 21-4. The prepared compound of formula 21-4 is deprotected to yield a compound of formula 21-5, which is then subjected to a reductive amination reaction or a substitution reaction, thereby preparing a compound of formula 21-6.

Compounds that are prepared according to reaction scheme 21 above are compounds 11680, 11681, 11682, 11683, 11684, 11686, 11687, 11688, 11689, 11690, 11691, 11692, 11693, 11694, 11695, 11696, 11697, 11698, 11699, 11725, 11726, 11727, 11728, 11790, 11791, 11792 and 11793.

[Reaction Scheme 22]

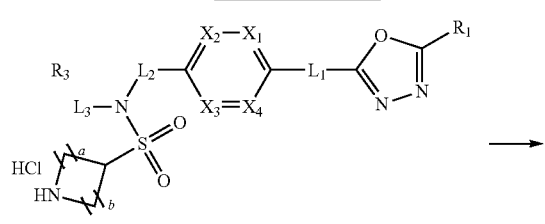

22-1

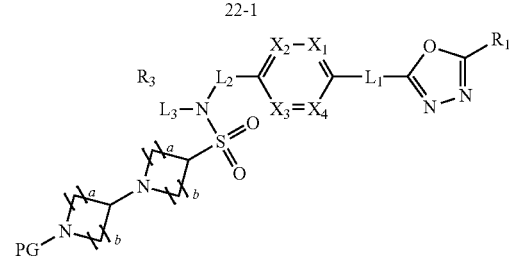

22-2

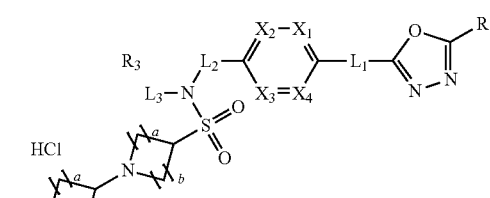

22-3

-continued

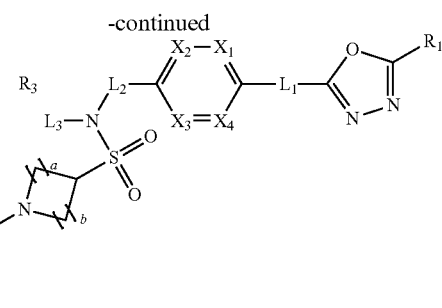

22-4

Reaction scheme 22 above shows a general method for synthesis of compounds having a sulfonamide structure. As shown therein, a compound of formula 22-1 is subjected to a reductive amination reaction to yield a compound of formula 22-2, which is then deprotected, thereby preparing a compound of formula 22-3. The prepared compound of formula 22-3 is subjected to a reductive amination reaction or a substitution reaction, thereby preparing a compound of formula 22-4.

Compounds that are prepared according to reaction scheme 22 above are compounds 11777, 11778, 11779, 11780, 11781, 11782, 11783, 11784, 11785 and 11836.

[Reaction Scheme 23]

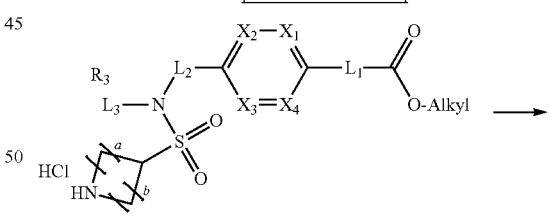

23-1

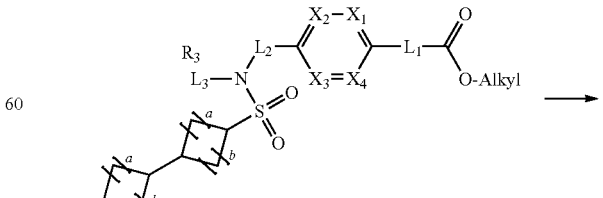

23-2

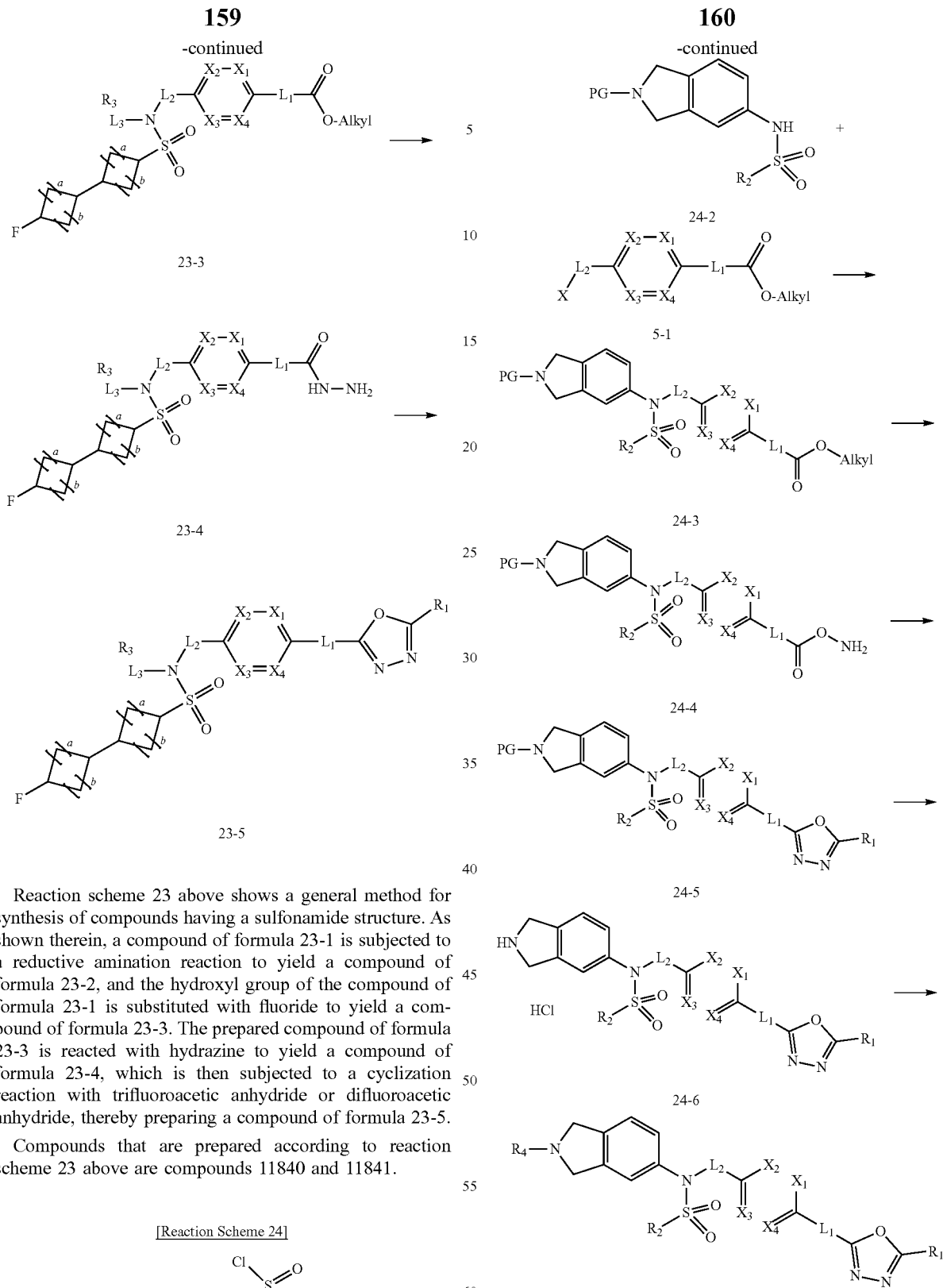
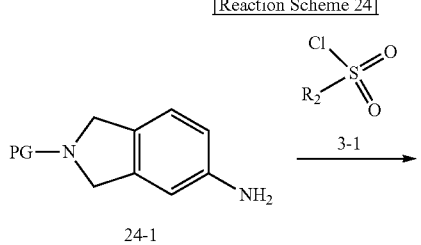

Reaction scheme 23 above shows a general method for synthesis of compounds having a sulfonamide structure. As shown therein, a compound of formula 23-1 is subjected to a reductive amination reaction to yield a compound of formula 23-2, and the hydroxyl group of the compound of formula 23-1 is substituted with fluoride to yield a compound of formula 23-3. The prepared compound of formula 23-3 is reacted with hydrazine to yield a compound of formula 23-4, which is then subjected to a cyclization reaction with trifluoroacetic anhydride or difluoroacetic anhydride, thereby preparing a compound of formula 23-5.

Compounds that are prepared according to reaction scheme 23 above are compounds 11840 and 11841.

Reaction scheme 24 above shows a general method for synthesis of compounds having a sulfonamide structure. As shown therein, a compound of formula 24-1 is subjected sequentially to a substitution reaction with a compound of formula 3-1 and a substitution reaction with a compound of formula 5-1 to obtain a compound of formula 24-3, which is then reacted with hydrazine to yield a compound of formula 24-4. Then, the prepared compound of formula 24-4 is subjected to a cyclization reaction with trifluoroacetic anhydride or difluoroacetic anhydride to yield a compound of formula 24-5, which is then deprotected, thereby preparing a compound of formula 24-6. Then, the prepared compound of formula 24-6 is subjected to a reductive amination reaction or a substitution reaction, thereby preparing a compound of formula 24-7.

Compounds that are prepared according to reaction scheme 24 above are compounds 11729, 11730, 11731, 11732, 11733, 11734, 11735 and 11736.

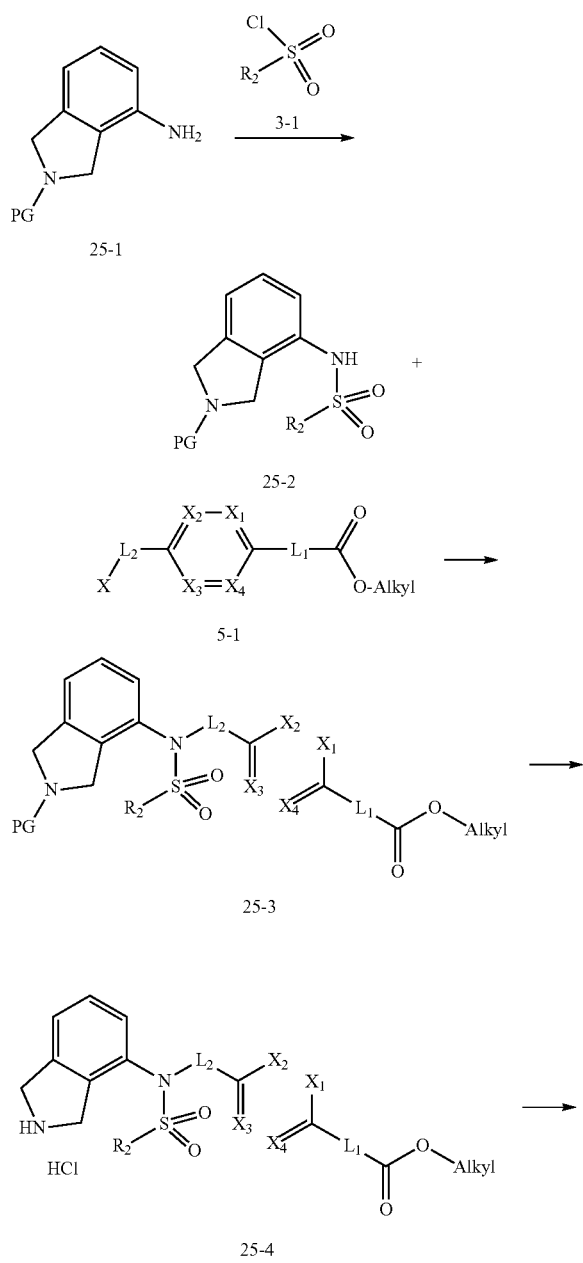

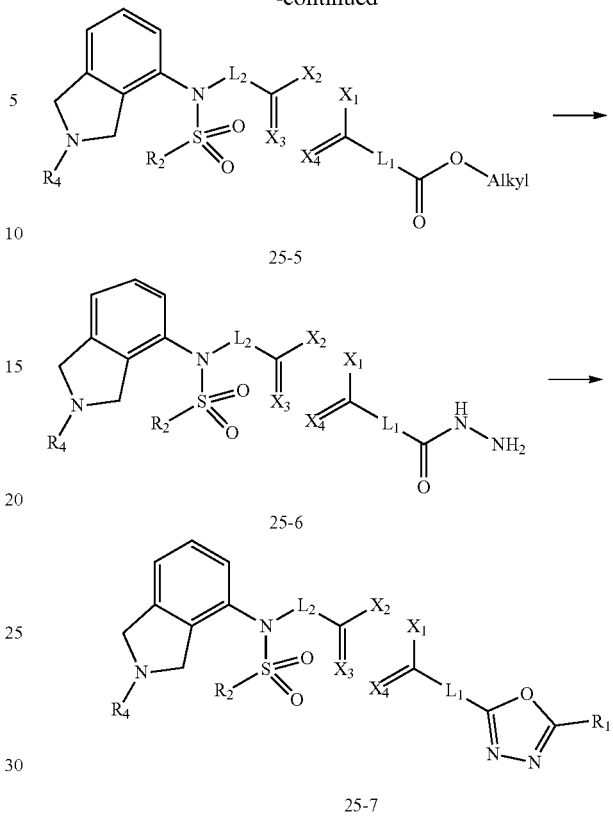

Reaction scheme 25 above shows a general method for synthesis of compounds having a sulfonamide structure. As shown therein, a compound of formula 25-1 is subjected sequentially to a substitution reaction with a compound of formula 3-1 and a substitution reaction with a compound of formula 5-1 to obtain a compound of formula 25-3. The compound of formula 25-4 is subjected to a reductive amination reaction or a substitution reaction to yield a compound of formula 25-5. Then, the compound of formula 25-5 is reacted with hydrazine to yield a compound of formula 25-6, which is then subjected to a cyclization reaction with trifluoroacetic anhydride or difluoroacetic anhydride, thereby preparing a compound of formula 25-7.

A compound that is prepared according to reaction scheme 25 above is compound 11712.

Compositions Comprising 1,3,4-Oxadiazole Sulfonamide Derivative Compounds, the Use Thereof and the Method of Treating Diseases The present invention provides a pharmaceutical composition for preventing or treating histone deacetylase 6 (HDAC6) activity-associated diseases, which contains, as an active ingredient, a compound represented by the following formula I, a stereoisomer thereof or a pharmaceutically acceptable salt thereof:

[Formula I]

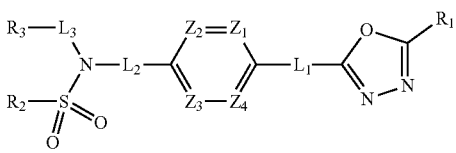

wherein formula I is as defined above.

The pharmaceutical composition according to the present invention exhibits a remarkable effect on the prevention or treatment of histone deacetylase 6 (HDAC6) activity-associated diseases by selectively inhibiting histone deacetylase 6 (HDAC6).

The histone deacetylase 6 (HDAC6) activity-associated diseases include infectious diseases such as prion disease; neoplasms such as benign tumor (e.g. myelodysplastic syndrome) or malignant tumor (e.g. multiple myeloma, lymphoma, leukemia, lung cancer, rectal cancer, colon cancer, prostate cancer, urothelial carcinoma, breast cancer, melanoma, skin cancer, liver cancer, brain cancer, gastric cancer, ovarian cancer, pancreatic cancer, head and neck cancer, oral cancer, or glioma); endocrine, nutritional and metabolic diseases such as Wilson's disease, amyloidosis or diabetes; mental and behavioral disorders such as depression or Rett's syndrome, and the like; neurological diseases such as atrophy of central nervous system (e.g. Huntington's disease, spinal muscular atrophy (SMA), spinocerebellar ataxia (SCA)), neurodegenerative disease (e.g. Alzheimer's disease), movement disorder (e.g. Parkinson's disease), neuropathy (e.g. hereditary neuropathy (Charcot-Marie-Tooth disease), sporadic neuropathy, inflammatory neuropathy, drug-induced neuropathy), motor neuron diseases (amyotrophic lateral sclerosis (ALS)), or demyelinating diseases of the central nervous system (e.g. multiple sclerosis (MS)), and the like; diseases of the eye and adnexa, such as uveitis; cardiovascular diseases such as atrial fibrillation or stroke and the like; respiratory diseases such as asthma; digestive diseases such as alcoholic liver disease, inflammatory bowel disease, Crohn's disease or ulcerative bowel disease, and the like; diseases of the skin and subcutaneous tissue, such as psoriasis; diseases of the musculoskeletal system and connective tissue, such as rheumatoid arthritis, osteoarthritis or systemic lupus erythematosus (SLE), and the like; or congenital malformations, deformations and chromosomal abnormalities, such as autosomal dominant polycystic kidney disease, as well as disorders or diseases associated with the abnormal function of histone deacetylase.

The pharmaceutically acceptable salt is as described above with respect to a pharmaceutically acceptable salt of the compound represented by formula I according to the present invention.

For administration, the pharmaceutical composition according to the present invention may further contain at least one pharmaceutically acceptable carrier in addition to the compound of formula I, an isomer thereof or a pharmaceutically acceptable salt thereof. The pharmaceutically acceptable carrier that is used in the present invention may be at least one of physiological saline, sterile water, Ringer solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, the composition can be formulated into injectable formulations such as solutions, suspensions, turbid fluid, etc, pills, capsules, granules or tablets using a diluent, a dispersing agent, a surfactant, a binder and a lubricant. Thus, the composition of the present invention may be in the form of patches, liquids, pills, capsules, granules, tablets, suppositories, etc. These formulations can be prepared either by conventional methods that are used for formulation in the art or by the method disclosed in Remington's Pharmaceutical Science (the latest edition), Mack Publishing Company, Easton Pa.

The pharmaceutical composition of the present invention may be administered orally or parenterally (e.g., intravenously, subcutaneously, intraperitoneally or topically) depending on the intended use. The dose of the pharmaceutical composition varies depending on the patient's weight, age, sex, health conditions and diet, the time of administration, the mode of administration, excretion rate, the severity of the disease, and the like. The daily dose of the compound of formula I according to the present invention may be about 1 to 1000 mg/kg, preferably 5 to 100 mg/kg, and may be administered once to several times a day.

The pharmaceutical composition of the present invention may further contain, in addition to the compound represented by formula I, a stereoisomer thereof or a pharmaceutically acceptable salt thereof, one or more active ingredients that exhibit medicinal efficacy identical or similar thereto.

The present invention also provides a method for preventing or treating a histone deacetylase-mediated disease, which comprises administering a therapeutically effective amount of the compound represented by formula I, a stereoisomer thereof or a pharmaceutically acceptable salt thereof.

As used herein, the term "therapeutically effective amount" refers to the amount of the compound represented by formula I, which is effective for the prevention or treatment of histone deacetylase 6 activity-associated diseases.

The present invention also provides a method of selectively inhibiting HDAC6, which comprises administering the compound of formula I, a stereoisomer thereof or a pharmaceutically acceptable salt thereof to mammals including humans.

The method of preventing or treating histone deacetylase 6 activity-associated disease according to the present invention includes inhibiting or averting the disease as well as addressing the disease itself, prior to the onset of symptoms by administering the compound represented by formula I. In the management of diseases, the magnitude of a prophylactic or therapeutic dose of a particular active ingredient will vary with the nature and severity of the disease or condition, and may also vary according to the route by which the active ingredient is administered. The dose and the dose frequency will also vary according to the age, body weight, and response of the individual patient. Suitable dosing regimens can be readily selected by those skilled in the art with due consideration of such factors. In addition, the method of preventing or treating histone deacetylase 6 activity-associated disease according to the present invention may further comprise administering a therapeutically effective amount of an additional active agent helpful for the treatment of the disease together with the compound represented by formula I, in which the additional active agent can exhibit a synergistic effect with the compound of formula I or an assistant effect.

The present invention is also intended to provide the use of the compound represented by formula I, a stereoisomer thereof or a pharmaceutically acceptable salt thereof, for the preparation of a medicament for treating histone deacetylase 6 activity-associated disease. For the preparation of the medicament, the compound represented by formula I may be mixed with a pharmaceutically acceptable adjuvant, diluent, carrier or the like, and combined with other active agents such that the active ingredients can have synergistic effects.

The particulars mentioned in the use, composition and treatment method of the present invention may be appropriately combined unless contradictory to one another.

Advantageous Effects of Invention

The compounds represented by formula I, stereoisomers thereof or pharmaceutically acceptable salts thereof can selectively inhibit HDAC6, and thus exhibit excellent effects on the prevention or treatment of histone deacetylase 6 activity-associated diseases.

MODE FOR THE INVENTION

Hereinafter, preferred examples will be presented to assist in the understanding of the present invention. However, these examples are provided only for a better understanding of the present invention and are not intended to limit the scope of the present invention.

Preparation of 1,3,4-Oxadiazole Sulfonamide Derivative Compounds

Specific methods for preparing the compounds of formula I are as follows.

EXAMPLE 1

Compound 11044: N-(2-fluoro-4-(5-(trifluoromethyl)-1,3,4-oxadiazol-2-yl)benzyl)-N-(pyridin-2-ylmethyl)methanesulfonamide

[Step 1] N-(pyridin-2-ylmethyl)methanesulfonamide

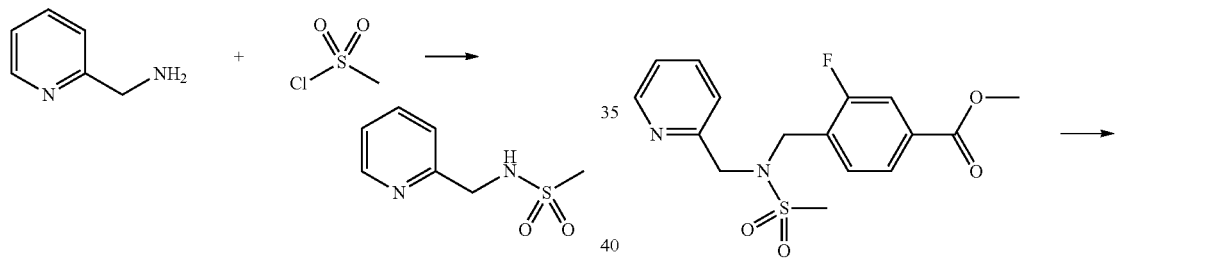

A solution of pyridin-2-ylmethanamine (1.000 g, 9.247 mmol), pyridine (0.821 mL, 10.172 mmol) and methanesulfonyl chloride (0.865 mL, 11.097 mmol) in dichloromethane (10 mL) was stirred at the room temperature for 12 hr. The precipitates were collected by filtration, washed by dichloromethane, and dried to give N-(pyridin-2-ylmethyl)methanesulfonamide as brown solid (1.050 g, 61.0%).

[Step 2] Methyl 3-fluoro-4-((N-(pyridin-2-ylmethyl)methylsulfonamido)methyl)benzoate

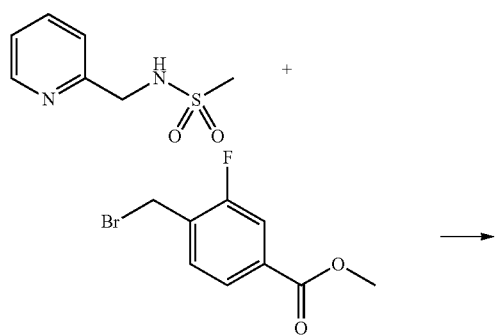

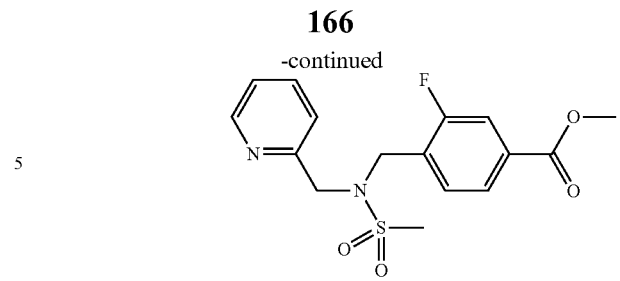

A solution of N-(pyridin-2-ylmethyl)methanesulfonamide (0.300 g, 1.611 mmol), NaH (60.00%, 0.077 g, 1.933 mmol) and methyl 4-(bromomethyl)-3-fluorobenzoate (0.438 g, 1.772 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethylacetate/hexane=0% to 40%) to give methyl 3-fluoro-4-((N-(pyridin-2-ylmethyl)methylsulfonamido)methyl)benzoate as white solid (0.290 g, 51.1%).

[Step 3] N-(2-fluoro-4-(hydrazinecarbonyl)benzyl)-N-(pyridin-2-ylmethyl)methanesulfonamide

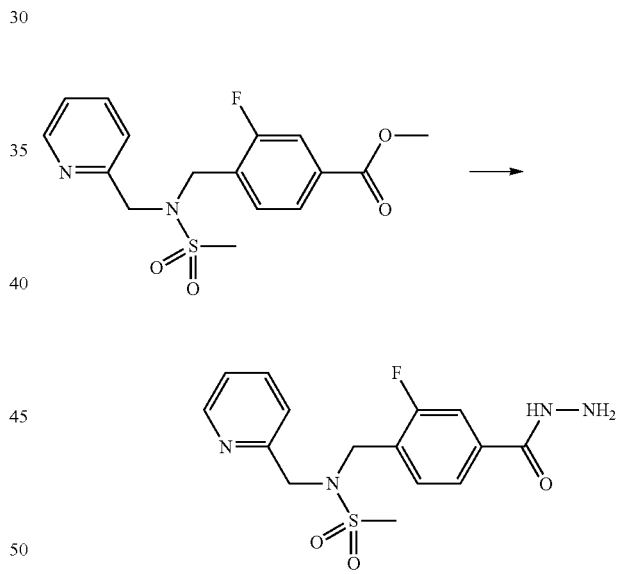

A mixture of methyl 3-fluoro-4-((N-(pyridin-2-ylmethyl)methylsulfonamido)methyl)benzoate (0.400 g, 1.135 mmol) and hydrazine hydrate (0.568 g, 11.351 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with saturated aqueous sodium chloride solution dried with anhydrous MgSO₄, filtered, and concentrated in vacuo. The title compound was used without further purification (N-(2-fluoro-4-(hydrazinecarbonyl)benzyl)-N-(pyridin-2-ylmethyl)methanesulfonamide, 0.370 g, 92.5%, yellow solid).

[Step 4] N-(2-fluoro-4-(2-(2,2,2-trifluoroacetyl)hydrazine-1-carbonyl)benzyl)-N-(pyridin-2-ylmethyl)methanesulfonamide

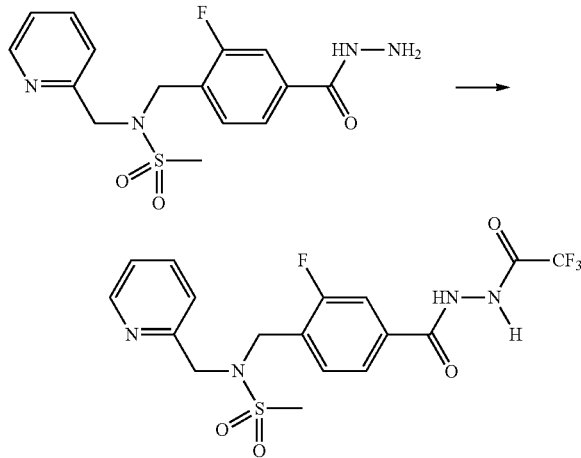

A solution of N-(2-fluoro-4-(hydrazinecarbonyl)benzyl)-N-(pyridin-2-ylmethyl)methanesulfonamide (0.370 g, 1.050 mmol), trifluoroacetic anhydride (TFAA, 0.131 mL, 0.945 mmol) and triethylamine (TEA, 0.220 mL, 1.575 mmol) in dichloromethane (10 mL) was stirred at the room temperature for 5 hr. Then, water was added to the reaction mixture, followed by extraction with dichloromethane. The organic layer was washed with saturated aqueous sodium chloride solution, dried with anhydrous MgSO$_4$, filtered, and concentrated in vacuo. The residue was chromatographed (SiO$_2$, 12 g cartridge; ethylacetate/hexane=0% to 40%) to give N-(2-fluoro-4-(2-(2,2,2-trifluoroacetyl)hydrazine-1-carbonyl)benzyl)-N-(pyridin-2-ylmethyl)methanesulfonamide as yellow solid (0.350 g, 74.3%).

[Step 5] Compound 11044

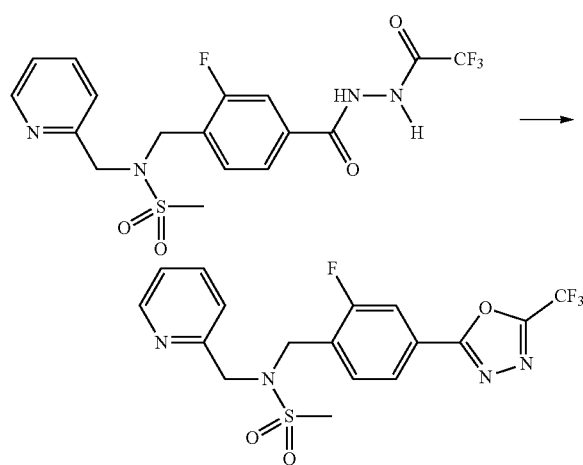

A solution of N-(2-fluoro-4-(2-(2,2,2-trifluoroacetyl)hydrazine-1-carbonyl)benzyl)-N-(pyridin-2-ylmethyl)methanesulfonamide (0.350 g, 0.781 mmol) and Burgess reagent (1-methoxy-N-triethylammoniosulfonyl-methanimidate, 0.279 g, 1.171 mmol) in tetrahydrofuran (10 mL) was stirred at 150° C. for 30 min, and cooled down to the room temperature to terminate the reaction. Then, water was added to the reaction mixture, followed by extraction with ethyl acetate. The organic layer was washed with saturated aqueous sodium chloride solution, dried with anhydrous MgSO$_4$, filtered, and concentrated in vacuo. The residue was chromatographed (SiO$_2$, 12 g cartridge; ethylacetate/hexane=0% to 30%) to give N-(2-fluoro-4-(5-(trifluoromethyl)-1,3,4-oxadiazol-2-yl)benzyl)-N-(pyridin-2-ylmethyl)methanesulfonamide as yellow solid (0.095 g, 28.3%).

$^1$H NMR (400 MHz, CDCl$_3$) δ 8.62-8.55 (m, 1H), 7.90 (dd, 1H, J=8.1, 1.7 Hz), 7.81-7.72 (m, 2H), 7.72-7.66 (m, 1H), 7.34-7.21 (m, 3H), 4.65 (s, 2H), 4.57 (s, 2H), 3.07 (s, 3H); LRMS (ES) m/z 431.1 (M$^+$+1).

EXAMPLE 2

Compound 11045: N-(pyridin-2-ylmethyl)-N-(4-(5-(trifluoromethyl)-1,3,4-oxadiazol-2-yl)benzyl)methanesulfonamide

[Step 1] methyl 4-((N-(pyridin-2-ylmethyl)methylsulfonamido)methyl)benzoate

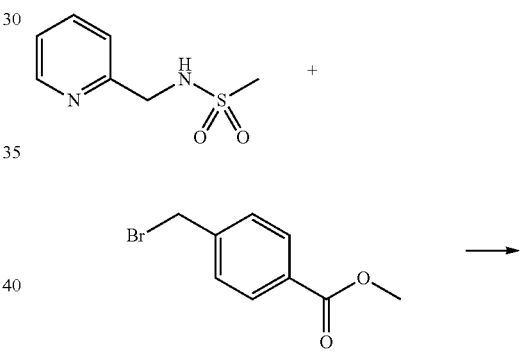

A solution of N-(pyridin-2-ylmethyl)methanesulfonamide (0.300 g, 1.611 mmol), NaH (60.00%, 0.077 g, 1.933 mmol) and methyl 4-(bromomethyl)benzoate (0.406 g, 1.772 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl4-((N-(pyridin-2-ylmethyl)methylsulfonamido)methyl)benzoate as yellow solid (0.270 g, 50.1%).

[Step 2] N-(4-(hydrazinecarbonyl)benzyl)-N-(pyridin-2-ylmethyl)methanesulfonamide

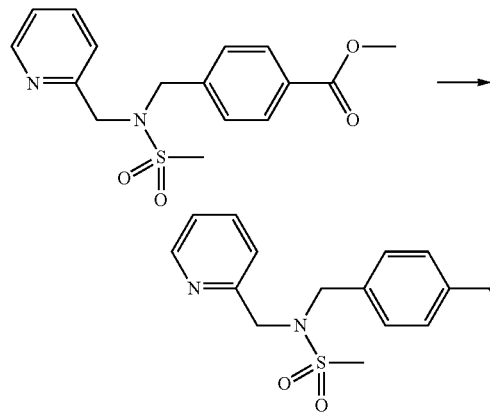

A mixture of methyl 4-((N-(pyridin-2-ylmethyl)methylsulfonamido)methyl)benzoate (0.420 g, 1.256 mmol) and hydrazine hydrate (0.629 g, 12.560 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with saturated aqueous sodium chloride solution, dried with anhydrous MgSO₄, filtered, and concentrated in vacuo. The title compound was used without further purification (N-(4-(hydrazinecarbonyl)benzyl)-N-(pyridin-2-ylmethyl)methanesulfonamide, 0.330 g, 78.6%, yellow solid).

[Step 3] N-(pyridin-2-ylmethyl)-N-(4-(2-(2,2,2-trifluoroacetyl)hydrazine-1-carbonyl)benzyl)methanesulfonamide

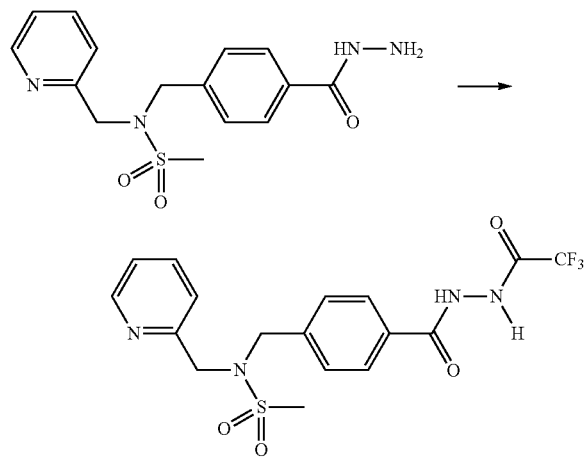

A solution of N-(4-(hydrazinecarbonyl)benzyl)-N-(pyridin-2-ylmethyl)methanesulfonamide (0.332 g, 0.993 mmol), TFAA (0.124 mL, 0.894 mmol) and TEA (0.208 mL, 1.489 mmol) in dichloromethane (10 mL) was stirred at the room temperature for 5 hr. Then, water was added to the reaction mixture, followed by extraction with dichloromethane. The organic layer was washed with saturated aqueous sodium chloride solution, dried with anhydrous MgSO₄, filtered, and concentrated in vacuo. The residue was chromatographed (SiO₂, 12 g cartridge; ethyl acetate/hexane=0% to 40%) to give N-(pyridin-2-ylmethyl)-N-(4-(2-(2,2,2-trifluoroacetyl)hydrazine-1-carbonyl)benzyl)methanesulfonamide as yellow solid (0.330 g, 77.2%).

[Step 4] Compound 11045

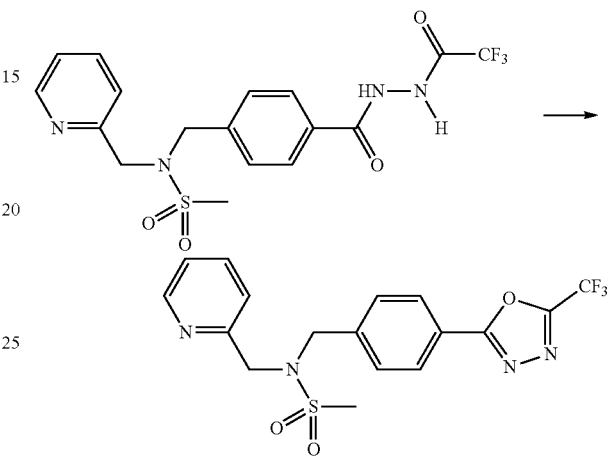

A mixture of N-(pyridin-2-ylmethyl)-N-(4-(2-(2,2,2-trifluoroacetyl)hydrazine-1-carbonyl)benzyl)methanesulfonamide (0.330 g, 0.767 mmol) and Burgess reagent (0.274 g, 1.150 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with saturated aqueous sodium chloride solution, dried with anhydrous MgSO₄, filtered, and concentrated in vacuo. The residue was chromatographed (SiO₂, 12 g cartridge; ethyl acetate/hexane=0% to 30%) to give N-(pyridin-2-ylmethyl)-N-(4-(5-(trifluoromethyl)-1,3,4-oxadiazol-2-yl)benzyl)methanesulfonamide as white solid (0.100 g, 31.6%).
¹H NMR (400 MHz, CDCl₃) δ 8.62-8.56 (m, 1H), 8.10-8.03 (m, 2H), 7.76-7.67 (m, 1H), 7.60-7.53 (m, 2H), 7.34-7.25 (m, 2H), 4.58 (s, 4H), 3.04 (s, 3H); LRMS (ES) m/z 413.1 (M⁺+1).

EXAMPLE 3

Compound 11078, 4-methoxy-N-(4-(5-(trifluoromethyl)-1,3,4-oxadiazol-2-yl)benzyl)benzenesulfonamide

[Step 1] tert-butyl (4-(hydrazinecarbonyl)benzyl)carbamate

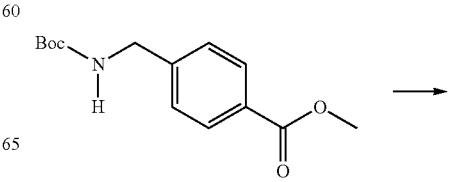

-continued

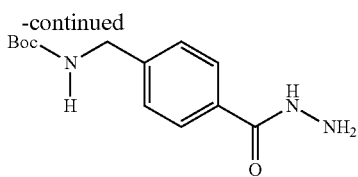

A mixture of methyl 4-(((tert-butoxycarbonyl)amino)methyl)benzoate (10.000 g, 37.692 mmol) and hydrazine monohydrate (9.661 g, 301.534 mmol) in ethanol (20 mL) prepared at the ambient temperature was heated at reflux for 20 hr, and cooled down to the ambient temperature, and concentrated under the reduced pressure to remove the solvent. The precipitates were collected by filtration, washed by water, and dried to give tert-butyl (4-(hydrazinecarbonyl)benzyl)carbamate as white solid (9.800 g, 98.0%).

[Step 2] tert-butyl (4-(2-(2,2,2-trifluoroacetyl)hydrazine-1-carbonyl)benzyl)carbamate

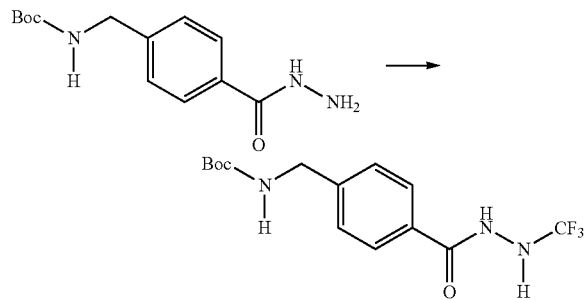

TEA (3.396 mL, 24.500 mmol) was added to a solution of tert-butyl (4-(hydrazinecarbonyl)benzyl)carbamate (5.000 g, 18.846 mmol) in dichloromethane (20 mL) at 0° C., and the mixture was stirred at the same temperature. The reaction mixture was treated with TFAA (2.760 mL, 20.730 mmol), and stirred for additional 3 hr at the room temperature. Then, water was added to the reaction mixture, followed by extraction with ethyl acetate. The organic layer was washed with saturated aqueous sodium chloride solution, dried with anhydrous MgSO₄, filtered, and concentrated in vacuo. The title compound was used without further purification (tert-butyl (4-(2-(2,2,2-trifluoroacetyl)hydrazine-1-carbonyl)benzyl)carbamate, 6.000 g, 88.1%, white solid).

[Step 3] tert-butyl (4-(5-(trifluoromethyl)-1,3,4-oxadiazol-2-yl)benzyl)carbamate

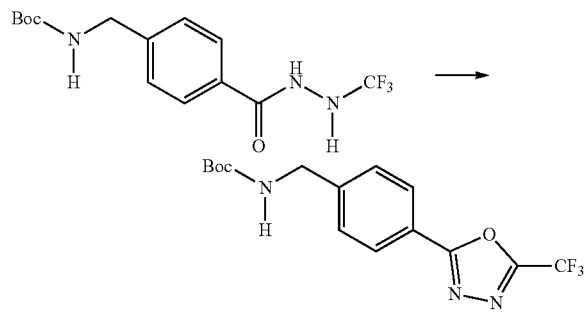

A mixture of tert-butyl 4-(2-(2,2,2-trifluoroacetyl)hydrazinecarbonyl)benzylcarbamate (6.990 g, 19.346 mmol) and Burgess reagent (7.438 g, 29.019 mmol) in tetrahydrofuran (25 mL) was heated at 150° C. for 30 min under the microwaves, and cooled down to the room temperature to terminate the reaction. Then, water was added to the reaction mixture, followed by extraction with ethyl acetate. The organic layer was washed with saturated aqueous sodium chloride solution, dried with anhydrous MgSO₄, filtered, and concentrated in vacuo. The residue was chromatographed (SiO₂, 80 g cartridge; ethyl acetate/hexane=0% to 20%) to give tert-butyl 4-(5-(trifluoromethyl)-1,3,4-oxadiazol-2-yl)benzylcarbamate as white solid (4.500 g, 67.8%).

[Step 4] (4-(5-(trifluoromethyl)-1,3,4-oxadiazol-2-yl)phenyl)methanamine hydrochloride

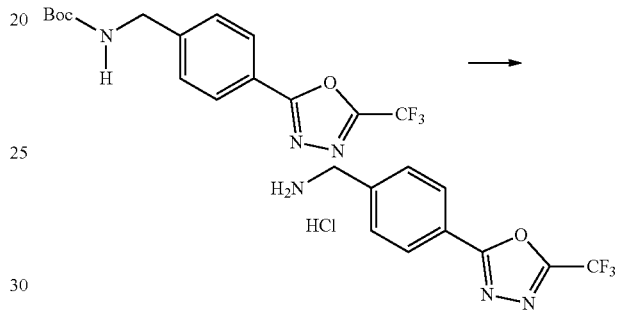

A solution of tert-butyl (4-(5-(trifluoromethyl)-1,3,4-oxadiazol-2-yl)benzyl)carbamate (3.760 g, 10.953 mmol) in dichloromethane (20 mL) was mixed with HCl (4.00 M solution, 3.012 mL, 12.048 mmol) at the room temperature. The reaction mixture was stirred at the same temperature for 8 hr. The precipitates were collected by filtration, washed by dichloromethane, and dried to give (4-(5-(trifluoromethyl)-1,3,4-oxadiazol-2-yl)phenyl)methanamine hydrochloride as white solid (2.800 g, 91.4%).

[Step 5] Compound 11078

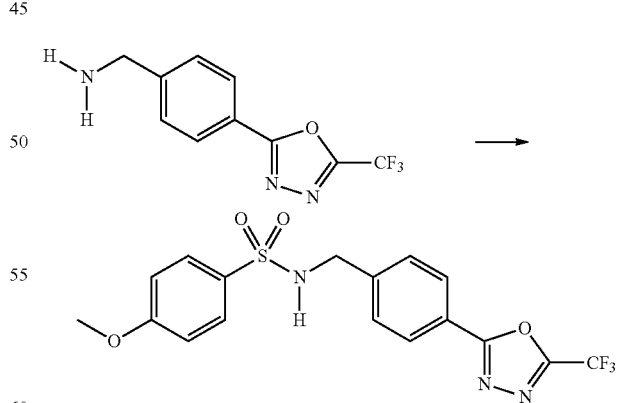

A solution of (4-(5-(trifluoromethyl)-1,3,4-oxadiazol-2-yl)phenyl)methanamine hydrochloride (0.050 g, 0.179 mmol), 4-methoxybenzene-1-sulfonyl chloride (0.041 g, 0.197 mmol) and pyridine (0.017 g, 0.215 mmol) in dichloromethane (10 mL) was stirred at the room temperature for 20 min. Then, aqueous 1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO₂, 12 g cartridge; ethyl acetate/hexane=0% to 10%) to give 4-methoxy-N-(4-(5-(trifluoromethyl)-1,3,4-oxadiazol-2-yl)benzyl)benzenesulfonamide as white solid (0.065 g, 87.9%).

$^1$H NMR (400 MHz, DMSO-$d_6$) δ 8.20 (s, 1H), 8.06-8.01 (m, 2H), 7.81-7.72 (m, 2H), 7.58-7.53 (m, 2H), 7.17-7.09 (m, 2H), 4.11 (s, 2H), 3.86 (d, 3H, J=0.9 Hz); LRMS (ES) m/z 414.0 (M$^+$+1).

EXAMPLE 4

Compound 11088: N-(pyridin-3-yl)-N-(4-(5-(trifluoromethyl)-1,3,4-oxadiazol-2-yl)benzyl)methanesulfonamide

[Step 1] N-(pyridin-3-yl)methanesulfonamide

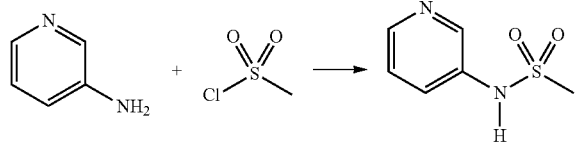

A solution of pyridin-3-amine (3.000 g, 31.874 mmol), pyridine (2.830 mL, 35.062 mmol) and methanesulfonyl chloride (4.381 g, 38.249 mmol) in dichloromethane (80 mL) was stirred at the room temperature for 12 hr. The precipitates were collected by filtration, washed by dichloromethane, and dried to give N-(pyridin-3-yl)methanesulfonamide as yellow solid (3.200 g, 58.3%).

[Step 2] methyl 4-((N-(pyridin-3-yl)methylsulfonamido)methyl)benzoate

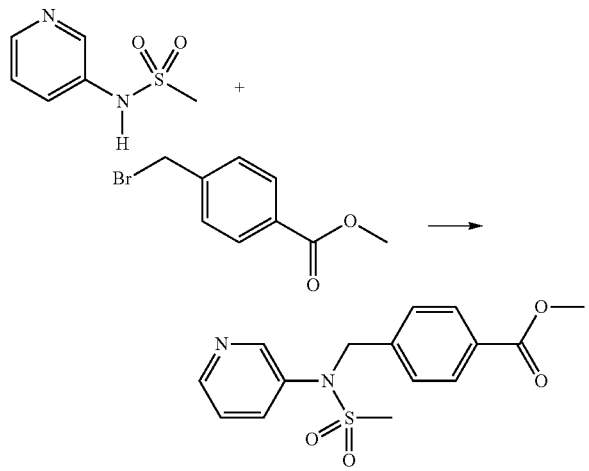

A solution of N-(pyridin-3-yl)methanesulfonamide (0.400 g, 2.323 mmol), NaH (60.00%, 0.111 g, 2.787 mmol) and methyl 4-(bromomethyl)benzoate (0.585 g, 2.555 mmol) in N,N-dimethylformide (10 mL) was stirred at the room temperature for 5 hr. Then, water was added to the reaction mixture, followed by extraction with ethyl acetate. The organic layer was washed with saturated aqueous sodium chloride solution, dried with anhydrous MgSO₄, filtered, and concentrated in vacuo. The residue was chromatographed (SiO₂, 12 g cartridge; ethyl acetate/hexane=0% to 30%) to give methyl 4-((N-(pyridin-3-yl)methylsulfonamido)methyl)benzoate as yellow solid (0.210 g, 28.2%).

[Step 3] N-(4-(hydrazinecarbonyl)benzyl)-N-(pyridin-3-yl)methanesulfonamide

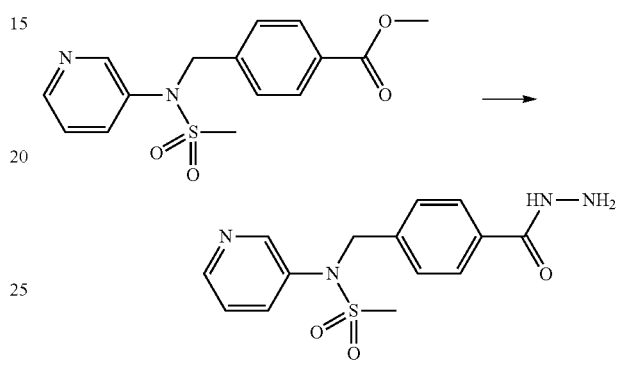

A solution of methyl 4-((N-(pyridin-3-yl)methylsulfonamido)methyl)benzoate (0.210 g, 0.656 mmol) and hydrazine hydrate (0.328 g, 6.555 mmol) in ethanol (10 mL) was stirred at 120° C. for 1 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(4-(hydrazinecarbonyl)benzyl)-N-(pyridin-3-yl)methanesulfonamide, 0.150 g, 71.4%, yellow solid).

[Step 4] N-(pyridin-3-yl)-N-(4-(2-(2,2,2-trifluoroacetyl)hydrazine-1-carbonyl)benzyl)methanesulfonamide

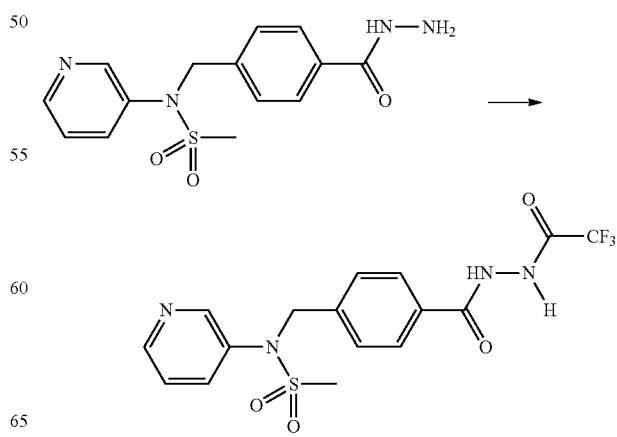

A solution of N-(4-(hydrazinecarbonyl)benzyl)-N-(pyridin-3-yl)methanesulfonamide (0.150 g, 0.468 mmol), trifluoroacetic anhydride (0.059 mL, 0.421 mmol) and triethylamine (0.098 mL, 0.702 mmol) in dichloromethane (5 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-(pyridin-3-yl)-N-(4-(2-(2,2,2-trifluoroacetyl)hydrazine-1-carbonyl)benzyl)methanesulfonamide as yellow oil (0.110 g, 56.4%).

[Step 5] Compound 11088

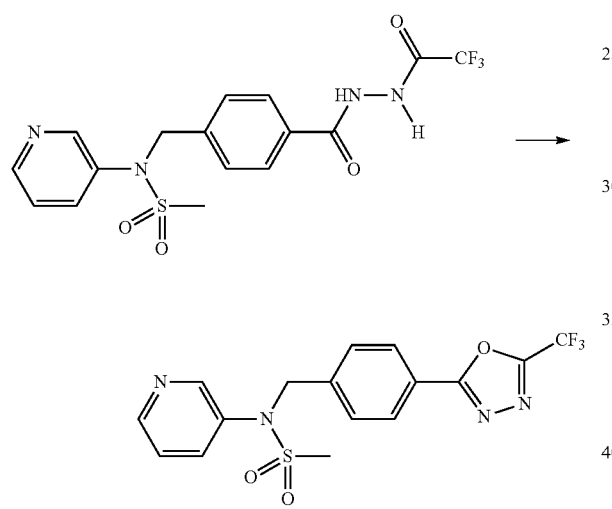

A mixture of N-(pyridin-3-yl)-N-(4-(2-(2,2,2-trifluoroacetyl)hydrazine-1-carbonyl)benzyl)methanesulfonamide (0.110 g, 0.264 mmol) and 1-methoxy-N-triethylammoniosulfonyl-methanimidate (Burgess reagent, 0.094 g, 0.396 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-(pyridin-3-yl)-N-(4-(5-(trifluoromethyl)-1,3,4-oxadiazol-2-yl)benzyl)methanesulfonamide as white solid (0.073 g, 69.4%).

$^1$H NMR (400 MHz, CDCl$_3$) δ 9.07 (s, 1H), 8.59 (s, 1H), 8.08 (d, 2H, J=8.3 Hz), 7.97 (d, 1H, J=8.5 Hz), 7.55 (d, 3H, J=8.1 Hz), 5.15 (s, 2H), 3.15 (s, 3H); LRMS (ES) m/z 399.19 (M$^+$+1).

EXAMPLE 5

Compound 11089: N-(2-fluoro-4-(5-(trifluoromethyl)-1,3,4-oxadiazol-2-yl)benzyl)-N-(pyridin-3-yl)methanesulfonamide

[Step 1] methyl 3-fluoro-4-((N-(pyridin-3-yl)methylsulfonamido)methyl)benzoate

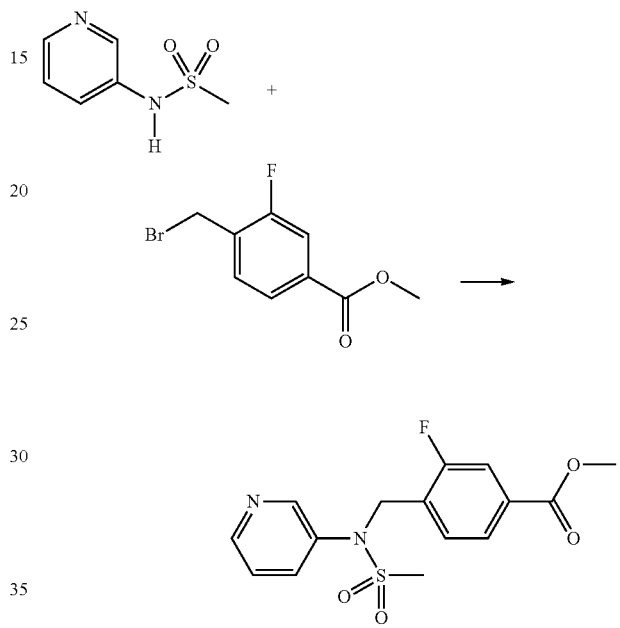

A solution of N-(pyridin-3-yl)methanesulfonamide (0.400 g, 2.323 mmol), NaH (60.00%, 0.111 g, 2.787 mmol) and methyl 4-(bromomethyl)-3-fluorobenzoate (0.631 g, 2.555 mmol) in N,N-dimethylformide (10 mL) was stirred at the room temperature for 5 hr. Then, water was added to the reaction mixture, followed by extraction with ethyl acetate. The organic layer was washed with saturated aqueous sodium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 3-fluoro-4-((N-(pyridin-3-yl)methylsulfonamido)methyl)benzoate as white solid (0.250 g, 31.8%).

[Step 2] N-(2-fluoro-4-(hydrazinecarbonyl)benzyl)-N-(pyridin-3-yl)methanesulfonamide

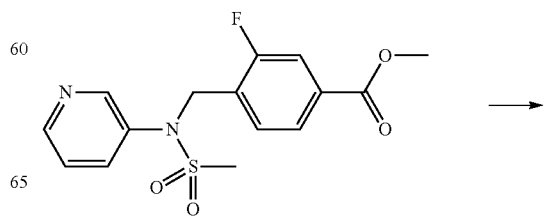

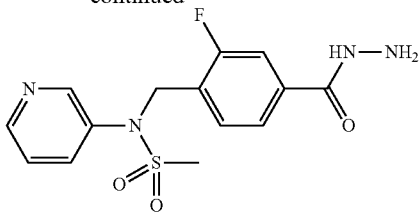

A mixture of methyl 3-fluoro-4-((N-(pyridin-3-yl)methylsulfonamido)methyl)benzoate (0.250 g, 0.739 mmol) and hydrazine hydrate (0.370 g, 7.389 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(pyridin-3-yl)methanesulfonamide, 0.200 g, 80.0%, yellow solid).

[Step 3] N-(2-fluoro-4-(2-(2,2,2-trifluoroacetyl)hydrazine-1-carbonyl)benzyl)-N-(pyridin-3-yl)methanesulfonamide

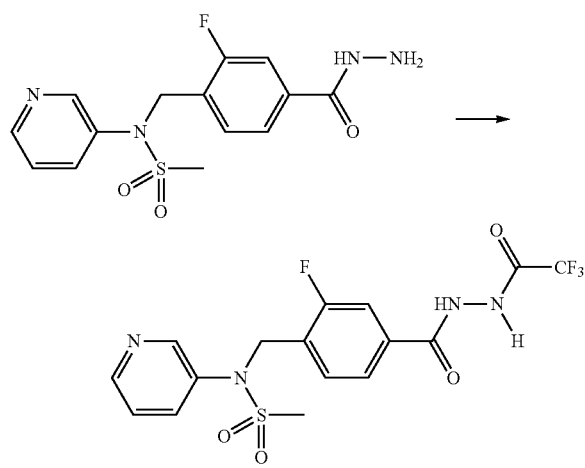

A solution of N-(2-fluoro-4-(hydrazinecarbonyl)benzyl)-N-(pyridin-3-yl)methanesulfonamide (0.200 g, 0.591 mmol), trifluoroacetic anhydride (0.074 mL, 0.532 mmol) and triethylamine (0.124 mL, 0.887 mmol) in dichloromethane (5 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-(2-fluoro-4-(2-(2,2,2-trifluoroacetyl)hydrazine-1-carbonyl)benzyl)-N-(pyridin-3-yl)methanesulfonamide as yellow oil (0.130 g, 50.6%).

[Step 4] Compound 11089

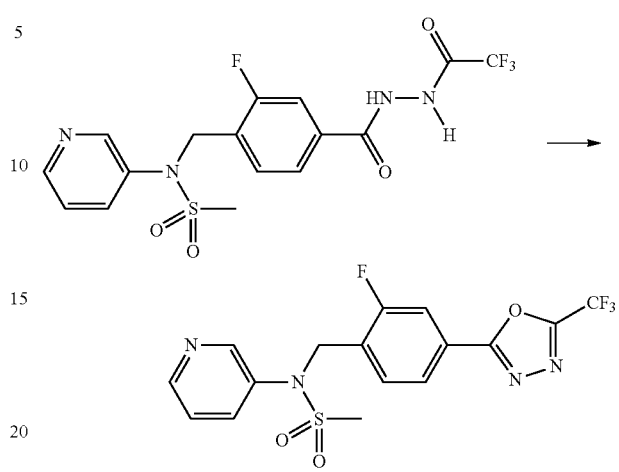

A mixture of N-(2-fluoro-4-(2-(2,2,2-trifluoroacetyl)hydrazine-1-carbonyl)benzyl)-N-(pyridin-3-yl)methanesulfonamide (0.130 g, 0.299 mmol) and 1-methoxy-N-triethylammoniosulfonyl-methanimidate (Burgess reagent, 0.107 g, 0.449 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 30%) to give N-(2-fluoro-4-(5-(trifluoromethyl)-1,3,4-oxadiazol-2-yl)benzyl)-N-(pyridin-3-yl)methane sulfonamide as yellow solid (0.091 g, 73.0%).

$^1$H NMR (400 MHz, CDCl$_3$) δ 8.70 (s, 1H), 8.58 (d, 1H, J=4.7 Hz), 7.91 (dd, 1H, J=8.0, 1.5 Hz), 7.81-7.73 (m, 2H), 7.69 (t, 1H, J=7.6 Hz), 7.40 (dd, 1H, J=8.3, 4.8 Hz), 5.09 (s, 2H), 3.09 (s, 3H); LRMS (ES) m/z 416.9 (M$^+$+1).

EXAMPLE 6

Compound 11120: N-(4-(5-(difluoromethyl)-1,3,4-oxadiazol-2-yl)-2-fluorobenzyl)-N-(pyridin-3-yl)methanesulfonamide

[Step 1] methyl 3-fluoro-4-((N-(pyridin-3-yl)methylsulfonamido)methyl)benzoate

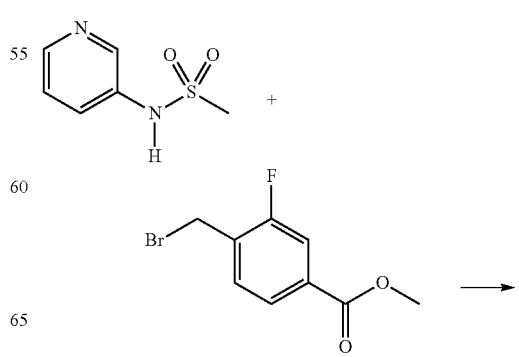

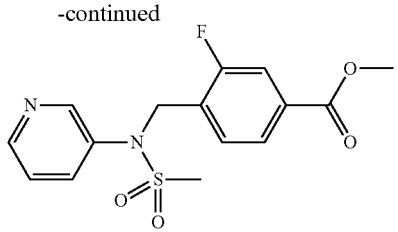

A solution of N-(pyridin-3-yl)methanesulfonamide (0.800 g, 4.646 mmol), sodium hydride (60.00%, 0.223 g, 5.575 mmol) and methyl 4-(bromomethyl)-3-fluorobenzoate (1.263 g, 5.110 mmol) in N,N-dimethylformide (20 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 3-fluoro-4-((N-(pyridin-3-yl)methylsulfonamido)methyl)benzoate as yellow solid (0.740 g, 47.1%).

[Step 2] N-(2-fluoro-4-(hydrazinecarbonyl)benzyl)-N-(pyridin-3-yl)methanesulfonamide

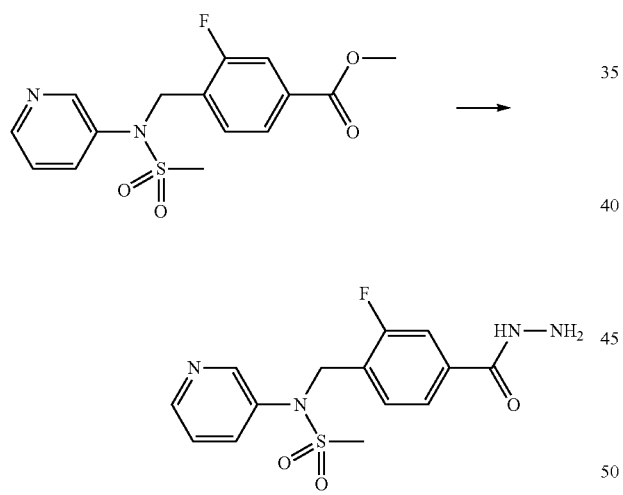

A mixture of methyl 3-fluoro-4-((N-(pyridin-3-yl)methylsulfonamido)methyl)benzoate (0.740 g, 2.187 mmol) and hydrazine hydrate (1.095 g, 21.871 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(pyridin-3-yl)methanesulfonamide, 0.610 g, 82.4%, yellow solid).

[Step 3] Compound 11120

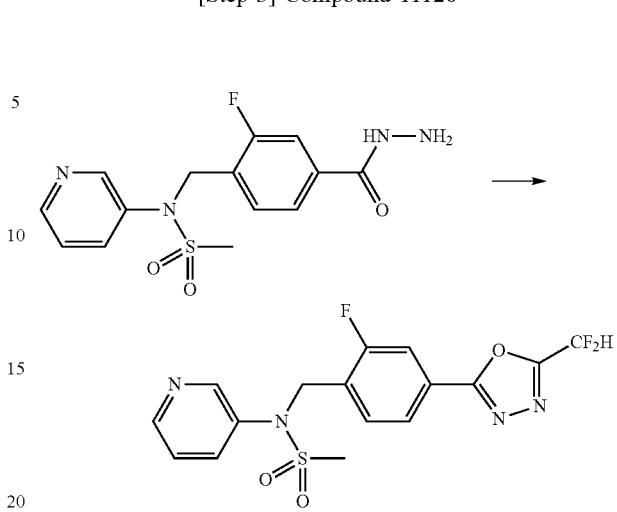

A solution of N-(2-fluoro-4-(hydrazinecarbonyl)benzyl)-N-(pyridin-3-yl)methanesulfonamide (0.080 g, 0.236 mmol), difluoroacetic anhydride (0.031 mL, 0.284 mmol) and triethylamine (0.066 mL, 0.473 mmol) in dichloromethane (1 mL) was stirred at the room temperature for 1 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(pyridin-3-yl)methanesulfonamide as white solid (0.041 g, 43.5%).

$^1$H NMR (400 MHz, CDCl$_3$) δ 8.92 (s, 1H), 8.65-8.59 (m, 1H), 8.02-7.95 (m, 1H), 7.92 (dd, 1H, J=8.0, 1.7 Hz), 7.78 (dd, 1H, J=10.0, 1.7 Hz), 7.67 (t, 1H, J=7.6 Hz), 7.59 (dd, 1H, J=8.4, 5.1 Hz), 7.06 (s, 0.2H), 6.93 (s, 0.4H), 6.80 (s, 0.2H), 5.13 (s, 2H), 3.13 (s, 3H); LRMS (ES) m/z 399.1 (M$^+$+1).

EXAMPLE 7

Compound 11121: N-(4-(5-(trifluoromethyl)-1,3,4-oxadiazol-2-yl)benzyl)methanesulfonamide

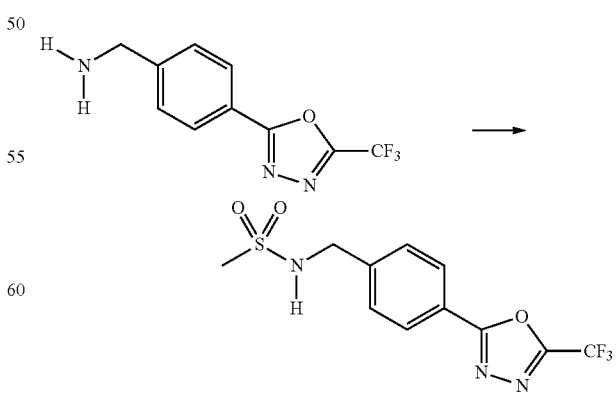

Triethylamine (0.032 mL, 0.232 mmol) was added to a solution of (4-(5-(trifluoromethyl)-1,3,4-oxadiazol-2-yl)

phenyl)methanamine hydrochloride (0.050 g, 0.179 mmol) in dichloromethane (2 mL) at the room temperature and the mixture was stirred at the same temperature for 10 min. The reaction mixture was treated with methanesulfonyl chloride (0.015 mL, 0.197 mmol), and stirred for additional 5 hr at the same temperature. Then, saturated aqueous ammonium chloride solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 50%) to give N-(4-(5-(trifluoromethyl)-1,3,4-oxadiazol-2-yl)benzyl)methanesulfonamide as white solid (0.055 g, 95.7%).

$^1$H NMR (400 MHz, DMSO-d$_6$) δ 8.17-8.07 (m, 2H), 7.77 (s, 1H), 7.66 (d, 2H, J=8.2 Hz), 4.32 (d, 2H, J=3.6 Hz), 2.96 (s, 3H); LRMS (ES) m/z 320.19 (M$^+$–1).

EXAMPLE 8

Compound 11128: N-(pyridin-2-ylmethyl)-N-((5-(5-(trifluoromethyl)-1,3,4-oxadiazol-2-yl)pyridin-2-yl)methyl)methanesulfonamide

[Step 1] methyl 6-((N-(pyridin-2-ylmethyl)methylsulfonamido)methyl)nicotinate

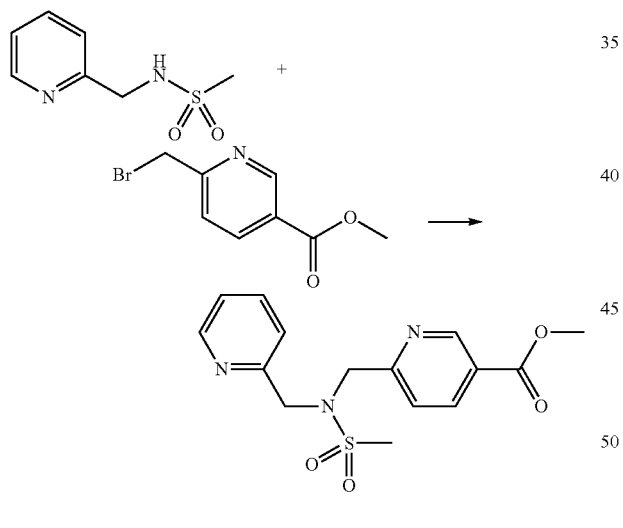

A solution of N-(pyridin-2-ylmethyl)methanesulfonamide (0.300 g, 1.611 mmol), sodium hydride (60.00%, 0.077 g, 1.933 mmol) and methyl 6-(bromomethyl)nicotinate (0.408 g, 1.772 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 6-((N-(pyridin-2-ylmethyl)methylsulfonamido)methyl)nicotinate as yellow solid (0.290 g, 53.7%).

[Step 2] N-((5-(hydrazinecarbonyl)pyridin-2-yl)methyl)-N-(pyridin-2-ylmethyl)methanesulfonamide

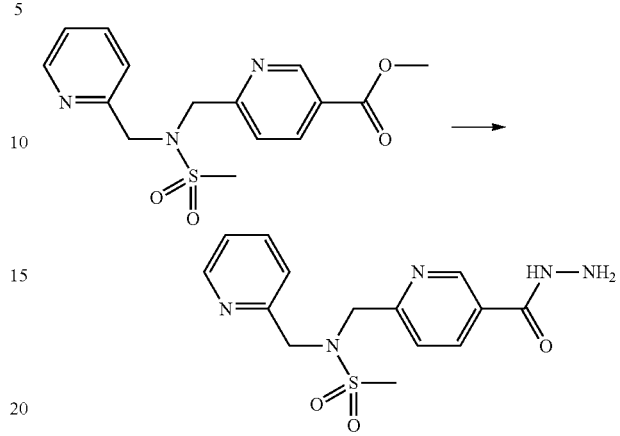

A mixture of methyl 6-((N-(pyridin-2-ylmethyl)methylsulfonamido)methyl)nicotinate (0.290 g, 0.865 mmol) and hydrazine hydrate (0.433 g, 8.647 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-((5-(hydrazinecarbonyl)pyridin-2-yl)methyl)-N-(pyridin-2-ylmethyl)methanesulfonamide, 0.110 g, 37.9%, white solid).

[Step 3] N-(pyridin-2-ylmethyl)-N-((5-(2-(2,2,2-trifluoroacetyl)hydrazine-1-carbonyl)pyridin-2-yl)methyl)methanesulfonamide

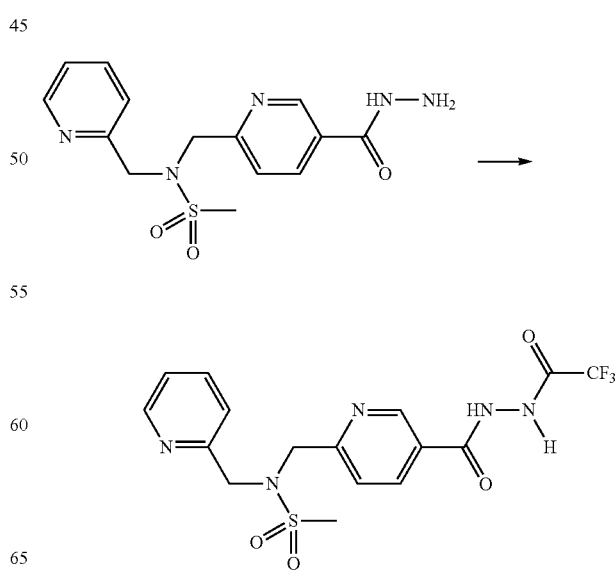

A solution of N-((5-(hydrazinecarbonyl)pyridin-2-yl)methyl)-N-(pyridin-2-ylmethyl)methanesulfonamide (0.110 g, 0.328 mmol), trifluoroacetic anhydride (0.041 mL, 0.295 mmol) and triethylamine (0.069 mL, 0.492 mmol) in dichloromethane (10 mL) was stirred at the room temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-(pyridin-2-ylmethyl)-N-((5-(2-(2,2,2-trifluoroacetyl)hydrazine-1-carbonyl)pyridin-2-yl)methyl)methanesulfonamide as yellow oil (0.091 g, 64.3%).

[Step 4] Compound 11128

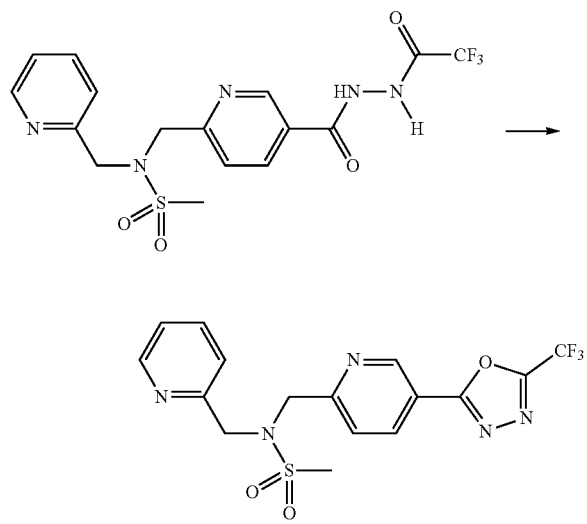

A mixture of N-(pyridin-2-ylmethyl)-N-((5-(2-(2,2,2-trifluoroacetyl)hydrazine-1-carbonyl)pyridin-2-yl)methyl)methanesulfonamide (0.091 g, 0.211 mmol) and 1-methoxy-N-triethylammoniosulfonyl-methanimidate (Burgess reagent, 0.075 g, 0.316 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(pyridin-2-ylmethyl)-N-((5-(5-(trifluoromethyl)-1,3,4-oxadiazol-2-yl)pyridin-2-yl)methyl)methanesulfonamide as white solid (0.021 g, 24.1%).

$^1$H NMR (400 MHz, CDCl$_3$) δ 9.27 (dd, 1H, J=2.2, 0.9 Hz), 8.61-8.54 (m, 1H), 8.43-8.35 (m, 1H), 7.76 (t, 1H, J=7.8 Hz), 7.67 (dd, 1H, J=8.2, 0.8 Hz), 7.46 (d, 1H, J=7.9 Hz), 7.29 (s, 1H), 4.73 (s, 2H), 4.67 (s, 2H), 3.16 (s, 3H); LRMS (ES) m/z 414.3 (M$^+$+1).

EXAMPLE 9

Compound 11129: N-(2-methoxy-4-(5-(trifluoromethyl)-1,3,4-oxadiazol-2-yl)benzyl)-N-(pyridin-3-yl)methanesulfonamide

[Step 1] methyl 3-methoxy-4-((N-(pyridin-3-yl)methylsulfonamido)methyl)benzoate

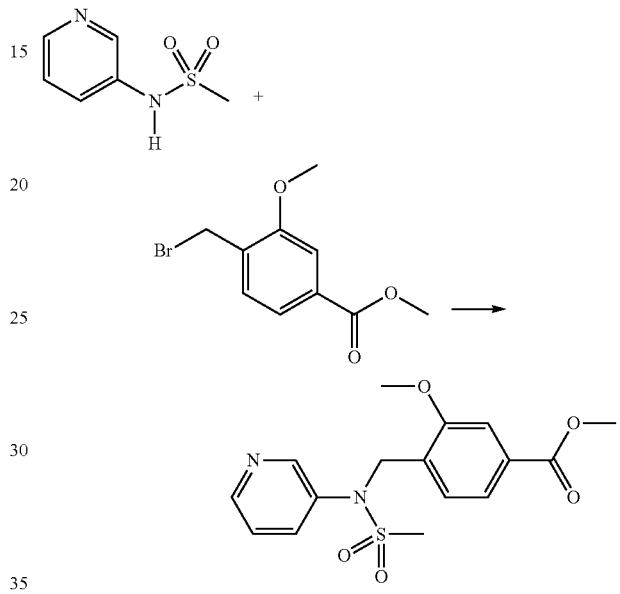

A solution of N-(pyridin-3-yl)methanesulfonamide (0.500 g, 2.904 mmol), sodium hydride (60.00%, 0.139 g, 3.484 mmol) and methyl 4-(bromomethyl)-3-methoxybenzoate (0.828 g, 3.194 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 3-methoxy-4-((N-(pyridin-3-yl)methylsulfonamido)methyl)benzoate as yellow solid (0.117 g, 11.5%).

[Step 2] N-(4-(hydrazinecarbonyl)-2-methoxybenzyl)-N-(pyridin-3-yl)methanesulfonamide

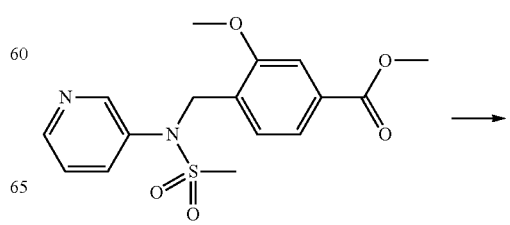

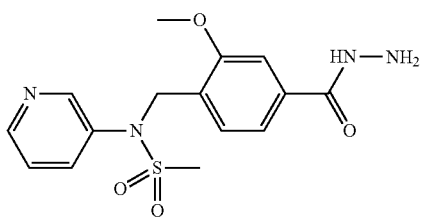

A mixture of methyl 3-methoxy-4-((N-(pyridin-3-yl)methylsulfonamido)methyl)benzoate (0.117 g, 0.334 mmol) and hydrazine hydrate (0.167 g, 3.339 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(4-(hydrazinecarbonyl)-2-methoxybenzyl)-N-(pyridin-3-yl)methanesulfonamide, 0.100 g, 85.5%, yellow oil).

[Step 3] N-(2-methoxy-4-(2-(2,2,2-trifluoroacetyl)hydrazine-1-carbonyl)benzyl)-N-(pyridin-3-yl)methanesulfonamide

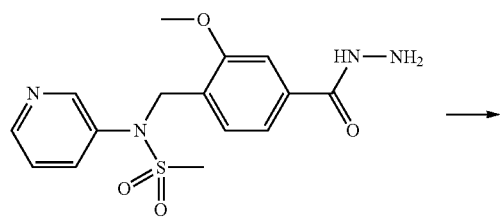

A solution of N-(4-(hydrazinecarbonyl)-2-methoxybenzyl)-N-(pyridin-3-yl)methanesulfonamide (0.100 g, 0.285 mmol), trifluoroacetic anhydride (0.036 mL, 0.257 mmol) and triethylamine (0.059 mL, 0.428 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-(2-methoxy-4-(2-(2,2,2-trifluoroacetyl)hydrazine-1-carbonyl)benzyl)-N-(pyridin-3-yl)methanesulfonamide as yellow oil (0.090 g, 70.6%).

[Step 4] Compound 11129

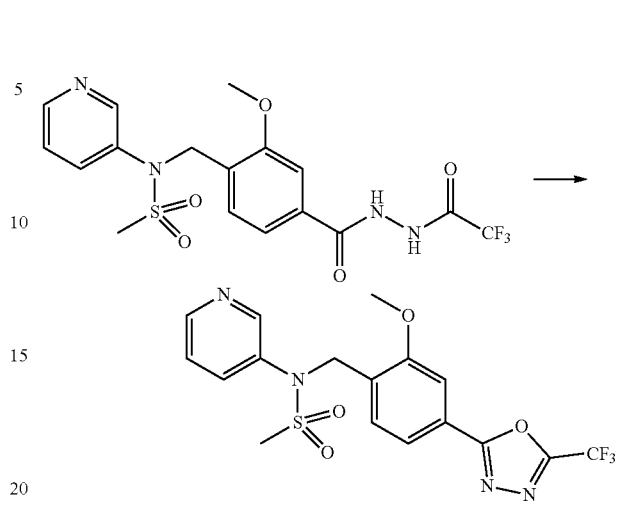

A mixture of N-(2-methoxy-4-(2-(2,2,2-trifluoroacetyl)hydrazine-1-carbonyl)benzyl)-N-(pyridin-3-yl)methanesulfonamide (0.090 g, 0.202 mmol) and 1-methoxy-N-triethylammoniosulfonyl-methanimidate (Burgess reagent, 0.072 g, 0.302 mmol) in tetrahydrofuran (10 mL) was heated at 150° C. for 30 min under the microwaves, cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 30%) to give N-(2-methoxy-4-(5-(trifluoromethyl)-1,3,4-oxadiazol-2-yl)benzyl)-N-(pyridin-3-yl)methanesulfonamide as white solid (0.036 g, 41.7%).

$^1$H NMR (400 MHz, CDCl$_3$) δ 8.76 (s, 1H), 8.56 (d, 1H, J=5.1 Hz), 8.01 (d, 1H, J=8.5 Hz), 7.67 (dd, 1H, J=7.9, 1.6 Hz), 7.61-7.52 (m, 3H), 5.08 (s, 2H), 3.90 (s, 3H), 3.09 (s, 3H); LRMS (ES) m/z 429.3 (M$^+$+1).

EXAMPLE 10

Compound 11133: N-(3-fluoro-4-(5-(trifluoromethyl)-1,3,4-oxadiazol-2-yl)benzyl)-N-(pyridin-3-yl)methanesulfonamide

[Step 1] methyl 2-fluoro-4-((pyridin-3-ylamino)methyl)benzoate

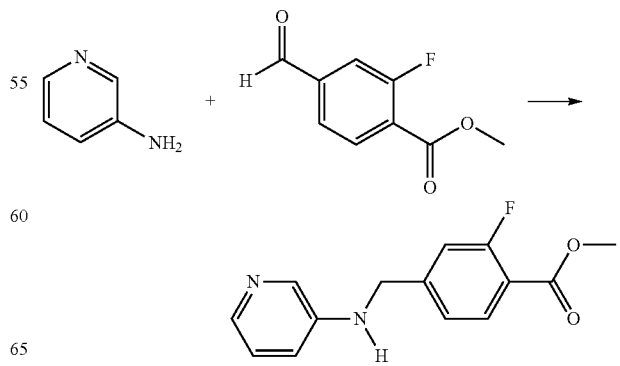

Methyl 2-fluoro-4-formylbenzoate (1.490 g, 8.181 mmol) and AcOH (0.501 mL, 8.181 mmol) were added to a solution of pyridin-3-amine (0.700 g, 7.437 mmol) in dichloromethane (20 mL) at the room temperature, and the mixture was stirred at the same temperature for 1 hr. The reaction mixture was treated with Na(OAc)$_3$BH (3.153 g, 14.875 mmol), and stirred for additional 12 hr at the same temperature. Then, water was added to the reaction mixture, followed by extraction with ethyl acetate. The organic layer was washed with saturated aqueous sodium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 2-fluoro-4-((pyridin-3-ylamino)methyl)benzoate as yellow oil (0.500 g, 25.8%).

[Step 2] methyl 2-fluoro-4-((N-(pyridin-3-yl)methylsulfonamido)methyl)benzoate

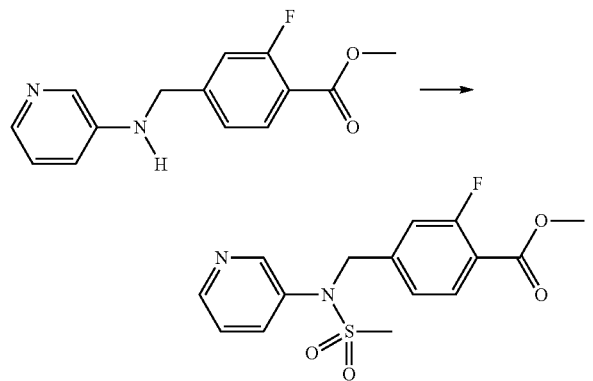

A solution of methyl 2-fluoro-4-((pyridin-3-ylamino)methyl)benzoate (0.500 g, 1.921 mmol), pyridine (0.171 mL, 2.113 mmol) and methanesulfonyl chloride (0.180 mL, 2.305 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The residue was chromatographed (SiO$_2$, 12 g cartridge; ethyl acetate/hexane=0% to 30%) to give methyl 2-fluoro-4-((N-(pyridin-3-yl)methylsulfonamido)methyl)benzoate as yellow solid (0.160 g, 24.6%).

[Step 3] N-(3-fluoro-4-(hydrazinecarbonyl)benzyl)-N-(pyridin-3-yl)methanesulfonamide

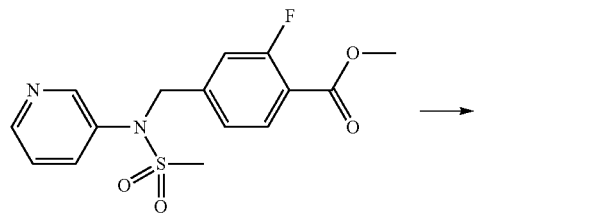

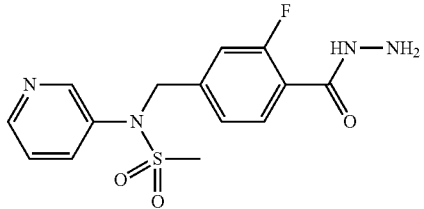

A mixture of methyl 2-fluoro-4-((N-(pyridin-3-yl)methylsulfonamido)methyl)benzoate (0.160 g, 0.473 mmol) and hydrazine hydrate (0.237 g, 4.729 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-fluoro-4-(hydrazinecarbonyl)benzyl)-N-(pyridin-3-yl)methanesulfonamide, 0.109 g, 68.1%, yellow oil).

[Step 4] N-(3-fluoro-4-(2-(2,2,2-trifluoroacetyl)hydrazine-1-carbonyl)benzyl)-N-(pyridin-3-yl)methanesulfonamide

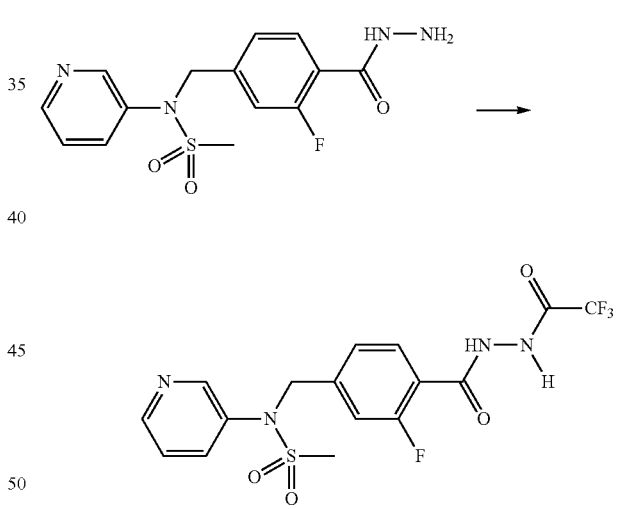

A solution of N-(3-fluoro-4-(hydrazinecarbonyl)benzyl)-N-(pyridin-3-yl)methanesulfonamide (0.109 g, 0.322 mmol), trifluoroacetic anhydride (0.040 mL, 0.290 mmol) and triethylamine (0.067 mL, 0.483 mmol) in dichloromethane (5 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 60%) to give N-(3-fluoro-4-(2-(2,2,2-trifluoroacetyl)hydrazine-1-carbonyl)benzyl)-N-(pyridin-3-yl)methanesulfonamide as yellow oil (0.071 g, 50.7%).

[Step 5] Compound 11133

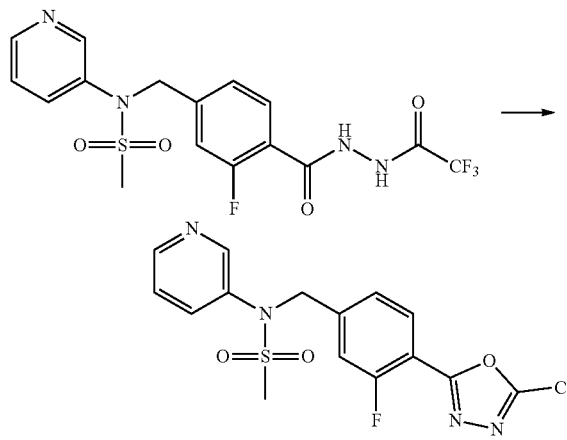

A mixture of N-(3-fluoro-4-(2-(2,2,2-trifluoroacetyl)hydrazine-1-carbonyl)benzyl)-N-(pyridin-3-yl)methanesulfonamide (0.071 g, 0.163 mmol) and 1-methoxy-N-triethylammoniosulfonyl-methanimidate (Burgess reagent, 0.058 g, 0.245 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(3-fluoro-4-(5-(trifluoromethyl)-1,3,4-oxadiazol-2-yl)benzyl)-N-(pyridin-3-yl)methanesulfonamide as yellow oil (0.031 g, 45.6%).

$^1$H NMR (400 MHz, CDCl$_3$) δ 9.24 (s, 1H), 8.60 (d, 1H, J=5.1 Hz), 8.13-8.02 (m, 2H), 7.67-7.54 (m, 1H), 7.37 (d, 2H, J=9.3 Hz), 5.19 (s, 2H), 3.16 (s, 3H); LRMS (ES) m/z 417.1 (M$^+$+1).

EXAMPLE 11

Compound 11151: N-phenyl-N-(4-(5-(trifluoromethyl)-1,3,4-oxadiazol-2-yl)benzyl)pyridine-3-sulfonamide

[Step 1] N-phenylpyridine-4-sulfonamide

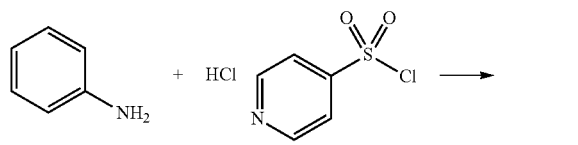

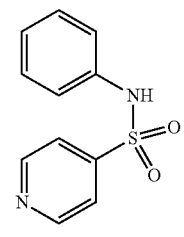

A solution of aniline (0.200 g, 2.147 mmol) and Pyridine (0.260 mL, 3.221 mmol) in dichloromethane (6 mL) was mixed with pyridine-4-sulfonyl chloride hydrochloride (0.483 g, 2.255 mmol) at the room temperature, and the reaction mixture was stirred at the same temperature for 10 hr. Then, saturated aqueous ammonium chloride solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-phenylpyridine-4-sulfonamide as yellow solid (0.250 g, 49.7%).

[Step 2] methyl 4-((N-phenylpyridine-3-sulfonamido)methyl)benzoate

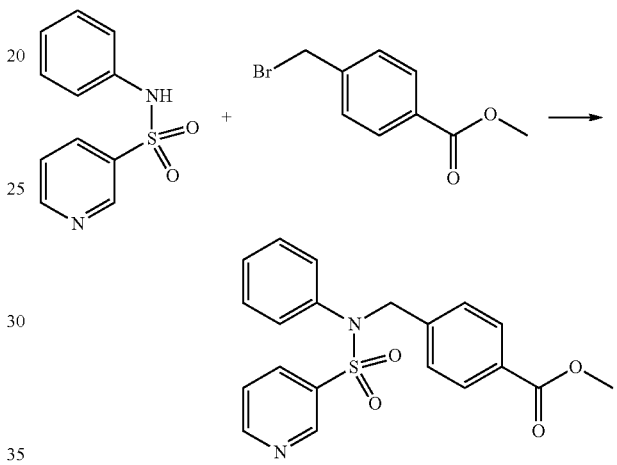

Sodium hydride (60.00%, 0.082 g, 2.049 mmol) was added to a solution of N-phenylpyridine-3-sulfonamide (0.400 g, 1.707 mmol) in N,N-dimethylformide (8 mL) at 0° C., and the mixture was stirred at the same temperature for 20 min. The reaction mixture was treated with methyl 4-(bromomethyl)benzoate (0.430 g, 1.878 mmol), and stirred for additional 8 hr at the room temperature. Then, saturated aqueous ammonium chloride solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 4-((N-phenylpyridine-3-sulfonamido)methyl)benzoate as white solid (0.380 g, 58.2%).

[Step 3] N-(4-(hydrazinecarbonyl)benzyl)-N-phenylpyridine-3-sulfonamide

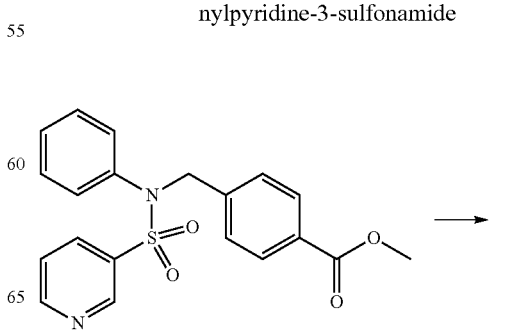

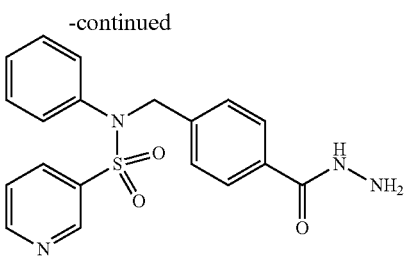

A mixture of methyl 4-((N-phenylpyridine-3-sulfonamido)methyl)benzoate (0.330 g, 0.863 mmol) and hydrazine hydrate (0.138 g, 4.315 mmol) in ethanol (6 mL) was heated at reflux for 16 hr, and cooled down to the ambient temperature, and concentrated under the reduced pressure. The precipitates were collected by filtration, washed by water, and dried to give N-(4-(hydrazinecarbonyl)benzyl)-N-phenylpyridine-3-sulfonamide as white solid (0.320 g, 97.0%).

[Step 4] Compound 11151

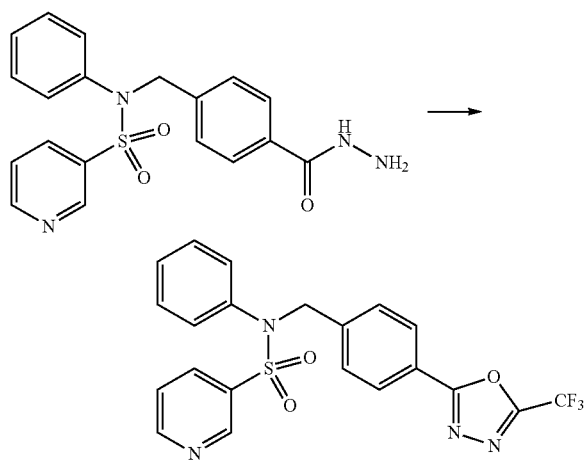

Triethylamine (0.075 mL, 0.544 mmol) was added to a solution of N-(4-(hydrazinecarbonyl)benzyl)-N-phenylpyridine-3-sulfonamide (0.160 g, 0.418 mmol) in tetrahydrofuran (8 mL) at the room temperature, and the mixture was stirred for 10 min at the same temperature. The reaction mixture was treated with trifluoroacetic anhydride (0.061 mL, 0.460 mmol), heated at reflux for 14 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 50%) to give N-phenyl-N-(4-(5-(trifluoromethyl)-1,3,4-oxadiazol-2-yl)benzyl)pyridine-3-sulfonamide as white solid (0.150 g, 77.9%).

$^1$H NMR (400 MHz, DMSO-d$_6$) δ 8.95 (dd, 1H, J=4.9, 1.6 Hz), 8.84 (dd, 1H, J=2.4, 0.8 Hz), 8.10 (ddd, 1H, J=8.1, 2.4, 1.6 Hz), 8.06-7.99 (m, 2H), 7.73 (ddd, 1H, J=8.1, 4.9, 0.8 Hz), 7.66-7.54 (m, 2H), 7.38-7.24 (m, 3H), 7.21-7.12 (m, 2H), 5.04 (s, 2H); LRMS (ES) m/z 462.0 (M$^+$+1).

EXAMPLE 12

Compound 11152: N-(4-(5-(difluoromethyl)-1,3,4-oxadiazol-2-yl)benzyl)-N-phenylpyridine-3-sulfonamide

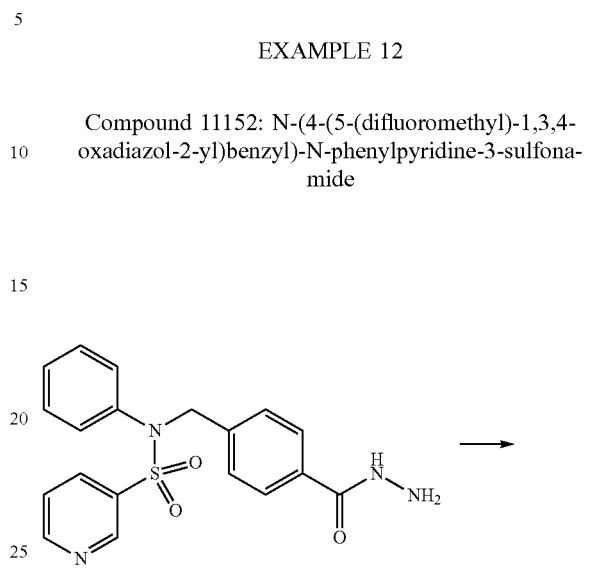

Triethylamine (0.075 mL, 0.544 mmol) was added to a solution of N-(4-(hydrazinecarbonyl)benzyl)-N-phenylpyridine-3-sulfonamide (0.160 g, 0.418 mmol) in tetrahydrofuran (8 mL) at the room temperature, and the mixture was stirred for 10 min at the same temperature. The reaction mixture was treated with 2,2-difluoroacetic anhydride (0.050 mL, 0.460 mmol), heated at reflux for 14 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 50%) to give N-(4-(5-(difluoromethyl)-1,3,4-oxadiazol-2-yl)benzyl)-N-phenylpyridine-3-sulfonamide as white solid (0.140 g, 75.6%).

$^1$H NMR (400 MHz, DMSO-d$_6$) δ 8.95 (dd, 1H, J=4.9, 1.6 Hz), 8.84 (dd, 1H, J=2.3, 0.8 Hz), 8.09 (ddd, 1H, J=8.1, 2.4, 1.6 Hz), 8.06-7.96 (m, 2H), 7.78-7.66 (m, 1H), 7.64-7.53 (m, 3H), 7.43 (s, OH), 7.38-7.26 (m, 3H), 7.21-7.12 (m, 2H), 5.03 (s, 2H); LRMS (ES) m/z 444.0 (M$^+$+1).

EXAMPLE 13

Compound 11153: N-(2-fluoro-4-(5-(trifluoromethyl)-1,3,4-oxadiazol-2-yl)benzyl)-N-phenylethanesulfonamide

[Step 1] methyl 3-fluoro-4-((N-phenylethylsulfonamido)methyl)benzoate

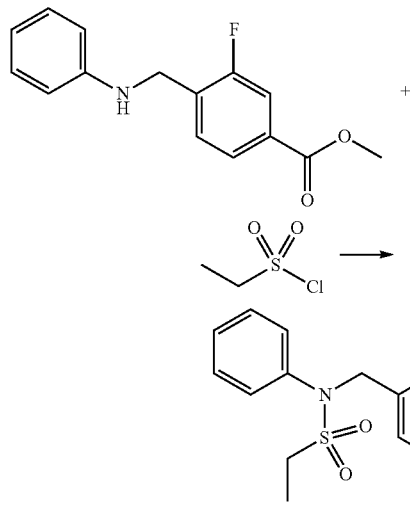

A solution of ethanesulfonyl chloride (0.219 mL, 2.314 mmol), N,N-dimethylpyridin-4-amine (DMAP, 0.071 g, 0.579 mmol) and pyridine (0.233 mL, 2.893 mmol) in dichloromethane (10 mL) was stirred at the room temperature for 30 min, and then mixed with methyl 3-fluoro-4-((phenylamino)methyl)benzoate (0.500 g, 1.928 mmol). The reaction mixture was heated at reflux for 5 hr, cooled down to the room temperature to terminate the reaction. Then, saturated aqueous ammonium chloride solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 25%) to give methyl 3-fluoro-4-((N-phenylethylsulfonamido)methyl)benzoate as white solid (0.450 g, 66.4%).

[Step 2] N-(2-fluoro-4-(hydrazinecarbonyl)benzyl)-N-phenylethanesulfonamide

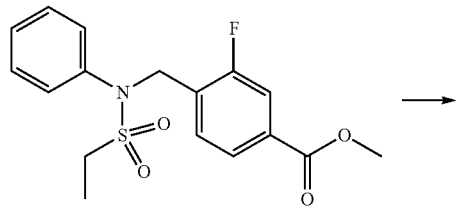

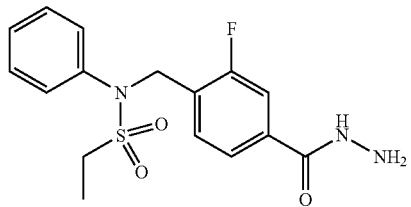

A mixture of methyl 3-fluoro-4-((N-phenylethylsulfonamido)methyl)benzoate (0.450 g, 1.281 mmol) and hydrazine hydrate (0.205 g, 6.403 mmol) in ethanol (8 mL) was heated at reflux for 16 hr, and cooled down to the ambient temperature, and concentrated under the reduced pressure to remove the solvent. The precipitates were collected by filtration, washed by water, and dried to give N-(2-fluoro-4-(hydrazinecarbonyl)benzyl)-N-phenylethanesulfonamide as white solid (0.420 g, 93.3%).

[Step 3] Compound 11153

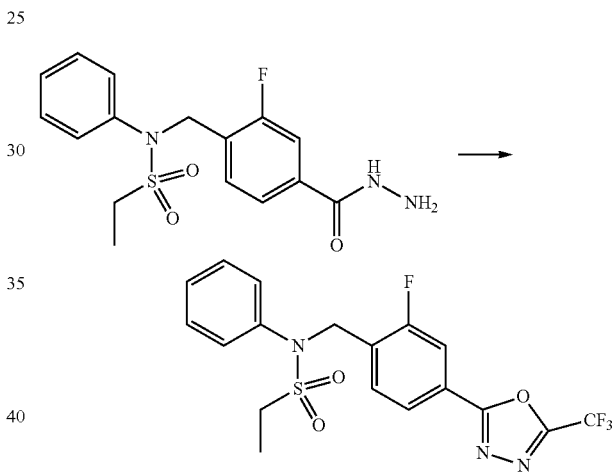

A solution of N-(2-fluoro-4-(hydrazinecarbonyl)benzyl)-N-phenylethanesulfonamide (0.080 g, 0.228 mmol) and triethylamine (0.041 mL, 0.296 mmol) in tetrahydrofuran (2 mL) was stirred at the room temperature for 10 min, and then mixed with trifluoroacetic anhydride (0.033 mL, 0.250 mmol). The reaction mixture was heated at reflux for 6 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO₂, 12 g cartridge; ethyl acetate/hexane=0% to 40%) to give N-(2-fluoro-4-(5-(trifluoromethyl)-1,3,4-oxadiazol-2-yl)benzyl)-N-phenylethanesulfonamide as white solid (0.075 g, 76.7%).

$^1$H NMR (400 MHz, DMSO-$d_6$) δ 7.91 (dd, 1H, J=8.0, 1.7 Hz), 7.84 (dd, 1H, J=10.1, 1.7 Hz), 7.71 (t, 1H, J=7.7 Hz), 7.51-7.43 (m, 2H), 7.44-7.30 (m, 3H), 5.11 (s, 2H), 3.31 (q, 2H, J=7.3 Hz), 1.33 (t, 3H, J=7.3 Hz); LRMS (ES) m/z 430.0 (M⁺+1).

EXAMPLE 14

Compound 11154: N-(4-(5-(difluoromethyl)-1,3,4-oxadiazol-2-yl)-2-fluorobenzyl)-N-phenylethanesulfonamide

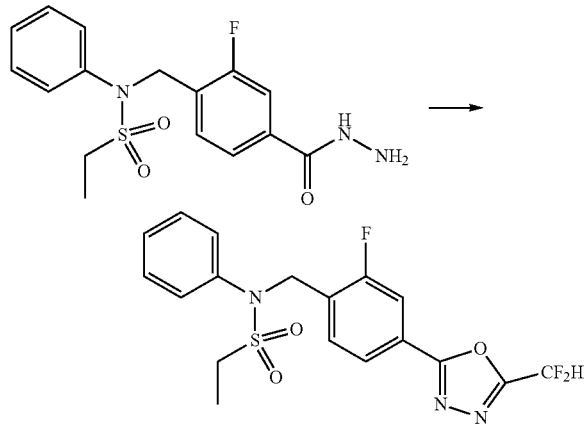

A solution of N-(2-fluoro-4-(hydrazinecarbonyl)benzyl)-N-phenylethanesulfonamide (0.080 g, 0.228 mmol) and triethylamine (0.041 mL, 0.296 mmol) in tetrahydrofuran (2 mL) was stirred at the room temperature for 10 min, and then mixed with 2,2-difluoroacetic anhydride (0.030 mL, 0.273 mmol). The reaction mixture was heated at reflux for 3 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-phenylethanesulfonamide as white solid (0.065 g, 69.4%).

$^1$H NMR (400 MHz, DMSO-d$_6$) δ 7.88 (dd, 1H, J=8.0, 1.7 Hz), 7.80 (dd, 1H, J=10.2, 1.7 Hz), 7.75-7.67 (m, 1H), 7.58-7.40 (m, 3H), 7.39 (dd, 2H, J=8.5, 6.9 Hz), 7.34-7.27 (m, 1H), 5.10 (s, 2H), 3.30 (q, 2H, J=7.4 Hz), 1.33 (t, 3H, J=7.3 Hz); LRMS (ES) m/z 412.3 (M$^+$+1).

EXAMPLE 15

Compound 11155: N-(3-fluorophenyl)-N-(4-(5-(trifluoromethyl)-1,3,4-oxadiazol-2-yl)benzyl)pyridine-3-sulfonamide

[Step 1] N-(3-fluorophenyl)-N-(4-(hydrazinecarbonyl)benzyl)pyridine-3-sulfonamide

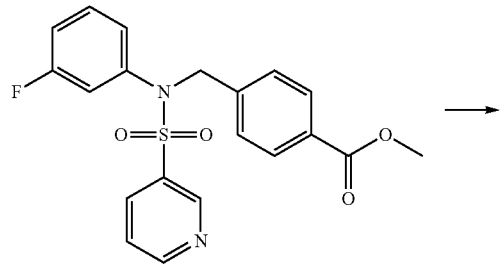

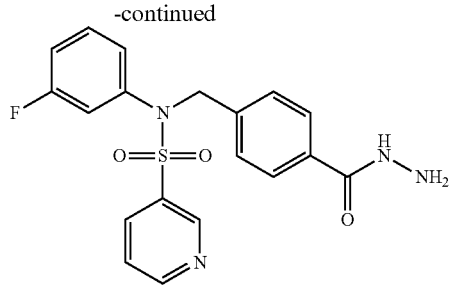

A mixture of methyl 4-((N-(3-fluorophenyl)pyridine-3-sulfonamido)methyl)benzoate (0.300 g, 0.749 mmol) and hydrazine hydrate (0.120 g, 3.746 mmol) in ethanol (6 mL) prepared at the ambient temperature was heated at reflux for 16 hr, and cooled down to the ambient temperature, and concentrated under the reduced pressure to remove the solvent. The residue was diluted with aqueous saturated sodium bicarbonate solution and stirred at the ambient temperature. The resulting precipitates were collected by filtration, washed by water, and dried to give N-(3-fluorophenyl)-N-(4-(hydrazinecarbonyl)benzyl)pyridine-3-sulfonamide as white solid (0.290 g, 96.7%).

[Step 2] Compound 11155

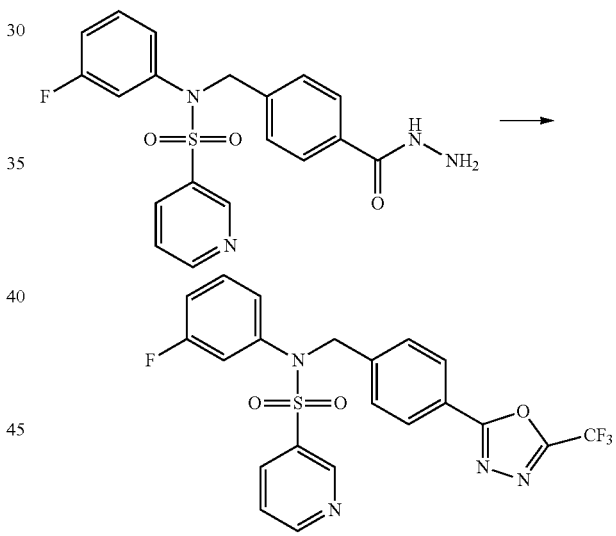

A solution of N-(3-fluorophenyl)-N-(4-(hydrazinecarbonyl)benzyl)pyridine-3-sulfonamide (0.100 g, 0.250 mmol) and triethylamine (0.045 mL, 0.325 mmol) in tetrahydrofuran (2 mL) was stirred at the room temperature for 10 min, and then mixed with trifluoroacetic anhydride (0.037 mL, 0.275 mmol). The reaction mixture was heated at reflux for 3 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 40%) to give N-(3-fluorophenyl)-N-(4-(5-(trifluoromethyl)-1,3,4-oxadiazol-2-yl)benzyl)pyridine-3-sulfonamide as white solid (0.060 g, 50.2%).

¹H NMR (400 MHz, DMSO-d₆) δ 8.97 (dd, 1H, J=4.9, 1.6 Hz), 8.87 (dd, 1H, J=2.4, 0.8 Hz), 8.11 (ddd, 1H, J=8.1, 2.4, 1.6 Hz), 8.05-7.95 (m, 2H), 7.74 (ddd, 1H, J=8.1, 4.9, 0.8 Hz), 7.69 (s, 0.2H), 7.62-7.57 (m, 2H), 7.56 (s, 0.5H), 7.43 (s, 0.2H), 7.37 (dd, 1H, J=8.2, 6.6 Hz), 7.21-7.11 (m, 2H), 7.07 (ddd, 1H, J=8.1, 2.0, 1.0 Hz), 5.04 (s, 2H); LRMS (ES) m/z 477.2 (M⁺−1).

EXAMPLE 16

Compound 11156: N-(4-(5-(difluoromethyl)-1,3,4-oxadiazol-2-yl)benzyl)-N-(3-fluorophenyl)pyridine-3-sulfonamide

[Step 1] N-(4-(2-(2,2-difluoroacetyl)hydrazine-1-carbonyl)benzyl)-N-(3-fluorophenyl)pyridine-3-sulfonamide

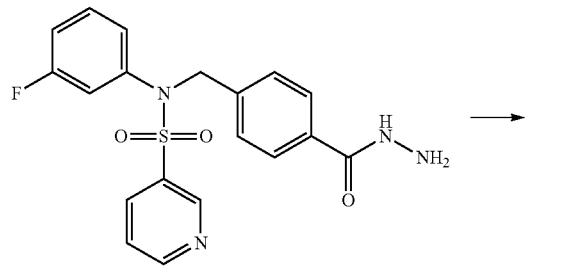

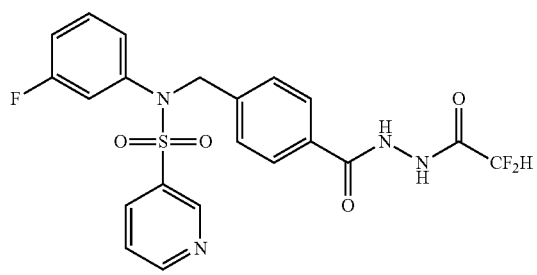

A solution of N-(3-fluorophenyl)-N-(4-(hydrazinecarbonyl)benzyl)pyridine-3-sulfonamide (0.100 g, 0.250 mmol) and triethylamine (0.045 mL, 0.325 mmol) in tetrahydrofuran (2 mL) was stirred at the room temperature for 10 min, and then mixed with 2,2-difluoroacetic anhydride (0.033 mL, 0.300 mmol). The reaction mixture was heated at reflux for 3 hr, and cooled down to the room temperature to terminate the reaction. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(4-(2-(2,2-difluoroacetyl)hydrazine-1-carbonyl)benzyl)-N-(3-fluorophenyl)pyridine-3-sulfonamide as white solid (0.080 g, 67.0%).

[Step 2] Compound 11156

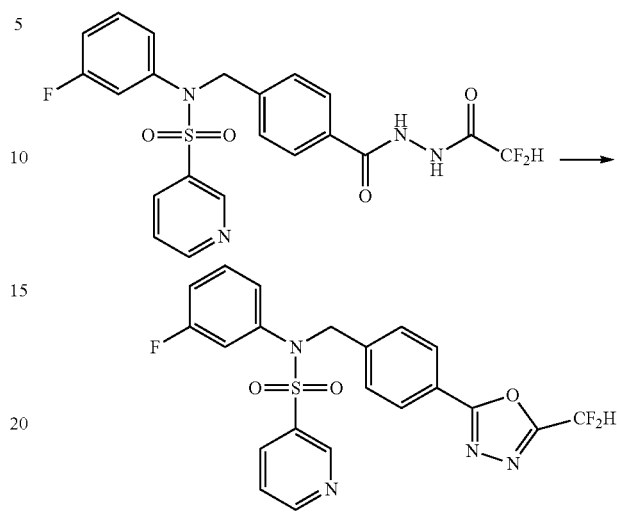

A mixture of N-(4-(2-(2,2-difluoroacetyl)hydrazine-1-carbonyl)benzyl)-N-(3-fluorophenyl)pyridine-3-sulfonamide (0.080 g, 0.167 mmol) and 1-methoxy-N-triethylammoniosulfonyl-methanimidate (Burgess reagent, 0.035 g, 0.201 mmol) in tetrahydrofuran (2 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(4-(5-(difluoromethyl)-1,3,4-oxadiazol-2-yl)benzyl)-N-(3-fluorophenyl)pyridine-3-sulfonamide as white solid (0.055 g, 71.4%).

¹H NMR (400 MHz, DMSO-d₆) δ 8.97 (dd, 1H, J=4.9, 1.5 Hz), 8.87 (d, 1H, J=2.3 Hz), 8.11 (ddd, 1H, J=8.1, 2.4, 1.6 Hz), 8.08-7.97 (m, 2H), 7.74 (ddd, 1H, J=8.0, 4.9, 0.8 Hz), 7.60 (d, 2H, J=8.2 Hz), 7.37 (td, 1H, J=8.1, 6.6 Hz), 7.22-7.10 (m, 2H), 7.10-7.02 (m, 1H), 5.05 (s, 2H); LRMS (ES) m/z 462.0 (M⁺+1).

EXAMPLE 17

Compound 11167: N-phenyl-N-(4-(5-(trifluoromethyl)-1,3,4-oxadiazol-2-yl)benzyl)methanesulfonamide

[Step 1] N-phenylmethanesulfonamide

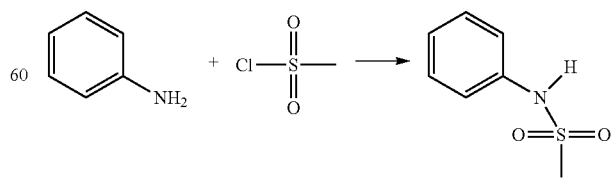

A solution of aniline (3.000 g, 32.213 mmol), pyridine (2.860 mL, 35.434 mmol) and methanesulfonyl chloride (3.012 mL, 38.656 mmol) in dichloromethane (80 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-phenylmethanesulfonamide, 4.100 g, 74.3%, white solid).

[Step 2] methyl 4-((N-phenylmethylsulfonamido)methyl)benzoate

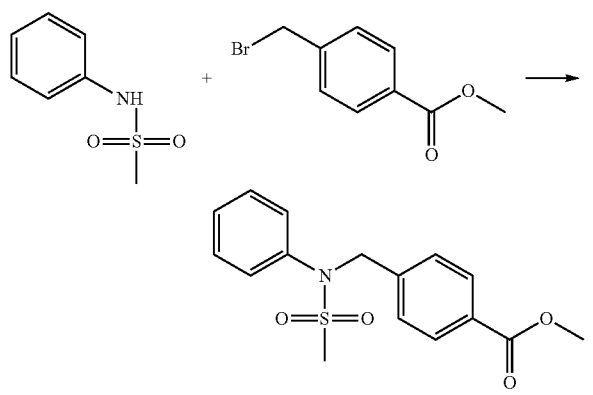

A solution of N-phenylmethanesulfonamide (0.800 g, 4.673 mmol), sodium hydride (60.00%, 0.224 g, 5.607 mmol) and methyl 4-(bromomethyl)benzoate (1.177 g, 5.140 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 4-((N-phenylmethylsulfonamido)methyl)benzoate as white solid (0.700 g, 46.9%).

[Step 3] N-(4-(hydrazinecarbonyl)benzyl)-N-phenylmethanesulfonamide

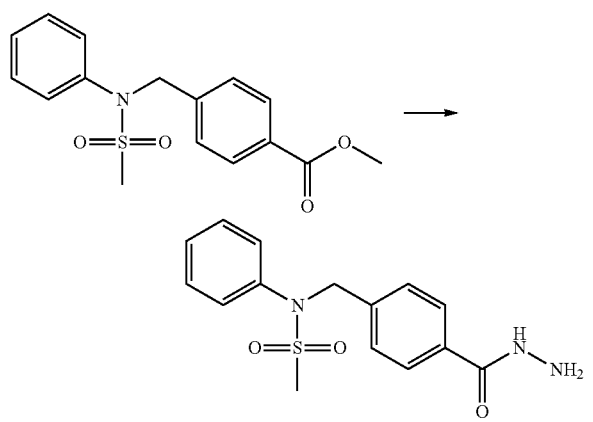

A mixture of methyl 4-((N-phenylmethylsulfonamido)methyl)benzoate (0.700 g, 2.192 mmol) and hydrazine hydrate (1.097 g, 21.917 mmol) in dichloromethane (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(4-(hydrazinecarbonyl)benzyl)-N-phenylmethanesulfonamide, 0.430 g, 61.4%, yellow oil).

[Step 4] Compound 11167

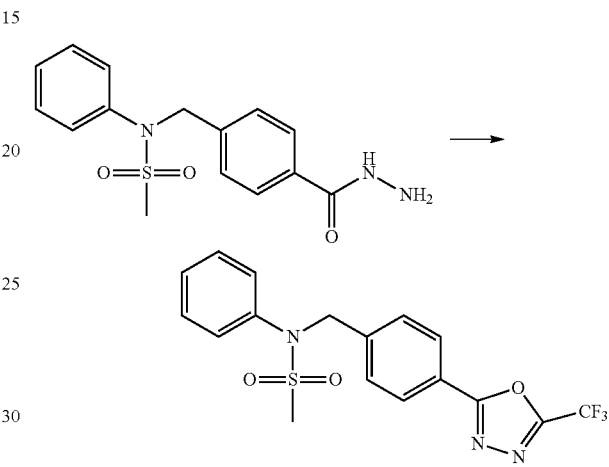

A solution of N-(4-(hydrazinecarbonyl)benzyl)-N-phenylmethanesulfonamide (0.200 g, 0.626 mmol), trifluoroacetic anhydride (0.096 mL, 0.689 mmol) and triethylamine (0.175 mL, 1.252 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-phenyl-N-(4-(5-(trifluoromethyl)-1,3,4-oxadiazol-2-yl)benzyl)methanesulfonamide as white solid (0.140 g, 56.3%).

$^1$H NMR (400 MHz, CDCl$_3$) δ 8.09-8.01 (m, 2H), 7.54-7.47 (m, 2H), 7.42-7.26 (m, 5H), 4.97 (s, 2H), 3.01 (s, 3H); LRMS (ES) m/z 398.1 (M$^+$+1).

EXAMPLE 18

Compound 11168: N-(4-(5-(difluoromethyl)-1,3,4-oxadiazol-2-yl)benzyl)-N-phenylmethanesulfonamide

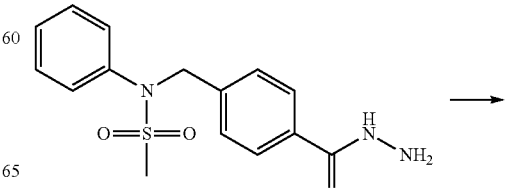

-continued

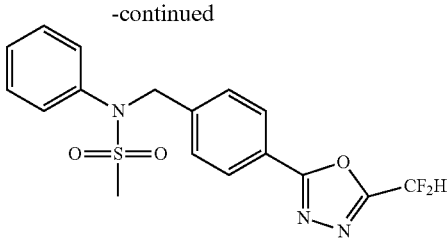

A solution of N-(4-(hydrazinecarbonyl)benzyl)-N-phenylmethanesulfonamide (0.200 g, 0.626 mmol), difluoroacetic anhydride (0.075 mL, 0.689 mmol) and triethylamine (0.131 mL, 0.939 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)benzyl)-N-phenylmethanesulfonamide as white solid (0.110 g, 46.3%).

$^1$H NMR (400 MHz, CDCl$_3$) δ 8.08-7.97 (m, 2H), 7.53-7.45 (m, 2H), 7.44-7.26 (m, 5H), 7.05 (s, 0.2H), 6.92 (s, 0.5H), 6.79 (s, 0.2H), 4.96 (s, 2H), 3.01 (s, 3H); LRMS (ES) m/z 380.0 (M$^+$+1).

EXAMPLE 19

Compound 11169: N-(2-fluoro-4-(5-(trifluoromethyl)-1,3,4-oxadiazol-2-yl)benzyl)-N-phenylmethanesulfonamide

[Step 1] methyl 3-fluoro-4-((N-phenylmethylsulfonamido)methyl)benzoate

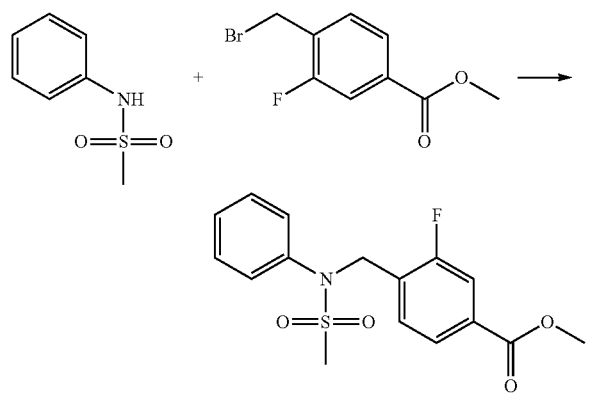

A solution of N-phenylmethanesulfonamide (0.800 g, 4.673 mmol), sodium hydride (60.00%, 0.224 g, 5.607 mmol) and methyl 4-(bromomethyl)-3-fluorobenzoate (1.270 g, 5.140 mmol) in N,N-dimethylformide (10 mL) was stirred at the room temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 3-fluoro-4-((N-phenylmethylsulfonamido)methyl)benzoate as yellow solid (0.752 g, 47.7%).

[Step 2] N-(2-fluoro-4-(hydrazinecarbonyl)benzyl)-N-phenylmethanesulfonamide

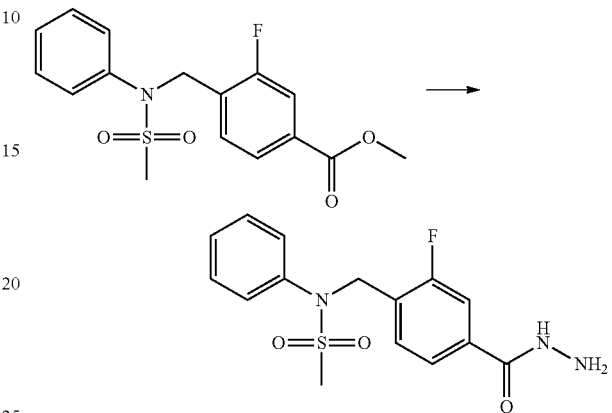

A mixture of methyl 3-fluoro-4-((N-phenylmethylsulfonamido)methyl)benzoate (0.752 g, 2.229 mmol) and hydrazine hydrate (1.116 g, 22.290 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-phenylmethanesulfonamide, 0.700 g, 93.1%, yellow oil).

[Step 3] N-(2-fluoro-4-(2-(2,2,2-trifluoroacetyl)hydrazine-1-carbonyl)benzyl)-N-phenylmethanesulfonamide

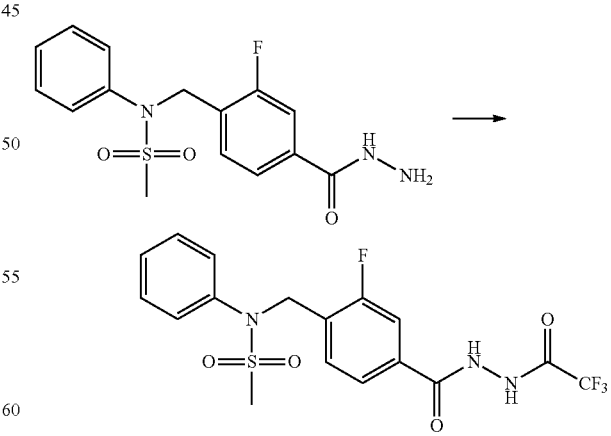

A solution of N-(2-fluoro-4-(hydrazinecarbonyl)benzyl)-N-phenylmethanesulfonamide (0.200 g, 0.593 mmol), trifluoroacetic anhydride (0.091 mL, 0.652 mmol) and triethylamine (0.124 mL, 0.889 mmol) in dichloromethane (10 mL) was stirred at the room temperature for 5 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The title compound was used without further purification (N-(2-fluoro-4-(2-(2,2,2-trifluoroacetyl)hydrazine-1-carbonyl)benzyl)-N-phenylmethanesulfonamide, 0.150 g, 58.4%, yellow oil).

[Step 4] Compound 11169

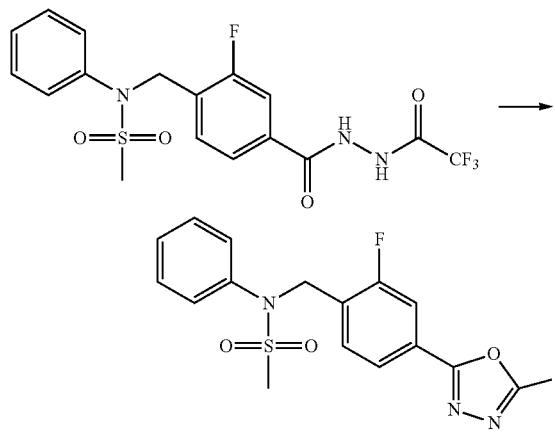

A mixture of N-(2-fluoro-4-(2-(2,2,2-trifluoroacetyl)hydrazine-1-carbonyl)benzyl)-N-phenylmethanesulfonamide (0.150 g, 0.346 mmol) and 1-methoxy-N-triethylammoniosulfonyl-methanimidate (Burgess reagent, 0.124 g, 0.519 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give N-(2-fluoro-4-(5-(trifluoromethyl)-1,3,4-oxadiazol-2-yl)benzyl)-N-phenylmethanesulfonamide as white solid (0.091 g, 63.3%).

¹H NMR (400 MHz, CDCl₃) δ 7.88 (dd, 1H, J=8.1, 1.7 Hz), 7.75 (dd, 1H, J=9.8, 1.6 Hz), 7.71 (t, 1H, J=7.6 Hz), 7.42-7.29 (m, 5H), 5.05 (s, 2H), 3.03 (s, 3H); LRMS (ES) m/z 416.3 (M⁺+1).

EXAMPLE 20

Compound 11170: N-(4-(5-(difluoromethyl)-1,3,4-oxadiazol-2-yl)-2-fluorobenzyl)-N-phenylmethanesulfonamide

[Step 1] N-(4-(2-(2,2-difluoroacetyl)hydrazine-1-carbonyl)-2-fluorobenzyl)-N-phenylmethanesulfonamide

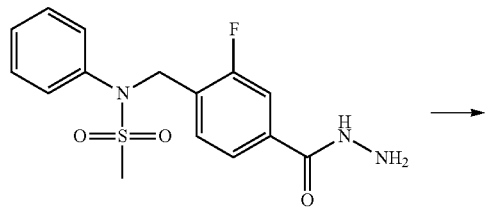

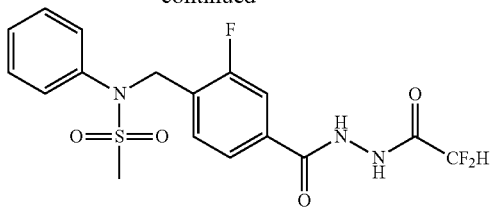

A solution of N-(2-fluoro-4-(hydrazinecarbonyl)benzyl)-N-phenylmethanesulfonamide (0.200 g, 0.593 mmol), difluoroacetic anhydride (0.071 mL, 0.652 mmol) and triethylamine (0.124 mL, 0.889 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(4-(2-(2,2-difluoroacetyl)hydrazine-1-carbonyl)-2-fluorobenzyl)-N-phenylmethane sulfonamide, 0.110 g, 44.7%, yellow oil).

[Step 2] Compound 11170

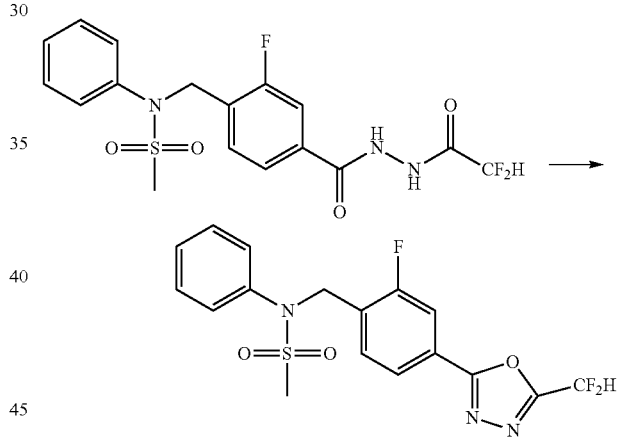

A mixture of N-(4-(2-(2,2-difluoroacetyl)hydrazine-1-carbonyl)-2-fluorobenzyl)-N-phenylmethanesulfonamide (0.110 g, 0.254 mmol) and 1-methoxy-N-triethylammoniosulfonyl-methanimidate (Burgess reagent, 0.091 g, 0.381 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(4-(5-(difluoromethyl)-1,3,4-oxadiazol-2-yl)-2-fluorobenzyl)-N-phenylmethanesulfonamide as white solid (0.071 g, 70.4%).

¹H NMR (400 MHz, CDCl₃) δ 7.88 (d, 1H, J=8.3 Hz), 7.75 (d, 1H, J=10.0 Hz), 7.68 (t, 1H, J=7.7 Hz), 7.42-7.29 (m, 5H), 7.05 (s, 0.2H), 6.92 (s, 0.5H), 6.79 (s, 0.2H), 5.04 (s, 2H), 3.03 (s, 3H); LRMS (ES) m/z 398.5 (M⁺+1).

EXAMPLE 21

Compound 11171: N-phenyl-N-((5-(5-(trifluoromethyl)-1,3,4-oxadiazol-2-yl)pyridin-2-yl)methyl)methanesulfonamide

[Step 1] methyl 6-((N-phenylmethylsulfonamido)methyl)nicotinate

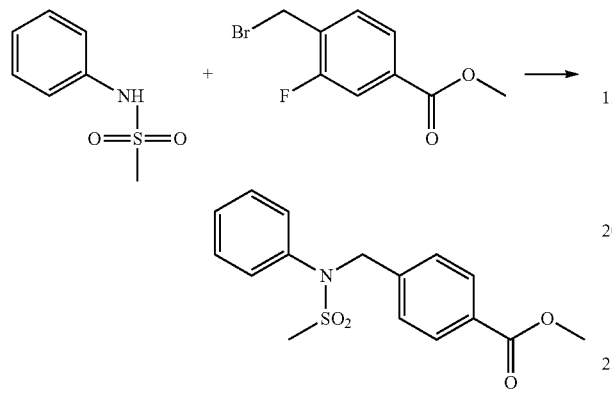

A solution of N-phenylmethanesulfonamide (0.800 g, 4.673 mmol), sodium hydride (60.00%, 0.224 g, 5.607 mmol) and methyl 6-(bromomethyl)nicotinate (1.182 g, 5.140 mmol) in N,N-dimethylformide (10 mL) was stirred at the room temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 6-((N-phenylmethylsulfonamido)methyl)nicotinate as yellow solid (0.323 g, 21.6%).

[Step 2] N-((5-(hydrazinecarbonyl)pyridin-2-yl)methyl)-N-phenylmethanesulfonamide

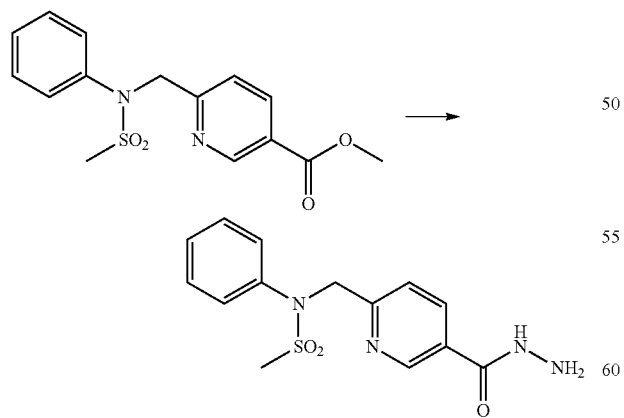

A mixture of methyl 6-((N-phenylmethylsulfonamido)methyl)nicotinate (0.323 g, 1.008 mmol) and hydrazine hydrate (0.505 g, 10.082 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-((5-(hydrazinecarbonyl)pyridin-2-yl)methyl)-N-phenylmethanesulfonamide, 0.300 g, 92.9%, yellow oil).

[Step 3] N-phenyl-N-((5-(2-(2,2,2-trifluoroacetyl)hydrazine-1-carbonyl)pyridin-2-yl)methyl)methanesulfonamide

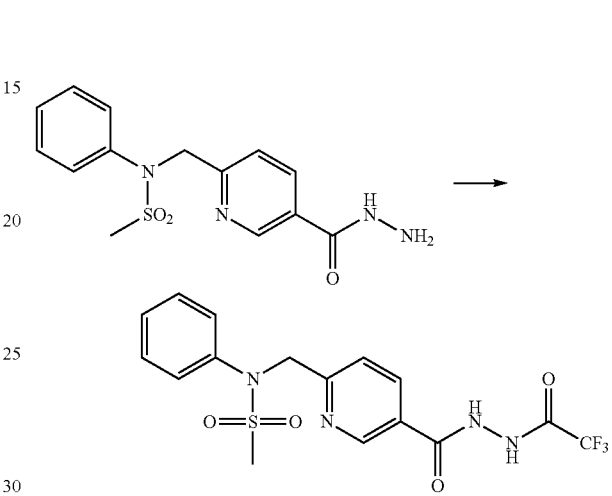

A solution of N-((5-(hydrazinecarbonyl)pyridin-2-yl)methyl)-N-phenylmethanesulfonamide (0.100 g, 0.312 mmol), trifluoroacetic anhydride (0.048 mL, 0.343 mmol) and triethylamine (0.065 mL, 0.468 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The title compound was used without further purification (N-phenyl-N-((5-(2-(2,2,2-trifluoroacetyl)hydrazine-1-carbonyl)pyridin-2-yl)methyl)methanesulfonamide, 0.083 g, 63.9%, yellow oil).

[Step 4] Compound 11171

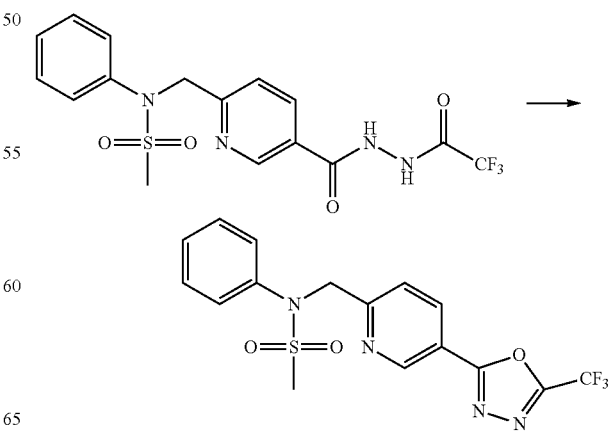

A mixture of N-phenyl-N-((5-(2-(2,2,2-trifluoroacetyl)hydrazine-1-carbonyl)pyridin-2-yl)methyl)methanesulfonamide (0.083 g, 0.199 mmol) and 1-methoxy-N-triethylammoniosulfonyl-methanimidate (Burgess reagent, 0.071 g, 0.299 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 60%) to give N-phenyl-N-((5-(5-(trifluoromethyl)-1,3,4-oxadiazol-2-yl)pyridin-2-yl)methyl)methanesulfonamide as yellow solid (0.053 g, 66.7%).

$^1$H NMR (400 MHz, CDCl$_3$) δ 9.25 (dd, 1H, J=2.3, 0.8 Hz), 8.40 (dd, 1H, J=8.3, 2.3 Hz), 7.76 (dd, 1H, J=8.2, 0.8 Hz), 7.46-7.34 (m, 4H), 7.35-7.29 (m, 1H), 5.18 (s, 2H), 3.08 (s, 3H); LRMS (ES) m/z 399.3 (M$^+$+1).

EXAMPLE 22

Compound 11172: N-((5-(5-(difluoromethyl)-1,3,4-oxadiazol-2-yl)pyridin-2-yl)methyl)-N-phenylmethanesulfonamide

[Step 1] N-((5-(2-(2,2-difluoroacetyl)hydrazine-1-carbonyl)pyridin-2-yl)methyl)-N-phenylmethanesulfonamide

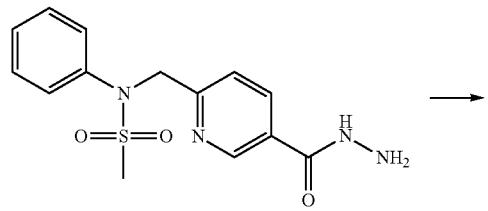

A solution of N-((5-(hydrazinecarbonyl)pyridin-2-yl)methyl)-N-phenylmethanesulfonamide (0.100 g, 0.312 mmol), difluoroacetic anhydride (0.037 mL, 0.343 mmol) and triethylamine (0.065 mL, 0.468 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-((5-(2-(2,2-difluoroacetyl)hydrazine-1-carbonyl)pyridin-2-yl)methyl)-N-phenylmethanesulfonamide, 0.083 g, 66.7%, yellow oil).

[Step 2] Compound 11172

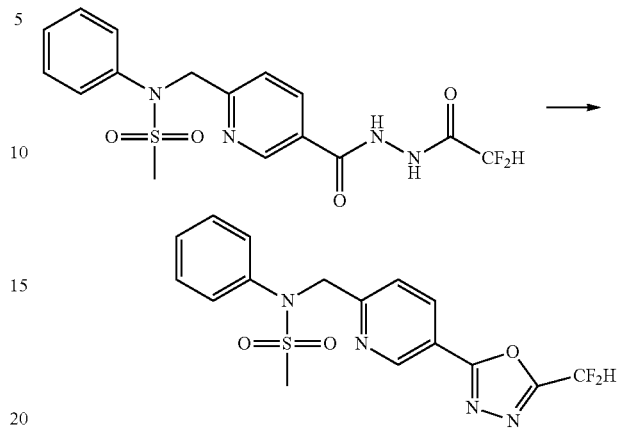

A mixture of N-((5-(2-(2,2-difluoroacetyl)hydrazine-1-carbonyl)pyridin-2-yl)methyl)-N-phenylmethanesulfonamide (0.083 g, 0.208 mmol) and 1-methoxy-N-triethylammoniosulfonyl-methanimidate (Burgess reagent, 0.074 g, 0.313 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-((5-(5-(difluoromethyl)-1,3,4-oxadiazol-2-yl)pyridin-2-yl)methyl)-N-phenylmethanesulfonamide as yellow solid (0.043 g, 54.3%).

$^1$H NMR (400 MHz, CDCl$_3$) δ 9.25 (dd, 1H, J=2.2, 0.9 Hz), 8.40 (dd, 1H, J=8.3, 2.2 Hz), 7.74 (dd, 1H, J=8.1, 0.8 Hz), 7.49-7.29 (m, 5H), 7.08 (s, 0.2H), 6.95 (s, 0.5H), 6.82 (s, 0.2H), 5.17 (s, 2H), 3.09 (s, 3H); LRMS (ES) m/z 381.2 (M$^+$+1).

[Step 3] Compound 11172 HCl Salt

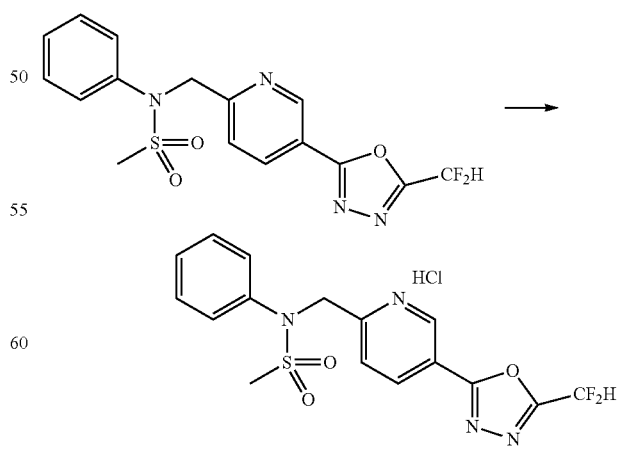

A solution of N-((5-(5-(difluoromethyl)-1,3,4-oxadiazol-2-yl)pyridin-2-yl)methyl)-N-phenylmethanesulfonamide (0.026 g, 0.068 mmol) and hydrogen chloride (1.00 M solution in EtOAc, 0.075 mL, 0.075 mmol) in ethyl acetate (2 mL) was stirred at the room temperature for 1 hr. The precipitates were collected by filtration, washed by ethyl acetate, and dried to give N-((5-(5-(difluoromethyl)-1,3,4-oxadiazol-2-yl)pyridin-2-yl)methyl)-N-phenylmethanesulfonamide hydrochloride as white solid (0.028 g, 98.3%).

EXAMPLE 23

Compound 11173: N-phenyl-N-((6-(5-(trifluoromethyl)-1,3,4-oxadiazol-2-yl)pyridin-3-yl)methyl)methanesulfonamide

[Step 1] methyl 5-((phenylamino)methyl)picolinate

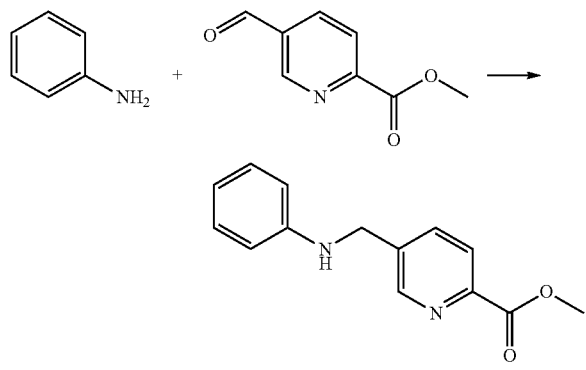

Methyl 5-formylpicolinate (0.975 g, 5.906 mmol) and acetic acid (0.338 mL, 5.906 mmol) were added to a solution of aniline (0.500 g, 5.369 mmol) in dichloromethane (20 mL) at the room temperature, and the mixture was stirred at the same temperature for 30 min. The reaction mixture was treated with sodium triacetoxyborohydride (2.276 g, 10.738 mmol), stirred for additional 12 hr at the same temperature. Then, water was added to the reaction mixture, followed by extraction with dichloromethane. The organic layer was washed with aqueous saturated sodium bicarbonate solution, dried with anhydrous MgSO₄, filtered, and concentrated in vacuo. The residue was chromatographed (SiO₂, 12 g cartridge; ethyl acetate/hexane=0% to 40%) to give methyl 5-((phenylamino)methyl)picolinate as yellow solid (0.672 g, 51.7%).

[Step 2] methyl 5-((N-phenylmethylsulfonamido)methyl)picolinate

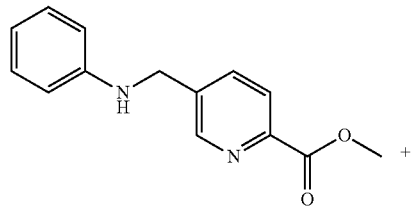

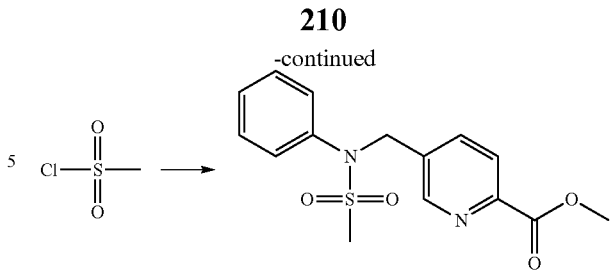

A solution of methyl 5-((phenylamino)methyl)picolinate (0.672 g, 2.774 mmol), triethylamine (0.773 mL, 5.547 mmol) and methanesulfonyl chloride (0.259 mL, 3.328 mmol) in dichloromethane (10 mL) was stirred at the room temperature for 5 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 30%) to give methyl 5-((N-phenylmethylsulfonamido)methyl)picolinate as yellow oil (0.620 g, 69.8%).

[Step 3] N-((6-(hydrazinecarbonyl)pyridin-3-yl)methyl)-N-phenylmethanesulfonamide

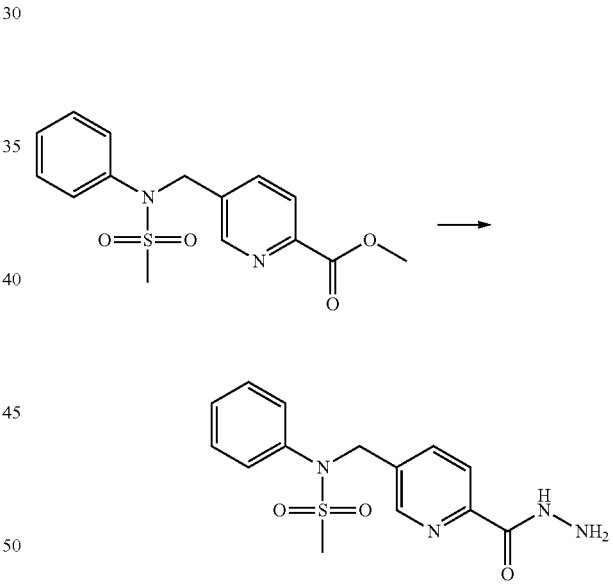

A mixture of methyl 5-((N-phenylmethylsulfonamido)methyl)picolinate (0.620 g, 1.935 mmol) and hydrazine hydrate (0.969 g, 19.353 mmol) in dichloromethane (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-((6-(hydrazinecarbonyl)pyridin-3-yl)methyl)-N-phenylmethanesulfonamide, 0.590 g, 95.2%, yellow oil).

[Step 4] Compound 11173

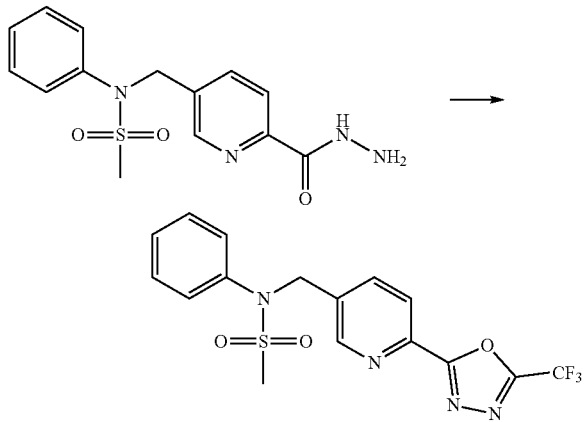

A solution of N-((6-(hydrazinecarbonyl)pyridin-3-yl)methyl)-N-phenylmethanesulfonamide (0.200 g, 0.624 mmol), trifluoroacetic anhydride (0.096 mL, 0.687 mmol) and triethylamine (0.131 mL, 0.936 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-phenyl-N-((6-(5-(trifluoromethyl)-1,3,4-oxadiazol-2-yl)pyridin-3-yl)methyl)methanesulfonamide as yellow solid (0.100 g, 40.2%).

$^1$H NMR (400 MHz, CDCl$_3$) δ 8.67-8.60 (m, 1H), 8.31-8.24 (m, 1H), 8.04-7.96 (m, 1H), 7.45-7.24 (m, 5H), 5.01 (s, 2H), 3.03 (s, 3H); LRMS (ES) m/z 399.0 (M$^+$+1).

EXAMPLE 24

Compound 11174: N-((6-(5-(difluoromethyl)-1,3,4-oxadiazol-2-yl)pyridin-3-yl)methyl)-N-phenylmethanesulfonamide

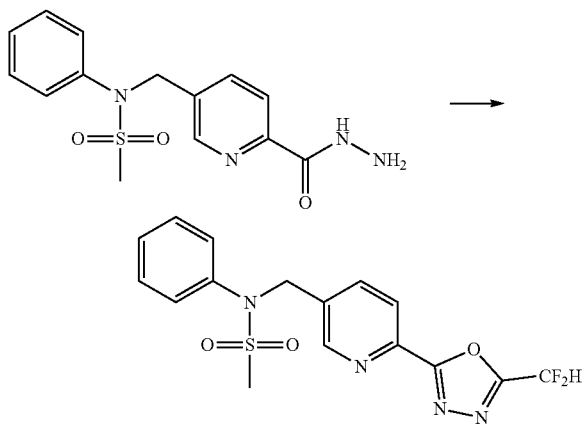

A solution of N-((6-(hydrazinecarbonyl)pyridin-3-yl)methyl)-N-phenylmethanesulfonamide (0.200 g, 0.624 mmol), difluoroacetic anhydride (0.075 mL, 0.687 mmol) and triethylamine (0.131 mL, 0.936 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-((6-(5-(difluoromethyl)-1,3,4-oxadiazol-2-yl)pyridin-3-yl)methyl)-N-phenylmethanesulfonamide as yellow solid (0.110 g, 46.3%).

$^1$H NMR (400 MHz, CDCl$_3$) δ 8.63 (dd, 1H, J=2.2, 0.8 Hz), 8.25 (d, 1H, J=8.1, 0.8 Hz), 8.02-7.95 (m, 1H), 7.41-7.29 (m, 5H), 7.07 (s, 0.2H), 6.94 (s, 0.5H), 6.81 (s, 0.2H), 5.01 (s, 2H), 3.03 (s, 3H); LRMS (ES) m/z 381.3 (M$^+$+1).

EXAMPLE 25

Compound 11175: N-(2-fluoro-4-(5-(trifluoromethyl)-1,3,4-oxadiazol-2-yl)benzyl)-N-(3-(trifluoromethyl)phenyl)methanesulfonamide

[Step 1]
N-(3-(trifluoromethyl)phenyl)methanesulfonamide

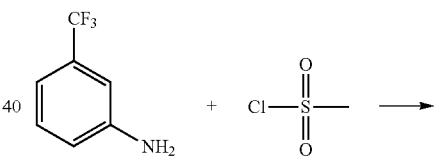

A solution of 3-(trifluoromethyl)aniline (1.000 g, 6.206 mmol), pyridine (0.551 mL, 6.827 mmol) and methanesulfonyl chloride (0.580 mL, 7.447 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(3-(trifluoromethyl)phenyl)methanesulfonamide, 1.050 g, 70.7%, yellow oil).

[Step 2] methyl 3-fluoro-4-((N-(3-(trifluoromethyl)phenyl)methylsulfonamido)methyl)benzoate

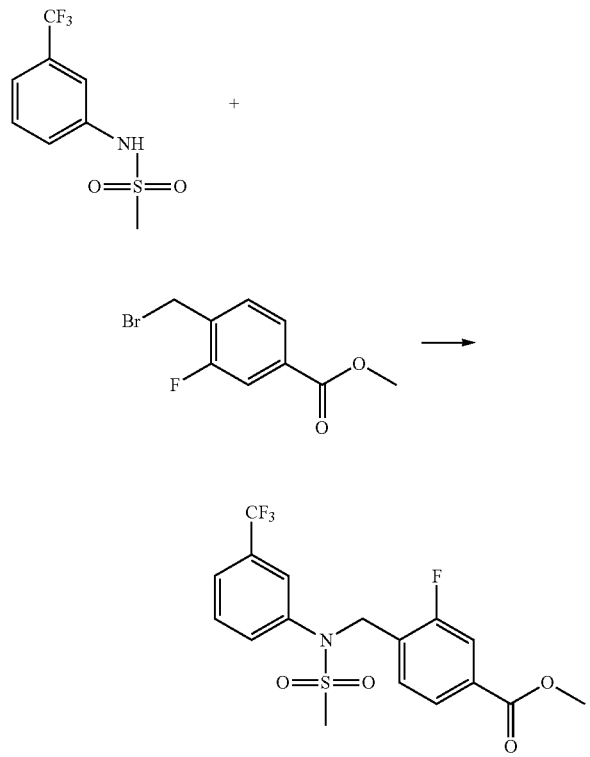

A solution of N-(3-(trifluoromethyl)phenyl)methanesulfonamide (0.500 g, 2.090 mmol), sodium hydride (60.00%, 0.100 g, 2.508 mmol) and methyl 4-(bromomethyl)-3-fluorobenzoate (0.568 g, 2.299 mmol) in N,N-dimethylformamide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 30%) to give methyl 3-fluoro-4-((N-(3-(trifluoromethyl)phenyl)methylsulfonamido)methyl)benzoate as yellow solid (0.600 g, 70.8%).

[Step 3] N-(2-fluoro-4-(hydrazinecarbonyl)benzyl)-N-(3-(trifluoromethyl)phenyl)methanesulfonamide

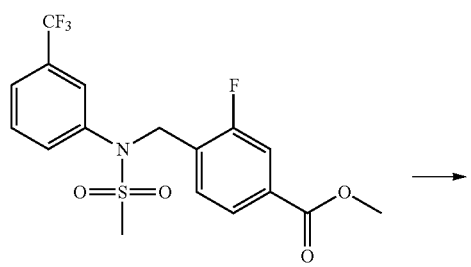

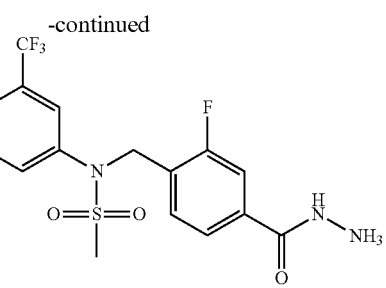

A mixture of methyl 3-fluoro-4-((N-(3-(trifluoromethyl)phenyl)methylsulfonamido)methyl)benzoate (0.665 g, 1.641 mmol) and hydrazine hydrate (0.821 g, 16.405 mmol) in dichloromethane (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(2-fluoro-4-(hydrazinecarbonyl)benzyl)-N-(3-(trifluoromethyl)phenyl)methanesulfonamide, 0.520 g, 78.2%, yellow oil).

[Step 4] N-(2-fluoro-4-(2-(2,2,2-trifluoroacetyl)hydrazine-1-carbonyl)benzyl)-N-(3-(trifluoromethyl)phenyl)methanesulfonamide

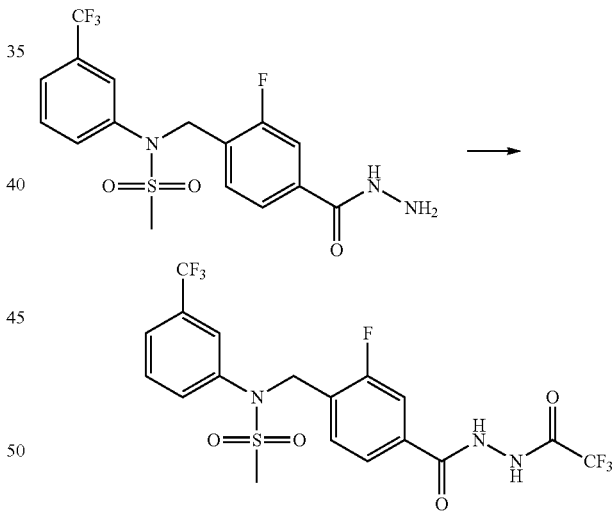

A solution of N-(2-fluoro-4-(hydrazinecarbonyl)benzyl)-N-(3-(trifluoromethyl)phenyl)methanesulfonamide (0.200 g, 0.493 mmol), trifluoroacetic anhydride (0.075 mL, 0.543 mmol) and triethylamine (0.103 mL, 0.740 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(2-fluoro-4-(2-(2,2,2-trifluoroacetyl)hydrazine-1-carbonyl)benzyl)-N-(3-(trifluoromethyl)phenyl)methanesulfonamide, 0.140 g, 56.6%, white solid).

[Step 5] Compound 11175

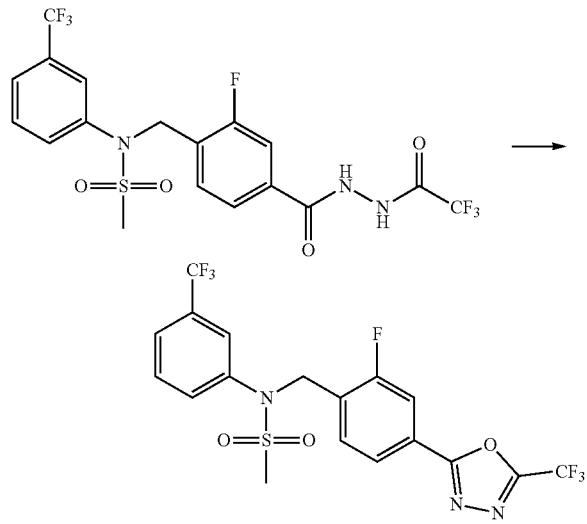

A mixture of N-(2-fluoro-4-(2-(2,2,2-trifluoroacetyl)hydrazine-1-carbonyl)benzyl)-N-(3-(trifluoromethyl)phenyl)methanesulfonamide (0.140 g, 0.279 mmol) and 1-methoxy-N-triethylammoniosulfonyl-methanimidate (Burgess reagent, 0.100 g, 0.419 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(2-fluoro-4-(5-(trifluoromethyl)-1,3,4-oxadiazol-2-yl)benzyl)-N-(3-(trifluoromethyl)phenyl)methanesulfonamide as yellow solid (0.094 g, 69.6%).

$^1$H NMR (400 MHz, CDCl$_3$) δ 7.89 (dt, 1H, J=8.1, 4.0 Hz), 7.81-7.72 (m, 1H), 7.68 (t, 1H, J=7.6 Hz), 7.63-7.56 (m, 2H), 7.56-7.45 (m, 2H), 5.07 (s, 2H), 3.06 (s, 3H); LRMS (ES) m/z 484.3 (M$^+$+1).

EXAMPLE 26

Compound 11176: N-(4-(5-(difluoromethyl)-1,3,4-oxadiazol-2-yl)-2-fluorobenzyl)-N-(3-(trifluoromethyl)phenyl)methanesulfonamide

[Step 1] N-(4-(2-(2,2-difluoroacetyl)hydrazine-1-carbonyl)-2-fluorobenzyl)-N-(3-(trifluoromethyl)phenyl)methanesulfonamide

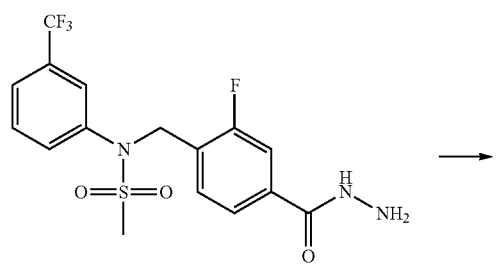

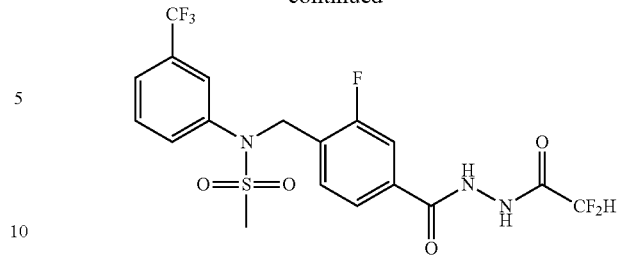

A solution of N-(2-fluoro-4-(hydrazinecarbonyl)benzyl)-N-(3-(trifluoromethyl)phenyl)methanesulfonamide (0.200 g, 0.493 mmol), difluoroacetic anhydride (0.059 mL, 0.543 mmol) and triethylamine (0.103 mL, 0.740 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-2-fluorobenzyl)-N-(3-(trifluoromethyl)phenyl) methanesulfonamide, 0.130 g, 54.5%, white solid).

[Step 2] Compound 11176

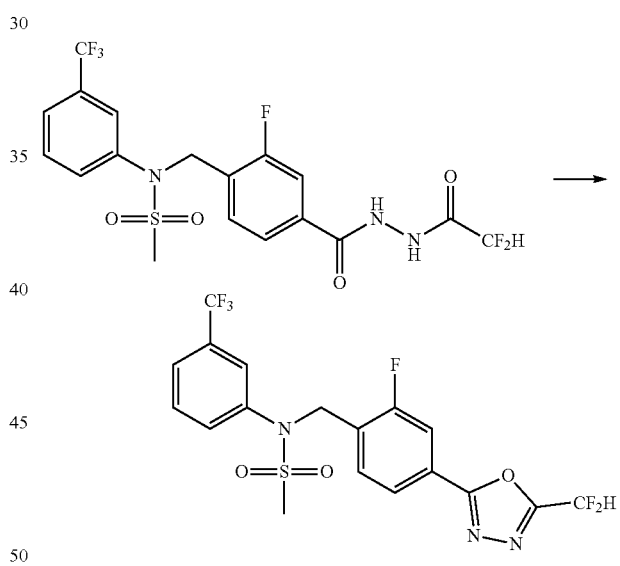

A mixture of N-(4-(2-(2,2-difluoroacetyl)hydrazine-1-carbonyl)-2-fluorobenzyl)-N-(3-(trifluoromethyl)phenyl) methanesulfonamide (0.130 g, 0.269 mmol) and 1-methoxy-N-triethylammoniosulfonyl-methanimidate (Burgess reagent, 0.096 g, 0.403 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(3-(trifluoromethyl)phenyl)methanesulfonamide as yellow solid (0.094 g, 75.1%).

¹H NMR (400 MHz, CDCl₃) δ 7.90 (dd, 1H, J=8.0, 1.7 Hz), 7.76 (dd, 1H, J=9.9, 1.7 Hz), 7.66 (t, 1H, J=7.6 Hz), 7.61-7.55 (m, 2H), 7.55-7.45 (m, 2H), 7.05 (s, 0.2H), 6.92 (s, 0.4H), 6.79 (s, 0.2H), 5.06 (s, 2H), 3.05 (s, 3H); LRMS (ES) m/z 466.2 (M⁺+1).

EXAMPLE 27

Compound 11177: N-(2-fluoro-4-(5-(trifluoromethyl)-1,3,4-oxadiazol-2-yl)benzyl)-N-(m-tolyl)methanesulfonamide

[Step 1] N-(m-tolyl)methanesulfonamide

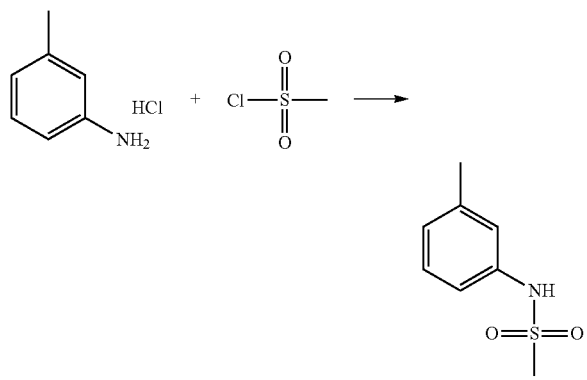

A solution of m-toluidine hydrochloride (1.000 g, 6.963 mmol), pyridine (0.618 mL, 7.660 mmol) and methanesulfonyl chloride (0.651 mL, 8.356 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO₄, filtered, and concentrated in vacuo. The title compound was used without further purification (N-(m-tolyl)methanesulfonamide, 1.100 g, 85.3%, white solid).

[Step 2] methyl 3-fluoro-4-((N-(m-tolyl)methylsulfonamido)methyl)benzoate

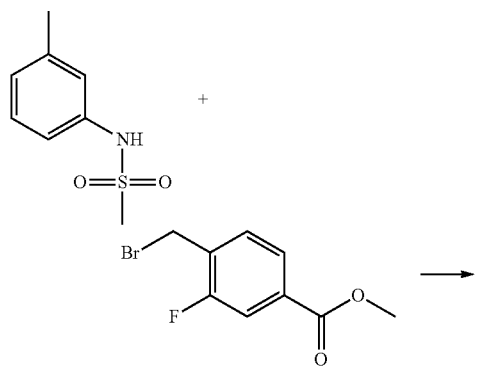

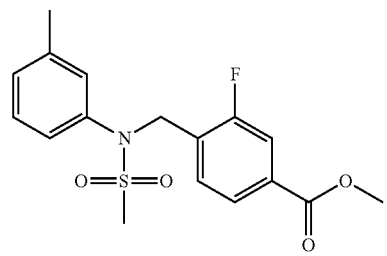

A solution of N-(m-tolyl)methanesulfonamide (0.500 g, 2.699 mmol), sodium hydride (60.00%, 0.130 g, 3.239 mmol) and methyl 4-(bromomethyl)-3-fluorobenzoate (0.734 g, 2.969 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 30%) to give methyl 3-fluoro-4-((N-(m-tolyl)methylsulfonamido)methyl)benzoate as yellow solid (0.630 g, 66.4%).

[Step 3] N-(2-fluoro-4-(hydrazinecarbonyl)benzyl)-N-(m-tolyl)methanesulfonamide

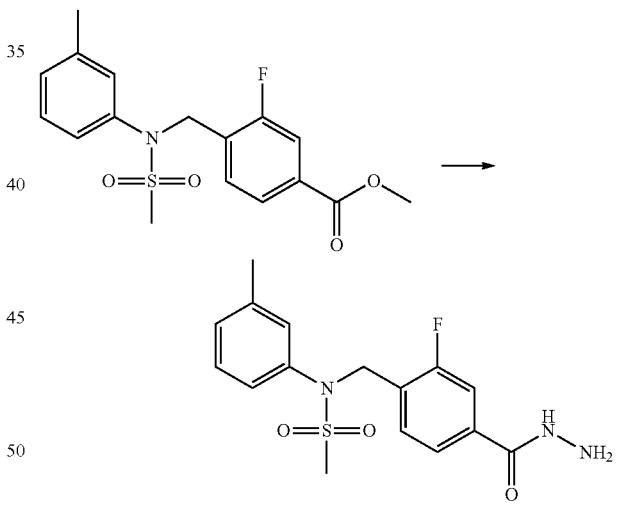

A mixture of methyl 3-fluoro-4-((N-(m-tolyl)methylsulfonamido)methyl)benzoate (0.630 g, 1.793 mmol) and hydrazine hydrate (0.898 g, 17.929 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(2-fluoro-4-(hydrazinecarbonyl)benzyl)-N-(m-tolyl)methanesulfonamide, 0.590 g, 93.7%, yellow oil).

219

[Step 4] N-(2-fluoro-4-(2-(2,2,2-trifluoroacetyl)hydrazine-1-carbonyl)benzyl)-N-(m-tolyl)methanesulfonamide

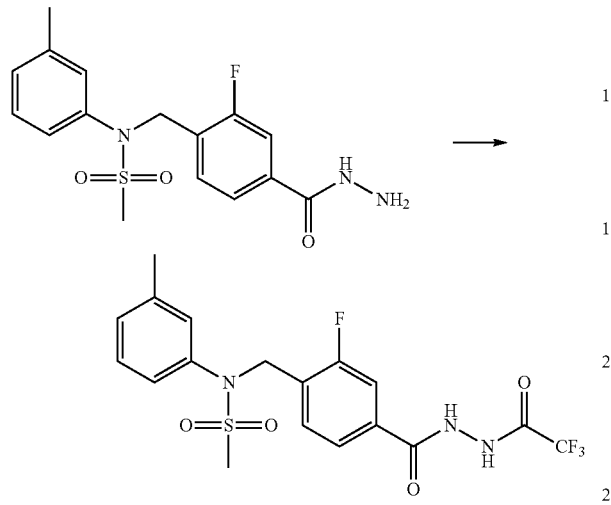

A solution of N-(2-fluoro-4-(hydrazinecarbonyl)benzyl)-N-(m-tolyl)methanesulfonamide (0.200 g, 0.569 mmol), trifluoroacetic anhydride (0.087 mL, 0.626 mmol) and triethylamine (0.119 mL, 0.854 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-fluoro-4-(2-(2,2,2-trifluoroacetyl)hydrazine-1-carbonyl)benzyl)-N-(m-tolyl)methanesulfonamide, 0.153 g, 60.1%, white solid).

[Step 5] Compound 11177

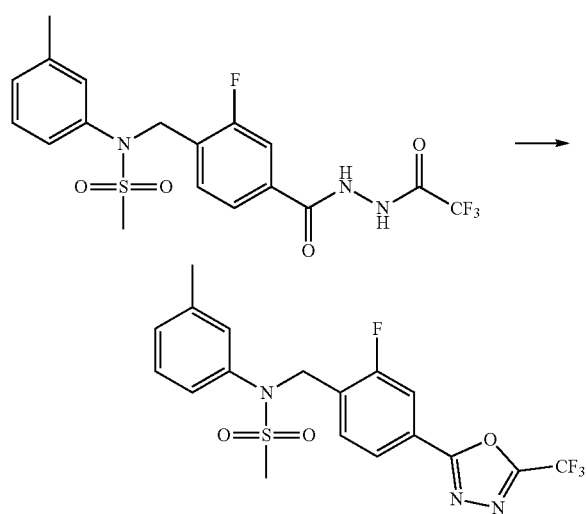

A mixture of N-(2-fluoro-4-(2-(2,2,2-trifluoroacetyl)hydrazine-1-carbonyl)benzyl)-N-(m-tolyl)methanesulfona-

220 mide (0.153 g, 0.342 mmol) and 1-methoxy-N-triethylammoniosulfonyl-methanimidate (Burgess reagent, 0.122 g, 0.513 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(2-fluoro-4-(5-(trifluoromethyl)-1,3,4-oxadiazol-2-yl)benzyl)-N-(m-tolyl)methanesulfonamide as yellow solid (0.100 g, 68.1%).

$^1$H NMR (400 MHz, CDCl$_3$) δ 7.88 (dd, 1H, J=8.1, 1.7 Hz), 7.79-7.67 (m, 2H), 7.30-7.09 (m, 4H), 5.03 (s, 2H), 3.02 (s, 3H), 2.34 (s, 3H); LRMS (ES) m/z 430.0 (M$^+$+1).

EXAMPLE 28

Compound 11178: N-(4-(5-(difluoromethyl)-1,3,4-oxadiazol-2-yl)-2-fluorobenzyl)-N-(m-tolyl)methanesulfonamide

[Step 1] N-(4-(2-(2,2-difluoroacetyl)hydrazine-1-carbonyl)-2-fluorobenzyl)-N-(m-tolyl)methanesulfonamide

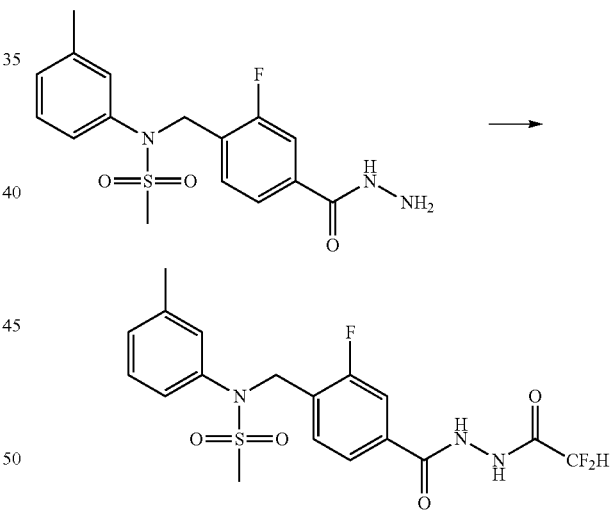

A solution of N-(2-fluoro-4-(hydrazinecarbonyl)benzyl)-N-(m-tolyl)methanesulfonamide (0.200 g, 0.569 mmol), difluoroacetic anhydride (0.068 mL, 0.626 mmol) and triethylamine (0.119 mL, 0.854 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-2-fluorobenzyl)-N-(m-tolyl)methanesulfonamide, 0.130 g, 53.2%, white solid).

[Step 2] Compound 11178

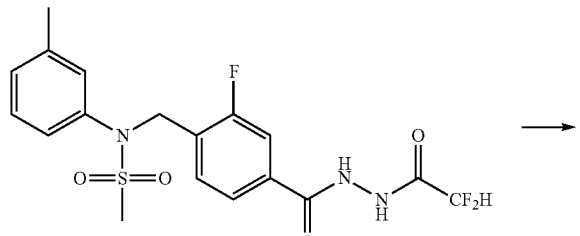

A mixture of N-(4-(2-(2,2-difluoroacetyl)hydrazine-1-carbonyl)-2-fluorobenzyl)-N-(m-tolyl)methanesulfonamide (0.130 g, 0.303 mmol) and 1-methoxy-N-triethylammoniosulfonyl-methanimidate (Burgess reagent, 0.108 g, 0.454 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(m-tolyl)methanesulfonamide as yellow solid (0.091 g, 73.1%).

$^1$H NMR (400 MHz, CDCl$_3$) δ 7.92-7.83 (m, 1H), 7.79-7.64 (m, 2H), 7.25 (dd, 1H, J=15.9, 8.2 Hz), 7.19-7.08 (m, 3H), 7.05 (s, 0.2H), 6.92 (S, 0.5H), 6.79 (s, 0.2H), 5.02 (s, 2H), 3.02 (s, 3H), 2.34 (s, 3H); LRMS (ES) m/z 412.0 (M$^+$+1).

EXAMPLE 29

Compound 11179: N-(2-fluoro-4-(5-(trifluoromethyl)-1,3,4-oxadiazol-2-yl)benzyl)-N-(3-methoxyphenyl)methanesulfonamide

[Step 1] N-(3-methoxyphenyl)methanesulfonamide

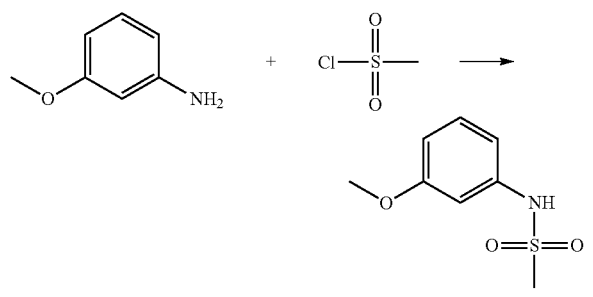

A solution of 3-methoxyaniline (1.000 g, 8.120 mmol), pyridine (0.721 mL, 8.931 mmol) and methanesulfonyl chloride (0.759 mL, 9.743 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(3-methoxyphenyl)methanesulfonamide, 0.920 g, 52.6%, yellow oil).

[Step 2] methyl 3-fluoro-4-((N-(3-methoxyphenyl)methylsulfonamido)methyl)benzoate

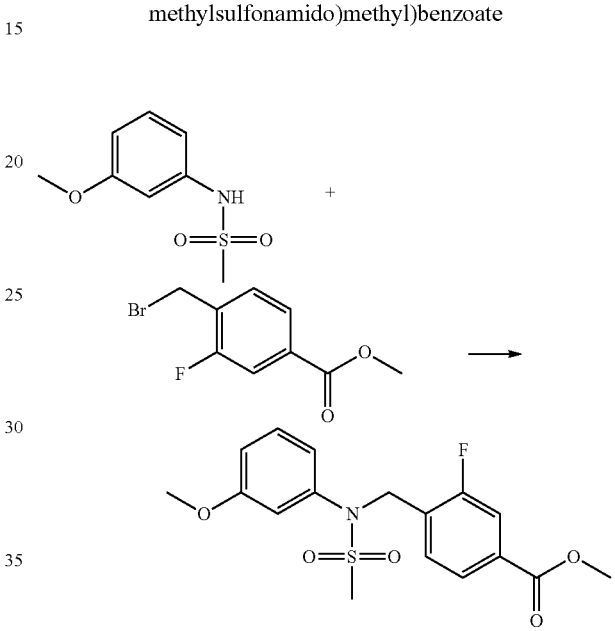

A solution of N-(3-methoxyphenyl)methanesulfonamide (0.700 g, 3.252 mmol), sodium hydride (60.00%, 0.156 g, 3.902 mmol) and methyl 4-(bromomethyl)-3-fluorobenzoate (0.884 g, 3.577 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 3-fluoro-4-((N-(3-methoxyphenyl)methylsulfonamido)methyl)benzoate as yellow solid (0.900 g, 75.3%).

[Step 3] N-(2-fluoro-4-(hydrazinecarbonyl)benzyl)-N-(3-methoxyphenyl)methanesulfonamide

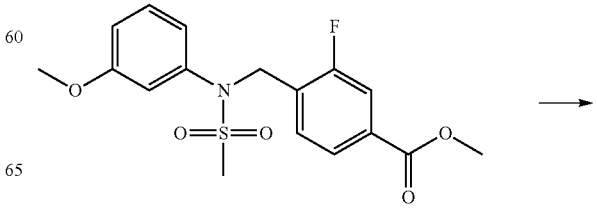

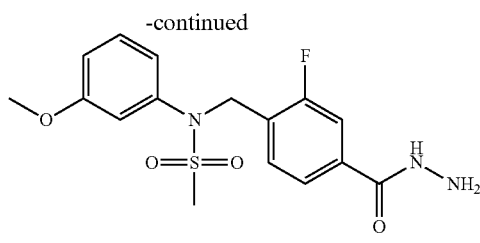

A mixture of methyl 3-fluoro-4-((N-(3-methoxyphenyl)methylsulfonamido)methyl)benzoate (0.973 g, 2.648 mmol) and hydrazine hydrate (1.326 g, 26.484 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(3-methoxyphenyl)methanesulfonamide, 0.830 g, 85.3%, yellow oil).

[Step 4] N-(2-fluoro-4-(2-(2,2,2-trifluoroacetyl)hydrazine-1-carbonyl)benzyl)-N-(3-methoxyphenyl)methanesulfonamide A solution of N-(2-fluoro-4-(hydrazinecarbonyl)benzyl)-N-(3-methoxyphenyl)methanesulfonamide (0.200 g, 0.544 mmol), trifluoroacetic anhydride (0.083 mL, 0.599 mmol) and triethylamine (0.114 mL, 0.817 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-fluoro-4-(2-(2,2,2-trifluoroacetyl)hydrazine-1-carbonyl)benzyl)-N-(3-methoxyphenyl)methanesulfonamide, 0.140 g, 55.5%, yellow solid).

[Step 5] Compound 11179

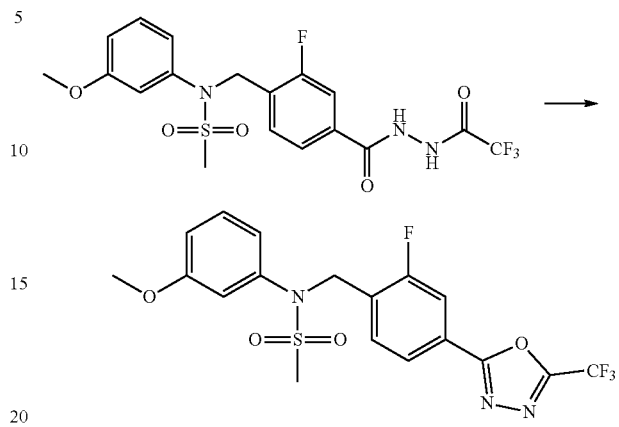

A mixture of N-(2-fluoro-4-(2-(2,2,2-trifluoroacetyl)hydrazine-1-carbonyl)benzyl)-N-(3-methoxyphenyl)methanesulfonamide (0.140 g, 0.302 mmol) and 1-methoxy-N-triethylammoniosulfonyl-methanimidate (Burgess reagent, 0.108 g, 0.453 mmol) in tetrahydrofuran (10 mL) was heated at 150° C. for 30 min under the microwaves, cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(2-fluoro-4-(5-(trifluoromethyl)-1,3,4-oxadiazol-2-yl)benzyl)-N-(3-methoxyphenyl)methanesulfonamide as white solid (0.100 g, 74.3%).

$^1$H NMR (400 MHz, CDCl$_3$) δ 7.90-7.82 (m, 1H), 7.79-7.65 (m, 2H), 7.31-7.20 (m, 1H), 6.96-6.80 (m, 3H), 5.03 (s, 2H), 3.77 (s, 3H), 3.02 (s, 3H); LRMS (ES) m/z 446.3 (M$^+$+1).

EXAMPLE 30

Compound 11180: N-(4-(5-(difluoromethyl)-1,3,4-oxadiazol-2-yl)-2-fluorobenzyl)-N-(3-methoxyphenyl)methanesulfonamide

[Step 1] N-(4-(2-(2,2-difluoroacetyl)hydrazine-1-carbonyl)-2-fluorobenzyl)-N-(3-methoxyphenyl)methanesulfonamide

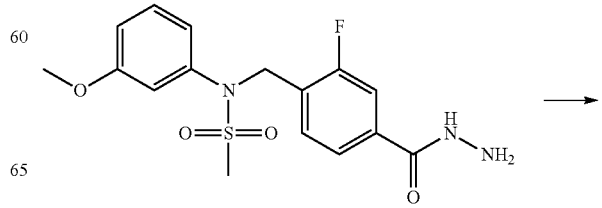

-continued

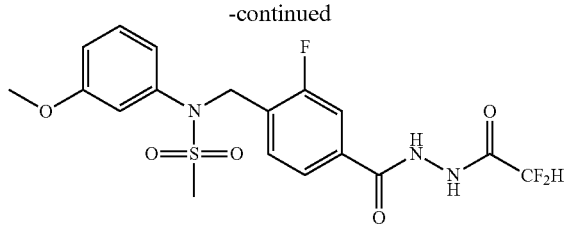

A solution of N-(2-fluoro-4-(hydrazinecarbonyl)benzyl)-N-(3-methoxyphenyl)methanesulfonamide (0.200 g, 0.544 mmol), difluoroacetic anhydride (0.065 mL, 0.599 mmol) and triethylamine (0.114 mL, 0.817 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-2-fluorobenzyl)-N-(3-methoxyphenyl)methanesulfonamide, 0.160 g, 66.0%, white solid).

[Step 2] Compound 11180

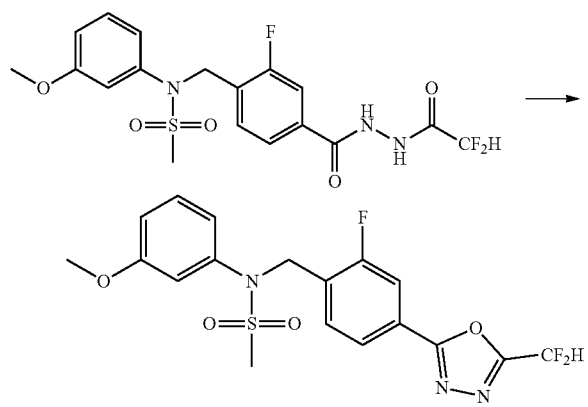

A mixture of N-(4-(2-(2,2-difluoroacetyl)hydrazine-1-carbonyl)-2-fluorobenzyl)-N-(3-methoxyphenyl)methanesulfonamide (0.160 g, 0.359 mmol) and 1-methoxy-N-triethylammoniosulfonyl-methanimidate (Burgess reagent, 0.128 g, 0.539 mmol) in dichloromethane (10 mL) was heated at 150° C. for 30 min under the microwaves, cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(3-methoxyphenyl)methanesulfonamide as white solid (0.120 g, 78.2%).
$^1$H NMR (400 MHz, CDCl$_3$) δ 7.88 (dd, 1H, J=7.9, 1.7 Hz), 7.75 (dd, 1H, J=10.0, 1.7 Hz), 7.68 (t, 1H, J=7.6 Hz), 7.31-7.22 (m, 1H), 7.05 (s, 0.2H), 6.95-6.81 (m, 3H), 6.79 (s, 0.2H), 5.03 (s, 2H), 3.78 (d, 3H, J=0.6 Hz), 3.03 (d, 3H, J=0.5 Hz); LRMS (ES) m/z 428.1 (M$^+$+1).

EXAMPLE 31

Compound 11181: N-(2-fluoro-4-(5-(trifluoromethyl)-1,3,4-oxadiazol-2-yl)benzyl)-N-(3-fluorophenyl)methanesulfonamide

[Step 1] N-(3-fluorophenyl)methanesulfonamide

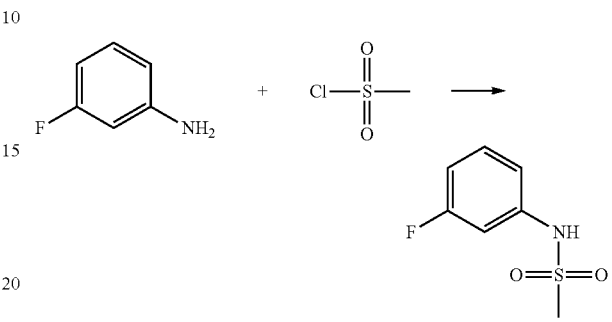

A solution of 3-fluoroaniline (0.800 g, 7.199 mmol), pyridine (0.639 mL, 7.919 mmol) and methanesulfonyl chloride (0.673 mL, 8.639 mmol) in dichloromethane (20 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(3-fluorophenyl)methanesulfonamide, 0.610 g, 44.8%, yellow oil).

[Step 2] methyl 3-fluoro-4-((N-(3-fluorophenyl)methylsulfonamido)methyl)benzoate

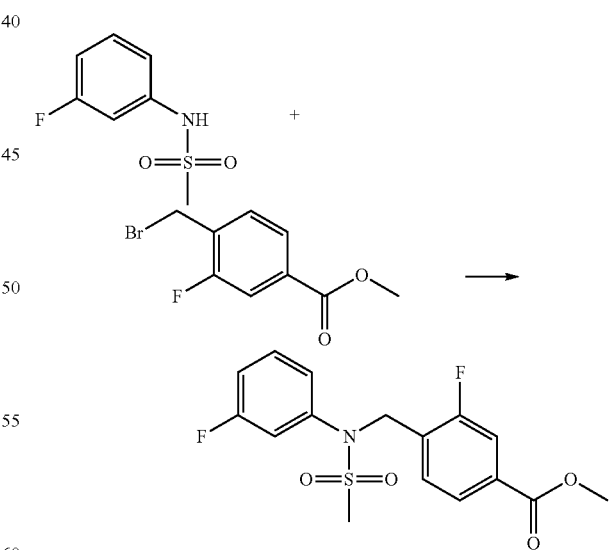

A solution of N-(3-fluorophenyl)methanesulfonamide (0.610 g, 3.224 mmol), sodium hydride (0.093 g, 3.869 mmol) and methyl 4-(bromomethyl)-3-fluorobenzoate (0.876 g, 3.547 mmol) in N,N-dimethylformide (10 mL) was stirred at the room temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (methyl 3-fluoro-4-((N-(3-fluorophenyl)methylsulfonamido)methyl)benzoate, 0.590 g, 51.5%, yellow oil).

[Step 3] N-(2-fluoro-4-(hydrazinecarbonyl)benzyl)-N-(3-fluorophenyl)methanesulfonamide

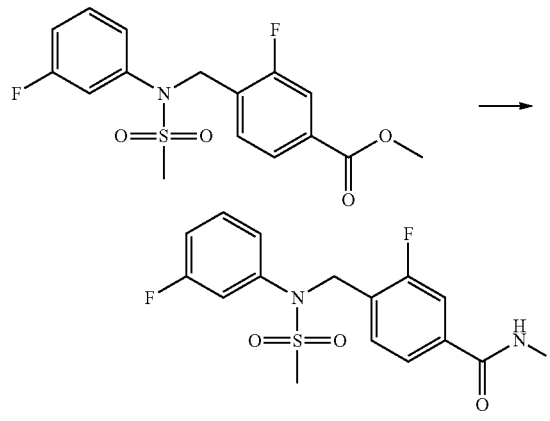

A mixture of methyl 3-fluoro-4-((N-(3-fluorophenyl)methylsulfonamido)methyl)benzoate (0.590 g, 1.660 mmol) and hydrazine hydrate (0.831 g, 16.603 mmol) in dichloromethane (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(3-fluorophenyl)methanesulfonamide, 0.500 g, 84.7%, yellow oil).

[Step 4] N-(2-fluoro-4-(2-(2,2,2-trifluoroacetyl)hydrazine-1-carbonyl)benzyl)-N-(3-fluorophenyl)methanesulfonamide

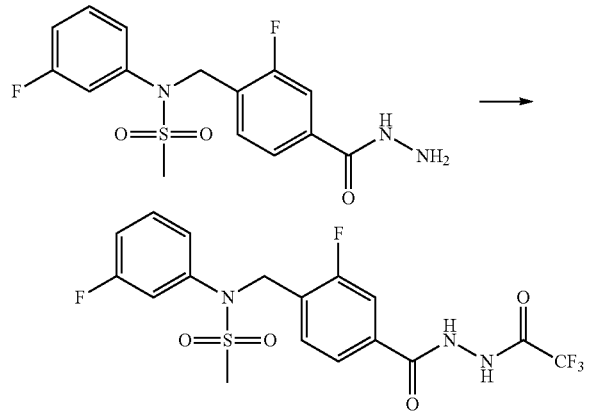

A solution of N-(2-fluoro-4-(hydrazinecarbonyl)benzyl)-N-(3-fluorophenyl)methanesulfonamide (0.200 g, 0.563 mmol), trifluoroacetic anhydride (0.086 mL, 0.619 mmol) and triethylamine (0.118 mL, 0.844 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-fluoro-4-(2-(2,2,2-trifluoroacetyl)hydrazine-1-carbonyl)benzyl)-N-(3-fluorophenyl)methanesulfonamide, 0.150 g, 59.0%, yellow solid).

[Step 5] Compound 11181

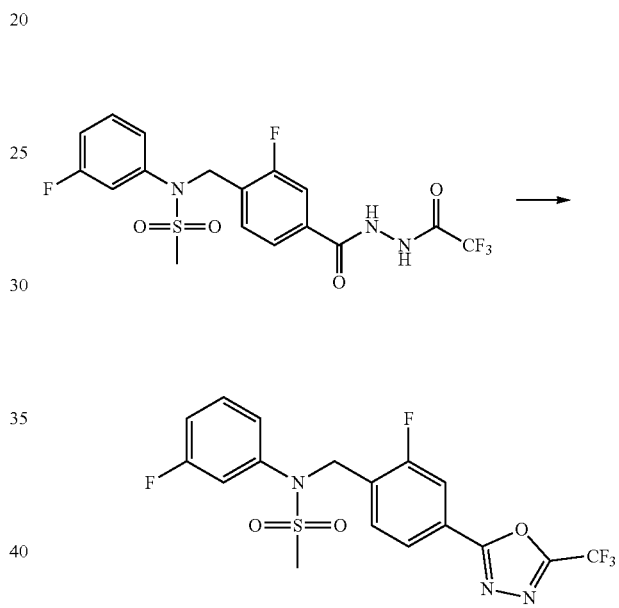

A mixture of N-(2-fluoro-4-(2-(2,2,2-trifluoroacetyl)hydrazine-1-carbonyl)benzyl)-N-(3-fluorophenyl)methanesulfonamide (0.150 g, 0.332 mmol) and 1-methoxy-N-triethylammoniosulfonyl-methanimidate (Burgess reagent, 0.119 g, 0.498 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(2-fluoro-4-(5-(trifluoromethyl)-1,3,4-oxadiazol-2-yl)benzyl)-N-(3-fluorophenyl)methanesulfonamide as white solid (0.091 g, 63.2%).

$^1$H NMR (400 MHz, CDCl$_3$) δ 7.89 (dd, 1H, J=8.1, 1.7 Hz), 7.77 (dd, 1H, J=9.8, 1.6 Hz), 7.68 (t, 1H, J=7.6 Hz), 7.39-7.30 (m, 1H), 7.18-6.99 (m, 3H), 5.04 (s, 2H), 3.05 (s, 3H); LRMS (ES) m/z 434.1 (M$^+$+1).

EXAMPLE 32

Compound 11182: N-(4-(5-(difluoromethyl)-1,3,4-oxadiazol-2-yl)-2-fluorobenzyl)-N-(3-fluorophenyl)methanesulfonamide

[Step 1] N-(4-(2-(2,2-difluoroacetyl)hydrazine-1-carbonyl)-2-fluorobenzyl)-N-(3-fluorophenyl)methanesulfonamide

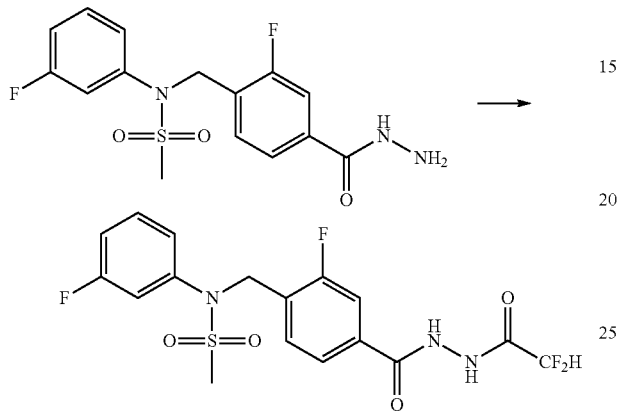

A solution of N-(2-fluoro-4-(hydrazinecarbonyl)benzyl)-N-(3-fluorophenyl)methanesulfonamide (0.200 g, 0.563 mmol), difluoroacetic anhydride (0.067 mL, 0.619 mmol) and triethylamine (0.118 mL, 0.844 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-2-fluorobenzyl)-N-(3-fluorophenyl)methanesulfonamide, 0.150 g, 61.5%, white solid).

[Step 2] Compound 11182

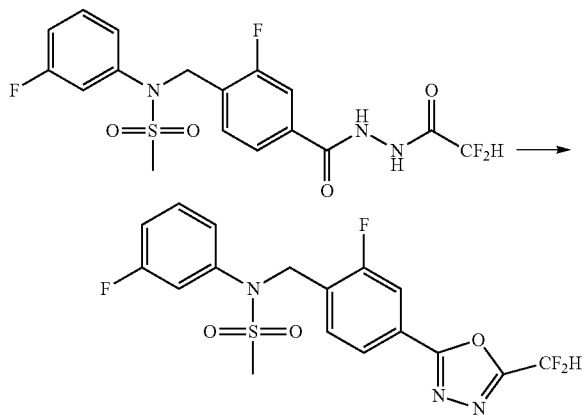

A mixture of N-(4-(2-(2,2-difluoroacetyl)hydrazine-1-carbonyl)-2-fluorobenzyl)-N-(3-fluorophenyl)methanesulfonamide (0.150 g, 0.346 mmol) and 1-methoxy-N-triethylammoniosulfonyl-methanimidate (Burgess reagent, 0.124 g, 0.519 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(3-fluorophenyl)methanesulfonamide as white solid (0.089 g, 61.9%).

$^1$H NMR (400 MHz, CDCl$_3$) δ 7.89 (dd, 1H, J=8.0, 1.7 Hz), 7.77 (dd, 1H, J=9.9, 1.7 Hz), 7.66 (t, 1H, J=7.6 Hz), 7.34 (td, 1H, J=8.2, 6.3 Hz), 7.18-6.98 (m, 3H), 6.92 (s, 0.5H), 6.79 (s, 0.2H), 5.03 (s, 2H), 3.04 (s, 3H); LRMS (ES) m/z 416.3 (M$^+$+1).

EXAMPLE 33

Compound 11183: N-(3-fluoro-4-(5-(trifluoromethyl)-1,3,4-oxadiazol-2-yl)benzyl)-N-phenylmethanesulfonamide

[Step 1] methyl 2-fluoro-4-((phenylamino)methyl)benzoate

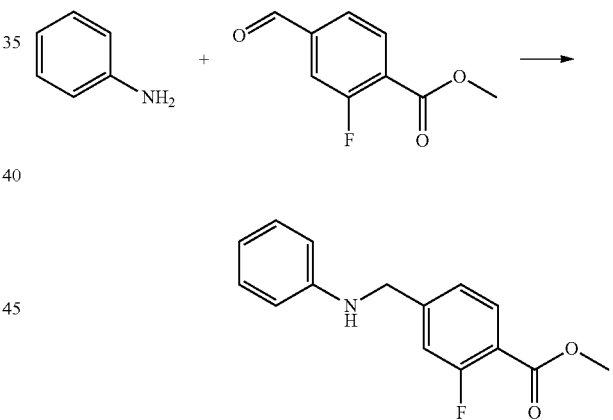

Methyl 2-fluoro-4-formylbenzoate (1.076 g, 5.906 mmol) and acetic acid (0.338 mL, 5.906 mmol) were added to a solution of aniline (0.500 g, 5.369 mmol) in dichloromethane (30 mL) at the room temperature, and the mixture was stirred at the same temperature for 30 min. The reaction mixture was treated with sodium triacetoxyborohydride (2.276 g, 10.738 mmol), and stirred for additional 12 hr at the same temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 2-fluoro-4-((phenylamino)methyl)benzoate as colorless oil (1.000 g, 71.8%).

231

[Step 2] methyl 2-fluoro-4-((N-phenylmethylsulfonamido)methyl)benzoate

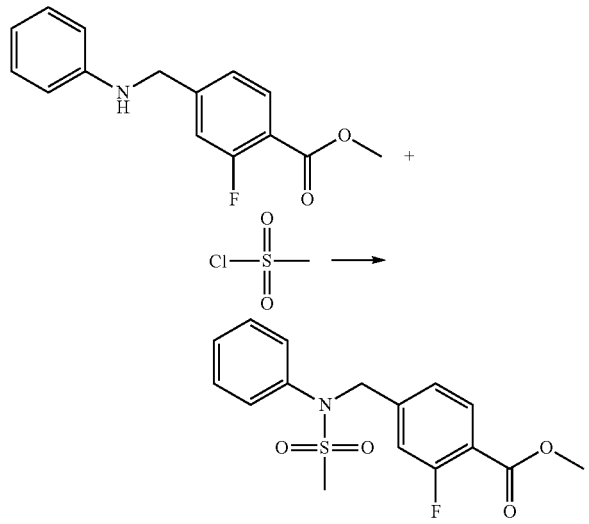

A solution of methyl 2-fluoro-4-((phenylamino)methyl)benzoate (0.540 g, 2.083 mmol), triethylamine (0.581 mL, 4.165 mmol) and methanesulfonyl chloride (0.195 mL, 2.499 mmol) in dichloromethane (10 mL) was stirred at the room temperature for 5 hr. Then, water was added to the reaction mixture, followed by extraction with dichloromethane. The organic layer was washed with aqueous saturated ammonium chloride solution, dried with anhydrous $MgSO_4$, filtered, and concentrated in vacuo. The residue was chromatographed ($SiO_2$, 12 g cartridge; ethyl acetate/hexane=0% to 35%) to give methyl 2-fluoro-4-((N-phenylmethylsulfonamido)methyl)benzoate as yellow solid (0.600 g, 85.4%).

[Step 3] N-(3-fluoro-4-(hydrazinecarbonyl)benzyl)-N-phenylmethanesulfonamide

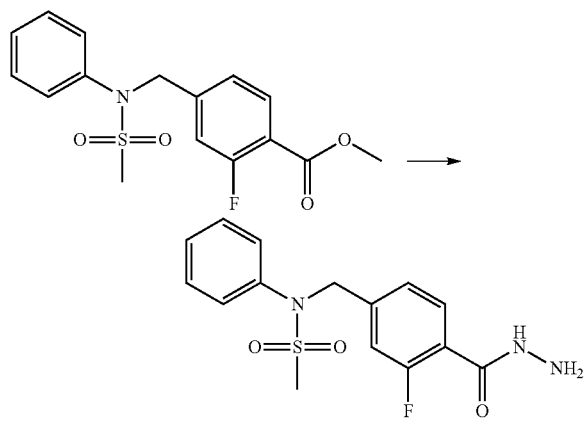

A mixture of methyl 2-fluoro-4-((N-phenylmethylsulfonamido)methyl)benzoate (0.600 g, 1.778 mmol) and hydrazine hydrate (0.890 g, 17.785 mmol) in dichloromethane (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The title compound was used without further purification (N-(3-fluoro-4-(hydrazinecarbonyl)benzyl)-N-phenylmethanesulfonamide, 0.520 g, 86.7%, yellow oil).

[Step 4] N-(3-fluoro-4-(2-(2,2,2-trifluoroacetyl)hydrazine-1-carbonyl)benzyl)-N-phenylmethanesulfonamide

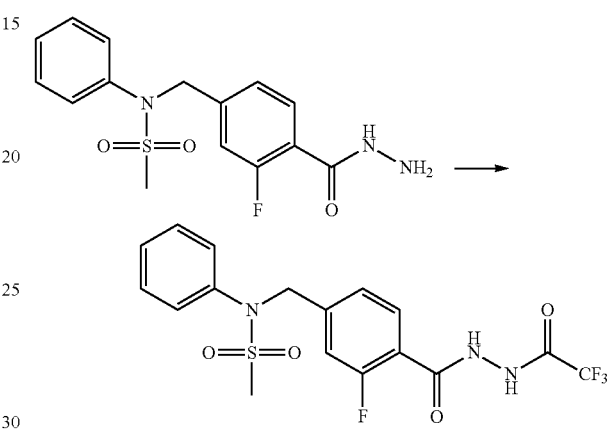

A solution of N-(3-fluoro-4-(hydrazinecarbonyl)benzyl)-N-phenylmethanesulfonamide (0.200 g, 0.593 mmol), trifluoroacetic anhydride (0.091 mL, 0.652 mmol) and triethylamine (0.124 mL, 0.889 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous $MgSO_4$, filtered, and concentrated in vacuo. The title compound was used without further purification (N-(3-fluoro-4-(2-(2,2,2-trifluoroacetyl)hydrazine-1-carbonyl)benzyl)-N-phenylmethanesulfonamide, 0.120 g, 46.7%, white solid).

[Step 5] Compound 11183

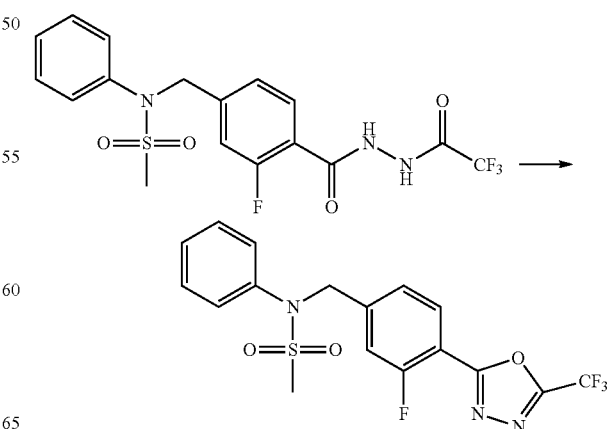

A mixture of N-(3-fluoro-4-(2-(2,2,2-trifluoroacetyl)hydrazine-1-carbonyl)benzyl)-N-phenylmethanesulfonamide (0.120 g, 0.277 mmol) and 1-methoxy-N-triethylammoniosulfonyl-methanimidate (Burgess reagent, 0.099 g, 0.415 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(3-fluoro-4-(5-(trifluoromethyl)-1,3,4-oxadiazol-2-yl)benzyl)-N-phenylmethanesulfonamide as white solid (0.079 g, 68.7%).

$^1$H NMR (400 MHz, CDCl$_3$) δ 8.05 (dd, 1H, J=8.2, 7.0 Hz), 7.46-7.25 (m, 7H), 4.96 (s, 2H), 3.02 (s, 3H); LRMS (ES) m/z 416.3 (M$^+$+1).

EXAMPLE 34

Compound 11184: N-(4-(5-(difluoromethyl)-1,3,4-oxadiazol-2-yl)-3-fluorobenzyl)-N-phenylmethanesulfonamide

[Step 1] N-(4-(2-(2,2-difluoroacetyl)hydrazine-1-carbonyl)-3-fluorobenzyl)-N-phenylmethanesulfonamide

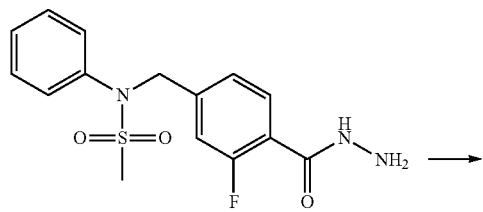

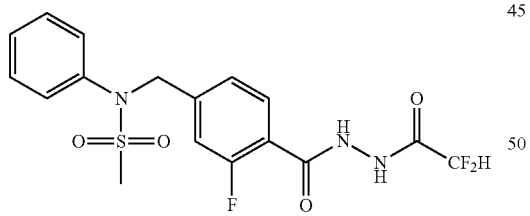

A solution of N-(3-fluoro-4-(hydrazinecarbonyl)benzyl)-N-phenylmethanesulfonamide (0.200 g, 0.593 mmol), difluoroacetic anhydride (0.071 mL, 0.652 mmol) and triethylamine (0.124 mL, 0.889 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-3-fluorobenzyl)-N-phenylmethanesulfonamide, 0.130 g, 52.8%, white solid).

[Step 2] Compound 11184

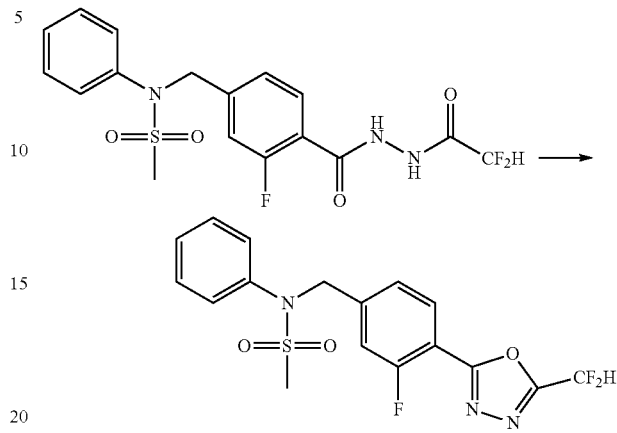

A solution of N-(4-(2-(2,2-difluoroacetyl)hydrazine-1-carbonyl)-3-fluorobenzyl)-N-phenylmethanesulfonamide (0.130 g, 0.313 mmol) and 1-methoxy-N-triethylammoniosulfonyl-methanimidate (Burgess reagent, 0.112 g, 0.469 mmol) in tetrahydrofuran (10 mL) was stirred at 150° C. for 30 min, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-3-fluorobenzyl)-N-phenylmethanesulfonamide as white solid (0.096 g, 77.2%).

$^1$H NMR (400 MHz, CDCl$_3$) δ 8.04 (dd, 1H, J=8.2, 7.0 Hz), 7.45-7.28 (m, 6H), 7.06 (s, OH), 6.94 (s, OH), 6.81 (s, OH), 4.96 (s, 2H), 3.02 (s, 3H); LRMS (ES) m/z 398.3 (M$^+$+1).

EXAMPLE 35

Compound 11186: N,N-bis(4-(5-(difluoromethyl)-1,3,4-oxadiazol-2-yl)benzyl)methanesulfonamide

[Step 1] dimethyl 4,4'-(azanediylbis(methylene))dibenzoate

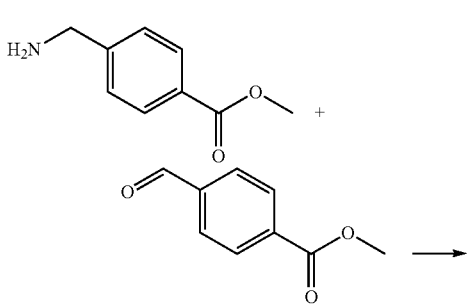

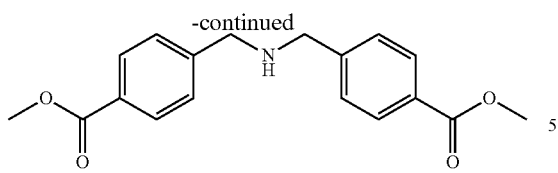

Acetic acid (0.099 mL, 1.731 mmol) was added to a solution of methyl 4-(aminomethyl)benzoate (0.260 g, 1.574 mmol) and methyl 4-formylbenzoate (0.284 g, 1.731 mmol) in dichloromethane (10 mL) at the room temperature, and the mixture was stirred at the same temperature for 30 min. The reaction mixture was treated with sodium triacetoxyborohydride (0.667 g, 3.148 mmol), and stirred for additional 12 hr at the same temperature. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 12 g cartridge; ethyl acetate/hexane=0% to 30%) to give dimethyl 4,4'-(azanediylbis(methylene))dibenzoate as white solid (0.248 g, 50.3%).

[Step 2] dimethyl 4,4'-(((methylsulfonyl)azanediyl)bis(methylene))dibenzoate

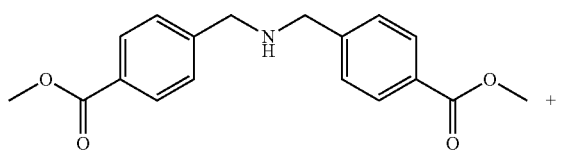
+
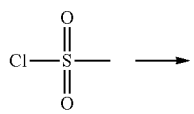
→
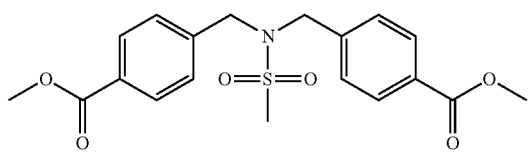

A solution of dimethyl 4,4'-(azanediylbis(methylene))dibenzoate (0.248 g, 0.791 mmol), triethylamine (0.165 mL, 1.187 mmol) and methanesulfonyl chloride (0.074 mL, 0.950 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 20%) to give dimethyl 4,4'-(((methylsulfonyl)azanediyl)bis(methylene))dibenzoate as white solid (0.250 g, 80.7%).

[Step 3] N,N-bis(4-(hydrazinecarbonyl)benzyl)methanesulfonamide

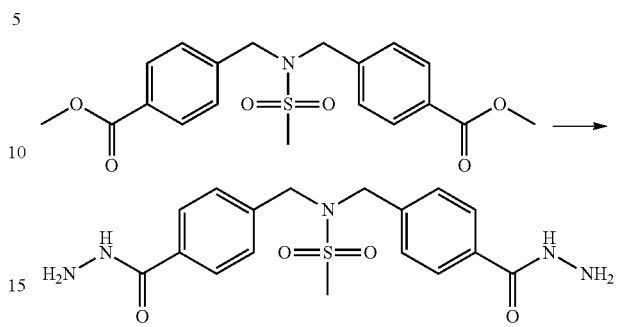

A mixture of dimethyl 4,4'-(((methylsulfonyl)azanediyl)bis(methylene))dibenzoate (0.250 g, 0.639 mmol) and hydrazine hydrate (0.320 g, 6.387 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N,N-bis(4-(hydrazinecarbonyl)benzyl)methanesulfonamide, 0.210 g, 84.0%, white solid).

[Step 4] Compound 11186

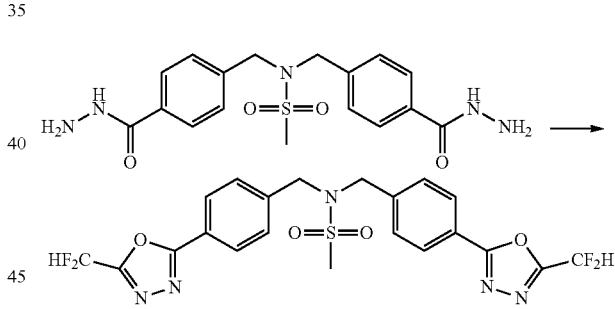

A solution of N,N-bis(4-(hydrazinecarbonyl)benzyl)methanesulfonamide (0.100 g, 0.255 mmol), difluoroacetic anhydride (0.033 mL, 0.307 mmol) and triethylamine (0.071 mL, 0.511 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N,N-bis(4-(5-(difluoromethyl)-1,3,4-oxadiazol-2-yl)benzyl)methanesulfonamide as white solid (0.079 g, 60.5%).

$^1$H NMR (400 MHz, CDCl$_3$) δ 8.10 (d, 4H, J=8.0 Hz), 7.48 (d, 4H, J=7.8 Hz), 7.07 (s, 0.3H), 6.94 (s, 0.8H), 6.81 (s, 0.4H), 4.49 (s, 4H), 2.96 (s, 3H); LRMS (ES) m/z 512.2 (M$^+$+1).

EXAMPLE 36

Compound 11190: N-(3-chlorophenyl)-N-(2-fluoro-4-(5-(trifluoromethyl)-1,3,4-oxadiazol-2-yl)benzyl)methanesulfonamide

[Step 1] N-(3-chlorophenyl)methanesulfonamide

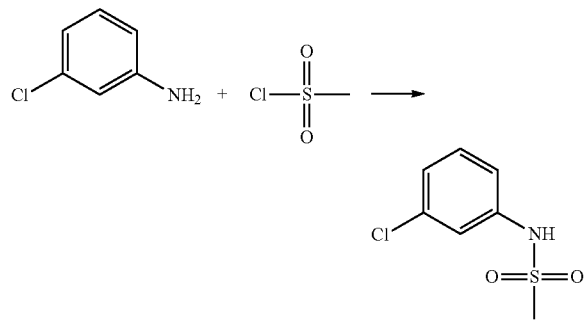

A solution of 3-chloroaniline (0.500 g, 3.919 mmol), pyridine (0.348 mL, 4.311 mmol) and methanesulfonyl chloride (0.366 mL, 4.703 mmol) in dichloromethane (10 mL) was stirred at the room temperature for 5 hr. Then, water was added to the reaction mixture, followed by extraction with dichloromethane. The organic layer was washed with aqueous 1N-hydrochloric acid solution, dried with anhydrous MgSO₄, filtered, and concentrated in vacuo. The title compound was used without further purification (N-(3-chlorophenyl)methanesulfonamide, 0.700 g, 86.8%, yellow solid).

[Step 2] methyl 4-((N-(3-chlorophenyl)methylsulfonamido)methyl)-3-fluorobenzoate

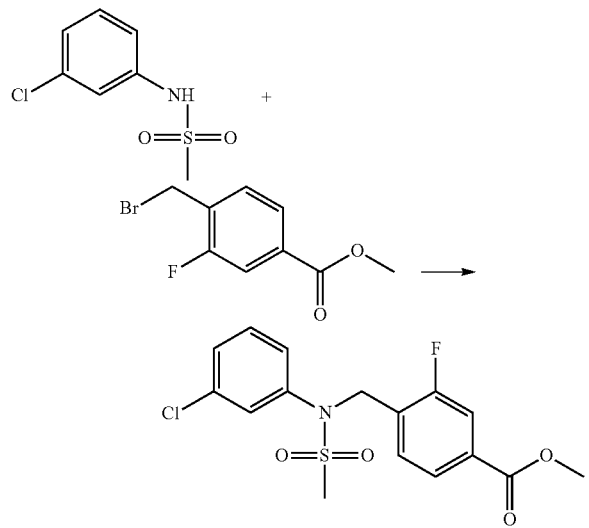

A solution of N-(3-chlorophenyl)methanesulfonamide (0.700 g, 3.404 mmol), sodium hydride (60.00%, 0.163 g, 4.084 mmol) and methyl 4-(bromomethyl)-3-fluorobenzoate (0.925 g, 3.744 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 30%) to give methyl 4-((N-(3-chlorophenyl)methylsulfonamido)methyl)-3-fluorobenzoate as yellow solid (0.640 g, 50.6%).

[Step 3] N-(3-chlorophenyl)-N-(2-fluoro-4-(hydrazinecarbonyl)benzyl)methanesulfonamide

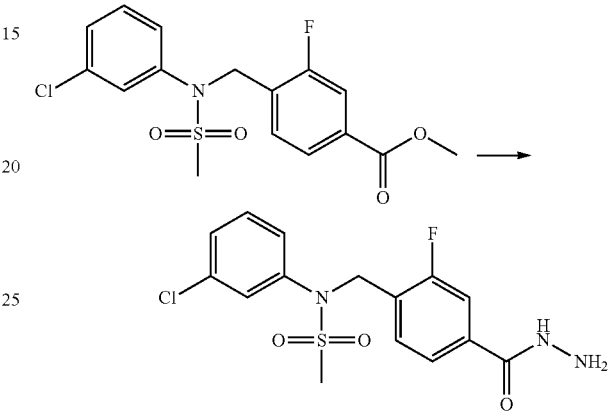

A mixture of methyl 4-((N-(3-chlorophenyl)methylsulfonamido)methyl)-3-fluorobenzoate (0.640 g, 1.721 mmol) and hydrazine hydrate (0.862 g, 17.213 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(3-chlorophenyl)-N-(2-fluoro-4-(hydrazinecarbonyl)benzyl)methanesulfonamide, 0.570 g, 89.1%, white solid).

[Step 4] N-(3-chlorophenyl)-N-(2-fluoro-4-(2-(2,2,2-trifluoroacetyl)hydrazine-1-carbonyl)benzyl)methanesulfonamide

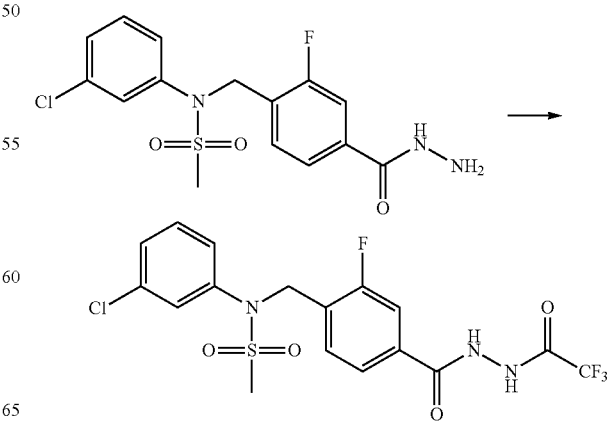

A solution of N-(3-chlorophenyl)-N-(2-fluoro-4-(hydrazinecarbonyl)benzyl)methanesulfonamide (0.250 g, 0.672 mmol), trifluoroacetic anhydride (0.112 mL, 0.807 mmol) and triethylamine (0.187 mL, 1.345 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(3-chlorophenyl)-N-(2-fluoro-4-(2-(2,2,2-trifluoroacetyl)hydrazine-1-carbonyl)benzyl)methanesulfonamide, 0.170 g, 54.0%, yellow solid).

[Step 5] Compound 11190

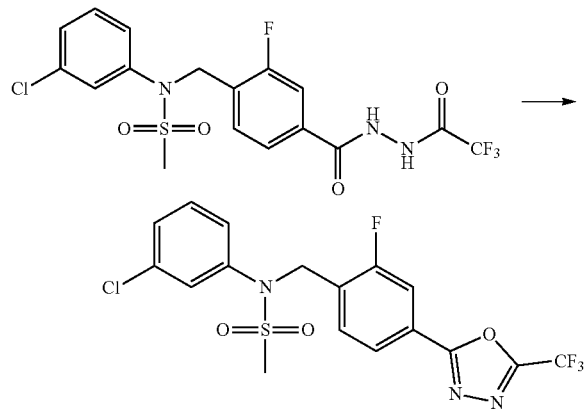

A mixture of N-(3-chlorophenyl)-N-(2-fluoro-4-(2-(2,2,2-trifluoroacetyl)hydrazine-1-carbonyl)benzyl)methanesulfonamide (0.170 g, 0.363 mmol) and 1-methoxy-N-triethylammoniosulfonyl-methanimidate (Burgess reagent, 0.130 g, 0.545 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 30%) to give N-(3-chlorophenyl)-N-(2-fluoro-4-(5-(trifluoromethyl)-1,3,4-oxadiazol-2-yl)benzyl)methanesulfonamide as white solid (0.110 g, 67.3%).

$^1$H NMR (400 MHz, CDCl$_3$) δ 7.90 (dd, 1H, J=8.0, 1.7 Hz), 7.78 (dd, 1H, J=9.9, 1.7 Hz), 7.68 (t, 1H, J=7.6 Hz), 7.39-7.27 (m, 3H), 7.32-7.19 (m, 1H), 5.03 (s, 2H), 3.04 (s, 3H); LRMS (ES) m/z 450.2 (M$^+$+1).

EXAMPLE 37

Compound 11191: N-(3-chlorophenyl)-N-(4-(5-(difluoromethyl)-1,3,4-oxadiazol-2-yl)-2-fluorobenzyl)methanesulfonamide

[Step 1] N-(3-chlorophenyl)-N-(4-(2-(2,2-difluoroacetyl)hydrazine-1-carbonyl)-2-fluorobenzyl)methanesulfonamide

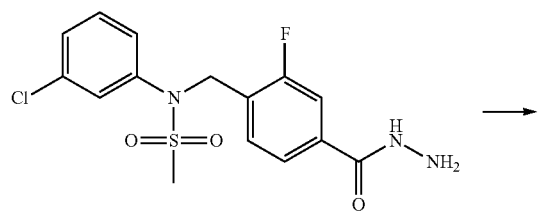

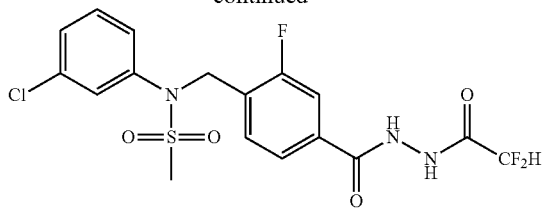

A solution of N-(3-chlorophenyl)-N-(2-fluoro-4-(hydrazinecarbonyl)benzyl)methanesulfonamide (0.250 g, 0.672 mmol), difluoroacetic anhydride (0.088 mL, 0.807 mmol) and triethylamine (0.187 mL, 1.345 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(3-chlorophenyl)-N-(4-(2-(2,2-difluoroacetyl)hydrazine-1-carbonyl)-2-fluorobenzyl)methanesulfonamide, 0.180 g, 59.5%, yellow solid).

[Step 2] Compound 11191

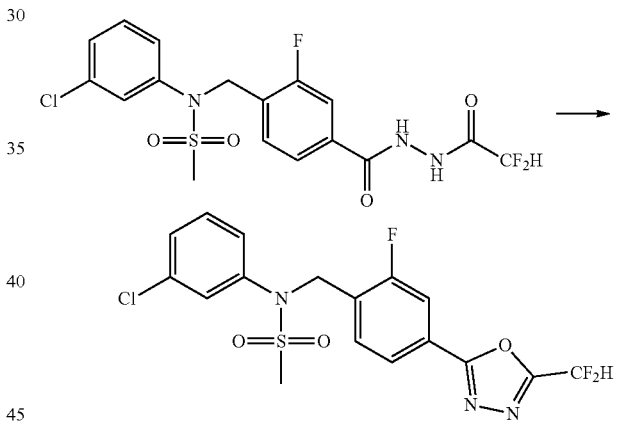

A mixture of N-(3-chlorophenyl)-N-(4-(2-(2,2-difluoroacetyl)hydrazine-1-carbonyl)-2-fluorobenzyl)methanesulfonamide (0.180 g, 0.400 mmol) and 1-methoxy-N-triethylammoniosulfonyl-methanimidate (Burgess reagent, 0.143 g, 0.600 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(3-chlorophenyl)-N-(4-(5-(difluoromethyl)-1,3,4-oxadiazol-2-yl)-2-fluorobenzyl)methanesulfonamide as white solid (0.120 g, 69.4%).

$^1$H NMR (400 MHz, CDCl$_3$) δ 7.89 (dd, 1H, J=8.0, 1.7 Hz), 7.76 (dd, 1H, J=10.0, 1.7 Hz), 7.65 (t, 1H, J=7.6 Hz), 7.39-7.18 (m, 4H), 7.05 (s, 0.2H), 6.93 (s, 0.5H), 6.80 (s, 0.2H), 5.02 (s, 2H), 3.04 (s, 3H); LRMS (ES) m/z 432.0 (M$^+$+1).

EXAMPLE 38

Compound 11192: N-(2-fluoro-4-(5-(trifluoromethyl)-1,3,4-oxadiazol-2-yl)benzyl)-N-(4-methoxyphenyl)methanesulfonamide

[Step 1] N-(4-methoxyphenyl)methanesulfonamide

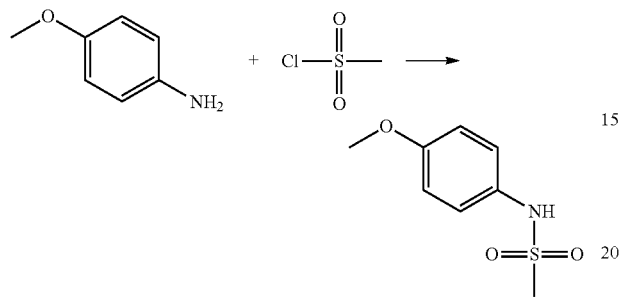

A solution of 4-methoxyaniline (0.600 g, 4.872 mmol), pyridine (0.424 g, 5.359 mmol) and methanesulfonyl chloride (0.670 g, 5.846 mmol) in dichloromethane (10 mL) was stirred at the room temperature for 5 hr. Then, water was added to the reaction mixture, followed by extraction with ethyl acetate. The organic layer was washed with aqueous 1N-hydrochloric acid solution, dried with anhydrous MgSO$_4$, filtered, and concentrated in vacuo. The title compound was used without further purification (N-(4-methoxyphenyl)methanesulfonamide, 0.840 g, 85.7%, yellow solid).

[Step 2] methyl 3-fluoro-4-((N-(4-methoxyphenyl)methylsulfonamido)methyl)benzoate

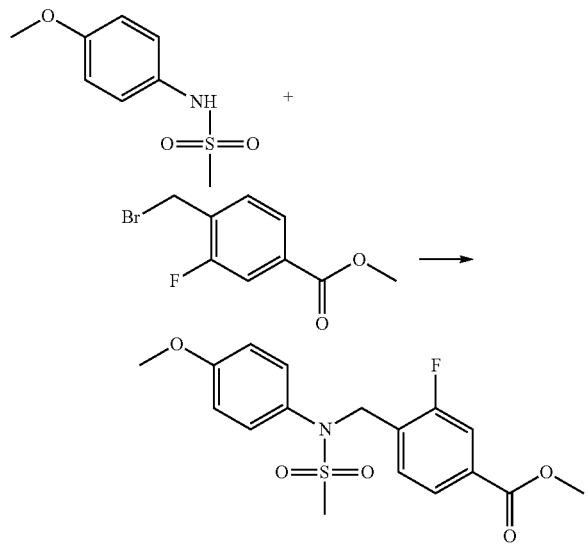

A solution of N-(4-methoxyphenyl)methanesulfonamide (1.000 g, 4.969 mmol), sodium hydride (60.00%, 0.239 g, 5.963 mmol) and methyl 4-(bromomethyl)-3-fluorobenzoate (1.350 g, 5.466 mmol) in N,N-dimethylformide (20 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 3-fluoro-4-((N-(4-methoxyphenyl)methylsulfonamido)methyl)benzoate as yellow solid (0.810 g, 44.4%).

[Step 3] N-(2-fluoro-4-(hydrazinecarbonyl)benzyl)-N-(4-methoxyphenyl)methanesulfonamide

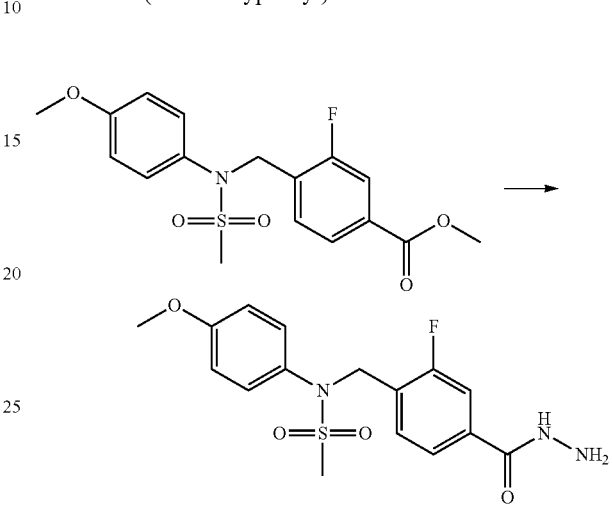

A mixture of methyl 3-fluoro-4-((N-(4-methoxyphenyl)methylsulfonamido)methyl)benzoate (0.810 g, 2.205 mmol) and hydrazine hydrate (1.104 g, 22.047 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(4-methoxyphenyl)methanesulfonamide, 0.700 g, 86.4%, white solid).

[Step 4] N-(2-fluoro-4-(2-(2,2,2-trifluoroacetyl)hydrazine-1-carbonyl)benzyl)-N-(4-methoxyphenyl)methanesulfonamide

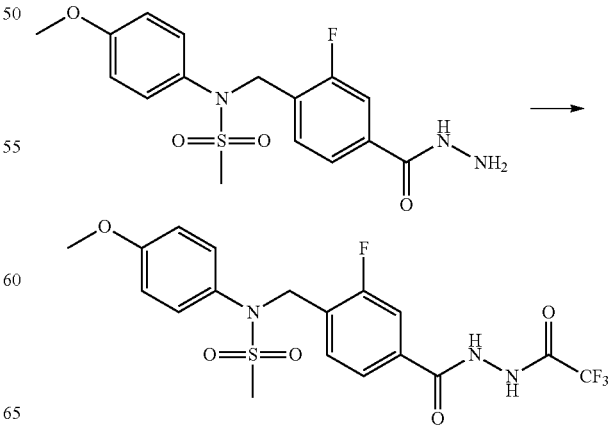

A solution of N-(2-fluoro-4-(hydrazinecarbonyl)benzyl)-N-(4-methoxyphenyl)methanesulfonamide (0.350 g, 0.953 mmol), trifluoroacetic anhydride (0.159 mL, 1.143 mmol) and triethylamine (0.264 mL, 1.905 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous $MgSO_4$, filtered, and concentrated in vacuo. The title compound was used without further purification (N-(2-fluoro-4-(2-(2,2,2-trifluoroacetyl)hydrazine-1-carbonyl)benzyl)-N-(4-methoxyphenyl)methanesulfonamide, 0.250 g, 56.6%, yellow solid).

[Step 5] Compound 11192

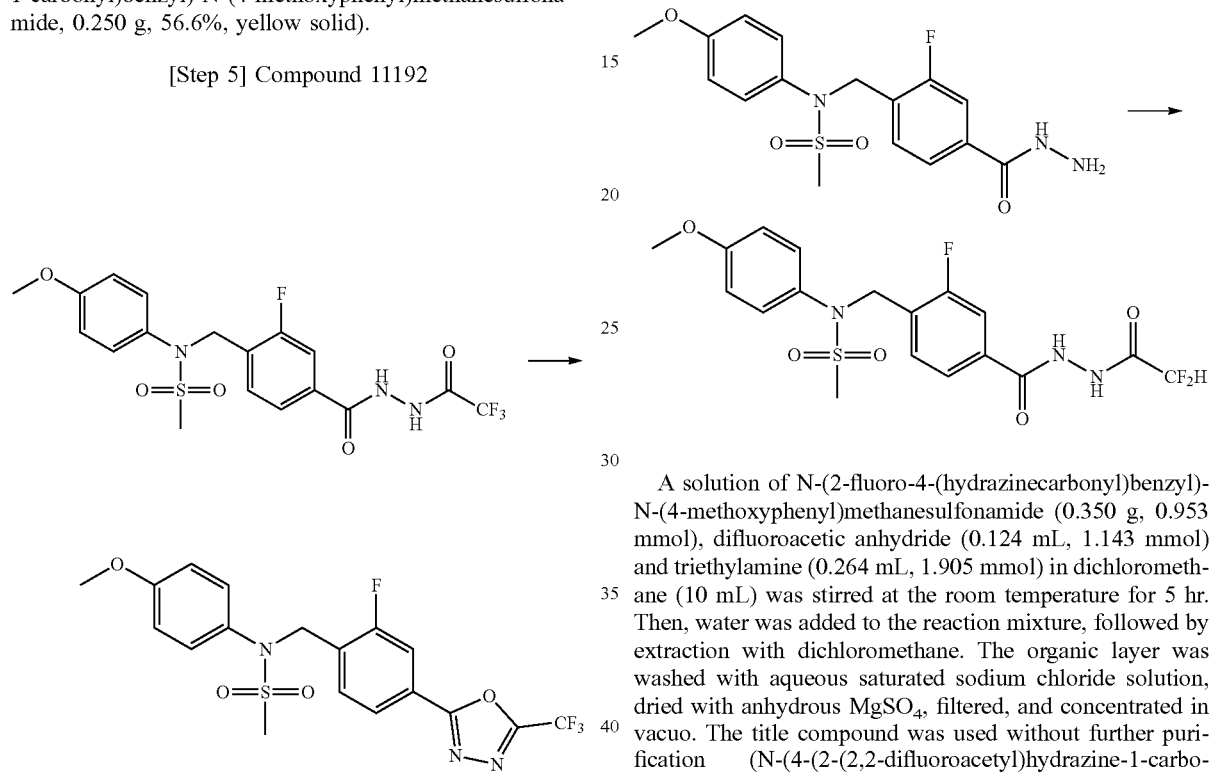

A mixture of N-(2-fluoro-4-(2-(2,2,2-trifluoroacetyl)hydrazine-1-carbonyl)benzyl)-N-(4-methoxyphenyl)methanesulfonamide (0.250 g, 0.539 mmol) and 1-methoxy-N-triethylammoniosulfonyl-methanimidate (Burgess reagent, 0.193 g, 0.809 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 4 g cartridge; ethyl acetate/hexane=0% to 40%) to give N-(2-fluoro-4-(5-(trifluoromethyl)-1,3,4-oxadiazol-2-yl)benzyl)-N-(4-methoxyphenyl)methanesulfonamide as yellow solid (0.190 g, 79.1%).

$^1$H NMR (400 MHz, $CDCl_3$) δ 7.88 (dd, 1H, J=8.0, 1.8 Hz), 7.78-7.65 (m, 2H), 7.26-7.16 (m, 2H), 6.92-6.81 (m, 2H), 4.98 (s, 2H), 3.79 (s, 3H), 3.01 (s, 3H); LRMS (ES) m/z 446.2 ($M^+$+1).

EXAMPLE 39

Compound 11193: N-(4-(5-(difluoromethyl)-1,3,4-oxadiazol-2-yl)-2-fluorobenzyl)-N-(4-methoxyphenyl)methanesulfonamide

[Step 1] N-(4-(2-(2,2-difluoroacetyl)hydrazine-1-carbonyl)-2-fluorobenzyl)-N-(4-methoxyphenyl)methanesulfonamide

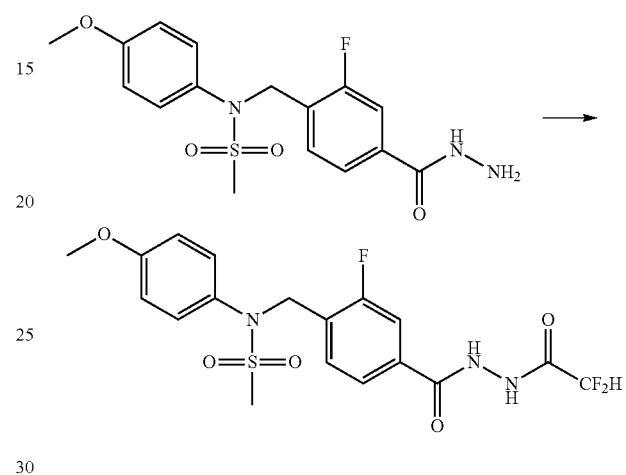

A solution of N-(2-fluoro-4-(hydrazinecarbonyl)benzyl)-N-(4-methoxyphenyl)methanesulfonamide (0.350 g, 0.953 mmol), difluoroacetic anhydride (0.124 mL, 1.143 mmol) and triethylamine (0.264 mL, 1.905 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous $MgSO_4$, filtered, and concentrated in vacuo. The title compound was used without further purification (N-(4-(2-(2,2-difluoroacetyl)hydrazine-1-carbonyl)-2-fluorobenzyl)-N-(4-methoxyphenyl)methanesulfonamide, 0.260 g, 61.3%, white solid).

[Step 2] Compound 11193

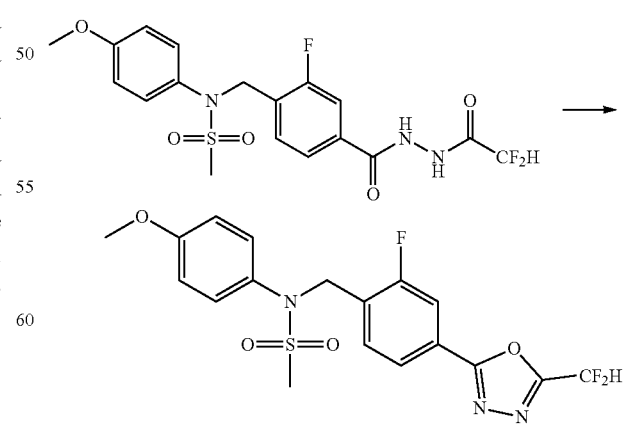

A mixture of N-(4-(2-(2,2-difluoroacetyl)hydrazine-1-carbonyl)-2-fluorobenzyl)-N-(4-methoxyphenyl)methanesulfonamide (0.260 g, 0.584 mmol) and 1-methoxy-N-triethylammoniosulfonyl-methanimidate (Burgess reagent, 0.209 g, 0.876 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 30%) to give N-(4-(5-(difluoromethyl)-1,3,4-oxadiazol-2-yl)-2-fluorobenzyl)-N-(4-methoxyphenyl)methanesulfonamide as yellow solid (0.180 g, 72.1%).

$^1$H NMR (400 MHz, CDCl$_3$) δ 7.88 (dd, 1H, J=8.0, 1.7 Hz), 7.75 (dd, 1H, J=9.9, 1.7 Hz), 7.67 (dd, 1H, J=8.0, 7.3 Hz), 7.26-7.16 (m, 2H), 7.05 (s, 0.2H), 6.92 (s, 0.5H), 6.89-6.82 (m, 2H), 6.80 (s, 0.2H), 4.98 (s, 2H), 3.79 (s, 3H), 3.01 (s, 3H); LRMS (ES) m/z 428.3 (M$^+$+1).

EXAMPLE 40

Compound 11194: N-(2-fluoro-4-(5-(trifluoromethyl)-1,3,4-oxadiazol-2-yl)benzyl)-N-(pyrimidin-5-yl)methanesulfonamide

[Step 1] N-(pyrimidin-5-yl)methanesulfonamide

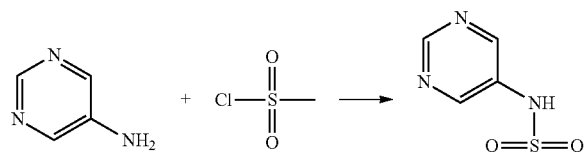

A solution of pyrimidin-5-amine (0.500 g, 5.257 mmol), pyridine (0.467 mL, 5.783 mmol) and methanesulfonyl chloride (0.492 mL, 6.308 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give N-(pyrimidin-5-yl)methanesulfonamide as yellow solid (0.610 g, 67.0%).

[Step 2] methyl 3-fluoro-4-((N-(pyrimidin-5-yl)methylsulfonamido)methyl)benzoate

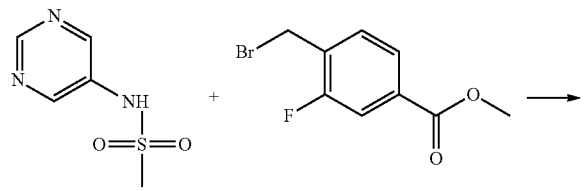

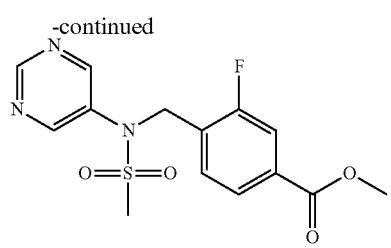

A solution of N-(pyrimidin-5-yl)methanesulfonamide (0.610 g, 3.522 mmol), sodium hydride (60.00%, 0.169 g, 4.227 mmol) and methyl 4-(bromomethyl)-3-fluorobenzoate (0.957 g, 3.874 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 3-fluoro-4-((N-(pyrimidin-5-yl)methylsulfonamido)methyl)benzoate as yellow solid (0.590 g, 49.4%).

[Step 3] N-(2-fluoro-4-(hydrazinecarbonyl)benzyl)-N-(pyrimidin-5-yl)methanesulfonamide

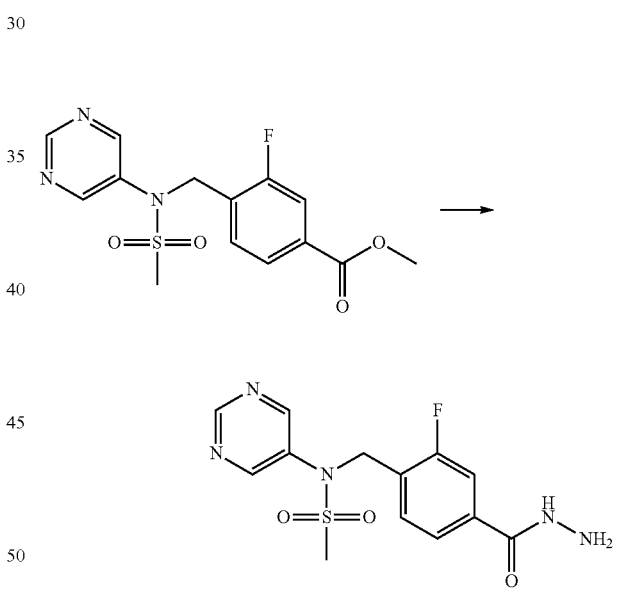

A mixture of methyl 3-fluoro-4-((N-(pyrimidin-5-yl)methylsulfonamido)methyl)benzoate (0.590 g, 1.739 mmol) and hydrazine hydrate (0.870 g, 17.387 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(pyrimidin-5-yl)methanesulfonamide, 0.520 g, 88.1%, white solid).

247

[Step 4] N-(2-fluoro-4-(2-(2,2,2-trifluoroacetyl)hydrazine-1-carbonyl)benzyl)-N-(pyrimidin-5-yl)methanesulfonamide

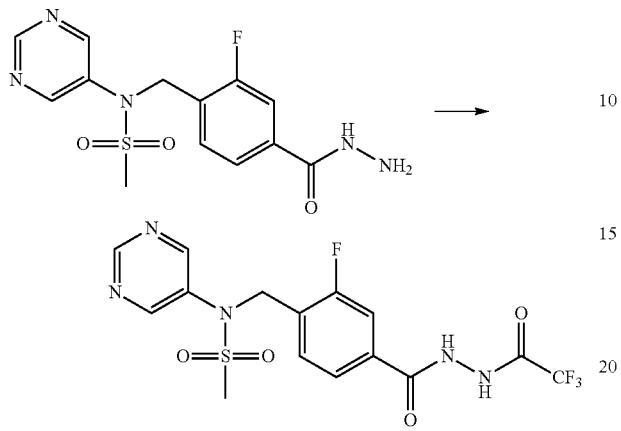

A solution of N-(2-fluoro-4-(hydrazinecarbonyl)benzyl)-N-(pyrimidin-5-yl)methanesulfonamide (0.245 g, 0.722 mmol), trifluoroacetic anhydride (0.121 mL, 0.866 mmol) and triethylamine (0.200 mL, 1.444 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(2-fluoro-4-(2-(2,2,2-trifluoroacetyl)hydrazine-1-carbonyl)benzyl)-N-(pyrimidin-5-yl)methanesulfonamide, 0.180 g, 57.3%, yellow solid).

[Step 5] Compound 11194

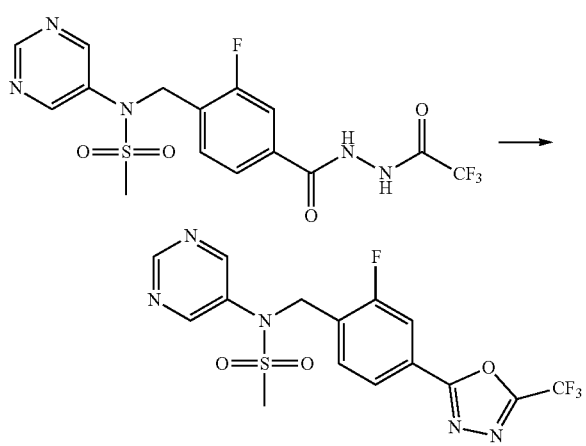

A mixture of N-(2-fluoro-4-(2-(2,2,2-trifluoroacetyl)hydrazine-1-carbonyl)benzyl)-N-(pyrimidin-5-yl)methanesulfonamide (0.180 g, 0.413 mmol) and 1-methoxy-N-triethylammoniosulfonyl-methanimidate (Burgess reagent, 0.148 g, 0.620 mmol) in tetrahydrofuran (10 mL) was heated at 150° C. for 30 min under the microwaves, and cooled down to the room temperature to terminate the reaction. Then, water was added to the reaction mixture, followed by

248 extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 60%) to give N-(2-fluoro-4-(5-(trifluoromethyl)-1,3,4-oxadiazol-2-yl)benzyl)-N-(pyrimidin-5-yl)methanesulfonamide as yellow solid (0.090 g, 52.2%).

$^1$H NMR (400 MHz, CDCl₃) δ 9.14 (d, 1H, J=0.6 Hz), 8.73 (s, 2H), 7.94 (dd, 1H, J=8.1, 1.6 Hz), 7.81 (dd, 1H, J=9.8, 1.7 Hz), 7.68 (t, 1H, J=7.6 Hz), 5.07 (s, 2H), 3.10 (s, 3H); LRMS (ES) m/z 418.3 (M⁺+1).

EXAMPLE 41

Compound 11195: N-(4-(5-(difluoromethyl)-1,3,4-oxadiazol-2-yl)-2-fluorobenzyl)-N-(pyrimidin-5-yl)methanesulfonamide

[Step 1] N-(4-(2-(2,2-difluoroacetyl)hydrazine-1-carbonyl)-2-fluorobenzyl)-N-(pyrimidin5-5yl)methanesulfonamide

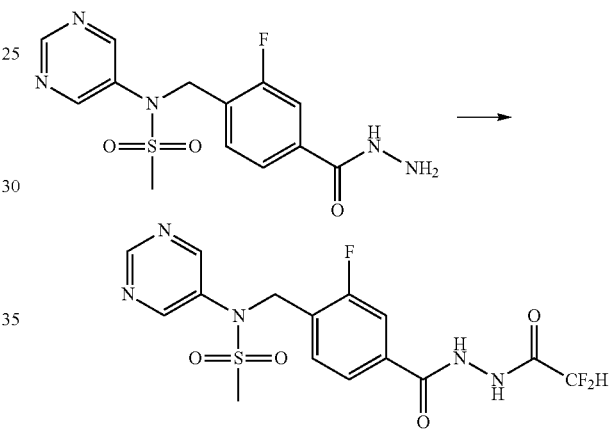

A solution of N-(2-fluoro-4-(hydrazinecarbonyl)benzyl)-N-(pyrimidin-5-yl)methanesulfonamide (0.245 g, 0.722 mmol), difluoroacetic anhydride (0.094 mL, 0.866 mmol) and triethylamine (0.200 mL, 1.444 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification N-(4-(2-(2,2-difluoroacetyl)hydrazine-1-carbonyl)-2-fluorobenzyl)-N-(pyrimidin5-5yl)methanesulfonamide, 0.170 g, 52.3%, yellow solid).

[Step 2] Compound 11195

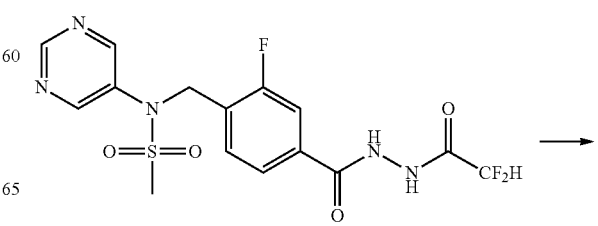

-continued

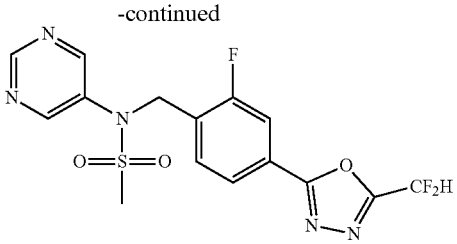

A mixture of N-(4-(2-(2,2-difluoroacetyl)hydrazine-1-carbonyl)-2-fluorobenzyl)-N-(pyrimidin-5-yl)methanesulfonamide (0.170 g, 0.407 mmol) and 1-methoxy-N-triethylammoniosulfonyl-methanimidate (Burgess reagent, 0.146 g, 0.611 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(4-(5-(difluoromethyl)-1,3,4-oxadiazol-2-yl)-2-fluorobenzyl)-N-(pyrimidin-5-yl)methanesulfonamide as yellow solid (0.100 g, 61.5%).

$^1$H NMR (400 MHz, CDCl$_3$) δ 9.12 (s, 1H), 8.70 (s, 2H), 7.91 (dd, 1H, J=8.1, 1.6 Hz), 7.78 (dd, 1H, J=10.0, 1.6 Hz), 7.64 (t, 1H, J=7.6 Hz), 7.04 (s, 0.04H), 6.91 (s, 0.06H), 6.78 (s, 0.2H), 5.04 (s, 2H), 3.08 (s, 3H); LRMS (ES) m/z 400.1 (M$^+$+1).

EXAMPLE 42

Compound 11196: N-(3-bromophenyl)-N-(2-fluoro-4-(5-(trifluoromethyl)-1,3,4-oxadiazol-2-yl)benzyl)methanesulfonamide

[Step 1] N-(3-bromophenyl)methanesulfonamide

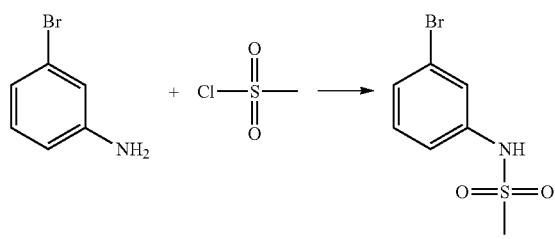

A solution of 3-bromoaniline (1.000 g, 5.813 mmol), pyridine (0.516 mL, 6.394 mmol) and methanesulfonyl chloride (0.799 g, 6.976 mmol) in dichloromethane (50 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The residue was chromatographed (SiO$_2$, 40 g cartridge; ethyl acetate/hexane=0% to 30%) to give N-(3-bromophenyl)methanesulfonamide as white solid (1.100 g, 75.7%).

[Step 2] methyl 4-((N-(3-bromophenyl)methylsulfonamido)methyl)-3-fluorobenzoate

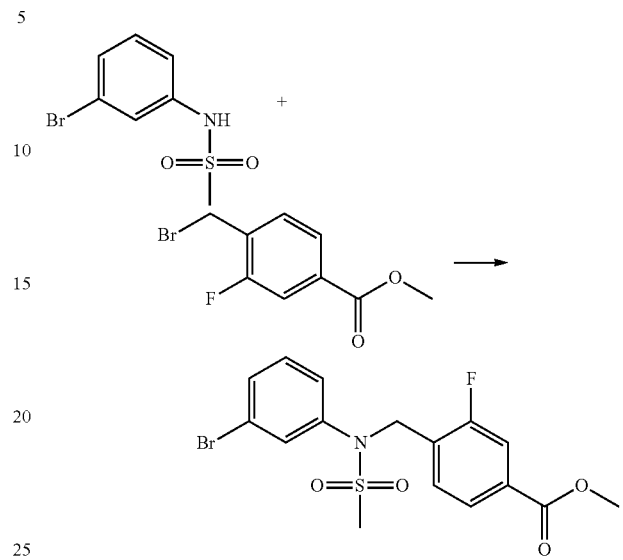

A solution of N-(3-bromophenyl)methanesulfonamide (0.500 g, 1.999 mmol), sodium hydride (60.00%, 0.096 g, 2.399 mmol) and methyl 4-(bromomethyl)-3-fluorobenzoate (0.543 g, 2.199 mmol) in N,N-dimethylformamide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 4-((N-(3-bromophenyl)methylsulfonamido)methyl)-3-fluorobenzoate as yellow solid (0.490 g, 58.9%).

[Step 3] N-(3-bromophenyl)-N-(2-fluoro-4-(hydrazinecarbonyl)benzyl)methanesulfonamide

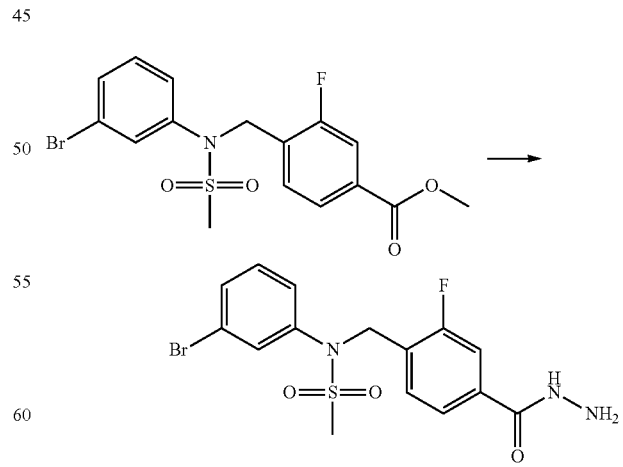

A mixture of methyl 4-((N-(3-bromophenyl)methylsulfonamido)methyl)-3-fluorobenzoate (0.490 g, 1.177 mmol) and hydrazine hydrate (0.589 g, 11.771 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-bromophenyl)-N-(2-fluoro-4-(hydrazinecarbonyl)benzyl)methanesulfonamide, 0.400 g, 81.6%, white solid).

[Step 4] Compound 11196

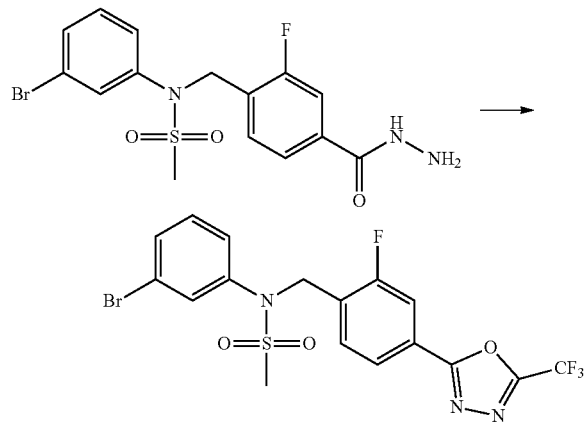

A solution of N-(3-bromophenyl)-N-(2-fluoro-4-(hydrazinecarbonyl)benzyl)methanesulfonamide (0.200 g, 0.480 mmol), trifluoroacetic anhydride (0.074 mL, 0.529 mmol) and triethylamine (0.100 mL, 0.721 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give N-(3-bromophenyl)-N-(2-fluoro-4-(5-(trifluoromethyl)-1,3,4-oxadiazol-2-yl)benzyl)methanesulfonamide as white solid (0.100 g, 42.1%).

$^1$H NMR (400 MHz, CDCl$_3$) δ 7.90 (dd, 1H, J=8.1, 1.7 Hz), 7.77 (dd, 1H, J=9.8, 1.6 Hz), 7.68 (dd, 1H, J=8.1, 7.2 Hz), 7.52 (t, 1H, J=1.9 Hz), 7.48-7.44 (m, 1H), 7.29-7.22 (m, 2H), 5.03 (s, 2H), 3.04 (s, 3H); LRMS (ES) m/z 496.2 (M$^+$+1).

EXAMPLE 43

Compound 11197: N-(3-bromophenyl)-N-(4-(5-(difluoromethyl)-1,3,4-oxadiazol-2-yl)-2-fluorobenzyl)methanesulfonamide

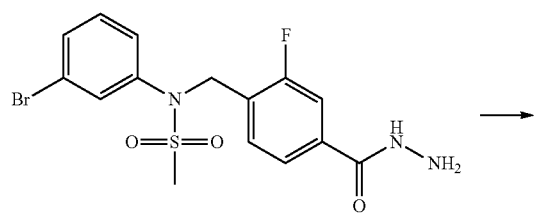

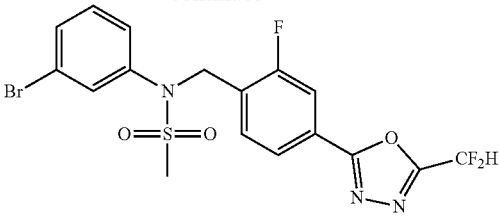

A solution of N-(3-bromophenyl)-N-(2-fluoro-4-(hydrazinecarbonyl)benzyl)methanesulfonamide (0.200 g, 0.480 mmol), difluoroacetic anhydride (0.057 mL, 0.529 mmol) and triethylamine (0.100 mL, 0.721 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(3-bromophenyl)-N-(4-(5-(difluoromethyl)-1,3,4-oxadiazol-2-yl)-2-fluorobenzyl)methanesulfonamide as yellow solid (0.130 g, 56.8%).

$^1$H NMR (400 MHz, CDCl$_3$) δ 7.89 (dd, 1H, J=8.0, 1.6 Hz), 7.77 (dt, 1H, J=10.0, 1.3 Hz), 7.65 (t, 1H, J=7.6 Hz), 7.54-7.49 (m, 1H), 7.48-7.42 (m, 1H), 7.32-7.20 (m, 2H), 7.05 (s, 0.2H), 6.93 (s, 0.5H), 6.80 (s, 0.2H), 5.02 (s, 2H), 3.04 (s, 3H); LRMS (ES) m/z 478.2 (M$^+$+1).

EXAMPLE 44

Compound 11216: N-(3-fluorophenyl)-N-((5-(5-(trifluoromethyl)-1,3,4-oxadiazol-2-yl)pyridin-2-yl)methyl)methanesulfonamide

[Step 1] methyl 6-(((3-fluorophenyl)amino)methyl)nicotinate

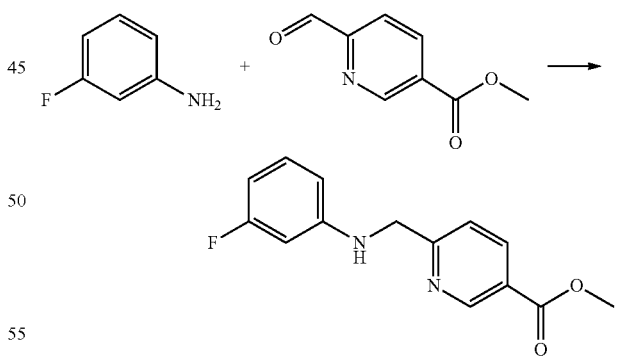

Acetic acid (0.283 mL, 4.950 mmol) was added to a solution of 3-fluoroaniline (0.500 g, 4.500 mmol) and methyl 6-formylnicotinate (0.817 g, 4.950 mmol) in dichloromethane (20 mL) at the room temperature, and the mixture was stirred at the same temperature for 30 min. The reaction mixture was treated with sodium triacetoxyborohydride (1.907 g, 8.999 mmol), and stirred for additional 12 hr at the same temperature. Then, water was added to the reaction mixture, followed by extraction with dichloromethane. The organic layer was washed with aqueous saturated sodium bicarbonate solution, dried with anhydrous MgSO₄, filtered, and concentrated in vacuo. The residue was chromatographed (SiO₂, 12 g cartridge; ethyl acetate/hexane=0% to 40%) to give methyl 6-(((3-fluorophenyl)amino)methyl)nicotinate as yellow oil (0.500 g, 42.7%).

[Step 2] methyl 6-((N-(3-fluorophenyl)methylsulfonamido)methyl)nicotinate

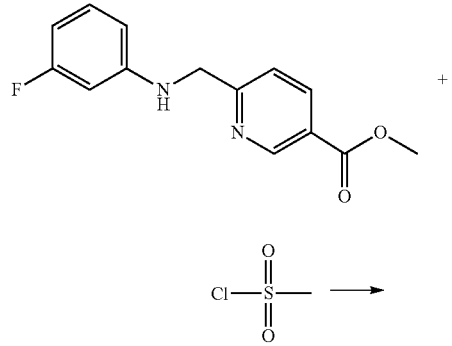

A solution of methyl 6-(((3-fluorophenyl)amino)methyl)nicotinate (0.500 g, 1.921 mmol), pyridine (0.186 mL, 2.305 mmol), N,N-dimethylpyridin-4-amine (DMAP, 0.012 g, 0.096 mmol) and methanesulfonyl chloride (0.180 mL, 2.305 mmol) in dichloromethane (10 mL) was stirred at 50° C. for 12 hr, and cooled down to the room temperature to terminate the reaction. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 40%) to give methyl 6-((N-(3-fluorophenyl)methylsulfonamido)methyl)nicotinate as yellow solid (0.380 g, 58.5%).

[Step 3] N-(3-fluorophenyl)-N-((5-(hydrazinecarbonyl)pyridin-2-yl)methyl)methanesulfonamide

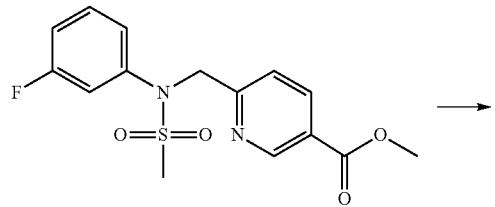

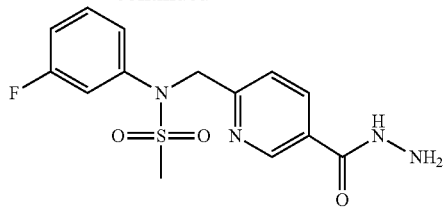

A mixture of methyl 6-((N-(3-fluorophenyl)methylsulfonamido)methyl)nicotinate (0.380 g, 1.123 mmol) and hydrazine hydrate (0.562 g, 11.231 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(3-fluorophenyl)-N-((5-(hydrazinecarbonyl)pyridin-2-yl)methyl)methanesulfonamide, 0.280 g, 73.7%, white solid).

[Step 4] Compound 11216

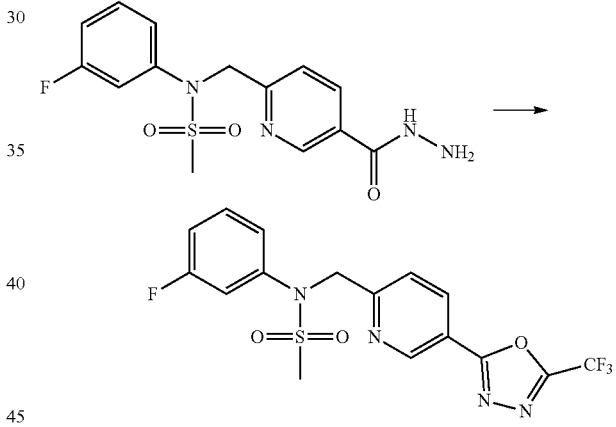

A solution of N-(3-fluorophenyl)-N-((5-(hydrazinecarbonyl)pyridin-2-yl)methyl)methanesulfonamide (0.090 g, 0.266 mmol), trifluoroacetic anhydride (0.041 mL, 0.293 mmol) and triethylamine (0.055 mL, 0.399 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(3-fluorophenyl)-N-((5-(5-(trifluoromethyl)-1,3,4-oxadiazol-2-yl)pyridin-2-yl)methyl)methanesulfonamide as white solid (0.043 g, 38.8%).

$^1$H NMR (400 MHz, CDCl₃) δ 9.27 (dd, 1H, J=2.3, 0.8 Hz), 8.41 (dd, 1H, J=8.2, 2.2 Hz), 7.73-7.66 (m, 1H), 7.38-7.31 (m, 1H), 7.26-7.17 (m, 2H), 7.07-6.97 (m, 1H), 5.16 (s, 2H), 3.10 (s, 3H); LRMS (ES) m/z 417.3 (M⁺+1).

EXAMPLE 45

Compound 11217: N-((5-(5-(difluoromethyl)-1,3,4-oxadiazol-2-yl)pyridin-2-yl)methyl)-N-(3-fluorophenyl)methanesulfonamide

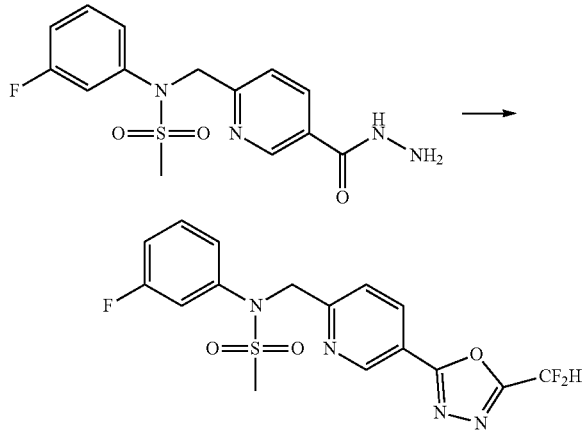

A solution of N-(3-fluorophenyl)-N-((5-(hydrazinecarbonyl)pyridin-2-yl)methyl)methanesulfonamide (0.090 g, 0.266 mmol), difluoroacetic anhydride (0.032 mL, 0.293 mmol) and triethylamine (0.055 mL, 0.399 mmol) in dichloromethane (10 mL) was stirred at the room temperature for 5 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 40%) to give N-((5-(5-(difluoromethyl)-1,3,4-oxadiazol-2-yl)pyridin-2-yl)methyl)-N-(3-fluorophenyl)methanesulfonamide as yellow solid (0.053 g, 50.0%).

$^1$H NMR (400 MHz, CDCl$_3$) δ 9.27 (dd, 1H, J=2.3, 0.9 Hz), 8.40 (dd, 1H, J=8.2, 2.2 Hz), 7.68 (dd, 1H, J=8.3, 0.8 Hz), 7.38-7.30 (m, 1H), 7.27-7.16 (m, 2H), 7.08 (s, 0.2H), 7.05-6.98 (m, 1H), 6.95 (s, 0.5H), 6.82 (s, 0.2H), 5.15 (s, 2H), 3.10 (s, 3H); LRMS (ES) m/z 399.0 (M$^+$+1).

EXAMPLE 46

Compound 11218: N-(2-fluoro-4-(5-(trifluoromethyl)-1,3,4-oxadiazol-2-yl)benzyl)-N-(2-(trifluoromethyl)phenyl)methanesulfonamide

[Step 1]
N-(2-(trifluoromethyl)phenyl)methanesulfonamide

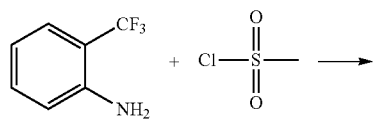

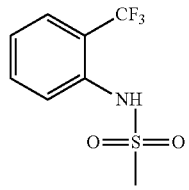

A solution of 2-(trifluoromethyl)aniline (1.000 g, 6.206 mmol), pyridine (0.551 mL, 6.827 mmol) and methanesulfonyl chloride (0.580 mL, 7.447 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO₄, filtered, and concentrated in vacuo. The title compound was used without further purification (N-(2-(trifluoromethyl)phenyl)methanesulfonamide, 1.100 g, 74.1%, yellow solid).

[Step 2] methyl 3-fluoro-4-((N-(2-(trifluoromethyl)phenyl)methylsulfonamido)methyl)benzoate

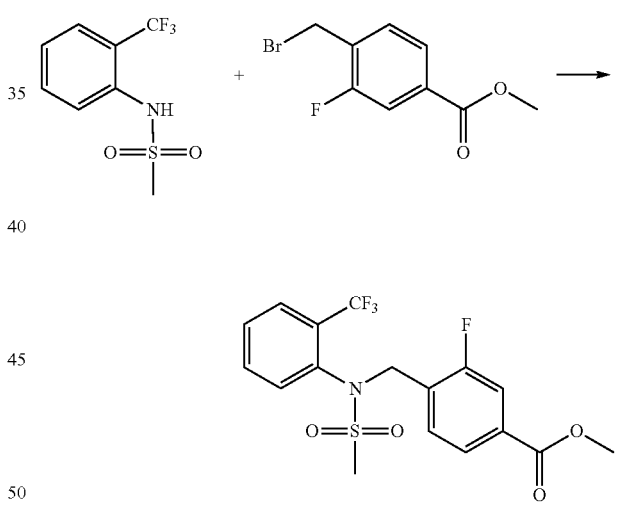

A solution of N-(2-(trifluoromethyl)phenyl)methanesulfonamide (0.500 g, 2.090 mmol), sodium hydride (60.00%, 0.100 g, 2.508 mmol) and methyl 4-(bromomethyl)-3-fluorobenzoate (0.568 g, 2.299 mmol) in N,N-dimethylformamide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 40%) to give methyl 3-fluoro-4-((N-(2-(trifluoromethyl)phenyl)methylsulfonamido)methyl)benzoate as yellow solid (0.610 g, 72.0%).

257

[Step 3] N-(2-fluoro-4-(hydrazinecarbonyl)benzyl)-N-(2-(trifluoromethyl)phenyl)methanesulfonamide

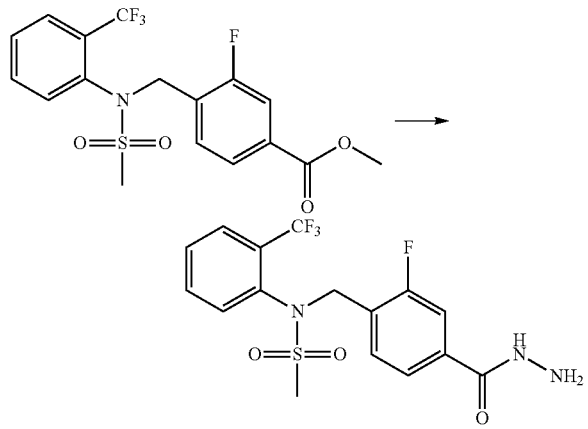

A mixture of methyl 3-fluoro-4-((N-(2-(trifluoromethyl)phenyl)methylsulfonamido)methyl)benzoate (0.610 g, 1.505 mmol) and hydrazine hydrate (0.753 g, 15.048 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(2-fluoro-4-(hydrazinecarbonyl)benzyl)-N-(2-(trifluoromethyl)phenyl)methanesulfonamide, 0.530 g, 86.9%, yellow solid).

[Step 4] Compound 11218

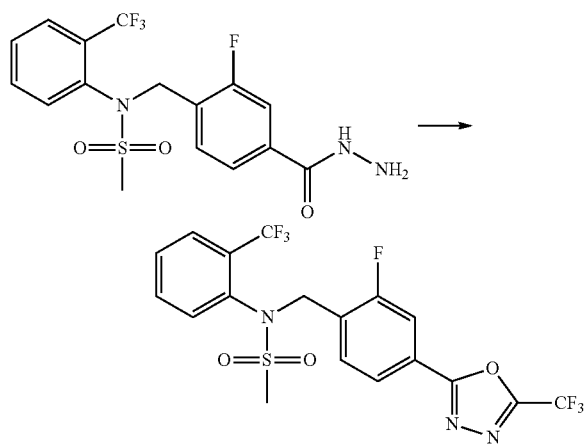

A solution of N-(2-fluoro-4-(hydrazinecarbonyl)benzyl)-N-(2-(trifluoromethyl)phenyl)methanesulfonamide (0.265 g, 0.654 mmol), trifluoroacetic anhydride (0.100 mL, 0.719 mmol) and triethylamine (0.136 mL, 0.981 mmol) in dichloromethane (10 mL) was stirred at the room temperature for 5 hr. Then, water was added to the reaction mixture, followed by extraction with dichloromethane. The organic layer was washed with aqueous saturated sodium chloride

258 solution, dried with anhydrous MgSO₄, filtered, and concentrated in vacuo. The residue was chromatographed (SiO₂, 4 g cartridge; ethyl acetate/hexane=0% to 40%) to give N-(2-fluoro-4-(5-(trifluoromethyl)-1,3,4-oxadiazol-2-yl)benzyl)-N-(2-(trifluoromethyl)phenyl)methanesulfonamide as white solid (0.190 g, 60.1%).

$^1$H NMR (400 MHz, CDCl₃) δ 7.87 (dd, 1H, J=8.0, 1.7 Hz), 7.79-7.70 (m, 2H), 7.66-7.57 (m, 1H), 7.56-7.46 (m, 2H), 7.31-7.21 (m, 1H), 5.01 (dd, 1H, J=14.7, 1.5 Hz), 4.86 (d, 1H, J=14.7 Hz), 3.12 (s, 3H); LRMS (ES) m/z 484.2 (M⁺+1).

EXAMPLE 47

Compound 11219: N-(4-(5-(difluoromethyl)-1,3,4-oxadiazol-2-yl)-2-fluorobenzyl)-N-(2-(trifluoromethyl)phenyl)methanesulfonamide

[Step 1] N-(4-(2-(2,2-difluoroacetyl)hydrazine-1-carbonyl)-2-fluorobenzyl)-N-(2-(trifluoromethyl)phenyl)methanesulfonamide

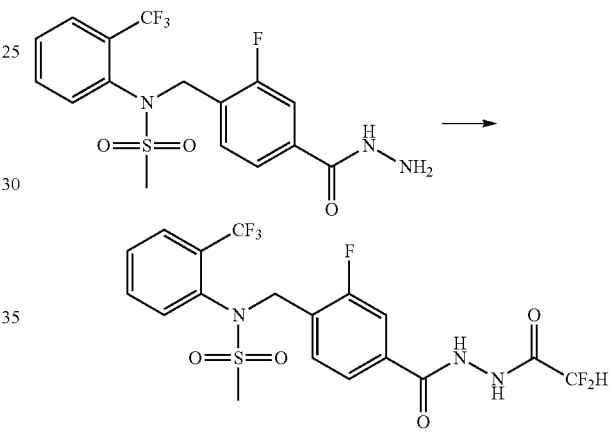

A solution of N-(2-fluoro-4-(hydrazinecarbonyl)benzyl)-N-(2-(trifluoromethyl)phenyl)methanesulfonamide (0.270 g, 0.666 mmol), difluoroacetic anhydride (0.087 mL, 0.799 mmol) and TEA (0.185 mL, 1.332 mmol) in (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(4-(2-(2,2-difluoroacetyl)hydrazine-1-carbonyl)-2-fluorobenzyl)-N-(2-(trifluoromethyl)phenyl)methanesulfonamide, 0.192 g, 59.6%, yellow solid).

[Step 2] Compound 11219

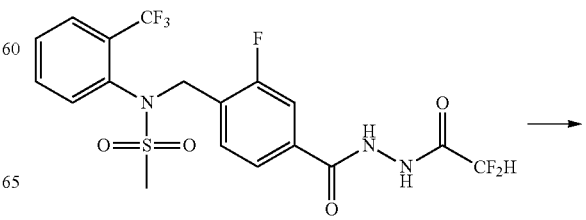

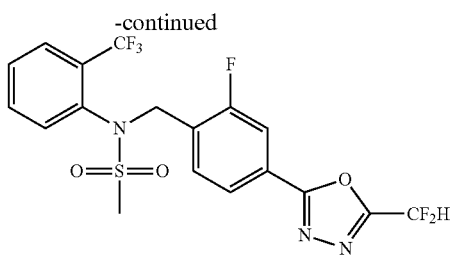

A mixture of N-(4-(2-(2,2-difluoroacetyl)hydrazine-1-carbonyl)-2-fluorobenzyl)-N-(2-(trifluoromethyl)phenyl)methanesulfonamide (0.192 g, 0.397 mmol) and 1-methoxy-N-triethylammoniosulfonyl-methanimidate (Burgess reagent, 0.142 g, 0.596 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 30%) to give N-(4-(5-(difluoromethyl)-1,3,4-oxadiazol-2-yl)-2-fluorobenzyl)-N-(2-(trifluoromethyl)phenyl)methanesulfonamide as yellow solid (0.110 g, 59.5%).

$^1$H NMR (400 MHz, CDCl$_3$) δ 7.87 (dd, 1H, J=8.0, 1.7 Hz), 7.79-7.70 (m, 2H), 7.59 (t, 1H, J=7.6 Hz), 7.55-7.46 (m, 2H), 7.27-7.21 (m, 1H), 7.06 (s, 0.2H), 6.93 (s, 0.5H), 6.80 (s, 0.2H), 5.00 (dd, 1H, J=14.8, 1.4 Hz), 4.86 (d, 1H, J=14.6 Hz), 3.12 (s, 3H); LRMS (ES) m/z 466.2 (M$^+$+1).

EXAMPLE 48

Compound 11220: N-(2-fluoro-4-(5-(trifluoromethyl)-1,3,4-oxadiazol-2-yl)benzyl)-N-(4-(trifluoromethyl)phenyl)methanesulfonamide

[Step 1] N-(4-(trifluoromethyl)phenyl)methanesulfonamide

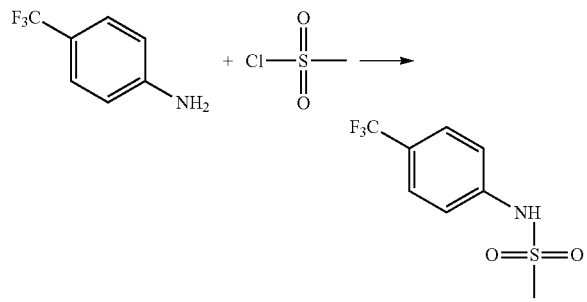

A solution of 4-(trifluoromethyl)aniline (1.000 g, 6.206 mmol), pyridine (0.551 mL, 6.827 mmol) and methanesulfonyl chloride (0.580 mL, 7.447 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(4-(trifluoromethyl)phenyl)methanesulfonamide, 1.200 g, 80.8%, yellow oil).

[Step 2] methyl 3-fluoro-4-((N-(4-(trifluoromethyl)phenyl)methylsulfonamido)methyl)benzoate

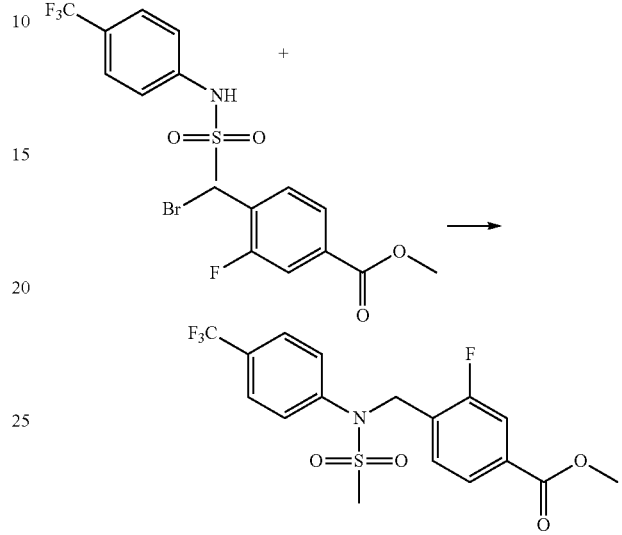

A solution of N-(4-(trifluoromethyl)phenyl)methanesulfonamide (0.500 g, 2.090 mmol), sodium hydride (60.00%, 0.100 g, 2.508 mmol) and methyl 4-(bromomethyl)-3-fluorobenzoate (0.568 g, 2.299 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 3-fluoro-4-((N-(4-(trifluoromethyl)phenyl)methylsulfonamido)methyl)benzoate as white solid (0.630 g, 74.4%).

[Step 3] N-(2-fluoro-4-(hydrazinecarbonyl)benzyl)-N-(4-(trifluoromethyl)phenyl)methanesulfonamide

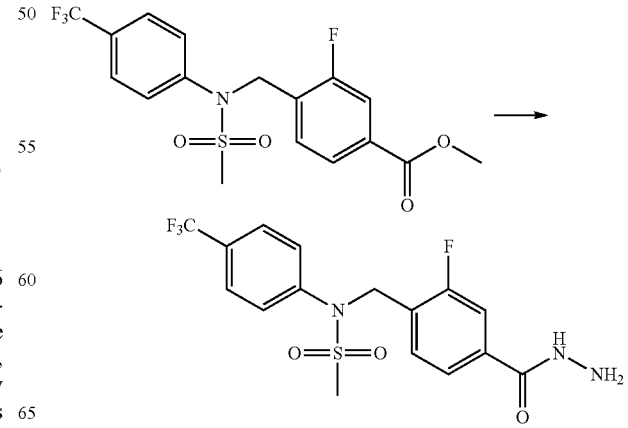

A solution of methyl 3-fluoro-4-((N-(4-(trifluoromethyl)phenyl)methylsulfonamido)methyl)benzoate (0.630 g, 1.554 mmol) and hydrazine hydrate (0.778 g, 15.542 mmol) in ethanol (10 mL) was stirred at 120° C. for 1 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(4-(trifluoromethyl)phenyl)methanesulfonamide, 0.600 g, 95.2%, yellow solid).

[Step 4] N-(2-fluoro-4-(2-(2,2,2-trifluoroacetyl)hydrazine-1-carbonyl)benzyl)-N-(4-(trifluoromethyl)phenyl)methanesulfonamide

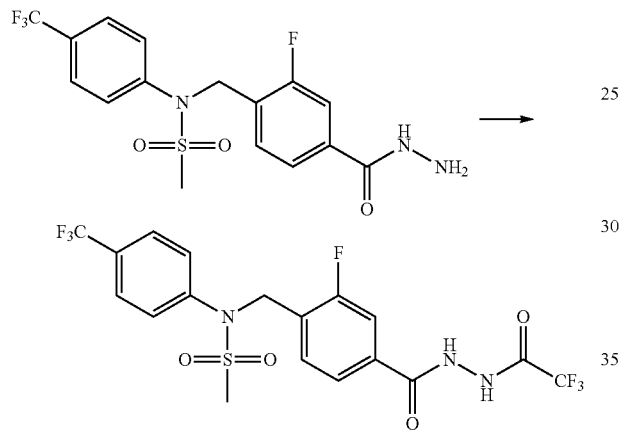

A solution of N-(2-fluoro-4-(hydrazinecarbonyl)benzyl)-N-(4-(trifluoromethyl)phenyl)methanesulfonamide (0.240 g, 0.592 mmol), trifluoroacetic anhydride (0.091 mL, 0.651 mmol) and triethylamine (0.123 mL, 0.888 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-fluoro-4-(2-(2,2,2-trifluoroacetyl)hydrazine-1-carbonyl)benzyl)-N-(4-(trifluoromethyl)phenyl)methanesulfonamide, 0.180 g, 60.6%, yellow solid).

[Step 5] Compound 11220

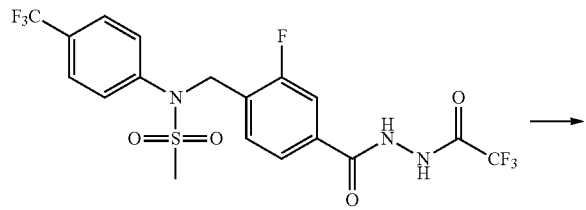

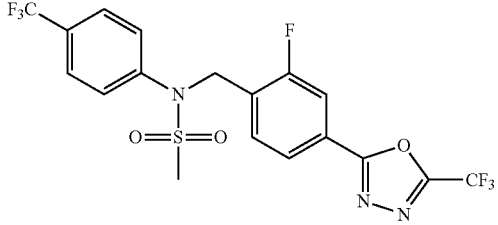

A mixture of N-(2-fluoro-4-(2-(2,2,2-trifluoroacetyl)hydrazine-1-carbonyl)benzyl)-N-(4-(trifluoromethyl)phenyl)methanesulfonamide (0.180 g, 0.359 mmol) and 1-methoxy-N-triethylammoniosulfonyl-methanimidate (Burgess reagent, 0.128 g, 0.539 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 30%) to give N-(2-fluoro-4-(5-(trifluoromethyl)-1,3,4-oxadiazol-2-yl)benzyl)-N-(4-(trifluoromethyl)phenyl)methanesulfonamide as yellow solid (0.130 g, 74.9%).
$^1$H NMR (400 MHz, CDCl$_3$) δ 7.89 (dd, 1H, J=8.1, 1.7 Hz), 7.78 (dd, 1H, J=9.8, 1.7 Hz), 7.72-7.60 (m, 3H), 7.52-7.45 (m, 2H), 5.09 (s, 2H), 3.05 (s, 3H); LRMS (ES) m/z 484.4 (M$^+$+1).

EXAMPLE 49

Compound 11221: N-(4-(5-(difluoromethyl)-1,3,4-oxadiazol-2-yl)-2-fluorobenzyl)-N-(4-(trifluoromethyl)phenyl)methanesulfonamide

[Step 1] N-(4-(2-(2,2-difluoroacetyl)hydrazine-1-carbonyl)-2-fluorobenzyl)-N-(4-(trifluoromethyl)phenyl)methanesulfonamide

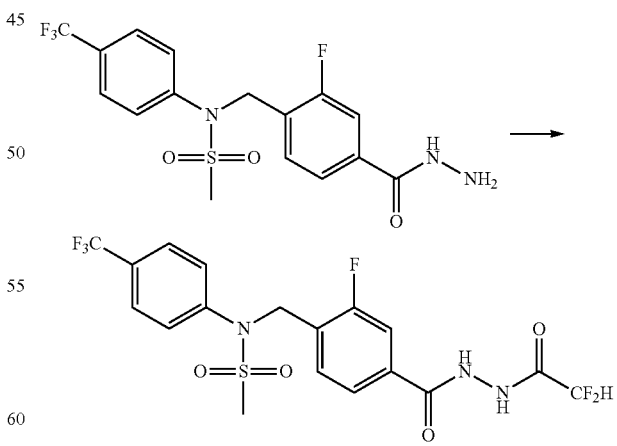

A solution of N-(2-fluoro-4-(hydrazinecarbonyl)benzyl)-N-(4-(trifluoromethyl)phenyl)methanesulfonamide (0.240 g, 0.592 mmol), difluoroacetic anhydride (0.077 mL, 0.710 mmol) and triethylamine (0.123 mL, 0.888 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(4-(2-(2,2-difluoroacetyl)hydrazine-1-carbonyl)-2-fluorobenzyl)-N-(4-(trifluoromethyl)phenyl)methanesulfonamide, 0.140 g, 48.9%, yellow solid).

[Step 2] Compound 11221

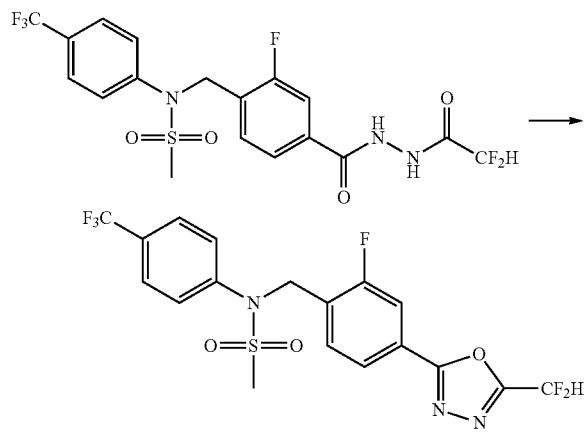

A mixture of N-(4-(2-(2,2-difluoroacetyl)hydrazine-1-carbonyl)-2-fluorobenzyl)-N-(4-(trifluoromethyl)phenyl)methanesulfonamide (0.140 g, 0.365 mmol) and 1-methoxy-N-triethylammoniosulfonyl-methanimidate (Burgess reagent, 0.131 g, 0.548 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 30%) to give N-(4-(5-(difluoromethyl)-1,3,4-oxadiazol-2-yl)-2-fluorobenzyl)-N-(4-(trifluoromethyl)phenyl)methanesulfonamide as yellow solid (0.092 g, 54.1%).

¹H NMR (400 MHz, CDCl₃) δ 7.89 (dd, 1H, J=8.1, 1.7 Hz), 7.77 (dd, 1H, J=10.0, 1.7 Hz), 7.70-7.60 (m, 3H), 7.52-7.44 (m, 2H), 7.05 (s, 0.2H), 6.92 (s, 0.5H), 6.79 (s, 0.2H), 5.08 (s, 2H), 3.05 (s, 3H); LRMS (ES) m/z 466.3 (M⁺+1).

EXAMPLE 50

Compound 11222: N-butyl-N-(4-(5-(trifluoromethyl)-1,3,4-oxadiazol-2-yl)benzyl)methanesulfonamide

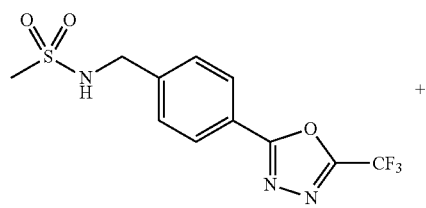

+

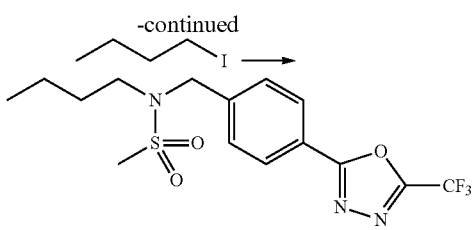

Sodium hydride (60.00%, 0.016 g, 0.405 mmol) was added to a solution of N-(4-(5-(trifluoromethyl)-1,3,4-oxadiazol-2-yl)benzyl)methanesulfonamide (0.100 g, 0.311 mmol) in N,N-dimethylformide (2 mL) at 0° C., and the mixture was stirred for 30 min. The reaction mixture was treated with 1-iodobutane (0.063 g, 0.342 mmol), and stirred at the same temperature for 30 min. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 25%) to give the crude product which was rechromatographed (SiO₂, 4 g cartridge; acetonitrile/aqueous 1%-formic acid solution=5% to 50%) to give N-butyl-N-(4-(5-(trifluoromethyl)-1,3,4-oxadiazol-2-yl)benzyl)methanesulfonamide as white solid (0.035 g, 29.8%).

¹H NMR (400 MHz, CDCl₃) δ 8.14-8.06 (m, 2H), 7.61-7.53 (m, 2H), 4.46 (s, 2H), 3.27-3.12 (m, 2H), 2.90 (s, 3H), 1.47 (ddt, 2H, J=9.3, 7.7, 3.4 Hz), 1.28-1.21 (m, 2H), 0.84 (t, 3H, J=7.3 Hz); LRMS (ES) m/z 378.3 (M⁺+1).

EXAMPLE 51

Compound 11225: N-(4-(5-(difluoromethyl)-1,3,4-oxadiazol-2-yl)-2-fluorobenzyl)-N-(3-fluorophenyl)pyridine-3-sulfonamide

[Step 1] N-(3-fluorophenyl)pyridine-3-sulfonamide

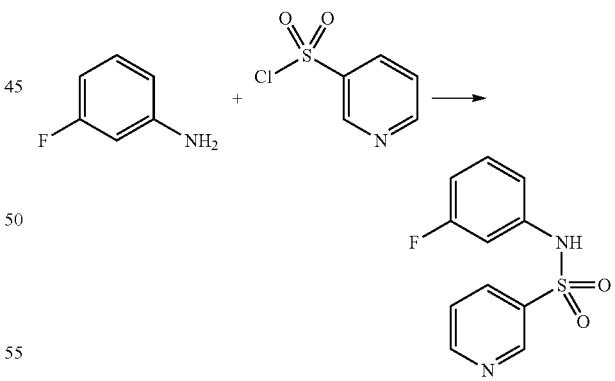

Triethylamine (1.622 mL, 11.699 mmol) was added to a solution of 3-fluoroaniline (1.000 g, 8.999 mmol) in dichloromethane (14 mL) at the room temperature, and the mixture was stirred at the same temperature for 10 min. The reaction mixture was treated with pyridine-3-sulfonyl chloride (1.758 g, 9.899 mmol), and stirred for additional 24 hr at the same temperature. The precipitates were collected by filtration, washed by diethylether, and dried to give N-(3-fluorophenyl)pyridine-3-sulfonamide as light yellow solid (1.900 g, 83.7%).

[Step 2] methyl 3-fluoro-4-((N-(3-fluorophenyl)pyridine-3-sulfonamido)methyl)benzoate

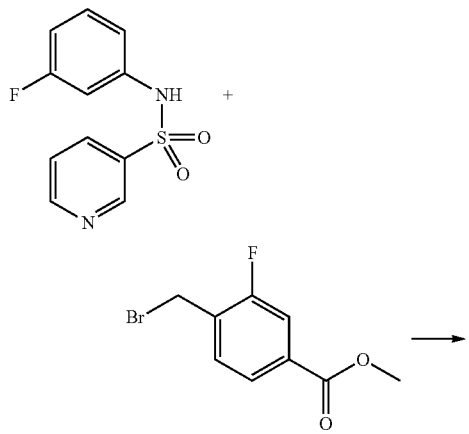

Sodium hydride (60.00%, 0.076 g, 1.903 mmol) was added to a solution of N-(3-fluorophenyl)pyridine-3-sulfonamide (0.400 g, 1.586 mmol) in N,N-dimethylformide (6 mL) at 0° C., and the mixture was stirred at the same temperature for 20 min. The reaction mixture was treated with methyl 4-(bromomethyl)-3-fluorobenzoate (0.411 g, 1.665 mmol), and stirred for additional 16 hr at the room temperature. Then, aqueous 1N-hydrochloric acid solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 3-fluoro-4-((N-(3-fluorophenyl)pyridine-3-sulfonamido)methyl)benzoate as white solid (0.250 g, 37.7%).

[Step 3] N-(2-fluoro-4-(hydrazinecarbonyl)benzyl)-N-(3-fluorophenyl)pyridine-3-sulfonamide

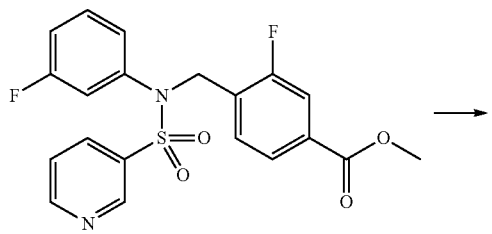

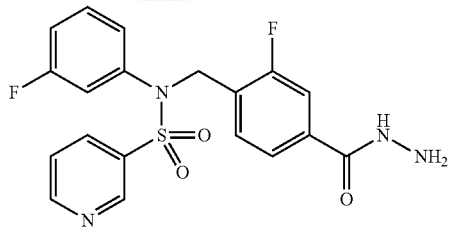

A mixture of methyl 3-fluoro-4-((N-(3-fluorophenyl)pyridine-3-sulfonamido)methyl)benzoate (0.250 g, 0.598 mmol) and hydrazine hydrate (0.057 g, 1.793 mmol) in ethanol (6 mL) prepared at the ambient temperature was heated at reflux for 24 hr, and cooled down to the ambient temperature. The reaction mixture was concentrated under the reduced pressure to remove the solvent. The residue was diluted with aqueous saturated sodium bicarbonate solution and stirred. The resulting precipitates were collected by filtration, washed by water, and dried to give N-(2-fluoro-4-(hydrazinecarbonyl)benzyl)-N-(3-fluorophenyl)pyridine-3-sulfonamide as white solid (0.220 g, 88.0%).

[Step 4] Compound 11225

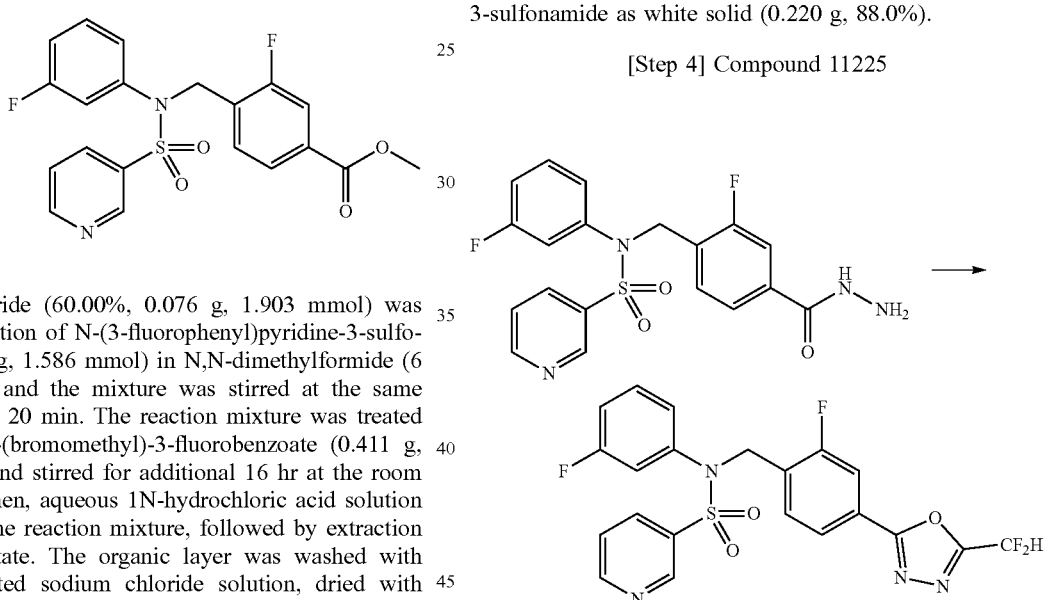

A solution of N-(2-fluoro-4-(hydrazinecarbonyl)benzyl)-N-(3-fluorophenyl)pyridine-3-sulfonamide (0.040 g, 0.096 mmol) and triethylamine (0.017 mL, 0.124 mmol) in tetrahydrofuran (2 mL) was stirred at the room temperature for 10 min, and then mixed with 2,2-difluoroacetic anhydride (0.012 mL, 0.115 mmol). The reaction mixture was heated at reflux for 8 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(3-fluorophenyl)pyridine-3-sulfonamide as white solid (0.035 g, 76.5%).
$^1$H NMR (400 MHz, DMSO-d$_6$) δ 8.96 (dd, 1H, J=4.9, 1.6 Hz), 8.87 (dd, 1H, J=2.4, 0.8 Hz), 8.11 (ddd, 1H, J=8.1, 2.4, 1.6 Hz), 7.91-7.78 (m, 2H), 7.78-7.69 (m, 2H), 7.68 (s, 0.25H), 7.56 (s, 0.5H), 7.44 (s, 0.25H), 7.39 (td, 1H, J=8.2, 6.6 Hz), 7.24-7.11 (m, 2H), 7.06 (ddd, 1H, J=8.0, 2.0, 0.9 Hz), 5.08 (s, 2H); LRMS (ES) m/z 480.1 (M$^+$+1).

EXAMPLE 52

Compound 11226: N-(benzo[d][1,3]dioxol-5-yl)-N-(2-fluoro-4-(5-(trifluoromethyl)-1,3,4-oxadiazol-2-yl)benzyl)methanesulfonamide

[Step 1] N-(benzo[d][1,3]dioxol-5-yl)methanesulfonamide

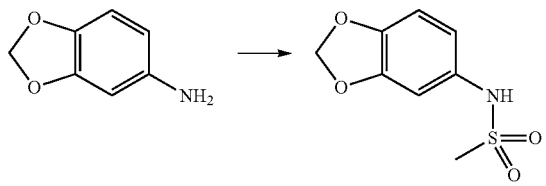

Triethylamine (1.314 mL, 9.479 mmol) was added to a solution of benzo[d][1,3]dioxol-5-amine (1.000 g, 7.292 mmol) in dichloromethane (14 mL) at the room temperature, and the mixture was stirred at the same temperature for 10 min. The reaction mixture was treated with methanesulfonyl chloride (0.621 mL, 8.021 mmol), and stirred for additional 24 hr at the same temperature. Then, aqueous 0.1N-hydrochloric acid solution was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(benzo[d][1,3]dioxol-5-yl)methanesulfonamide, 1.400 g, 89.2%, light yellow solid).

[Step 2] methyl 4-((N-(benzo[d][1,3]dioxol-5-yl)methylsulfonamido)methyl)-3-fluorobenzoate

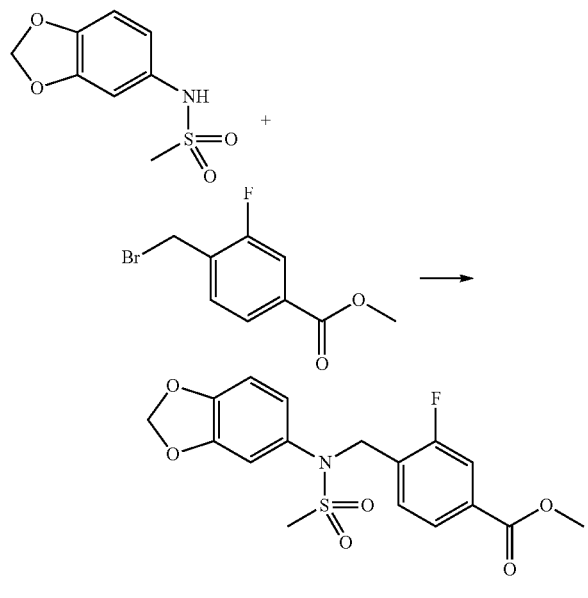

Sodium hydride (60.00%, 0.067 g, 1.673 mmol) was added to a solution of N-(benzo[d][1,3]dioxol-5-yl)methanesulfonamide (0.300 g, 1.394 mmol) in N,N-dimethylformamide (4 mL) at 0° C., and the mixture was stirred at the same temperature for 20 min. The reaction mixture was treated with methyl 4-(bromomethyl)-3-fluorobenzoate (0.362 g, 1.464 mmol), and stirred for additional 16 hr at the room temperature. Then, aqueous 1N-hydrochloric acid solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 4-((N-(benzo[d][1,3]dioxol-5-yl)methylsulfonamido)methyl)-3-fluorobenzoate as white solid (0.210 g, 39.5%).

[Step 3] N-(benzo[d][1,3]dioxol-5-yl)-N-(2-fluoro-4-(hydrazinecarbonyl)benzyl)methanesulfonamide

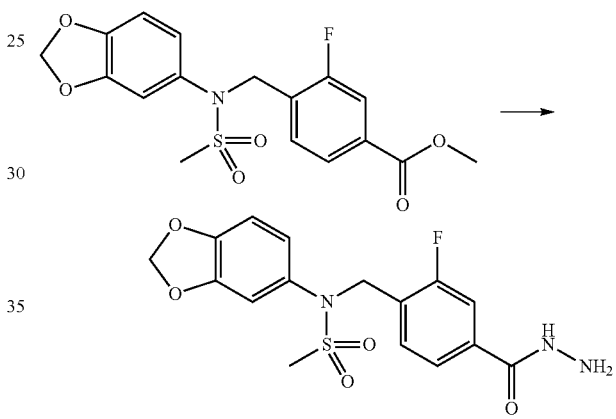

A mixture of methyl 4-((N-(benzo[d][1,3]dioxol-5-yl)methylsulfonamido)methyl)-3-fluorobenzoate (0.210 g, 0.551 mmol) and hydrazine hydrate (0.053 g, 1.652 mmol) in ethanol (6 mL) prepared at the ambient temperature was heated at reflux for 24 hr, cooled down to the ambient temperature, and concentrated under the reduced pressure to remove the solvent. The residue was diluted with aqueous saturated sodium bicarbonate solution and stirred. The resulting precipitates were collected by filtration, washed by water, and dried to give N-(benzo[d][1,3]dioxol-5-yl)-N-(2-fluoro-4-(hydrazinecarbonyl)benzyl)methanesulfonamide as white solid (0.190 g, 90.5%).

[Step 4] Compound 11226

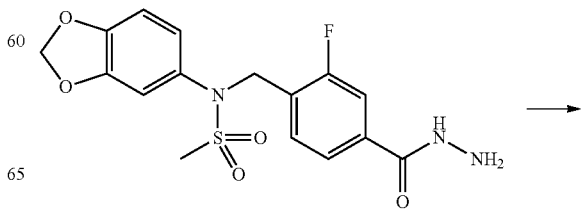

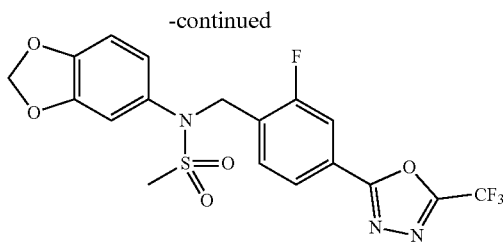

A solution of N-(benzo[d][1,3]dioxol-5-yl)-N-(2-fluoro-4-(hydrazinecarbonyl)benzyl)methanesulfonamide (0.055 g, 0.144 mmol) and triethylamine (0.026 mL, 0.187 mmol) in tetrahydrofuran (2 mL) was stirred at the room temperature for 10 min, and then mixed with trifluoroacetic anhydride (0.021 mL, 0.159 mmol). The reaction mixture was heated at reflux for 8 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 40%) to give N-(benzo[d][1,3]dioxol-5-yl)-N-(2-fluoro-4-(5-(trifluoromethyl)-1,3,4-oxadiazol-2-yl)benzyl)methanesulfonamide as white solid (0.040 g, 60.4%).

$^1$H NMR (400 MHz, DMSO-d6) δ 7.98-7.80 (m, 2H), 7.72 (t, 1H, J=7.7 Hz), 6.99-6.86 (m, 2H), 6.06 (s, 2H), 4.99 (s, 2H), 3.15 (s, 3H); LRMS (ES) m/z 460.2 (M$^+$+1).

EXAMPLE 53

Compound 11227: N-(benzo[d][1,3]dioxol-5-yl)-N-(4-(5-(difluoromethyl)-1,3,4-oxadiazol-2-yl)-2-fluorobenzyl)methanesulfonamide

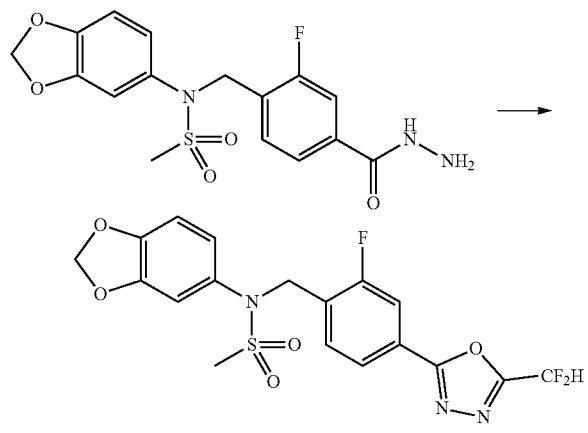

A solution of N-(benzo[d][1,3]dioxol-5-yl)-N-(2-fluoro-4-(hydrazinecarbonyl)benzyl)methanesulfonamide (0.055 g, 0.144 mmol) and triethylamine (0.026 mL, 0.187 mmol) in tetrahydrofuran (2 mL) was stirred at the room temperature for 10 min, and then mixed with 2,2-difluoroacetic anhydride (0.019 mL, 0.173 mmol). The reaction mixture was heated at reflux for 8 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 40%) to give N-(benzo[d][1,3]dioxol-5-yl)-N-(4-(5-(difluoromethyl)-1,3,4-oxadiazol-2-yl)-2-fluorobenzyl)methanesulfonamide as white solid (0.035 g, 55.0%).

$^1$H NMR (400 MHz, DMSO-d6) δ 7.90 (dd, 1H, J=8.0, 1.7 Hz), 7.82 (dd, 1H, J=10.3, 1.6 Hz), 7.71 (t, 1H, J=6.8 Hz), 7.69 (s, 0.25H), 7.57 (d, 0.5H), 7.44 (s, 0.25H), 7.10 (s, 1H), 6.96-6.85 (m, 2H), 6.06 (s, 2H), 4.98 (s, 2H), 3.14 (d, 3H, J=0.7 Hz); LRMS (ES) m/z 442.2 (M$^+$+1).

EXAMPLE 54

Compound 11229: N-(4-(5-(difluoromethyl)-1,3,4-oxadiazol-2-yl)-2-fluorobenzyl)-N-phenylcyclohexanesulfonamide

[Step 1] N-phenylcyclohexanesulfonamide

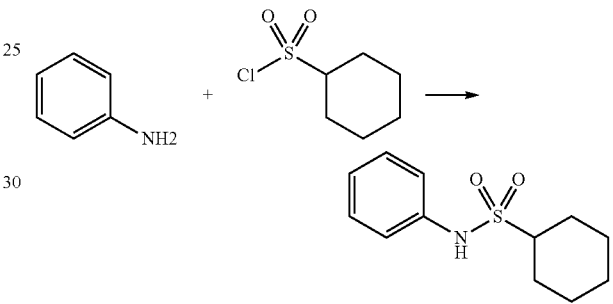

A mixture of aniline (0.500 g, 5.369 mmol) and pyridine (0.520 mL, 6.443 mmol) in dichloromethane (10 mL) was treated at the room temperature with cyclohexanesulfonyl chloride (1.079 g, 5.906 mmol), and stirred at the same temperature for 5 min. The reaction mixture was stirred at the same temperature for additional 2 hr. Then, water was added to the reaction mixture, followed by extraction with dichloromethane. The organic layer was washed with aqueous 0.1N-hydrochloric acid solution, dried with anhydrous MgSO$_4$, filtered, and concentrated in vacuo. The title compound was used without further purification (N-phenylcyclohexanesulfonamide, 1.400 g, 109.0%, brown solid).

[Step 2] Compound 11229

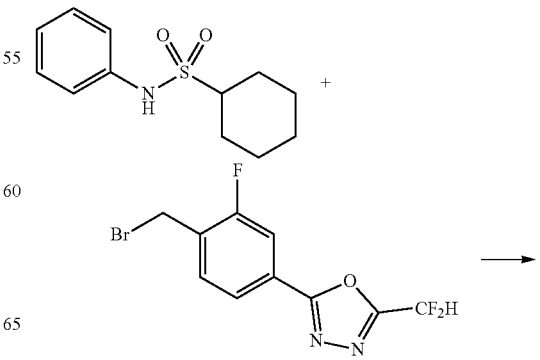

-continued

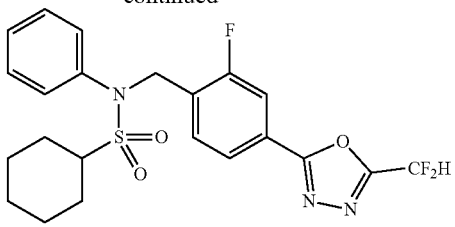

A mixture of 2-(4-(bromomethyl)-3-fluorophenyl)-5-(difluoromethyl)-1,3,4-oxadiazole (0.050 g, 0.154 mmol) and N-phenylcyclohexanesulfonamide (0.040 g, 0.169 mmol) in N,N-dimethylformide (10 mL) was treated at the room temperature with NaH (60.00%, 0.007 g, 0.185 mmol), and stirred at the same temperature for 5 min. The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 20%) to give N-(4-(5-(difluoromethyl)-1,3,4-oxadiazol-2-yl)-2-fluorobenzyl)-N-phenylcyclohexanesulfonamide as white solid (0.070 g, 97.8%).

$^1$H NMR (400 MHz, CDCl$_3$) δ 7.88-7.86 (m, 1H), 7.74-7.69 (m, 2H), 7.35-7.27 (m, 5H), 6.91 (t, 1H, J=52.0 Hz), 5.08 (brs, 2H), 3.05-3.00 (m, 1H), 2.23-2.14 (m, 2H), 1.92 (m, 2H), 1.72-1.66 (m, 4H), 1.28-1.24 (m, 2H); LRMS (ES) m/z 466.30 (M$^+$+1).

EXAMPLE 55

Compound 11230: N-(4-(5-(difluoromethyl)-1,3,4-oxadiazol-2-yl)-2-fluorobenzyl)-N-phenylbutane-2-sulfonamide

[Step 1] N-phenylbutane-2-sulfonamide

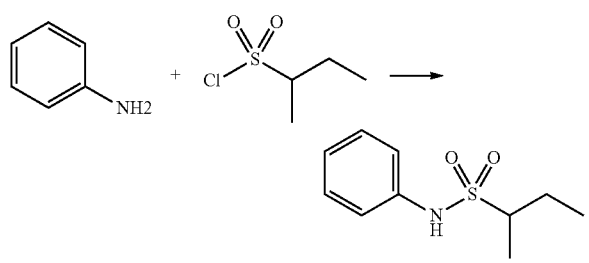

A mixture of aniline (0.078 mL, 0.859 mmol) and pyridine (0.083 mL, 1.031 mmol) in dichloromethane (10 mL) was treated at the room temperature with butane-2-sulfonyl chloride (0.148 g, 0.945 mmol). The reaction mixture was stirred at the same temperature for 12 hr. Then, water was added to the reaction mixture, followed by extraction with dichloromethane. The organic layer was washed with aqueous 0.1N-hydrochloric acid solution, dried with anhydrous MgSO$_4$, filtered, and concentrated in vacuo. The residue was chromatographed (SiO$_2$, 12 g cartridge; ethyl acetate/hexane=0% to 30%) to give N-phenylbutane-2-sulfonamide as yellow solid (0.160 g, 87.3%).

[Step 2] Compound 11230

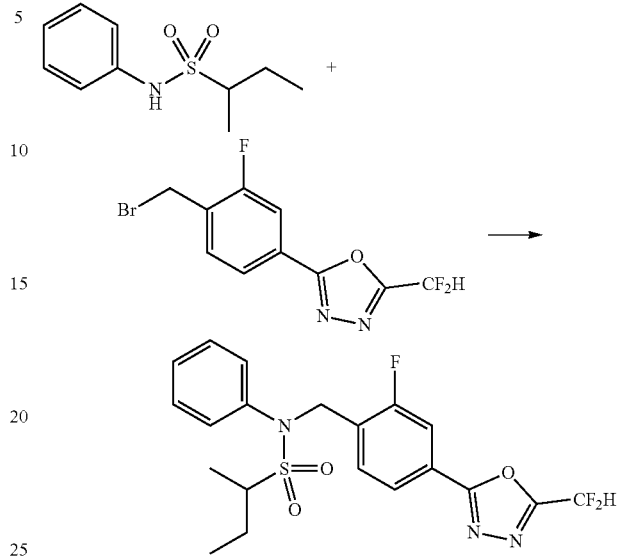

A solution of 2-(4-(bromomethyl)-3-fluorophenyl)-5-(difluoromethyl)-1,3,4-oxadiazole (0.050 g, 0.154 mmol) and N-phenylbutane-2-sulfonamide (0.036 g, 0.169 mmol) in dichloromethane (10 mL) was mixed at the room temperature with sodium hydride (60.00%, 0.007 g, 0.185 mmol). The reaction mixture was stirred at the same temperature for 12 hr. Then, water was added to the reaction mixture, followed by extraction with dichloromethane. The organic layer was washed with aqueous 0.1N-hydrochloric acid solution, dried with anhydrous MgSO$_4$, filtered, and concentrated in vacuo. The residue was chromatographed (SiO$_2$, 12 g cartridge; ethyl acetate/hexane=0% to 20%) to give N-(4-(5-(difluoromethyl)-1,3,4-oxadiazol-2-yl)-2-fluorobenzyl)-N-phenylbutane-2-sulfonamide as white solid (0.045 g, 64.0%).

$^1$H NMR (400 MHz, CDCl$_3$) δ 7.88-7.86 (m, 1H), 7.74-7.69 (m, 2H), 7.35-7.27 (m, 5H), 6.91 (t, 1H, J=52.0 Hz), 5.11-5.08 (m, 2H), 3.09-3.04 (m, 1H), 2.13-2.07 (m, 1H), 1.74-1.64 (m, 1H), 1.44 (d, 3H, J=8.0 Hz), 1.03 (t, 3H, J=8.0 Hz); LRMS (ES) m/z m/z 440.23 (M$^+$+1).

EXAMPLE 56

Compound 11231: methyl 2-(N-(4-(5-(difluoromethyl)-1,3,4-oxadiazol-2-yl)-2-fluorobenzyl)-N-phenylsulfamoyl)acetate

[Step 1] methyl 2-(N-phenylsulfamoyl)acetate

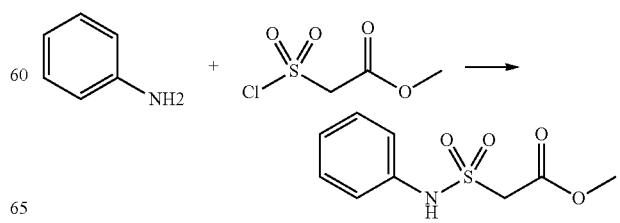

A mixture of aniline (0.147 mL, 1.611 mmol) and pyridine (0.156 mL, 1.933 mmol) in dichloromethane (10 mL) was treated at the room temperature with methyl 2-(chlorosulfonyl)acetate (0.306 g, 1.772 mmol). The reaction mixture was stirred at the same temperature for 12 hr. Then, water was added to the reaction mixture, followed by extraction with dichloromethane. The organic layer was washed with aqueous 0.1N-hydrochloric acid solution, dried with anhydrous MgSO₄, filtered, and concentrated in vacuo. The title compound was used without further purification. (methyl 2-(N-phenylsulfamoyl)acetate, 0.300 g, 75.3%, brown solid).

[Step 2] Compound 11231

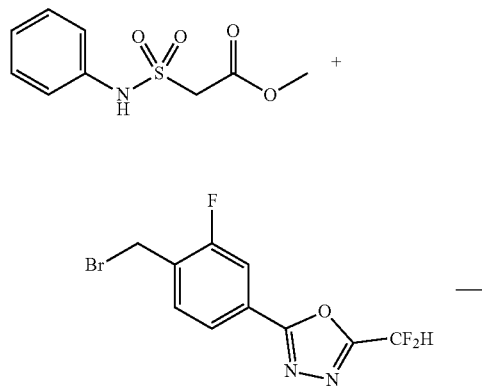

A solution of 2-(4-(bromomethyl)-3-fluorophenyl)-5-(difluoromethyl)-1,3,4-oxadiazole (0.050 g, 0.154 mmol), methyl 2-(N-phenylsulfamoyl)acetate (0.039 g, 0.169 mmol) and sodium hydride (60.00%, 0.007 g, 0.185 mmol) in dichloromethane (10 mL) was stirred at the room temperature for 12. Then, water was added to the reaction mixture, followed by extraction with dichloromethane. The organic layer was washed with aqueous 0.1N-hydrochloric acid solution, dried with anhydrous MgSO₄, filtered, and concentrated in vacuo. The residue was chromatographed (SiO₂, 12 g cartridge; ethyl acetate/hexane=0% to 20%) to give methyl 2-(N-(4-(5-(difluoromethyl)-1,3,4-oxadiazol-2-yl)-2-fluorobenzyl)-N-phenylsulfamoyl)acetate as light-yellow oil (0.035 g, 50.0%).

$^1$H NMR (400 MHz, CDCl₃) δ 7.89-7.87 (m, 1H), 7.72-7.66 (m, 2H), 7.47-7.45 (m, 2H), 7.40-7.28 (m, 3H), 6.91 (t, 1H, J=52.0 Hz), 5.12 (s, 2H), 4.07 (s, 2H), 3.87 (s, 3H); LRMS (ES) m/z 454.27 (M⁺−1).

EXAMPLE 57

Compound 11248: N-(2-fluoro-4-(5-(trifluoromethyl)-1,3,4-oxadiazol-2-yl)benzyl)-N-(o-tolyl)methanesulfonamide

[Step 1] N-(o-tolyl)methanesulfonamide

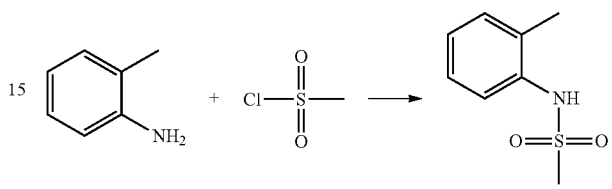

A solution of o-toluidine (1.000 g, 9.332 mmol), pyridine (0.829 mL, 10.265 mmol) and methanesulfonyl chloride (0.873 mL, 11.198 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO₄, filtered, and concentrated in vacuo. The title compound was used without further purification (N-(o-tolyl)methanesulfonamide, 0.910 g, 52.6%, yellow solid).

[Step 2] methyl 3-fluoro-4-((N-(o-tolyl)methylsulfonamido)methyl)benzoate

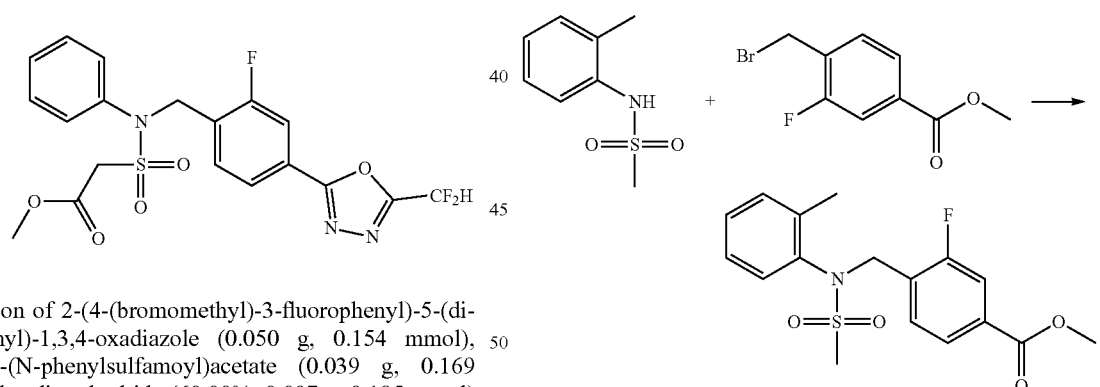

A solution of N-(o-tolyl)methanesulfonamide (0.500 g, 2.699 mmol), sodium hydride (60.00%, 0.130 g, 3.239 mmol) and methyl 4-(bromomethyl)-3-fluorobenzoate (0.734 g, 2.969 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 40%) to give methyl 3-fluoro-4-((N-(o-tolyl)methylsulfonamido)methyl)benzoate as yellow solid (0.610 g, 64.3%).

[Step 3] N-(2-fluoro-4-(hydrazinecarbonyl)benzyl)-N-(o-tolyl)methanesulfonamide

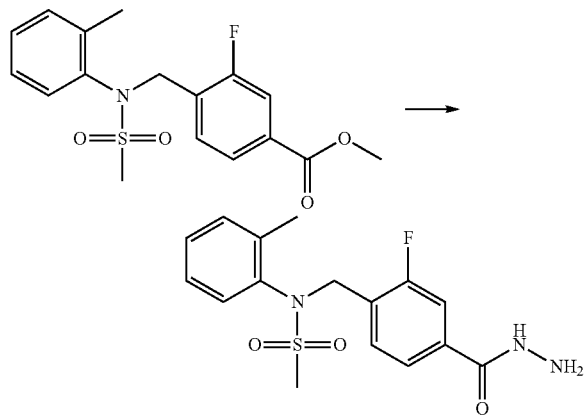

A mixture of methyl 3-fluoro-4-((N-(o-tolyl)methylsulfonamido)methyl)benzoate (0.610 g, 1.736 mmol) and hydrazine hydrate (0.869 g, 17.360 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(o-tolyl)methanesulfonamide, 0.530 g, 86.9%, yellow solid).

[Step 4] N-(2-fluoro-4-(2-(2,2,2-trifluoroacetyl)hydrazine-1-carbonyl)benzyl)-N-(o-tolyl)methanesulfonamide

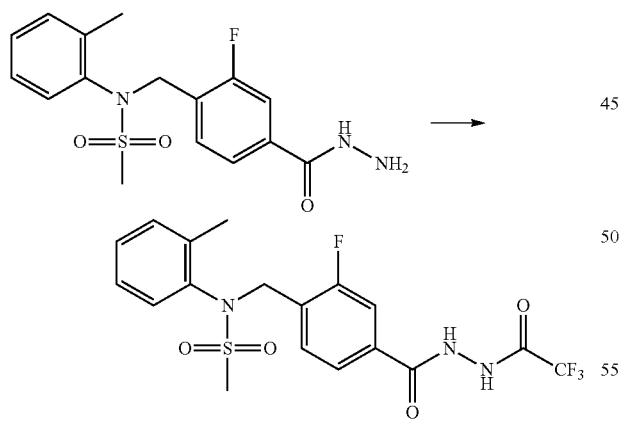

A solution of N-(2-fluoro-4-(hydrazinecarbonyl)benzyl)-N-(o-tolyl)methanesulfonamide (0.260 g, 0.740 mmol), trifluoroacetic anhydride (0.113 mL, 0.814 mmol) and triethylamine (0.154 mL, 1.110 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-fluoro-4-(2-(2,2,2-trifluoroacetyl)hydrazine-1-carbonyl)benzyl)-N-(o-tolyl)methanesulfonamide, 0.190 g, 57.4%, yellow solid).

[Step 5] Compound 11248

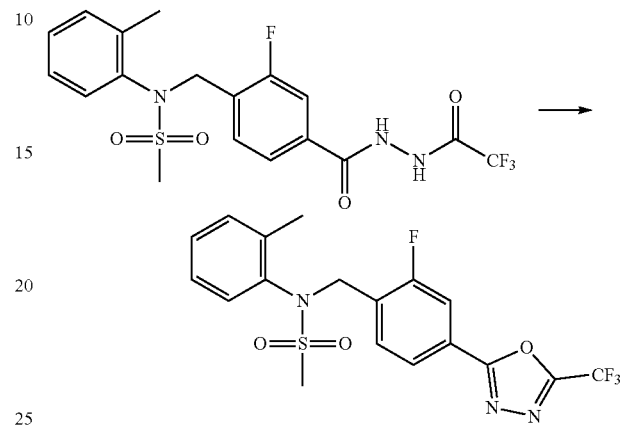

A mixture of N-(2-fluoro-4-(2-(2,2,2-trifluoroacetyl)hydrazine-1-carbonyl)benzyl)-N-(o-tolyl)methanesulfonamide (0.190 g, 0.425 mmol) and 1-methoxy-N-triethylammoniosulfonyl-methanimidate (Burgess reagent, 0.152 g, 0.637 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(2-fluoro-4-(5-(trifluoromethyl)-1,3,4-oxadiazol-2-yl)benzyl)-N-(o-tolyl)methanesulfonamide as white solid (0.100 g, 54.8%).

$^1$H NMR (400 MHz, CDCl$_3$) δ 7.85 (dd, 1H, J=8.1, 2.0 Hz), 7.80-7.72 (m, 1H), 7.61-7.51 (m, 1H), 7.28-7.15 (m, 4H), 4.92 (s, 2H), 3.07 (s, 3H), 2.23 (s, 3H); LRMS (ES) m/z 430.3 (M$^+$+1).

EXAMPLE 58

Compound 11249: N-(4-(5-(difluoromethyl)-1,3,4-oxadiazol-2-yl)-2-fluorobenzyl)-N-(o-tolyl)methanesulfonamide

[Step 1] N-(4-(2-(2,2-difluoroacetyl)hydrazine-1-carbonyl)-2-fluorobenzyl)-N-(o-tolyl)methanesulfonamide

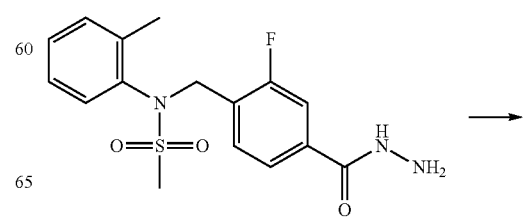

-continued

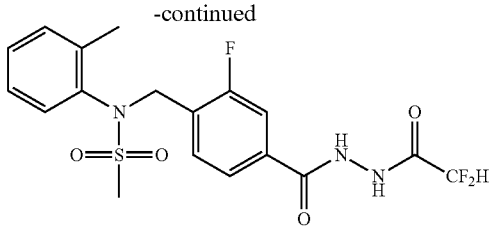

A solution of N-(2-fluoro-4-(hydrazinecarbonyl)benzyl)-N-(o-tolyl)methanesulfonamide (0.260 g, 0.740 mmol), difluoroacetic anhydride (0.097 mL, 0.888 mmol) and triethylamine (0.205 mL, 1.480 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-2-fluorobenzyl)-N-(o-tolyl)methanesulfonamide, 0.180 g, 56.7%, yellow solid).

[Step 2] Compound 11249

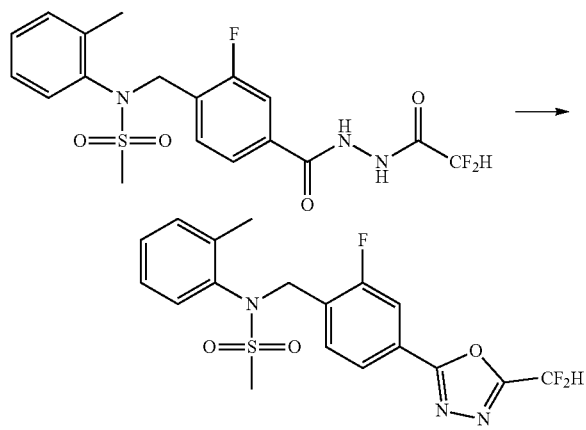

A mixture of N-(4-(2-(2,2-difluoroacetyl)hydrazine-1-carbonyl)-2-fluorobenzyl)-N-(o-tolyl)methanesulfonamide (0.180 g, 0.419 mmol) and 1-methoxy-N-triethylammoniosulfonyl-methanimidate (Burgess reagent, 0.150 g, 0.629 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(o-tolyl)methanesulfonamide as white solid (0.110 g, 63.8%).
$^1$H NMR (400 MHz, CDCl$_3$) δ 7.84 (dd, 1H, J=8.0, 1.7 Hz), 7.74 (dd, 1H, J=9.7, 1.7 Hz), 7.57-7.47 (m, 1H), 7.27-7.15 (m, 4H), 7.05 (s, 0.2H), 6.92 (s, 0.5H), 6.80 (s, 0.2H), 4.91 (s, 2H), 3.06 (s, 3H), 2.22 (s, 3H); LRMS (ES) m/z 412.3 (M$^+$+1).

EXAMPLE 59

Compound 11250: N-(2-fluoro-4-(5-(trifluoromethyl)-1,3,4-oxadiazol-2-yl)benzyl)-N-(2-methoxyphenyl)methanesulfonamide

[Step 1] N-(2-methoxyphenyl)methanesulfonamide

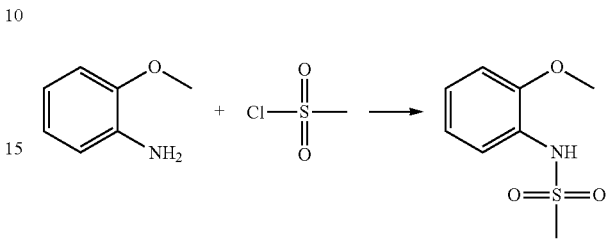

A solution of 2-methoxyaniline (1.000 g, 8.120 mmol), pyridine (0.721 mL, 8.931 mmol) and methanesulfonyl chloride (0.759 mL, 9.743 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(2-methoxyphenyl)methanesulfonamide, 0.920 g, 56.3%, brown solid).

[Step 2] methyl 3-fluoro-4-((N-(2-methoxyphenyl)methylsulfonamido)methyl)benzoate

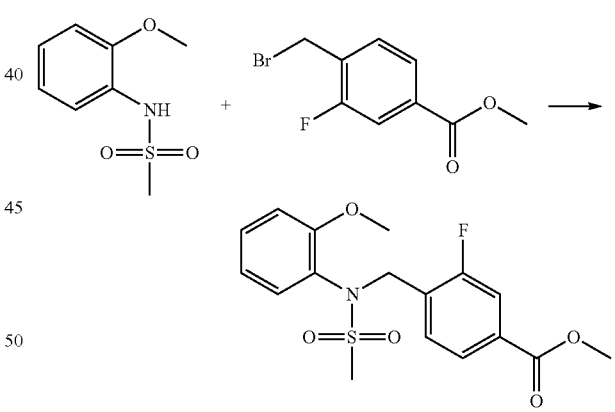

A solution of N-(2-methoxyphenyl)methanesulfonamide (0.500 g, 2.485 mmol), sodium hydride (60.00%, 0.119 g, 2.982 mmol) and methyl 4-(bromomethyl)-3-fluorobenzoate (0.675 g, 2.733 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 3-fluoro-4-((N-(2-methoxyphenyl)methylsulfonamido)methyl)benzoate as yellow solid (0.630 g, 69.0%).

[Step 3] N-(2-fluoro-4-(hydrazinecarbonyl)benzyl)-N-(2-methoxyphenyl)methanesulfonamide

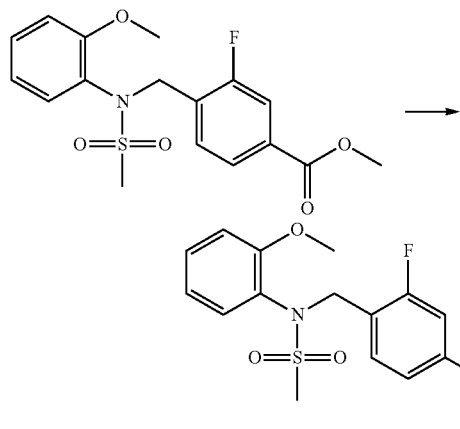

A solution of methyl 3-fluoro-4-((N-(2-methoxyphenyl)methylsulfonamido)methyl)benzoate (0.630 g, 1.715 mmol) and hydrazine hydrate (0.858 g, 17.148 mmol) in ethanol (10 mL) was stirred at 120° C. for 1 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(2-fluoro-4-(hydrazinecarbonyl)benzyl)-N-(2-methoxyphenyl)methanesulfonamide, 0.520 g, 82.5%, yellow solid).

[Step 4] N-(2-fluoro-4-(2-(2,2,2-trifluoroacetyl)hydrazine-1-carbonyl)benzyl)-N-(2-methoxyphenyl)methanesulfonamide

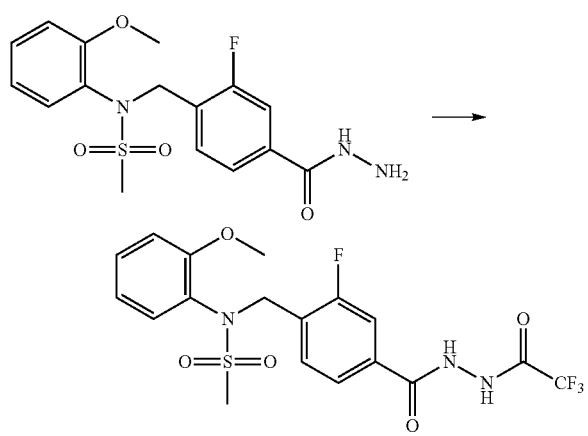

A solution of N-(2-fluoro-4-(hydrazinecarbonyl)benzyl)-N-(2-methoxyphenyl)methanesulfonamide (0.260 g, 0.708 mmol), trifluoroacetic anhydride (0.108 mL, 0.778 mmol) and triethylamine (0.147 mL, 1.062 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(2-fluoro-4-(2-(2,2,2-trifluoroacetyl)hydrazine-1-carbonyl)benzyl)-N-(2-methoxyphenyl)methanesulfonamide, 0.210 g, 64.0%, yellow solid).

[Step 5] Compound 11250

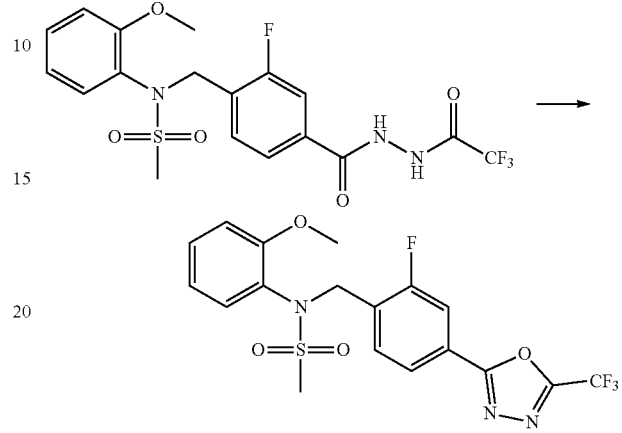

A mixture of N-(2-fluoro-4-(2-(2,2,2-trifluoroacetyl)hydrazine-1-carbonyl)benzyl)-N-(2-methoxyphenyl)methanesulfonamide (0.210 g, 0.453 mmol) and 1-methoxy-N-triethylammoniosulfonyl-methanimidate (Burgess reagent, 0.162 g, 0.680 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(2-fluoro-4-(5-(trifluoromethyl)-1,3,4-oxadiazol-2-yl)benzyl)-N-(2-methoxyphenyl)methanesulfonamide as white solid (0.130 g, 64.4%).

$^1$H NMR (400 MHz, CDCl₃) δ 7.87 (dd, 1H, J=8.0, 1.8 Hz), 7.80-7.67 (m, 2H), 7.36-7.26 (m, 1H), 7.24-7.15 (m, 1H), 7.02-6.94 (m, 1H), 6.93-6.82 (m, 1H), 4.97 (s, 2H), 3.94 (d, 3H, J=0.9 Hz), 3.04 (d, 3H, J=1.0 Hz); LRMS (ES) m/z 446.0 (M⁺+1).

EXAMPLE 60

Compound 11251: N-(4-(5-(difluoromethyl)-1,3,4-oxadiazol-2-yl)-2-fluorobenzyl)-N-(2-methoxyphenyl)methanesulfonamide

[Step 1] N-(4-(2-(2,2-difluoroacetyl)hydrazine-1-carbonyl)-2-fluorobenzyl)-N-(2-methoxyphenyl)methanesulfonamide

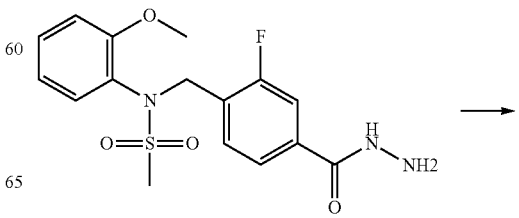

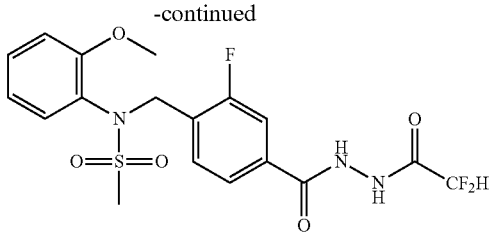

A solution of N-(2-fluoro-4-(hydrazinecarbonyl)benzyl)-N-(2-methoxyphenyl)methanesulfonamide (0.260 g, 0.708 mmol), difluoroacetic anhydride (0.092 mL, 0.849 mmol) and triethylamine (0.196 mL, 1.415 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-2-fluorobenzyl)-N-(2-methoxyphenyl)methanesulfonamide, 0.210 g, 66.6%, yellow solid).

[Step 2] Compound 11251

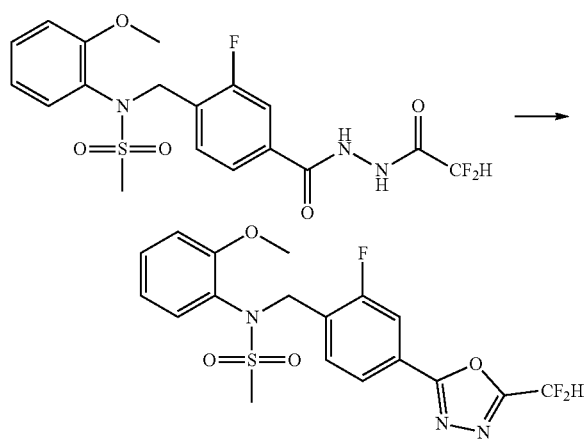

A mixture of N-(4-(2-(2,2-difluoroacetyl)hydrazine-1-carbonyl)-2-fluorobenzyl)-N-(2-methoxyphenyl)methanesulfonamide (0.210 g, 0.471 mmol) and 1-methoxy-N-triethylammoniosulfonyl-methanimidate (Burgess reagent, 0.169 g, 0.707 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(2-methoxyphenyl)methanesulfonamide as white solid (0.126 g, 62.5%).
$^1$H NMR (400 MHz, CDCl$_3$) δ 7.91-7.83 (m, 1H), 7.77-7.66 (m, 2H), 7.36-7.26 (m, 1H), 7.22-7.15 (m, 1H), 7.05 (s, 0.2H), 7.00-6.94 (m, 1H), 6.92 (s, 0.5H), 6.91-6.83 (m, 1H), 6.79 (s, 0.2H), 4.97 (s, 2H), 3.94 (s, 3H), 3.04 (s, 3H); LRMS (ES) m/z 428.1 (M$^+$+1).

EXAMPLE 61

Compound 11252: N-(4-(5-(difluoromethyl)-1,3,4-oxadiazol-2-yl)-2-fluorobenzyl)-N-phenylpyridine-3-sulfonamide

[Step 1] N-phenylpyridine-3-sulfonamide

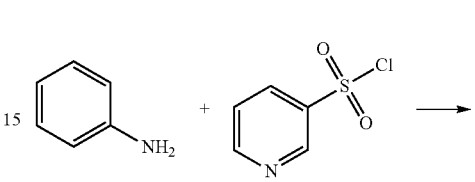

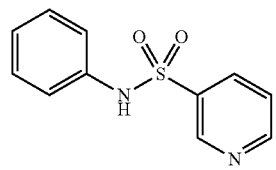

A solution of pyridine-3-sulfonyl chloride (2.002 g, 11.275 mmol) and pyridine (1.274 g, 16.107 mmol) in dichloromethane (14 mL) was stirred at the room temperature for 20 min, and mixed with aniline (1.000 g, 10.738 mmol). The reaction mixture was stirred at the same temperature for additional 24 hr. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The title compound was used without further purification (N-phenylpyridine-3-sulfonamide, 2.300 g, 91.4%, orange solid).

[Step 2] 3-fluoro-4-methylbenzohydrazide

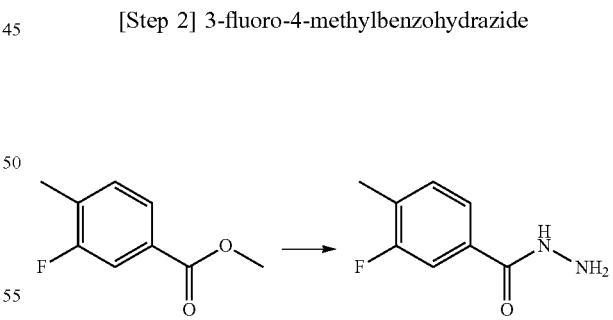

A mixture of methyl 3-fluoro-4-methylbenzoate (10.000 g, 59.464 mmol) and hydrazine hydrate (9.526 g, 297.318 mmol) in ethanol (20 mL) prepared at the ambient temperature was heated at reflux for 16 hr, and cooled down to the ambient temperature, and concentrated under the reduced pressure to remove the solvent. The precipitates were collected by filtration, washed by water, and dried to give 3-fluoro-4-methylbenzohydrazide as white solid (9.500 g, 95.0%).

[Step 3] N'-(2,2-difluoroacetyl)-3-fluoro-4-methyl-benzohydrazide

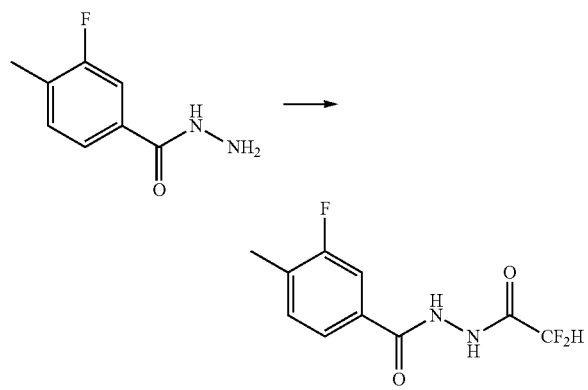

A solution of 3-fluoro-4-methylbenzohydrazide (4.000 g, 23.785 mmol) and triethylamine (4.286 mL, 30.921 mmol) in tetrahydrofuran (12 mL) was stirred at the room temperature for 10 min, and then mixed with 2,2-difluoroacetic anhydride (3.105 mL, 28.543 mmol). The reaction mixture was heated at reflux for 8 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 24 g cartridge; ethyl acetate/hexane=0% to 30%) to give N'-(2,2-difluoroacetyl)-3-fluoro-4-methylbenzohydrazide as white solid (4.900 g, 83.7%).

[Step 4] 2-(difluoromethyl)-5-(3-fluoro-4-methylphenyl)-1,3,4-oxadiazole

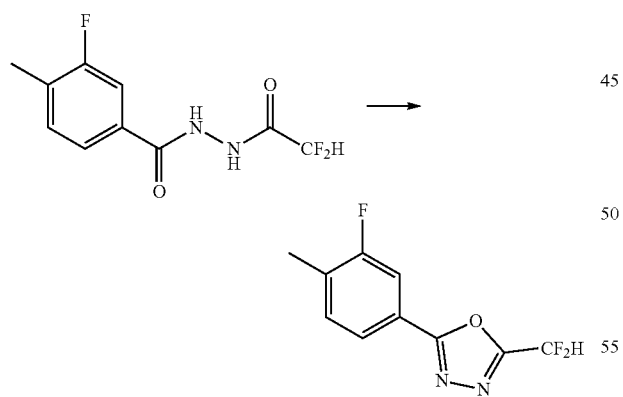

A mixture of N'-(2,2-difluoroacetyl)-3-fluoro-4-methylbenzohydrazide (4.800 g, 19.497 mmol) and 1-methoxy-N-triethylammoniosulfonyl-methanimidate (Burgess reagent, 3.563 g, 20.472 mmol) in tetrahydrofuran (25 mL) prepared at the ambient temperature was heated at reflux for 16 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 15%) to give 2-(difluoromethyl)-5-(3-fluoro-4-methylphenyl)-1,3,4-oxadiazole as white solid (2.830 g, 63.6%).

[Step 5] 2-(4-(bromomethyl)-3-fluorophenyl)-5-(difluoromethyl)-1,3,4-oxadiazole

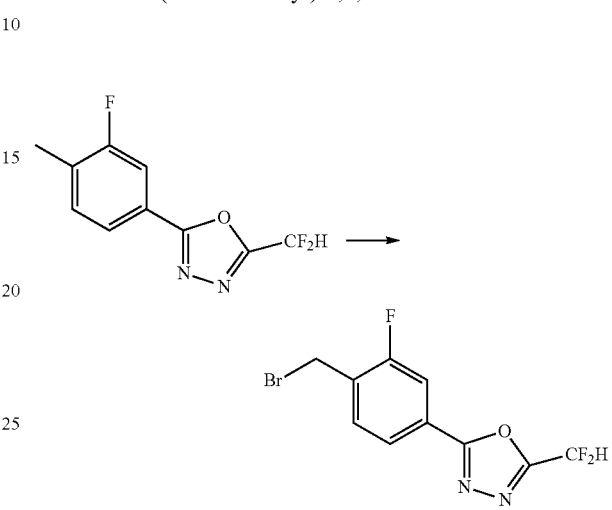

A mixture of 2-(difluoromethyl)-5-(3-fluoro-4-methylphenyl)-1,3,4-oxadiazole (2.830 g, 12.403 mmol), 1-bromopyrrolidine-2,5-dione (NBS, 2.317 g, 13.023 mmol) and Azobisisobutyronitrile (AIBN, 0.102 g, 0.620 mmol) in dichloromethane (20 mL) prepared at the ambient temperature was heated at reflux for 24 hr, and cooled down to the ambient temperature. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 10%) to give 2-(4-(bromomethyl)-3-fluorophenyl)-5-(difluoromethyl)-1,3,4-oxadiazole as white solid (2.900 g, 76.1%).

[Step 6] Compound 11252

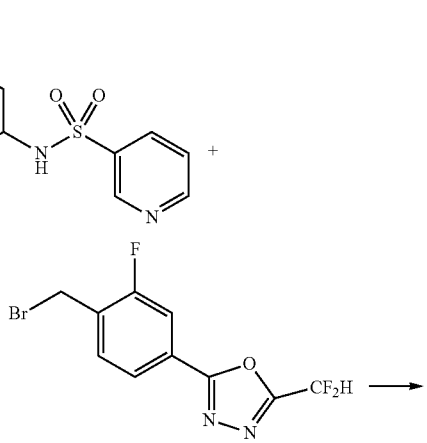

285

-continued

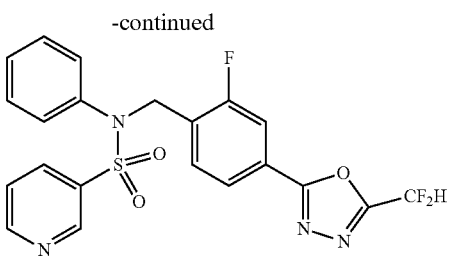

Sodium hydride (60.00%, 0.007 g, 0.179 mmol) was added to a solution of N-phenylpyridine-3-sulfonamide (0.035 g, 0.149 mmol) in N,N-dimethylformide (1 mL) at 0° C., and the mixture was stirred at the same temperature for 20 min. The reaction mixture was treated with 2-(4-(bromomethyl)-3-fluorophenyl)-5-(difluoromethyl)-1,3,4-oxadiazole (0.048 g, 0.157 mmol), and stirred for additional 16 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-phenylpyridine-3-sulfonamide as white solid (0.055 g, 80.0%).

$^1$H NMR (400 MHz, CDCl$_3$) δ 8.94-8.85 (m, 2H), 7.96-7.84 (m, 2H), 7.74-7.66 (m, 2H), 7.52-7.46 (m, 1H), 7.35-7.24 (m, 3H), 7.05 (ddd, 2H, J=6.7, 3.1, 1.1 Hz), 7.04-6.76 (m, 1H), 4.95 (s, 2H); LRMS (ES) m/z 461.0 (M$^+$+1).

EXAMPLE 62

Compound 11253: N-(2-fluoro-4-(5-(trifluoromethyl)-1,3,4-oxadiazol-2-yl)benzyl)-N-(6-(trifluoromethyl)pyridin-2-yl)pyridine-3-sulfonamide

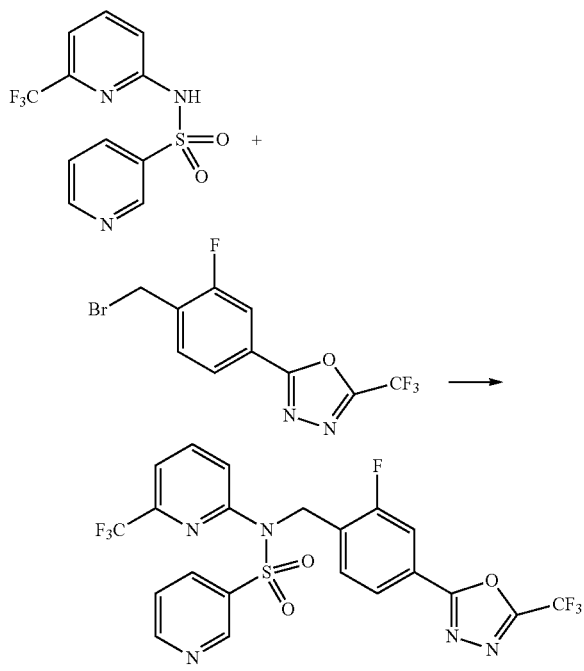

286

Sodium hydride (60.00%, 0.007 g, 0.178 mmol) was added to a solution of N-(6-(trifluoromethyl)pyridin-2-yl)pyridine-3-sulfonamide (0.045 g, 0.148 mmol) in N,N-dimethylformide (1 mL) at 0° C., and the mixture was stirred at the same temperature for 30 min. The reaction mixture was treated with 2-(4-(bromomethyl)-3-fluorophenyl)-5-(trifluoromethyl)-1,3,4-oxadiazole (0.051 g, 0.156 mmol), and stirred for additional 16 hr at the room temperature. Then, aqueous 0.1N-hydrochloric acid solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 60%) to give N-(2-fluoro-4-(5-(trifluoromethyl)-1,3,4-oxadiazol-2-yl)benzyl)-N-(6-(trifluoromethyl)pyridin-2-yl)pyridine-3-sulfonamide as white solid (0.045 g, 55.4%).

$^1$H NMR (400 MHz, CDCl$_3$) δ 8.95 (d, 1H, J=2.4 Hz), 8.87 (dd, 1H, J=4.9, 1.6 Hz), 8.02 (dt, 1H, J=8.0, 2.0 Hz), 7.90 (t, 1H, J=7.9 Hz), 7.82 (dd, 1H, J=8.0, 1.7 Hz), 7.79-7.71 (m, 2H), 7.63 (t, 1H, J=7.6 Hz), 7.54-7.47 (m, 2H), 5.22 (s, 2H); LRMS (ES) m/z 546.18 (M$^+$−1).

EXAMPLE 63

Compound 11254: N-(3-acetylphenyl)-N-(4-(5-(difluoromethyl)-1,3,4-oxadiazol-2-yl)-2-fluorobenzyl)methanesulfonamide

[Step 1] N-(3-acetylphenyl)methanesulfonamide

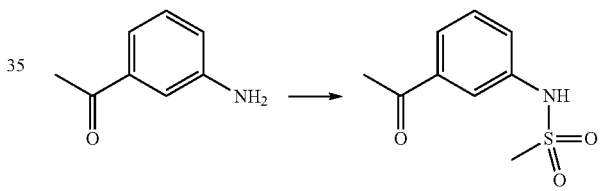

Triethylamine (1.333 mL, 9.618 mmol) was added to a solution of 1-(3-aminophenyl)ethan-1-one (1.000 g, 7.398 mmol) in dichloromethane (14 mL) at the room temperature, and the mixture was stirred at the same temperature for 10 min. The reaction mixture was treated with methanesulfonyl chloride (0.630 mL, 8.138 mmol), and stirred for additional 24 hr at the same temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 24 g cartridge; ethyl acetate/hexane=0% to 30%) to give N-(3-acetylphenyl)methanesulfonamide as white solid (0.750 g, 47.5%).

[Step 2] Compound 11254

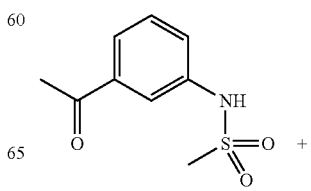

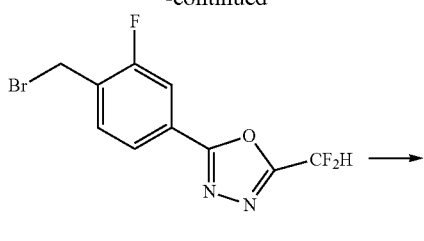

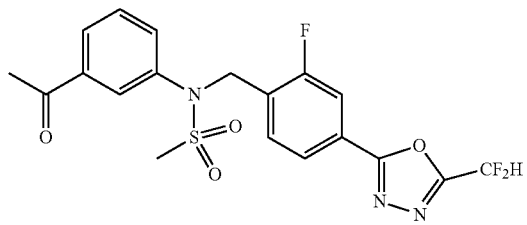

Sodium hydride (60.00%, 0.007 g, 0.169 mmol) was added to a solution of N-(3-acetylphenyl)methanesulfonamide (0.030 g, 0.141 mmol) in N,N-dimethylformide (1 mL) at 0° C., and the mixture was stirred at the same temperature for 30 min. The reaction mixture was treated with 2-(4-(bromomethyl)-3-fluorophenyl)-5-(difluoromethyl)-1,3,4-oxadiazole (0.045 g, 0.148 mmol), and stirred for additional 16 hr at the room temperature. Then, aqueous 0.1N-hydrochloric acid solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(3-acetylphenyl)-N-(4-(5-(difluoromethyl)-1,3,4-oxadiazol-2-yl)-2-fluorobenzyl)methanesulfonamide as white solid (0.030 g, 48.5%).

$^1$H NMR (400 MHz, CDCl₃) δ 7.92 (t, 1H, J=1.9 Hz), 7.89-7.82 (m, 2H), 7.72 (dd, 1H, J=9.9, 1.7 Hz), 7.64 (t, 1H, J=7.6 Hz), 7.52 (ddd, 1H, J=8.0, 2.3, 1.2 Hz), 7.45 (t, 1H, J=7.8 Hz), 6.89 (t, 1H, J=51.7 Hz), 5.04 (s, 2H), 3.02 (s, 3H), 2.58 (s, 3H); LRMS (ES) m/z 438.16 (M⁺−1).

EXAMPLE 64

Compound 11255: N-(2-fluoro-4-(5-(trifluoromethyl)-1,3,4-oxadiazol-2-yl)benzyl)-N-(3-fluorophenyl)tetrahydro-2H-thiopyran-4-sulfonamide 1,1-dioxide

[Step 1] N-(3-fluorophenyl)tetrahydro-2H-thiopyran-4-sulfonamide 1,1-dioxide

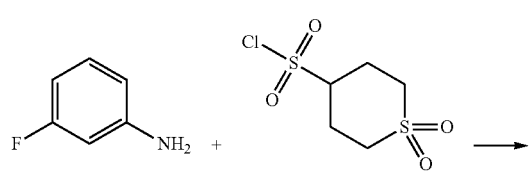

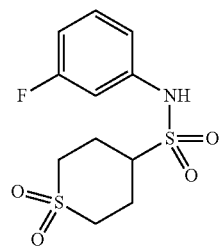

Triethylamine (0.162 mL, 1.170 mmol) was added to a solution of aniline (0.100 g, 0.900 mmol) in dichloromethane (4 mL) at 0° C., and the mixture was stirred at the same temperature for 10 min. The reaction mixture was treated with tetrahydro-2H-thiopyran-4-sulfonyl chloride 1,1-dioxide (0.209 g, 0.900 mmol), and stirred for additional 25 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO₂, 12 g cartridge; ethyl acetate/hexane=0% to 50%) to give N-(3-fluorophenyl)tetrahydro-2H-thiopyran-4-sulfonamide 1,1-dioxide as white solid (0.250 g, 90.4%).

[Step 2] methyl 3-fluoro-4-(((N-(3-fluorophenyl)-1,1-dioxidotetrahydro-2H-thiopyran)-4-sulfonamido)methyl)benzoate

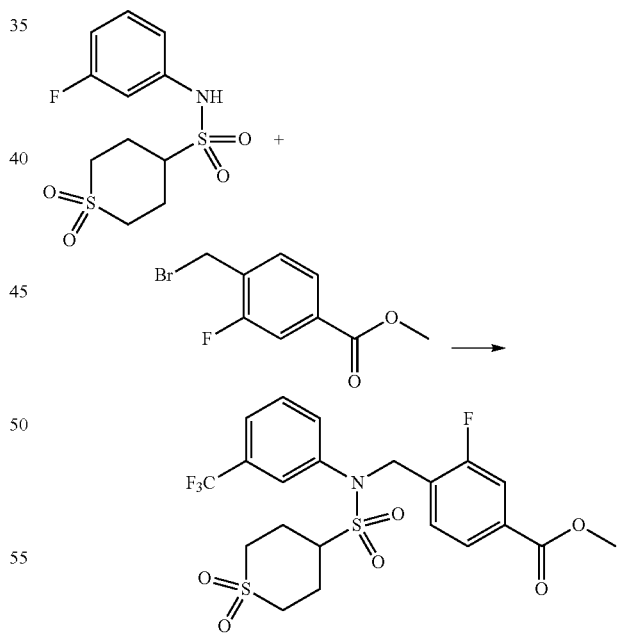

Sodium hydride (60.00%, 0.041 g, 1.032 mmol) was added to a solution of N-(3-fluorophenyl)tetrahydro-2H-thiopyran-4-sulfonamide 1,1-dioxide (0.244 g, 0.794 mmol) in N,N-dimethylformide (6 mL) at 0° C., and stirred at the same temperature for 20 min. The reaction mixture was treated with methyl 4-(bromomethyl)-3-fluorobenzoate (0.216 g, 0.873 mmol), and stirred at the same temperature for 20 min. Then, aqueous 1N-hydrochloric acid solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 30%) to give methyl 3-fluoro-4-(((N-(3-fluorophenyl)-1,1-dioxidotetrahydro-2H-thiopyran)-4-sulfonamido)methyl)benzoate as colorlessness oil (0.220 g, 58.5%).

[Step 3] N-(2-fluoro-4-(hydrazinecarbonyl)benzyl)-N-(3-fluorophenyl)tetrahydro-2H-thiopyran-4-sulfonamide 1,1-dioxide

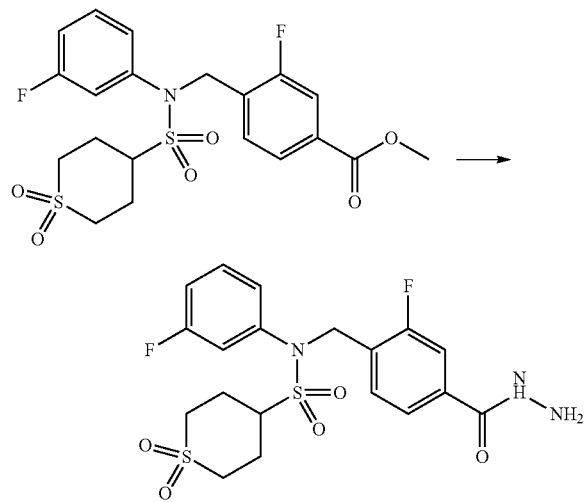

A mixture of methyl 3-fluoro-4-(((N-(3-fluorophenyl)-1,1-dioxidotetrahydro-2H-thiopyran)-4-sulfonamido)methyl)benzoate (0.220 g, 0.465 mmol) and hydrazine hydrate (0.074 g, 2.323 mmol) in ethanol (8 mL) prepared at the ambient temperature was heated at reflux for 18 hr, and cooled down to the ambient temperature, and concentrated under the reduced pressure to remove the solvent. The residue was diluted with water and stirred. The resulting precipitates were collected by filtration, washed by water, and dried to give N-(2-fluoro-4-(hydrazinecarbonyl)benzyl)-N-(3-fluorophenyl)tetrahydro-2H-thiopyran-4-sulfonamide 1,1-dioxide as white solid (0.200 g, 90.9%).

[Step 4] Compound 11255

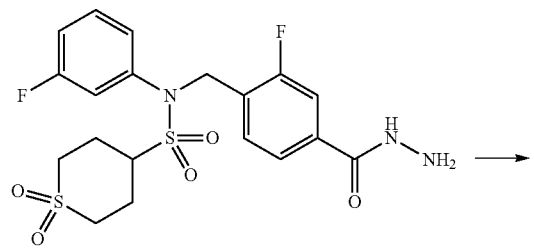

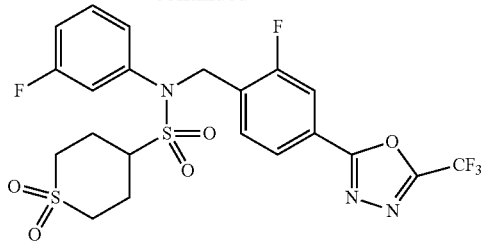

A solution of N-(2-fluoro-4-(hydrazinecarbonyl)benzyl)-N-(3-fluorophenyl)tetrahydro-2H-thiopyran-4-sulfonamide 1,1-dioxide (0.070 g, 0.148 mmol) and triethylamine (0.027 mL, 0.192 mmol) in tetrahydrofuran (2 mL) was stirred at the room temperature for 10 min, and then mixed with trifluoroacetic anhydride (0.022 mL, 0.163 mmol). The reaction mixture was heated at reflux for 16 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO₂, 4 g cartridge; ethyl acetate/hexane=0% to 30%) to give N-(2-fluoro-4-(5-(trifluoromethyl)-1,3,4-oxadiazol-2-yl)benzyl)-N-(3-fluorophenyl)tetrahydro-2H-thiopyran-4-sulfonamide 1,1-dioxide as white solid (0.065 g, 79.7%).
¹H NMR (400 MHz, DMSO-d₆) δ 7.93 (dd, 1H, J=8.0, 1.7 Hz), 7.85 (dd, 1H, J=10.1, 1.7 Hz), 7.68 (t, 1H, J=7.7 Hz), 7.51-7.39 (m, 2H), 7.35-7.30 (m, 1H), 7.22-7.15 (m, 1H), 5.18 (s, 2H), 3.76 (t, 1H, J=11.7 Hz), 3.51-3.43 (m, 2H), 3.37-3.29 (m, 2H), 3.23 (d, 2H, J=13.8 Hz), 2.18 (q, 2H, J=12.6 Hz); LRMS (ES) m/z 552.3 (M⁺+1).

EXAMPLE 65

Compound 11256: N-(4-(5-(difluoromethyl)-1,3,4-oxadiazol-2-yl)-2-fluorobenzyl)-N-(3-fluorophenyl)tetrahydro-2H-thiopyran-4-sulfonamide 1,1-dioxide

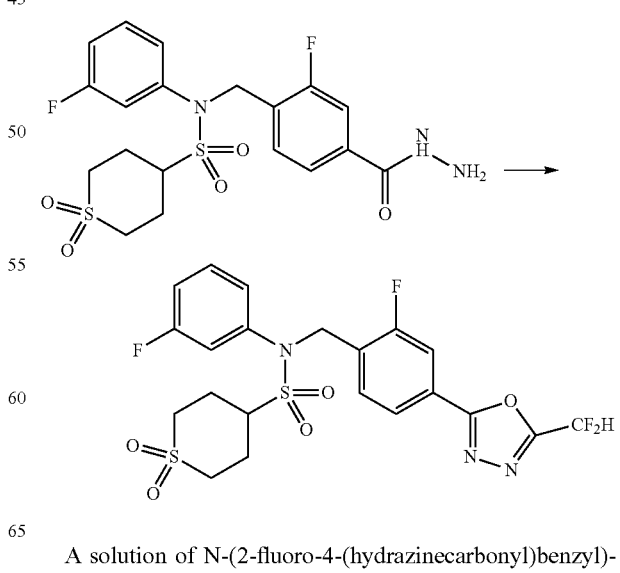

A solution of N-(2-fluoro-4-(hydrazinecarbonyl)benzyl)-N-(3-fluorophenyl)tetrahydro-2H-thiopyran-4-sulfonamide 1,1-dioxide (0.070 g, 0.148 mmol) and triethylamine (0.027 mL, 0.192 mmol) in tetrahydrofuran (2 mL) was stirred at the room temperature for 10 min, and then mixed with 2,2-difluoroacetic anhydride (0.019 mL, 0.177 mmol). The reaction mixture was heated at reflux for 16 hr, and cooled down to the room temperature to terminate the reaction. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 30%) to give N-(4-(5-(difluoromethyl)-1,3,4-oxadiazol-2-yl)-2-fluorobenzyl)-N-(3-fluorophenyl)tetrahydro-2H-thiopyran-4-sulfonamide 1,1-dioxide as white solid (0.070 g, 88.8%).

$^1$H NMR (400 MHz, DMSO-d$_6$) δ 7.90 (dd, 1H, J=8.0, 1.7 Hz), 7.82 (dd, 1H, J=10.1, 1.7 Hz), 7.68 (d, 1H, J=8.2 Hz), 7.65 (s, 0.25H), 7.56 (s, 0.5H), 7.49 (m, 0.25H), 7.49-7.37 (m, 2H), 7.33 (dd, 1H, J=8.2, 1.9 Hz), 7.19 (td, 1H, J=8.2, 2.2 Hz), 5.17 (s, 2H), 3.75 (t, 1H, J=11.8 Hz), 3.53-3.41 (m, 2H), 3.36-3.28 (m, 2H), 3.23 (d, 2H, J=13.6 Hz), 2.18 (q, 2H, J=12.6 Hz); LRMS (ES) m/z 534.3 (M$^+$+1).

EXAMPLE 66

Compound 11271: N-(4-chlorophenyl)-N-(2-fluoro-4-(5-(trifluoromethyl)-1,3,4-oxadiazol-2-yl)benzyl)methanesulfonamide

[Step 1] N-(4-chlorophenyl)methanesulfonamide

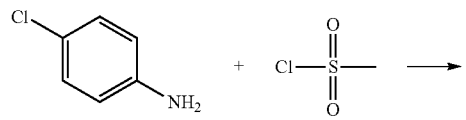

A solution of 4-chloroaniline (1.000 g, 7.839 mmol), pyridine (0.696 mL, 8.623 mmol) and methanesulfonyl chloride (0.733 mL, 9.407 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(4-chlorophenyl)methanesulfonamide, 0.950 g, 58.9%, brown solid).

[Step 2] methyl 4-((N-(4-chlorophenyl)methylsulfonamido)methyl)-3-fluorobenzoate

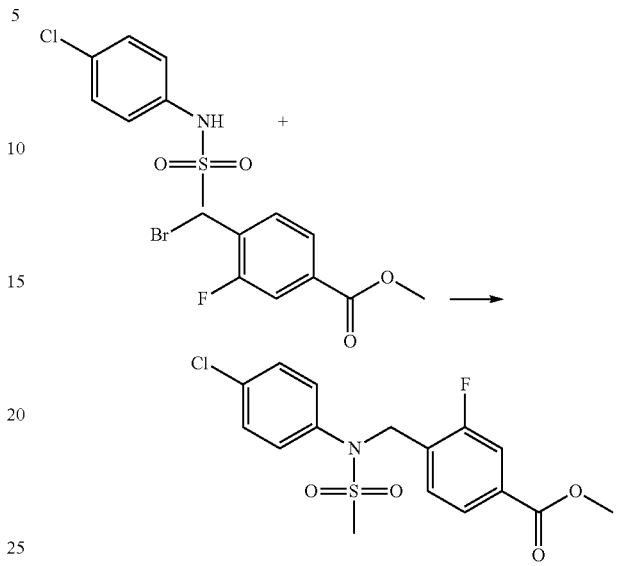

A solution of N-(4-chlorophenyl)methanesulfonamide (0.500 g, 2.431 mmol), sodium hydride (60.00%, 0.117 g, 2.917 mmol) and methyl 4-(bromomethyl)-3-fluorobenzoate (0.661 g, 2.674 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 4-((N-(4-chlorophenyl)methylsulfonamido)methyl)-3-fluorobenzoate as yellow solid (0.690 g, 76.3%).

[Step 3] N-(4-chlorophenyl)-N-(2-fluoro-4-(hydrazinecarbonyl)benzyl)methanesulfonamide

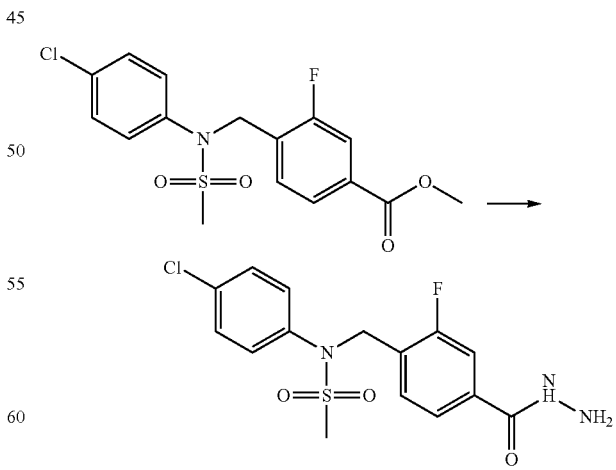

A mixture of methyl 4-((N-(4-chlorophenyl)methylsulfonamido)methyl)-3-fluorobenzoate (0.690 g, 1.856 mmol) and hydrazine hydrate (0.929 g, 18.558 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(4-chlorophenyl)-N-(2-fluoro-4-(hydrazinecarbonyl)benzyl)methanesulfonamide, 0.580 g, 84.1%, yellow solid).

[Step 4] Compound 11271

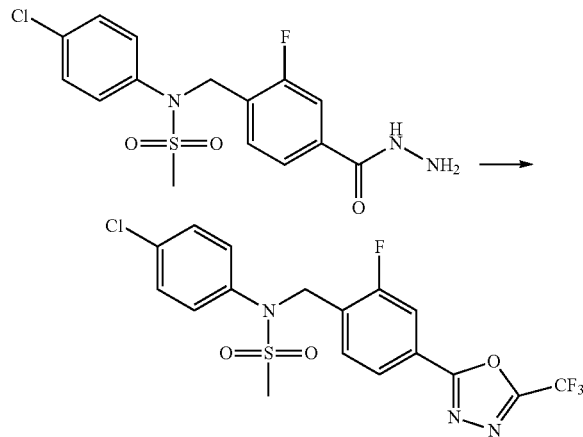

A solution of N-(4-chlorophenyl)-N-(2-fluoro-4-(hydrazinecarbonyl)benzyl)methanesulfonamide (0.300 g, 0.807 mmol), trifluoroacetic anhydride (0.123 mL, 0.888 mmol) and triethylamine (0.169 mL, 1.210 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-chlorophenyl)-N-(2-fluoro-4-(5-(trifluoromethyl)-1,3,4-oxadiazol-2-yl)benzyl)methanesulfonamide, 0.120 g, 33.1%, white solid).

$^1$H NMR (400 MHz, CDCl$_3$) δ 7.88 (dd, 1H, J=8.0, 1.7 Hz), 7.76 (dd, 1H, J=9.8, 1.7 Hz), 7.67 (t, 1H, J=7.6 Hz), 7.38-7.29 (m, 2H), 7.31-7.22 (m, 2H), 5.01 (s, 2H), 3.02 (s, 3H); LRMS (ES) m/z 450.3 (M$^+$+1).

EXAMPLE 67

Compound 11272: N-(2-fluoro-4-(5-(trifluoromethyl)-1,3,4-oxadiazol-2-yl)benzyl)-N-(5-fluoropyridin-3-yl)methanesulfonamide

[Step 1]
N-(5-fluoropyridin-3-yl)methanesulfonamide

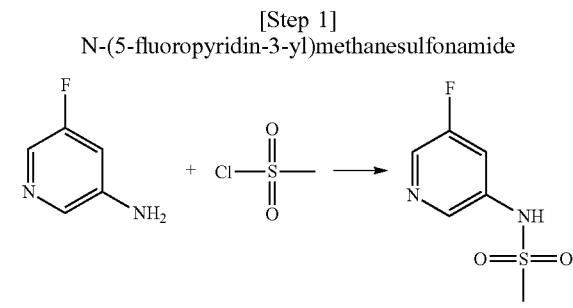

A solution of 5-fluoropyridin-3-amine (1.000 g, 8.920 mmol), pyridine (0.792 mL, 9.812 mmol) and methanesulfonyl chloride (0.834 mL, 10.704 mmol) in dichloromethane (20 mL) was stirred at the room temperature for 5 hr. The precipitates were collected by filtration, washed by saturated aqueous dichloromethane solution, and dried to give N-(5-fluoropyridin-3-yl)methanesulfonamide as yellow solid (0.890 g, 52.5%).

[Step 2] methyl 3-fluoro-4-((N-(5-fluoropyridin-3-yl)methylsulfonamido)methyl)benzoate

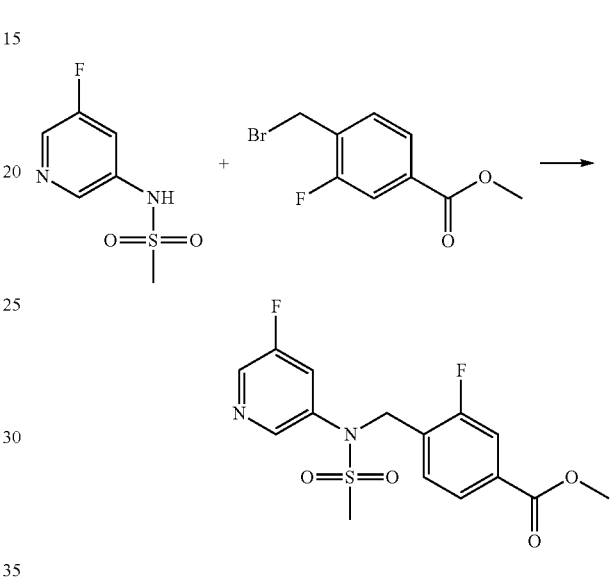

A solution of N-(5-fluoropyridin-3-yl)methanesulfonamide (0.380 g, 1.998 mmol), sodium hydride (60.00%, 0.096 g, 2.398 mmol) and methyl 4-(bromomethyl)-3-fluorobenzoate (0.543 g, 2.198 mmol) in N,N-dimethylformamide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 3-fluoro-4-((N-(5-fluoropyridin-3-yl)methylsulfonamido)methyl)benzoate as yellow solid (0.510 g, 71.6%).

[Step 3] N-(2-fluoro-4-(hydrazinecarbonyl)benzyl)-N-(5-fluoropyridin-3-yl)methanesulfonamide

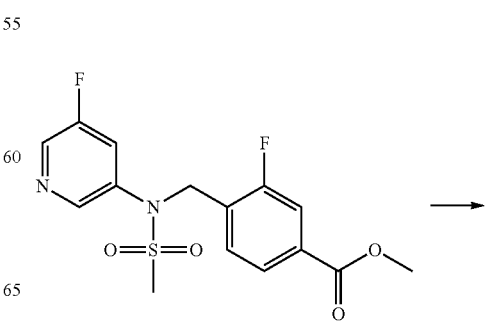

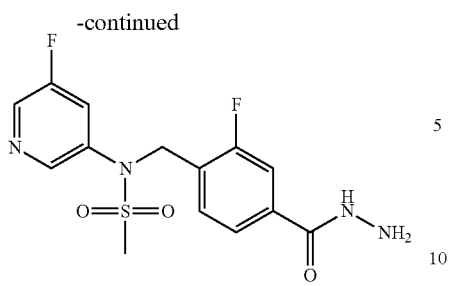

A mixture of methyl 3-fluoro-4-((N-(5-fluoropyridin-3-yl)methylsulfonamido)methyl)benzoate (0.510 g, 1.431 mmol) and hydrazine hydrate (0.716 g, 14.312 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(5-fluoropyridin-3-yl)methanesulfonamide, 0.440 g, 86.3%, yellow solid).

[Step 4] Compound 11272

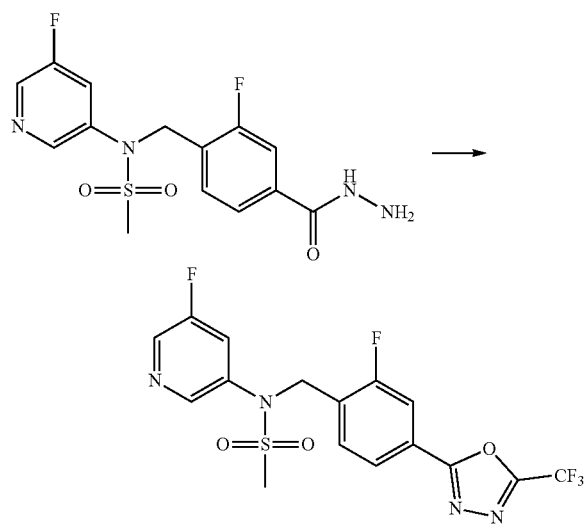

A solution of N-(2-fluoro-4-(hydrazinecarbonyl)benzyl)-N-(5-fluoropyridin-3-yl)methanesulfonamide (0.220 g, 0.617 mmol), trifluoroacetic anhydride (0.094 mL, 0.679 mmol) and triethylamine (0.129 mL, 0.926 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was obtained without further purification (N-(2-fluoro-4-(5-(trifluoromethyl)-1,3,4-oxadiazol-2-yl)benzyl)-N-(5-fluoropyridin-3-yl)methanesulfonamide, 0.110 g, 41.0%, yellow solid).

$^1$H NMR (400 MHz, CDCl$_3$) δ 8.48-8.42 (m, 2H), 7.92 (dd, 1H, J=8.1, 1.7 Hz), 7.80 (dd, 1H, J=9.8, 1.7 Hz), 7.67 (t, 1H, J=7.6 Hz), 7.52-7.43 (m, 1H), 5.07 (s, 2H), 3.09 (s, 3H); LRMS (ES) m/z 435.1 (M$^+$+1).

EXAMPLE 68

Compound 11273: N-(2-fluoro-4-(5-(trifluoromethyl)-1,3,4-oxadiazol-2-yl)benzyl)-N-(2-fluorophenyl)methanesulfonamide

[Step 1] N-(2-fluorophenyl)methanesulfonamide

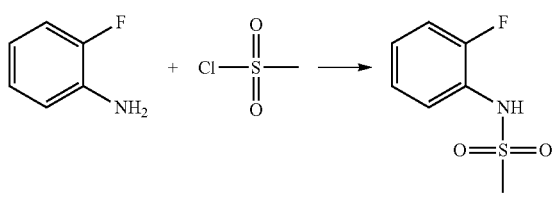

A solution of 2-fluoroaniline (1.000 g, 8.999 mmol), pyridine (0.799 mL, 9.899 mmol) and methanesulfonyl chloride (0.841 mL, 10.799 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(2-fluorophenyl)methanesulfonamide, 0.900 g, 52.9%, yellow solid).

[Step 2] methyl 3-fluoro-4-((N-(2-fluorophenyl)methylsulfonamido)methyl)benzoate

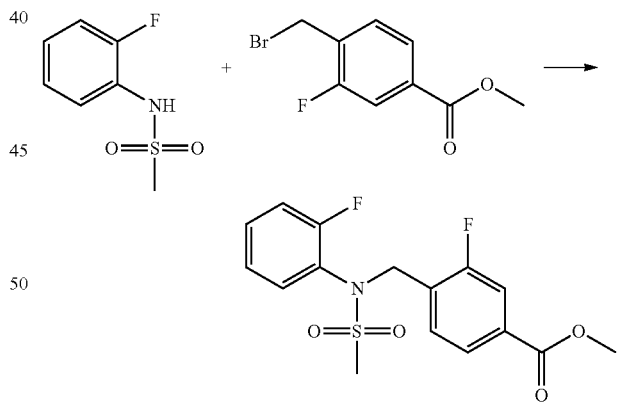

A solution of N-(2-fluorophenyl)methanesulfonamide (0.500 g, 2.643 mmol), sodium hydride (60.00%, 0.127 g, 3.171 mmol) and methyl 4-(bromomethyl)-3-fluorobenzoate (0.718 g, 2.907 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 3-fluoro-4-((N-

(2-fluorophenyl)methylsulfonamido)methyl)benzoate as yellow solid (0.630 g, 67.1%).

[Step 3] N-(2-fluoro-4-(hydrazinecarbonyl)benzyl)-N-(2-fluorophenyl)methanesulfonamide

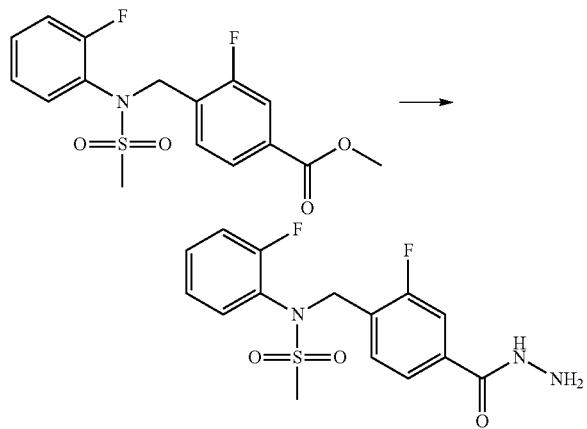

A mixture of methyl 3-fluoro-4-((N-(2-fluorophenyl)methylsulfonamido)methyl)benzoate (0.680 g, 1.914 mmol) and hydrazine hydrate (0.958 g, 19.136 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(2-fluoro-4-(hydrazinecarbonyl)benzyl)-N-(2-fluorophenyl)methanesulfonamide, 0.590 g, 86.8%, white solid).

[Step 4] N-(2-fluoro-4-(2-(2,2,2-trifluoroacetyl)hydrazine-1-carbonyl)benzyl)-N-(2-fluorophenyl)methanesulfonamide

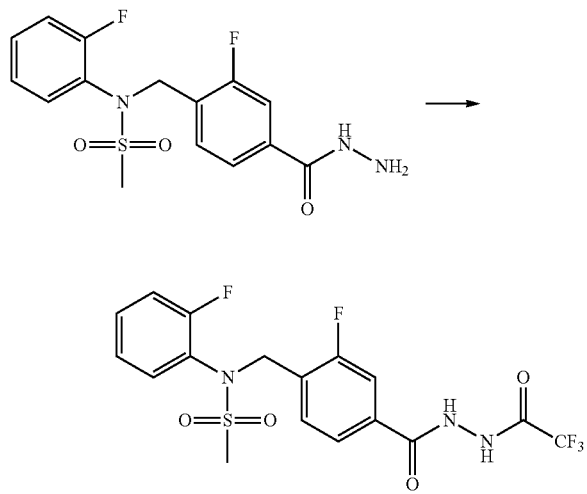 [SMILES: CS(=O)(=O)N(Cc1ccc(C(=O)NN)cc1F)c1ccccc1Cl ; CS(=O)(=O)N(Cc1ccc(C(=O)NNC(=O)C(F)(F)F)cc1F)c1ccccc1Cl]

A solution of N-(2-fluoro-4-(hydrazinecarbonyl)benzyl)-N-(2-fluorophenyl)methanesulfonamide (0.290 g, 0.816 mmol), trifluoroacetic anhydride (0.125 mL, 0.898 mmol) and triethylamine (0.170 mL, 1.224 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(2-fluoro-4-(2-(2,2,2-trifluoroacetyl)hydrazine-1-carbonyl)benzyl)-N-(2-fluorophenyl)methanesulfonamide, 0.210 g, 57.0%, yellow solid).

[Step 5] Compound 11273

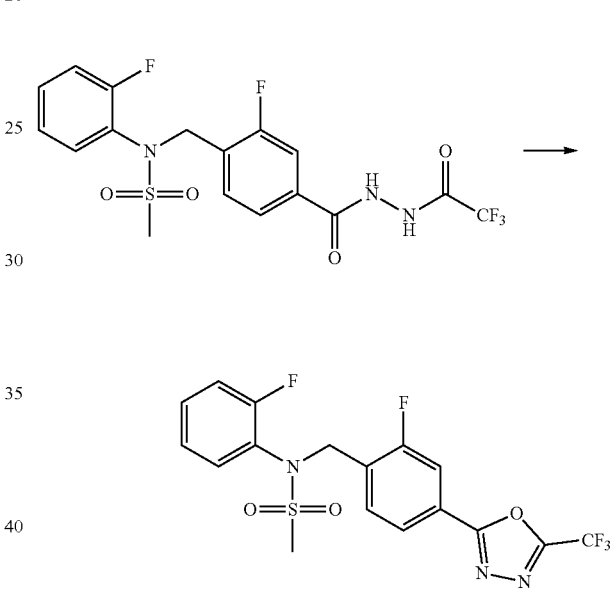

A solution of N-(2-fluoro-4-(2-(2,2,2-trifluoroacetyl)hydrazine-1-carbonyl)benzyl)-N-(2-fluorophenyl)methanesulfonamide (0.210 g, 0.465 mmol) in tetrahydrofuran (10 mL) was treated with 1-methoxy-N-triethylammoniosulfonyl-methanimidate (Burgess reagent, 0.166 g, 0.698 mmol), heated at 150° C. under the microwaves for 30 min, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(2-fluoro-4-(5-(trifluoromethyl)-1,3,4-oxadiazol-2-yl)benzyl)-N-(2-fluorophenyl)methanesulfonamide as yellow solid (0.150 g, 74.4%).

$^1$H NMR (400 MHz, CDCl₃) δ 7.89 (dd, 1H, J=8.0, 1.7 Hz), 7.79-7.67 (m, 2H), 7.41-7.30 (m, 1H), 7.32-7.23 (m, 1H), 7.22-7.07 (m, 2H), 5.00 (s, 2H), 3.09 (s, 3H); LRMS (ES) m/z 434.0 (M⁺+1).

EXAMPLE 69

Compound 11274: N-(2-fluoro-4-(5-(trifluoromethyl)-1,3,4-oxadiazol-2-yl)benzyl)-N-(2-fluorophenyl)methanesulfonamide

[Step 1] N-(4-(2-(2,2-difluoroacetyl)hydrazine-1-carbonyl)-2-fluorobenzyl)-N-(2-fluorophenyl)methanesulfonamide

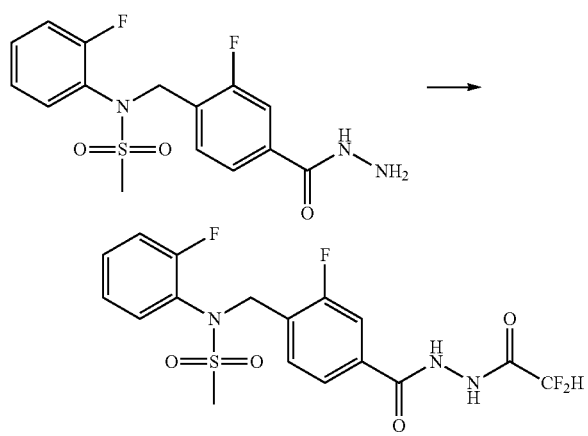

A solution of N-(2-fluoro-4-(hydrazinecarbonyl)benzyl)-N-(2-fluorophenyl)methanesulfonamide (0.290 g, 0.816 mmol), difluoroacetic anhydride (0.098 mL, 0.898 mmol) and triethylamine (0.170 mL, 1.224 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(4-(2-(2,2-difluoroacetyl)hydrazine-1-carbonyl)-2-fluorobenzyl)-N-(2-fluorophenyl)methanesulfonamide, 0.200 g, 56.5%, yellow solid).

[Step 2] Compound 11274

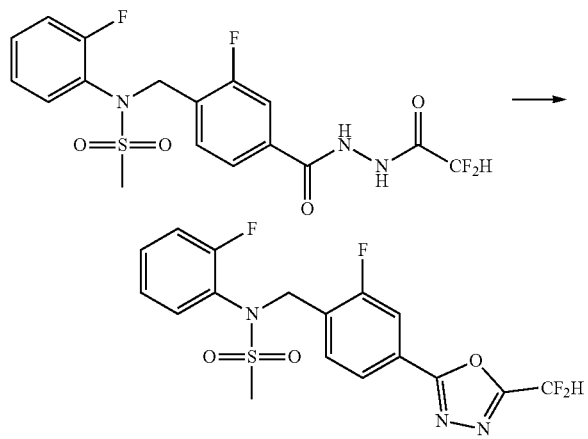

A mixture of N-(4-(2-(2,2-difluoroacetyl)hydrazine-1-carbonyl)-2-fluorobenzyl)-N-(2-fluorophenyl)methanesulfonamide (0.200 g, 0.461 mmol) and 1-methoxy-N-triethylammoniosulfonyl-methanimidate (Burgess reagent, 0.165 g, 0.692 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(2-fluoro-4-(5-(trifluoromethyl)-1,3,4-oxadiazol-2-yl)benzyl)-N-(2-fluorophenyl)methanesulfonamide as yellow solid (0.110 g, 57.4%).

$^1$H NMR (400 MHz, CDCl₃) δ 7.89 (dd, 1H, J=8.0, 1.7 Hz), 7.74 (dd, 1H, J=9.9, 1.6 Hz), 7.68 (t, 1H, J=7.6 Hz), 7.38-7.31 (m, 1H), 7.30-7.24 (m, 1H), 7.20-7.08 (m, 2H), 7.05 (s, 0.2H), 6.92 (s, 0.5H), 6.80 (s, 0.2H), 4.99 (s, 2H), 3.09 (s, 3H); LRMS (ES) m/z 416.3 (M⁺+1).

EXAMPLE 70

Compound 11275: N-(2-fluoro-4-(5-(trifluoromethyl)-1,3,4-oxadiazol-2-yl)benzyl)-N-(4-fluorophenyl)methanesulfonamide

[Step 1] N-(4-fluorophenyl)methanesulfonamide

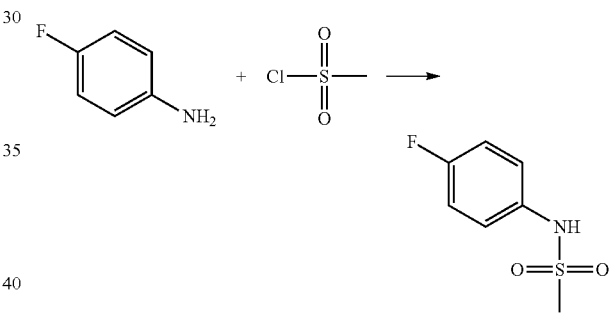

A solution of 4-fluoroaniline (1.000 g, 8.999 mmol), pyridine (0.799 mL, 9.899 mmol) and methanesulfonyl chloride (0.841 mL, 10.799 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO₄, filtered, and concentrated in vacuo. The title compound was used without further purification (N-(4-fluorophenyl)methanesulfonamide, 0.960 g, 56.4%, brown solid).

[Step 2] methyl 3-fluoro-4-((N-(4-fluorophenyl)methylsulfonamido)methyl)benzoate

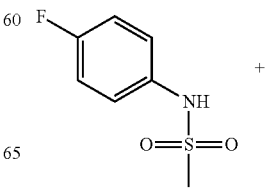
+

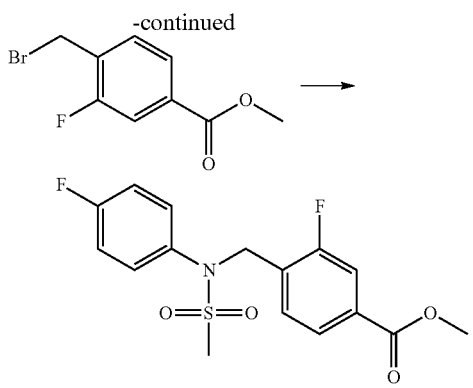

A solution of N-(4-fluorophenyl)methanesulfonamide (0.500 g, 2.643 mmol), sodium hydride (60.00%, 0.127 g, 3.171 mmol) and methyl 4-(bromomethyl)-3-fluorobenzoate (0.718 g, 2.907 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 3-fluoro-4-((N-(4-fluorophenyl)methylsulfonamido)methyl)benzoate as yellow solid (0.690 g, 73.5%).

[Step 3] N-(2-fluoro-4-(hydrazinecarbonyl)benzyl)-N-(4-fluorophenyl)methanesulfonamide

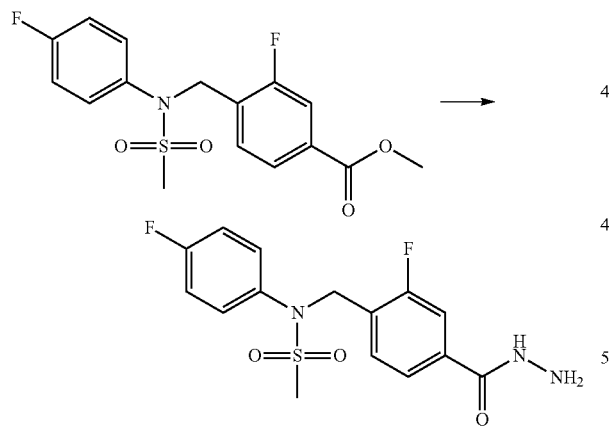

A mixture of methyl 3-fluoro-4-((N-(4-fluorophenyl)methylsulfonamido)methyl)benzoate (0.690 g, 1.942 mmol) and hydrazine hydrate (0.972 g, 19.417 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(4-fluorophenyl)methanesulfonamide, 0.610 g, 88.4%, yellow solid).

[Step 4] N-(2-fluoro-4-(2-(2,2,2-trifluoroacetyl)hydrazine-1-carbonyl)benzyl)-N-(4-fluorophenyl)methanesulfonamide

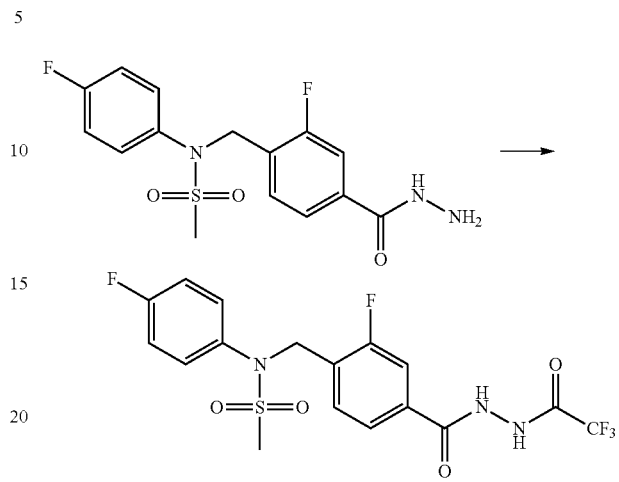

A solution of N-(2-fluoro-4-(hydrazinecarbonyl)benzyl)-N-(4-fluorophenyl)methanesulfonamide (0.300 g, 0.844 mmol), trifluoroacetic anhydride (0.129 mL, 0.929 mmol) and triethylamine (0.176 mL, 1.266 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-fluoro-4-(2-(2,2,2-trifluoroacetyl)hydrazine-1-carbonyl)benzyl)-N-(4-fluorophenyl)methanesulfonamide, 0.210 g, 55.1%, yellow solid).

[Step 5] Compound 11275

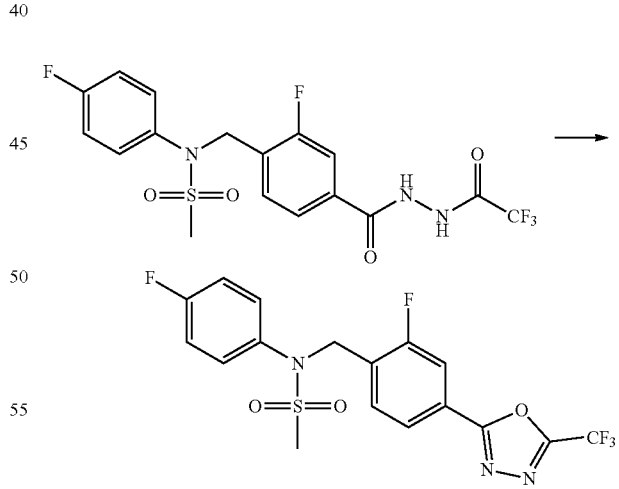

A mixture of N-(2-fluoro-4-(2-(2,2,2-trifluoroacetyl)hydrazine-1-carbonyl)benzyl)-N-(4-fluorophenyl)methanesulfonamide (0.210 g, 0.465 mmol) and 1-methoxy-N-triethylammoniosulfonyl-methanimidate (Burgess reagent, 0.166 g, 0.698 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(2-fluoro-4-(5-(trifluoromethyl)-1,3,4-oxadiazol-2-yl)benzyl)-N-(4-fluorophenyl)methanesulfonamide as white solid (0.140 g, 69.4%).

$^1$H NMR (400 MHz, CDCl$_3$) δ 7.89 (dd, 1H, J=8.0, 1.7 Hz), 7.76 (dd, 1H, J=9.8, 1.6 Hz), 7.68 (t, 1H, J=7.6 Hz), 7.35-7.23 (m, 2H), 7.13-7.00 (m, 2H), 5.00 (s, 2H), 3.03 (s, 3H); LRMS (ES) m/z 434.2 (M$^+$+1).

EXAMPLE 71

Compound 11276: N-(4-(5-(difluoromethyl)-1,3,4-oxadiazol-2-yl)-2-fluorobenzyl)-N-(4-fluorophenyl)methanesulfonamide

[Step 1] N-(4-(2-(2,2-difluoroacetyl)hydrazine-1-carbonyl)-2-fluorobenzyl)-N-(4-fluorophenyl)methanesulfonamide

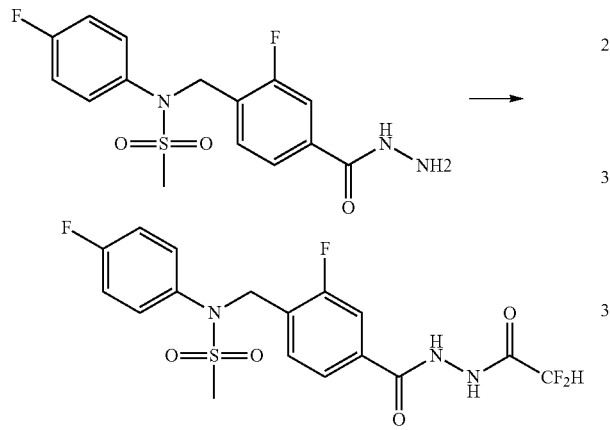

A solution of N-(2-fluoro-4-(hydrazinecarbonyl)benzyl)-N-(4-fluorophenyl)methanesulfonamide (0.300 g, 0.844 mmol), difluoroacetic anhydride (0.101 mL, 0.929 mmol) and triethylamine (0.176 mL, 1.266 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-2-fluorobenzyl)-N-(4-fluorophenyl)methanesulfonamide, 0.230 g, 62.9%, yellow solid).

[Step 2] Compound 11276

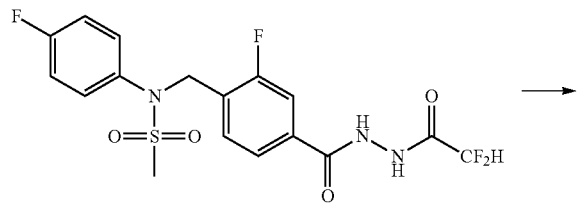

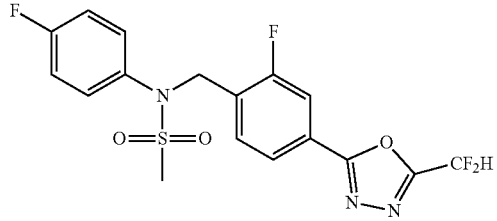

A mixture of N-(4-(2-(2,2-difluoroacetyl)hydrazine-1-carbonyl)-2-fluorobenzyl)-N-(4-fluorophenyl)methanesulfonamide (0.230 g, 0.531 mmol) and 1-methoxy-N-triethylammoniosulfonyl-methanimidate (Burgess reagent, 0.190 g, 0.796 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(4-fluorophenyl)methanesulfonamide as yellow solid (0.140 g, 63.5%).

$^1$H NMR (400 MHz, CDCl$_3$) δ 7.89 (dd, 1H, J=8.0, 1.7 Hz), 7.76 (dd, 1H, J=9.9, 1.7 Hz), 7.65 (t, 1H, J=7.6 Hz), 7.34-7.24 (m, 2H), 7.11-7.00 (m, 2H), 6.93 (s, 0.5H), 6.80 (s, 0.2H), 4.99 (s, 2H), 3.03 (s, 3H); LRMS (ES) m/z 416.3 (M$^+$+1).

EXAMPLE 72

Compound 11277: N-(4-bromophenyl)-N-(2-fluoro-4-(5-(trifluoromethyl)-1,3,4-oxadiazol-2-yl)benzyl)methanesulfonamide

[Step 1] N-(4-bromophenyl)methanesulfonamide

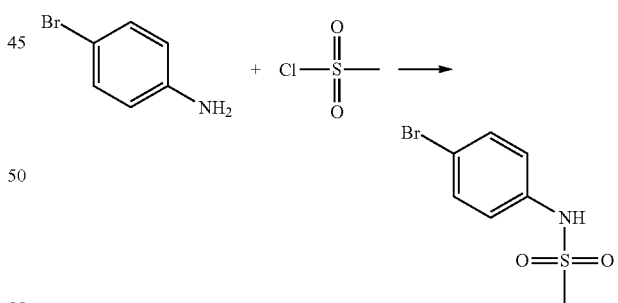

A solution of 4-bromoaniline (1.000 g, 5.813 mmol), pyridine (0.516 mL, 6.395 mmol) and methanesulfonyl chloride (0.544 mL, 6.976 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(4-bromophenyl)methanesulfonamide, 0.960 g, 66.0%, yellow solid).

[Step 2] methyl 4-((N-(4-bromophenyl)methylsulfonamido)methyl)-3-fluorobenzoate

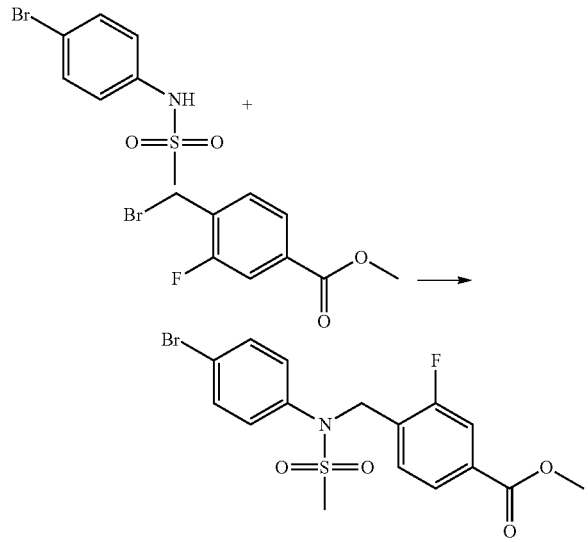

A solution of N-(4-bromophenyl)methanesulfonamide (0.500 g, 1.999 mmol), sodium hydride (60.00%, 0.096 g, 2.399 mmol) and methyl 4-(bromomethyl)-3-fluorobenzoate (0.543 g, 2.199 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 4-((N-(4-bromophenyl)methylsulfonamido)methyl)-3-fluorobenzoate as yellow solid (0.680 g, 81.7%).

[Step 3] N-(4-bromophenyl)-N-(2-fluoro-4-(hydrazinecarbonyl)benzyl)methanesulfonamide

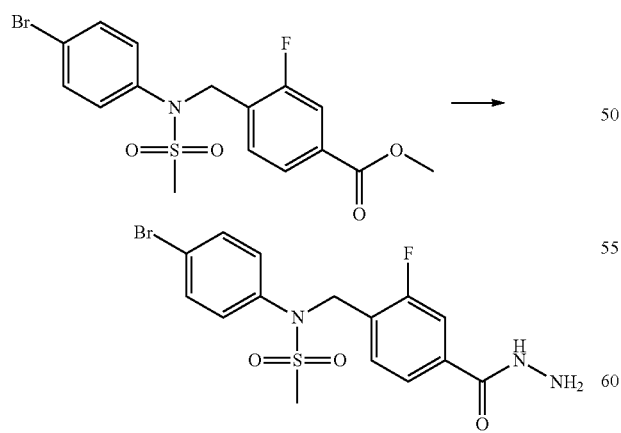

A mixture of methyl 4-((N-(4-bromophenyl)methylsulfonamido)methyl)-3-fluorobenzoate (0.680 g, 1.634 mmol) and hydrazine hydrate (0.818 g, 16.336 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(4-bromophenyl)-N-(2-fluoro-4-(hydrazinecarbonyl)benzyl)methanesulfonamide, 0.650 g, 95.6%, white solid).

[Step 4] N-(4-bromophenyl)-N-(2-fluoro-4-(2-(2,2,2-trifluoroacetyl)hydrazine-1-carbonyl)benzyl)methanesulfonamide

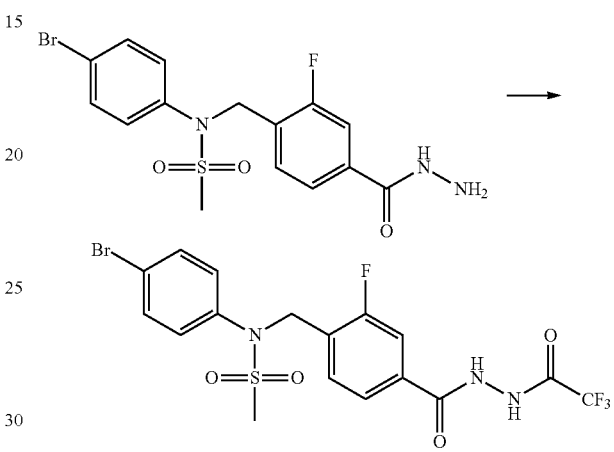

A solution of N-(4-bromophenyl)-N-(2-fluoro-4-(hydrazinecarbonyl)benzyl)methanesulfonamide (0.290 g, 0.697 mmol), trifluoroacetic anhydride (0.108 mL, 0.766 mmol) and triethylamine (0.117 mL, 0.836 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-bromophenyl)-N-(2-fluoro-4-(2-(2,2,2-trifluoroacetyl)hydrazine-1-carbonyl)benzyl)methanesulfonamide, 0.258 g, 72.3%, yellow solid).

[Step 5] Compound 11277

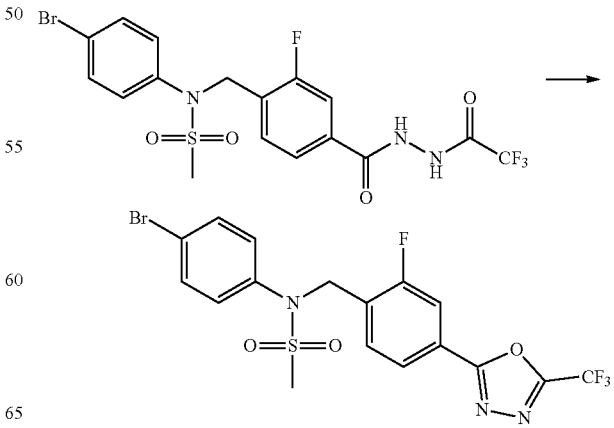

A solution of N-(4-bromophenyl)-N-(2-fluoro-4-(2-(2,2,2-trifluoroacetyl)hydrazine-1-carbonyl)benzyl)methanesulfonamide (0.290 g, 0.566 mmol) and 1-methoxy-N-triethylammoniosulfonyl-methanimidate (Burgess reagent, 0.202 g, 0.849 mmol) in tetrahydrofuran (10 mL) was stirred at 150° C. for 30 min, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 30%) to give N-(4-bromophenyl)-N-(2-fluoro-4-(5-(trifluoromethyl)-1,3,4-oxadiazol-2-yl)benzyl)methanesulfonamide as yellow solid (0.190 g, 67.9%).

$^1$H NMR (400 MHz, CDCl$_3$) δ 7.92-7.85 (m, 1H), 7.76 (dd, 1H, J=9.9, 1.7 Hz), 7.71-7.62 (m, 1H), 7.54-7.45 (m, 2H), 7.24-7.17 (m, 2H), 5.01 (s, 2H), 3.02 (s, 3H); LRMS (ES) m/z 496.2 (M$^+$+1).

EXAMPLE 73

Compound 11278: N-(4-bromophenyl)-N-(4-(5-(difluoromethyl)-1,3,4-oxadiazol-2-yl)-2-fluorobenzyl)methanesulfonamide

[Step 1] N-(4-bromophenyl)-N-(4-(2-(2,2-difluoroacetyl)hydrazine-1-carbonyl)-2-fluorobenzyl)methanesulfonamide

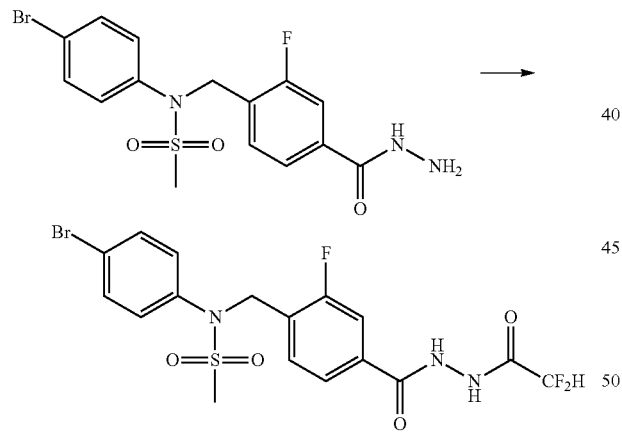

A solution of N-(4-bromophenyl)-N-(2-fluoro-4-(hydrazinecarbonyl)benzyl)methanesulfonamide (0.300 g, 0.721 mmol), difluoroacetic anhydride (0.138 g, 0.793 mmol) and triethylamine (0.121 mL, 0.865 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-bromophenyl)-N-(4-(2-(2,2-difluoroacetyl)hydrazine-1-carbonyl)-2-fluorobenzyl)methanesulfonamide, 0.240 g, 67.4%, yellow solid).

[Step 2] Compound 11278

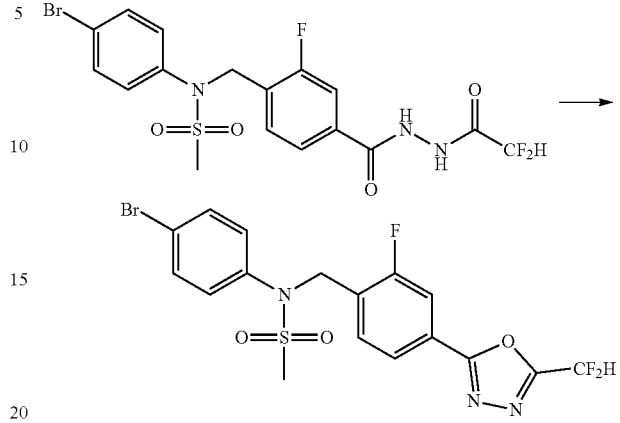

A mixture of N-(4-bromophenyl)-N-(4-(2-(2,2-difluoroacetyl)hydrazine-1-carbonyl)-2-fluorobenzyl)methanesulfonamide (0.240 g, 0.486 mmol) and 1-methoxy-N-triethylammoniosulfonyl-methanimidate (Burgess reagent, 0.174 g, 0.728 mmol) in dichloromethane (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-bromophenyl)-N-(4-(5-(difluoromethyl)-1,3,4-oxadiazol-2-yl)-2-fluorobenzyl)methanesulfonamide as white solid (0.150 g, 64.9%).

$^1$H NMR (400 MHz, CDCl$_3$) δ 7.89 (dd, 1H, J=8.1, 1.7 Hz), 7.76 (dd, 1H, J=9.9, 1.7 Hz), 7.64 (t, 1H, J=7.6 Hz), 7.54-7.45 (m, 2H), 7.25-7.16 (m, 2H), 7.05 (s, 0.2H), 6.93 (s, 0.5H), 6.80 (s, 0.2H), 5.01 (s, 2H), 3.02 (s, 3H); LRMS (ES) m/z 476.2 (M$^+$+1).

EXAMPLE 74

Compound 11279: N-(2-chlorophenyl)-N-(2-fluoro-4-(5-(trifluoromethyl)-1,3,4-oxadiazol-2-yl)benzyl)methanesulfonamide

[Step 1] N-(2-chlorophenyl)methanesulfonamide

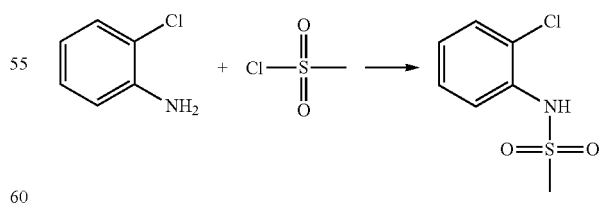

A solution of 2-chloroaniline (1.000 g, 7.839 mmol), pyridine (0.696 mL, 8.623 mmol) and methanesulfonyl chloride (0.733 mL, 9.407 mmol) in dichloromethane (10 mL) was stirred at the room temperature for 12 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(2-chlorophenyl)methanesulfonamide, 0.940 g, 58.3%, yellow solid).

[Step 2] methyl 4-((N-(2-chlorophenyl)methylsulfonamido)methyl)-3-fluorobenzoate

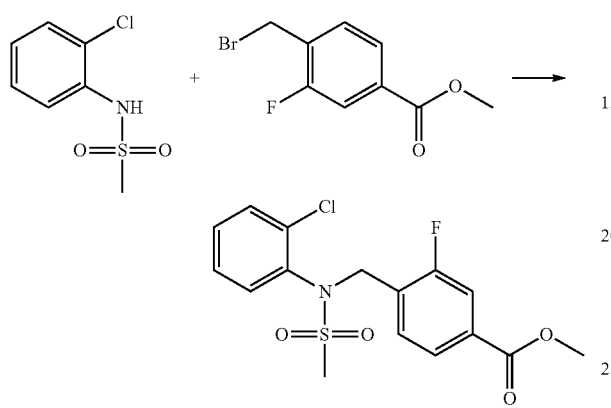

A solution of N-(2-chlorophenyl)methanesulfonamide (0.500 g, 2.431 mmol), sodium hydride (60.00%, 0.117 g, 2.917 mmol) and methyl 4-(bromomethyl)-3-fluorobenzoate (0.661 g, 2.674 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 4-((N-(2-chlorophenyl)methylsulfonamido)methyl)-3-fluorobenzoate as yellow solid (0.640 g, 70.8%).

[Step 3] N-(2-chlorophenyl)-N-(2-fluoro-4-(hydrazinecarbonyl)benzyl)methanesulfonamide

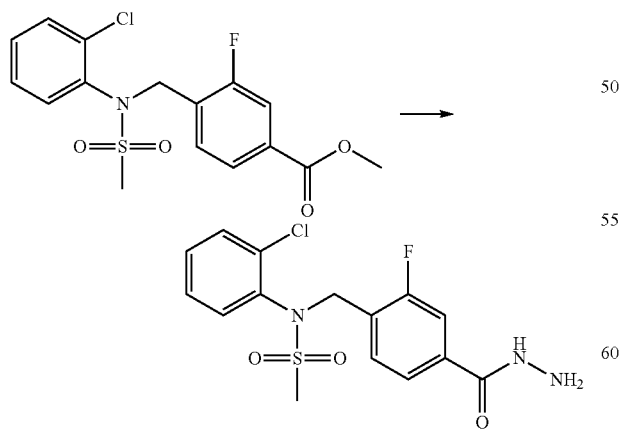

A mixture of methyl 4-((N-(2-chlorophenyl)methylsulfonamido)methyl)-3-fluorobenzoate (0.640 g, 1.721 mmol) and hydrazine hydrate (0.862 g, 17.213 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(2-chlorophenyl)-N-(2-fluoro-4-(hydrazinecarbonyl)benzyl)methanesulfonamide, 0.580 g, 90.6%, yellow solid).

[Step 4] N-(2-chlorophenyl)-N-(2-fluoro-4-(2-(2,2,2-trifluoroacetyl)hydrazine-1-carbonyl)benzyl)methanesulfonamide

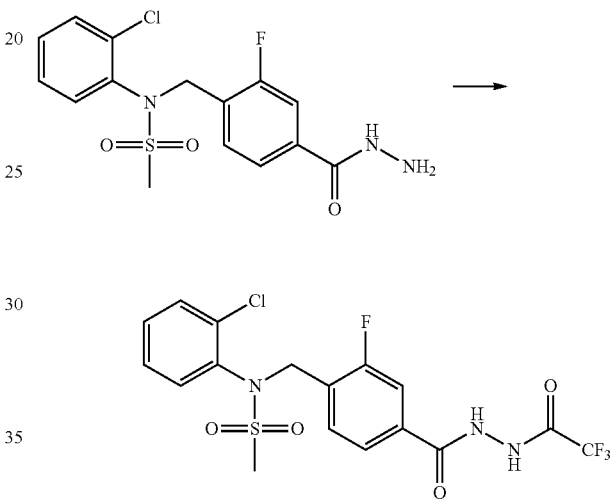

A solution of N-(2-chlorophenyl)-N-(2-fluoro-4-(hydrazinecarbonyl)benzyl)methanesulfonamide (0.290 g, 0.780 mmol), trifluoroacetic anhydride (0.121 mL, 0.858 mmol) and triethylamine (0.130 mL, 0.936 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-chlorophenyl)-N-(2-fluoro-4-(2-(2,2,2-trifluoroacetyl)hydrazine-1-carbonyl)benzyl)methanesulfonamide, 0.200 g, 54.8%, yellow solid).

[Step 5] Compound 11279

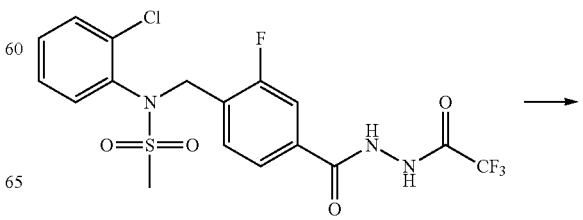

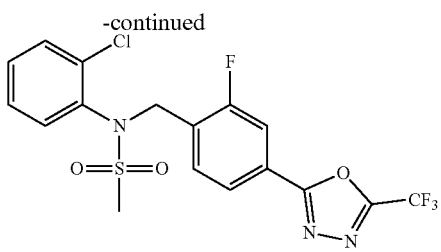

A mixture of N-(2-chlorophenyl)-N-(2-fluoro-4-(2-(2,2,2-trifluoroacetyl)hydrazine-1-carbonyl)benzyl)methanesulfonamide (0.200 g, 0.428 mmol) and 1-methoxy-N-triethylammoniosulfonyl-methanimidate (Burgess reagent, 0.153 g, 0.641 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(2-chlorophenyl)-N-(2-fluoro-4-(5-(trifluoromethyl)-1,3,4-oxadiazol-2-yl)benzyl)methanesulfonamide as yellow solid (0.120 g, 65.0%).
$^1$H NMR (400 MHz, CDCl$_3$) δ 7.89 (dd, 1H, J=8.0, 1.7 Hz), 7.77-7.66 (m, 2H), 7.52-7.44 (m, 1H), 7.36-7.17 (m, 3H), 5.04 (s, 2H), 3.14 (s, 3H); LRMS (ES) m/z 450.0 (M$^+$+1).

EXAMPLE 75

Compound 11280: N-(2-chlorophenyl)-N-(4-(5-(difluoromethyl)-1,3,4-oxadiazol-2-yl)-2-fluorobenzyl)methanesulfonamide

[Step 1] N-(2-chlorophenyl)-N-(4-(2-(2,2-difluoroacetyl)hydrazine-1-carbonyl)-2-fluorobenzyl)methanesulfonamide

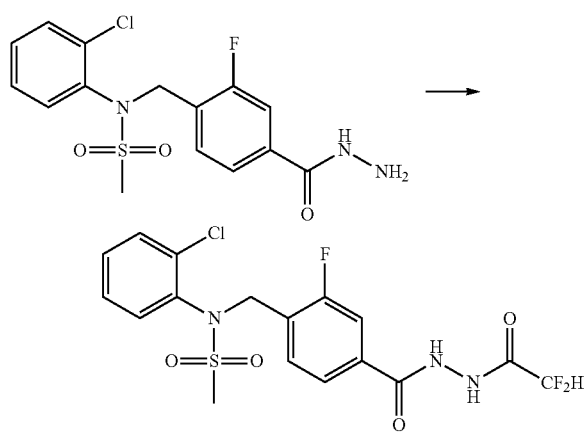

A solution of N-(2-chlorophenyl)-N-(2-fluoro-4-(hydrazinecarbonyl)benzyl)methanesulfonamide (0.290 g, 0.780 mmol), difluoroacetic anhydride (0.093 mL, 0.858 mmol) and triethylamine (0.130 mL, 0.936 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-chlorophenyl)-N-(4-(2-(2,2-difluoroacetyl)hydrazine-1-carbonyl)-2-fluorobenzyl)methanesulfonamide, 0.220 g, 62.7%, yellow solid).

[Step 2] Compound 11280

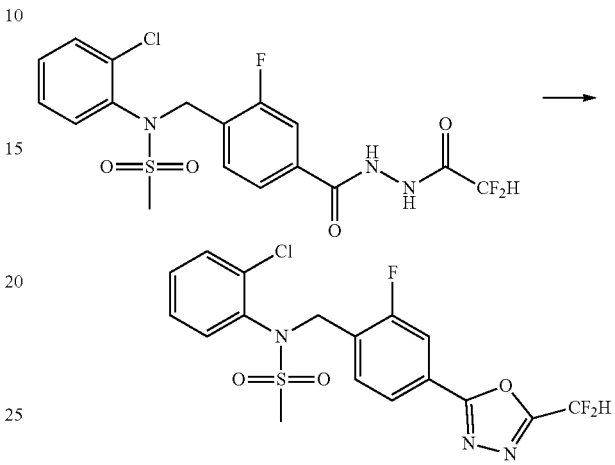

A mixture of N-(2-chlorophenyl)-N-(4-(2-(2,2-difluoroacetyl)hydrazine-1-carbonyl)-2-fluorobenzyl)methanesulfonamide (0.220 g, 0.489 mmol) and 1-methoxy-N-triethylammoniosulfonyl-methanimidate (Burgess reagent, 0.175 g, 0.734 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(2-chlorophenyl)-N-(4-(5-(difluoromethyl)-1,3,4-oxadiazol-2-yl)-2-fluorobenzyl)methanesulfonamide as yellow solid (0.130 g, 61.6%).
$^1$H NMR (400 MHz, CDCl$_3$) δ 7.91-7.82 (m, 1H), 7.78-7.62 (m, 2H), 7.53-7.43 (m, 1H), 7.36-7.26 (m, 1H), 7.26-7.17 (m, 2H), 7.06 (s, 0.2H), 6.93 (s, 0.5H), 6.80 (s, 0.2H), 5.02 (s, 2H), 3.13 (s, 3H); LRMS (ES) m/z 432.2 (M$^+$+1).

EXAMPLE 76

Compound 11281: N-(4-chlorophenyl)-N-(4-(5-(difluoromethyl)-1,3,4-oxadiazol-2-yl)-2-fluorobenzyl)methanesulfonamide

[Step 1] N-(4-chlorophenyl)-N-(4-(2-(2,2-difluoroacetyl)hydrazine-1-carbonyl)-2-fluorobenzyl)methanesulfonamide

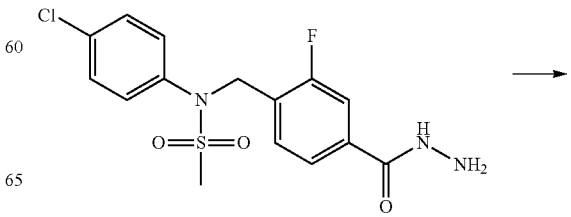

-continued

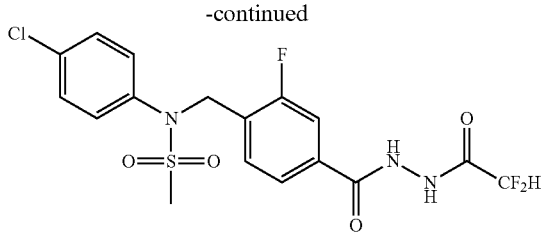

A solution of N-(4-chlorophenyl)-N-(2-fluoro-4-(hydrazinecarbonyl)benzyl)methanesulfonamide (0.300 g, 0.807 mmol), difluoroacetic anhydride (0.097 mL, 0.888 mmol) and triethylamine (0.135 mL, 0.968 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous $MgSO_4$, filtered, and concentrated in vacuo. The title compound was used without further purification (N-(4-chlorophenyl)-N-(4-(2-(2,2-difluoroacetyl) hydrazine-1-carbonyl)-2-fluorobenzyl)methanesulfonamide, 0.240 g, 66.1%, yellow solid).

[Step 2] Compound 11281

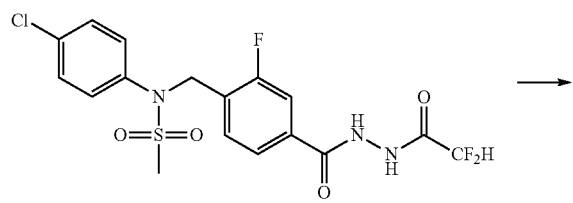

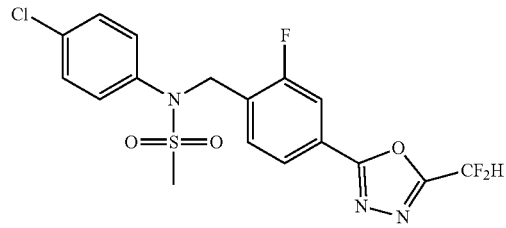

A mixture of N-(4-chlorophenyl)-N-(4-(2-(2,2-difluoroacetyl)hydrazine-1-carbonyl)-2-fluorobenzyl)methanesulfonamide (0.240 g, 0.534 mmol) and 1-methoxy-N-triethylammoniosulfonyl-methanimidate (Burgess reagent, 0.191 g, 0.800 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 12 g cartridge; ethyl acetate/hexane=0% to 40%) to give N-(4-chlorophenyl)-N-(4-(5-(difluoromethyl)-1,3,4-oxadiazol-2-yl)-2-fluorobenzyl) methanesulfonamide as yellow solid (0.140 g, 60.8%).

$^1$H NMR (400 MHz, $CDCl_3$) δ 7.93-7.85 (m, 1H), 7.80-7.72 (m, 1H), 7.65 (t, 1H, J=7.7 Hz), 7.37-7.30 (m, 2H), 7.30-7.22 (m, 2H), 7.05 (s, 0.2H), 6.93 (s, 0.5H), 6.80 (s, 0.2H), 5.01 (s, 2H), 3.02 (s, 3H); LRMS (ES) m/z 432.2 ($M^+$+1).

EXAMPLE 77

Compound 11282: N-(2-fluoro-4-(5-(trifluoromethyl)-1,3,4-oxadiazol-2-yl)benzyl)-N-(p-tolyl)methanesulfonamide

[Step 1] N-(p-tolyl)methanesulfonamide

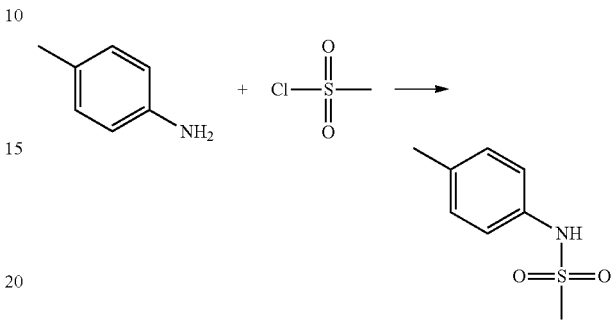

A solution of p-toluidine (1.000 g, 9.332 mmol), pyridine (0.829 mL, 10.265 mmol) and methanesulfonyl chloride (0.873 mL, 11.198 mmol) in dichloromethane (10 mL) was stirred at the room temperature for 5 hr. Then, water was added to the reaction mixture, followed by extraction with dichloromethane. The organic layer was washed with aqueous 1N-hydrochloric acid solution, dried with anhydrous $MgSO_4$, filtered, and concentrated in vacuo. The title compound was used without further purification (N-(p-tolyl) methanesulfonamide, 1.100 g, 63.6%, yellow solid).

[Step 2] methyl 3-fluoro-4-((N-(p-tolyl)methylsulfonamido)methyl)benzoate

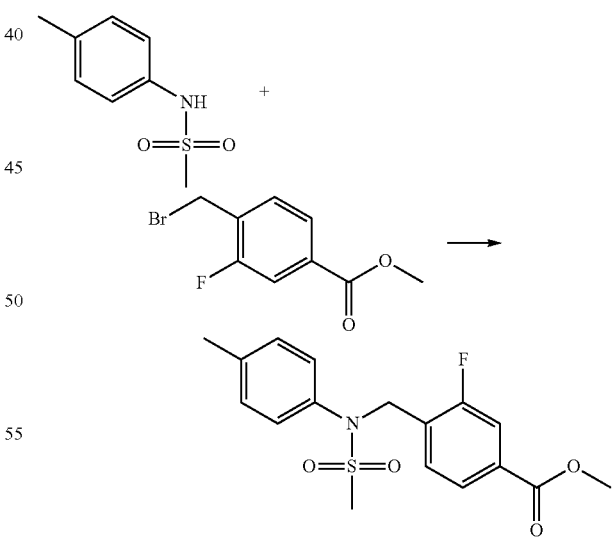

A solution of N-(p-tolyl)methanesulfonamide (0.500 g, 2.699 mmol), sodium hydride (60.00%, 0.130 g, 3.239 mmol) and methyl 4-(bromomethyl)-3-fluorobenzoate (0.734 g, 2.969 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 30%) to give methyl 3-fluoro-4-((N-(p-tolyl)methylsulfonamido)methyl)benzoate as white solid (0.660 g, 69.6%).

[Step 3] N-(2-fluoro-4-(hydrazinecarbonyl)benzyl)-N-(p-tolyl)methanesulfonamide

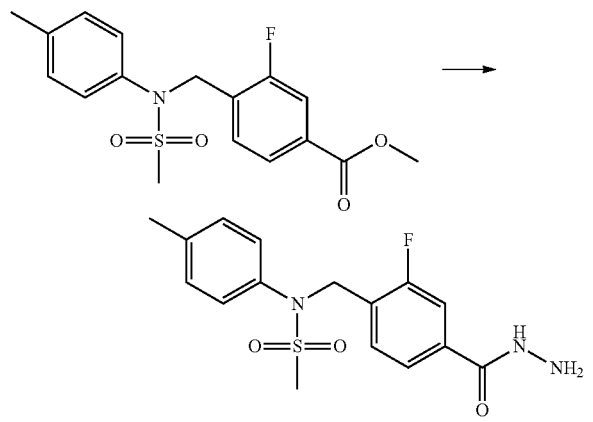

A mixture of methyl 3-fluoro-4-((N-(p-tolyl)methylsulfonamido)methyl)benzoate (0.660 g, 1.878 mmol) and hydrazine hydrate (0.940 g, 18.783 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(2-fluoro-4-(hydrazinecarbonyl)benzyl)-N-(p-tolyl)methanesulfonamide, 0.540 g, 81.8%, white solid).

[Step 4] N-(2-fluoro-4-(2-(2,2,2-trifluoroacetyl)hydrazine-1-carbonyl)benzyl)-N-(p-tolyl)methanesulfonamide

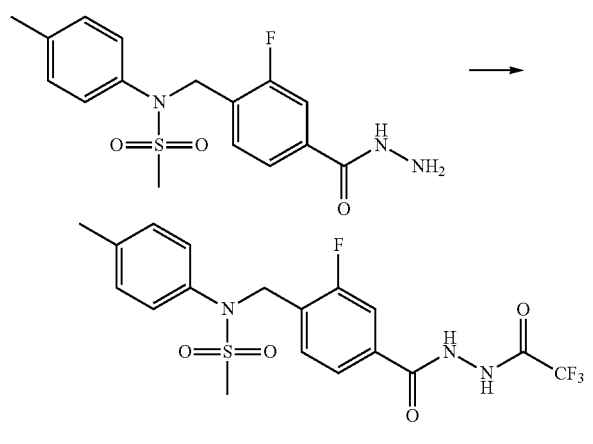

A solution of N-(2-fluoro-4-(hydrazinecarbonyl)benzyl)-N-(p-tolyl)methanesulfonamide (0.270 g, 0.768 mmol), trifluoroacetic anhydride (0.118 mL, 0.845 mmol) and triethylamine (0.161 mL, 1.153 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(2-fluoro-4-(2-(2,2,2-trifluoroacetyl)hydrazine-1-carbonyl)benzyl)-N-(p-tolyl)methanesulfonamide, 0.190 g, 55.3%, white solid).

[Step 5] Compound 11282

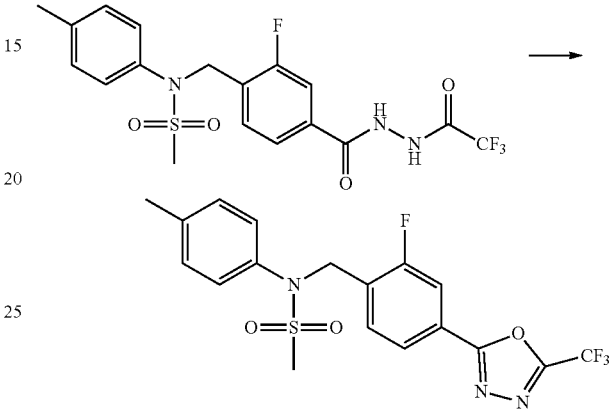

A mixture of N-(2-fluoro-4-(2-(2,2,2-trifluoroacetyl)hydrazine-1-carbonyl)benzyl)-N-(p-tolyl)methanesulfonamide (0.190 g, 0.425 mmol) and 1-methoxy-N-triethylammoniosulfonyl-methanimidate (Burgess reagent, 0.152 g, 0.637 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-(2-fluoro-4-(5-(trifluoromethyl)-1,3,4-oxadiazol-2-yl)benzyl)-N-(p-tolyl)methanesulfonamide as yellow solid (0.110 g, 60.3%).
¹H NMR (400 MHz, CDCl₃) δ 7.88 (dd, 1H, J=8.0, 1.7 Hz), 7.79-7.65 (m, 2H), 7.25-7.08 (m, 4H), 5.02 (s, 2H), 3.01 (s, 3H), 2.33 (s, 3H); LRMS (ES) m/z 430.3 (M⁺+1).

EXAMPLE 78

Compound 11283: N-(4-(5-(difluoromethyl)-1,3,4-oxadiazol-2-yl)-2-fluorobenzyl)-N-(p-tolyl)methanesulfonamide

[Step 1] N-(4-(2-(2,2-difluoroacetyl)hydrazine-1-carbonyl)-2-fluorobenzyl)-N-(p-tolyl)methanesulfonamide

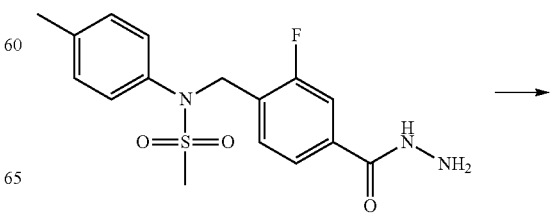

-continued

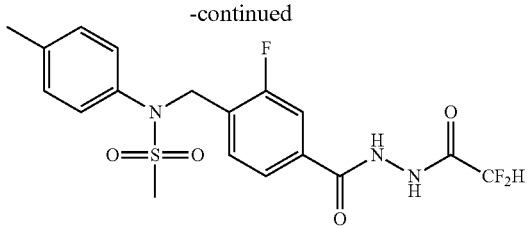

A solution of N-(2-fluoro-4-(hydrazinecarbonyl)benzyl)-N-(p-tolyl)methanesulfonamide (0.270 g, 0.768 mmol), difluoroacetic anhydride (0.092 mL, 0.845 mmol) and triethylamine (0.129 mL, 0.922 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(4-(2-(2,2-difluoroacetyl)hydrazine-1-carbonyl)-2-fluorobenzyl)-N-(p-tolyl)methanesulfonamide, 0.210 g, 63.6%, yellow solid).

[Step 2] Compound 11283

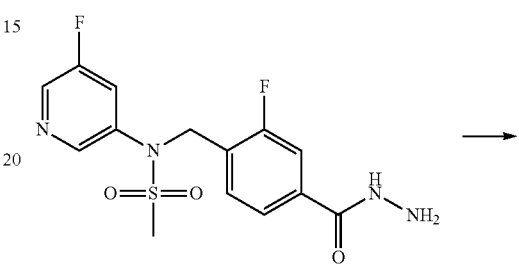

A mixture of N-(4-(2-(2,2-difluoroacetyl)hydrazine-1-carbonyl)-2-fluorobenzyl)-N-(p-tolyl)methanesulfonamide (0.210 g, 0.489 mmol) and 1-methoxy-N-triethylammoniosulfonyl-methanimidate (Burgess reagent, 0.175 g, 0.734 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(p-tolyl)methanesulfonamide as yellow solid (0.120 g, 59.6%).

$^1$H NMR (400 MHz, CDCl$_3$) δ 7.87 (dd, 1H, J=8.1, 1.6 Hz), 7.74 (dd, 1H, J=9.9, 1.7 Hz), 7.68 (t, 1H, J=7.7 Hz), 7.25-7.12 (m, 4H), 7.05 (s, 0.2H), 6.92 (s, 0.5H), 6.79 (s, 0.2H), 5.01 (s, 2H), 3.01 (s, 3H), 2.33 (s, 3H); LRMS (ES) m/z 412.4 (M$^+$+1).

EXAMPLE 79

Compound 11284: N-(4-(5-(difluoromethyl)-1,3,4-oxadiazol-2-yl)-2-fluorobenzyl)-N-(5-fluoropyridin-3-yl)methanesulfonamide

[Step 1] N-(4-(2-(2,2-difluoroacetyl)hydrazine-1-carbonyl)-2-fluorobenzyl)-N-(5-fluoropyridin-3-yl)methanesulfonamide

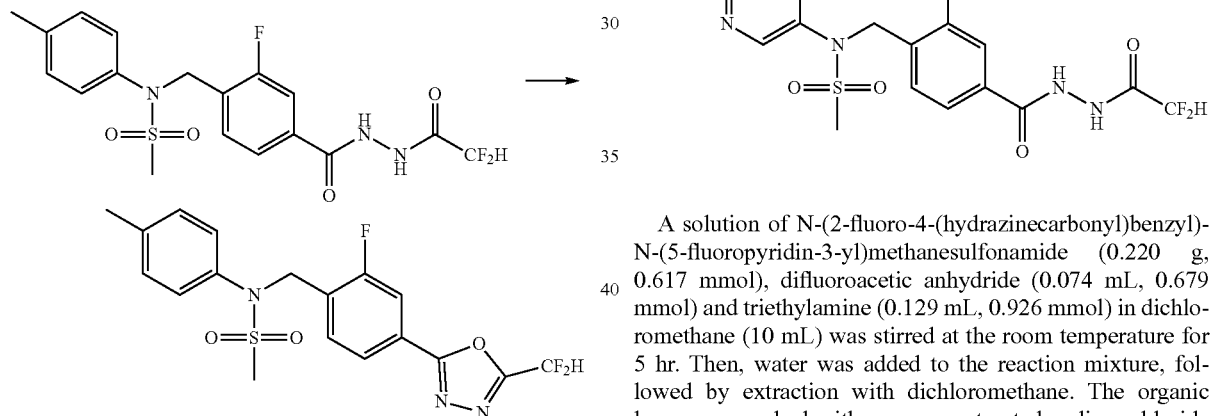

A solution of N-(2-fluoro-4-(hydrazinecarbonyl)benzyl)-N-(5-fluoropyridin-3-yl)methanesulfonamide (0.220 g, 0.617 mmol), difluoroacetic anhydride (0.074 mL, 0.679 mmol) and triethylamine (0.129 mL, 0.926 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-(4-(2-(2,2-difluoroacetyl)hydrazine-1-carbonyl)-2-fluorobenzyl)-N-(5-fluoropyridin-3-yl)methanesulfonamide as yellow solid (0.140 g, 52.2%).

[Step 2] Compound 11284

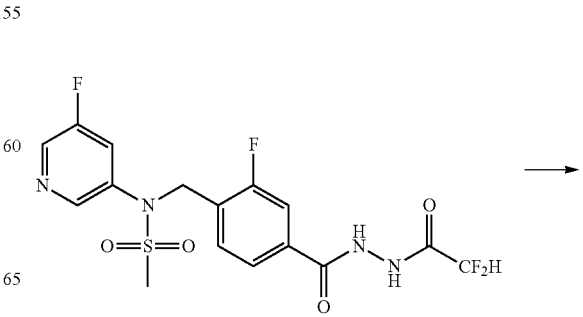

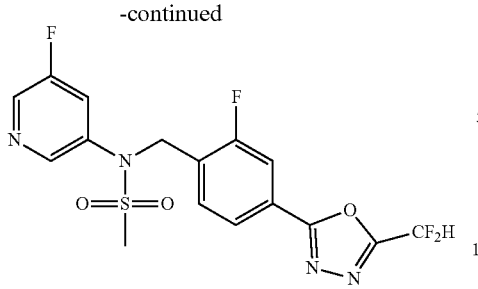

A mixture of N-(4-(2-(2,2-difluoroacetyl)hydrazine-1-carbonyl)-2-fluorobenzyl)-N-(5-fluoropyridin-3-yl)methanesulfonamide (0.140 g, 0.322 mmol) and 1-methoxy-N-triethylammoniosulfonyl-methanimidate (Burgess reagent, 0.115 g, 0.483 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 4 g cartridge; ethyl acetate/hexane=0% to 40%) to give N-(4-(5-(difluoromethyl)-1,3,4-oxadiazol-2-yl)-2-fluorobenzyl)-N-(5-fluoropyridin-3-yl)methanesulfonamide as yellow solid (0.086 g, 64.1%).

$^1$H NMR (400 MHz, $CDCl_3$) δ 8.46 (s, 2H), 7.92 (dd, 1H, J=8.1, 1.7 Hz), 7.80 (dd, 1H, J=9.8, 1.3 Hz), 7.65 (t, 1H, J=7.7 Hz), 7.54-7.43 (m, 1H), 7.06 (s, 0.2H), 6.93 (s, 0.5H), 6.80 (s, 0.2H), 5.07 (s, 2H), 3.09 (d, 3H, J=1.1 Hz); LRMS (ES) m/z 417.3 (M$^+$+1).

EXAMPLE 80

Compound 11287: methyl 3-(N-(4-(5-(difluoromethyl)-1,3,4-oxadiazol-2-yl)-2-fluorobenzyl)-N-phenylsulfamoyl)propanoate

[Step 1] methyl 3-(N-phenylsulfamoyl)propanoate

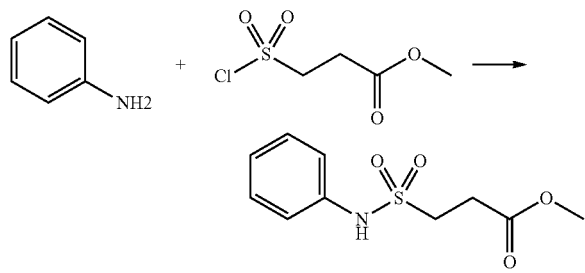

A solution of aniline (0.490 mL, 5.369 mmol) and pyridine (0.520 mL, 6.443 mmol) in dichloromethane (10 mL) was mixed at the room temperature with methyl 3-(chlorosulfonyl)propanoate (1.102 g, 5.906 mmol). The reaction mixture was stirred at the same temperature for 12 hr. Then, water was added to the reaction mixture, followed by extraction with dichloromethane. The organic layer was washed with aqueous 0.1N-hydrochloric acid solution, dried with anhydrous $MgSO_4$, filtered, and concentrated in vacuo. The title compound was used without further purification (methyl 3-(N-phenylsulfamoyl)propanoate, 1.000 g, 71.3%, brown solid).

[Step 2] Compound 11287

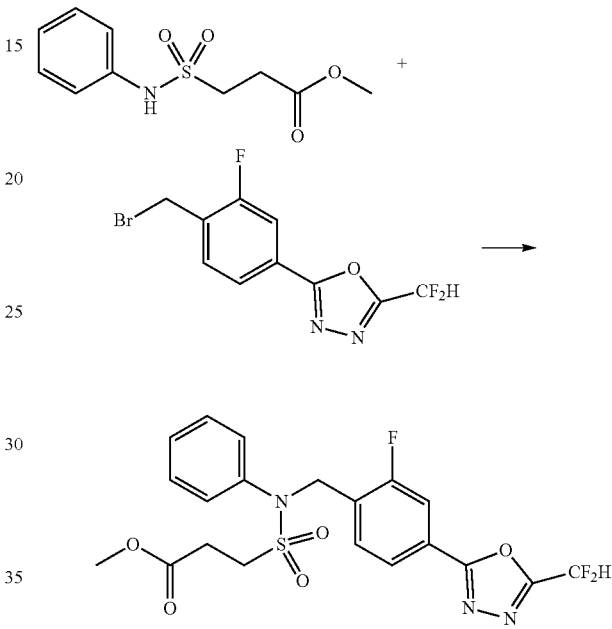

Sodium hydride (60.00%, 0.014 g, 0.345 mmol) was added to a solution of methyl 3-(N-phenylsulfamoyl)propanoate (0.070 g, 0.288 mmol) in N,N-dimethylformide (1 mL) at 0° C., and the mixture was stirred at the same temperature for 20 min. The reaction mixture was treated with 2-(4-(bromomethyl)-3-fluorophenyl)-5-(difluoromethyl)-1,3,4-oxadiazole (0.093 g, 0.302 mmol), and stirred for additional 16 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed ($SiO_2$, 4 g cartridge; ethyl acetate/hexane=0% to 30%) to give methyl 3-(N-(4-(5-(difluoromethyl)-1,3,4-oxadiazol-2-yl)-2-fluorobenzyl)-N-phenylsulfamoyl)propanoate as white solid (0.085 g, 62.9%).

$^1$H NMR (400 MHz, DMSO-d6) δ 7.88 (dd, 1H, J=8.1, 1.7 Hz), 7.80 (dd, 1H, J=10.2, 1.7 Hz), 7.73-7.67 (m, 1H), 7.66 (s, 0.25H), 7.56 (s, 0.5H), 7.50 (s, 0.25H), 7.50-7.45 (m, 2H), 7.44-7.36 (m, 2H), 7.36-7.29 (m, 1H), 5.11 (s, 2H), 3.67 (s, 3H), 3.59 (t, 2H, J=7.4 Hz), 2.84 (t, 2H, J=7.4 Hz); LRMS (ES) m/z 470.2 (M$^+$+1).

EXAMPLE 81

Compound 11288: N-(4-(5-(difluoromethyl)-1,3,4-oxadiazol-2-yl)-2-fluorobenzyl)-3-methoxy-N-phenylbutane-1-sulfonamide

[Step 1] 3-methoxy-2-methyl-N-phenylpropane-1-sulfonamide

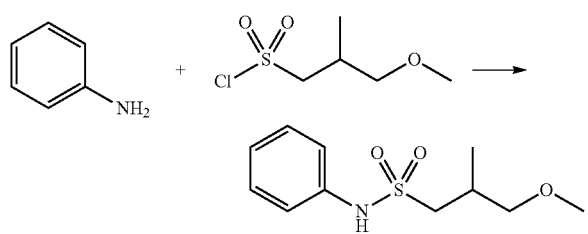

A solution of aniline (0.245 mL, 2.684 mmol) and pyridine (0.259 mL, 3.221 mmol) in dichloromethane (10 mL) was mixed at the room temperature with 3-methoxy-2-methylpropane-1-sulfonyl chloride (0.551 g, 2.953 mmol). The reaction mixture was stirred at the same temperature for 12 hr. Then, water was added to the reaction mixture, followed by extraction with dichloromethane. The organic layer was washed with aqueous 0.1N-hydrochloric acid solution, dried with anhydrous MgSO$_4$, filtered, and concentrated in vacuo. The title compound was used without further purification (3-methoxy-2-methyl-N-phenylpropane-1-sulfonamide, 0.500 g, 76.5%, brown solid).

[Step 2] Compound 11288

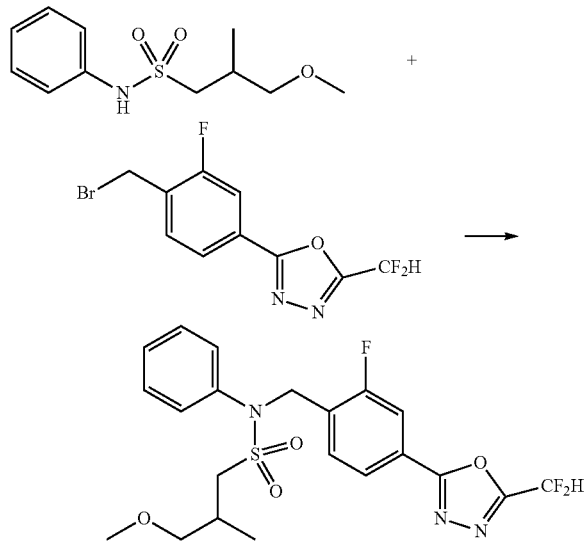

Sodium hydride (60.00%, 0.012 g, 0.296 mmol) was added to a solution of 3-methoxy-2-methyl-N-phenylpropane-1-sulfonamide (0.060 g, 0.247 mmol) in N,N-dimethylformide (1 mL) at 0° C., and the mixture was stirred at the same temperature for 20 min. The reaction mixture was treated with 2-(4-(bromomethyl)-3-fluorophenyl)-5-(difluoromethyl)-1,3,4-oxadiazole (0.080 g, 0.259 mmol), and stirred for additional 16 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 30%) to give N-(4-(5-(difluoromethyl)-1,3,4-oxadiazol-2-yl)-2-fluorobenzyl)-3-methoxy-N-phenylbutane-1-sulfonamide as white solid (0.045 g, 38.9%).

$^1$H NMR (400 MHz, DMSO-d$_6$) 400 MHz): δ 7.88 (dd, 1H, J=8.1, 1.7 Hz), 7.80 (dd, 1H, J=10.2, 1.7 Hz), 7.70 (d, 1H, J=8.0 Hz), 7.67 (s, 0.25H), 7.56 (s, 0.5H), 7.53-7.44 (m, 2H), 7.43 (s, 0.25H), 7.43-7.34 (m, 2H), 7.36-7.27 (m, 1H), 5.09 (s, 2H), 3.49-3.40 (m, 2H), 3.33-3.22 (m, 4H), 3.12 (dd, 1H, J=14.0, 8.2 Hz), 2.32 (tt, 1H, J=12.8, 6.1 Hz), 1.08 (d, 3H, J=6.8 Hz); LRMS (ES) m/z 468.17 (M$^+$−1).

EXAMPLE 82

Compound 11289: N-(4-(5-(difluoromethyl)-1,3,4-oxadiazol-2-yl)-2-fluorobenzyl)-N-phenylpropane-1-sulfonamide

[Step 1] N-phenylpropane-1-sulfonamide

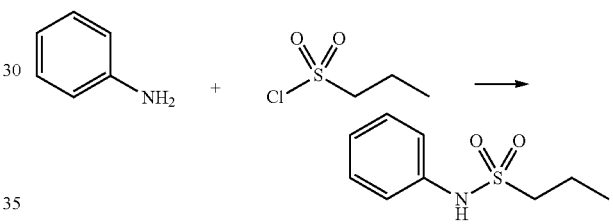

A solution of aniline (0.490 mL, 5.369 mmol) and propane-1-sulfonyl chloride (0.628 g, 5.637 mmol) in dichloromethane (10 mL) was stirred at the room temperature for 5 min, and mixed with triethylamine (1.497 mL, 10.738 mmol). The reaction mixture was stirred at the same temperature for additional 12 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 20%) to give N-phenylpropane-1-sulfonamide as light yellow oil (0.130 g, 12.2%).

[Step 2] Compound 11289

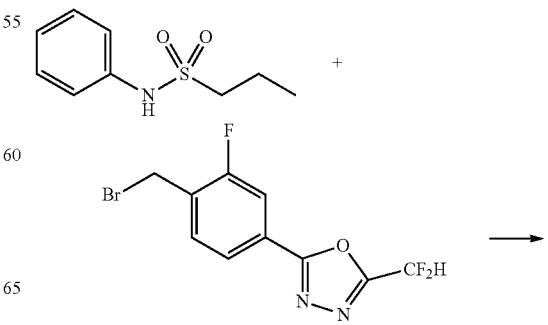

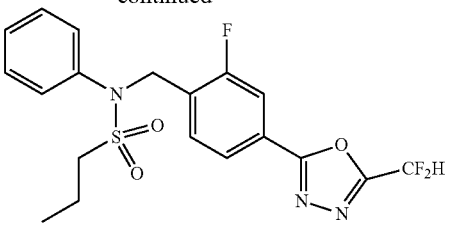

Sodium hydride (60.00%, 0.011 g, 0.271 mmol) was added to a solution of N-phenylpropane-1-sulfonamide (0.045 g, 0.226 mmol) in N,N-dimethylformide (1 mL) at 0° C., and the mixture was stirred at the same temperature for 20 min. The reaction mixture was treated with 2-(4-(bromomethyl)-3-fluorophenyl)-5-(difluoromethyl)-1,3,4-oxadiazole (0.073 g, 0.237 mmol), and stirred for additional 16 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 15%) to give N-(4-(5-(difluoromethyl)-1,3,4-oxadiazol-2-yl)-2-fluorobenzyl)-N-phenylpropane-1-sulfonamide as white solid (0.060 g, 62.5%).

$^1$H NMR (400 MHz, CDCl$_3$) δ 7.87 (dd, 1H, J=8.1, 1.6 Hz), 7.77-7.65 (m, 2H), 7.41-7.27 (m, 5H), 6.92 (t, 1H, J=51.7 Hz), 5.06 (s, 2H), 3.17-2.99 (m, 2H), 2.06-1.83 (m, 2H), 1.09 (t, 3H, J=7.4 Hz); LRMS (ES) m/z 424.32 (M$^+$−1).

EXAMPLE 83

Compound 11290: N-(4-(5-(difluoromethyl)-1,3,4-oxadiazol-2-yl)-2-fluorobenzyl)-N-phenylbutane-1-sulfonamide

[Step 1] N-phenylbutane-1-sulfonamide

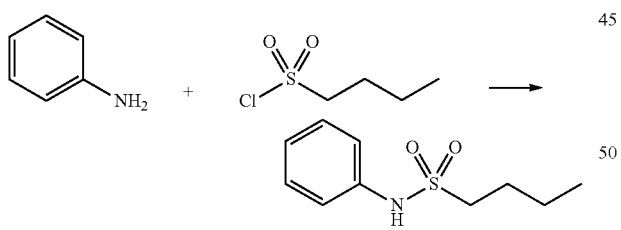

A solution of aniline (0.490 mL, 5.369 mmol) and butane-1-sulfonyl chloride (0.883 g, 5.637 mmol) in dichloromethane (10 mL) was stirred at the room temperature for 5 min, and mixed with triethylamine (1.497 mL, 10.738 mmol). The reaction mixture was stirred at the same temperature for additional 12 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 20%) to give N-phenylbutane-1-sulfonamide as light yellow oil (0.460 g, 40.2%).

[Step 2] Compound 11290

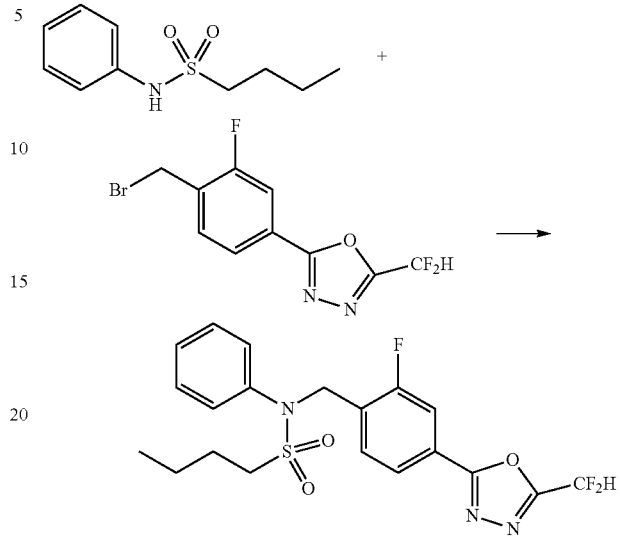

Sodium hydride (60.00%, 0.010 g, 0.253 mmol) was added to a solution of N-phenylbutane-1-sulfonamide (0.045 g, 0.211 mmol) in N,N-dimethylformide (1 mL) at 0° C., and the mixture was stirred at the same temperature for 20 min. The reaction mixture was treated with 2-(4-(bromomethyl)-3-fluorophenyl)-5-(difluoromethyl)-1,3,4-oxadiazole (0.068 g, 0.222 mmol), and stirred for additional 16 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 15%) to give N-(4-(5-(difluoromethyl)-1,3,4-oxadiazol-2-yl)-2-fluorobenzyl)-N-phenylbutane-1-sulfonamide as white solid (0.060 g, 64.7%).

$^1$H NMR (400 MHz, CDCl$_3$) δ 7.87 (dd, 1H, J=8.0, 1.7 Hz), 7.78-7.63 (m, 2H), 7.42-7.25 (m, 5H), 6.92 (t, 1H, J=51.7 Hz), 5.06 (s, 2H), 3.15-3.03 (m, 2H), 1.98-1.79 (m, 2H), 1.48 (h, 2H, J=7.4 Hz), 0.97 (t, 3H, J=7.3 Hz); LRMS (ES) m/z 440.2 (M$^+$+1).

EXAMPLE 84

Compound 11291: N-(4-(5-(difluoromethyl)-1,3,4-oxadiazol-2-yl)-2-fluorobenzyl)-N-phenylcyclopropanesulfonamide

[Step 1] N-phenylcyclopropanesulfonamide

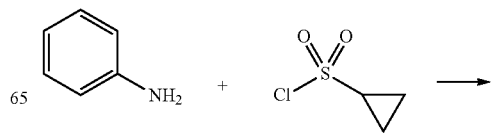

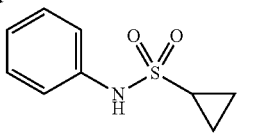

A solution of Aniline (0.500 g, 5.369 mmol) and Et3N (1.630 g, 16.107 mmol) in dichloromethane (10 mL) was stirred at the room temperature for 10 min, and mixed with cyclopropanesulfonyl chloride (1.510 g, 10.738 mmol). The reaction mixture was stirred at the same temperature for additional 12 hr. Then, water was added to the reaction mixture, followed by extraction with dichloromethane. The organic layer was washed with saturated aqueous sodium chloride solution, dried with anhydrous MgSO₄, filtered, and concentrated in vacuo. The residue was chromatographed (SiO₂, 12 g cartridge; ethyl acetate/hexane=0% to 50%) to give N-phenylcyclopropanesulfonamide as white solid (0.650 g, 61.4%).

[Step 2] Compound 11291

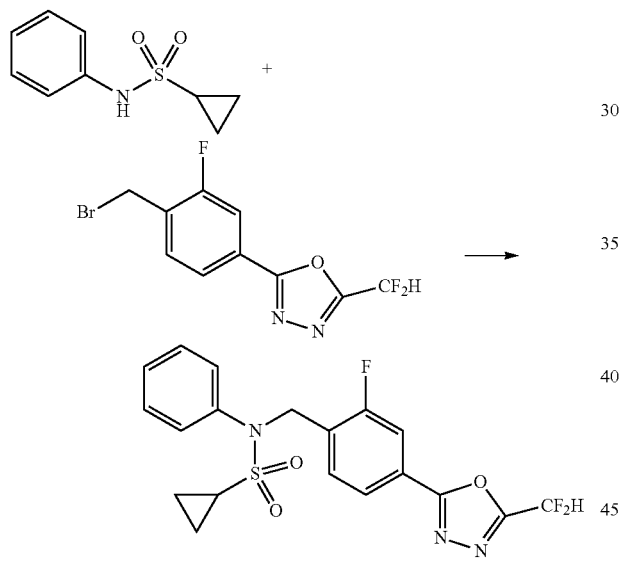

Sodium hydride (60.00%, 0.011 g, 0.274 mmol) was added to a solution of N-phenylcyclopropanesulfonamide (0.045 g, 0.228 mmol) in N,N-dimethylformide (1 mL) at 0° C., and the mixture was stirred at the same temperature for 20 min. The reaction mixture was treated with 2-(4-(bromomethyl)-3-fluorophenyl)-5-(difluoromethyl)-1,3,4-oxadiazole (0.074 g, 0.240 mmol), and stirred for additional 16 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO₂, 4 g cartridge; ethyl acetate/hexane=0% to 20%) to give N-(4-(5-(difluoromethyl)-1,3,4-oxadiazol-2-yl)-2-fluorobenzyl)-N-phenylcyclopropanesulfonamide as white solid (0.055 g, 56.9%).

¹H NMR (400 MHz, CDCl₃) δ 7.87 (dd, 1H, J=8.1, 1.6 Hz), 7.76-7.65 (m, 2H), 7.41-7.26 (m, 5H), 6.92 (t, 1H, J=51.7 Hz), 5.07 (s, 2H), 2.51 (tt, 1H, J=8.0, 4.8 Hz), 1.18-1.11 (m, 2H), 1.06-0.98 (m, 2H); LRMS (ES) m/z 424.3 (M⁺+1).

EXAMPLE 85

Compound 11292: N-cyclohexyl-N-(4-(5-(difluoromethyl)-1,3,4-oxadiazol-2-yl)-2-fluorobenzyl)methanesulfonamide

[Step 1] N-cyclohexylmethanesulfonamide

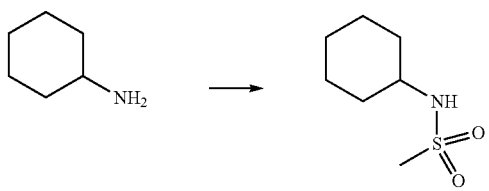

A solution of methanesulfonyl chloride (0.858 mL, 11.091 mmol) and pyridine (1.221 mL, 15.124 mmol) in dichloromethane (16 mL) was stirred at the room temperature for 10 min, and mixed with cyclohexanamine (1.000 g, 10.083 mmol). The reaction mixture was stirred at the same temperature for additional 24 hr. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The title compound was used without further purification (N-cyclohexylmethanesulfonamide, 1.700 g, 95.1%, yellow solid).

[Step 2] Compound 11292

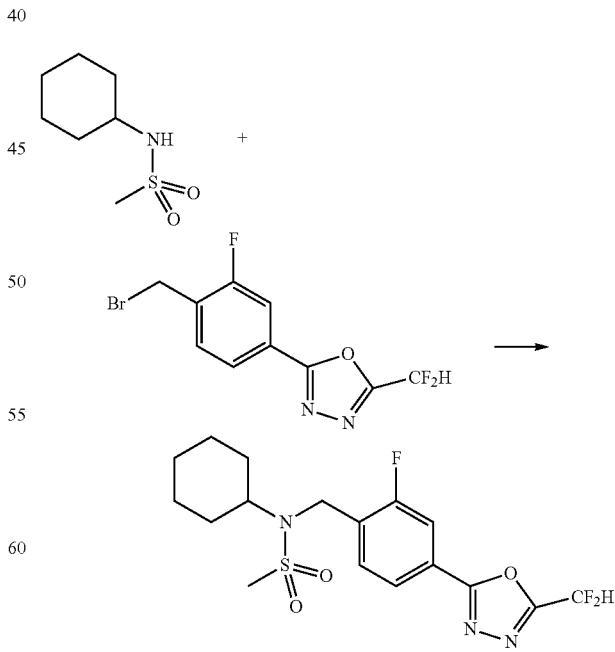

Sodium hydride (60.00%, 0.014 g, 0.338 mmol) was added to a solution of N-cyclohexylmethanesulfonamide (0.050 g, 0.282 mmol) in N,N-dimethylformide (1 mL) at 0° C., and the mixture was stirred at the same temperature for 20 min. The reaction mixture was treated with 2-(4-(bromomethyl)-3-fluorophenyl)-5-(difluoromethyl)-1,3,4-oxadiazole (0.087 g, 0.282 mmol), and stirred for additional 16 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 30%) to give N-cyclohexyl-N-(4-(5-(difluoromethyl)-1,3,4-oxadiazol-2-yl)-2-fluorobenzyl)methanesulfonamide as light yellow oil (0.080 g, 70.3%).

$^1$H NMR (400 MHz, CDCl$_3$) δ 7.88 (dd, 1H, J=8.2, 1.6 Hz), 7.84-7.72 (m, 2H), 6.91 (t, 1H, J=51.7 Hz), 4.49 (s, 2H), 3.74 (tt, 1H, J=11.3, 2.9 Hz), 2.94 (d, 3H, J=9.4 Hz), 1.87-1.66 (m, 4H), 1.66-1.52 (m, 1H), 1.31 (qt, 4H, J=12.6, 6.9 Hz), 1.01 (dt, 1H, J=9.5, 6.3 Hz); LRMS (ES) m/z 404.0 (M$^+$+1).

EXAMPLE 86

Compound 11323: N-((5-(5-(trifluoromethyl)-1,3,4-oxadiazol-2-yl)pyridin-2-yl)methyl)-N-(3-(trifluoromethyl)phenyl)methanesulfonamide

[Step 1] methyl 6-((N-(3-(trifluoromethyl)phenyl)methylsulfonamido)methyl)nicotinate

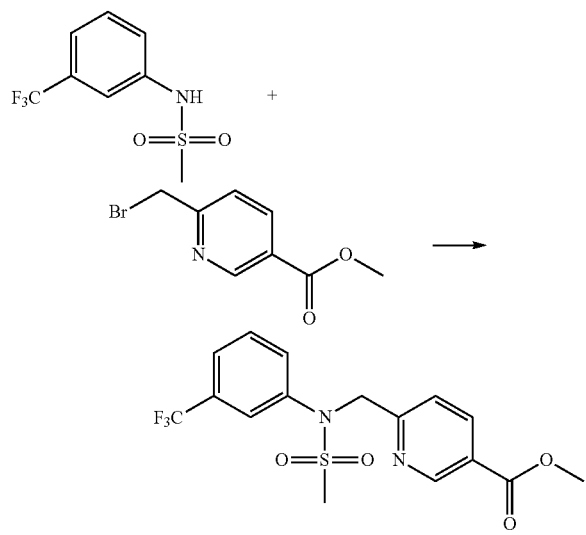

A solution of N-(3-(trifluoromethyl)phenyl)methanesulfonamide (0.500 g, 2.090 mmol), sodium hydride (60.00%, 0.100 g, 2.508 mmol) and methyl 6-(bromomethyl)nicotinate (0.529 g, 2.299 mmol) in N,N-dimethylformide (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 6-((N-(3-(trifluoromethyl)phenyl)methylsulfonamido)methyl)nicotinate as yellow solid (0.400 g, 49.3%).

[Step 2] N-((5-(hydrazinecarbonyl)pyridin-2-yl)methyl)-N-(3-(trifluoromethyl)phenyl)methanesulfonamide

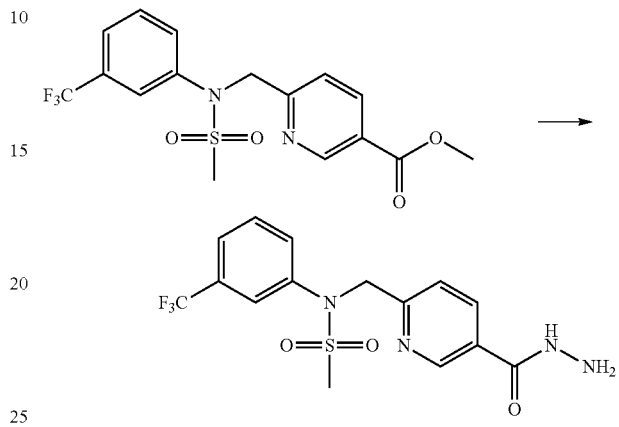

A mixture of methyl 6-((N-(3-(trifluoromethyl)phenyl)methylsulfonamido)methyl)nicotinate (0.400 g, 1.030 mmol) and hydrazine hydrate (0.516 g, 10.300 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-((5-(hydrazinecarbonyl)pyridin-2-yl)methyl)-N-(3-(trifluoromethyl)phenyl)methanesulfonamide, 0.300 g, 75.0%, yellow solid).

[Step 3] Compound 11323

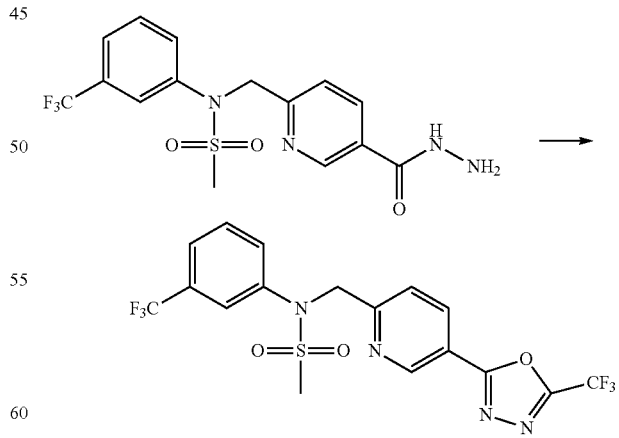

A solution of N-((5-(hydrazinecarbonyl)pyridin-2-yl)methyl)-N-(3-(trifluoromethyl)phenyl)methanesulfonamide (0.150 g, 0.386 mmol), trifluoroacetic anhydride (0.060 mL, 0.425 mmol) and triethylamine (0.081 mL, 0.579 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 40%) to give N-((5-(5-(trifluoromethyl)-1,3,4-oxadiazol-2-yl)pyridin-2-yl)methyl)-N-(3-(trifluoromethyl)phenyl)methanesulfonamide as yellow solid (0.067 g, 37.2%).

¹H NMR (400 MHz, CDCl₃) δ 9.28 (dd, 1H, J=2.3, 0.8 Hz), 8.41 (dd, 1H, J=8.2, 2.2 Hz), 7.76-7.62 (m, 3H), 7.62-7.47 (m, 2H), 5.18 (s, 2H), 3.10 (s, 3H); LRMS (ES) m/z 467.3 (M⁺+1).

EXAMPLE 87

Compound 11324: N-((5-(5-(difluoromethyl)-1,3,4-oxadiazol-2-yl)pyridin-2-yl)methyl)-N-(3-(trifluoromethyl)phenyl)methanesulfonamide

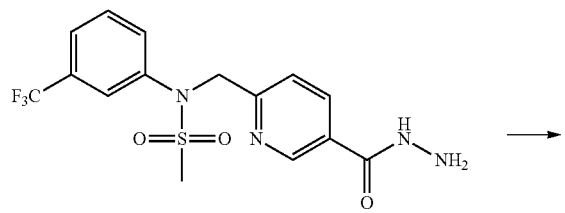

A mixture of N-((5-(hydrazinecarbonyl)pyridin-2-yl)methyl)-N-(3-(trifluoromethyl)phenyl)methanesulfonamide (0.150 g, 0.386 mmol), difluoroacetic anhydride (0.050 mL, 0.463 mmol) and triethylamine (0.081 mL, 0.579 mmol) in dichloromethane (10 mL) was heated at 150° C. for 30 min under the microwaves, and cooled down to the room temperature to terminate the reaction. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 40%) to give N-((5-(5-(difluoromethyl)-1,3,4-oxadiazol-2-yl)pyridin-2-yl)methyl)-N-(3-(trifluoromethyl)phenyl)methanesulfonamide as yellow solid (0.074 g, 42.7%).

¹H NMR (400 MHz, CDCl₃) δ 9.28 (dd, 1H, J=2.2, 0.9 Hz), 8.42 (dd, 1H, J=8.2, 2.2, 0.8 Hz), 7.73 (dq, 1H, J=3.0, 0.8 Hz), 7.70-7.62 (m, 2H), 7.62-7.45 (m, 2H), 7.08 (s, 0.2H), 6.95 (s, 0.5H), 6.83 (s, 0.2H), 5.18 (s, 2H), 3.10 (d, 3H, J=0.7 Hz); LRMS (ES) m/z 449.3 (M⁺+1).

EXAMPLE 88

Compound 11338: tert-butyl 4-(N-(4-(5-(difluoromethyl)-1,3,4-oxadiazol-2-yl)-2-fluorobenzyl)methylsulfonamido)piperidine-1-carboxylate

[Step 1] tert-butyl 4-(methylsulfonamido)piperidine-1-carboxylate

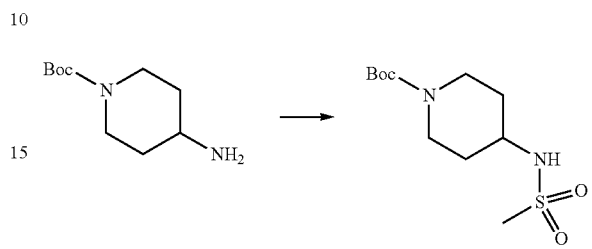

A solution of methanesulfonyl chloride (0.425 mL, 5.492 mmol) and pyridine (0.605 mL, 7.490 mmol) in dichloromethane (14 mL) was stirred at the room temperature for 20 min, and mixed with tert-butyl 4-aminopiperidine-1-carboxylate (1.000 g, 4.993 mmol). The reaction mixture was stirred at the same temperature for additional 24 hr. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The title compound was used without further purification (tert-butyl 4-(methylsulfonamido)piperidine-1-carboxylate, 1.300 g, 93.5%, white solid).

[Step 2] tert-butyl 4-(N-(2-fluoro-4-(methoxycarbonyl)benzyl)methylsulfonamido)piperidine-1-carboxylate

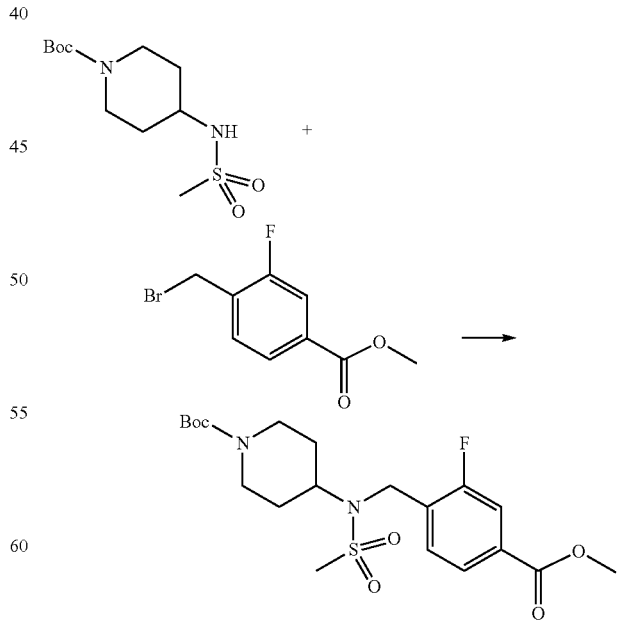

Sodium hydride (60.00%, 0.172 g, 4.311 mmol) was added to a solution of tert-butyl 4-(methylsulfonamido) piperidine-1-carboxylate (1.000 g, 3.592 mmol) in N,N- dimethylformide (8 mL) at 0° C., and the mixture was stirred at the same temperature for 20 min. The reaction mixture was treated with methyl 4-(bromomethyl)-3-fluorobenzoate (0.932 g, 3.772 mmol), and stirred for additional 16 hr at the room temperature. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 20%) to give tert-butyl 4-(N-(2-fluoro-4-(methoxycarbonyl)benzyl) methylsulfonamido)piperidine-1-carboxylate as white solid (1.200 g, 75.1%).

[Step 3] tert-butyl 4-(N-(2-fluoro-4-(hydrazinecarbonyl)benzyl)methylsulfonamido)piperidine-1-carboxylate

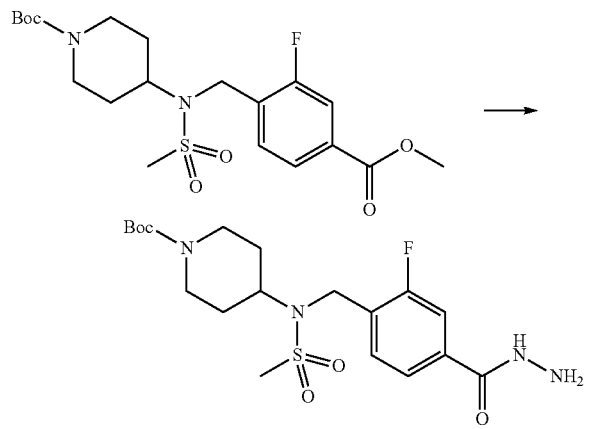

A mixture of tert-butyl 4-(N-(2-fluoro-4-(methoxycarbonyl)benzyl)methylsulfonamido)piperidine-1-carboxylate (1.200 g, 2.700 mmol) and hydrazine hydrate (0.394 mL, 8.099 mmol) in ethanol (10 mL) prepared at the ambient temperature was heated at reflux for 24 hr, and cooled down to the ambient temperature, and concentrated under the reduced pressure to remove the solvent. Then, water was added to the reaction mixture, followed by extraction with dichloromethane. The bi-phasic mixture was passed through a plastic frit to remove the solid residues and the aqueous layer, and the organic layer collected was concentrated in vacuo. The title compound was used without further purification (tert-butyl 4-(N-(2-fluoro-4-(hydrazinecarbonyl)benzyl)methylsulfonamido)piperidine-1-carboxylate, 1.100 g, 91.7%, white solid).

[Step 4] Compound 11338

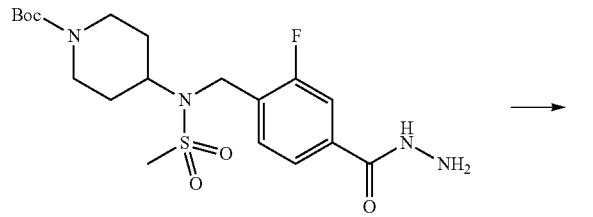

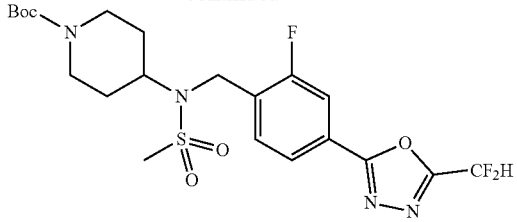

Triethylamine (0.122 mL, 0.877 mmol) was added to a solution of tert-butyl 4-(N-(2-fluoro-4-(hydrazinecarbonyl) benzyl)methylsulfonamido)piperidine-1-carboxylate (0.300 g, 0.675 mmol) in dichloromethane (8 mL) at the room temperature, and the mixture was stirred for 20 min at the same temperature. The reaction mixture was treated with 2,2-difluoroacetic anhydride (0.088 mL, 0.810 mmol), heated at reflux for 16 hr, and cooled down to the room temperature to terminate the reaction. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 40%) to give tert-butyl 4-(N-(4-(5-(difluoromethyl)-1,3,4-oxadiazol-2-yl)-2-fluorobenzyl)methylsulfonamido)piperidine-1-carboxylate as light yellow oil (0.280 g, 82.2%).
$^1$H NMR (400 MHz, CDCl$_3$) δ 7.91 (dd, 1H, J=8.2, 1.6 Hz), 7.83-7.77 (m, 2H), 6.92 (t, 1H, J=51.7 Hz), 4.50 (s, 2H), 4.11 (q, 2H, J=7.2 Hz), 3.92 (tt, 1H, J=12.1, 3.8 Hz), 2.94 (s, 3H), 2.71 (t, 2H, J=12.8 Hz), 1.70 (t, 2H, J=13.6 Hz), 1.64-1.48 (m, 2H), 1.42 (s, 9H); LRMS (ES) m/z 405.33 (M$^+$+1).

EXAMPLE 89

Compound 11345: N-(benzo[d][1,3]dioxol-5-yl)-N-((5-(5-(difluoromethyl)-1,3,4-oxadiazol-2-yl)pyridin-2-yl)methyl)methanesulfonamide

[Step 1] methyl 6-((benzo[d][1,3]dioxol-5-ylamino)methyl)nicotinate

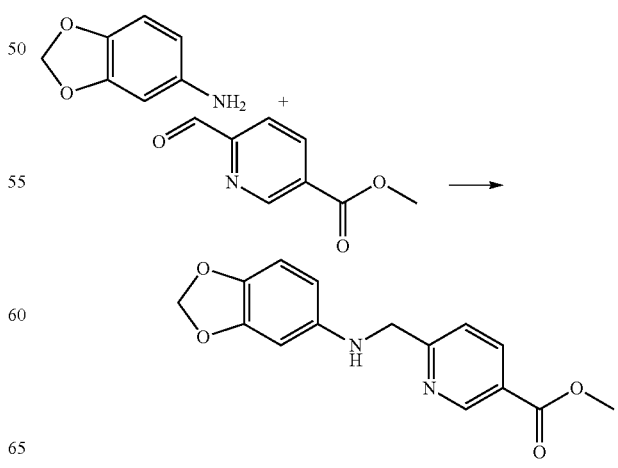

333

Acetic acid (0.150 mL, 2.625 mmol) was added to a solution of benzo[d][1,3]dioxol-5-amine (0.300 g, 2.188 mmol) and methyl 6-formylnicotinate (0.379 g, 2.297 mmol) in dichloromethane (10 mL) at the room temperature, and the mixture was stirred at the same temperature for 30 min. The reaction mixture was treated with sodium triacetoxyborohydride (0.927 g, 4.375 mmol), and stirred for additional 12 hr at the same temperature. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 40%) to give methyl 6-((benzo[d][1,3]dioxol-5-ylamino)methyl)nicotinate as yellow solid (0.492 g, 78.6%).

[Step 2] methyl 6-((N-(benzo[d][1,3]dioxol-5-yl)methylsulfonamido)methyl)nicotinate

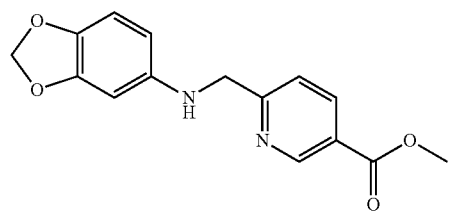

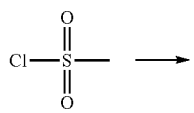

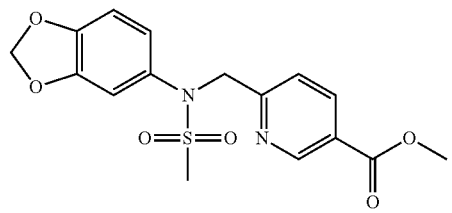

A mixture of methyl 6-((benzo[d][1,3]dioxol-5-ylamino)methyl)nicotinate (0.490 g, 1.712 mmol), triethylamine (0.477 mL, 3.423 mmol) and methanesulfonyl chloride (0.160 mL, 2.054 mmol) in dichloromethane (10 mL) prepared at the ambient temperature was heated at reflux for 15 hr, and cooled down to the ambient temperature. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 40 g cartridge; ethyl acetate/hexane=0% to 30%) to give methyl 6-((N-(benzo[d][1,3]dioxol-5-yl)methylsulfonamido)methyl)nicotinate as brown oil (0.216 g, 34.6%).

334

[Step 3] N-(benzo[d][1,3]dioxol-5-yl)-N-((5-(hydrazinecarbonyl)pyridin-2-yl)methyl)methanesulfonamide

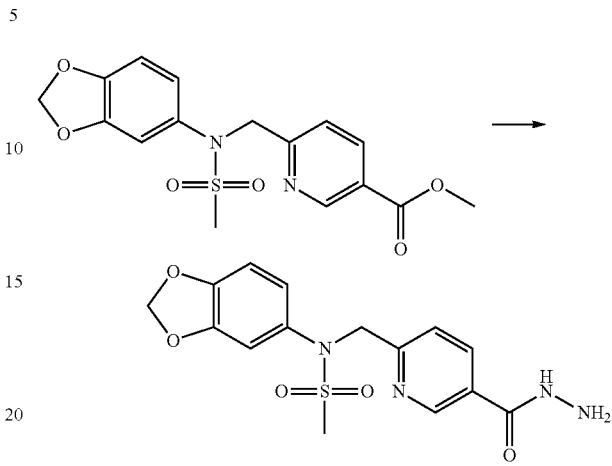

A mixture of methyl 6-((N-(benzo[d][1,3]dioxol-5-yl)methylsulfonamido)methyl)nicotinate (0.216 g, 0.593 mmol) and hydrazine hydrate (50.00% solution, 0.165 mL, 1.778 mmol) in ethanol (10 mL) was stirred at the ambient temperature for 1 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(benzo[d][1,3]dioxol-5-yl)-N-((5-(hydrazinecarbonyl)pyridin-2-yl)methyl)methanesulfonamide, 0.131 g, 60.6%, white foamy solid).

[Step 4] Compound 11345

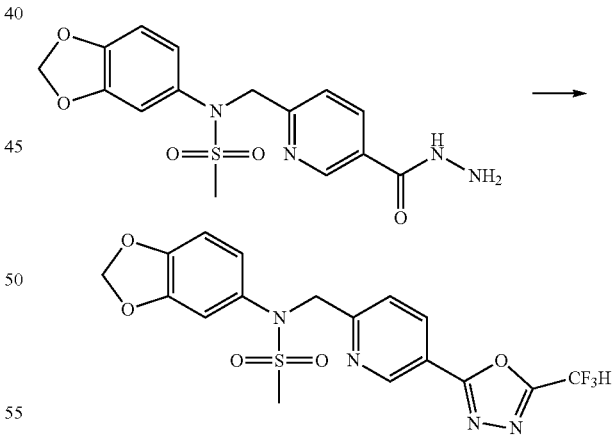

A mixture of N-(benzo[d][1,3]dioxol-5-yl)-N-((5-(hydrazinecarbonyl)pyridin-2-yl)methyl)methanesulfonamide (0.135 g, 0.371 mmol), difluoroacetic anhydride (0.060 mL, 0.556 mmol) and triethylamine (0.155 mL, 1.112 mmol) in dichloromethane (5 mL) prepared at the ambient temperature was heated at reflux for 36 hr, and cooled down to the ambient temperature, and concentrated under the reduced pressure to remove the solvent. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=10% to 50%) to give N-(benzo[d][1,3]dioxol-5-yl)-N-((5-(5-(difluoromethyl)-1,3,4-oxadiazol-2-yl)pyridin-2-yl)methyl)methanesulfonamide as brown solid (0.097 g, 61.7%).

¹H NMR (400 MHz, CDCl₃) δ 9.23 (d, 1H, J=2.2 Hz), 8.37 (dd, 1H, J=8.2, 2.2 Hz), 7.67 (d, 1H, J=8.2 Hz), 7.26 (s, 0.4H), 7.06 (s, 0.2H), 6.93 (s, 0.5H), 6.88-6.76 (m, 2H), 6.72 (d, 1H, J=8.2 Hz), 5.96 (s, 2H), 5.04 (s, 2H), 3.06 (s, 3H); LRMS (ES) m/z 425.24 (M⁺+1).

EXAMPLE 90

Compound 11346: N-((5-(5-(difluoromethyl)-1,3,4-oxadiazol-2-yl)pyridin-2-yl)methyl)-N-(4-methoxyphenyl)methanesulfonamide

[Step 1] methyl 6-(((4-methoxyphenyl)amino)methyl)nicotinate

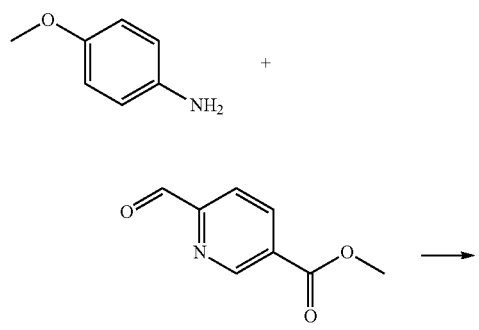

Acetic acid (0.167 mL, 2.923 mmol) was added to a solution of 4-methoxyaniline (0.300 g, 2.436 mmol) and methyl 6-formylnicotinate (0.422 g, 2.558 mmol) in dichloromethane (10 mL) at the room temperature, and the mixture was stirred at the same temperature for 30 min. The reaction mixture was treated with sodium triacetoxyborohydride (1.033 g, 4.872 mmol), and stirred for additional 12 hr at the same temperature. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 40%) to give methyl 6-(((4-methoxyphenyl)amino)methyl)nicotinate as yellow solid (0.537 g, 81.0%).

[Step 2] methyl 6-((N-(4-methoxyphenyl)methylsulfonamido)methyl)nicotinate

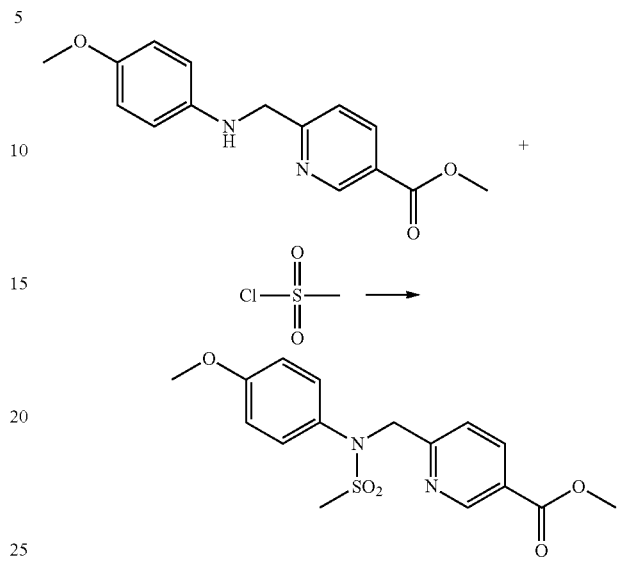

A solution of methyl 6-(((4-methoxyphenyl)amino)methyl)nicotinate (0.530 g, 1.946 mmol), triethylamine (0.543 mL, 3.893 mmol) and methanesulfonyl chloride (0.182 mL, 2.336 mmol) in dichloromethane (10 mL) was stirred at the room temperature for 5 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 30%) to give methyl 6-((N-(4-methoxyphenyl)methylsulfonamido)methyl)nicotinate as pale brown solid (0.305 g, 44.7%).

[Step 3] N-((5-(hydrazinecarbonyl)pyridin-2-yl)methyl)-N-(4-methoxyphenyl)methanesulfonamide

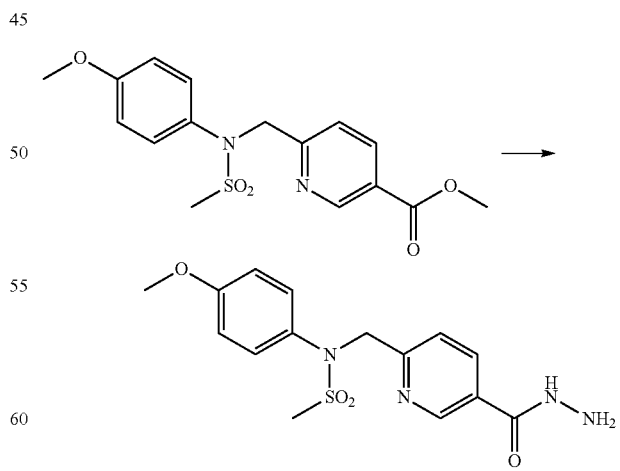

A mixture of methyl 6-((N-(4-methoxyphenyl)methylsulfonamido)methyl)nicotinate (0.305 g, 0.870 mmol) and hydrazine hydrate (50.00% solution, 0.242 mL, 2.611 mmol) in ethanol (10 mL) was stirred at the ambient temperature for 1 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-((5-(hydrazinecarbonyl)pyridin-2-yl)methyl)-N-(4-methoxyphenyl)methanesulfonamide as white solid (0.282 g, 92.5%)

[Step 4] Compound 11346

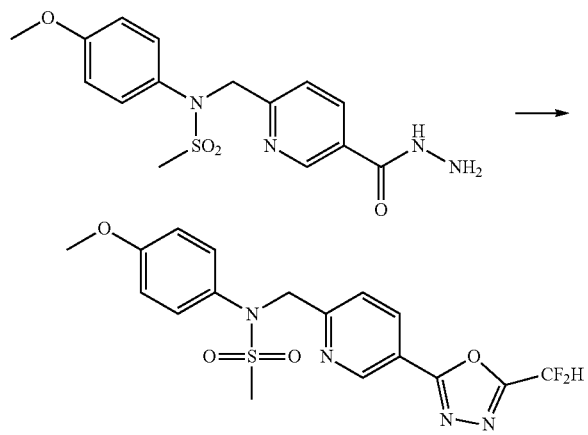

A mixture of N-((5-(hydrazinecarbonyl)pyridin-2-yl)methyl)-N-(4-methoxyphenyl)methanesulfonamide (0.282 g, 0.805 mmol), difluoroacetic anhydride (0.131 mL, 1.207 mmol) and triethylamine (0.337 mL, 2.414 mmol) in dichloromethane (5 mL) was heated at reflux for 36 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=10% to 50%) to give N-((5-(5-(difluoromethyl)-1,3,4-oxadiazol-2-yl)pyridin-2-yl)methyl)-N-(4-methoxyphenyl)methanesulfonamide as brown solid (0.228 g, 69.0%).

$^1$H NMR (400 MHz, CDCl$_3$) δ 9.22 (dd, 1H, J=2.2, 0.9 Hz), 8.37 (dd, 1H, J=8.3, 2.2 Hz), 7.71 (d, 1H, J=8.2 Hz), 7.34-7.21 (m, 2H), 7.06 (s, 0.2H), 6.93 (s, 0.4H), 6.88-6.81 (m, 2H), 6.80 (s, 0.2H), 5.08 (s, 2H), 3.76 (s, 3H), 3.05 (s, 3H); LRMS (ES) m/z 411.28 (M$^+$+1).

EXAMPLE 91

Compound 11347: N-(5-bromopyridin-2-yl)-N-(4-(5-(difluoromethyl)-1,3,4-oxadiazol-2-yl)benzyl)methanesulfonamide

[Step 1] Methyl 4-((N-(5-bromopyridin-2-yl)methylsulfonamido)methyl)benzoate

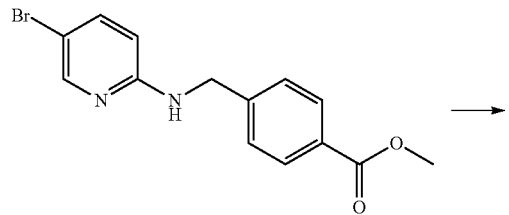

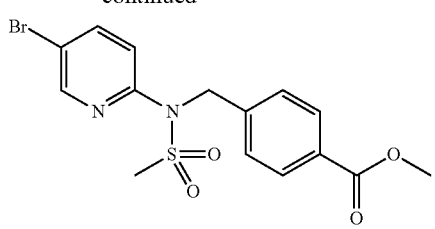

A solution of methanesulfonyl chloride (0.106 mL, 1.370 mmol), N,N-dimethylpyridin-4-amine (DMAP, 0.046 g, 0.374 mmol) and pyridine (0.151 mL, 1.868 mmol) in dichloromethane (10 mL) was stirred at the room temperature for 20 min, and then mixed with methyl 4-(((5-bromopyridin-2-yl)amino)methyl)benzoate (0.400 g, 1.245 mmol). The reaction mixture was heated at reflux for 24 hr, and cooled down to the room temperature to terminate the reaction. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 15%) to give methyl 4-((N-(5-bromopyridin-2-yl)methylsulfonamido)methyl)benzoate as yellow solid (0.350 g, 70.4%).

[Step 2] N-(5-bromopyridin-2-yl)-N-(4-(hydrazinecarbonyl)benzyl)methanesulfonamide

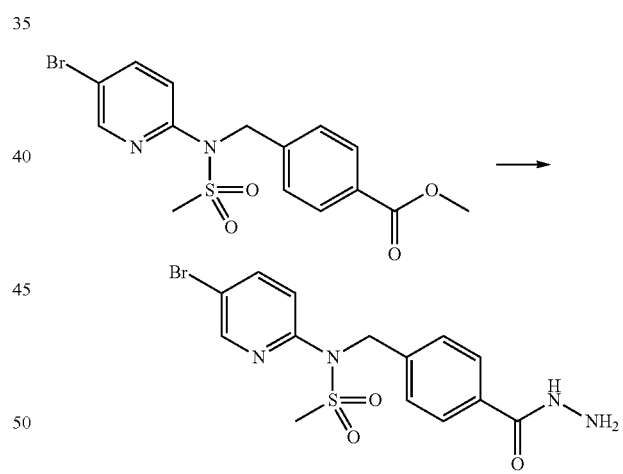

A mixture of methyl 4-((N-(5-bromopyridin-2-yl)methylsulfonamido)methyl)benzoate (0.350 g, 0.877 mmol) and hydrazine hydrate (0.084 g, 2.630 mmol) in ethanol (8 mL) prepared at the ambient temperature was heated at reflux for 24 hr, and cooled down to the ambient temperature, and concentrated under the reduced pressure to remove the solvent. The residue was diluted with aqueous saturated sodium bicarbonate solution and stirred. The resulting precipitates were collected by filtration, washed by water, and dried to give N-(5-bromopyridin-2-yl)-N-(4-(hydrazinecarbonyl)benzyl)methanesulfonamide as white solid (0.290 g, 82.9%).

339

[Step 3] Compound 11347

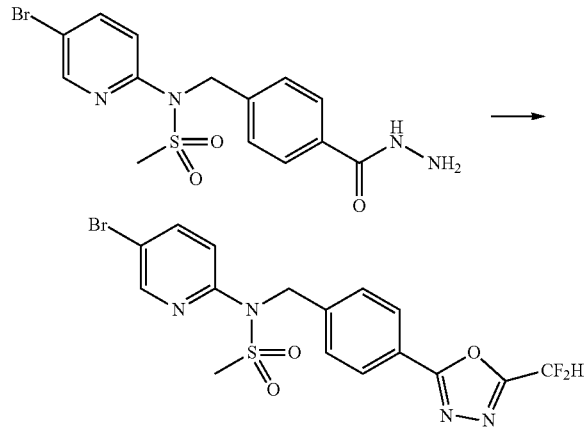

Triethylamine (0.032 mL, 0.234 mmol) was added to a solution of N-(5-bromopyridin-2-yl)-N-(4-(hydrazinecarbonyl)benzyl)methanesulfonamide (0.072 g, 0.180 mmol) in tetrahydrofuran (1 mL) at the room temperature, and the mixture was stirred for 10 min at the same temperature. The reaction mixture was treated with 2,2-difluoroacetic anhydride (0.024 mL, 0.216 mmol), heated at reflux for 6 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 40%) to give the crude product which was rechromatographed (SiO$_2$ plate, 20×20×1 mm; ethyl acetate/hexane=30%) to give N-(5-bromopyridin-2-yl)-N-(4-(5-(difluoromethyl)-1,3,4-oxadiazol-2-yl)benzyl)methanesulfonamide as white solid (0.035 g, 42.3%).

$^1$H NMR (400 MHz, CDCl$_3$) δ 8.39-8.31 (m, 1H), 8.08-7.99 (m, 2H), 7.61 (dd, 1H, J=8.7, 2.6 Hz), 7.56-7.46 (m, 2H), 7.32-7.26 (m, 2H), 6.89 (t, 1H, J=51.7 Hz), 5.16 (s, 2H), 3.07 (s, 3H); LRMS (ES) m/z 461.1 (M$^+$+1).

EXAMPLE 92

Compound 11348: N-(5-chloropyridin-2-yl)-N-(4-(5-(difluoromethyl-1,3,4-oxadiazol-2-yl)benzyl)methanesulfonamide

[Step 1] methyl 4-((N-(5-chloropyridin-2-yl)methylsulfonamido)methyl)benzoate

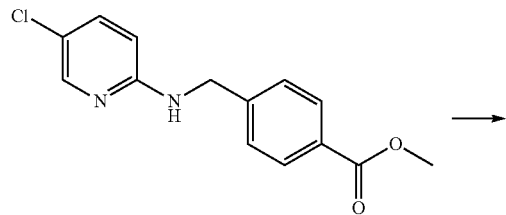

340

-continued

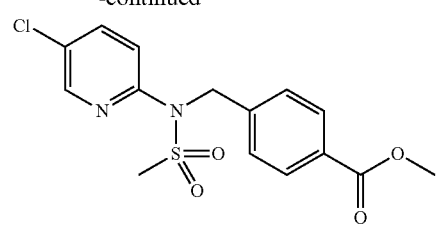

A solution of methanesulfonyl chloride (0.123 mL, 1.590 mmol), N,N-dimethylpyridin-4-amine (DMAP, 0.053 g, 0.434 mmol) and pyridine (0.175 mL, 2.168 mmol) in dichloromethane (10 mL) was stirred at the room temperature for 20 min, and then mixed with methyl 4-(((5-chloropyridin-2-yl)amino)methyl)benzoate (0.400 g, 1.446 mmol). The reaction mixture was heated at reflux for 24 hr, and cooled down to the room temperature to terminate the reaction. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 15%) to give methyl 4-((N-(5-chloropyridin-2-yl)methylsulfonamido)methyl)benzoate as white solid (0.320 g, 62.4%).

[Step 2] N-(5-chloropyridin-2-yl)-N-(4-(hydrazinecarbonyl)benzyl)methanesulfonamide

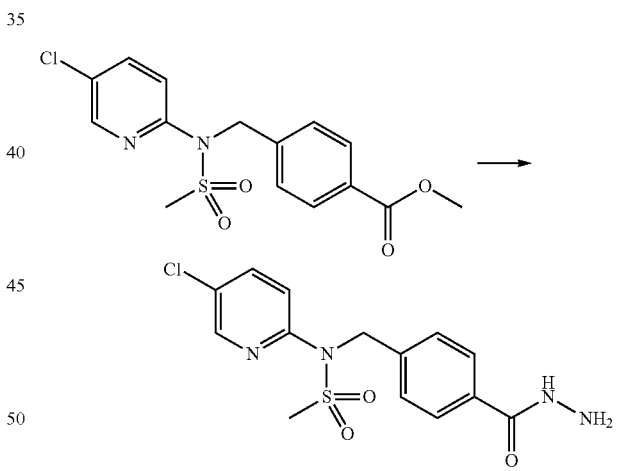

A mixture of methyl 4-((N-(5-chloropyridin-2-yl)methylsulfonamido)methyl)benzoate (0.320 g, 0.902 mmol) and hydrazine hydrate (0.087 g, 2.706 mmol) in ethanol (8 mL) prepared at the ambient temperature was heated at reflux for 24 hr, and cooled down to the ambient temperature, and concentrated under the reduced pressure to remove the solvent. The residue was diluted with aqueous saturated sodium bicarbonate solution and stirred. The resulting precipitates were collected by filtration, washed by water, and dried to give N-(5-chloropyridin-2-yl)-N-(4-(hydrazinecarbonyl)benzyl)methanesulfonamide as white solid (0.280 g, 87.5%).

[Step 3] Compound 11348

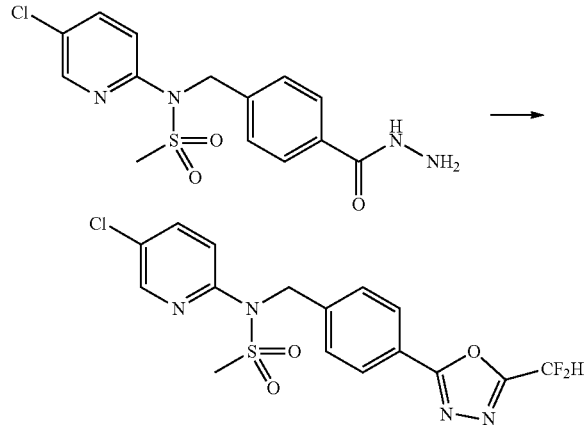

N-(5-chloropyridin-2-yl)-N-(4-(hydrazinecarbonyl)benzyl)methanesulfonamide (0.074 g, 0.207 mmol) in tetrahydrofuran (1 mL) was stirred for 10 min at the room temperature. The reaction mixture was treated with 2,2-difluoroacetic anhydride (0.027 mL, 0.249 mml), and heated at reflux for 6 hr. The reaction mixture was cooled down to the room temperature to terminate the reaction. Then, water was added to the reaction mixture, followed by extraction with ethyl acetate. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 30%) to give N-(5-chloropyridin-2-yl)-N-(4-(5-(difluoromethyl-1,3,4-oxadiazol-2-yl)benzyl)methanesulfonamide as white solid (0.030 g, 34.9%).

$^1$H NMR (400 MHz, CDCl$_3$) δ 8.48 (dd, 1H, J=2.6, 0.7 Hz), 8.09-8.00 (m, 2H), 7.77 (ddd, 1H, J=8.6, 2.5, 0.6 Hz), 7.54 (d, 2H, J=8.2 Hz), 7.30-7.27 (m, 1H), 6.92 (t, 1H, J=51.7 Hz), 5.19 (s, 2H), 3.10 (s, 3H); LRMS (ES) m/z 415.2 (M$^+$+1).

EXAMPLE 93

Compound 11350: N-((5-(5-(difluoromethyl)-1,3,4-oxadiazol-2-yl)pyridin-2-yl)methyl)-N-phenyltetrahydro-2H-thiopyran-4-sulfonamide 1,1-dioxide

[Step 1]
N-phenyltetrahydro-2H-thiopyran-4-sulfonamide 1,1-dioxide

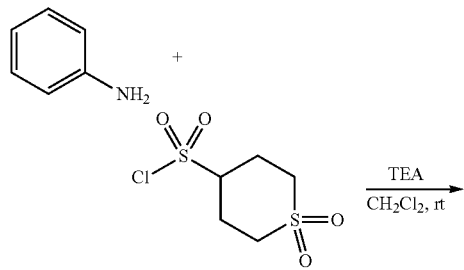

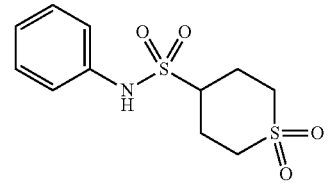

Triethylamine (0.193 mL, 1.396 mmol) was added to a solution of aniline (0.100 g, 1.074 mmol) in dichloromethane (6 mL) at 0° C., and the mixture was stirred at the same temperature for 20 min. The reaction mixture was treated with tetrahydro-2H-thiopyran-4-sulfonyl chloride 1,1-dioxide (0.250 g, 1.074 mmol), and stirred for additional 16 hr at the room temperature. Then, aqueous 0.1N-hydrochloric acid solution was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-phenyltetrahydro-2H-thiopyran-4-sulfonamide 1,1-dioxide, 0.310 g, 99.8%, white solid).

[Step 2] methyl 6-(((1,1-dioxido-N-phenyltetrahydro-2H-thiopyran)-4-sulfonamido)methyl)nicotinate

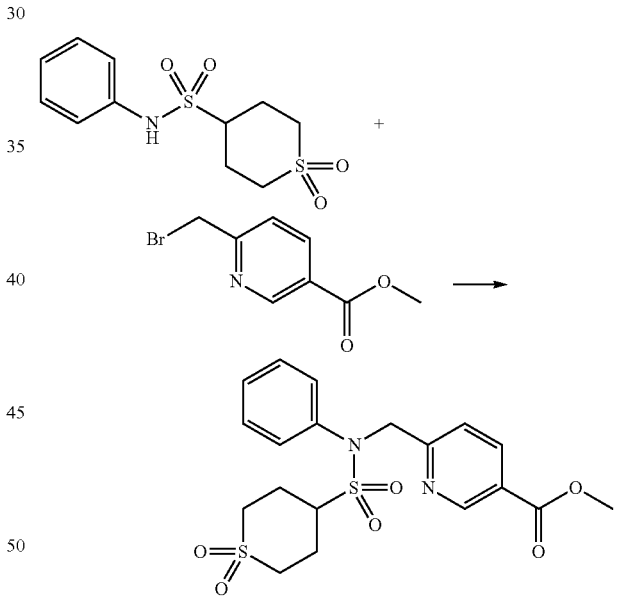

A solution of methyl 6-(bromomethyl)nicotinate (0.125 g, 0.544 mmol) and potassium iodide (0.017 g, 0.104 mmol) in N,N-dimethylformide (2 mL) was stirred at the room temperature for 20 min, and mixed with N-phenyltetrahydro-2H-thiopyran-4-sulfonamide 1,1-dioxide (0.150 g, 0.518 mmol) and potassium carbonate (0.086 g, 0.622 mmol). The reaction mixture was stirred at the same temperature for additional 24 hr. Then, aqueous 0.1N-hydrochloric acid solution was added to the reaction mixture, followed by extraction with ethyl acetate. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 60%) to give methyl 6-(((1,1-dioxido-N-phenyltetrahydro-2H-thiopyran)-4-sulfonamido)methyl)nicotinate as white solid (0.200 g, 87.9%).

[Step 3] N-((5-(hydrazinecarbonyl)pyridin-2-yl)methyl)-N-phenyltetrahydro-2H-thiopyran-4-sulfonamide 1,1-dioxide

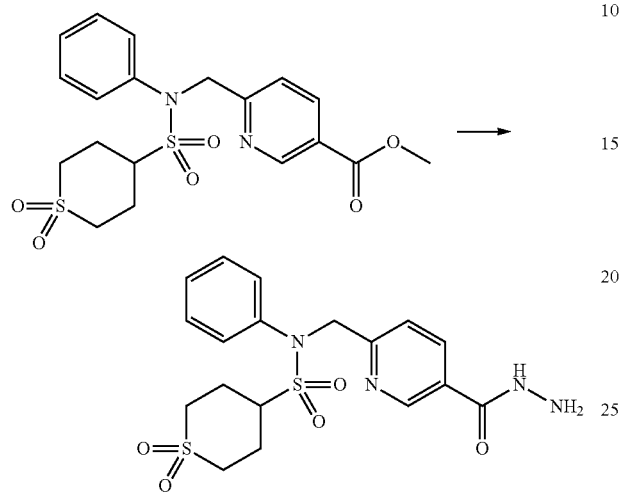

A mixture of methyl 6-(((1,1-dioxido-N-phenyltetrahydro-2H-thiopyran)-4-sulfonamido)methyl)nicotinate (0.200 g, 0.456 mmol) and hydrazine hydrate (0.067 mL, 1.368 mmol) in ethanol (4 mL) prepared at the ambient temperature was heated at reflux for 16 hr, and cooled down to the ambient temperature, and concentrated under the reduced pressure to remove the solvent. The precipitates were collected by filtration, washed by water, and dried to give N-((5-(hydrazinecarbonyl)pyridin-2-yl)methyl)-N-phenyltetrahydro-2H-thiopyran-4-sulfonamide 1,1-dioxide as white solid (0.180 g, 90.0%).

[Step 4] Compound 11350

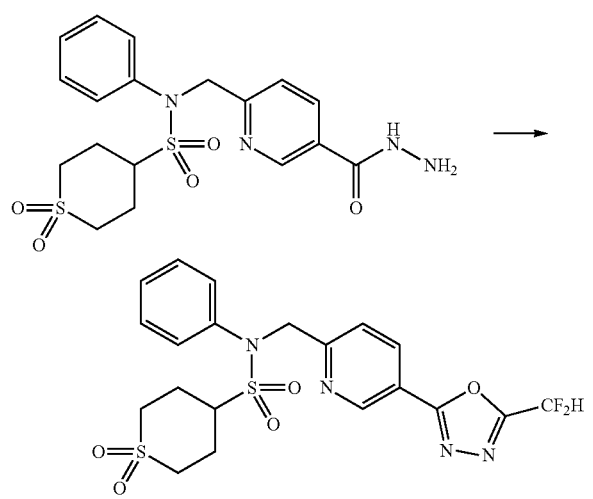

Triethylamine (0.057 mL, 0.410 mmol) was added to a solution of N-((5-(hydrazinecarbonyl)pyridin-2-yl)methyl)-N-phenyltetrahydro-2H-thiopyran-4-sulfonamide 1,1-dioxide (0.090 g, 0.205 mmol) in tetrahydrofuran (1 mL) at the room temperature, and the mixture was stirred for 10 min at the same temperature. The reaction mixture was treated with 2,2-difluoroacetic anhydride (0.033 mL, 0.308 mmol), heated at reflux for 6 hr, and cooled down to the room temperature to terminate the reaction. Then, water was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-N-phenyltetrahydro-2H-thiopyran-4-sulfonamide 1,1-dioxide as white solid (0.070 g, 68.4%)
$^1$H NMR (400 MHz, CDCl$_3$) δ 9.24 (d, 1H, J=2.1 Hz), 8.37 (dd, 1H, J=8.2, 2.2 Hz), 7.59 (d, 1H, J=8.2 Hz), 7.45-7.28 (m, 5H), 6.95 (t, 1H, J=51.6 Hz), 5.16 (s, 2H), 3.45 (p, 1H, J=6.3 Hz), 3.41-3.28 (m, 2H), 3.05-2.94 (m, 2H), 2.64 (q, 4H, J=6.3 Hz); LRMS (ES) m/z 499.3 (M$^+$+1).

EXAMPLE 94

Compound 11351: N-cyclohexyl-N-((5-(5-(difluoromethyl)-1,3,4-oxadiazol-2-yl)pyridin-2-yl)methyl)methanesulfonamide

[Step 1] Methyl 6-((N-cyclohexylmethylsulfonamido)methyl)nicotinate

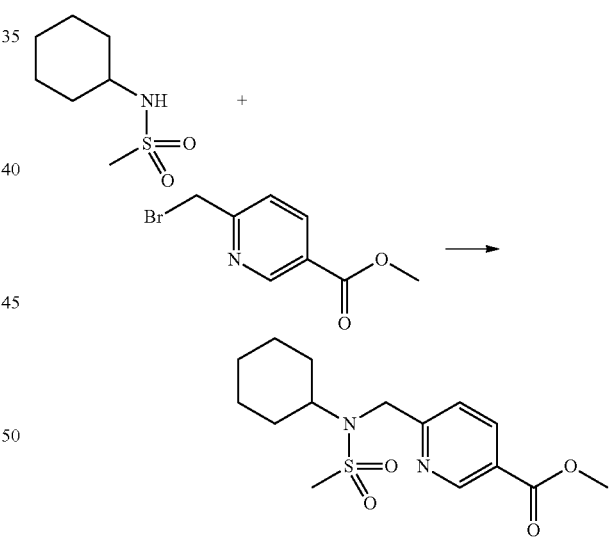

A solution of methyl 6-(bromomethyl)nicotinate (0.164 g, 0.711 mmol) and potassium iodide (0.022 g, 0.135 mmol) in N,N-dimethylformide (2 mL) was stirred at the room temperature for 20 min, and mixed with N-cyclohexylmethanesulfonamide (0.120 g, 0.677 mmol) and potassium carbonate (0.112 g, 0.812 mmol). The reaction mixture was stirred at the same temperature for additional 24 hr. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 40%) to give methyl 6-((N-cyclohexylmethylsulfonamido)methyl)nicotinate as white solid (0.210 g, 95.0%).

[Step 2] N-cyclohexyl-N-((5-(hydrazinecarbonyl)pyridin-2-yl)methyl)methanesulfonamide

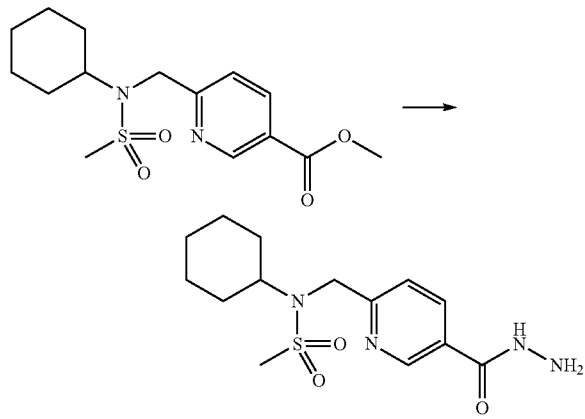

A mixture of methyl 6-((N-cyclohexylmethylsulfonamido)methyl)nicotinate (0.210 g, 0.643 mmol) and hydrazine hydrate (0.094 mL, 1.930 mmol) prepared at the ambient temperature in ethanol (4 mL) was heated at reflux for 16 hr, and cooled down to the ambient temperature, and concentrated under the reduced pressure to remove the solvent. The precipitates were collected by filtration, washed by water, and dried to give N-cyclohexyl-N-((5-(hydrazinecarbonyl)pyridin-2-yl)methyl)methanesulfonamide as white solid (0.180 g, 85.7%).

[Step 3] Compound 11351

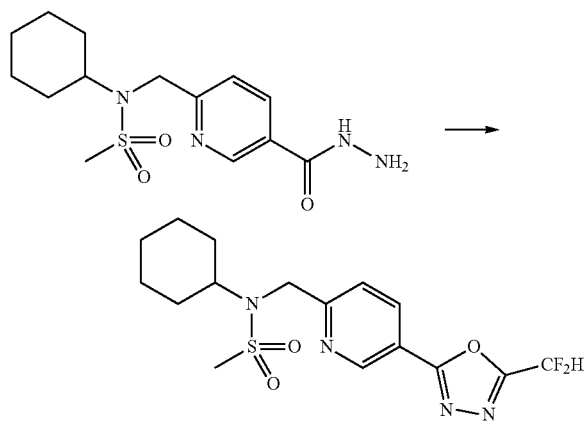

Triethylamine (0.077 mL, 0.551 mmol) was added to a solution of N-cyclohexyl-N-((5-(hydrazinecarbonyl)pyridin-2-yl)methyl)methanesulfonamide (0.090 g, 0.276 mmol) in tetrahydrofuran (1 mL) at the room temperature, and the mixture was stirred for 10 min at the same temperature. The reaction mixture was treated with 2,2-difluoroacetic anhydride (0.045 mL, 0.414 mmol), heated at reflux for 6 hr, and cooled down to the room temperature to terminate the reaction. Then, water was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 50%) to give N-cyclohexyl-N-((5-(5-(difluoromethyl)-1,3,4-oxadiazol-2-yl)pyridin-2-yl)methyl)methanesulfonamide as white solid (0.070 g, 65.7%).

$^1$H NMR (400 MHz, CDCl$_3$) δ 9.21 (dd, 1H, J=2.3, 0.8 Hz), 8.36 (dd, 1H, J=8.3, 2.2 Hz), 7.80 (dd, 1H, J=8.3, 0.8 Hz), 6.93 (t, 1H, J=51.6 Hz), 4.59 (s, 2H), 3.86-3.69 (m, 1H), 3.00 (s, 3H), 1.84-1.66 (m, 4H), 1.59 (d, 1H, J=13.6 Hz), 1.31 (td, 4H, J=9.4, 2.8 Hz), 1.07-0.88 (m, 1H); LRMS (ES) m/z 387.0 (M$^+$+1).

EXAMPLE 95

Compound 11352: N-(3-chlorophenyl)-N-((5-(5-(difluoromethyl)-1,3,4-oxadiazol-2-yl)pyridin-2-yl)methyl)methanesulfonamide

[Step 1] Methyl 6-((N-(3-chlorophenyl)methylsulfonamido)methyl)nicotinate

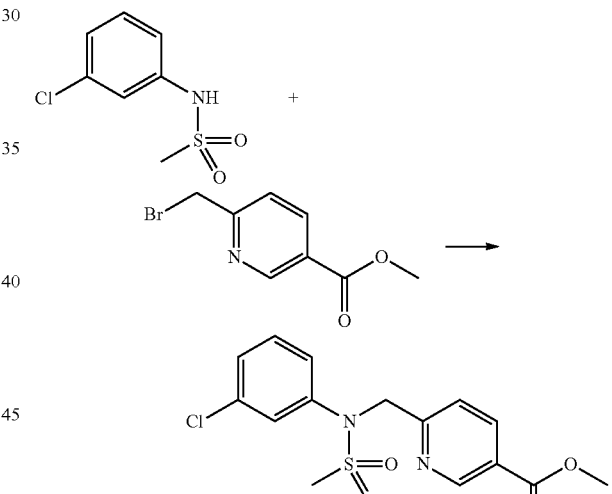

A solution of methyl 6-(bromomethyl)nicotinate (0.294 g, 1.276 mmol) and potassium iodide (0.040 g, 0.243 mmol) in N,N-dimethylformide (4 mL) was stirred at the room temperature for 20 min, and mixed with N-(3-chlorophenyl)methanesulfonamide (0.250 g, 1.216 mmol) and potassium carbonate (0.202 g, 1.459 mmol). The reaction mixture was stirred at the same temperature for additional 24 hr. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 40%) to give methyl 6-((N-(3-chlorophenyl)methylsulfonamido)methyl)nicotinate as light yellow solid (0.292 g, 67.7%).

347

[Step 2] (N-(3-chlorophenyl)-N-((5-(hydrazinecarbonyl)pyridin-2-yl)methyl)methanesulfonamide

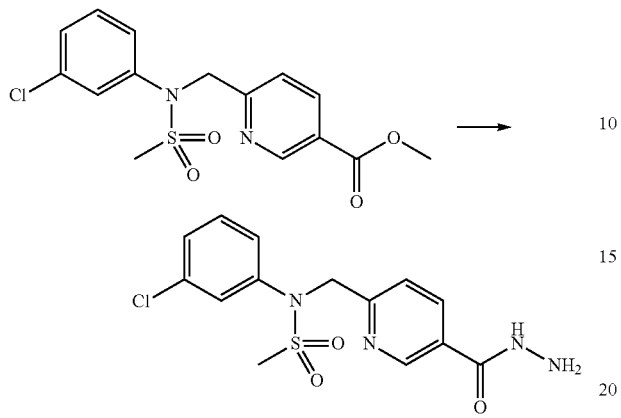

A mixture of methyl 6-((N-(3-chlorophenyl)methylsulfonamido)methyl)nicotinate (0.292 g, 0.823 mmol) and hydrazine hydrate (0.087 mL, 2.469 mmol) in ethanol (6 mL) prepared at ambient temperature was heated at reflux for 16 hr, and cooled down to the ambient temperature, and concentrated under the reduced pressure to remove the solvent. The title compound was used without further purification (N-(3-chlorophenyl)-N-((5-(hydrazinecarbonyl)pyridin-2-yl)methyl)methanesulfonamide, 0.250 g, 85.6%, white solid).

[Step 3] N-(3-chlorophenyl)-N-((5-(2-(2,2-difluoroacetyl)hydrazine-1-carbonyl)pyridin-2-yl)methyl) methanesulfonamide

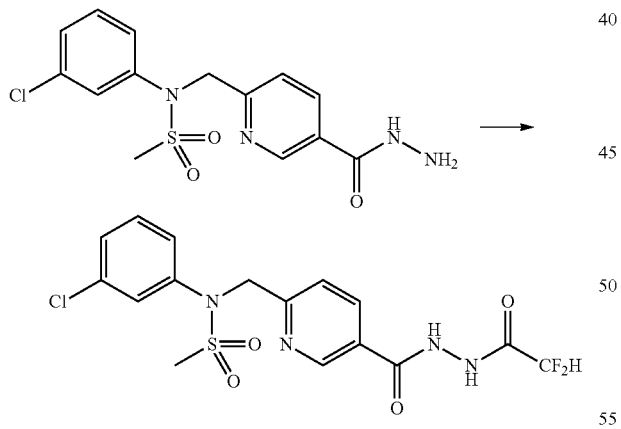

Triethylamine (0.112 mL, 0.803 mmol) was added to a solution of N-(3-chlorophenyl)-N-((5-(hydrazinecarbonyl)pyridin-2-yl)methyl)methanesulfonamide (0.190 g, 0.535 mmol) in tetrahydrofuran (3 mL) at the room temperature, and the mixture was stirred for 10 min at the same temperature. The reaction mixture was treated with 2,2-difluoroacetic anhydride (0.070 mL, 0.643 mmol), heated at reflux for 16 hr, and cooled down to the room temperature to terminate the reaction. Then, water was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 50%) to give N-(3-chlorophenyl)-N-((5-(2-(2,2-difluoroacetyl)hydrazine-1-carbonyl)pyridin-2-yl) methyl)methanesulfonamide as white solid (0.210 g, 90.6%).

[Step 4] Compound 11352

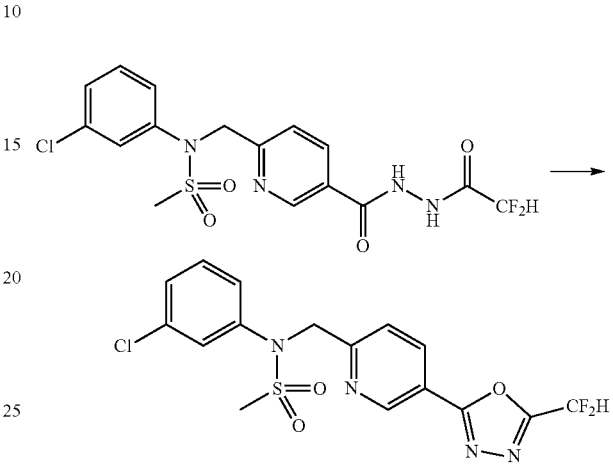

A mixture of N-(3-chlorophenyl)-N-((5-(2-(2,2-difluoroacetyl)hydrazine-1-carbonyl)pyridin-2-yl)methyl)methanesulfonamide (0.110 g, 0.254 mmol) and 1-methoxy-N-triethylammoniosulfonyl-methanimidate (Burgess reagent, 0.073 g, 0.305 mmol) in tetrahydrofuran (6 mL) was heated at 130° C. for 30 min under the microwaves. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(3-chlorophenyl)-N-((5-(5-(difluoromethyl)-1,3,4-oxadiazol-2-yl)pyridin-2-yl) methyl)methanesulfonamide as white solid (0.080 g, 75.9%).

$^1$H NMR (400 MHz, CDCl$_3$) δ 9.27 (dd, 1H, J=2.3, 0.8 Hz), 8.41 (dd, 1H, J=8.2, 2.2 Hz), 7.67 (dd, 1H, J=8.2, 0.9 Hz), 7.47 (dt, 1H, J=2.6, 1.1 Hz), 7.36-7.26 (m, 4H), 6.95 (t, 1H, J=51.6 Hz), 5.14 (s, 2H), 3.10 (s, 3H); LRMS (ES) m/z 417.0 (M$^+$+1).

EXAMPLE 96

Compound 11353: N-((5-(5-(difluoromethyl)-1,3,4-oxadiazol-2-yl)pyridin-2-yl)methyl)-N-(pyridin-3-yl) methanesulfonamide

[Step 1] methyl 6-((N-(pyridin-3-yl)methylsulfonamido)methyl)nicotinate

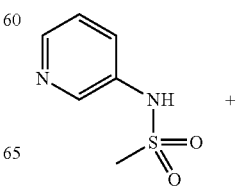

-continued

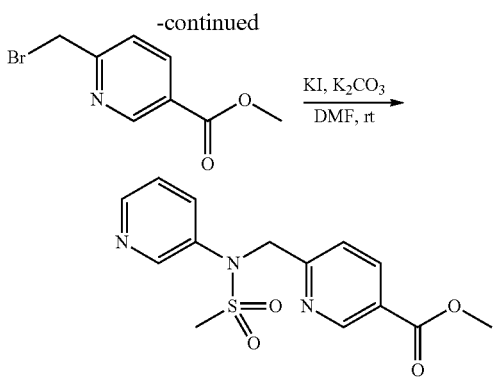

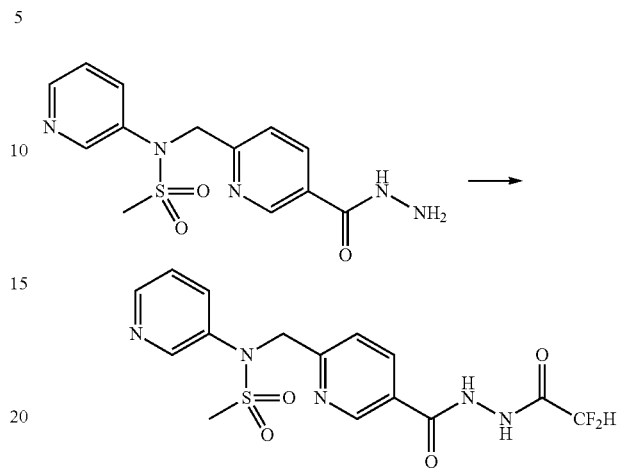

A solution of methyl 6-(bromomethyl)nicotinate (0.168 g, 0.732 mmol) and potassium iodide (0.023 g, 0.139 mmol) in N,N-dimethylformide (2 mL) was stirred at the room temperature for 20 min, and mixed with N-(pyridin-3-yl)methanesulfonamide (0.120 g, 0.697 mmol) and potassium carbonate (0.116 g, 0.836 mmol). The reaction mixture was stirred at the same temperature for additional 24 hr. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; methanol/dichloromethane=0% to 5%) to give methyl 6-((N-(pyridin-3-yl)methylsulfonamido)methyl)nicotinate as yellow solid (0.140 g, 62.5%).

[Step 2] N-((5-(hydrazinecarbonyl)pyridin-2-yl)methyl)-N-(pyridin-3-yl)methanesulfonamide

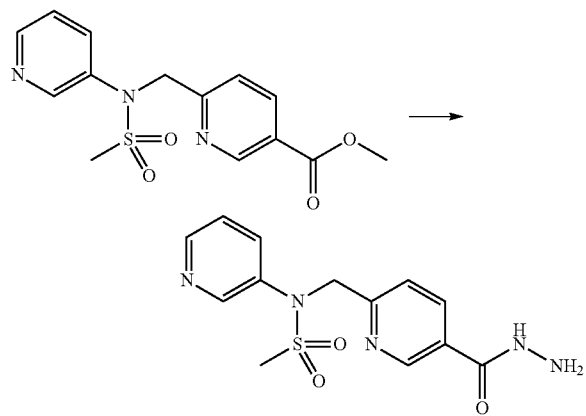

A mixture of methyl 6-((N-(pyridin-3-yl)methylsulfonamido)methyl)nicotinate (0.140 g, 0.436 mmol) and hydrazine hydrate (0.064 mL, 1.307 mmol) in ethanol (4 mL) prepared at the ambient temperature was heated at reflux for 16 hr, and cooled down to the ambient temperature, and concentrated under the reduced pressure to remove the solvent. The title compound was used without further purification (N-((5-(hydrazinecarbonyl)pyridin-2-yl)methyl)-N-(pyridin-3-yl)methanesulfonamide, 0.135 g, 96.4%, light yellow oil).

[Step 3] N-((5-(2-(2,2-difluoroacetyl)hydrazine-1-carbonyl)pyridin-2-yl)methyl)-N-(pyridin-3-yl)methanesulfonamide Triethylamine (0.117 mL, 0.840 mmol) was added to a solution of N-((5-(hydrazinecarbonyl)pyridin-2-yl)methyl)-N-(pyridin-3-yl)methanesulfonamide (0.135 g, 0.420 mmol) in tetrahydrofuran (1 mL) at the room temperature, and the mixture was stirred for 10 min at the same temperature. The reaction mixture was treated with 2,2-difluoroacetic anhydride (0.069 mL, 0.630 mmol), heated at reflux for 6 hr, and cooled down to the room temperature to terminate the reaction. Then, water was added to the reaction mixture, followed by extraction with ethyl acetate. The bi-phasic mixture was passed through a plastic frit to remove the solid residues and the aqueous layer, and the organic layer collected was concentrated in vacuo. The residue was chromatographed (SiO$_2$, 4 g cartridge; methanol/dichloromethane=0% to 5%) to give N-((5-(2-(2,2-difluoroacetyl)hydrazine-1-carbonyl)pyridin-2-yl)methyl)-N-(pyridin-3-yl)methanesulfonamide as yellow oil (0.070 g, 43.7%).

[Step 4] Compound 11353

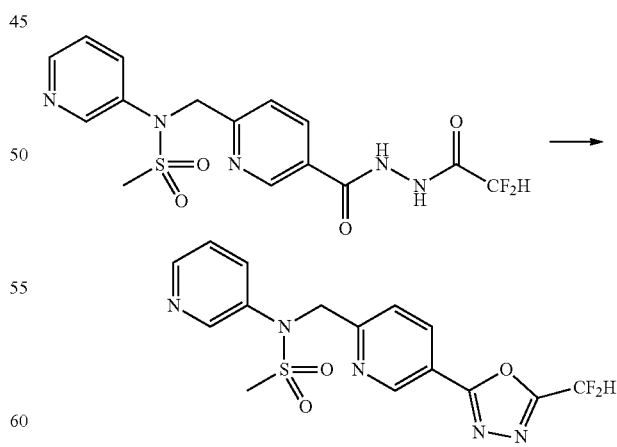

A mixture of N-((5-(2-(2,2-difluoroacetyl)hydrazine-1-carbonyl)pyridin-2-yl)methyl)-N-(pyridin-3-yl)methanesulfonamide (0.070 g, 0.184 mmol) and 1-methoxy-N-triethylammoniosulfonyl-methanimidate (Burgess reagent, 0.052 g, 0.220 mmol) in tetrahydrofuran (2 mL) was heated at 130°

C. for 30 min under the microwaves. Then, water was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO₂, 4 g cartridge; methanol/dichloromethane=0% to 5%) to give N-((5-(5-(difluoromethyl)-1,3,4-oxadiazol-2-yl)pyridin-2-yl)methyl)-N-(pyridin-3-yl)methanesulfonamide as light yellow oil (0.025 g, 35.7%).

¹H NMR (400 MHz, CDCl₃) δ 9.28 (d, J=1.7 Hz, 1H), 8.89 (d, J=2.1 Hz, 1H), 8.57 (dd, J=5.0, 1.2 Hz, 1H), 8.42 (dd, J=8.2, 2.2 Hz, 1H), 8.15 (d, J=9.0 Hz, 1H), 7.54 (m, 1H), 6.94 (t, J=51.6 Hz, 1H), 5.19 (s, 2H), 3.10 (s, 3H); LRMS (ES) m/z 382.27 (M⁺+1).

EXAMPLE 97

Compound 11354: N-(3-bromophenyl)-N-((5-(5-(difluoromethyl)-1,3,4-oxadiazol-2-yl)pyridin-2-yl)methyl)methanesulfonamide

[Step 1] methyl 6-((N-(3-bromophenyl)methylsulfonamido)methyl)nicotinate

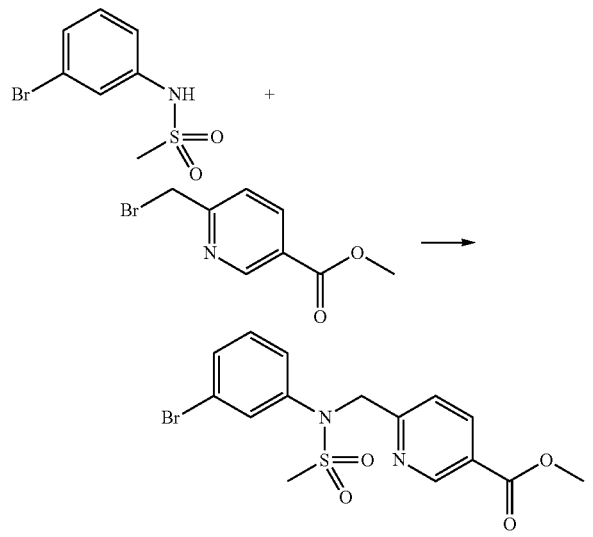

A solution of methyl 6-(bromomethyl)nicotinate (0.193 g, 0.840 mmol) and potassium iodide (0.027 g, 0.160 mmol) in N,N-dimethylformide (3 mL) was stirred at the room temperature for 20 min, and mixed with N-(3-bromophenyl)methanesulfonamide (0.200 g, 0.800 mmol) and potassium carbonate (0.144 g, 1.040 mmol). The reaction mixture was stirred at the same temperature for additional 24 hr. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO₂, 12 g cartridge; ethyl acetate/hexane=0% to 40%) to give methyl 6-((N-(3-bromophenyl)methylsulfonamido)methyl)nicotinate as white solid (0.270 g, 84.6%).

[Step 2] N-(3-bromophenyl)-N-((5-(hydrazinecarbonyl)pyridin-2-yl)methyl)methanesulfonamide


A mixture of methyl 6-((N-(3-bromophenyl)methylsulfonamido)methyl)nicotinate (0.270 g, 0.676 mmol) and hydrazine monohydrate (0.099 mL, 2.029 mmol) in ethanol (6 mL) prepared at the ambient temperature was heated at reflux for 8 hr, and cooled down to the ambient temperature, and concentrated under the reduced pressure to remove the solvent. The precipitates were collected by filtration, washed by water, and dried to give N-(3-bromophenyl)-N-((5-(hydrazinecarbonyl)pyridin-2-yl)methyl)methanesulfonamide as white solid (0.250 g, 92.6%).

[Step 3] Compound 11354

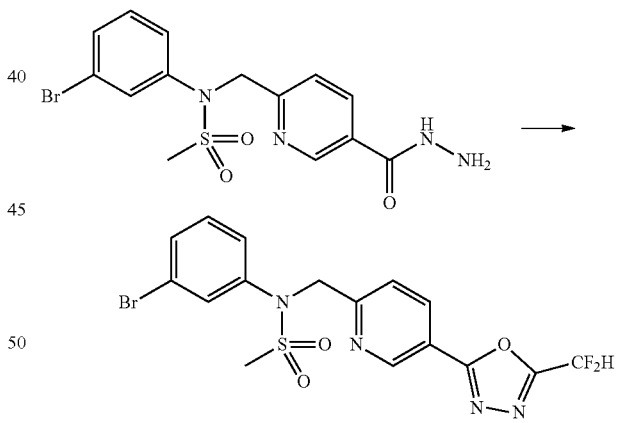

Triethylamine (0.042 mL, 0.304 mmol) was added to a solution of N-(3-bromophenyl)-N-((5-(hydrazinecarbonyl)pyridin-2-yl)methyl)methanesulfonamide (0.061 g, 0.152 mmol) in tetrahydrofuran (2 mL) at the room temperature, and the mixture was stirred for 20 min at the same temperature. The reaction mixture was treated with 2,2-difluoroacetic anhydride (0.025 mL, 0.228 mmol), heated at reflux for 8 hr, and cooled down to the room temperature to terminate the reaction. Then, water was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 50%) to give N-(3-bromophenyl)-N-((5-(5-(difluoromethyl)-1,3,4-oxadiazol-2-yl)pyridin-2-yl)methyl)methanesulfonamide as white solid (0.055 g, 78.8%).

$^1$H NMR (400 MHz, CDCl$_3$) δ 9.26 (d, J=1.7 Hz, 1H), 8.40 (dd, J=8.2, 2.1 Hz, 1H), 7.67 (d, J=8.2 Hz, 1H), 7.61 (m, 1H), 7.44~7.37 (m, 2H), 7.24 (t, J=8.0 Hz, 1H), 6.95 (t, J=51.6 Hz, 1H), 5.13 (s, 2H), 3.09 (s, 3H); LRMS (ES) m/z 491.06 (M$^+$+1).

EXAMPLE 98

Compound 11355: N-((5-(5-(difluoromethyl)-1,3,4-oxadiazol-2-yl)pyridin-2-yl)methyl)-N-(m-tolyl)methanesulfonamide

[Step 1] 6-((N-(m-tolyl)methylsulfonamido)methyl)nicotinate

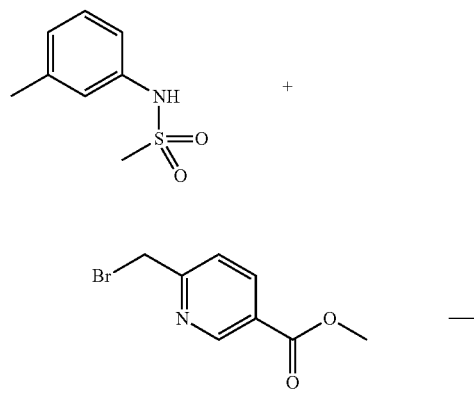

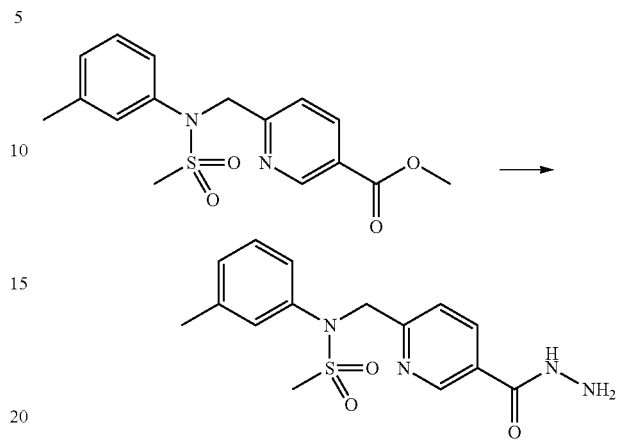

A solution of methyl 6-(bromomethyl)nicotinate (0.196 g, 0.850 mmol) and potassium iodide (0.027 g, 0.162 mmol) in N,N-dimethylformide (3 mL) was stirred at the room temperature for 20 min, and mixed with N-(m-tolyl)methanesulfonamide (0.150 g, 0.810 mmol) and potassium carbonate (0.145 g, 1.053 mmol). The reaction mixture was stirred at the same temperature for additional 24 hr. Then, aqueous 0.1N-hydrochloric acid solution was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 12 g cartridge; ethyl acetate/hexane=0% to 50%) to give methyl 6-((N-(m-tolyl)methylsulfonamido)methyl)nicotinate as white solid (0.200 g, 73.9%).

[Step 2] N-((5-(hydrazinecarbonyl)pyridin-2-yl)methyl)-N-(m-tolyl)methanesulfonamide A mixture of methyl 6-((N-(m-tolyl)methylsulfonamido)methyl)nicotinate (0.200 g, 0.598 mmol) and hydrazine monohydrate (0.087 mL, 1.794 mmol) in ethanol (3 mL) prepared at the ambient temperature was heated at reflux for 8 hr, cooled down to the ambient temperature, and concentrated under the reduced pressure to remove the solvent. Then, water was added to the concentrates, followed by extraction with dichloromethane. The organic layer was washed with aqueous saturated sodium chloride solution, dried with anhydrous MgSO$_4$, filtered, and concentrated in vacuo. The title compound was used without further purification (N-((5-(hydrazinecarbonyl)pyridin-2-yl)methyl)-N-(m-tolyl)methanesulfonamide, 0.190 g, 95.0%, white solid).

[Step 3] Compound 11355

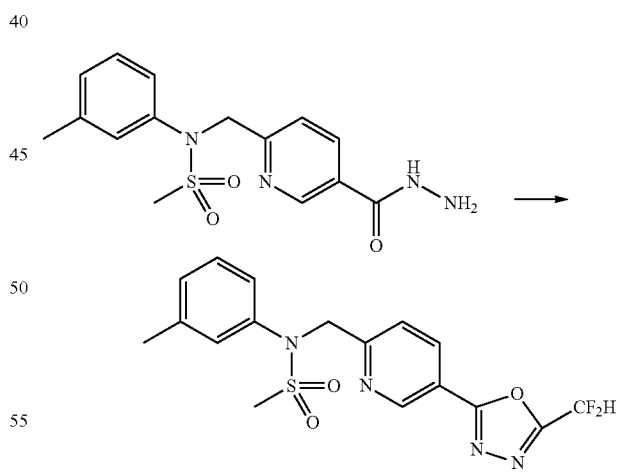

Triethylamine (0.055 mL, 0.391 mmol) was added to a solution of N-((5-(hydrazinecarbonyl)pyridin-2-yl)methyl)-N-(m-tolyl)methanesulfonamide (0.065 g, 0.196 mmol) in tetrahydrofuran (2 mL) at the room temperature, and the mixture was stirred for 20 min at the same temperature. The reaction mixture was treated with 2,2-difluoroacetic anhydride (0.032 mL, 0.293 mmol), heated at reflux for 8 hr, and cooled down to the room temperature to terminate the reaction. Then, water was added to the reaction mixture, followed by extraction with dichloromethane. The bi-phasic mixture was passed through a plastic frit to remove the solid residues and the aqueous layer, and the organic layer collected was concentrated in vacuo. The residue was chromatographed (SiO$_2$, 4 g cartridge; ethyl acetate/hexane=0% to 50%) to give N-((5-(5-(difluoromethyl)-1,3,4-oxadiazol-2-yl)pyridin-2-yl)methyl)-N-(m-tolyl)methane sulfonamide as white solid (0.048 g, 62.2%).

$^1$H NMR (400 MHz, CDCl$_3$) δ 9.23 (d, J=2.0 Hz, 1H), 8.39 (dd, J=8.3, 2.2 Hz, 1H), 7.75 (d, J=8.3 Hz, 1H), 7.28~7.18 (m, 3H), 6.95 (t, J=51.6 Hz, 1H), 5.14 (s, 2H), 3.07 (s, 3H); LRMS (ES) m/z 394.99 (M$^+$+1).

EXAMPLE 99

Compound 11366: N-(3-bromophenyl)-N-((5-(5-(difluoromethyl)-1,3,4-oxadiazol-2-yl)pyridin-2-yl)methyl)ethanesulfonamide

[Step 1] N-(3-bromophenyl)ethanesulfonamide

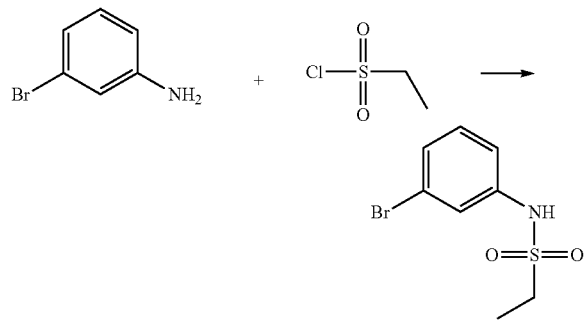

A solution of 3-bromoaniline (3.000 g, 17.439 mmol), pyridine (1.545 mL, 19.183 mmol) and ethanesulfonyl chloride (2.148 mL, 22.670 mmol) in dichloromethane (100 mL) was stirred at the room temperature for 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 40%) to give N-(3-bromophenyl)ethanesulfonamide as colorless oil (4.000 g, 86.8%).

[Step 2] methyl 6-((N-(3-bromophenyl)ethylsulfonamido)methyl)nicotinate

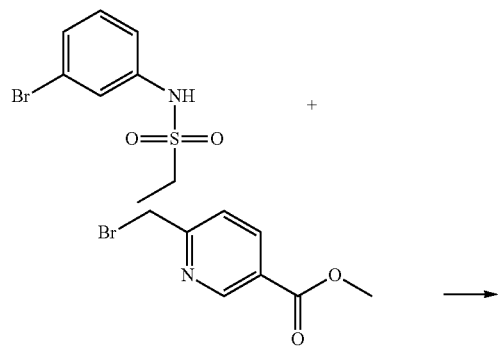

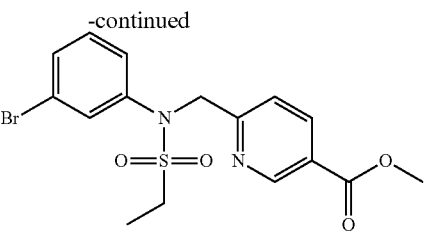

A solution of methyl 6-(bromomethyl)nicotinate (0.479 g, 2.082 mmol) and potassium iodide (0.063 g, 0.379 mmol) in N,N-dimethylformide (30 mL) was stirred at the room temperature for 30 min, and mixed with N-(3-bromophenyl)ethanesulfonamide (0.500 g, 1.893 mmol) and potassium carbonate (0.392 g, 2.839 mmol). The reaction mixture was stirred at 50° C. for additional 12 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 6-((N-(3-bromophenyl)ethylsulfonamido)methyl)nicotinate as yellow solid (0.582 g, 74.4%).

[Step 3] N-(3-bromophenyl)-N-((5-(hydrazinecarbonyl)pyridin-2-yl)methyl)methanesulfonamide

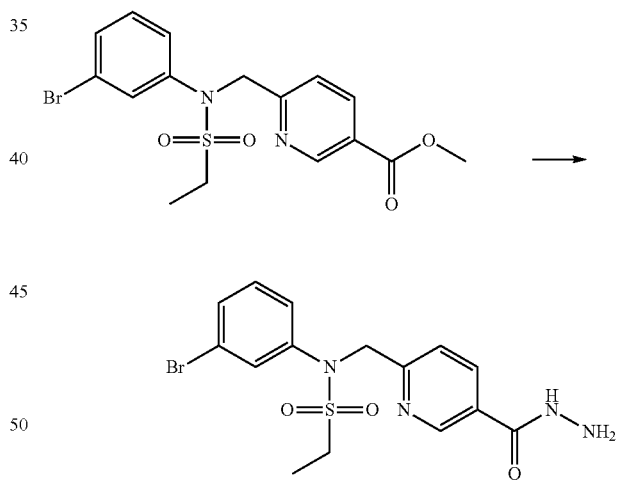

A mixture of methyl 6-((N-(3-bromophenyl)methylsulfonamido)methyl)nicotinate (0.582 g, 1.458 mmol) and hydrazine hydrate (0.730 g, 14.577 mmol) in ethanol (40 mL) was heated at reflux for 5 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-bromophenyl)-N-((5-(hydrazinecarbonyl)pyridin-2-yl)methyl)methanesulfonamide, 0.500 g, 85.9%, colorless oil).

[Step 4] Compound 11366

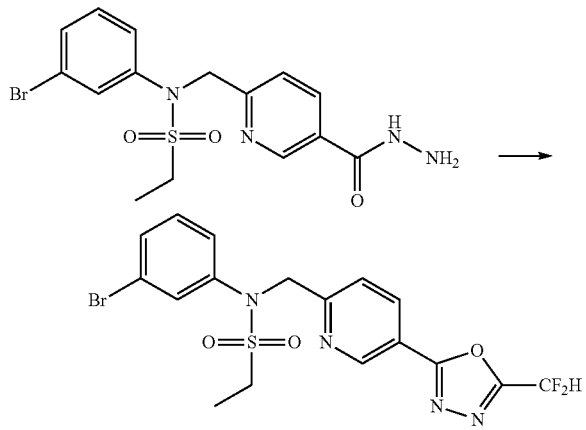

A mixture of N-(3-bromophenyl)-N-((5-(hydrazinecarbonyl)pyridin-2-yl)methyl)methanesulfonamide (0.500 g, 1.210 mmol), triethylamine (0.843 mL, 6.049 mmol) and difluoroacetic anhydride (0.329 mL, 3.025 mmol) in tetrahydrofuran (10 mL) prepared at ambient temperature was heated at reflux for 12 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 40%) to give N-(3-bromophenyl)-N-((5-(5-(difluoromethyl)-1,3,4-oxadiazol-2-yl)pyridin-2-yl)methyl)ethanesulfonamide as colorless oil (0.430 g, 74.8%).

$^1$H NMR (400 MHz, CDCl$_3$) δ 9.25 (d, 1H, J=1.8 Hz), 8.40 (dd, 1H, J=8.2, 2.3 Hz), 7.70 (d, 1H, J=8.3 Hz), 7.63-7.62 (m, 1H), 7.43-7.37 (m, 2H), 7.24-7.20 (m, 1H), 7.07 (s, 0.2H), 6.95 (s, 0.5H), 6.82 (s, 0.8H), 5.16 (s, 2H), 3.21 (q, 2H, J=7.4 Hz), 1.48-1.41 (m, 3H); LRMS (ES) m/z 473.0 (M$^+$+1).

EXAMPLE 100

Compound 11367: N-((5-(5-(difluoromethyl)-1,3,4-oxadiazol-2-yl)pyridin-2-yl)methyl)-1-methyl-N-phenylpiperidine-4-sulfonamide

[Step 1] tert-butyl 4-(N-phenylsulfamoyl)piperidine-1-carboxylate

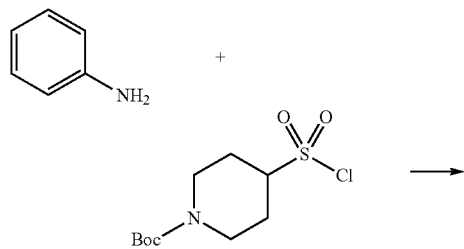

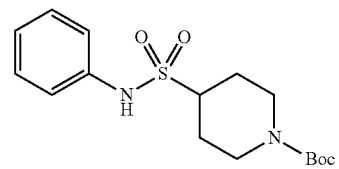

Triethylamine (1.946 mL, 13.959 mmol) was added to a solution of aniline (0.980 mL, 10.738 mmol) in dichloromethane (10 mL) at the room temperature, and the mixture was stirred at the same temperature for 20 min. The reaction mixture was treated with tert-butyl 4-(chlorosulfonyl)piperidine-1-carboxylate (3.199 g, 11.275 mmol), and stirred for additional 16 hr at the same temperature. Then, aqueous 0.1N-hydrochloric acid solution was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (tert-butyl 4-(N-phenylsulfamoyl)piperidine-1-carboxylate, 3.600 g, 98.5%, white solid).

[Step 2] methyl 6-(((1-(tert-butoxycarbonyl)-N-phenylpiperidine)-4-sulfonamido)methyl)nicotinate

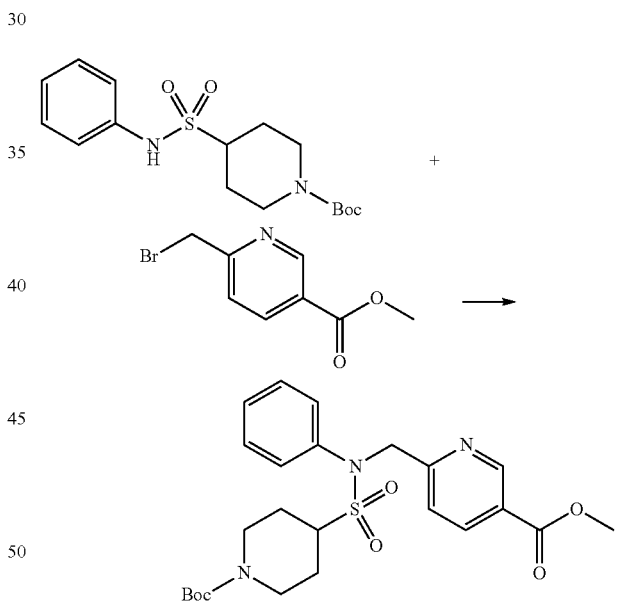

A solution of methyl 6-(bromomethyl)nicotinate (0.710 g, 3.084 mmol) and potassium iodide (0.098 g, 0.587 mmol) in N,N-dimethylformide (6 mL) was stirred at the room temperature for 30 min, and mixed with tert-butyl 4-(N-phenylsulfamoyl)piperidine-1-carboxylate (1.000 g, 2.937 mmol) and potassium carbonate (0.487 g, 3.525 mmol). The reaction mixture was stirred at the same temperature for additional 24 hr. The reaction mixture was diluted with water, and stirred at the ambient temperature. The resulting precipitates were collected by filtration, washed by water solution, and dried to give methyl 6-(((1-(tert-butoxycarbonyl)-N-phenylpiperidine)-4-sulfonamido)methyl)nicotinate as brown solid (1.350 g, 93.9%).

359

[Step 3] methyl 6-((N-phenylpiperidine-4-sulfonamido)methyl)nicotinate hydrochloride

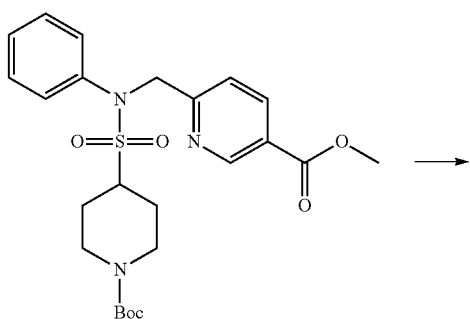

A solution of methyl 6-(((1-(tert-butoxycarbonyl)-N-phenylpiperidine)-4-sulfonamido)methyl)nicotinate (0.436 g, 0.891 mmol) and hydrochloric acid (4.00 M solution in 1,4-dioxane, 0.891 mL, 3.562 mmol) in dichloromethane (10 mL) was stirred at the room temperature for 1 hr, and concentrated under the reduced pressure to remove the solvent. The title compound was used without further purification (methyl 6-((N-phenylpiperidine-4-sulfonamido)methyl)nicotinate hydrochloride, 0.350 g, 92.3%, yellow solid).

[Step 4] methyl 6-(((1-methyl-N-phenylpiperidine)-4-sulfonamido)methyl)nicotinate

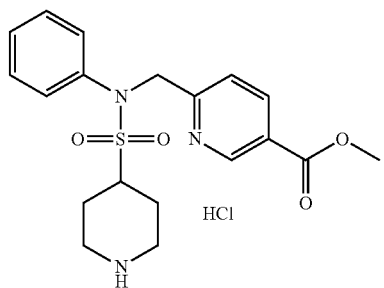

360

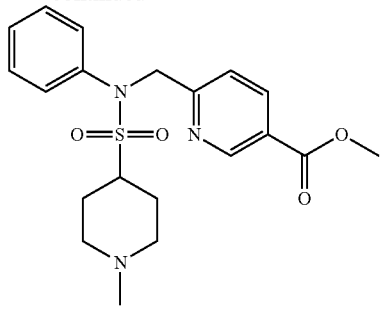

Acetic acid (0.032 mL, 0.563 mmol) was added to a solution of methyl 6-((N-phenylpiperidine-4-sulfonamido)methyl)nicotinate hydrochloride (0.200 g, 0.470 mmol) and formaldehyde (0.141 g, 4.696 mmol) in dichloromethane (10 mL) at the room temperature, and the mixture was stirred at the same temperature for 30 min. The reaction mixture was treated with sodium triacetoxyborohydride (0.199 g, 0.939 mmol), and stirred for additional 12 hr at the same temperature. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; ethyl acetate/hexane=0% to 40%) to give methyl 6-(((1-methyl-N-phenylpiperidine)-4-sulfonamido)methyl)nicotinate as yellow oil (0.142 g, 74.9%).

[Step 5] N-((5-(hydrazinecarbonyl)pyridin-2-yl)methyl)-1-methyl-N-phenylpiperidine-4-sulfonamide

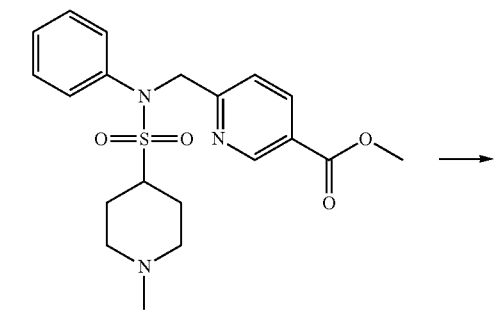

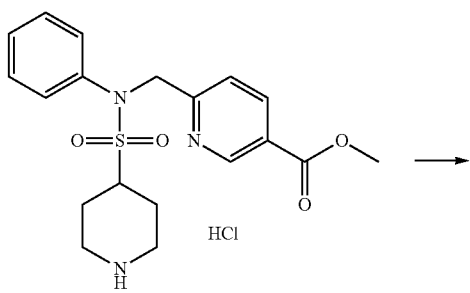

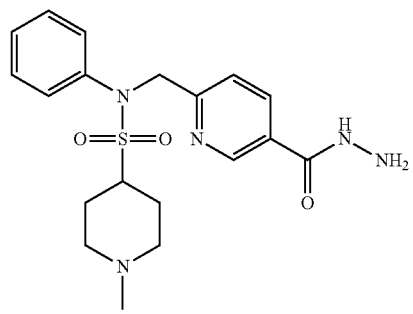

A mixture of methyl 6-(((1-methyl-N-phenylpiperidine)-4-sulfonamido)methyl)nicotinate (0.142 g, 0.352 mmol) and hydrazine monohydrate (0.171 mL, 3.519 mmol) in ethanol (10 mL) prepared at the ambient temperature was heated at reflux for 12 hr, and cooled down to the ambient temperature, and concentrated under the reduced pressure to remove the solvent. The title compound was used without further purification (N-((5-(hydrazinecarbonyl)pyridin-2-yl)methyl)-1-methyl-N-phenylpiperidine-4-sulfonamide, 0.130 g, 91.5%, yellow solid).

[Step 6] Compound 11367

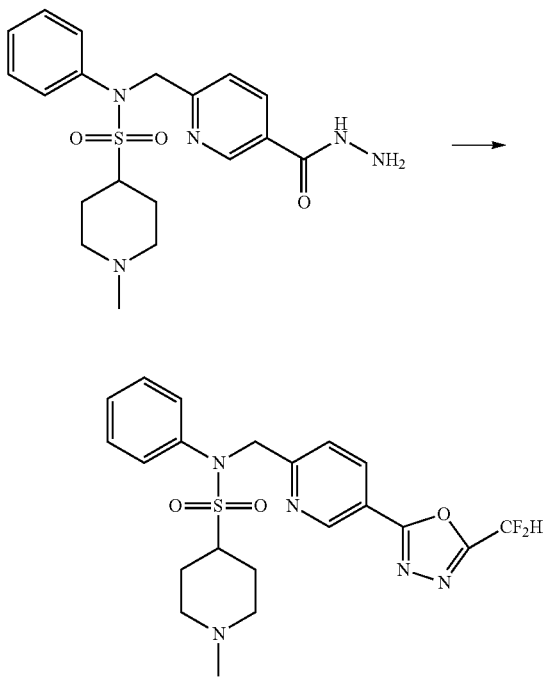

A mixture of N-((5-(hydrazinecarbonyl)pyridin-2-yl)methyl)-1-methyl-N-phenylpiperidine-4-sulfonamide (0.130 g, 0.322 mmol), difluoroacetic anhydride (0.062 g, 0.354 mmol) and triethylamine (0.054 mL, 0.387 mmol) in tetrahydrofuran (10 mL) prepared at the ambient temperature was heated at reflux for 5 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-((5-(5-(difluoromethyl)-1,3,4-oxadiazol-2-yl)pyridin-2-yl)methyl)-1-methyl-N-phenylpiperidine-4-sulfonamide as yellow solid (0.094 g, 62.9%).

$^1$H NMR (400 MHz, CDCl$_3$) δ 9.29-9.20 (m, 1H), 8.41-8.37 (m, 1H), 7.60-7.47 (m, 2H), 7.36-7.29 (m, 4H), 7.08 (s, 0.2H), 6.95 (s, 0.5H), 6.82 (s, 0.2H), 5.14 (s, 2H), 3.68-3.65 (m, 2H), 3.45-3.35 (m, 3H), 3.17-3.10 (m, 2H), 2.84 (s, 3H), 2.64-2.49 (m, 2H); LRMS (ES) m/z 464.4 (M$^+$+1).

EXAMPLE 101

Compound 11368: N-((5-(5-(difluoromethyl)-1,3,4-oxadiazol-2-yl)pyridin-2-yl)methyl)-1-ethyl-N-phenylpiperidine-4-sulfonamide

[Step 1] methyl 6-(((1-ethyl-N-phenylpiperidine)-4-sulfonamido)methyl)nicotinate

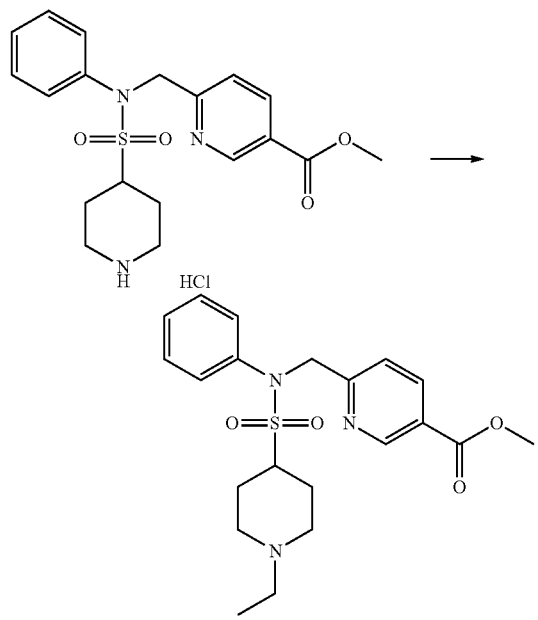

Acetic acid (0.032 mL, 0.563 mmol) was added to a solution of methyl 6-((N-phenylpiperidine-4-sulfonamido)methyl)nicotinate hydrochloride (0.200 g, 0.470 mmol) and acetaldehyde (0.207 g, 4.696 mmol) in dichloromethane (10 mL) at the room temperature, and the mixture was stirred at the same temperature for 30 min. The reaction mixture was treated with sodium triacetoxyborohydride (0.199 g, 0.939 mmol), and stirred for additional 12 hr at the same temperature. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; ethyl acetate/hexane=0% to 50%) to give methyl 6-(((1-ethyl-N-phenylpiperidine)-4-sulfonamido)methyl)nicotinate as yellow oil (0.139 g, 70.9%).

[Step 2] 1-ethyl-N-((5-(hydrazinecarbonyl)pyridin-2-yl)methyl)-N-phenylpiperidine-4-sulfonamide

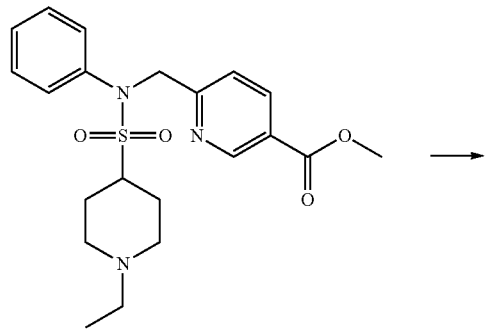

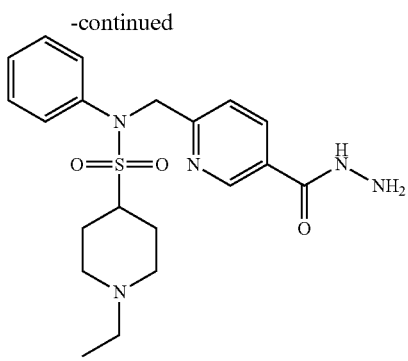

A mixture of methyl 6-(((1-ethyl-N-phenylpiperidine)-4-sulfonamido)methyl)nicotinate (0.139 g, 0.333 mmol) and hydrazine monohydrate (0.162 mL, 3.329 mmol) in ethanol (10 mL) prepared at the ambient temperature was heated at reflux for 12 hr, cooled down to the ambient temperature, and concentrated under the reduced pressure to remove the solvent. The title compound was used without further purification (1-ethyl-N-((5-(hydrazinecarbonyl)pyridin-2-yl)methyl)-N-phenylpiperidine-4-sulfonamide, 0.120 g, 86.3%, white solid).

[Step 3] Compound 11368

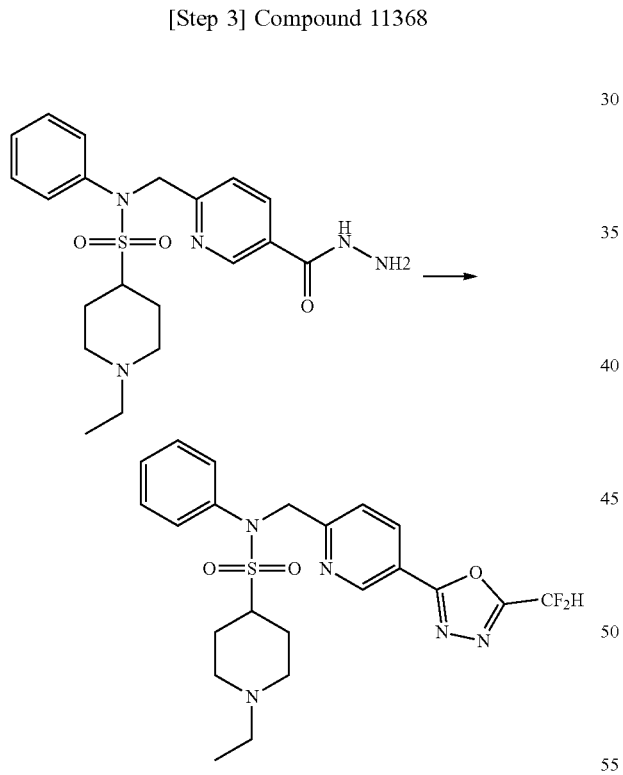

A mixture of 1-ethyl-N-((5-(hydrazinecarbonyl)pyridin-2-yl)methyl)-N-phenylpiperidine-4-sulfonamide (0.120 g, 0.287 mmol), difluoroacetic anhydride (0.055 g, 0.316 mmol) and triethylamine (0.048 mL, 0.345 mmol) in tetrahydrofuran (10 mL) prepared at the ambient temperature was heated at reflux for 5 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-((5-(5-(difluoromethyl)-1,3,4-oxadiazol-2-yl)pyridin-2-yl)methyl)-1-ethyl-N-phenylpiperidine-4-sulfonamide as white solid (0.082 g, 59.7%).

$^1$H NMR (400 MHz, CDCl$_3$) δ 9.30-9.20 (m, 1H), 8.40-8.34 (m, 1H), 7.55-7.54 (m, 1H), 7.47-7.45 (m, 1H), 7.41-7.29 (m, 4H), 7.08 (s, 0.2H), 6.95 (s, 0.5H), 6.82 (s, 0.2H), 5.14 (s, 2H), 3.80-3.65 (m, 2H), 3.45-3.31 (m, 2H), 3.29-3.07 (m, 3H), 2.70-2.61 (m, 2H), 2.55-2.50 (m, 2H), 1.41-1.26 (m, 3H); LRMS (ES) m/z 478.4 (M$^+$+1).

EXAMPLE 102

Compound 11372: N-(4-(5-(difluoromethyl)-1,3,4-oxadiazol-2-yl)-2-fluorobenzyl)-1-methyl-N-phenylpiperidine-4-sulfonamide

[Step 1] tert-butyl 4-(N-(2-fluoro-4-(methoxycarbonyl)benzyl)-N-phenylsulfamoyl)piperidine-1-carboxylate

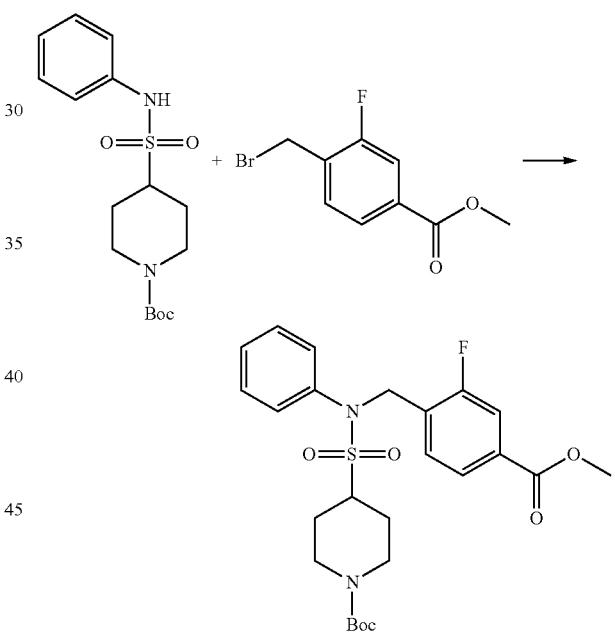

A solution of methyl 4-(bromomethyl)-3-fluorobenzoate (0.610 g, 2.467 mmol) and potassium iodide (0.039 g, 0.235 mmol) in N,N-dimethylformamide (8 mL) was stirred at the room temperature for 30 min, and mixed with tert-butyl 4-(N-phenylsulfamoyl)piperidine-1-carboxylate (0.800 g, 2.350 mmol) and potassium carbonate (0.422 g, 3.055 mmol). The reaction mixture was stirred at the same temperature for additional 24 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 70%) to give tert-butyl 4-(N-(2-fluoro-4-(methoxycarbonyl)benzyl)-N-phenylsulfamoyl)piperidine-1-carboxylate as white solid (1.100 g, 92.4%).

[Step 2] methyl 3-fluoro-4-((N-phenylpiperidine-4-sulfonamido)methyl)benzoate hydrochloride

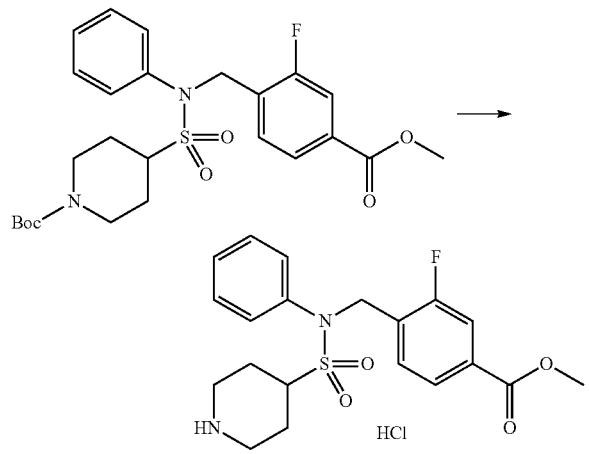

A solution of tert-butyl 4-(N-(2-fluoro-4-(methoxycarbonyl)benzyl)-N-phenylsulfamoyl)piperidine-1-carboxylate (1.100 g, 2.171 mmol) in dichloromethane (10 mL) was mixed at the room temperature with hydrochloric acid (0.158 g, 4.343 mmol). The reaction mixture was stirred at the same temperature for 5 hr. The precipitates were collected by filtration, washed by dichloromethane, and dried to give methyl 3-fluoro-4-((N-phenylpiperidine-4-sulfonamido)methyl)benzoate hydrochloride as white solid (0.850 g, 88.4%).

[Step 3] methyl 3-fluoro-4-(((1-methyl-N-phenylpiperidine)-4-sulfonamido)methyl)benzoate

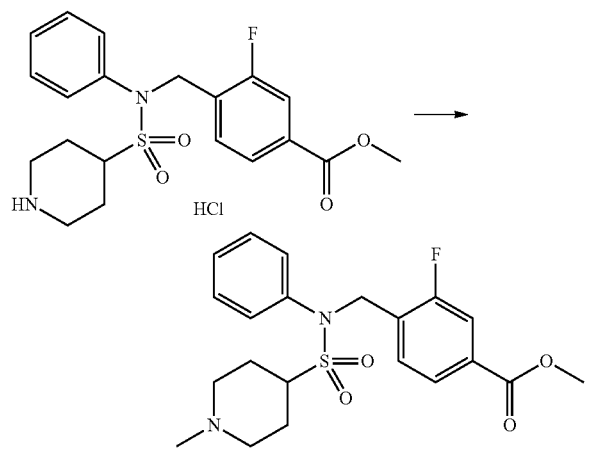

A solution of methyl 3-fluoro-4-((N-phenylpiperidine-4-sulfonamido)methyl)benzoate hydrochloride (0.100 g, 0.226 mmol), formaldehyde (0.034 g, 1.129 mmol) and acetic acid (0.006 mL, 0.113 mmol) in methanol (2 mL) was stirred at the room temperature for 20 min, and mixed with sodium cyanoborohydride (0.043 g, 0.677 mmol). The reaction mixture was stirred at the same temperature for additional 5 hr, and concentrated under the reduced pressure to remove the solvent. Then, saturated aqueous sodium bicarbonate solution was added to the concentrate, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give methyl 3-fluoro-4-(((1-methyl-N-phenylpiperidine)-4-sulfonamido)methyl)benzoate as white solid (0.080 g, 84.3%).

[Step 4] N-(2-fluoro-4-(hydrazinecarbonyl)benzyl)-1-methyl-N-phenylpiperidine-4-sulfonamide

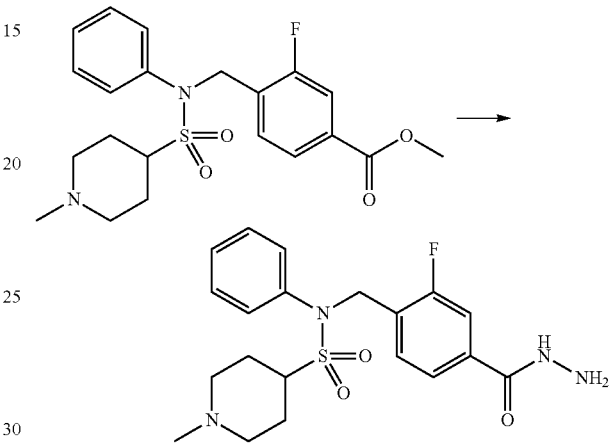

A mixture of methyl 3-fluoro-4-(((1-methyl-N-phenylpiperidine)-4-sulfonamido)methyl)benzoate (0.080 g, 0.190 mmol) and hydrazine monohydrate (0.028 mL, 0.571 mmol) in ethanol (3 mL) prepared at the ambient temperature was heated at reflux for 16 hr, cooled down to the ambient temperature, and concentrated under the reduced pressure to remove the solvent. The residue was diluted with aqueous saturated sodium bicarbonate solution and stirred. The resulting precipitates were collected by filtration, washed by water, and dried to give N-(2-fluoro-4-(hydrazinecarbonyl)benzyl)-1-methyl-N-phenylpiperidine-4-sulfonamide as white solid (0.075 g, 93.8%).

[Step 5] Compound 11372

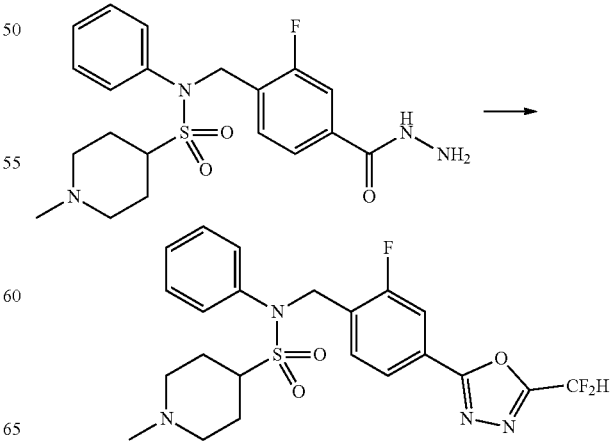

Triethylamine (0.046 mL, 0.327 mmol) was added to solution of N-(2-fluoro-4-(hydrazinecarbonyl)benzyl)-1-methyl-N-phenylpiperidine-4-sulfonamide (0.069 g, 0.164 mmol) in tetrahydrofuran (2 mL) at the room temperature, and the mixture was stirred for 10 min at the same temperature. The reaction mixture was treated with 2,2-difluoroacetic anhydride (0.027 mL, 0.245 mmol), heated at reflux for 5 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-1-methyl-N-phenylpiperidine-4-sulfonamide as white solid (0.055 g, 70.0%).

$^1$H NMR (400 MHz, CDCl$_3$) δ 7.85 (dd, 1H, J=8.0, 1.6 Hz), 7.69 (d, 1H, J=16.4 Hz), 7.62 (t, 1H, J=7.4 Hz), 7.37-7.26 (m, 5H), 7.02 (s, 0.25H), 6.89 (s, 0.5H), 6.76 (s, 0.25H), 5.06 (s, 2H), 3.19 (m, 3H), 2.51-2.42 (m, 4H), 2.28-2.04 (m, 5H); LRMS (ES) m/z 481.21 (M$^+$+1).

EXAMPLE 103

Compound 11373: N-(4-(5-(difluoromethyl)-1,3,4-oxadiazol-2-yl)-2-fluorobenzyl)-1-ethyl-N-phenylpiperidine-4-sulfonamide

[Step 1] methyl 4-(((1-ethyl-N-phenylpiperidine)-4-sulfonamido)methyl)-3-fluorobenzoate

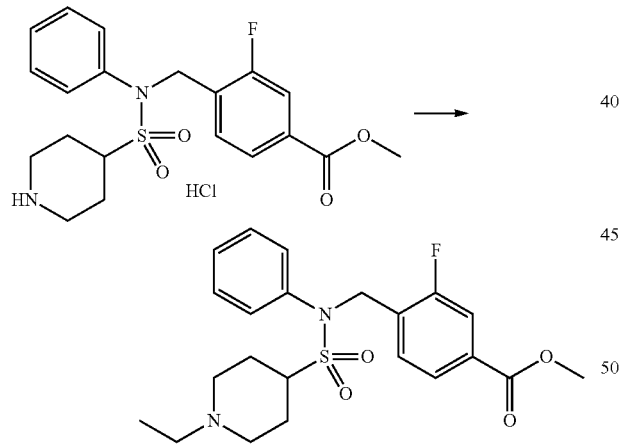

A solution of methyl 3-fluoro-4-((N-phenylpiperidine-4-sulfonamido)methyl)benzoate hydrochloride (0.100 g, 0.226 mmol) and acetaldehyde (0.038 mL, 0.677 mmol) in methanol (2 mL) was stirred at the room temperature for 20 min, and mixed with sodium cyanoborohydride (0.043 g, 0.677 mmol). The reaction mixture was stirred at the same temperature for additional 5 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 100%) to give methyl 4-(((1-ethyl-N-phenylpiperidine)-4-sulfonamido)methyl)-3-fluorobenzoate as white solid (0.080 g, 81.5%).

[Step 2] 1-ethyl-N-(2-fluoro-4-(hydrazinecarbonyl)benzyl)-N-phenylpiperidine-4-sulfonamide

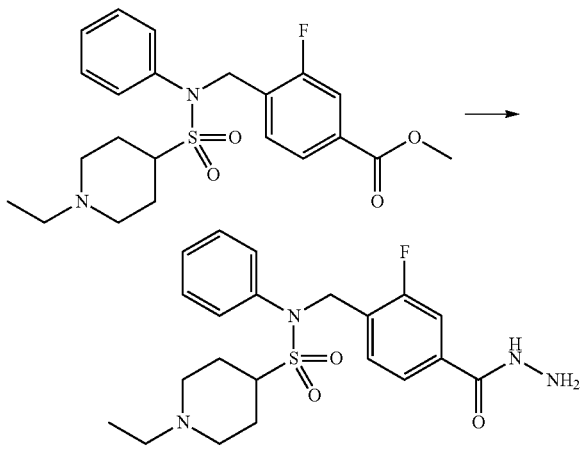

A mixture of methyl 4-(((1-ethyl-N-phenylpiperidine)-4-sulfonamido)methyl)-3-fluorobenzoate (0.080 g, 0.184 mmol) and hydrazine monohydrate (0.045 mL, 0.921 mmol) in ethanol (3 mL) prepared at the ambient temperature was heated at reflux for 18 hr, cooled down to the ambient temperature, and concentrated under the reduced pressure to remove the solvent. The residue was diluted with aqueous saturated sodium bicarbonate solution and stirred. The resulting precipitates were collected by filtration, washed by water, and dried to give 1-ethyl-N-(2-fluoro-4-(hydrazinecarbonyl)benzyl)-N-phenylpiperidine-4-sulfonamide as white solid (0.070 g, 87.5%).

[Step 3] Compound 11373

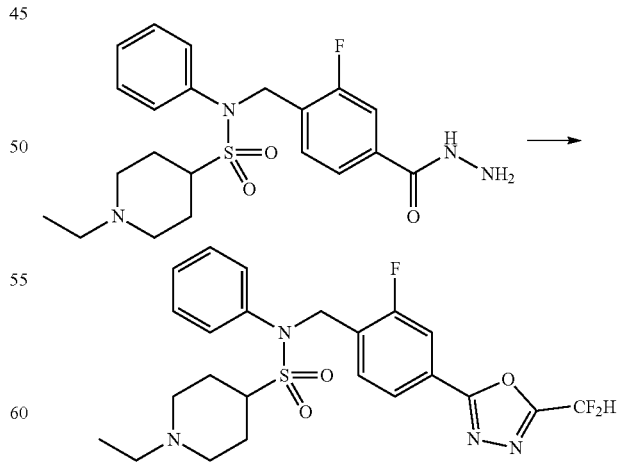

Triethylamine (0.040 mL, 0.289 mmol) was added to solution of 1-ethyl-N-(2-fluoro-4-(hydrazinecarbonyl)benzyl)-N-phenylpiperidine-4-sulfonamide (0.063 g, 0.145 mmol) in tetrahydrofuran (2 mL) at the room temperature, and the mixture was stirred for 10 min at the same temperature. The reaction mixture was treated with 2,2-difluoroacetic anhydride (0.024 mL, 0.217 mmol), heated at reflux for 5 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-1-ethyl-N-phenylpiperidine-4-sulfonamide as white solid (0.055 g, 77.0%).

$^1$H NMR (400 MHz, CDCl$_3$) δ 7.85 (dd, 1H, J=8.1, 1.6 Hz), 7.69 (dd, 1H, J=9.8, 1.4 Hz), 7.64 (t, 1H, J=6.7 Hz), 7.33-7.02 (m, 5H), 7.02 (s, 0.25H), 6.89 (s, 0.5H), 6.76 (s, 0.25H), 5.06 (s, 2H), 3.21 (m, 3H), 2.65 (m, 3H), 2.24 (m, 5H), 1.24 (m, 3H); LRMS (ES) m/z 495.18 (M$^+$+1).

EXAMPLE 104

Compound 11377, N-(4-(5-(difluoromethyl)-1,3,4-oxadiazol-2-yl)-2-fluorobenzyl)-1-(2-hydroxy-2-methylpropyl)-N-phenylpiperidine-4-sulfonamide

[Step 1] ethyl 3-fluoro-4-(((1-(2-hydroxy-2-methylpropyl)-N-phenylpiperidine)-4-sulfonamido)methyl)benzoate

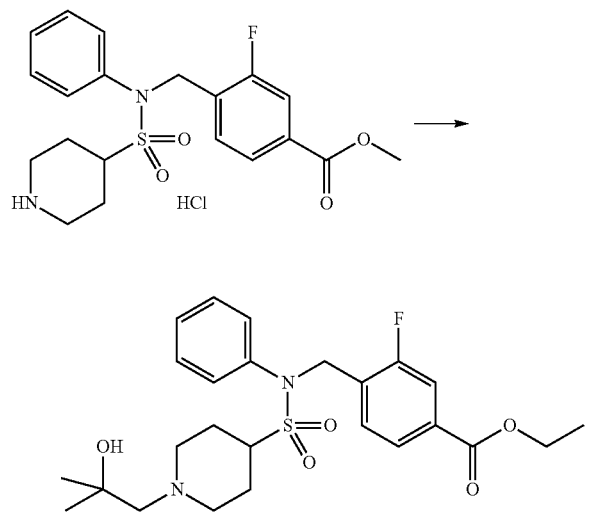

A mixture of methyl 3-fluoro-4-((N-phenylpiperidine-4-sulfonamido)methyl)benzoate hydrochloride (0.090 g, 0.203 mmol), 2,2-dimethyloxirane (0.073 g, 1.016 mmol) and potassium carbonate (0.056 g, 0.406 mmol) in ethanol (6 mL) was heated at 120° C. for 30 min under the microwaves. Then, the reaction mixture was concentrated under the reduced pressure to remove the solvent. The precipitates were collected by filtration, washed by water, and dried to give ethyl 3-fluoro-4-(((1-(2-hydroxy-2-methylpropyl)-N-phenylpiperidine)-4-sulfonamido)methyl)benzoate as white solid (0.080 g, 79.9%).

[Step 2] N-(2-fluoro-4-(hydrazinecarbonyl)benzyl)-1-(2-hydroxy-2-methylpropyl)-N-phenylpiperidine-4-sulfonamide


A mixture of ethyl 3-fluoro-4-(((1-(2-hydroxy-2-methylpropyl)-N-phenylpiperidine)-4-sulfonamido)methyl)benzoate (0.080 g, 0.162 mmol) and hydrazine monohydrate (0.039 mL, 0.812 mmol) in ethanol (2 mL) prepared at the ambient temperature was heated at reflux for 16 hr, cooled down to the ambient temperature, and concentrated under the reduced pressure to remove the solvent. The residue was diluted with aqueous saturated sodium bicarbonate solution and stirred. The resulting precipitates were collected by filtration, washed by water, and dried to give N-(2-fluoro-4-(hydrazinecarbonyl)benzyl)-1-(2-hydroxy-2-methylpropyl)-N-phenylpiperidine-4-sulfonamide as white solid (0.065 g, 83.6%).

[Step 3] Compound 11377

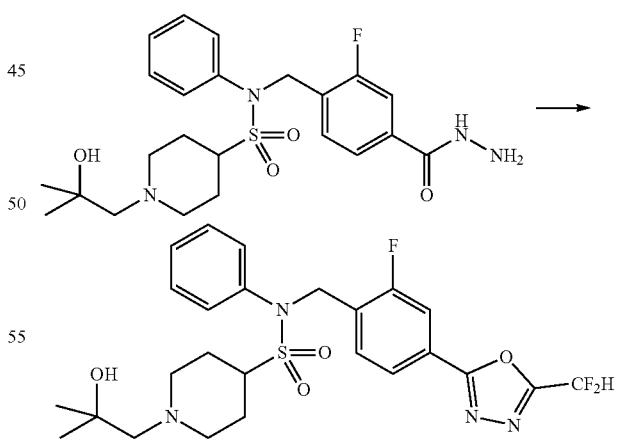

Triethylamine (0.025 mL, 0.180 mmol) was added to solution of N-(2-fluoro-4-(hydrazinecarbonyl)benzyl)-1-(2-hydroxy-2-methylpropyl)-N-phenylpiperidine-4-sulfonamide (0.043 g, 0.090 mmol) in tetrahydrofuran (3 mL) at the room temperature, and the mixture was stirred for 10 min at the same temperature. The reaction mixture was treated with 2,2-difluoroacetic anhydride (0.015 mL, 0.135 mmol), heated at reflux for 5 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 70%) to give N-(4-(5-(difluoromethyl)-1,3,4-oxadiazol-2-yl)-2-fluorobenzyl)-1-(2-hydroxy-2-methylpropyl)-N-phenylpiperidine-4-sulfonamide as white solid (0.015 g, 31.0%).

$^1$H NMR (400 MHz, CDCl$_3$) δ 7.85 (dd, 1H, J=8.0, 1.5 Hz), 7.70 (dd, 1H, J=9.9, 1.5 Hz), 7.63 (t, 1H, J=7.6 Hz), 7.35-7.27 (m, 5H), 7.02 (s, 0.25H), 6.89 (s, 0.5H), 6.76 (s, 0.25H), 5.05 (s, 2H), 3.24 (m, 2H), 3.14 (m, 1H), 2.63-2.54 (m, 4H), 2.23-2.16 (m, 4H), 1.25 (S, 6H); LRMS (ES) m/z 539.54 (M$^+$+1).

EXAMPLE 105

Compound 11386, N-(4-((4-acetylpiperazin-1-yl)methyl)phenyl)-N-((5-(5-(difluoromethyl)-1,3,4-oxadiazol-2-yl)pyridin-2-yl)methyl)ethanesulfonamide

[Step 1] tert-butyl 4-(4-nitrobenzyl)piperazine-1-carboxylate

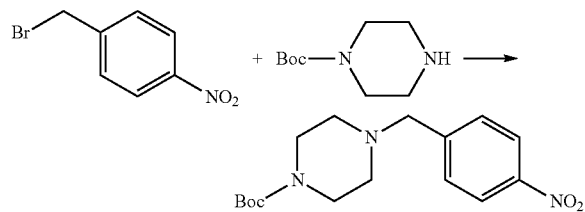

A solution of 1-(bromomethyl)-4-nitrobenzene (1.000 g, 4.629 mmol), N,N-diisopropylethylamine (1.209 mL, 6.943 mmol) and tert-butyl piperazine-1-carboxylate (0.948 g, 5.092 mmol) in acetonitrile (50 mL) was stirred at the room temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 20%) to give tert-butyl 4-(4-nitrobenzyl)piperazine-1-carboxylate as yellow oil (1.100 g, 73.9%).

[Step 2] tert-butyl 4-(4-aminobenzyl)piperazine-1-carboxylate

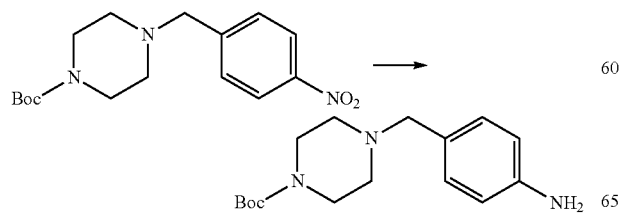

A solution of tert-butyl 4-(4-nitrobenzyl)piperazine-1-carboxylate (1.100 g, 3.423 mmol), ammonium chloride (0.915 g, 17.114 mmol) and Zn dust (1.119 g, 17.114 mmol) in tetrahydrofuran (20 mL)/water (20 mL) was stirred at the room temperature for 12 hr. The reaction mixture was filtered to remove solids. Then, water was added to the filtrate, followed by extraction with ethyl acetate. The organic layer was washed with aqueous saturated sodium chloride solution, dried with anhydrous MgSO$_4$, filtered, and concentrated in vacuo. The title compound was used without further purification (tert-butyl 4-(4-aminobenzyl)piperazine-1-carboxylate, 0.900 g, 90.2%, yellow solid).

[Step 3] tert-butyl 4-(4-(ethylsulfonamido)benzyl)piperazine-1-carboxylate

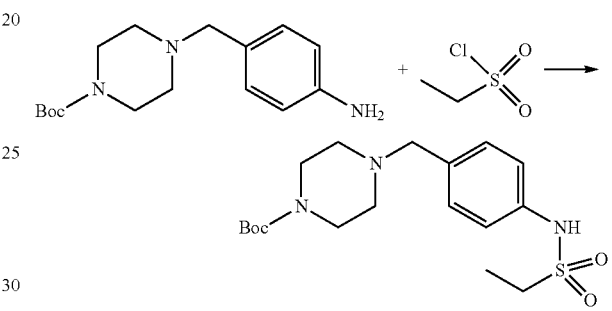

A solution of tert-butyl 4-(4-aminobenzyl)piperazine-1-carboxylate (0.900 g, 3.089 mmol), pyridine (0.299 mL, 3.706 mmol) and ethanesulfonyl chloride (0.477 g, 3.706 mmol) in dichloromethane (30 mL) was stirred at the room temperature for 12 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give tert-butyl 4-(4-(ethylsulfonamido)benzyl)piperazine-1-carboxylate as yellow solid (0.800 g, 67.5%).

[Step 4] tert-butyl 4-(4-(N-((5-(methoxycarbonyl)pyridin-2-yl)methyl)ethylsulfonamido)benzyl)piperazine-1-carboxylate

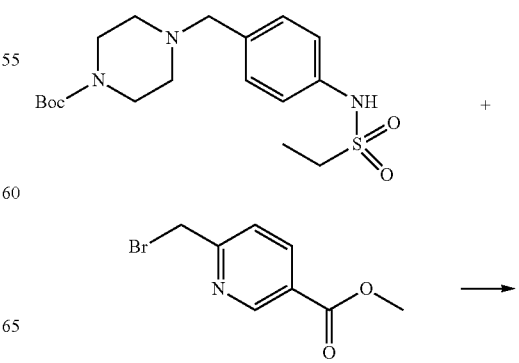

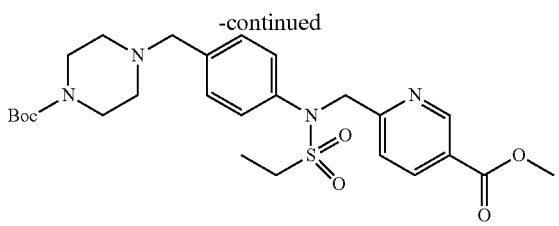

A solution of methyl 6-(bromomethyl)nicotinate (0.528 g, 2.295 mmol) and potassium iodide (0.069 g, 0.417 mmol) in N,N-dimethylformide (20 mL) was stirred at the room temperature for 30 min, and mixed with tert-butyl 4-(4-(ethylsulfonamido)benzyl)piperazine-1-carboxylate (0.800 g, 2.086 mmol) and potassium carbonate (0.432 g, 3.129 mmol). The reaction mixture was stirred at 50° C. for additional 12 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 40%) to give tert-butyl 4-(4-(N-((5-(methoxycarbonyl)pyridin-2-yl)methyl)ethylsulfonamido)benzyl)piperazine-1-carboxylate as yellow solid (0.623 g, 56.1%).

[Step 5] methyl 6-((N-(4-(piperazin-1-ylmethyl)phenyl)ethylsulfonamido)methyl)nicotinate hydrochloride

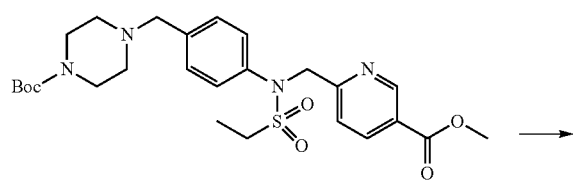

A solution of tert-butyl 4-(4-(N-((5-(methoxycarbonyl)pyridin-2-yl)methyl)ethylsulfonamido)benzyl)piperazine-1-carboxylate (0.623 g, 1.170 mmol) and hydrochloric acid (4.00 M solution in 1,4-dioxane, 1.170 mL, 4.678 mmol) in dichloromethane (30 mL) was stirred at the room temperature for 5 hr. The reaction mixture was concentrated under the reduced pressure to remove the solvent, and then, the title compound was used without further purification (methyl 6-((N-(4-(piperazin-1-ylmethyl)phenyl)ethylsulfonamido)methyl)nicotinate hydrochloride, 0.500 g, 91.2%, yellow solid).

[Step 6] methyl 6-((N-(4-((4-acetylpiperazin-1-yl)methyl)phenyl)ethylsulfonamido)methyl)nicotinate

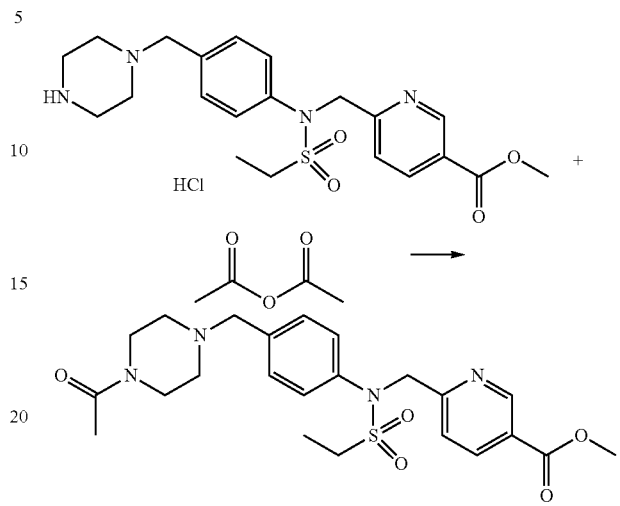

A solution of methyl 6-((N-(4-(piperazin-1-ylmethyl)phenyl)ethylsulfonamido)methyl)nicotinate hydrochloride (0.150 g, 0.320 mmol), triethylamine (0.067 mL, 0.480 mmol) and acetic anhydride (0.042 g, 0.416 mmol) in dichloromethane (5 mL) was stirred at the room temperature for 5 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 12 g cartridge; methanol/dichloromethane=0% to 5%) to give methyl 6-((N-(4-((4-acetylpiperazin-1-yl)methyl)phenyl)ethylsulfonamido)methyl)nicotinate as yellow oil (0.090 g, 59.3%).

[Step 7] N-(4-((4-acetylpiperazin-1-yl)methyl)phenyl)-N-((5-(hydrazinecarbonyl)pyridin-2-yl)methyl)ethanesulfonamide

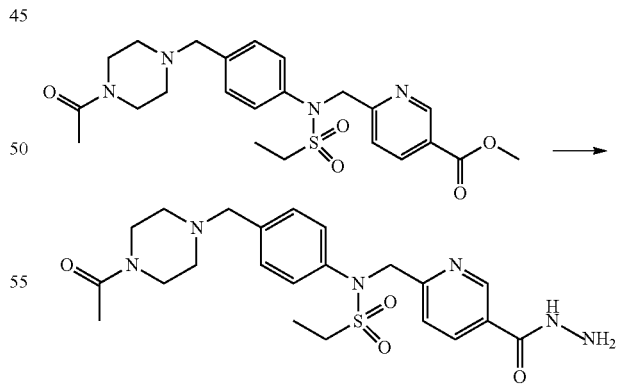

A solution of methyl 6-((N-(4-((4-acetylpiperazin-1-yl)methyl)phenyl)ethylsulfonamido)methyl)nicotinate (0.090 g, 0.190 mmol) and hydrazine hydrate (0.095 g, 1.896 mmol) in ethanol (5 mL) was stirred at 90° C. for 12 hr, and cooled down to the room temperature to terminate the reaction. Then, water was added to the reaction mixture, followed by extraction with dichloromethane. The organic layer was washed with aqueous saturated sodium bicarbonate solution, dried with anhydrous MgSO₄, filtered, and concentrated in vacuo. The title compound was used without further purification (N-(4-((4-acetylpiperazin-1-yl)methyl)phenyl)-N-((5-(hydrazinecarbonyl)pyridin-2-yl)methyl)ethanesulfonamide, 0.071 g, 78.9%, white solid).

[Step 8] Compound 11386

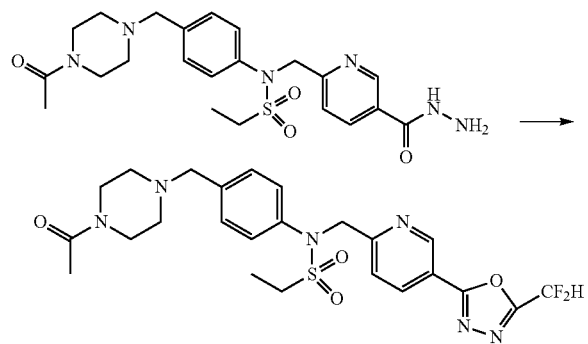

A mixture of N-(4-((4-acetylpiperazin-1-yl)methyl)phenyl)-N-((5-(hydrazinecarbonyl)pyridin-2-yl)methyl)ethanesulfonamide (0.072 g, 0.152 mmol), triethylamine (0.085 mL, 0.607 mmol) and 2,2-difluoroacetic anhydride (0.033 mL, 0.303 mmol) in tetrahydrofuran (10 mL) prepared at the room temperature was heated at reflux for 5 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give N-(4-((4-acetylpiperazin-1-yl)methyl)phenyl)-N-((5-(5-(difluoromethyl)-1,3,4-oxadiazol-2-yl)pyridin-2-yl)methyl)ethanesulfonamide as yellow solid (0.026 g, 32.1%).
$^1$H NMR (400 MHz, CDCl₃) δ 9.23 (dd, 1H, J=2.2, 0.9 Hz), 8.39 (dd, 1H, J=8.2, 2.2 Hz), 7.77 (d, 1H, J=8.3 Hz), 7.39 (s, 4H), 6.95 (m, 1H), 5.18 (s, 2H), 3.62 (s, 3H), 3.50 (s, 3H), 3.22 (q, 2H, J=7.4 Hz), 2.43 (s, 4H), 2.09 (s, 3H), 1.47 (t, 3H, J=7.4 Hz); LRMS (ES) m/z 535.34 (M⁺+1).

EXAMPLE 106

Compound 11387, N-((5-(5-(difluoromethyl)-1,3,4-oxadiazol-2-yl)pyridin-2-yl)methyl)-N-(4-((4-(methylsulfonyl)piperazin-1-yl)methyl)phenyl)ethanesulfonamide

[Step 1] methyl 6-((N-(4-((4-(methylsulfonyl)piperazin-1-yl)methyl)phenyl)ethylsulfonamido)methyl)nicotinate

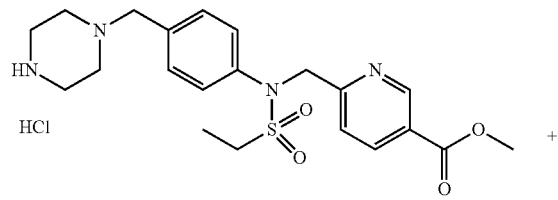

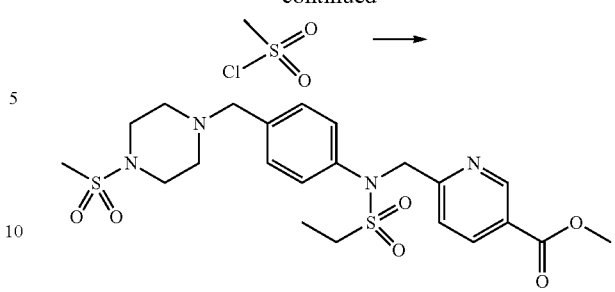

A solution of methyl 6-((N-(4-(piperazin-1-ylmethyl)phenyl)ethylsulfonamido)methyl)nicotinate hydrochloride (0.150 g, 0.320 mmol), triethylamine (0.067 mL, 0.480 mmol) and methanesulfonyl chloride (0.032 mL, 0.416 mmol) in dichloromethane (5 mL) was stirred at the room temperature for 5 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 12 g cartridge; methanol/dichloromethane=0% to 5%) to give methyl 6-((N-(4-((4-(methylsulfonyl)piperazin-1-yl)methyl)phenyl)ethylsulfonamido)methyl)nicotinate as yellow oil (0.094 g, 57.6%).

[Step 2] N-((5-(hydrazinecarbonyl)pyridin-2-yl)methyl)-N-(4-((4-(methylsulfonyl)piperazin-1-yl)methyl)phenyl)ethanesulfonamide

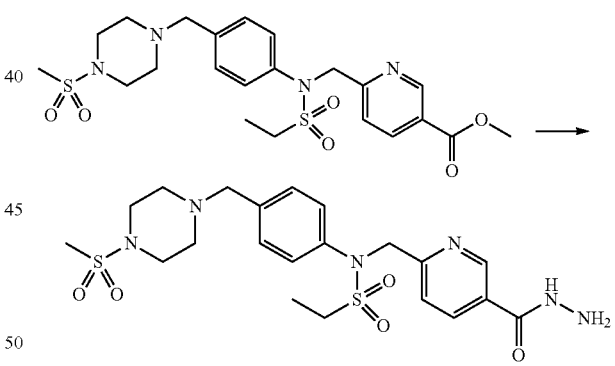

A solution of methyl 6-((N-(4-((4-(methylsulfonyl)piperazin-1-yl)methyl)phenyl)ethylsulfonamido)methyl)nicotinate (0.094 g, 0.184 mmol) and hydrazine hydrate (0.092 g, 1.841 mmol) in ethanol (5 mL) was stirred at 90° C. for 12 hr, and cooled down to the room temperature to terminate the reaction. Then, water was added to the reaction mixture, followed by extraction with dichloromethane. The organic layer was washed with aqueous saturated sodium bicarbonate solution, dried with anhydrous MgSO₄, filtered, and concentrated in vacuo. The title compound was used without further purification (N-((5-(hydrazinecarbonyl)pyridin-2-yl)methyl)-N-(4-((4-(methylsulfonyl)piperazin-1-yl)methyl)phenyl)ethanesulfonamide, 0.069 g, 73.4%, white solid).

[Step 3] Compound 11387

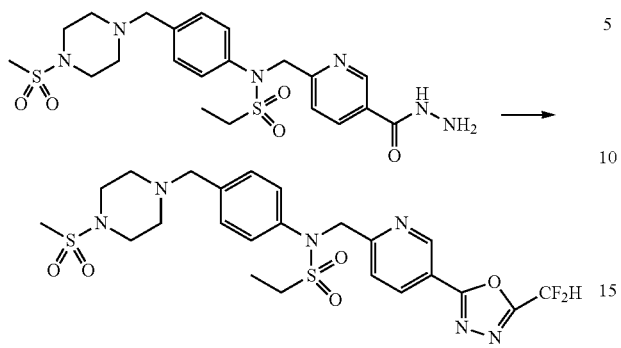

A mixture of N-((5-(hydrazinecarbonyl)pyridin-2-yl)methyl)-N-(4-((4-(methylsulfonyl)piperazin-1-yl)methyl)phenyl)ethanesulfonamide (0.090 g, 0.176 mmol), triethylamine (0.098 mL, 0.705 mmol) and 2,2-difluoroacetic anhydride (0.038 mL, 0.353 mmol) in tetrahydrofuran (10 mL) prepared at the room temperature was heated at reflux for 5 hr, and cooled down to the ambient temperature. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-N-(4-((4-(methylsulfonyl)piperazin-1-yl)methyl)phenyl)ethanesulfonamide as yellow solid (0.031 g, 30.8%).

$^1$H NMR (400 MHz, CDCl$_3$) δ 9.22 (td, 1H, J=2.2, 0.9 Hz), 8.39 (dd, 1H, J=8.2, 2.2 Hz), 7.70 (ddd, 1H, J=8.2, 4.7, 0.9 Hz), 7.53-7.44 (m, 2H), 7.46-7.37 (m, 2H), 7.11-6.80 (m, 1H), 5.17 (s, 2H), 3.72 (s, 1H), 3.55-3.50 (m, 3H), 3.22 (q, 2H, J=7.4 Hz), 3.06 (s, 4H), 2.84 (s, 3H), 1.44 (s, 5H); LRMS (ES) m/z 571.37 (M$^+$+1).

EXAMPLE 107

Compound 11388, N-(3-((4-acetylpiperazin-1-yl)methyl)phenyl)-N-((5-(5-(difluoromethyl)-1,3,4-oxadiazol-2-yl)pyridin-2-yl)methyl)ethanesulfonamide

[Step 1] tert-butyl 4-(3-nitrobenzyl)piperazine-1-carboxylate

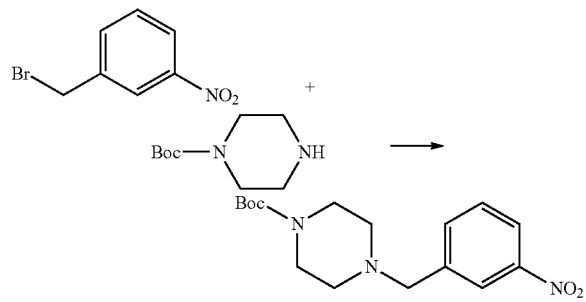

A solution of 1-(bromomethyl)-3-nitrobenzene (1.000 g, 4.629 mmol), N,N-diisopropylethylamine (1.209 mL, 6.943 mmol) and tert-butyl piperazine-1-carboxylate (0.948 g, 5.092 mmol) in acetonitrile (20 mL) was stirred at the room temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 20%) to give tert-butyl 4-(3-nitrobenzyl)piperazine-1-carboxylate as yellow oil (1.050 g, 70.6%).

[Step 2] tert-butyl 4-(3-aminobenzyl)piperazine-1-carboxylate

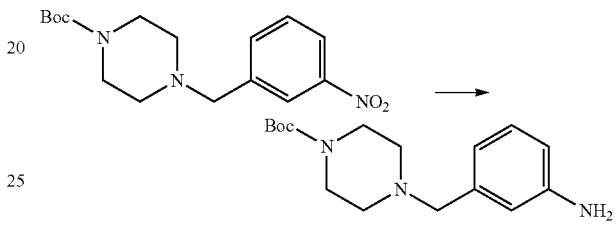

A solution of tert-butyl 4-(3-nitrobenzyl)piperazine-1-carboxylate (1.050 g, 3.267 mmol), ammonium chloride (0.874 g, 16.336 mmol) and Zinc dust (1.068 g, 16.336 mmol) in tetrahydrofuran (20 mL)/water (20 mL) was stirred at the room temperature for 12 hr. The reaction mixture was filtered to remove solids. Then, water was added to the filtrate, followed by extraction with ethyl acetate. The organic layer was washed with aqueous saturated sodium chloride solution, dried with anhydrous MgSO$_4$, filtered, and concentrated in vacuo. The title compound was used without further purification (tert-butyl 4-(3-aminobenzyl)piperazine-1-carboxylate, 0.940 g, 98.7%, yellow solid).

[Step 3] tert-butyl 4-(3-(ethylsulfonamido)benzyl)piperazine-1-carboxylate

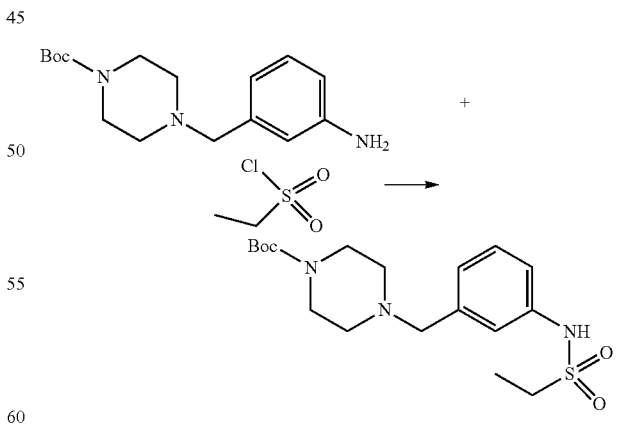

A solution of tert-butyl 4-(3-aminobenzyl)piperazine-1-carboxylate (0.940 g, 3.226 mmol), pyridine (0.312 mL, 3.871 mmol) and ethanesulfonyl chloride (0.456 g, 3.548 mmol) in dichloromethane (30 mL) was stirred at the room temperature for 12 hr. Then, water was added to the reaction mixture, followed by extraction with dichloromethane. The organic layer was washed with aqueous saturated ammonium chloride solution, separated, dried with anhydrous MgSO₄, filtered, and concentrated in vacuo. The residue was chromatographed (SiO₂, 12 g cartridge; ethyl acetate/hexane=0% to 40%) to give tert-butyl 4-(3-(ethylsulfonamido)benzyl)piperazine-1-carboxylate as yellow solid (1.080 g, 87.3%).

[Step 4] tert-butyl 4-(3-(N-((5-(methoxycarbonyl)pyridin-2-yl)methyl)ethylsulfonamido)benzyl)piperazine-1-carboxylate

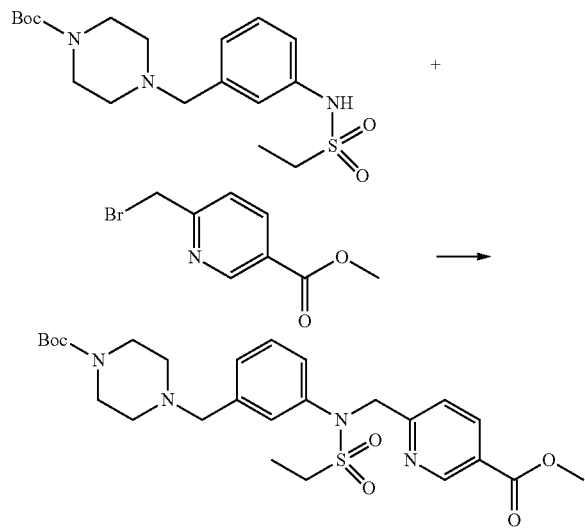

A solution of methyl 6-(bromomethyl)nicotinate (0.713 g, 3.098 mmol) and potassium iodide (0.093 g, 0.563 mmol) in N,N-dimethylformide (30 mL) was stirred at the room temperature for 30 min, and mixed with tert-butyl 4-(3-(ethylsulfonamido)benzyl)piperazine-1-carboxylate (1.080 g, 2.816 mmol) and potassium carbonate (0.584 g, 4.224 mmol). The reaction mixture was stirred at 50° C. for additional 12 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 40%) to give tert-butyl 4-(3-(N-((5-(methoxycarbonyl)pyridin-2-yl)methyl)ethylsulfonamido)benzyl)piperazine-1-carboxylate as yellow solid (0.616 g, 41.1%).

[Step 5] methyl 6-((N-(3-(piperazin-1-ylmethyl)phenyl)ethylsulfonamido)methyl)nicotinate hydrochloride

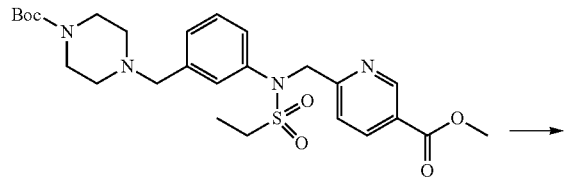

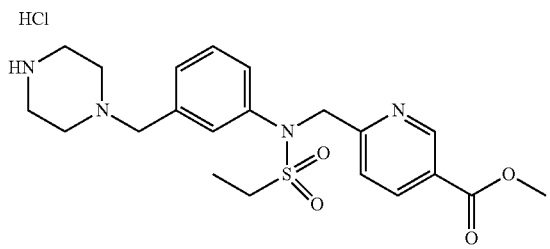

A solution of tert-butyl 4-(3-(N-((5-(methoxycarbonyl)pyridin-2-yl)methyl)ethylsulfonamido)benzyl)piperazine-1-carboxylate (0.616 g, 1.156 mmol) and hydrochloric acid (4.00 M solution in 1,4-dioxane, 1.156 mL, 4.626 mmol) in dichloromethane (20 mL) was stirred at the room temperature for 5 hr, and concentrated under the reduced pressure to remove the solvent. The title compound was used without further purification (methyl 6-((N-(3-(piperazin-1-ylmethyl)phenyl)ethylsulfonamido)methyl)nicotinate hydrochloride, 0.520 g, 95.9%, yellow solid).

[Step 6] methyl 6-((N-(3-((4-acetylpiperazin-1-yl)methyl)phenyl)ethylsulfonamido)methyl)nicotinate

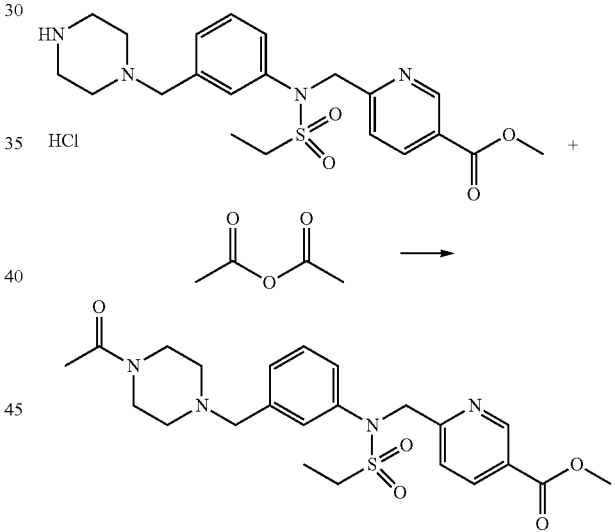

A solution of methyl 6-((N-(3-(piperazin-1-ylmethyl)phenyl)ethylsulfonamido)methyl)nicotinate hydrochloride (0.150 g, 0.320 mmol), triethylamine (0.067 mL, 0.480 mmol) and acetic anhydride (0.039 g, 0.384 mmol) in dichloromethane (5 mL) was stirred at the room temperature for 5 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 12 g cartridge; methanol/dichloromethane=0% to 5%) to give methyl 6-((N-(3-((4-acetylpiperazin-1-yl)methyl)phenyl)ethylsulfonamido)methyl)nicotinate as yellow solid (0.094 g, 61.9%).

381

[Step 7] N-(3-((4-acetylpiperazin-1-yl)methyl)phenyl)-N-((5-(hydrazinecarbonyl)pyridin-2-yl)methyl)ethanesulfonamide

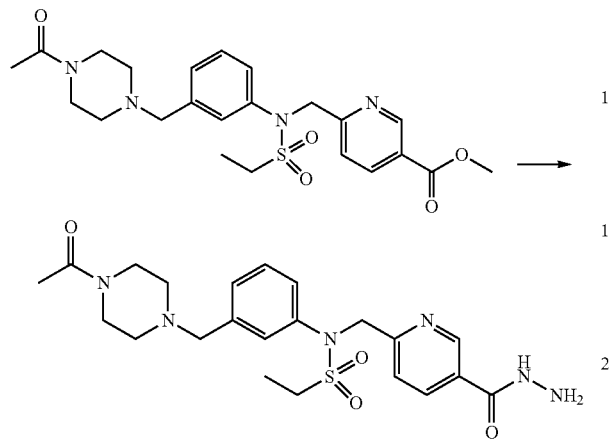

A solution of methyl 6-((N-(3-((4-acetylpiperazin-1-yl)methyl)phenyl)ethylsulfonamido)methyl)nicotinate (0.094 g, 0.198 mmol) and hydrazine hydrate (0.099 g, 1.981 mmol) in ethanol (10 mL) was stirred at 90° C. for 5 hr, and cooled down to the room temperature to terminate the reaction. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(3-((4-acetylpiperazin-1-yl)methyl)phenyl)-N-((5-(hydrazinecarbonyl)pyridin-2-yl)methyl)ethanesulfonamide, 0.064 g, 68.1%, white solid).

[Step 8] Compound 11388

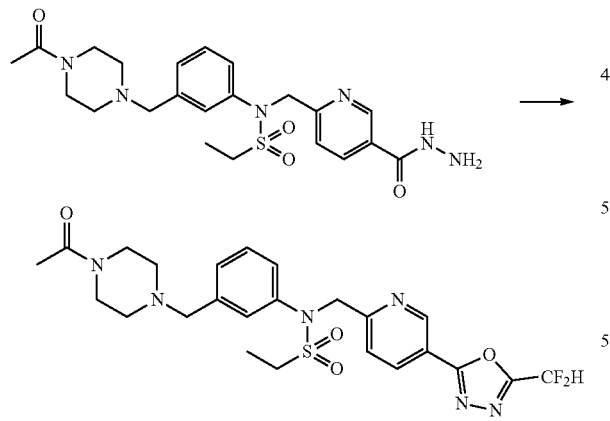

A mixture of N-(3-((4-acetylpiperazin-1-yl)methyl)phenyl)-N-((5-(hydrazinecarbonyl)pyridin-2-yl)methyl)ethanesulfonamide (0.061 g, 0.129 mmol), triethylamine (0.072 mL, 0.514 mmol) and 2,2-difluoroacetic anhydride (0.028 mL, 0.257 mmol) in tetrahydrofuran (10 mL) prepared at the room temperature was heated at reflux for 5 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; methanol/dichloromethane=0% to 5%) to give N-(3-((4-acetylpiperazin-1-yl)methyl)phenyl)-N-((5-(5-(difluoromethyl)-1,3,4-oxadiazol-2-yl)pyridin-2-yl)methyl)ethanesulfonamide as yellow solid (0.018 g, 26.2%).

$^1$H NMR (400 MHz, CDCl$_3$) δ 9.21 (d, 1H, J=2.2 Hz), 8.38 (dd, 1H, J=8.2, 2.2 Hz), 7.76 (d, 1H, J=8.2 Hz), 7.44 (s, 1H), 7.35-7.23 (m, 3H), 7.13-6.77 (m, 1H), 5.18 (s, 2H), 3.88-3.33 (m, 6H), 3.21 (q, 2H, J=7.4 Hz), 2.40 (s, 4H), 2.08 (s, 3H), 1.46 (t, 3H, J=7.4 Hz); LRMS (ES) m/z 535.47 (M$^+$+1).

EXAMPLE 108

Compound 11389, N-(4-(5-(difluoromethyl)-1,3,4-oxadiazol-2-yl)-2-fluorobenzyl)-N-(4-(5-(trifluoromethyl)-1,2,4-oxadiazol-3-yl)benzyl)methanesulfonamide

[Step 1] (tert-butyl (4-cyanobenzyl)carbamate

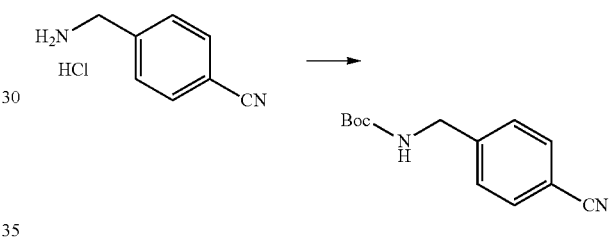

Triethylamine (4.932 mL, 35.583 mmol) was added to solution of 4-(aminomethyl)benzonitrile hydrochloride (5.000 g, 29.652 mmol) in dichloromethane (20 mL) at the room temperature, and the mixture was stirred for 10 min at the same temperature. The reaction mixture was treated at the same temperature with Di-tert-butyl dicarbonate (6.795 g, 31.135 mmol) and stirred for additional 5 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (tert-butyl (4-cyanobenzyl)carbamate, 6.850 g, 99.5%, white solid).

[Step 2] tert-butyl (Z)-4-(N'-hydroxycarbamimidoyl)benzylcarbamate

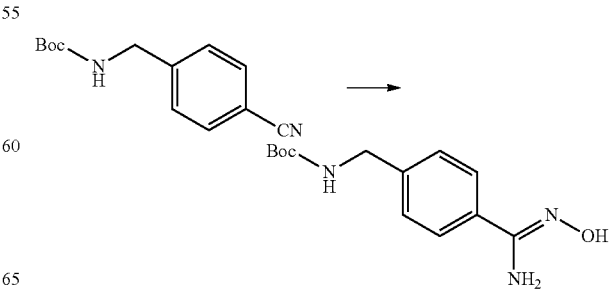

A mixture of tert-butyl 4-cyanobenzylcarbamate (6.800 g, 29.275 mmol), NH2OH (6.103 g, 87.825 mmol), Na2CO3 (9.309 g, 87.825 mmol) and NH2OH (50.00% solution in water, 5.372 mL, 87.825 mmol) in ethanol (20 mL) prepared at the room temperature was heated at reflux for 14 hr, cooled down to the ambient temperature, and concentrated under the reduced pressure to remove the solvent. The residue was diluted with aqueous saturated sodium bicarbonate solution and stirred. The resulting precipitates were collected by filtration, washed by water, and dried to give tert-butyl (Z)-4-(N'-hydroxycarbamimidoyl)benzylcarbamate as white solid (7.500 g, 96.6%).

[Step 3] tert-butyl (4-(5-(trifluoromethyl)-1,2,4-oxadiazol-3-yl)benzyl)carbamate

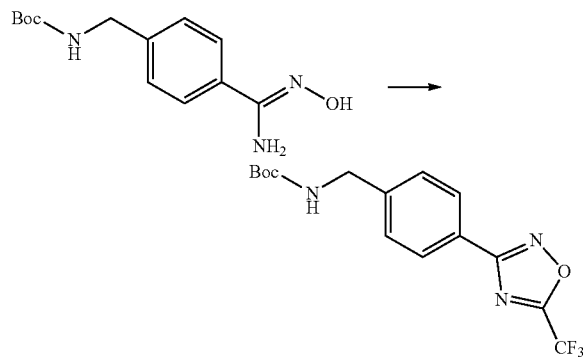

Triethylamine (5.298 mL, 38.219 mmol) was added to solution of tert-butyl (Z)-(4-(N'-hydroxycarbamimidoyl)benzyl)carbamate (7.800 g, 29.400 mmol) in N,N-dimethylformide (25 mL) at 0° C., and the mixture was stirred at the same temperature. The reaction mixture was treated at 80° C. with Trifluoroacetic anhydride (TFAA, 4.305 mL, 32.340 mmol), stirred for additional 2 hr, cooled down to the room temperature to terminate the reaction and concentrated under the reduced pressure to terminate the reaction. Then, aqueous ammonium chloride solution was added to the reaction mixture, followed by extraction with ethyl acetate. The organic layer was washed with brine, dried with anhydrous MgSO4, filtered, and concentrated in vacuo. The residue was chromatographed (SiO2, 80 g cartridge; ethyl acetate/hexane=0% to 30%) to give tert-butyl (4-(5-(trifluoromethyl)-1,2,4-oxadiazol-3-yl)benzyl)carbamate as colorlessness oil (5.240 g, 51.9%).

[Step 4] (4-(5-(trifluoromethyl)-1,2,4-oxadiazol-3-yl)phenyl)methanamine hydrochloride

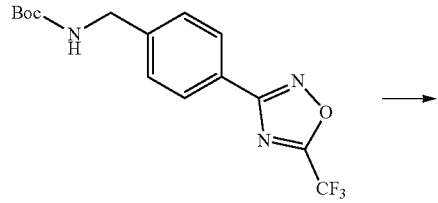

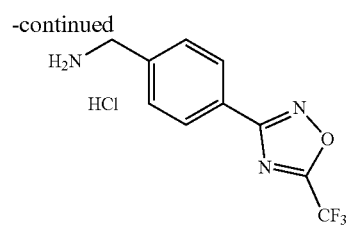

A solution of tert-butyl (4-(5-(trifluoromethyl)-1,2,4-oxadiazol-3-yl)benzyl)carbamate (5.240 g, 15.263 mmol) in dichloromethane (20 mL) prepared at the room temperature was mixed with HCl (4.00 M solution, 4.197 mL, 16.789 mmol). The reaction mixture was stirred at the same temperature for 1 hr. The precipitates were collected by filtration, washed by dichloromethane, and dried to give (4-(5-(trifluoromethyl)-1,2,4-oxadiazol-3-yl)phenyl)methanamine hydrochloride as white solid (3.900 g, 91.4%).

[Step 5] N-(4-(5-(trifluoromethyl)-1,2,4-oxadiazol-3-yl)benzyl)methanesulfonamide

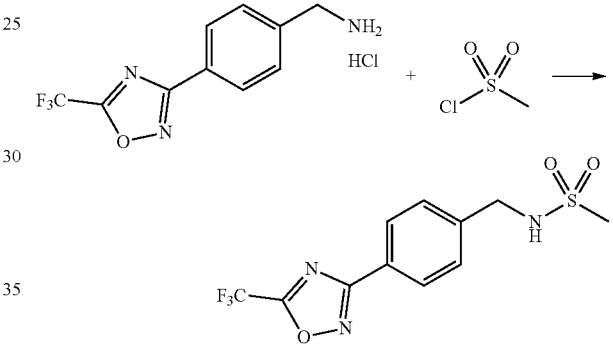

Triethylamine (0.060 mL, 0.429 mmol) was added to solution of (4-(5-(trifluoromethyl)-1,2,4-oxadiazol-3-yl)phenyl)methanamine hydrochloride (0.100 g, 0.358 mmol) in dichloromethane (4 mL) at the room temperature, and the mixture was stirred for 10 min at the same temperature. The reaction mixture was treated at the same temperature with methanesulfonyl chloride (0.028 mL, 0.358 mmol) and stirred for additional 3 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(5-(trifluoromethyl)-1,2,4-oxadiazol-3-yl)benzyl)methanesulfonamide, 0.110 g, 95.7%, white solid).

[Step 6] N-(4-(2-(2,2-difluoroacetyl)hydrazine-1-carbonyl)-2-fluorobenzyl)-N-(4-(5-(trifluoromethyl)-1,2,4-oxadiazol-3-yl)benzyl)methanesulfonamide

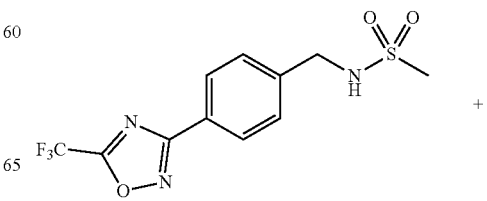

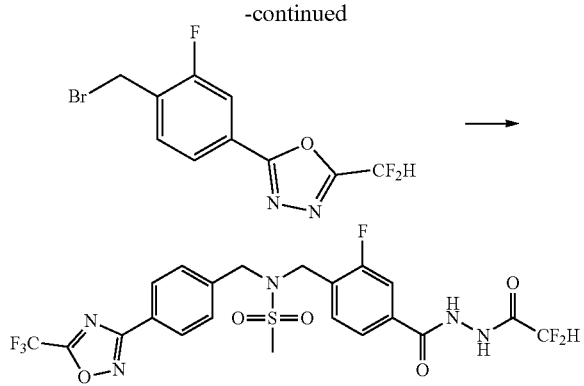

A solution of 2-(4-(bromomethyl)-3-fluorophenyl)-5-(difluoromethyl)-1,3,4-oxadiazole (0.043 g, 0.141 mmol) and potassium iodide (0.004 g, 0.027 mmol) in N,N-dimethylformide (2 mL) was stirred at the room temperature for 30 min, and mixed with N-(4-(5-(trifluoromethyl)-1,2,4-oxadiazol-3-yl)benzyl)methanesulfonamide (0.043 g, 0.134 mmol) and potassium carbonate (0.028 g, 0.201 mmol). The reaction mixture was stirred at the same temperature for additional 8 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 35%) to give N-(4-(2-(2,2-difluoroacetyl)hydrazine-1-carbonyl)-2-fluorobenzyl)-N-(4-(5-(trifluoromethyl)-1,2,4-oxadiazol-3-yl)benzyl)methanesulfonamide as yellow solid (0.050 g, 66.1%).

[Step 7] Compound 11389

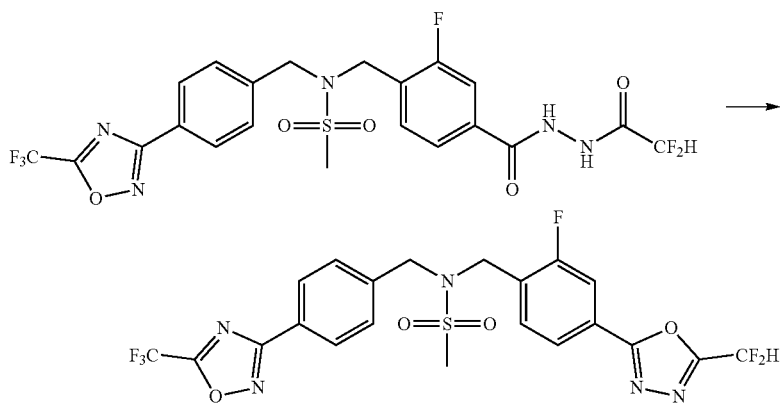

A mixture of N-(4-(2-(2,2-difluoroacetyl)hydrazine-1-carbonyl)-2-fluorobenzyl)-N-(4-(5-(trifluoromethyl)-1,2,4-oxadiazol-3-yl)benzyl)methanesulfonamide (0.050 g, 0.088 mmol) and 1-methoxy-N-triethylammoniosulfonyl-methanimidate (Burgess reagent, 0.063 g, 0.265 mmol) in tetrahydrofuran (4 mL) was heated at 130° C. for 30 min under the microwaves. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 25%) to give N-(4-(5-(difluoromethyl)-1,3,4-oxadiazol-2-yl)-2-fluorobenzyl)-N-(4-(5-(trifluoromethyl)-1,2,4-oxadiazol-3-yl)benzyl)methanesulfonamide as white solid (0.025 g, 51.6%).

$^1$H NMR (400 MHz, DMSO-D6) δ 7.94 (d, 2H, J=8.3 Hz), 7.78 (dd, 1H, J=25.9, 17.9 Hz), 7.70-7.67 (m, 1.25H), 7.62 (t, 5H, J=7.8 Hz), 7.56 (s, 0.5H), 7.50 (d, 1H, J=8.3 Hz), 7.43 (s, 0.25H), 4.60 (s, 2H), 4.55 (s, 2H), 3.17 (s, 3H); LRMS (ES) m/z 548.38 (M$^+$+1).

EXAMPLE 109

Compound 11390, N-((5-(5-(difluoromethyl)-1,3,4-oxadiazol-2-yl)pyridin-2-yl)methyl)-N-phenyltetrahydro-2H-pyran-4-sulfonamide

[Step 1] N-phenyltetrahydro-2H-pyran-4-sulfonamide

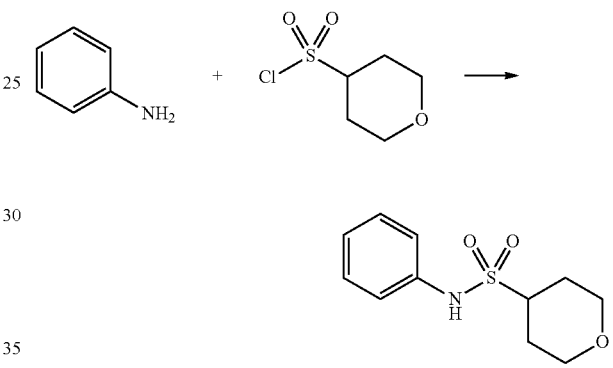

A solution of aniline (0.294 mL, 3.221 mmol) and triethylamine (0.539 mL, 3.866 mmol) in dichloromethane (8 mL) was stirred at 0° C. for 10 min, and mixed with tetrahydro-2H-pyran-4-sulfonyl chloride (0.624 g, 3.382 mmol). The reaction mixture was stirred at the room temperature for additional 6 hr. Then, aqueous 0.1N-hydrochloric acid solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed

387

(SiO₂, 12 g cartridge; ethyl acetate/hexane=0% to 40%) to give N-phenyltetrahydro-2H-pyran-4-sulfonamide as light yellow oil (0.650 g, 83.6%).

[Step 2] methyl 6-(((N-phenyltetrahydro-2H-pyran)-4-sulfonamido)methyl)nicotinate

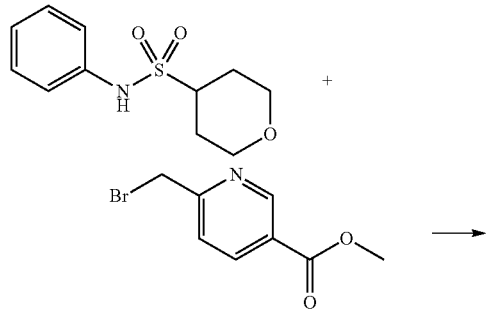

A solution of methyl 6-(bromomethyl)nicotinate (0.497 g, 2.158 mmol) and potassium iodide (0.068 g, 0.411 mmol) in N,N-dimethylformide (8 mL) was stirred at the room temperature for 20 min, and mixed with N-phenyltetrahydro-2H-pyran-4-sulfonamide (0.496 g, 2.055 mmol) and potassium carbonate (0.369 g, 2.672 mmol). The reaction mixture was stirred at the same temperature for additional 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 40%) to give methyl 6-(((N-phenyltetrahydro-2H-pyran)-4-sulfonamido)methyl)nicotinate as yellow solid (0.650 g, 81.0%).

[Step 3] N-((5-(hydrazinecarbonyl)pyridin-2-yl)methyl)-N-phenyltetrahydro-2H-pyran-4-sulfonamide

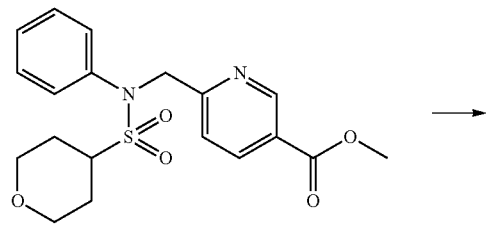

388

-continued

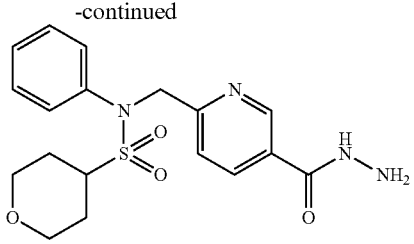

A mixture of methyl 6-(((N-phenyltetrahydro-2H-pyran)-4-sulfonamido)methyl)nicotinate (0.650 g, 1.665 mmol) and hydrazine monohydrate (0.405 mL, 8.324 mmol) in ethanol (10 mL) prepared at the room temperature was heated at reflux for 8 hr, cooled down to the ambient temperature, and concentrated under the reduced pressure to remove the solvent. The residue was diluted with aqueous saturated sodium bicarbonate solution and stirred. The resulting precipitates were collected by filtration, washed by water, and dried to give N-((5-(hydrazinecarbonyl)pyridin-2-yl)methyl)-N-phenyltetrahydro-2H-pyran-4-sulfonamide as white solid (0.580 g, 89.2%).

[Step 4] Compound 11390

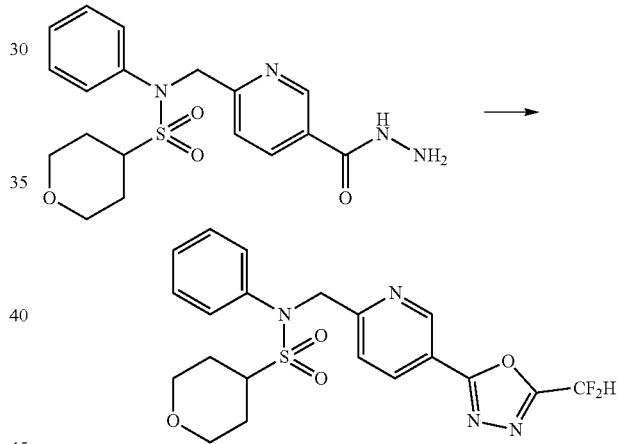

Triethylamine (0.039 mL, 0.277 mmol) was added to solution of N-((5-(hydrazinecarbonyl)pyridin-2-yl)methyl)-N-phenyltetrahydro-2H-pyran-4-sulfonamide (0.054 g, 0.138 mmol) in tetrahydrofuran (2 mL) at the room temperature, and the mixture was stirred for 10 min at the same temperature. The reaction mixture was treated with 2,2-difluoroacetic anhydride (0.023 mL, 0.207 mmol), heated at reflux for 3 hr, and cooled down to the room temperature to terminate the reaction. Then, aqueous saturated sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 40%) to give N-((5-(5-(difluoromethyl)-1,3,4-oxadiazol-2-yl)pyridin-2-yl)methyl)-N-phenyltetrahydro-2H-pyran-4-sulfonamide as white solid (0.055 g, 88.3%).

¹H NMR (400 MHz, CDCl₃) δ 9.18 (d, 1H, J=2.2 Hz), 8.38 (dd, 1H, J=8.2, 2.2 Hz), 7.75 (d, 1H, J=8.2 Hz), 7.40 (m, 2 Hz), 7.35 (m, 2H), 7.25 (m, 1 Hz), 7.05 (s, 0.25H), 6.92 (s, 0.5H), 6.79 (s, 0.25H), 5.20 (s, 2H), 4.11-4.07 (m, 2H), 3.39-3.30 (m, 3H), 2.20-1.99 (m, 4H); LRMS (ES) m/z 451.35 (M$^+$+1).

EXAMPLE 110

Compound 11392, N-(4-(5-(difluoromethyl)-1,3,4-oxadiazol-2-yl)-2-fluorobenzyl)-N-(3-((1,1-dioxido-thiomorpholino)methyl)phenyl)ethanesulfonamide

[Step 1] 4-(3-nitrobenzyl)thiomorpholine 1,1-dioxide

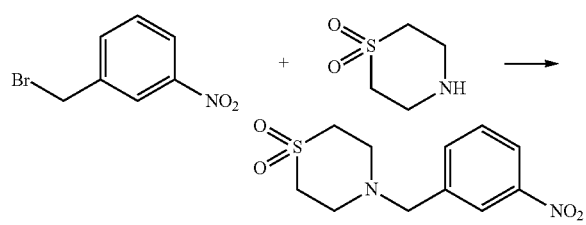

A solution of 1-(bromomethyl)-3-nitrobenzene (2.400 g, 11.110 mmol), thiomorpholine 1,1-dioxide (1.427 g, 10.554 mmol) and N,N-diisopropylethylamine (2.516 mL, 14.442 mmol) in acetonitrile (16 mL) was stirred at the room temperature for 24 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give 4-(3-nitrobenzyl)thiomorpholine 1,1-dioxide as yellow solid (2.800 g, 93.2%).

[Step 2] 4-(3-aminobenzyl)thiomorpholine 1,1-dioxide

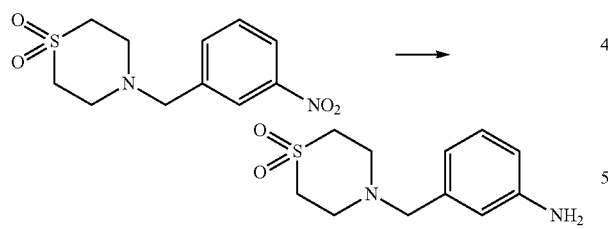

A solution of 4-(3-nitrobenzyl)thiomorpholine 1,1-dioxide (2.750 g, 10.174 mmol), zinc (2.661 g, 40.696 mmol) and ammonium chloride (2.177 g, 40.696 mmol) in tetrahydrofuran (10 mL)/water (5 mL) was stirred at the room temperature for 16 hr. The reaction mixture was filtered by paper filter to remove solids. Then, saturated aqueous sodium bicarbonate solution was added to filtrate, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give 4-(3-aminobenzyl)thiomorpholine 1,1-dioxide as yellow solid (2.100 g, 85.9%).

[Step 3] N-(3-((1,1-dioxidothiomorpholino)methyl) phenyl)ethanesulfonamide

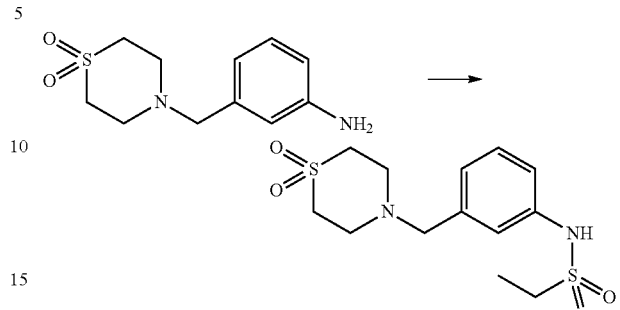

A solution of 4-(3-aminobenzyl)thiomorpholine 1,1-dioxide (1.000 g, 4.161 mmol) and pyridine (0.402 mL, 4.993 mmol) in dichloromethane (20 mL) was mixed at 0° C. with ethanesulfonyl chloride (0.387 mL, 4.369 mmol), and stirred at the same temperature for 20 min. The reaction mixture was stirred at the room temperature for additional 16 hr. Then, aqueous 0.1N-hydrochloric acid solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give N-(3-((1,1-dioxidothiomorpholino)methyl)phenyl)ethanesulfonamide as light yellow solid (1.200 g, 86.8%).

[Step 4] methyl 4-((N-(3-((1,1-dioxidothiomorpholino)methyl)phenyl)ethylsulfonamido)methyl)-3-fluorobenzoate

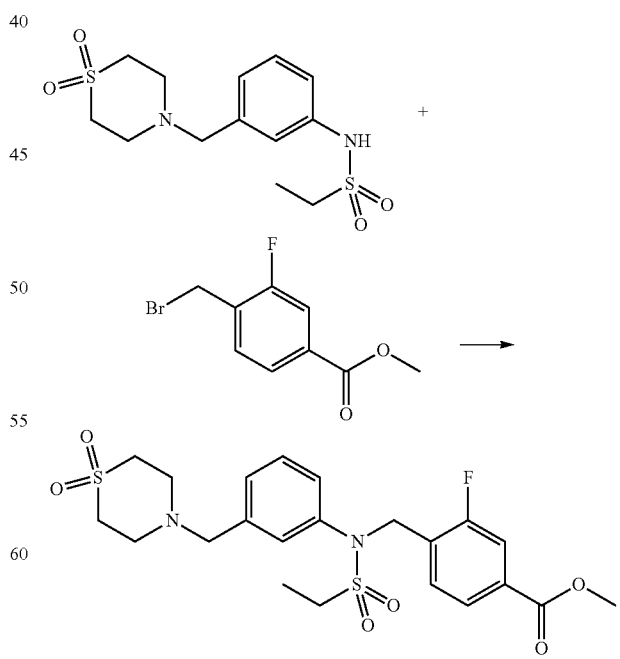

A solution of methyl 4-(bromomethyl)-3-fluorobenzoate (0.531 g, 2.148 mmol) and potassium iodide (0.068 g, 0.409 mmol) in N,N-dimethylformide (8 mL) was stirred at the room temperature for 20 min, and mixed with N-(3-((1,1-dioxidothiomorpholino)methyl)phenyl)ethanesulfonamide (0.680 g, 2.046 mmol) and potassium carbonate (0.368 g, 2.659 mmol). The reaction mixture was stirred at the same temperature for additional 8 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 40 g cartridge; ethyl acetate/hexane=0% to 70%) to give methyl 4-((N-(3-((1,1-dioxidothiomorpholino)methyl)phenyl)ethylsulfonamido)methyl)-3-fluorobenzoate as white solid (0.880 g, 86.3%).

[Step 5] N-(3-((1,1-dioxidothiomorpholino)methyl)phenyl)-N-(2-fluoro-4-(hydrazinecarbonyl)benzyl)ethanesulfonamide

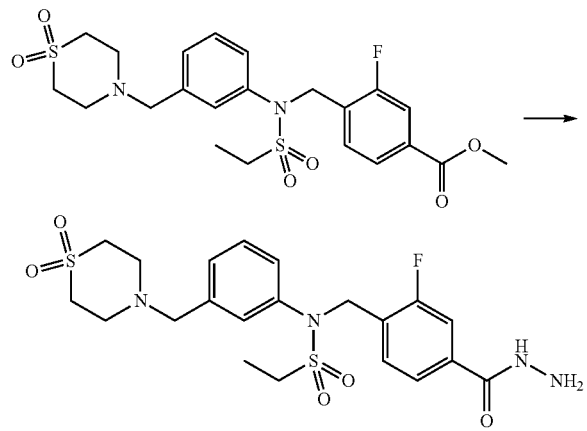

A mixture of methyl 4-((N-(3-((1,1-dioxidothiomorpholino)methyl)phenyl)ethylsulfonamido)methyl)-3-fluorobenzoate (0.880 g, 1.765 mmol) and hydrazine monohydrate (0.257 mL, 5.295 mmol) in ethanol (8 mL) prepared at the room temperature was heated at reflux for 14 hr, cooled down to the ambient temperature, and concentrated under the reduced pressure to remove the solvent. The residue was diluted with aqueous saturated sodium bicarbonate solution and stirred. The resulting precipitates were collected by filtration, washed with water, and dried to give N-(3-((1,1-dioxidothiomorpholino)methyl)phenyl)-N-(2-fluoro-4-(hydrazinecarbonyl)benzyl)ethanesulfonamide as white solid (0.850 g, 96.6%).

[Step 6] Compound 11392

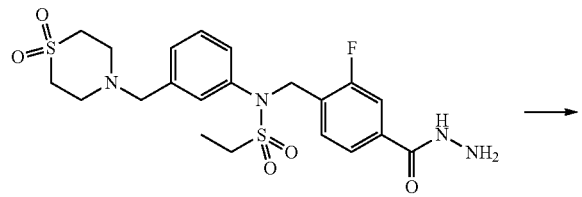

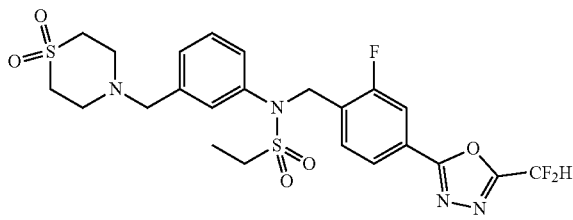

Triethylamine (0.028 mL, 0.201 mmol) was added to solution of N-(3-((1,1-dioxidothiomorpholino)methyl)phenyl)-N-(2-fluoro-4-(hydrazinecarbonyl)benzyl)ethanesulfonamide (0.050 g, 0.100 mmol) in tetrahydrofuran (2 mL) at the room temperature, and the mixture was stirred for 10 min at the same temperature. The reaction mixture was treated with 2,2-difluoroacetic anhydride (0.016 mL, 0.150 mmol), heated at reflux for 5 hr, and cooled down to the room temperature to terminate the reaction. Then, aqueous saturated sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 80%) to give N-(4-(5-(difluoromethyl)-1,3,4-oxadiazol-2-yl)-2-fluorobenzyl)-N-(3-((1,1-dioxidothiomorpholino)methyl)phenyl)ethanesulfonamide as white solid (0.045 g, 80.3%).

$^1$H NMR (400 MHz, CDCl$_3$) δ 7.86 (dd, 1H, J=8.1, 1.5 Hz), 7.84-7.66 (m, 2H), 7.32-7.28 (m, 2 Hz), 7.25-7.21 (m, 2 Hz), 7.02 (s, 0.25H), 6.89 (s, 0.5H), 6.77 (s, 0.25H), 5.03 (s, 2H), 3.62 (m, 2H), 3.13 (q, 2H, J=7.4 Hz), 3.02 (m, 4H), 2.87 (m, 4H), 1.45 (t, 3H, J=7.4 Hz); LRMS (ES) m/z 560.47 (M$^+$+1).

EXAMPLE 111

Compound 11402: N-(4-((4-acetylpiperazin-1-yl)methyl)phenyl)-N-(4-(5-(difluoromethyl)-1,3,4-oxadiazol-2-yl)-2-fluorobenzyl)ethanesulfonamide

[Step 1] tert-butyl 4-(4-(N-(2-fluoro-4-(methoxycarbonyl)benzyl)ethylsulfonamido)benzyl)piperazine-1-carboxylate

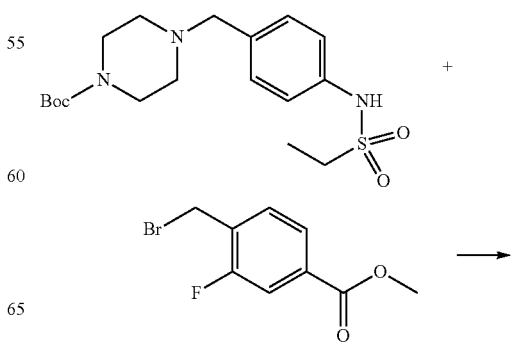

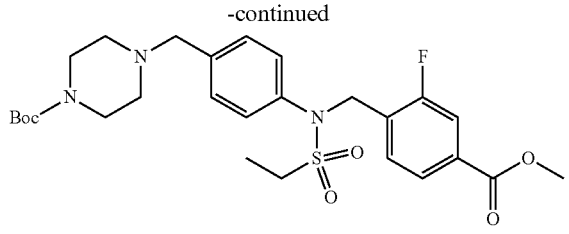

A solution of methyl 4-(bromomethyl)-3-fluorobenzoate (0.454 g, 1.836 mmol) and potassium iodide (0.055 g, 0.334 mmol) in N,N-dimethylformide (30 mL) was stirred at the room temperature for 30 min, and mixed with tert-butyl 4-(4-(ethylsulfonamido)benzyl)piperazine-1-carboxylate (0.640 g, 1.669 mmol) and potassium carbonate (0.346 g, 2.503 mmol). The reaction mixture was stirred at 50° C. for additional 12 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 30%) to give tert-butyl 4-(4-(N-(2-fluoro-4-(methoxycarbonyl)benzyl)ethylsulfonamido)benzyl)piperazine-1-carboxylate as yellow solid (0.780 g, 85.0%).

[Step 2] methyl 3-fluoro-4-((N-(4-(piperazin-1-ylmethyl)phenyl)ethylsulfonamido)methyl)benzoate hydrochloride

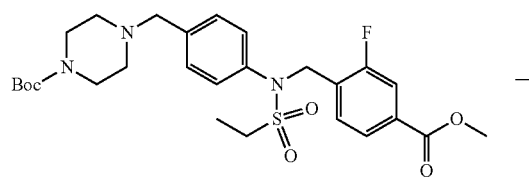

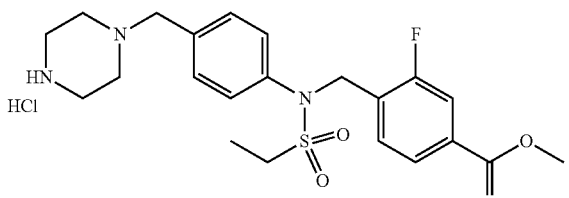

A solution of tert-butyl 4-(4-(N-(2-fluoro-4-(methoxycarbonyl)benzyl)ethylsulfonamido)benzyl)piperazine-1-carboxylate (0.780 g, 1.419 mmol) and hydrochloric acid (4.00 M solution in 1,4-dioxane, 1.419 mL, 5.676 mmol) in dichloromethane (10 mL) was stirred at the room temperature for 5 hr, and concentrated under the reduced pressure to remove the solvent. The title compound was used without further purification (methyl 3-fluoro-4-((N-(4-(piperazin-1-ylmethyl)phenyl)ethylsulfonamido)methyl)benzoate hydrochloride, 0.680 g, 98.6%, white solid).

[Step 3] methyl 4-((N-(4-((4-acetylpiperazin-1-yl)methyl)phenyl)ethylsulfonamido)methyl)-3-fluorobenzoate

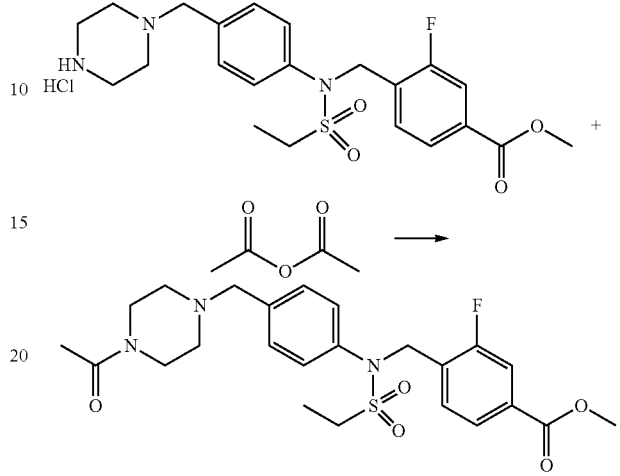

A solution of methyl 3-fluoro-4-((N-(4-(piperazin-1-ylmethyl)phenyl)ethylsulfonamido)methyl)benzoate hydrochloride (0.200 g, 0.412 mmol), triethylamine (0.086 mL, 0.617 mmol) and acetic anhydride (0.047 mL, 0.494 mmol) in dichloromethane (5 mL) was stirred at the room temperature for 5 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The title compound was used without further purification (methyl 4-((N-(4-((4-acetylpiperazin-1-yl)methyl)phenyl)ethylsulfonamido)methyl)-3-fluorobenzoate, 0.130 g, 64.3%, yellow oil).

[Step 4] N-(4-((4-acetylpiperazin-1-yl)methyl)phenyl)-N-(2-fluoro-4-(hydrazinecarbonyl)benzyl)ethanesulfonamide

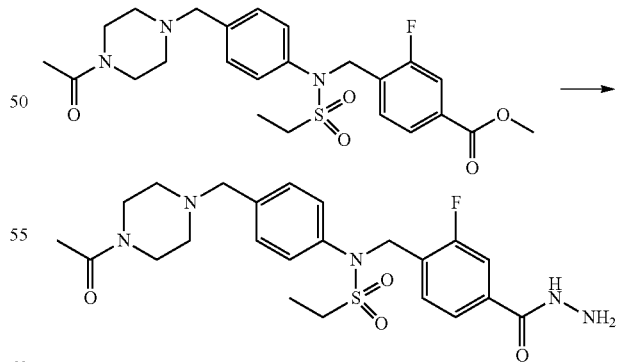

A solution of methyl 4-((N-(4-((4-acetylpiperazin-1-yl)methyl)phenyl)ethylsulfonamido)methyl)-3-fluorobenzoate (0.130 g, 0.264 mmol) and hydrazine monohydrate (0.129 mL, 2.645 mmol) in ethanol (5 mL) was stirred at the room temperature for 12 hr. Then, water was added to the reaction mixture, followed by extraction with dichloromethane. The organic layer was washed with aqueous saturated sodium bicarbonate solution, dried with anhydrous MgSO₄, filtered, and concentrated in vacuo. The title compound was used without further purification (N-(4-((4-acetylpiperazin-1-yl)methyl)phenyl)-N-(2-fluoro-4-(hydrazinecarbonyl)benzyl)ethanesulfonamide, 0.096 g, 73.8%, yellow solid).

[Step 5] Compound 11402

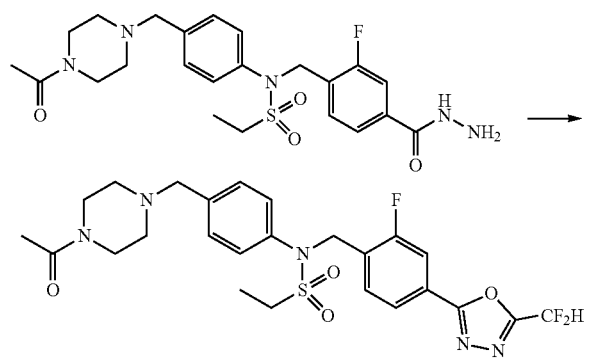

A mixture of N-(4-((4-acetylpiperazin-1-yl)methyl)phenyl)-N-(2-fluoro-4-(hydrazinecarbonyl)benzyl)ethanesulfonamide (0.096 g, 0.195 mmol), triethylamine (0.109 mL, 0.781 mmol) and 2,2-difluoroacetic anhydride (0.042 mL, 0.391 mmol) in tetrahydrofuran (10 mL) prepared at the room temperature was heated at reflux for 5 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give N-(4-((4-acetylpiperazin-1-yl)methyl)phenyl)-N-(4-(5-(difluoromethyl)-1,3,4-oxadiazol-2-yl)-2-fluorobenzyl)ethanesulfonamide as yellow oil (0.021 g, 19.5%).

¹H NMR (400 MHz, CDCl₃) δ 7.88 (dd, 1H, J=8.0, 1.7 Hz), 7.76-7.66 (m, 2H), 7.30 (t, 4H, J=4.7 Hz), 7.10-6.72 (m, 1H), 5.05 (s, 2H), 3.62 (s, 2H), 3.52-3.42 (m, 4H), 3.20-3.08 (m, 2H), 2.41 (s, 4H), 2.08 (d, 3H, J=1.5 Hz), 1.51-1.39 (m, 3H); LRMS (ES) m/z 552.45 (M⁺+1).

EXAMPLE 112

Compound 11403, N-(3-((4-acetylpiperazin-1-yl)methyl)phenyl)-N-(4-(5-(difluoromethyl)-1,3,4-oxadiazol-2-yl)-2-fluorobenzyl)ethanesulfonamide

[Step 1] tert-butyl 4-(3-(N-(2-fluoro-4-(methoxycarbonyl)benzyl)ethylsulfonamido)benzyl)piperazine-1-carboxylate

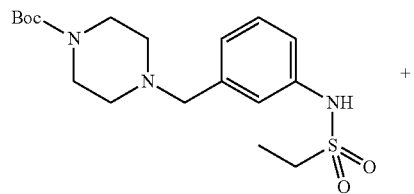

+

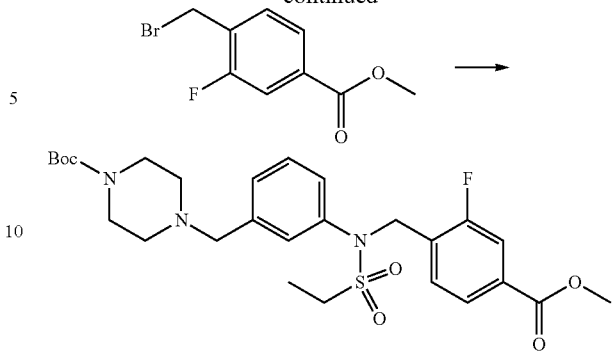

A solution of methyl 4-(bromomethyl)-3-fluorobenzoate (0.454 g, 1.836 mmol) and potassium iodide (0.055 g, 0.334 mmol) in N,N-dimethylformide (30 mL) was stirred at the room temperature for 30 min, and mixed with tert-butyl 4-(3-(ethylsulfonamido)benzyl)piperazine-1-carboxylate (0.640 g, 1.669 mmol) and potassium carbonate (0.346 g, 2.503 mmol). The reaction mixture was stirred at 50° C. for additional 12 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 30%) to give tert-butyl 4-(3-(N-(2-fluoro-4-(methoxycarbonyl)benzyl)ethylsulfonamido)benzyl)piperazine-1-carboxylate as yellow solid (0.780 g, 85.0%).

[Step 2] methyl 3-fluoro-4-((N-(3-(piperazin-1-ylmethyl)phenyl)ethylsulfonamido)methyl)benzoate hydrochloride

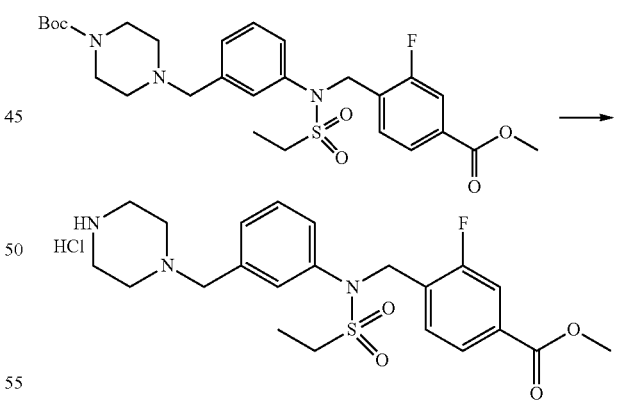

A solution of tert-butyl 4-(3-(N-(2-fluoro-4-(methoxycarbonyl)benzyl)ethylsulfonamido)benzyl)piperazine-1-carboxylate (0.780 g, 1.419 mmol) and hydrochloric acid (4.00 M solution in 1,4-dioxane, 1.419 mL, 5.676 mmol) in dichloromethane (10 mL) was stirred at the room temperature for 5 hr, and concentrated under the reduced pressure to remove the solvent. The title compound was used without further purification (methyl 3-fluoro-4-((N-(3-(piperazin-1-ylmethyl)phenyl)ethylsulfonamido)methyl)benzoate hydrochloride, 0.680 g, 98.6%, white solid).

[Step 3] methyl 4-((N-(3-((4-acetylpiperazin-1-yl)methyl)phenyl)ethylsulfonamido)methyl)-3-fluorobenzoate

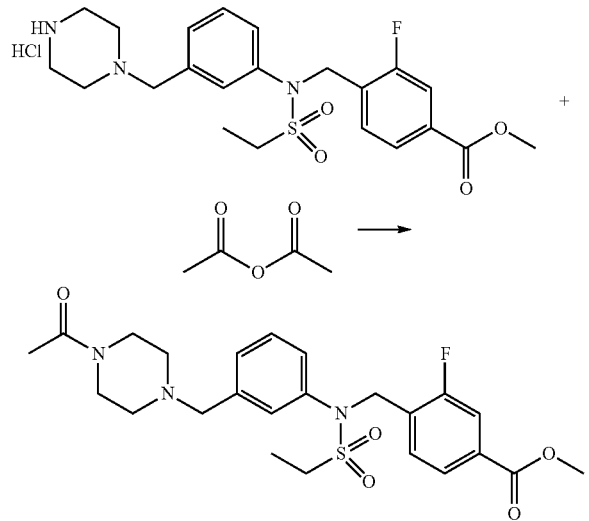

A solution of methyl 3-fluoro-4-((N-(3-(piperazin-1-ylmethyl)phenyl)ethylsulfonamido)methyl)benzoate hydrochloride (0.200 g, 0.412 mmol), triethylamine (0.086 mL, 0.617 mmol) and acetic anhydride (0.050 mL, 0.535 mmol) in dichloromethane (5 mL) was stirred at the room temperature for 5 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 12 g cartridge; methanol/dichloromethane=0% to 5%) to give methyl 4-((N-(3-((4-acetylpiperazin-1-yl)methyl)phenyl)ethylsulfonamido)methyl)-3-fluorobenzoate as yellow oil (0.160 g, 79.1%).

[Step 4] N-(3-((4-acetylpiperazin-1-yl)methyl)phenyl)-N-(2-fluoro-4-(hydrazinecarbonyl)benzyl)ethanesulfonamide

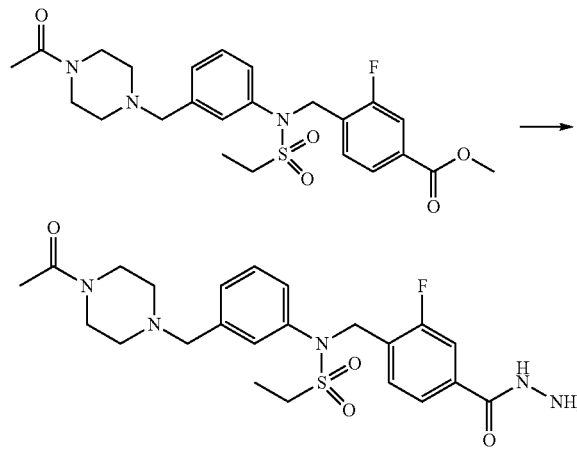

A solution of methyl 4-((N-(3-((4-acetylpiperazin-1-yl)methyl)phenyl)ethylsulfonamido)methyl)-3-fluorobenzoate (0.160 g, 0.325 mmol) and hydrazine monohydrate (0.158 mL, 3.255 mmol) in ethanol (5 mL) was stirred at 90° C. for 12 hr and cooled down to the room temperature to terminate the reaction. Then, water was added to the reaction mixture, followed by extraction with dichloromethane. The organic layer was washed with aqueous saturated sodium bicarbonate solution, dried with anhydrous MgSO₄, filtered, and concentrated in vacuo. The title compound was used without further purification (N-(3-((4-acetylpiperazin-1-yl)methyl)phenyl)-N-(2-fluoro-4-(hydrazinecarbonyl)benzyl)ethanesulfonamide, 0.096 g, 60.0%, yellow solid).

[Step 5] Compound 11403

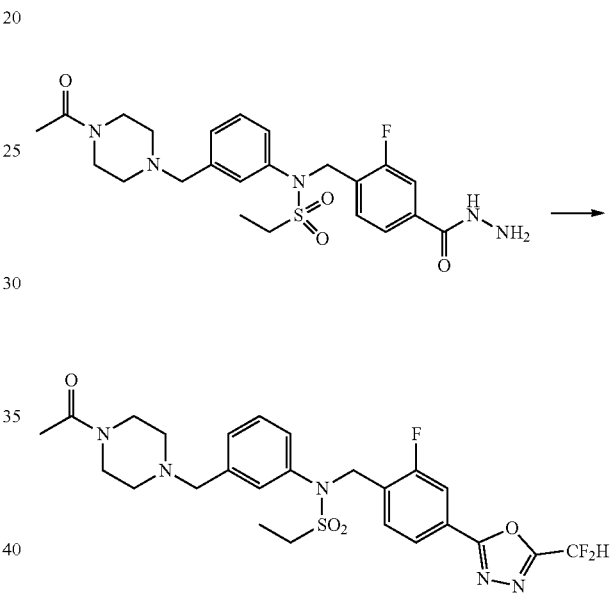

A mixture of N-(3-((4-acetylpiperazin-1-yl)methyl)phenyl)-N-(2-fluoro-4-(hydrazinecarbonyl)benzyl)ethanesulfonamide (0.096 g, 0.195 mmol), triethylamine (0.109 mL, 0.781 mmol) and 2,2-difluoroacetic anhydride (0.042 mL, 0.391 mmol) in tetrahydrofuran (10 mL) prepared at the room temperature was heated at reflux for 5 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give N-(3-((4-acetylpiperazin-1-yl)methyl)phenyl)-N-(4-(5-(difluoromethyl)-1,3,4-oxadiazol-2-yl)-2-fluorobenzyl)ethanesulfonamide as white solid (0.021 g, 19.5%).

$^1$H NMR (400 MHz, CDCl$_3$) δ 7.85 (dd, 1H, J=8.0, 1.6 Hz), 7.73-7.63 (m, 2H), 7.34-7.25 (m, 2H), 7.27-7.18 (m, 2H), 7.11-6.77 (m, 1H), 5.05 (s, 2H), 3.57 (d, 2H, J=6.2 Hz), 3.51-3.39 (m, 4H), 3.15 (q, 2H, J=7.4 Hz), 2.33 (t, 4H, J=10.2 Hz), 2.06 (s, 3H), 1.45 (t, 3H, J=7.4 Hz); LRMS (ES) m/z 552.51 (M$^+$+1).

EXAMPLE 113

Compound 11404, N-(4-(5-(difluoromethyl)-1,3,4-oxadiazol-2-yl)-2-fluorobenzyl)-N-(3-((4-(methylsulfonyl)piperazin-1-yl)methyl)phenyl)ethanesulfonamide

[Step 1] methyl 3-fluoro-4-((N-(3-((4-(methylsulfonyl)piperazin-1-yl)methyl)phenyl)ethylsulfonamido)methyl)benzoate

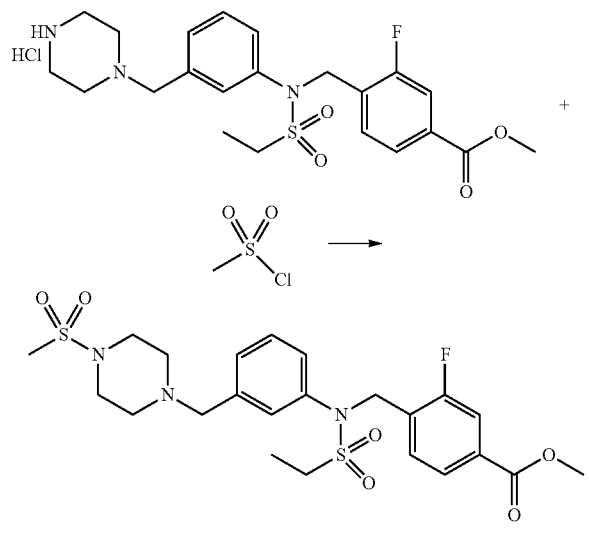

A solution of methyl 3-fluoro-4-((N-(3-(piperazin-1-ylmethyl)phenyl)ethylsulfonamido)methyl)benzoate hydrochloride (0.200 g, 0.412 mmol), triethylamine (0.086 mL, 0.617 mmol) and methanesulfonyl chloride (0.041 mL, 0.535 mmol) in dichloromethane (5 mL) was stirred at the room temperature for 5 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 12 g cartridge; methanol/dichloromethane=0% to 5%) to give methyl 3-fluoro-4-((N-(3-((4-(methylsulfonyl)piperazin-1-yl)methyl)phenyl)ethylsulfonamido)methyl)benzoate as yellow oil (0.130 g, 59.9%).

[Step 2] N-(2-fluoro-4-(hydrazinecarbonyl)benzyl)-N-(3-((4-(methylsulfonyl)piperazin-1-yl)methyl)phenyl)ethanesulfonamide

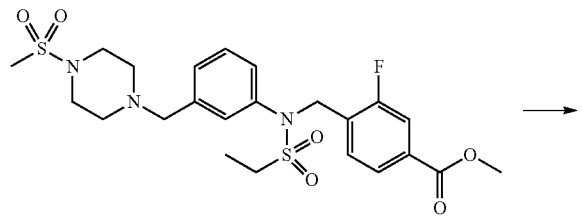

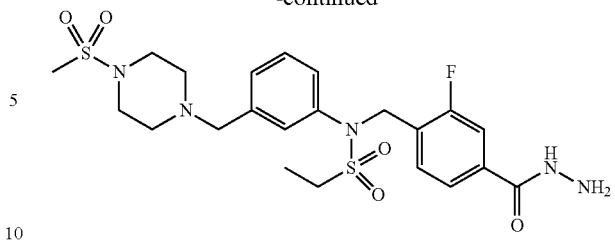

A solution of methyl 3-fluoro-4-((N-(3-((4-(methylsulfonyl)piperazin-1-yl)methyl)phenyl)ethylsulfonamido)methyl)benzoate (0.130 g, 0.246 mmol) and hydrazine monohydrate (0.120 mL, 2.464 mmol) in ethanol (10 mL) was stirred at 90° C. for 12 hr, and cooled down to the room temperature to terminate the reaction. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(2-fluoro-4-(hydrazinecarbonyl)benzyl)-N-(3-((4-(methylsulfonyl)piperazin-1-yl)methyl)phenyl)ethanesulfonamide, 0.092 g, 70.8%, yellow solid).

[Step 3] Compound 11404

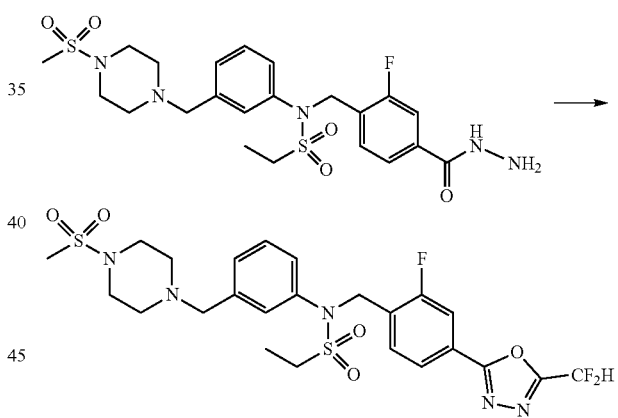

A mixture of N-(2-fluoro-4-(hydrazinecarbonyl)benzyl)-N-(3-((4-(methylsulfonyl)piperazin-1-yl)methyl)phenyl)ethanesulfonamide (0.160 g, 0.303 mmol), triethylamine (0.169 mL, 1.213 mmol) and 2,2-difluoroacetic anhydride (0.066 mL, 0.606 mmol) in tetrahydrofuran (10 mL) prepared at the room temperature was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(3-((4-(methylsulfonyl)piperazin-1-yl)methyl)phenyl)ethanesulfonamide as yellow oil (0.110 g, 61.7%).

$^1$H NMR (400 MHz, CDCl$_3$) δ 7.86 (dd, 1H, J=8.0, 1.7 Hz), 7.73-7.63 (m, 2H), 7.36-7.16 (m, 4H), 7.11-6.75 (m,

1H), 5.04 (s, 2H), 3.52 (s, 2H), 3.21-3.10 (m, 6H), 2.78 (s, 3H), 2.45 (s, 4H), 1.51-1.40 (m, 3H); LRMS (ES) m/z 588.48 (M$^+$+1).

EXAMPLE 114

Compound 11405, N-(4-(5-(difluoromethyl)-1,3,4-oxadiazol-2-yl)-2-fluorobenzyl)-N-(3-((4-methylpiperazin-1-yl)methyl)phenyl)ethanesulfonamide

[Step 1] methyl 3-fluoro-4-((N-(3-((4-methylpiperazin-1-yl)methyl)phenyl)ethylsulfonamido)methyl)benzoate

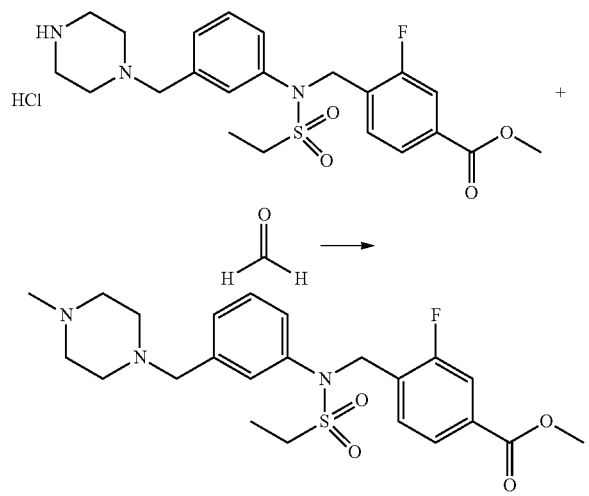

A solution of methyl 3-fluoro-4-((N-(3-(piperazin-1-ylmethyl)phenyl)ethylsulfonamido)methyl)benzoate hydrochloride (0.200 g, 0.412 mmol), formaldehyde (0.037 g, 1.235 mmol) and acetic acid (0.026 mL, 0.453 mmol) in dichloromethane (5 mL) was stirred at the room temperature for 30 min, and mixed with sodium triacetoxyborohydride (0.131 g, 0.617 mmol). The reaction mixture was stirred at the same temperature for additional 5 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 12 g cartridge; methanol/dichloromethane=0% to 5%) to give methyl 3-fluoro-4-((N-(3-((4-methylpiperazin-1-yl)methyl)phenyl)ethylsulfonamido)methyl)benzoate as yellow oil (0.120 g, 62.9%).

[Step 2] N-(2-fluoro-4-(hydrazinecarbonyl)benzyl)-N-(3-((4-methylpiperazin-1-yl)methyl)phenyl)ethanesulfonamide

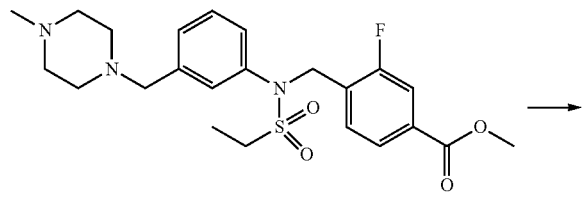

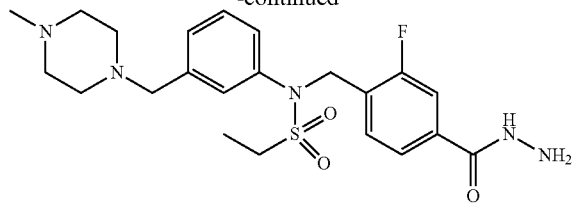

A solution of methyl 3-fluoro-4-((N-(3-((4-methylpiperazin-1-yl)methyl)phenyl)ethylsulfonamido)methyl)benzoate (0.120 g, 0.259 mmol) and hydrazine monohydrate (0.126 mL, 2.589 mmol) in ethanol (5 mL) was stirred at 90° C. for 12 hr, and cooled down to the room temperature to terminate the reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-(2-fluoro-4-(hydrazinecarbonyl)benzyl)-N-(3-((4-methylpiperazin-1-yl)methyl)phenyl)ethanesulfonamide, 0.089 g, 74.2%, yellow solid).

[Step 3] Compound 11405

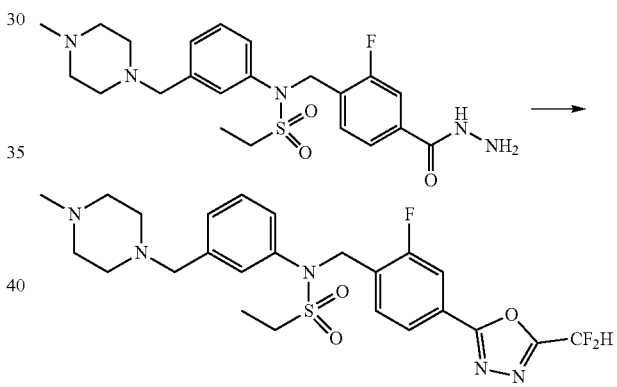

A mixture of N-(2-fluoro-4-(hydrazinecarbonyl)benzyl)-N-(3-((4-methylpiperazin-1-yl)methyl)phenyl)ethanesulfonamide (0.150 g, 0.324 mmol), triethylamine (0.180 mL, 1.294 mmol) and 2,2-difluoroacetic anhydride (0.070 mL, 0.647 mmol) in tetrahydrofuran (10 mL) prepared at the room temperature was heated at reflux for 12 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(3-((4-methylpiperazin-1-yl)methyl)phenyl)ethanesulfonamide as yellow oil (0.090 g, 53.1%).

$^1$H NMR (400 MHz, CDCl$_3$) δ 7.87 (dd, 1H, J=8.1, 1.7 Hz), 7.75-7.65 (m, 2H), 7.34-7.18 (m, 4H), 7.12-6.73 (m, 1H), 5.06 (s, 2H), 3.50 (s, 2H), 3.15 (q, 2H, J=7.4 Hz), 2.71-2.40 (m, 8H), 2.37 (s, 3H), 1.47 (t, 3H, J=7.4 Hz); LRMS (ES) m/z 524.50 (M$^+$+1).

EXAMPLE 115

Compound 11406, N-(3-((4-acetylpiperazin-1-yl)methyl)phenyl)-N-(2-fluoro-4-(5-(trifluoromethyl)-1,3,4-oxadiazol-2-yl)benzyl)ethanesulfonamide

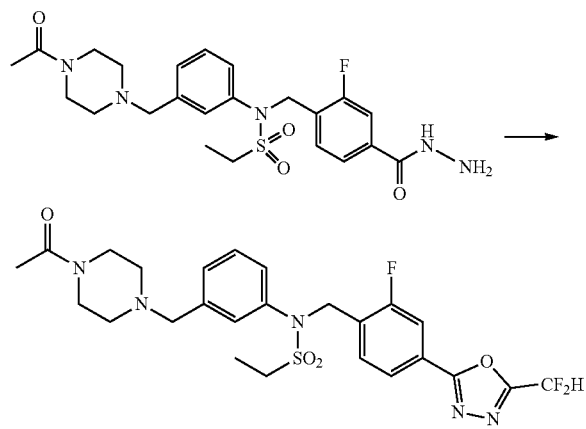

A mixture of N-(3-((4-acetylpiperazin-1-yl)methyl)phenyl)-N-(2-fluoro-4-(hydrazinecarbonyl)benzyl)ethanesulfonamide (0.052 g, 0.106 mmol), triethylamine (0.059 mL, 0.423 mmol) and trifluoroacetic anhydride (0.030 mL, 0.212 mmol) in tetrahydrofuran (10 mL) prepared at the room temperature was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 100%) to give N-(3-((4-acetylpiperazin-1-yl)methyl)phenyl)-N-(2-fluoro-4-(5-(trifluoromethyl)-1,3,4-oxadiazol-2-yl)benzyl)ethanesulfonamide as yellow solid (0.021 g, 34.9%).

$^1$H NMR (400 MHz, CDCl$_3$) δ 7.88 (dd, 1H, J=8.0, 1.6 Hz), 7.77-7.68 (m, 2H), 7.61 (s, 1H), 7.48-7.32 (m, 3H), 5.07 (s, 2H), 4.18 (s, 2H), 3.85 (s, 2H), 3.18 (q, 3H, J=7.4 Hz), 3.07 (s, 5H), 2.13 (s, 3H), 1.46 (t, 3H, J=7.4 Hz); LRMS (ES) m/z 570.56 (M$^+$+1).

EXAMPLE 116

Compound 11411, N-(3-chloro-4-fluorophenyl)-N-((5-(5-(difluoromethyl)-1,3,4-oxadiazol-2-yl)pyridin-2-yl)methyl)ethanesulfonamide

[Step 1] N-(3-chloro-4-fluorophenyl)ethanesulfonamide

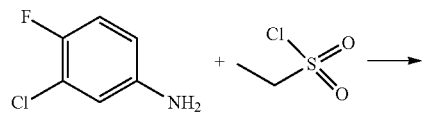

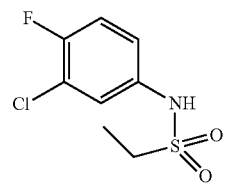

A solution of 3-chloro-4-fluoroaniline (2.000 g, 13.740 mmol), pyridine (1.328 mL, 16.488 mmol) and ethanesulfonyl chloride (1.943 g, 15.114 mmol) in dichloromethane (100 mL) was stirred at the room temperature for 5 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(3-chloro-4-fluorophenyl)ethanesulfonamide, 2.100 g, 64.3%, black solid).

[Step 2] methyl 6-((N-(3-chloro-4-fluorophenyl)ethylsulfonamido)methyl)nicotinate

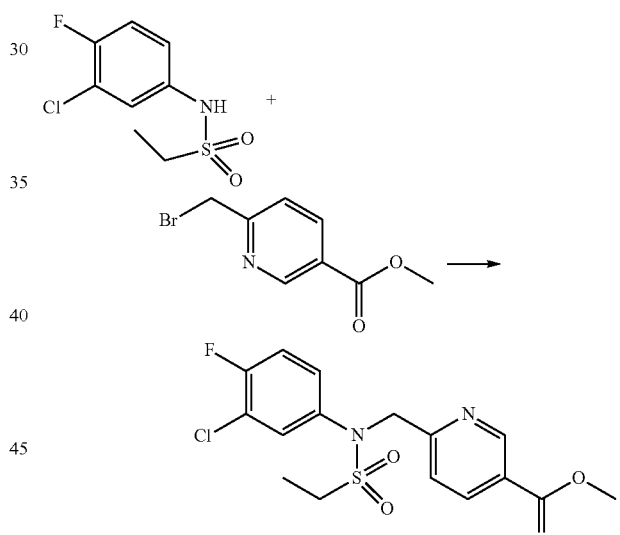

A solution of methyl 6-(bromomethyl)nicotinate (0.658 g, 2.861 mmol) and potassium iodide (0.086 g, 0.520 mmol) in N,N-dimethylformide (30 mL) was mixed at 50° C. with N-(3-chloro-4-fluorophenyl)ethanesulfonamide (0.600 g, 2.601 mmol) and potassium carbonate (0.539 g, 3.902 mmol). The reaction mixture was stirred at the same temperature for 12 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 6-((N-(3-chloro-4-fluorophenyl)ethylsulfonamido)methyl)nicotinate as yellow solid (0.510 g, 50.7%).

405

[Step 3] N-(3-chloro-4-fluorophenyl)-N-((5-(hydrazinecarbonyl)pyridin-2-yl)methyl)ethanesulfonamide

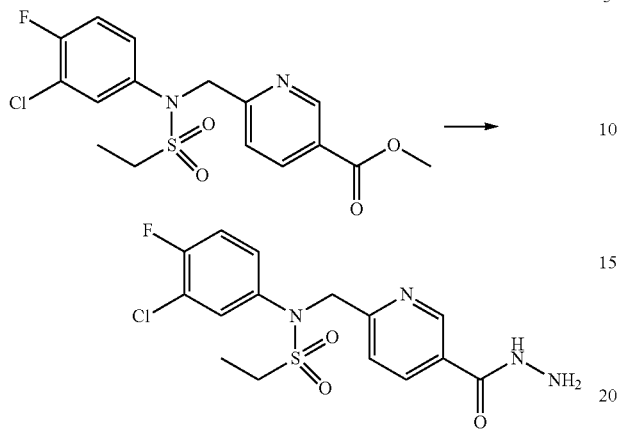

A solution of methyl 6-((N-(3-chloro-4-fluorophenyl)ethylsulfonamido)methyl)nicotinate (0.510 g, 1.318 mmol) and hydrazine monohydrate (0.641 mL, 13.184 mmol) in ethanol (10 mL) was stirred at 90° C. for 12 hr, cooled down to the room temperature to terminate the reaction and concentrated under the reduced pressure to remove the solvent. The title compound was used without further purification (N-(3-chloro-4-fluorophenyl)-N-((5-(hydrazinecarbonyl)pyridin-2-yl)methyl)ethanesulfonamide, 0.300 g, 58.8%, white solid).

[Step 4] Compound 11411

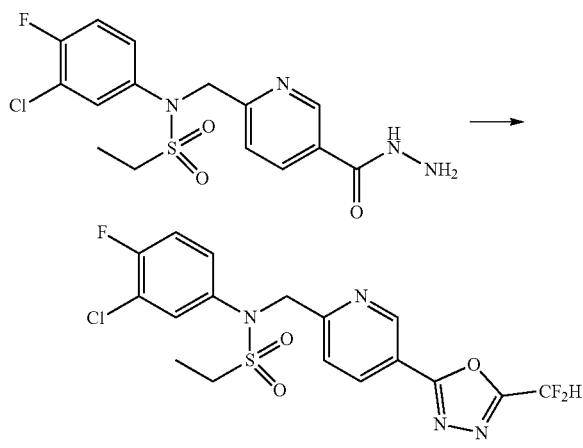

A solution of N-(3-chloro-4-fluorophenyl)-N-((5-(hydrazinecarbonyl)pyridin-2-yl)methyl)ethanesulfonamide (0.150 g, 0.388 mmol), triethylamine (0.216 mL, 1.551 mmol) and 2,2-difluoroacetic anhydride (0.084 mL, 0.776 mmol) in tetrahydrofuran (10 mL) was stirred at 90° C. for 5 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give

406

N-(3-chloro-4-fluorophenyl)-N-((5-(5-(difluoromethyl)-1,3,4-oxadiazol-2-yl)pyridin-2-yl)methyl)ethanesulfonamide as white solid (0.092 g, 53.1%).

$^1$H NMR (400 MHz, CDCl$_3$) δ 9.26 (dd, 1H, J=2.3, 0.9 Hz), 8.42 (ddd, 1H, J=8.3, 2.3, 0.7 Hz), 7.70 (dd, 1H, J=8.2, 0.9 Hz), 7.54 (ddd, 1H, J=6.5, 2.7, 0.7 Hz), 7.38-7.26 (m, 1H), 7.16-7.09 (m, 1H), 7.09-6.81 (m, 1H), 5.13 (s, 2H), 3.21 (qd, 2H, J=7.4, 0.7 Hz), 1.45 (td, 3H, J=7.4, 0.8 Hz); LRMS (ES) m/z 447.44 (M$^+$+1).

EXAMPLE 117

Compound 11412, N-((5-(5-(difluoromethyl)-1,3,4-oxadiazol-2-yl)pyridin-2-yl)methyl)-N-phenylethanesulfonamide

[Step 1] N-phenylethanesulfonamide

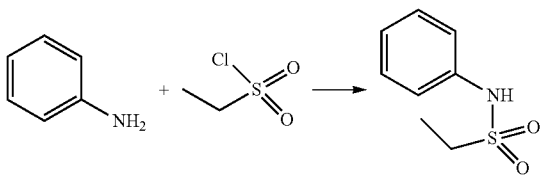

Triethylamine (1.946 mL, 13.959 mmol) was added to solution of aniline (0.980 mL, 10.738 mmol) in dichloromethane (12 mL) prepared at 0° C., and the mixture was stirred for 20 min at the same temperature. The reaction mixture was treated with ethanesulfonyl chloride (1.119 mL, 11.811 mmol and stirred for additional 24 hr at the room temperature. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 40 g cartridge; ethyl acetate/hexane=0% to 15%) to give N-phenylethanesulfonamide as yellow oil (1.400 g, 70.4%).

[Step 2] methyl 6-((N-phenylethylsulfonamido)methyl)nicotinate

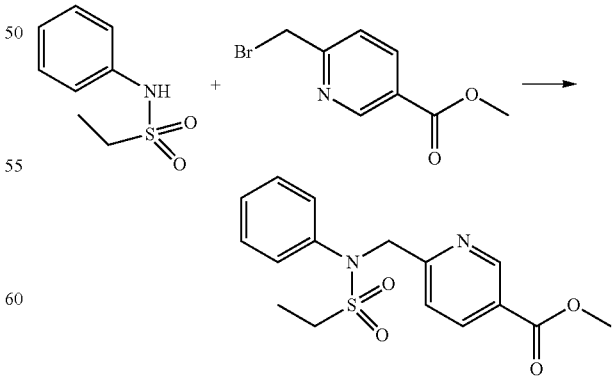

A solution of methyl 6-(bromomethyl)nicotinate (0.710 g, 3.088 mmol) and potassium iodide (0.093 g, 0.561 mmol) in N,N-dimethylformide (30 mL) was mixed at the room temperature with N-phenylethanesulfonamide (0.520 g, 2.807 mmol) and potassium carbonate (0.582 g, 4.211 mmol). The reaction mixture was stirred at the same temperature for 12 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 100%) to give methyl 6-((N-phenylethylsulfonamido) methyl)nicotinate as yellow solid (0.500 g, 53.3%).

[Step 3] N-((5-(hydrazinecarbonyl)pyridin-2-yl) methyl)-N-phenylethanesulfonamide

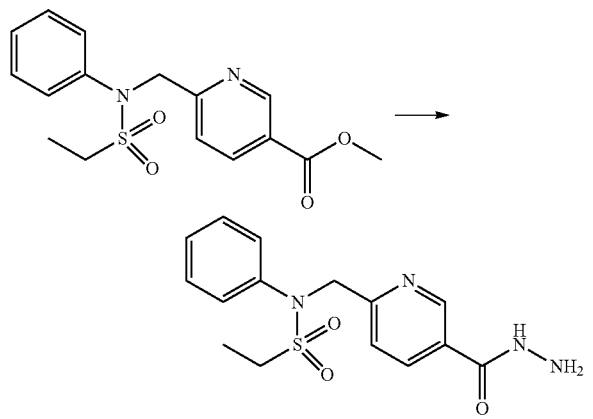

A solution of methyl 6-((N-phenylethylsulfonamido) methyl)nicotinate (0.300 g, 0.897 mmol) and hydrazine monohydrate (0.436 mL, 8.972 mmol) in ethanol (10 mL) was stirred at 90° C. for 12 hr, cooled down to the room temperature to terminate the reaction, and concentrated under the reduced pressure to remove the solvent. The title compound was used without further purification (N-((5-(hydrazinecarbonyl)pyridin-2-yl)methyl)-N-phenylethanesulfonamide, 0.220 g, 73.3%, white solid).

[Step 4] Compound 11412

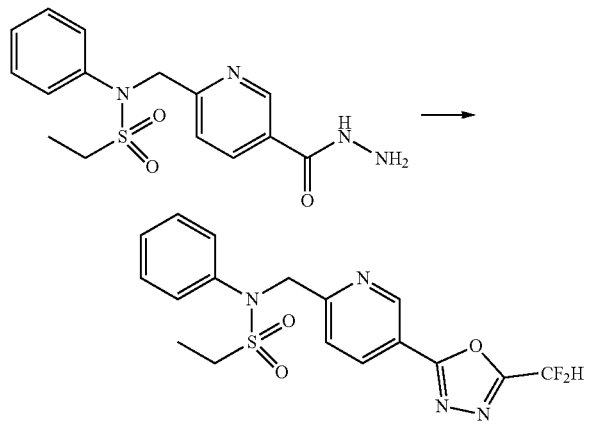

A solution of N-((5-(hydrazinecarbonyl)pyridin-2-yl) methyl)-N-phenylethanesulfonamide (0.220 g, 0.658 mmol), triethylamine (0.367 mL, 2.632 mmol) and 2,2-difluoroacetic anhydride (0.143 mL, 1.316 mmol) in tetrahydrofuran (10 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 50%) to give N-((5-(5-(difluoromethyl)-1,3,4-oxadiazol-2-yl)pyridin-2-yl)methyl)-N-phenylethanesulfonamide as white solid (0.120 g, 46.2%).

¹H NMR (400 MHz, CDCl₃) δ 9.23 (dd, 1H, J=2.2, 0.8 Hz), 8.42 (dd, 1H, J=8.3, 2.2 Hz), 7.80 (dd, 1H, J=8.3, 0.8 Hz), 7.48-7.24 (m, 5H), 7.09-6.80 (m, 1H), 5.22 (s, 2H), 3.21 (q, 2H, J=7.4 Hz), 1.46 (t, 3H, J=7.4 Hz); LRMS (ES) m/z 395.43 (M⁺+1).

EXAMPLE 118

Compound 11426, N-((5-(5-(difluoromethyl)-1,3,4-oxadiazol-2-yl)pyridin-2-yl)methyl)-1-(methylsulfonyl)-N-phenylpiperidine-4-sulfonamide

[Step 1] methyl 6-(((1-(methylsulfonyl)-N-phenylpiperidine)-4-sulfonamido)methyl)nicotinate

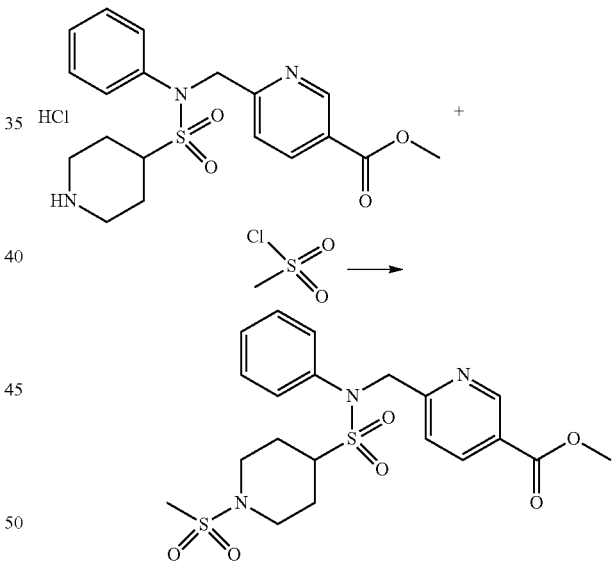

A solution of methyl 6-((N-phenylpiperidine-4-sulfonamido)methyl)nicotinate hydrochloride (0.165 g, 0.387 mmol), triethylamine (0.081 mL, 0.581 mmol) and methanesulfonyl chloride (0.036 mL, 0.465 mmol) in dichloromethane (10 mL) was stirred at the room temperature for 5 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 80%) to give methyl 6-(((1-(methylsulfonyl)-N-phenylpiperidine)-4-sulfonamido)methyl)nicotinate as yellow solid (0.110 g, 60.7%).

[Step 2] N-((5-(hydrazinecarbonyl)pyridin-2-yl)methyl)-1-(methylsulfonyl)-N-phenylpiperidine-4-sulfonamide

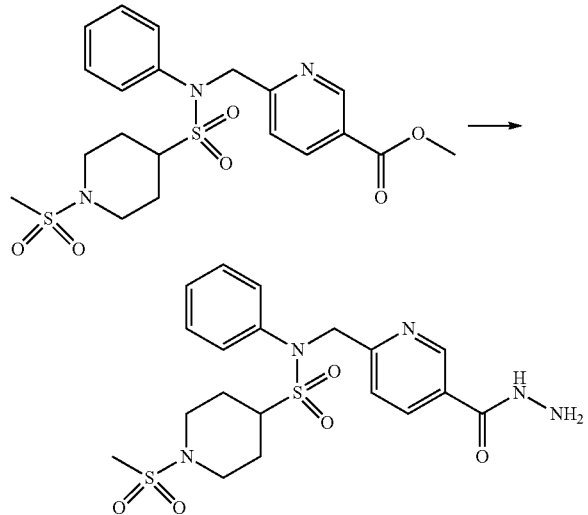

A solution of methyl 6-(((1-(methylsulfonyl)-N-phenylpiperidine)-4-sulfonamido)methyl)nicotinate (0.110 g, 0.235 mmol) and hydrazine monohydrate (0.118 g, 2.353 mmol) in ethanol (10 mL) was stirred at the room temperature for 12 hr and concentrated under the reduced pressure to remove the solvent. Then, water was added to the concentrate, followed by extraction with dichloromethane. The organic layer was washed with aqueous saturated sodium bicarbonate solution, dried with anhydrous MgSO₄, filtered, and concentrated in vacuo. The title compound was used without further purification (N-((5-(hydrazinecarbonyl)pyridin-2-yl)methyl)-1-(methylsulfonyl)-N-phenylpiperidine-4-sulfonamide, 0.086 g, 78.2%, yellow solid).

[Step 3] Compound 11426

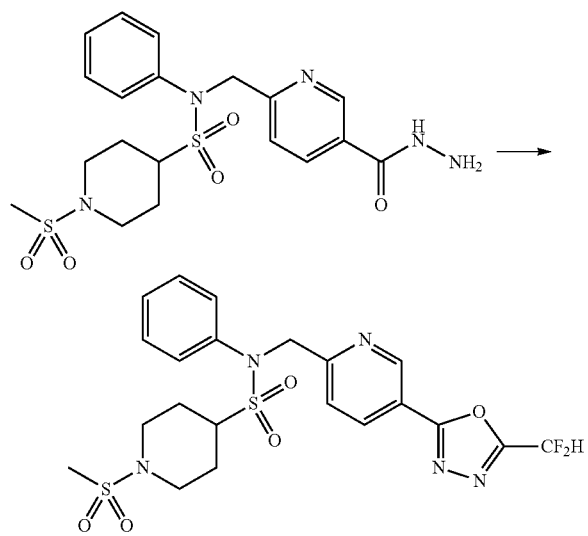

A mixture of N-((5-(hydrazinecarbonyl)pyridin-2-yl)methyl)-1-(methylsulfonyl)-N-phenylpiperidine-4-sulfonamide (0.086 g, 0.184 mmol), triethylamine (0.103 mL, 0.736 mmol) and 2,2-difluoroacetic anhydride (0.040 mL, 0.368 mmol) in tetrahydrofuran (10 mL) prepared at the room temperature was heated at reflux for 12 hr and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; methanol/dichloromethane=0% to 5%) to give N-((5-(5-(difluoromethyl)-1,3,4-oxadiazol-2-yl)pyridin-2-yl)methyl)-1-(methylsulfonyl)-N-phenylpiperidine-4-sulfonamide as yellow solid (0.053 g, 54.6%).

$^1$H NMR (400 MHz, CDCl$_3$) δ 9.23 (s, 1H), 8.40 (dd, 1H, J=8.3, 2.2 Hz), 7.71 (d, 1H, J=8.2 Hz), 7.46-7.32 (m, 3H), 7.34-7.26 (m, 2H), 7.11-6.78 (m, 1H), 5.21 (s, 2H), 3.96-3.88 (m, 2H), 3.31-3.21 (m, 1H), 2.86-2.76 (m, 5H), 2.32-2.23 (m, 2H), 2.15-2.01 (m, 2H); LRMS (ES) m/z 528.51 (M$^+$+1).

EXAMPLE 119

Compound 11427, N-(4-(5-(difluoromethyl)-1,3,4-oxadiazol-2-yl)-2-fluorobenzyl)-N-(3-(1-methylpiperidin-4-yl)phenyl)ethanesulfonamide

[Step 1] tert-butyl 4-(3-(ethylsulfonamido)phenyl)-3,6-dihydropyridine-1(2H)-carboxylate

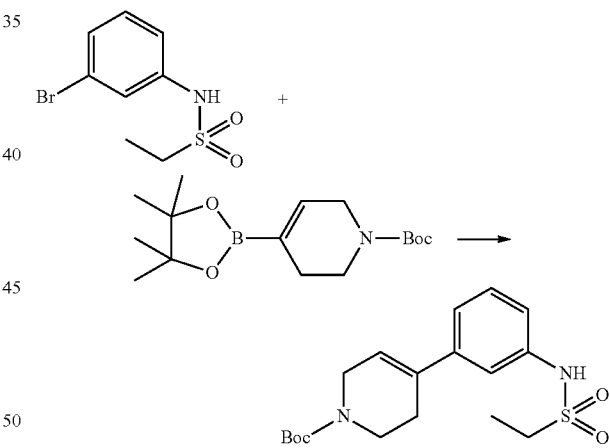

A mixture of N-(3-bromophenyl)ethanesulfonamide (1.000 g, 3.786 mmol), tert-butyl 4-(4,4,5,5-tetramethyl-1,3,2-dioxaborolan-2-yl)-3,6-dihydropyridine-1(2H)-carboxylate (1.288 g, 4.164 mmol), [1,1'-Bis(di-tert-butylphosphino)-ferrocene]palladium(II)Dichloride (0.247 g, 0.379 mmol) and sodium carbonate (0.602 g, 5.679 mmol) in 1,4-dioxane (50 mL)/water (10 mL) prepared at the room temperature was heated at reflux for 12 hr, cooled down to the ambient temperature and filtered through a celite pad to remove solids. Then, water was added to the filtrate, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=0% to 30%) to give tert-butyl 4-(3-(ethylsulfonamido)phenyl)-3,6-dihydropyridine-1(2H)-carboxylate as yellow solid (1.300 g, 93.7%).

[Step 2] tert-butyl 4-(3-(ethylsulfonamido)phenyl)piperidine-1-carboxylate

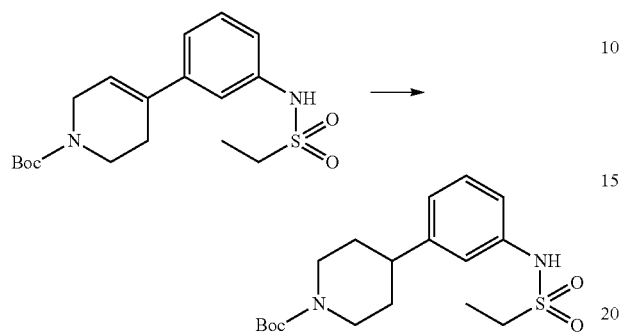

A solution of tert-butyl 4-(3-(ethylsulfonamido)phenyl)-3,6-dihydropyridine-1(2H)-carboxylate (0.900 g, 2.456 mmol) in Pd/C (50 mg) and methanol (20 mL) was stirred at the room temperature for 12 hr under the presence of H2 gas and filtered through a celite pad to remove solids. Then, water was added to the filtrate, followed by extraction with ethyl acetate. The organic layer was washed with aqueous saturated sodium chloride solution, dried with anhydrous MgSO$_4$, filtered, and concentrated in vacuo. The title compound was used without further purification (tert-butyl 4-(3-(ethylsulfonamido)phenyl)piperidine-1-carboxylate, 0.820 g, 90.6%, yellow solid).

[Step 3] tert-butyl 4-(3-(N-(2-fluoro-4-(methoxycarbonyl)benzyl)ethylsulfonamido)phenyl)piperidine-1-carboxylate

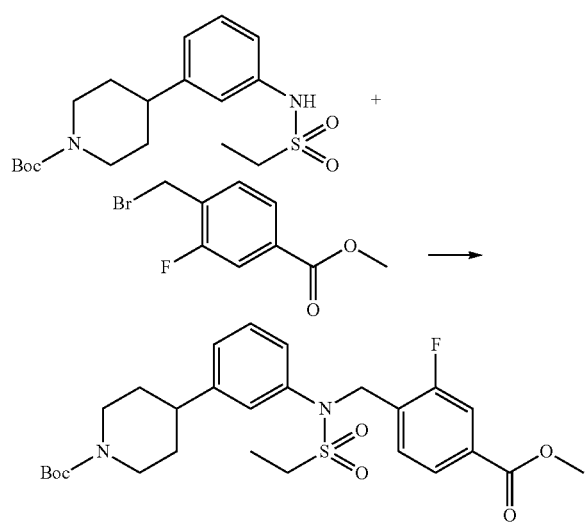

A solution of methyl 4-(bromomethyl)-3-fluorobenzoate (0.605 g, 2.448 mmol) and potassium iodide (0.074 g, 0.445 mmol) in N,N-dimethylformide (10 mL) was stirred at the room temperature for 30 min, and mixed with tert-butyl 4-(3-(ethylsulfonamido)phenyl)piperidine-1-carboxylate (0.820 g, 2.225 mmol) and potassium carbonate (0.461 g, 3.338 mmol). The reaction mixture was stirred at 50° C. for additional 12 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give tert-butyl 4-(3-(N-(2-fluoro-4-(methoxycarbonyl)benzyl)ethylsulfonamido)phenyl)piperidine-1-carboxylate as yellow solid (0.900 g, 75.6%).

[Step 4] methyl 3-fluoro-4-((N-(3-(piperidin-4-yl)phenyl)ethylsulfonamido)methyl)benzoate hydrochloride

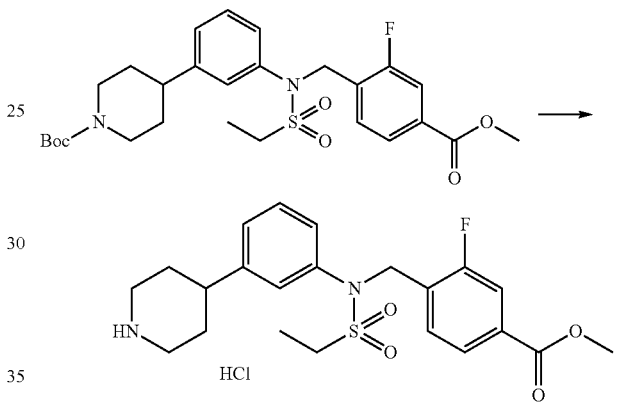

A solution of tert-butyl 4-(3-(N-(2-fluoro-4-(methoxycarbonyl)benzyl)ethylsulfonamido)phenyl)piperidine-1-carboxylate (0.900 g, 1.683 mmol) and hydrochloric acid (4.00 M solution in 1,4-dioxane, 1.683 mL, 6.734 mmol) in dichloromethane (10 mL) was stirred at the room temperature for 5 hr, and concentrated under the reduced pressure to remove the solvent. The title compound was used without further purification (methyl 3-fluoro-4-((N-(3-(piperidin-4-yl)phenyl)ethylsulfonamido)methyl)benzoate hydrochloride, 0.750 g, 94.6%, yellow solid).

[Step 5] methyl 3-fluoro-4-((N-(3-(1-methylpiperidin-4-yl)phenyl)ethylsulfonamido)methyl)benzoate

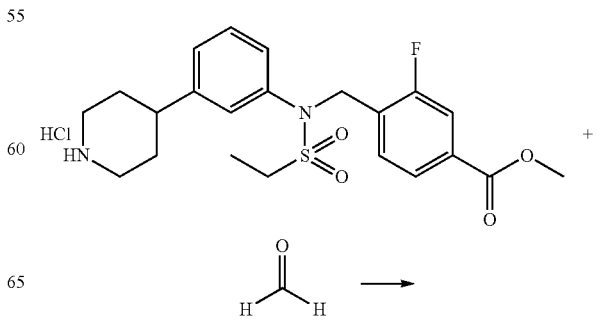

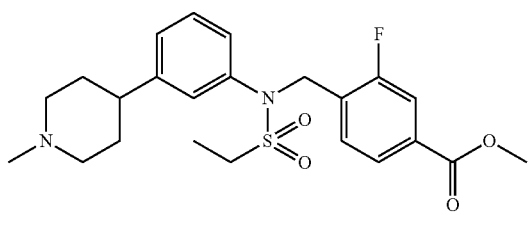

A solution of methyl 3-fluoro-4-((N-(3-(piperidin-4-yl)phenyl)ethylsulfonamido)methyl)benzoate hydrochloride (0.300 g, 0.637 mmol), formaldehyde (0.057 g, 1.911 mmol) and acetic acid (0.044 mL, 0.764 mmol) in dichloromethane (10 mL) was stirred at the room temperature for 30 min, and mixed with sodium triacetoxyborohydride (0.202 g, 0.955 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 12 g cartridge; methanol/dichloromethane=0% to 5%) to give methyl 3-fluoro-4-((N-(3-(1-methylpiperidin-4-yl)phenyl)ethylsulfonamido)methyl)benzoate as yellow solid (0.264 g, 92.4%).

[Step 6] N-(2-fluoro-4-(hydrazinecarbonyl)benzyl)-N-(3-(1-methylpiperidin-4-yl)phenyl)ethanesulfonamide

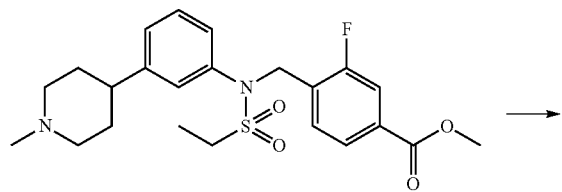

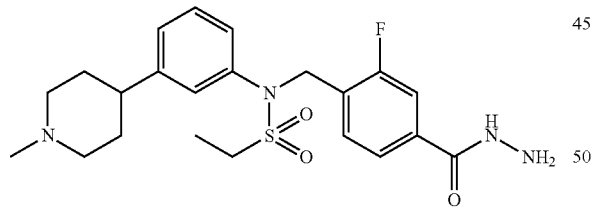

A solution of methyl 3-fluoro-4-((N-(3-(1-methylpiperidin-4-yl)phenyl)ethylsulfonamido)methyl)benzoate (0.264 g, 0.589 mmol) and hydrazine monohydrate (0.286 mL, 5.886 mmol) in ethanol (10 mL) was stirred at 90° C. for 12 hr and cooled down to the room temperature to terminate the reaction. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(2-fluoro-4-(hydrazinecarbonyl)benzyl)-N-(3-(1-methylpiperidin-4-yl)phenyl)ethanesulfonamide, 0.176 g, 66.7%, yellow solid).

[Step 7] Compound 11427

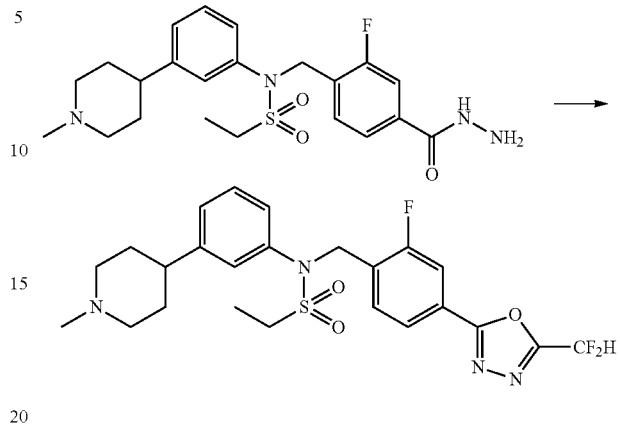

A solution of N-(2-fluoro-4-(hydrazinecarbonyl)benzyl)-N-(3-(1-methylpiperidin-4-yl)phenyl)ethanesulfonamide (0.176 g, 0.392 mmol), triethylamine (0.219 mL, 1.569 mmol) and 2,2-difluoroacetic anhydride (0.085 mL, 0.785 mmol) in dichloromethane (10 mL) was stirred at the room temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(3-(1-methylpiperidin-4-yl)phenyl)ethanesulfonamide as yellow solid (0.098 g, 49.1%).

$^1$H NMR (400 MHz, CDCl$_3$) δ 7.87 (dd, 1H, J=8.0, 1.7 Hz), 7.76-7.64 (m, 2H), 7.29 (d, 1H, J=15.5 Hz), 7.24-7.11 (m, 3H), 7.08-6.73 (m, 1H), 5.05 (s, 2H), 3.14 (q, 4H, J=7.4 Hz), 2.54 (tt, 1H, J=11.9, 3.8 Hz), 2.48 (s, 3H), 2.35-2.24 (m, 2H), 2.07-1.91 (m, 2H), 1.89-1.81 (m, 2H), 1.46 (t, 3H, J=7.4 Hz); LRMS (ES) m/z 509.40 (M$^+$+1).

EXAMPLE 120

Compound 11428, N-((5-(5-(difluoromethyl)-1,3,4-oxadiazol-2-yl)pyridin-2-yl)methyl)-N-phenyltetrahydrofuran-3-sulfonamide

[Step 1] N-phenyltetrahydrofuran-3-sulfonamide

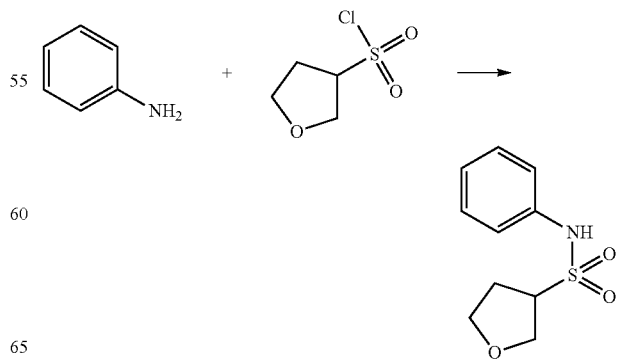

A solution of aniline (0.147 mL, 1.611 mmol), triethylamine (0.337 mL, 2.416 mmol) and tetrahydrofuran-3-sulfonyl chloride (0.330 g, 1.933 mmol) in dichloromethane (10 mL) was stirred at the room temperature for 5 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give N-phenyltetrahydrofuran-3-sulfonamide as yellow solid (0.300 g, 82.0%).

[Step 2] methyl 6-(((N-phenyltetrahydrofuran)-3-sulfonamido)methyl)nicotinate

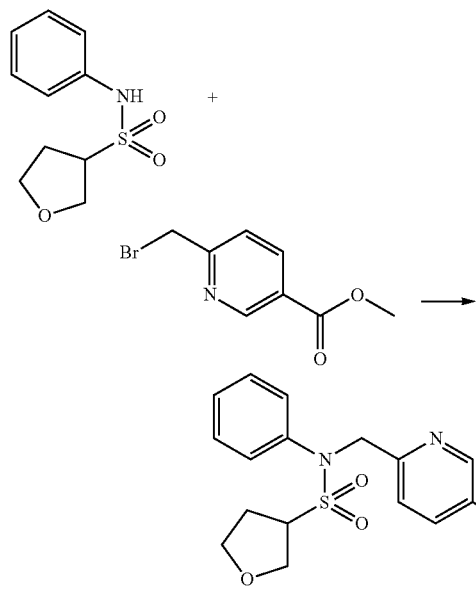

A solution of N-phenyltetrahydrofuran-3-sulfonamide (0.300 g, 1.320 mmol), potassium carbonate (0.274 g, 1.980 mmol), methyl 6-(bromomethyl)nicotinate (0.334 g, 1.452 mmol) and potassium iodide (0.110 g, 0.660 mmol) in N,N-dimethylformide (10 mL) was stirred at the room temperature for 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 70%) to give methyl 6-(((N-phenyltetrahydrofuran)-3-sulfonamido)methyl)nicotinate as yellow solid (0.120 g, 24.2%).

[Step 3] N-((5-(hydrazinecarbonyl)pyridin-2-yl)methyl)-N-phenyltetrahydrofuran-3-sulfonamide

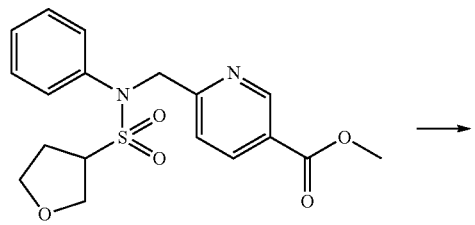

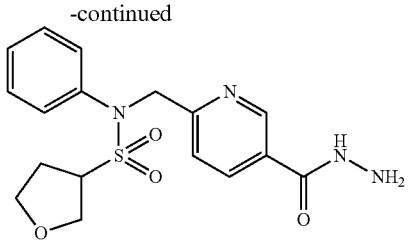

A solution of methyl 6-(((N-phenyltetrahydrofuran)-3-sulfonamido)methyl)nicotinate (0.120 g, 0.319 mmol) and hydrazine monohydrate (0.155 mL, 3.188 mmol) in ethanol (10 mL) was stirred at 90° C. for 12 hr cooled down to the room temperature to terminate the reaction and concentrated under the reduced pressure to remove the solvent. Then, water was added to the concentrate, followed by extraction with dichloromethane. The organic layer was washed with aqueous saturated sodium bicarbonate solution, dried with anhydrous MgSO$_4$, filtered, and concentrated in vacuo. The title compound was used without further purification (N-((5-(hydrazinecarbonyl)pyridin-2-yl)methyl)-N-phenyltetrahydrofuran-3-sulfonamide, 0.082 g, 68.3%, white solid).

[Step 4] Compound 11428

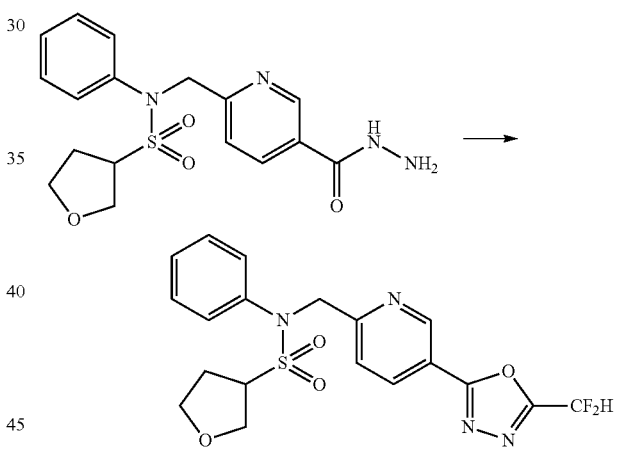

A solution of N-((5-(hydrazinecarbonyl)pyridin-2-yl)methyl)-N-phenyltetrahydrofuran-3-sulfonamide (0.082 g, 0.218 mmol), triethylamine (0.121 mL, 0.871 mmol) and 2,2-difluoroacetic anhydride (0.047 mL, 0.436 mmol) in tetrahydrofuran (10 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give N-((5-(5-(difluoromethyl)-1,3,4-oxadiazol-2-yl)pyridin-2-yl)methyl)-N-phenyltetrahydrofuran-3-sulfonamide as yellow solid (0.051 g, 53.6%).

$^1$H NMR (400 MHz, CDCl$_3$) δ 9.23 (dd, 1H, J=2.3, 0.9 Hz), 8.39 (dd, 1H, J=8.3, 2.2 Hz), 7.72 (dd, 1H, J=8.2, 0.8 Hz), 7.47-7.25 (m, 5H), 7.11-6.77 (m, 1H), 5.28-5.13 (m, 2H), 4.20-3.91 (m, 4H), 3.85 (ddd, 1H, J=8.8, 7.3, 6.1 Hz), 2.45-2.20 (m, 2H); LRMS (ES) m/z 437.41 (M$^+$+1).

EXAMPLE 121

Compound 11429, N-(3-chloro-4-fluorophenyl)-N-((5-(5-(trifluoromethyl)-1,3,4-oxadiazol-2-yl)pyridin-2-yl)methyl)ethanesulfonamide

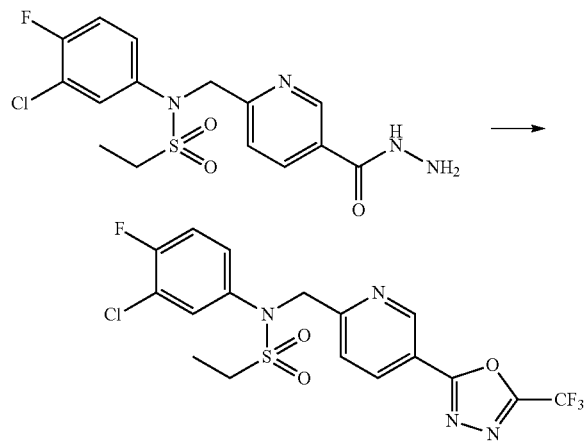

A solution of N-(3-chloro-4-fluorophenyl)-N-((5-(hydrazinecarbonyl)pyridin-2-yl)methyl)ethanesulfonamide (0.068 g, 0.176 mmol), triethylamine (0.098 mL, 0.703 mmol) and trifluoroacetic anhydride (0.050 mL, 0.352 mmol) in tetrahydrofuran (10 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 50%) to give N-(3-chloro-4-fluorophenyl)-N-((5-(5-(trifluoromethyl)-1,3,4-oxadiazol-2-yl)pyridin-2-yl)methyl)ethanesulfonamide as yellow solid (0.042 g, 51.4%).

$^1$H NMR (400 MHz, CDCl$_3$) δ 9.26 (dd, 1H, J=2.3, 0.8 Hz), 8.42 (dd, 1H, J=8.2, 2.2 Hz), 7.70 (dd, 1H, J=8.3, 0.8 Hz), 7.54 (dd, 1H, J=6.4, 2.7 Hz), 7.34 (ddd, 1H, J=8.9, 4.1, 2.7 Hz), 7.12 (t, 1H, J=8.6 Hz), 5.13 (s, 2H), 3.20 (q, 2H, J=7.4 Hz), 1.45 (t, 3H, J=7.4 Hz); LRMS (ES) m/z 465.30 (M$^+$+1).

EXAMPLE 122

Compound 11430, N-phenyl-N-((5-(5-(trifluoromethyl)-1,3,4-oxadiazol-2-yl)pyridin-2-yl)methyl)ethanesulfonamide

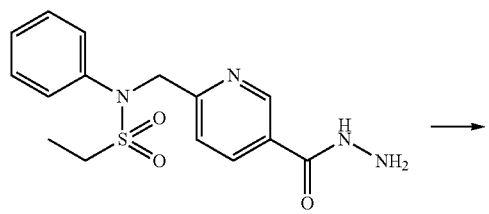

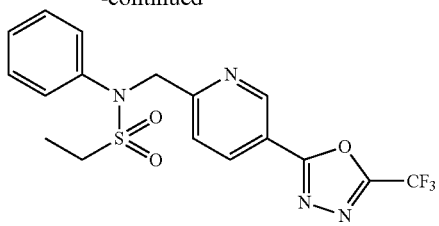

A solution of N-((5-(hydrazinecarbonyl)pyridin-2-yl)methyl)-N-phenylethanesulfonamide (0.056 g, 0.167 mmol), triethylamine (0.093 mL, 0.670 mmol) and trifluoroacetic anhydride (0.047 mL, 0.335 mmol) in tetrahydrofuran (10 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 60%) to give N-phenyl-N-((5-(5-(trifluoromethyl)-1,3,4-oxadiazol-2-yl)pyridin-2-yl)methyl)ethanesulfonamide as yellow solid (0.036 g, 52.1%).

$^1$H NMR (400 MHz, CDCl$_3$) δ 9.22 (dd, 1H, J=2.2, 0.8 Hz), 8.38 (dd, 1H, J=8.3, 2.2 Hz), 7.78 (dt, 1H, J=8.3, 0.7 Hz), 7.47-7.40 (m, 2H), 7.45-7.32 (m, 2H), 7.36-7.24 (m, 1H), 5.20 (s, 2H), 3.20 (q, 2H, J=7.4 Hz), 1.50-1.41 (m, 3H); LRMS (ES) m/z 413.0 (M$^+$+1).

EXAMPLE 123

Compound 11431, N-phenyl-N-((5-(5-(trifluoromethyl)-1,3,4-oxadiazol-2-yl)pyridin-2-yl)methyl)tetrahydro-2H-pyran-4-sulfonamide

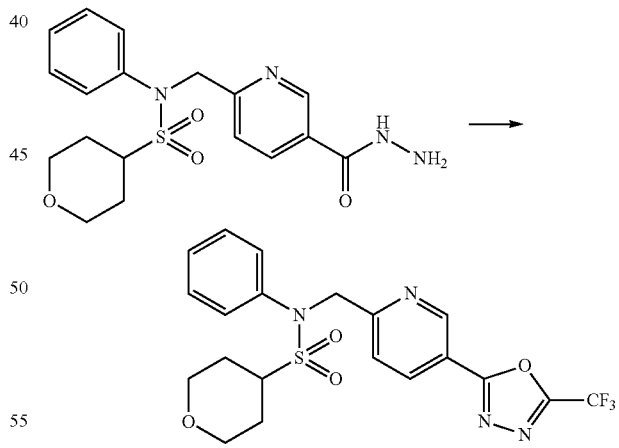

A solution of N-((5-(hydrazinecarbonyl)pyridin-2-yl)methyl)-N-phenyltetrahydro-2H-pyran-4-sulfonamide (0.095 g, 0.243 mmol), triethylamine (0.136 mL, 0.973 mmol) and trifluoroacetic anhydride (0.069 mL, 0.487 mmol) in tetrahydrofuran (10 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 60%) to give N-phenyl-N-((5-(5-(trifluoromethyl)-1,3,4-oxadiazol-2-yl)pyridin-2-yl)methyl)tetrahydro-2H-pyran-4-sulfonamide as white solid (0.056 g, 49.1%).

$^1$H NMR (400 MHz, CDCl$_3$) δ 9.20 (dt, 1H, J=2.1, 1.0 Hz), 8.39 (dt, 1H, J=8.3, 2.0 Hz), 7.78 (dt, 1H, J=8.3, 1.1 Hz), 7.43 (ddd, 2H, J=8.3, 1.8, 0.8 Hz), 7.44-7.32 (m, 2H), 7.36-7.21 (m, 1H), 5.22 (d, 2H, J=1.5 Hz), 4.19-4.07 (m, 2H), 3.46-3.28 (m, 3H), 2.10-1.96 (m, 4H); LRMS (ES) m/z 469.30 (M$^+$+1).

EXAMPLE 124

Compound 11432, N-(3-chloro-4-fluorophenyl)-N-((5-(5-(trifluoromethyl)-1,3,4-oxadiazol-2-yl)pyridin-2-yl)methyl)methanesulfonamide

[Step 1]
N-(3-chloro-4-fluorophenyl)methanesulfonamide

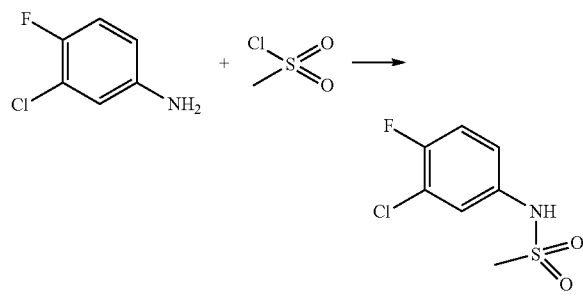

A solution of 3-chloro-4-fluoroaniline (2.000 g, 13.740 mmol), pyridine (1.217 mL, 15.114 mmol) and methanesulfonyl chloride (1.276 mL, 16.488 mmol) in dichloromethane (80 mL) was stirred at the room temperature for 5 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(3-chloro-4-fluorophenyl)methanesulfonamide, 2.600 g, 84.6%, black solid).

[Step 2] methyl 6-((N-(3-chloro-4-fluorophenyl)methylsulfonamido)methyl)nicotinate

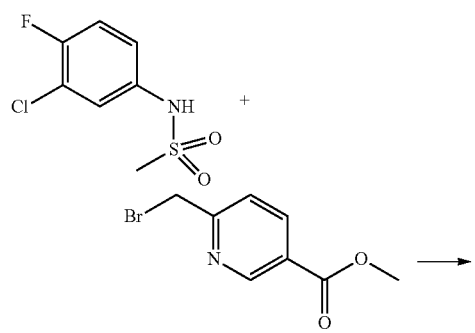

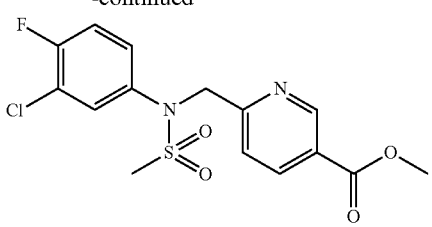

A solution of methyl 6-(bromomethyl)nicotinate (0.339 g, 1.476 mmol) and potassium iodide (0.111 g, 0.671 mmol) in N,N-dimethylformide (10 mL) was stirred at the room temperature for 30 min, and mixed with N-(3-chloro-4-fluorophenyl)methanesulfonamide (0.300 g, 1.341 mmol) and potassium carbonate (0.278 g, 2.012 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 6-((N-(3-chloro-4-fluorophenyl)methylsulfonamido)methyl)nicotinate as yellow solid (0.290 g, 58.0%).

[Step 3] N-(3-chloro-4-fluorophenyl)-N-((5-(hydrazinecarbonyl)pyridin-2-yl)methyl)methanesulfonamide

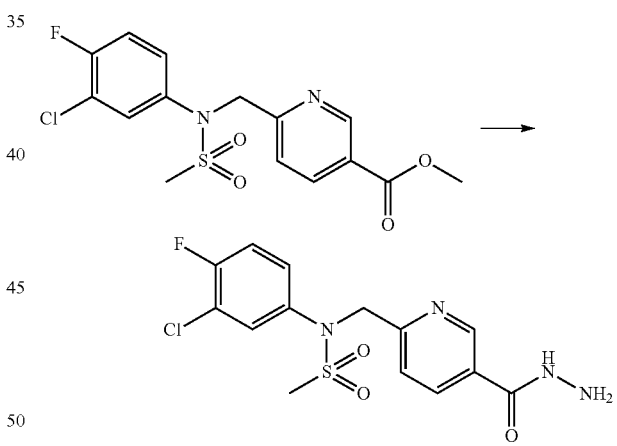

A solution of methyl 6-((N-(3-chloro-4-fluorophenyl)methylsulfonamido)methyl)nicotinate (0.100 g, 0.268 mmol) and hydrazine monohydrate (0.130 mL, 2.682 mmol) in ethanol (10 mL) was stirred at 90° C. for 12 hr, cooled down to the room temperature to terminate the reaction and concentrated under the reduced pressure to remove the solvent. Then, water was added to the concentrate, followed by extraction with dichloromethane. The organic layer was washed with aqueous saturated sodium bicarbonate solution, dried with anhydrous MgSO$_4$, filtered, and concentrated in vacuo. The title compound was used without further purification (N-(3-chloro-4-fluorophenyl)-N-((5-(hydrazinecarbonyl)pyridin-2-yl)methyl)methanesulfonamide, 0.071 g, 71.0%, yellow solid).

[Step 4] Compound 11432

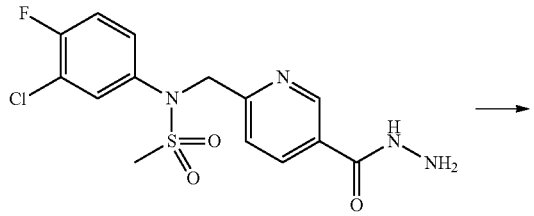

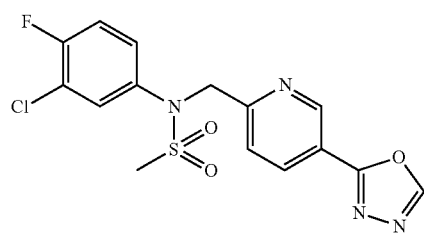

A solution of N-(3-chloro-4-fluorophenyl)-N-((5-(hydrazinecarbonyl)pyridin-2-yl)methyl)methanesulfonamide (0.071 g, 0.190 mmol), triethylamine (0.106 mL, 0.762 mmol) and trifluoroacetic anhydride (0.054 mL, 0.381 mmol) in tetrahydrofuran (10 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(3-chloro-4-fluorophenyl)-N-((5-(5-(trifluoromethyl)-1,3,4-oxadiazol-2-yl)pyridin-2-yl)methyl)methanesulfonamide as yellow solid (0.036 g, 41.9%).

$^1$H NMR (400 MHz, CDCl$_3$) δ 9.29 (dd, 1H, J=2.3, 0.8 Hz), 8.43 (dd, 1H, J=8.2, 2.2 Hz), 7.67 (dt, 1H, J=8.3, 0.7 Hz), 7.54 (dd, 1H, J=6.4, 2.7 Hz), 7.41-7.26 (m, 1H), 7.14 (t, 1H, J=8.6 Hz), 5.11 (s, 2H), 3.09 (d, 3H, J=0.4 Hz); LRMS (ES) m/z 451.38 (M$^+$+1).

EXAMPLE 125

Compound 11433, N-(3-chloro-4-fluorophenyl)-N-((5-(5-(difluoromethyl)-1,3,4-oxadiazol-2-yl)pyridin-2-yl)methyl)methanesulfonamide

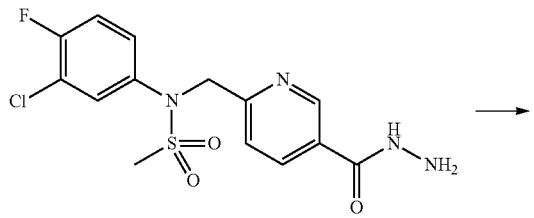

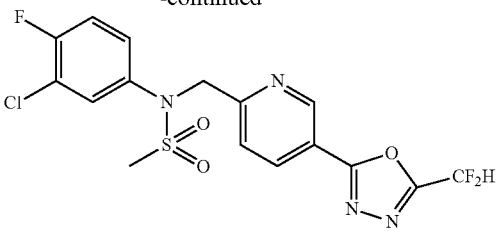

A solution of N-(3-chloro-4-fluorophenyl)-N-((5-(hydrazinecarbonyl)pyridin-2-yl)methyl)methanesulfonamide (0.070 g, 0.188 mmol), triethylamine (0.105 mL, 0.751 mmol) and 2,2-difluoroacetic anhydride (0.047 mL, 0.376 mmol) in tetrahydrofuran (10 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(3-chloro-4-fluorophenyl)-N-((5-(5-(difluoromethyl)-1,3,4-oxadiazol-2-yl)pyridin-2-yl)methyl)methanesulfonamide as yellow solid (0.046 g, 56.6%).

$^1$H NMR (400 MHz, CDCl$_3$) δ 9.29 (d, 1H, J=2.1 Hz), 8.42 (dd, 1H, J=8.2, 2.2 Hz), 7.65 (dd, 1H, J=8.1, 0.8 Hz), 7.54 (dd, 1H, J=6.5, 2.7 Hz), 7.34 (ddd, 1H, J=8.8, 4.1, 2.7 Hz), 7.14 (t, 1H, J=8.7 Hz), 7.10-6.81 (m, 1H), 5.10 (s, 2H), 3.09 (s, 3H); LRMS (ES) m/z 433.40 (M$^+$+1).

EXAMPLE 126

Compound 11447, 1-(1-acetylazetidin-3-yl)-N-(3-chloro-4-fluorophenyl)-N-(4-(5-(difluoromethyl)-1,3,4-oxadiazol-2-yl)-2-fluorobenzyl)piperidine-4-sulfonamide

[Step 1] tert-butyl 4-(N-(3-chloro-4-fluorophenyl)sulfamoyl)piperidine-1-carboxylate

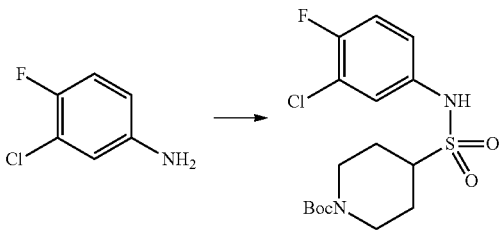 [SMILES: Nc1ccc(F)c(Cl)c1 ; CC(C)(C)OC(=O)N1CCC(S(=O)(=O)Nc2ccc(F)c(Cl)c2)CC1]

A mixture of 3-chloro-4-fluoroaniline (2.200 g, 15.114 mmol) and tert-butyl 4-(chlorosulfonyl)piperidine-1-carboxylate (4.289 g, 15.114 mmol) in dichloromethane (20 mL) was treated at the room temperature with triethylamine (2.528 mL, 18.137 mmol). The reaction mixture was stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=10% to 30%) to give tert-butyl 4-(N-(3-chloro-4-fluorophenyl)sulfamoyl)piperidine-1-carboxylate as pale purple solid (2.940 g, 49.5%).

423

[Step 2] tert-butyl 4-(N-(3-chloro-4-fluorophenyl)-N-(2-fluoro-4-(methoxycarbonyl)benzyl)sulfamoyl)piperidine-1-carboxylate

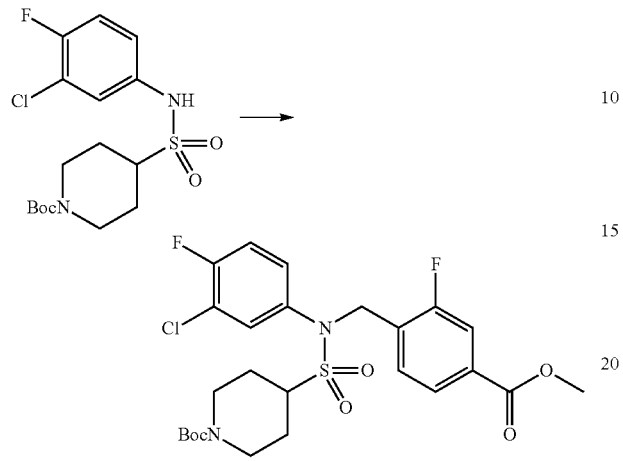

A mixture of tert-butyl 4-(N-(3-chloro-4-fluorophenyl)sulfamoyl)piperidine-1-carboxylate (1.500 g, 3.818 mmol), methyl 4-(bromomethyl)-3-fluorobenzoate (1.132 g, 4.582 mmol), potassium carbonate (0.792 g, 5.727 mmol) and potassium iodide (0.951 g, 5.727 mmol) in N,N-dimethylformide (10 mL) was stirred at the room temperature for 16 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=20% to 50%) to give tert-butyl 4-(N-(3-chloro-4-fluorophenyl)-N-(2-fluoro-4-(methoxycarbonyl)benzyl)sulfamoyl)piperidine-1-carboxylate as white solid (1.860 g, 87.1%).

[Step 3] methyl 4-((N-(3-chloro-4-fluorophenyl)piperidine-4-sulfonamido)methyl)-3-fluorobenzoate hydrochloride

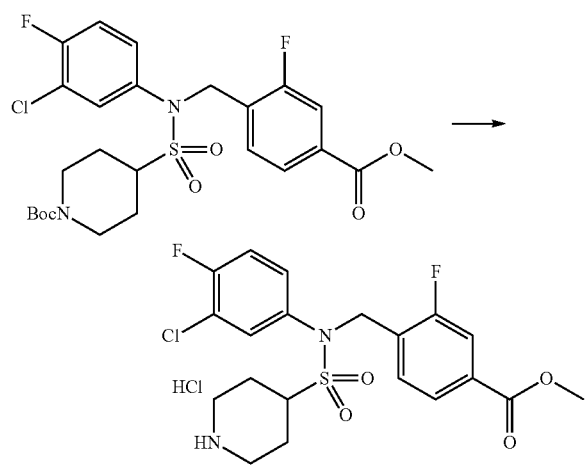

424

A solution of tert-butyl 4-(N-(3-chloro-4-fluorophenyl)-N-(2-fluoro-4-(methoxycarbonyl)benzyl)sulfamoyl)piperidine-1-carboxylate (1.860 g, 3.327 mmol) in 1,4-dioxane (8 mL) was mixed at the room temperature with hydrochloric acid (4.00 M solution in 1,4-dioxane, 8.318 mL, 33.273 mmol), and stirred at the same temperature for 1 hr. The reaction mixture was diluted with ethyl acetate (10 mL) and hexane (50 mL) and stirred. The resulting precipitates were collected by filtration, washed by hexane, and dried to give methyl 4-((N-(3-chloro-4-fluorophenyl)piperidine-4-sulfonamido)methyl)-3-fluorobenzoate hydrochloride as beige solid (1.620 g, 98.3%).

[Step 4] tert-butyl 3-(4-(N-(3-chloro-4-fluorophenyl)-N-(2-fluoro-4-(methoxycarbonyl)benzyl)sulfamoyl)piperidin-1-yl)azetidine-1-carboxylate

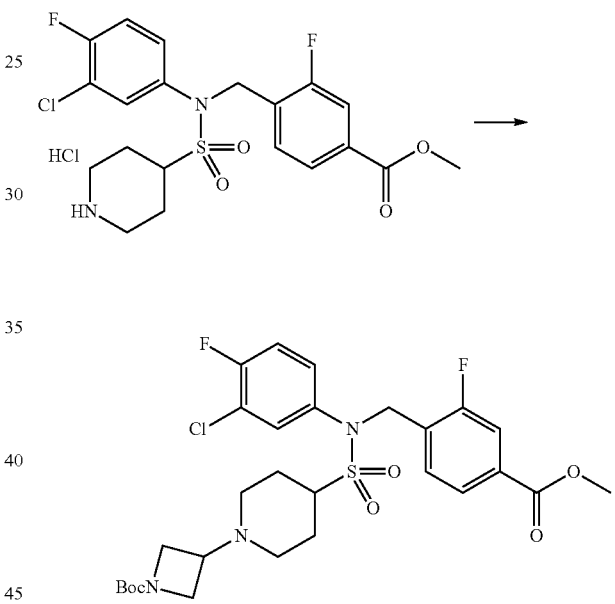

A mixture of methyl 4-((N-(3-chloro-4-fluorophenyl)piperidine-4-sulfonamido)methyl)-3-fluorobenzoate hydrochloride (1.300 g, 2.624 mmol), tert-butyl 3-oxoazetidine-1-carboxylate (0.674 g, 3.937 mmol) and N,N-diisopropylethylamine (0.686 mL, 3.937 mmol) in dichloromethane (50 mL) was treated at the room temperature with sodium triacetoxyborohydride (1.112 g, 5.249 mmol) and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=40% to 70%) to give tert-butyl 3-(4-(N-(3-chloro-4-fluorophenyl)-N-(2-fluoro-4-(methoxycarbonyl)benzyl)sulfamoyl)piperidin-1-yl)azetidine-1-carboxylate as white solid (1.178 g, 73.1%).

[Step 5] tert-butyl 3-(4-(N-(3-chloro-4-fluorophenyl)-N-(2-fluoro-4-(hydrazinecarbonyl)benzyl)sulfamoyl)piperidin-1-yl)azetidine-1-carboxylate

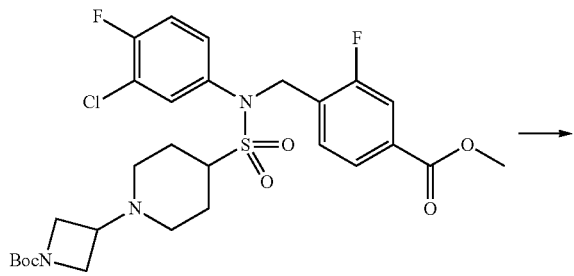

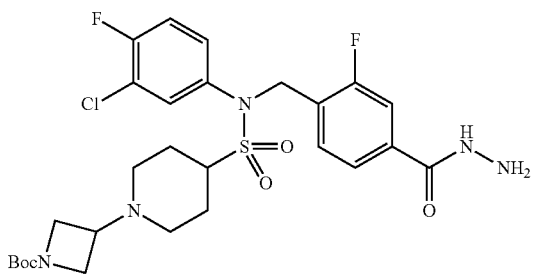

tert-butyl 3-(4-(N-(3-chloro-4-fluorophenyl)-N-(2-fluoro-4-(methoxycarbonyl)benzyl)sulfamoyl)piperidin-1-yl)azetidine-1-carboxylate (1.178 g, 1.918 mmol) and hydrazine monohydrate (0.932 mL, 19.183 mmol) were mixed at the room temperature in ethanol (20 mL), stirred at 110° C. for 2 hr, cooled down to the room temperature to terminate the reaction and concentrated under the reduced pressure to remove the solvent. The residue was diluted with water (100 mL) and stirred. The resulting precipitates were collected by filtration, washed by water, and dried to give tert-butyl 3-(4-(N-(3-chloro-4-fluorophenyl)-N-(2-fluoro-4-(hydrazinecarbonyl)benzyl)sulfamoyl)piperidin-1-yl)azetidine-1-carboxylate as white solid (1.149 g, 97.5%).

[Step 6] tert-butyl 3-(4-(N-(3-chloro-4-fluorophenyl)-N-(4-(2-(2,2-difluoroacetyl)hydrazine-1-carbonyl)-2-fluorobenzyl)sulfamoyl)piperidin-1-yl)azetidine-1-carboxylate

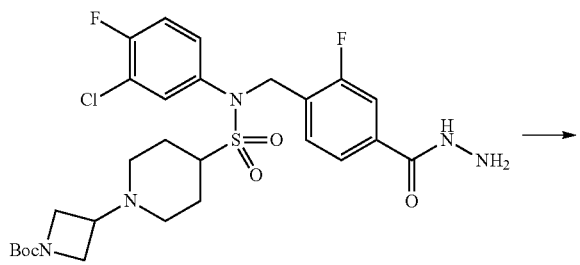

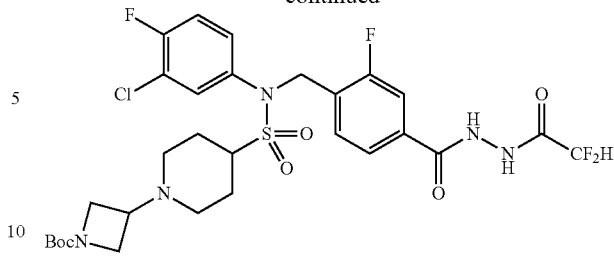

A solution of tert-butyl 3-(4-(N-(3-chloro-4-fluorophenyl)-N-(2-fluoro-4-(hydrazinecarbonyl)benzyl)sulfamoyl)piperidin-1-yl)azetidine-1-carboxylate (1.149 g, 1.871 mmol) in tetrahydrofuran (30 mL) was mixed at 70° C. with 2,2-difluoroacetic anhydride (0.244 mL, 2.245 mmol) and N,N-diisopropylethylamine (0.489 mL, 2.807 mmol), stirred at the same temperature for 1 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=30% to 60%) to give tert-butyl 3-(4-(N-(3-chloro-4-fluorophenyl)-N-(4-(2-(2,2-difluoroacetyl)hydrazine-1-carbonyl)-2-fluorobenzyl)sulfamoyl)piperidin-1-yl)azetidine-1-carboxylate as white solid (1.058 g, 81.7%).

[Step 7] tert-butyl 3-(4-(N-(3-chloro-4-fluorophenyl)-N-(4-(5-(difluoromethyl)-1,3,4-oxadiazol-2-yl)-2-fluorobenzyl)sulfamoyl)piperidin-1-yl)azetidine-1-carboxylate

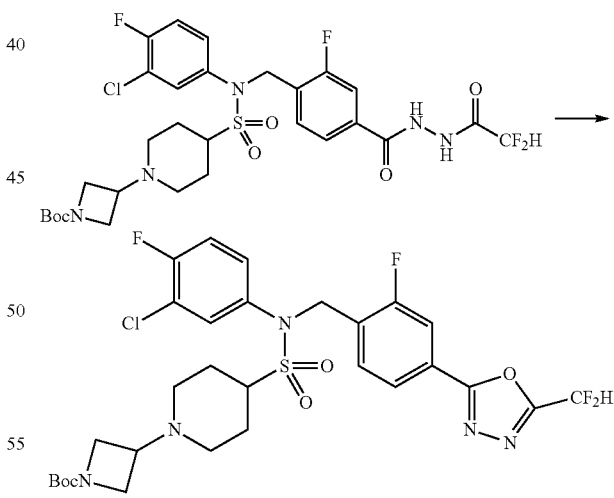

A solution of tert-butyl 3-(4-(N-(3-chloro-4-fluorophenyl)-N-(4-(2-(2,2-difluoroacetyl)hydrazine-1-carbonyl)-2-fluorobenzyl)sulfamoyl)piperidin-1-yl)azetidine-1-carboxylate (1.000 g, 1.445 mmol) in dichloromethane (30 mL) was mixed at the room temperature with methanesulfonyl chloride (0.134 mL, 1.734 mmol) and N,N-diisopropylethylamine (0.377 mL, 2.167 mmol) and stirred at the same temperature for 1 hr. Then, saturated aqueous ammonium chloride solution was added to the reaction mixture, followed by extraction with ethyl acetate. The organic layer was washed with aqueous saturated sodium bicarbonate solution, dried with anhydrous MgSO$_4$, filtered, and concentrated in vacuo. The residue was chromatographed (SiO$_2$, 40 g cartridge; ethyl acetate/hexane=40% to 70%) to give tert-butyl 3-(4-(N-(3-chloro-4-fluorophenyl)-N-(4-(5-(difluoromethyl)-1,3,4-oxadiazol-2-yl)-2-fluorobenzyl)sulfamoyl)piperidin-1-yl)azetidine-1-carboxylate as light yellow solid (0.680 g, 69.8%).

[Step 8] 1-(azetidin-3-yl)-N-(3-chloro-4-fluorophenyl)-N-(4-(5-(difluoromethyl)-1,3,4-oxadiazol-2-yl)-2-fluorobenzyl)piperidine-4-sulfonamide dihydrochloride

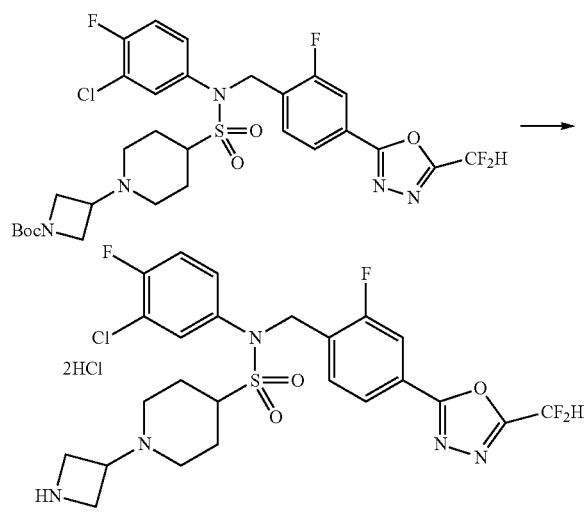

A solution of tert-butyl 3-(4-(N-(3-chloro-4-fluorophenyl)-N-(4-(5-(difluoromethyl)-1,3,4-oxadiazol-2-yl)-2-fluorobenzyl)sulfamoyl)piperidin-1-yl)azetidine-1-carboxylate (0.680 g, 1.009 mmol) in 1,4-dioxane (10 mL) was mixed at the room temperature with hydrochloric acid (4.00 M solution in 1,4-dioxane, 5.044 mL, 20.175 mmol) and stirred at the same temperature for 1 hr. The reaction mixture was diluted with ethyl acetate (10 mL) and hexane (70 mL) and stirred. The resulting precipitates were collected by filtration, washed by hexane, and dried to give 1-(azetidin-3-yl)-N-(3-chloro-4-fluorophenyl)-N-(4-(5-(difluoromethyl)-1,3,4-oxadiazol-2-yl)-2-fluorobenzyl)piperidine-4-sulfonamide dihydrochloride as white solid (0.620 g, 95.0%).

[Step 9] Compound 11447

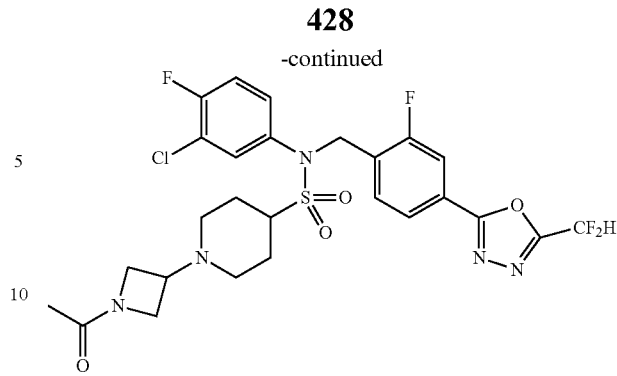

A slurry of 1-(azetidin-3-yl)-N-(3-chloro-4-fluorophenyl)-N-(4-(5-(difluoromethyl)-1,3,4-oxadiazol-2-yl)-2-fluorobenzyl)piperidine-4-sulfonamide dihydrochloride (0.050 g, 0.077 mmol) in dichloromethane (5 mL) was mixed at the room temperature with acetyl chloride (0.008 mL, 0.116 mmol) and N,N-diisopropylethylamine (0.047 mL, 0.271 mmol) and stirred at the same temperature for 3 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give 1-(1-acetylazetidin-3-yl)-N-(3-chloro-4-fluorophenyl)-N-(4-(5-(difluoromethyl)-1,3,4-oxadiazol-2-yl)-2-fluorobenzyl)piperidine-4-sulfonamide as beige solid (0.023 g, 48.3%).

$^1$H NMR (400 MHz, DMSO-d6) δ 7.88 (dd, 2H, J=7.9, 1.6 Hz), 7.83-7.75 (m, 2H), 7.71-7.62 (m, 1.25H), 7.54 (s, 0.5H), 7.51-7.47 (m, 1H), 7.44-7.36 (m, 1.25H), 5.12 (s, 2H), 4.10 (t, 1H, J=7.9 Hz), 3.92 (dd, 1H, J=8.6, 5.0 Hz), 3.82 (t, 1H, J=8.5 Hz), 3.63 (m, 1H), 3.12-3.06 (m, 1H), 2.89 (t, 2H, J=12.8 Hz), 2.11 (d, 2H, J=11.2 Hz), 2.01-1.89 (m, 2H), 1.89 (s, 3H), 1.75-1.71 (m, 2H); LRMS (ES) m/z 616.5 (M$^+$+1).

EXAMPLE 127

Compound 11448, N-(3-chloro-4-fluorophenyl)-N-(4-(5-(difluoromethyl)-1,3,4-oxadiazol-2-yl)-2-fluorobenzyl)-1-(1-(methylsulfonyl)azetidin-3-yl)piperidine-4-sulfonamide

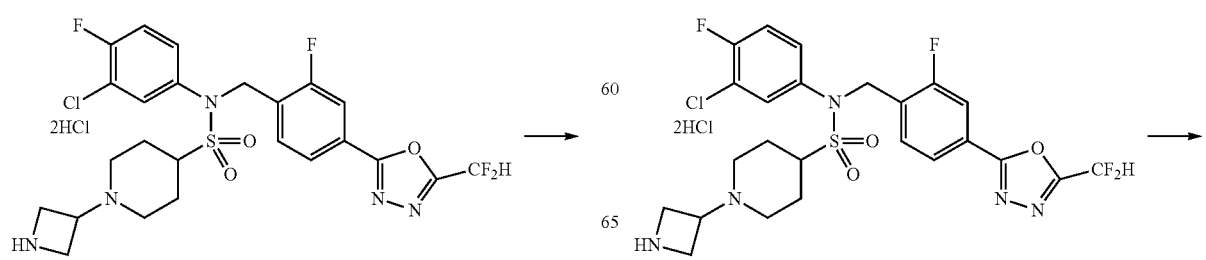

429
-continued

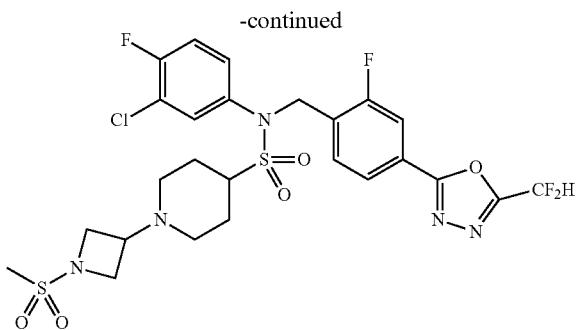

A slurry of 1-(azetidin-3-yl)-N-(3-chloro-4-fluorophenyl)-N-(4-(5-(difluoromethyl)-1,3,4-oxadiazol-2-yl)-2-fluorobenzyl)piperidine-4-sulfonamide dihydrochloride (0.050 g, 0.077 mmol) in dichloromethane (5 mL) was mixed at the room temperature with methanesulfonyl chloride (0.009 mL, 0.116 mmol) and N,N-diisopropylethylamine (0.047 mL, 0.271 mmol) and stirred at the same temperature for 3 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 12 g cartridge; ethyl acetate/hexane=50% to 80%) to give N-(3-chloro-4-fluorophenyl)-N-(4-(5-(difluoromethyl)-1,3,4-oxadiazol-2-yl)-2-fluorobenzyl)-1-(1-(methylsulfonyl)azetidin-3-yl)piperidine-4-sulfonamide as light yellow solid (0.026 g, 51.6%).

$^1$H NMR (400 MHz, DMSO-d6) δ 7.88 (dd, 1H, J=8.0, 1.7 Hz), 7.83-7.75 (m, 2H), 7.70-7.61 (m, 1.25H), 7.54 (s, 0.5H), 7.49 (m, 1H), 7.44-7.36 (m, 1.25H), 5.12 (s, 2H), 3.85 (t, 2H, J=7.7 Hz), 3.75 (dd, 2H, J=8.4, 6.0 Hz), 3.16 (q, 1H, J=6.5 Hz), 3.00 (s, 3H), 2.87 (d, 2H, J=11.0 Hz), 2.10 (d, 2H, J=12.1 Hz), 1.97-1.86 (m, 2H), 1.76-1.62 (m, 2H); LRMS (ES) m/z 652.4 ($M^+$+1).

EXAMPLE 128

Compound 11451, N-(3-chloro-4-fluorophenyl)-N-(4-(5-(difluoromethyl)-1,3,4-oxadiazol-2-yl)-2-fluorobenzyl)-1-(1-methylazetidin-3-yl)piperidine-4-sulfonamide

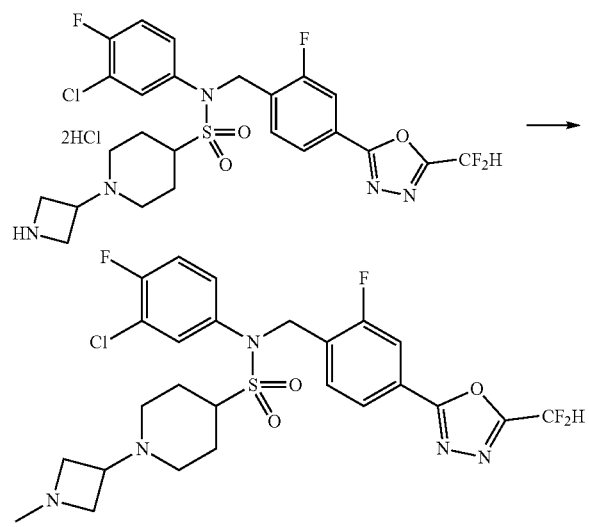

430

A mixture of 1-(azetidin-3-yl)-N-(3-chloro-4-fluorophenyl)-N-(4-(5-(difluoromethyl)-1,3,4-oxadiazol-2-yl)-2-fluorobenzyl)piperidine-4-sulfonamide dihydrochloride (0.100 g, 0.155 mmol) and formaldehyde (37.00% solution in water, 0.023 mL, 0.309 mmol) in dichloromethane (5 mL) was treated at the room temperature with sodium triacetoxyborohydride (0.066 g, 0.309 mmol) and stirred at the same temperature for 3 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 12 g cartridge; methanol/dichloromethane=0% to 15%) to give the crude product, and then the crude product was dissolved in ethyl acetate (1 mL) and hexane (10 mL) and stirred. The resulting precipitates were collected by filtration, washed by hexane, and dried to give N-(3-chloro-4-fluorophenyl)-N-(4-(5-(difluoromethyl)-1,3,4-oxadiazol-2-yl)-2-fluorobenzyl)-1-(1-methylazetidin-3-yl)piperidine-4-sulfonamide as light yellow solid (0.022 g, 24.2%).

$^1$H NMR (400 MHz, DMSO-d6) δ 7.87 (dd, 2H, J=8.0, 1.7 Hz), 7.83-7.74 (m, 2H), 7.70-7.61 (m, 1.25H), 7.54 (s, 0.5H), 7.48 (m, 1H), 7.45-7.35 (m, 1.25H), 5.11 (s, 2H), 3.50-3.47 (m, 2H), 2.92-2.86 (m, 3H), 2.79 (d, 2H, J=11.2 Hz), 2.31 (s, 3H), 2.08-2.04 (m, 2H), 1.83 (t, 2H, J=11.5 Hz), 1.67 (dt, 2H, J=12.2, 6.3 Hz); LRMS (ES) m/z 588.6 ($M^+$+1).

EXAMPLE 129

Compound 11452, N-(3-chloro-4-fluorophenyl)-N-(4-(5-(difluoromethyl)-1,3,4-oxadiazol-2-yl)-2-fluorobenzyl)-1-(1-(2-hydroxyacetyl)azetidin-3-yl)piperidine-4-sulfonamide

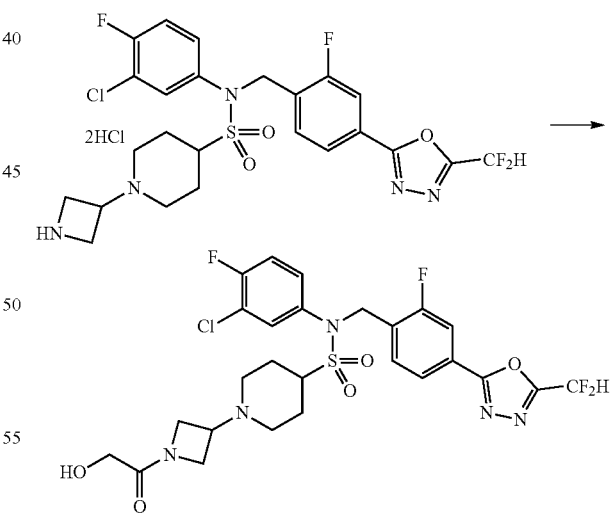

A mixture of 1-(azetidin-3-yl)-N-(3-chloro-4-fluorophenyl)-N-(4-(5-(difluoromethyl)-1,3,4-oxadiazol-2-yl)-2-fluorobenzyl)piperidine-4-sulfonamide dihydrochloride (0.100 g, 0.155 mmol), 2-hydroxyacetic acid (0.013 g, 0.170 mmol) and 1H-benzo[d][1,2,3]triazol-1-ol (HOBt, 0.031 g, 0.232 mmol) in dichloromethane (5 mL) was treated at the room temperature with 1-Ethyl-3-(3-dimethylaminopropyl)carbodiimide (EDC, 0.036 g, 0.232 mmol) and N,N-diisopropylethylamine (0.121 mL, 0.696 mmol) and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 10%) to give the crude product, and then the crude product was dissolved in ethyl acetate (1 mL) and hexane (10 mL) and stirred. The resulting precipitates were collected by filtration, washed by hexane, and dried to give N-(3-chloro-4-fluorophenyl)-N-(4-(5-(difluoromethyl)-1,3,4-oxadiazol-2-yl)-2-fluorobenzyl)-1-(1-(2-hydroxyacetyl)azetidin-3-yl)piperidine-4-sulfonamide as light yellow solid (0.041 g, 42.0%).

$^1$H NMR (400 MHz, DMSO-d6) δ 7.87 (dd, 1H, J=8.0, 1.7 Hz), 7.83-7.75 (m, 2H), 7.70-7.62 (m, 1.25H), 7.54 (s, 0.5H), 7.49 (m, 1H), 7.44-7.35 (m, 1.25H), 5.12 (s, 2H), 4.88 (t, 1H, J=6.0 Hz), 4.16 (m, 1H), 3.98 (m, 1H), 3.91-3.87 (m, 2H), 3.69 (dd, 1H, J=10.0, 5.1 Hz), 3.37 (m, 1H), 3.14 (dq, 1H, J=12.4, 6.6, 5.9 Hz), 2.92-2.84 (m, 2H), 2.10 (d, 2H, J=12.0 Hz), 1.93-1.86 (m, 2H), 1.77-1.62 (m, 2H); LRMS (ES) m/z 632.6 (M⁺+1).

EXAMPLE 130

Compound 11460, N-((5-(5-(difluoromethyl)-1,3,4-oxadiazol-2-yl)pyridin-2-yl)methyl)-N-(3-fluoro-4-methylphenyl)ethanesulfonamide

[Step 1]
N-(3-fluoro-4-methylphenyl)ethanesulfonamide

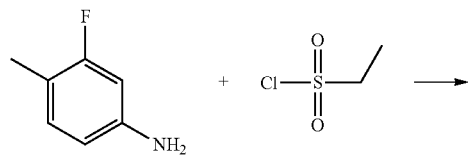

A solution of 3-fluoro-4-methylaniline (0.457 mL, 3.995 mmol), pyridine (0.483 mL, 5.993 mmol) and ethanesulfonyl chloride (0.453 mL, 4.794 mmol) in dichloromethane (10 mL) was stirred at the room temperature for 18 hr. Then, water was added to the reaction mixture, followed by extraction with ethyl acetate. The organic layer was washed with aqueous 1M-hydrochloric acid solution, dried with anhydrous MgSO₄, filtered, and concentrated in vacuo. The residue was chromatographed (SiO₂, 12 g cartridge; ethyl acetate/hexane=0% to 80%) to give N-(3-fluoro-4-methylphenyl)ethanesulfonamide as yellow solid (0.623 g, 71.8%).

[Step 2] Methyl 6-((N-(3-fluoro-4-methylphenyl)ethylsulfonamido)methyl)nicotinate

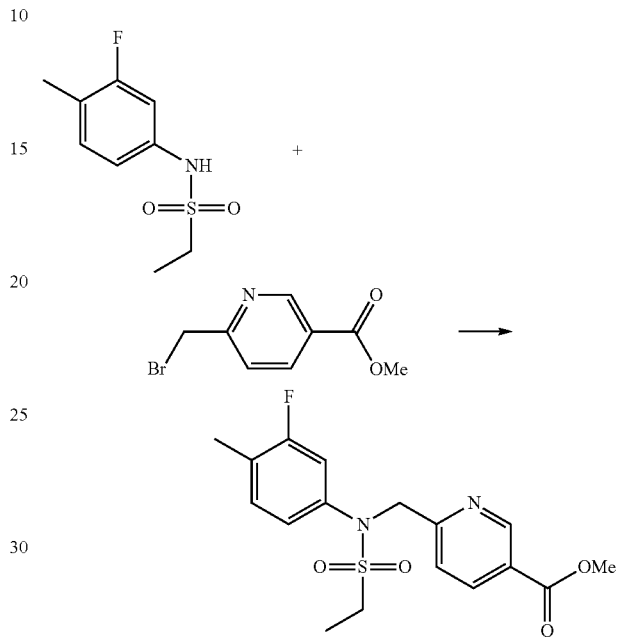

A solution of N-(3-fluoro-4-methylphenyl)ethanesulfonamide (0.250 g, 1.151 mmol), methyl 6-(bromomethyl)nicotinate (0.318 g, 1.381 mmol), potassium carbonate (0.239 g, 1.726 mmol) and potassium iodide (0.019 g, 0.115 mmol) in N,N-dimethylformide (10 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 100%) to give methyl 6-((N-(3-fluoro-4-methylphenyl)ethylsulfonamido)methyl)nicotinate as white solid (0.290 g, 68.8%).

[Step 3] N-(3-fluoro-4-methylphenyl)-N-((5-(hydrazinecarbonyl)pyridin-2-yl)methyl)ethanesulfonamide

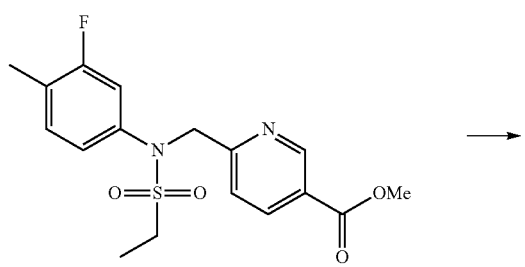

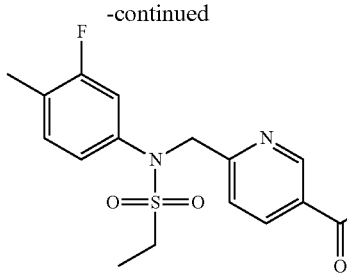

Methyl 6-4N-(3-fluoro-4-methylphenyl)ethylsulfonamido)methyl)nicotinate (0.290 g, 0.791 mmol) and hydrazine monohydrate (1.154 mL, 23.744 mmol) were mixed at the room temperature in ethanol (8 mL)/water (2 mL), stirred at 90° C. for 18 hr, cooled down to the room temperature to terminate the reaction and concentrated under the reduced pressure to remove the solvent. The title compound was used without further purification (N-(3-fluoro-4-methylphenyl)-N-((5-(hydrazinecarbonyl)pyridin-2-yl)methyl)ethanesulfonamide, 0.259 g, 89.3%, yellow solid).

[Step 4] N-((5-(2-(2,2-difluoroacetyl)hydrazine-1-carbonyl)pyridin-2-yl)methyl)-N-(3-fluoro-4-methylphenyl)ethanesulfonamide

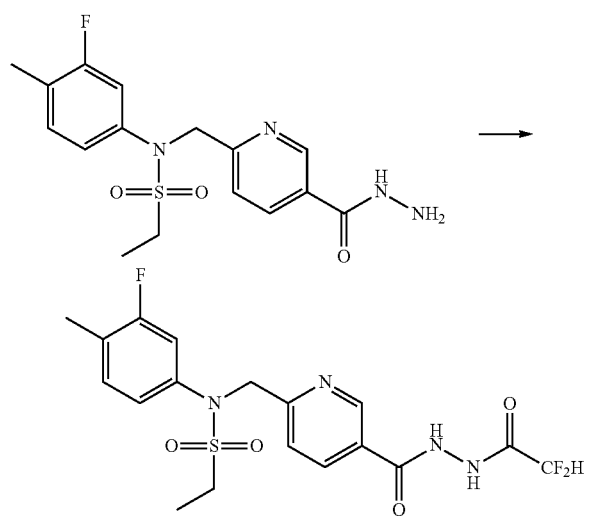

A solution of N-(3-fluoro-4-methylphenyl)-N-((5-(hydrazinecarbonyl)pyridin-2-yl)methyl)ethanesulfonamide (0.080 g, 0.218 mmol) and triethylamine (0.046 mL, 0.328 mmol) in tetrahydrofuran (10 mL) was mixed at the room temperature with 2,2-difluoroacetic anhydride (0.029 mL, 0.262 mmol), stirred at 50° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-((5-(2-(2,2-difluoroacetyl)hydrazine-1-carbonyl)pyridin-2-yl)methyl)-N-(3-fluoro-4-methylphenyl)ethanesulfonamide, 0.087 g, 89.7%, yellow oil).

[Step 5] Compound 11460

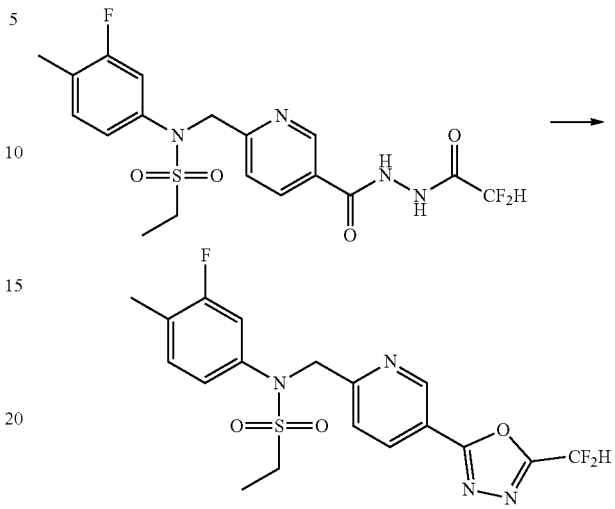

A mixture of N-((5-(2-(2,2-difluoroacetyl)hydrazine-1-carbonyl)pyridin-2-yl)methyl)-N-(3-fluoro-4-methylphenyl)ethanesulfonamide (0.090 g, 0.203 mmol) and 1-methoxy-N-triethylammoniosulfonyl-methanimidate (Burgess reagent, 0.145 g, 0.608 mmol) in tetrahydrofuran (10 mL) was heated at 150° C. for 30 min under the microwaves, cooled down to the room temperature. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 100%) to give N-((5-(5-(difluoromethyl)-1,3,4-oxadiazol-2-yl)pyridin-2-yl)methyl)-N-(3-fluoro-4-methylphenyl)ethanesulfonamide as yellow solid (0.050 g, 57.9%).

$^1$H NMR (400 MHz, CDCl₃) δ 9.21 (dd, 1H, J=2.2, 0.9 Hz), 8.37 (dd, 1H, J=8.2, 2.2 Hz), 7.75-7.66 (m, 1H), 7.16-7.07 (m, 3H), 6.86 (d, 1H, J=51.6 Hz), 5.14 (s, 2H), 3.18 (q, 2H, J=7.4 Hz), 2.20 (d, 3H, J=1.9 Hz), 1.42 (t, 3H, J=7.4 Hz); LRMS (ES) m/z 427.3 (M⁺+1).

EXAMPLE 131

Compound 11461, N-((5-(5-(difluoromethyl)-1,3,4-oxadiazol-2-yl)pyridin-2-yl)methyl)-N-(4-fluoro-3-methylphenyl)ethanesulfonamide

[Step 1]
N-(4-fluoro-3-methylphenyl)ethanesulfonamide

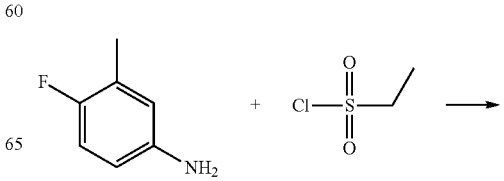

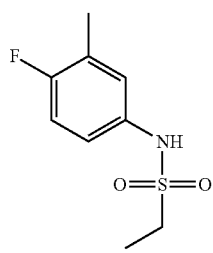

A solution of 4-fluoro-3-methylaniline (0.500 g, 3.995 mmol), pyridine (0.483 mL, 5.993 mmol) and ethanesulfonyl chloride (0.453 mL, 4.794 mmol) in dichloromethane (10 mL) was stirred at the room temperature for 18 hr. Then, water was added to the reaction mixture, followed by extraction with ethyl acetate. The organic layer was washed with aqueous 1M-hydrochloric acid solution, dried with anhydrous MgSO₄, filtered, and concentrated in vacuo. The residue was chromatographed (SiO₂, 12 g cartridge; ethyl acetate/hexane=0% to 80%) to give N-(4-fluoro-3-methylphenyl)ethanesulfonamide as yellow solid (0.633 g, 72.9%).

[Step 2] methyl 6-4N-(4-fluoro-3-methylphenyl) ethylsulfonamido)methyl)nicotinate

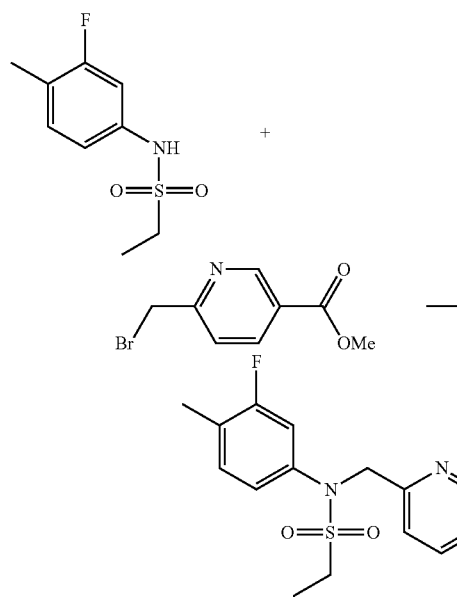

A solution of N-(4-fluoro-3-methylphenyl)ethanesulfonamide (0.250 g, 1.151 mmol), methyl 6-(bromomethyl)nicotinate (0.318 g, 1.381 mmol), potassium carbonate (0.239 g, 1.726 mmol) and potassium iodide (0.019 g, 0.115 mmol) in N,N-dimethylformide (10 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 100%) to give methyl 6-((N-(4-fluoro-3-methylphenyl)ethylsulfonamido)methyl)nicotinate as white solid (0.230 g, 54.6%).

[Step 3] N-(4-fluoro-3-methylphenyl)-N-((5-(hydrazinecarbonyl)pyridin-2-yl)methyl)ethanesulfonamide

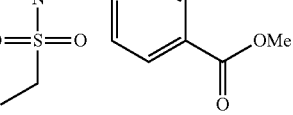

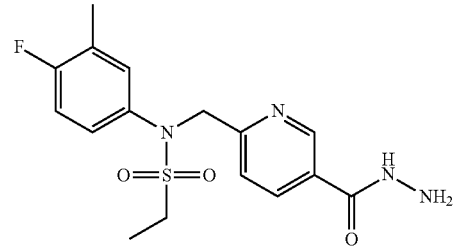

Methyl 6-((N-(4-fluoro-3-methylphenyl)ethylsulfonamido)methyl)nicotinate (0.230 g, 0.628 mmol) and hydrazine monohydrate (0.915 mL, 18.831 mmol) were mixed at the room temperature in ethanol (8 mL)/water (2 mL), stirred at 90° C. for 18 hr, cooled down to the room temperature to terminate the reaction and concentrated under the reduced pressure to remove the solvent. The title compound was used without further purification (N-(4-fluoro-3-methylphenyl)-N-((5-(hydrazinecarbonyl)pyridin-2-yl)methyl)ethanesulfonamide, 0.222 g, 96.5%, yellow solid).

[Step 4] N-((5-(2-(2,2-difluoroacetyl)hydrazine-1-carbonyl)pyridin-2-yl)methyl)-N-(4-fluoro-3-methylphenyl)ethanesulfonamide

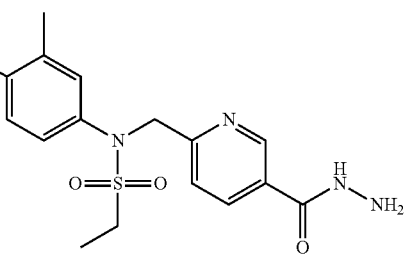

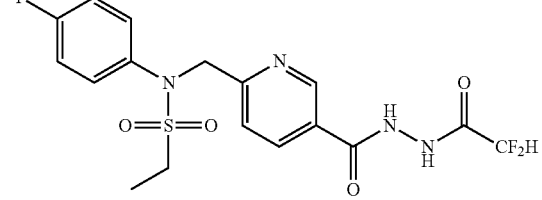

A solution of N-(4-fluoro-3-methylphenyl)-N-((5-(hydrazinecarbonyl)pyridin-2-yl)methyl)ethanesulfonamide (0.080 g, 0.218 mmol) and triethylamine (0.046 mL, 0.328 mmol) in tetrahydrofuran (10 mL) was mixed at the room temperature with 2,2-difluoroacetic anhydride (0.029 mL, 0.262 mmol), stirred at 50° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-((5-(2-(2,2-difluoroacetyl)hydrazine-1-carbonyl)pyridin-2-yl)methyl)-N-(4-fluoro-3-methylphenyl)ethanesulfonamide, 0.088 g, 94.5%, yellow oil).

[Step 5] Compound 11461

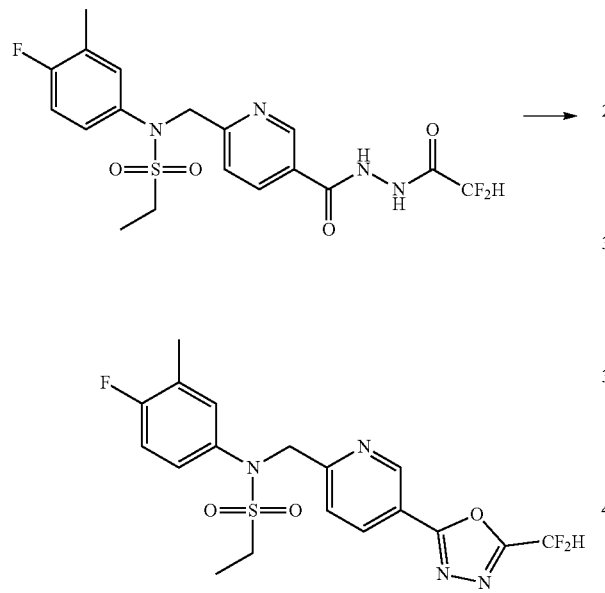

A mixture of N-((5-(2-(2,2-difluoroacetyl)hydrazine-1-carbonyl)pyridin-2-yl)methyl)-N-(4-fluoro-3-methylphenyl)ethanesulfonamide (0.090 g, 0.203 mmol) and 1-methoxy-N-triethylammoniosulfonyl-methanimidate (Burgess reagent, 0.145 g, 0.608 mmol) in tetrahydrofuran (10 mL) was heated at 150° C. for 30 min under the microwaves, cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 100%) to give N-((5-(5-(difluoromethyl)-1,3,4-oxadiazol-2-yl)pyridin-2-yl)methyl)-N-(4-fluoro-3-methylphenyl)ethanesulfonamide as yellow solid (0.070 g, 81.1%).

$^1$H NMR (400 MHz, CDCl$_3$) δ 9.21 (dd, 1H, J=2.2, 0.8 Hz), 8.39 (dd, 1H, J=8.3, 2.2 Hz), 7.74 (dd, 1H, J=8.3, 0.9 Hz), 7.25-7.12 (m, 2H), 7.07-6.78 (m, 2H), 5.12 (s, 2H), 3.17 (q, 2H, J=7.4 Hz), 2.22 (d, 3H, J=2.0 Hz), 1.44 (t, 3H, J=7.4 Hz); LRMS (ES) m/z 427.3 (M$^+$+1)

EXAMPLE 132

Compound 11462, N-((5-(5-(difluoromethyl)-1,3,4-oxadiazol-2-yl)pyridin-2-yl)methyl)-N-(3,4-difluorophenyl)ethanesulfonamide

[Step 1] N-(3,4-difluorophenyl)ethanesulfonamide

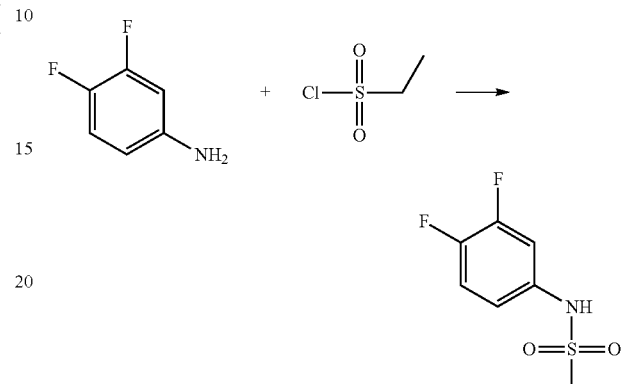

A solution of 3,4-difluoroaniline (0.384 mL, 3.873 mmol), pyridine (0.468 mL, 5.809 mmol) and ethanesulfonyl chloride (0.439 mL, 4.647 mmol) in dichloromethane (10 mL) was stirred at the room temperature for 18 hr. Then, water was added to the reaction mixture, followed by extraction with ethyl acetate. The organic layer was washed with aqueous 1M-hydrochloric acid solution, dried with anhydrous MgSO$_4$, filtered, and concentrated in vacuo. The residue was chromatographed (SiO$_2$, 12 g cartridge; ethyl acetate/hexane=0% to 80%) to give N-(3,4-difluorophenyl)ethanesulfonamide as yellow solid (0.670 g, 78.2%).

[Step 2] Methyl 6-((N-(3,4-difluorophenyl)ethylsulfonamido)methyl)nicotinate

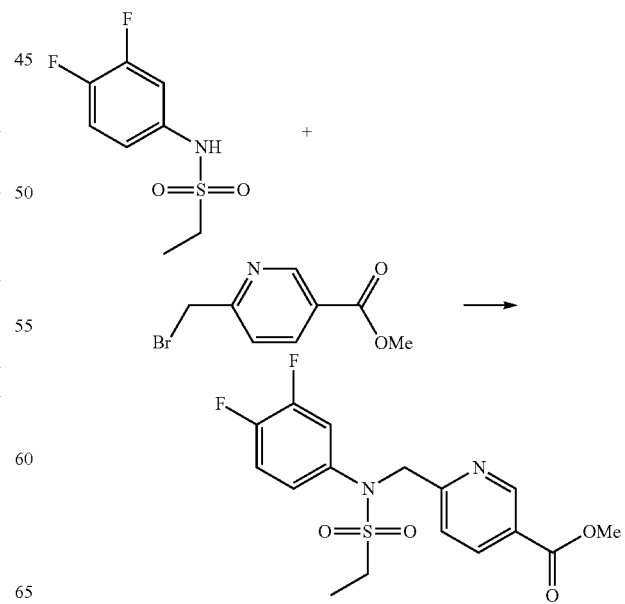

A solution of N-(3,4-difluorophenyl)ethanesulfonamide (0.250 g, 1.130 mmol), methyl 6-(bromomethyl)nicotinate (0.312 g, 1.356 mmol), potassium carbonate (0.234 g, 1.695 mmol) and potassium iodide (0.019 g, 0.113 mmol) in N,N-dimethylformide (10 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 100%) to give methyl 6-((N-(3,4-difluorophenyl)ethylsulfonamido)methyl)nicotinate as yellow solid (0.151 g, 36.1%).

[Step 3] N-(3,4-difluorophenyl)-N-((5-(hydrazinecarbonyl)pyridin-2-yl)methyl)ethanesulfonamide

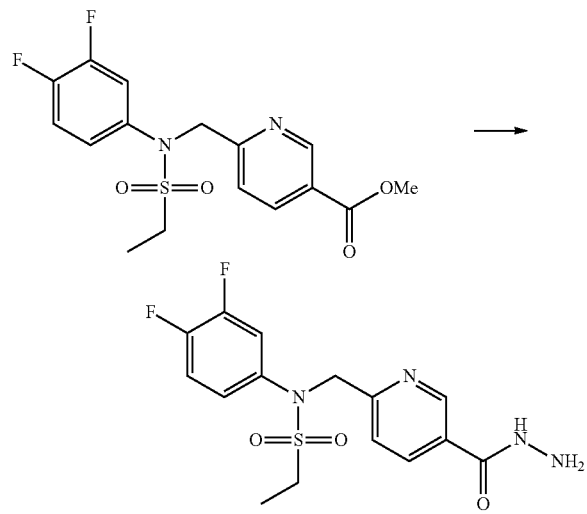

Methyl 6-((N-(3,4-difluorophenyl)ethylsulfonamido)methyl)nicotinate (0.160 g, 0.432 mmol) and hydrazine monohydrate (0.630 mL, 12.960 mmol) were mixed at the room temperature in ethanol (8 mL)/water (2 mL), stirred at 90° C. for 18 hr, cooled down to the room temperature to terminate the reaction and concentrated under the reduced pressure to remove the solvent. The title compound was used without further purification (N-(3,4-difluorophenyl)-N-((5-(hydrazinecarbonyl)pyridin-2-yl)methyl)ethanesulfonamide, 0.152 g, 95.0%, yellow solid).

[Step 4] N-((5-(2-(2,2-difluoroacetyl)hydrazine-1-carbonyl)pyridin-2-yl)methyl)-N-(3,4-difluorophenyl)ethanesulfonamide

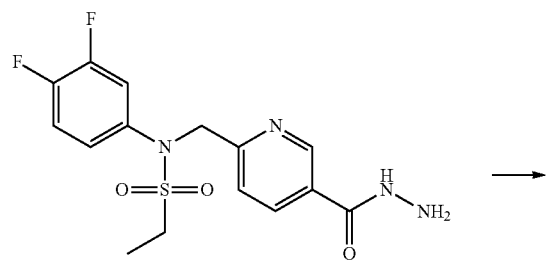

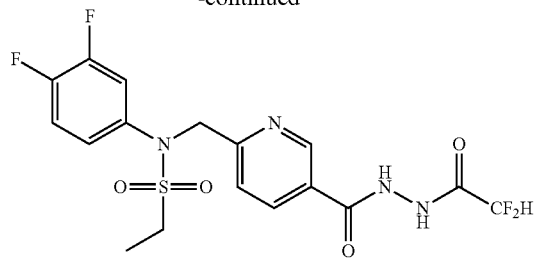

A solution of N-(3,4-difluorophenyl)-N-((5-(hydrazinecarbonyl)pyridin-2-yl)methyl)ethanesulfonamide (0.080 g, 0.216 mmol) and triethylamine (0.045 mL, 0.324 mmol) in tetrahydrofuran (10 mL) was mixed at the room temperature with 2,2-difluoroacetic anhydride (0.028 mL, 0.259 mmol), stirred at 50° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-((5-(2-(2,2-difluoroacetyl)hydrazine-1-carbonyl)pyridin-2-yl)methyl)-N-(3,4-difluorophenyl)ethanesulfonamide, 0.090 g, 92.9%, yellow oil).

[Step 5] Compound 11462

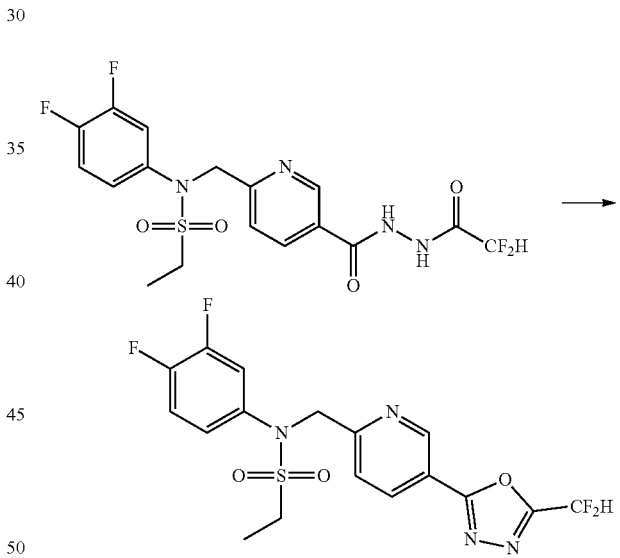

A mixture of N-((5-(2-(2,2-difluoroacetyl)hydrazine-1-carbonyl)pyridin-2-yl)methyl)-N-(3,4-difluorophenyl)ethanesulfonamide (0.090 g, 0.201 mmol) and 1-methoxy-N-triethylammoniosulfonyl-methanimidate (Burgess reagent, 0.143 g, 0.602 mmol) in tetrahydrofuran (10 mL) was heated at 150° C. for 30 min under the microwaves, cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 100%) to give N-((5-(5-(difluoromethyl)-1,3,4-oxadiazol-2-yl)pyridin-2-yl)methyl)-N-(3,4-difluorophenyl)ethanesulfonamide as yellow solid (0.053 g, 61.4%).

¹H NMR (400 MHz, CDCl₃) δ 9.24 (dd, 1H, J=2.2, 0.8 Hz), 8.42 (dd, 1H, J=8.2, 2.2 Hz), 7.69 (dd, 1H, J=8.2, 0.8 Hz), 7.32 (ddd, 1H, J=11.0, 7.0, 2.6 Hz), 7.22-7.08 (m, 2H), 6.93 (t, 1H, J=51.6 Hz), 5.13 (s, 2H), 3.18 (q, 2H, J=7.4 Hz), 1.42 (t, 3H, J=7.4 Hz); LRMS (ES) m/z 431.3 (M⁺+1).

EXAMPLE 133

Compound 11463, N-((5-(5-(difluoromethyl)-1,3,4-oxadiazol-2-yl)pyridin-2-yl)methyl)-N-(3,5-difluorophenyl)ethanesulfonamide

[Step 1] N-(3,5-difluorophenyl)ethanesulfonamide

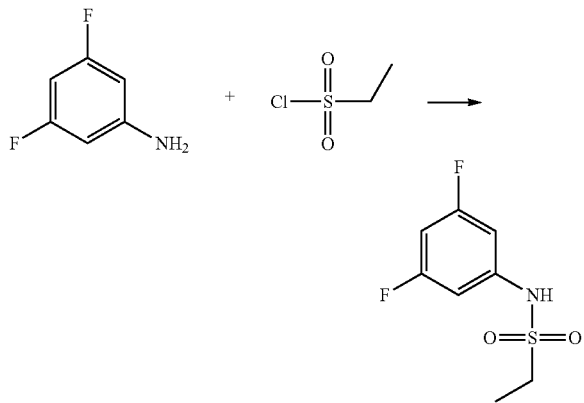

A solution of 3,5-difluoroaniline (0.500 g, 3.873 mmol), pyridine (0.468 mL, 5.809 mmol) and ethanesulfonyl chloride (0.439 mL, 4.647 mmol) in dichloromethane (10 mL) was stirred at the room temperature for 18 hr. Then, water was added to the reaction mixture, followed by extraction with ethyl acetate. The organic layer was washed with aqueous 1M-hydrochloric acid solution, dried with anhydrous MgSO₄, filtered, and concentrated in vacuo. The residue was chromatographed (SiO₂, 12 g cartridge; ethyl acetate/hexane=0% to 80%) to give N-(3,5-difluorophenyl)ethanesulfonamide as yellow solid (0.611 g, 71.3%).

[Step 2] Methyl 6-((N-(3,5-difluorophenyl)ethylsulfonamido)methyl)nicotinate

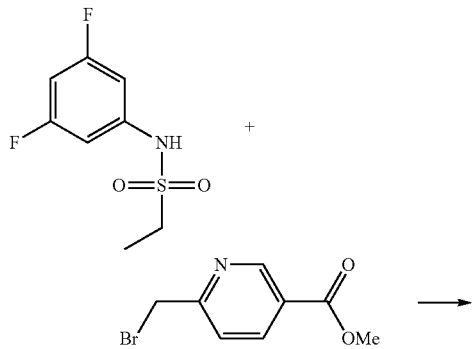

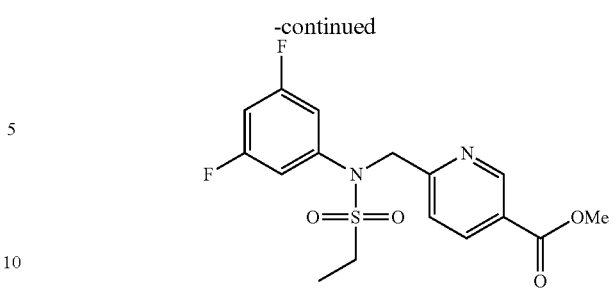

A solution of N-(3,5-difluorophenyl)ethanesulfonamide (0.250 g, 1.130 mmol), methyl 6-(bromomethyl)nicotinate (0.312 g, 1.356 mmol), potassium carbonate (0.234 g, 1.695 mmol) and potassium iodide (0.019 g, 0.113 mmol) in N,N-dimethylformide (10 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 100%) to give methyl 6-((N-(3,5-difluorophenyl)ethylsulfonamido)methyl)nicotinate as yellow solid (0.175 g, 41.8%).

[Step 3] N-(3,5-difluorophenyl)-N-((5-(hydrazinecarbonyl)pyridin-2-yl)methyl)ethanesulfonamide

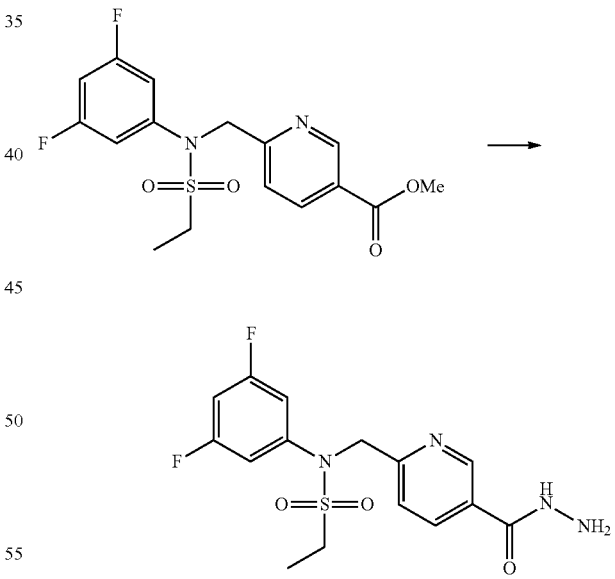

Methyl 6-((N-(3,5-difluorophenyl)ethylsulfonamido)methyl)nicotinate (0.180 g, 0.486 mmol) and hydrazine monohydrate (0.709 mL, 14.580 mmol) were mixed at the room temperature in ethanol (8 mL)/water (2 mL), stirred at 90° C. for 18 hr, cooled down to the room temperature to terminate the reaction and concentrated under the reduced pressure to remove the solvent. The title compound was used without further purification (N-(3,5-difluorophenyl)-N-((5-(hydrazinecarbonyl)pyridin-2-yl)methyl)ethanesulfonamide, 0.177 g, 98.3%, yellow solid).

443

[Step 4] N-((5-(2-(2,2-difluoroacetyl)hydrazine-1-carbonyl)pyridin-2-yl)methyl)-N-(3,5-difluorophenyl)ethanesulfonamide

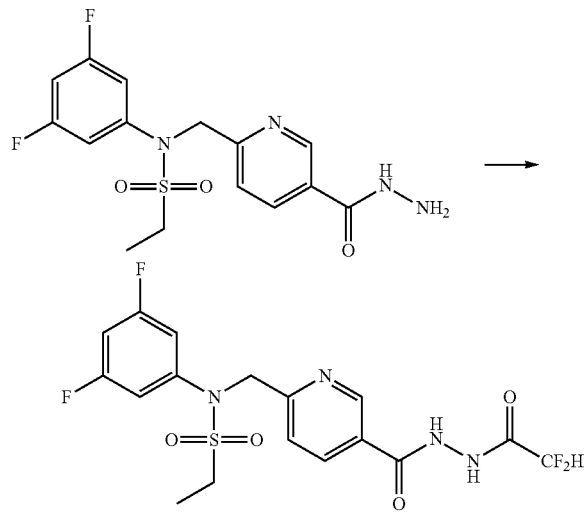

A solution of N-(3,5-difluorophenyl)-N-((5-(hydrazinecarbonyl)pyridin-2-yl)methyl)ethanesulfonamide (0.080 g, 0.216 mmol) and triethylamine (0.045 mL, 0.324 mmol) in tetrahydrofuran (10 mL) was mixed at the room temperature with 2,2-difluoroacetic anhydride (0.028 mL, 0.259 mmol), stirred at 50° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-((5-(2-(2,2-difluoroacetyl)hydrazine-1-carbonyl)pyridin-2-yl)methyl)-N-(3,5-difluorophenyl)ethanesulfonamide, 0.092 g, 95.0%, yellow oil).

[Step 5] Compound 11463

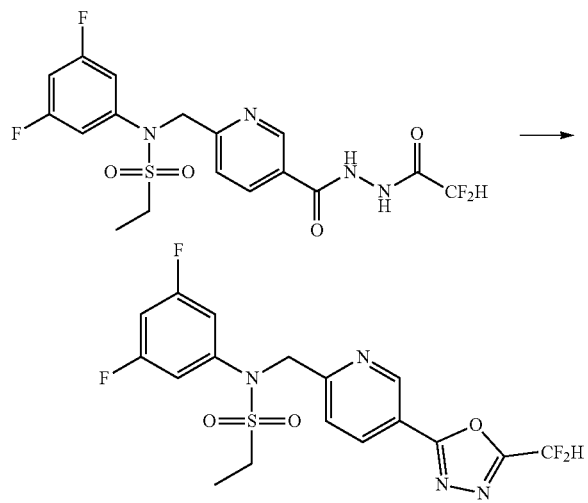

444

A mixture of N-((5-(2-(2,2-difluoroacetyl)hydrazine-1-carbonyl)pyridin-2-yl)methyl)-N-(3,5-difluorophenyl)ethanesulfonamide (0.090 g, 0.201 mmol) and 1-methoxy-N-triethylammoniosulfonyl-methanimidate (Burgess reagent, 0.143 g, 0.602 mmol) in tetrahydrofuran (10 mL) was heated at 150° C. for 30 min under the microwaves, cooled down to the room temperature. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 100%) to give N-((5-(5-(difluoromethyl)-1,3,4-oxadiazol-2-yl)pyridin-2-yl)methyl)-N-(3,5-difluorophenyl)ethanesulfonamide as yellow solid (0.046 g, 53.2%).

$^1$H NMR (400 MHz, CDCl$_3$) δ 9.25 (dd, 1H, J=2.2, 0.9 Hz), 8.39 (dd, 1H, J=8.3, 2.2 Hz), 7.65 (d, 1H, J=8.2 Hz), 7.10-7.00 (m, 2H), 6.87 (d, 1H, J=51.6 Hz), 6.70 (tt, 1H, J=8.6, 2.3 Hz), 5.16 (s, 2H), 3.22 (q, 2H, J=7.4 Hz), 1.41 (t, 3H, J=7.4 Hz); LRMS (ES) m/z 431.2 (M⁺+1).

EXAMPLE 134

Compound 11497, N-(3-chloro-4-fluorophenyl)-N-((5-(5-(difluoromethyl)-1,3,4-oxadiazol-2-yl)pyridin-2-yl)methyl)tetrahydro-2H-thiopyran-4-sulfonamide 1,1-dioxide

[Step 1] N-(3-chloro-4-fluorophenyl)tetrahydro-2H-thiopyran-4-sulfonamide 1,1-dioxide

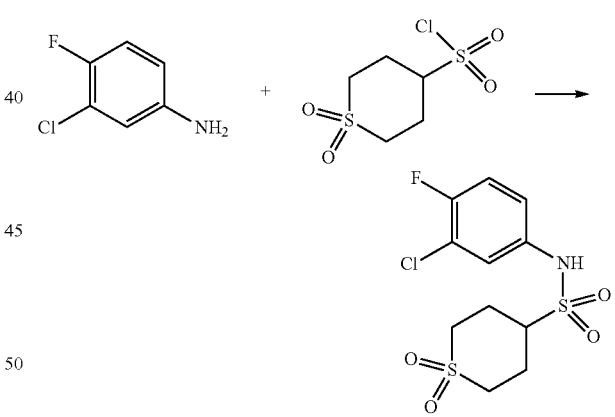

A solution of 3-chloro-4-fluoroaniline (0.300 g, 2.061 mmol), triethylamine (0.575 mL, 4.122 mmol) and tetrahydro-2H-thiopyran-4-sulfonyl chloride 1,1-dioxide (0.528 g, 2.267 mmol) in dichloromethane (10 mL) was stirred at the room temperature for 5 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 20%) to give N-(3-chloro-4-fluorophenyl)tetrahydro-2H-thiopyran-4-sulfonamide 1,1-dioxide as yellow solid (0.265 g, 37.6%).

445

[Step 2] methyl 6-(((N-(3-chloro-4-fluorophenyl)-1,1-dioxidotetrahydro-2H-thiopyran)-4-sulfonamido)methyl)nicotinate

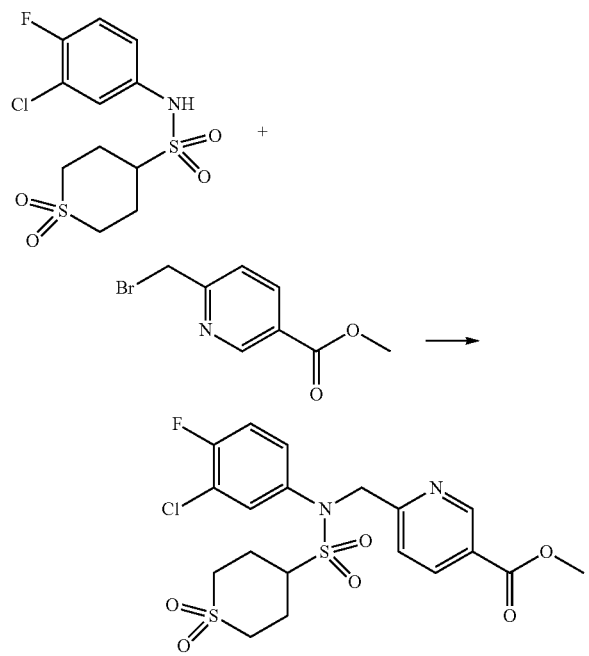

A solution of N-(3-chloro-4-fluorophenyl)tetrahydro-2H-thiopyran-4-sulfonamide 1,1-dioxide (0.265 g, 0.775 mmol), potassium carbonate (0.161 g, 1.163 mmol), methyl 6-(bromomethyl)nicotinate (0.196 g, 0.853 mmol) and potassium iodide (0.064 g, 0.388 mmol) in N,N-dimethylformide (15 mL) was stirred at the room temperature for 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 60%) to give methyl 6-(((N-(3-chloro-4-fluorophenyl)-1,1-dioxidotetrahydro-2H-thiopyran)-4-sulfonamido)methyl)nicotinate as yellow solid (0.370 g, 97.2%).

[Step 3] N-(3-chloro-4-fluorophenyl)-N-((5-(hydrazinecarbonyl)pyridin-2-yl)methyl)tetrahydro-2H-thiopyran-4-sulfonamide 1,1-dioxide

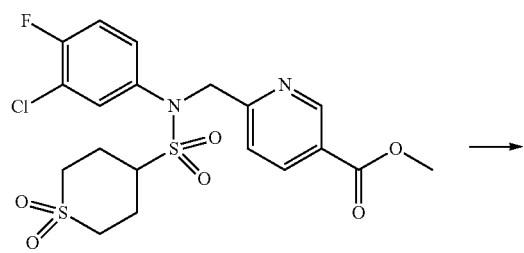

446

-continued

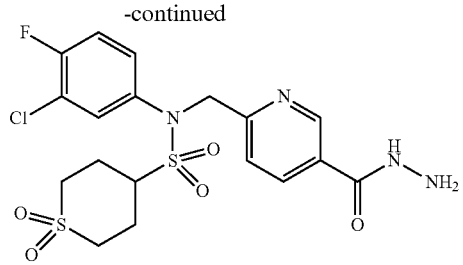

A solution of methyl 6-(((N-(3-chloro-4-fluorophenyl)-1,1-dioxidotetrahydro-2H-thiopyran)-4-sulfonamido)methyl)nicotinate (0.370 g, 0.754 mmol) and hydrazine monohydrate (0.377 g, 7.536 mmol) in ethanol (5 mL) was stirred at 90° C. for 12 hr, cooled down to the room temperature to terminate the reaction and concentrated under the reduced pressure to remove the solvent. The residue was diluted with sodium bicarbonate (20 mL) and stirred. The resulting precipitates were collected by filtration, washed by water, and dried to give N-(3-chloro-4-fluorophenyl)-N-((5-(hydrazinecarbonyl)pyridin-2-yl)methyl)tetrahydro-2H-thiopyran-4-sulfonamide 1,1-dioxide as white solid (0.220 g, 59.5%).

[Step 4] N-(3-chloro-4-fluorophenyl)-N-((5-(2-(2,2-difluoroacetyl)hydrazine-1-carbonyl)pyridin-2-yl)methyl)tetrahydro-2H-thiopyran-4-sulfonamide 1,1-dioxide

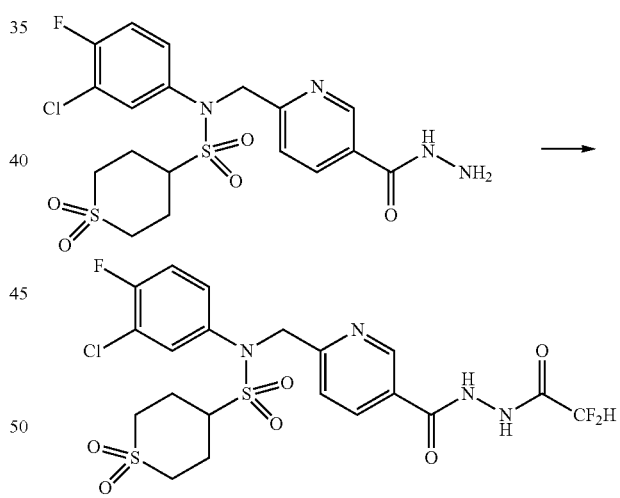

A solution of N-(3-chloro-4-fluorophenyl)-N-((5-(hydrazinecarbonyl)pyridin-2-yl)methyl)tetrahydro-2H-thiopyran-4-sulfonamide 1,1-dioxide (0.220 g, 0.448 mmol), triethylamine (0.250 mL, 1.792 mmol) and 2,2-difluoroacetic anhydride (0.111 mL, 0.896 mmol) in tetrahydrofuran (10 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The title compound was used without further purification (N-(3-chloro-4-fluorophenyl)-N-((5-(2-(2,2-difluoroacetyl)hydrazine-1-carbonyl)pyridin-2-yl)methyl)tetrahydro-2H-thiopyran-4-sulfonamide 1,1-dioxide, 0.140 g, 54.9%, yellow solid).

[Step 5] Compound 11497

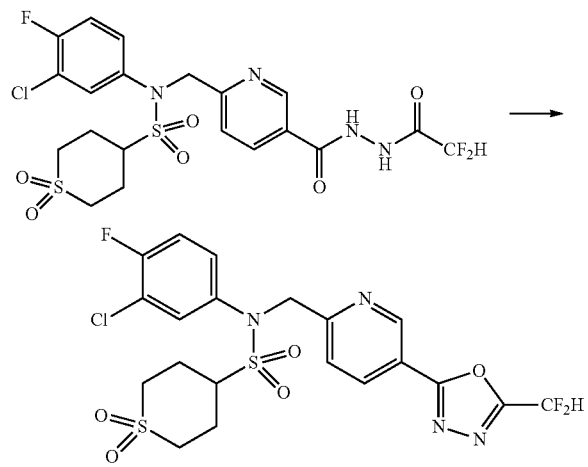

A solution of N-(3-chloro-4-fluorophenyl)-N-((5-(2-(2,2-difluoroacetyl)hydrazine-1-carbonyl)pyridin-2-yl)methyl) tetrahydro-2H-thiopyran-4-sulfonamide 1,1-dioxide (0.140 g, 0.246 mmol) and 1-methoxy-N-triethylammoniosulfonylmethanimidate (Burgess reagent, 0.176 g, 0.738 mmol) in tetrahydrofuran (15 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 60%) to give N-(3-chloro-4-fluorophenyl)-N-((5-(5-(difluoromethyl)-1,3,4-oxadiazol-2-yl)pyridin-2-yl)methyl)tetrahydro-2H-thiopyran-4-sulfonamide 1,1-dioxide as white solid (0.095 g, 70.1%).
¹H NMR (400 MHz, CDCl₃) δ 9.30 (dd, 1H, J=2.2, 0.9 Hz), 8.42 (dd, 1H, J=8.2, 2.2 Hz), 7.57-7.48 (m, 2H), 7.35-7.27 (m, 1H), 7.13 (t, 1H, J=8.6 Hz), 7.10-6.82 (m, 1H), 5.09 (s, 2H), 3.49-3.31 (m, 3H), 3.07-2.95 (m, 2H), 2.70-2.61 (m, 4H); LRMS (ES) m/z 551.45 (M⁺+1).

EXAMPLE 135

Compound 11501, N-(3-chloro-4-fluorophenyl)-N-((5-(5-(difluoromethyl)-1,3,4-oxadiazol-2-yl)pyridin-2-yl)methyl)-1-(oxetan-3-yl)piperidine-4-sulfonamide

[Step 1] methyl 6-(((1-(tert-butoxycarbonyl)-N-(3-chloro-4-fluorophenyl)piperidine)-4-sulfonamido) methyl)nicotinate

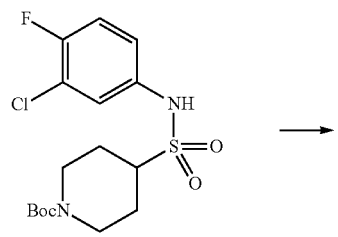

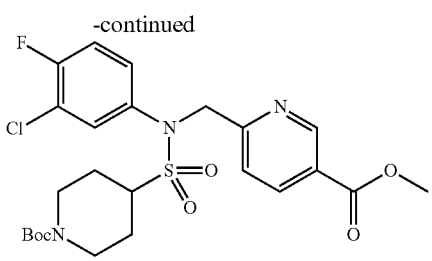

tert-butyl 4-(N-(3-chloro-4-fluorophenyl)sulfamoyl)piperidine-1-carboxylate (1.440 g, 3.665 mmol), methyl 6-(bromomethyl)nicotinate (1.012 g, 4.398 mmol), potassium carbonate (0.760 g, 5.498 mmol) and potassium iodide (0.913 g, 5.498 mmol) were mixed at the room temperature in N,N-dimethylformide (30 mL) and then stirred at the same temperature for 16 hr. Then, saturated aqueous ammonium chloride solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 80 g cartridge; ethyl acetate/hexane=20% to 50%) to give methyl 6-(((1-(tert-butoxycarbonyl)-N-(3-chloro-4-fluorophenyl)piperidine)-4-sulfonamido)methyl)nicotinate as beige solid (1.920 g, 96.6%).

[Step 2] methyl 6-((N-(3-chloro-4-fluorophenyl) piperidine-4-sulfonamido)methyl)nicotinate dihydrochloride

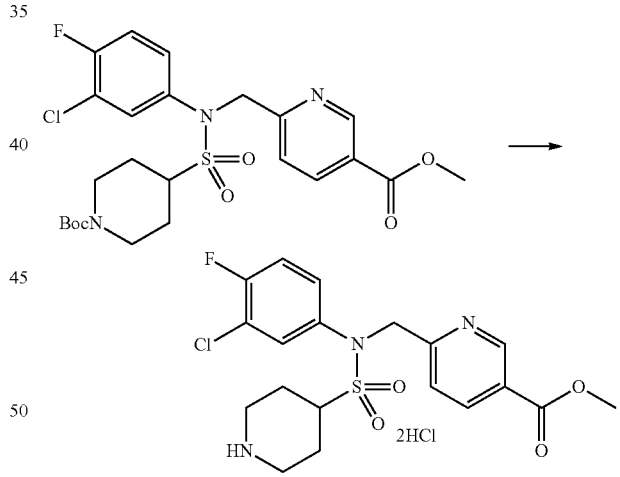

A solution of methyl 6-(((1-(tert-butoxycarbonyl)-N-(3-chloro-4-fluorophenyl)piperidine)-4-sulfonamido)methyl) nicotinate (1.920 g, 3.542 mmol) in 1,4-dioxane (10 mL) was mixed at the room temperature with hydrochloric acid (4.00 M solution in 1,4-dioxane, 8.856 mL, 35.423 mmol), stirred at the same temperature for 3 hr, and concentrated under the reduced pressure to remove the solvent. The residue was diluted with ethyl acetate (20 mL) and hexane (20 mL) and stirred. The resulting precipitates were collected by filtration, washed by hexane, and dried to give methyl 6-((N-(3-chloro-4-fluorophenyl)piperidine-4-sulfonamido)methyl)nicotinate dihydrochloride as brown solid (1.760 g, 96.5%).

449

[Step 3] methyl 6-(((N-(3-chloro-4-fluorophenyl)-1-(oxetan-3-yl)piperidine)-4-sulfonamido)methyl)nicotinate

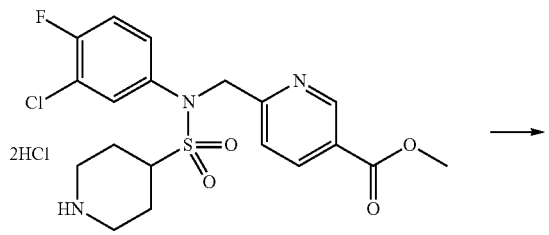

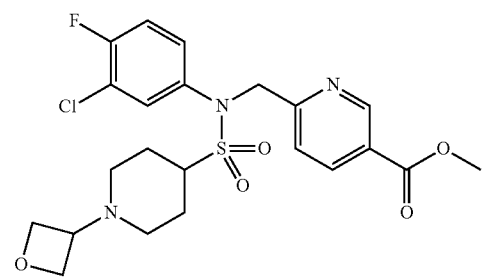

A mixture of methyl 6-((N-(3-chloro-4-fluorophenyl)piperidine-4-sulfonamido)methyl)nicotinate dihydrochloride (0.300 g, 0.583 mmol), oxetan-3-one (0.084 g, 1.165 mmol) and N,N-diisopropylethylamine (0.254 mL, 1.457 mmol) in dichloromethane (20 mL) was treated at the room temperature with sodium triacetoxyborohydride (0.247 g, 1.165 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=50% to 80%) to give methyl 6-(((N-(3-chloro-4-fluorophenyl)-1-(oxetan-3-yl)piperidine)-4-sulfonamido)methyl)nicotinate as beige solid (0.286 g, 98.6%).

[Step 4] N-(3-chloro-4-fluorophenyl)-N-((5-(hydrazinecarbonyl)pyridin-2-yl)methyl)-1-(oxetan-3-yl)piperidine-4-sulfonamide

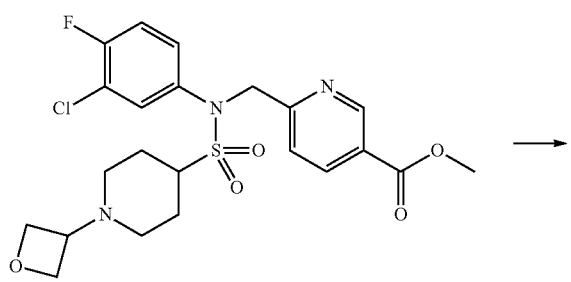

450

-continued

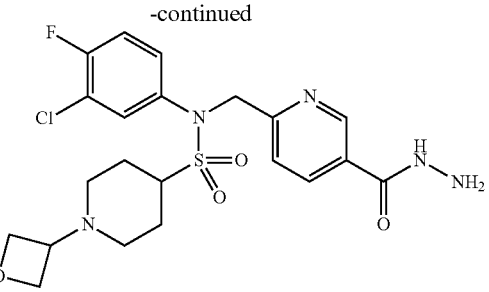

A slurry of methyl 6-(((N-(3-chloro-4-fluorophenyl)-1-(oxetan-3-yl)piperidine)-4-sulfonamido)methyl)nicotinate (0.286 g, 0.574 mmol) in ethanol (5 mL) was mixed at the room temperature with hydrazine monohydrate (0.558 mL, 11.487 mmol), stirred at 110° C. for 16 hr, cooled down to the room temperature to terminate the reaction and concentrated under the reduced pressure to remove the solvent. The residue was diluted with ethyl acetate (5 mL) and hexane (30 mL) and stirred. The resulting precipitates were collected by filtration, washed by hexane, and dried to give N-(3-chloro-4-fluorophenyl)-N-((5-(hydrazinecarbonyl)pyridin-2-yl)methyl)-1-(oxetan-3-yl)piperidine-4-sulfonamide as white solid (0.243 g, 85.0%).

[Step 5] Compound 11501

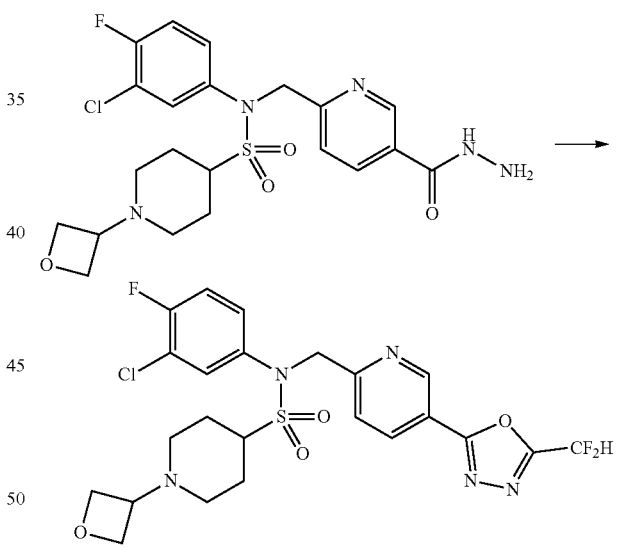

A solution of N-(3-chloro-4-fluorophenyl)-N-((5-(hydrazinecarbonyl)pyridin-2-yl)methyl)-1-(oxetan-3-yl)piperidine-4-sulfonamide (0.243 g, 0.488 mmol) in tetrahydrofuran (10 mL) was mixed at 70° C. with 2,2-difluoroacetic anhydride (0.152 mL, 1.220 mmol) and N,N-diisopropylethylamine (0.255 mL, 1.464 mmol). The reaction mixture was stirred at the same temperature for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=60% to 90%) to give the crude product, and then the crude product was dissolved in dichloromethane (3 mL) and hexane (30 mL) and stirred. The resulting precipitates were collected by filtration, washed by hexane, and dried to give N-(3-chloro-4-fluorophenyl)-N-((5-(5-(difluoromethyl)-1,3,4-oxadiazol-2-yl)pyridin-2-yl)methyl)-1-(oxetan-3-yl)piperidine-4-sulfonamide as white solid (0.126 g, 46.3%).

$^1$H NMR (400 MHz, DMSO-d6) δ 9.11 (s, 1H), 8.42 (m, 1H), 7.83 (m, 1H), 7.73-7.69 (m, 1.25H), 7.56-7.54 (m, 1.5H), 7.46-7.36 (m, 1.25H), 5.18 (s, 2H), 4.53 (t, 2H, J=6.5 Hz), 4.42 (t, 2H, J=6.1 Hz), 3.44 (m, 1H), 2.80 (d, 2H, J=10.9 Hz), 2.11 (d, 2H, J=11.9 Hz), 1.86 (t, 2H, J=11.7 Hz), 1.72 (t, 2H, J=12.1 Hz); LRMS (ES) m/z 558.5 (M$^+$+1).

EXAMPLE 136

Compound 11502, 1-(1-acetylazetidin-3-yl)-N-(3-chloro-4-fluorophenyl)-N-((5-(5-(difluoromethyl)-1,3,4-oxadiazol-2-yl)pyridin-2-yl)methyl)piperidine-4-sulfonamide

[Step 1] methyl 6-(((1-(1-(tert-butoxycarbonyl)azetidin-3-yl)-N-(3-chloro-4-fluorophenyl)piperidine)-4-sulfonamido)methyl)nicotinate

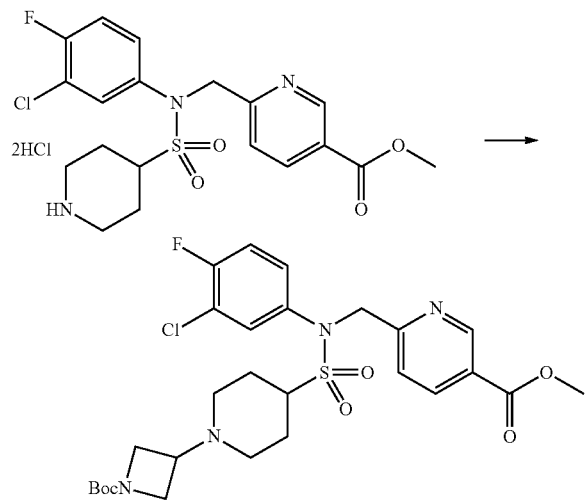

A mixture of methyl 6-((N-(3-chloro-4-fluorophenyl)piperidine-4-sulfonamido)methyl)nicotinate dihydrochloride (1.600 g, 3.108 mmol), tert-butyl 3-oxoazetidine-1-carboxylate (0.798 g, 4.662 mmol) and N,N-diisopropylethylamine (1.353 mL, 7.770 mmol) in dichloromethane (50 mL) was treated at the room temperature with sodium triacetoxyborohydride (1.317 g, 6.216 mmol) and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=30% to 60%) to give methyl 6-(((1-(1-(tert-butoxycarbonyl)azetidin-3-yl)-N-(3-chloro-4-fluorophenyl)piperidine)-4-sulfonamido)methyl) nicotinate as beige solid (1.520 g, 81.9%).

[Step 2] methyl 6-(((1-(azetidin-3-yl)-N-(3-chloro-4-fluorophenyl)piperidine)-4-sulfonamido)methyl) nicotinate trihydrochloride

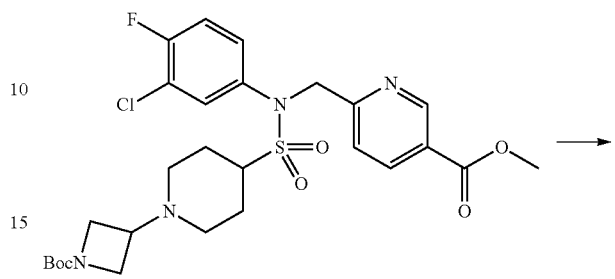

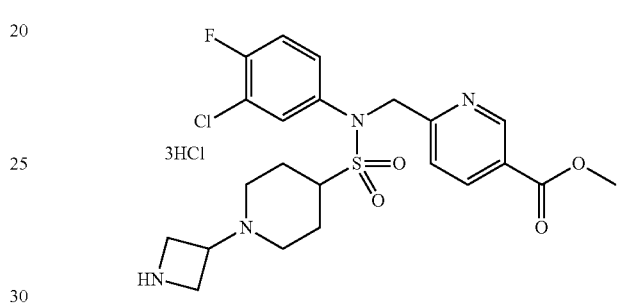

A solution of methyl 6-(((1-(1-(tert-butoxycarbonyl)azetidin-3-yl)-N-(3-chloro-4-fluorophenyl)piperidine)-4-sulfonamido)methyl)nicotinate (1.520 g, 2.546 mmol) in 1,4-dioxane (20 mL) was mixed at the room temperature with hydrochloric acid (4.00 M solution in 1,4-dioxane, 9.546 mL, 38.185 mmol), stirred at the same temperature for 3 hr, and concentrated under the reduced pressure to remove the solvent. The residue was diluted with ethyl acetate (20 mL) and hexane (50 mL) and stirred. The resulting precipitates were collected by filtration, washed by hexane, and dried to give methyl 6-(((1-(azetidin-3-yl)-N-(3-chloro-4-fluorophenyl)piperidine)-4-sulfonamido)methyl)nicotinate trihydrochloride as beige solid (1.420 g, 92.0%).

[Step 3] Methyl 6-(((1-(1-acetylazetidin-3-yl)-N-(3-chloro-4-fluorophenyl)piperidine)-4-sulfonamido) methyl)nicotinate

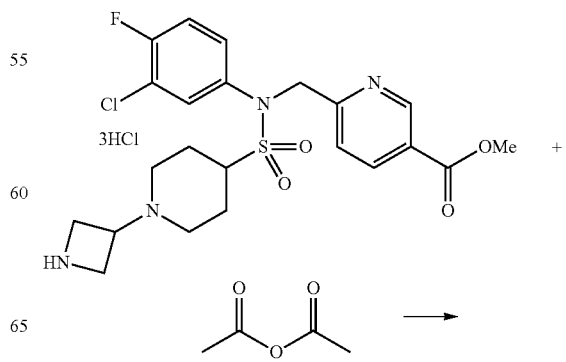

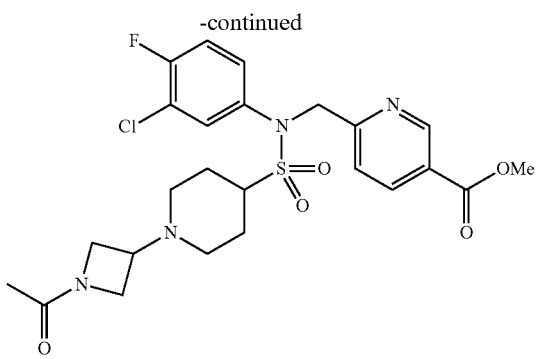

A solution of methyl 6-(((1-(azetidin-3-yl)-N-(3-chloro-4-fluorophenyl)piperidine)-4-sulfonamido)methyl)nicotinate trihydrochloride (0.300 g, 0.604 mmol) and N,N-diisopropylethylamine (0.210 mL, 1.207 mmol) in dichloromethane (10 mL) was mixed at the room temperature with acetic anhydride (0.085 mL, 0.905 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 12 g cartridge; methanol/dichloromethane=0% to 15%) to give methyl 6-(((1-(1-acetylazetidin-3-yl)-N-(3-chloro-4-fluorophenyl)piperidine)-4-sulfonamido)methyl)nicotinate as colorless oil (0.320 g, 98.3%).

[Step 4] 1-(1-acetylazetidin-3-yl)-N-(3-chloro-4-fluorophenyl)-N-((5-(hydrazinecarbonyl)pyridin-2-yl)methyl)piperidine-4-sulfonamide

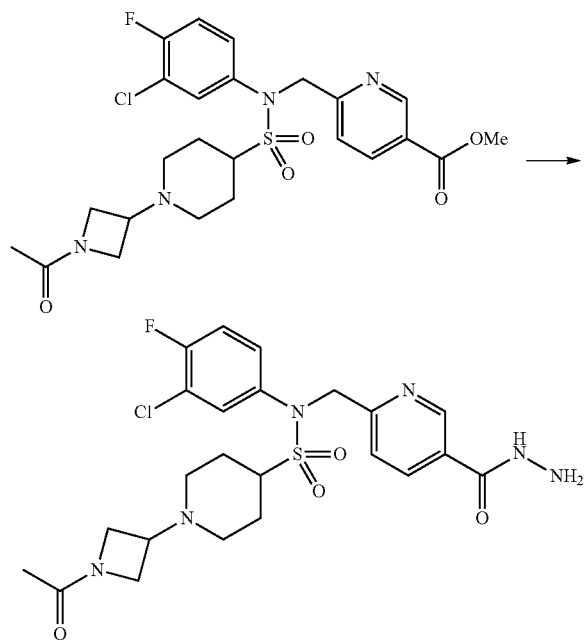

Methyl 6-(((1-(1-acetylazetidin-3-yl)-N-(3-chloro-4-fluorophenyl)piperidine)-4-sulfonamido)methyl)nicotinate (0.330 g, 0.612 mmol) and hydrazine monohydrate (0.893 mL, 18.367 mmol) were mixed at the room temperature in ethanol (8 mL)/water (2 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The title compound was used without further purification (1-(1-acetylazetidin-3-yl)-N-(3-chloro-4-fluorophenyl)-N-((5-(hydrazinecarbonyl)pyridin-2-yl)methyl)piperidine-4-sulfonamide, 0.288 g, 87.3%, white solid).

[Step 5] Compound 11502

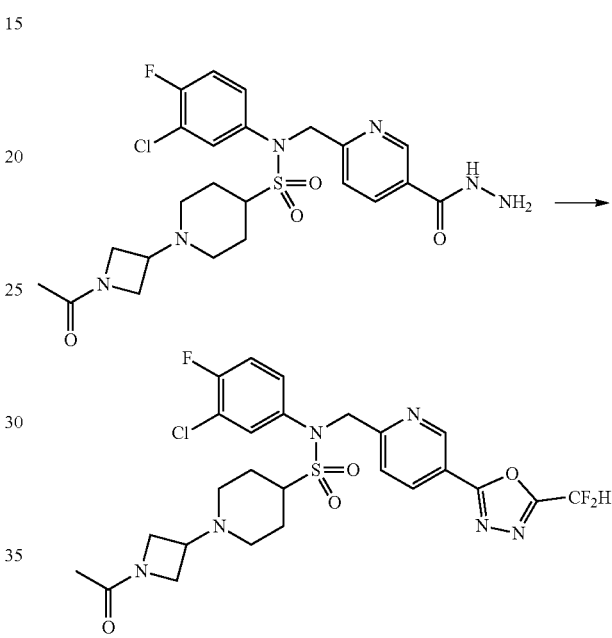

A solution of 1-(1-acetylazetidin-3-yl)-N-(3-chloro-4-fluorophenyl)-N-((5-(hydrazinecarbonyl)pyridin-2-yl)methyl)piperidine-4-sulfonamide (0.288 g, 0.534 mmol) and triethylamine (0.223 mL, 1.603 mmol) in tetrahydrofuran (10 mL) was mixed at room temperature with 2,2-difluoroacetic anhydride (0.199 mL, 1.603 mmol). The reaction mixture was stirred at 80° C. for 1 hr and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 12 g cartridge; methanol/dichloromethane=0% to 20%) to give 1-(1-acetylazetidin-3-yl)-N-(3-chloro-4-fluorophenyl)-N-((5-(5-(difluoromethyl)-1,3,4-oxadiazol-2-yl)pyridin-2-yl)methyl)piperidine-4-sulfonamide as white solid (0.020 g, 6.2%).

$^1$H NMR (400 MHz, $CDCl_3$) δ 9.20 (dd, 1H, J=2.2, 0.8 Hz), 8.37 (dd, 1H, J=8.2, 2.2 Hz), 7.63 (dd, 1H, J=8.2, 0.8 Hz), 7.49 (dd, 1H, J=6.4, 2.7 Hz), 7.29 (ddd, 1H, J=8.9, 4.1, 2.7 Hz), 7.12-7.03 (m, 1H), 6.86 (d, 1H, J=51.6 Hz), 5.09 (d, 2H, J=1.6 Hz), 4.12 (t, 1H, J=7.8 Hz), 4.05-3.91 (m, 2H), 3.84 (dd, 1H, J=10.0, 5.3 Hz), 3.20-3.06 (m, 2H), 3.00-2.89 (m, 1H), 2.16 (d, 1H, J=13.5 Hz), 1.95 (td, 6H, J=12.7, 10.8, 5.1 Hz), 1.86 (s, 3H); LRMS (ES) m/z 599.5 ($M^+$+1).

EXAMPLE 137

Compound 11503, N-(3-chloro-4-fluorophenyl)-N-((5-(5-(difluoromethyl)-1,3,4-oxadiazol-2-yl)pyridin-2-yl)methyl)-1-(1-(methylsulfonyl)azetidin-3-yl)piperidine-4-sulfonamide

[Step 1] methyl 6-(((N-(3-chloro-4-fluorophenyl)-1-(1-(methylsulfonyl)azetidin-3-yl)piperidine)-4-sulfonamido)methyl)nicotinate

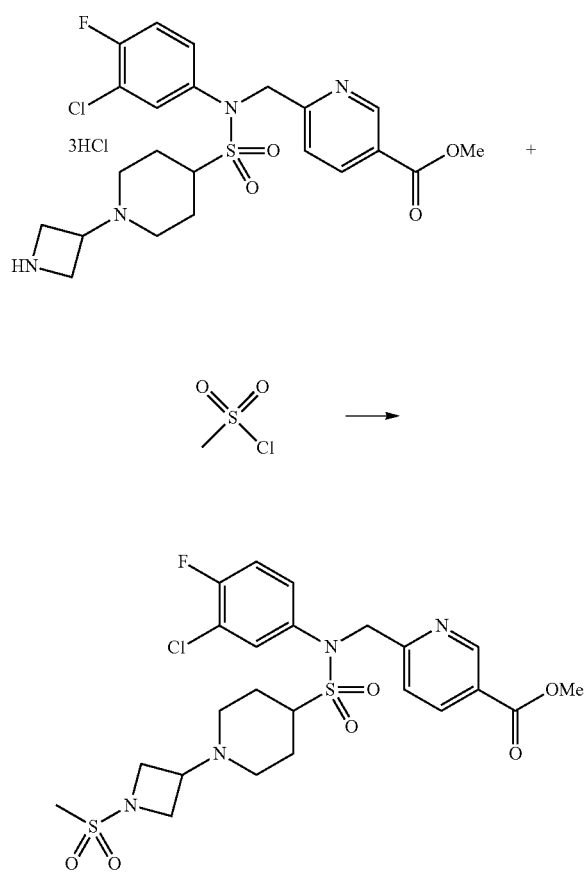

A solution of methyl 6-(((1-(azetidin-3-yl)-N-(3-chloro-4-fluorophenyl)piperidine)-4-sulfonamido)methyl)nicotinate trihydrochloride (0.300 g, 0.604 mmol) and N,N-diisopropylethylamine (0.210 mL, 1.207 mmol) in dichloromethane (10 mL) was mixed at the room temperature with methanesulfonyl chloride (0.070 mL, 0.905 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 15%) to give methyl 6-(((N-(3-chloro-4-fluorophenyl)-1-(1-(methylsulfonyl)azetidin-3-yl)piperidine)-4-sulfonamido)methyl)nicotinate as yellow solid (0.280 g, 80.7%).

[Step 2] N-(3-chloro-4-fluorophenyl)-N-((5-(hydrazinecarbonyl)pyridin-2-yl)methyl)-1-(1-(methylsulfonyl)azetidin-3-yl)piperidine-4-sulfonamide

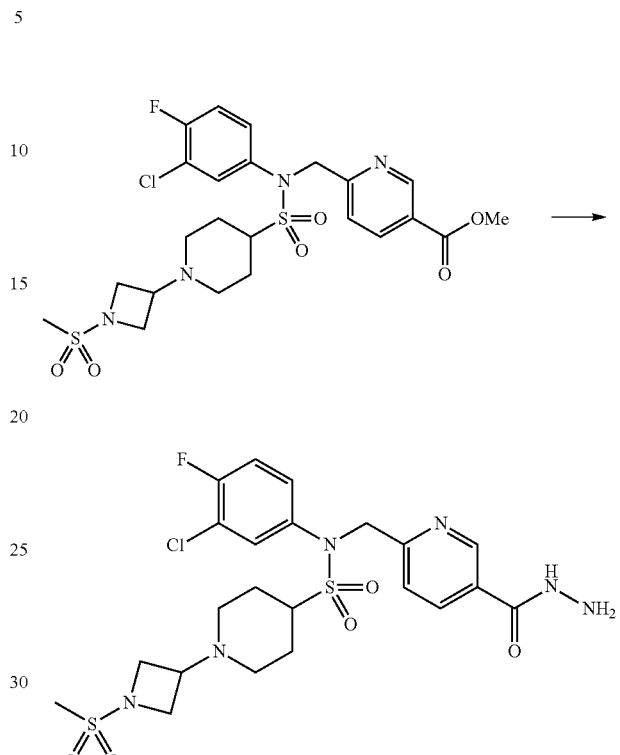

methyl 6-(((N-(3-chloro-4-fluorophenyl)-1-(1-(methylsulfonyl)azetidin-3-yl)piperidine)-4-sulfonamido)methyl)nicotinate (0.280 g, 0.487 mmol) and hydrazine monohydrate (0.710 mL, 14.607 mmol) were mixed at the room temperature in ethanol (8 mL)/water (2 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(3-chloro-4-fluorophenyl)-N-((5-(hydrazinecarbonyl)pyridin-2-yl)methyl)-1-(1-(methylsulfonyl)azetidin-3-yl)piperidine-4-sulfonamide, 0.245 g, 87.5%, white solid).

[Step 3] Compound 11503

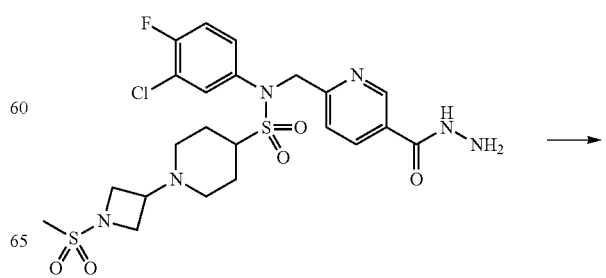

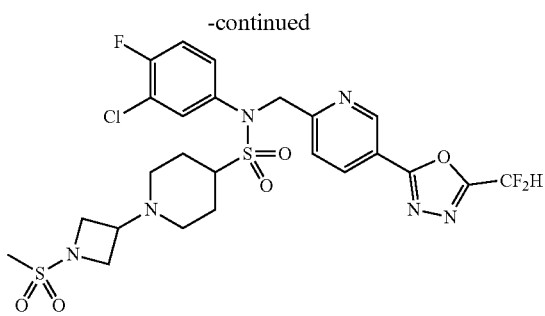

A solution of N-(3-chloro-4-fluorophenyl)-N-((5-(hydrazinecarbonyl)pyridin-2-yl)methyl)-1-(1-(methylsulfonyl)azetidin-3-yl)piperidine-4-sulfonamide (0.245 g, 0.426 mmol) and triethylamine (0.178 mL, 1.278 mmol) in tetrahydrofuran (10 mL) was mixed at the room temperature with 2,2-difluoroacetic anhydride (0.159 mL, 1.278 mmol), stirred at 80° C. for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 20%) to give N-(3-chloro-4-fluorophenyl)-N-((5-(5-(difluoromethyl)-1,3,4-oxadiazol-2-yl)pyridin-2-yl)methyl)-1-(1-(methylsulfonyl)azetidin-3-yl)piperidine-4-sulfonamide as white solid (0.120 g, 44.4%).

$^1$H NMR (400 MHz, CDCl$_3$) δ 9.19 (dd, 1H, J=2.3, 0.8 Hz), 8.35 (dd, 1H, J=8.2, 2.2 Hz), 7.61 (dd, 1H, J=8.3, 0.9 Hz), 7.48 (dd, 1H, J=6.4, 2.7 Hz), 7.33-7.27 (m, 2H), 7.10-7.05 (m, 2H), 7.05-6.78 (m, 1H), 5.07 (s, 2H), 3.85 (ddd, 4H, J=30.8, 8.0, 6.6 Hz), 3.18 (q, 1H, J=6.6 Hz), 3.10 (s, 1H), 2.87 (s, 3H), 2.12 (s, 2H), 1.93 (t, 4H, J=9.7 Hz); LRMS (ES) m/z 635.5 (M$^+$+1).

EXAMPLE 138

Compound 11504, N-(4-chloro-3-methylphenyl)-N-((5-(5-(difluoromethyl)-1,3,4-oxadiazol-2-yl)pyridin-2-yl)methyl)ethanesulfonamide

[Step 1] N-(4-chloro-3-methylphenyl)ethanesulfonamide

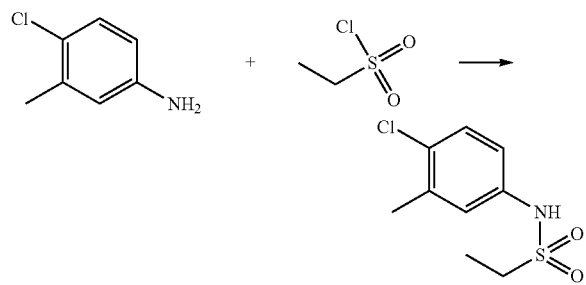

A solution of 4-chloro-3-methylaniline (0.500 g, 3.531 mmol) and pyridine (0.427 mL, 5.297 mmol) in dichloromethane (20 mL) was mixed at the room temperature with ethanesulfonyl chloride (0.400 mL, 4.237 mmol) and stirred at the same temperature for 12 hr. Then, aqueous 1M-hydrochloric acid solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=5% to 50%) to give N-(4-chloro-3-methylphenyl)ethanesulfonamide as beige solid (0.440 g, 53.3%).

[Step 2] methyl 6-((N-(4-chloro-3-methylphenyl)ethylsulfonamido)methyl)nicotinate

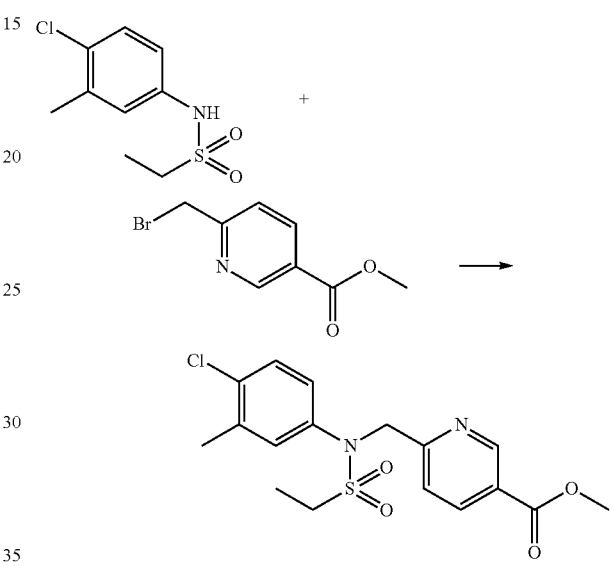

A solution of N-(4-chloro-3-methylphenyl)ethanesulfonamide (0.200 g, 0.856 mmol), potassium carbonate (0.177 g, 1.284 mmol), methyl 6-(bromomethyl)nicotinate (0.217 g, 0.941 mmol) and potassium iodide (0.071 g, 0.428 mmol) in N,N-dimethylformide (10 mL) was stirred at the room temperature for 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 6-((N-(4-chloro-3-methylphenyl)ethylsulfonamido)methyl)nicotinate as yellow solid (0.150 g, 45.8%).

[Step 3] N-(4-chloro-3-methylphenyl)-N-((5-(hydrazinecarbonyl)pyridin-2-yl)methyl)ethanesulfonamide

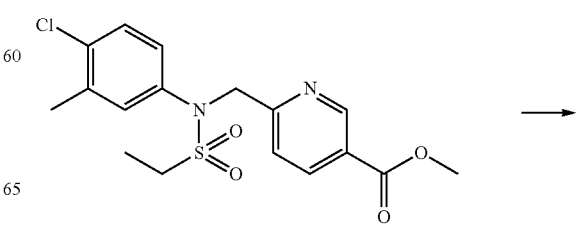

-continued

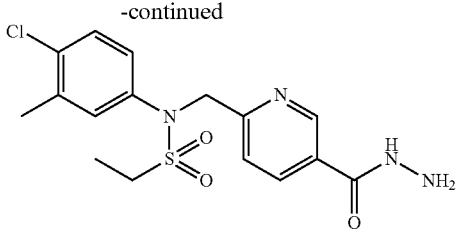

A solution of methyl 6-((N-(4-chloro-3-methylphenyl)ethylsulfonamido)methyl)nicotinate (0.150 g, 0.392 mmol) and hydrazine monohydrate (0.190 mL, 3.918 mmol) in ethanol (10 mL) was stirred at 90° C. for 12 hr and cooled down to the room temperature to terminate the reaction. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(4-chloro-3-methylphenyl)-N-((5-(hydrazinecarbonyl)pyridin-2-yl)methyl)ethanesulfonamide, 0.077 g, 51.3%, yellow oil).

[Step 4] Compound 11504

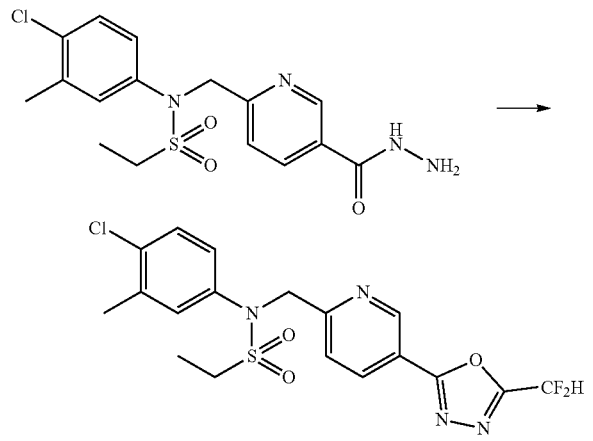

A solution of N-(4-chloro-3-methylphenyl)-N-((5-(hydrazinecarbonyl)pyridin-2-yl)methyl)ethanesulfonamide (0.077 g, 0.201 mmol), triethylamine (0.112 mL, 0.804 mmol) and 2,2-difluoroacetic anhydride (0.050 mL, 0.402 mmol) in tetrahydrofuran (5 mL) was stirred at 90° C. for 5 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 20%) to give N-(4-chloro-3-methylphenyl)-N-((5-(5-(difluoromethyl)-1,3,4-oxadiazol-2-yl)pyridin-2-yl)methyl)ethanesulfonamide as yellow solid (0.035 g, 39.3%).
$^1$H NMR (400 MHz, CDCl$_3$) δ 9.23 (dd, 1H, J=2.2, 0.9 Hz), 8.41 (dd, 1H, J=8.2, 2.2 Hz), 7.75 (dd, 1H, J=8.2, 0.9 Hz), 7.35-7.26 (m, 2H), 7.19 (ddd, 1H, J=8.6, 2.7, 0.7 Hz), 7.10-6.80 (m, 1H), 5.16 (s, 2H), 3.20 (q, 2H, J=7.4 Hz), 2.35 (s, 3H), 1.46 (t, 3H, J=7.4 Hz); LRMS (ES) m/z 443.3 (M$^+$+1).

EXAMPLE 139

Compound 11505, N-(3-chloro-4-methylphenyl)-N-((5-(5-(difluoromethyl)-1,3,4-oxadiazol-2-yl)pyridin-2-yl)methyl)ethanesulfonamide

[Step 1] N-(3-chloro-4-methylphenyl)ethanesulfonamide

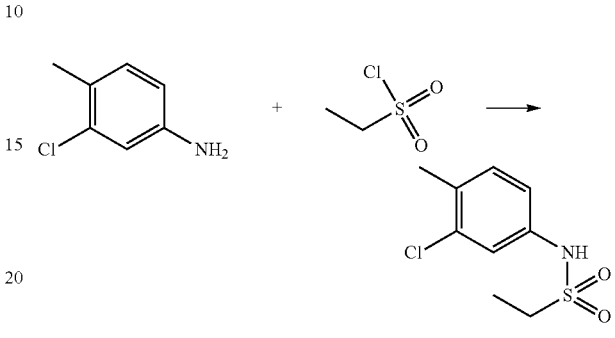

A solution of 3-chloro-4-methylaniline (0.500 g, 3.531 mmol), ethanesulfonyl chloride (0.501 mL, 5.297 mmol) and pyridine (0.341 mL, 4.237 mmol) in dichloromethane (15 mL) was stirred at the room temperature for 18 hr. Then, water was added to the reaction mixture, followed by extraction with ethyl acetate. The organic layer was washed with aqueous 1M-hydrochloric acid solution, dried with anhydrous MgSO$_4$, filtered, and concentrated in vacuo. The residue was chromatographed (SiO$_2$, 12 g cartridge; ethyl acetate/hexane=0% to 80%) to give N-(3-chloro-4-methylphenyl)ethanesulfonamide as red solid (0.528 g, 64.0%).

[Step 2] methyl 6-((N-(3-chloro-4-methylphenyl)ethylsulfonamido)methyl)nicotinate

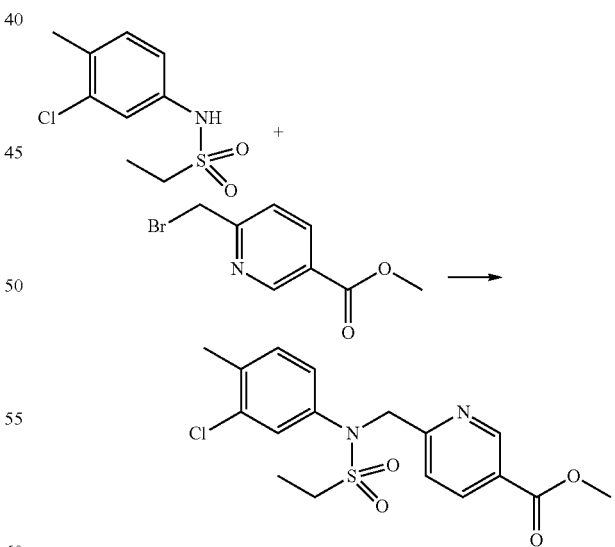

A solution of methyl 6-(bromomethyl)nicotinate (0.217 g, 0.941 mmol) and potassium iodide (0.071 g, 0.428 mmol) in N,N-dimethylformide (10 mL) was mixed at the room temperature with N-(3-chloro-4-methylphenyl)ethanesulfonamide (0.200 g, 0.856 mmol) and potassium carbonate (0.177 g, 1.284 mmol). The reaction mixture was stirred at the same temperature for 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 6-((N-(3-chloro-4-methylphenyl)ethylsulfonamido)methyl)nicotinate as yellow solid (0.140 g, 42.7%).

[Step 3] N-(3-chloro-4-methylphenyl)-N-((5-(hydrazinecarbonyl)pyridin-2-yl)methyl)ethanesulfonamide

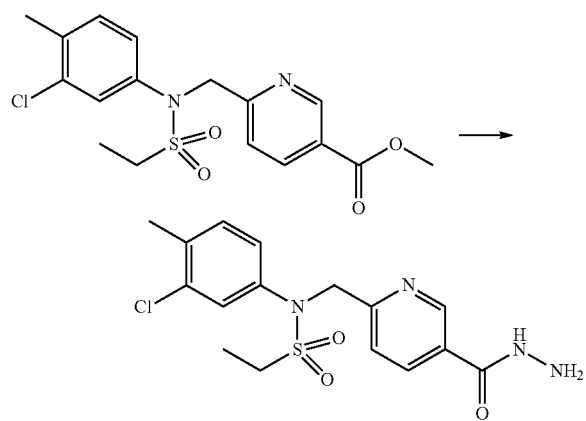

A solution of methyl 6-((N-(3-chloro-4-methylphenyl)ethylsulfonamido)methyl)nicotinate (0.140 g, 0.366 mmol) and hydrazine monohydrate (0.178 mL, 3.657 mmol) in ethanol (10 mL) was stirred at 90° C. for 12 hr, cooled down to the room temperature to terminate the reaction and concentrated under the reduced pressure to remove the solvent. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(3-chloro-4-methylphenyl)-N-((5-(hydrazinecarbonyl)pyridin-2-yl)methyl)ethanesulfonamide, 0.088 g, 62.9%, yellow oil).

[Step 4] Compound 11505

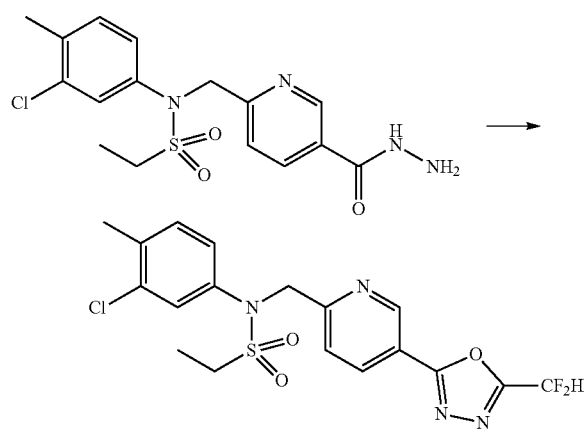

A solution of N-(3-chloro-4-methylphenyl)-N-((5-(hydrazinecarbonyl)pyridin-2-yl)methyl)ethanesulfonamide (0.088 g, 0.230 mmol), triethylamine (0.128 mL, 0.919 mmol) and 2,2-difluoroacetic anhydride (0.057 mL, 0.460 mmol) in tetrahydrofuran (5 mL) was stirred at 90° C. for 5 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 20%) to give the title compound as yellow oil (0.055 g, 54.0%).

$^1$H NMR (400 MHz, CDCl$_3$) δ 9.23 (dd, 1H, J=2.2, 0.9 Hz), 8.40 (dd, 1H, J=8.3, 2.2 Hz), 7.73 (dd, 1H, J=8.3, 0.9 Hz), 7.44 (d, 1H, J=2.1 Hz), 7.33-7.16 (m, 2H), 7.10-6.80 (m, 1H), 5.14 (s, 2H), 3.20 (q, 2H, J=7.4 Hz), 2.33 (s, 3H), 1.45 (t, 3H, J=7.4 Hz); LRMS (ES) m/z 443.43 (M$^+$+1).

EXAMPLE 140

Compound 11506, N-(3,5-dichlorophenyl)-N-((5-(5-(difluoromethyl)-1,3,4-oxadiazol-2-yl)pyridin-2-yl)methyl)ethanesulfonamide

[Step 1] N-(3,5-dichlorophenyl)ethanesulfonamide

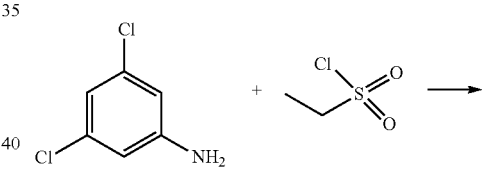

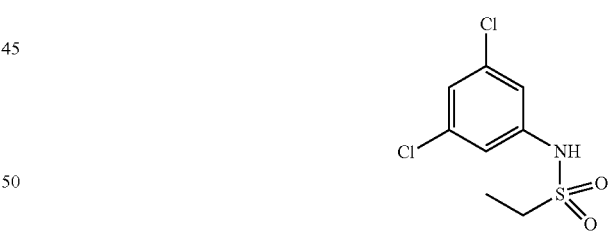

A solution of 3,5-dichloroaniline (0.500 g, 3.086 mmol) and pyridine (0.298 mL, 3.703 mmol) in dichloromethane (15 mL) was mixed at the room temperature with ethanesulfonyl chloride (0.437 mL, 4.629 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 30%) to give N-(3,5-dichlorophenyl)ethanesulfonamide as white solid (0.638 g, 81.3%)

[Step 2] methyl 6-((N-(3,5-dichlorophenyl)ethylsulfonamido)methyl)nicotinate

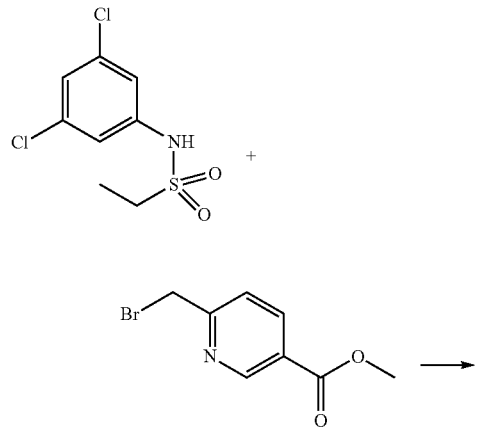

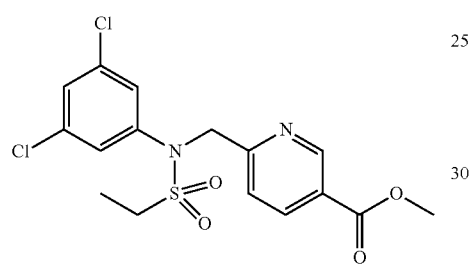

A solution of methyl 6-(bromomethyl)nicotinate (0.199 g, 0.866 mmol) and potassium iodide (0.065 g, 0.393 mmol) in N,N-dimethylformide (10 mL) was mixed at the room temperature with N-(3,5-dichlorophenyl)ethanesulfonamide (0.200 g, 0.787 mmol) and potassium carbonate (0.163 g, 1.180 mmol). The reaction mixture was stirred at the same temperature for 12 hr. Then, water was added to the reaction mixture, followed by extraction with ethyl acetate. The organic layer was washed with aqueous saturated ammonium chloride solution, dried with anhydrous MgSO4, filtered, and concentrated in vacuo. The residue was chromatographed (SiO2, 12 g cartridge; ethyl acetate/hexane=0% to 40%) to give methyl 6-((N-(3,5-dichlorophenyl)ethylsulfonamido)methyl)nicotinate as yellow solid (0.160 g, 50.4%).

[Step 3] N-(3,5-dichlorophenyl)-N-((5-(hydrazinecarbonyl)pyridin-2-yl)methyl)ethanesulfonamide

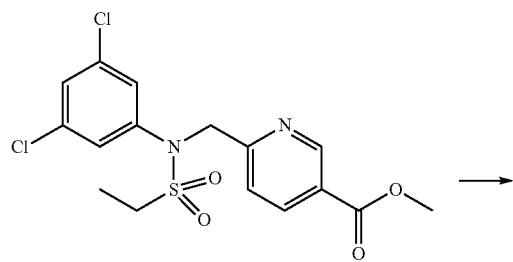

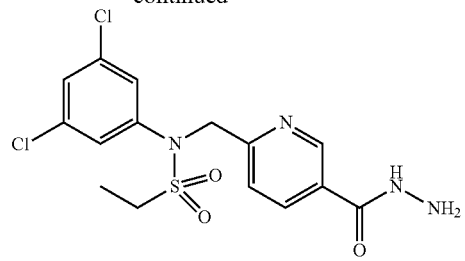

A solution of methyl 6-((N-(3,5-dichlorophenyl)ethylsulfonamido)methyl)nicotinate (0.160 g, 0.397 mmol) and hydrazine monohydrate (0.193 mL, 3.968 mmol) in ethanol (10 mL) was stirred at 90° C. for 12 hr, cooled down to the room temperature to terminate the reaction and concentrated under the reduced pressure to remove the solvent. Then, water was added to the concentrate, followed by extraction with dichloromethane. The organic layer was washed with aqueous saturated sodium bicarbonate solution, dried with anhydrous MgSO4, filtered, and concentrated in vacuo. The title compound was used without further purification (N-(3,5-dichlorophenyl)-N-((5-(hydrazinecarbonyl)pyridin-2-yl)methyl)ethanesulfonamide, 0.087 g, 54.4%, yellow oil).

[Step 4] Compound 11506

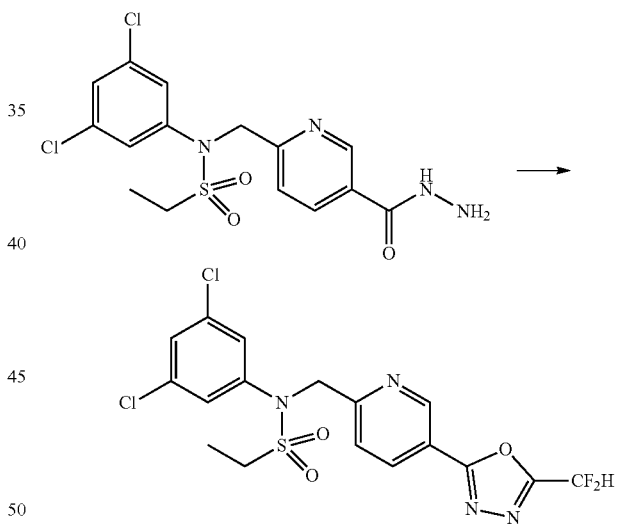

A solution of N-(3,5-dichlorophenyl)-N-((5-(hydrazinecarbonyl)pyridin-2-yl)methyl)ethanesulfonamide (0.087 g, 0.216 mmol), triethylamine (0.120 mL, 0.863 mmol) and 2,2-difluoroacetic anhydride (0.054 mL, 0.431 mmol) in tetrahydrofuran (5 mL) was stirred at 90° C. for 5 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO4, filtered, and concentrated in vacuo. The residue was chromatographed (SiO2, 4 g cartridge; ethyl acetate/hexane=0% to 20%) to give N-(3,5-dichlorophenyl)-N-((5-(5-(difluoromethyl)-1,3,4-oxadiazol-2-yl)pyridin-2-yl)methyl)ethanesulfonamide as yellow oil (0.039 g, 39.0%).

$^1$H NMR (400 MHz, CDCl$_3$) δ 9.28 (dd, 1H, J=2.2, 0.9 Hz), 8.43 (dd, 1H, J=8.2, 2.2 Hz), 7.67 (dt, 1H, J=8.2, 0.7 Hz), 7.41 (d, 2H, J=1.8 Hz), 7.28 (d, 1H, J=1.8 Hz), 7.10-6.81 (m, 1H), 5.15 (s, 2H), 3.23 (q, 2H, J=7.4 Hz), 1.45 (t, 3H, J=7.4 Hz); LRMS (ES) m/z 463.35 (M$^+$+1).

EXAMPLE 141

Compound 11507, N-(3,4-dichlorophenyl)-N-((5-(5-(difluoromethyl)-1,3,4-oxadiazol-2-yl)pyridin-2-yl)methyl)ethanesulfonamide

[Step 1] N-(3,4-dichlorophenyl)ethanesulfonamide

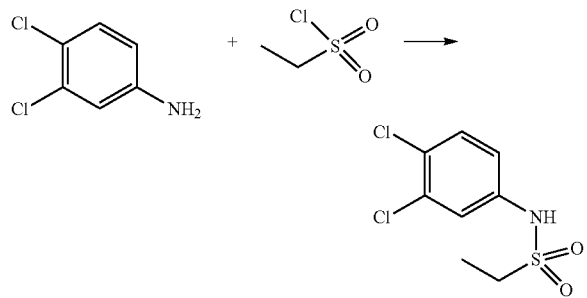

A solution of 3,4-dichloroaniline (0.500 g, 3.086 mmol) and pyridine (0.373 mL, 4.629 mmol) in dichloromethane (20 mL) was mixed at the room temperature with ethanesulfonyl chloride (0.350 mL, 3.703 mmol) and stirred at the same temperature for 12 hr. Then, aqueous 1M-hydrochloric acid solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=5% to 50%) to give N-(3,4-dichlorophenyl)ethanesulfonamide as red solid (0.430 g, 54.8%).

[Step 2] methyl 6-4N-(3,4-dichlorophenyl)ethylsulfonamido)methyl)nicotinate

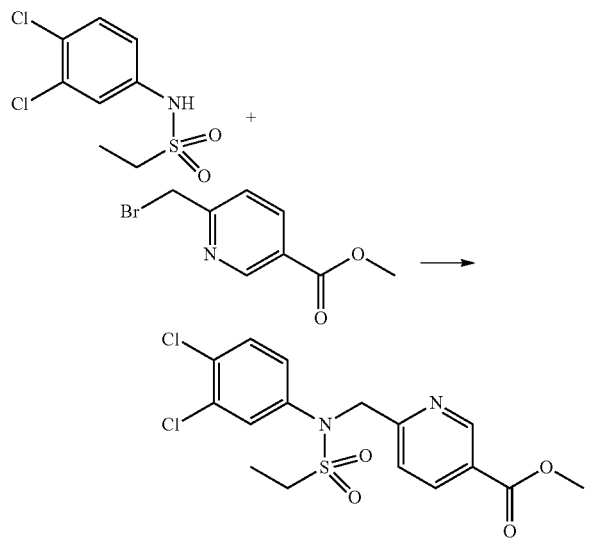

A solution of methyl 6-(bromomethyl)nicotinate (0.199 g, 0.866 mmol) and potassium iodide (0.065 g, 0.393 mmol) in N,N-dimethylformide (10 mL) was mixed at the room temperature with N-(3,4-dichlorophenyl)ethanesulfonamide (0.200 g, 0.787 mmol) and potassium carbonate (0.163 g, 1.180 mmol). The reaction mixture was stirred at the same temperature for 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 6-((N-(3,4-dichlorophenyl)ethylsulfonamido)methyl)nicotinate as yellow solid (0.110 g, 34.7%).

[Step 3] N-(3,4-dichlorophenyl)-N-((5-(hydrazinecarbonyl)pyridin-2-yl)methyl)ethanesulfonamide

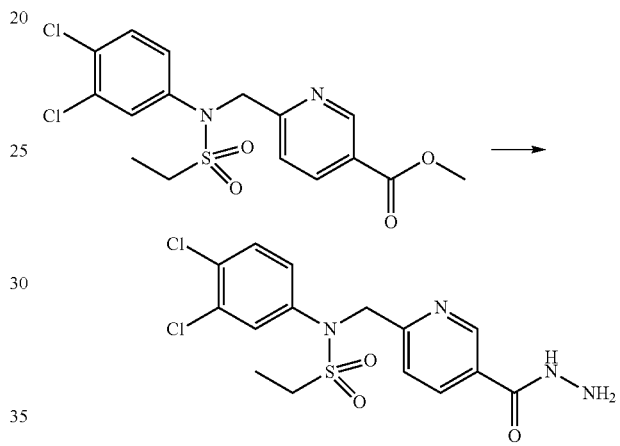

A solution of methyl 6-((N-(3,4-dichlorophenyl)ethylsulfonamido)methyl)nicotinate (0.110 g, 0.273 mmol) and hydrazine monohydrate (0.133 mL, 2.728 mmol) in ethanol (10 mL) was stirred at 90° C. for 12 hr, cooled down to the room temperature to terminate the reaction and concentrated under the reduced pressure to remove the solvent. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(3,4-dichlorophenyl)-N-((5-(hydrazinecarbonyl)pyridin-2-yl)methyl)ethanesulfonamide, 0.046 g, 41.8%, yellow oil).

[Step 4] N-(3,4-dichlorophenyl)-N-((5-(2-(2,2-difluoroacetyl)hydrazine-1-carbonyl)pyridin-2-yl)methyl)ethanesulfonamide

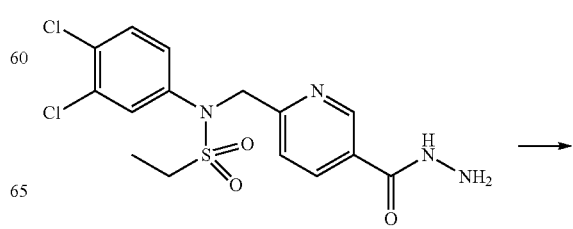

-continued

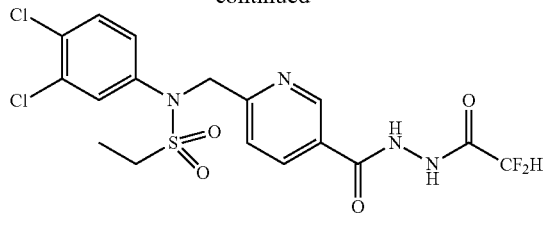

A solution of N-(3,4-dichlorophenyl)-N-((5-(hydrazinecarbonyl)pyridin-2-yl)methyl)ethanesulfonamide (0.046 g, 0.114 mmol), triethylamine (0.064 mL, 0.456 mmol) and 2,2-difluoroacetic anhydride (0.028 mL, 0.228 mmol) in tetrahydrofuran (5 mL) was stirred at 90° C. for 5 hr, and cooled down to the room temperature to terminate the reaction. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(3,4-dichlorophenyl)-N-((5-(2-(2,2-difluoroacetyl)hydrazine-1-carbonyl)pyridin-2-yl)methyl)ethanesulfonamide, 0.029 g, 52.8%, yellow oil).

[Step 5] Compound 11507

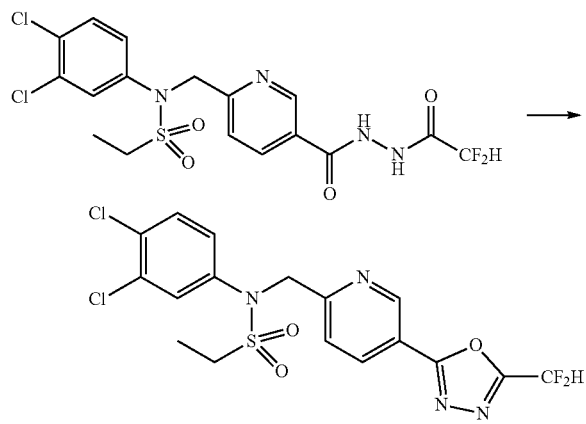

A solution of N-(3,4-dichlorophenyl)-N-((5-(2-(2,2-difluoroacetyl)hydrazine-1-carbonyl)pyridin-2-yl)methyl)ethanesulfonamide (0.029 g, 0.060 mmol) and 1-methoxy-N-triethylammoniosulfonyl-methanimidate (Burgess reagent, 0.029 g, 0.121 mmol) in tetrahydrofuran (5 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 50%) to give N-(3,4-dichlorophenyl)-N-((5-(5-(difluoromethyl)-1,3,4-oxadiazol-2-yl)pyridin-2-yl)methyl)ethanesulfonamide as yellow solid (0.012 g, 43.0%).

$^1$H NMR (400 MHz, CDCl$_3$) δ 9.26 (dd, 1H, J=2.2, 0.9 Hz), 8.41 (dd, 1H, J=8.2, 2.2 Hz), 7.68 (dd, 1H, J=8.2, 0.9 Hz), 7.60 (d, 1H, J=2.5 Hz), 7.42 (d, 1H, J=8.7 Hz), 7.36-7.25 (m, 1H), 7.16-6.77 (m, 1H), 5.15 (s, 2H), 3.21 (q, 2H, J=7.4 Hz), 1.49-1.38 (m, 3H); LRMS (ES) m/z 463.35 (M$^+$+1).

EXAMPLE 142

Compound 11508, N-(3-chloro-5-methylphenyl)-N-((5-(5-(difluoromethyl)-1,3,4-oxadiazol-2-yl)pyridin-2-yl)methyl)ethanesulfonamide

[Step 1]
N-(3-chloro-5-methylphenyl)ethanesulfonamide

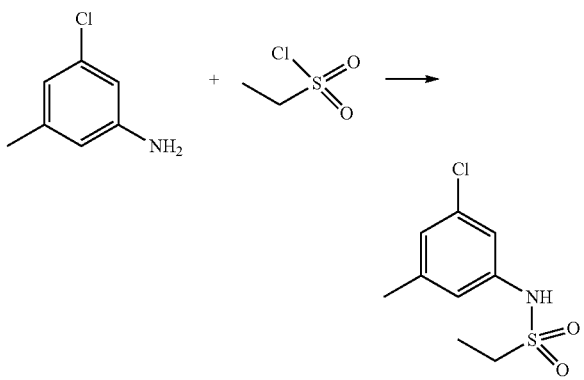

A solution of 3-chloro-5-methylaniline (0.500 g, 3.531 mmol) and pyridine (0.427 mL, 5.297 mmol) in dichloromethane (20 mL) was mixed at the room temperature with ethanesulfonyl chloride (0.400 mL, 4.237 mmol), and stirred at the same temperature for 12 hr. Then, aqueous 1M-hydrochloric acid solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; ethyl acetate/hexane=5% to 50%) to give N-(3-chloro-5-methylphenyl)ethanesulfonamide as beige solid (0.380 g, 46.0%).

[Step 2] methyl 6-((N-(3-chloro-5-methylphenyl)ethylsulfonamido)methyl)nicotinate

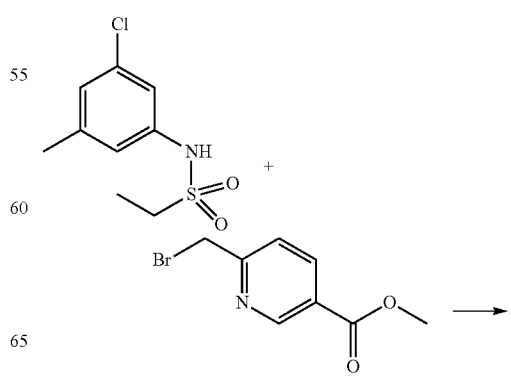

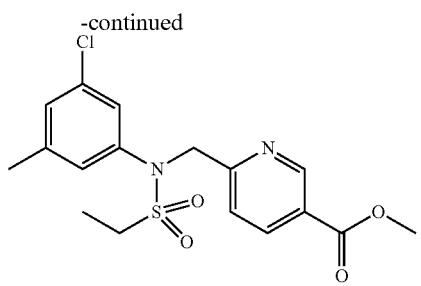

A solution of methyl 6-(bromomethyl)nicotinate (0.217 g, 0.941 mmol) and potassium iodide (0.071 g, 0.428 mmol) in N,N-dimethylformide (10 mL) was mixed at the room temperature with N-(3-chloro-5-methylphenyl)ethanesulfonamide (0.200 g, 0.856 mmol) and potassium carbonate (0.177 g, 1.284 mmol). The reaction mixture was stirred at the same temperature for 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 50%) to give methyl 6-((N-(3-chloro-5-methylphenyl)ethylsulfonamido)methyl)nicotinate as yellow solid (0.130 g, 39.7%).

[Step 3] N-(3-chloro-5-methylphenyl)-N-((5-(hydrazinecarbonyl)pyridin-2-yl)methyl)ethanesulfonamide

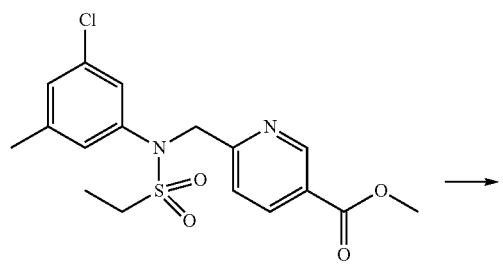

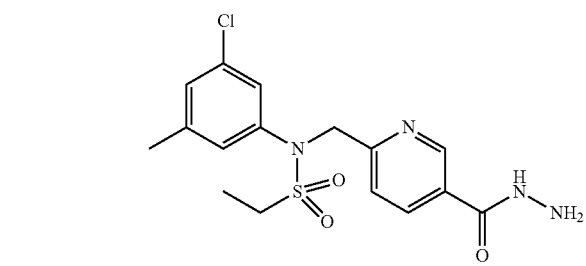

A solution of methyl 6-((N-(3-chloro-5-methylphenyl)ethylsulfonamido)methyl)nicotinate (0.130 g, 0.340 mmol) and hydrazine monohydrate (0.165 mL, 3.395 mmol) in ethanol (10 mL) was stirred at 90° C. for 12 hr, cooled down to the room temperature to terminate the reaction and concentrated under the reduced pressure to remove the solvent. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(3-chloro-5-methylphenyl)-N-((5-(hydrazinecarbonyl)pyridin-2-yl)methyl)ethanesulfonamide, 0.063 g, 48.5%, yellow oil).

[Step 4] N-(3-chloro-5-methylphenyl)-N-((5-(2-(2,2-difluoroacetyl)hydrazine-1-carbonyl)pyridin-2-yl)methyl)ethanesulfonamide

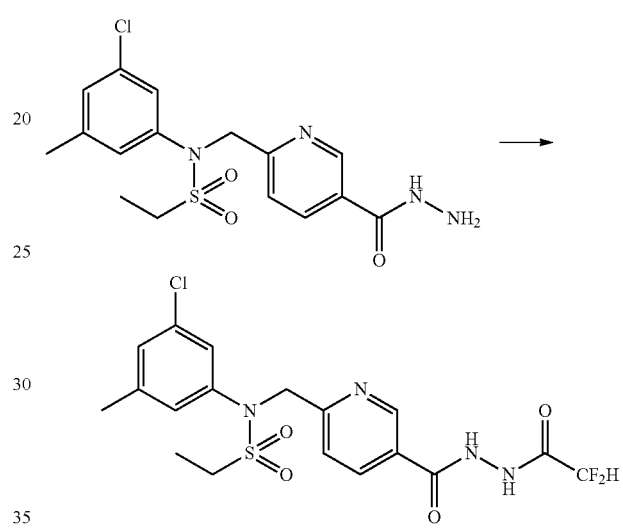

A solution of N-(3-chloro-5-methylphenyl)-N-((5-(hydrazinecarbonyl)pyridin-2-yl)methyl)ethanesulfonamide (0.063 g, 0.165 mmol), triethylamine (0.092 mL, 0.658 mmol) and 2,2-difluoroacetic anhydride (0.041 mL, 0.329 mmol) in tetrahydrofuran (5 mL) was stirred at 90° C. for 5 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The title compound was used without further purification (N-(3-chloro-5-methylphenyl)-N-((5-(2-(2,2-difluoroacetyl)hydrazine-1-carbonyl)pyridin-2-yl)methyl)ethanesulfonamide, 0.034 g, 44.8%, yellow oil).

[Step 5] Compound 11508

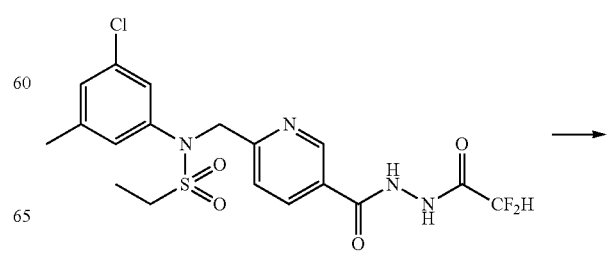

-continued

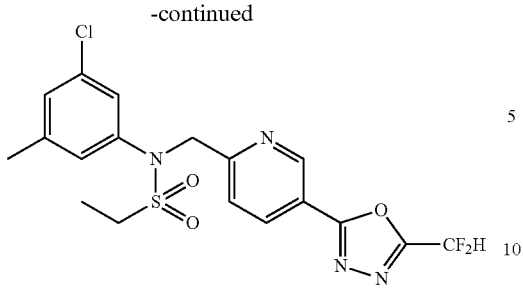

A solution of N-(3-chloro-5-methylphenyl)-N-((5-(2-(2,2-difluoroacetyl)hydrazine-1-carbonyl)pyridin-2-yl)methyl)ethanesulfonamide (0.034 g, 0.074 mmol) and 1-methoxy-N-triethylammoniosulfonyl-methanimidate (Burgess reagent, 0.035 g, 0.148 mmol) in tetrahydrofuran (5 mL) was stirred at 90° C. for 5 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(3-chloro-5-methylphenyl)-N-((5-(5-(difluoromethyl)-1,3,4-oxadiazol-2-yl)pyridin-2-yl)methyl)ethanesulfonamide as yellow solid (0.026 g, 79.6%).

$^1$H NMR (400 MHz, CDCl$_3$) δ 9.25 (dd, 1H, J=2.2, 0.9 Hz), 8.41 (dd, 1H, J=8.2, 2.2 Hz), 7.73 (dd, 1H, J=8.2, 0.8 Hz), 7.26 (td, 1H, J=2.0, 0.6 Hz), 7.16 (ddt, 1H, J=2.3, 1.5, 0.8 Hz), 7.12-7.06 (m, 1H), 7.02-6.79 (m, 1H), 5.15 (s, 2H), 3.21 (q, 2H, J=7.4 Hz), 2.32 (s, 3H), 1.46 (t, 3H, J=7.4 Hz); LRMS (ES) m/z 443.36 (M$^+$+1).

EXAMPLE 143

Compound 11514, N-(3-chloro-4-fluorophenyl)-N-(4-(5-(difluoromethyl)-1,3,4-oxadiazol-2-yl)-2-fluorobenzyl)-2-(pyrrolidin-1-yl)ethane-1-sulfonamide

[Step 1] N-(3-chloro-4-fluorophenyl)ethenesulfonamide

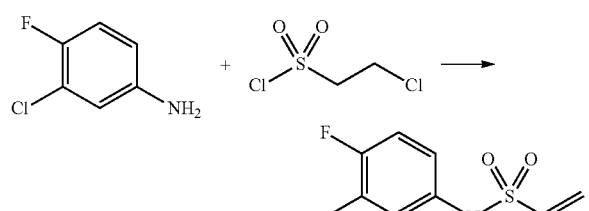

A solution of 3-chloro-4-fluoroaniline (3.000 g, 20.610 mmol) and 2-chloroethane-1-sulfonyl chloride (2.369 mL, 22.671 mmol) in dichloromethane (14 mL) was mixed at the room temperature with pyridine (2.158 mL, 26.793 mmol) and stirred at the same temperature for 6 hr. Then, aqueous 0.1N-hydrochloric acid solution was added to the reaction mixture, followed by extraction with dichloromethane The bi-phasic mixture was passed through a plastic frit to remove the solid residues and aqueous layer, and the organic layer collected was concentrated in vacuo. The residue was chromatographed (SiO$_2$, 24 g cartridge; ethyl acetate/hexane=0% to 20%) to give N-(3-chloro-4-fluorophenyl)ethenesulfonamide as gray solid (3.800 g, 78.2%).

[Step 2] methyl 4-((N-(3-chloro-4-fluorophenyl)vinylsulfonamido)methyl)-3-fluorobenzoate

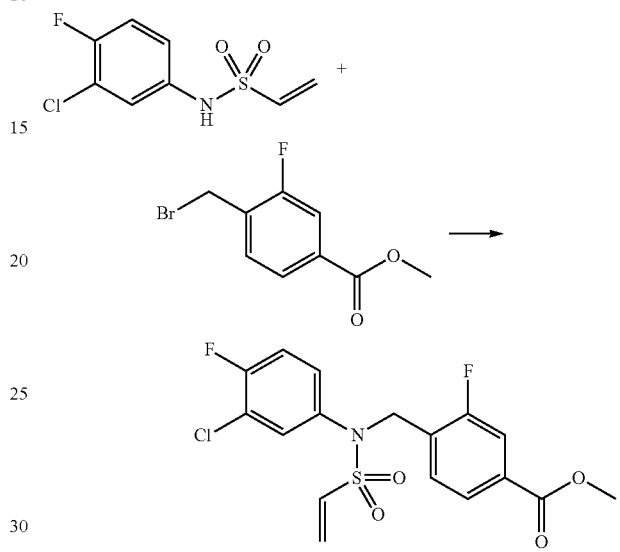

A solution of N-(3-chloro-4-fluorophenyl)ethenesulfonamide (2.000 g, 8.487 mmol), methyl 4-(bromomethyl)-3-fluorobenzoate (3.145 g, 12.730 mmol) and potassium carbonate (1.290 g, 9.335 mmol) in N,N-dimethylformide (10 mL) was stirred at the room temperature for 16 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 24 g cartridge; ethyl acetate/hexane=0% to 30%) to give methyl 4-((N-(3-chloro-4-fluorophenyl)vinylsulfonamido)methyl)-3-fluorobenzoate as light yellow solid (2.700 g, 91.1%).

[Step 3] methyl 4-(((N-(3-chloro-4-fluorophenyl)-2-(pyrrolidin-1-yl)ethyl)sulfonamido)methyl)-3-fluorobenzoate

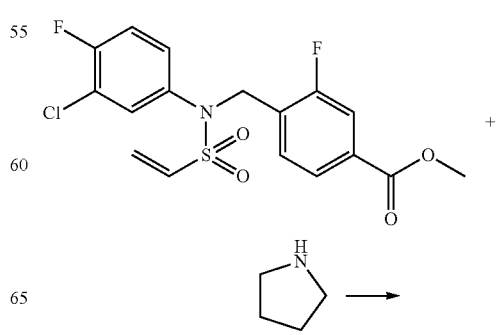

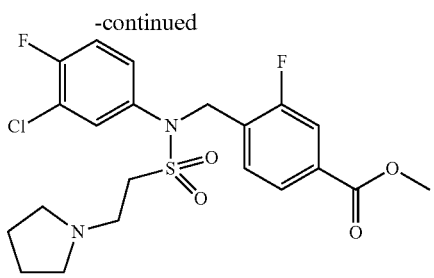

A solution of methyl 4-((N-(3-chloro-4-fluorophenyl)vinylsulfonamido)methyl)-3-fluorobenzoate (0.200 g, 0.498 mmol), N,N-diisopropylethylamine (0.104 mL, 0.597 mmol) and pyrrolidine (0.071 g, 0.995 mmol) in tetrahydrofuran (5 mL) was stirred at the room temperature for 5 hr. Then, water was added to the reaction mixture, followed by extraction with ethyl acetate. The organic layer was washed with aqueous saturated ammonium chloride solution, dried with anhydrous $MgSO_4$, filtered, and concentrated in vacuo. The residue was chromatographed ($SiO_2$, 12 g cartridge; ethyl acetate/hexane=0% to 60%) to give methyl 4-(((N-(3-chloro-4-fluorophenyl)-2-(pyrrolidin-1-yl)ethyl)sulfonamido)methyl)-3-fluorobenzoate as yellow solid (0.150 g, 63.7%).

[Step 4] N-(3-chloro-4-fluorophenyl)-N-(2-fluoro-4-(hydrazinecarbonyl)benzyl)-2-(pyrrolidin-1-yl)ethane-1-sulfonamide

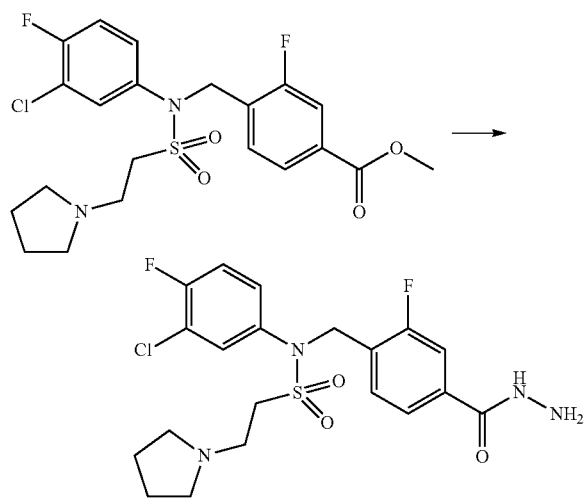

A solution of methyl 4-(((N-(3-chloro-4-fluorophenyl)-2-(pyrrolidin-1-yl)ethyl)sulfonamido)methyl)-3-fluorobenzoate (0.150 g, 0.317 mmol) and hydrazine monohydrate (0.154 mL, 3.172 mmol) in ethanol (10 mL) was stirred at 90° C. for 12 hr, cooled down to the room temperature to terminate the reaction and concentrated under the reduced pressure to remove the solvent. The residue was diluted with sodium bicarbonate (10 mL) and water (5 mL) and stirred. The resulting precipitates were collected by filtration, washed by water, and dried to give N-(3-chloro-4-fluorophenyl)-N-(2-fluoro-4-(hydrazinecarbonyl)benzyl)-2-(pyrrolidin-1-yl)ethane-1-sulfonamide as white solid (0.100 g, 66.7%).

[Step 5] Compound 11514

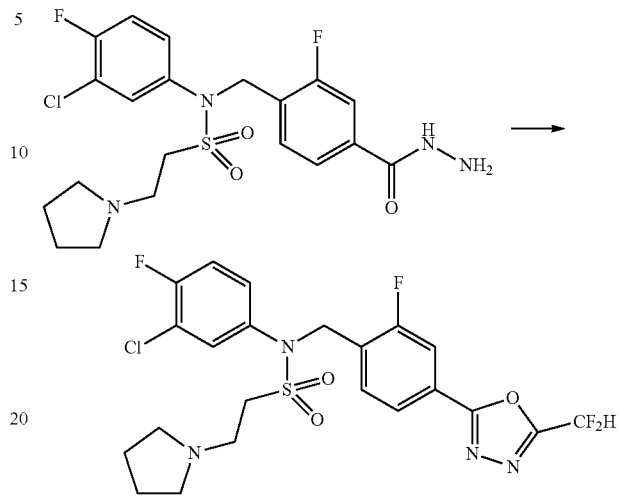

A solution of N-(3-chloro-4-fluorophenyl)-N-(2-fluoro-4-(hydrazinecarbonyl)benzyl)-2-(pyrrolidin-1-yl)ethane-1-sulfonamide (0.100 g, 0.211 mmol), triethylamine (0.147 mL, 1.057 mmol) and 2,2-difluoroacetic anhydride (0.079 mL, 0.634 mmol) in tetrahydrofuran (10 mL) was stirred at 90° C. for 5 hr and cooled down to the room temperature to terminate the reaction. Then, water was added to the reaction mixture, followed by extraction with ethyl acetate. The organic layer was washed with aqueous saturated ammonium chloride solution, dried with anhydrous $MgSO_4$, filtered, and concentrated in vacuo. The residue was chromatographed ($SiO_2$, 4 g cartridge; ethyl acetate/hexane=0% to 50%) to give N-(3-chloro-4-fluorophenyl)-N-(4-(5-(difluoromethyl)-1,3,4-oxadiazol-2-yl)-2-fluorobenzyl)-2-(pyrrolidin-1-yl)ethane-1-sulfonamide as yellow oil (0.045 g, 39.9%).
$^1$H NMR (400 MHz, $CDCl_3$) δ 7.90 (dd, 1H, J=8.1, 1.6 Hz), 7.75 (dd, 1H, J=9.9, 1.7 Hz), 7.67 (dd, 1H, J=8.0, 7.2 Hz), 7.51 (dd, 1H, J=6.4, 2.6 Hz), 7.25 (ddd, 1H, J=8.8, 4.2, 2.7 Hz), 7.10 (t, 1H, J=8.6 Hz), 7.06-6.77 (m, 1H), 5.04 (s, 2H), 3.32 (dd, 2H, J=7.4, 6.5 Hz), 3.05 (dd, 2H, J=7.4, 6.4 Hz), 2.75-2.49 (m, 4H), 1.96-1.84 (m, 4H); LRMS (ES) m/z 533.40 ($M^+$+1).

EXAMPLE 144

Compound 11518, N-((5-(5-(difluoromethyl)-1,3,4-oxadiazol-2-yl)pyrazin-2-yl)methyl)-N-phenylmethanesulfonamide

[Step 1] methyl 5-(bromomethyl)pyrazine-2-carboxylate

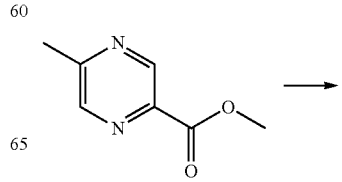

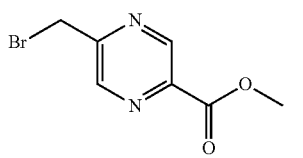

A mixture of methyl 5-methylpyrazine-2-carboxylate (3.000 g, 19.717 mmol), 1-bromopyrrolidine-2,5-dione (NBS, 3.685 g, 20.703 mmol) and Azobisisobutyronitrile (AIBN, 1.295 g, 7.887 mmol) in carbon tetrachloride (20 mL) prepared at the room temperature was heated at reflux for 10 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 15%) to give methyl 5-(bromomethyl)pyrazine-2-carboxylate as gray solid (1.500 g, 32.9%).

[Step 2] methyl 5-((N-phenylmethylsulfonamido)methyl)pyrazine-2-carboxylate

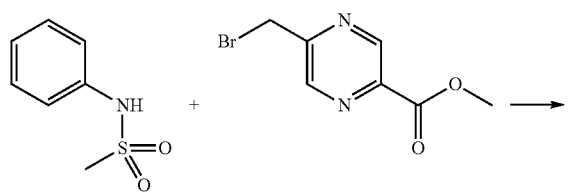

A solution of methyl 5-(bromomethyl)pyrazine-2-carboxylate (0.567 g, 2.453 mmol) and potassium iodide (0.039 g, 0.234 mmol) in N,N-dimethylformide (6 mL) was stirred at the room temperature for 30 min, and mixed with N-phenylmethanesulfonamide (0.400 g, 2.336 mmol) and potassium carbonate (0.420 g, 3.037 mmol). The reaction mixture was stirred at the same temperature for additional 8 hr. The reaction mixture was diluted with water and stirred. The resulting precipitates were collected by filtration, washed by water, and dried to give methyl 5-((N-phenylmethylsulfonamido)methyl)pyrazine-2-carboxylate as white solid (0.710 g, 94.6%).

[Step 3] N-((5-(hydrazinecarbonyl)pyrazin-2-yl)methyl)-N-phenylmethanesulfonamide

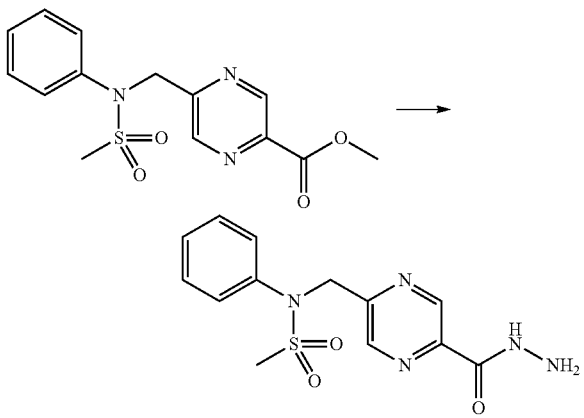

A solution of methyl 5-((N-phenylmethylsulfonamido)methyl)pyrazine-2-carboxylate (0.400 g, 1.245 mmol) and potassium carbonate (0.860 g, 6.224 mmol) in ethanol (4 mL) was mixed at the room temperature with hydrazine monohydrate (0.605 mL, 12.447 mmol). The reaction mixture was heated at reflux for 2 hr, cooled down to the room temperature to terminate the reaction and concentrated under the reduced pressure to remove the solvent. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (N-((5-(hydrazinecarbonyl)pyrazin-2-yl)methyl)-N-phenylmethanesulfonamide, 0.350 g, 87.5%, white solid).

[Step 4] Compound 11518

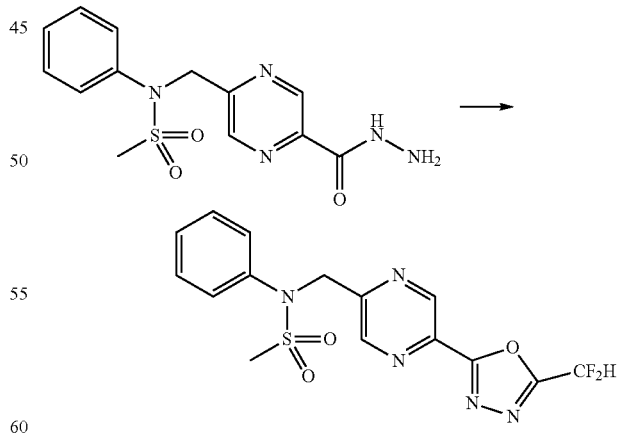

A solution of N-((5-(hydrazinecarbonyl)pyrazin-2-yl)methyl)-N-phenylmethanesulfonamide (0.100 g, 0.311 mmol) and triethylamine (0.130 mL, 0.934 mmol) in tetrahydrofuran (5 mL) was mixed at the room temperature with 2,2-difluoroacetic anhydride (0.085 mL, 0.685 mmol). The reaction mixture was heated at reflux for 5 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 60%) to give N-((5-(5-(difluoromethyl)-1,3,4-oxadiazol-2-yl)pyrazin-2-yl)methyl)-N-phenylmethanesulfonamide as white solid (0.070 g, 59.0%).

$^1$H NMR (400 MHz, CDCl$_3$) δ 9.39 (d, 1H, J=1.4 Hz), 8.90 (d, 1H, J=1.4 Hz), 7.41-7.35 (m, 4 Hz), 7.32 (m, 1 Hz), 7.07 (s, 0.25H), 6.94 (s, 0.5H), 6.81 (s, 0.25H), 5.19 (s, 2H), 3.05 (s, 3H); LRMS (ES) m/z 382.34 (M$^+$+1).

EXAMPLE 145

Compound 11520, N-(4-(5-(difluoromethyl)-1,3,4-oxadiazol-2-yl)-2-fluorobenzyl)-N-(1-methyl-1H-indazol-4-yl)ethanesulfonamide

[Step 1] N-(1-methyl-1H-indazol-4-yl)ethanesulfonamide

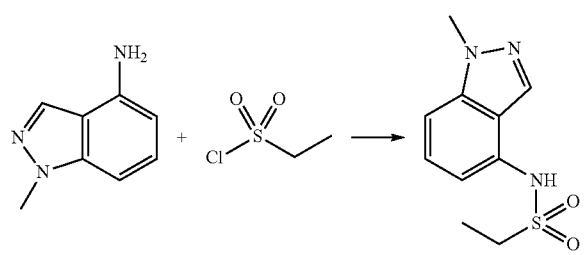

A solution of 1-methyl-1H-indazol-4-amine (0.300 g, 2.038 mmol), pyridine (0.197 mL, 2.446 mmol) and ethanesulfonyl chloride (0.231 mL, 2.446 mmol) in dichloromethane (20 mL) was stirred at the room temperature for 5 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(1-methyl-1H-indazol-4-yl)ethanesulfonamide, 0.350 g, 71.8%, yellow oil).

[Step 2] methyl 3-fluoro-4-((N-(1-methyl-1H-indazol-4-yl)ethylsulfonamido)methyl)benzoate

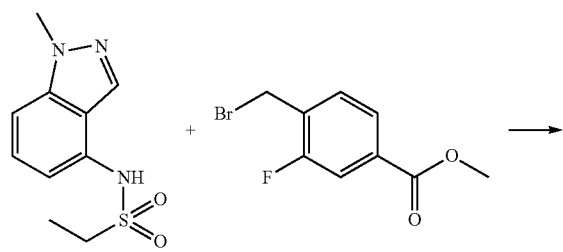

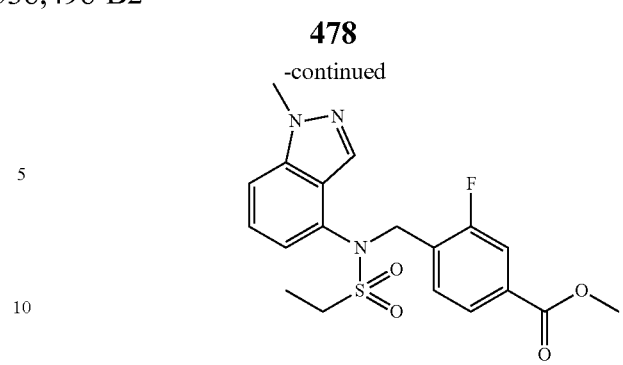

A solution of methyl 4-(bromomethyl)-3-fluorobenzoate (0.216 g, 0.873 mmol) and potassium iodide (0.066 g, 0.397 mmol) in N,N-dimethylformide (20 mL) was stirred at the room temperature for 30 min, and mixed with N-(1-methyl-1H-indazol-4-yl)ethanesulfonamide (0.190 g, 0.794 mmol) and potassium carbonate (0.165 g, 1.191 mmol). The reaction mixture was stirred at 50° C. for additional 12 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 3-fluoro-4-((N-(1-methyl-1H-indazol-4-yl)ethylsulfonamido)methyl)benzoate as yellow solid (0.250 g, 77.7%).

[Step 3] N-(2-fluoro-4-(hydrazinecarbonyl)benzyl)-N-(1-methyl-1H-indazol-4-yl)ethanesulfonamide

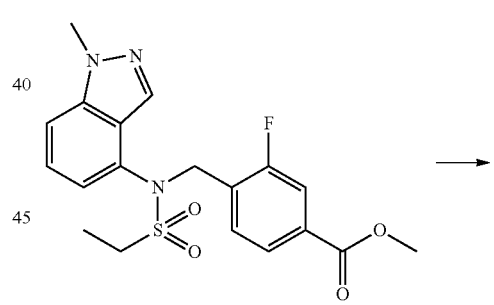

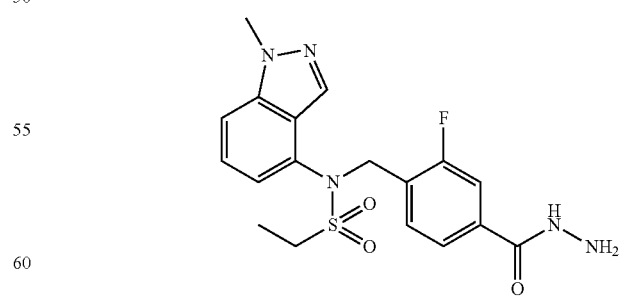

A solution of methyl 3-fluoro-4-((N-(1-methyl-1H-indazol-4-yl)ethylsulfonamido)methyl)benzoate (0.250 g, 0.617 mmol) and hydrazine monohydrate (0.300 mL, 6.166 mmol) in ethanol (15 mL) was stirred at 90° C. for 12 hr, cooled down to the room temperature to terminate the reaction and concentrated under the reduced pressure to remove the solvent. Then, water was added to the concentrate, followed by extraction with dichloromethane. The organic layer was washed with aqueous saturated sodium bicarbonate solution, dried with anhydrous MgSO₄, filtered, and concentrated in vacuo. The title compound was used without further purification (N-(2-fluoro-4-(hydrazinecarbonyl)benzyl)-N-(1-methyl-1H-indazol-4-yl)ethanesulfonamide, 0.200 g, 80.0%, yellow oil).

[Step 4] Compound 11520

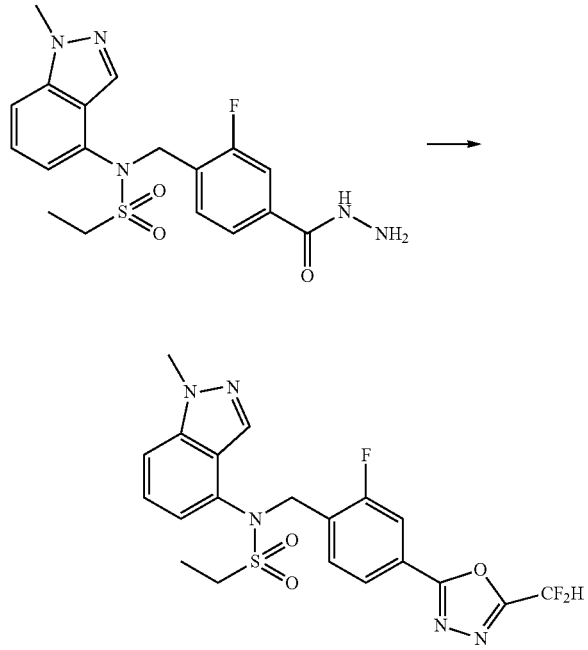 [SMILES: CCS(=O)(=O)N(Cc1ccc(C(=O)NN)cn1)c1cccc2c1cnn2C ; CCS(=O)(=O)N(Cc1ccc(-c2nnc(C(F)F)o2)cn1)c1cccc2c1cnn2C]

A mixture of N-(2-fluoro-4-(hydrazinecarbonyl)benzyl)-N-(1-methyl-1H-indazol-4-yl)ethanesulfonamide (0.200 g, 0.493 mmol), triethylamine (0.344 mL, 2.466 mmol) and 2,2-difluoroacetic anhydride (0.184 mL, 1.480 mmol) in tetrahydrofuran (15 mL) prepared at the room temperature was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 40%) to give N-(4-(5-(difluoromethyl)-1,3,4-oxadiazol-2-yl)-2-fluorobenzyl)-N-(1-methyl-1H-indazol-4-yl)ethanesulfonamide as white solid (0.110 g, 47.9%).

¹H NMR (400 MHz, CDCl₃) δ 8.01 (d, 1H, J=0.9 Hz), 7.82 (dt, 1H, J=8.1, 1.5 Hz), 7.71-7.62 (m, 2H), 7.42-7.30 (m, 2H), 7.13 (dd, 1H, J=7.0, 1.1 Hz), 7.07-6.74 (m, 1H), 5.17 (s, 2H), 4.08 (s, 3H), 3.20 (q, 2H, J=7.4 Hz), 1.48 (td, 3H, J=7.4, 1.1 Hz); LRMS (ES) m/z 466.42 (M⁺+1).

EXAMPLE 146

Compound 11521, N-(4-(5-(difluoromethyl)-1,3,4-oxadiazol-2-yl)-2-fluorobenzyl)-N-(1-methyl-1H-indazol-6-yl)ethanesulfonamide

[Step 1] N-(1-methyl-1H-indazol-6-yl)ethanesulfonamide

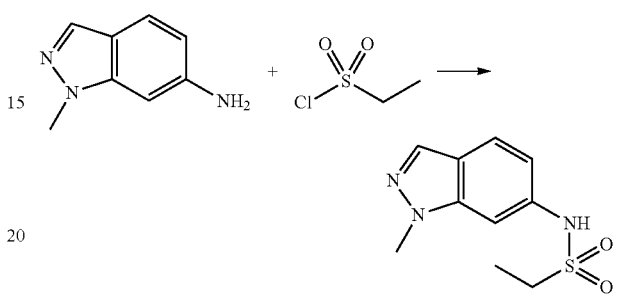

A solution of 1-methyl-1H-indazol-6-amine (0.300 g, 2.038 mmol), pyridine (0.197 mL, 2.446 mmol) and ethanesulfonyl chloride (0.231 mL, 2.446 mmol) in dichloromethane (20 mL) was stirred at the room temperature for 5 hr. Then, water was added to the reaction mixture, followed by extraction with dichloromethane. The organic layer was washed with aqueous 1N-hydrochloric acid solution, dried with anhydrous MgSO₄, filtered, and concentrated in vacuo. The title compound was used without further purification (N-(1-methyl-1H-indazol-6-yl)ethanesulfonamide, 0.360 g, 73.8%, yellow oil).

[Step 2] methyl 3-fluoro-4-((N-(1-methyl-1H-indazol-6-yl)ethylsulfonamido)methyl)benzoate

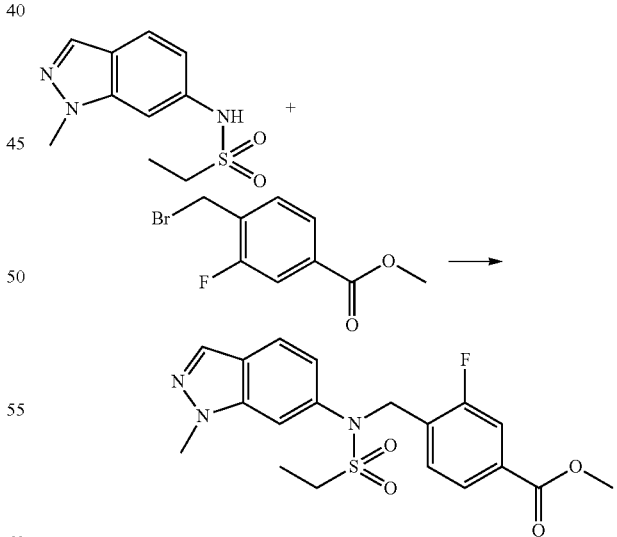

A solution of methyl 4-(bromomethyl)-3-fluorobenzoate (0.261 g, 1.057 mmol) and potassium iodide (0.080 g, 0.481 mmol) in N,N-dimethylformide (20 mL) was stirred at the room temperature for 30 min, and mixed with N-(1-methyl-1H-indazol-6-yl)ethanesulfonamide (0.230 g, 0.961 mmol) and potassium carbonate (0.199 g, 1.442 mmol). The reaction mixture was stirred at 50° C. for additional 12 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 3-fluoro-4-((N-(1-methyl-1H-indazol-6-yl)ethylsulfonamido)methyl)benzoate as yellow oil (0.200 g, 51.3%).

[Step 3] N-(2-fluoro-4-(hydrazinecarbonyl)benzyl)-N-(1-methyl-1H-indazol-6-yl)ethanesulfonamide

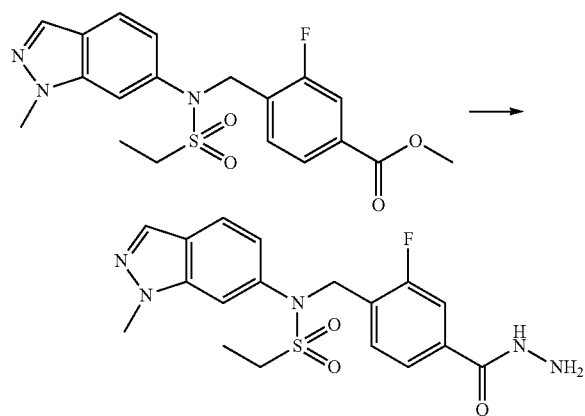

A solution of methyl 3-fluoro-4-((N-(1-methyl-1H-indazol-6-yl)ethylsulfonamido)methyl)benzoate (0.200 g, 0.493 mmol) and hydrazine monohydrate (0.240 mL, 4.933 mmol) in ethanol (20 mL) was stirred at 90° C. for 12 hr, cooled down to the room temperature to terminate the reaction and concentrated under the reduced pressure to remove the solvent. Then, water was added to the concentrate, followed by extraction with dichloromethane. The organic layer was washed with aqueous saturated sodium bicarbonate solution, dried with anhydrous MgSO$_4$, filtered, and concentrated in vacuo. The title compound was used without further purification (N-(2-fluoro-4-(hydrazinecarbonyl)benzyl)-N-(1-methyl-1H-indazol-6-yl)ethanesulfonamide, 0.180 g, 90.0%, white solid).

[Step 4] Compound 11521

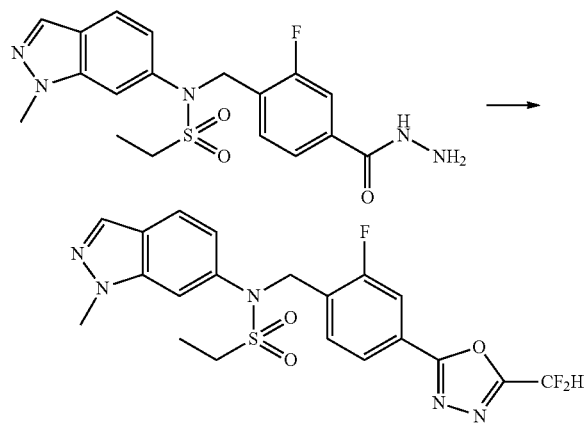

A mixture of N-(2-fluoro-4-(hydrazinecarbonyl)benzyl)-N-(1-methyl-1H-indazol-6-yl)ethanesulfonamide (0.180 g, 0.444 mmol), triethylamine (0.309 mL, 2.220 mmol) and 2,2-difluoroacetic anhydride (0.166 mL, 1.332 mmol) in tetrahydrofuran (15 mL) prepared at the room temperature was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)-2-fluorobenzyl)-N-(1-methyl-1H-indazol-6-yl)ethanesulfonamide as yellow oil (0.130 g, 62.9%).

$^1$H NMR (400 MHz, CDCl$_3$) δ 7.96 (d, 1H, J=1.0 Hz), 7.88 (dd, 1H, J=8.0, 1.6 Hz), 7.77-7.66 (m, 3H), 7.42 (dt, 1H, J=1.8, 0.8 Hz), 7.11 (dd, 1H, J=8.6, 1.8 Hz), 7.06-6.76 (m, 1H), 5.16 (s, 2H), 4.04 (s, 3H), 3.17 (q, 2H, J=7.4 Hz), 1.49 (d, 3H, J=7.3 Hz); LRMS (ES) m/z 466.30 (M$^+$+1).

EXAMPLE 147

Compound 11522, N-(4-(5-(difluoromethyl)-1,3,4-oxadiazol-2-yl)-2-fluorobenzyl)-N-(1-methyl-1H-indazol-7-yl)ethanesulfonamide

[Step 1] N-(1-methyl-1H-indazol-7-yl)ethanesulfonamide

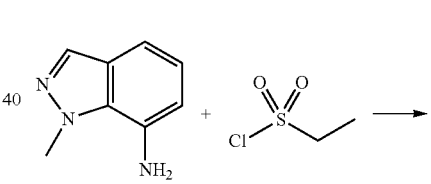

A solution of 1-methyl-1H-indazol-7-amine (0.500 g, 3.397 mmol), pyridine (0.328 mL, 4.077 mmol) and ethanesulfonyl chloride (0.385 mL, 4.077 mmol) in dichloromethane (20 mL) was stirred at the room temperature for 5 hr. Then, water was added to the reaction mixture, followed by extraction with dichloromethane. The organic layer was washed with aqueous 1N-hydrochloric acid solution, dried with anhydrous MgSO$_4$, filtered, and concentrated in vacuo. The title compound was used without further purification (N-(1-methyl-1H-indazol-7-yl)ethanesulfonamide, 0.550 g, 67.7%, yellow solid).

483

[Step 2] methyl 3-fluoro-4-((N-(1-methyl-1H-indazol-7-yl)ethylsulfonamido)methyl)benzoate

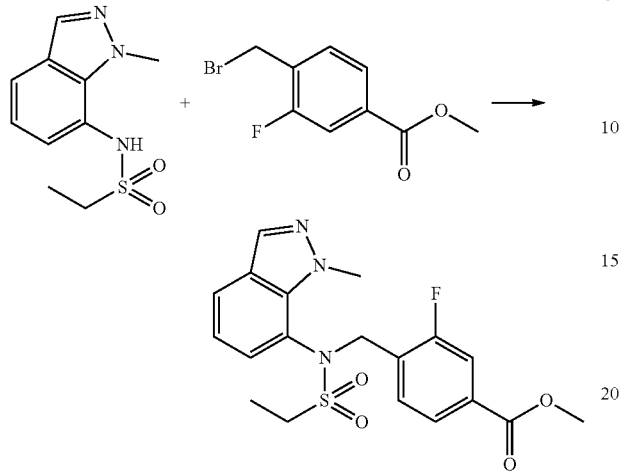

A solution of methyl 4-(bromomethyl)-3-fluorobenzoate (0.227 g, 0.919 mmol) and potassium iodide (0.069 g, 0.418 mmol) in N,N-dimethylformide (10 mL) was stirred at the room temperature for 30 min, and mixed with N-(1-methyl-1H-indazol-7-yl)ethanesulfonamide (0.200 g, 0.836 mmol) and potassium carbonate (0.173 g, 1.254 mmol). The reaction mixture was stirred at 50° C. for additional 12 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 40%) to give methyl 3-fluoro-4-((N-(1-methyl-1H-indazol-7-yl)ethylsulfonamido)methyl)benzoate as yellow oil (0.240 g, 70.8%).

[Step 3] N-(2-fluoro-4-(hydrazinecarbonyl)benzyl)-N-(1-methyl-1H-indazol-7-yl)ethanesulfonamide

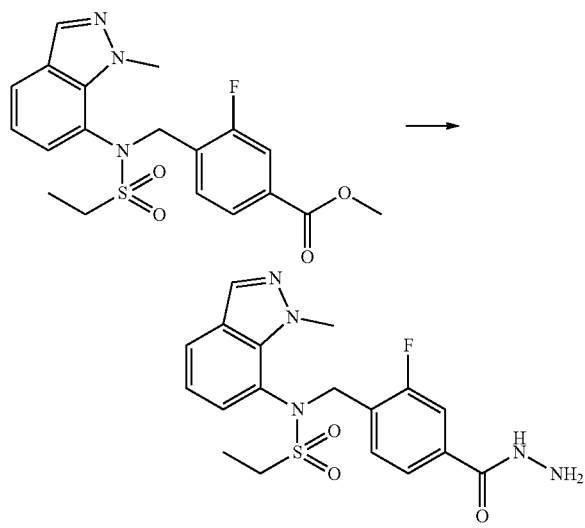

484

A solution of methyl 3-fluoro-4-((N-(1-methyl-1H-indazol-7-yl)ethylsulfonamido)methyl)benzoate (0.240 g, 0.592 mmol) and hydrazine monohydrate (0.288 mL, 5.919 mmol) in ethanol (20 mL) was stirred at 90° C. for 12 hr, cooled down to the room temperature to terminate the reaction and concentrated under the reduced pressure to remove the solvent. Then, water was added to the concentrate, followed by extraction with ethyl acetate. The organic layer was washed with aqueous saturated ammonium chloride solution, dried with anhydrous MgSO₄, filtered, and concentrated in vacuo. The title compound was used without further purification (N-(2-fluoro-4-(hydrazinecarbonyl)benzyl)-N-(1-methyl-1H-indazol-7-yl)ethanesulfonamide, 0.200 g, 83.3%, yellow oil).

[Step 4] Compound 11522

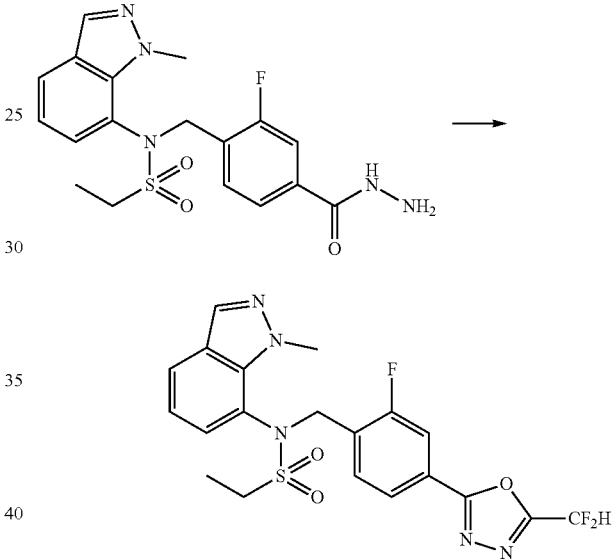

A mixture of N-(2-fluoro-4-(hydrazinecarbonyl)benzyl)-N-(1-methyl-1H-indazol-7-yl)ethanesulfonamide (0.200 g, 0.493 mmol), triethylamine (0.344 mL, 2.466 mmol) and 2,2-difluoroacetic anhydride (0.184 mL, 1.480 mmol) in tetrahydrofuran (15 mL) was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 40%) to give N-(4-(5-(difluoromethyl)-1,3,4-oxadiazol-2-yl)-2-fluorobenzyl)-N-(1-methyl-1H-indazol-7-yl)ethanesulfonamide as yellow oil (0.150 g, 65.3%).

$^1$H NMR (400 MHz, CDCl₃) δ7.98 (d, 1H, J=1.5 Hz), 7.80 (dd, 1H, J=8.0, 1.7 Hz), 7.78-7.71 (m, 2H), 7.42 (t, 1H, J=7.6 Hz), 7.27-7.20 (m, 1H), 7.12 (dd, 1H, J=8.0, 7.4 Hz), 7.07-6.76 (m, 1H), 5.07 (d, 2H, J=1.0 Hz), 4.13 (s, 3H), 3.29 (qd, 2H, J=7.4, 1.8 Hz), 1.52 (t, 3H, J=7.4 Hz); LRMS (ES) m/z 466.42 (M⁺+1).

EXAMPLE 148

Compound 11539, N-((5-(5-(difluoromethyl)-1,3,4-oxadiazol-2-yl)pyridin-2-yl)methyl)-N-(1-methyl-1H-indazol-4-yl)ethanesulfonamide

[Step 1] methyl 6-((N-(1-methyl-1H-indazol-4-yl)ethylsulfonamido)methyl)nicotinate

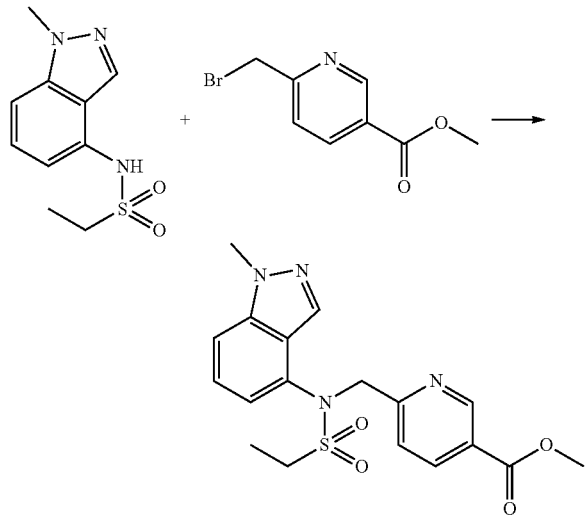

A solution of methyl 6-(bromomethyl)nicotinate (0.159 g, 0.690 mmol) and potassium iodide (0.052 g, 0.313 mmol) in N,N-dimethylformide (15 mL) was mixed at the room temperature with N-(1-methyl-1H-indazol-4-yl)ethanesulfonamide (0.150 g, 0.627 mmol) and potassium carbonate (0.130 g, 0.940 mmol). The reaction mixture was stirred at the same temperature for 12 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 40%) to give methyl 6-((N-(1-methyl-1H-indazol-4-yl)ethylsulfonamido)methyl)nicotinate as yellow oil (0.190 g, 78.0%).

[Step 2] N-((5-(hydrazinecarbonyl)pyridin-2-yl)methyl)-N-(1-methyl-1H-indazol-4-yl)ethanesulfonamide

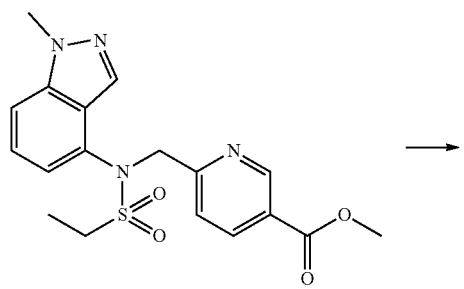

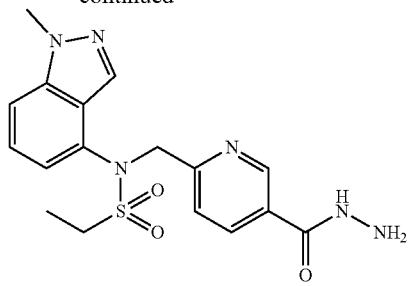

A solution of methyl 6-((N-(1-methyl-1H-indazol-4-yl)ethylsulfonamido)methyl)nicotinate (0.190 g, 0.489 mmol) and hydrazine monohydrate (0.245 g, 4.891 mmol) in ethanol (10 mL) was stirred at 90° C. for 12 hr, cooled down to the room temperature to terminate the reaction and concentrated under the reduced pressure to remove the solvent. The residue was diluted with water (10 mL) and sodium bicarbonate (5 mL) and stirred. The resulting precipitates were collected by filtration, washed by water, and dried to give N-((5-(hydrazinecarbonyl)pyridin-2-yl)methyl)-N-(1-methyl-1H-indazol-4-yl)ethanesulfonamide as white solid (0.150 g, 78.9%).

[Step 3] Compound 11539

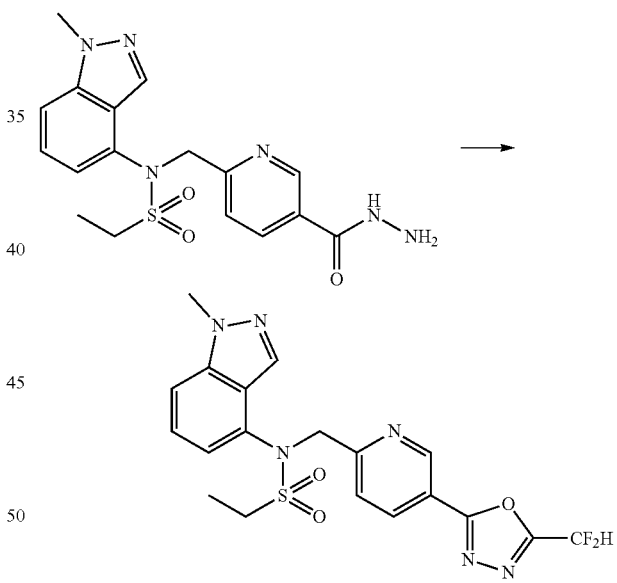

A mixture of N-((5-(hydrazinecarbonyl)pyridin-2-yl)methyl)-N-(1-methyl-1H-indazol-4-yl)ethanesulfonamide (0.080 g, 0.206 mmol), triethylamine (0.144 mL, 1.030 mmol) and 2,2-difluoroacetic anhydride (0.077 mL, 0.618 mmol) in tetrahydrofuran (5 mL) prepared at the room temperature was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 40%) to give N-((5-(5-(difluoromethyl)-1,3,4-oxadiazol- 2-yl)pyridin-2-yl)methyl)-N-(1-methyl-1H-indazol-4-yl)ethanesulfonamide as yellow oil (0.056 g, 60.6%).

$^1$H NMR (400 MHz, CDCl$_3$) δ 9.17 (dd, 1H, J=2.2, 0.9 Hz), 8.35 (dd, 1H, J=8.3, 2.3 Hz), 8.08 (d, 1H, J=0.8 Hz), 7.78 (dd, 1H, J=8.3, 0.9 Hz), 7.42-7.26 (m, 2H), 7.21 (dd, 1H, J=6.6, 1.5 Hz), 7.10-6.76 (m, 1H), 5.28 (s, 2H), 4.08 (s, 3H), 3.26 (q, 2H, J=7.4 Hz), 1.48 (t, 3H, J=7.4 Hz); LRMS (ES) m/z 449.40 (M$^+$+1).

EXAMPLE 149

Compound 11540, N-((5-(5-(difluoromethyl)-1,3,4-oxadiazol-2-yl)pyridin-2-yl)methyl)-N-(1-methyl-1H-indazol-6-yl)ethanesulfonamide

[Step 1] methyl 6-((N-(1-methyl-1H-indazol-6-yl)ethylsulfonamido)methyl)nicotinate

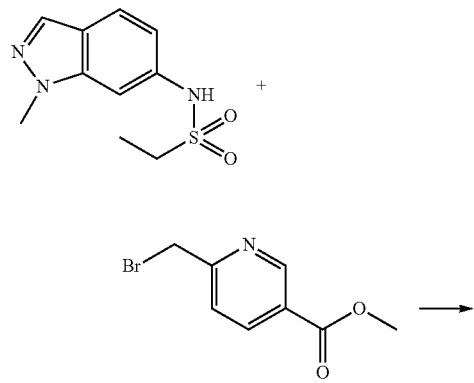

A solution of methyl 6-(bromomethyl)nicotinate (0.212 g, 0.919 mmol) and potassium iodide (0.069 g, 0.418 mmol) in N,N-dimethylformide (15 mL) was mixed at 50° C. with N-(1-methyl-1H-indazol-6-yl)ethanesulfonamide (0.200 g, 0.836 mmol) and potassium carbonate (0.173 g, 1.254 mmol). The reaction mixture was stirred at the same temperature for 12 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 40%) to give methyl 6-((N-(1-methyl-1H-indazol-6-yl)ethylsulfonamido)methyl)nicotinate as yellow solid (0.220 g, 67.8%).

[Step 2] N-((5-(hydrazinecarbonyl)pyridin-2-yl)methyl)-N-(1-methyl-1H-indazol-6-yl)ethanesulfonamide

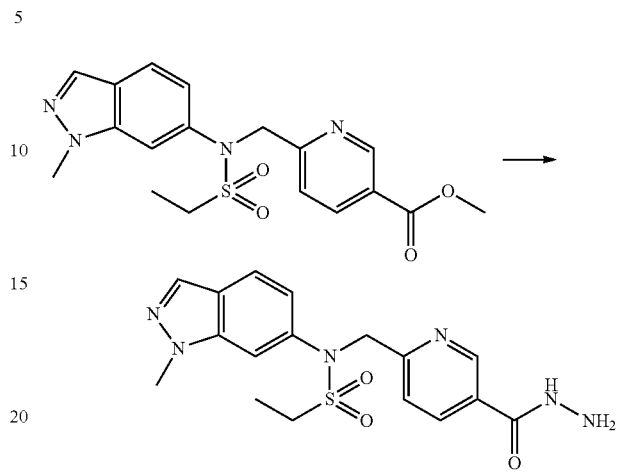

A solution of methyl 6-((N-(1-methyl-1H-indazol-6-yl)ethylsulfonamido)methyl)nicotinate (0.200 g, 0.515 mmol) and hydrazine monohydrate (0.258 g, 5.149 mmol) in ethanol (20 mL) was stirred at 90° C. for 12 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with water (10 mL) and sodium bicarbonate (5 mL) and stirred. The resulting precipitates were collected by filtration, washed by water, and dried to give N-((5-(hydrazinecarbonyl)pyridin-2-yl)methyl)-N-(1-methyl-1H-indazol-6-yl)ethanesulfonamide as yellow solid (0.170 g, 85.0%).

[Step 3] Compound 11540

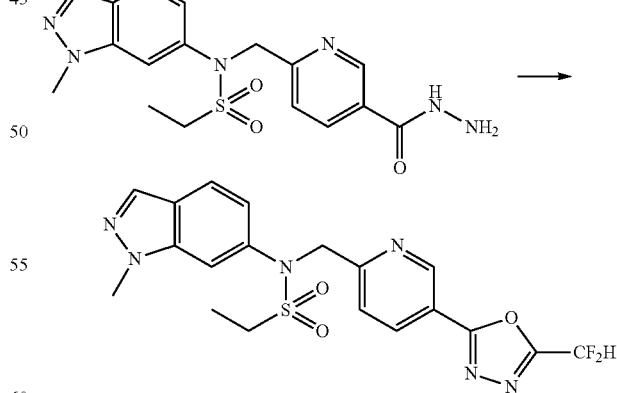

A mixture of N-((5-(hydrazinecarbonyl)pyridin-2-yl)methyl)-N-(1-methyl-1H-indazol-6-yl)ethanesulfonamide (0.100 g, 0.257 mmol), triethylamine (0.179 mL, 1.287 mmol) and 2,2-difluoroacetic anhydride (0.096 mL, 0.772 mmol) in tetrahydrofuran (10 mL) prepared at the room temperature was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 50%) to give N-((5-(5-(difluoromethyl)-1,3,4-oxadiazol-2-yl)pyridin-2-yl)methyl)-N-(1-methyl-1H-indazol-6-yl)ethanesulfonamide as white solid (0.089 g, 77.1%).

¹H NMR (400 MHz, CDCl₃) δ 9.22 (dd, 1H, J=2.2, 0.9 Hz), 8.38 (dd, 1H, J=8.2, 2.2 Hz), 7.95 (d, 1H, J=1.0 Hz), 7.78 (dd, 1H, J=8.3, 0.9 Hz), 7.70 (dd, 1H, J=8.6, 0.7 Hz), 7.54 (dt, 1H, J=1.7, 0.9 Hz), 7.19 (dd, 1H, J=8.6, 1.8 Hz), 7.10-6.75 (m, 1H), 5.27 (s, 2H), 4.06 (s, 3H), 3.23 (q, 2H, J=7.4 Hz), 1.47 (t, 3H, J=7.4 Hz); LRMS (ES) m/z 449.34 (M⁺+1).

EXAMPLE 150

Compound 11541, N-((5-(5-(difluoromethyl)-1,3,4-oxadiazol-2-yl)pyridin-2-yl)methyl)-N-(1-methyl-1H-indazol-7-yl)ethanesulfonamide

[Step 1] methyl 6-((N-(1-methyl-1H-indazol-7-yl)ethylsulfonamido)methyl)nicotinate

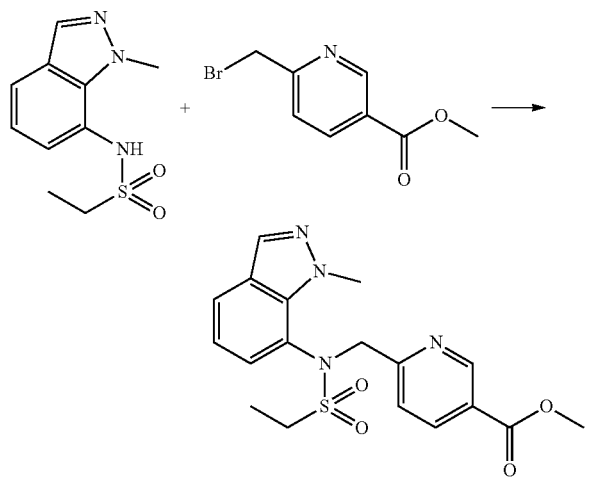

A solution of methyl 6-(bromomethyl)nicotinate (0.212 g, 0.919 mmol) and potassium iodide (0.069 g, 0.418 mmol) in N,N-dimethylformide (15 mL) was mixed at 50° C. with N-(1-methyl-1H-indazol-7-yl)ethanesulfonamide (0.200 g, 0.836 mmol) and potassium carbonate (0.173 g, 1.254 mmol). The reaction mixture was stirred at the same temperature for 12 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 40%) to give methyl 6-((N-(1-methyl-1H-indazol-7-yl)ethylsulfonamido)methyl)nicotinate as yellow solid (0.230 g, 70.8%).

[Step 2] N-((5-(hydrazinecarbonyl)pyridin-2-yl)methyl)-N-(1-methyl-1H-indazol-7-yl)ethanesulfonamide

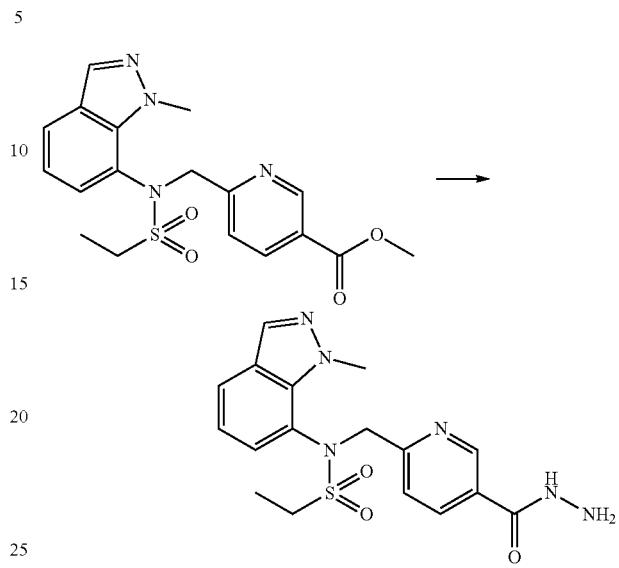

A solution of methyl 6-((N-(1-methyl-1H-indazol-7-yl)ethylsulfonamido)methyl)nicotinate (0.230 g, 0.592 mmol) and hydrazine monohydrate (0.296 g, 5.921 mmol) in ethanol (20 mL) was stirred at 90° C. for 12 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with water (10 mL) and sodium bicarbonate (5 mL) and stirred. The resulting precipitates were collected by filtration, washed by water, and dried to give N-((5-(hydrazinecarbonyl)pyridin-2-yl)methyl)-N-(1-methyl-1H-indazol-7-yl)ethanesulfonamide as yellow solid (0.180 g, 78.3%).

[Step 3] Compound 11541

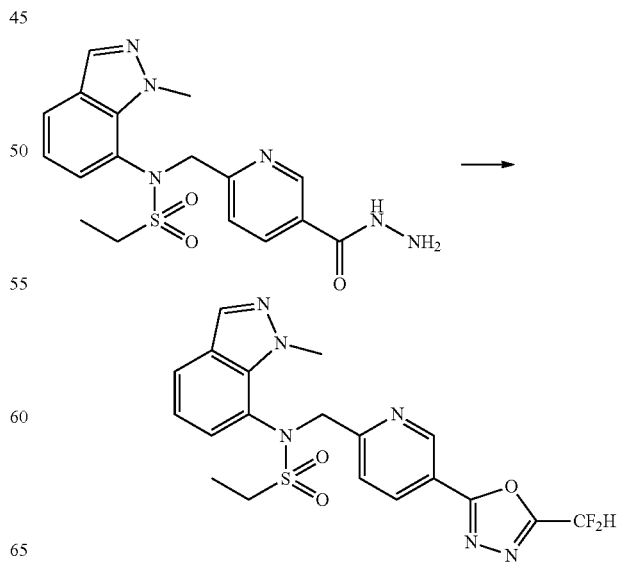

A mixture of N-((5-(hydrazinecarbonyl)pyridin-2-yl)methyl)-N-(1-methyl-1H-indazol-7-yl)ethanesulfonamide (0.050 g, 0.129 mmol), triethylamine (0.090 mL, 0.644 mmol) and 2,2-difluoroacetic anhydride (0.048 mL, 0.386 mmol) in tetrahydrofuran (10 mL) prepared at the room temperature was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give N-((5-(5-(difluoromethyl)-1,3,4-oxadiazol-2-yl)pyridin-2-yl)methyl)-N-(1-methyl-1H-indazol-7-yl)ethanesulfonamide as yellow oil (0.039 g, 67.6%).

$^1$H NMR (400 MHz, CDCl$_3$) δ 9.34 (dd, 1H, J=2.2, 0.8 Hz), 8.33 (dd, 1H, J=8.1, 2.3 Hz), 8.01 (s, 1H), 7.71 (dd, 1H, J=8.0, 1.0 Hz), 7.36 (dd, 1H, J=8.1, 0.9 Hz), 7.17 (dd, 1H, J=7.4, 1.0 Hz), 7.02 (dd, 1H, J=8.0, 7.4 Hz), 6.97-6.81 (m, 1H), 5.39 (d, 1H, J=15.1 Hz), 4.91 (d, 1H, J=15.1 Hz), 4.33 (s, 3H), 3.61 (dq, 1H, J=13.6, 7.5 Hz), 3.42 (dq, 1H, J=13.5, 7.4 Hz), 1.51 (t, 3H, J=7.4 Hz); LRMS (ES) m/z 449.46 (M$^+$+1).

EXAMPLE 151

Compound 11552, N-(3-chloro-4-fluorophenyl)-N-(4-(5-(difluoromethyl)-1,3,4-oxadiazol-2-yl)-2-fluorobenzyl)-2-(4-methylpiperazin-1-yl)ethane-1-sulfonamide

[Step 1] tert-butyl 4-(2-(N-(3-chloro-4-fluorophenyl)-N-(2-fluoro-4-(methoxycarbonyl)benzyl)sulfamoyl)ethyl)piperazine-1-carboxylate

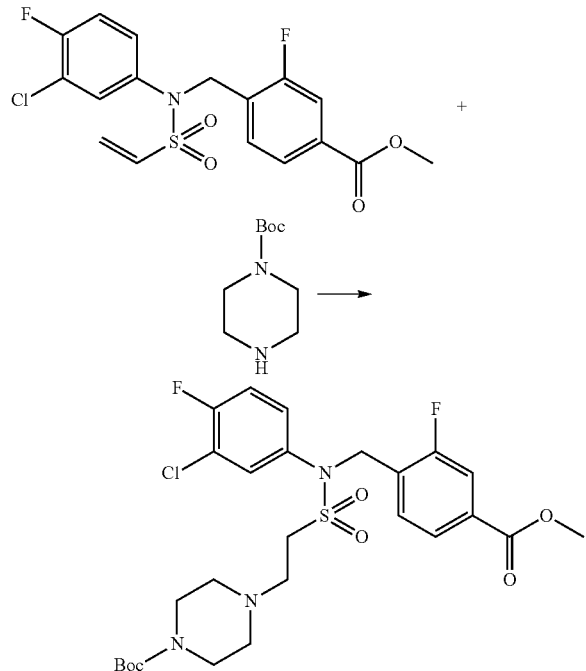

A solution of methyl 4-((N-(3-chloro-4-fluorophenyl)vinylsulfonamido)methyl)-3-fluorobenzoate (1.000 g, 2.489 mmol), N,N-diisopropylethylamine (0.650 mL, 3.733 mmol) and tert-butyl piperazine-1-carboxylate (0.603 g, 3.235 mmol) in tetrahydrofuran (5 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give tert-butyl 4-(2-(N-(3-chloro-4-fluorophenyl)-N-(2-fluoro-4-(methoxycarbonyl)benzyl)sulfamoyl)ethyl)piperazine-1-carboxylate as white solid (1.300 g, 88.8%).

[Step 2] methyl 4-(((N-(3-chloro-4-fluorophenyl)-2-(piperazin-1-yl)ethyl)sulfonamido)methyl)-3-fluorobenzoate hydrochloride

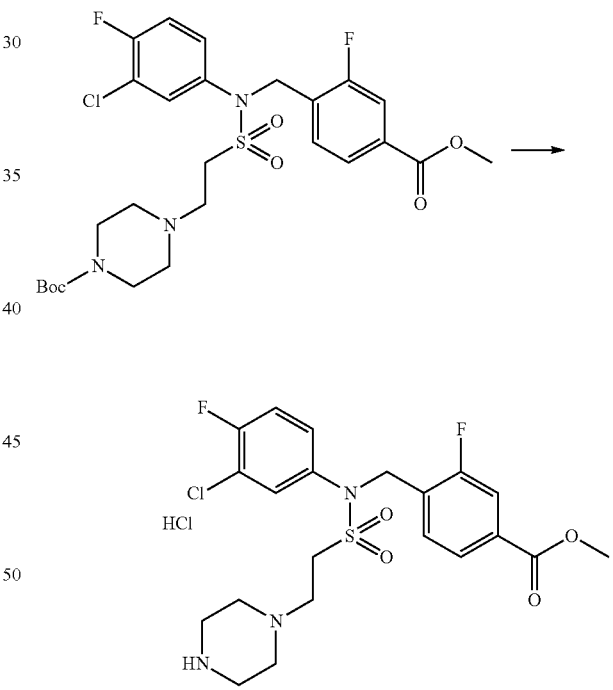

A solution of tert-butyl 4-(2-(N-(3-chloro-4-fluorophenyl)-N-(2-fluoro-4-(methoxycarbonyl)benzyl)sulfamoyl)ethyl)piperazine-1-carboxylate (1.300 g, 2.211 mmol) and hydrogen chloride (4.00 M solution in 1,4-dioxane, 1.105 mL, 4.421 mmol) in dichloromethane (50 mL) was stirred at the room temperature for 5 hr. The precipitates were collected by filtration, washed by dichloromethane, and dried to give methyl 4-(((N-(3-chloro-4-fluorophenyl)-2-(piperazin-1-yl)ethyl)sulfonamido)methyl)-3-fluorobenzoate hydrochloride as white solid (1.150 g, 99.2%).

[Step 3] methyl 4-(((N-(3-chloro-4-fluorophenyl)-2-(4-methylpiperazin-1-yl)ethyl)sulfonamido)methyl)-3-fluorobenzoate

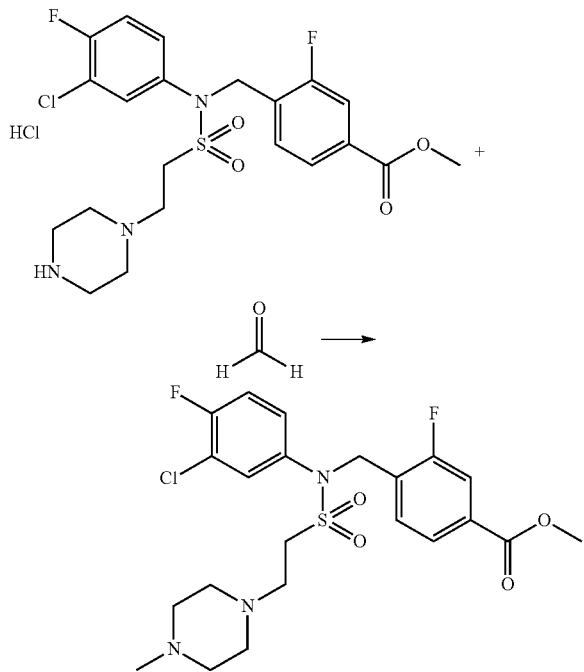

A solution of methyl 4-(((N-(3-chloro-4-fluorophenyl)-2-(piperazin-1-yl)ethyl)sulfonamido)methyl)-3-fluorobenzoate hydrochloride (0.200 g, 0.381 mmol), formaldehyde (0.023 g, 0.763 mmol) and acetic acid (0.024 mL, 0.420 mmol) in dichloromethane (10 mL) was mixed at the room temperature with sodium triacetoxyborohydride (0.162 g, 0.763 mmol). The reaction mixture was stirred at the same temperature for 12 hr. Then, water was added to the reaction mixture, followed by extraction with dichloromethane. The organic layer was washed with aqueous saturated sodium bicarbonate solution, dried with anhydrous MgSO₄, filtered, and concentrated in vacuo. The residue was chromatographed (SiO₂, 12 g cartridge; methanol/dichloromethane=0% to 5%) to give methyl 4-(((N-(3-chloro-4-fluorophenyl)-2-(4-methylpiperazin-1-yl)ethyl)sulfonamido)methyl)-3-fluorobenzoate as yellow oil (0.150 g, 78.4%).

[Step 4] N-(3-chloro-4-fluorophenyl)-N-(2-fluoro-4-(hydrazinecarbonyl)benzyl)-2-(4-methylpiperazin-1-yl)ethane-1-sulfonamide

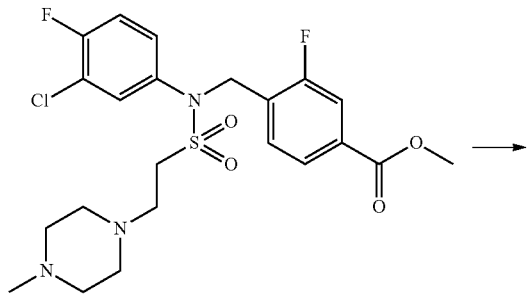

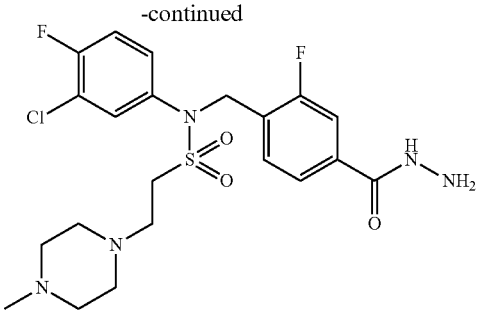

A solution of methyl 4-(((N-(3-chloro-4-fluorophenyl)-2-(4-methylpiperazin-1-yl)ethyl)sulfonamido)methyl)-3-fluorobenzoate (0.150 g, 0.299 mmol) and hydrazine monohydrate (0.145 mL, 2.988 mmol) in ethanol (20 mL) was stirred at 90° C. for 12 hr, cooled down to the room temperature to terminate the reaction and concentrated under the reduced pressure to remove the solvent. The residue was diluted with water (10 mL) and sodium bicarbonate (5 mL) and stirred. The resulting precipitates were collected by filtration, washed by water, and dried to give N-(3-chloro-4-fluorophenyl)-N-(2-fluoro-4-(hydrazinecarbonyl)benzyl)-2-(4-methylpiperazin-1-yl)ethane-1-sulfonamide as white solid (0.120 g, 80.0%).

[Step 5] Compound 11552

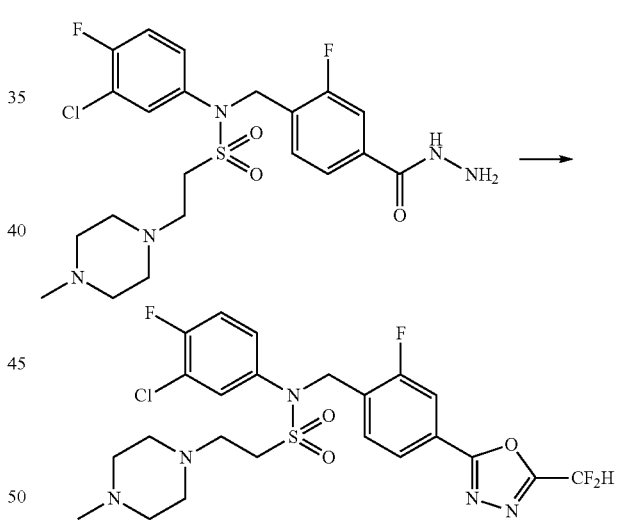

A mixture of N-(3-chloro-4-fluorophenyl)-N-(2-fluoro-4-(hydrazinecarbonyl)benzyl)-2-(4-methylpiperazin-1-yl)ethane-1-sulfonamide (0.080 g, 0.159 mmol), triethylamine (0.111 mL, 0.797 mmol) and 2,2-difluoroacetic anhydride (0.059 mL, 0.478 mmol) in tetrahydrofuran (10 mL) was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give N-(3-chloro-4-fluorophenyl)-N-(4-(5-(difluoromethyl)-1,3,4-oxadiazol-2-yl)-2-fluorobenzyl)-2-(4-methylpiperazin-1-yl)ethane-1-sulfonamide as white solid (0.056 g, 62.5%).

$^1$H NMR (400 MHz, CDCl$_3$) δ 7.91 (dd, 1H, J=7.9, 1.6 Hz), 7.76 (dd, 1H, J=9.9, 1.6 Hz), 7.66 (t, 1H, J=7.6 Hz), 7.50 (dd, 1H, J=6.5, 2.6 Hz), 7.24 (ddd, 1H, J=8.8, 4.1, 2.7 Hz), 7.11 (t, 1H, J=8.6 Hz), 7.07-6.74 (m, 1H), 5.03 (s, 2H), 3.28 (t, 2H, J=6.9 Hz), 2.94 (t, 2H, J=6.9 Hz), 2.59 (s, 8H), 2.36 (s, 3H); LRMS (ES) m/z 562.47 (M$^+$+1).

EXAMPLE 152

Compound 11553, 2-(4-acetylpiperazin-1-yl)-N-(3-chloro-4-fluorophenyl)-N-(4-(5-(difluoromethyl)-1,3,4-oxadiazol-2-yl)-2-fluorobenzyl)ethane-1-sulfonamide

[Step 1] methyl 4-(((2-(4-acetylpiperazin-1-yl)-N-(3-chloro-4-fluorophenyl)ethyl)sulfonamido)methyl)-3-fluorobenzoate

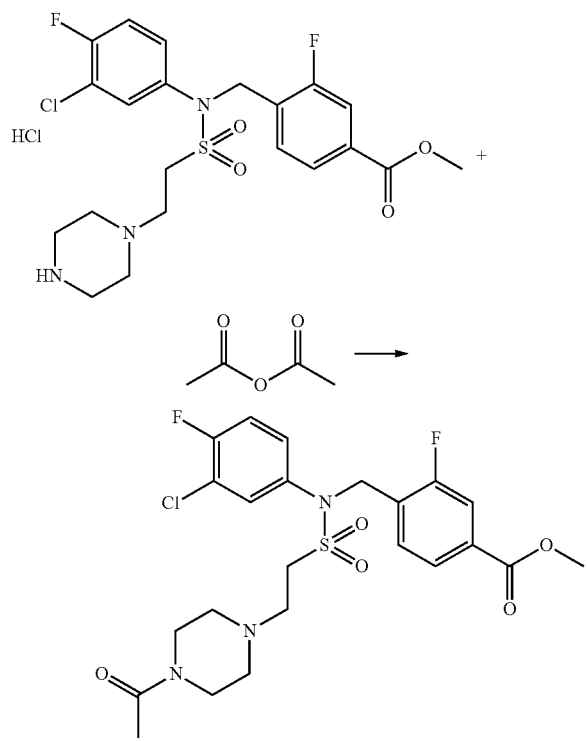

A solution of methyl 4-(((N-(3-chloro-4-fluorophenyl)-2-(piperazin-1-yl)ethyl)sulfonamido)methyl)-3-fluorobenzoate hydrochloride (0.200 g, 0.381 mmol), triethylamine (0.080 mL, 0.572 mmol) and acetic anhydride (0.047 mL, 0.496 mmol) in dichloromethane (10 mL) was stirred at the room temperature for 5 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 80%) to give methyl 4-(((2-(4-acetylpiperazin-1-yl)-N-(3-chloro-4-fluorophenyl)ethyl)sulfonamido)methyl)-3-fluorobenzoate as yellow oil (0.160 g, 79.2%).

[Step 2] 2-(4-acetylpiperazin-1-yl)-N-(3-chloro-4-fluorophenyl)-N-(2-fluoro-4-(hydrazinecarbonyl)benzyl)ethane-1-sulfonamide

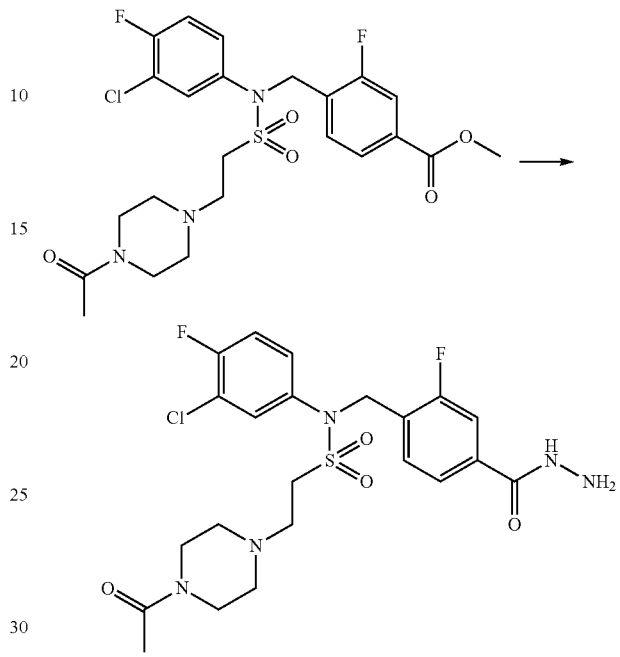

A solution of methyl 4-(((2-(4-acetylpiperazin-1-yl)-N-(3-chloro-4-fluorophenyl)ethyl)sulfonamido)methyl)-3-fluorobenzoate (0.160 g, 0.302 mmol) and hydrazine monohydrate (0.147 mL, 3.019 mmol) in ethanol (20 mL) was stirred at 90° C. for 12 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with water (10 mL) and sodium bicarbonate (5 mL) and stirred. The resulting precipitates were collected by filtration, washed by water, and dried to give 2-(4-acetylpiperazin-1-yl)-N-(3-chloro-4-fluorophenyl)-N-(2-fluoro-4-(hydrazinecarbonyl)benzyl)ethane-1-sulfonamide as white solid (0.130 g, 81.2%).

[Step 3] Compound 11553

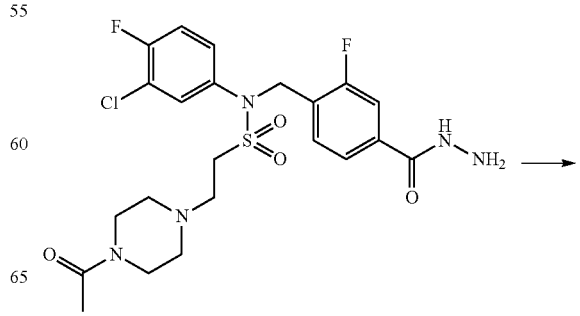

-continued

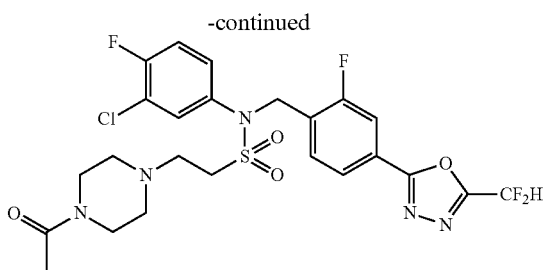

A mixture of 2-(4-acetylpiperazin-1-yl)-N-(3-chloro-4-fluorophenyl)-N-(2-fluoro-4-(hydrazinecarbonyl)benzyl)ethane-1-sulfonamide (0.080 g, 0.151 mmol), triethylamine (0.105 mL, 0.755 mmol) and 2,2-difluoroacetic anhydride (0.056 mL, 0.453 mmol) in tetrahydrofuran (10 mL) prepared at the room temperature was heated at reflux for 12 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give 2-(4-acetylpiperazin-1-yl)-N-(3-chloro-4-fluorophenyl)-N-(4-(5-(difluoromethyl)-1,3,4-oxadiazol-2-yl)-2-fluorobenzyl)ethane-1-sulfonamide as yellow solid (0.051 g, 57.3%).

$^1$H NMR (400 MHz, CDCl$_3$) δ 7.91 (dd, 1H, J=8.1, 1.7 Hz), 7.77 (dd, 1H, J=9.9, 1.6 Hz), 7.64 (t, 1H, J=7.6 Hz), 7.45 (dd, 1H, J=6.4, 2.6 Hz), 7.22 (ddd, 1H, J=8.9, 4.2, 2.6 Hz), 7.12 (t, 1H, J=8.6 Hz), 7.08-6.77 (m, 1H), 5.01 (s, 2H), 3.68 (t, 2H, J=5.1 Hz), 3.57-3.49 (m, 2H), 3.29 (dd, 2H, J=8.1, 6.1 Hz), 2.94 (dd, 2H, J=8.0, 6.1 Hz), 2.57-2.45 (m, 4H), 2.12 (s, 3H); LRMS (ES) m/z 590.42 (M$^+$+1).

EXAMPLE 153

Compound 11554, N-(3-chloro-4-fluorophenyl)-N-(4-(5-(difluoromethyl)-1,3,4-oxadiazol-2-yl)-2-fluorobenzyl)-2-(4-(methylsulfonyl)piperazin-1-yl)ethane-1-sulfonamide

[Step 1] methyl 4-(((N-(3-chloro-4-fluorophenyl)-2-(4-(methylsulfonyl)piperazin-1-yl)ethyl)sulfonamido)methyl)-3-fluorobenzoate

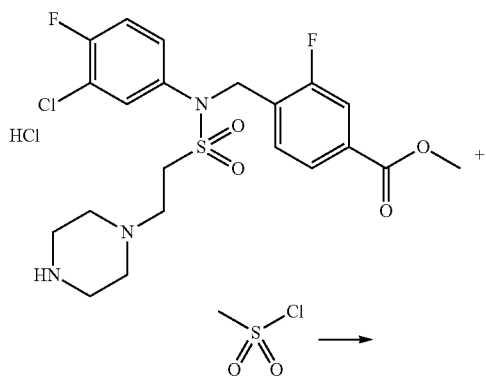

-continued

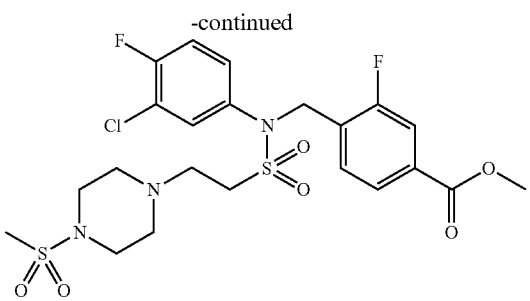

A solution of methyl 4-(((N-(3-chloro-4-fluorophenyl)-2-(piperazin-1-yl)ethyl)sulfonamido)methyl)-3-fluorobenzoate hydrochloride (0.200 g, 0.381 mmol), triethylamine (0.106 mL, 0.763 mmol) and methanesulfonyl chloride (0.038 mL, 0.496 mmol) in dichloromethane (10 mL) was stirred at the room temperature for 5 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 12 g cartridge; methanol/dichloromethane=0% to 5%) to give methyl 4-(((N-(3-chloro-4-fluorophenyl)-2-(4-(methylsulfonyl)piperazin-1-yl)ethyl)sulfonamido)methyl)-3-fluorobenzoate as yellow solid (0.180 g, 83.4%).

[Step 2] N-(3-chloro-4-fluorophenyl)-N-(2-fluoro-4-(hydrazinecarbonyl)benzyl)-2-(4-(methylsulfonyl)piperazin-1-yl)ethane-1-sulfonamide

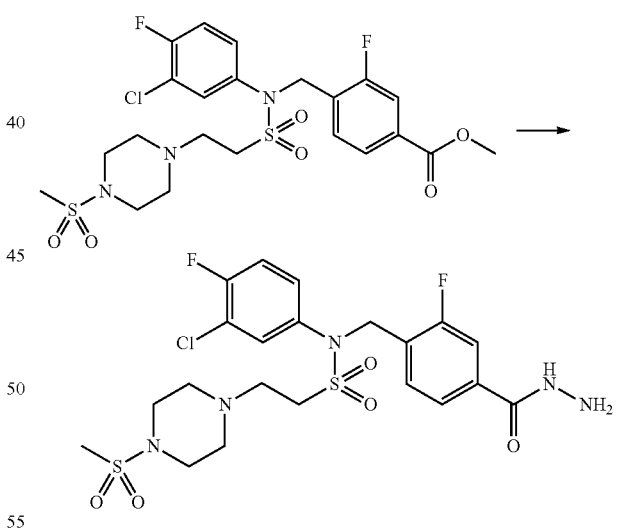

A solution of methyl 4-(((N-(3-chloro-4-fluorophenyl)-2-(4-(methylsulfonyl)piperazin-1-yl)ethyl)sulfonamido)methyl)-3-fluorobenzoate (0.180 g, 0.318 mmol) and hydrazine monohydrate (0.155 mL, 3.180 mmol) in ethanol (10 mL) was stirred at 90° C. for 12 hr, cooled down to the room temperature to terminate the reaction and concentrated under the reduced pressure to remove the solvent. The residue was diluted with water (10 mL) and sodium bicarbonate (5 mL) and stirred. The resulting precipitates were collected by filtration, washed by water, and dried to give N-(3-chloro-4-fluorophenyl)-N-(2-fluoro-4-(hydrazinecarbonyl)benzyl)-

2-(4-(methylsulfonyl)piperazin-1-yl)ethane-1-sulfonamide as white solid (0.130 g, 72.2%).

[Step 3] Compound 11554

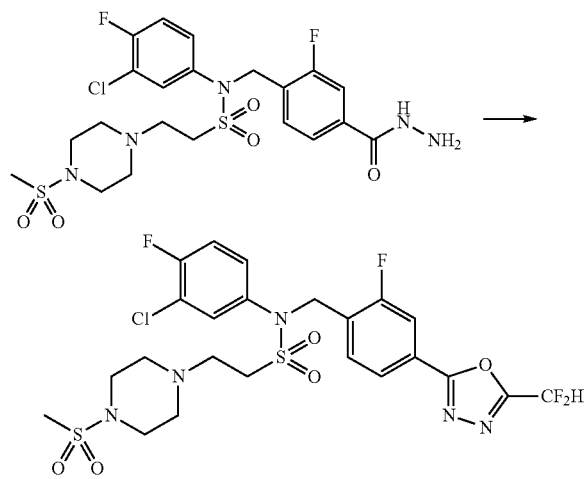

A mixture of N-(3-chloro-4-fluorophenyl)-N-(2-fluoro-4-(hydrazinecarbonyl)benzyl)-2-(4-(methylsulfonyl)piperazin-1-yl)ethane-1-sulfonamide (0.080 g, 0.141 mmol), triethylamine (0.098 mL, 0.707 mmol) and 2,2-difluoroacetic anhydride (0.053 mL, 0.424 mmol) in tetrahydrofuran (5 mL) prepared at the room temperature was heated at reflux for 12 hr, and cooled down to the ambient temperature. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give N-(3-chloro-4-fluorophenyl)-N-(4-(5-(difluoromethyl)-1,3,4-oxadiazol-2-yl)-2-fluorobenzyl)-2-(4-(methylsulfonyl)piperazin-1-yl)ethane-1-sulfonamide as yellow solid (0.034 g, 38.4%).

$^1$H NMR (400 MHz, CDCl$_3$) δ 7.95-7.86 (m, 1H), 7.81-7.73 (m, 1H), 7.63 (t, 1H, J=7.7 Hz), 7.44 (dt, 1H, J=6.5, 2.2 Hz), 7.27-7.16 (m, 1H), 7.17-7.07 (m, 1H), 7.08-6.75 (m, 1H), 5.01 (s, 2H), 3.34-3.25 (m, 6H), 2.98 (td, 2H, J=7.0, 1.7 Hz), 2.82 (s, 3H), 2.68-2.61 (m, 4H); LRMS (ES) m/z 626.39 (M$^+$+1).

EXAMPLE 154

Compound 11564, N-((5-(5-(difluoromethyl)-1,3,4-oxadiazol-2-yl)pyrimidin-2-yl)methyl)-N-phenyl-methanesulfonamide

[Step 1] methyl 2-(bromomethyl)pyrimidine-5-carboxylate

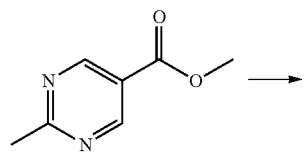

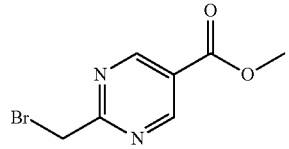

A mixture of methyl 2-methylpyrimidine-5-carboxylate (1.000 g, 6.572 mmol), 1-bromopyrrolidine-2,5-dione (NBS, 1.228 g, 6.901 mmol) and Azobisisobutyronitrile (AIBN, 0.432 g, 2.629 mmol) in carbon tetrachloride (6 mL) prepared at the room temperature was heated at reflux for 10 hr, and cooled down to the ambient temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 24 g cartridge; ethyl acetate/hexane=0% to 15%) to give methyl 2-(bromomethyl)pyrimidine-5-carboxylate as gray solid (0.390 g, 25.7%).

[Step 2] methyl 2-((N-phenylmethylsulfonamido)methyl)pyrimidine-5-carboxylate

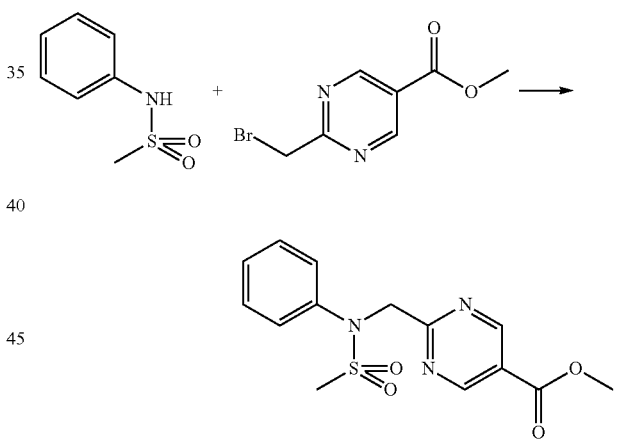

A solution of methyl 2-(bromomethyl)pyrimidine-5-carboxylate (0.383 g, 1.656 mmol) and potassium iodide (0.026 g, 0.158 mmol) in N,N-dimethylformide (4 mL) was mixed at the room temperature with N-phenylmethanesulfonamide (0.270 g, 1.577 mmol) and potassium carbonate (0.262 g, 1.892 mmol). The reaction mixture was stirred at the same temperature for 30 min. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 80%) to give methyl 2-((N-phenylmethylsulfonamido)methyl)pyrimidine-5-carboxylate as white solid (0.370 g, 73.0%).

501

[Step 3] N-((5-(hydrazinecarbonyl)pyrimidin-2-yl)methyl)-N-phenylmethanesulfonamide

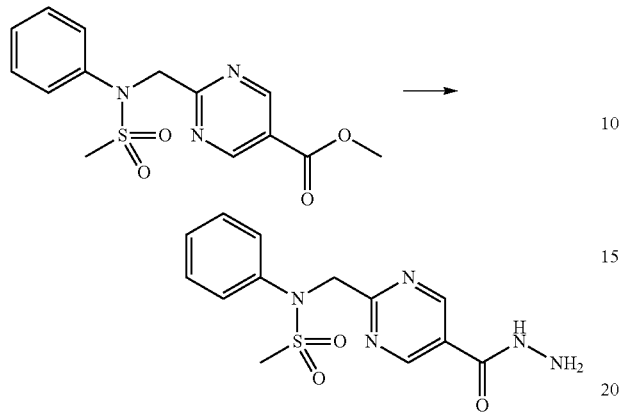

A mixture of methyl 2-((N-phenylmethylsulfonamido)methyl)pyrimidine-5-carboxylate (0.200 g, 0.622 mmol) and hydrazine monohydrate (0.151 mL, 3.112 mmol) in ethanol (5 mL) prepared at the room temperature was heated at reflux for 5 hr, cooled down to the ambient temperature, and concentrated under the reduced pressure to remove the solvent. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-((5-(hydrazinecarbonyl)pyrimidin-2-yl)methyl)-N-phenylmethanesulfonamide, 0.150 g, 75.0%, white solid).

[Step 4] Compound 11564

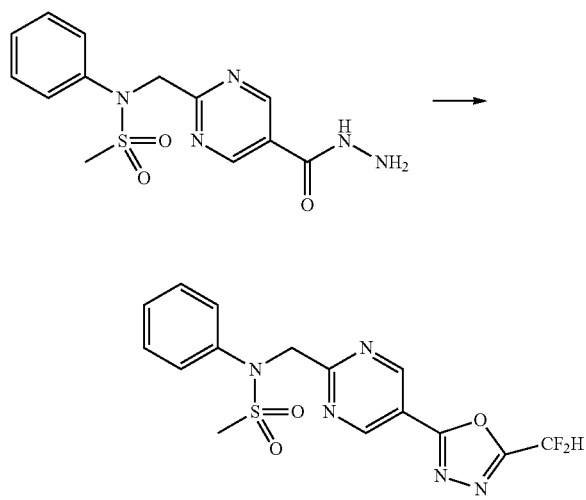

A solution of N-((5-(hydrazinecarbonyl)pyrimidin-2-yl)methyl)-N-phenylmethanesulfonamide (0.070 g, 0.218 mmol), triethylamine (0.152 mL, 1.089 mmol) and 2,2-difluoroacetic anhydride (0.081 mL, 0.653 mmol) in tetrahydrofuran (5 mL) was stirred at 90° C. for 5 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 60%) to give N-((5-(5-(difluoromethyl)-1,3,4-oxadiazol-2-yl)pyrimidin-2-yl)methyl)-N-phenylmethanesulfonamide as yellow solid (0.049 g, 59.0%).

$^1$H NMR (400 MHz, CDCl$_3$) δ 9.43 (s, 2H), 7.54-7.46 (m, 2H), 7.43-7.27 (m, 3H), 7.17-6.79 (m, 1H), 5.30 (s, 2H), 3.24 (s, 3H); LRMS (ES) m/z 382.34 (M$^+$+1).

EXAMPLE 155

Compound 11565, N-phenyl-N-((5-(5-(trifluoromethyl)-1,3,4-oxadiazol-2-yl)pyrimidin-2-yl)methyl)methanesulfonamide

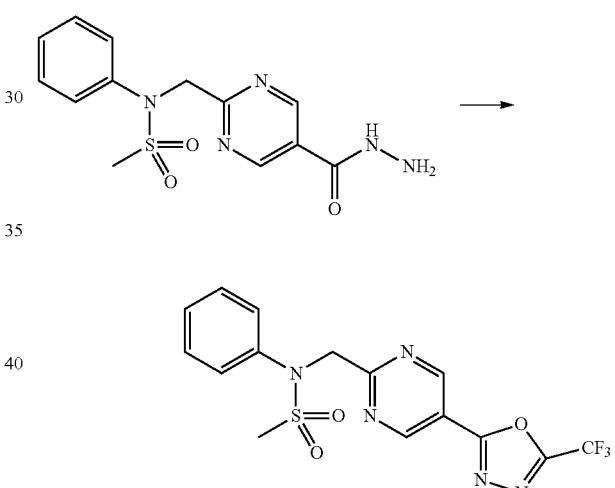

A solution of N-((5-(hydrazinecarbonyl)pyrimidin-2-yl)methyl)-N-phenylmethanesulfonamide (0.056 g, 0.174 mmol), triethylamine (0.121 mL, 0.871 mmol) and trifluoroacetic anhydride (0.074 mL, 0.523 mmol) in tetrahydrofuran (5 mL) was stirred at 90° C. for 5 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 12 g cartridge; methanol/dichloromethane=0% to 5%) to give N-phenyl-N-((5-(5-(trifluoromethyl)-1,3,4-oxadiazol-2-yl)pyrimidin-2-yl)methyl)methanesulfonamide as white solid (0.031 g, 44.5%).

$^1$H NMR (400 MHz, CDCl$_3$) δ 9.44 (s, 2H), 7.55-7.46 (m, 2H), 7.43-7.27 (m, 3H), 5.31 (s, 2H), 3.23 (s, 3H); LRMS (ES) m/z 400.30 (M$^+$+1).

EXAMPLE 156

Compound 11566, N-((6-(5-(difluoromethyl)-1,3,4-oxadiazol-2-yl)pyridazin-3-yl)methyl)-N-phenyl-methanesulfonamide

[Step 1] methyl 6-(bromomethyl)pyridazine-3-carboxylate

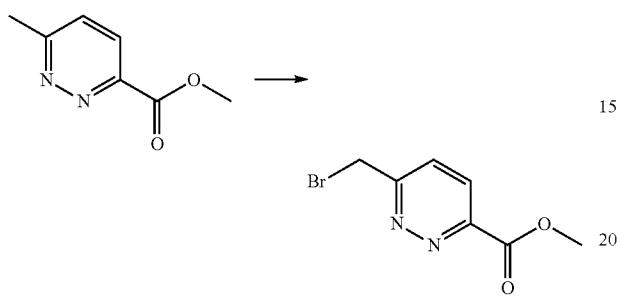

A mixture of methyl 6-methylpyridazine-3-carboxylate (1.000 g, 6.572 mmol), 1-bromopyrrolidine-2,5-dione (NBS, 1.228 g, 6.901 mmol) and Azobisisobutyronitrile (AIBN, 0.432 g, 2.629 mmol) in carbon tetrachloride (6 mL) prepared at the room temperature was heated at reflux for 10 hr, and cooled down to the ambient temperature. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 24 g cartridge; ethyl acetate/hexane=0% to 15%) to give methyl 6-(bromomethyl)pyridazine-3-carboxylate as white solid (0.490 g, 32.3%).

[Step 2] methyl 6-((N-phenylmethylsulfonamido)methyl)pyridazine-3-carboxylate

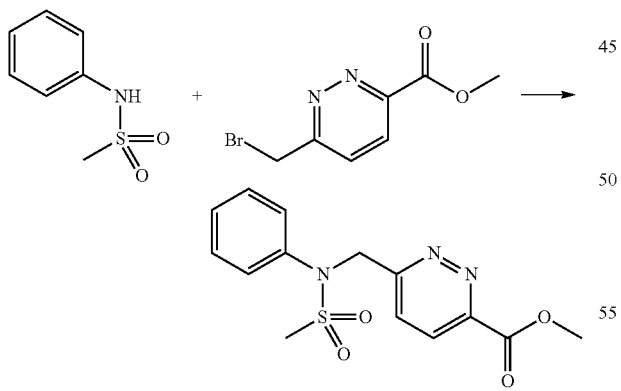

A solution of methyl 6-(bromomethyl)pyridazine-3-carboxylate (0.468 g, 2.024 mmol) and potassium iodide (0.032 g, 0.193 mmol) in N,N-dimethylformide (5 mL) was stirred at the room temperature for 30 min, and mixed with N-phenylmethanesulfonamide (0.330 g, 1.927 mmol) and potassium carbonate (0.346 g, 2.506 mmol). The reaction mixture was stirred at the same temperature for additional 24 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 70%) to give methyl 6-((N-phenylmethylsulfonamido)methyl)pyridazine-3-carboxylate as white solid (0.450 g, 72.7%).

[Step 3] N-((6-(hydrazinecarbonyl)pyridazin-3-yl)methyl)-N-phenylmethanesulfonamide

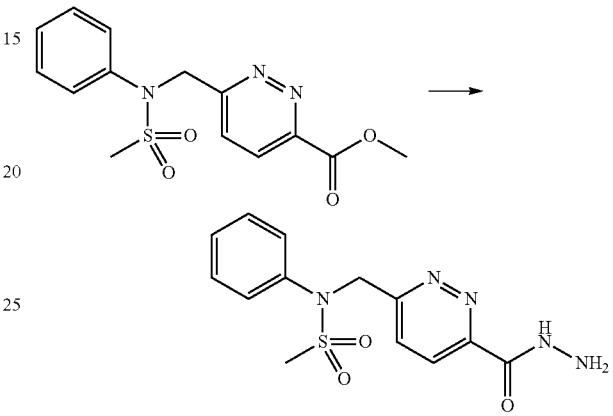

A mixture of methyl 6-((N-phenylmethylsulfonamido)methyl)pyridazine-3-carboxylate (0.200 g, 0.622 mmol) and hydrazine monohydrate (0.151 mL, 3.112 mmol) in ethanol (5 mL) prepared at the room temperature was heated at reflux for 3 hr, cooled down to the ambient temperature, and concentrated under the reduced pressure to remove the solvent. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (N-(((6-(hydrazinecarbonyl)pyridazin-3-yl)methyl)-N-phenylmethanesulfonamide, 0.150 g, 75.0%, white solid).

[Step 4] Compound 11566

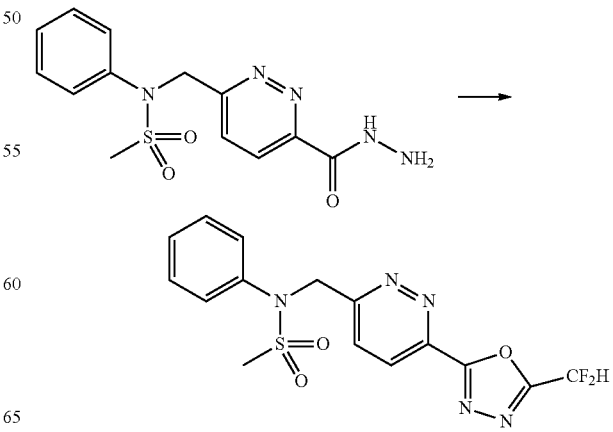

A solution of N-((6-(hydrazinecarbonyl)pyridazin-3-yl)methyl)-N-phenylmethanesulfonamide (0.080 g, 0.249 mmol), triethylamine (0.173 mL, 1.245 mmol) and 2,2-difluoroacetic anhydride (0.093 mL, 0.747 mmol) in dichloromethane (5 mL) was stirred at 90° C. for 5 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 60%) to give N-((6-(5-(difluoromethyl)-1,3,4-oxadiazol-2-yl)pyridazin-3-yl)methyl)-N-phenylmethanesulfonamide as white solid (0.059 g, 62.1%).

$^1$H NMR (400 MHz, CDCl₃) δ 8.42 (d, 1H, J=8.8 Hz), 8.01 (d, 1H, J=8.8 Hz), 7.47-7.41 (m, 2H), 7.42-7.36 (m, 2H), 7.35-7.29 (m, 1H), 7.14-6.82 (m, 1H), 5.40 (s, 2H), 3.10 (s, 3H); LRMS (ES) m/z 381.90 (M⁺+1).

EXAMPLE 157

Compound 11567, N-phenyl-N-((6-(5-(trifluoromethyl)-1,3,4-oxadiazol-2-yl)pyridazin-3-yl)methyl)methanesulfonamide

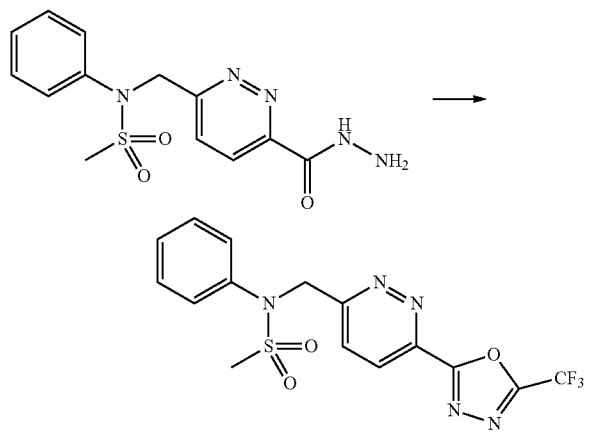

A solution of N-((6-(hydrazinecarbonyl)pyridazin-3-yl)methyl)-N-phenylmethanesulfonamide (0.067 g, 0.208 mmol), triethylamine (0.145 mL, 1.042 mmol) and trifluoroacetic anhydride (0.088 mL, 0.625 mmol) in dichloromethane (5 mL) was stirred at 90° C. for 5 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 60%) to give N-phenyl-N-((6-(5-(trifluoromethyl)-1,3,4-oxadiazol-2-yl)pyridazin-3-yl)methyl)methanesulfonamide as white solid (0.042 g, 50.4%).

$^1$H NMR (400 MHz, CDCl₃) δ 8.44 (d, 1H, J=8.8 Hz), 8.03 (d, 1H, J=8.8 Hz), 7.48-7.34 (m, 4H), 7.37-7.28 (m, 1H), 5.40 (s, 2H), 3.10 (s, 3H); LRMS (ES) m/z 400.2 (M⁺+1).

EXAMPLE 158

Compound 11573, N-phenyl-N-((5-(5-(trifluoromethyl)-1,3,4-oxadiazol-2-yl)pyrazin-2-yl)methyl)methanesulfonamide

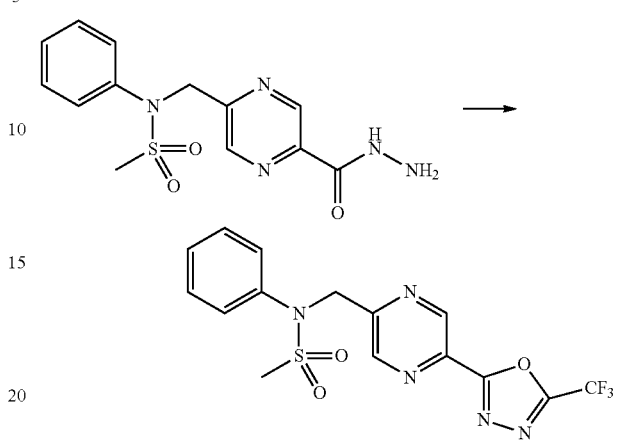

A solution of N-((5-(hydrazinecarbonyl)pyrazin-2-yl)methyl)-N-phenylmethanesulfonamide (0.080 g, 0.249 mmol) and triethylamine (0.104 mL, 0.747 mmol) in tetrahydrofuran (5 mL) was mixed at the room temperature with trifluoroacetic anhydride (0.077 mL, 0.548 mmol). The reaction mixture was heated at reflux for 5 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; ethyl acetate/hexane=0% to 60%) to give N-phenyl-N-((5-(5-(trifluoromethyl)-1,3,4-oxadiazol-2-yl)pyrazin-2-yl)methyl)methanesulfonamide as white solid (0.055 g, 55.3%).

$^1$H NMR (400 MHz, CDCl₃) δ 9.40 (d, 1H, J=1.4 Hz), 8.92 (d, 1H, J=1.5 Hz), 7.41-7.35 (m, 4H), 7.33-7.29 (m, 1H), 5.19 (s, 2H), 3.00 (s, 3H); LRMS (ES) m/z 400.32 (M⁺+1).

EXAMPLE 159

Compound 11582, N-(3-chloro-4-fluorophenyl)-N-(4-(5-(difluoromethyl)-1,3,4-oxadiazol-2-yl)-2-fluorobenzyl)-2-(4-(1-(methylsulfonyl)azetidin-3-yl)piperazin-1-yl)ethane-1-sulfonamide

[Step 1] tert-butyl 3-(4-(2-(N-(3-chloro-4-fluorophenyl)-N-(2-fluoro-4-(methoxycarbonyl)benzyl)sulfamoyl)ethyl)piperazin-1-yl)azetidine-1-carboxylate

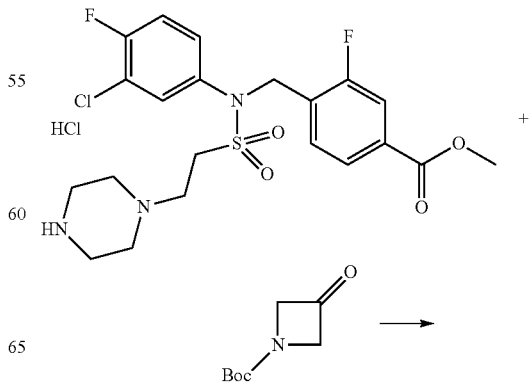

507

-continued

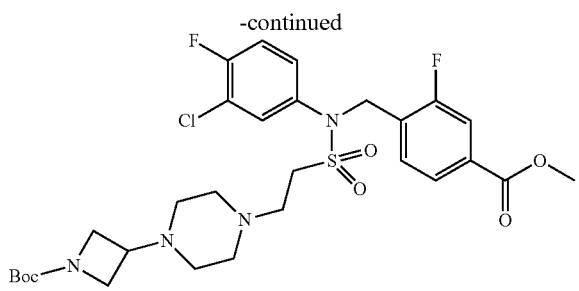

A solution of methyl 4-(((N-(3-chloro-4-fluorophenyl)-2-(piperazin-1-yl)ethyl)sulfonamido)methyl)-3-fluorobenzoate hydrochloride (0.400 g, 0.763 mmol), tert-butyl 3-oxoazetidine-1-carboxylate (0.157 g, 0.915 mmol), acetic acid (0.065 mL, 1.144 mmol) and sodium triacetoxyborohydride (0.323 g, 1.526 mmol) in dichloromethane (20 mL) was stirred at the room temperature for 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 12 g cartridge; methanol/dichloromethane=0% to 5%) to give tert-butyl 3-(4-(2-(N-(3-chloro-4-fluorophenyl)-N-(2-fluoro-4-(methoxycarbonyl)benzyl)sulfamoyl)ethyl)piperazin-1-yl)azetidine-1-carboxylate as white solid (0.350 g, 71.3%).

[Step 2] methyl 4-(((2-(4-(azetidin-3-yl)piperazin-1-yl)-N-(3-chloro-4-fluorophenyl)ethyl)sulfonamido)methyl)-3-fluorobenzoate hydrochloride

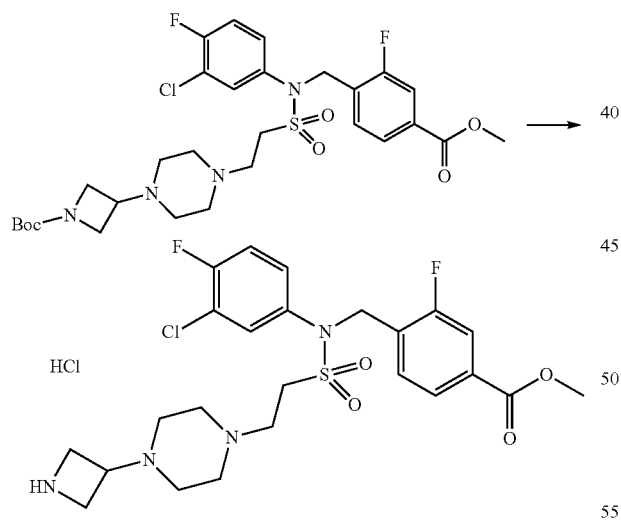

A solution of tert-butyl 3-(4-(2-(N-(3-chloro-4-fluorophenyl)-N-(2-fluoro-4-(methoxycarbonyl)benzyl)sulfamoyl)ethyl)piperazin-1-yl)azetidine-1-carboxylate (0.350 g, 0.544 mmol) and hydrogen chloride (4.00 M solution in 1,4-dioxane, 0.272 mL, 1.088 mmol) in dichloromethane (20 mL) was stirred at the room temperature for 12 hr. The precipitates were collected by filtration, washed by dichloromethane, and dried to give methyl 4-(((2-(4-(azetidin-3-yl)piperazin-1-yl)-N-(3-chloro-4-fluorophenyl)ethyl)sulfonamido)methyl)-3-fluorobenzoate hydrochloride as white solid (0.300 g, 95.1%).

[Step 3] methyl 4-(((N-(3-chloro-4-fluorophenyl)-2-(4-(1-(methylsulfonyl)azetidin-3-yl)piperazin-1-yl)ethyl)sulfonamido)methyl)-3-fluorobenzoate

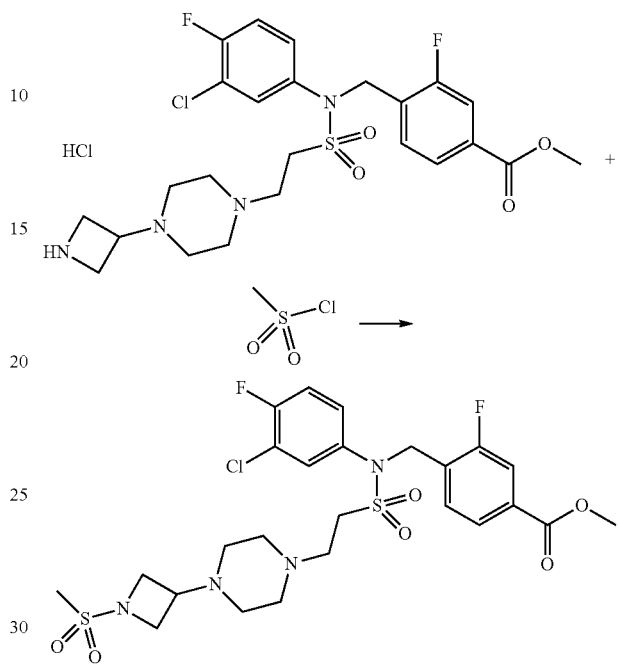

A solution of methyl 4-(((2-(4-(azetidin-3-yl)piperazin-1-yl)-N-(3-chloro-4-fluorophenyl)ethyl)sulfonamido)methyl)-3-fluorobenzoate hydrochloride (0.100 g, 0.173 mmol), triethylamine (0.036 mL, 0.259 mmol) and methanesulfonyl chloride (0.016 mL, 0.207 mmol) in dichloromethane (10 mL) was stirred at the room temperature for 5 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give methyl 4-(((N-(3-chloro-4-fluorophenyl)-2-(4-(1-(methylsulfonyl)azetidin-3-yl)piperazin-1-yl)ethyl)sulfonamido)methyl)-3-fluorobenzoate as white solid (0.083 g, 77.4%).

[Step 4] N-(3-chloro-4-fluorophenyl)-N-(2-fluoro-4-(hydrazinecarbonyl)benzyl)-2-(4-(1-(methylsulfonyl)azetidin-3-yl)piperazin-1-yl)ethane-1-sulfonamide

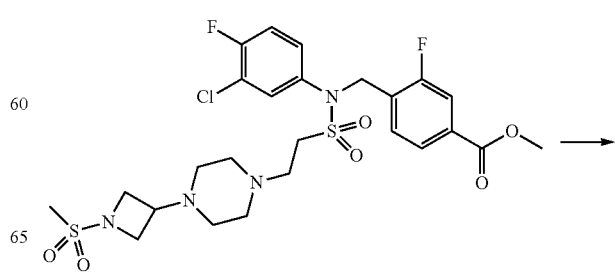

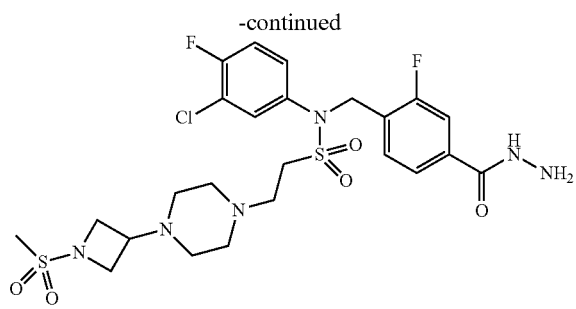

A solution of methyl 4-(((N-(3-chloro-4-fluorophenyl)-2-(4-(1-(methylsulfonyl)azetidin-3-yl)piperazin-1-yl)ethyl)sulfonamido)methyl)-3-fluorobenzoate (0.100 g, 0.161 mmol) and hydrazine monohydrate (0.078 mL, 1.610 mmol) in ethanol (10 mL) was stirred at 90° C. for 12 hr, and cooled down to the room temperature to terminate the reaction, and concentrated under the reduced pressure to remove the solvent. The concentrate was diluted with water (10 mL) and sodium bicarbonate (5 mL) and stirred. The resulting precipitates were collected by filtration and dried to give N-(3-chloro-4-fluorophenyl)-N-(2-fluoro-4-(hydrazinecarbonyl)benzyl)-2-(4-(1-(methylsulfonyl)azetidin-3-yl)piperazin-1-yl)ethane-1-sulfonamide as white solid (0.083 g, 83.0%).

[Step 5] Compound 11582

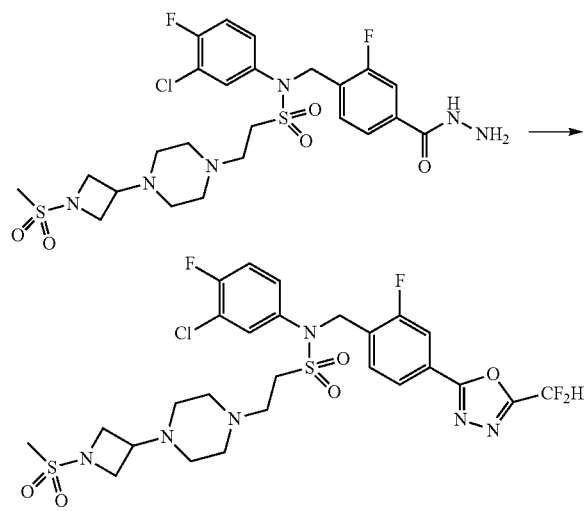

A solution of N-(3-chloro-4-fluorophenyl)-N-(2-fluoro-4-(hydrazinecarbonyl)benzyl)-2-(4-(1-(methylsulfonyl)azetidin-3-yl)piperazin-1-yl)ethane-1-sulfonamide (0.070 g, 0.113 mmol), triethylamine (0.079 mL, 0.563 mmol) and 2,2-difluoroacetic anhydride (0.042 mL, 0.338 mmol) in tetrahydrofuran (10 mL) was stirred at 90° C. for 5 hr and cooled down to the room temperature to terminate the reaction Then, aqueous 1.0 N-hydrochloric acid solution was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 12 g cartridge; methanol/dichloromethane=0% to 5%) to give N-(3-chloro-4-fluorophenyl)-N-(4-(5-(difluoromethyl)-1,3,4-oxadiazol-2-yl)-2-fluorobenzyl)-2-(4-(1-(methylsulfonyl)azetidin-3-yl)piperazin-1-yl)ethane-1-sulfonamide as white solid (0.041 g, 53.4%).

$^1$H NMR (400 MHz, CDCl$_3$) δ 7.90 (dd, 1H, J=8.0, 1.6 Hz), 7.76 (dd, 1H, J=9.8, 1.6 Hz), 7.64 (t, 1H, J=7.6 Hz), 7.47 (dd, 1H, J=6.4, 2.6 Hz), 7.28-7.20 (m, 1H), 7.11 (t, 1H, J=8.6 Hz), 7.08-6.77 (m, 1H), 5.02 (s, 2H), 3.99-3.84 (m, 4H), 3.35-3.30 (m, 2H), 3.31-3.20 (m, 1H), 2.97 (t, 2H, J=7.1 Hz), 2.91 (s, 3H), 2.63 (s, 4H), 2.50 (s, 4H); LRMS (ES) m/z 681.52 (M$^+$+1).

EXAMPLE 160

Compound 11583, N-(3-chloro-4-fluorophenyl)-N-(4-(5-(difluoromethyl)-1,3,4-oxadiazol-2-yl)-2-fluorobenzyl)-2-(4-(oxetan-3-yl)piperazin-1-yl)ethane-1-sulfonamide

[Step 1] methyl 4-(((N-(3-chloro-4-fluorophenyl)-2-(4-(oxetan-3-yl)piperazin-1-yl)ethyl)sulfonamido)methyl)-3-fluorobenzoate

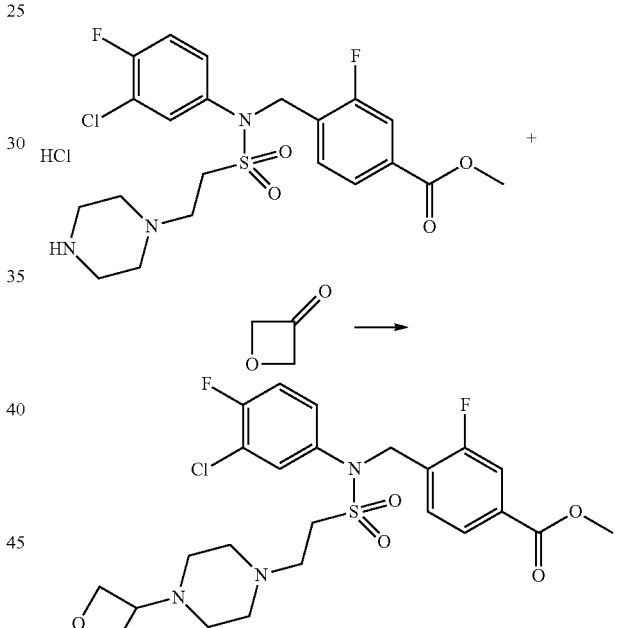

A solution of methyl 4-(((N-(3-chloro-4-fluorophenyl)-2-(piperazin-1-yl)ethyl)sulfonamido)methyl)-3-fluorobenzoate hydrochloride (0.200 g, 0.381 mmol), oxetan-3-one (0.036 g, 0.496 mmol) and acetic acid (0.024 mL, 0.420 mmol) in dichloromethane (10 mL) was mixed at the room temperature with sodium triacetoxyborohydride (0.162 g, 0.763 mmol). The reaction mixture was stirred at the same temperature for 30 min. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; methanol/dichloromethane=0% to 5%) to give methyl 4-(((N-(3-chloro-4-fluorophenyl)-2-(4-(oxetan-3-yl)piperazin-1-yl)ethyl)sulfonamido)methyl)-3-fluorobenzoate as yellow solid (0.150 g, 72.3%).

[Step 2] N-(3-chloro-4-fluorophenyl)-N-(2-fluoro-4-(hydrazinecarbonyl)benzyl)-2-(4-(oxetan-3-yl)piperazin-1-yl)ethane-1-sulfonamide

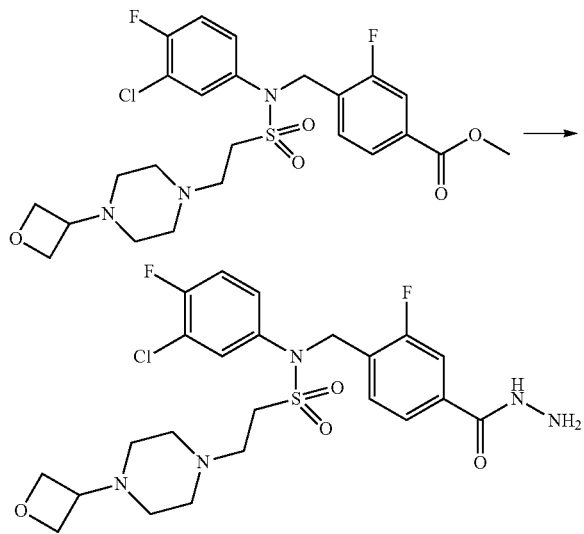

A solution of methyl 4-(((N-(3-chloro-4-fluorophenyl)-2-(4-(oxetan-3-yl)piperazin-1-yl)ethyl)sulfonamido)methyl)-3-fluorobenzoate (0.150 g, 0.276 mmol) and hydrazine monohydrate (0.134 mL, 2.757 mmol) in ethanol (10 mL) was stirred at 90° C. for 12 hr, cooled down to the room temperature to terminate the reaction and concentrated under the reduced pressure to remove the solvent. The residue was diluted with water (10 mL) and sodium bicarbonate (5 mL) and stirred. The resulting precipitates were collected by filtration, washed by water, and dried to give N-(3-chloro-4-fluorophenyl)-N-(2-fluoro-4-(hydrazinecarbonyl)benzyl)-2-(4-(oxetan-3-yl)piperazin-1-yl)ethane-1-sulfonamide as white solid (0.120 g, 80.0%).

[Step 3] Compound 11583

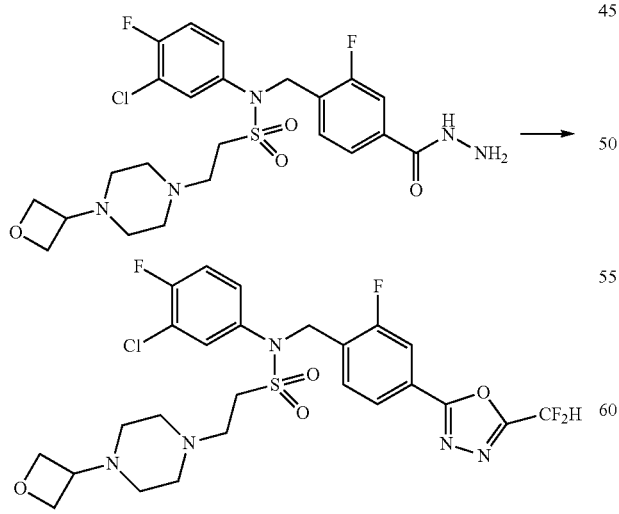

A solution of N-(3-chloro-4-fluorophenyl)-N-(2-fluoro-4-(hydrazinecarbonyl)benzyl)-2-(4-(oxetan-3-yl)piperazin-1-yl)ethane-1-sulfonamide (0.070 g, 0.129 mmol), triethylamine (0.090 mL, 0.643 mmol) and 2,2-difluoroacetic anhydride (0.048 mL, 0.386 mmol) in tetrahydrofuran (10 mL) was stirred at 90° C. for 5 hr and cooled down to the room temperature to terminate the reaction Then, aqueous 1.0 N-hydrochloric acid solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(3-chloro-4-fluorophenyl)-N-(4-(5-(difluoromethyl)-1,3,4-oxadiazol-2-yl)-2-fluorobenzyl)-2-(4-(oxetan-3-yl)piperazin-1-yl)ethane-1-sulfonamide as white solid (0.040 g, 51.5%).

$^1$H NMR (400 MHz, CDCl$_3$) δ 7.91 (dd, 1H, J=8.1, 1.7 Hz), 7.77 (dd, 1H, J=9.9, 1.7 Hz), 7.65 (t, 1H, J=7.6 Hz), 7.48 (dd, 1H, J=6.4, 2.7 Hz), 7.27-7.21 (m, 1H), 7.11 (t, 1H, J=8.6 Hz), 7.07-6.77 (m, 1H), 5.02 (s, 2H), 4.68 (dt, 4H, J=22.2, 6.4 Hz), 3.64-3.53 (m, 1H), 3.34 (s, 2H), 2.99 (t, 2H, J=7.0 Hz), 2.68 (s, 4H), 2.50 (s, 4H); LRMS (ES) m/z 604.45 (M$^+$+1).

EXAMPLE 161

Compound 11588, N-(4-(5-(difluoromethyl)-1,3,4-oxadiazol-2-yl)-2-fluorobenzyl)-3-morpholino-N-phenylpropane-1-sulfonamide

[Step 1] 3-chloro-N-phenylpropane-1-sulfonamide

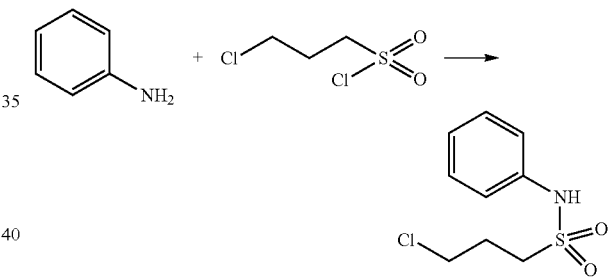

A solution of aniline (0.980 mL, 10.738 mmol), triethylamine (1.796 mL, 12.885 mmol) and 3-chloropropane-1-sulfonyl chloride (2.091 g, 11.811 mmol) in dichloromethane (30 mL) was stirred at the room temperature for 5 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 24 g cartridge; ethyl acetate/hexane=0% to 5%) to give 3-chloro-N-phenylpropane-1-sulfonamide as yellow oil (2.000 g, 79.7%).

[Step 2] methyl 4-(((3-chloro-N-phenylpropyl)sulfonamido)methyl)-3-fluorobenzoate

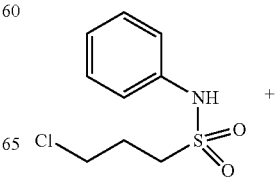

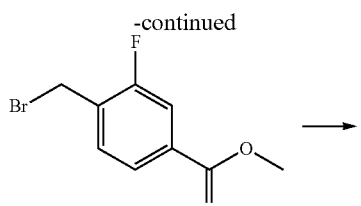

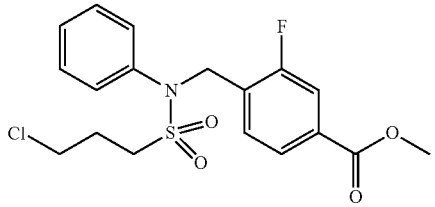

A solution of 3-chloro-N-phenylpropane-1-sulfonamide (2.000 g, 8.558 mmol), potassium carbonate (1.774 g, 12.836 mmol), methyl 4-(bromomethyl)-3-fluorobenzoate (2.326 g, 9.413 mmol) and potassium iodide (0.710 g, 4.279 mmol) in N,N-dimethylformide (5 mL) was stirred at the room temperature for 30 min and for additional 12 hr at 50° C., then, cooled down to the room temperature to terminate the reaction. Then, water was added to the reaction mixture, followed by extraction with ammonium chloride. The organic layer was washed with aqueous saturated sodium chloride solution, dried with anhydrous MgSO$_4$, filtered, and concentrated in vacuo. The residue was chromatographed (SiO$_2$, 24 g cartridge; ethyl acetate/hexane=0% to 30%) to give methyl 4-(((3-chloro-N-phenylpropyl)sulfonamido) methyl)-3-fluorobenzoate as yellow oil (2.800 g, 81.8%).

[Step 3] methyl 3-fluoro-4-(((3-morpholino-N-phenylpropyl)sulfonamido)methyl)benzoate

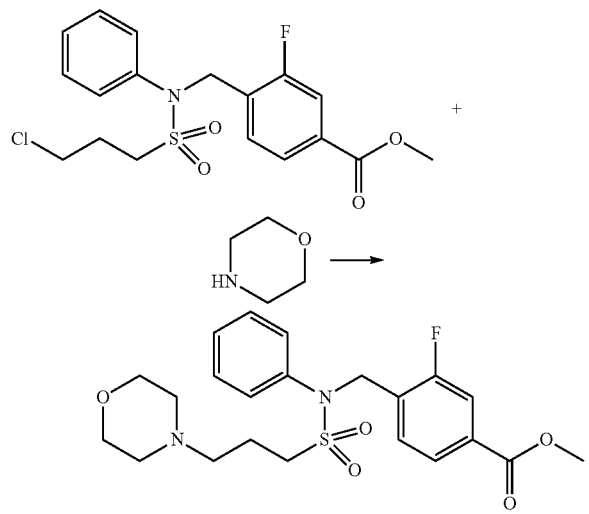

A solution of methyl 4-(((3-chloro-N-phenylpropyl)sulfonamido)methyl)-3-fluorobenzoate (0.200 g, 0.500 mmol), potassium iodide (0.042 g, 0.250 mmol), potassium carbonate (0.104 g, 0.750 mmol) and morpholine (0.056 mL, 0.650 mmol) in N,N-dimethylformide (10 mL) was stirred at 50° C. for 12 hr and cooled down to the room temperature to terminate the reaction. Then, aqueous 1.0 N-hydrochloric acid solution was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give methyl 3-fluoro-4-(((3-morpholino-N-phenylpropyl)sulfonamido) methyl)benzoate as yellow oil (0.110 g, 48.8%).

[Step 4] N-(2-fluoro-4-(hydrazinecarbonyl)benzyl)-3-morpholino-N-phenylpropane-1-sulfonamide


A solution of methyl 3-fluoro-4-(((3-morpholino-N-phenylpropyl)sulfonamido)methyl)benzoate (0.100 g, 0.222 mmol) and hydrazine monohydrate (0.108 mL, 2.220 mmol) in ethanol (10 mL) was stirred at 90° C. for 12 hr, cooled down to the room temperature to terminate the reaction and concentrated under the reduced pressure to remove the solvent. The residue was diluted with water (5 mL) and aqueous saturated sodium bicarbonate solution (3 mL) and stirred. The resulting precipitates were collected by filtration and dried to give N-(2-fluoro-4-(hydrazinecarbonyl)benzyl)-3-morpholino-N-phenylpropane-1-sulfonamide as white solid (0.089 g, 89.0%).

[Step 5] Compound 11588


A solution of N-(2-fluoro-4-(hydrazinecarbonyl)benzyl)-3-morpholino-N-phenylpropane-1-sulfonamide (0.089 g, 0.198 mmol), triethyl amine (0.138 mL, 0.988 mmol) and 2,2-difluoroacetic anhydride (0.074 mL, 0.593 mmol) in tetrahydrofuran (5 mL) was stirred at the room temperature for 18 hr Then, aqueous 1.0 N-hydrochloric acid solution was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give N-(4-(5-(difluoromethyl)-1,3,4-oxadiazol-2-yl)-2-fluorobenzyl)-3-morpholino-N-phenylpropane-1-sulfonamide as yellow oil (0.040 g, 39.7%).

¹H NMR (400 MHz, CDCl₃) δ 7.85 (dd, 1H, J=8.0, 1.7 Hz), 7.73 (dd, 1H, J=9.9, 1.6 Hz), 7.59 (t, 1H, J=7.6 Hz), 7.41-7.27 (m, 5H), 7.07-6.75 (m, 1H), 5.04 (s, 2H), 4.01 (t, 4H, J=4.8 Hz), 3.31 (t, 4H, J=6.9 Hz), 3.21 (t, 4H, J=7.8 Hz), 2.51-2.31 (m, 2H); LRMS (ES) m/z 511.40 (M⁺+1).

EXAMPLE 162

Compound 11589, N-(4-(5-(difluoromethyl)-1,3,4-oxadiazol-2-yl)-2-fluorobenzyl)-3-(4-methylpiperazin-1-yl)-N-phenylpropane-1-sulfonamide

[Step 1] methyl 3-fluoro-4-(((3-(4-methylpiperazin-1-yl)-N-phenylpropyl)sulfonamido)methyl)benzoate

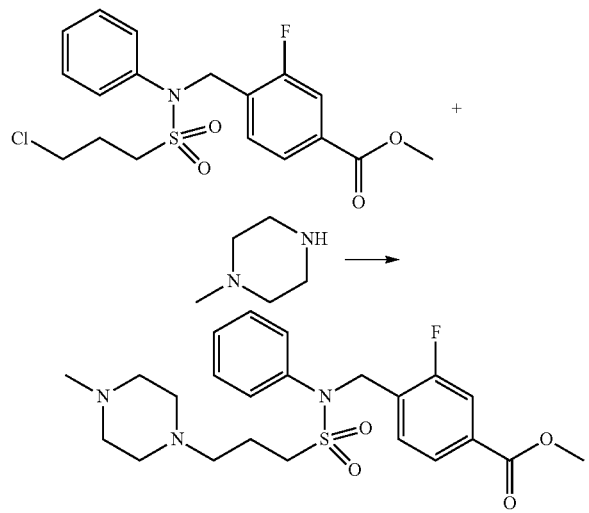

A solution of methyl 4-(((3-chloro-N-phenylpropyl)sulfonamido)methyl)-3-fluorobenzoate (0.200 g, 0.500 mmol), potassium iodide (0.042 g, 0.250 mmol), potassium carbonate (0.104 g, 0.750 mmol) and 1-methylpiperazine (0.072 mL, 0.650 mmol) in N,N-dimethylformamide (10 mL) was stirred at 50° C. for 12 hr and cooled down to the room temperature to terminate the reaction. Then, aqueous 1.0 N-hydrochloric acid solution was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give methyl methyl 3-fluoro-4-(((3-(4-methylpiperazin-1-yl)-N-phenylpropyl)sulfonamido)methyl)benzoate as yellow oil (0.160 g, 71.2%).

[Step 2] N-(2-fluoro-4-(hydrazinecarbonyl)benzyl)-3-(4-methylpiperazin-1-yl)-N-phenylpropane-1-sulfonamide

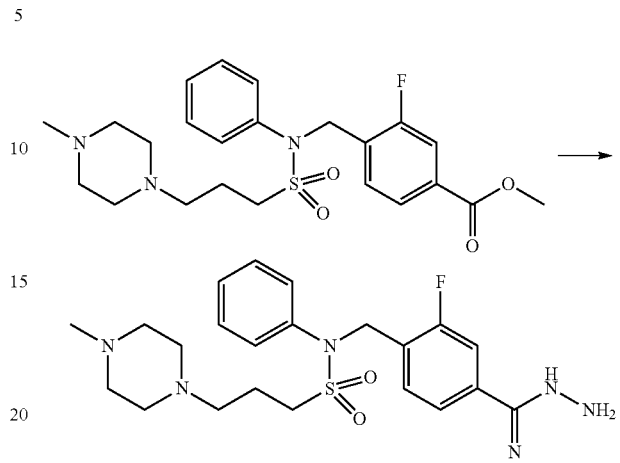

A solution of methyl 3-fluoro-4-(((3-(4-methylpiperazin-1-yl)-N-phenylpropyl)sulfonamido)methyl)benzoate (0.088 g, 0.190 mmol) and hydrazine monohydrate (0.092 mL, 1.898 mmol) in ethanol (10 mL) was stirred at 90° C. for 12 hr, cooled down to the room temperature to terminate the reaction and concentrated under the reduced pressure to remove the solvent. The residue was diluted with water (5 mL) and sodium bicarbonate (2 mL) and stirred. The resulting precipitates were collected by filtration and dried to give N-(2-fluoro-4-(hydrazinecarbonyl)benzyl)-3-(4-methylpiperazin-1-yl)-N-phenylpropane-1-sulfonamide as white solid (0.070 g, 79.5%).

[Step 3] Compound 11589

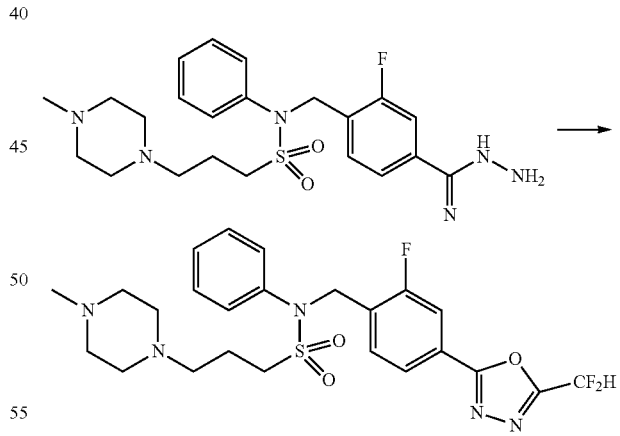

A solution of N-(2-fluoro-4-(hydrazinecarbonyl)benzyl)-3-(4-methylpiperazin-1-yl)-N-phenylpropane-1-sulfonamide (0.070 g, 0.151 mmol), triethylamine (0.105 mL, 0.755 mmol) and 2,2-difluoroacetic anhydride (0.079 g, 0.453 mmol) in tetrahydrofuran (5 mL) was stirred at 90° C. for 5 hr and cooled down to the room temperature to terminate the reaction Then, aqueous 1.0 N-hydrochloric acid solution was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give N-(4-(5-(difluoromethyl)-1,3,4-oxadiazol-2-yl)-2-fluorobenzyl)-3-(4-methylpiperazin-1-yl)-N-phenylpropane-1-sulfonamide as white solid (0.031 g, 39.2%).

¹H NMR (400 MHz, CDCl₃) δ 7.87 (dd, 1H, J=8.1, 1.6 Hz), 7.74 (dd, 1H, J=9.9, 1.6 Hz), 7.63 (t, 1H, J=7.6 Hz), 7.42-7.27 (m, 5H), 7.08-6.76 (m, 1H), 5.06 (s, 2H), 3.28-3.19 (m, 4H), 3.07-3.02 (m, 4H), 2.80-2.72 (m, 5H), 2.21-2.08 (m, 4H); LRMS (ES) m/z 524.44 (M⁺+1).

EXAMPLE 163

Compound 11605, N-((2-(5-(difluoromethyl)-1,3,4-oxadiazol-2-yl)pyrimidin-5-yl)methyl)-N-phenylmethanesulfonamide

[Step 1] methyl 5-(bromomethyl)pyrimidine-2-carboxylate

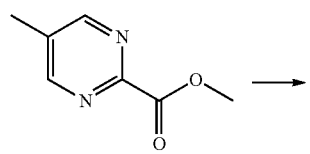

A mixture of methyl 5-methylpyrimidine-2-carboxylate (0.500 g, 3.286 mmol), 1-bromopyrrolidine-2,5-dione (NBS, 0.643 g, 3.615 mmol) and Azobisisobutyronitrile (AIBN, 0.216 g, 1.314 mmol) in carbon tetrachloride (4 mL) prepared at the room temperature was heated at reflux for 10 hr, and cooled down to the ambient temperature. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 30%) to give methyl 5-(bromomethyl)pyrimidine-2-carboxylate as white solid (0.380 g, 50.0%).

[Step 2] methyl 5-((N-phenylmethylsulfonamido)methyl)pyrimidine-2-carboxylate

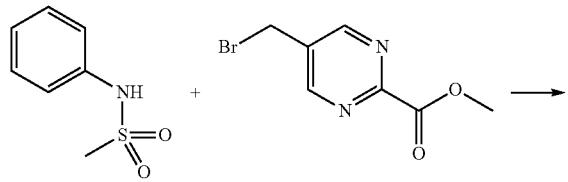

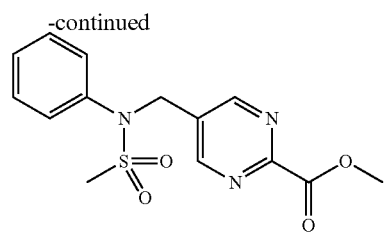

A solution of methyl 5-(bromomethyl)pyrimidine-2-carboxylate (0.270 g, 1.168 mmol) and potassium iodide (0.019 g, 0.117 mmol) in N,N-dimethylformide (5 mL) was stirred at the room temperature for 20 min, and mixed with N-phenylmethanesulfonamide (0.200 g, 1.168 mmol) and potassium carbonate (0.194 g, 1.402 mmol). The reaction mixture was stirred at the same temperature for additional 8 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; ethyl acetate/hexane=0% to 80%) to give methyl 5-((N-phenylmethylsulfonamido)methyl)pyrimidine-2-carboxylate as light yellow solid (0.220 g, 58.6%).

[Step 3] N-((2-(hydrazinecarbonyl)pyrimidin-5-yl)methyl)-N-phenylmethanesulfonamide

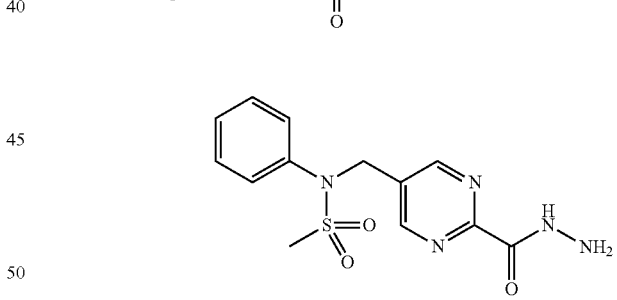

A mixture of methyl 5-((N-phenylmethylsulfonamido)methyl)pyrimidine-2-carboxylate (0.220 g, 0.685 mmol) and hydrazine monohydrate (0.166 mL, 3.423 mmol) in ethanol (4 mL) prepared at the room temperature was heated at reflux for 5 hr, cooled down to the ambient temperature, and concentrated under the reduced pressure to remove the solvent. Then, saturated aqueous sodium bicarbonate solution was added to the concentrate, followed by extraction with dichloromethane. The organic layer was washed with aqueous saturated sodium chloride solution, dried with anhydrous MgSO₄, filtered, and concentrated in vacuo. The title compound was used without further purification (N-((2-(hydrazinecarbonyl)pyrimidin-5-yl)methyl)-N-phenylmethanesulfonamide, 0.190 g, 86.4%, white solid).

519

[Step 4] Compound 11605

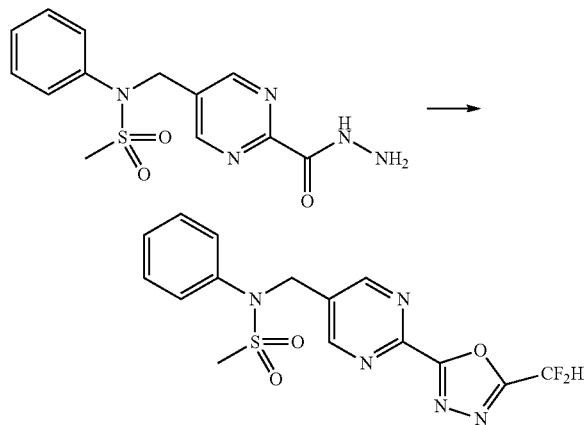

A solution of N-((2-(hydrazinecarbonyl)pyrimidin-5-yl)methyl)-N-phenylmethanesulfonamide (0.045 g, 0.140 mmol) and triethylamine (0.059 mL, 0.420 mmol) in tetrahydrofuran (1.5 mL) was mixed at the room temperature with 2,2-difluoroacetic anhydride (0.038 mL, 0.308 mmol), stirred at 60° C. for 2 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 50%) to give N-((2-(5-(difluoromethyl)-1,3,4-oxadiazol-2-yl)pyrimidin-5-yl)methyl)-N-phenylmethanesulfonamide as white solid (0.040 g, 74.9%).

$^1$H NMR (400 MHz, CDCl$_3$) δ 8.87 (s, 2H), 7.41-7.34 (m, 3H), 7.31 (d, 2H, J=9.8 Hz), 7.07 (s, 0.25H), 6.94 (s, 0.5H), 6.81 (s, 0.25H), 5.00 (s, 2H), 3.01 (s, 3H); LRMS (ES) m/z 382.34 (M$^+$+1).

EXAMPLE 164

Compound 11606, N-phenyl-N-((2-(5-(trifluoromethyl)-1,3,4-oxadiazol-2-yl)pyrimidin-5-yl)methyl)methanesulfonamide

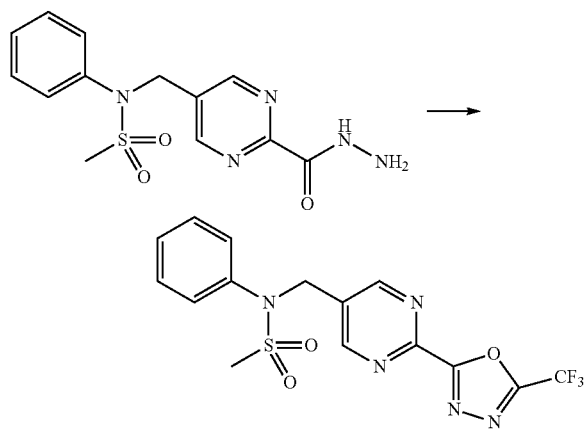

A solution of N-((2-(hydrazinecarbonyl)pyrimidin-5-yl)methyl)-N-phenylmethanesulfonamide (0.030 g, 0.093 mmol) and triethylamine (0.039 mL, 0.280 mmol) in tetrahydrofuran (1.5 mL) was mixed at the room temperature with trifluoroacetic anhydride (0.029 mL, 0.205 mmol), stirred at 60° C. for 2 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 50%) to give N-phenyl-N-((2-(5-(trifluoromethyl)-1,3,4-oxadiazol-2-yl)pyrimidin-5-yl)methyl)methanesulfonamide as white solid (0.028 g, 75.1%).

$^1$H NMR (400 MHz, CDCl$_3$) δ 8.89 (s, 2H), 7.42-7.28 (m, 5H), 5.00 (s, 2H), 3.01 (s, 3H); LRMS (ES) m/z 400.38 (M$^+$+1).

EXAMPLE 165

Compound 11625, N-(4-(5-(difluoromethyl)-1,3,4-oxadiazol-2-yl)-2-fluorobenzyl)-1-(oxetan-3-yl)-N-phenylpiperidine-4-sulfonamide

[Step 1] methyl 3-fluoro-4-(((1-(oxetan-3-yl)-N-phenylpiperidine)-4-sulfonamido)methyl)benzoate

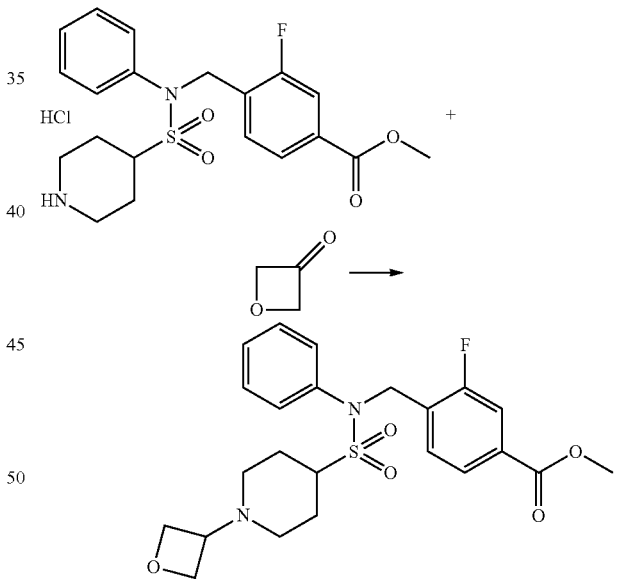

A solution of methyl 3-fluoro-4-((N-phenylpiperidine-4-sulfonamido)methyl)benzoate hydrochloride (0.100 g, 0.226 mmol), oxetan-3-one (0.020 g, 0.271 mmol) and acetic acid (0.014 mL, 0.248 mmol) in dichloromethane (10 mL) was stirred at the room temperature for 30 min, and mixed with sodium triacetoxyborohydride (0.096 g, 0.452 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 12 g cartridge; ethyl acetate/hexane=0% to 60%) to give methyl 3-fluoro-4-(((1-(oxetan-3-yl)-N-phenylpiperidine)-4-sulfonamido)methyl)benzoate as white solid (0.090 g, 86.2%).

[Step 2] N-(2-fluoro-4-(hydrazinecarbonyl)benzyl)-1-(oxetan-3-yl)-N-phenylpiperidine-4-sulfonamide

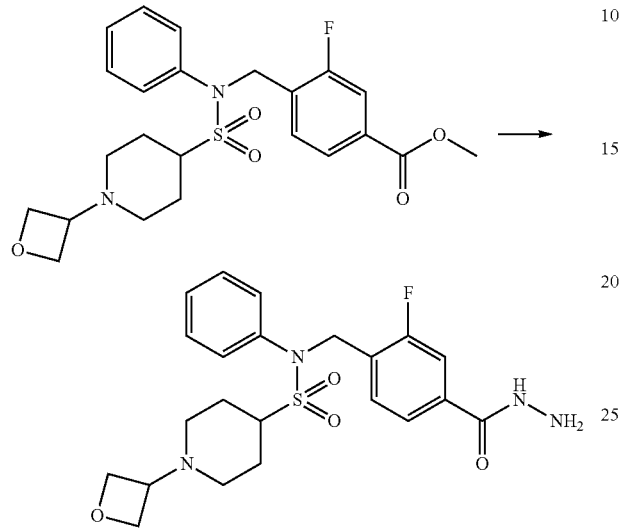

A solution of methyl 3-fluoro-4-(((1-(oxetan-3-yl)-N-phenylpiperidine)-4-sulfonamido)methyl)benzoate (0.100 g, 0.216 mmol) and hydrazine monohydrate (0.105 mL, 2.162 mmol) in ethanol (10 mL) was stirred at the room temperature for 18 hr, and concentrated under the reduced pressure to remove the solvent. The residue was diluted with water (10 mL) and sodium bicarbonate (5 mL) and stirred. The resulting precipitates were collected by filtration, washed by hexane, and dried to give N-(2-fluoro-4-(hydrazinecarbonyl)benzyl)-1-(oxetan-3-yl)-N-phenylpiperidine-4-sulfonamide as white solid (0.089 g, 89.0%).

[Step 3] compound 11625

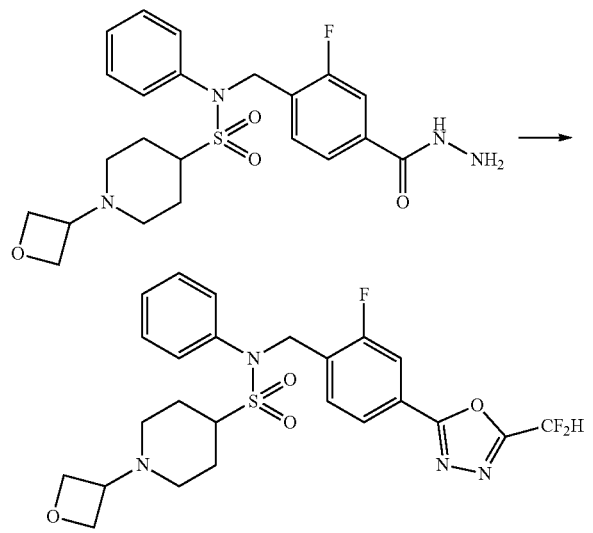

A solution of N-(2-fluoro-4-(hydrazinecarbonyl)benzyl)-1-(oxetan-3-yl)-N-phenylpiperidine-4-sulfonamide (0.050 g, 0.108 mmol), triethylamine (0.075 mL, 0.540 mmol) and 2,2-difluoroacetic anhydride (0.040 mL, 0.324 mmol) in tetrahydrofuran (10 mL) was stirred at the room temperature for 5 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 70%) to give N-(4-(5-(difluoromethyl)-1,3,4-oxadiazol-2-yl)-2-fluorobenzyl)-1-(oxetan-3-yl)-N-phenylpiperidine-4-sulfonamide as white solid (0.023 g, 40.7%).

$^1$H NMR (400 MHz, CDCl$_3$) δ 7.87 (dd, 1H, J=8.1, 1.6 Hz), 7.73 (dd, 1H, J=9.9, 1.6 Hz), 7.60 (t, 1H, J=7.6 Hz), 7.41-7.27 (m, 5H), 7.10-6.75 (m, 1H), 5.07 (s, 2H), 4.98-4.91 (m, 2H), 4.74 (t, 2H, J=7.2 Hz), 3.93 (s, 1H), 3.37-3.16 (m, 3H), 2.65-2.60 (m, 2H), 2.48-2.43 (m, 2H), 2.40-2.31 (m, 2H); LRMS (ES) m/z 523.38 (M$^+$+1).

EXAMPLE 166

Compound 11628, N-(4-(5-(difluoromethyl)-1,3,4-oxadiazol-2-yl)benzyl)-N-(pyridin-3-yl)methanesulfonamide

[Step 1] methyl 4-((N-(pyridin-3-yl)methylsulfonamido)methyl)benzoate

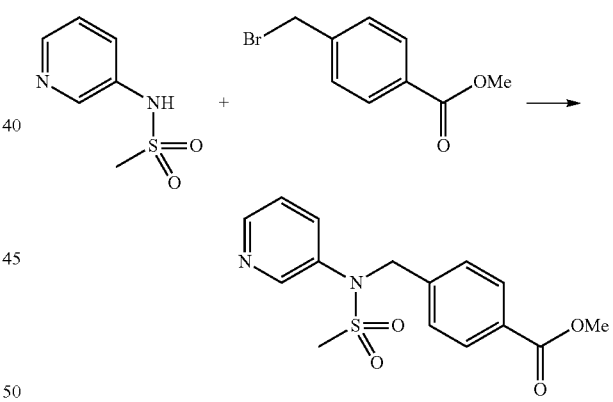

N-(pyridin-3-yl)methanesulfonamide (1.000 g, 5.807 mmol), methyl 4-(bromomethyl)benzoate (1.995 g, 8.711 mmol), potassium carbonate (1.204 g, 8.711 mmol) and potassium iodide (0.096 g, 0.581 mmol) were mixed at the room temperature in N,N-dimethylformide (20 mL), stirred at 50° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 80%) to give methyl 4-((N-(pyridin-3-yl)methylsulfonamido)methyl)benzoate as red solid (1.510 g, 81.2%).

523

[Step 2] N-(4-(hydrazinecarbonyl)benzyl)-N-(pyridin-3-yl)methanesulfonamide

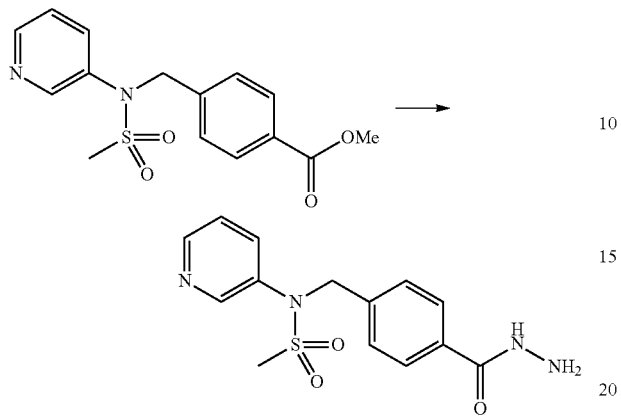

Methyl 4-((N-(pyridin-3-yl)methylsulfonamido)methyl)benzoate (1.500 g, 4.682 mmol) and hydrazine monohydrate (5.689 mL, 117.056 mmol) were mixed at the room temperature in ethanol (20 mL)/water (5 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(4-(hydrazinecarbonyl)benzyl)-N-(pyridin-3-yl)methanesulfonamide, 1.120 g, 74.7%, yellow solid).

[Step 3] Compound 11628

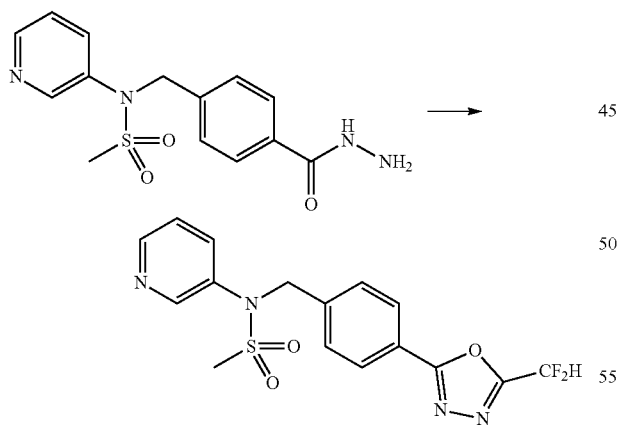

A solution of N-(4-(hydrazinecarbonyl)benzyl)-N-(pyridin-3-yl)methanesulfonamide (0.200 g, 0.624 mmol) and triethylamine (0.261 mL, 1.873 mmol) in tetrahydrofuran (10 mL) was mixed at the room temperature with 2,2-difluoroacetic anhydride (0.233 mL, 1.873 mmol), stirred at 80° C. for 1 hr and cooled down to the room temperature to terminate the reaction. Then, water was added to the reaction mixture, followed by extraction with ethyl acetate. The organic layer was washed with aqueous saturated sodium

524 chloride solution, dried with anhydrous MgSO₄, filtered, and concentrated in vacuo. The residue was chromatographed (SiO₂ plate, 20×20×1 mm; methanol/dichloromethane=10%) to give N-(4-(5-(difluoromethyl)-1,3,4-oxadiazol-2-yl)benzyl)-N-(pyridin-3-yl)methanesulfonamide as white solid (0.023 g, 9.7%).

$^1$H NMR (400 MHz, DMSO-d6) δ 8.57 (d, 1H, J=2.4 Hz), 8.43 (dd, J=4.8, 1.1 Hz, 1H), 7.98 (d, 2H, J=8.2 Hz), 7.90 (d, 1H, J=8.2 Hz), 7.65-7.38 (m, 4H), 5.03 (s, 2H), 3.20 (s, 3H); LRMS (ES) m/z 380.9 (M$^+$+1).

EXAMPLE 167

Compound 11629, N-(4-(5-(difluoromethyl)-1,3,4-oxadiazol-2-yl)benzyl)-N-phenyl-2-(piperidin-1-yl)ethane-1-sulfonamide

[Step 1] N-phenylethenesulfonamide

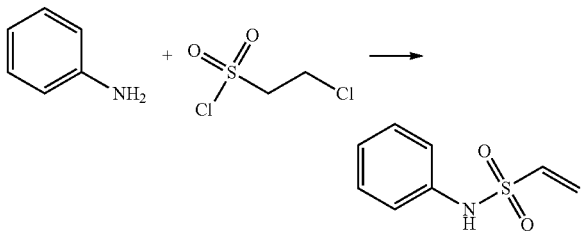

A solution of aniline (0.980 mL, 10.738 mmol), 2-chloroethane-1-sulfonyl chloride (1.233 mL, 11.811 mmol) and pyridine (1.730 mL, 21.475 mmol) in dichloromethane (20 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=0% to 20%) to give N-phenylethenesulfonamide as yellow oil (0.945 g, 48.0%).

[Step 2] methyl 4-((N-phenylvinylsulfonamido)methyl)benzoate

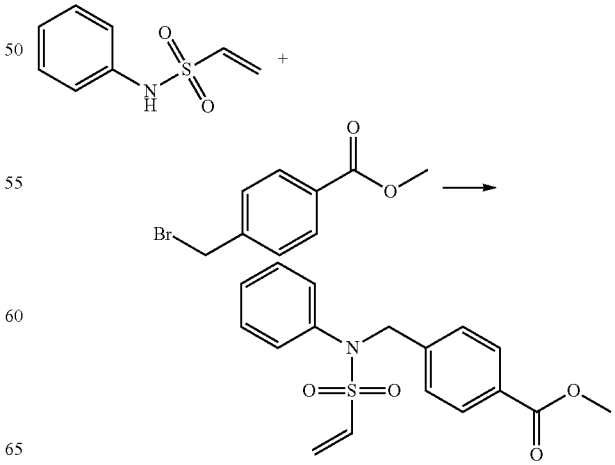

A solution of N-phenylethenesulfonamide (0.945 g, 5.157 mmol), methyl 4-(bromomethyl)benzoate (1.300 g, 5.673 mmol), potassium iodide (0.428 g, 2.579 mmol) and potassium carbonate (1.069 g, 7.736 mmol) in N,N-dimethylformamide (50 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 20%) to give methyl 4-((N-phenylvinylsulfonamido)methyl)benzoate as light green solid (1.500 g, 87.8%).

[Step 3] methyl 4-(((N-phenyl-2-(piperidin-1-yl)ethyl)sulfonamido)methyl)benzoate

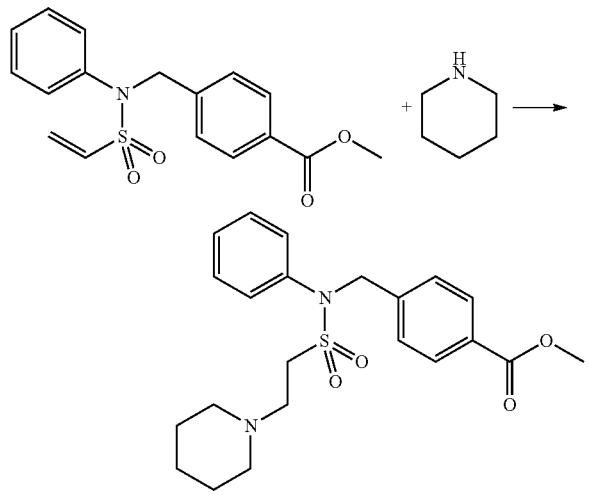

A solution of methyl 4-((N-phenylvinylsulfonamido)methyl)benzoate (0.300 g, 0.905 mmol), piperidine (0.179 mL, 1.811 mmol) and N,N-Diisopropylethylamine (0.189 mL, 1.086 mmol) in tetrahydrofuran (5 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=20% to 80%) to give methyl 4-(((N-phenyl-2-(piperidin-1-yl)ethyl)sulfonamido)methyl)benzoate as white solid (0.334 g, 88.7%).

[Step 4] N-(4-(hydrazinecarbonyl)benzyl)-N-phenyl-2-(piperidin-1-yl)ethane-1-sulfonamide

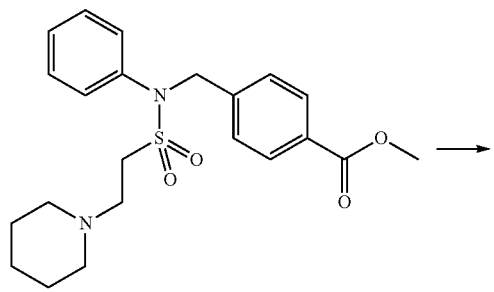

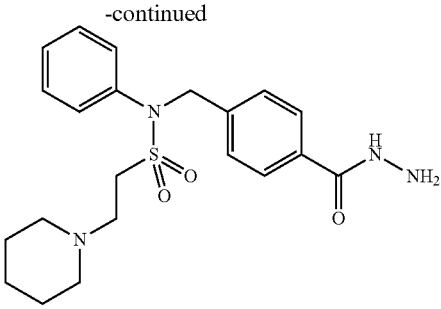

A solution of methyl 4-(((N-phenyl-2-(piperidin-1-yl)ethyl)sulfonamido)methyl)benzoate (0.334 g, 0.803 mmol) and hydrazine hydrate (0.402 g, 8.028 mmol) in ethanol (10 mL) was stirred at 90° C. for 12 hr, cooled down to the room temperature to terminate the reaction and concentrated under the reduced pressure to remove the solvent. The residue was diluted with sodium bicarbonate (10 mL) and water (5 mL) and stirred. The resulting precipitates were collected by filtration, washed by water, and dried to give N-(4-(hydrazinecarbonyl)benzyl)-N-phenyl-2-(piperidin-1-yl)ethane-1-sulfonamide as white solid (0.273 g, 81.7%).

[Step 5] Compound 11629

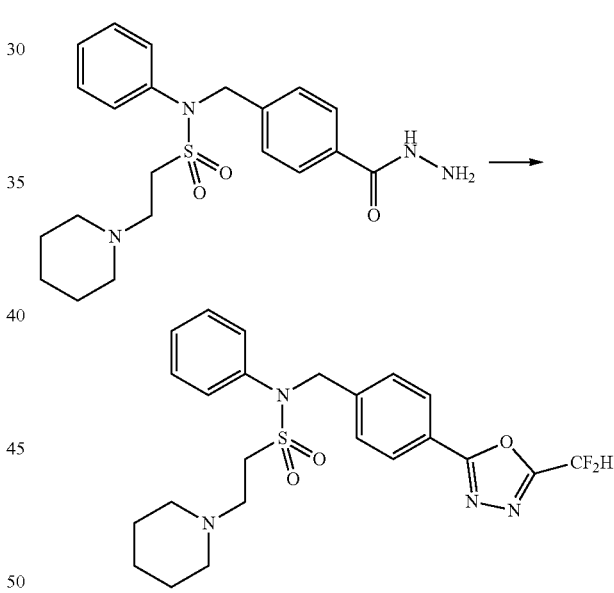

A solution of N-(4-(hydrazinecarbonyl)benzyl)-N-phenyl-2-(piperidin-1-yl)ethane-1-sulfonamide (0.100 g, 0.240 mmol), triethylamine (0.167 mL, 1.200 mmol) and 2,2-difluoroacetic anhydride (0.090 mL, 0.720 mmol) in tetrahydrofuran (5 mL) was stirred at 90° C. for 12 hr, cooled down to the room temperature to terminate the reaction and concentrated under the reduced pressure to remove the solvent. Then, water was added to the concentrate, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(4-(5-(difluoromethyl)-1,3,4-oxadiazol-2-yl)benzyl)-N-phenyl-2-(piperidin-1-yl)ethane-1-sulfonamide as white solid (0.035 g, 30.8%).

¹H NMR (400 MHz, CDCl₃) δ8.02 (d, 2H, J=8.4 Hz), 7.46 (d, 2H, J=8.4 Hz), 7.47~7.28 (m, 5H), 6.91 (t, 1H, J=51.7 Hz), 5.00 (s, 2H), 3.58~3.56 (m, 2H), 3.06 (t, 2H, J=7.1 Hz), 2.70 (brs, 4H), 1.79 (brs, 4H), 1.55 (brs, 2H); LRMS (ES) m/z 477.3 (M⁺+1).

EXAMPLE 168

Compound 11630, N-(4-(5-(difluoromethyl)-1,3,4-oxadiazol-2-yl)benzyl)-2-(4-methylpiperazin-1-yl)-N-phenylethane-1-sulfonamide

[Step 1] methyl 4-(((2-(4-methylpiperazin-1-yl)-N-phenylethyl)sulfonamido)methyl)benzoate

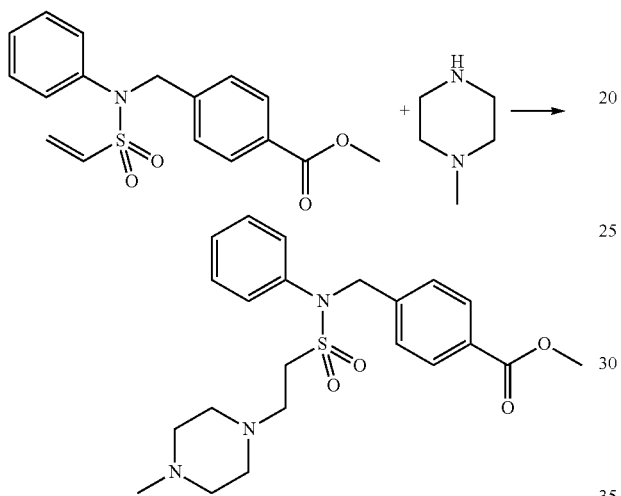

A solution of methyl 4-((N-phenylvinylsulfonamido)methyl)benzoate (0.300 g, 0.905 mmol), 1-methylpiperazine (0.202 mL, 1.811 mmol) and N,N-Diisopropylethylamine (0.189 mL, 1.086 mmol) in tetrahydrofuran (5 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=20% to 80%) to give methyl 4-(((2-(4-methylpiperazin-1-yl)-N-phenylethyl)sulfonamido)methyl)benzoate as white solid (0.362 g, 92.7%).

[Step 2] N-(4-(hydrazinecarbonyl)benzyl)-2-(4-methylpiperazin-1-yl)-N-phenylethane-1-sulfonamide

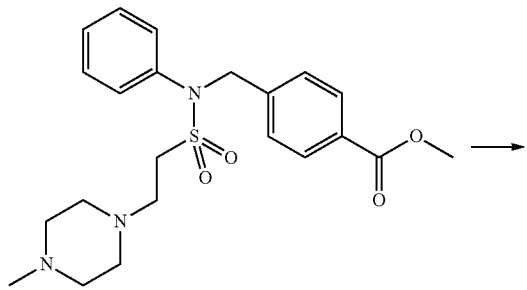

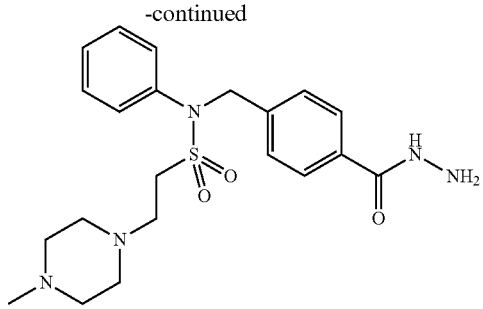

A solution of methyl 4-(((2-(4-methylpiperazin-1-yl)-N-phenylethyl)sulfonamido)methyl)benzoate (0.362 g, 0.840 mmol) and hydrazine hydrate (0.420 g, 8.395 mmol) in ethanol (10 mL) was stirred at 90° C. for 12 hr, cooled down to the room temperature to terminate the reaction and concentrated under the reduced pressure to remove the solvent. The residue was diluted with sodium bicarbonate (10 mL) and water (5 mL) and stirred. The resulting precipitates were collected by filtration, washed by water, and dried to give N-(4-(hydrazinecarbonyl)benzyl)-2-(4-methylpiperazin-1-yl)-N-phenylethane-1-sulfonamide as white solid (0.237 g, 65.5%).

[Step 3] Compound 11630

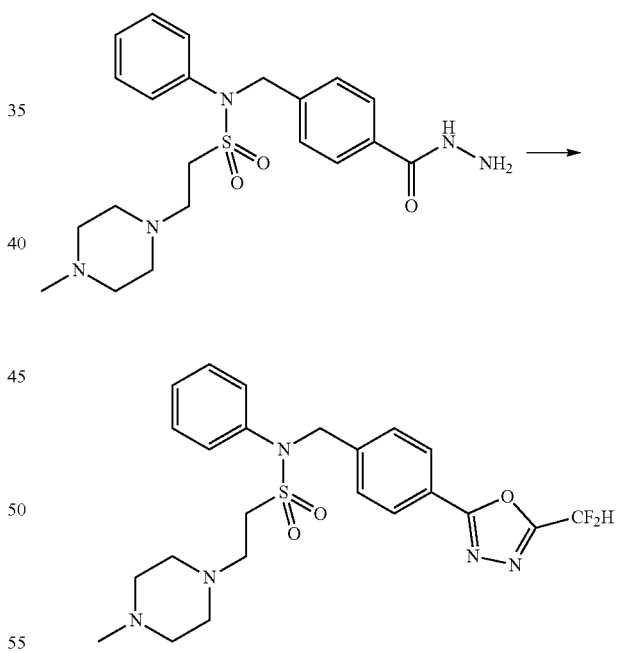

A solution of N-(4-(hydrazinecarbonyl)benzyl)-2-(4-methylpiperazin-1-yl)-N-phenylethane-1-sulfonamide (0.100 g, 0.232 mmol), triethylamine (0.161 mL, 1.159 mmol) and 2,2-difluoroacetic anhydride (0.086 mL, 0.695 mmol) in tetrahydrofuran (5 mL) was stirred at 90° C. for 12 hr, cooled down to the room temperature to terminate the reaction and concentrated under the reduced pressure to remove the solvent. Then, water was added to the concentrate, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 50%) to give N-(4-(5-(difluoromethyl)-1,3,4-oxadiazol-2-yl)benzyl)-2-(4-methylpiperazin-1-yl)-N-phenylethane-1-sulfonamide as colorless oil (0.033 g, 28.7%).

¹H NMR (400 MHz, CDCl₃) δ8.04 (d, 2H, J=8.4 Hz), 7.47 (d, 2H, J=8.6 Hz), 7.36~7.30 (m, 5H), 6.92 (t, 1H, J=51.7 Hz), 4.97 (s, 2H), 3.29 (dd, 2H, J=8.3, 6.2 Hz), 3.01 (dd, 2H, J=8.2, 6.3 Hz), 2.79 (brs, 8H), 2.57 (s, 3H); LRMS (ES) m/z 492.3 (M⁺+1).

EXAMPLE 169

Compound 11631, tert-butyl 4-(2-(N-(4-(5-(difluoromethyl)-1,3,4-oxadiazol-2-yl)benzyl)-N-phenylsulfamoyl)ethyl)piperazine-1-carboxylate

[Step 1] tert-butyl 4-(2-(N-(4-(methoxycarbonyl)benzyl)-N-phenylsulfamoyl)ethyl)piperazine-1-carboxylate

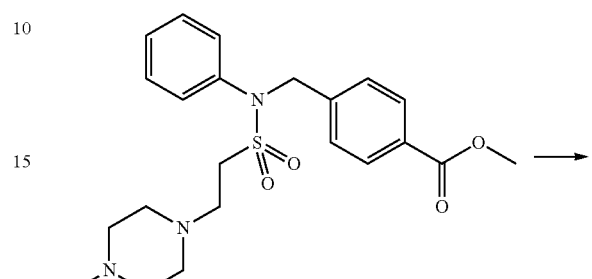

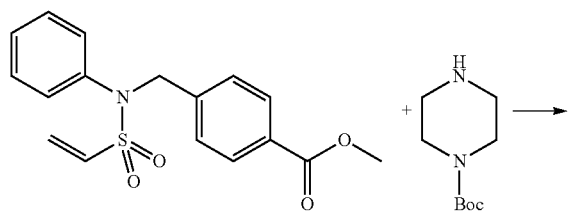

A solution of methyl 4-((N-phenylvinylsulfonamido)methyl)benzoate (0.300 g, 0.905 mmol), tert-butyl piperazine-1-carboxylate (0.337 g, 1.811 mmol) and N,N-Diisopropylethylamine (0.189 mL, 1.086 mmol) in tetrahydrofuran (5 mL) was stirred at the room temperature for 5 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=20% to 80%) to give tert-butyl 4-(2-(N-(4-(methoxycarbonyl)benzyl)-N-phenylsulfamoyl)ethyl)piperazine-1-carboxylate as white solid (0.411 g, 87.7%).

[Step 2] tert-butyl 4-(2-(N-(4-(hydrazinecarbonyl)benzyl)-N-phenylsulfamoyl)ethyl)piperazine-1-carboxylate A solution of tert-butyl 4-(2-(N-(4-(methoxycarbonyl)benzyl)-N-phenylsulfamoyl)ethyl)piperazine-1-carboxylate (0.411 g, 0.794 mmol) and hydrazine hydrate (0.397 g, 7.936 mmol) in ethanol (10 mL) was stirred at 90° C. for 12 hr, cooled down to the room temperature to terminate the reaction and concentrated under the reduced pressure to remove the solvent. The residue was diluted with sodium bicarbonate (10 mL) and water (5 mL) and stirred. The resulting precipitates were collected by filtration, washed by water, and dried to give tert-butyl 4-(2-(N-(4-(hydrazinecarbonyl)benzyl)-N-phenylsulfamoyl)ethyl)piperazine-1-carboxylate as white solid (0.344 g, 83.8%).

[Step 3] Compound 11631

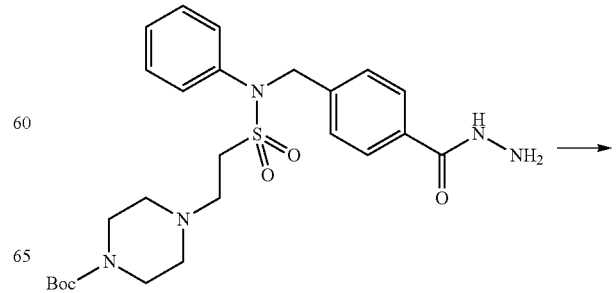

531

-continued

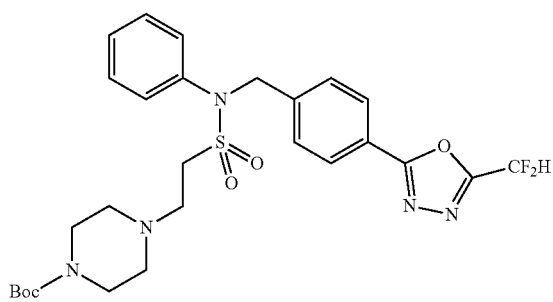

A solution of tert-butyl 4-(2-(N-(4-(hydrazinecarbonyl)benzyl)-N-phenylsulfamoyl)ethyl)piperazine-1-carboxylate (0.240 g, 0.464 mmol), triethylamine (0.323 mL, 2.318 mmol) and 2,2-difluoroacetic anhydride (0.173 mL, 1.391 mmol) in tetrahydrofuran (5 mL) was stirred at 90° C. for 18 hr, cooled down to the room temperature to terminate the reaction and concentrated under the reduced pressure to remove the solvent. Then, water was added to the concentrate, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give tert-butyl 4-(2-(N-(4-(5-(difluoromethyl)-1,3,4-oxadiazol-2-yl)benzyl)-N-phenylsulfamoyl)ethyl)piperazine-1-carboxylate as yellow oil (0.199 g, 74.3%).

$^1$H NMR (400 MHz, CDCl$_3$) δ8.03 (d, 2H, J=8.5 Hz), 7.46 (d, 2H, J=8.6 Hz), 7.37~7.28 (m, 5H), 6.92 (t, 1H, J=51.7 Hz), 4.98 (s, 2H), 3.54 (brs, 4H), 3.41 (brs, 2H), 3.00 (t, 2H, J=7.3 Hz), 2.56 (brs, 4H), 1.48 (s, 9H); LRMS (ES) m/z 578.3 (M$^+$+1).

EXAMPLE 170

Compound 11632, N-(4-(5-(difluoromethyl)-1,3,4-oxadiazol-2-yl)benzyl)-2-((3S,5R)-3,5-dimethylpiperazin-1-yl)-N-phenylethane-1-sulfonamide

[Step 1] methyl 4-(((2-((3S,5R)-3,5-dimethylpiperazin-1-yl)-N-phenylethyl)sulfonamido)methyl)benzoate

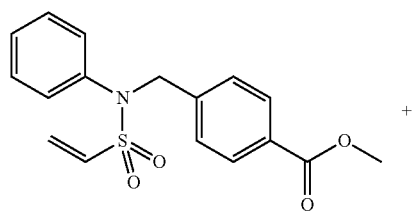

+

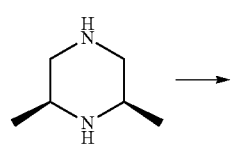

→

532

-continued

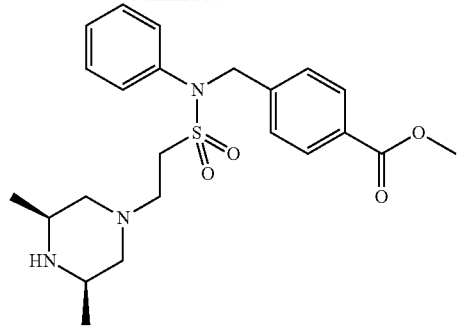

A solution of methyl 4-((N-phenylvinylsulfonamido)methyl)benzoate (0.300 g, 0.905 mmol), (2S,6R)-2,6-dimethylpiperazine (0.207 g, 1.811 mmol) and N,N-Diisopropylethylamine (0.189 mL, 1.086 mmol) in tetrahydrofuran (5 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 10%) to give methyl 4-(((2-((3S,5R)-3,5-dimethylpiperazin-1-yl)-N-phenylethyl)sulfonamido)methyl)benzoate as white solid (0.403 g, 99.9%).

[Step 2] 2-((3S,5R)-3,5-dimethylpiperazin-1-yl)-N-(4-(hydrazinecarbonyl)benzyl)-N-phenylethane-1-sulfonamide

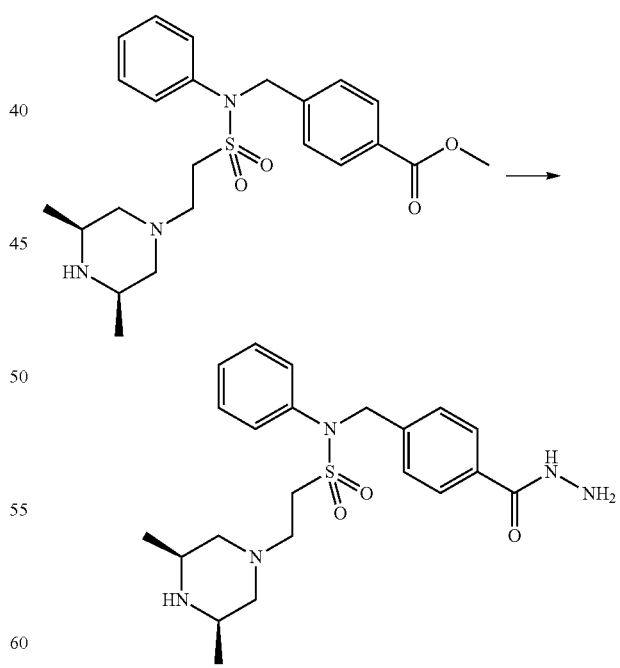

A solution of methyl 4-(((2-((3S,5R)-3,5-dimethylpiperazin-1-yl)-N-phenylethyl)sulfonamido)methyl)benzoate (0.403 g, 0.904 mmol) and hydrazine hydrate (0.453 g, 9.042 mmol) in ethanol (10 mL) was stirred at 90° C. for 12 hr, cooled down to the room temperature to terminate the reaction and concentrated under the reduced pressure to remove the solvent. The residue was diluted with sodium bicarbonate (10 mL) and water (5 mL) and stirred. The resulting precipitates were collected by filtration, washed by water, and dried to give 2-((3S,5R)-3,5-dimethylpiperazin-1-yl)-N-(4-(hydrazinecarbonyl)benzyl)-N-phenylethane-1-sulfonamide as yellow solid (0.263 g, 65.3%).

[Step 3] N-(4-(2-(2,2-difluoroacetyl)hydrazine-1-carbonyl)benzyl)-2-((3S,5R)-3,5-dimethylpiperazin-1-yl)-N-phenylethane-1-sulfonamide

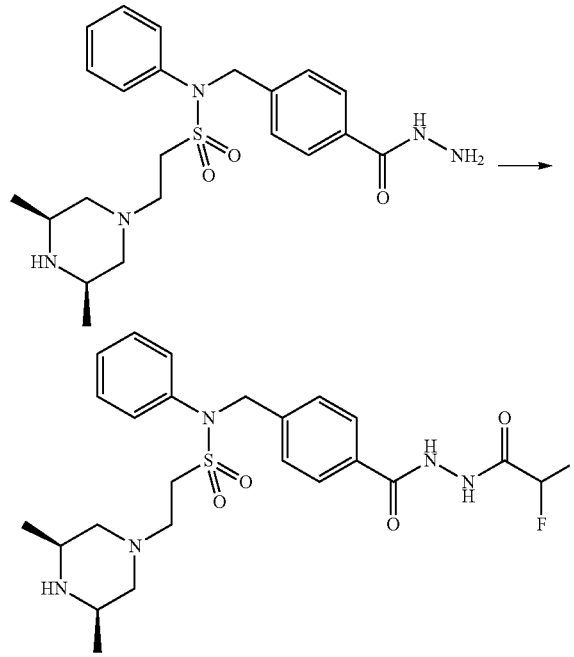

A solution of 2-((3S,5R)-3,5-dimethylpiperazin-1-yl)-N-(4-(hydrazinecarbonyl)benzyl)-N-phenylethane-1-sulfonamide (0.100 g, 0.224 mmol), triethylamine (0.156 mL, 1.122 mmol) and 2,2-difluoroacetic anhydride (0.084 mL, 0.673 mmol) in tetrahydrofuran (5 mL) was stirred at 90° C. for 12 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The title compound was used without further purification N-(4-(2-(2,2-difluoroacetyl)hydrazine-1-carbonyl)benzyl)-2-((3S,5R)-3,5-dimethylpiperazin-1-yl)-N-phenylethane-1-sulfonamide, 0.125 g, 106.4%, yellow oil).

[Step 4] Compound 11632

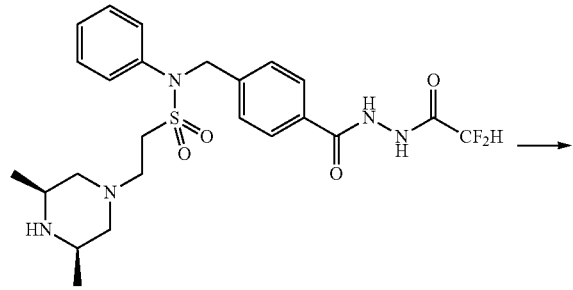

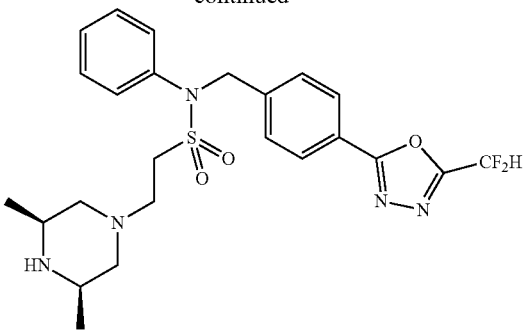

A mixture of N-(4-(2-(2,2-difluoroacetyl)hydrazine-1-carbonyl)benzyl)-2-((3S,5R)-3,5-dimethylpiperazin-1-yl)-N-phenylethane-1-sulfonamide (0.125 g, 0.239 mmol) and 1-methoxy-N-triethylammoniosulfonyl-methanimidate (Burgess reagent, 0.171 g, 0.716 mmol) in tetrahydrofuran (2 mL) was heated at 150° C. for 0.5 hr under the microwaves, cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)benzyl)-2-((3S,5R)-3,5-dimethylpiperazin-1-yl)-N-phenylethane-1-sulfonamide as yellow solid (0.015 g, 12.0%).

$^1$H NMR (400 MHz, CDCl$_3$+CD3OD) δ7.99~7.97 (m, 2H), 7.42 (d, 2H, J=8.1 Hz), 7.31~7.28 (m, 5H), 6.88 (t, 1H, J=51.9 Hz), 4.93 (s, 2H), 3.39~3.36 (m, 4H), 3.12~2.96 (m, 4H), 2.74~2.46 (m, 4H), 1.37 (s, 6H). LRMS (ES) m/z 506.4 (M$^+$+1).

EXAMPLE 171

Compound 11633, 2-(4-acetylpiperazin-1-yl)-N-(4-(5-(difluoromethyl)-1,3,4-oxadiazol-2-yl)benzyl)-N-phenylethane-1-sulfonamide

[Step 1] N-(4-(5-(difluoromethyl)-1,3,4-oxadiazol-2-yl)benzyl)-N-phenyl-2-(piperazin-1-yl)ethane-1-sulfonamide hydrochloride

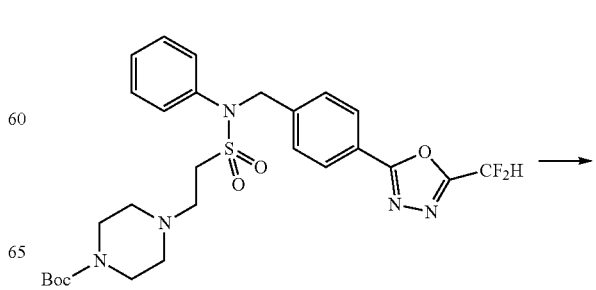

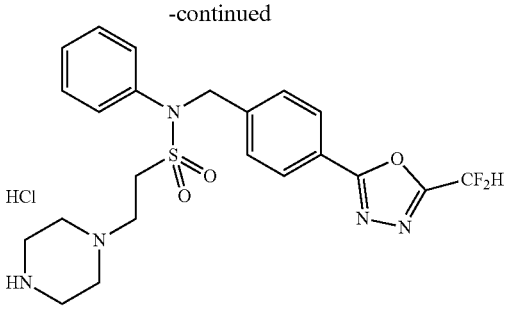

A solution of tert-butyl 4-(2-(N-(4-(5-(difluoromethyl)-1,3,4-oxadiazol-2-yl)benzyl)-N-phenylsulfamoyl)ethyl)piperazine-1-carboxylate (0.150 g, 0.290 mmol) and hydrogen chloride (4.00 M solution in 1,4-dioxane, 0.362 mL, 1.449 mmol) in 1,4-dioxane (5 mL) was stirred at the room temperature for 2 hr, and concentrated under the reduced pressure to remove the solvent. The residue was diluted with diethylether (10 mL) and stirred. The resulting precipitates were collected by filtration, washed by diethylether, and dried to give N-(4-(5-(difluoromethyl)-1,3,4-oxadiazol-2-yl)benzyl)-N-phenyl-2-(piperazin-1-yl)ethane-1-sulfonamide hydrochloride as white solid (0.146 g, 98.0%).

[Step 2] Compound 11633

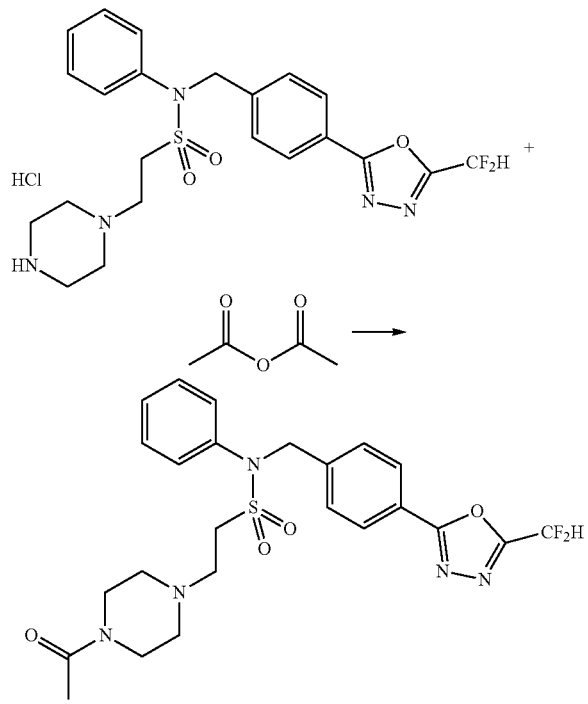

A solution of N-(4-(5-(difluoromethyl)-1,3,4-oxadiazol-2-yl)benzyl)-N-phenyl-2-(piperazin-1-yl)ethane-1-sulfonamide hydrochloride (0.050 g, 0.097 mmol), acetic anhydride (0.014 mL, 0.146 mmol) and triethylamine (0.041 mL, 0.292 mmol) in dichloromethane (5 mL) was stirred at the room temperature for 5 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=30% to 100%) to give 2-(4-acetylpiperazin-1-yl)-N-(4-(5-(difluoromethyl)-1,3,4-oxadiazol-2-yl)benzyl)-N-phenylethane-1-sulfonamide as white solid (0.033 g, 65.3%).

$^1$H NMR (400 MHz, CDCl$_3$) δ8.04 (d, 2H, J=8.1 Hz), 7.46 (d, 2H, J=8.2 Hz), 7.37~7.31 (m, 5H), 6.92 (t, 1H, J=51.8 Hz), 4.99 (s, 2H), 3.75~3.70 (m, 4H), 3.63~3.49 (m, 2H), 3.10~3.05 (m, 2H), 2.72~2.50 (m, 4H), 2.12 (s, 3H); LRMS (ES) m/z 520.3 (M$^+$+1).

EXAMPLE 172

Compound 11634, N-(4-(5-(difluoromethyl)-1,3,4-oxadiazol-2-yl)benzyl)-2-(4-(methylsulfonyl)piperazin-1-yl)-N-phenylethane-1-sulfonamide

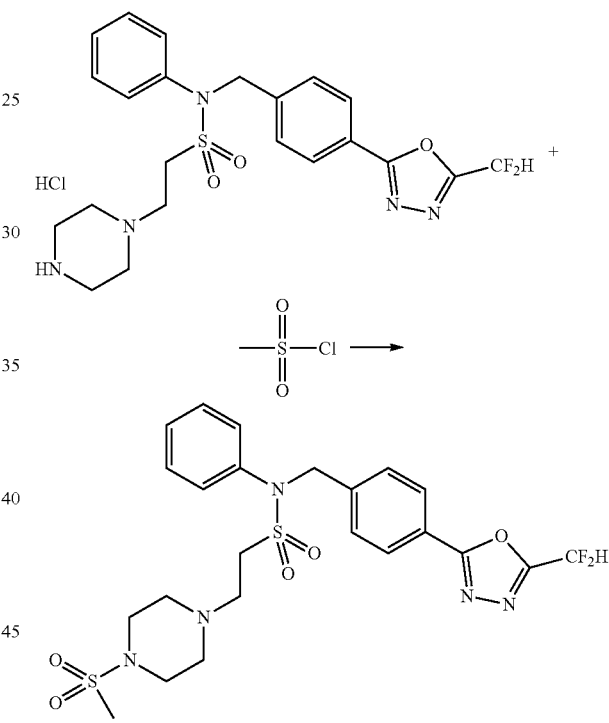

A solution of N-(4-(5-(difluoromethyl)-1,3,4-oxadiazol-2-yl)benzyl)-N-phenyl-2-(piperazin-1-yl)ethane-1-sulfonamide hydrochloride (0.050 g, 0.097 mmol), methanesulfonyl chloride (0.011 mL, 0.146 mmol) and triethylamine (0.041 mL, 0.292 mmol) in dichloromethane (5 mL) was stirred at the room temperature for 5 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=30% to 80%) to give N-(4-(5-(difluoromethyl)-1,3,4-oxadiazol-2-yl)benzyl)-2-(4-(methylsulfonyl)piperazin-1-yl)-N-phenylethane-1-sulfonamide as white solid (0.041 g, 75.3%).

$^1$H NMR (400 MHz, CDCl$_3$) δ8.4 Hz, 2H), 7.46 (d, 2H, J=8.5 Hz), 7.38~7.29 (m, 5H), 6.92 (t, 1H, J=51.7 Hz), 4.98

(s, 2H), 3.40~3.37 (m, 6H), 3.06~3.05 (m, 2H), 2.83 (s, 3H), 2.74 (brs, 4H); LRMS (ES) m/z 556.3 (M⁺+1).

EXAMPLE 173

Compound 11636, N-(4-(5-(difluoromethyl)-1,3,4-oxadiazol-2-yl)benzyl)-N-(pyrimidin-5-yl)methanesulfonamide

[Step 1] methyl 4-((N-(pyrimidin-5-yl)methylsulfonamido)methyl)benzoate

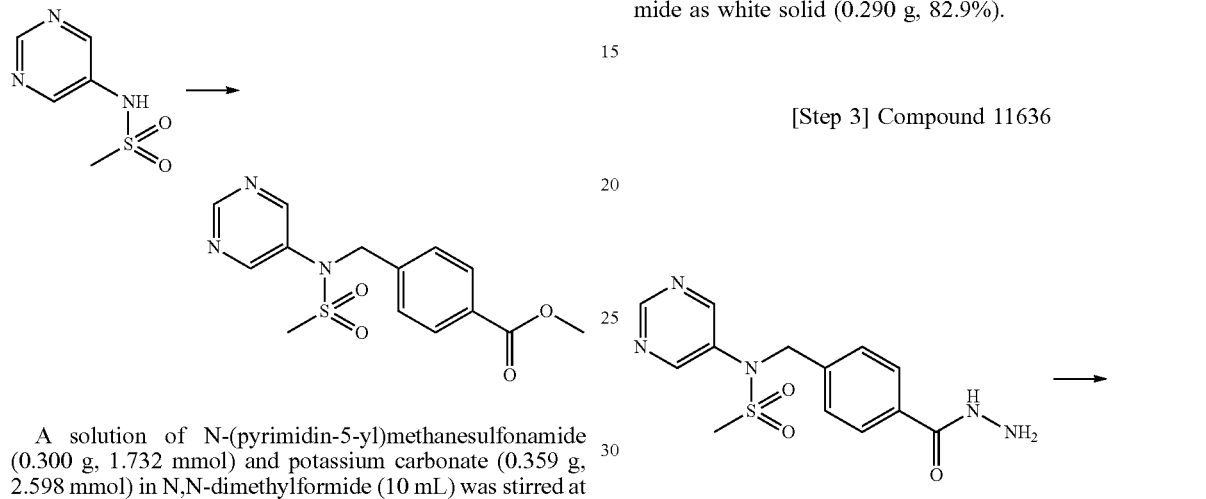

A solution of N-(pyrimidin-5-yl)methanesulfonamide (0.300 g, 1.732 mmol) and potassium carbonate (0.359 g, 2.598 mmol) in N,N-dimethylformide (10 mL) was stirred at the room temperature for 30 min, and mixed with methyl 4-(bromomethyl)benzoate (0.436 g, 1.905 mmol) and potassium iodide (0.144 g, 0.866 mmol). The reaction mixture was stirred at 50° C. for additional 12 hr and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 50%) to give methyl 4-((N-(pyrimidin-5-yl)methylsulfonamido)methyl)benzoate as white solid (0.350 g, 62.9%).

[Step 2] N-(4-(hydrazinecarbonyl)benzyl)-N-(pyrimidin-5-yl)methanesulfonamide

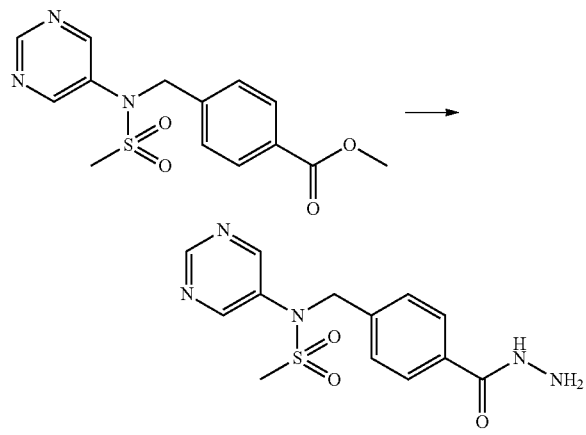

A solution of methyl 4-((N-(pyrimidin-5-yl)methylsulfonamido)methyl)benzoate (0.350 g, 1.089 mmol) and hydrazine monohydrate (0.529 mL, 10.892 mmol) in ethanol (20 mL) was stirred at 90° C. for 12 hr, cooled down to the room temperature to terminate the reaction and concentrated under the reduced pressure to remove the solvent. The residue was diluted with water (10 mL) and sodium bicarbonate (5 mL) and stirred. The resulting precipitates were collected by filtration, washed by hexane, and dried to give N-(4-(hydrazinecarbonyl)benzyl)-N-(pyrimidin-5-yl)methanesulfonamide as white solid (0.290 g, 82.9%).

[Step 3] Compound 11636

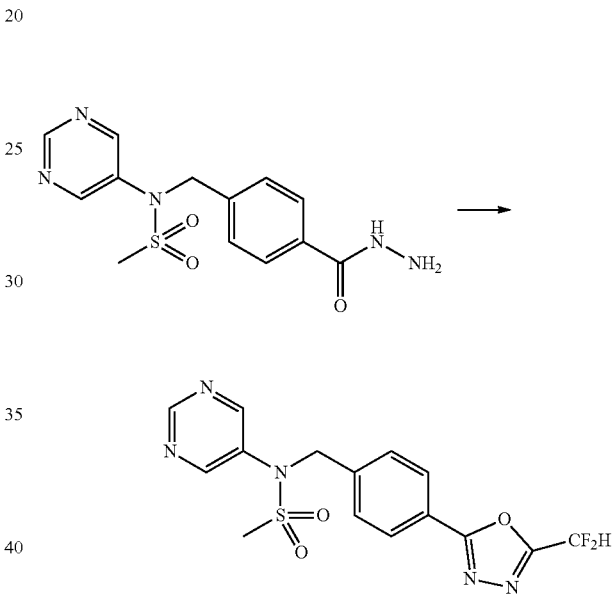

A mixture of N-(4-(hydrazinecarbonyl)benzyl)-N-(pyrimidin-5-yl)methanesulfonamide (0.100 g, 0.311 mmol), triethylamine (0.217 mL, 1.556 mmol) and 2,2-difluoroacetic anhydride (0.116 mL, 0.934 mmol) in tetrahydrofuran (10 mL) prepared at the room temperature was heated at reflux for 12 hr, and cooled down to the ambient temperature. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 60%) to give N-(4-(5-(difluoromethyl)-1,3,4-oxadiazol-2-yl)benzyl)-N-(pyrimidin-5-yl)methanesulfonamide as white solid (0.073 g, 61.5%).

¹H NMR (400 MHz, MeOD) δ 9.00 (s, 1H), 8.86 (s, 2H), 8.08 (d, 2H, J=6.6 Hz), 7.62 (d, 2H, J=8.4 Hz), 7.34 (s, 0.3H), 7.21 (s, 0.5H), 7.08 (s, 0.3H), 5.14 (s, 2H), 3.20 (s, 3H); LRMS (ES) m/z 382.2 (M⁺+1).

EXAMPLE 174

Compound 11637, N-(4-(5-(difluoromethyl)-1,3,4-oxadiazol-2-yl)benzyl)-1-methyl-N-phenylpiperidine-4-sulfonamide

[Step 1] tert-butyl 4-(N-(4-(methoxycarbonyl)benzyl)-N-phenylsulfamoyl)piperidine-1-carboxylate

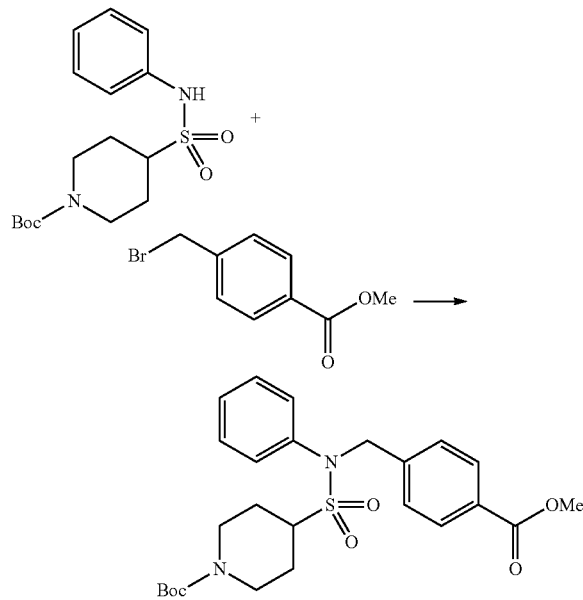

tert-butyl 4-(N-phenylsulfamoyl)piperidine-1-carboxylate (0.600 g, 1.763 mmol), methyl 4-(bromomethyl)benzoate (0.606 g, 2.644 mmol), potassium carbonate (0.487 g, 3.526 mmol) and potassium iodide (0.029 g, 0.176 mmol) were mixed at the room temperature in N,N-dimethylformide (15 mL), stirred at 50° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 80%) to give tert-butyl 4-(N-(4-(methoxycarbonyl)benzyl)-N-phenylsulfamoyl)piperidine-1-carboxylate as white solid (0.855 g, 99.3%).

[Step 2] methyl 4-((N-phenylpiperidine-4-sulfonamido)methyl)benzoate hydrochloride

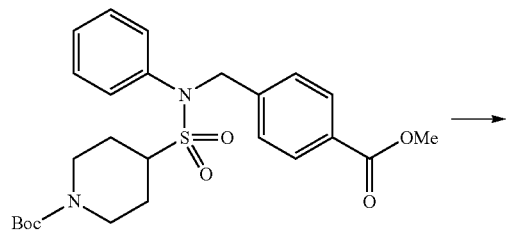

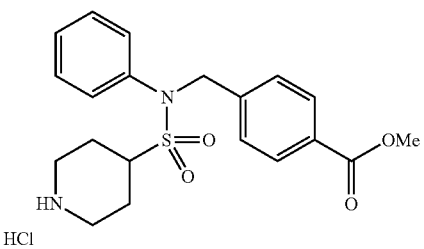

A solution of tert-butyl 4-(N-(4-(methoxycarbonyl)benzyl)-N-phenylsulfamoyl)piperidine-1-carboxylate (0.855 g, 1.750 mmol) in dichloromethane (15 mL) was mixed at the room temperature with hydrochloric acid (4.00 M solution, 1.750 mL, 7.000 mmol). The reaction mixture was stirred at the same temperature for 18 hr, and concentrated under the reduced pressure to remove the solvent. The precipitates were collected by filtration, washed by dichloromethane, and dried to give methyl 4-((N-phenylpiperidine-4-sulfonamido)methyl)benzoate hydrochloride as white solid (0.558 g, 75.0%).

[Step 3] methyl 4-(((1-methyl-N-phenylpiperidine)-4-sulfonamido)methyl)benzoate

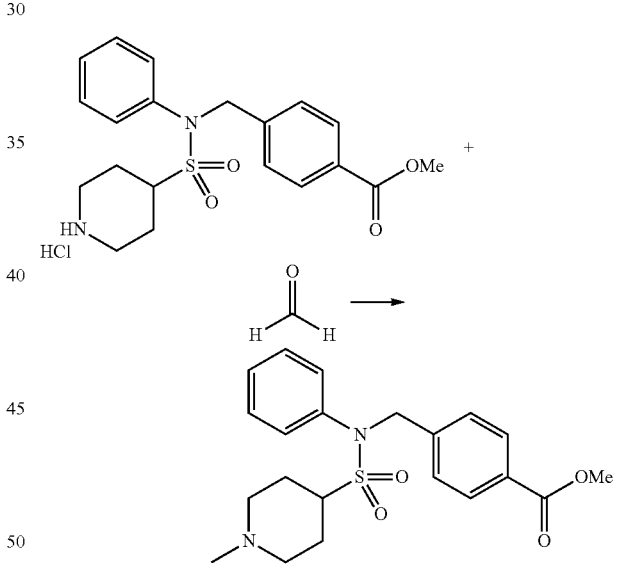

A solution of methyl 4-((N-phenylpiperidine-4-sulfonamido)methyl)benzoate hydrochloride (0.100 g, 0.235 mmol) and paraformaldehyde (0.011 g, 0.353 mmol) in dichloromethane (10 mL) was mixed at the room temperature with sodium triacetoxyborohydride (0.100 g, 0.471 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 15%) to give methyl 4-(((1-methyl-N-phenylpiperidine)-4-sulfonamido)methyl)benzoate as white solid (0.067 g, 70.7%).

[Step 4] N-(4-(hydrazinecarbonyl)benzyl)-1-methyl-N-phenylpiperidine-4-sulfonamide

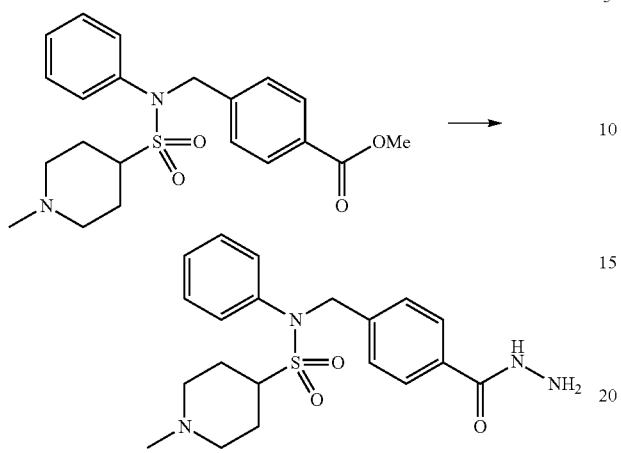

Methyl 4-(((1-methyl-N-phenylpiperidine)-4-sulfonamido)methyl)benzoate (0.067 g, 0.166 mmol) and hydrazine monohydrate (0.243 mL, 4.994 mmol) were mixed at the room temperature in ethanol (16 mL)/water (4 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(4-(hydrazinecarbonyl) benzyl)-1-methyl-N-phenylpiperidine-4-sulfonamide, 0.050 g, 74.6%, white solid).

[Step 5] Compound 11637

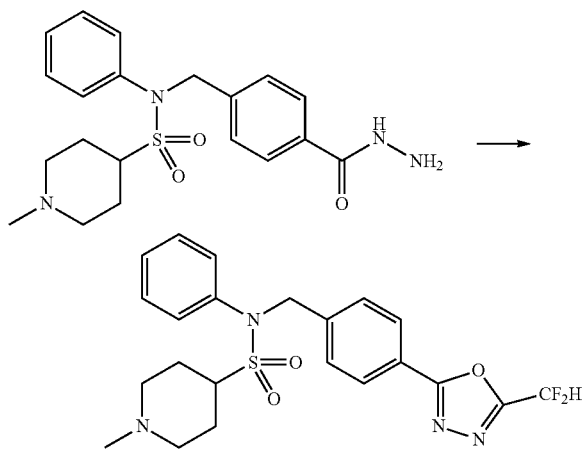

A solution of N-(4-(hydrazinecarbonyl)benzyl)-1-methyl-N-phenylpiperidine-4-sulfonamide (0.050 g, 0.124 mmol) and triethylamine (0.035 mL, 0.248 mmol) in tetrahydrofuran (10 mL) was mixed at the room temperature with 2,2-difluoroacetic anhydride (0.046 mL, 0.373 mmol), stirred at 80° C. for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 15%) to give N-(4-(5-(difluoromethyl)-1,3,4-oxadiazol-2-yl)benzyl)-1-methyl-N-phenylpiperidine-4-sulfonamide as white solid (0.017 g, 29.6%).

$^1$H NMR (400 MHz, CDCl$_3$) δ 8.00 (d, 2H, J=8.4 Hz), 7.42 (d, 2H, J=8.4 Hz), 7.42-7.23 (m, 5H), 7.01 (s, 0.25H), 6.88 (s, 0.5H), 6.75 (s, 0.25H), 4.98 (s, 2H), 3.20-3.0 (m, 3H), 2.51-2.38 (m, 3H), 2.38-2.10 (m, 6H); LRMS (ES) m/z 463.3 (M$^+$+1).

EXAMPLE 175

Compound 11638, N-(4-(5-(difluoromethyl)-1,3,4-oxadiazol-2-yl)benzyl)-1-isopropyl-N-phenylpiperidine-4-sulfonamide

[Step 1] Methyl 4-(((1-isopropyl-N-phenylpiperidine)-4-sulfonamido)methyl)benzoate

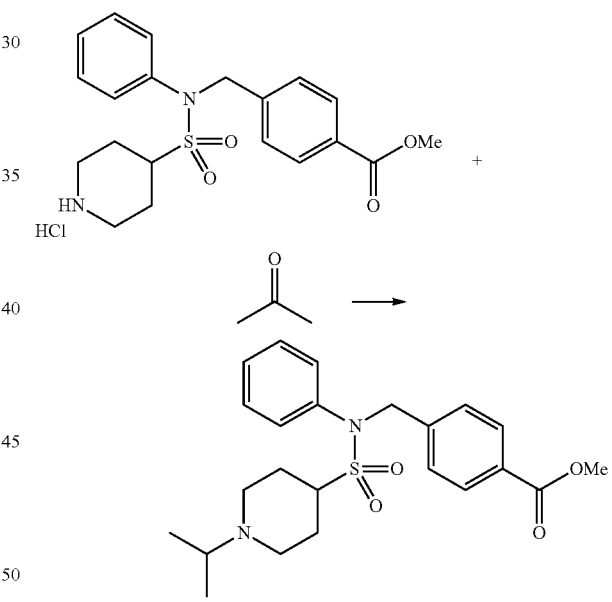

A solution of methyl 4-((N-phenylpiperidine-4-sulfonamido)methyl)benzoate hydrochloride (0.100 g, 0.235 mmol) and propan-2-one (0.021 mL, 0.282 mmol) in dichloromethane (10 mL) was mixed at the room temperature with sodium triacetoxyborohydride (0.100 g, 0.471 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give methyl 4-(((1-isopropyl-N-phenylpiperidine)-4-sulfonamido)methyl)benzoate as white solid (0.078 g, 77.0%).

543

[Step 2] N-(4-(hydrazinecarbonyl)benzyl)-1-isopropyl-N-phenylpiperidine-4-sulfonamide

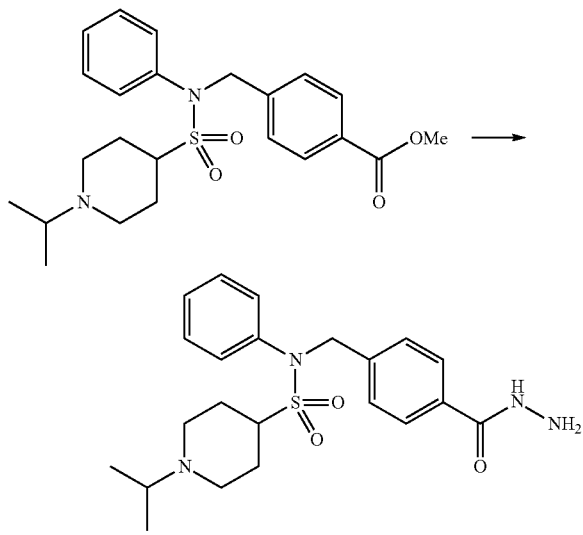

Methyl 4-(((1-isopropyl-N-phenylpiperidine)-4-sulfonamido)methyl)benzoate (0.078 g, 0.181 mmol) and hydrazine monohydrate (0.264 mL, 5.435 mmol) were mixed at the room temperature in ethanol (16 mL)/water (4 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(4-(hydrazinecarbonyl)benzyl)-1-isopropyl-N-phenylpiperidine-4-sulfonamide, 0.061 g, 78.2%, white solid).

[Step 3] Compound 11638

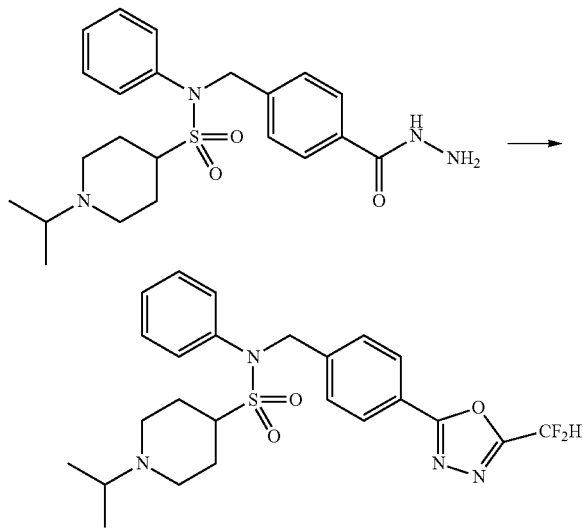

A solution of N-(4-(hydrazinecarbonyl)benzyl)-1-isopropyl-N-phenylpiperidine-4-sulfonamide (0.061 g, 0.142 mmol) and triethylamine (0.039 mL, 0.283 mmol) in tetrahydrofuran (10 mL) was mixed at the room temperature with 2,2-difluoroacetic anhydride (0.053 mL, 0.425 mmol), stirred at 80° C. for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give N-(4-(5-(difluoromethyl)-1,3,4-oxadiazol-2-yl)benzyl)-1-isopropyl-N-phenylpiperidine-4-sulfonamide as white solid (0.044 g, 63.3%).

$^1$H NMR (400 MHz, CDCl$_3$) δ 8.00 (d, 2H, J=8.2 Hz), 7.42 (d, 2H, J=8.2 Hz), 7.30-7.24 (m, 5H), 7.01 (s, 0.25H), 6.88 (s, 0.5H), 6.75 (s, 0.25H), 4.99 (s, 2H), 3.45-2.88 (m, 4H), 2.65-1.82 (m, 6H), 1.53-0.89 (m, 6H); LRMS (ES) m/z 491.3 (M$^+$+1).

EXAMPLE 176

Compound 11639, 1-cyclobutyl-N-(4-(5-(difluoromethyl)-1,3,4-oxadiazol-2-yl)benzyl)-N-phenylpiperidine-4-sulfonamide

[Step 1] methyl 4-(((1-cyclobutyl-N-phenylpiperidine)-4-sulfonamido)methyl)benzoate

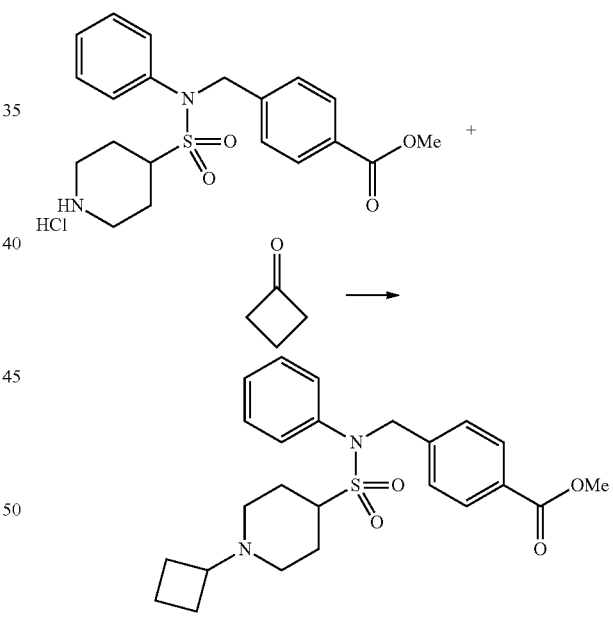

A solution of methyl 4-((N-phenylpiperidine-4-sulfonamido)methyl)benzoate hydrochloride (0.100 g, 0.235 mmol) and cyclobutanone (0.021 mL, 0.282 mmol) in dichloromethane (10 mL) was mixed at the room temperature with sodium triacetoxyborohydride (0.100 g, 0.471 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give methyl 4-(((1-cyclobutyl-N-phenylpiperidine)-4-sulfonamido)methyl)benzoate as white solid (0.084 g, 80.7%).

[Step 2] 1-cyclobutyl-N-(4-(hydrazinecarbonyl)benzyl)-N-phenylpiperidine-4-sulfonamide

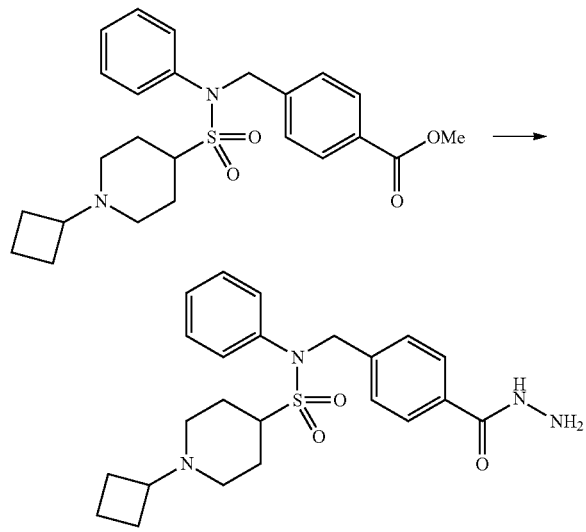

Methyl 4-(((1-cyclobutyl-N-phenylpiperidine)-4-sulfonamido)methyl)benzoate (0.084 g, 0.190 mmol) and hydrazine monohydrate (0.277 mL, 5.694 mmol) were mixed at the room temperature in ethanol (16 mL)/water (4 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (1-cyclobutyl-N-(4-(hydrazinecarbonyl)benzyl)-N-phenylpiperidine-4-sulfonamide, 0.078 g, 92.9%, white solid).

[Step 3] Compound 11639

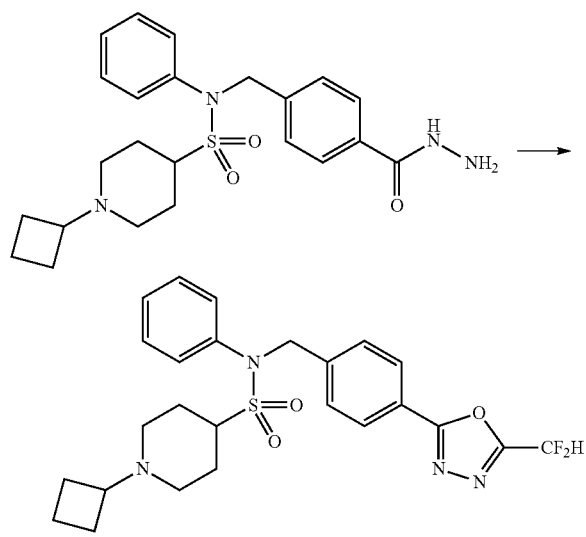

A solution of 1-cyclobutyl-N-(4-(hydrazinecarbonyl)benzyl)-N-phenylpiperidine-4-sulfonamide (0.078 g, 0.176 mmol) and triethylamine (0.049 mL, 0.352 mmol) in tetrahydrofuran (10 mL) was mixed at the room temperature with 2,2-difluoroacetic anhydride (0.066 mL, 0.529 mmol), stirred at 80° C. for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give 1-cyclobutyl-N-(4-(5-(difluoromethyl)-1,3,4-oxadiazol-2-yl)benzyl)-N-phenylpiperidine-4-sulfonamide as white solid (0.058 g, 65.5%).

$^1$H NMR (400 MHz, CDCl$_3$) δ 7.99 (d, 2H, J=8.4 Hz), 7.42 (d, 2H, J=8.4 Hz), 7.32-7.21 (m, 5H), 7.01 (s, 0.25H), 6.88 (s, 0.5H), 6.75 (s, 0.25H), 4.97 (s, 2H), 3.18-2.91 (m, 3H), 2.83-2.62 (m, 2H), 2.25-1.85 (m, 8H), 1.85-1.60 (m, 4H); LRMS (ES) m/z 503.2 (M$^+$+1).

EXAMPLE 177

Compound 11645, N-(4-(5-(difluoromethyl)-1,3,4-oxadiazol-2-yl)benzyl)-N-phenyl-2-(pyrrolidin-1-yl)ethane-1-sulfonamide

[Step 1] methyl 4-(((N-phenyl-2-(pyrrolidin-1-yl)ethyl)sulfonamido)methyl)benzoate

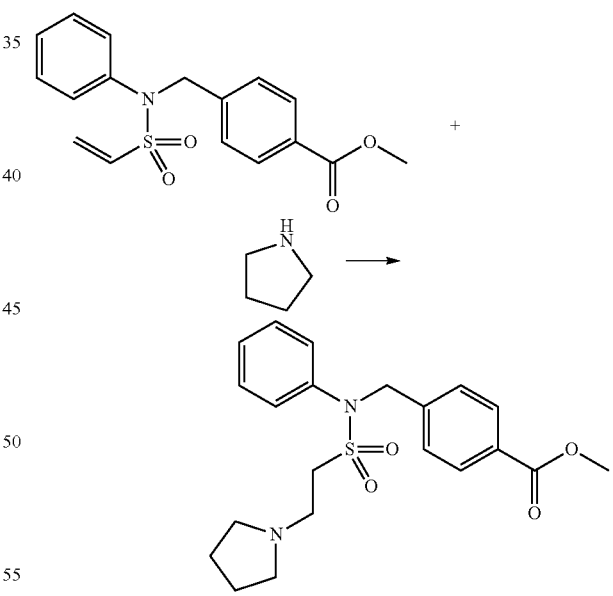

A solution of methyl 4-((N-phenylvinylsulfonamido)methyl)benzoate (0.200 g, 0.604 mmol), pyrrolidine (0.086 g, 1.207 mmol) and N,N-Diisopropylethylamine (0.126 mL, 0.724 mmol) in tetrahydrofuran (5 mL) was stirred at the room temperature for 5 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/ hexane=20% to 80%) to give methyl 4-(((N-phenyl-2-(pyrrolidin-1-yl)ethyl)sulfonamido)methyl)benzoate as white solid (0.173 g, 71.1%).

[Step 2] N-(4-(hydrazinecarbonyl)benzyl)-N-phenyl-2-(pyrrolidin-1-yl)ethane-1-sulfonamide as white solid

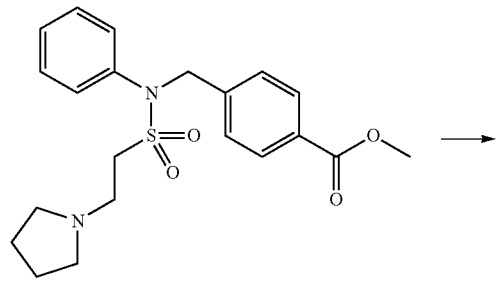

A solution of methyl 4-(((N-phenyl-2-(pyrrolidin-1-yl)ethyl)sulfonamido)methyl)benzoate (0.173 g, 0.429 mmol) and hydrazine hydrate (0.215 g, 4.288 mmol) in ethanol (10 mL) was stirred at 90° C. for 12 hr, cooled down to the room temperature to terminate the reaction and concentrated under the reduced pressure to remove the solvent. The residue was diluted with aqueous saturated sodium bicarbonate solution (10 mL) and water (5 mL) and stirred. The resulting precipitates were collected by filtration, washed by water, and dried to give N-(4-(hydrazinecarbonyl)benzyl)-N-phenyl-2-(pyrrolidin-1-yl)ethane-1-sulfonamide as white solid (0.173 g, 99.9%).

[Step 3] Compound 11645

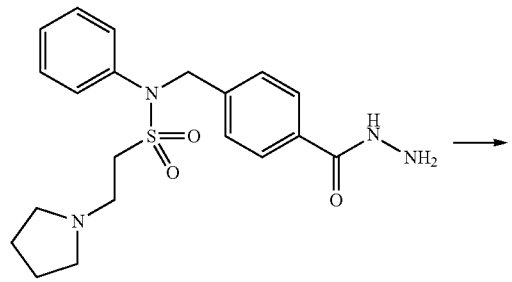

-continued

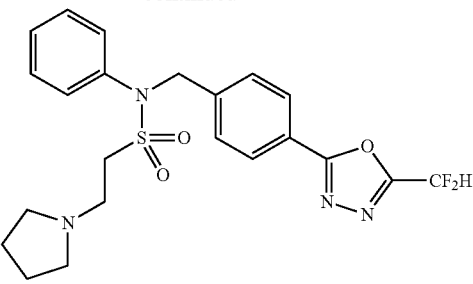

A solution of N-(4-(hydrazinecarbonyl)benzyl)-N-phenyl-2-(pyrrolidin-1-yl)ethane-1-sulfonamide (0.650 g, 1.615 mmol), triethylamine (1.125 mL, 8.074 mmol) and 2,2-difluoroacetic anhydride (0.602 mL, 4.845 mmol) in tetrahydrofuran (2 mL) was stirred at 90° C. for 0.5 hr, cooled down to the room temperature to terminate the reaction and concentrated under the reduced pressure to remove the solvent. Then, water was added to the concentrate, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 50%) to give N-(4-(5-(difluoromethyl)-1,3,4-oxadiazol-2-yl)benzyl)-N-phenyl-2-(pyrrolidin-1-yl)ethane-1-sulfonamide as white solid (0.020 g, 2.7%).

$^1$H NMR (400 MHz, CDCl$_3$) δ8.03 (d, 2H, J=8.3 Hz), 7.47 (d, 2H, J=8.2 Hz), 7.35~7.28 (m, 5H), 6.91 (t, 1H, J=51.7 Hz), 4.99 (s, 2H), 3.51 (brs, 2H), 3.15 (t, 2H, J=7.4 Hz), 2.78 (brs, 4H), 1.94 (brs, 4H); LRMS (ES) m/z 463.3 (M$^+$+1).

EXAMPLE 178

Compound 11646, N-(4-(5-(difluoromethyl)-1,3,4-oxadiazol-2-yl)benzyl)-N-phenyl-2-((3S,5R)-3,4,5-trimethylpiperazin-1-yl)ethane-1-sulfonamide

[Step 1] methyl 4-(((N-phenyl-2-((3S,5R)-3,4,5-trimethylpiperazin-1-yl)ethyl)sulfonamido)methyl)benzoate

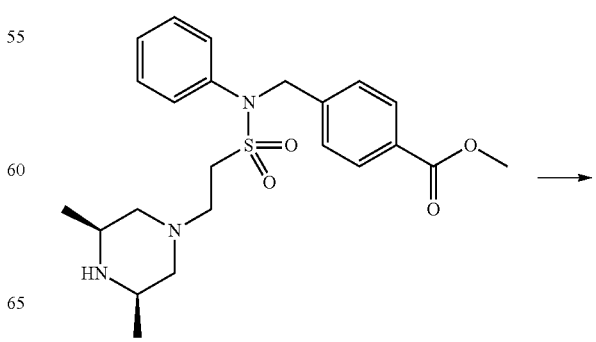

-continued

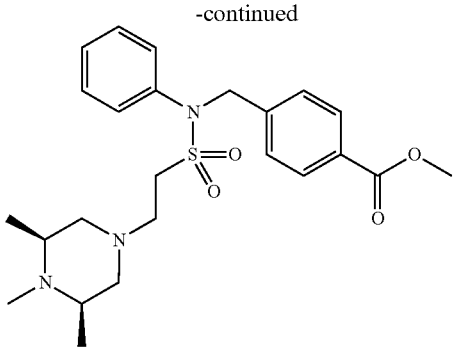

A solution of methyl 4-(((2-((3S,5R)-3,5-dimethylpiperazin-1-yl)-N-phenylethyl)sulfonamido)methyl)benzoate (0.500 g, 1.122 mmol) and formaldehyde (0.413 mL, 11.221 mmol) in acetonitrile (5 mL) was mixed at the room temperature with sodium triacetoxyborohydride (1.189 g, 5.611 mmol). The reaction mixture was stirred at the same temperature for 12 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give methyl 4-(((N-phenyl-2-((3S,5R)-3,4,5-trimethylpiperazin-1-yl)ethyl)sulfonamido)methyl)benzoate as white solid (0.309 g, 59.9%).

[Step 2] N-(4-(hydrazinecarbonyl)benzyl)-N-phenyl-2-((3S,5R)-3,4,5-trimethylpiperazin-1-yl)ethane-1-sulfonamide

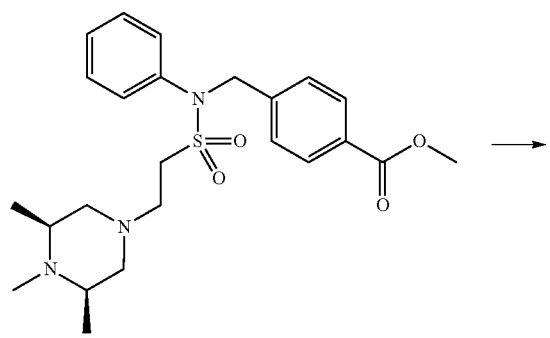

A solution of methyl 4-(((N-phenyl-2-((3S,5R)-3,4,5-trimethylpiperazin-1-yl)ethyl)sulfonamido)methyl)benzoate (0.160 g, 0.348 mmol) and hydrazine hydrate (0.174 g, 3.481 mmol) in ethanol (3 mL) was stirred at 90° C. for 18 hr, cooled down to the room temperature to terminate the reaction and concentrated under the reduced pressure to remove the solvent. The residue was diluted with sodium bicarbonate (20 mL) and water (10 mL) and stirred. The resulting precipitates were collected by filtration, washed by water, and dried to give N-(4-(hydrazinecarbonyl)benzyl)-N-phenyl-2-((3S,5R)-3,4,5-trimethylpiperazin-1-yl)ethane-1-sulfonamide as white solid (0.078 g, 48.8%).

[Step 3] Compound 11646

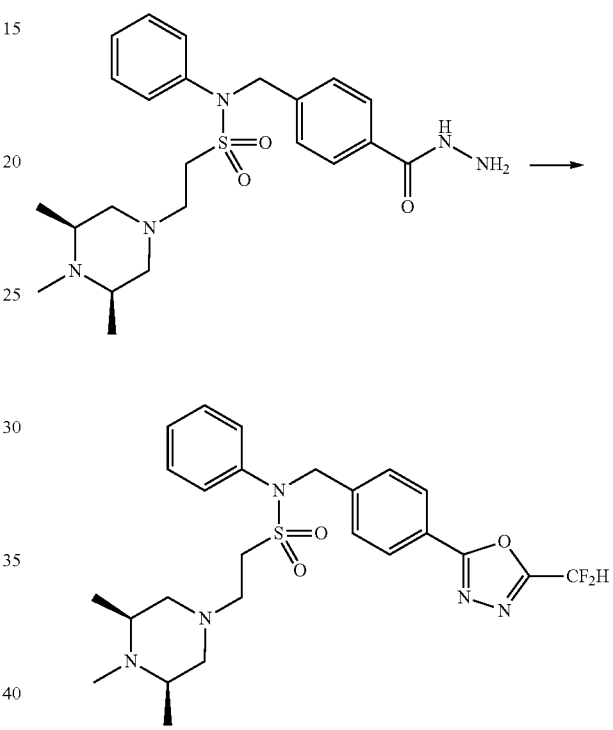

A solution of N-(4-(hydrazinecarbonyl)benzyl)-N-phenyl-2-((3S,5R)-3,4,5-trimethylpiperazin-1-yl)ethane-1-sulfonamide (0.078 g, 0.170 mmol), triethylamine (0.118 mL, 0.849 mmol) and 2,2-difluoroacetic anhydride (0.063 mL, 0.509 mmol) in tetrahydrofuran (3 mL) was stirred at 90° C. for 1 hr, cooled down to the room temperature to terminate the reaction and concentrated under the reduced pressure to remove the solvent. Then, aqueous N-sodium bicarbonate solution was added to the concentrate, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)benzyl)-N-phenyl-2-((3S,5R)-3,4,5-trimethylpiperazin-1-yl)ethane-1-sulfonamide as yellow oil (0.068 g, 76.7%).

$^1$H NMR (400 MHz, CDCl$_3$) δ8.04 (d, 2H, J=8.4 Hz), 7.47 (d, 2H, J=8.4 Hz), 7.38~7.29 (m, 5H), 6.92 (t, 1H, J=51.7 Hz), 4.97 (s, 2H), 3.32 (t, 2H, J=7.0 Hz), 3.14 (brs, 2H), 3.06 (t, 2H, J=7.0 Hz), 2.88~2.85 (m, 4H), 2.80 (s, 3H), 1.47 (d, 6H, J=5.8 Hz); LRMS (ES) m/z 520.3 (M$^+$+1).

EXAMPLE 179

Compound 11647, N-(4-(5-(difluoromethyl)-1,3,4-oxadiazol-2-yl)benzyl)-N-phenyl-3-(pyrrolidin-1-yl)propane-1-sulfonamide

[Step 1] 3-chloro-N-phenylpropane-1-sulfonamide

A solution of aniline (1.961 mL, 21.475 mmol), 3-chloropropane-1-sulfonyl chloride (2.865 mL, 23.623 mmol) and pyridine (3.460 mL, 42.951 mmol) in dichloromethane (5 mL) was stirred at the room temperature for 18 hr. Then, aqueous N-hydrochloric acid solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 30%) to give 3-chloro-N-phenylpropane-1-sulfonamide as yellow oil (3.160 g, 63.0%).

[Step 2] methyl 4-(((3-chloro-N-phenylpropyl)sulfonamido)methyl)benzoate

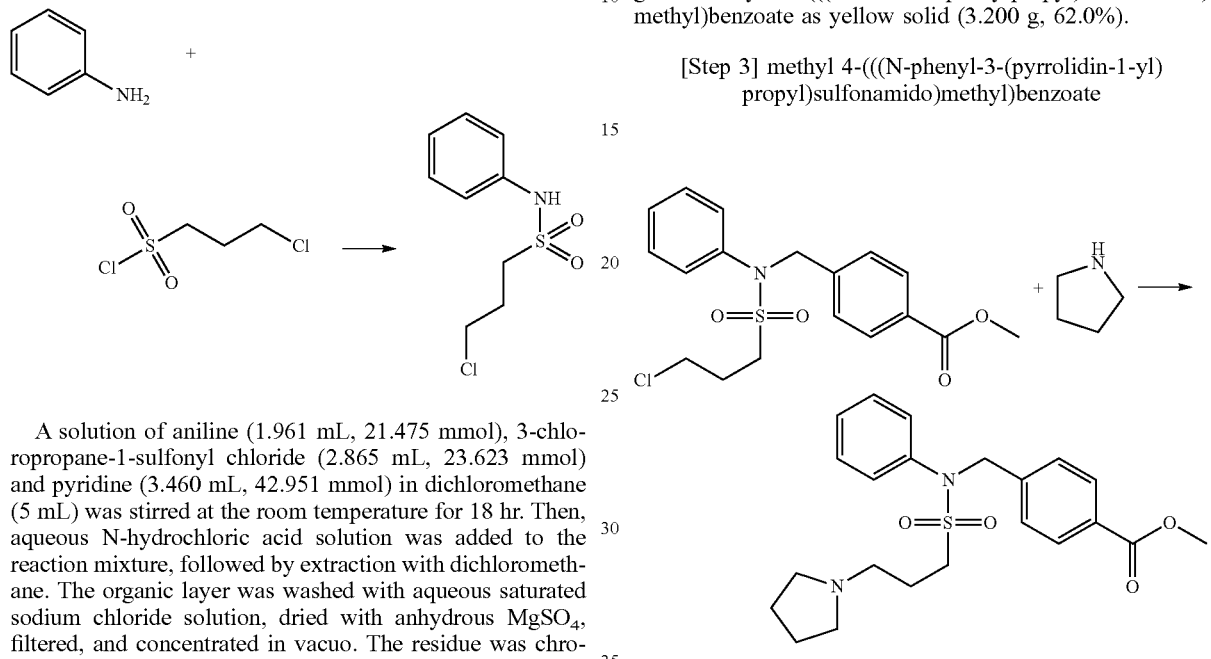

A solution of 3-chloro-N-phenylpropane-1-sulfonamide (3.160 g, 13.521 mmol), methyl 4-(bromomethyl)benzoate (3.407 g, 14.873 mmol), potassium iodide (1.122 g, 6.761 mmol) and potassium carbonate (2.803 g, 20.282 mmol) in N,N-dimethylformide (20 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 80 g cartridge; ethyl acetate/hexane=0% to 50%) to give methyl 4-(((3-chloro-N-phenylpropyl)sulfonamido)methyl)benzoate as yellow solid (3.200 g, 62.0%).

[Step 3] methyl 4-(((N-phenyl-3-(pyrrolidin-1-yl)propyl)sulfonamido)methyl)benzoate

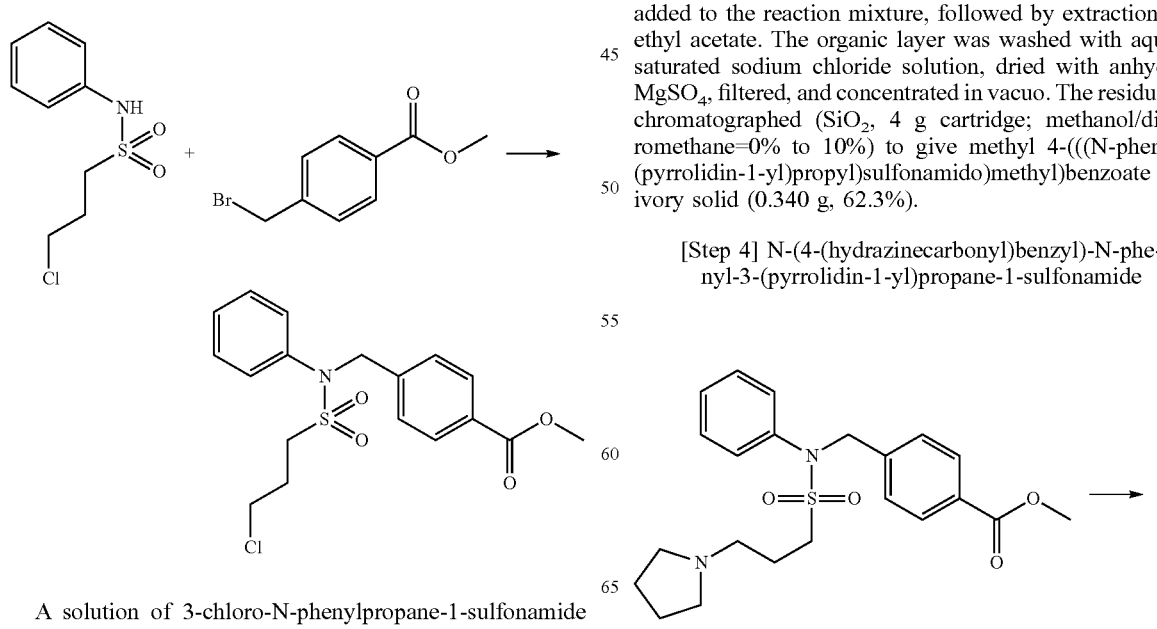

A solution of methyl 4-(((3-chloro-N-phenylpropyl)sulfonamido)methyl)benzoate (0.500 g, 1.309 mmol), pyrrolidine (0.186 g, 2.619 mmol) and N,N-Diisopropylethylamine (0.274 mL, 1.571 mmol) in tetrahydrofuran (5 mL) was stirred at the room temperature for 18 hr and then for additional 2 hr at 90° C., and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 10%) to give methyl 4-(((N-phenyl-3-(pyrrolidin-1-yl)propyl)sulfonamido)methyl)benzoate as ivory solid (0.340 g, 62.3%).

[Step 4] N-(4-(hydrazinecarbonyl)benzyl)-N-phenyl-3-(pyrrolidin-1-yl)propane-1-sulfonamide

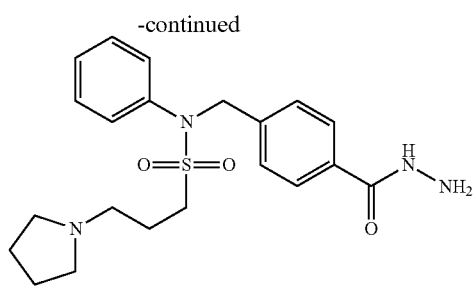

A solution of methyl 4-(((N-phenyl-3-(pyrrolidin-1-yl)propyl)sulfonamido)methyl)benzoate (0.200 g, 0.480 mmol) and hydrazine hydrate (0.240 g, 4.801 mmol) in ethanol (3 mL) was stirred at 90° C. for 18 hr, cooled down to the room temperature to terminate the reaction and concentrated under the reduced pressure to remove the solvent. The residue was diluted with sodium bicarbonate (20 mL) and water (10 mL) and stirred. The resulting precipitates were collected by filtration, washed by water, and dried to give N-(4-(hydrazinecarbonyl)benzyl)-N-phenyl-3-(pyrrolidin-1-yl)propane-1-sulfonamide as white solid (0.181 g, 90.5%).

[Step 5] Compound 11647

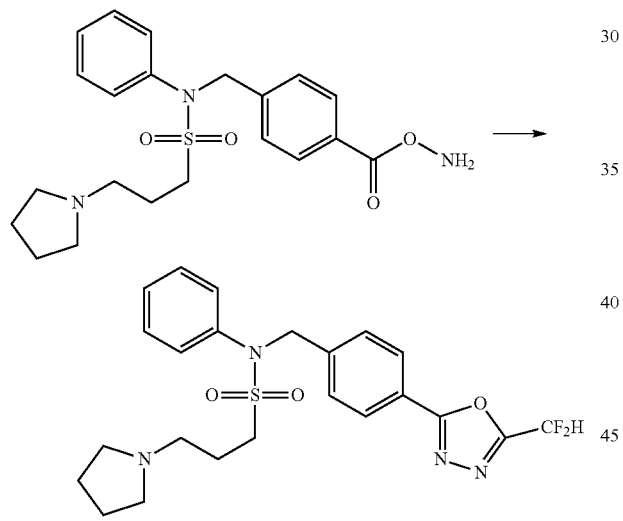

A solution of N-(4-(hydrazinecarbonyl)benzyl)-N-phenyl-3-(pyrrolidin-1-yl)propane-1-sulfonamide (0.092 g, 0.221 mmol), triethylamine (0.154 mL, 1.104 mmol) and 2,2-difluoroacetic anhydride (0.082 mL, 0.663 mmol) in tetrahydrofuran (3 mL) was stirred at 90° C. for 1 hr, cooled down to the room temperature to terminate the reaction and concentrated under the reduced pressure to remove the solvent. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)benzyl)-N-phenyl-3-(pyrrolidin-1-yl)propane-1-sulfonamide as yellow oil (0.071 g, 67.3%).

$^1$H NMR (400 MHz, CDCl$_3$) δ8.01 (d, 2H, J=8.5 Hz), 7.45 (d, 2H, J=8.6 Hz), 7.36~7.25 (m, 5H), 6.91 (t, 1H, J=51.7 Hz), 4.98 (s, 2H), 3.80~3.79 (m, 2H), 3.33~3.26 (m, 4H), 2.80×2.79 (m, 2H), 2.42×2.35 (m, 2H), 2.10×2.05 (m, 4H); LRMS (ES) m/z 447.1 (M$^+$+1).

EXAMPLE 180

Compound 11648, N-(4-(5-(difluoromethyl)-1,3,4-oxadiazol-2-yl)benzyl)-3-(4-(methylsulfonyl)piperazin-1-yl)-N-phenylpropane-1-sulfonamide

[Step 1] tert-butyl 4-(3-(N-(4-(methoxycarbonyl)benzyl)-N-phenylsulfamoyl)propyl)piperazine-1-carboxylate

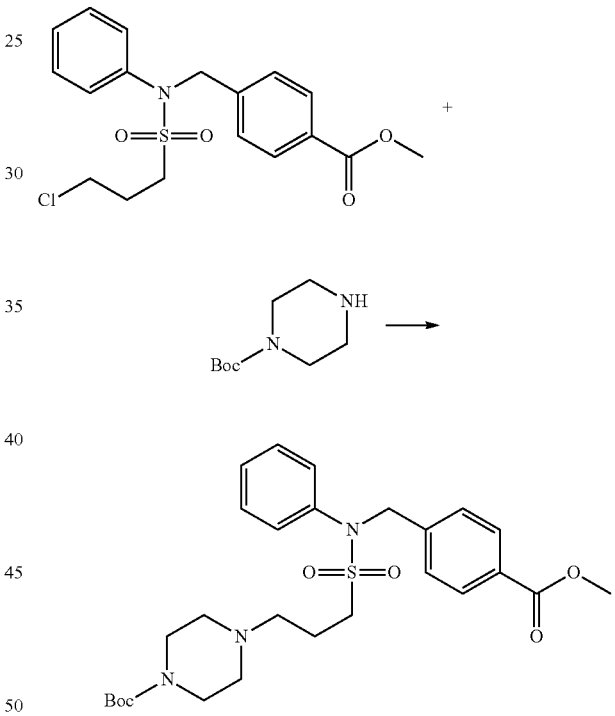

A solution of methyl 4-(((3-chloro-N-phenylpropyl)sulfonamido)methyl)benzoate (0.978 g, 2.561 mmol), tert-butyl piperazine-1-carboxylate (0.954 g, 5.122 mmol) and potassium carbonate (0.531 g, 3.842 mmol) in N,N-dimethylformide (5 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give tert-butyl 4-(3-(N-(4-(methoxycarbonyl)benzyl)-N-phenylsulfamoyl)propyl)piperazine-1-carboxylate as white solid (1.190 g, 87.4%).

555

[Step 2] methyl 4-(((N-phenyl-3-(piperazin-1-yl)propyl)sulfonamido)methyl)benzoate hydrochloride

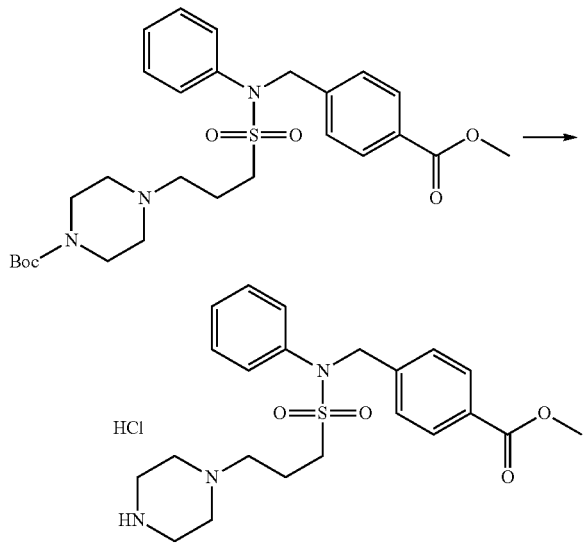

A solution of tert-butyl 4-(3-(N-(4-(methoxycarbonyl)benzyl)-N-phenylsulfamoyl)propyl)piperazine-1-carboxylate (1.190 g, 2.238 mmol) and hydrochloric acid (4.00 M solution, 2.798 mL, 11.191 mmol) in 1,4-dioxane (5 mL) was stirred at the room temperature for 2 hr, and concentrated under the reduced pressure to remove the solvent. The residue was diluted with diethylether (20 mL) and stirred. The resulting precipitates were collected by filtration, washed by diethylether, and dried to give methyl 4-(((N-phenyl-3-(piperazin-1-yl)propyl)sulfonamido)methyl)benzoate hydrochloride as white solid (0.932 g, 89.0%).

[Step 3] methyl 4-(((3-(4-(methylsulfonyl)piperazin-1-yl)-N-phenylpropyl)sulfonamido)methyl)benzoate

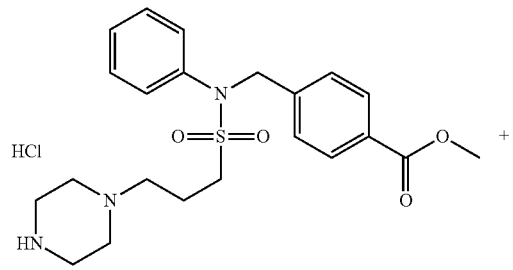
+
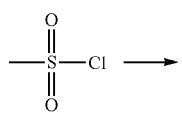

556

-continued

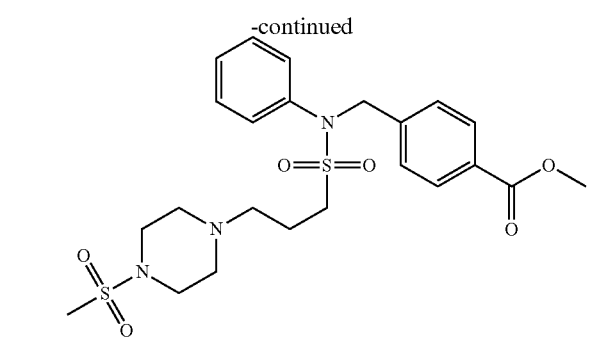

A solution of methyl 4-(((N-phenyl-3-(piperazin-1-yl)propyl)sulfonamido)methyl)benzoate hydrochloride (0.300 g, 0.641 mmol), methanesulfonyl chloride (0.074 mL, 0.962 mmol) and triethylamine (0.268 mL, 1.923 mmol) in dichloromethane (2 mL) was stirred at the room temperature for 3 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 4-(((3-(4-(methylsulfonyl)piperazin-1-yl)-N-phenylpropyl)sulfonamido)methyl)benzoate as white solid (0.131 g, 40.2%).

[Step 4] N-(4-(hydrazinecarbonyl)benzyl)-3-(4-(methylsulfonyl)piperazin-1-yl)-N-phenylpropane-1-sulfonamide

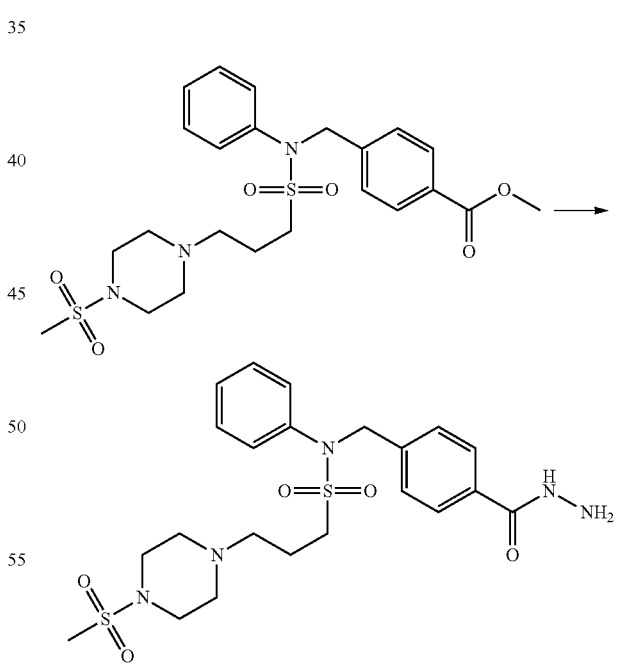

A solution of methyl 4-(((3-(4-(methylsulfonyl)piperazin-1-yl)-N-phenylpropyl)sulfonamido)methyl)benzoate (0.131 g, 0.257 mmol) and hydrazine hydrate (0.129 g, 2.57 mmol) in ethanol (3 mL) was stirred at 90° C. for 18 hr, cooled down to the room temperature to terminate the reaction and concentrated under the reduced pressure to remove the solvent. The residue was diluted with sodium bicarbonate (20 mL) and water (10 mL), and stirred. The resulting precipitates were collected by filtration, washed by water, and dried to give N-(4-(hydrazinecarbonyl)benzyl)-3-(4-(methylsulfonyl)piperazin-1-yl)-N-phenylpropane-1-sulfonamide as white solid (0.056 g, 42.7%).

[Step 5] Compound 11648

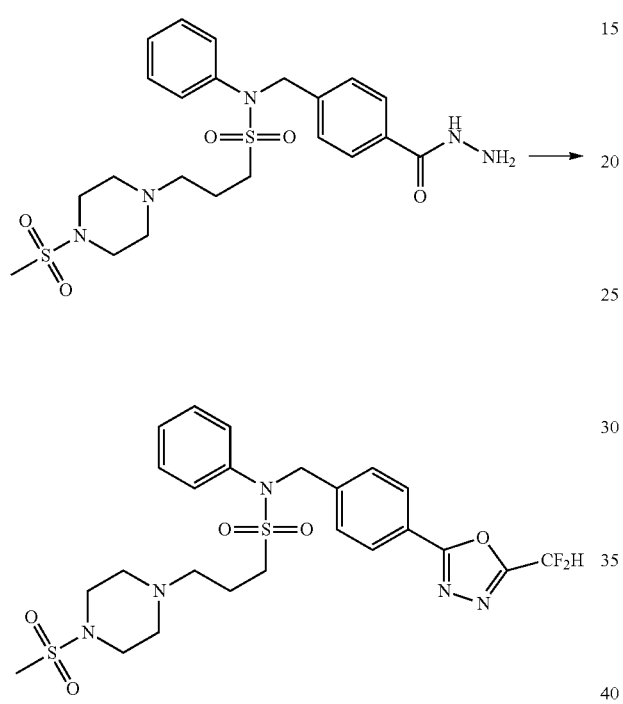

A solution of N-(4-(hydrazinecarbonyl)benzyl)-3-(4-(methylsulfonyl)piperazin-1-yl)-N-phenylpropane-1-sulfonamide (0.056 g, 0.110 mmol), triethylamine (0.077 mL, 0.549 mmol) and 2,2-difluoroacetic anhydride (0.041 mL, 0.330 mmol) in tetrahydrofuran (3 mL) was stirred at 90° C. for 1 hr, cooled down to the room temperature to terminate the reaction and concentrated under the reduced pressure to remove the solvent. Then, aqueous N-sodium bicarbonate solution was added to the concentrate, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)benzyl)-3-(4-(methylsulfonyl)piperazin-1-yl)-N-phenylpropane-1-sulfonamide as white solid (0.059 g, 93.6%).

$^1$H NMR (400 MHz, CDCl$_3$) δ8.02 (d, 2H, J=8.4 Hz), 7.44 (d, 2H, J=8.5 Hz), 7.35~7.27 (m, 5H), 6.92 (t, 1H, J=51.7 Hz), 4.96 (s, 2H), 3.59 (brs, 4H), 3.26 (t, 2H, J=7.1 Hz), 3.22~3.12 (m, 6H), 2.87 (s, 3H), 2.37~2.30 (m, 2H); LRMS (ES) m/z 570.3 (M$^+$+1).

EXAMPLE 181

Compound 11655, N-(4-(5-(difluoromethyl)-1,3,4-oxadiazol-2-yl)benzyl)-2-morpholino-N-phenylethanesulfonamide

[Step 1] methyl 4-((2-morpholino-N-phenylethylsulfonamido)methyl)benzoate

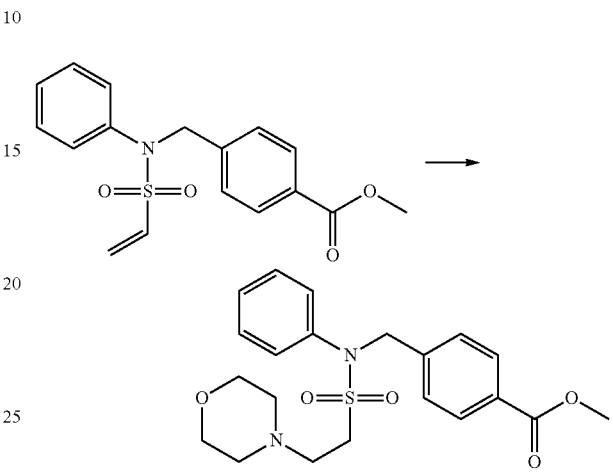

A solution of methyl 4-((N-phenylvinylsulfonamido)methyl)benzoate (0.300 g, 0.905 mmol), morpholine (0.078 mL, 0.905 mmol) and N,N-Diisopropylethylamine (0.312 mL, 1.811 mmol) in dichloromethane (10 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give methyl 4-((2-morpholino-N-phenylethylsulfonamido)methyl)benzoate as white solid (0.250 g, 66.0%).

[Step 2] N-(4-(hydrazinecarbonyl)benzyl)-2-morpholino-N-phenylethanesulfonamide

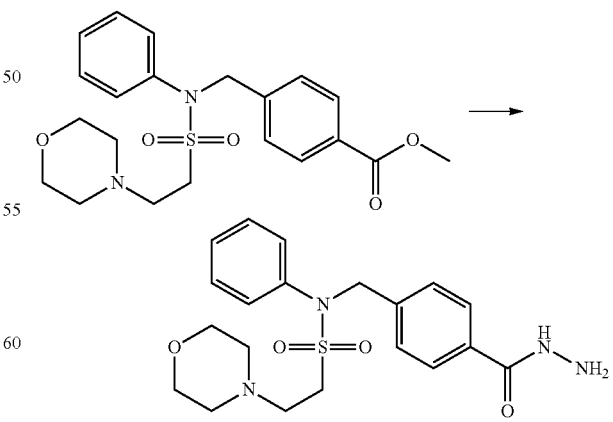

A solution of methyl 4-((2-morpholino-N-phenylethylsulfonamido)methyl)benzoate (0.250 g, 0.597 mmol) and hydrazine (0.375 mL, 11.947 mmol) in ethanol (10 mL) was stirred at 80° C. for 6 hr, cooled down to the room temperature to terminate the reaction and concentrated under the reduced pressure to remove the solvent. The concentrate was crystallized at the room temperature using water (10 mL). The resulting precipitates were filtered and dried to give N-(4-(hydrazinecarbonyl)benzyl)-2-morpholino-N-phenylethanesulfonamide as white solid (0.180 g, 72.0%).

[Step 3] Compound 11655

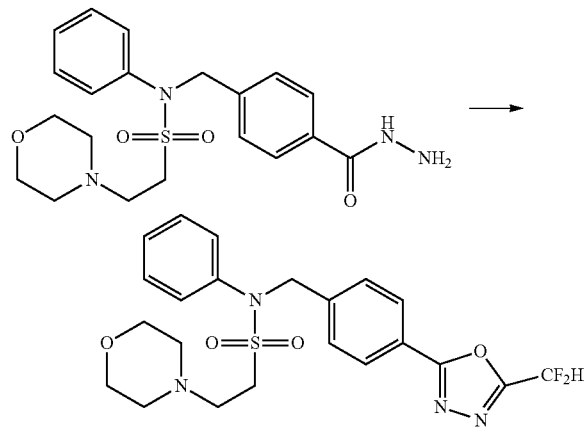

A mixture of N-(4-(hydrazinecarbonyl)benzyl)-2-morpholino-N-phenylethanesulfonamide (0.180 g, 0.430 mmol), 2,2-difluoroacetic anhydride (0.160 mL, 1.290 mmol) and triethylamine (0.300 mL, 2.150 mmol) in tetrahydrofuran (10 mL) prepared at the room temperature was heated at reflux for 12 hr, and cooled down to the ambient temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)benzyl)-2-morpholino-N-phenylethanesulfonamide as white solid (0.179 g, 87.0%).

$^1$H NMR (400 MHz, CDCl$_3$) δ 7.99 (d, 2H, J=8.3 Hz), 7.54-7.52 (m, 2H), 7.45-7.33 (m, 4H), 7.26 (t, 1H, J=7.3 Hz), 6.21 (t, 1H, J=53.5 Hz), 5.04 (s, 2H), 3.64-3.61 (m, 4H), 3.53-3.49 (m, 2H), 2.89-2.85 (m, 2H), 2.60-2.56 (m, 4H); LRMS (ES) m/z 479.0 (M$^+$+1).

EXAMPLE 182

Compound 11656, 3-(4-acetylpiperazin-1-yl)-N-(4-(5-(difluoromethyl)-1,3,4-oxadiazol-2-yl)benzyl)-N-phenylpropane-1-sulfonamide

[Step 1] methyl 4-(((3-(4-acetylpiperazin-1-yl)-N-phenylpropyl)sulfonamido)methyl)benzoate

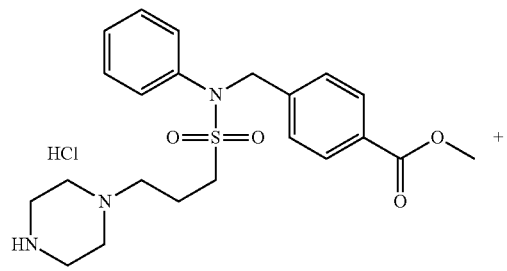

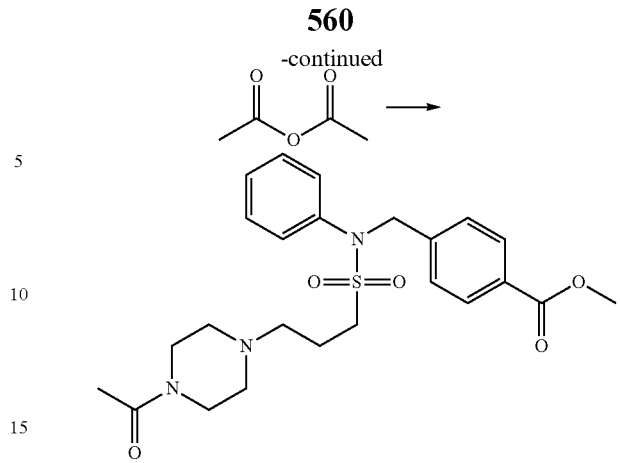

A solution of methyl 4-(((N-phenyl-3-(piperazin-1-yl)propyl)sulfonamido)methyl)benzoate hydrochloride (0.300 g, 0.641 mmol), acetic anhydride (0.091 mL, 0.962 mmol) and triethylamine (0.268 mL, 1.923 mmol) in dichloromethane (2 mL) was stirred at the room temperature for 3 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 4-(((3-(4-acetylpiperazin-1-yl)-N-phenylpropyl)sulfonamido)methyl)benzoate as colorless oil (0.201 g, 66.2%).

[Step 2] 3-(4-acetylpiperazin-1-yl)-N-(4-(hydrazinecarbonyl)benzyl)-N-phenylpropane-1-sulfonamide

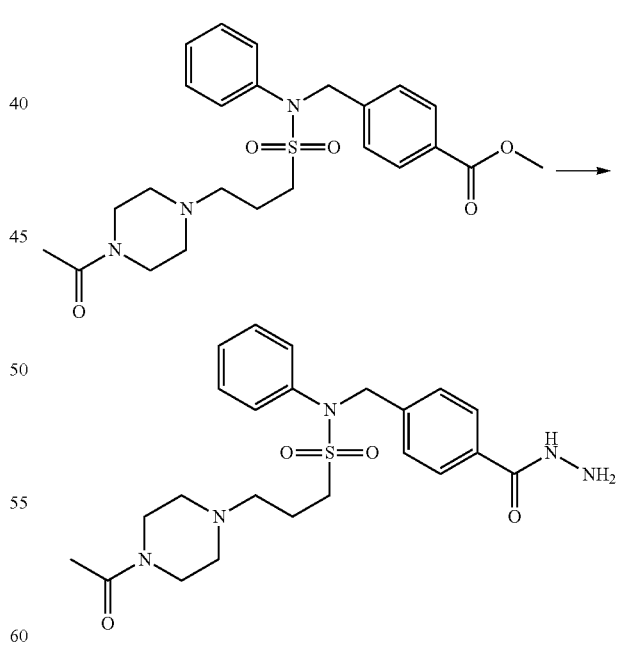

A solution methyl 4-(((3-(4-acetylpiperazin-1-yl)-N-phenylpropyl)sulfonamido)methyl)benzoate (0.118 g, 0.249 mmol) and hydrazine hydrate (0.116 g, 2.315 mmol) in ethanol (3 ml) were stirred at 90° C. for 18 hr, cooled down to the room temperature to terminate the reaction and concentrated under the reduced pressure to remove the solvent. The concentrate was diluted aqueous N-sodium bicarbonate solution (20 ml) and water (10 ml), and stirred. The resulting precipitates were collected by filtration and dried to give 3-(4-acetylpiperazin-1-yl)-N-(4-(hydrazinecarbonyl)benzyl)-N-phenylpropane-1-sulfonamide as white solid (0.078 g, 71.1%).

[Step 3] Compound 11656

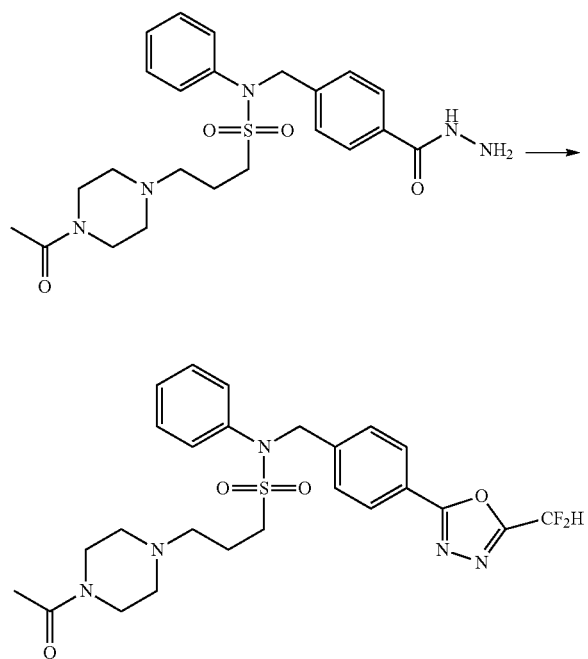

A solution of 3-(4-acetylpiperazin-1-yl)-N-(4-(hydrazinecarbonyl)benzyl)-N-phenylpropane-1-sulfonamide (0.118 g, 0.249 mmol), triethylamine (0.174 mL, 1.246 mmol) and 2,2-difluoroacetic anhydride (0.093 mL, 0.747 mmol) in tetrahydrofuran (3 mL) was stirred at 90° C. for 1 hr, cooled down to the room temperature to terminate the reaction and concentrated under the reduced pressure to remove the solvent. Then, aqueous N-sodium bicarbonate solution was added to the concentrate, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give 3-(4-acetylpiperazin-1-yl)-N-(4-(5-(difluoromethyl)-1,3,4-oxadiazol-2-yl)benzyl)-N-phenylpropane-1-sulfonamide as yellow solid (0.020 g, 15.2%).

$^1$H NMR (400 MHz, CDCl$_3$) δ8.04 (d, 2H, J=8.2 Hz), 7.48 (d, 2H, J=8.1 Hz), 7.38~7.28 (m, 5H), 6.92 (t, 1H, J=51.8 Hz), 5.00 (s, 2H), 3.73~7.64 (m, 4H), 3.29 (m, 2H), 2.81~2.60 (m, 6H), 2.28~2.24 (m, 2H), 2.12 (s, 3H); LRMS (ES) m/z 534.2 (M$^+$+1).

EXAMPLE 183

Compound 11657, N-(4-(5-(difluoromethyl)-1,3,4-oxadiazol-2-yl)benzyl)-N-phenyl-3-(piperidin-1-yl)propane-1-sulfonamide

[Step 1] methyl 4-(((N-phenyl-3-(piperidin-1-yl)propyl)sulfonamido)methyl)benzoate

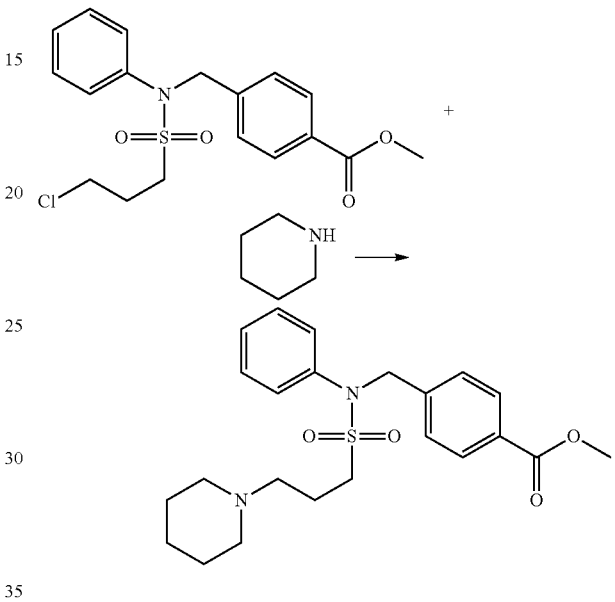

A solution of methyl 4-(((3-chloro-N-phenylpropyl)sulfonamido)methyl)benzoate (0.500 g, 1.309 mmol), piperidine (0.259 mL, 2.619 mmol) and potassium carbonate (0.271 g, 1.964 mmol) in N,N-dimethylformide (3 mL) was stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 10%) to give methyl 4-(((N-phenyl-3-(piperidin-1-yl)propyl)sulfonamido)methyl)benzoate as white solid (0.127 g, 22.5%).

[Step 2] N-(4-(hydrazinecarbonyl)benzyl)-N-phenyl-3-(piperidin-1-yl)propane-1-sulfonamide

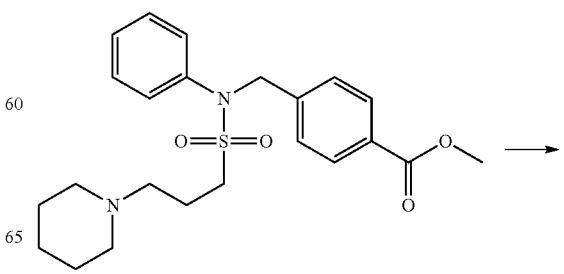

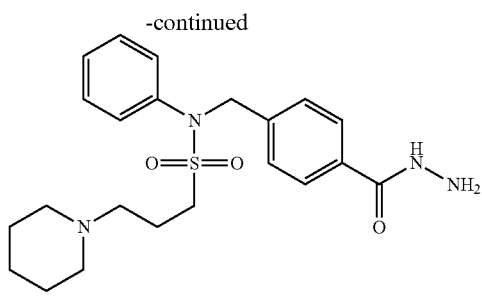

A solution of methyl 4-(((N-phenyl-3-(piperidin-1-yl)propyl)sulfonamido)methyl)benzoate (0.127 g, 0.295 mmol) and hydrazine hydrate (0.148 g, 2.950 mmol) in ethanol (3 mL) was stirred at 90° C. for 18 hr, cooled down to the room temperature to terminate the reaction and concentrated under the reduced pressure to remove the solvent. The residue was diluted with sodium bicarbonate (20 mL) and water (10 mL) and stirred. The resulting precipitates were collected by filtration, washed by water, and dried to give N-(4-(hydrazinecarbonyl)benzyl)-N-phenyl-3-(piperidin-1-yl)propane-1-sulfonamide as white solid (0.123 g, 96.8%).

[Step 3] Compound 11657

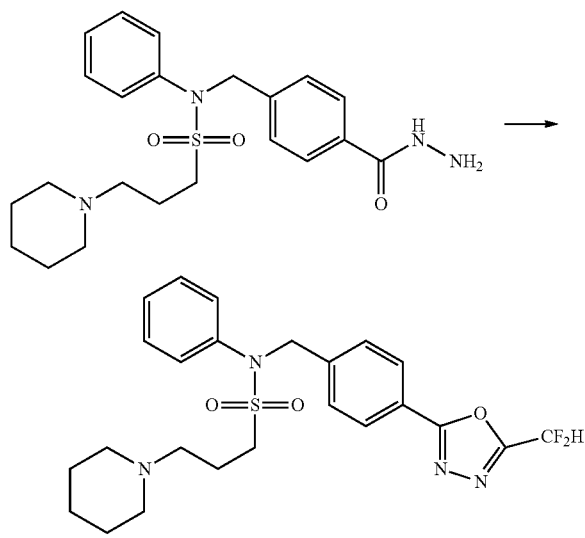

A solution of N-(4-(hydrazinecarbonyl)benzyl)-N-phenyl-3-(piperidin-1-yl)propane-1-sulfonamide (0.123 g, 0.286 mmol), triethylamine (0.198 mL, 1.43 mmol) and 2,2-difluoroacetic anhydride (0.107 mL, 0.858 mmol) in tetrahydrofuran (3 mL) was stirred at 90° C. for 1 hr, cooled down to the room temperature to terminate the reaction and concentrated under the reduced pressure to remove the solvent. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)benzyl)-N-phenyl-3-(piperidin-1-yl)propane-1-sulfonamide as yellow oil (0.081 g, 58.0%).

$^1$H NMR (400 MHz, CDCl$_3$) δ8.03 (d, 2H, J=8.4 Hz), 7.47 (d, 2H, J=8.4 Hz), 7.36~7.26 (m, 5H), 6.91 (t, 1H, J=51.7 Hz), 4.99 (s, 2H), 3.24~3.17 (m, 2H), 2.64~2.59 (m, 6H), 2.21~2.15 (m, 2H), 1.70~1.69 (m, 4H), 1.51-1.36 (m, 2H); LRMS (ES) m/z 491.3 (M$^+$+1).

EXAMPLE 184

Compound 11658, N-(4-(5-(difluoromethyl)-1,3,4-oxadiazol-2-yl)benzyl)-3-(4-methylpiperazin-1-yl)-N-phenylpropane-1-sulfonamide

[Step 1] methyl 4-(((3-(4-methylpiperazin-1-yl)-N-phenylpropyl)sulfonamido)methyl)benzoate

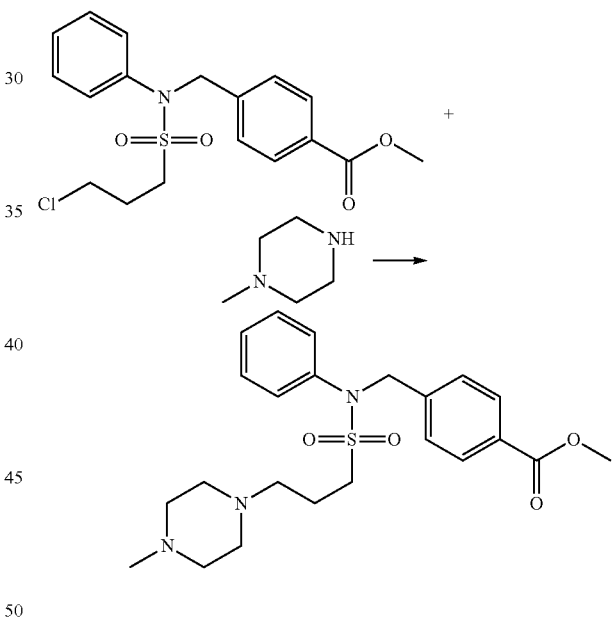

A solution of methyl 4-(((3-chloro-N-phenylpropyl)sulfonamido)methyl)benzoate (0.500 g, 1.309 mmol), 1-methylpiperazine (0.291 mL, 2.619 mmol) and potassium carbonate (0.271 g, 1.964 mmol) in N,N-dimethylformide (3 mL) was stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 10%) to give methyl 4-(((3-(4-methylpiperazin-1-yl)-N-phenylpropyl)sulfonamido)methyl)benzoate as white solid (0.464 g, 79.6%).

[Step 2] N-(4-(hydrazinecarbonyl)benzyl)-3-(4-methylpiperazin-1-yl)-N-phenylpropane-1-sulfonamide

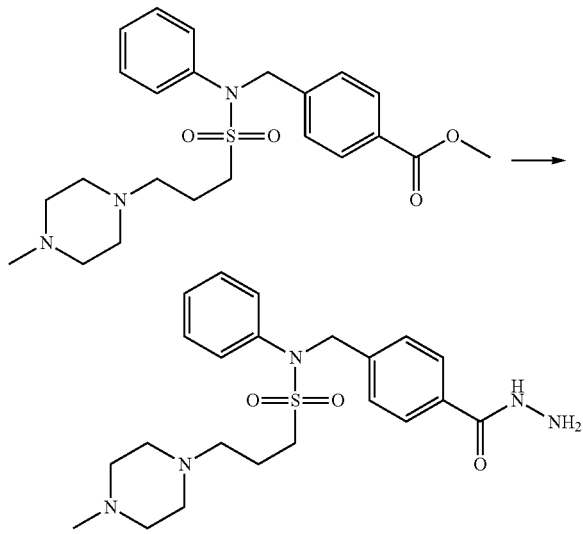

A solution of methyl 4-(((3-(4-methylpiperazin-1-yl)-N-phenylpropyl)sulfonamido)methyl)benzoate (0.200 g, 0.449 mmol) and hydrazine hydrate (0.225 g, 4.489 mmol) in ethanol (3 mL) was stirred at 90° C. for 18 hr, cooled down to the room temperature to terminate the reaction and concentrated under the reduced pressure to remove the solvent. The residue was diluted with sodium bicarbonate (20 mL) and water (10 mL) and stirred. The resulting precipitates were collected by filtration, washed by water, and dried to give N-(4-(hydrazinecarbonyl)benzyl)-3-(4-methylpiperazin-1-yl)-N-phenylpropane-1-sulfonamide as white solid (0.116 g, 58.0%).

[Step 3] Compound 11658

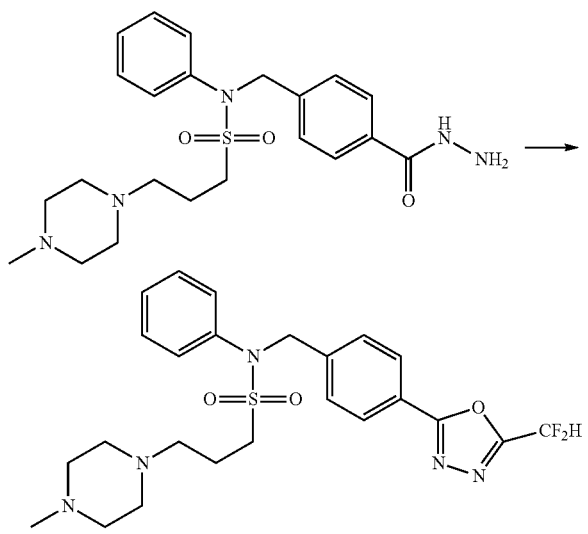

A solution of N-(4-(hydrazinecarbonyl)benzyl)-3-(4-methylpiperazin-1-yl)-N-phenylpropane-1-sulfonamide (0.116 g, 0.260 mmol), triethylamine (0.181 mL, 1.302 mmol) and 2,2-difluoroacetic anhydride (0.097 mL, 0.781 mmol) in tetrahydrofuran (3 mL) was stirred at 90° C. for 1 hr, cooled down to the room temperature to terminate the reaction and concentrated under the reduced pressure to remove the solvent. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)benzyl)-3-(4-methylpiperazin-1-yl)-N-phenylpropane-1-sulfonamide as yellow oil (0.068 g, 51.6%).

$^1$H NMR (400 MHz, CDCl$_3$) δ8.04 (d, 2H, J=8.3 Hz), 7.47 (d, 2H, J=8.3 Hz), 7.37~7.27 (m, 5H), 6.91 (t, 1H, J=51.7 Hz), 4.98 (s, 2H), 3.20~3.13 (m, 2H), 2.61~2.54 (m, 8H), 2.54~2.49 (m, 2H), 2.44 (s, 3H), 2.09~2.03 (m, 2H); LRMS (ES) m/z 506.4 (M$^+$+1).

EXAMPLE 185

Compound 11663, 2-(4-benzylpiperazin-1-yl)-N-(4-(5-(difluoromethyl)-1,3,4-oxadiazol-2-yl)benzyl)-N-phenylethanesulfonamide

[Step 1] methyl 4-((2-(4-benzylpiperazin-1-yl)-N-phenylethylsulfonamido)methyl)benzoate

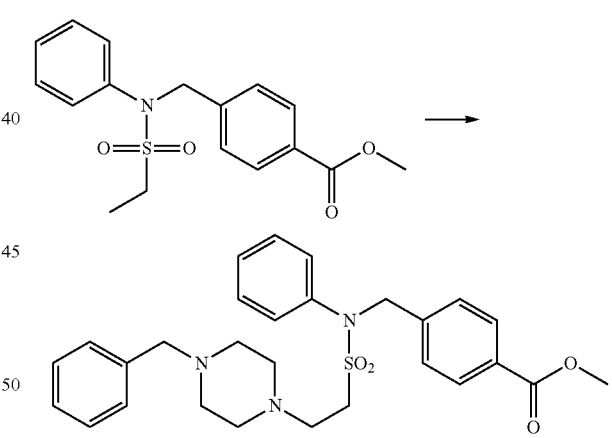

A solution of methyl 4-((N-phenylvinylsulfonamido)methyl)benzoate (0.500 g, 1.509 mmol), 1-benzylpiperazine (0.258 mL, 1.509 mmol) and N,N-Diisopropylethylamine (0.520 mL, 3.018 mmol) in dichloromethane (10 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give methyl 4-((2-(4-benzylpiperazin-1-yl)-N-phenylethylsulfonamido)methyl)benzoate as white solid (0.430 g, 56.1%).

567

[Step 2] 2-(4-benzylpiperazin-1-yl)-N-(4-(hydrazinecarbonyl)benzyl)-N-phenylethanesulfonamide

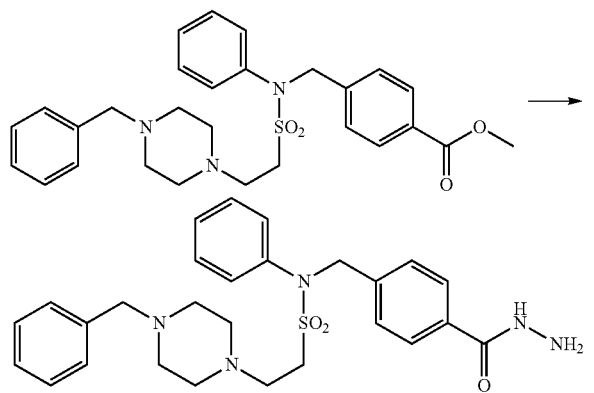

A solution of methyl 4-((2-(4-benzylpiperazin-1-yl)-N-phenylethylsulfonamido)methyl)benzoate (0.200 g, 0.394 mmol) and hydrazine (0.247 mL, 7.880 mmol) in ethanol (10 mL) was stirred at 80° C. for 6 hr, cooled down to the room temperature to terminate the reaction and concentrated under the reduced pressure to remove the solvent. The crude product was crystallized at the room temperature using water (20 mL). The resulting precipitates were filtered and dried to give 2-(4-benzylpiperazin-1-yl)-N-(4-(hydrazinecarbonyl)benzyl)-N-phenylethanesulfonamide as white solid (0.160 g, 80.0%).

[Step 3] compound 11663

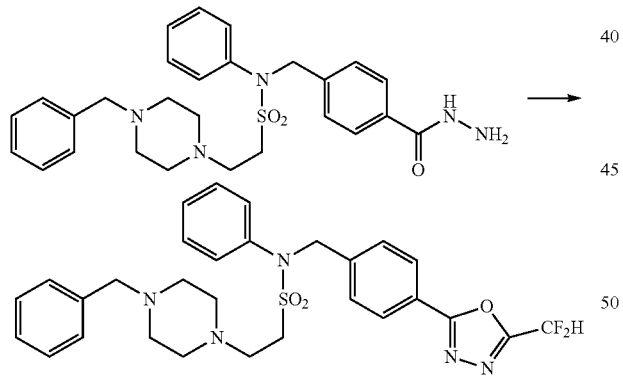

A mixture of 2-(4-benzylpiperazin-1-yl)-N-(4-(hydrazinecarbonyl)benzyl)-N-phenylethanesulfonamide (0.160 g, 0.315 mmol), 2,2-Difluoroacetic anhydride (0.118 mL, 0.946 mmol) and triethylamine (0.220 mL, 1.576 mmol) in tetrahydrofuran (10 mL) prepared at the room temperature was heated at reflux for 12 hr, and cooled down to the ambient temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to

568

5%) to give 2-(4-benzylpiperazin-1-yl)-N-(4-(5-(difluoromethyl)-1,3,4-oxadiazol-2-yl)benzyl)-N-phenylethanesulfonamide as white solid (0.060 g, 33.5%).

$^1$H NMR (400 MHz, DMSO-d6) δ7.98 (d, 2H, J=8.3 Hz), 7.52 (d, 2H, J=8.4 Hz), 7.41-7.24 (m, 11H), 5.03 (s, 2H), 3.91-3.88 (m, 2H), 3.49 (t, 2H, J=7.0 Hz), 2.88-2.65 (m, 6H); LRMS (ES) m/z 568.1 (M$^+$+1).

EXAMPLE 186

Compound 11665, N-(4-(5-(difluoromethyl)-1,3,4-oxadiazol-2-yl)benzyl)-N-phenyl-3-((3R,5S)-3,4,5-trimethylpiperazin-1-yl)propane-1-sulfonamide

[Step 1] methyl 4-(((3-((3R,5S)-3,5-dimethylpiperazin-1-yl)-N-phenylpropyl)sulfonamido)methyl)benzoate A solution of methyl 4-(((3-chloro-N-phenylpropyl)sulfonamido)methyl)benzoate (0.500 g, 1.309 mmol), (2R,6S)-2,6-dimethylpiperazine (0.299 g, 2.619 mmol) and potassium carbonate (0.271 g, 1.964 mmol) in N,N-dimethylformide (3 mL) was stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 10%) to give methyl 4-(((3-((3R,5S)-3,5-dimethylpiperazin-1-yl)-N-phenylpropyl)sulfonamido)methyl)benzoate as white solid (0.515 g, 85.6%).

569

[Step 2] methyl 4-(((N-phenyl-3-((3R,5S)-3,4,5-trimethylpiperazin-1-yl)propyl)sulfonamido)methyl)benzoate

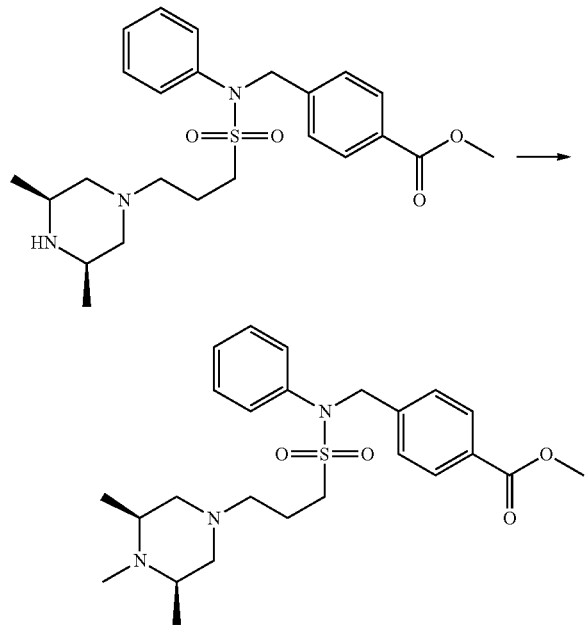

A solution of methyl 4-(((3-((3R,5S)-3,5-dimethylpiperazin-1-yl)-N-phenylpropyl)sulfonamido)methyl)benzoate (0.200 g, 0.435 mmol), paraformaldehyde (0.131 g, 4.352 mmol) and sodium triacetoxyborohydride (0.461 g, 2.176 mmol) in acetonitrile (5 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 10%) to give methyl 4-(((N-phenyl-3-((3R,5S)-3,4,5-trimethylpiperazin-1-yl)propyl)sulfonamido)methyl)benzoate as yellow solid (0.063 g, 30.3%).

[Step 3] N-(4-(hydrazinecarbonyl)benzyl)-N-phenyl-3-((3R,5S)-3,4,5-trimethylpiperazin-1-yl)propane-1-sulfonamide

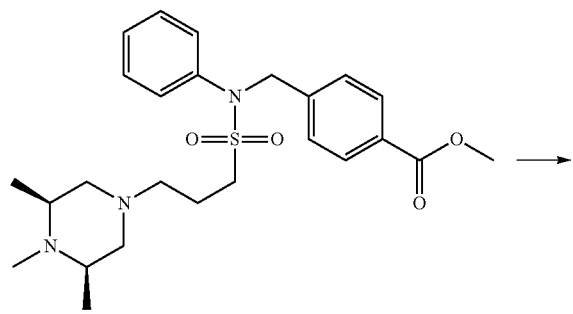

570

-continued

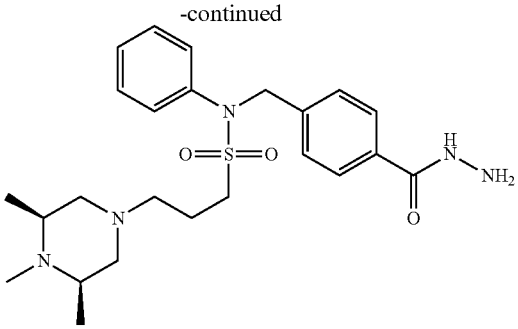

A solution of methyl 4-(((N-phenyl-3-((3R,5S)-3,4,5-trimethylpiperazin-1-yl)propyl)sulfonamido)methyl)benzoate (0.063 g, 0.133 mmol) and hydrazine hydrate (0.067 g, 1.330 mmol) in ethanol (5 mL) was stirred at 90° C. for 18 hr, cooled down to the room temperature to terminate the reaction and concentrated under the reduced pressure to remove the solvent. The residue was diluted with sodium bicarbonate (20 mL) and water (10 mL) and stirred. The resulting precipitates were collected by filtration, washed by water, and dried to give N-(4-(hydrazinecarbonyl)benzyl)-N-phenyl-3-((3R,5S)-3,4,5-trimethylpiperazin-1-yl)propane-1-sulfonamide as white solid (0.041 g, 64.4%).

[Step 4] Compound 11665

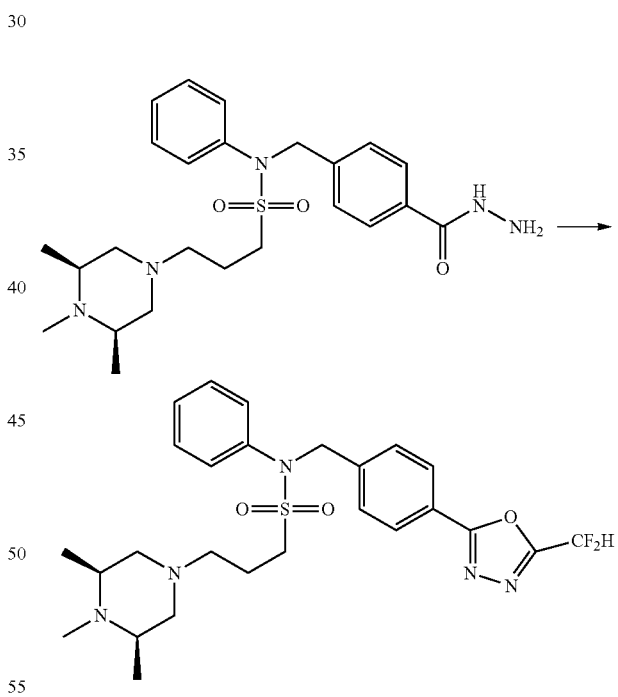

A solution of N-(4-(hydrazinecarbonyl)benzyl)-N-phenyl-3-((3R,5S)-3,4,5-trimethylpiperazin-1-yl)propane-1-sulfonamide (0.041 g, 0.086 mmol), triethylamine (0.060 mL, 0.429 mmol) and 2,2-difluoroacetic anhydride (0.032 mL, 0.257 mmol) in tetrahydrofuran (3 mL) was stirred at 90° C. for 1 hr, cooled down to the room temperature to terminate the reaction and concentrated under the reduced pressure to remove the solvent. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 10%) to give N-(4-(5-(difluoromethyl)-1,3,4-oxadiazol-2-yl)benzyl)-N-phenyl-3-((3R,5S)-3,4,5-trimethylpiperazin-1-yl)propane-1-sulfonamide as colorless oil (0.031 g, 67.3%).

¹H NMR (400 MHz, CDCl₃) δ8.04 (dt, 2H, J=8.5, 1.8 Hz), 7.47 (d, 2H, J=8.6 Hz), 7.37~7.26 (m, 5H), 6.91 (t, 1H, J=51.7 Hz), 4.98 (s, 2H), 3.19~3.15 (m, 2H), 2.72 (d, 2H, J=10.6 Hz), 2.42 (t, 2H, J=6.8 Hz), 2.35 (brs, 4H), 2.09~2.01 (m, 4H), 1.16 (d, 6H, J=5.1 Hz); LRMS (ES) m/z 534.1 (M⁺+1).

EXAMPLE 187

Compound 11668, N-((adamantan-1-yl)methyl)-N-(4-(5-(difluoromethyl)-1,3,4-oxadiazol-2-yl)benzyl)methanesulfonamide

[Step 1] methyl 4-((((adamantan-1-yl)methyl)amino)methyl)benzoate

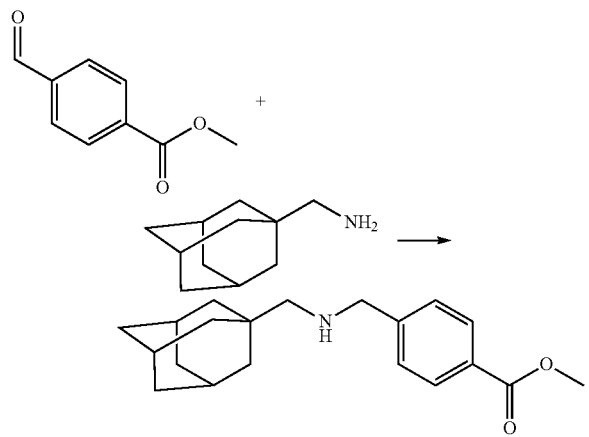

A mixture of methyl 4-formylbenzoate (0.500 g, 3.046 mmol) and (adamantan-1-yl)methanamine (0.654 mL, 3.960 mmol) in dichloromethane (20 mL) was treated at the room temperature with sodium triacetoxyborohydride (1.291 g, 6.092 mmol), and stirred at the same temperature for 3 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=30% to 70%) to give methyl 4-((((adamantan-1-yl)methyl)amino)methyl)benzoate as colorless oil (0.860 g, 90.1%).

[Step 2] methyl 4-((N-((adamantan-1-yl)methyl)methylsulfonamido)methyl)benzoate

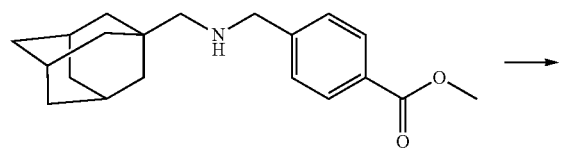

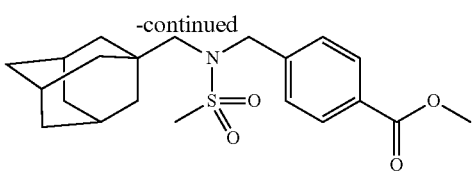

A solution of methyl 4-((((adamantan-1-yl)methyl)amino)methyl)benzoate (0.860 g, 2.744 mmol) in dichloromethane (50 mL) was mixed at the room temperature with methanesulfonyl chloride (0.276 mL, 3.567 mmol) and triethylamine (0.574 mL, 4.116 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=20% to 50%) to give methyl 4-((N-((adamantan-1-yl)methyl)methylsulfonamido)methyl)benzoate as beige solid (0.956 g, 89.0%).

[Step 3] N-((adamantan-1-yl)methyl)-N-(4-(hydrazinecarbonyl)benzyl)methanesulfonamide

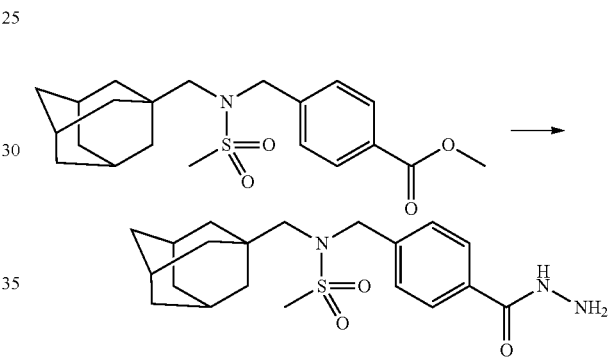

A solution of methyl 4-((N-((adamantan-1-yl)methyl)methylsulfonamido)methyl)benzoate (0.956 g, 2.442 mmol) in tetrahydrofuran (7 mL)/ethanol (7 mL) was mixed at the room temperature with hydrazine monohydrate (2.373 mL, 48.834 mmol). The reaction mixture was heated at reflux for 18 hr, cooled down to the room temperature to terminate the reaction and concentrated under the reduced pressure to remove the solvent. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with ethyl acetate (10 mL) and hexane (50 mL) and stirred. The resulting precipitates were collected by filtration, washed by hexane, and dried to give N-((adamantan-1-yl)methyl)-N-(4-(hydrazinecarbonyl)benzyl)methanesulfonamide as white solid (0.935 g, 97.8%).

[Step 4] Compound 11668

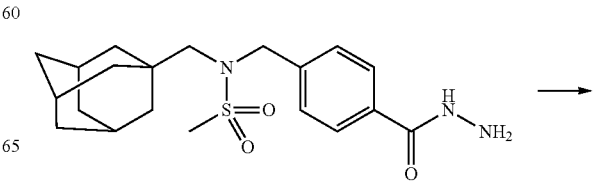

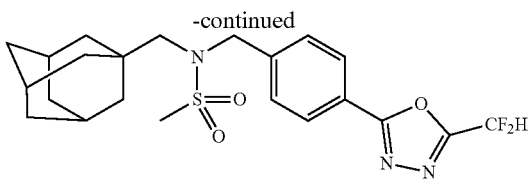

A mixture of N-((adamantan-1-yl)methyl)-N-(4-(hydrazinecarbonyl)benzyl)methanesulfonamide (0.300 g, 0.766 mmol) and triethylamine (0.427 mL, 3.065 mmol) in tetrahydrofuran (20 mL) was treated at the room temperature with 2,2-difluoroacetic anhydride (0.286 mL, 2.299 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=20% to 50%) to give the concentrate, and then the concentrate was dissolved in ethyl acetate (5 mL) and hexane (30 mL) and stirred. The resulting precipitates were collected by filtration, washed by hexane, and dried to give N-((adamantan-1-yl)methyl)-N-(4-(5-(difluoromethyl)-1,3,4-oxadiazol-2-yl)benzyl)methanesulfonamide as white solid (0.262 g, 75.7%).

$^1$H NMR (400 MHz, DMSO-d6) δ 8.07 (d, 2H, J=8.4 Hz), 7.68 (s, 0.25H), 7.65 (d, 2H, J=8.4 Hz), 7.55 (s, 0.5H), 7.42 (s, 0.25H), 4.51 (s, 2H), 2.97 (s, 3H), 2.93 (s, 2H), 1.86 (s, 3H), 1.64-1.56 (m, 3H), 1.53-1.47 (m, 3H), 1.47-1.41 (m, 6H); LRMS (ES) m/z 452.1 (M$^+$+1).

EXAMPLE 188

Compound 11669, N-((adamantan-1-yl)methyl)-N-((5-(5-(difluoromethyl)-1,3,4-oxadiazol-2-yl)pyridin-2-yl)methyl)methanesulfonamide

[Step 1] methyl 6-((((adamantan-1-yl)methyl)amino)methyl)nicotinate

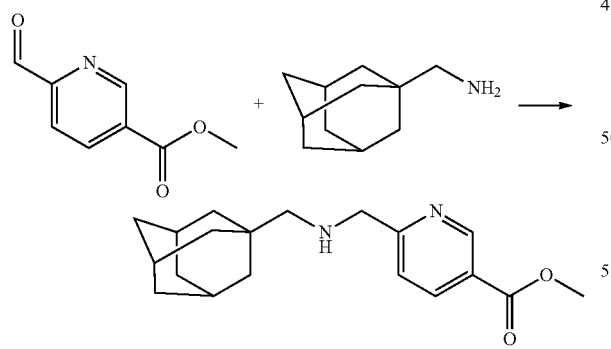

A mixture of methyl 6-formylnicotinate (0.320 g, 1.938 mmol) and (adamantan-1-yl)methanamine (0.416 mL, 2.519 mmol) in dichloromethane (20 mL) was treated at the room temperature with sodium triacetoxyborohydride (0.821 g, 3.875 mmol), and stirred at the same temperature for 3 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=30% to 70%) to give methyl 6-((((adamantan-1-yl)methyl)amino)methyl)nicotinate as yellow oil (0.530 g, 87.0%).

[Step 2] methyl 6-((N-((adamantan-1-yl)methyl)methylsulfonamido)methyl)nicotinate

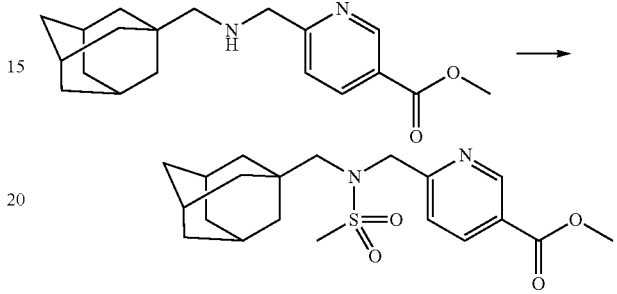

A solution of methyl 6-((((adamantan-1-yl)methyl)amino)methyl)nicotinate (0.530 g, 1.686 mmol) in dichloromethane (50 mL) was mixed at the room temperature with methanesulfonyl chloride (0.170 mL, 2.191 mmol) and triethylamine (0.352 mL, 2.528 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=30% to 70%) to give methyl 6-((N-((adamantan-1-yl)methyl)methylsulfonamido)methyl)nicotinate as yellow solid (0.510 g, 77.1%).

[Step 3] N-((adamantan-1-yl)methyl)-N-((5-(hydrazinecarbonyl)pyridin-2-yl)methyl)methanesulfonamide

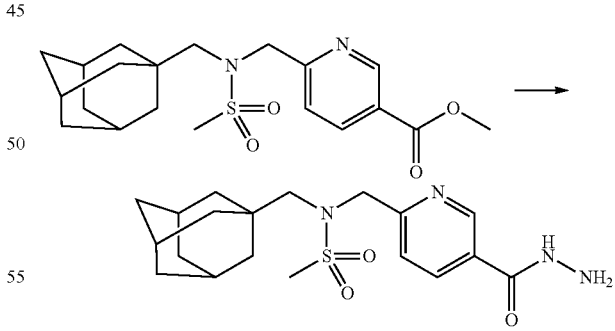

A solution of methyl 6-((N-((adamantan-1-yl)methyl)methylsulfonamido)methyl)nicotinate (0.510 g, 1.299 mmol) in tetrahydrofuran (7 mL)/ethanol (7 mL) was mixed at the room temperature with hydrazine monohydrate (1.263 mL, 25.987 mmol). The reaction mixture was heated at reflux for 18 hr, cooled down to the room temperature to terminate the reaction and concentrated under the reduced pressure to remove the solvent. Then, water was added to the reaction mixture, followed by extraction with ethyl acetate.

The organic layer was washed with aqueous saturated sodium chloride solution, dried with anhydrous MgSO$_4$, filtered, and concentrated in vacuo. The residue was diluted with ethyl acetate (10 mL) and hexane (50 mL) and stirred. The resulting precipitates were collected by filtration, washed by hexane, and dried to give N-((adamantan-1-yl)methyl)-N-((5-(hydrazinecarbonyl)pyridin-2-yl)methyl)methanesulfonamide as white solid (0.365 g, 71.6%).

[Step 4] Compound 11669

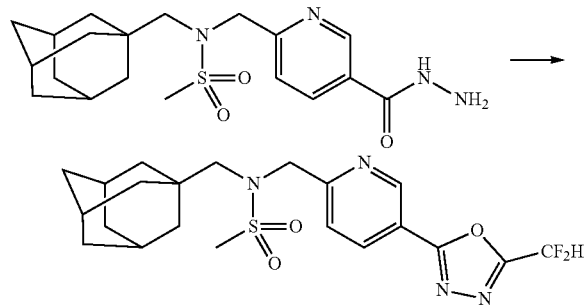

A mixture of N-((adamantan-1-yl)methyl)-N-((5-(hydrazinecarbonyl)pyridin-2-yl)methyl)methanesulfonamide (0.300 g, 0.764 mmol) and triethylamine (0.426 mL, 3.057 mmol) in tetrahydrofuran (20 mL) was treated at the room temperature with 2,2-difluoroacetic anhydride (0.285 mL, 2.293 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=30% to 60%) to give the concentrate, and then the concentrate was dissolved in ethyl acetate (5 mL) and hexane (30 mL) and stirred. The resulting precipitates were collected by filtration, washed by hexane, and dried to give N-((adamantan-1-yl)methyl)-N-((5-(5-(difluoromethyl)-1,3,4-oxadiazol-2-yl)pyridin-2-yl)methyl)methanesulfonamide as white solid (0.241 g, 69.7%).

$^1$H NMR (400 MHz, DMSO-d6) δ 9.17 (dd, 1H, J=2.2, 0.8 Hz), 8.50 (dd, 1H, J=8.3, 2.3 Hz), 7.83 (dd, 1H, J=8.3, 0.9 Hz), 7.58 (t, 1H, J=51.3 Hz), 4.61 (s, 2H), 3.01 (s, 3H), 2.96 (s, 2H), 1.88 (s, 3H), 1.66-1.58 (m, 3H), 1.57-1.51 (m, 3H), 1.50-1.45 (m, 6H); LRMS (ES) m/z 453.3 (M$^+$+1).

EXAMPLE 189

Compound 11675, N-(4-(5-(difluoromethyl)-1,3,4-oxadiazol-2-yl)benzyl)-2-(4-methylpiperidin-1-yl)-N-phenylethanesulfonamide

[Step 1] methyl 4-((2-(4-methylpiperidin-1-yl)-N-phenylethylsulfonamido)methyl)benzoate

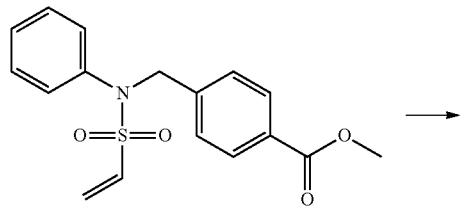

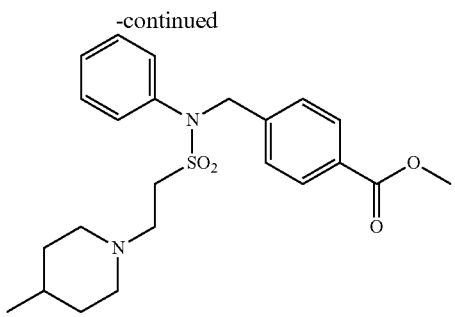

A solution of methyl 4-((N-phenylvinylsulfonamido)methyl)benzoate (0.200 g, 0.604 mmol), 4-methylpiperidine (0.060 g, 0.604 mmol) and N,N-Diisopropylethylamine (0.208 mL, 1.207 mmol) in dichloromethane (10 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=5% to 10%) to give methyl 4-((2-(4-methylpiperidin-1-yl)-N-phenylethylsulfonamido)methyl)benzoate as white solid (0.230 g, 88.5%).

[Step 2] N-(4-(hydrazinecarbonyl)benzyl)-2-(4-methylpiperidin-1-yl)-N-phenylethanesulfonamide

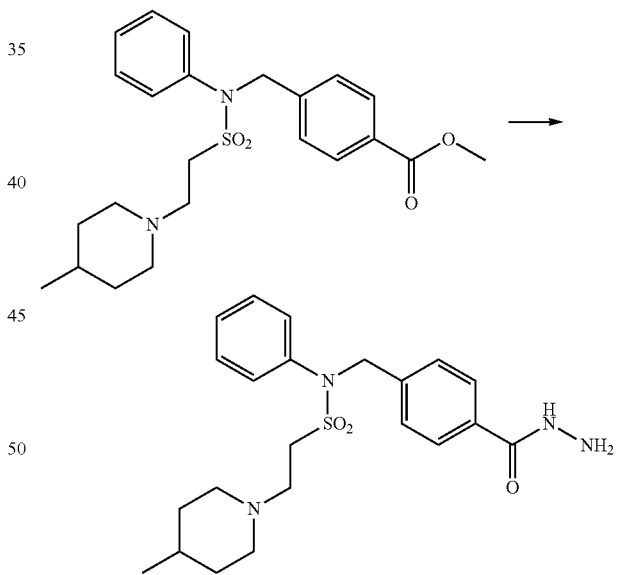

A mixture of methyl 4-((2-(4-methylpiperidin-1-yl)-N-phenylethylsulfonamido)methyl)benzoate (0.230 g, 0.534 mmol) and hydrazine (0.335 mL, 10.684 mmol) in ethanol (5 mL) prepared at the room temperature was heated at reflux for 6 hr, cooled down to the ambient temperature, and concentrated under the reduced pressure to remove the solvent. The residue was diluted with water (20 mL) and stirred. The resulting precipitates were collected by filtration and dried to give N-(4-(hydrazinecarbonyl)benzyl)-2-(4-methylpiperidin-1-yl)-N-phenylethanesulfonamide as white solid (0.160 g, 69.6%).

[Step 3] Compound 11675

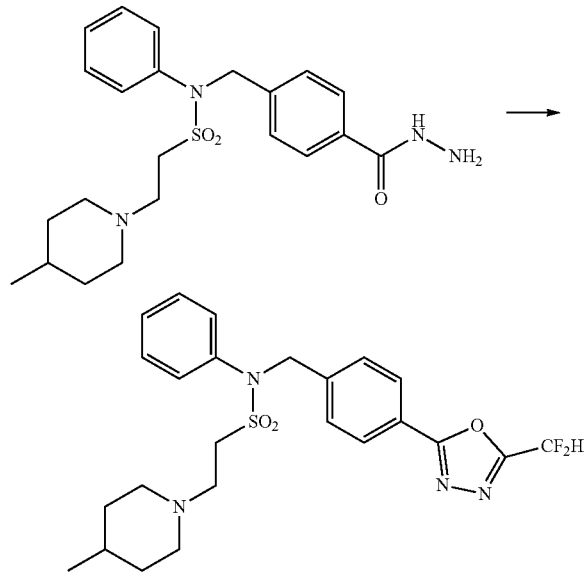

A mixture of N-(4-(hydrazinecarbonyl)benzyl)-2-(4-methylpiperidin-1-yl)-N-phenylethanesulfonamide (0.160 g, 0.372 mmol), 2,2-difluoroacetic anhydride (0.139 mL, 1.115 mmol) and triethylamine (0.259 mL, 1.858 mmol) in tetrahydrofuran (10 mL) prepared at the room temperature was heated at reflux for 12 hr, and cooled down to the ambient temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)benzyl)-2-(4-methylpiperidin-1-yl)-N-phenylethanesulfonamide as white solid (0.060 g, 32.9%).

$^1$H NMR (400 MHz, CDCl$_3$) δ 8.00 (d, 2H, J=8.1 Hz), 7.43 (d, 2H, J=8.0 Hz), 7.33-7.27 (m, 5H), 6.91 (t, 1H, J=51.9 Hz), 4.96 (s, 2H), 3.84-3.75 (m, 2H), 3.58-3.48 (m, 2H), 3.40-3.36 (m, 2H), 2.66 (m, 2H), 1.86-1.84 (m, 2H), 1.65 (m, 2H), 1.27 (t, 1H, J=1.3 Hz), 1.03-1.02 (m, 3H); LRMS (ES) m/z 491.8 (M$^+$+1).

EXAMPLE 190

Compound 11676, (1-(2-(N-(4-(5-(difluoromethyl)-1,3,4-oxadiazol-2-yl)benzyl)-N-Phenylsulfamoyl)ethyl)piperidin-4-yl)methyl 2,2-difluoroacetate

[Step 1] methyl 4-((2-(4-(hydroxymethyl)piperidin-1-yl)-N-phenylethylsulfonamido)methyl)benzoate

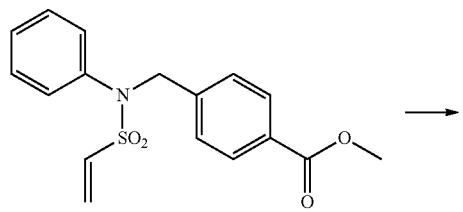

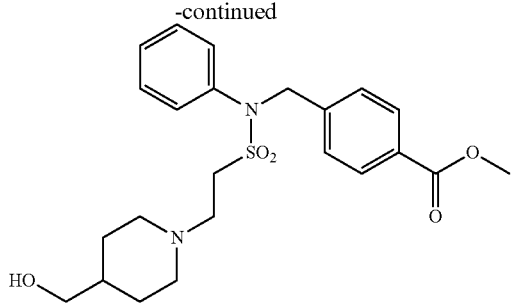

A solution of methyl 4-((N-phenylvinylsulfonamido)methyl)benzoate (0.200 g, 0.604 mmol), piperidin-4-yl-methanol (0.070 g, 0.604 mmol) and N,N-Diisopropylethylamine (0.208 mL, 1.207 mmol) in dichloromethane (10 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=5% to 10%) to give methyl 4-((2-(4-(hydroxymethyl)piperidin-1-yl)-N-phenylethylsulfonamido)methyl)benzoate as white solid (0.180 g, 66.8%).

[Step 2] N-(4-(hydrazinecarbonyl)benzyl)-2-(4-(hydroxymethyl)piperidin-1-yl)-N-phenylethanesulfonamide

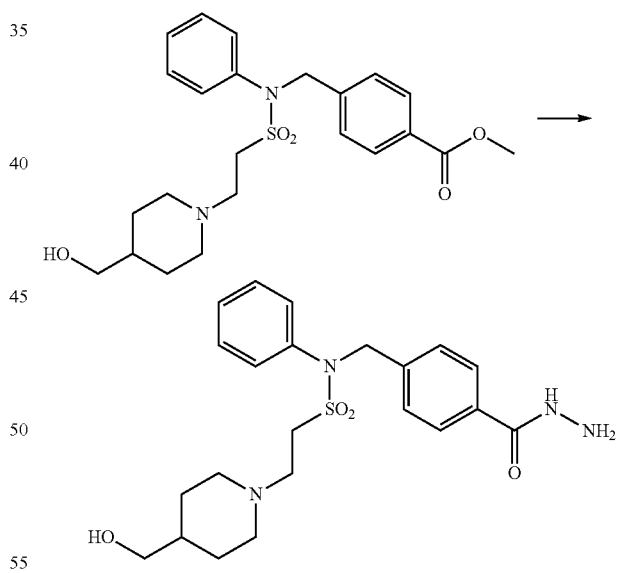

A mixture of methyl 4-((2-(4-(hydroxymethyl)piperidin-1-yl)-N-phenylethylsulfonamido)methyl)benzoate (0.180 g, 0.403 mmol) and hydrazine (0.253 mL, 8.062 mmol) in ethanol (5 mL) prepared at the room temperature was heated at reflux for 6 hr, cooled down to the ambient temperature, and concentrated under the reduced pressure to remove the solvent. The residue was diluted with water (20 mL) and stirred. The resulting precipitates were collected by filtration and dried to give N-(4-(hydrazinecarbonyl)benzyl)-2-(4-(hydroxymethyl)piperidin-1-yl)-N-phenylethanesulfonamide as white solid (0.100 g, 55.6%).

[Step 3] Compound 11676

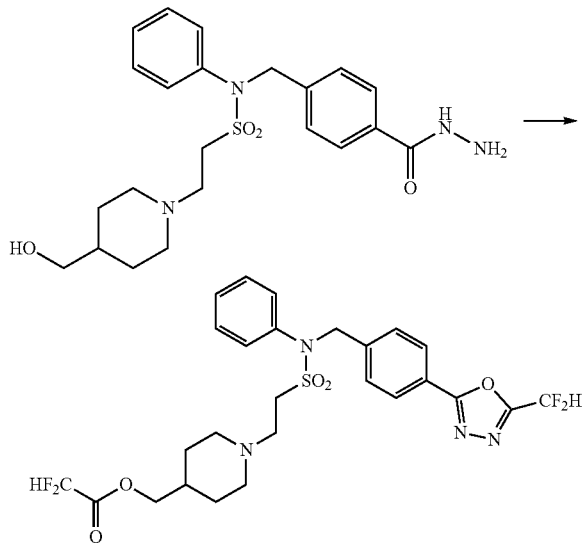

A mixture of N-(4-(hydrazinecarbonyl)benzyl)-2-(4-(hydroxymethyl)piperidin-1-yl)-N-phenylethanesulfonamide (0.100 g, 0.224 mmol), 2,2-difluoroacetic anhydride (0.084 mL, 0.672 mmol) and triethylamine (0.156 mL, 1.120 mmol) in tetrahydrofuran (10 mL) prepared at the room temperature was heated at reflux for 12 hr, and cooled down to the ambient temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give (1-(2-(N-(4-(5-(difluoromethyl)-1,3,4-oxadiazol-2-yl)benzyl)-N-Phenylsulfamoyl)ethyl)piperidin-4-yl)methyl 2,2-difluoroacetate as white solid (0.050 g, 38.2%).
$^1$H NMR (400 MHz, CDCl$_3$) δ 8.02 (d, 2H, J=8.3 Hz), 7.44 (d, 2H, J=8.0 Hz), 7.37-7.28 (m, 5H), 6.91 (t, 1H, J=51.7 Hz), 5.96 (t, 1H, J=53.1 Hz), 4.97 (d, 2H), 4.22 (d, 2H, J=6.1 Hz), 3.84-3.81 (m, 2H), 3.69-3.65 (m, 2H), 3.44-3.40 (m, 2H), 2.77 (m, 2H), 2.02-1.78 (m, 5H); LRMS (ES) m/z 585.9 (M$^+$+1).

EXAMPLE 191

Compound 11677, tert-butyl 2,2-difluoroacetyl(1-(2-(N-(4-(5-(difluoromethyl)-1,3,4-oxadiazol-2-yl)benzyl)-N-phenylsulfamoyl)ethyl)piperidin-4-yl)carbamate

[Step 1] methyl 4-((2-(4-(tert-butoxycarbonylamino)piperidin-1-yl)-N-phenylethylsulfonamido)methyl)benzoate

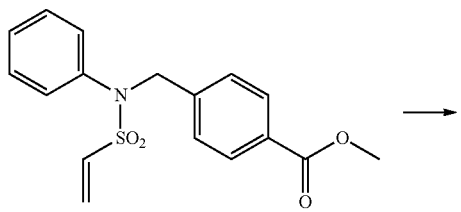

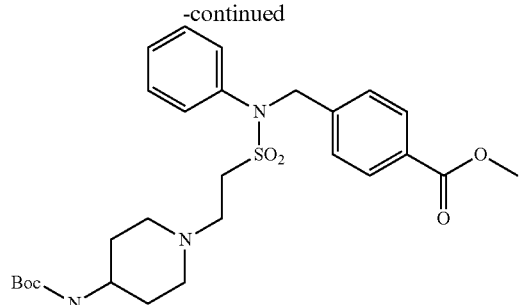

A solution of methyl 4-((N-phenylvinylsulfonamido)methyl)benzoate (0.200 g, 0.604 mmol), tert-butyl piperidin-4-ylcarbamate (0.121 g, 0.604 mmol) and N,N-Diisopropylethylamine (0.208 mL, 1.207 mmol) in dichloromethane (10 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=5% to 10%) to give methyl 4-((2-(4-(tert-butoxycarbonylamino)piperidin-1-yl)-N-phenylethylsulfonamido)methyl)benzoate as white solid (0.220 g, 68.6%).

[Step 2] tert-butyl 1-(2-(N-(4-(hydrazinecarbonyl)benzyl)-N-phenylsulfamoyl)ethyl)piperidin-4-ylcarbamate

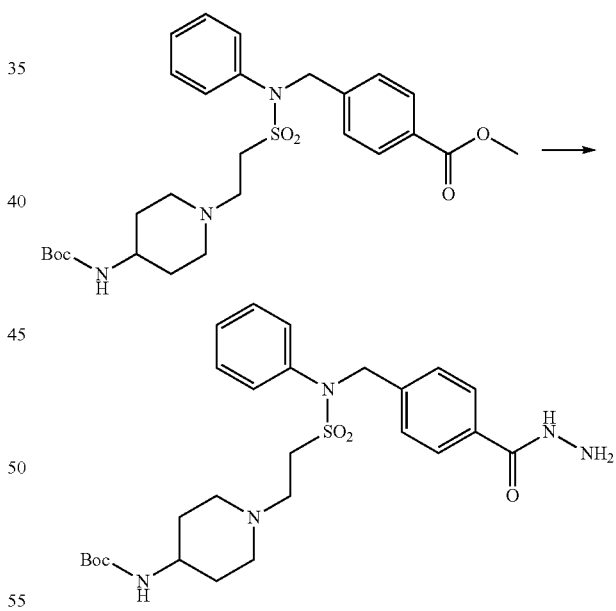

A mixture of methyl 4-((2-(4-(tert-butoxycarbonylamino)piperidin-1-yl)-N-phenylethylsulfonamido)methyl)benzoate (0.220 g, 0.414 mmol) and hydrazine (0.260 mL, 8.276 mmol) in ethanol (5 mL) prepared at the room temperature was heated at reflux for 6 hr, cooled down to the ambient temperature, and concentrated under the reduced pressure to remove the solvent. The residue was diluted with water (20 mL) and stirred. The resulting precipitates were collected by filtration and dried to give tert-butyl 1-(2-(N-(4-(hydrazinecarbonyl)benzyl)-N-phenylsulfamoyl)ethyl)piperidin-4-ylcarbamate as white solid (0.120 g, 54.5%).

581

[Step 3] Compound 11677

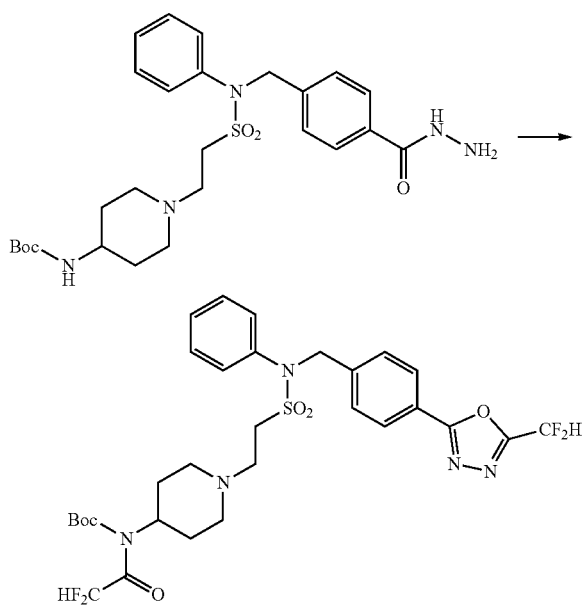

A mixture of give tert-butyl 1-(2-(N-(4-(hydrazinecarbonyl)benzyl)-N-phenylsulfamoyl)ethyl)piperidin-4-ylcarbamate (0.120 g, 0.226 mmol), 2,2-difluoroacetic anhydride (0.084 mL, 0.677 mmol) and triethylamine (0.157 mL, 1.129 mmol) in tetrahydrofuran (10 mL) prepared at the room temperature was heated at reflux for 12 hr, and cooled down to the ambient temperature. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO$_2$, 12 g cartridge; methanol/dichloromethane=0% to 5%) to give tert-butyl 2,2-difluoroacetyl(1-(2-(N-(4-(5-(difluoromethyl)-1,3,4-oxadiazol-2-yl)benzyl)-N-phenylsulfamoyl)ethyl)piperidin-4-yl)carbamate as white solid (0.050 g, 33.1%).

$^1$H NMR (400 MHz, CDCl$_3$) δ 8.01 (d, 2H, J=8.2 Hz), 7.43 (d, 2H, J=8.2 Hz), 7.33-7.28 (m, 5H), 6.91 (t, 1H, J=51.7 Hz), 5.87 (t, 1H, J=54.6 Hz), 4.95 (d, 2H), 4.60 (m, 1H), 3.79-3.70 (m, 4H), 3.47-3.44 (m, 2H), 2.95-2.84 (m, 4H), 1.89 (m, 2H), 1.58-1.44 (m, 9H); LRMS (ES) m/z 670.4 (M$^+$+1).

EXAMPLE 192

Compound 11678, 2-(5-(2,2-difluoroacetyl)-1H-imidazol-1-yl)-N-(4-(5-(difluoromethyl)-1,3,4-oxadiazol-2-yl)benzyl)-N-phenylethane-1-sulfonamide

[Step 1] methyl 4-((2-(1H-imidazol-1-yl)-N-phenylethylsulfonamido)methyl)benzoate

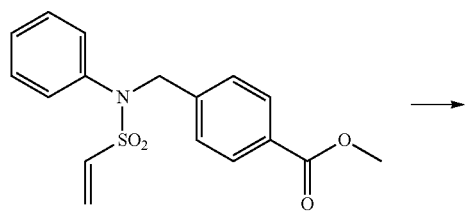

582

-continued

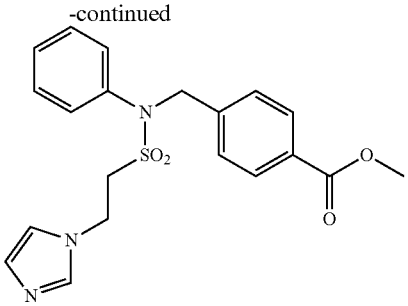

A solution of methyl 4-((N-phenylvinylsulfonamido)methyl)benzoate (0.200 g, 0.604 mmol), 1H-imidazole (0.041 g, 0.604 mmol) and N,N-Diisopropylethylamine (0.208 mL, 1.207 mmol) in dichloromethane (10 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO$_2$, 12 g cartridge; methanol/dichloromethane=5% to 10%) to give methyl 4-((2-(1H-imidazol-1-yl)-N-phenylethylsulfonamido)methyl)benzoate as white solid (0.210 g, 87.1%).

[Step 2] N-(4-(hydrazinecarbonyl)benzyl)-2-(1H-imidazol-1-yl)-N-phenylethanesulfonamide

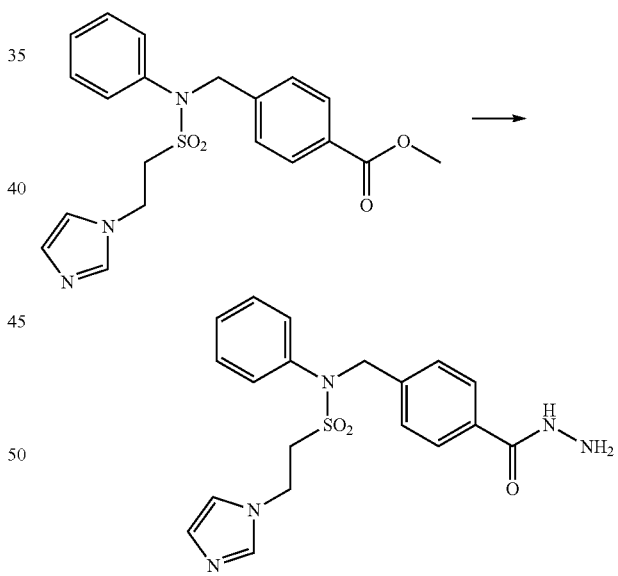

A mixture of methyl 4-((2-(1H-imidazol-1-yl)-N-phenylethylsulfonamido)methyl)benzoate (0.210 g, 0.526 mmol) and hydrazine (0.330 mL, 10.514 mmol) in ethanol (5 mL) prepared at the room temperature was heated at reflux for 6 hr, cooled down to the ambient temperature, and concentrated under the reduced pressure to remove the solvent. The residue was diluted with water (20 mL) and stirred. The resulting precipitates were collected by filtration and dried to give N-(4-(hydrazinecarbonyl)benzyl)-2-(1H-imidazol-1-yl)-N-phenylethanesulfonamide as white solid (0.130 g, 61.9%).

[Step 3] Compound 11678

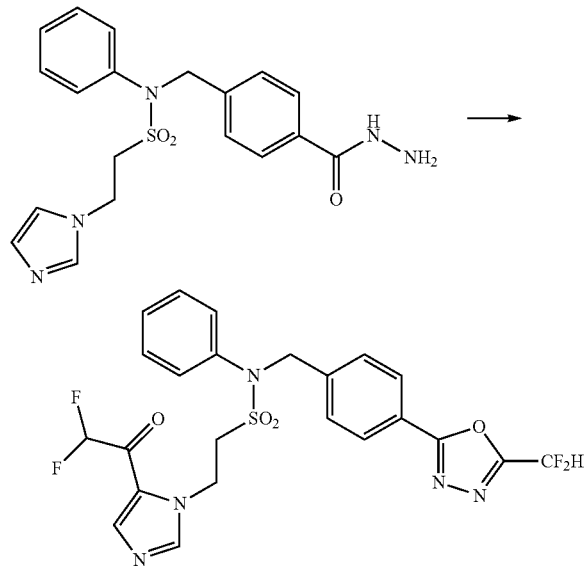

A mixture of N-(4-(hydrazinecarbonyl)benzyl)-2-(1H-imidazol-1-yl)-N-phenylethane sulfonamide (0.130 g, 0.325 mmol), 2,2-difluoroacetic anhydride (0.121 mL, 0.976 mmol) and triethylamine (0.227 mL, 1.627 mmol) in tetrahydrofuran (10 mL) prepared at the room temperature was heated at reflux for 12 hr, and cooled down to the ambient temperature. Then, water was added to the reaction mixture, followed by extraction with dichloromethane. The organic layer was washed with aqueous saturated sodium chloride solution, dried with anhydrous MgSO4, filtered, and concentrated in vacuo. The residue was chromatographed (SiO2, 12 g cartridge; methanol/dichloromethane=0% to 5%) to give 2-(5-(2,2-difluoroacetyl)-1H-imidazol-1-yl)-N-(4-(5-(difluoromethyl)-1,3,4-oxadiazol-2-yl)benzyl)-N-phenylethane-1-sulfonamide as white solid (0.040 g, 22.9%).

$^1$H NMR (400 MHz, DMSO-d6) δ7.99 (d, 2H), 7.97 (s, 1H), 7.53-7.52 (m, 3H), 7.43-7.29 (m, 5H), 7.09 (t, 1H, J=51.7 Hz), 6.25 (t, 1H, J=54.6 Hz), 5.03 (s, 1H), 4.88-4.84 (m, 2H), 3.85-3.82 (m, 2H); LRMS (ES) m/z 583.3 (M$^+$+1).

EXAMPLE 193

Compound 11679, N-(4-(5-(difluoromethyl)-1,3,4-oxadiazol-2-yl)benzyl)-2-(4-(3-hydroxypropyl)piperazin-1-yl)-N-phenylethane-1-sulfonamide

[Step 1] methyl 4-((2-(4-(3-hydroxypropyl)piperazin-1-yl)-N-phenylethylsulfonamido)methyl)benzoate

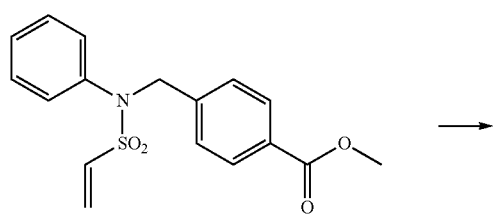

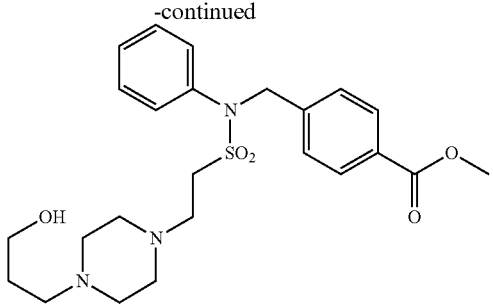

A solution of methyl 4-((N-phenylvinylsulfonamido)methyl)benzoate (0.200 g, 0.604 mmol), 3-(piperazin-1-yl)propan-1-ol (0.087 g, 0.604 mmol) and N,N-Diisopropylethylamine (0.208 mL, 1.207 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO4, filtered, and concentrated in vacuo. The residue was chromatographed (SiO2, 12 g cartridge; methanol/dichloromethane=5% to 10%) to give methyl 4-((2-(4-(3-hydroxypropyl)piperazin-1-yl)-N-phenylethylsulfonamido)methyl)benzoate as white solid (0.230 g, 80.1%).

[Step 2] N-(4-(hydrazinecarbonyl)benzyl)-2-(4-(3-hydroxypropyl)piperazin-1-yl)-N-phenylethanesulfonamide

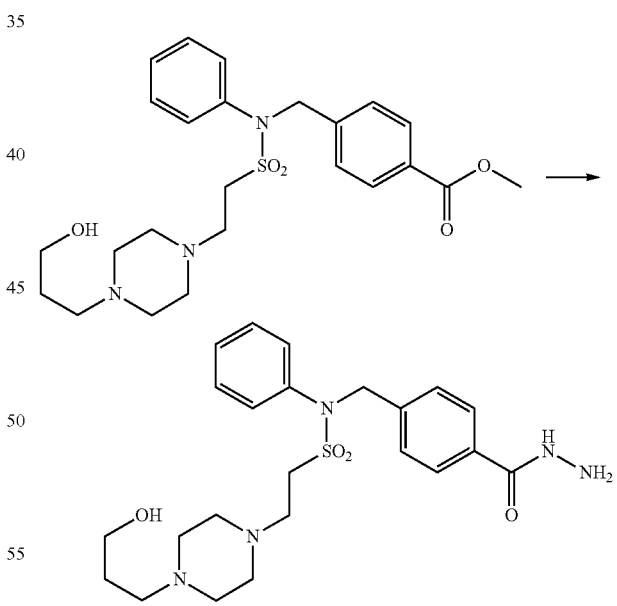

A mixture of methyl 4-((2-(4-(3-hydroxypropyl)piperazin-1-yl)-N-phenylethylsulfonamido)methyl)benzoate (0.230 g, 0.484 mmol) and hydrazine (0.304 mL, 9.672 mmol) in ethanol (5 mL) prepared at the room temperature was heated at reflux for 6 hr, cooled down to the ambient temperature, and concentrated under the reduced pressure to remove the solvent. The residue was diluted with water (20 mL) and stirred. The resulting precipitates were collected by filtration and dried to give N-(4-(hydrazinecarbonyl)benzyl)-2-(4-(3-hydroxypropyl)piperazin-1-yl)-N-phenyle-thanesulfonamide as white solid (0.140 g, 60.9%).

[Step 3] Compound 11679

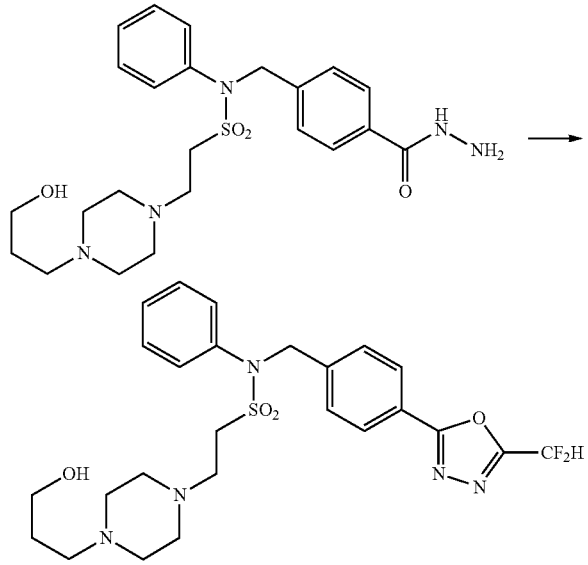

A mixture of N-(4-(hydrazinecarbonyl)benzyl)-2-(4-(3-hydroxypropyl)piperazin-1-yl)-N-phenylethanesulfonamide (0.140 g, 0.294 mmol), 2,2-difluoroacetic anhydride (0.110 mL, 0.883 mmol) and triethylamine (0.205 mL, 1.472 mmol) in tetrahydrofuran (10 mL) prepared at the room temperature was heated at reflux for 12 hr, and cooled down to the ambient temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)benzyl)-2-(4-(3-hydroxypropyl)piperazin-1-yl)-N-phenylethane-1-sulfonamide as white solid (0.080 g, 50.7%).

$^1$H NMR (400 MHz, DMSO-d6) δ8.03-7.98 (m, 2H), 7.55-7.53 (m, 2H), 7.44-7.24 (m, 5H), 5.86 (t, 1H, J=55.2 Hz), 5.04 (s, 2H), 3.51-3.39 (m, 6H), 3.38-3.20 (m, 4H), 2.94-2.91 (m, 4H), 2.68 (m, 2H), 1.99-1.78 (m, 2H); LRMS (ES) m/z 534.9 (M$^+$+1).

EXAMPLE 194

Compound 11680, N-(4-(5-(difluoromethyl)-1,3,4-oxadiazol-2-yl)benzyl)-1-(oxetan-3-yl)-N-phenylpiperidine-4-sulfonamide

[Step 1] tert-butyl 4-(N-(4-(hydrazinecarbonyl)benzyl)-N-phenylsulfamoyl)piperidine-1-carboxylate

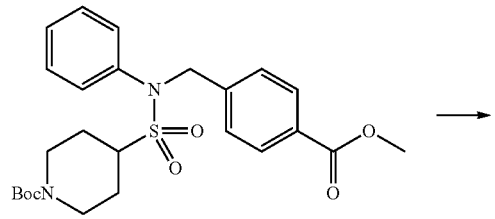

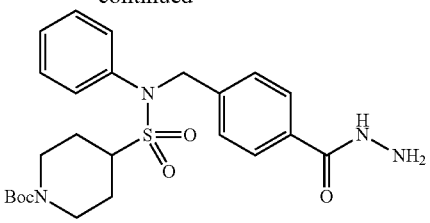

tert-butyl 4-(N-(4-(methoxycarbonyl)benzyl)-N-phenylsulfamoyl)piperidine-1-carboxylate (0.830 g, 1.699 mmol) and hydrazine monohydrate (2.477 mL, 50.962 mmol) in tetrahydrofuran (7 mL)/ethanol (7 mL) was mixed at the room temperature, heated at 120° C. under the microwaves for 90 min, cooled down to the room temperature, and concentrated under the reduced pressure to remove the solvent. The residue was diluted with ethyl acetate (20 mL) and hexane (40 mL) and stirred. The resulting precipitates were collected by filtration, washed by hexane, and dried to give tert-butyl 4-(N-(4-(hydrazinecarbonyl)benzyl)-N-phenylsulfamoyl)piperidine-1-carboxylate as white solid (0.720 g, 86.7%).

[Step 2] tert-butyl 4-(N-(4-(2-(2,2-difluoroacetyl)hydrazine-1-carbonyl)benzyl)-N-phenylsulfamoyl)piperidine-1-carboxylate

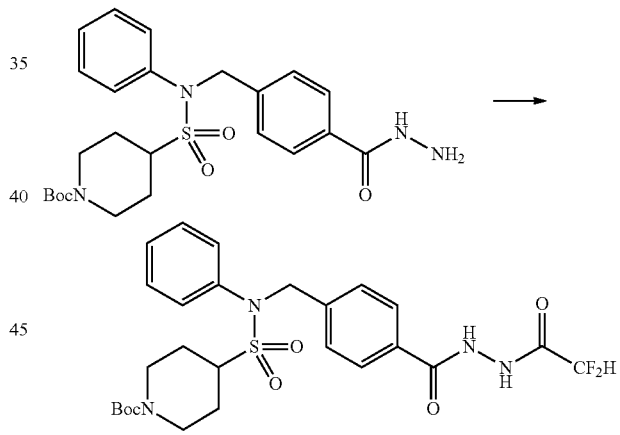

A mixture of tert-butyl 4-(N-(4-(hydrazinecarbonyl)benzyl)-N-phenylsulfamoyl)piperidine-1-carboxylate (0.720 g, 1.474 mmol) and triethylamine (1.027 mL, 7.368 mmol) in tetrahydrofuran (20 mL) was treated at the room temperature with 2,2-difluoroacetic anhydride (0.550 mL, 4.421 mmol), stirred at 70° C. for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=30% to 60%) to give tert-butyl 4-(N-(4-(2-(2,2-difluoroacetyl)hydrazine-1-carbonyl)benzyl)-N-phenylsulfamoyl)piperidine-1-carboxylate as white solid (0.610 g, 73.1%).

[Step 3] tert-butyl 4-(N-(4-(5-(difluoromethyl)-1,3,4-oxadiazol-2-yl)benzyl)-N-phenylsulfamoyl)piperidine-1-carboxylate

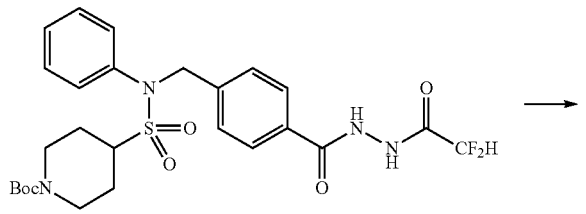

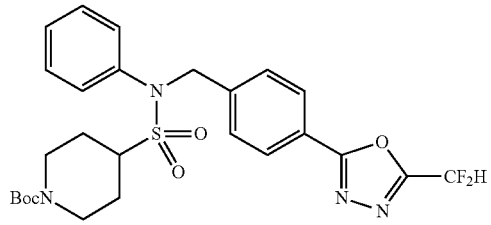

A mixture of tert-butyl 4-(N-(4-(2-(2,2-difluoroacetyl)hydrazine-1-carbonyl)benzyl)-N-phenylsulfamoyl)piperidine-1-carboxylate (0.610 g, 1.077 mmol) and triethylamine (0.450 mL, 3.230 mmol) in dichloromethane (30 mL) was treated at the room temperature with methanesulfonyl chloride (0.208 mL, 2.691 mmol), and stirred at the same temperature for 1 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give tert-butyl 4-(N-(4-(5-(difluoromethyl)-1,3,4-oxadiazol-2-yl)benzyl)-N-phenylsulfamoyl)piperidine-1-carboxylate as white solid (0.360 g, 61.0%).

[Step 4] N-(4-(5-(difluoromethyl)-1,3,4-oxadiazol-2-yl)benzyl)-N-phenylpiperidine-4-sulfonamide hydrochloride

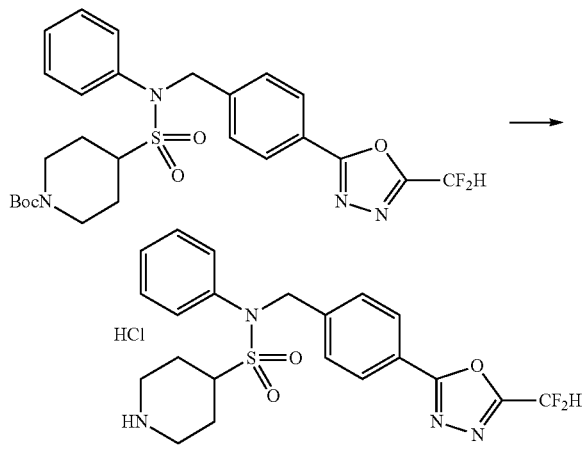

A solution of tert-butyl 4-(N-(4-(5-(difluoromethyl)-1,3,4-oxadiazol-2-yl)benzyl)-N-phenylsulfamoyl)piperidine-1-carboxylate (0.360 g, 0.656 mmol) in 1,4-dioxane (10 mL) was mixed at the room temperature with hydrochloric acid (4.00 M solution in 1,4-dioxane, 4.922 mL, 19.686 mmol), stirred at the same temperature for 1 hr, and concentrated under the reduced pressure to remove the solvent. The residue was diluted with ethyl acetate (20 mL) and hexane (20 mL) and stirred. The resulting precipitates were collected by filtration, washed by hexane, and dried to give N-(4-(5-(difluoromethyl)-1,3,4-oxadiazol-2-yl)benzyl)-N-phenylpiperidine-4-sulfonamide hydrochloride as white solid (0.290 g, 91.1%).

[Step 5] Compound 11680

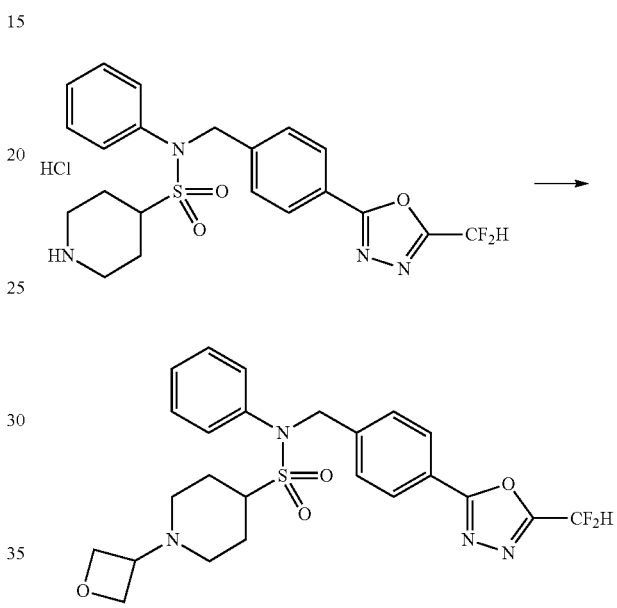

A mixture of N-(4-(5-(difluoromethyl)-1,3,4-oxadiazol-2-yl)benzyl)-N-phenylpiperidine-4-sulfonamide hydrochloride (0.100 g, 0.206 mmol), oxetan-3-one (0.074 g, 1.031 mmol) and N,N-diisopropylethylamine (0.072 mL, 0.412 mmol) in dichloromethane (5 mL) was treated at the room temperature with sodium triacetoxyborohydride (0.087 g, 0.412 mmol) and stirred at the same temperature for 18 hr. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give the concentrate, and then the concentrate was dissolved in ethyl acetate (3 mL) and hexane (30 mL) and stirred. The resulting precipitates were collected by filtration, washed by hexane, and dried to give N-(4-(5-(difluoromethyl)-1,3,4-oxadiazol-2-yl)benzyl)-1-(oxetan-3-yl)-N-phenylpiperidine-4-sulfonamide as white solid (0.062 g, 59.6%).

$^1$H NMR (400 MHz, DMSO-d6) δ 8.00 (d, 2H, J=8.3 Hz), 7.65 (s, 0.25H), 7.55-7.47 (m, 2.5H), 7.47-7.39 (m, 2.25H), 7.33 (t, 2H, J=7.7 Hz), 7.23 (t, 1H, J=7.3 Hz), 5.08 (s, 2H), 4.53 (t, 2H, J=6.5 Hz), 4.42 (t, 2H, J=6.1 Hz), 3.44 (m, 1H), 3.29 (m, 1H), 2.79 (d, 2H, J=10.9 Hz), 2.08 (d, 2H, J=12.3 Hz), 1.84 (t, 2H, J=11.5 Hz), 1.80-1.66 (m, 2H); LRMS (ES) m/z 505.3 (M$^+$+1).

EXAMPLE 195

Compound 11681, N-(3-chlorophenyl)-N-(4-(5-(difluoromethyl)-1,3,4-oxadiazol-2-yl)benzyl)-1-(oxetan-3-yl)piperidine-4-sulfonamide

[Step 1] tert-butyl 4-(N-(3-chlorophenyl)sulfamoyl)piperidine-1-carboxylate

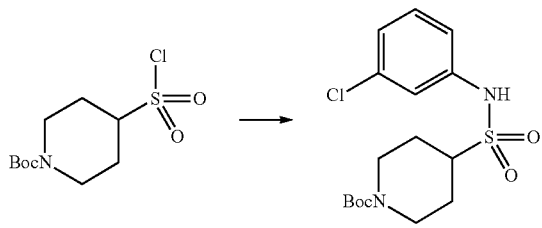 [SMILES: CC(C)(C)OC(=O)N1CCC(S(=O)(=O)Cl)CC1 ; CC(C)(C)OC(=O)N1CCC(S(=O)(=O)Nc2cccc(Cl)c2)CC1]

A solution of tert-butyl 4-(chlorosulfonyl)piperidine-1-carboxylate (3.000 g, 10.572 mmol) in dichloromethane (50 mL) was mixed at the room temperature with 3-chloroaniline (1.618 g, 12.686 mmol) and triethylamine (2.210 mL, 15.858 mmol), and stirred at the same temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=20% to 50%) to give the concentrate, and then the concentrate was dissolved in ethyl acetate (10 mL) and hexane (100 mL) and stirred. The resulting precipitates were collected by filtration, washed by hexane, and dried to give tert-butyl 4-(N-(3-chlorophenyl)sulfamoyl)piperidine-1-carboxylate as white solid (0.860 g, 21.7%).

[Step 2] tert-butyl 4-(N-(3-chlorophenyl)-N-(4-(methoxycarbonyl)benzyl)sulfamoyl)piperidine-1-carboxylate

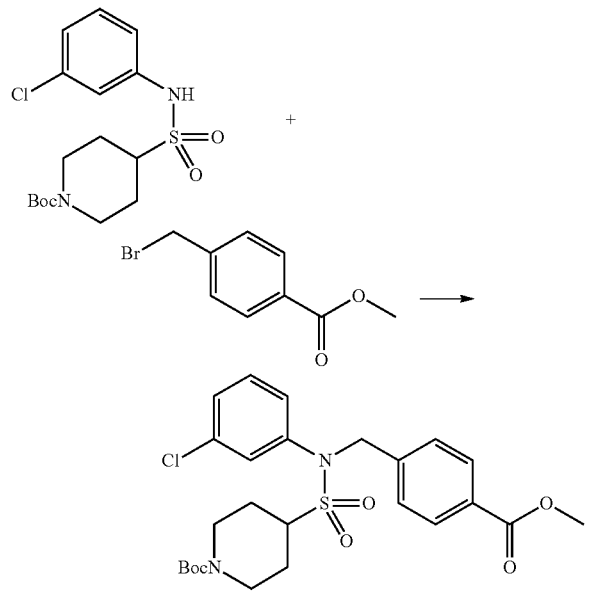

A mixture of tert-butyl 4-(N-(3-chlorophenyl)sulfamoyl)piperidine-1-carboxylate (0.400 g, 1.067 mmol), methyl 4-(bromomethyl)benzoate (0.318 g, 1.387 mmol), potassium carbonate (0.295 g, 2.134 mmol) and potassium iodide (0.354 g, 2.134 mmol) in N,N-dimethylformide (10 mL) was stirred at the room temperature for 6 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=20% to 50%) to give tert-butyl 4-(N-(3-chlorophenyl)-N-(4-(methoxycarbonyl)benzyl)sulfamoyl)piperidine-1-carboxylate as beige solid (0.430 g, 77.0%).

[Step 3] tert-butyl 4-(N-(3-chlorophenyl)-N-(4-(hydrazinecarbonyl)benzyl)sulfamoyl)piperidine-1-carboxylate

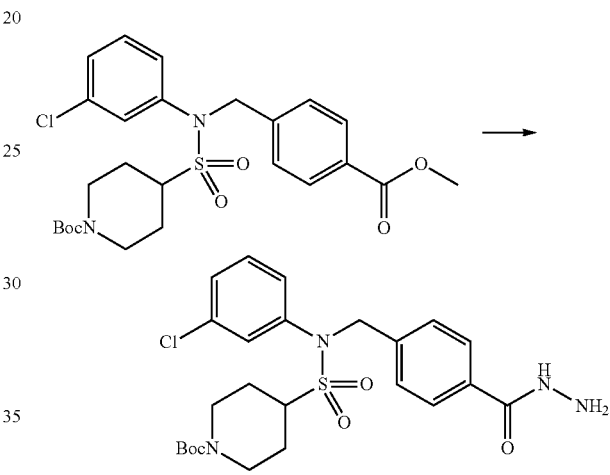

A solution of tert-butyl 4-(N-(3-chlorophenyl)-N-(4-(methoxycarbonyl)benzyl)sulfamoyl)piperidine-1-carboxylate (0.430 g, 0.822 mmol) in tetrahydrofuran (7 mL)/ethanol (7 mL) was mixed at the room temperature with hydrazine monohydrate (1.199 mL, 24.664 mmol). The reaction mixture was heated at reflux for 18 hr, cooled down to the room temperature to terminate the reaction and concentrated under the reduced pressure to remove the solvent. The residue was diluted with water (50 mL) and stirred. The resulting precipitates were collected by filtration, washed by water, and dried to give tert-butyl 4-(N-(3-chlorophenyl)-N-(4-(hydrazinecarbonyl)benzyl)sulfamoyl)piperidine-1-carboxylate as white solid (0.369 g, 85.8%).

[Step 4] tert-butyl 4-(N-(3-chlorophenyl)-N-(4-(5-(difluoromethyl)-1,3,4-oxadiazol-2-yl)benzyl)sulfamoyl)piperidine-1-carboxylate

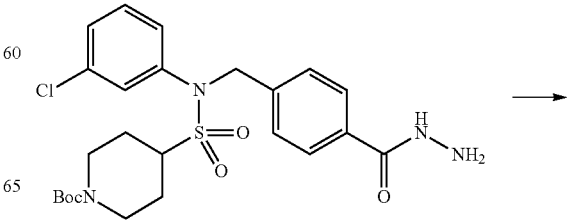

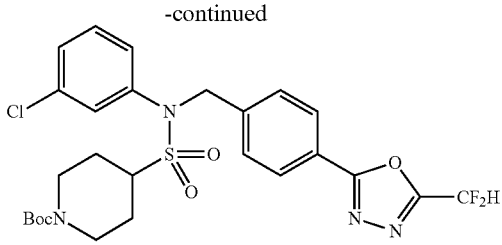

A mixture of tert-butyl 4-(N-(3-chlorophenyl)-N-(4-(hydrazinecarbonyl)benzyl)sulfamoyl)piperidine-1-carboxylate (0.369 g, 0.705 mmol) and triethylamine (0.393 mL, 2.822 mmol) in tetrahydrofuran (10 mL) was treated at the room temperature with 2,2-difluoroacetic anhydride (0.263 mL, 2.116 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=20% to 50%) to give tert-butyl 4-(N-(3-chlorophenyl)-N-(4-(5-(difluoromethyl)-1,3,4-oxadiazol-2-yl)benzyl)sulfamoyl)piperidine-1-carboxylate as white solid (0.352 g, 85.6%).

[Step 5] N-(3-chlorophenyl)-N-(4-(5-(difluoromethyl)-1,3,4-oxadiazol-2-yl)benzyl)piperidine-4-sulfonamide hydrochloride

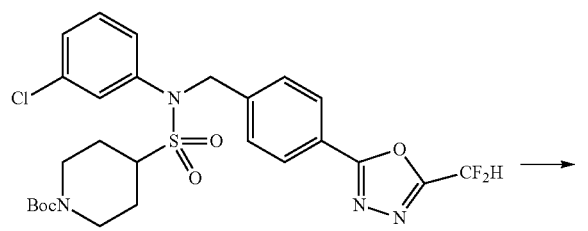

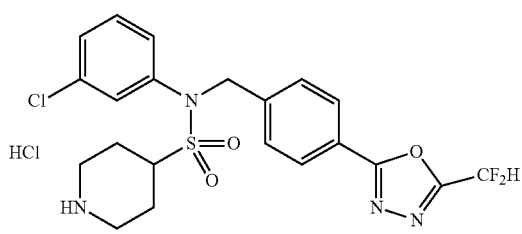

A solution of tert-butyl 4-(N-(3-chlorophenyl)-N-(4-(5-(difluoromethyl)-1,3,4-oxadiazol-2-yl)benzyl)sulfamoyl)piperidine-1-carboxylate (0.352 g, 0.604 mmol) in 1,4-dioxane (2 mL) was mixed at the room temperature with hydrochloric acid (4.00 M solution in 1,4-dioxane, 3.019 mL, 12.074 mmol), and stirred at the same temperature for 1 hr. The reaction mixture was diluted with ethyl acetate (5 mL) and hexane (20 mL) and stirred. The resulting precipitates were collected by filtration, washed by hexane, and dried to give N-(3-chlorophenyl)-N-(4-(5-(difluoromethyl)-1,3,4-oxadiazol-2-yl)benzyl)piperidine-4-sulfonamide hydrochloride as white solid (0.290 g, 92.5%).

[Step 6] Compound 11681

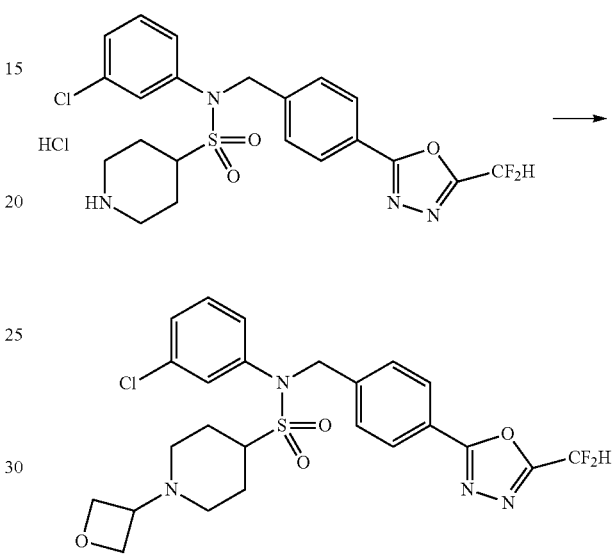

A mixture of N-(3-chlorophenyl)-N-(4-(5-(difluoromethyl)-1,3,4-oxadiazol-2-yl)benzyl)piperidine-4-sulfonamide hydrochloride (0.100 g, 0.193 mmol), oxetan-3-one (0.069 g, 0.963 mmol) and N,N-diisopropylethylamine (0.067 mL, 0.385 mmol) in dichloromethane (5 mL) was treated at the room temperature with sodium triacetoxyborohydride (0.082 g, 0.385 mmol), and stirred at the same temperature for 18 hr. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give the concentrate, and then the concentrate was dissolved in ethyl acetate (3 mL) and hexane (30 mL) and stirred. The resulting precipitates were collected by filtration, washed by hexane, and dried to give N-(3-chlorophenyl)-N-(4-(5-(difluoromethyl)-1,3,4-oxadiazol-2-yl)benzyl)-1-(oxetan-3-yl)piperidine-4-sulfonamide as white solid (0.068 g, 65.5%).

$^1$H NMR (400 MHz, DMSO-d6) δ 8.00 (d, 2H, J=8.4 Hz), 7.66 (s, 0.25H), 7.59-7.53 (t, 1H, J=2.0 Hz), 7.53-7.48 (m, 2.5H), 7.44 (ddd, 1H, J=7.9, 2.1, 1.1 Hz), 7.40 (s, 0.25H), 7.35 (t, 1H, J=8.0 Hz), 7.29 (ddd, 1H, J=8.1, 2.1, 1.2 Hz), 5.12 (s, 2H), 4.53 (t, 2H, J=6.5 Hz), 4.42 (t, 2H, J=6.1 Hz), 3.40 (m, 1H), 3.31 (m, 1H), 2.80 (d, 2H, J=11.1 Hz), 2.12-2.00 (m, 2H), 1.86 (t, 2H, J=11.4 Hz), 1.79-1.65 (m, 2H); LRMS (ES) m/z 539.2 (M$^+$+1).

EXAMPLE 196

Compound 11682, N-(4-(5-(difluoromethyl)-1,3,4-oxadiazol-2-yl)benzyl)-1-(oxetan-3-yl)-N-(m-tolyl)piperidine-4-sulfonamide

[Step 1] tert-butyl 4-(N-(m-tolyl)sulfamoyl)piperidine-1-carboxylate

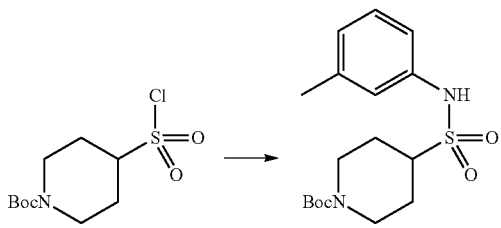 [SMILES: CC(C)(C)OC(=O)N1CCC(S(=O)(=O)Cl)CC1 ; Cc1cccc(NS(=O)(=O)C2CCN(C(=O)OC(C)(C)C)CC2)c1]

A solution of tert-butyl 4-(chlorosulfonyl)piperidine-1-carboxylate (3.000 g, 10.572 mmol) in dichloromethane (50 mL) was mixed at the room temperature with m-toluidine hydrochloride (1.822 g, 12.686 mmol) and triethylamine (3.684 mL, 26.430 mmol), and stirred at the same temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give the concentrate, and then the concentrate was dissolved in ethyl acetate (10 mL) and hexane (100 mL) and stirred. The resulting precipitates were collected by filtration, washed by hexane, and dried to give tert-butyl 4-(N-(m-tolyl)sulfamoyl)piperidine-1-carboxylate as white solid (1.880 g, 50.2%).

[Step 2] tert-butyl 4-(N-(4-(methoxycarbonyl)benzyl)-N-(m-tolyl)sulfamoyl)piperidine-1-carboxylate

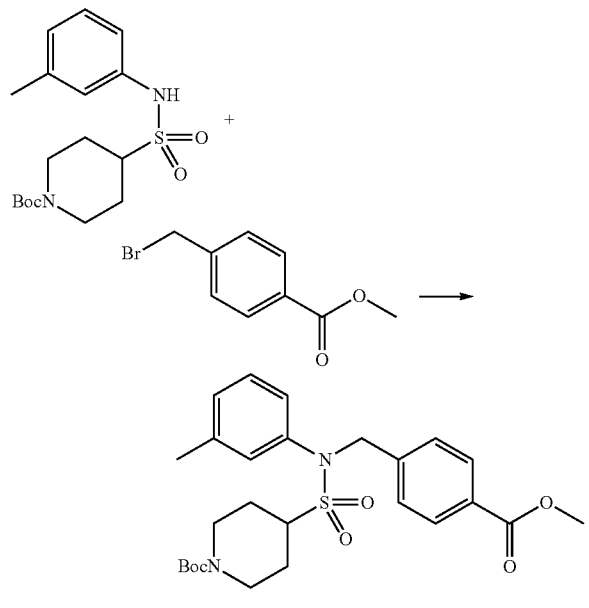

A mixture of tert-butyl 4-(N-(m-tolyl)sulfamoyl)piperidine-1-carboxylate (0.880 g, 2.483 mmol), methyl 4-(bromomethyl)benzoate (0.739 g, 3.227 mmol), potassium carbonate (0.686 g, 4.965 mmol) and potassium iodide (0.824 g, 4.965 mmol) in N,N-dimethylformamide (20 mL) was stirred at the room temperature for 6 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give tert-butyl 4-(N-(4-(methoxycarbonyl)benzyl)-N-(m-tolyl)sulfamoyl)piperidine-1-carboxylate as beige solid (0.930 g, 74.5%).

[Step 3] tert-butyl 4-(N-(4-(hydrazinecarbonyl)benzyl)-N-(m-tolyl)sulfamoyl)piperidine-1-carboxylate

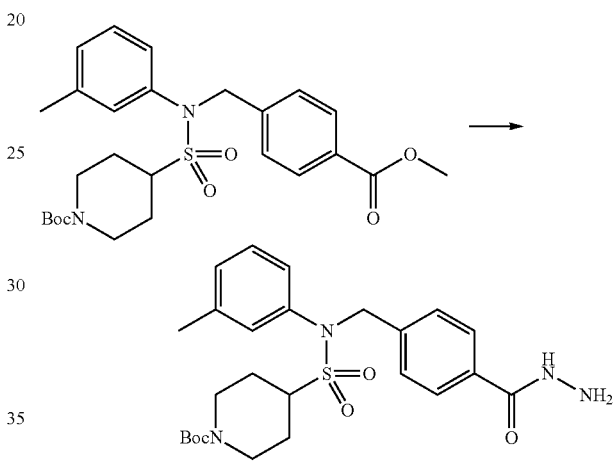

A solution of tert-butyl 4-(N-(4-(methoxycarbonyl)benzyl)-N-(m-tolyl)sulfamoyl)piperidine-1-carboxylate (0.930 g, 1.850 mmol) in tetrahydrofuran (20 mL)/ethanol (20 mL) was mixed at the room temperature with hydrazine monohydrate (2.698 mL, 55.508 mmol). The reaction mixture was heated at reflux for 18 hr, cooled down to the room temperature to terminate the reaction and concentrated under the reduced pressure to remove the solvent. The residue was diluted with water (50 mL) and stirred. The resulting precipitates were collected by filtration, washed by water, and dried to give tert-butyl 4-(N-(4-(hydrazinecarbonyl)benzyl)-N-(m-tolyl)sulfamoyl)piperidine-1-carboxylate as white solid (0.866 g, 93.1%).

[Step 4] tert-butyl 4-(N-(4-(5-(difluoromethyl)-1,3,4-oxadiazol-2-yl)benzyl)-N-(m-tolyl)sulfamoyl)piperidine-1-carboxylate

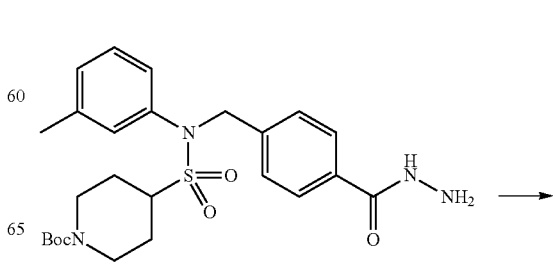

-continued

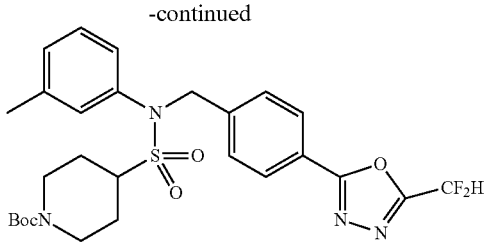

A reaction mixture of tert-butyl 4-(N-(4-(hydrazinecarbonyl)benzyl)-N-(m-tolyl)sulfamoyl)piperidine-1-carboxylate (0.866 g, 1.723 mmol) and triethylamine (0.961 mL, 6.892 mmol) in tetrahydrofuran (20 mL) was treated at the room temperature with 2,2-difluoroacetic anhydride (0.643 mL, 5.169 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give tert-butyl 4-(N-(4-(5-(difluoromethyl)-1,3,4-oxadiazol-2-yl)benzyl)-N-(m-tolyl)sulfamoyl)piperidine-1-carboxylate as white solid (0.823 g, 84.9%).

[Step 5] N-(4-(5-(difluoromethyl)-1,3,4-oxadiazol-2-yl)benzyl)-N-(m-tolyl)piperidine-4-sulfonamide hydrochloride

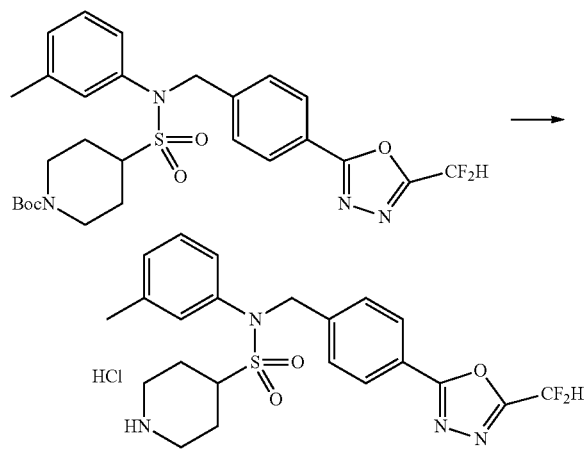

A suspension of tert-butyl 4-(N-(4-(5-(difluoromethyl)-1,3,4-oxadiazol-2-yl)benzyl)-N-(m-tolyl)sulfamoyl)piperidine-1-carboxylate (0.823 g, 1.463 mmol) in 1,4-dioxane (5 mL) was mixed at the room temperature with hydrochloric acid (4.00 M solution in 1,4-dioxane, 5.485 mL, 21.942 mmol), and stirred at the same temperature for 1 hr. The reaction mixture was diluted with ethyl acetate (10 mL) and hexane (30 mL) and stirred. The resulting precipitates were collected by filtration, washed by hexane, and dried to give N-(4-(5-(difluoromethyl)-1,3,4-oxadiazol-2-yl)benzyl)-N-(m-tolyl)piperidine-4-sulfonamide hydrochloride as white solid (0.723 g, 99.1%).

[Step 6] Compound 11682

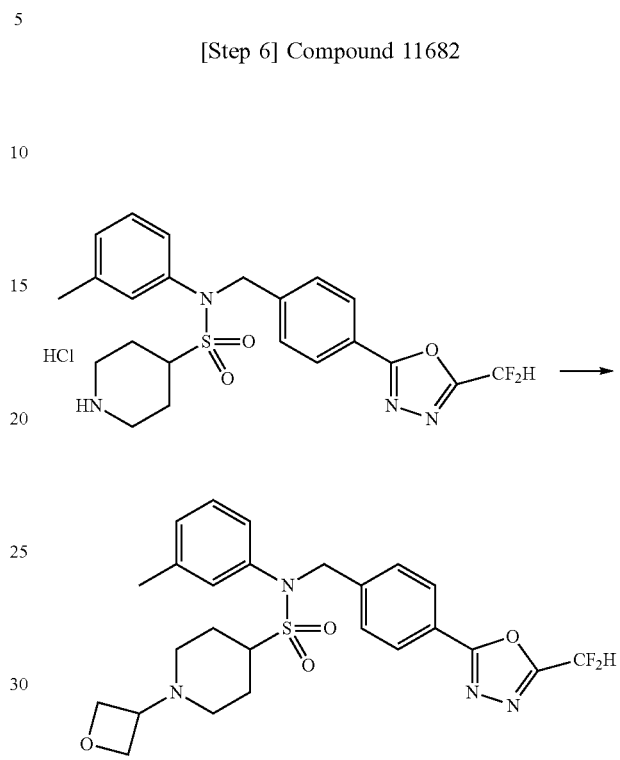

A mixture of N-(4-(5-(difluoromethyl)-1,3,4-oxadiazol-2-yl)benzyl)-N-(m-tolyl)piperidine-4-sulfonamide hydrochloride (0.100 g, 0.200 mmol), oxetan-3-one (0.072 g, 1.002 mmol) and N,N-diisopropylethylamine (0.070 mL, 0.401 mmol) in dichloromethane (5 mL) was treated at the room temperature with sodium triacetoxyborohydride (0.085 g, 0.401 mmol), and stirred at the same temperature for 18 hr. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give the concentrate, and then the concentrate was dissolved in ethyl acetate (3 mL) and hexane (30 mL) and stirred. The resulting precipitates were collected by filtration, washed by hexane, and dried to give N-(4-(5-(difluoromethyl)-1,3,4-oxadiazol-2-yl)benzyl)-1-(oxetan-3-yl)-N-(m-tolyl)piperidine-4-sulfonamide as white solid (0.072 g, 69.3%).

$^1$H NMR (400 MHz, DMSO-d6) δ 7.98 (d, 2H, J=8.3 Hz), 7.66 (s, 0.25H), 7.56-7.47 (m, 2.5H), 7.40 (s, 0.25H), 7.27-7.17 (m, 3H), 7.04 (d, 1H, J=6.9 Hz), 5.06 (s, 2H), 4.53 (t, 2H, J=6.5 Hz), 4.42 (t, 2H, J=6.1 Hz), 3.40 (m, 1H), 3.25 (m, 1H), 2.80 (d, 2H, J=10.8 Hz), 2.25 (s, 3H), 2.14-2.02 (m, 2H), 1.81 (t, 2H, J=11.5 Hz), 1.79-1.69 (m, 2H); LRMS (ES) m/z 519.3 (M$^+$+1).

EXAMPLE 197

Compound 11683, N-(3-chlorophenyl)-N-((5-(5-(difluoromethyl)-1,3,4-oxadiazol-2-yl)pyridin-2-yl)methyl)-1-(oxetan-3-yl)piperidine-4-sulfonamide

[Step 1] methyl 6-(((1-(tert-butoxycarbonyl)-N-(3-chlorophenyl)piperidine)-4-sulfonamido)methyl)nicotinate

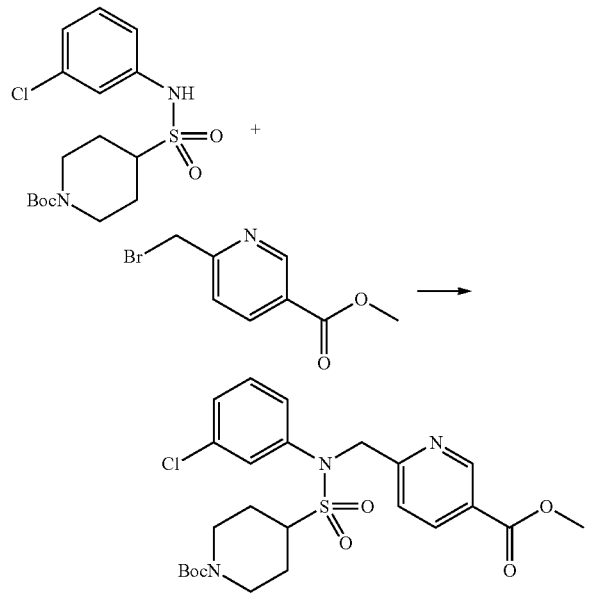

A mixture of tert-butyl 4-(N-(3-chlorophenyl)sulfamoyl)piperidine-1-carboxylate (0.460 g, 1.227 mmol), methyl 6-(bromomethyl)nicotinate (0.367 g, 1.595 mmol), potassium carbonate (0.339 g, 2.454 mmol) and potassium iodide (0.407 g, 2.454 mmol) in N,N-dimethylformide (10 mL) was stirred at the room temperature for 6 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=30% to 60%) to give methyl 6-(((1-(tert-butoxycarbonyl)-N-(3-chlorophenyl)piperidine)-4-sulfonamido)methyl)nicotinate as white solid (0.436 g, 67.8%).

[Step 2] tert-butyl 4-(N-(3-chlorophenyl)-N-((5-(hydrazinecarbonyl)pyridin-2-yl)methyl)sulfamoyl)piperidine-1-carboxylate

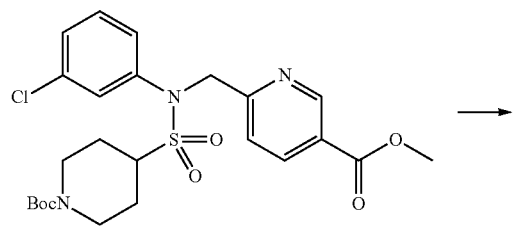

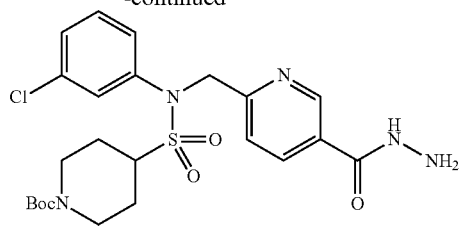

A solution of methyl 6-(((1-(tert-butoxycarbonyl)-N-(3-chlorophenyl)piperidine)-4-sulfonamido)methyl)nicotinate (0.436 g, 0.832 mmol) in tetrahydrofuran (7 mL)/ethanol (7 mL) was mixed at the room temperature with hydrazine monohydrate (1.213 mL, 24.960 mmol). The reaction mixture was heated at reflux for 18 hr, cooled down to the room temperature to terminate the reaction and concentrated under the reduced pressure to remove the solvent. The residue was diluted with water (50 mL) and stirred. The resulting precipitates were collected by filtration, washed by water, and dried to give tert-butyl 4-(N-(3-chlorophenyl)-N-((5-(hydrazinecarbonyl)pyridin-2-yl)methyl)sulfamoyl)piperidine-1-carboxylate as white solid (0.275 g, 63.1%).

[Step 3] tert-butyl 4-(N-(3-chlorophenyl)-N-((5-(5-(difluoromethyl)-1,3,4-oxadiazol-2-yl)pyridin-2-yl)methyl)sulfamoyl)piperidine-1-carboxylate A reaction mixture of tert-butyl 4-(N-(3-chlorophenyl)-N-((5-(hydrazinecarbonyl)pyridin-2-yl)methyl)sulfamoyl)piperidine-1-carboxylate (0.275 g, 0.525 mmol) and triethylamine (0.293 mL, 2.099 mmol) in tetrahydrofuran (10 mL) was treated at the room temperature with 2,2-difluoroacetic anhydride (0.196 mL, 1.574 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=20% to 50%) to give tert-butyl 4-(N-(3-chlorophenyl)-N-((5-(5-(difluoromethyl)-1,3,4-oxadiazol-2-yl)pyridin-2-yl)methyl)sulfamoyl)piperidine-1-carboxylate as white solid (0.230 g, 75.0%).

[Step 4] N-(3-chlorophenyl)-N-((5-(5-(difluoromethyl)-1,3,4-oxadiazol-2-yl)pyridin-2-yl)methyl)piperidine-4-sulfonamide dihydrochloride

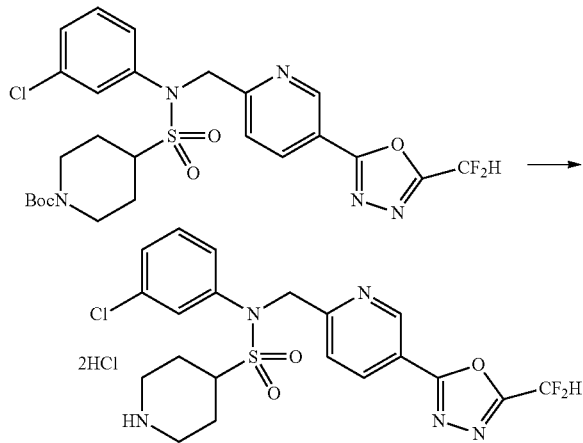

A solution of tert-butyl 4-(N-(3-chlorophenyl)-N-((5-(5-(difluoromethyl)-1,3,4-oxadiazol-2-yl)pyridin-2-yl)methyl)sulfamoyl)piperidine-1-carboxylate (0.230 g, 0.394 mmol) in 1,4-dioxane (2 mL) was mixed at the room temperature with hydrochloric acid (4.00 M solution in 1,4-dioxane, 1.969 mL, 7.876 mmol), and stirred at the same temperature for 1 hr. The reaction mixture was diluted with ethyl acetate (5 mL) and hexane (20 mL) and stirred. The resulting precipitates were collected by filtration, washed by hexane, and dried to give N-(3-chlorophenyl)-N-((5-(5-(difluoromethyl)-1,3,4-oxadiazol-2-yl)pyridin-2-yl)methyl)piperidine-4-sulfonamide dihydrochloride as white solid (0.206 g, 93.9%).

[Step 5] Compound 11683

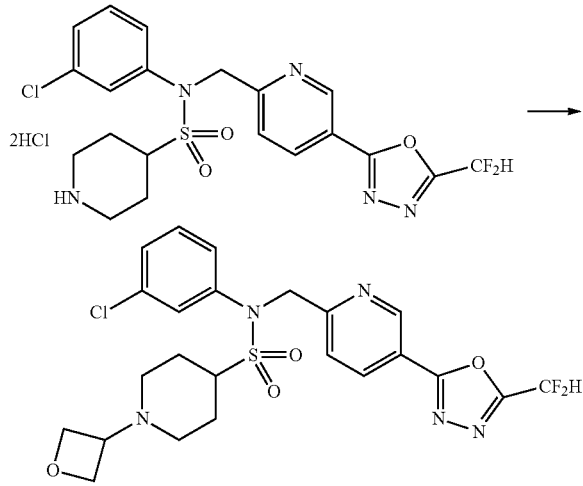

A mixture of N-(3-chlorophenyl)-N-((5-(5-(difluoromethyl)-1,3,4-oxadiazol-2-yl)pyridin-2-yl)methyl)piperidine-4-sulfonamide dihydrochloride (0.100 g, 0.180 mmol), oxetan-3-one (0.065 g, 0.898 mmol) and N,N-diisopropylethylamine (0.094 mL, 0.539 mmol) in dichloromethane (5 mL) was treated at the room temperature with sodium triacetoxyborohydride (0.076 g, 0.359 mmol), and stirred at the same temperature for 18 hr. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 10%) to give the concentrate, and then the concentrate was dissolved in ethyl acetate (3 mL) and hexane (30 mL) and stirred. The resulting precipitates were collected by filtration, washed by hexane, and dried to give N-(3-chlorophenyl)-N-((5-(5-(difluoromethyl)-1,3,4-oxadiazol-2-yl)pyridin-2-yl)methyl)-1-(oxetan-3-yl)piperidine-4-sulfonamide as white solid (0.076 g, 78.4%).

$^1$H NMR (400 MHz, DMSO-d6) δ 9.10 (d, 1H, J=2.2 Hz), 8.41 (m, 1H), 7.72-7.67 (m, 1.25H), 7.64 (t, 1H, J=2.1 Hz), 7.56 (s, 0.5H), 7.51 (m, 1H), 7.43 (s, 0.25H), 7.37 (t, 1H, J=8.0 Hz), 7.31 (m, 1H), 5.21 (s, 2H), 4.52 (t, 2H, J=6.5 Hz), 4.42 (t, 2H, J=6.1 Hz), 3.47-3.38 (m, 2H), 2.80 (d, 2H, J=11.1 Hz), 2.11 (d, 2H, J=12.5 Hz), 1.85 (t, 2H, J=11.4 Hz), 1.77-1.64 (m, 2H); LRMS (ES) m/z 540.2 (M⁺+1).

EXAMPLE 198

Compound 11684, N-((5-(5-(difluoromethyl)-1,3,4-oxadiazol-2-yl)pyridin-2-yl)methyl)-1-(oxetan-3-yl)-N-(m-tolyl)piperidine-4-sulfonamide

[Step 1] methyl 6-(((1-(tert-butoxycarbonyl)-N-(m-tolyl)piperidine)-4-sulfonamido)methyl)nicotinate

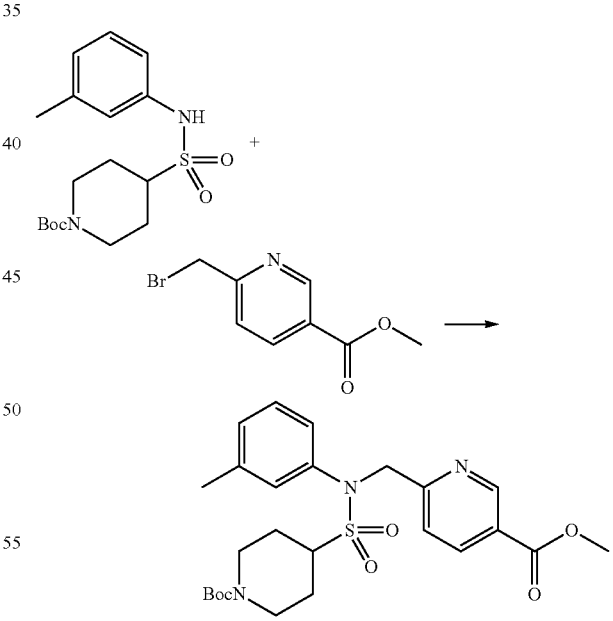

A mixture of tert-butyl 4-(N-(m-tolyl)sulfamoyl)piperidine-1-carboxylate (1.000 g, 2.821 mmol), methyl 6-(bromomethyl)nicotinate (0.844 g, 3.667 mmol), potassium carbonate (0.780 g, 5.642 mmol) and potassium iodide (0.937 g, 5.642 mmol) in N,N-dimethylformide (20 mL) was stirred at the room temperature for 6 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=30% to 60%) to give methyl 6-(((1-(tert-butoxycarbonyl)-N-(m-tolyl)piperidine)-4-sulfonamido)methyl)nicotinate as white solid (1.230 g, 86.6%).

[Step 2] tert-butyl 4-(N-((5-(hydrazinecarbonyl)pyridin-2-yl)methyl)-N-(m-tolyl)sulfamoyl)piperidine-1-carboxylate

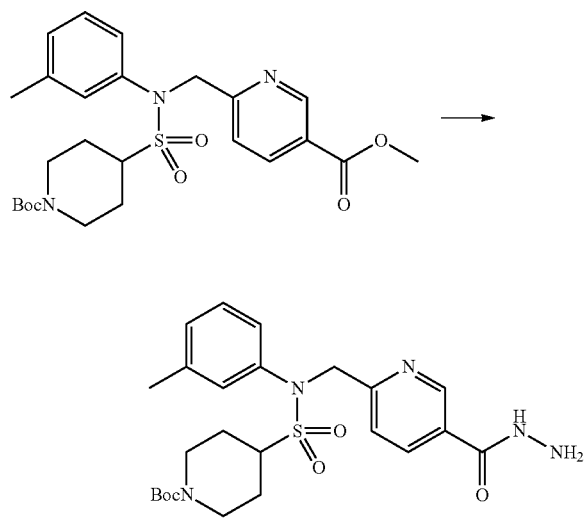

A solution of methyl 6-(((1-(tert-butoxycarbonyl)-N-(m-tolyl)piperidine)-4-sulfonamido)methyl)nicotinate (1.230 g, 2.442 mmol) in tetrahydrofuran (7 mL)/ethanol (7 mL) was mixed at the room temperature with hydrazine monohydrate (3.561 mL, 73.271 mmol). The reaction mixture was heated at reflux for 18 hr, cooled down to the room temperature to terminate the reaction and concentrated under the reduced pressure to remove the solvent. The residue was diluted with water (50 mL) and stirred. The resulting precipitates were collected by filtration, washed by water, and dried to give tert-butyl 4-(N-((5-(hydrazinecarbonyl)pyridin-2-yl)methyl)-N-(m-tolyl)sulfamoyl)piperidine-1-carboxylate as white solid (0.961 g, 78.1%).

[Step 3] tert-butyl 4-(N-((5-(5-(difluoromethyl)-1,3,4-oxadiazol-2-yl)pyridin-2-yl)methyl)-N-(m-tolyl)sulfamoyl)piperidine-1-carboxylate

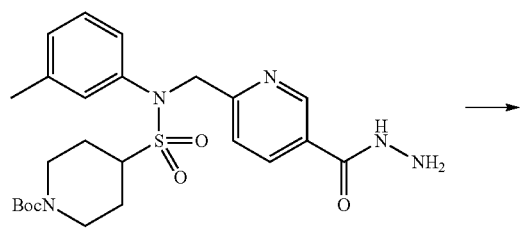

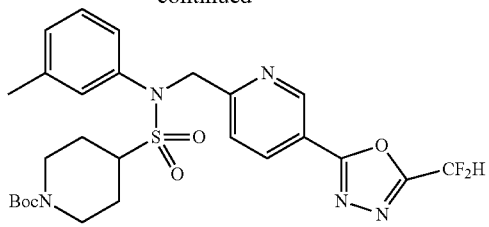

A mixture of tert-butyl 4-(N-((5-(hydrazinecarbonyl)pyridin-2-yl)methyl)-N-(m-tolyl)sulfamoyl)piperidine-1-carboxylate (0.961 g, 1.908 mmol) and triethylamine (1.064 mL, 7.633 mmol) in tetrahydrofuran (20 mL) was treated at the room temperature with 2,2-difluoroacetic anhydride (0.712 mL, 5.725 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=20% to 50%) to give tert-butyl 4-(N-((5-(5-(difluoromethyl)-1,3,4-oxadiazol-2-yl)pyridin-2-yl)methyl)-N-(m-tolyl)sulfamoyl)piperidine-1-carboxylate as white solid (0.910 g, 84.6%).

[Step 4] N-((5-(5-(difluoromethyl)-1,3,4-oxadiazol-2-yl)pyridin-2-yl)methyl)-N-(m-tolyl)piperidine-4-sulfonamide dihydrochloride

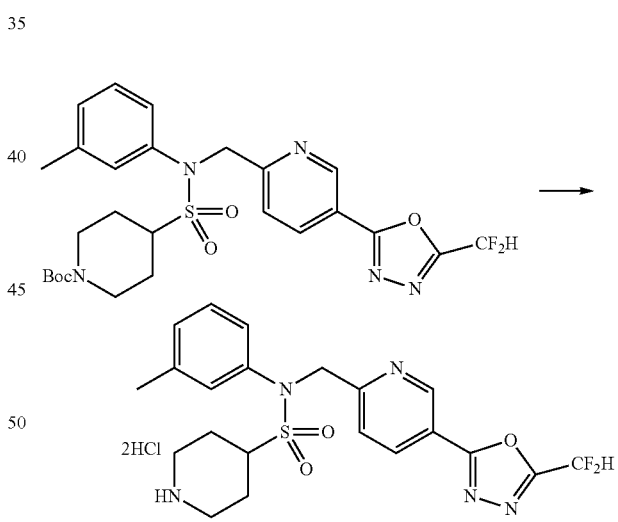

A solution of tert-butyl 4-(N-((5-(5-(difluoromethyl)-1,3,4-oxadiazol-2-yl)pyridin-2-yl)methyl)-N-(m-tolyl)sulfamoyl)piperidine-1-carboxylate (0.910 g, 1.615 mmol) in 1,4-dioxane (5 mL) was mixed at the room temperature with hydrochloric acid (4.00 M solution in 1,4-dioxane, 6.055 mL, 24.218 mmol), and stirred at the same temperature for 1 hr. The reaction mixture was diluted with ethyl acetate (10 mL) and hexane (30 mL) and stirred. The resulting precipitates were collected by filtration, washed by hexane, and dried to give N-((5-(5-(difluoromethyl)-1,3,4-oxadiazol-2-yl)pyridin-2-yl)methyl)-N-(m-tolyl)piperidine-4-sulfonamide dihydrochloride as white solid (0.843 g, 97.3%).

603

[Step 5] Compound 11684

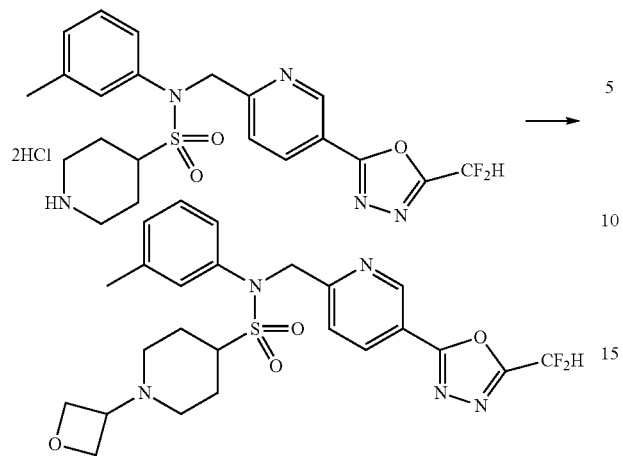

A mixture of N-((5-(5-(difluoromethyl)-1,3,4-oxadiazol-2-yl)pyridin-2-yl)methyl)-N-(m-tolyl)piperidine-4-sulfonamide dihydrochloride (0.100 g, 0.186 mmol), oxetan-3-one (0.067 g, 0.932 mmol) and N,N-diisopropylethylamine (0.097 mL, 0.559 mmol) in dichloromethane (5 mL) was treated at the room temperature with sodium triacetoxyborohydride (0.079 g, 0.373 mmol), and stirred at the same temperature for 18 hr. Then, saturated aqueous sodium bicarbonate solution was added to the reaction mixture, followed by extraction with ammonium chloride. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 10%) to give the concentrate, and then the concentrate was dissolved in ethyl acetate (3 mL) and hexane (30 mL) and stirred. The resulting precipitates were collected by filtration, washed by hexane, and dried to give N-((5-(5-(difluoromethyl)-1,3,4-oxadiazol-2-yl)pyridin-2-yl)methyl)-1-(oxetan-3-yl)-N-(m-tolyl)piperidine-4-sulfonamide as white solid (0.049 g, 50.6%).

$^1$H NMR (400 MHz, DMSO-d6) δ 9.09 (dd, 1H, J=2.1, 0.8 Hz), 8.41 (dd, 1H, J=8.3, 2.3 Hz), 7.71 (d, 1H, J=8.6 Hz), 7.56 (t, 1H, J=51.3 Hz), 7.33 (s, 1H), 7.30 (d, 1H, J=8.0 Hz), 7.22 (t, 1H, J=7.7 Hz), 7.06 (d, 1H, J=7.5 Hz), 5.15 (s, 2H), 4.52 (t, 2H, J=6.5 Hz), 4.42 (t, 2H, J=6.1 Hz), 3.40 (m, 1H), 3.26 (m, 1H), 2.79 (d, 2H, J=11.0 Hz), 2.26 (s, 3H), 2.11 (d, 2H, J=12.2 Hz), 1.84 (t, 2H, J=11.4 Hz), 1.79-1.64 (m, 2H); LRMS (ES) m/z 520.3 (M⁺+1).

EXAMPLE 199

Compound 11685, N-(4-(5-(difluoromethyl)-1,3,4-oxadiazol-2-yl)benzyl)-3-(dimethylamino)-N-phenylpropane-1-sulfonamide

[Step 1] methyl 4-(((3-(azetidin-1-yl)-N-phenylpropyl)sulfonamido)methyl)benzoate

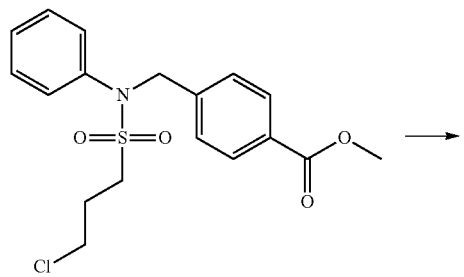

604

-continued

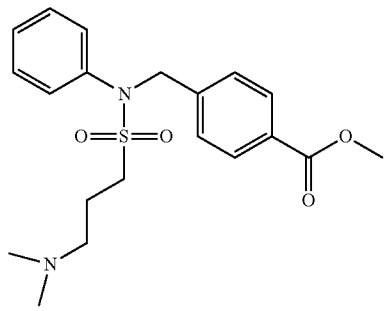

A solution of methyl 4-(((3-chloro-N-phenylpropyl)sulfonamido)methyl)benzoate (0.250 g, 0.655 mmol), azetidine hydrochloride (0.122 g, 1.309 mmol) and potassium carbonate (0.136 g, 0.982 mmol) in N,N-dimethylformide (3 mL) was stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 30%) to give methyl 4-(((3-(azetidin-1-yl)-N-phenylpropyl)sulfonamido)methyl)benzoate as white solid (0.108 g, 42.3%).

[Step 2] 3-(dimethylamino)-N-(4-(hydrazinecarbonyl)benzyl)-N-phenylpropane-1-sulfonamide

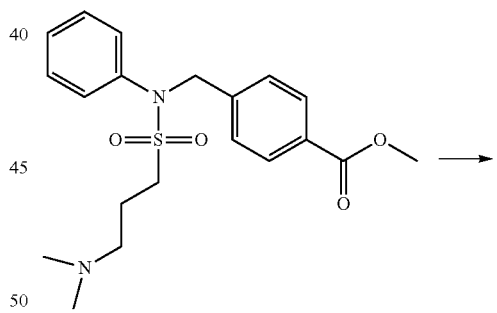

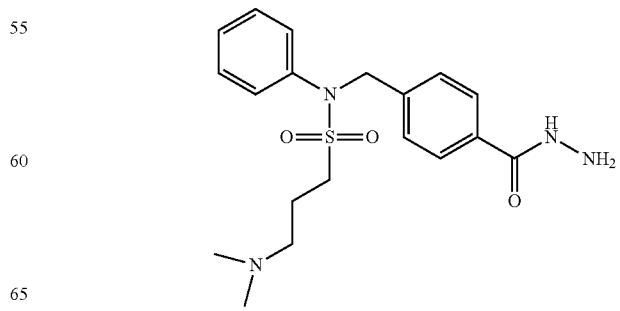

A solution of methyl 4-(((3-(dimethylamino)-N-phenyl-propyl)sulfonamido)methyl)benzoate (0.108 g, 0.277 mmol) and hydrazine monohydrate (0.134 mL, 2.766 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give 3-(dimethylamino)-N-(4-(hydrazinecarbonyl)benzyl)-N-phenylpropane-1-sulfonamide as white solid (0.099 g, 91.5%).

[Step 3] Compound 11685

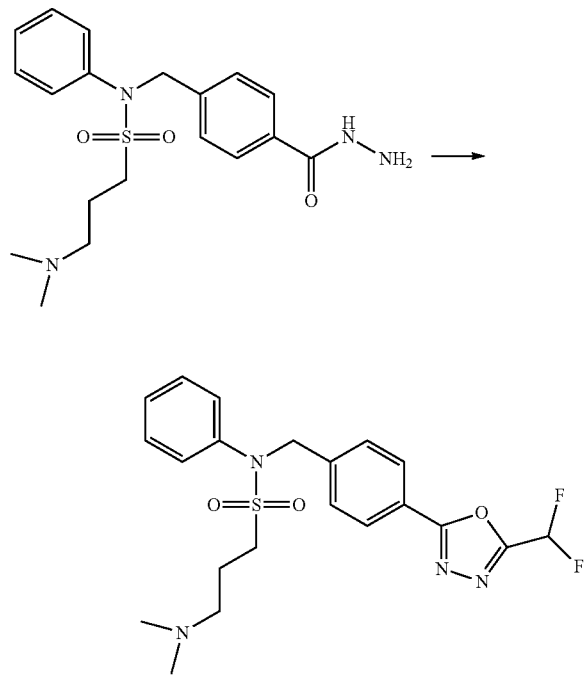

A solution of 3-(dimethylamino)-N-(4-(hydrazinecarbonyl)benzyl)-N-phenylpropane-1-sulfonamide (0.099 g, 0.253 mmol), 2,2-difluoroacetic anhydride (0.314 mL, 2.528 mmol) and triethylamine (0.176 mL, 1.264 mmol) in tetrahydrofuran (5 mL) was stirred at 80° C. for 1 hr and cooled down to the room temperature to terminate the reaction. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)benzyl)-3-(dimethylamino)-N-phenylpropane-1-sulfonamide as white solid (0.023 g, 20.2%).

$^1$H NMR (400 MHz, CD3OD) δ8.03 (d, 2H, J=8.4 Hz), 7.55 (d, 2H, J=8.4 Hz), 7.43~7.26 (m, 5H), 7.21 (t, 1H, J=51.7 Hz), 5.05 (s, 2H), 3.28 (t, 2H, J=7.6 Hz), 2.60 (t, 2H, J=7.5 Hz), 2.36 (s, 6H), 2.11~2.03 (m, 2H); LRMS (ES) m/z 451.3 (M$^+$+1).

EXAMPLE 200

Compound 11686, 1-(bicyclo[2.2.1]heptan-2-yl)-N-((5-(5-(difluoromethyl)-1,3,4-oxadiazol-2-yl)pyridin-2-yl)methyl)-N-(m-tolyl)piperidine-4-sulfonamide

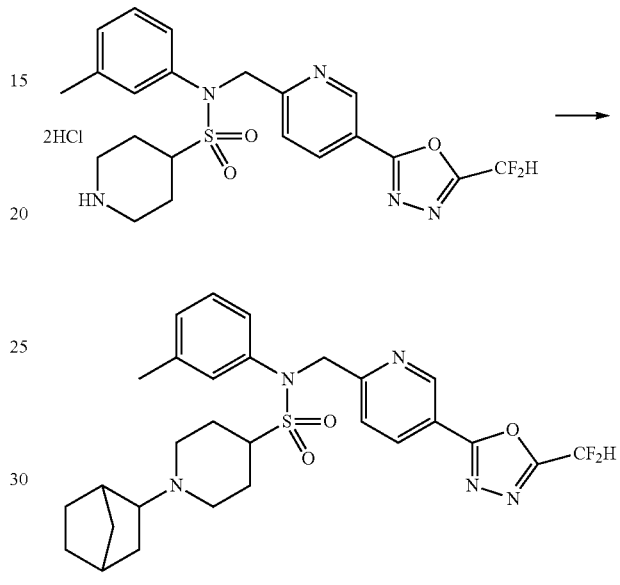

A mixture of N-((5-(5-(difluoromethyl)-1,3,4-oxadiazol-2-yl)pyridin-2-yl)methyl)-N-(m-tolyl)piperidine-4-sulfonamide dihydrochloride (0.050 g, 0.093 mmol), bicyclo[2.2.1]heptan-2-one (0.021 g, 0.186 mmol) and N,N-diisopropylethylamine (0.041 mL, 0.233 mmol) in dichloromethane (5 mL) was treated at the room temperature with sodium triacetoxyborohydride (0.040 g, 0.186 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=50% to 80%) to give the concentrate, and then the concentrate was dissolved in ethyl acetate (3 mL) and hexane (30 mL) and stirred. The resulting precipitates were collected by filtration, washed by hexane, and dried to give 1-(bicyclo[2.2.1]heptan-2-yl)-N-((5-(5-(difluoromethyl)-1,3,4-oxadiazol-2-yl)pyridin-2-yl)methyl)-N-(m-tolyl)piperidine-4-sulfonamide as white solid (0.039 g, 75.0%).

$^1$H NMR (400 MHz, DMSO-d6) δ 9.09 (dd, 1H, J=2.4, 0.8 Hz), 8.42 (dd, 1H, J=8.3, 2.3 Hz), 7.71 (d, 1H, J=8.3 Hz), 7.56 (t, 1H, J=51.2 Hz), 7.33 (s, 1H), 7.29 (d, 1H, J=8.2 Hz), 7.22 (t, 1H, J=7.7 Hz), 7.06 (d, 1H, J=7.5 Hz), 5.15 (s, 2H), 3.25 (m, 1H), 3.03-2.89 (m, 2H), 2.29-2.24 (m, 4H), 2.19 (m, 1H), 2.15-2.04 (m, 3H), 1.84-1.62 (m, 6H), 1.43 (m, 1H), 1.32 (m, 1H), 1.27-1.13 (m, 3H), 0.81 (m, 1H); LRMS (ES) m/z 558.3 (M$^+$+1).

EXAMPLE 201

Compound 11687, 1-(4,4-difluorocyclohexyl)-N-((5-(5-(difluoromethyl)-1,3,4-oxadiazol-2-yl)pyridin-2-yl)methyl)-N-(m-tolyl)piperidine-4-sulfonamide

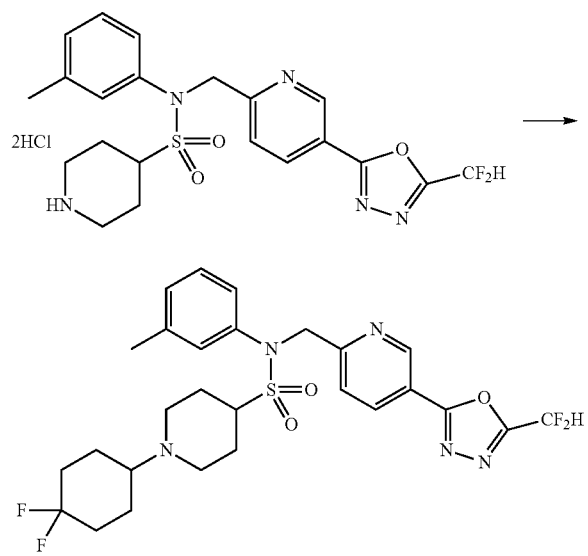

A mixture of N-((5-(5-(difluoromethyl)-1,3,4-oxadiazol-2-yl)pyridin-2-yl)methyl)-N-(m-tolyl)piperidine-4-sulfonamide dihydrochloride (0.050 g, 0.093 mmol), 4,4-difluorocyclohexan-1-one (0.025 g, 0.186 mmol) and N,N-diisopropylethylamine (0.041 mL, 0.233 mmol) in dichloromethane (5 mL) was treated at the room temperature with sodium triacetoxyborohydride (0.040 g, 0.186 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 4 g cartridge; ethyl acetate/hexane=50% to 80%) to give the concentrate, and then the concentrate was dissolved in ethyl acetate (3 mL) and hexane (30 mL) and stirred. The resulting precipitates were collected by filtration, washed by hexane, and dried to give 1-(4,4-difluorocyclohexyl)-N-((5-(5-(difluoromethyl)-1,3,4-oxadiazol-2-yl)pyridin-2-yl)methyl)-N-(m-tolyl)piperidine-4-sulfonamide as white solid (0.036 g, 66.4%).

$^1$H NMR (400 MHz, DMSO-d6) δ 9.09 (m, 1H), 8.41 (dd, 1H, J=8.3, 2.3 Hz), 7.71 (d, 1H, J=8.2 Hz), 7.56 (t, 1H, J=51.3 Hz), 7.33 (s, 1H), 7.29 (d, 1H, J=8.3 Hz), 7.22 (t, 1H, J=7.7 Hz), 7.06 (d, 1H, J=7.6 Hz), 5.15 (s, 2H), 3.41 (m, 1H), 3.25 (m, 1H), 2.92 (d, 2H, J=11.1 Hz), 2.26 (s, 3H), 2.19 (t, 2H, J=11.4 Hz), 2.13-1.98 (m, 4H), 1.87-1.62 (m, 6H), 1.58-1.47 (m, 2H); LRMS (ES) m/z 582.3 ($M^+$+1).

EXAMPLE 202

Compound 11688, N-((5-(5-(difluoromethyl)-1,3,4-oxadiazol-2-yl)pyridin-2-yl)methyl)-1-((1r,4r)-4-fluorocyclohexyl)-N-(m-tolyl)piperidine-4-sulfonamide

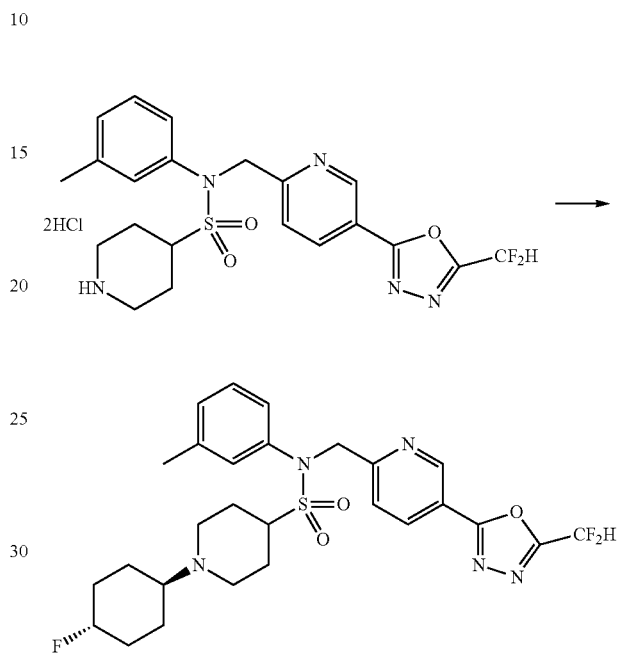

A mixture of N-((5-(5-(difluoromethyl)-1,3,4-oxadiazol-2-yl)pyridin-2-yl)methyl)-N-(m-tolyl)piperidine-4-sulfonamide dihydrochloride (0.050 g, 0.093 mmol), 4-fluorocyclohexan-1-one (0.022 g, 0.186 mmol) and N,N-diisopropylethylamine (0.041 mL, 0.233 mmol) in dichloromethane (5 mL) was treated at the room temperature with sodium triacetoxyborohydride (0.040 g, 0.186 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 4 g cartridge; ethyl acetate/hexane=60% to 90%) to give N-((5-(5-(difluoromethyl)-1,3,4-oxadiazol-2-yl)pyridin-2-yl)methyl)-1-((1r,4r)-4-fluorocyclohexyl)-N-(m-tolyl)piperidine-4-sulfonamide as white solid (0.008 g, 15.2%).

$^1$H NMR (400 MHz, DMSO-d6) δ 9.09 (m, 1H), 8.41 (dd, 1H, J=8.3, 2.3 Hz), 7.71 (d, 1H, J=8.3 Hz), 7.56 (t, 1H, J=51.3 Hz), 7.33 (s, 1H), 7.29 (d, 1H, J=8.0 Hz), 7.22 (t, 1H, J=7.7 Hz), 7.05 (d, 1H, J=7.7 Hz), 5.14 (s, 2H), 4.63-4.36 (ddt, 1H, J=49.3, 10.0, 5.5 Hz), 3.21 (m, 1H), 2.91 (d, 2H, J=11.1 Hz), 2.33 (m, 1H), 2.26 (s, 3H), 2.23-2.12 (m, 2H), 2.12-1.99 (m, 4H), 1.77-1.69 (m, 2H), 1.69-1.58 (m, 2H), 1.47-1.26 (m, 4H); LRMS (ES) m/z 564.2 ($M^+$+1).

EXAMPLE 203

Compound 11689, N-((5-(5-(difluoromethyl)-1,3,4-oxadiazol-2-yl)pyridin-2-yl)methyl)-1-((1s,4s)-4-fluorocyclohexyl)-N-(m-tolyl)piperidine-4-sulfonamide

EXAMPLE 204

Compound 11690, N-((5-(5-(difluoromethyl)-1,3,4-oxadiazol-2-yl)pyridin-2-yl)methyl)-N-(m-tolyl)-1-((1r,4r)-4-(trifluoromethyl)cyclohexyl)piperidine-4-sulfonamide

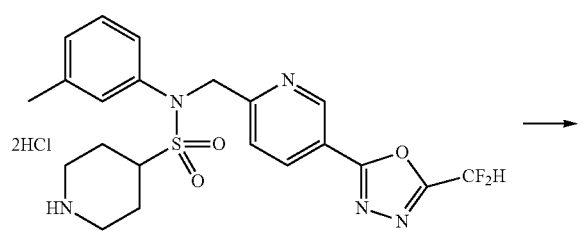

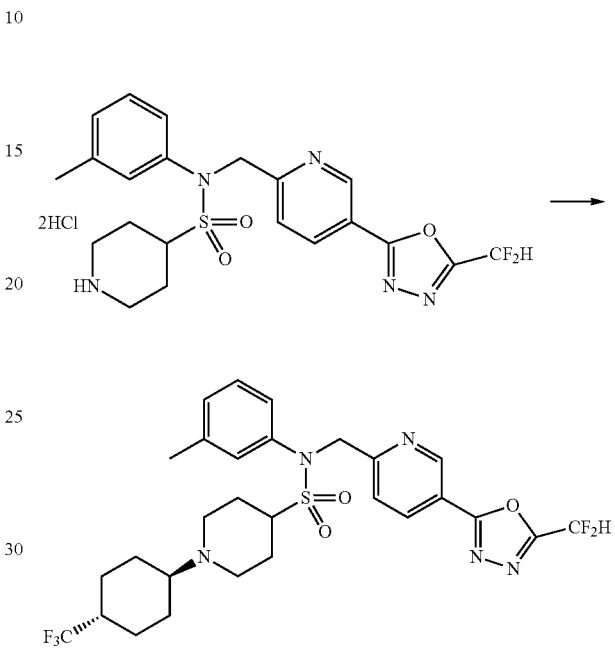

A mixture of N-((5-(5-(difluoromethyl)-1,3,4-oxadiazol-2-yl)pyridin-2-yl)methyl)-N-(m-tolyl)piperidine-4-sulfonamide dihydrochloride (0.050 g, 0.093 mmol), 4-fluorocyclohexan-1-one (0.022 g, 0.186 mmol) and N,N-diisopropylethylamine (0.041 mL, 0.233 mmol) in dichloromethane (5 mL) was treated at the room temperature with sodium triacetoxyborohydride (0.040 g, 0.186 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 4 g cartridge; ethyl acetate/hexane=60% to 90%) to give N-((5-(5-(difluoromethyl)-1,3,4-oxadiazol-2-yl)pyridin-2-yl)methyl)-1-((1s,4s)-4-fluorocyclohexyl)-N-(m-tolyl)piperidine-4-sulfonamide as light yellow solid (0.011 g, 20.9%).

$^1$H NMR (400 MHz, DMSO-d6) δ 9.09 (d, 1H, J=2.2 Hz), 8.41 (dd, 1H, J=8.2, 2.3 Hz), 7.71 (d, 1H, J=8.4 Hz), 7.56 (t, 1H, J=51.2 Hz), 7.37-7.27 (m, 2H), 7.22 (t, 1H, J=7.7 Hz), 7.06 (d, 1H, J=7.6 Hz), 5.15 (s, 2H), 4.76 (d, 1H, J=48.7 Hz), 3.22 (m, 1H), 2.93 (d, 2H, J=11.1 Hz), 2.37 (m, 1H), 2.28-2.17 (m, 5H), 2.09 (d, 2H, J=12.0 Hz), 1.96-1.88 (m, 2H), 1.73-1.61 (m, 2H), 1.60-1.43 (m, 6H); LRMS (ES) m/z 564.2 ($M^+$+1).

A mixture of N-((5-(5-(difluoromethyl)-1,3,4-oxadiazol-2-yl)pyridin-2-yl)methyl)-N-(m-tolyl)piperidine-4-sulfonamide dihydrochloride (0.050 g, 0.093 mmol), 4-(trifluoromethyl)cyclohexan-1-one (0.031 g, 0.186 mmol) and N,N-diisopropylethylamine (0.041 mL, 0.233 mmol) in dichloromethane (5 mL) was treated at the room temperature with sodium triacetoxyborohydride (0.040 g, 0.186 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 4 g cartridge; ethyl acetate/hexane=60% to 90%) to give N-((5-(5-(difluoromethyl)-1,3,4-oxadiazol-2-yl)pyridin-2-yl)methyl)-N-(m-tolyl)-1-((1r,4r)-4-(trifluoromethyl)cyclohexyl)piperidine-4-sulfonamide as white solid (0.009 g, 15.7%).

$^1$H NMR (400 MHz, DMSO-d6) δ 9.09 (d, 1H, J=2.2 Hz), 8.41 (dd, 1H, J=8.3, 2.3 Hz), 7.72 (d, 1H, J=8.2 Hz), 7.56 (t, 1H, J=51.3 Hz), 7.33 (s, 1H), 7.29 (d, 1H, J=8.4 Hz), 7.22 (t, 1H, J=7.7 Hz), 7.06 (d, 1H, J=7.5 Hz), 5.16 (s, 2H), 3.28 (m, 1H), 3.08 (d, 2H, J=11.3 Hz), 2.33 (m, 1H), 2.26 (s, 3H), 2.23 (m, 1H), 2.15-2.06 (m, 2H), 1.96-1.82 (m, 4H), 1.75-1.58 (m, 4H), 1.57-1.48 (m, 2H), 1.42 (t, 2H, J=12.6 Hz); LRMS (ES) m/z 614.3 ($M^+$+1).

EXAMPLE 205

Compound 11691, N-((5-(5-(difluoromethyl)-1,3,4-oxadiazol-2-yl)pyridin-2-yl)methyl)-N-(m-tolyl)-1-((1s,4s)-4-(trifluoromethyl)cyclohexyl)piperidine-4-sulfonamide

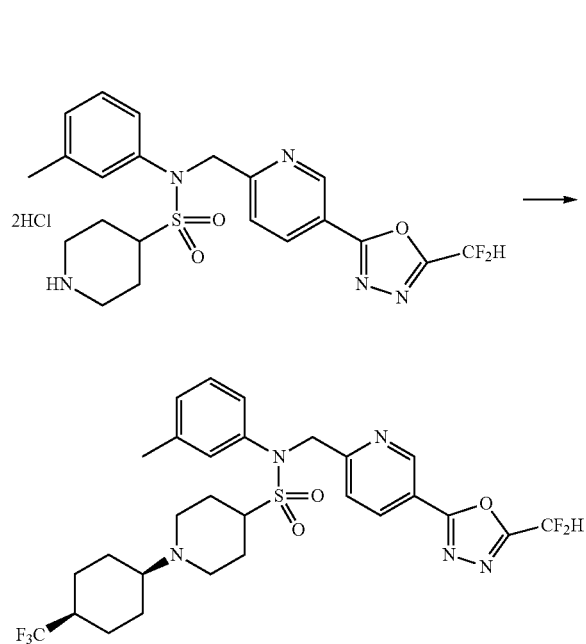

A mixture of N-((5-(5-(difluoromethyl)-1,3,4-oxadiazol-2-yl)pyridin-2-yl)methyl)-N-(m-tolyl)piperidine-4-sulfonamide dihydrochloride (0.050 g, 0.093 mmol), 4-(trifluoromethyl)cyclohexan-1-one (0.031 g, 0.186 mmol) and N,N-diisopropylethylamine (0.041 mL, 0.233 mmol) in dichloromethane (5 mL) was treated at the room temperature with sodium triacetoxyborohydride (0.040 g, 0.186 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=60% to 90%) to give N-((5-(5-(difluoromethyl)-1,3,4-oxadiazol-2-yl)pyridin-2-yl)methyl)-N-(m-tolyl)-1-((1s,4s)-4-(trifluoromethyl)cyclohexyl)piperidine-4-sulfonamide as white solid (0.010 g, 17.5%).

$^1$H NMR (400 MHz, DMSO-d6) δ 9.09 (d, 1H, J=2.3 Hz), 8.41 (dd, 1H, J=8.2, 2.3 Hz), 7.71 (d, 1H, J=8.2 Hz), 7.56 (t, 1H, J=51.3 Hz), 7.33 (s, 1H), 7.29 (m, 1H), 7.22 (t, 1H, J=7.7 Hz), 7.05 (d, 1H, J=7.4 Hz), 5.15 (s, 2H), 3.21 (m, 1H), 2.90 (d, 2H, J=11.1 Hz), 2.33 (m, 1H), 2.30-2.18 (m, 6H), 2.08 (d, 2H, J=11.8 Hz), 1.91-1.86 (m, 2H), 1.84-1.76 (m, 2H), 1.72-1.58 (m, 2H), 1.37-1.13 (m, 4H); LRMS (ES) m/z 614.3 (M$^+$+1).

EXAMPLE 206

Compound 11692, N-((5-(5-(difluoromethyl)-1,3,4-oxadiazol-2-yl)pyridin-2-yl)methyl)-1-(tetrahydro-2H-pyran-4-yl)-N-(m-tolyl)piperidine-4-sulfonamide

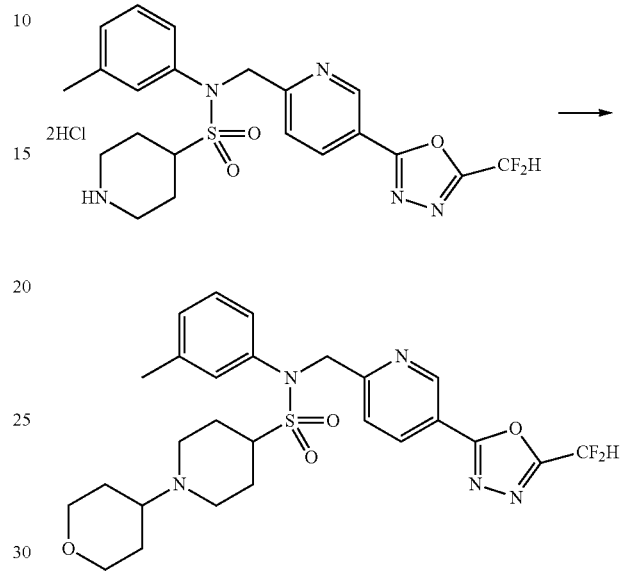

A mixture of N-((5-(5-(difluoromethyl)-1,3,4-oxadiazol-2-yl)pyridin-2-yl)methyl)-N-(m-tolyl)piperidine-4-sulfonamide dihydrochloride (0.050 g, 0.093 mmol), tetrahydro-4H-pyran-4-one (0.019 g, 0.186 mmol) and N,N-diisopropylethylamine (0.041 mL, 0.233 mmol) in dichloromethane (5 mL) was treated at the room temperature with sodium triacetoxyborohydride (0.040 g, 0.186 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=70% to 100%) to give the concentrate, and then the concentrate was dissolved in ethyl acetate (3 mL) and hexane (30 mL) and stirred. The resulting precipitates were collected by filtration, washed by hexane, and dried to give N-((5-(5-(difluoromethyl)-1,3,4-oxadiazol-2-yl)pyridin-2-yl)methyl)-1-(tetrahydro-2H-pyran-4-yl)-N-(m-tolyl)piperidine-4-sulfonamide as white solid (0.044 g, 86.2%).

$^1$H NMR (400 MHz, DMSO-d6) δ 9.09 (d, 1H, J=2.2 Hz), 8.42 (dd, 1H, J=8.3, 2.2 Hz), 7.71 (d, 1H, J=8.1 Hz), 7.56 (t, 1H, J=51.3 Hz), 7.33 (s, 1H), 7.30 (d, 1H, J=8.7 Hz), 7.22 (t, 1H, J=7.7 Hz), 7.06 (d, 1H, J=7.5 Hz), 5.15 (s, 2H), 3.87 (d, 2H, J=8.7 Hz), 3.31-3.21 (m, 4H), 2.97 (d, 2H, J=11.2 Hz), 2.26 (s, 3H), 2.21-2.05 (m, 4H), 1.73-1.59 (m, 4H), 1.49-1.33 (m, 2H); LRMS (ES) m/z 548.0 (M$^+$+1).

EXAMPLE 207

Compound 11693, 1-(bicyclo[2.2.1]heptan-2-yl)-N-(4-(5-(difluoromethyl)-1,3,4-oxadiazol-2-yl)benzyl)-N-(m-tolyl)piperidine-4-sulfonamide

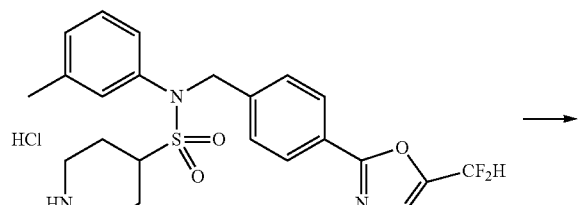

A mixture of N-(4-(5-(difluoromethyl)-1,3,4-oxadiazol-2-yl)benzyl)-N-(m-tolyl)piperidine-4-sulfonamide hydrochloride (0.050 g, 0.100 mmol), bicyclo[2.2.1]heptan-2-one (0.022 g, 0.200 mmol) and N,N-diisopropylethylamine (0.026 mL, 0.150 mmol) in dichloromethane (5 mL) was treated at the room temperature with sodium triacetoxyborohydride (0.042 g, 0.200 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=50% to 80%) to give the concentrate, and then the concentrate was dissolved in ethyl acetate (3 mL) and hexane (30 mL) and stirred. The resulting precipitates were collected by filtration, washed by hexane, and dried to give 1-(bicyclo[2.2.1]heptan-2-yl)-N-(4-(5-(difluoromethyl)-1,3,4-oxadiazol-2-yl)benzyl)-N-(m-tolyl)piperidine-4-sulfonamide as white solid (0.026 g, 46.6%).

$^1$H NMR (400 MHz, DMSO-d6) δ 7.98 (d, 2H, J=8.3 Hz), 7.66 (s, 0.25H), 7.56-7.47 (m, 2.5H), 7.40 (s, 0.25H), 7.28-7.16 (m, 3H), 7.04 (d, 1H, J=6.6 Hz), 5.06 (s, 2H), 3.19 (m, 1H), 3.03-2.89 (m, 2H), 2.27-2.23 (m, 4H), 2.20 (m, 1H), 2.13 (m, 1H), 2.05 (d, 2H, J=11.0 Hz), 1.84-1.63 (m, 6H), 1.45 (m, 1H), 1.32 (m, 1H), 1.27-1.13 (m, 3H), 0.83 (m, 1H); LRMS (ES) m/z 557.0 (M$^+$+1).

EXAMPLE 208

Compound 11694, 1-(4,4-difluorocyclohexyl)-N-(4-(5-(difluoromethyl)-1,3,4-oxadiazol-2-yl)benzyl)-N-(m-tolyl)piperidine-4-sulfonamide

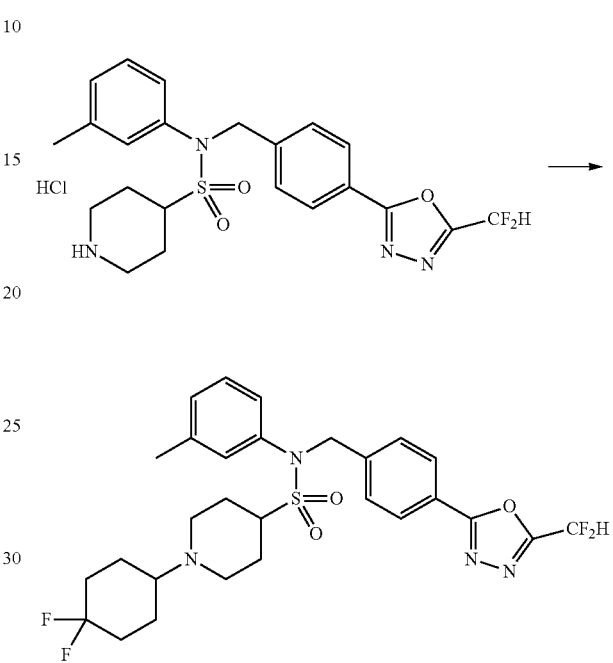

A mixture of N-(4-(5-(difluoromethyl)-1,3,4-oxadiazol-2-yl)benzyl)-N-(m-tolyl)piperidine-4-sulfonamide hydrochloride (0.050 g, 0.100 mmol), 4,4-difluorocyclohexan-1-one (0.027 g, 0.200 mmol) and N,N-diisopropylethylamine (0.026 mL, 0.150 mmol) in dichloromethane (5 mL) was treated at the room temperature with sodium triacetoxyborohydride (0.042 g, 0.200 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=50% to 80%) to give the concentrate, and then the concentrate was dissolved in ethyl acetate (3 mL) and hexane (30 mL) and stirred. The resulting precipitates were collected by filtration, washed by hexane, and dried to give 1-(4,4-difluorocyclohexyl)-N-(4-(5-(difluoromethyl)-1,3,4-oxadiazol-2-yl)benzyl)-N-(m-tolyl)piperidine-4-sulfonamide as white solid (0.037 g, 63.6%).

$^1$H NMR (400 MHz, DMSO-d6) δ 7.98 (d, 2H, J=8.4 Hz), 7.66 (s, 0.25H), 7.55-7.47 (m, 2.5H), 7.40 (s, 0.25H), 7.27-7.18 (m, 3H), 7.04 (d, 1H, J=6.7 Hz), 5.05 (s, 2H), 3.31 (m, 1H), 3.17 (m, 1H), 2.93 (d, 2H, J=11.1 Hz), 2.25 (s, 3H), 2.19 (t, 2H, J=11.4 Hz), 2.11-1.98 (m, 4H), 1.88-1.61 (m, 6H), 1.58-1.47 (m, 2H); LRMS (ES) m/z 581.2 (M$^+$+1).

EXAMPLE 209

Compound 11695, N-(4-(5-(difluoromethyl)-1,3,4-oxadiazol-2-yl)benzyl)-1-((1r,4r)-4-fluorocyclohexyl)-N-(m-tolyl)piperidine-4-sulfonamide

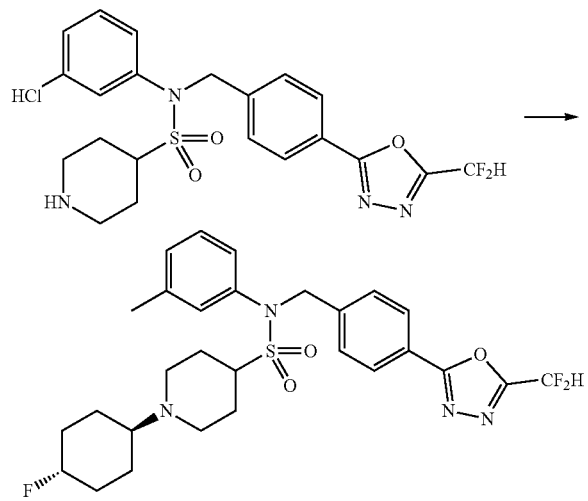

A mixture of N-(4-(5-(difluoromethyl)-1,3,4-oxadiazol-2-yl)benzyl)-N-(m-tolyl)piperidine-4-sulfonamide hydrochloride (0.050 g, 0.100 mmol), 4-fluorocyclohexan-1-one (0.023 g, 0.200 mmol) and N,N-diisopropylethylamine (0.026 mL, 0.150 mmol) in dichloromethane (5 mL) was treated at the room temperature with sodium triacetoxyborohydride (0.042 g, 0.200 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=60% to 90%) to give N-(4-(5-(difluoromethyl)-1,3,4-oxadiazol-2-yl)benzyl)-1-((1r,4r)-4-fluorocyclohexyl)-N-(m-tolyl)piperidine-4-sulfonamide as white solid (0.011 g, 19.5%).

$^1$H NMR (400 MHz, DMSO-d6) δ 7.98 (d, 2H, J=8.4 Hz), 7.66 (s, 0.25H), 7.55-7.47 (m, 2.5H), 7.40 (s, 0.25H), 7.27-7.15 (m, 3H), 7.04 (m, 1H), 5.05 (s, 2H), 4.49 (dt, 1H, J=10.3, 5.6 Hz), 3.16 (m, 1H), 2.91 (d, 2H, J=11.1 Hz), 2.35 (m, 1H), 2.25 (s, 3H), 2.22-2.12 (m, 2H), 2.09-1.98 (m, 4H), 1.77-1.58 (m, 4H), 1.50-1.26 (m, 4H); LRMS (ES) m/z 563.2 (M$^+$+1).

EXAMPLE 210

Compound 11696, N-(4-(5-(difluoromethyl)-1,3,4-oxadiazol-2-yl)benzyl)-1-((1s,4s)-4-fluorocyclohexyl)-N-(m-tolyl)piperidine-4-sulfonamide

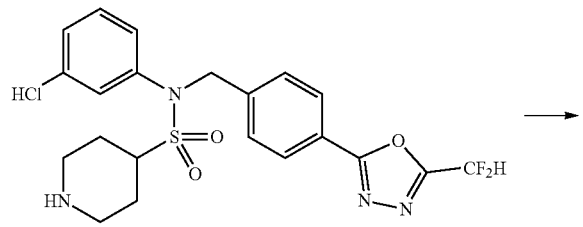

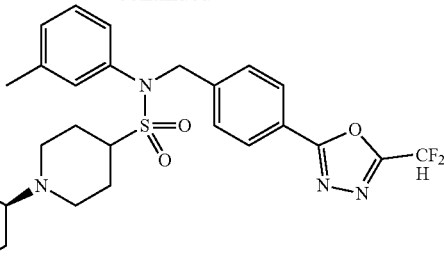

A mixture of N-(4-(5-(difluoromethyl)-1,3,4-oxadiazol-2-yl)benzyl)-N-(m-tolyl)piperidine-4-sulfonamide hydrochloride (0.050 g, 0.100 mmol), 4-fluorocyclohexan-1-one (0.023 g, 0.200 mmol) and N,N-diisopropylethylamine (0.026 mL, 0.150 mmol) in dichloromethane (5 mL) was treated at the room temperature with sodium triacetoxyborohydride (0.042 g, 0.200 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=60% to 90%) to give N-(4-(5-(difluoromethyl)-1,3,4-oxadiazol-2-yl)benzyl)-1-((1s,4s)-4-fluorocyclohexyl)-N-(m-tolyl)piperidine-4-sulfonamide as white solid (0.013 g, 23.1%).

$^1$H NMR (400 MHz, DMSO-d6) δ 7.98 (d, 2H, J=8.4 Hz), 7.66 (s, 0.25H), 7.55-7.47 (m, 2.5H), 7.40 (s, 0.25H), 7.28-7.16 (m, 3H), 7.04 (m, 1H), 5.06 (s, 2H), 4.76 (d, 1H, J=49.0 Hz), 3.17 (m, 1H), 2.93 (d, 2H, J=11.1 Hz), 2.36 (m, 1H), 2.27-2.12 (m, 5H), 2.11-2.03 (m, 2H), 2.02-1.88 (m, 2H), 1.74-1.62 (m, 2H), 1.59-1.38 (m, 6H); LRMS (ES) m/z 563.3 (M$^+$+1).

EXAMPLE 211

Compound 11697, N-(4-(5-(difluoromethyl)-1,3,4-oxadiazol-2-yl)benzyl)-N-(m-tolyl)-1-((1r,4r)-4-(trifluoromethyl)cyclohexyl)piperidine-4-sulfonamide

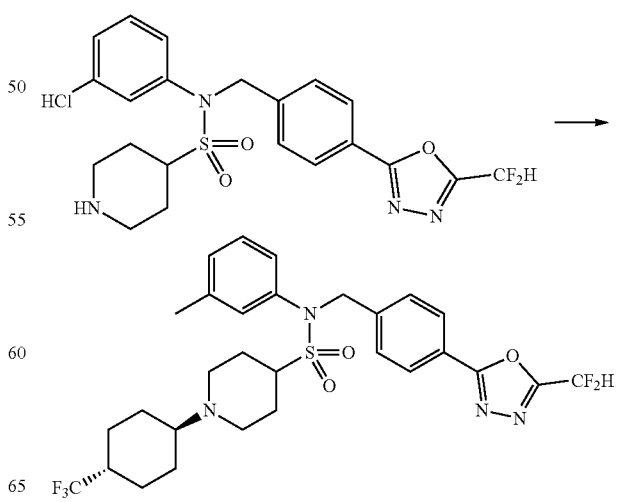

A mixture of N-(4-(5-(difluoromethyl)-1,3,4-oxadiazol-2-yl)benzyl)-N-(m-tolyl)piperidine-4-sulfonamide hydrochloride (0.050 g, 0.100 mmol), 4-(trifluoromethyl)cyclohexan-1-one (0.033 g, 0.200 mmol) and N,N-diisopropylethylamine (0.026 mL, 0.150 mmol) in dichloromethane (5 mL) was treated at the room temperature with sodium triacetoxyborohydride (0.042 g, 0.200 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=60% to 90%) to give N-(4-(5-(difluoromethyl)-1,3,4-oxadiazol-2-yl)benzyl)-N-(m-tolyl)-1-((1r,4r)-4-(trifluoromethyl)cyclohexyl)piperidine-4-sulfonamide as white solid (0.013 g, 21.2%).

$^1$H NMR (400 MHz, DMSO-d6) δ 7.98 (d, 2H, J=8.4 Hz), 7.66 (s, 0.25H), 7.55-7.47 (m, 2.5H), 7.40 (s, 0.25H), 7.29-7.15 (m, 3H), 7.04 (m, 1H), 5.06 (s, 2H), 3.21 (m, 1H), 3.09 (d, 2H, J=11.3 Hz), 2.34 (m, 1H), 2.27-2.20 (m, 4H), 2.07 (d, 2H, J=12.3 Hz), 1.96-1.85 (m, 4H), 1.75-1.58 (m, 4H), 1.57-1.48 (m, 2H), 1.42 (t, 2H, J=12.5 Hz); LRMS (ES) m/z 613.3 (M$^+$+1).

EXAMPLE 212

Compound 11698, N-(4-(5-(difluoromethyl)-1,3,4-oxadiazol-2-yl)benzyl)-N-(m-tolyl)-1-((1s,4s)-4-(trifluoromethyl)cyclohexyl)piperidine-4-sulfonamide

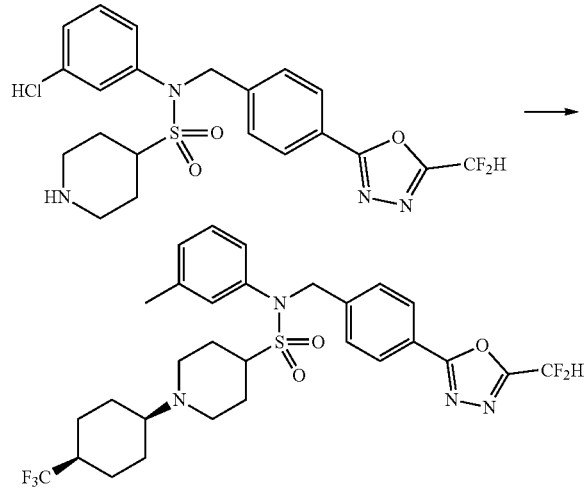

A mixture of N-(4-(5-(difluoromethyl)-1,3,4-oxadiazol-2-yl)benzyl)-N-(m-tolyl)piperidine-4-sulfonamide hydrochloride (0.050 g, 0.100 mmol), 4-(trifluoromethyl)cyclohexan-1-one (0.033 g, 0.200 mmol) and N,N-diisopropylethylamine (0.026 mL, 0.150 mmol) in dichloromethane (5 mL) was treated at the room temperature with sodium triacetoxyborohydride (0.042 g, 0.200 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=60% to 90%) to give N-(4-(5-(difluoromethyl)-1,3,4-oxadiazol-2-yl)benzyl)-N-(m-tolyl)-1-((1s,4s)-4-(trifluoromethyl)cyclohexyl)piperidine-4-sulfonamide as white solid (0.016 g, 26.1%).

$^1$H NMR (400 MHz, DMSO-d6) δ 7.98 (d, 2H, J=8.4 Hz), 7.66 (s, 0.25H), 7.55-7.47 (m, 2.5H), 7.40 (s, 0.25H), 7.27-7.16 (m, 3H), 7.04 (d, 1H, J=6.8 Hz), 5.05 (s, 2H), 3.15 (m, 1H), 2.90 (d, 2H, J=11.0 Hz), 2.34 (m, 1H), 2.29-2.14 (m, 6H), 2.06 (d, 2H, J=11.8 Hz), 1.93-1.75 (m, 4H), 1.72-1.61 (m, 2H), 1.34-1.21 (m, 4H); LRMS (ES) m/z 613.3 (M$^+$+1).

EXAMPLE 213

Compound 11699, N-(4-(5-(difluoromethyl)-1,3,4-oxadiazol-2-yl)benzyl)-1-(tetrahydro-2H-pyran-4-yl)-N-(m-tolyl)piperidine-4-sulfonamide

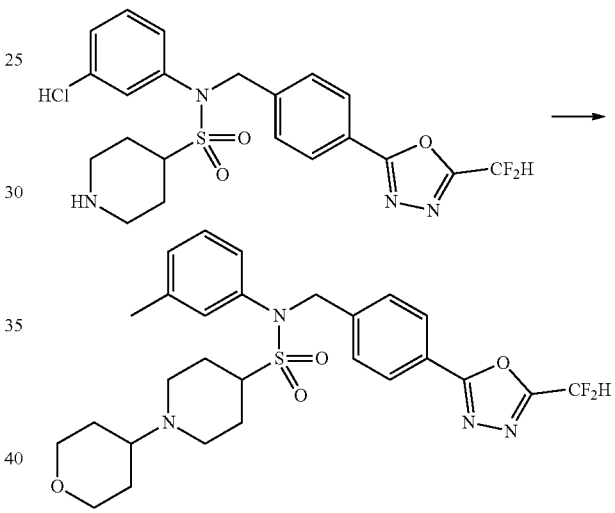

A mixture of N-(4-(5-(difluoromethyl)-1,3,4-oxadiazol-2-yl)benzyl)-N-(m-tolyl)piperidine-4-sulfonamide hydrochloride (0.050 g, 0.100 mmol), tetrahydro-4H-pyran-4-one (0.020 g, 0.200 mmol) and N,N-diisopropylethylamine (0.026 mL, 0.150 mmol) in dichloromethane (5 mL) was treated at the room temperature with sodium triacetoxyborohydride (0.042 g, 0.200 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=70% to 100%) to give the concentrate, and then the concentrate was dissolved in ethyl acetate (3 mL) and hexane (30 mL) and stirred. The resulting precipitates were collected by filtration, washed by hexane, and dried to give N-(4-(5-(difluoromethyl)-1,3,4-oxadiazol-2-yl)benzyl)-1-(tetrahydro-2H-pyran-4-yl)-N-(m-tolyl)piperidine-4-sulfonamide as white solid (0.030 g, 54.8%).

$^1$H NMR (400 MHz, DMSO-d6) δ 7.98 (d, 2H, J J=8.4 Hz), 7.66 (s, 0.25H), 7.55-7.47 (m, 2.5H), 7.40 (s, 0.25H), 7.27-7.16 (m, 3H), 7.04 (d, 1H, J=6.6 Hz), 5.06 (s, 2H), 3.92-3.84 (m, 2H), 3.31-3.22 (m, 2H), 3.18 (m, 1H), 2.98 (d, 2H, J=11.0 Hz), 2.45 (m, 1H), 2.25 (s, 3H), 2.16 (t, 2H, J=11.4 Hz), 2.07 (d, 2H, J=12.4 Hz), 1.74-1.59 (m, 4H), 1.49-1.34 (qd, 2H, J=12.0, 4.4 Hz); LRMS (ES) m/z 547.3 (M$^+$+1).

EXAMPLE 214

Compound 11700, N-(4-(5-(difluoromethyl)-1,3,4-oxadiazol-2-yl)benzyl)-2-(3-hydroxypiperidin-1-yl)-N-phenylethanesulfonamide

[Step 1] methyl 4-((2-(3-hydroxypiperidin-1-yl)-N-phenylethylsulfonamido)methyl)benzoate

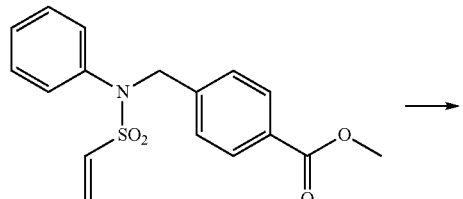

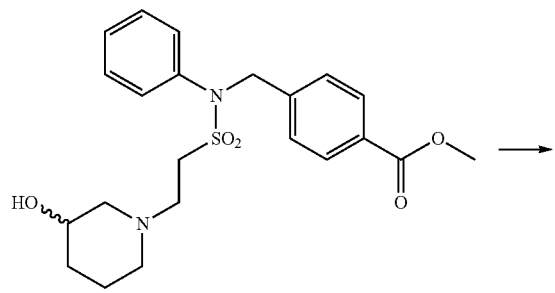

A solution of methyl 4-((N-phenylvinylsulfonamido)methyl)benzoate (0.200 g, 0.604 mmol), piperidin-3-ol (0.082 g, 0.604 mmol) and N,N-Diisopropylethylamine (0.208 mL, 1.207 mmol) in dichloromethane (10 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=5% to 10%) to give methyl 4-((2-(3-hydroxypiperidin-1-yl)-N-phenylethylsulfonamido)methyl)benzoate as white solid (0.220 g, 84.3%).

[Step 2] N-(4-(hydrazinecarbonyl)benzyl)-2-(3-hydroxypiperidin-1-yl)-N-phenylethanesulfonamide

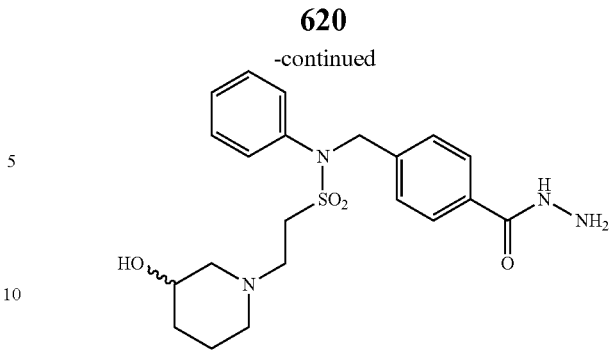

A mixture of methyl 4-((2-(3-hydroxypiperidin-1-yl)-N-phenylethylsulfonamido)methyl)benzoate (0.220 g, 0.509 mmol) and hydrazine (0.319 mL, 10.173 mmol) in ethanol (5 mL) prepared at the room temperature was heated at reflux for 6 hr, cooled down to the ambient temperature, and concentrated under the reduced pressure to remove the solvent. The residue was diluted with water (20 mL) and stirred. The resulting precipitates were collected by filtration and dried to give N-(4-(hydrazinecarbonyl)benzyl)-2-(3-hydroxypiperidin-1-yl)-N-phenylethanesulfonamide as white solid (0.130 g, 59.1%).

[Step 3] Compound 11700

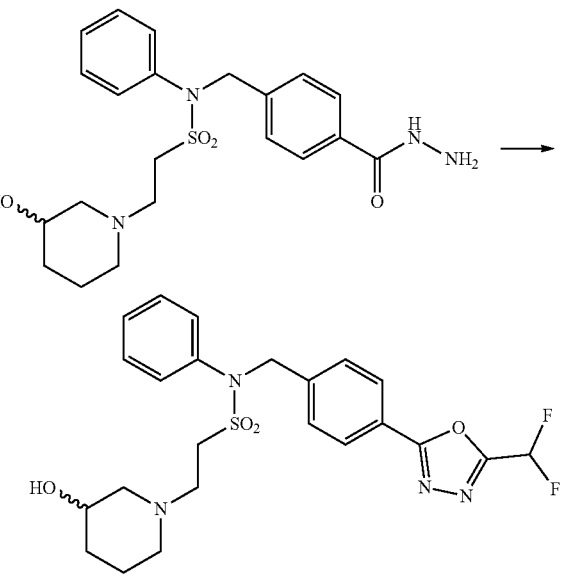

A mixture of N-(4-(hydrazinecarbonyl)benzyl)-2-(3-hydroxypiperidin-1-yl)-N-phenylethanesulfonamide (0.130 g, 0.301 mmol), 2,2-difluoroacetic anhydride (0.112 mL, 0.902 mmol) and Triethylamine (0.209 mL, 1.503 mmol) in tetrahydrofuran (10 mL) was heated at reflux for 12 hr, cooled down to the ambient temperature, and concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)benzyl)-2-(3-hydroxypiperidin-1-yl)-N-phenylethanesulfonamide as yellow solid (0.001 g, 0.7%).

¹H NMR (400 MHz, CD3OD) δ8.03 (d, 2H, J=8.44 Hz), 7.56 (d, 2H, J=8.48 Hz), 7.45-7.29 (m, 5H), 7.21 (t, 1H, J=51.6 Hz), 5.07 (s, 2H), 3.75-3.65 (m, 2H), 3.44-3.40 (m, 2H), 2.93-2.89 (m, 1H), 2.23-2.12 (m, 1H), 2.14-2.01 (m, 1H), 1.95-1.85 (m, 1H), 1.91-1.86 (m, 1H), 1.86-1.78 (m, 1H), 1.82-1.77 (m, 1H), 1.64-1.50 (m, 1H), 1.32-1.24 (m, 1H); LRMS (ES) m/z 493.3 (M⁺+1).

EXAMPLE 215

Compound 11705, (S)—N-(4-(5-(difluoromethyl)-1,3,4-oxadiazol-2-yl)benzyl)-3-(3-fluoropyrrolidin-1-yl)-N-phenylpropane-1-sulfonamide

[Step 1] methyl (S)-4-(((3-(3-fluoropyrrolidin-1-yl)-N-phenylpropyl)sulfonamido)methyl)benzoate

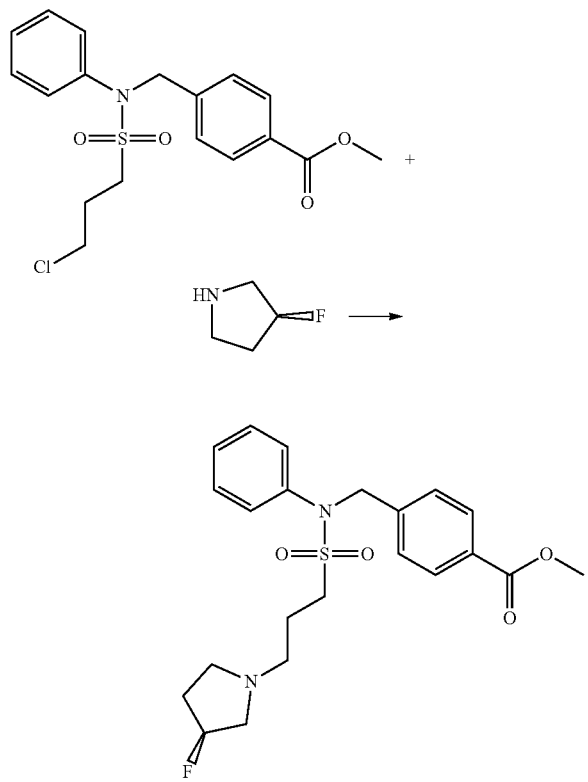

A solution of methyl 4-(((3-chloro-N-phenylpropyl)sulfonamido)methyl)benzoate (0.250 g, 0.655 mmol), (S)-3-fluoropyrrolidin hydrochloride (0.123 g, 0.982 mmol) and potassium carbonate (0.136 g, 0.982 mmol) in N,N-dimethylformide (3 mL) was stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; methanol/dichloromethane=0% to 5%) to give methyl (S)-4-(((3-(3-fluoropyrrolidin-1-yl)-N-phenylpropyl)sulfonamido)methyl)benzoate as colorless oil (0.162 g, 57.0%).

[Step 2] (S)-3-(3-fluoropyrrolidin-1-yl)-N-(4-(hydrazinecarbonyl)benzyl)-N-phenylpropane-1-sulfonamide

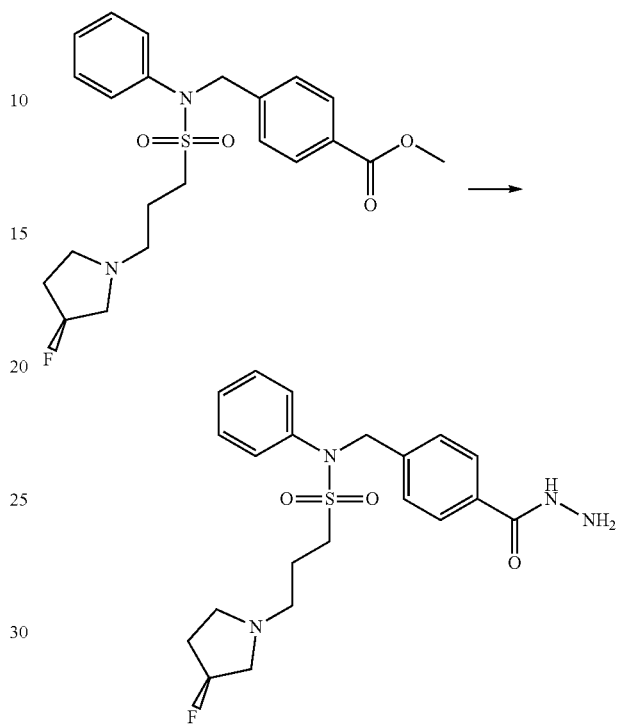

A solution of methyl (S)-4-(((3-(3-fluoropyrrolidin-1-yl)-N-phenylpropyl)sulfonamido)methyl)benzoate (0.162 g, 0.373 mmol) and hydrazine monohydrate (0.181 mL, 3.730 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give (S)-3-(3-fluoropyrrolidin-1-yl)-N-(4-(hydrazinecarbonyl)benzyl)-N-phenylpropane-1-sulfonamide as white solid (0.106 g, 65.4%).

[Step 3] Compound 11705

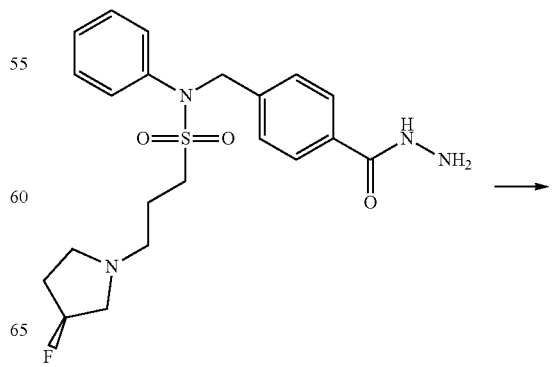

-continued

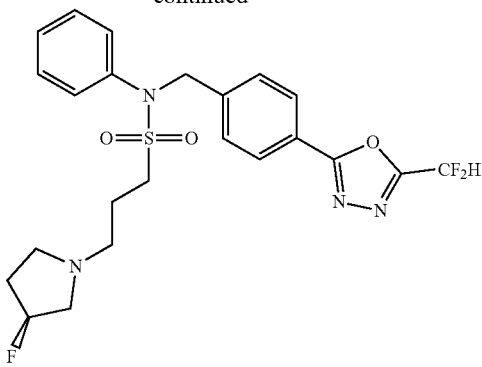

A solution of (S)-3-(3-fluoropyrrolidin-1-yl)-N-(4-(hydrazinecarbonyl)benzyl)-N-phenylpropane-1-sulfonamide (0.106 g, 0.244 mmol), 2,2-difluoroacetic anhydride (0.303 mL, 2.439 mmol) and triethylamine (0.170 mL, 1.220 mmol) in tetrahydrofuran (5 mL) was stirred at 80° C. for 1 hr and cooled down to the room temperature to terminate the reaction. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give (S)—N-(4-(5-(difluoromethyl)-1,3,4-oxadiazol-2-yl)benzyl)-3-(3-fluoropyrrolidin-1-yl)-N-phenylpropane-1-sulfonamide as colorless oil (0.059 g, 49.0%).

$^1$H NMR (400 MHz, CD3OD) δ8.00 (d, 2H, J=8.4 Hz), 7.54 (d, 2H, J=8.6 Hz), 7.43~7.25 (m, 5H), 7.21 (t, 1H, J=51.7 Hz), 5.26~5.09 (m, 1H), 5.05 (s, 2H), 3.31~3.26 (m, 2H), 2.99~2.88 (m, 2H), 2.69 (dd, 1H, J=11.7, 4.9 Hz), 2.65~2.59 (m, 2H), 2.41 (q, 1H, J=8.0 Hz), 2.28~2.14 (m, 1H), 2.12~2.03 (m, 2H), 2.02~1.93 (m, 1H); LRMS (ES) m/z 495.3 (M$^+$+1).

EXAMPLE 216

Compound 11706, N-(4-(5-(difluoromethyl)-1,3,4-oxadiazol-2-yl)benzyl)-3-(3,3-difluoropyrrolidin-1-yl)-N-phenylpropane-1-sulfonamide

[Step 1] methyl 4-(((3-(3,3-difluoropyrrolidin-1-yl)-N-phenylpropyl)sulfonamido)methyl)benzoate

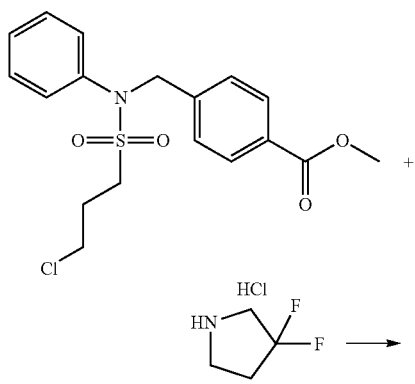

-continued

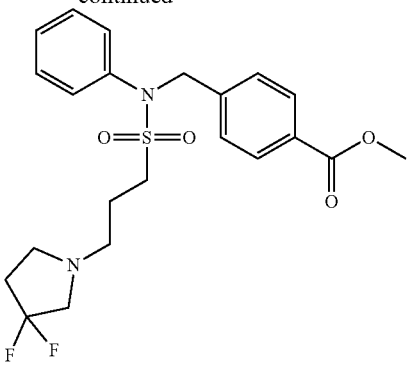

A solution of methyl 4-(((3-chloro-N-phenylpropyl)sulfonamido)methyl)benzoate (0.250 g, 0.655 mmol), 3,3-difluoropyrrolidin hydrochloride (0.188 g, 1.309 mmol) and potassium carbonate (0.136 g, 0.982 mmol) in N,N-dimethylformide (3 mL) was stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give methyl 4-(((3-(3,3-difluoropyrrolidin-1-yl)-N-phenylpropyl)sulfonamido) methyl)benzoate as yellow oil (0.277 g, 93.5%).

[Step 2] 3-(3,3-difluoropyrrolidin-1-yl)-N-(4-(hydrazinecarbonyl)benzyl)-N-phenylpropane-1-sulfonamide

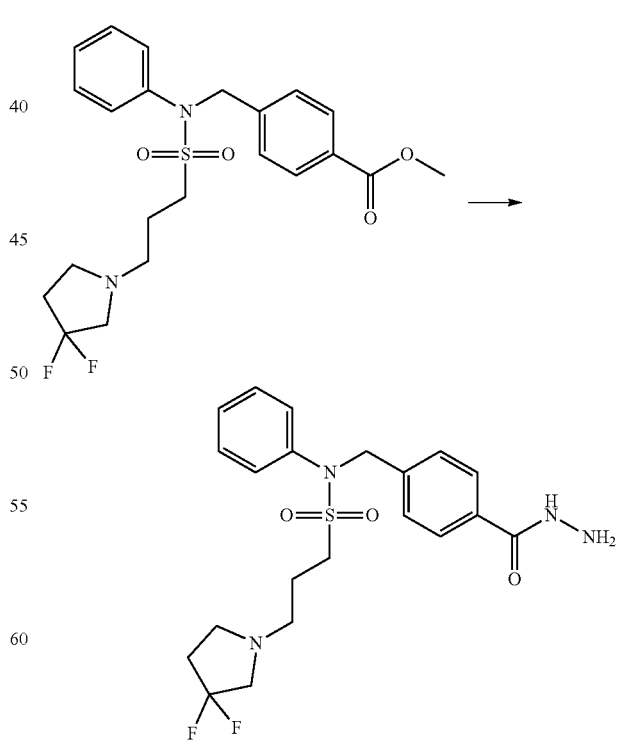

A solution of methyl 4-(((3-(3,3-difluoropyrrolidin-1-yl)-N-phenylpropyl)sulfonamido)methyl)benzoate (0.277 g, 0.612 mmol) and hydrazine monohydrate (0.297 mL, 6.119 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give 3-(3,3-difluoropyrrolidin-1-yl)-N-(4-(hydrazinecarbonyl)benzyl)-N-phenylpropane-1-sulfonamide as white solid (0.139 g, 50.2%).

[Step 3] Compound 11706

A solution of 3-(3,3-difluoropyrrolidin-1-yl)-N-(4-(hydrazinecarbonyl)benzyl)-N-phenylpropane-1-sulfonamide (0.139 g, 0.307 mmol), 2,2-difluoroacetic anhydride (0.382 mL, 3.072 mmol) and triethylamine (0.214 mL, 1.536 mmol) in tetrahydrofuran (5 mL) was stirred at 80° C. for 1 hr and cooled down to the room temperature to terminate the reaction. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 10%) to give N-(4-(5-(difluoromethyl)-1,3,4-oxadiazol-2-yl)benzyl)-3-(3,3-difluoropyrrolidin-1-yl)-N-phenylpropane-1-sulfonamide as colorless oil (0.079 g, 49.9%).

$^1$H NMR (400 MHz, CD3OD) δ7.99 (d, 2H, J=8.5 Hz), 7.53 (d, 2H, J=8.5 Hz), 7.42~7.26 (m, 5H), 7.20 (t, 1H, J=51.7 Hz), 5.05 (s, 2H), 4.22 (t, 2H, J=6.1 Hz), 3.68 (q, 2H, J=11.6 Hz), 3.61~3.54 (m, 2H), 3.32~3.30 (m, 2H), 2.44~2.34 (m, 2H), 2.25~2.18 (m, 2H); LRMS (ES) m/z 557.3 (M⁺+1).

EXAMPLE 217

Compound 11707, (S)—N-(4-(5-(difluoromethyl)-1,3,4-oxadiazol-2-yl)benzyl)-3-(2-methylpyrrolidin-1-yl)-N-phenylpropane-1-sulfonamide

[Step 1] methyl (S)-4-(((3-(2-methylpyrrolidin-1-yl)-N-phenylpropyl)sulfonamido)methyl)benzoate

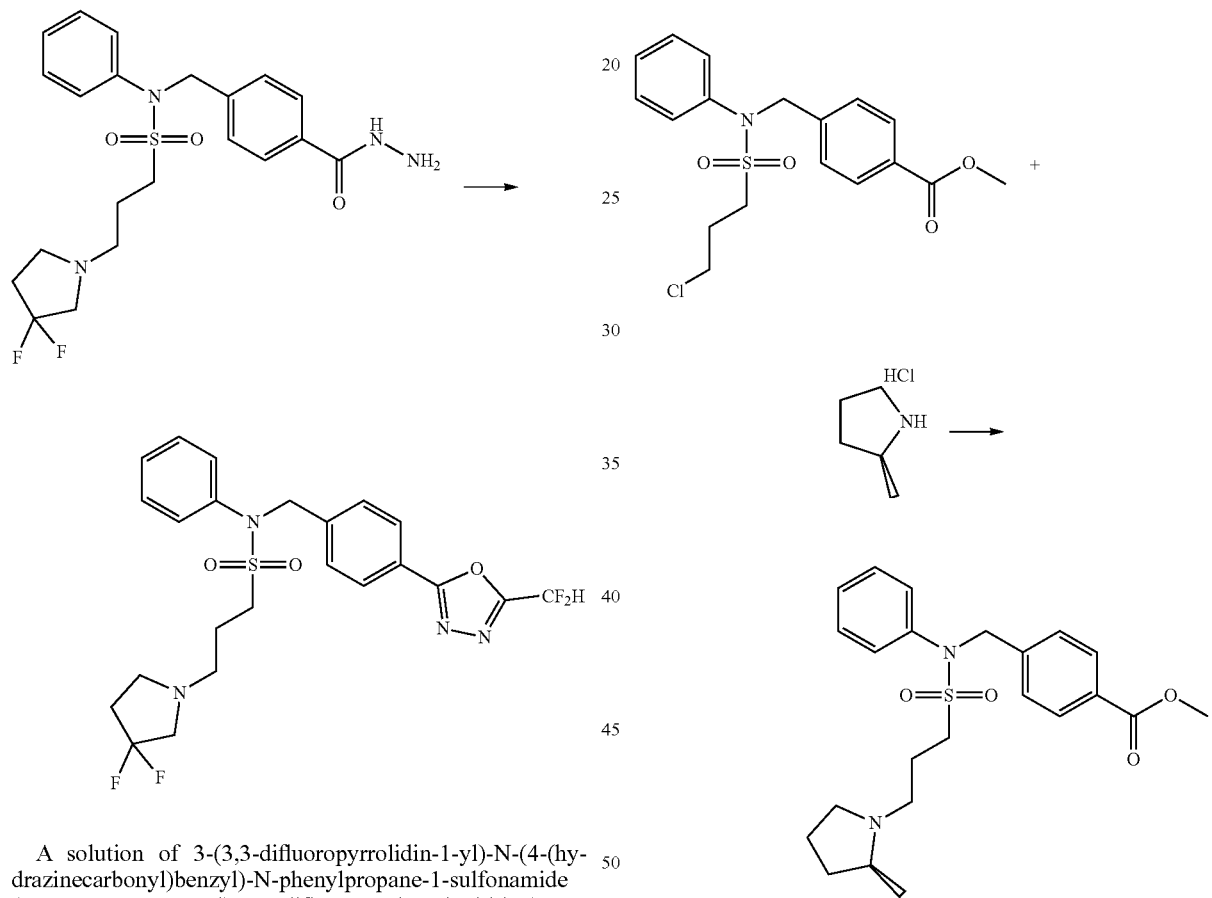

A solution of methyl 4-(((3-chloro-N-phenylpropyl)sulfonamido)methyl)benzoate (0.250 g, 0.655 mmol), (S)-2-methylpyrrolidine hydrochloride (0.076 g, 0.622 mmol) and potassium carbonate (0.136 g, 0.982 mmol) in N,N-dimethylformide (3 mL) was stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; methanol/dichloromethane=0% to 5%) to give methyl (S)-4-(((3-(2-methylpyrrolidin-1-yl)-N-phenylpropyl)sulfonamido) methyl)benzoate as white solid (0.158 g, 56.0%).

627

[Step 2] (S)—N-(4-(hydrazinecarbonyl)benzyl)-3-(2-methylpyrrolidin-1-yl)-N-phenylpropane-1-sulfonamide

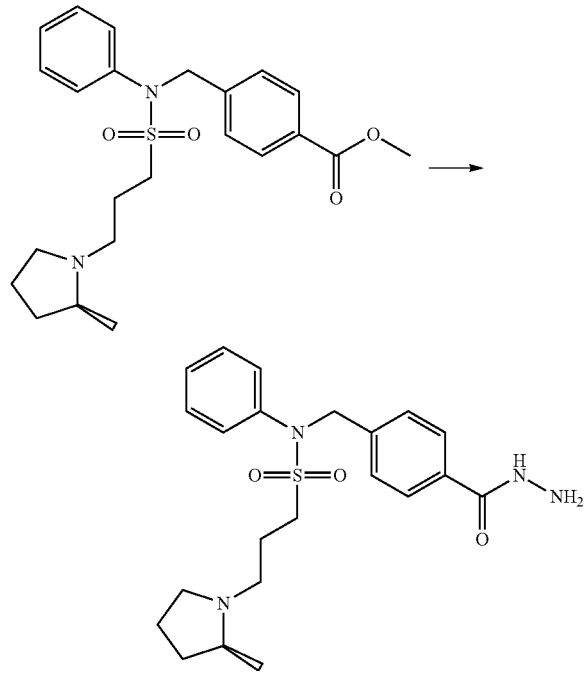

A solution of methyl (S)-4-(((3-(2-methylpyrrolidin-1-yl)-N-phenylpropyl)sulfonamido)methyl)benzoate (0.158 g, 0.367 mmol) and hydrazine monohydrate (0.178 mL, 3.667 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give (S)—N-(4-(hydrazinecarbonyl)benzyl)-3-(2-methylpyrrolidin-1-yl)-N-phenylpropane-1-sulfonamide as white solid (0.110 g, 69.7%).

[Step 3] Compound 11707

628

-continued

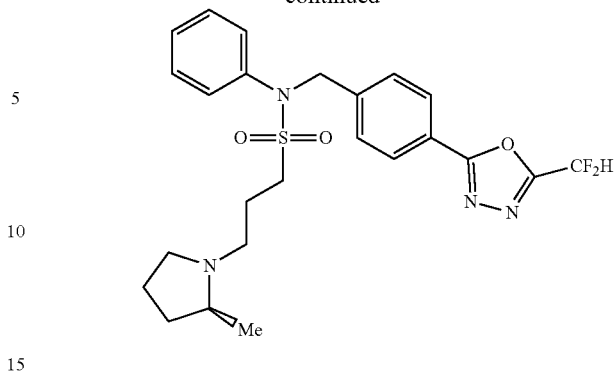

A solution of (S)—N-(4-(hydrazinecarbonyl)benzyl)-3-(2-methylpyrrolidin-1-yl)-N-phenylpropane-1-sulfonamide (0.110 g, 0.255 mmol), 2,2-difluoroacetic anhydride (0.318 mL, 2.555 mmol) and triethylamine (0.178 mL, 1.277 mmol) in tetrahydrofuran (5 mL) was stirred at 80° C. for 1 hr, and cooled down to the room temperature to terminate the reaction. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give (S)—N-(4-(5-(difluoromethyl)-1,3,4-oxadiazol-2-yl)benzyl)-3-(2-methylpyrrolidin-1-yl)-N-phenylpropane-1-sulfonamide as yellow solid (0.083 g, 66.4%).

$^1$H NMR (400 MHz, CD3OD) δ8.00 (d, 2H, J=8.5 Hz), 7.54 (d, 2H, J=8.5 Hz), 7.43~7.27 (m, 5H), 7.22 (t, 1H, J=51.7 Hz), 5.05 (s, 2H), 3.74 (brs, 1H), 3.55 (brs, 1H), 3.47~3.39 (m, 3H), 3.16~3.14 (m, 2H), 2.34~2.26 (m, 3H), 2.11~2.08 (m, 2H), 1.79~1.76 (m, 1H), 1.45 (d, 3H, J=5.4 Hz); LRMS (ES) m/z 491.3 (M$^+$+1).

EXAMPLE 218

Compound 11708, N-(4-(5-(difluoromethyl)-1,3,4-oxadiazol-2-yl)benzyl)-3-hydroxy-N-phenylpropane-1-sulfonamide

[Step 1] methyl (R)-4-(((3-(3-fluoropyrrolidin-1-yl)-N-phenylpropyl)sulfonamido)methyl)benzoate

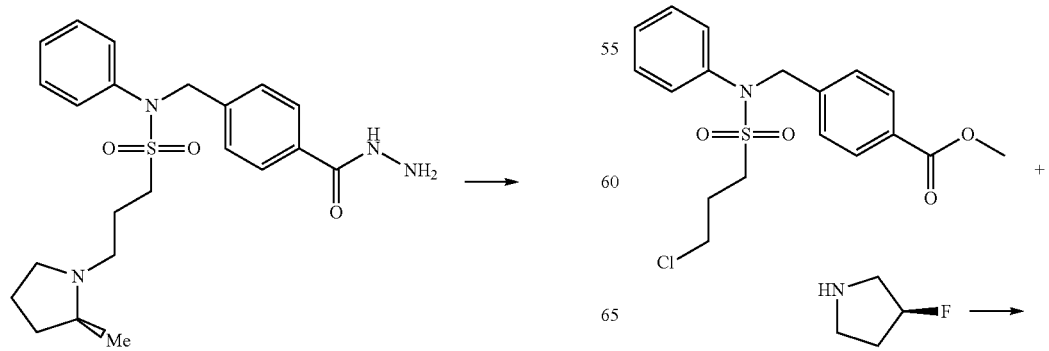

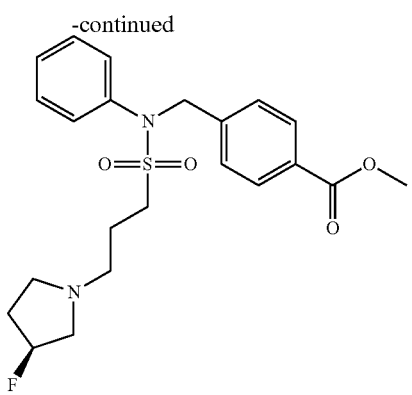

A solution of methyl 4-(((3-chloro-N-phenylpropyl)sulfonamido)methyl)benzoate (0.250 g, 0.655 mmol), (R)-3-fluoropyrrolidin hydrochloride (0.123 g, 0.982 mmol) and potassium carbonate (0.136 g, 0.982 mmol) in N,N-dimethylformide (3 mL) was stirred at 80° C. for 18 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; methanol/dichloromethane=0% to 5%) to give methyl (R)-4-(((3-(3-fluoropyrrolidin-1-yl)-N-phenylpropyl)sulfonamido)methyl)benzoate as colorless oil (0.225 g, 79.1%).

[Step 2] N-(4-(hydrazinecarbonyl)benzyl)-3-hydroxy-N-phenylpropane-1-sulfonamide

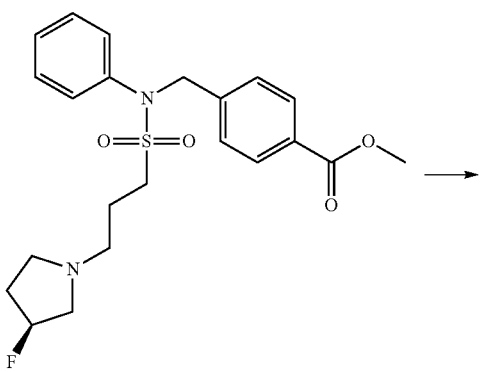

A solution of methyl (R)-4-(((3-(3-fluoropyrrolidin-1-yl)-N-phenylpropyl)sulfonamido)methyl)benzoate (0.225 g, 0.518 mmol) and hydrazine monohydrate (0.252 mL, 5.178 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give N-(4-(hydrazinecarbonyl)benzyl)-3-hydroxy-N-phenylpropane-1-sulfonamide as white solid (0.180 g, 95.7%).

[Step 3] Compound 11708

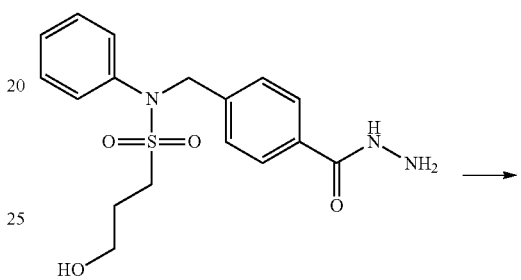

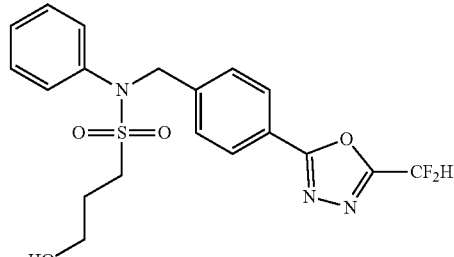

A solution of N-(4-(hydrazinecarbonyl)benzyl)-3-hydroxy-N-phenylpropane-1-sulfonamide (0.100 g, 0.275 mmol), 2,2-difluoroacetic anhydride (0.342 mL, 2.752 mmol) and triethylamine (0.192 mL, 1.376 mmol) in tetrahydrofuran (5 mL) was stirred at 80° C. for 1 hr, and cooled down to the room temperature to terminate the reaction. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 10%) to give N-(4-(5-(difluoromethyl)-1,3,4-oxadiazol-2-yl)benzyl)-3-hydroxy-N-phenylpropane-1-sulfonamide as colorless oil (0.036 g, 30.9%).

¹H NMR (400 MHz, CD3OD) δ8.04 (d, 2H, J=8.5 Hz), 7.48 (d, 2H, J=8.6 Hz), 7.35~7.28 (m, 5H), 6.92 (t, 1H, J=51.7 Hz), 4.98 (s, 2H), 3.82 (t, 2H, J=5.9 Hz), 3.27 (dd, 1H, J=8.8, 6.2 Hz), 2.29~2.12 (m, 2H), 1.74 (brs, 1H); LRMS (ES) m/z 424.3 (M⁺+1).

EXAMPLE 219

Compound 11709, 3-(N-(4-(5-(difluoromethyl)-1,3,4-oxadiazol-2-yl)benzyl)-N-phenylsulfamoyl)propyl 2,2-difluoroacetate

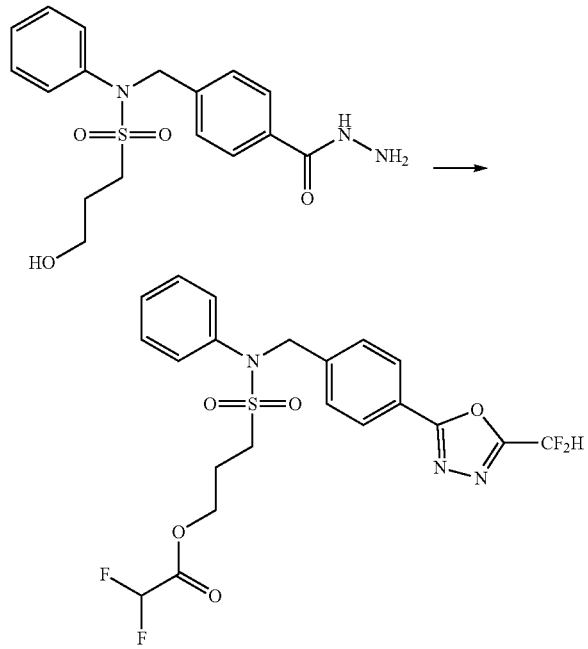

A solution of N-(4-(hydrazinecarbonyl)benzyl)-3-hydroxy-N-phenylpropane-1-sulfonamide (0.080 g, 0.220 mmol), 2,2-difluoroacetic anhydride (0.274 mL, 2.201 mmol) and triethylamine (0.153 mL, 1.101 mmol) in tetrahydrofuran (5 mL) was stirred at 80° C. for 1 hr, and cooled down to the room temperature to terminate the reaction. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=20% to 80%) to give 3-(N-(4-(5-(difluoromethyl)-1,3,4-oxadiazol-2-yl)benzyl)-N-phenylsulfamoyl) propyl 2,2-difluoroacetate as colorless oil (0.029 g, 26.5%).

$^1$H NMR (400 MHz, CD3OD) δ8.02 (d, 2H, J=8.6 Hz), 7.54 (d, 2H, J=8.6 Hz), 7.42~7.26 (m, 5H), 7.21 (t, 1H, J=51.6 Hz), 5.05 (s, 2H), 4.43 (t, 2H, J=6.3 Hz), 3.37~3.35 (m, 2H), 2.32~2.25 (m, 2H); LRMS (ES) m/z 502.1 (M$^+$+1).

EXAMPLE 220

Compound 11710, N-((5-(5-(difluoromethyl)-1,3,4-oxadiazol-2-yl)pyridin-2-yl)methyl)-N-phenyl-3-(pyrrolidin-1-yl)propane-1-sulfonamide

[Step 1] methyl 6-(((3-chloro-N-phenylpropyl)sulfonamido)methyl)nicotinate

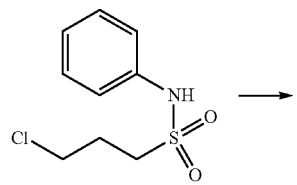

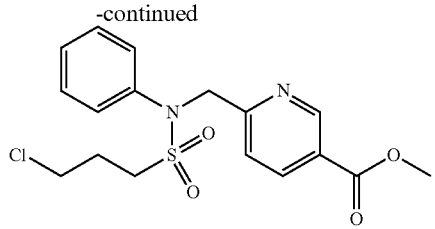

A solution of 3-chloro-N-phenylpropane-1-sulfonamide (2.000 g, 8.558 mmol) and potassium carbonate (1.774 g, 12.836 mmol) in N,N-dimethylformide (100 mL) was stirred at the room temperature for 30 min, and mixed with methyl 4-(bromomethyl)-3-fluorobenzoate (2.067 g, 8.985 mmol) and potassium iodide (0.710 g, 4.279 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 24 g cartridge; ethyl acetate/hexane=0% to 50%) to give methyl 6-(((3-chloro-N-phenylpropyl)sulfonamido)methyl)nicotinate as yellow solid (2.000 g, 61.0%).

[Step 2] methyl 6-(((N-phenyl-3-(pyrrolidin-1-yl)propyl)sulfonamido)methyl)nicotinate

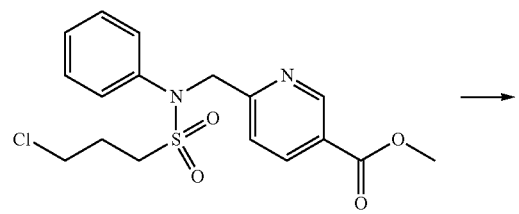

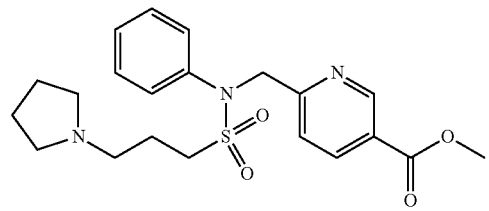

A solution of methyl 6-(((3-chloro-N-phenylpropyl)sulfonamido)methyl)nicotinate (0.200 g, 0.522 mmol), N,N-Diisopropylethylamine (0.136 mL, 0.784 mmol) and pyrrolidine (0.074 g, 1.045 mmol) in tetrahydrofuran (10 mL) was stirred at 70° C. for 12 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give methyl 6-(((N-phenyl-3-(pyrrolidin-1-yl)propyl)sulfonamido)methyl)nicotinate as yellow solid (0.130 g, 59.6%).

633

[Step 3] N-((5-(hydrazinecarbonyl)pyridin-2-yl)methyl)-N-phenyl-3-(pyrrolidin-1-yl)propane-1-sulfonamide

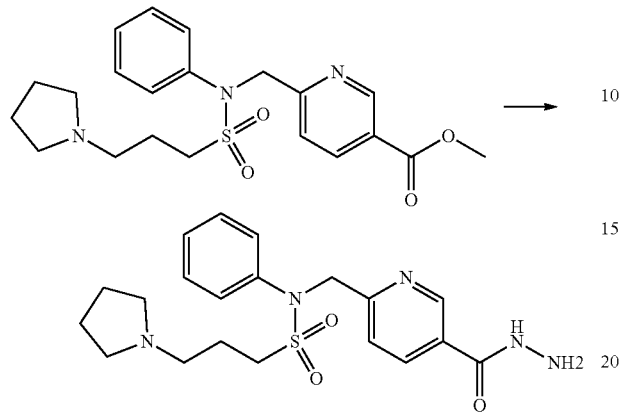

A solution of methyl 6-(((N-phenyl-3-(pyrrolidin-1-yl)propyl)sulfonamido)methyl)nicotinate (0.130 g, 0.311 mmol) and hydrazine monohydrate (0.151 mL, 3.114 mmol) in ethanol (10 mL) was stirred at 90° C. for 12 hr, cooled down to the room temperature to terminate the reaction, and concentrated under the reduced pressure to remove the solvent. The residue was diluted with water (5 mL) and sodium bicarbonate (3 mL) and stirred. The resulting precipitates were collected by filtration and dried to give N-((5-(hydrazinecarbonyl)pyridin-2-yl)methyl)-N-phenyl-3-(pyrrolidin-1-yl)propane-1-sulfonamide as white solid (0.098 g, 75.4%).

[Step 4] Compound 11710

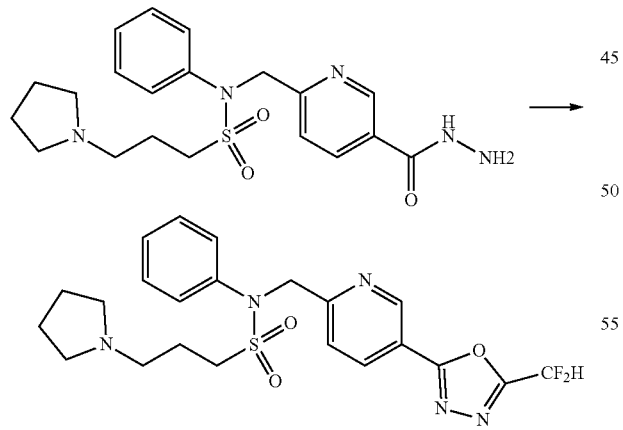

A solution of N-((5-(hydrazinecarbonyl)pyridin-2-yl)methyl)-N-phenyl-3-(pyrrolidin-1-yl)propane-1-sulfonamide (0.070 g, 0.168 mmol), triethylamine (0.117 mL, 0.838 mmol) and 2,2-difluoroacetic anhydride (0.063 mL, 0.503 mmol) in tetrahydrofuran (10 mL) was stirred at 70° C. for 12 hr, and cooled down to the room temperature to terminate

634 the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-N-phenyl-3-(pyrrolidin-1-yl)propane-1-sulfonamide as yellow solid (0.049 g, 61.2%).

$^1$H NMR (400 MHz, CDCl$_3$) δ 9.24 (s, 1H), 8.38-8.36 (m, 1H), 7.69 (d, 1H, J=8.3 Hz), 7.45-7.28 (m, 5H), 7.07 (s, 0.2H), 6.94 (s, 0.5H), 6.81 (s, 0.3H), 5.17 (s, 2H), 3.14-3.37 (m, 2H), 2.95-2.90 (m, 6H), 2.32-2.30 (m, 2H), 2.06-1.98 (m, 4H); LRMS (ES) m/z 478.3 (M$^+$+1).

EXAMPLE 221

Compound 11711, N-(3-chloro-4-fluorophenyl)-N-((5-(5-(difluoromethyl)-1,3,4-oxadiazol-2-yl)pyridin-2-yl)methyl)-3-morpholinopropane-1-sulfonamide

[Step 1] 3-chloro-N-(3-chloro-4-fluorophenyl)propane-1-sulfonamide

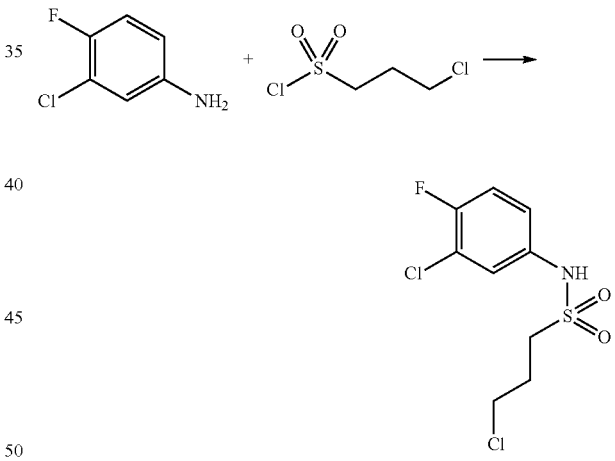

A solution of 3-chloro-4-fluoroaniline (5.000 g, 34.350 mmol) and pyridine (5.534 mL, 68.700 mmol) in dichloromethane (50 mL) was mixed at the room temperature with 3-chloropropane-1-sulfonyl chloride (4.594 mL, 37.785 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 80 g cartridge; ethyl acetate/hexane=0% to 30%) to give 3-chloro-N-(3-chloro-4-fluorophenyl)propane-1-sulfonamide as brown solid (8.700 g, 88.5%).

635

[Step 2] Methyl 6-(((3-chloro-N-(3-chloro-4-fluoro-phenyl)propyl)sulfonamido)methyl)nicotinate

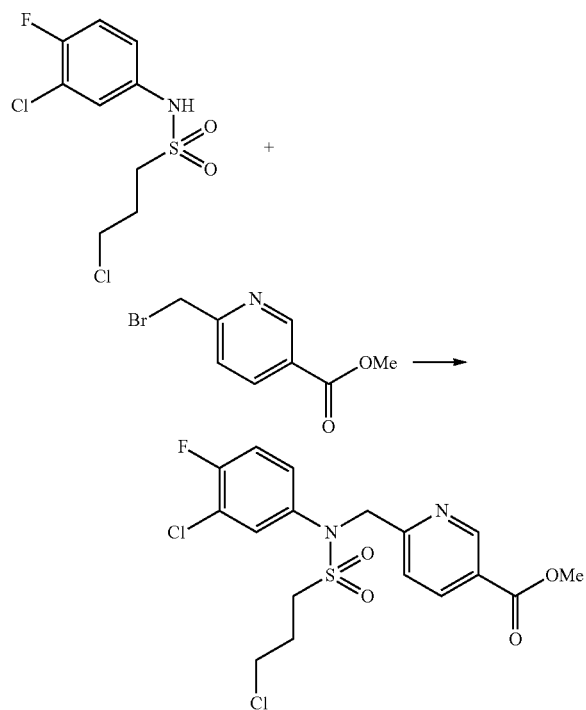

3-chloro-N-(3-chloro-4-fluorophenyl)propane-1-sulfonamide (2.500 g, 8.737 mmol), methyl 6-(bromomethyl)nicotinate (2.010 g, 8.737 mmol), potassium carbonate (2.415 g, 17.474 mmol) and potassium iodide (0.725 g, 4.368 mmol) were mixed at the room temperature in N,N-dimethylformide (20 mL), stirred at 50° C. for 18 hr, and cooled down to the room temperature to terminate the reaction. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 40 g cartridge; ethyl acetate/hexane=0% to 80%) to give methyl 6-(((3-chloro-N-(3-chloro-4-fluorophenyl)propyl)sulfonamido)methyl)nicotinate as res oil (3.800 g, 99.9%).

[Step 3] methyl 6-(((N-(3-chloro-4-fluorophenyl)-3-morpholinopropyl)sulfonamido)methyl)nicotinate

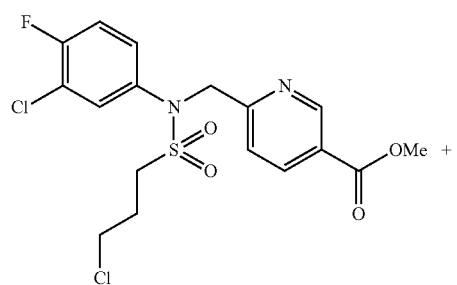

636

-continued

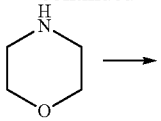

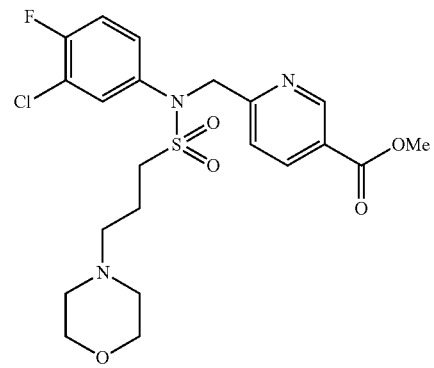

Methyl 6-(((3-chloro-N-(3-chloro-4-fluorophenyl)propyl)sulfonamido)methyl)nicotinate (0.200 g, 0.459 mmol), morpholine (0.048 mL, 0.551 mmol), potassium carbonate (0.127 g, 0.919 mmol) and potassium iodide (0.008 g, 0.046 mmol) were mixed at the room temperature in N,N-dimethylformide (15 mL), stirred at 80° C. for 18 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 80%) to give methyl 6-(((N-(3-chloro-4-fluorophenyl)-3-morpholinopropyl)sulfonamido)methyl)nicotinate as yellow oil (0.058 g, 26.0%).

[Step 4] N-(3-chloro-4-fluorophenyl)-N-((5-(hydrazinecarbonyl)pyridin-2-yl)methyl)-3-morpholinopropane-1-sulfonamide

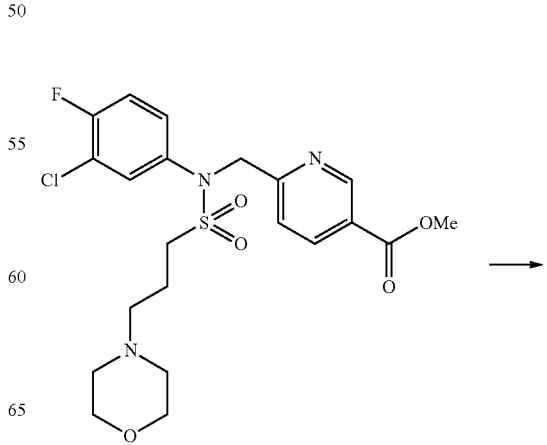

-continued

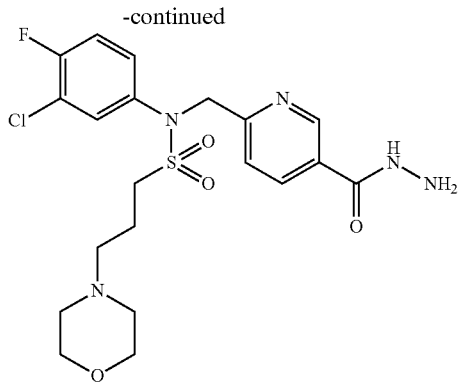

methyl 6-(((N-(3-chloro-4-fluorophenyl)-3-morpholinopropyl)sulfonamido)methyl)nicotinate (0.058 g, 0.119 mmol) and hydrazine monohydrate (0.174 mL, 3.581 mmol) were mixed at the room temperature in ethanol (10 mL), stirred at 70° C. for 18 hr, cooled down to the room temperature to terminate the reaction and concentrated under the reduced pressure to remove the solvent. The title compound was used without further purification (N-(3-chloro-4-fluorophenyl)-N-((5-(hydrazinecarbonyl)pyridin-2-yl)methyl)-3-morpholinopropane-1-sulfonamide, 0.057 g, 98.3%, white solid).

[Step 5] Compound 11711

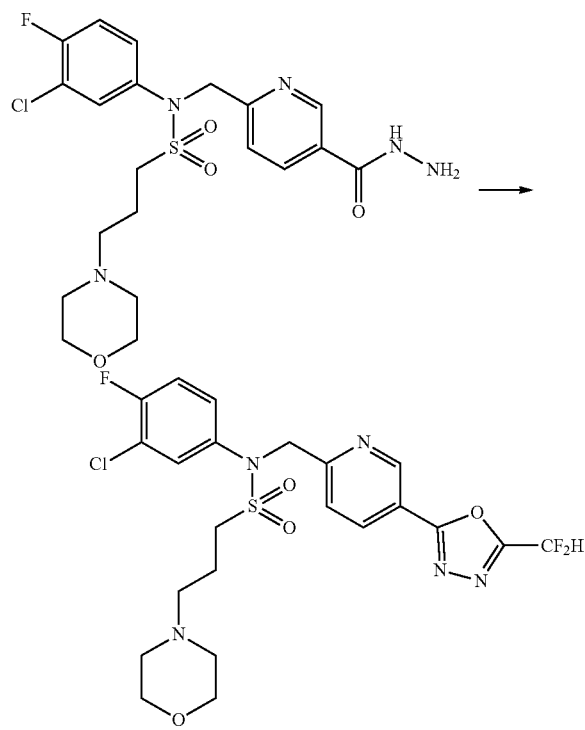

A solution of N-(3-chloro-4-fluorophenyl)-N-((5-(hydrazinecarbonyl)pyridin-2-yl)methyl)-3-morpholinopropane-1-sulfonamide (0.057 g, 0.117 mmol) and triethylamine (0.033 mL, 0.235 mmol) in tetrahydrofuran (10 mL) was mixed at the room temperature with 2,2-difluoroacetic anhydride (0.044 mL, 0.352 mmol), stirred at 80° C. for 2 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give N-(3-chloro-4-fluorophenyl)-N-((5-(5-(difluoromethyl)-1,3,4-oxadiazol-2-yl)pyridin-2-yl)methyl)-3-morpholinopropane-1-sulfonamide as yellow solid (0.025 g, 39.0%).

$^1$H NMR (400 MHz, CDCl$_3$) δ 9.23-9.22 (m, 1H), 8.38 (dd, 1H, J=8.2, 2.2 Hz), 7.63 (d, 1H, J=8.2 Hz), 7.52-7.50 (m, 1H), 7.33-7.29 (m, 1H), 7.11-7.06 (m, 1H), 7.06 (s, 0.25H), 6.93 (s, 0.5H), 6.80 (s, 0.25H), 5.07 (s, 2H); LRMS (ES) m/z 546.3 (M$^+$+1).

EXAMPLE 222

Compound 11712, N-((5-(5-(difluoromethyl)-1,3,4-oxadiazol-2-yl)pyridin-2-yl)methyl)-N-(2-methylisoindolin-4-yl)ethanesulfonamide

[Step 1] tert-butyl 4-(ethylsulfonamido)isoindoline-2-carboxylate

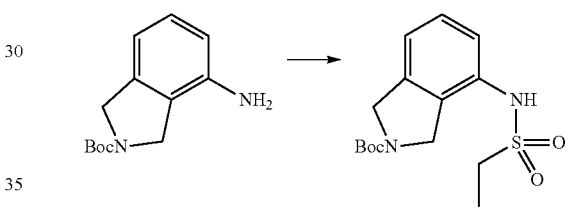

A solution of tert-butyl 4-aminoisoindoline-2-carboxylate (2.000 g, 8.536 mmol) in dichloromethane (50 mL) was mixed at the room temperature with ethanesulfonyl chloride (0.887 mL, 9.390 mmol) and triethylamine (1.785 mL, 12.804 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=10% to 30%) to give tert-butyl 4-(ethylsulfonamido)isoindoline-2-carboxylate as white solid (2.770 g, 99.4%).

[Step 2] tert-butyl 4-(N-((5-(methoxycarbonyl)pyridin-2-yl)methyl)ethylsulfonamido)isoindoline-2-carboxylate

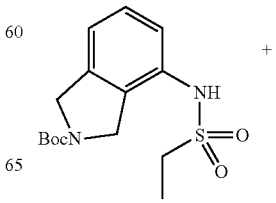 +

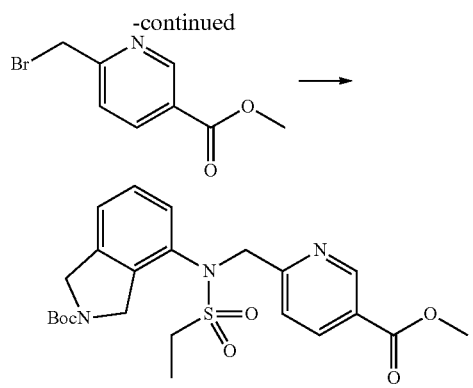

A mixture of tert-butyl 4-(ethylsulfonamido)isoindoline-2-carboxylate (1.380 g, 4.228 mmol), methyl 6-(bromomethyl)nicotinate (1.264 g, 5.496 mmol), potassium iodide (1.404 g, 8.456 mmol) and potassium carbonate (1.169 g, 8.456 mmol) in N,N-dimethylformide (20 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give tert-butyl 4-(N-((5-(methoxycarbonyl)pyridin-2-yl)methyl)ethylsulfonamido)isoindoline-2-carboxylate as brown solid (0.506 g, 25.2%).

[Step 3] methyl 6-((N-(isoindolin-4-yl)ethylsulfonamido)methyl)nicotinate dihydrochloride

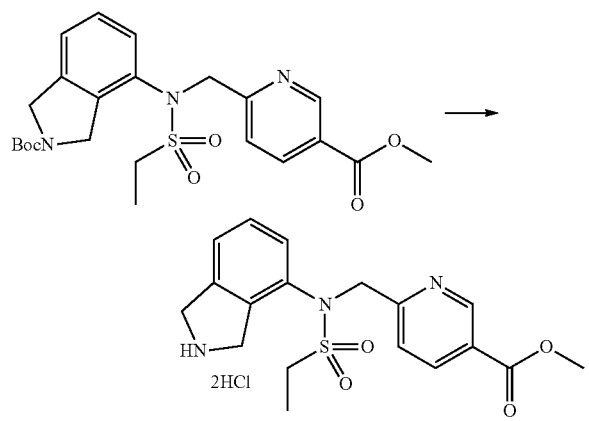

A solution of tert-butyl 4-(N-((5-(methoxycarbonyl)pyridin-2-yl)methyl)ethylsulfonamido)isoindoline-2-carboxylate (0.506 g, 1.064 mmol) in 1,4-dioxane (5 mL) was mixed at the room temperature with hydrochloric acid (4.00 M solution in 1,4-dioxane, 5.320 mL, 21.280 mmol), stirred at the same temperature for 3 hr, and concentrated under the reduced pressure to remove the solvent. The residue was diluted with ethyl acetate (10 mL) and hexane (10 mL) and stirred. The resulting precipitates were collected by filtration, washed by hexane, and dried to give methyl 6-((N-(isoindolin-4-yl)ethylsulfonamido)methyl)nicotinate dihydrochloride as brown solid (0.420 g, 88.0%).

[Step 4] methyl 6-((N-(2-methylisoindolin-4-yl)ethylsulfonamido)methyl)nicotinate

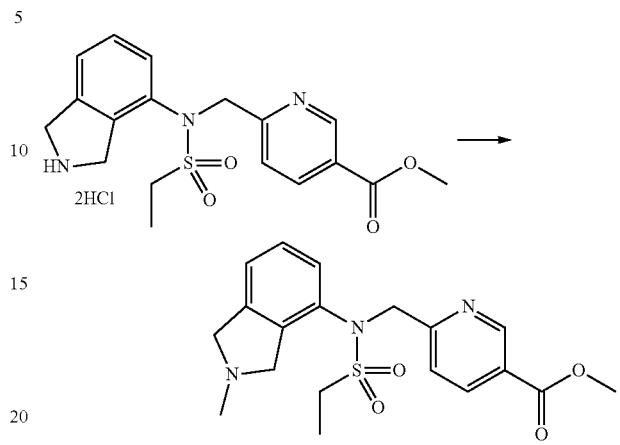

A mixture of methyl 6-((N-(isoindolin-4-yl)ethylsulfonamido)methyl)nicotinate dihydrochloride (0.200 g, 0.446 mmol), paraformaldehyde (0.067 g, 2.230 mmol) and N,N-diisopropylethylamine (0.194 mL, 1.115 mmol) in dichloromethane (10 mL) was treated at the room temperature with sodium triacetoxyborohydride (0.189 g, 0.892 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give methyl 6-((N-(2-methylisoindolin-4-yl)ethylsulfonamido)methyl)nicotinate as brown solid (0.077 g, 44.3%).

[Step 5] N-((5-(hydrazinecarbonyl)pyridin-2-yl)methyl)-N-(2-methylisoindolin-4-yl)ethanesulfonamide

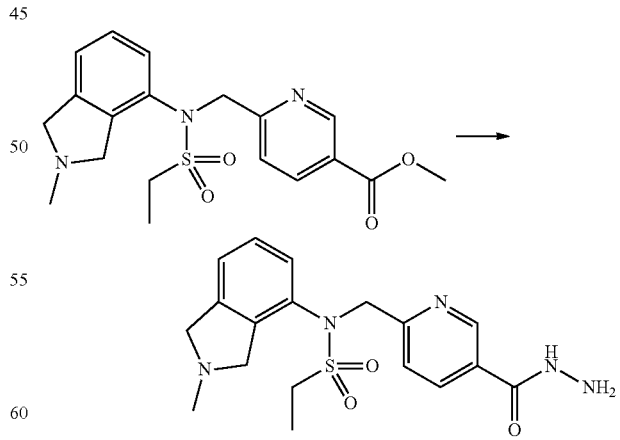

methyl 6-((N-(2-methylisoindolin-4-yl)ethylsulfonamido)methyl)nicotinate (0.077 g, 0.198 mmol) and hydrazine monohydrate (0.480 mL, 9.885 mmol) were mixed at the room temperature in ethanol (5 mL), stirred at 110° C. for 18 hr, cooled down to the room temperature to terminate the reaction and concentrated under the reduced pressure to remove the solvent. The title compound was used without further purification (N-((5-(hydrazinecarbonyl)pyridin-2-yl)methyl)-N-(2-methylisoindolin-4-yl)ethanesulfonamide, 0.077 g, 100.0%, brown solid).

[Step 6] Compound 11712

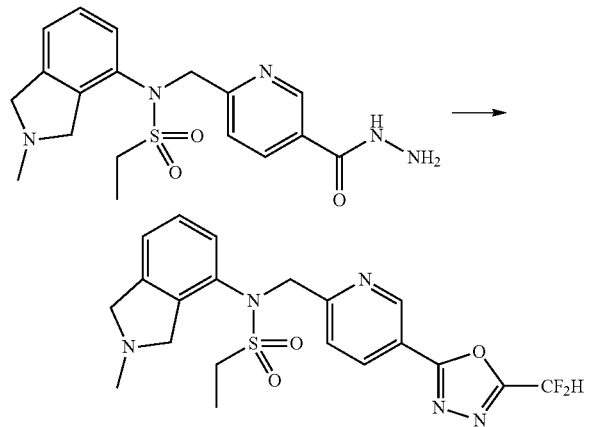

A solution of N-((5-(hydrazinecarbonyl)pyridin-2-yl)methyl)-N-(2-methylisoindolin-4-yl)ethanesulfonamide (0.077 g, 0.198 mmol) in tetrahydrofuran (10 mL) was mixed at the room temperature with 2,2-difluoroacetic anhydride (0.074 mL, 0.593 mmol) and triethylamine (0.110 mL, 0.791 mmol). The reaction mixture was heated at reflux for 1 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 10%) to give N-((5-(5-(difluoromethyl)-1,3,4-oxadiazol-2-yl)pyridin-2-yl)methyl)-N-(2-methylisoindolin-4-yl)ethanesulfonamide as beige solid (0.046 g, 51.8%).

$^1$H NMR (400 MHz, DMSO-d6) δ 9.10 (m, 1H), 8.42 (dd, 1H, J=8.2, 2.3 Hz), 7.73-7.65 (m, 1.25H), 7.56 (s, 0.5H), 7.43 (s, 0.25H), 7.32 (d, 1H, J=7.6 Hz), 7.21 (t, 1H, J=7.6 Hz), 7.16 (d, 1H, J=7.3 Hz), 5.00 (s, 2H), 3.85 (s, 2H), 3.76 (s, 2H), 3.48-3.40 (m, 2H), 2.41 (s, 3H), 1.31 (t, 3H, J=7.3 Hz); LRMS (ES) m/z 450.3 (M⁺+1).

EXAMPLE 223

Compound 11717, N-(4-(5-(difluoromethyl)-1,3,4-oxadiazol-2-yl)benzyl)-2-(4-(2-hydroxyethyl)piperazin-1-yl)-N-phenylethanesulfonamide

[Step 1] Methyl 4-(((2-(4-(2-hydroxyethyl)piperazin-1-yl)-N-phenylethyl)sulfonamido)methyl)benzoate

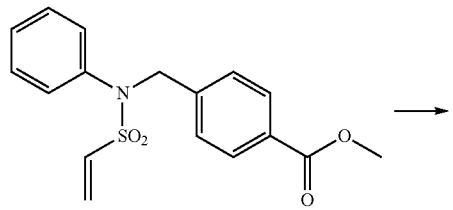

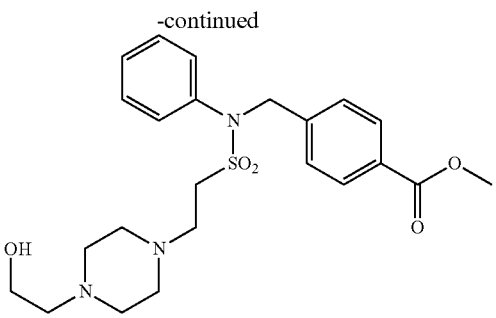

A solution of methyl 4-((N-phenylvinylsulfonamido)methyl)benzoate (0.300 g, 0.905 mmol), 2-(piperazin-1-yl)ethanol (0.122 mL, 0.996 mmol) and N,N-diisopropylethylamine (0.312 mL, 1.811 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give methyl 4-(((2-(4-(2-hydroxyethyl)piperazin-1-yl)-N-phenylethyl)sulfonamido)methyl)benzoate as white solid (0.350 g, 83.8%).

[Step 2] N-(4-(hydrazinecarbonyl)benzyl)-2-(4-(2-hydroxyethyl)piperazin-1-yl)-N-phenylethanesulfonamide

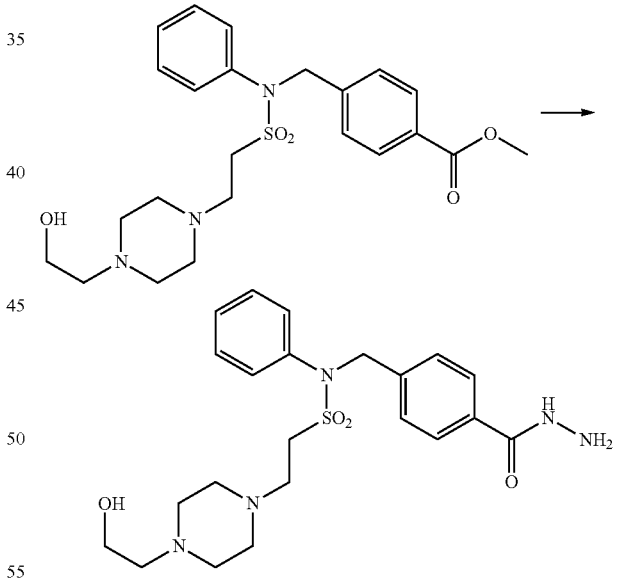

A solution of methyl 4-(((2-(4-(2-hydroxyethyl)piperazin-1-yl)-N-phenylethyl)sulfonamido)methyl)benzoate (0.350 g, 0.758 mmol) and hydrazine (0.476 mL, 15.166 mmol) in ethanol (5 mL) prepared at the room temperature was heated at the reflux for 12 hr, cooled down to the room temperature to terminate the reaction and concentrated under the reduced pressure to remove the solvent. The resulting precipitates were collected by filtration and dried to give N-(4-(hydrazinecarbonyl)benzyl)-2-(4-(2-hydroxyethyl)piperazin-1-yl)-N-phenylethanesulfonamide as white solid (0.130 g, 37.1%).

[Step 3] Compound 11717

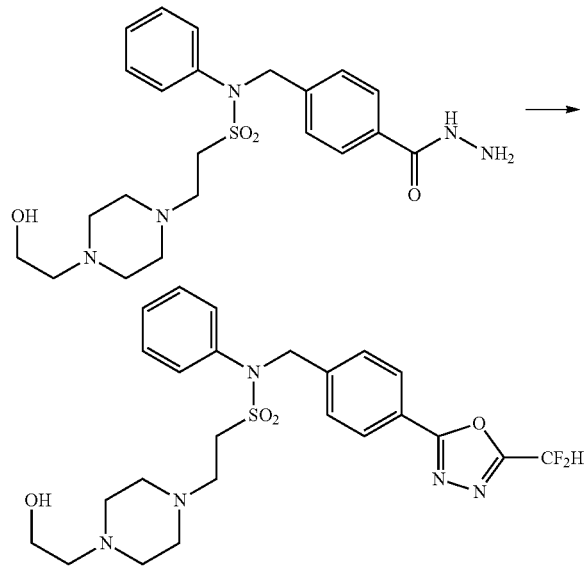

A mixture of N-(4-(hydrazinecarbonyl)benzyl)-2-(4-(2-hydroxyethyl)piperazin-1-yl)-N-phenylethanesulfonamide (0.130 g, 0.282 mmol), 2,2-difluoroacetic anhydride (0.105 mL, 0.845 mmol) and triethylamine (0.196 mL, 1.408 mmol) in tetrahydrofuran (5 mL) was heated at reflux for 6 hr, and cooled down to the ambient temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-2-(4-(2-hydroxyethyl)piperazin-1-yl)-N-phenylethanesulfonamide as orange solid (0.070 g, 47.7%).

$^1$H NMR (400 MHz, DMSO-d6) δ7.99 (d, 2H, J=8.4 Hz), 7.54-7.52 (m, 2H), 7.43-7.24 (m, 6H), 5.04 (s, 2H), 3.77-3.76 (m, 2H), 3.49-3.45 (m, 4H), 3.18 (m, 2H), 3.04 (m, 4H), 2.84 (m, 2H), 2.50 (m, 2H); LRMS (ES) m/z 522.0 (M$^+$+1).

EXAMPLE 224

Compound 11718, N-((5-(5-(difluoromethyl)-1,3,4-oxadiazol-2-yl)pyridin-2-yl)methyl)-3-morpholino-N-phenylpropane-1-sulfonamide

[Step 1] methyl 6-(((3-morpholino-N-phenylpropyl)sulfonamido)methyl)nicotinate

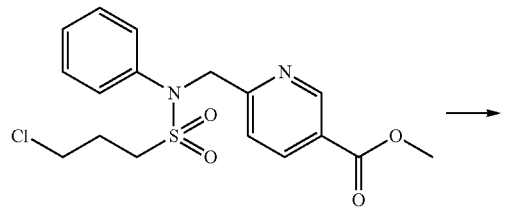

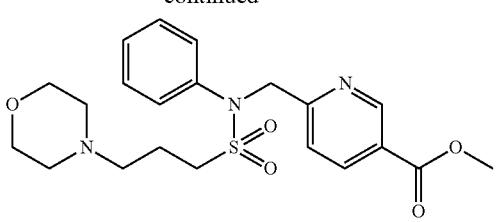

A solution of methyl 6-(((3-chloro-N-phenylpropyl)sulfonamido)methyl)nicotinate (0.150 g, 0.392 mmol), N,N-diisopropylethylamine (0.341 mL, 1.959 mmol) and morpholine (0.102 mL, 1.175 mmol) in tetrahydrofuran (10 mL) was stirred at 70° C. for 18 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give methyl 6-(((3-morpholino-N-phenylpropyl) sulfonamido)methyl)nicotinate as yellow solid (0.080 g, 47.1%).

[Step 2] N-((5-(hydrazinecarbonyl)pyridin-2-yl)methyl)-3-morpholino-N-phenylpropane-1-sulfonamide

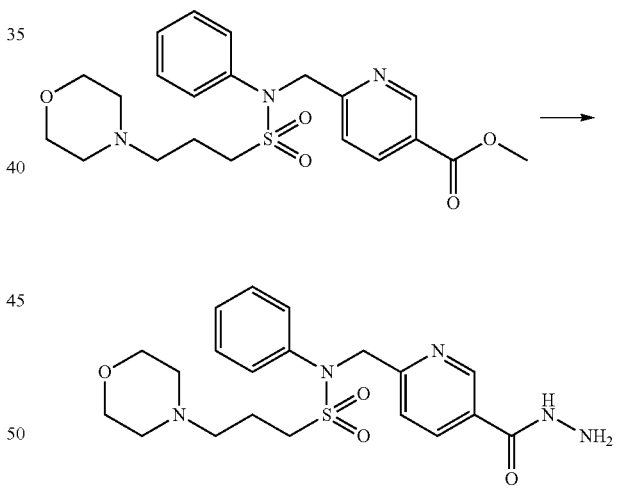

A solution of methyl 6-(((3-morpholino-N-phenylpropyl) sulfonamido)methyl)nicotinate (0.080 g, 0.185 mmol) and hydrazine monohydrate (0.090 mL, 1.845 mmol) in ethanol (10 mL) was stirred at 90° C. for 12 hr and cooled down to the room temperature to terminate the reaction. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-((5-(hydrazinecarbonyl)pyridin-2-yl)methyl)-3-morpholino-N-phenylpropane-1-sulfonamide, 0.069 g, 86.2%, white solid).

[Step 3] Compound 11718

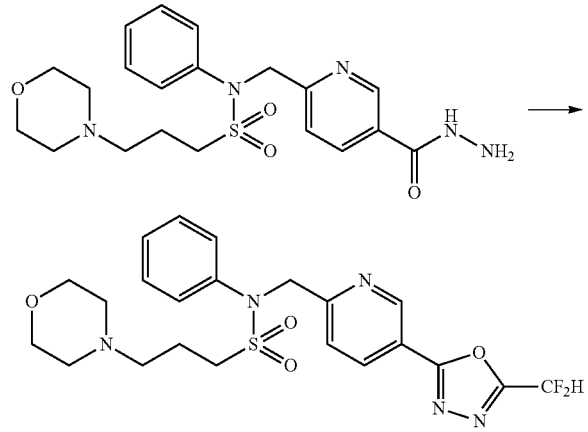

A solution of N-((5-(hydrazinecarbonyl)pyridin-2-yl)methyl)-3-morpholino-N-phenylpropane-1-sulfonamide (0.100 g, 0.231 mmol), triethylamine (0.161 mL, 1.153 mmol) and 2,2-difluoroacetic anhydride (0.086 mL, 0.692 mmol) in tetrahydrofuran (10 mL) was stirred at 70° C. for 12 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-3-morpholino-N-phenylpropane-1-sulfonamide as yellow solid (0.041 g, 36.0%).

$^1$H NMR (400 MHz, CDCl$_3$) δ 9.25-9.24 (m, 1H), 8.38-8.36 (m, 1H), 7.73-7.70 (m, 1H), 7.44-7.30 (m, 5H), 5.17 (s, 2H), 3.76-3.73 (m, 4H), 3.33-3.29 (m, 2H), 2.55-2.46 (m, 6H), 2.16-2.14 (m, 2H); LRMS (ES) m/z 494.3 (M$^+$+1).

EXAMPLE 225

Compound 11719, N-((5-(5-(difluoromethyl)-1,3,4-oxadiazol-2-yl)pyridin-2-yl)methyl)-3-(3,3-difluoropyrrolidin-1-yl)-N-phenylpropane-1-sulfonamide

[Step 1] methyl 6-(((3-(3,3-difluoropyrrolidin-1-yl)-N-phenylpropyl)sulfonamido)methyl)nicotinate

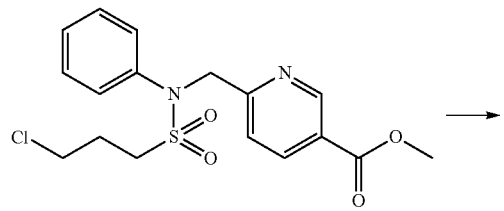

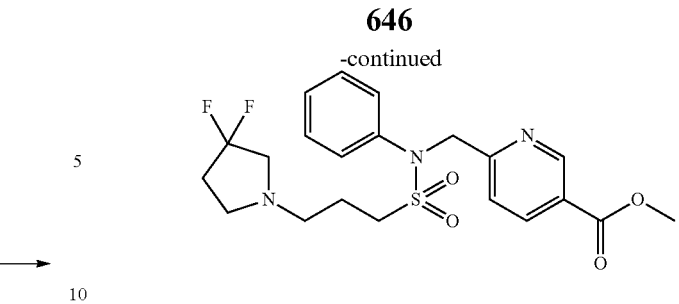

A solution of methyl 6-(((3-chloro-N-phenylpropyl)sulfonamido)methyl)nicotinate (0.150 g, 0.392 mmol), N,N-diisopropylethylamine (0.341 mL, 1.959 mmol) and 3,3-difluoropyrrolidin (0.126 g, 1.175 mmol) in tetrahydrofuran (10 mL) was stirred at 70° C. for 18 hr and cooled down to the room temperature to terminate the reaction. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give methyl 6-(((3-(3,3-difluoropyrrolidin-1-yl)-N-phenylpropyl)sulfonamido)methyl)nicotinate as yellow solid (0.049 g, 27.6%).

[Step 2] 3-(3,3-difluoropyrrolidin-1-yl)-N-((5-(hydrazinecarbonyl)pyridin-2-yl)methyl)-N-phenylpropane-1-sulfonamide

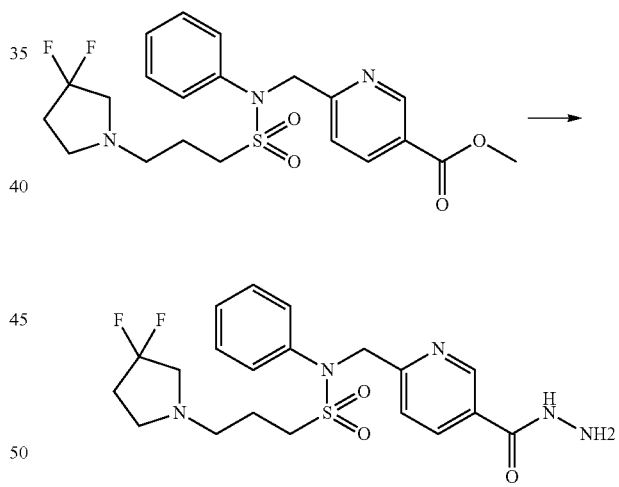

A solution of methyl 6-(((3-(3,3-difluoropyrrolidin-1-yl)-N-phenylpropyl)sulfonamido)methyl)nicotinate (0.049 g, 0.108 mmol) and hydrazine monohydrate (0.053 mL, 1.080 mmol) in ethanol (5 mL) was stirred at 90° C. for 12 hr, cooled down to the room temperature to terminate the reaction and concentrated under the reduced pressure to remove the solvent. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (3-(3,3-difluoropyrrolidin-1-yl)-N-((5-(hydrazinecarbonyl)pyridin-2-yl)methyl)-N-phenylpropane-1-sulfonamide, 0.023 g, 46.9%, yellow solid).

647

[Step 3] Compound 11719

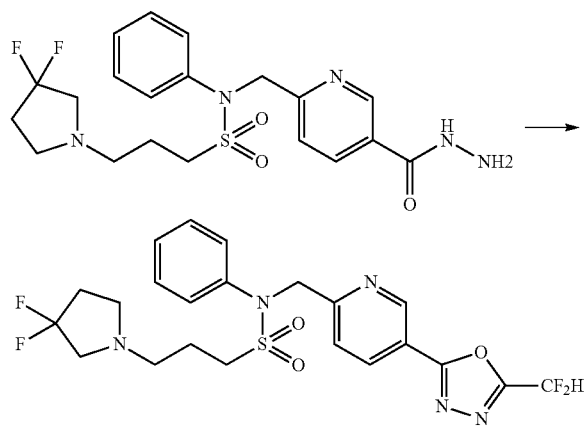

A solution of 3-(3,3-difluoropyrrolidin-1-yl)-N-((5-(hydrazinecarbonyl)pyridin-2-yl)methyl)-N-phenylpropane-1-sulfonamide (0.057 g, 0.126 mmol), triethylamine (0.088 mL, 0.628 mmol) and 2,2-difluoroacetic anhydride (0.047 mL, 0.377 mmol) in tetrahydrofuran (10 mL) was stirred at 70° C. for 12 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-3-(3,3-difluoropyrrolidin-1-yl)-N-phenylpropane-1-sulfonamide as yellow solid (0.019 g, 29.4%).

$^1$H NMR (400 MHz, CDCl$_3$) δ 9.23-9.22 (m, 1H), 8.38-8.36 (m, 1H), 7.72-7.70 (m, 1H), 7.44-7.27 (m, 5H), 7.07 (s, 0.2H), 6.94 (s, 0.5H), 6.81 (s, 0.2H), 5.16 (s, 2H), 3.31-3.28 (m, 2H), 2.97-2.91 (m, 2H), 2.79 (brs, 2H), 2.66 (brs, 2H), 2.35-2.25 (m, 2H), 2.11-2.04 (m, 2H); LRMS (ES) m/z 514.3 (M$^+$+1).

EXAMPLE 226

Compound 11721, N-(3-chloro-4-fluorophenyl)-N-((5-(5-(difluoromethyl)-1,3,4-oxadiazol-2-yl)pyridin-2-yl)methyl)-3-(pyrrolidin-1-yl)propane-1-sulfonamide

[Step 1] Methyl 6-(((N-(3-chloro-4-fluorophenyl)-3-(pyrrolidin-1-yl)propyl)sulfonamido)methyl)nicotinate

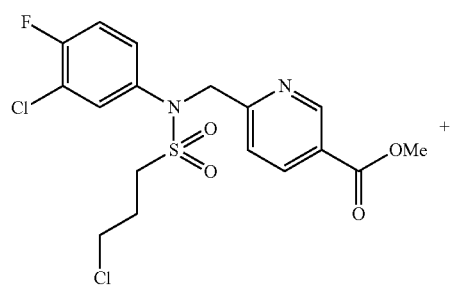

648

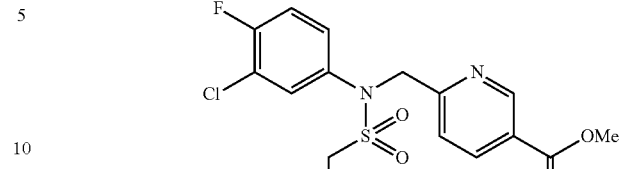

methyl 6-(((3-chloro-N-(3-chloro-4-fluorophenyl)propyl)sulfonamido)methyl)nicotinate (0.200 g, 0.459 mmol), pyrrolidine (0.057 mL, 0.689 mmol) and N,N-diisopropylethylamine (0.160 mL, 0.919 mmol) were mixed at the room temperature in tetrahydrofuran (10 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 20%) to give methyl 6-(((N-(3-chloro-4-fluorophenyl)-3-(pyrrolidin-1-yl)propyl)sulfonamido)methyl)nicotinate as yellow solid (0.123 g, 57.0%).

[Step 2] N-(3-chloro-4-fluorophenyl)-N-((5-(hydrazinecarbonyl)pyridin-2-yl)methyl)-3-(pyrrolidin-1-yl)propane-1-sulfonamide

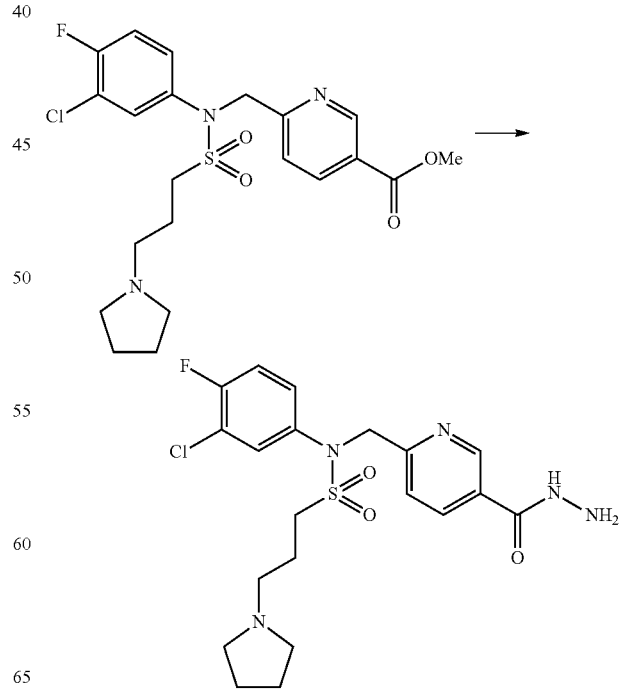

methyl 6-(((N-(3-chloro-4-fluorophenyl)-3-(pyrrolidin-1-yl)propyl)sulfonamido)methyl)nicotinate (0.123 g, 0.262 mmol) and hydrazine monohydrate (0.382 mL, 7.852 mmol) were mixed at the room temperature in ethanol (10 mL), stirred at 70° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chloro-4-fluorophenyl)-N-((5-(hydrazinecarbonyl)pyridin-2-yl)methyl)-3-(pyrrolidin-1-yl)propane-1-sulfonamide, 0.121 g, 98.4%, colorless oil).

[Step 3] Compound 11721

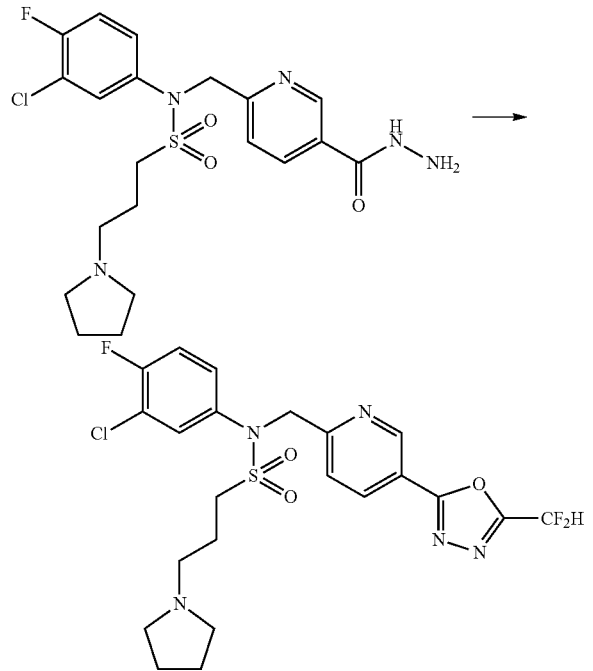

A solution of N-(3-chloro-4-fluorophenyl)-N-((5-(hydrazinecarbonyl)pyridin-2-yl)methyl)-3-(pyrrolidin-1-yl)propane-1-sulfonamide (0.130 g, 0.277 mmol) and triethylamine (0.116 mL, 0.830 mmol) in tetrahydrofuran (10 mL) was mixed at the room temperature with 2,2-difluoroacetic anhydride (0.103 mL, 0.830 mmol), stirred at 70° C. for 2 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 20%) to give N-(3-chloro-4-fluorophenyl)-N-((5-(5-(difluoromethyl)-1,3,4-oxadiazol-2-yl)pyridin-2-yl)methyl)-3-(pyrrolidin-1-yl)propane-1-sulfonamide as yellow solid (0.056 g, 38.2%).

$^1$H NMR (400 MHz, CDCl$_3$) δ 9.21-9.21 (m, 1H), 8.36 (dd, 1H, J=8.2, 2.2 Hz), 7.63 (d, 1H, J=8.2 Hz), 7.52-7.50 (m, 1H), 7.32-7.28 (m, 1H), 7.10-7.06 (m, 1H), 7.05 (s, 0.25H), 6.92 (s, 0.5H), 6.79 (s, 0.25H), 5.07 (s, 2H), 3.30-3.26 (m, 2H), 2.70-2.66 (m, 2H), 2.65-2.58 (m, 4H), 2.14-2.02 (m, 2H), 1.86-1.81 (m, 4H); LRMS (ES) m/z 530.2 (M$^+$+1).

EXAMPLE 227

Compound 11722, N-(3-chloro-4-fluorophenyl)-N-(4-(5-(difluoromethyl)-1,3,4-oxadiazol-2-yl)benzyl)-3-(pyrrolidin-1-yl)propane-1-sulfonamide

[Step 1] Methyl 4-(((3-chloro-N-(3-chloro-4-fluorophenyl)propyl)sulfonamido)methyl)benzoate

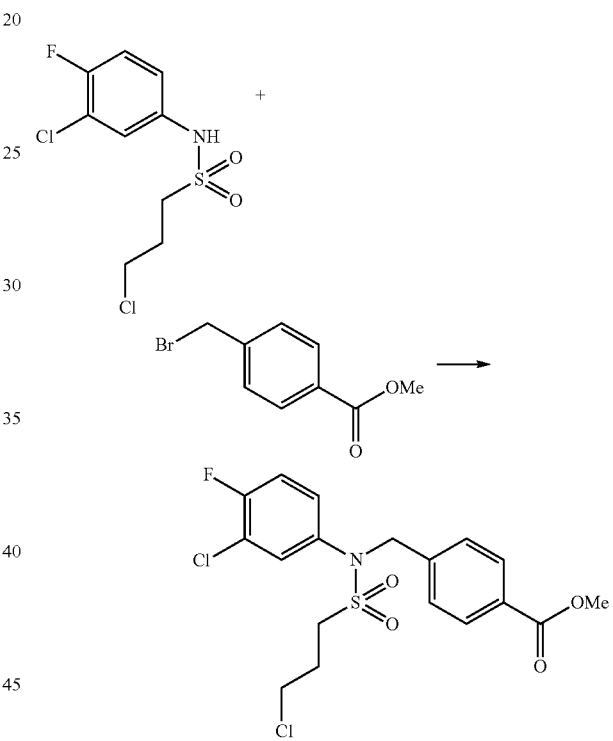

3-chloro-N-(3-chloro-4-fluorophenyl)propane-1-sulfonamide (3.000 g, 10.484 mmol), methyl 4-(bromomethyl)benzoate (2.522 g, 11.009 mmol), potassium iodide (0.870 g, 5.242 mmol) and potassium carbonate (2.898 g, 20.969 mmol) were mixed at the room temperature in N,N-dimethylformide (20 mL), stirred at 50° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give methyl 4-(((3-chloro-N-(3-chloro-4-fluorophenyl)propyl)sulfonamido)methyl)benzoate as yellow solid (4.500 g, 98.8%).

[Step 2] Methyl 4-(((N-(3-chloro-4-fluorophenyl)-3-(pyrrolidin-1-yl)propyl)sulfonamido)methyl)benzoate

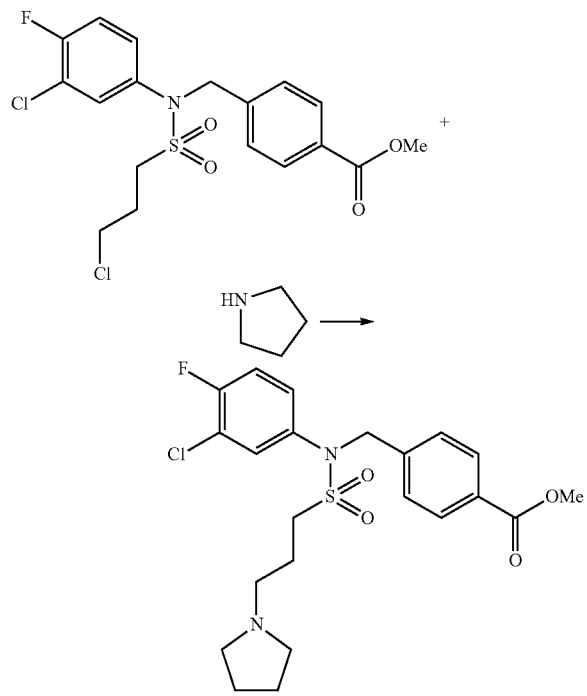

Methyl 4-(((3-chloro-N-(3-chloro-4-fluorophenyl)propyl)sulfonamido)methyl)benzoate (0.200 g, 0.461 mmol), pyrrolidine (0.076 mL, 0.921 mmol) and N,N-diisopropylethylamine (0.160 mL, 0.921 mmol) were mixed at the room temperature in tetrahydrofuran (10 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 20%) to give methyl 4-(((N-(3-chloro-4-fluorophenyl)-3-(pyrrolidin-1-yl)propyl)sulfonamido)methyl)benzoate as yellow solid (0.135 g, 62.5%).

[Step 3] N-(3-chloro-4-fluorophenyl)-N-(4-(hydrazinecarbonyl)benzyl)-3-(pyrrolidin-1-yl)propane-1-sulfonamide

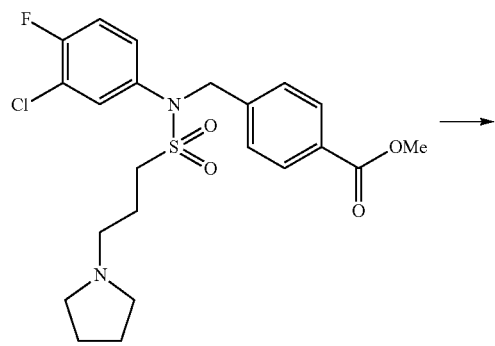

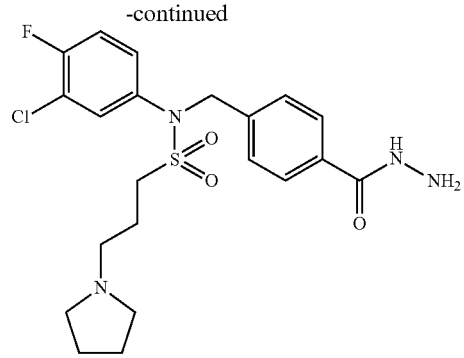

Methyl 4-(((N-(3-chloro-4-fluorophenyl)-3-(pyrrolidin-1-yl)propyl)sulfonamido)methyl)benzoate (0.135 g, 0.288 mmol) and hydrazine monohydrate (0.420 mL, 8.636 mmol) were mixed at the room temperature in ethanol (10 mL), stirred at 70° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chloro-4-fluorophenyl)-N-(4-(hydrazinecarbonyl)benzyl)-3-(pyrrolidin-1-yl)propane-1-sulfonamide, 0.130 g, 96.3%, colorless oil).

[Step 4] Compound 11722

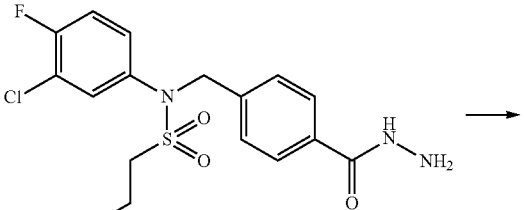

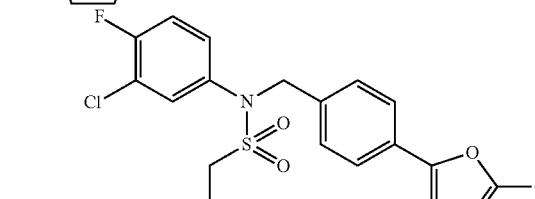

A solution of N-(3-chloro-4-fluorophenyl)-N-(4-(hydrazinecarbonyl)benzyl)-3-(pyrrolidin-1-yl)propane-1-sulfonamide (0.130 g, 0.277 mmol) and triethylamine (0.116 mL, 0.832 mmol) in tetrahydrofuran (10 mL) was mixed at the room temperature with 2,2-difluoroacetic anhydride (0.103 mL, 0.832 mmol), stirred at 70° C. for 2 hr and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 4 g cartridge; methanol/dichloromethane=0% to 20%) to give N-(3-chloro-4-fluorophenyl)-N-(4-(5-(difluoromethyl)-1,3,4-oxadiazol-2-yl)benzyl)-3-(pyrrolidin-1-yl)propane-1-sulfonamide as yellow solid (0.063 g, 43.0%).

$^1$H NMR (400 MHz, $CDCl_3$) δ 8.02-8.00 (m, 2H), 7.43 (d, 2H, J=8.4 Hz), 7.37 (dd, 1H, J=6.4, 2.6 Hz), 7.18-7.14 (m, 1H), 7.07-7.03 (m, 1H), 7.02 (s, 0.25H), 6.89 (s, 0.5H), 6.76 (s, 0.25H), 4.90 (s, 2H), 3.23-3.19 (m, 2H), 2.65-2.62 (m, 2H), 2.60-2.50 (m, 4H), 2.13-2.02 (m, 2H), 1.86-1.77 (m, 4H); LRMS (ES) m/z 529.3 (M$^+$+1).

EXAMPLE 228

Compound 11723, N-(3-chloro-4-fluorophenyl)-N-(4-(5-(difluoromethyl)-1,3,4-oxadiazol-2-yl)benzyl)-3-morpholinopropane-1-sulfonamide

[Step 1] Methyl 4-(((N-(3-chloro-4-fluorophenyl)-3-morpholinopropyl)sulfonamido)methyl)benzoate

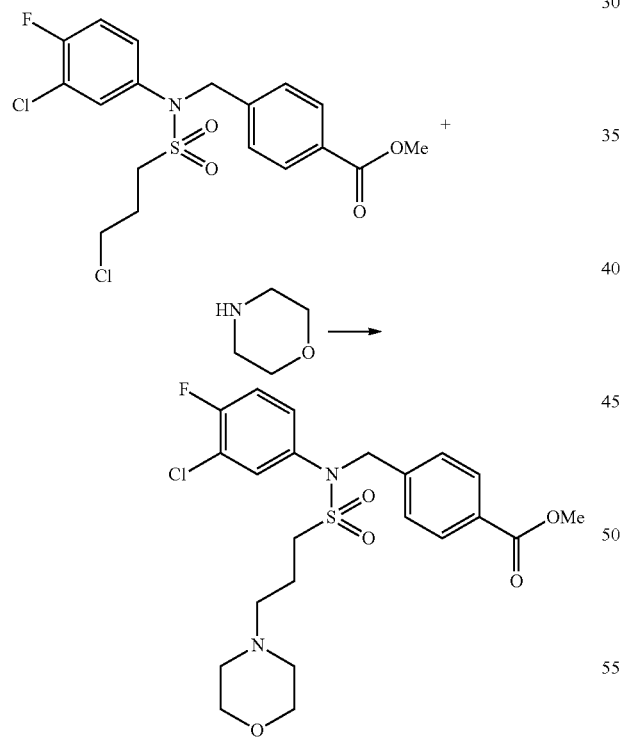

Methyl 4-(((3-chloro-N-(3-chloro-4-fluorophenyl)propyl) sulfonamido)methyl)benzoate (0.200 g, 0.461 mmol), morpholine (0.060 mL, 0.691 mmol) and N,N-diisopropylethylamine (0.160 mL, 0.921 mmol) were mixed at the room temperature in tetrahydrofuran (10 mL), stirred at 80° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 4 g cartridge; methanol/dichloromethane=0% to 20%) to give methyl 4-(((N-(3-chloro-4-fluorophenyl)-3-morpholinopropyl)sulfonamido)methyl)benzoate as yellow solid (0.031 g, 13.9%)

[Step 2] N-(3-chloro-4-fluorophenyl)-N-(4-(hydrazinecarbonyl)benzyl)-3-morpholinopropane-1-sulfonamide

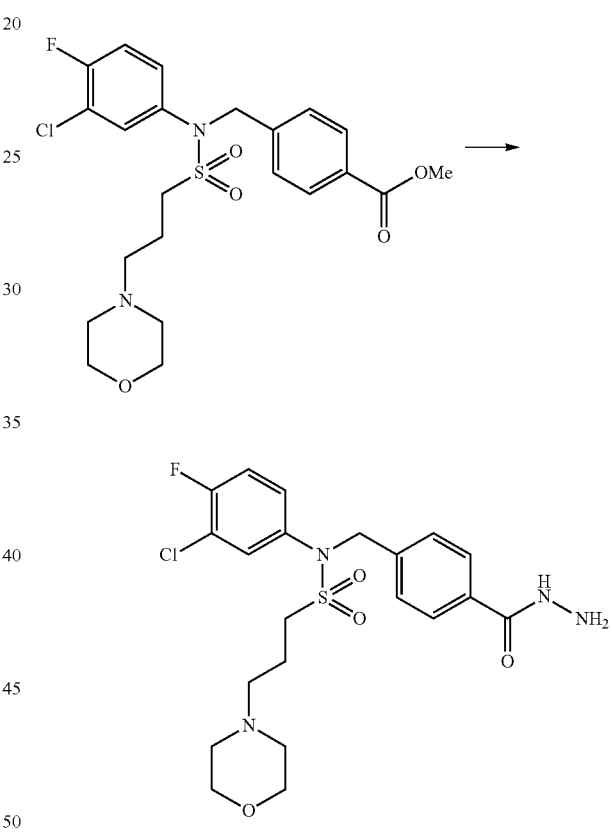

methyl 4-(((N-(3-chloro-4-fluorophenyl)-3-morpholinopropyl)sulfonamido)methyl)benzoate (0.031 g, 0.064 mmol) and hydrazine monohydrate (0.093 mL, 1.918 mmol) were mixed at the room temperature in ethanol (10 mL), stirred at 70° C. for 18 hr and cooled down to the room temperature to terminate the reaction. Then, water was added to the reaction mixture, followed by extraction with ethyl acetate. The organic layer was washed with aqueous saturated sodium chloride solution, dried with anhydrous $MgSO_4$, filtered, and concentrated in vacuo. The title compound was used without further purification (N-(3-chloro-4-fluorophenyl)-N-(4-(hydrazinecarbonyl)benzyl)-3-morpholinopropane-1-sulfonamide, 0.030 g, 96.8%, colorless oil).

655
[Step 3] Compound 11723

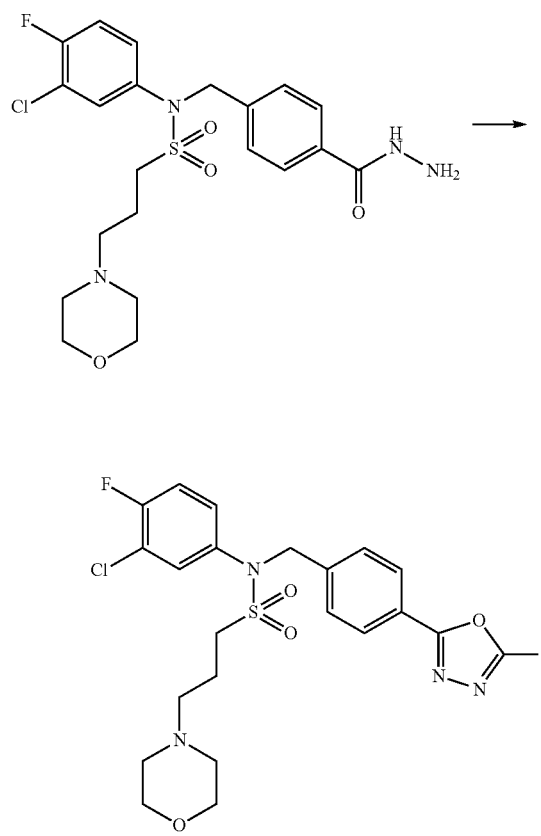

A solution of N-(3-chloro-4-fluorophenyl)-N-(4-(hydrazinecarbonyl)benzyl)-3-morpholinopropane-1-sulfonamide (0.030 g, 0.062 mmol) and triethylamine (0.026 mL, 0.186 mmol) in tetrahydrofuran (10 mL) was mixed at the room temperature with 2,2-difluoroacetic anhydride (0.023 mL, 0.186 mmol), stirred at 70° C. for 2 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; methanol/dichloromethane=0% to 20%) to give N-(3-chloro-4-fluorophenyl)-N-(4-(5-(difluoromethyl)-1,3,4-oxadiazol-2-yl)benzyl)-3-morpholinopropane-1-sulfonamide as yellow oil (0.020 g, 59.3%).

$^1$H NMR (400 MHz, CDCl₃) δ 8.05-8.01 (m, 2H), 7.44 (d, 2H, J=8.4 Hz), 7.37 (dd, 1H, J=6.4, 2.6 Hz), 7.18-7.14 (m, 1H), 7.10-7.05 (m, 1H), 7.02 (s, 0.25H), 6.90 (s, 0.5H), 6.77 (s, 0.25H), 4.91 (s, 2H), 3.83-3.62 (m, 4H), 3.29-3.18 (m, 2H), 2.62-2.40 (m, 6H), 2.18-2.05 (m, 2H); LRMS (ES) m/z 545.2 (M⁺+1).

656
EXAMPLE 229

Compound 11724, (R)—N-(4-(5-(difluoromethyl)-1,3,4-oxadiazol-2-yl)benzyl)-3-(3-fluoropyrrolidin-1-yl)-N-phenylpropane-1-sulfonamide

[Step 1] (R)-3-(3-fluoropyrrolidin-1-yl)-N-(4-(hydrazinecarbonyl)benzyl)-N-phenylpropane-1-sulfonamide

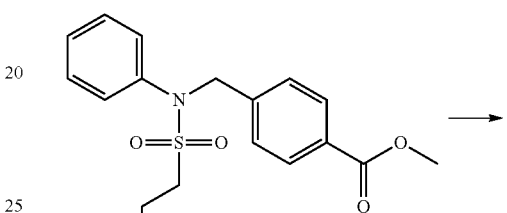

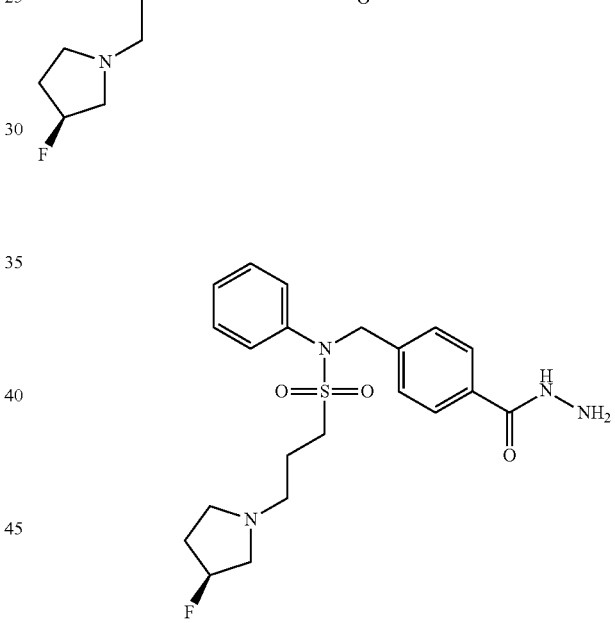

A solution of methyl (R)-4-(((3-(3-fluoropyrrolidin-1-yl)-N-phenylpropyl)sulfonamido)methyl)benzoate (0.095 g, 0.219 mmol) and hydrazine monohydrate (0.106 mL, 2.186 mmol) in ethanol (2 mL) was stirred at 80° C. for 18 hr and cooled down to the room temperature to terminate the reaction. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification ((R)-3-(3-fluoropyrrolidin-1-yl)-N-(4-(hydrazinecarbonyl)benzyl)-N-phenylpropane-1-sulfonamide, 0.078 g, 82.1%, yellow oil).

[Step 2] (R)—N-(4-(2-(2,2-difluoroacetyl)hydrazine-1-carbonyl)benzyl)-3-(3-fluoropyrrolidin-1-yl)-N-phenylpropane-1-sulfonamide

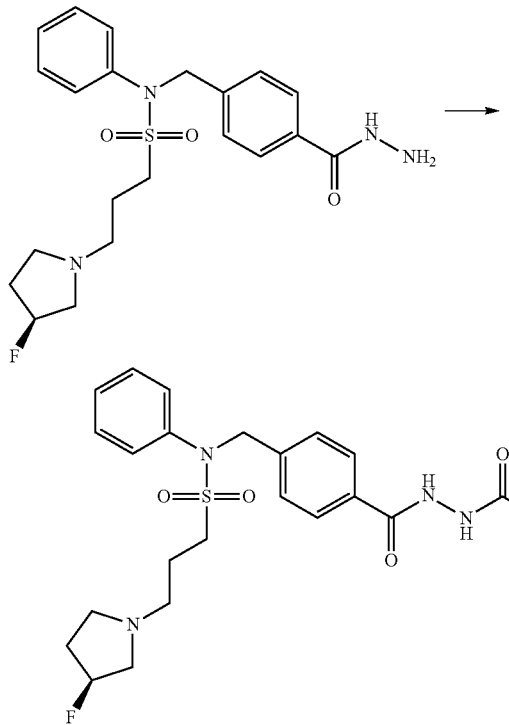

A solution of (R)-3-(3-fluoropyrrolidin-1-yl)-N-(4-(hydrazinecarbonyl)benzyl)-N-phenylpropane-1-sulfonamide (0.078 g, 0.180 mmol), 2,2-difluoroacetic anhydride (0.045 mL, 0.359 mmol) and triethylamine (0.050 mL, 0.359 mmol) in tetrahydrofuran (2 mL) was stirred at 80° C. for 0.5 hr and cooled down to the room temperature to terminate the reaction. Then, aqueous N-sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give (R)—N-(4-(2-(2,2-difluoroacetyl)hydrazine-1-carbonyl)benzyl)-3-(3-fluoropyrrolidin-1-yl)-N-phenylpropane-1-sulfonamide as white solid (0.058 g, 63.0%).

[Step 3] Compound 11724

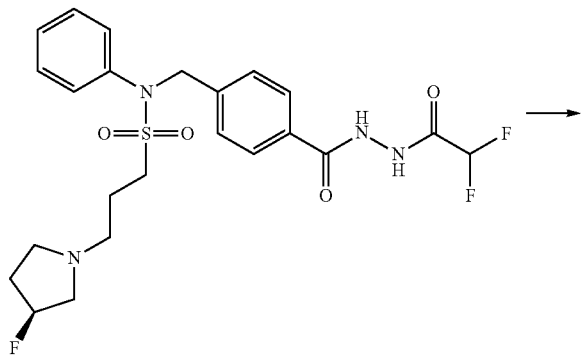

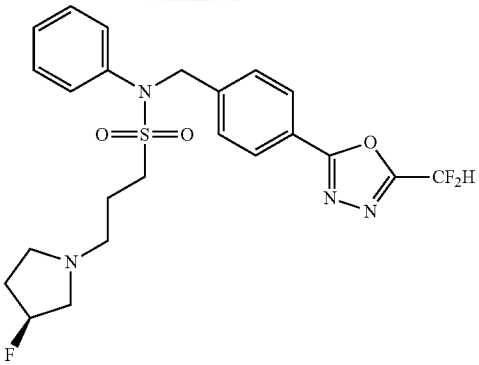

A solution of (R)—N-(4-(2-(2,2-difluoroacetyl)hydrazine-1-carbonyl)benzyl)-3-(3-fluoropyrrolidin-1-yl)-N-phenylpropane-1-sulfonamide (0.058 g, 0.113 mmol), methanesulfonyl chloride (0.026 mL, 0.339 mmol) and triethylamine (0.032 mL, 0.226 mmol) in dichloromethane (2 mL) was stirred at the room temperature for 0.5 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give (R)—N-(4-(5-(difluoromethyl)-1,3,4-oxadiazol-2-yl)benzyl)-3-(3-fluoropyrrolidin-1-yl)-N-phenylpropane-1-sulfonamide as yellow oil (0.008 g, 14.3%).

$^1$H NMR (400 MHz, CD3OD) δ8.03 (d, 2H, J=8.5 Hz), 7.56 (d, 2H, J=8.6 Hz), 7.43~7.26 (m, 5H), 7.21 (t, 1H, J=51.6 Hz), 5.30~5.16 (m, 1H), 5.06 (s, 2H), 3.14~3.02 (m, 2H), 2.91~2.83 (m, 1H), 2.79~2.72 (m, 2H), 2.63~2.57 (m, 1H), 2.40~2.17 (m, 2H), 2.15~2.00 (m, 4H); LRMS (ES) m/z 495.3 (M$^+$+1).

EXAMPLE 230

Compound 11725, N-(3-chlorophenyl)-N-(4-(5-(difluoromethyl)-1,3,4-oxadiazol-2-yl)benzyl)-1-((1r,4r)-4-fluorocyclohexyl)piperidine-4-sulfonamide

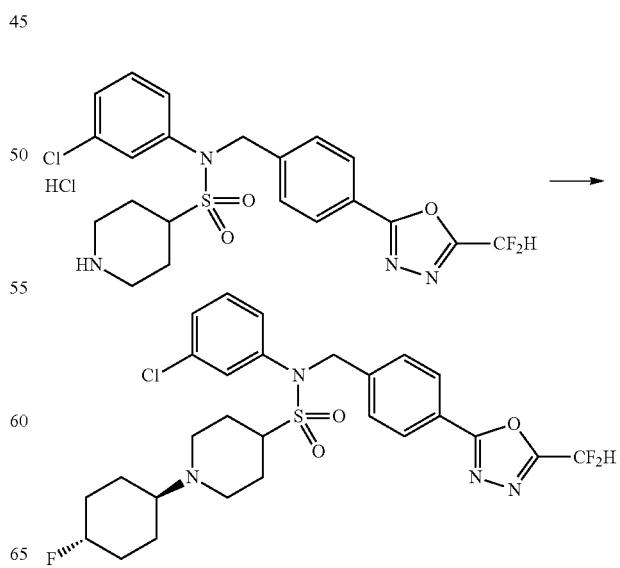

A mixture of N-(3-chlorophenyl)-N-(4-(5-(difluoromethyl)-1,3,4-oxadiazol-2-yl)benzyl)piperidine-4-sulfonamide hydrochloride (0.150 g, 0.289 mmol), 4-fluorocyclohexan-1-one (0.101 g, 0.866 mmol) and N,N-diisopropylethylamine (0.101 mL, 0.578 mmol) in dichloromethane (6 mL) was treated at the room temperature with sodium triacetoxyborohydride (0.122 g, 0.578 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=80% to 100%) to give N-(3-chlorophenyl)-N-(4-(5-(difluoromethyl)-1,3,4-oxadiazol-2-yl)benzyl)-1-((1r,4r)-4-fluorocyclohexyl)piperidine-4-sulfonamide as white solid (0.047 g, 27.9%).

$^1$H NMR (400 MHz, DMSO-d6) δ 7.99 (d, 2H, J=8.4 Hz), 7.66 (s, 0.25H), 7.57-7.47 (m, 3.5H), 7.44 (m, 1H), 7.40 (s, 0.25H), 7.35 (t, 1H, J=8.0 Hz), 7.29 (m, 1H), 5.11 (s, 2H), 4.48 (m, 1H), 3.28 (m, 1H), 2.91 (d, 2H, J=11.1 Hz), 2.33 (m, 1H), 2.24-2.14 (m, 2H), 2.10-1.94 (m, 4H), 1.77-1.57 (m, 4H), 1.48-1.28 (m, 4H); LRMS (ES) m/z 583.2 (M$^+$+1).

EXAMPLE 231

Compound 11726, N-(3-chlorophenyl)-N-(4-(5-(difluoromethyl)-1,3,4-oxadiazol-2-yl)benzyl)-1-((1s,4s)-4-fluorocyclohexyl)piperidine-4-sulfonamide

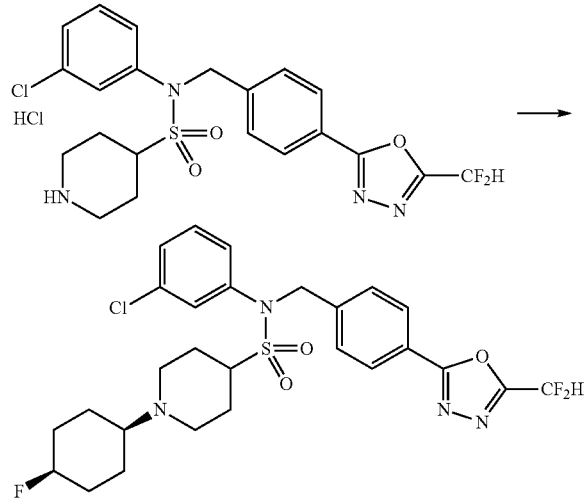

A mixture of N-(3-chlorophenyl)-N-(4-(5-(difluoromethyl)-1,3,4-oxadiazol-2-yl)benzyl)piperidine-4-sulfonamide hydrochloride (0.150 g, 0.289 mmol), 4-fluorocyclohexan-1-one (0.101 g, 0.866 mmol) and N,N-diisopropylethylamine (0.101 mL, 0.578 mmol) in dichloromethane (6 mL) was treated at the room temperature with sodium triacetoxyborohydride (0.122 g, 0.578 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=80% to 100%) to give N-(3-chlorophenyl)-N-(4-(5-(difluoromethyl)-1,3,4-oxadiazol-2-yl)benzyl)-1-((1s,4s)-4-fluorocyclohexyl)piperidine-4-sulfonamide as white solid (0.036 g, 21.4%).

$^1$H NMR (400 MHz, DMSO-d6) δ 7.99 (d, 2H, J=8.4 Hz), 7.66 (s, 0.25H), 7.58-7.48 (m, 3.5H), 7.46 (m, 1H), 7.40 (s, 0.25H), 7.35 (t, 1H, J=8.0 Hz), 7.29 (m, 1H), 5.11 (s, 2H), 4.76 (d, 1H, J=48.8 Hz), 3.28 (m, 1H), 2.93 (d, 2H, J=11.1 Hz), 2.36 (m, 1H), 2.29-2.15 (m, 2H), 2.11-2.03 (d, 2H, J=11.4 Hz), 2.01-1.84 (m, 2H), 1.66 (qd, 2H, J=12.2, 3.9 Hz), 1.60-1.40 (m, 6H); LRMS (ES) m/z 583.3 (M$^+$+1).

EXAMPLE 232

Compound 11727, N-(3-chlorophenyl)-N-((5-(5-(difluoromethyl)-1,3,4-oxadiazol-2-yl)pyridin-2-yl)methyl)-1-((1r,4r)-4-fluorocyclohexyl)piperidine-4-sulfonamide

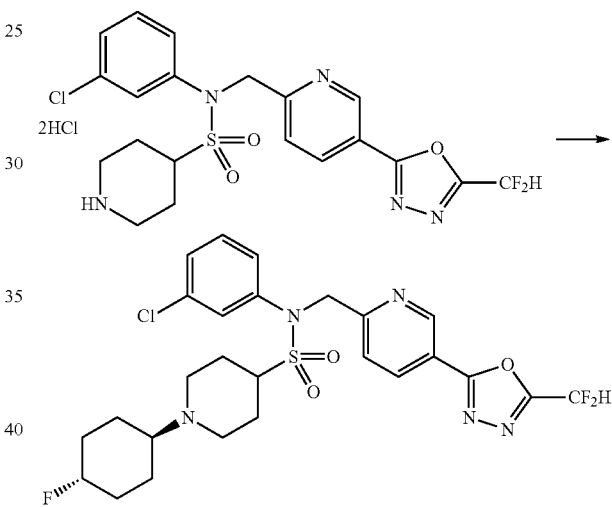

A mixture of N-(3-chlorophenyl)-N-((5-(5-(difluoromethyl)-1,3,4-oxadiazol-2-yl)pyridin-2-yl)methyl)piperidine-4-sulfonamide dihydrochloride (0.100 g, 0.180 mmol), 4-fluorocyclohexan-1-one (0.063 g, 0.539 mmol) and N,N-diisopropylethylamine (0.094 mL, 0.539 mmol) in dichloromethane (10 mL) was treated at the room temperature with sodium triacetoxyborohydride (0.076 g, 0.359 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=80% to 100%) to give N-(3-chlorophenyl)-N-((5-(5-(difluoromethyl)-1,3,4-oxadiazol-2-yl)pyridin-2-yl)methyl)-1-((1r,4r)-4-fluorocyclohexyl)piperidine-4-sulfonamide as white solid (0.032 g, 30.5%).

$^1$H NMR (400 MHz, DMSO-d6) δ 9.10 (dd, 1H, J=2.2, 0.8 Hz), 8.41 (dd, 1H, J=8.3, 2.3 Hz), 7.72-7.65 (m, 1.25H), 7.62 (t, 1H, J=2.1 Hz), 7.56 (s, 0.5H), 7.50 (ddd, 1H, J=8.0, 2.2, 1.1 Hz), 7.43 (s, 0.25H), 7.37 (t, 1H, J=8.0 Hz), 7.30 (ddd, 1H, J=8.1, 2.1, 1.1 Hz), 5.20 (s, 2H), 4.49 (m, 1H), 3.31 (m, 1H), 2.91 (d, 2H, J=11.2 Hz), 2.33 (m, 1H), 2.19 (t, 2H, J=11.4 Hz), 2.11-1.97 (m, 4H), 1.77-1.57 (m, 4H), 1.46-1.29 (m, 4H); LRMS (ES) m/z 584.3 (M$^+$+1).

EXAMPLE 233

Compound 11728, N-(3-chlorophenyl)-N-((5-(5-(difluoromethyl)-1,3,4-oxadiazol-2-yl)pyridin-2-yl)methyl)-1-((1s,4s)-4-fluorocyclohexyl)piperidine-4-sulfonamide

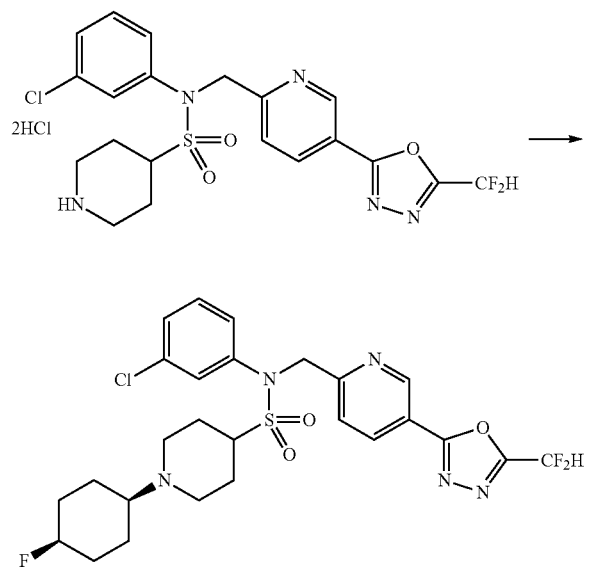 [SMILES: O=S(=O)(C1CCNCC1)N(Cc1ccc(-c2nnc(C(F)F)o2)cn1)c1cccc(Cl)c1 ; O=S(=O)(C1CCN([C@H]2CC[C@H](F)CC2)CC1)N(Cc1ccc(-c2nnc(C(F)F)o2)cn1)c1cccc(Cl)c1]

A mixture of N-(3-chlorophenyl)-N-((5-(5-(difluoromethyl)-1,3,4-oxadiazol-2-yl)pyridin-2-yl)methyl)piperidine-4-sulfonamide dihydrochloride (0.100 g, 0.180 mmol), 4-fluorocyclohexan-1-one (0.063 g, 0.539 mmol) and N,N-diisopropylethylamine (0.094 mL, 0.539 mmol) in dichloromethane (10 mL) was treated at the room temperature with sodium triacetoxyborohydride (0.076 g, 0.359 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=80% to 100%) to give N-(3-chlorophenyl)-N-((5-(5-(difluoromethyl)-1,3,4-oxadiazol-2-yl)pyridin-2-yl)methyl)-1-((1s,4s)-4-fluorocyclohexyl)piperidine-4-sulfonamide as white solid (0.033 g, 31.5%).

$^1$H NMR (400 MHz, DMSO-d6) δ 9.10 (dd, 1H, J=2.3, 0.9 Hz), 8.41 (dd, 1H, J=8.2, 2.3 Hz), 7.74-7.67 (m, 1.25H), 7.63 (t, 1H, J=2.0 Hz), 7.56 (s, 0.5H), 7.50 (ddd, 1H, J=8.1, 2.2, 1.2 Hz), 7.43 (s, 0.25H), 7.37 (t, 1H, J=8.0 Hz), 7.31 (ddd, 1H, J=8.1, 2.1, 1.1 Hz), 5.20 (s, 2H), 4.76 (d, 1H, J=48.9 Hz), 3.28 (m, 1H), 2.93 (d, 2H, J=11.2 Hz), 2.36 (m, 1H), 2.29-2.19 (m, 2H), 2.13-2.05 (m, 2H), 1.99-1.87 (m, 2H), 1.71-1.60 (m, 2H), 1.60-1.42 (m, 6H); LRMS (ES) m/z 584.2 (M$^+$+1).

EXAMPLE 234

Compound 11729, N-(4-(5-(difluoromethyl)-1,3,4-oxadiazol-2-yl)benzyl)-N-(2-methylisoindolin-5-yl)methanesulfonamide

[Step 1] tert-butyl 5-(methylsulfonamido)isoindoline-2-carboxylate

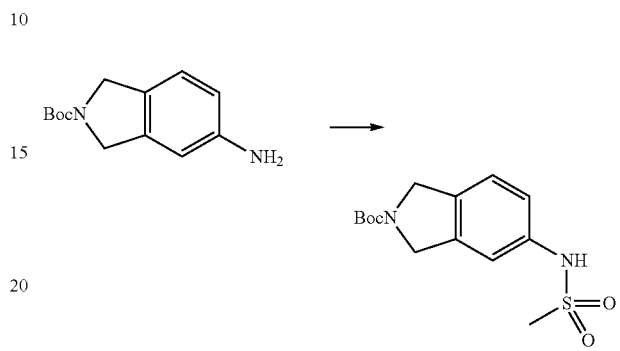

A solution of tert-butyl 5-aminoisoindoline-2-carboxylate (2.000 g, 8.536 mmol) in dichloromethane (50 mL) was mixed at the room temperature with methanesulfonyl chloride (0.661 mL, 8.536 mmol) and triethylamine (1.428 mL, 10.243 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give tert-butyl 5-(methylsulfonamido)isoindoline-2-carboxylate as white solid (2.220 g, 83.3%).

[Step 2] tert-butyl 5-(N-(4-(methoxycarbonyl)benzyl)methylsulfonamido)isoindoline-2-carboxylate

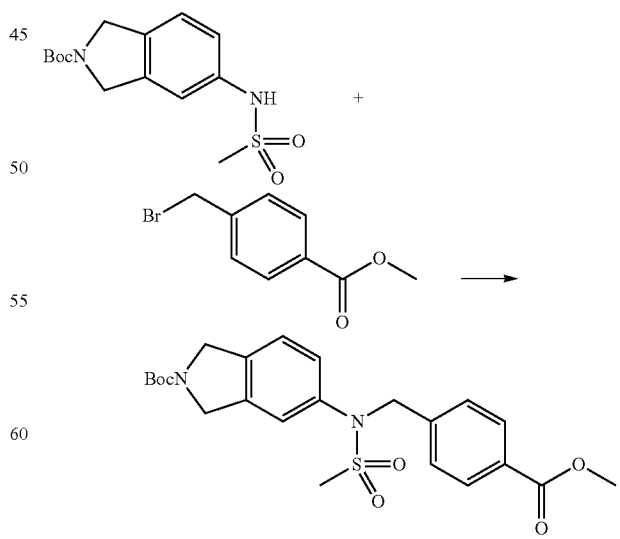

A mixture of tert-butyl 5-(methylsulfonamido)isoindoline-2-carboxylate (0.800 g, 2.561 mmol), methyl 4-(bromomethyl)benzoate (0.763 g, 3.329 mmol), potassium iodide (0.850 g, 5.122 mmol) and potassium carbonate (0.708 g, 5.122 mmol) in N,N-dimethylformide (15 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=30% to 60%) to give tert-butyl 5-(N-(4-(methoxycarbonyl)benzyl)methylsulfonamido)isoindoline-2-carboxylate as white solid (1.000 g, 84.8%)

[Step 3] tert-butyl 5-(N-(4-(hydrazinecarbonyl)benzyl)methylsulfonamido)isoindoline-2-carboxylate

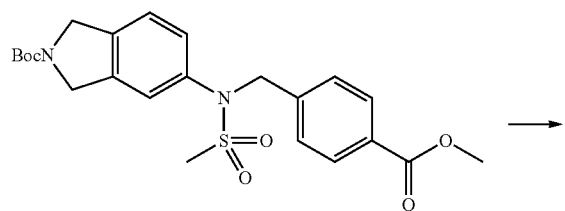

A solution of tert-butyl 5-(N-(4-(methoxycarbonyl)benzyl)methylsulfonamido)isoindoline-2-carboxylate (1.000 g, 2.171 mmol) in tetrahydrofuran (10 mL)/ethanol (10 mL) was mixed at the room temperature with hydrazine monohydrate (2.111 mL, 43.426 mmol). The reaction mixture was heated at reflux for 18 hr, cooled down to the room temperature to terminate the reaction and concentrated under the reduced pressure to remove the solvent. The title compound was used without further purification (tert-butyl 5-(N-(4-(hydrazinecarbonyl)benzyl)methylsulfonamido)isoindoline-2-carboxylate, 0.914 g, 91.4%, white solid).

[Step 4] tert-butyl 5-(N-(4-(5-(difluoromethyl)-1,3,4-oxadiazol-2-yl)benzyl)methylsulfonamido)isoindoline-2-carboxylate

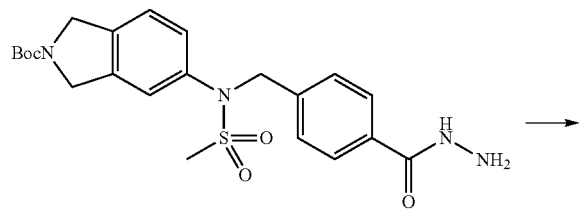

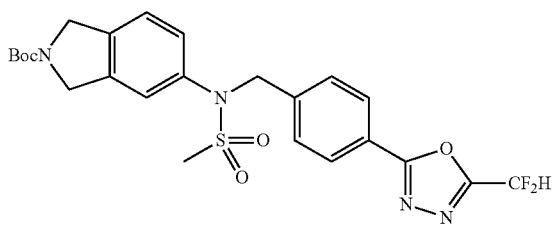

A solution of tert-butyl 5-(N-(4-(hydrazinecarbonyl)benzyl)methylsulfonamido)isoindoline-2-carboxylate (0.914 g, 1.985 mmol) in tetrahydrofuran (30 mL) was mixed at 50° C. with 2,2-difluoroacetic anhydride (0.987 mL, 7.938 mmol) and triethylamine (1.383 mL, 9.923 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give tert-butyl 5-(N-(4-(5-(difluoromethyl)-1,3,4-oxadiazol-2-yl)benzyl)methylsulfonamido)isoindoline-2-carboxylate as white solid (0.963 g, 93.2%).

[Step 5] N-(4-(5-(difluoromethyl)-1,3,4-oxadiazol-2-yl)benzyl)-N-(isoindolin-5-yl)methanesulfonamide hydrochloride

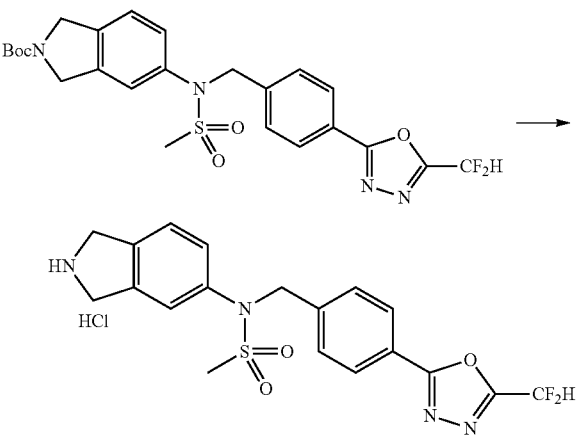

A solution of tert-butyl 5-(N-(4-(5-(difluoromethyl)-1,3,4-oxadiazol-2-yl)benzyl)methylsulfonamido)isoindoline-2-carboxylate (0.963 g, 1.850 mmol) in 1,4-dioxane (10 mL) was mixed at the room temperature with hydrochloric acid (4.00 M solution in 1,4-dioxane, 4.625 mL, 18.500 mmol), and stirred at the same temperature for 1 hr. The reaction mixture was diluted with ethyl acetate (5 mL) and hexane (30 mL) and stirred. The resulting precipitates were collected by filtration, washed by hexane, and dried to give N-(4-(5-(difluoromethyl)-1,3,4-oxadiazol-2-yl)benzyl)-N-(isoindolin-5-yl)methanesulfonamide hydrochloride as beige solid (0.835 g, 98.8%).

665

[Step 6] Compound 11729

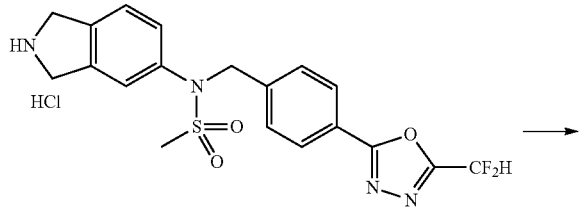

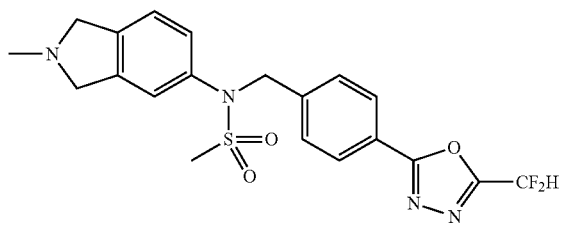

A mixture of N-(4-(5-(difluoromethyl)-1,3,4-oxadiazol-2-yl)benzyl)-N-(isoindolin-5-yl)methanesulfonamide hydrochloride (0.050 g, 0.109 mmol), paraformaldehyde (0.016 g, 0.547 mmol) and N,N-diisopropylethylamine (0.038 mL, 0.219 mmol) in dichloromethane (5 mL) was treated at the room temperature with sodium triacetoxyborohydride (0.046 g, 0.219 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)benzyl)-N-(2-methylisoindolin-5-yl)methanesulfonamide as light yellow solid (0.013 g, 27.3%).

$^1$H NMR (400 MHz, DMSO-d6) δ 7.98 (d, 2H, J=8.3 Hz), 7.67 (s, 0.25H), 7.58-7.51 (m, 2.5H), 7.41 (s, 0.25H), 7.31 (s, 1H), 7.24 (dd, 1H, J=8.0, 2.0 Hz), 7.19 (d, 1H, J=8.0 Hz), 4.96 (s, 2H), 3.81 (s, 2H), 3.80 (s, 2H), 3.12 (s, 3H), 2.48 (s, 3H); LRMS (ES) m/z 435.3 (M$^+$+1).

EXAMPLE 235

Compound 11730, N-(4-(5-(difluoromethyl)-1,3,4-oxadiazol-2-yl)benzyl)-N-(2-isopropylisoindolin-5-yl)methanesulfonamide

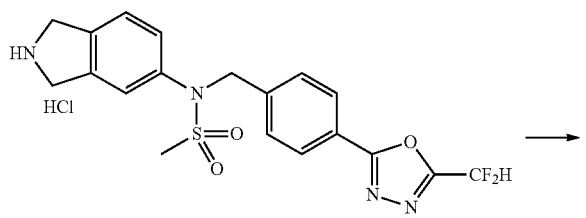

666

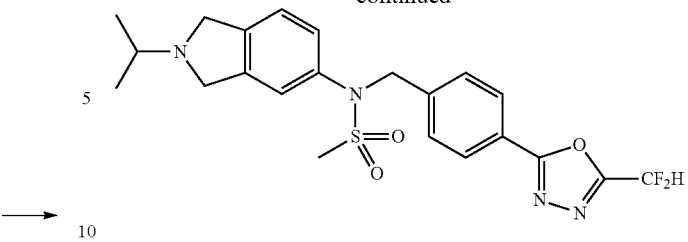

A mixture of N-(4-(5-(difluoromethyl)-1,3,4-oxadiazol-2-yl)benzyl)-N-(isoindolin-5-yl)methanesulfonamide hydrochloride (0.050 g, 0.109 mmol), acetone (0.040 mL, 0.547 mmol) and N,N-diisopropylethylamine (0.038 mL, 0.219 mmol) in dichloromethane (5 mL) was treated at the room temperature with sodium triacetoxyborohydride (0.046 g, 0.219 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)benzyl)-N-(2-isopropylisoindolin-5-yl)methanesulfonamide as beige solid (0.016 g, 31.6%).

$^1$H NMR (400 MHz, DMSO-d6) δ 7.98 (d, 2H, J=7.9 Hz), 7.66 (s, 0.25H), 7.60-7.50 (m, 2.5H), 7.41 (s, 0.25H), 7.29 (s, 1H), 7.26-7.15 (m, 2H), 4.96 (s, 2H), 3.78 (s, 4H), 3.14 (s, 3H), 2.65 (p, 1H, J=6.2 Hz), 1.05 (d, 6H, J=6.2 Hz); LRMS (ES) m/z 463.3 (M$^+$+1).

EXAMPLE 236

Compound 11731, N-(4-(5-(difluoromethyl)-1,3,4-oxadiazol-2-yl)benzyl)-N-(2-(oxetan-3-yl)isoindolin-5-yl)methanesulfonamide

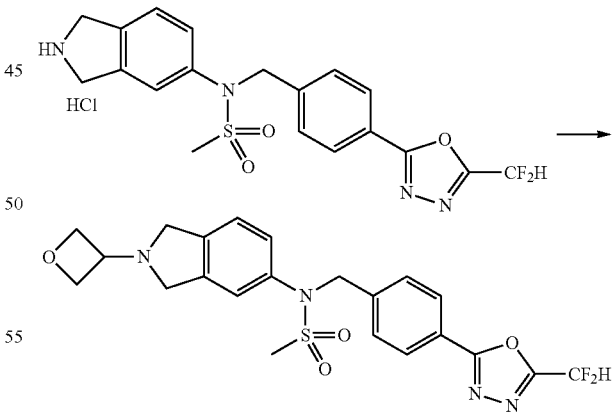

A mixture of N-(4-(5-(difluoromethyl)-1,3,4-oxadiazol-2-yl)benzyl)-N-(isoindolin-5-yl)methanesulfonamide hydrochloride (0.050 g, 0.109 mmol), oxetan-3-one (0.039 g, 0.547 mmol) and N,N-diisopropylethylamine (0.038 mL, 0.219 mmol) in dichloromethane (5 mL) was treated at the room temperature with sodium triacetoxyborohydride (0.046 g, 0.219 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 5%) to give N-(4-(5-(difluoromethyl)-1,3,4-oxadiazol-2-yl)benzyl)-N-(2-(oxetan-3-yl)isoindolin-5-yl)methanesulfonamide as beige solid (0.027 g, 51.8%).

¹H NMR (400 MHz, DMSO-d6) δ 7.98 (d, 2H, J=8.2 Hz), 7.66 (s, 0.25H), 7.59-7.51 (m, 2.5H), 7.31 (s, 0.25H), 7.26 (s, 1H), 7.28-7.15 (m, 2H), 4.96 (s, 2H), 4.61 (t, 2H, J=6.6 Hz), 4.52 (t, 2H, J=5.9 Hz), 3.93 (p, 1H, J=6.1 Hz), 3.81 (s, 4H), 3.12 (s, 3H); LRMS (ES) m/z 477.3 (M⁺+1).

EXAMPLE 237

Compound 11732, N-(2-acetylisoindolin-5-yl)-N-(4-(5-(difluoromethyl)-1,3,4-oxadiazol-2-yl)benzyl) methanesulfonamide

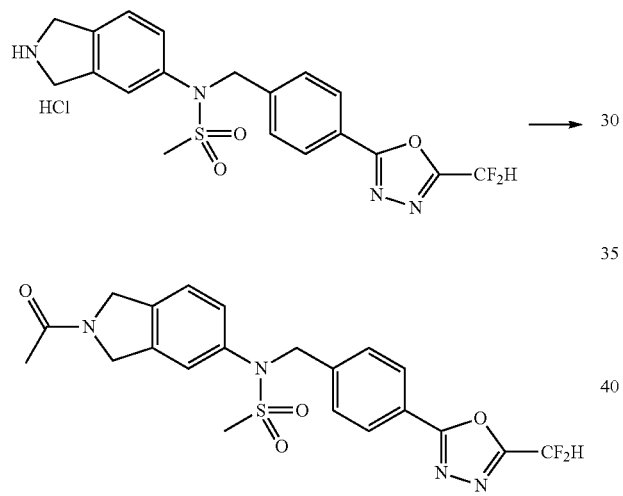

A mixture of N-(4-(5-(difluoromethyl)-1,3,4-oxadiazol-2-yl)benzyl)-N-(isoindolin-5-yl)methanesulfonamide hydrochloride (0.050 g, 0.109 mmol) in dichloromethane (5 mL) was treated at the room temperature with acetyl chloride (0.023 mL, 0.328 mmol) and N,N-diisopropylethylamine (0.038 mL, 0.219 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 5%) to give N-(2-acetylisoindolin-5-yl)-N-(4-(5-(difluoromethyl)-1,3,4-oxadiazol-2-yl)benzyl)methanesulfonamide as white solid (0.038 g, 75.1%).

¹H NMR (400 MHz, DMSO-d6) δ 7.98 (d, 2H, J=7.9 Hz), 7.66 (s, 0.25H), 7.59-7.51 (m, 2.5H), 7.47-7.36 (m, 1.25H), 7.36-7.25 (m, 2H), 4.98 (s, 2H), 4.76 (s, 2H), 4.55 (d, 2H, J=6.0 Hz), 3.14 (s, 3H), 2.02 (s, 3H); LRMS (ES) m/z 463.3 (M⁺+1).

EXAMPLE 238

Compound 11733, N-((5-(5-(difluoromethyl)-1,3,4-oxadiazol-2-yl)pyridin-2-yl)methyl)-N-(2-methyl-isoindolin-5-yl)methanesulfonamide

[Step 1] tert-butyl 5-(N-((5-(methoxycarbonyl)pyridin-2-yl)methyl)methylsulfonamido)isoindoline-2-carboxylate

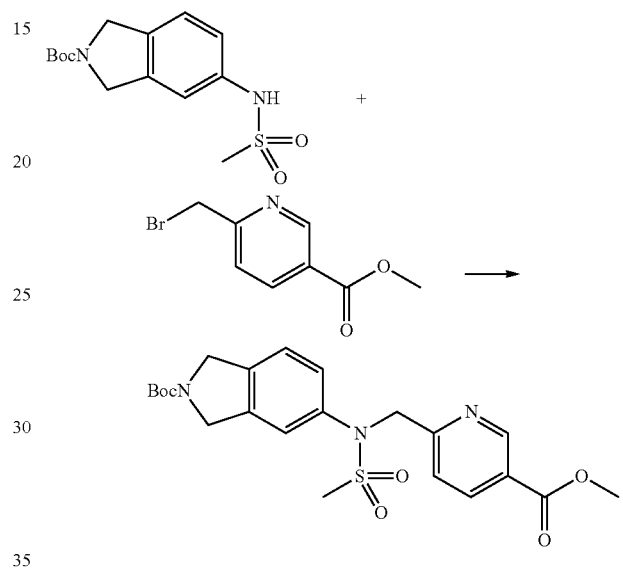

A mixture of tert-butyl 5-(methylsulfonamido)isoindoline-2-carboxylate (1.420 g, 4.546 mmol), methyl 6-(bromomethyl)nicotinate (1.360 g, 5.909 mmol), potassium iodide (1.509 g, 9.091 mmol) and potassium carbonate (1.256 g, 9.091 mmol) in N,N-dimethylformamide (20 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=40% to 70%) to give tert-butyl 5-(N-((5-(methoxycarbonyl)pyridin-2-yl)methyl)methylsulfonamido)isoindoline-2-carboxylate as brown solid (1.826 g, 87.0%).

[Step 2] tert-butyl 5-(N-((5-(hydrazinecarbonyl)pyridin-2-yl)methyl)methylsulfonamido)isoindoline-2-carboxylate

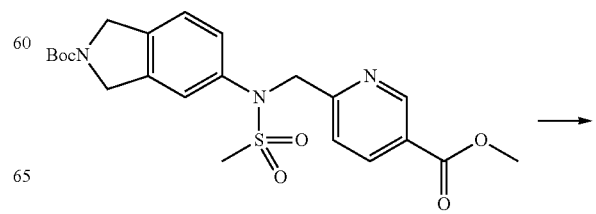

-continued

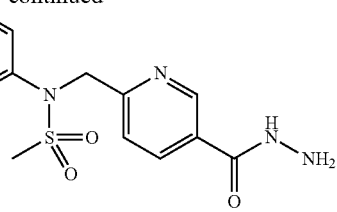

A solution of tert-butyl 5-(N-((5-(methoxycarbonyl)pyridin-2-yl)methyl)methylsulfonamido)isoindoline-2-carboxylate (1.826 g, 3.956 mmol) in tetrahydrofuran (15 mL)/ethanol (15 mL) was mixed at the room temperature with hydrazine monohydrate (3.846 mL, 79.128 mmol). The reaction mixture was heated at reflux for 18 hr, cooled down to the room temperature to terminate the reaction and concentrated under the reduced pressure to remove the solvent. The title compound was used without further purification (tert-butyl 5-(N-((5-(hydrazinecarbonyl)pyridin-2-yl)methyl)methylsulfonamido)isoindoline-2-carboxylate, 1.757 g, 96.2%, beige solid).

[Step 3] tert-butyl 5-(N-((5-(5-(difluoromethyl)-1,3,4-oxadiazol-2-yl)pyridin-2-yl)methyl)methylsulfonamido)isoindoline-2-carboxylate

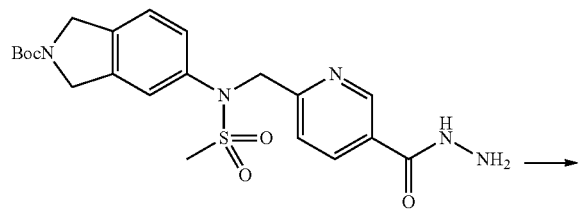

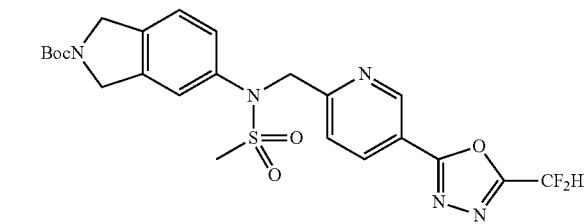

A solution of tert-butyl 5-(N-((5-(hydrazinecarbonyl)pyridin-2-yl)methyl)methylsulfonamido)isoindoline-2-carboxylate (1.757 g, 3.807 mmol) in tetrahydrofuran (50 mL) was mixed at 50° C. with 2,2-difluoroacetic anhydride (1.893 mL, 15.227 mmol) and triethylamine (2.653 mL, 19.034 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=30% to 70%) to give tert-butyl 5-(N-((5-(5-(difluoromethyl)-1,3,4-oxadiazol-2-yl)pyridin-2-yl)methyl)methylsulfonamido)isoindoline-2-carboxylate as white solid (1.518 g, 76.5%).

[Step 4] N-((5-(5-(difluoromethyl)-1,3,4-oxadiazol-2-yl)pyridin-2-yl)methyl)-N-(isoindolin-5-yl)methanesulfonamide dihydrochloride

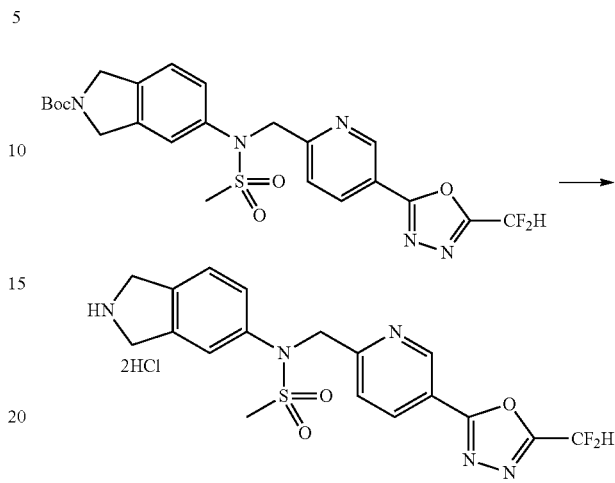

A solution of tert-butyl 5-(N-((5-(5-(difluoromethyl)-1,3,4-oxadiazol-2-yl)pyridin-2-yl)methyl)methylsulfonamido)isoindoline-2-carboxylate (1.518 g, 2.911 mmol) in 1,4-dioxane (15 mL) was mixed at the room temperature with hydrochloric acid (4.00 M solution in 1,4-dioxane, 7.277 mL, 29.106 mmol), and stirred at the same temperature for 1 hr. The reaction mixture was diluted with ethyl acetate (10 mL) and hexane (50 mL) and stirred. The resulting precipitates were collected by filtration, washed by hexane, and dried to give N-((5-(5-(difluoromethyl)-1,3,4-oxadiazol-2-yl)pyridin-2-yl)methyl)-N-(isoindolin-5-yl)methanesulfonamide dihydrochloride as beige solid (1.320 g, 91.7%).

[Step 5] Compound 11733

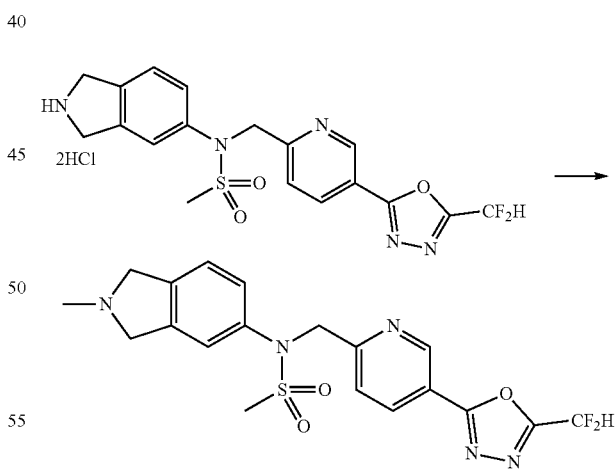

A mixture of N-((5-(5-(difluoromethyl)-1,3,4-oxadiazol-2-yl)pyridin-2-yl)methyl)-N-(isoindolin-5-yl)methanesulfonamide dihydrochloride (0.050 g, 0.101 mmol), paraformaldehyde (0.015 g, 0.506 mmol) and N,N-diisopropylethylamine (0.035 mL, 0.202 mmol) in dichloromethane (5 mL) was treated at the room temperature with sodium triacetoxyborohydride (0.043 g, 0.202 mmol), and stirred at the same temperature for 18 hr. Then, saturated aqueousسodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give N-((5-(5-(difluoromethyl)-1,3,4-oxadiazol-2-yl)pyridin-2-yl)methyl)-N-(2-methylisoindolin-5-yl)methanesulfonamide as beige solid (0.018 g, 40.9%).

$^1$H NMR (400 MHz, DMSO-d6) δ 9.10 (d, 1H, J=2.2 Hz), 8.41 (dd, 1H, J=8.2, 2.2 Hz), 7.75 (d, 1H, J J=8.3 Hz), 7.57 (t, 1H, J=51.2 Hz), 7.36 (s, 1H), 7.28 (dd, 1H, J=8.1, 1.9 Hz), 7.20 (d, 1H, J=8.0 Hz), 5.07 (s, 2H), 3.78 (s, 2H), 3.76 (s, 2H), 3.16 (s, 3H), 2.45 (s, 3H); LRMS (ES) m/z 436.0 (M$^+$+1).

EXAMPLE 239

Compound 11734, N-((5-(5-(difluoromethyl)-1,3,4-oxadiazol-2-yl)pyridin-2-yl)methyl)-N-(2-isopropylisoindolin-5-yl)methanesulfonamide

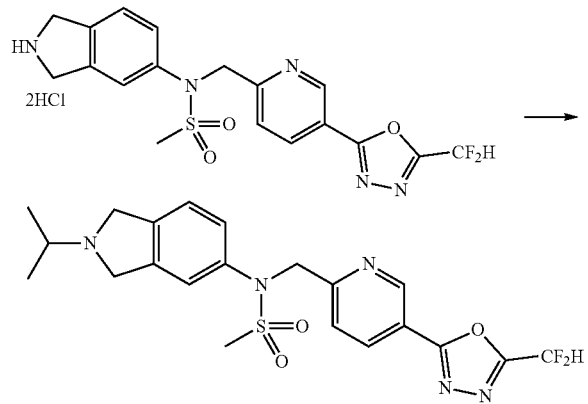

A mixture of N-((5-(5-(difluoromethyl)-1,3,4-oxadiazol-2-yl)pyridin-2-yl)methyl)-N-(isoindolin-5-yl)methanesulfonamide dihydrochloride (0.050 g, 0.101 mmol), acetone (0.037 mL, 0.506 mmol) and N,N-diisopropylethylamine (0.035 mL, 0.202 mmol) in dichloromethane (5 mL) was treated at the room temperature with sodium triacetoxyborohydride (0.043 g, 0.202 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give N-((5-(5-(difluoromethyl)-1,3,4-oxadiazol-2-yl)pyridin-2-yl)methyl)-N-(2-isopropylisoindolin-5-yl)methanesulfonamide as white solid (0.039 g, 83.2%).

$^1$H NMR (400 MHz, DMSO-d6) δ 9.10 (d, 1H, J=2.2 Hz), 8.40 (dd, 1H, J=8.2, 2.3 Hz), 7.74 (d, 1H, J=8.3 Hz), 7.56 (t, 1H, J=51.3 Hz), 7.35 (s, 1H), 7.27 (dd, 1H, J=8.0, 2.0 Hz), 7.20 (d, 1H, J=8.1 Hz), 5.07 (s, 2H), 3.80 (s, 2H), 3.79 (s, 2H), 3.16 (s, 3H), 2.66 (p, 1H, J=6.2 Hz), 1.06 (d, 6H, J=6.2 Hz); LRMS (ES) m/z 464.1 (M$^+$+1).

EXAMPLE 240

Compound 11735, N-((5-(5-(difluoromethyl)-1,3,4-oxadiazol-2-yl)pyridin-2-yl)methyl)-N-(2-(oxetan-3-yl)isoindolin-5-yl)methanesulfonamide

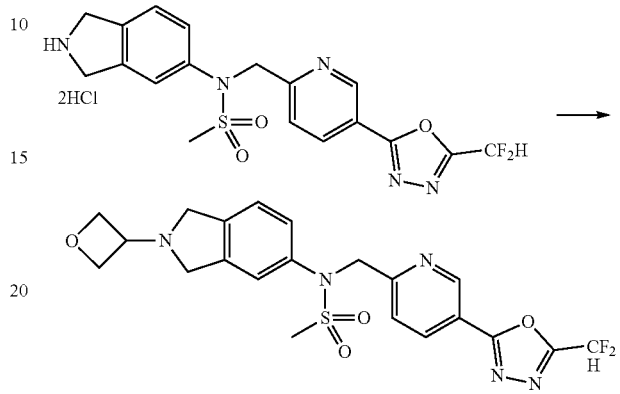

A mixture of N-((5-(5-(difluoromethyl)-1,3,4-oxadiazol-2-yl)pyridin-2-yl)methyl)-N-(isoindolin-5-yl)methanesulfonamide dihydrochloride (0.050 g, 0.101 mmol), oxetan-3-one (0.036 g, 0.506 mmol) and N,N-diisopropylethylamine (0.035 mL, 0.202 mmol) in dichloromethane (5 mL) was treated at the room temperature with sodium triacetoxyborohydride (0.043 g, 0.202 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-((5-(5-(difluoromethyl)-1,3,4-oxadiazol-2-yl)pyridin-2-yl)methyl)-N-(2-(oxetan-3-yl)isoindolin-5-yl)methanesulfonamide as brown solid (0.012 g, 24.8%).

$^1$H NMR (400 MHz, DMSO-d6) δ 9.11 (d, 1H, J=2.2 Hz), 8.41 (dd, 1H, J=8.2, 2.3 Hz), 7.75 (d, 1H, J J=8.3 Hz), 7.57 (t, 1H, J=51.2 Hz), 7.38 (s, 1H), 7.30 (dd, 1H, J=8.0, 2.0 Hz), 7.23 (d, 1H, J=8.0 Hz), 5.08 (s, 2H), 4.62 (t, 2H, J=6.5 Hz), 4.53 (t, 2H, J=5.7 Hz), 3.94 (p, 1H, J=6.1 Hz), 3.83 (s, 2H), 3.82 (s, 2H), 3.17 (s, 3H); LRMS (ES) m/z 478.3 (M$^+$+1).

EXAMPLE 241

Compound 11736, N-(2-acetylisoindolin-5-yl)-N-((5-(5-(difluoromethyl)-1,3,4-oxadiazol-2-yl)pyridin-2-yl)methyl)methanesulfonamide

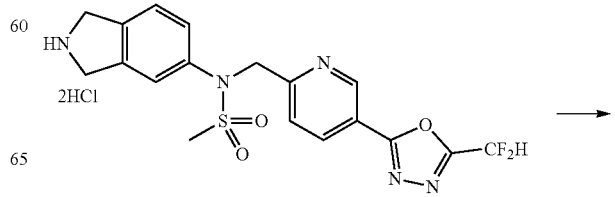

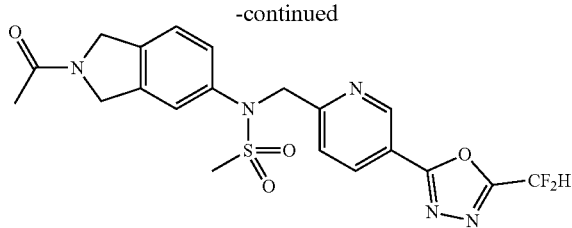

A mixture of N-((5-(5-(difluoromethyl)-1,3,4-oxadiazol-2-yl)pyridin-2-yl)methyl)-N-(isoindolin-5-yl)methanesulfonamide dihydrochloride (0.050 g, 0.101 mmol) in dichloromethane (5 mL) was treated at the room temperature with acetyl chloride (0.022 mL, 0.303 mmol) and N,N-diisopropylethylamine (0.035 mL, 0.202 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(2-acetylisoindolin-5-yl)-N-((5-(5-(difluoromethyl)-1,3,4-oxadiazol-2-yl)pyridin-2-yl)methyl)methanesulfonamide as white solid (0.036 g, 76.8%).

$^1$H NMR (400 MHz, DMSO-d6) δ 9.11 (d, 1H, J=2.2 Hz), 8.41 (dd, 1H, J=8.2, 2.2 Hz), 7.75 (dd, 1H, J=8.3, 3.2 Hz), 7.70 (s, 0.25H), 7.57 (s, 0.5H), 7.52-7.42 (m, 1.25H), 7.39 (td, 1H, J=8.0, 2.1 Hz), 7.33 (t, 1H, J=8.4 Hz), 5.10 (s, 2H), 4.78 (d, 2H, J=5.3 Hz), 4.56 (d, 2H, J=5.2 Hz), 3.19 (s, 3H), 2.03 (s, 3H); LRMS (ES) m/z 464.3 (M$^+$+1).

EXAMPLE 242

Compound 11737, N-(4-(5-(difluoromethyl)-1,3,4-oxadiazol-2-yl)benzyl)-2-(4-methyl-1,4-diazepan-1-yl)-N-phenylethanesulfonamide

[Step 1] 4-(chloromethyl)benzohydrazide

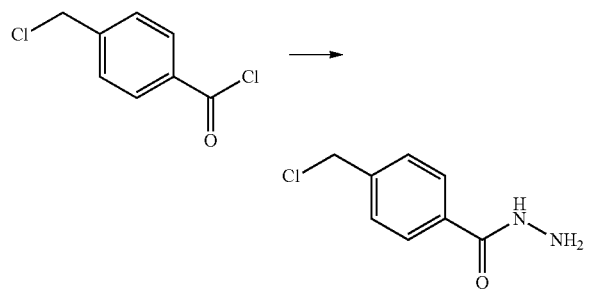

A solution of 4-(chloromethyl)benzoyl chloride (7.200 g, 38.087 mmol) and hydrazine (11.954 mL, 380.872 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The precipitates were collected by filtration and dried to give 4-(chloromethyl)benzohydrazide as white solid (7.000 g, 99.5%).

[Step 2] 2-(4-(chloromethyl)phenyl)-5-(difluoromethyl)-1,3,4-oxadiazole

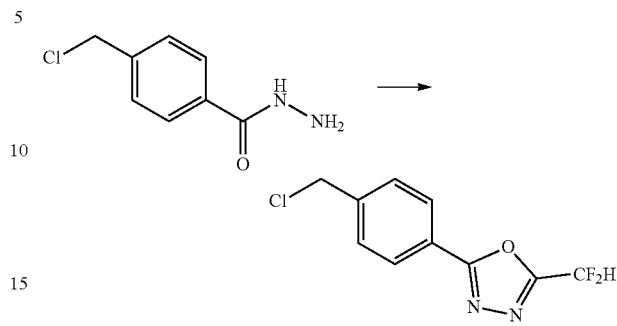

A solution of 4-(chloromethyl)benzohydrazide (7.300 g, 39.541 mmol), 2,2-difluoroacetic anhydride (14.747 mL, 118.622 mmol) and triethylamine (27.556 mL, 197.703 mmol) in tetrahydrofuran (5 mL) was stirred at the room temperature for 18 hr, and concentrated under the reduced pressure to remove the solvent. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=5% to 10%) to give 2-(4-(chloromethyl)phenyl)-5-(difluoromethyl)-1,3,4-oxadiazole as white solid (5.012 g, 51.8%).

[Step 3] N-(4-(5-(difluoromethyl)-1,3,4-oxadiazol-2-yl)benzyl)-N-phenylethenesulfonamide

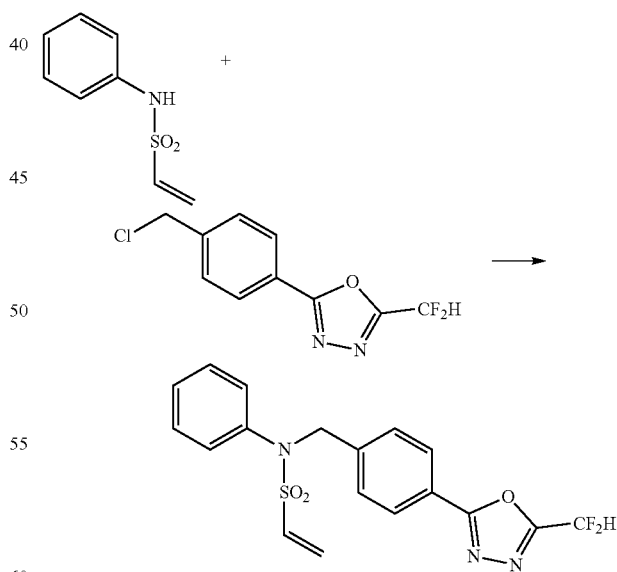

A solution of N-phenylethenesulfonamide (0.200 g, 1.092 mmol), 2-(4-(chloromethyl)phenyl)-5-(difluoromethyl)-1,3,4-oxadiazole (0.267 g, 1.092 mmol), potassium carbonate (0.151 g, 1.092 mmol) and potassium iodide (0.018 g, 0.109 mmol) in N,N-dimethylformide (5 mL) was stirred at the room temperature for 18 hr, and concentrated under the reduced pressure to remove the solvent. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 10%) to give N-(4-(5-(difluoromethyl)-1,3,4-oxadiazol-2-yl)benzyl)-N-phenylethenesulfonamide as white solid (0.220 g, 51.5%).

[Step 4] Compound 11737

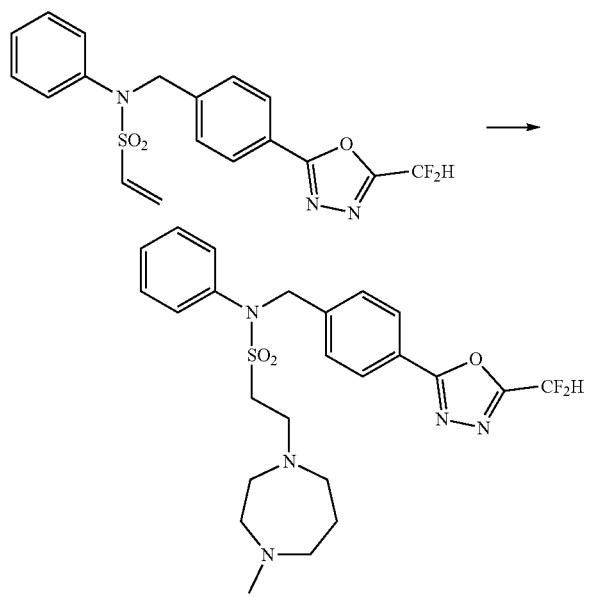

A solution of N-(4-(5-(difluoromethyl)-1,3,4-oxadiazol-2-yl)benzyl)-N-phenylethenesulfonamide (0.100 g, 0.255 mmol), 1-methylhomopiperazine (0.035 mL, 0.281 mmol) and N,N-Diisopropylethylamine (0.088 mL, 0.511 mmol) in dichloromethane (5 mL) was stirred at the room temperature for 18 hr, and concentrated under the reduced pressure to remove the solvent. The residue was chromatographed (SiO₂, 12 g cartridge; methanol/dichloromethane=3% to 5%) to give N-(4-(5-(difluoromethyl)-1,3,4-oxadiazol-2-yl)benzyl)-2-(4-methyl-1,4-diazepan-1-yl)-N-phenylethanesulfonamide as white solid (0.016 g, 12.4%).

¹H NMR (400 MHz, DMSO-d6) δ 7.98 (d, 2H, J=8.4 Hz), 7.54-7.52 (m, 2H), 7.45-7.25 (m, 6H), 5.04 (s, 2H), 3.42-3.39 (m, 2H), 2.94-2.90 (m, 2H), 2.70-2.67 (m, 4H), 2.57-2.56 (m, 4H), 2.27 (s, 3H), 1.71 (m, 2H); LRMS (ES) m/z 507.0 (M⁺+1).

EXAMPLE 243

Compound 11738, 2-(azetidin-1-yl)-N-(4-(5-(difluoromethyl)-1,3,4-oxadiazol-2-yl)benzyl)-N-phenylethanesulfonamide

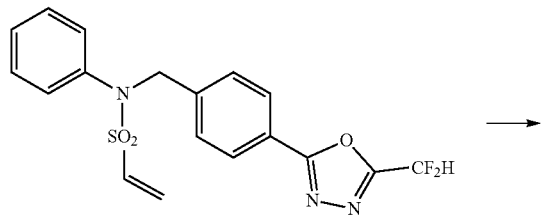

-continued

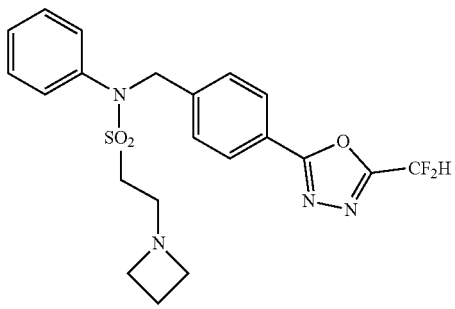

A solution of N-(4-(5-(difluoromethyl)-1,3,4-oxadiazol-2-yl)benzyl)-N-phenylethenesulfonamide (0.100 g, 0.255 mmol), azetidine (0.026 g, 0.281 mmol) and N,N-diisopropylethylamine (0.088 mL, 0.511 mmol) in dichloromethane (5 mL) was stirred at the room temperature for 18 hr, and concentrated under the reduced pressure to remove the solvent. The residue was chromatographed (SiO₂, 12 g cartridge; methanol/dichloromethane=3% to 5%) to give 2-(azetidin-1-yl)-N-(4-(5-(difluoromethyl)-1,3,4-oxadiazol-2-yl)benzyl)-N-phenylethanesulfonamide as white solid (0.045 g, 39.3%).

¹H NMR (400 MHz, DMSO-d6) δ8.98 (d, 2H, J=8.4 Hz), 7.54-7.52 (m, 2H), 7.44-7.23 (m, 6H), 5.03 (s, 2H), 3.24-3.20 (m, 2H), 3.13 (t, 4H, J=6.9 Hz), 2.77-2.73 (m, 2H), 2.00-1.93 (m, 2H); LRMS (ES) m/z 449.2 (M⁺+1).

EXAMPLE 244

Compound 11739, N-(4-(5-(difluoromethyl)-1,3,4-oxadiazol-2-yl)benzyl)-N-(thiazol-2-yl)methanesulfonamide

[Step 1] N-(thiazol-2-yl)methanesulfonamide

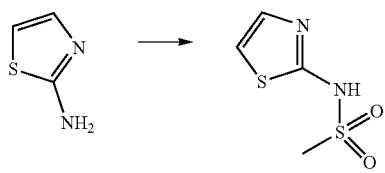

A solution of thiazol-2-amine (0.500 g, 4.993 mmol), pyridine (0.603 mL, 7.490 mmol) and methanesulfonyl chloride (0.502 mL, 6.491 mmol) in dichloromethane (20 mL) was stirred at the room temperature for 5 hr. Then, water was added to the reaction mixture, followed by extraction with dichloromethane. The organic layer was washed with aqueous 1N-hydrochloric acid solution, dried with anhydrous MgSO₄, filtered, and concentrated in vacuo. The title compound was used without further purification (N-(thiazol-2-yl)methanesulfonamide, 0.390 g, 43.8%, yellow solid).

[Step 2] methyl 4-((N-(thiazol-2-yl)methylsulfonamido)methyl)benzoate

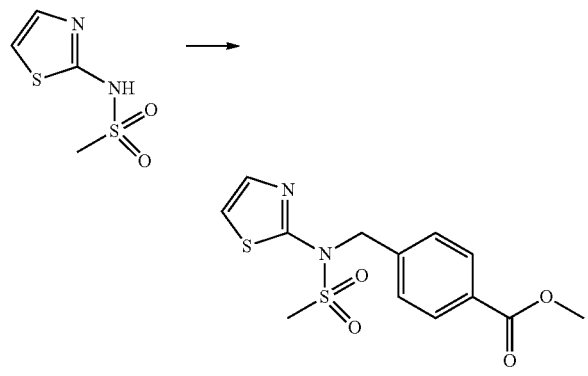

A solution of N-(thiazol-2-yl)methanesulfonamide (0.300 g, 1.683 mmol) and potassium carbonate (0.349 g, 2.525 mmol) in N,N-dimethylformamide (20 mL) was mixed at the room temperature with methyl 4-(bromomethyl)benzoate (4.240 g, 1.852 mmol) and potassium iodide (0.140 g, 0.842 mmol). The reaction mixture was stirred at the same temperature for 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 20%) to give methyl 4-((N-(thiazol-2-yl)methylsulfonamido)methyl)benzoate as yellow solid (0.210 g, 38.2%).

[Step 3] N-(4-(hydrazinecarbonyl)benzyl)-N-(thiazol-2-yl)methanesulfonamide

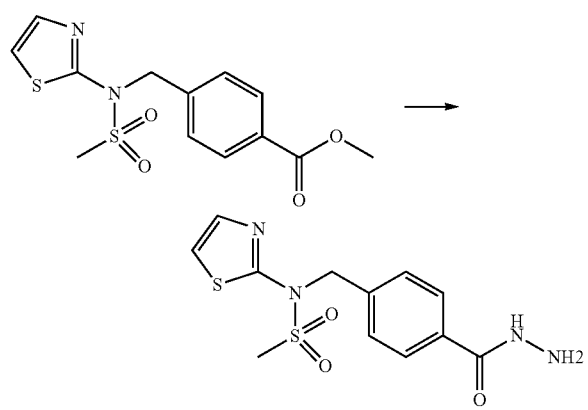

A solution of methyl 4-((N-(thiazol-2-yl)methylsulfonamido)methyl)benzoate (0.210 g, 0.643 mmol) and hydrazine monohydrate (0.313 mL, 6.434 mmol) in ethanol (10 mL) was stirred at 90° C. for 12 hr, cooled down to the room temperature to terminate the reaction and concentrated under the reduced pressure to remove the solvent. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(4-(hydrazinecarbonyl)benzyl)-N-(thiazol-2-yl)methanesulfonamide, 0.130 g, 61.9%, white solid).

[Step 4] Compound 11739

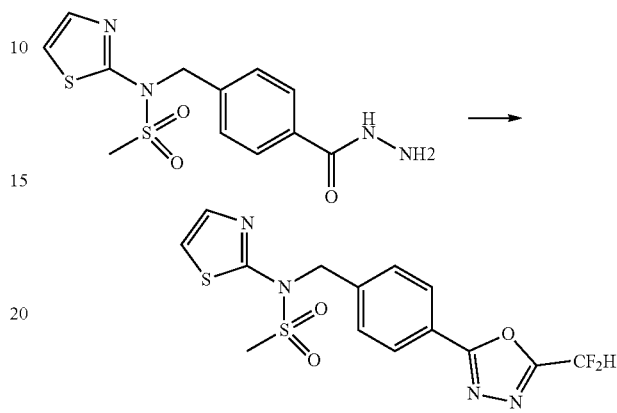

A solution of N-(4-(hydrazinecarbonyl)benzyl)-N-(thiazol-2-yl)methanesulfonamide (0.130 g, 0.398 mmol), triethylamine (0.278 mL, 1.991 mmol) and 2,2-difluoroacetic anhydride (0.149 mL, 1.195 mmol) in tetrahydrofuran (10 mL) was stirred at 70° C. for 12 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(4-(5-(difluoromethyl)-1,3,4-oxadiazol-2-yl)benzyl)-N-(thiazol-2-yl)methanesulfonamide as white solid (0.059 g, 38.3%).

$^1$H NMR (400 MHz, CDCl$_3$) δ 8.10 (d, 2H, J=8.4 Hz), 7.67 (d, 2H, J=8.5 Hz), 7.51 (d, 1H, J=3.6 Hz), 7.06 (d, 1H, J=3.6 Hz), 7.05 (s, 0.3H), 6.92 (s, 0.5H), 6.79 (s, 0.3H), 5.28 (s, 2H), 3.11 (s, 3H); LRMS (ES) m/z 387.2 (M$^+$+1).

EXAMPLE 245

Compound 11740, N-(benzo[d]thiazol-2-yl)-N-(4-(5-(difluoromethyl)-1,3,4-oxadiazol-2-yl)benzyl)methanesulfonamide

[Step 1] N-(benzo[d]thiazol-2-yl)methanesulfonamide

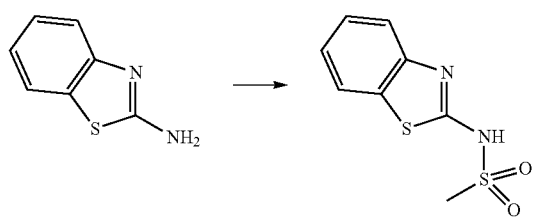

A solution of benzo[d]thiazol-2-amine (0.500 g, 3.329 mmol), pyridine (0.402 mL, 4.993 mmol) and methanesulfonyl chloride (0.335 mL, 4.328 mmol) in dichloromethane (20 mL) was stirred at the room temperature for 5 hr. Then, water was added to the reaction mixture, followed by extraction with dichloromethane. The organic layer was washed with aqueous 1N-hydrochloric acid solution, dried with anhydrous MgSO₄, filtered, and concentrated in vacuo. The title compound was used without further purification (N-(benzo[d]thiazol-2-yl)methanesulfonamide, 0.390 g, 51.3%, yellow solid).

[Step 2] methyl 4-((N-(benzo[d]thiazol-2-yl)methyl-sulfonamido)methyl)benzoate

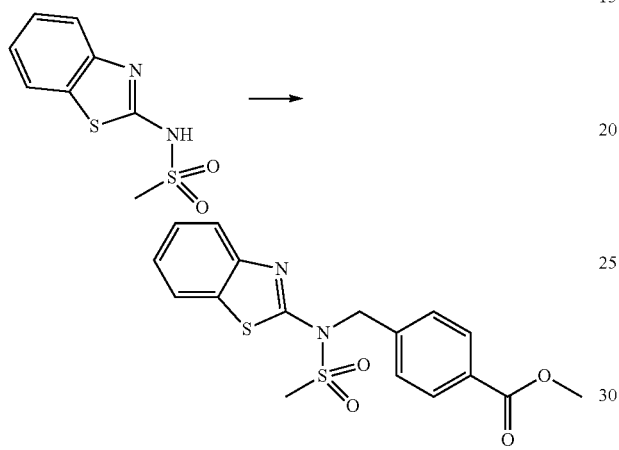

A solution of N-(benzo[d]thiazol-2-yl)methanesulfonamide (0.250 g, 1.095 mmol) and potassium carbonate (0.227 g, 1.643 mmol) in N,N-dimethylformide (20 mL) was mixed at the room temperature with methyl 4-(bromomethyl)benzoate (0.276 g, 1.205 mmol) and potassium iodide (0.091 g, 0.548 mmol). The reaction mixture was stirred at the same temperature for 12 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 12 g cartridge; ethyl acetate/hexane=0% to 40%) to give methyl 4-((N-(benzo[d]thiazol-2-yl)methylsulfonamido)methyl)benzoate as yellow solid (0.190 g, 46.1%).

[Step 3] N-(benzo[d]thiazol-2-yl)-N-(4-(hydrazinecarbonyl)benzyl)methanesulfonamide

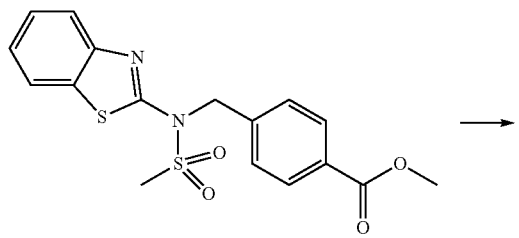

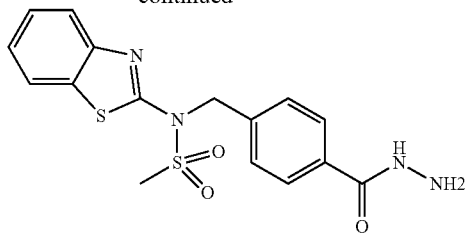

A solution of methyl 4-((N-(benzo[d]thiazol-2-yl)methylsulfonamido)methyl)benzoate (0.190 g, 0.505 mmol) and hydrazine monohydrate (0.245 mL, 5.047 mmol) in ethanol (10 mL) was stirred at 90° C. for 12 hr, cooled down to the room temperature to terminate the reaction and concentrated under the reduced pressure to remove the solvent. Then, water was added to the reaction mixture, followed by extraction with dichloromethane. The organic layer was washed with aqueous saturated sodium bicarbonate solution, dried with anhydrous MgSO₄, filtered, and concentrated in vacuo. The title compound was used without further purification (N-(benzo[d]thiazol-2-yl)-N-(4-(hydrazinecarbonyl)benzyl)methanesulfonamide, 0.090 g, 47.4%, yellow solid).

[Step 4] Compound 11740

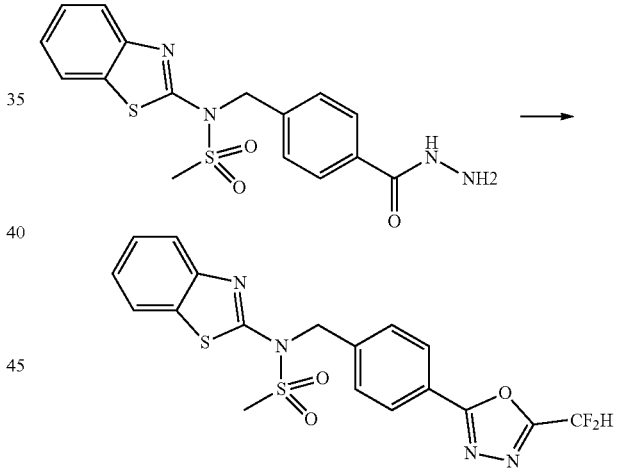

A solution of N-(benzo[d]thiazol-2-yl)-N-(4-(hydrazinecarbonyl)benzyl)methanesulfonamide (0.090 g, 0.239 mmol), triethylamine (0.167 mL, 1.195 mmol) and 2,2-difluoroacetic anhydride (0.089 mL, 0.717 mmol) in tetrahydrofuran (10 mL) was stirred at 70° C. for 12 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 50%) to give N-(benzo[d]thiazol-2-yl)-N-(4-(5-(difluoromethyl)-1,3,4-oxadiazol-2-yl)benzyl)methanesulfonamide as yellow solid (0.039 g, 37.4%).

¹H NMR (400 MHz, CDCl₃) δ 8.11 (d, 2H, J=6.8 Hz), 7.86-7.84 (m, 1H), 7.76 (d, 3H, J=7.3 Hz), 7.48-7.46 (m,

1H), 7.44-7.32 (m, 1H), 7.04 (s, 0.2H), 6.92 (s, 0.4H), 6.79 (s, 0.2H), 5.45 (s, 2H), 3.14 (s, 3H); LRMS (ES) m/z 437.2 (M$^+$+1).

EXAMPLE 246

Compound 11741, N-(4-(5-(difluoromethyl)-1,3,4-oxadiazol-2-yl)benzyl)-N-(oxazol-2-yl)methanesulfonamide

[Step 1] N-(oxazol-2-yl)methanesulfonamide

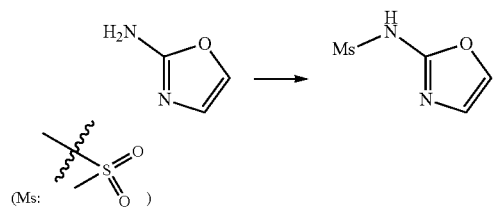

A solution of oxazol-2-amine (0.300 g, 3.568 mmol), methanesulfonyl chloride (0.304 mL, 3.925 mmol) and triethylamine (0.746 mL, 5.352 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(oxazol-2-yl)methanesulfonamide as yellow oil (0.150 g, 25.9%).

[Step 2] methyl 4-((N-(oxazol-2-yl)methylsulfonamido)methyl)benzoate

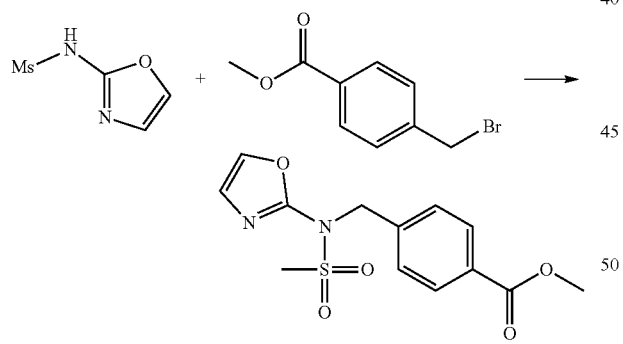

A solution of N-(oxazol-2-yl)methanesulfonamide (0.200 g, 1.233 mmol), methyl 4-(bromomethyl)benzoate (0.339 g, 1.480 mmol), potassium carbonate (0.205 g, 1.480 mmol) and potassium iodide (0.102 g, 0.617 mmol) in N,N-dimethylformide (3 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give methyl 4-((N-(oxazol-2-yl)methylsulfonamido)methyl)benzoate as white solid (0.106 g, 27.7%).

[Step 3] N-(4-(hydrazinecarbonyl)benzyl)-N-(oxazol-2-yl)methanesulfonamide

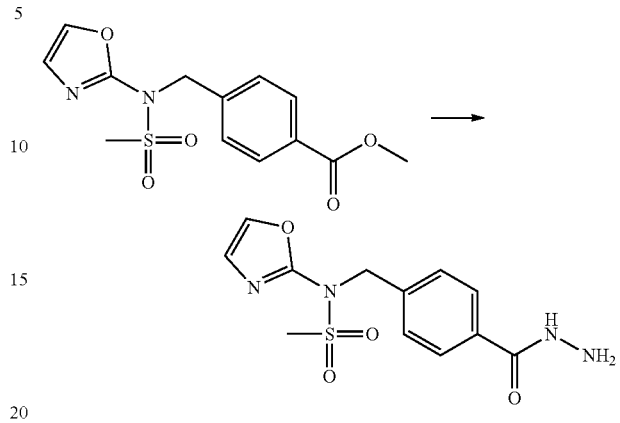

A solution of methyl 4-((N-(oxazol-2-yl)methylsulfonamido)methyl)benzoate (0.106 g, 0.342 mmol) and hydrazine monohydrate (0.166 mL, 3.416 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give N-(4-(hydrazinecarbonyl)benzyl)-N-(oxazol-2-yl)methanesulfonamide as white solid (0.075 g, 70.8%).

[Step 4] Compound 11741

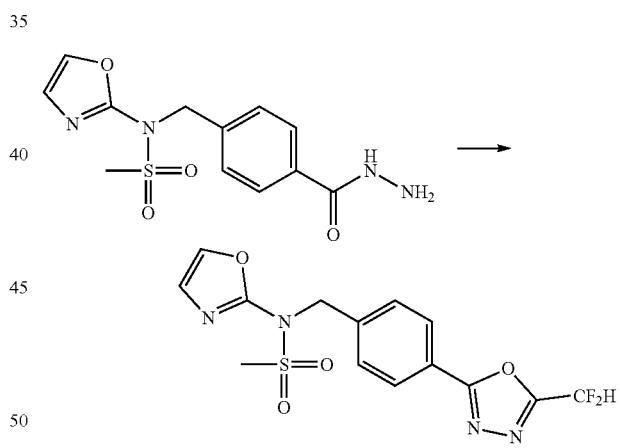

A solution of N-(4-(hydrazinecarbonyl)benzyl)-N-(oxazol-2-yl)methanesulfonamide (0.075 g, 0.242 mmol), 2,2-difluoroacetic anhydride (0.090 mL, 0.725 mmol) and triethylamine (0.101 mL, 0.725 mmol) in tetrahydrofuran (2 mL) was stirred at 80° C. for 0.5 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)benzyl)-N-(oxazol-2-yl)methanesulfonamide as white solid (0.034 g, 38.0%).

¹H NMR (400 MHz, CD3OD) δ8.11 (d, 2H, J=8.1 Hz), 7.74 (s, 1H), 7.64 (d, 2H, J=8.0 Hz), 7.10 (s, 1H), 7.23 (t, 1H, J=51.8 Hz), 5.13 (s, 2H), 3.38 (s, 3H); LRMS (ES) m/z 371.2 (M⁺+1).

EXAMPLE 247

Compound 11742, N-(4-(5-(difluoromethyl)-1,3,4-oxadiazol-2-yl)benzyl)-N-(1-isopropyl-1H-indazol-6-yl)methanesulfonamide

[Step 1] N-(1-isopropyl-1H-indazol-6-yl)methanesulfonamide

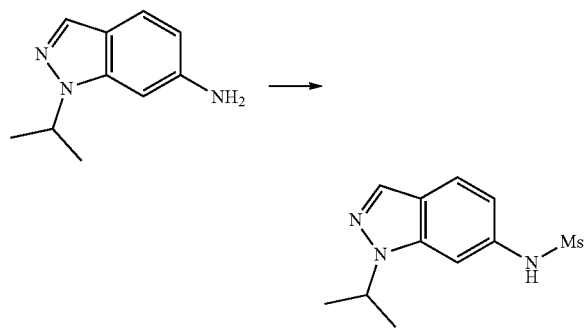

A solution of 1-isopropyl-1H-indazol-6-amine (0.300 g, 1.712 mmol), methanesulfonyl chloride (0.146 mL, 1.883 mmol) and triethylamine (0.358 mL, 2.568 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give N-(1-isopropyl-1H-indazol-6-yl)methanesulfonamide as orange solid (0.407 g, 93.8%).

[Step 2] methyl 4-((N-(1-isopropyl-1H-indazol-6-yl)methylsulfonamido)methyl)benzoate

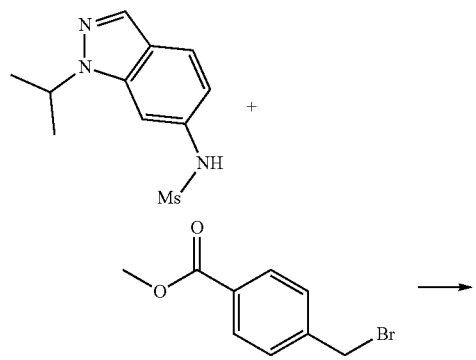

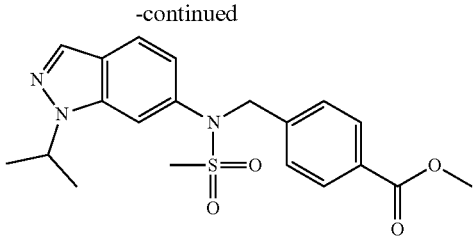

A solution of N-(1-isopropyl-1H-indazol-6-yl)methanesulfonamide (0.200 g, 0.790 mmol), methyl 4-(bromomethyl)benzoate (0.217 g, 0.947 mmol), potassium carbonate (0.131 g, 0.947 mmol) and potassium iodide (0.066 g, 0.395 mmol) in N,N-dimethylformamide (3 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give methyl 4-((N-(1-isopropyl-1H-indazol-6-yl)methylsulfonamido)methyl)benzoate as yellow solid (0.251 g, 79.3%).

[Step 3] N-(4-(hydrazinecarbonyl)benzyl)-N-(1-isopropyl-1H-indazol-6-yl)methanesulfonamide

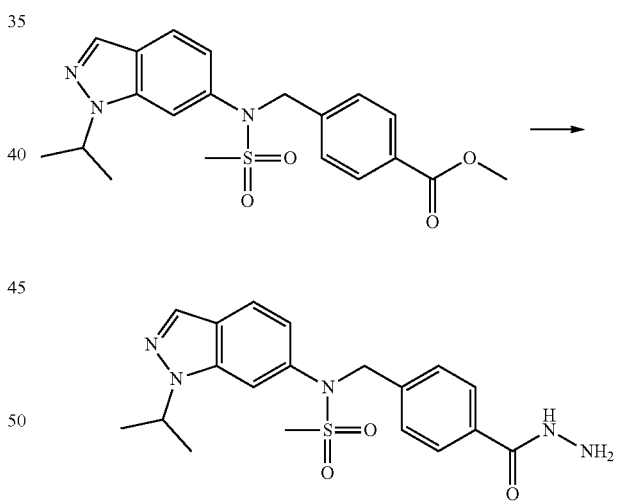

A solution of methyl 4-((N-(1-isopropyl-1H-indazol-6-yl)methylsulfonamido)methyl)benzoate (0.251 g, 0.625 mmol) and hydrazine monohydrate (0.304 mL, 6.252 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give N-(4-(hydrazinecarbonyl)benzyl)-N-(1-isopropyl-1H-indazol-6-yl)methanesulfonamide as white solid (0.242 g, 96.6%).

[Step 4] Compound 11741

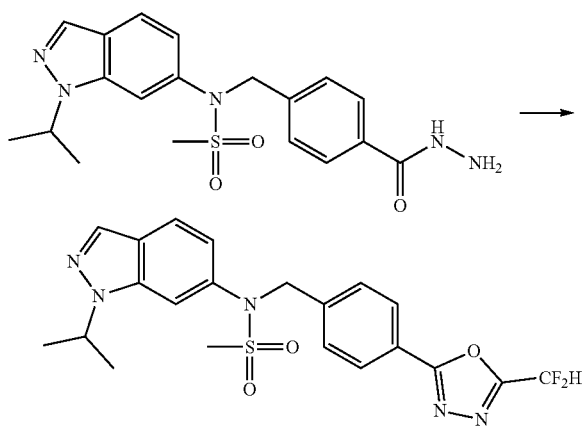

A solution of N-(4-(hydrazinecarbonyl)benzyl)-N-(1-isopropyl-1H-indazol-6-yl)methanesulfonamide (0.080 g, 0.199 mmol), 2,2-difluoroacetic anhydride (0.074 mL, 0.598 mmol) and triethylamine (0.083 mL, 0.598 mmol) in tetrahydrofuran (2 mL) was stirred at 80° C. for 0.5 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)benzyl)-N-(1-isopropyl-1H-indazol-6-yl)methanesulfonamide as white solid (0.075 g, 82.0%).
$^1$H NMR (400 MHz, CD3OD) δ8.01 (d, 2H, J=8.3 Hz), 7.99 (s, 1H), 7.73 (d, 1H, J=8.6 Hz), 7.62 (s, 1H), 7.58 (d, 2H, J=8.2 Hz), 7.19 (t, 1H, J=51.7 Hz), 7.22 (dd, 1H, J=8.7, 1.3 Hz), 4.93-4.87 (m, 1H), 3.33 (s, 3H), 1.50 (d, 6H, J=6.6 Hz); LRMS (ES) m/z 462.2 (M$^+$+1).

EXAMPLE 248

Compound 11743, N-(4-(5-(difluoromethyl)-1,3,4-oxadiazol-2-yl)benzyl)-N-(1-ethyl-1H-indazol-6-yl)methanesulfonamide

[Step 1]
N-(1-ethyl-1H-indazol-6-yl)methanesulfonamide

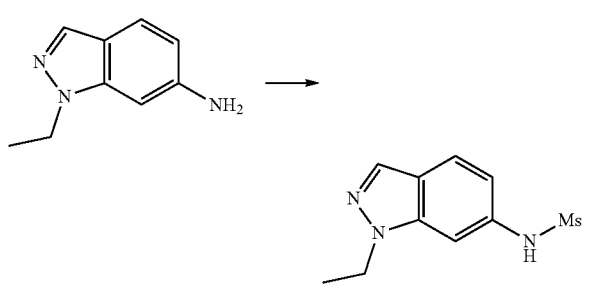

A solution of 1-ethyl-1H-indazol-6-amine (0.350 g, 2.171 mmol), methanesulfonyl chloride (0.185 mL, 2.388 mmol) and triethylamine (0.454 mL, 3.257 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(1-ethyl-1H-indazol-6-yl)methanesulfonamide as pink solid (0.508 g, 97.7%).

[Step 2] methyl 4-((N-(1-ethyl-1H-indazol-6-yl)methylsulfonamido)methyl)benzoate

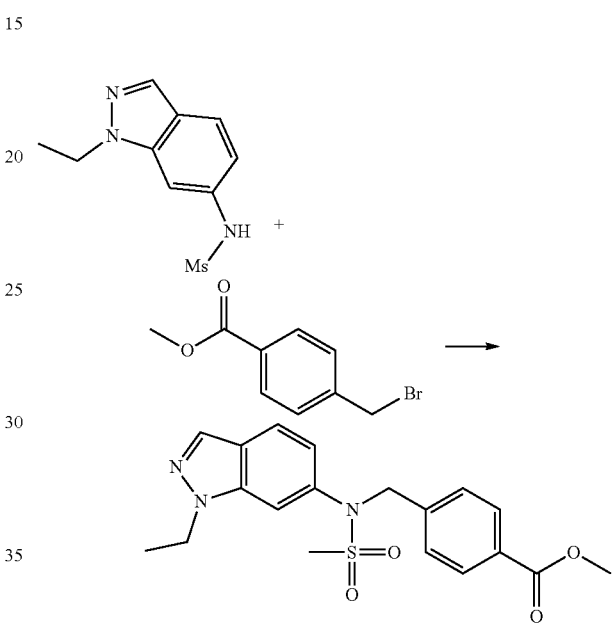

A solution of N-(1-ethyl-1H-indazol-6-yl)methanesulfonamide (0.200 g, 0.836 mmol), methyl 4-(bromomethyl)benzoate (0.230 g, 1.003 mmol), potassium carbonate (0.139 g, 1.003 mmol) and potassium iodide (0.069 g, 0.418 mmol) in N,N-dimethylformide (3 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give methyl 4-((N-(1-ethyl-1H-indazol-6-yl)methylsulfonamido)methyl)benzoate as ivory solid (0.223 g, 68.9%).

[Step 3] N-(1-ethyl-1H-indazol-6-yl)-N-(4-(hydrazinecarbonyl)benzyl)methanesulfonamide

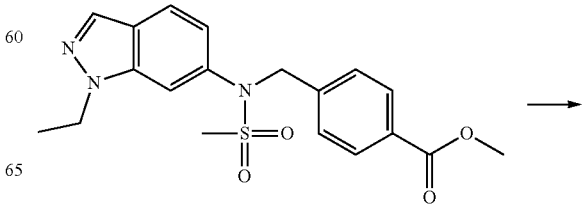

-continued

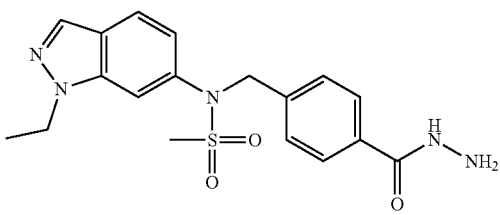

A solution of methyl 4-((N-(1-ethyl-1H-indazol-6-yl)methylsulfonamido)methyl)benzoate (0.223 g, 0.576 mmol) and hydrazine monohydrate (0.280 mL, 5.756 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give N-(1-ethyl-1H-indazol-6-yl)-N-(4-(hydrazinecarbonyl)benzyl)methanesulfonamide as white solid (0.205 g, 91.8%).

[Step 4] Compound 11743

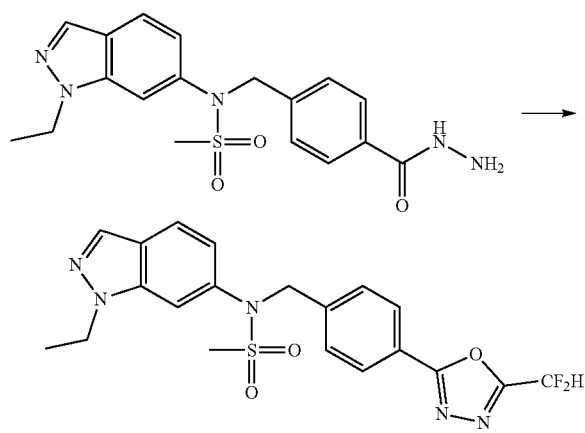

A solution of N-(1-ethyl-1H-indazol-6-yl)-N-(4-(hydrazinecarbonyl)benzyl)methanesulfonamide (0.080 g, 0.206 mmol), 2,2-difluoroacetic anhydride (0.077 mL, 0.619 mmol) and triethylamine (0.086 mL, 0.619 mmol) in tetrahydrofuran (2 mL) was stirred at 80° C. for 0.5 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)benzyl)-N-(1-ethyl-1H-indazol-6-yl)methanesulfonamide as white solid (0.054 g, 58.9%).

$^1$H NMR (400 MHz, CD3OD) δ8.01 (d, 2H, J=8.3 Hz), 7.92 (s, 1H), 7.74 (d, 1H, J=8.6 Hz), 7.63 (s, 1H), 7.59 (d, 2H, J=8.2 Hz), 7.19 (t, 1H, J=51.7 Hz), 7.23 (dd, 1H, J=8.6, 1.7 Hz), 5.10 (s, 2H), 4.42 (q, 2H, J=7.2 Hz), 3.13 (s, 3H), 1.41 (t, 3H, J=7.2 Hz); LRMS (ES) m/z 448.2 (M$^+$+1).

EXAMPLE 249

Compound 11744, N-(4-(5-(difluoromethyl)-1,3,4-oxadiazol-2-yl)benzyl)-N-(2-isopropylbenzo[d]thiazol-6-yl)methanesulfonamide

[Step 1] N-(2-isopropylbenzo[d]thiazol-6-yl)methanesulfonamide

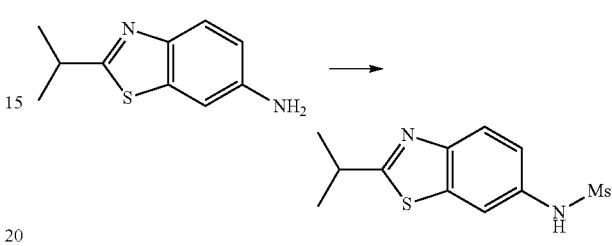

A solution of 2-isopropylbenzo[d]thiazol-6-amine (0.250 g, 1.300 mmol), methanesulfonyl chloride (0.111 mL, 1.430 mmol) and triethylamine (0.272 mL, 1.950 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(2-isopropylbenzo[d]thiazol-6-yl)methanesulfonamide as orange solid (0.307 g, 87.2%).

[Step 2] methyl 4-((N-(2-isopropylbenzo[d]thiazol-6-yl)methylsulfonamido)methyl)benzoate

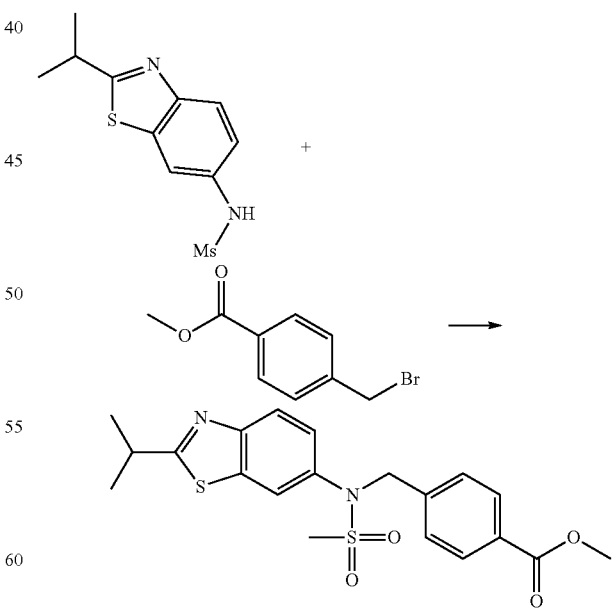

A solution of N-(2-isopropylbenzo[d]thiazol-6-yl)methanesulfonamide (0.300 g, 1.110 mmol), methyl 4-(bromomethyl)benzoate (0.305 g, 1.332 mmol), potassium carbonate (0.184 g, 1.332 mmol) and potassium iodide (0.092 g, 0.555 mmol) in N,N-dimethylformide (3 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give methyl 4-((N-(2-isopropylbenzo[d]thiazol-6-yl)methylsulfonamido)methyl)benzoate as pink solid (0.415 g, 89.3%).

[Step 3] N-(4-(hydrazinecarbonyl)benzyl)-N-(2-isopropylbenzo[d]thiazol-6-yl)methanesulfonamide

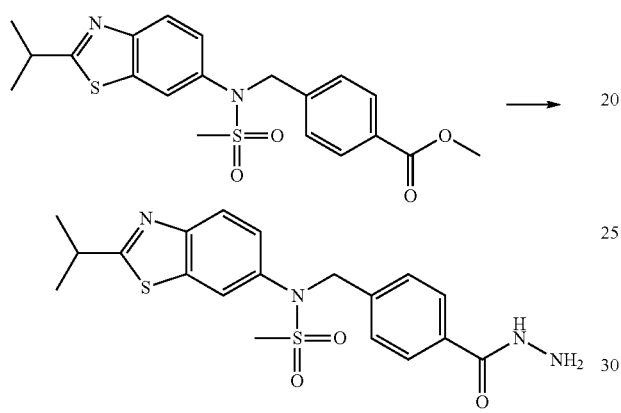

A solution of methyl 4-((N-(2-isopropylbenzo[d]thiazol-6-yl)methylsulfonamido)methyl)benzoate (0.415 g, 0.992 mmol) and hydrazine monohydrate (0.482 mL, 9.916 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give N-(4-(hydrazinecarbonyl)benzyl)-N-(2-isopropylbenzo[d]thiazol-6-yl)methanesulfonamide as orange solid (0.307 g, 74.0%).

[Step 4] Compound 11744

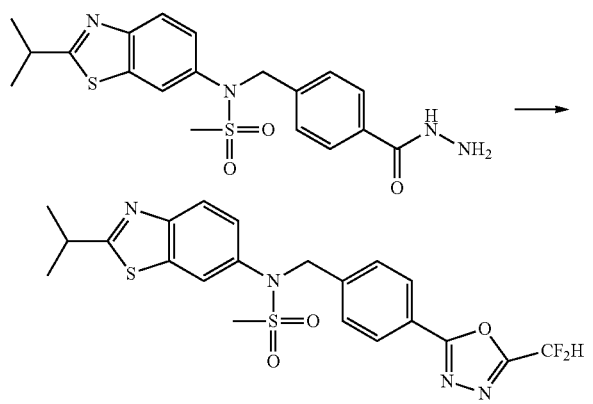

A solution of N-(4-(hydrazinecarbonyl)benzyl)-N-(2-isopropylbenzo[d]thiazol-6-yl)methanesulfonamide (0.080 g, 0.191 mmol), 2,2-difluoroacetic anhydride (0.071 mL, 0.573 mmol) and triethylamine (0.080 mL, 0.573 mmol) in tetrahydrofuran (2 mL) was stirred at 80° C. for 0.5 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)benzyl)-N-(2-isopropylbenzo[d]thiazol-6-yl)methanesulfonamide as ivory solid (0.057 g, 62.3%).

$^1$H NMR (400 MHz, CD3OD) δ8.01 (d, 1H, J=1.8 Hz), 7.98 (d, 2H, J=8.3 Hz), 7.86 (d, 1H, J=8.7 Hz), 7.57~7.53 (m, 3H), 7.19 (t, 1H, J=51.7 Hz), 5.07 (s, 2H), 3.43~3.36 (m, 1H), 3.12 (s, 3H), 1.43 (d, 6H, J=6.9 Hz); LRMS (ES) m/z 479.3 (M$^+$+1).

EXAMPLE 250

Compound 11745, N-(4-(5-(difluoromethyl)-1,3,4-oxadiazol-2-yl)benzyl)-N-(1,3-dimethyl-2-oxo-2,3-dihydro-1H-benzo[d]imidazol-5-yl) methanesulfonamide

[Step 1] N-(1,3-dimethyl-2-oxo-2,3-dihydro-1H-benzo[d]imidazol-5-yl)methanesulfonamide

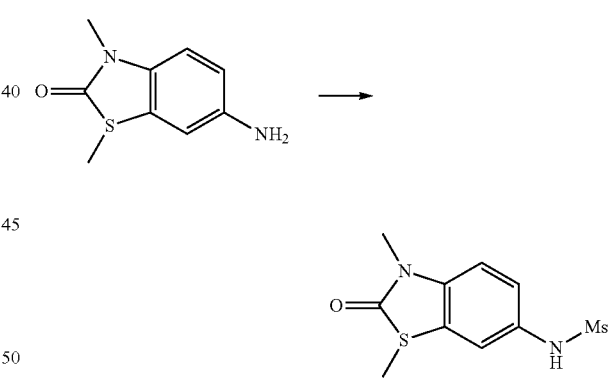

A solution of 5-amino-1,3-dimethyl-1,3-dihydro-2H-benzo[d]imidazol-2-one (0.350 g, 1.975 mmol), methanesulfonyl chloride (0.168 mL, 2.173 mmol) and triethylamine (0.413 mL, 2.963 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(1,3-dimethyl-2-oxo-2,3-dihydro-1H-benzo[d]imidazol-5-yl)methanesulfonamide as pink solid (0.432 g, 85.6%).

691

[Step 2] methyl 4-((N-(1,3-dimethyl-2-oxo-2,3-di-hydro-1H-benzo[d]imidazol-5-yl)methylsulfonamido)methyl)benzoate

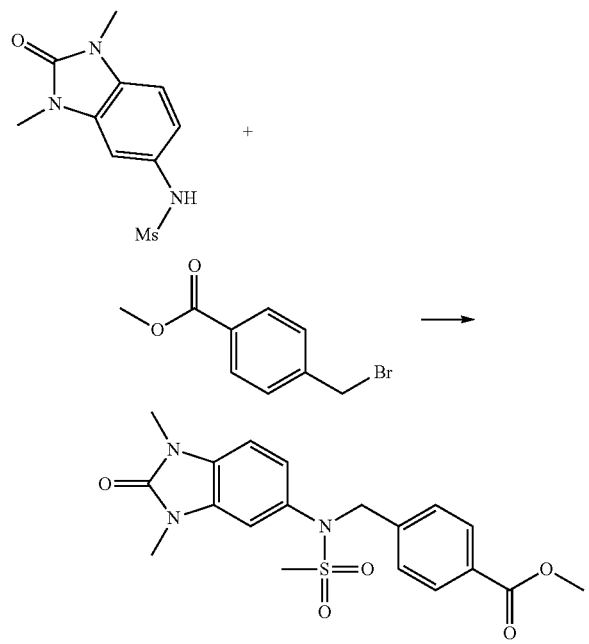

A solution of N-(1,3-dimethyl-2-oxo-2,3-dihydro-1H-benzo[d]imidazol-5-yl)methanesulfonamide (0.200 g, 0.783 mmol), methyl 4-(bromomethyl)benzoate (0.215 g, 0.940 mmol), potassium carbonate (0.130 g, 0.940 mmol) and potassium iodide (0.065 g, 0.392 mmol) in N,N-dimethylformide (3 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give methyl 4-((N-(1,3-dimethyl-2-oxo-2,3-dihydro-1H-benzo[d]imidazol-5-yl)methylsulfonamido)methyl)benzoate as yellow solid (0.291 g, 92.1%).

[Step 3] N-(1,3-dimethyl-2-oxo-2,3-dihydro-1H-benzo[d]imidazol-5-yl)-N-(4-(hydrazinecarbonyl)benzyl)methanesulfonamide

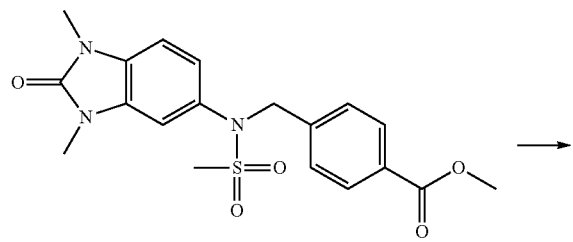

692

-continued

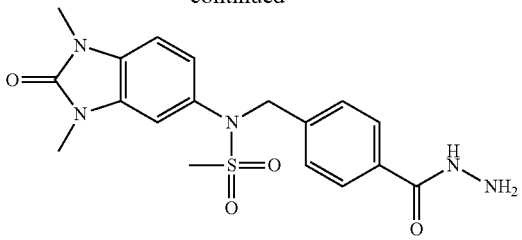

A solution of methyl 4-((N-(1,3-dimethyl-2-oxo-2,3-dihydro-1H-benzo[d]imidazol-5-yl)methylsulfonamido)methyl)benzoate (0.291 g, 0.721 mmol) and hydrazine monohydrate (0.351 mL, 7.213 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give N-(1,3-dimethyl-2-oxo-2,3-dihydro-1H-benzo[d]imidazol-5-yl)-N-(4-(hydrazinecarbonyl)benzyl)methanesulfonamide as yellow solid (0.188 g, 64.5%).

[Step 4] Compound 11745

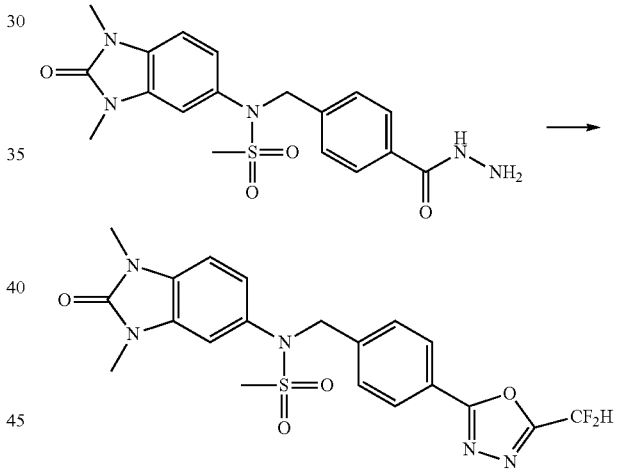

A solution of N-(1,3-dimethyl-2-oxo-2,3-dihydro-1H-benzo[d]imidazol-5-yl)-N-(4-(hydrazinecarbonyl)benzyl)methanesulfonamide (0.080 g, 0.198 mmol), 2,2-difluoroacetic anhydride (0.074 mL, 0.595 mmol) and triethylamine (0.083 mL, 0.595 mmol) in tetrahydrofuran (2 mL) was stirred at 80° C. for 0.5 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; methanol/dichloromethane=0% to 5%) to give N-(4-(5-(difluoromethyl)-1,3,4-oxadiazol-2-yl)benzyl)-N-(1,3-dimethyl-2-oxo-2,3-dihydro-1H-benzo[d]imidazol-5-yl) methanesulfonamide as white solid (0.083 g, 90.6%).

¹H NMR (400 MHz, CD3OD) δ7.99 (d, 2H, J=8.4 Hz), 7.55 (d, 2H, J=8.4 Hz), 7.20 (t, 1H, J=51.7 Hz), 7.19~7.15

693

(m, 2H), 7.06 (d, 1H, J=8.3 Hz), 5.01 (s, 2H), 3.35 (s, 3H), 3.33 (s, 3H), 3.10 (s, 3H); LRMS (ES) m/z 464.2 (M$^+$+1).

EXAMPLE 251

Compound 11746, N-(4-(5-(difluoromethyl)-1,3,4-oxadiazol-2-yl)benzyl)-N-(1,3-dimethyl-1H-indazol-5-yl)methanesulfonamide

[Step 1] N-(1,3-dimethyl-1H-indazol-5-yl)methanesulfonamide

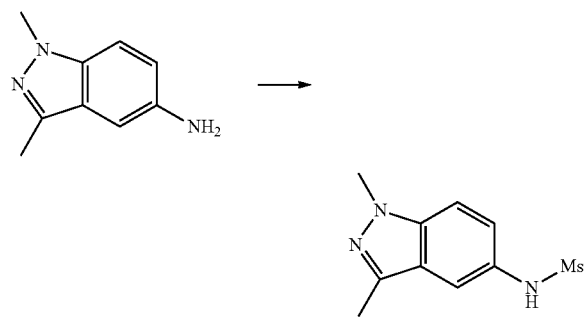

A solution of 1,3-dimethyl-1H-indazol-5-amine (0.250 g, 1.551 mmol), methanesulfonyl chloride (0.132 mL, 1.706 mmol) and triethylamine (0.324 mL, 2.326 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give N-(1,3-dimethyl-1H-indazol-5-yl)methanesulfonamide as white solid (0.220 g, 59.3%).

[Step 2] methyl 4-((N-(1,3-dimethyl-1H-indazol-5-yl)methylsulfonamido)methyl)benzoate

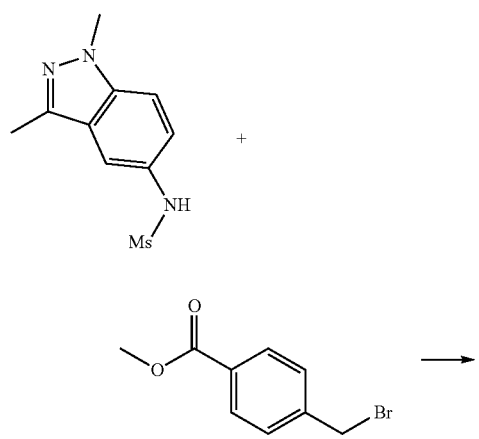

694

-continued

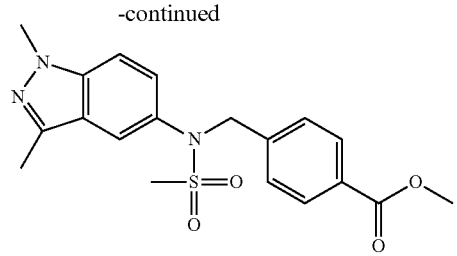

A solution of N-(1,3-dimethyl-1H-indazol-5-yl)methanesulfonamide (0.250 g, 1.045 mmol), methyl 4-(bromomethyl)benzoate (0.287 g, 1.254 mmol), potassium carbonate (0.173 g, 1.254 mmol) and potassium iodide (0.087 g, 0.522 mmol) in N,N-dimethylformide (3 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 50%) to give methyl 4-((N-(1,3-dimethyl-1H-indazol-5-yl)methylsulfonamido)methyl)benzoate as yellow solid (0.341 g, 84.2%).

[Step 3] N-(1,3-dimethyl-1H-indazol-5-yl)-N-(4-(hydrazinecarbonyl)benzyl)methanesulfonamide

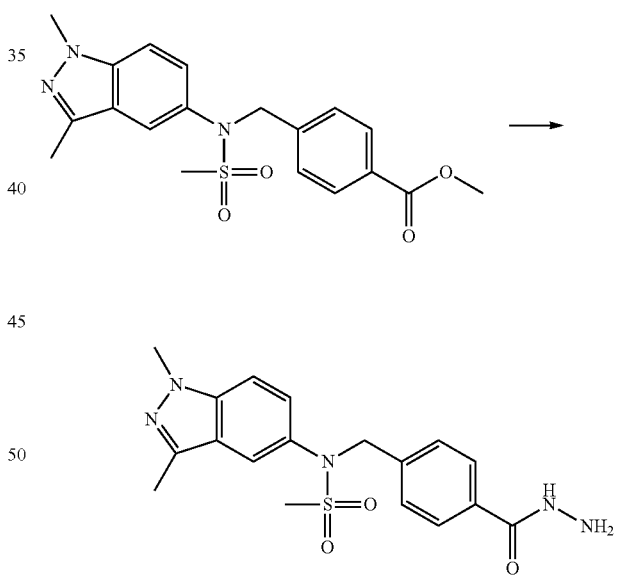

A solution of methyl 4-((N-(1,3-dimethyl-1H-indazol-5-yl)methylsulfonamido)methyl)benzoate (0.341 g, 0.880 mmol) and hydrazine monohydrate (0.428 mL, 8.801 mmol) in ethanol (3 mL) was stirred at 80° C. for 18 hr, cooled down to the room temperature to terminate the reaction and concentrated under the reduced pressure to remove the solvent. The residue was diluted with sodium bicarbonate (5 mL) and stirred. The resulting precipitates were collected by filtration and dried to give N-(1,3-dimethyl-1H-indazol-5-yl)-N-(4-(hydrazinecarbonyl)benzyl)methanesulfonamide as white solid (0.280 g, 82.0%).

695

[Step 4] Compound 11746

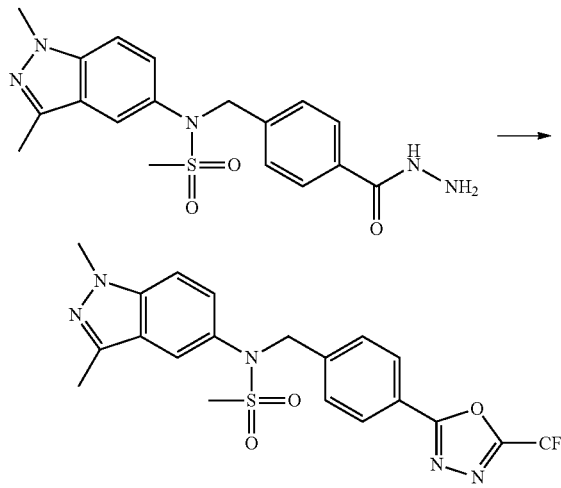

A solution of N-(1,3-dimethyl-1H-indazol-5-yl)-N-(4-(hydrazinecarbonyl)benzyl)methanesulfonamide (0.080 g, 0.206 mmol), 2,2-difluoroacetic anhydride (0.077 mL, 0.619 mmol) and triethylamine (0.086 mL, 0.619 mmol) in tetrahydrofuran (2 mL) was stirred at 80° C. for 0.5 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)benzyl)-N-(1,3-dimethyl-1H-indazol-5-yl)methanesulfonamide as white solid (0.078 g, 84.5%).

$^1$H NMR (400 MHz, CD3OD) δ7.97 (d, 2H, J=8.2 Hz), 7.75 (s, 1H), 7.54 (d, 2H, J=8.2 Hz), 7.42~7.37 (m, 2H), 7.19 (t, 1H, J=51.7 Hz), 5.04 (s, 2H), 3.93 (s, 3H), 3.10 (s, 3H), 2.48 (s, 3H); LRMS (ES) m/z 448.3 (M$^+$+1).

EXAMPLE 252

Compound 11747, N-(4-(5-(difluoromethyl)-1,3,4-oxadiazol-2-yl)-2-fluorobenzyl)-N-(2,3-dihydro-1H-inden-5-yl)methanesulfonamide

[Step 1]
N-(2,3-dihydro-1H-inden-5-yl)methanesulfonamide

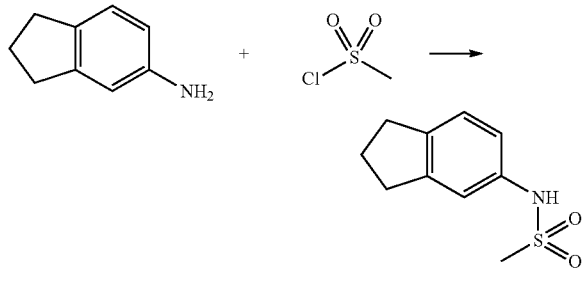

696

A solution of 2,3-dihydro-1H-inden-5-amine (0.500 g, 3.754 mmol) and pyridine (0.605 mL, 7.508 mmol) in dichloromethane (20 mL) was mixed at the room temperature with methanesulfonyl chloride (0.320 mL, 4.129 mmol). The reaction mixture was stirred at the same temperature for 18 hr. Then, aqueous 1M-hydrochloric acid solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 80%) to give N-(2,3-dihydro-1H-inden-5-yl)methanesulfonamide as yellow solid (0.660 g, 83.2%).

[Step 2] Compound 11747

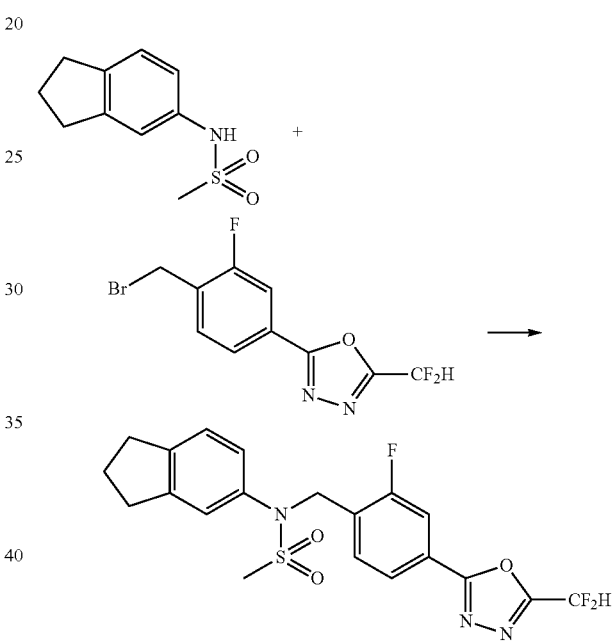

N-(2,3-dihydro-1H-inden-5-yl)methanesulfonamide (0.200 g, 0.947 mmol), 2-(4-(bromomethyl)-3-fluorophenyl)-5-(difluoromethyl)-1,3,4-oxadiazole (0.320 g, 1.041 mmol), potassium carbonate (0.262 g, 1.893 mmol) and potassium iodide (0.047 g, 0.284 mmol) were mixed at the room temperature in N,N-dimethylformide (10 mL) and then stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 50%) to give N-(4-(5-(difluoromethyl)-1,3,4-oxadiazol-2-yl)-2-fluorobenzyl)-N-(2,3-dihydro-1H-inden-5-yl)methanesulfonamide as yellow solid (0.240 g, 58.0%).

$^1$H NMR (400 MHz, CDCl$_3$) δ 7.87-7.84 (m, 1H), 7.73-7.66 (m, 2H), 7.17-7.15 (m, 2H), 7.05-7.02 (m, 1H), 7.03 (s, 0.25H), 6.89 (s, 0.5H), 6.76 (s, 0.25H), 4.98 (s, 2H), 2.99 (s, 3H), 2.88-2.83 (m, 4H), 2.11-1.02 (m, 2H); LRMS (ES) m/z 438.1 (M$^+$+1).

EXAMPLE 253

Compound 11748, (R)—N-(4-(5-(difluoromethyl)-1,3,4-oxadiazol-2-yl)-2-fluorobenzyl)-N-(2,3-dihydro-1H-inden-1-yl)methanesulfonamide

[Step 1] (R)—N-(2,3-dihydro-1H-inden-1-yl)methanesulfonamide

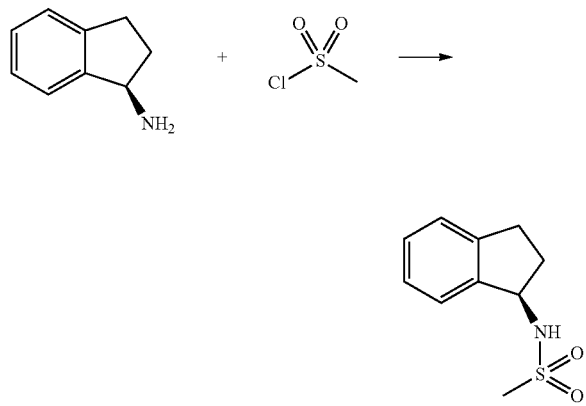

A solution of (R)-2,3-dihydro-1H-inden-1-amine (0.500 g, 3.754 mmol) and pyridine (0.605 mL, 7.508 mmol) in dichloromethane (20 mL) was mixed at the room temperature with methanesulfonyl chloride (0.320 mL, 4.129 mmol). The reaction mixture was stirred at the same temperature for 18 hr. Then, aqueous 1M-hydrochloric acid solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 50%) to give (R)—N-(2,3-dihydro-1H-inden-1-yl)methanesulfonamide as white solid (0.407 g, 51.3%).

[Step 2] Compound 11748

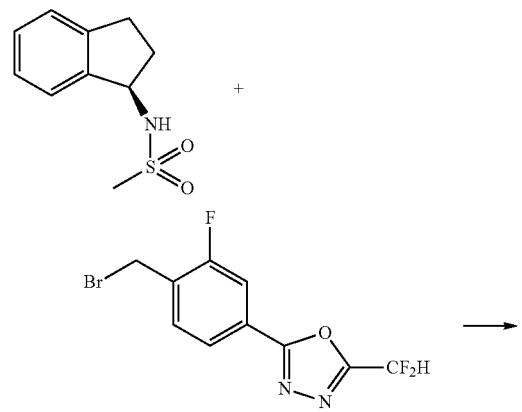

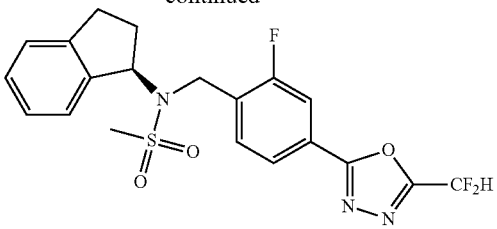

(R)—N-(2,3-dihydro-1H-inden-1-yl)methanesulfonamide (0.200 g, 0.947 mmol), 2-(4-(bromomethyl)-3-fluorophenyl)-5-(difluoromethyl)-1,3,4-oxadiazole (0.320 g, 1.041 mmol), potassium carbonate (0.262 g, 1.893 mmol) and potassium iodide (0.047 g, 0.284 mmol) were mixed at the room temperature in N,N-dimethylformide (10 mL) and then stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 30%) to give (R)—N-(4-(5-(difluoromethyl)-1,3,4-oxadiazol-2-yl)-2-fluorobenzyl)-N-(2,3-dihydro-1H-inden-1-yl)methanesulfonamide as white solid (0.017 g, 4.1%).

$^1$H NMR (400 MHz, CDCl$_3$) δ 7.83-7.81 (m, 1H), 7.72-7.68 (m, 1H), 7.57 (dd, 1H, J=10.2, 1.6 Hz), 7.21-7.14 (m, 3H), 7.07-7.04 (m, 1H), 7.03 (s, 0.25H), 6.90 (s, 0.5H), 6.77 (s, 0.25H), 5.62-5.58 (m, 1H), 4.43-4.29 (m, 2H), 3.05 (s, 3H), 2.98-2.81 (m, 2H), 2.54-2.45 (m, 1H), 2.06-1.97 (m, 1H); LRMS (ES) m/z 438.3 (M⁺+1).

EXAMPLE 254

Compound 11749, (S)—N-(4-(5-(difluoromethyl)-1,3,4-oxadiazol-2-yl)-2-fluorobenzyl)-N-(2,3-dihydro-1H-inden-1-yl)methanesulfonamide

[Step 1] (S)—N-(2,3-dihydro-1H-inden-1-yl)methanesulfonamide

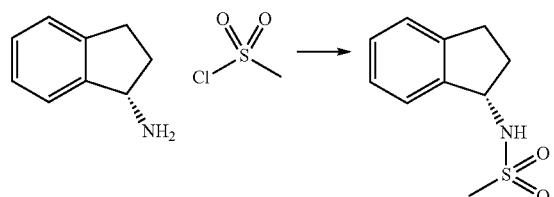

A solution of (S)-2,3-dihydro-1H-inden-1-amine (0.500 g, 3.754 mmol) and pyridine (0.605 mL, 7.508 mmol) in dichloromethane (20 mL) was mixed at the room temperature with methanesulfonyl chloride (0.320 mL, 4.129 mmol). The reaction mixture was stirred at the same temperature for 18 hr. Then, aqueous 1M-hydrochloric acid solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 50%) to give (S)—N-(2,3-dihydro-1H-inden-1-yl)methanesulfonamide as white solid (0.542 g, 68.3%).

[Step 2] Compound 11749

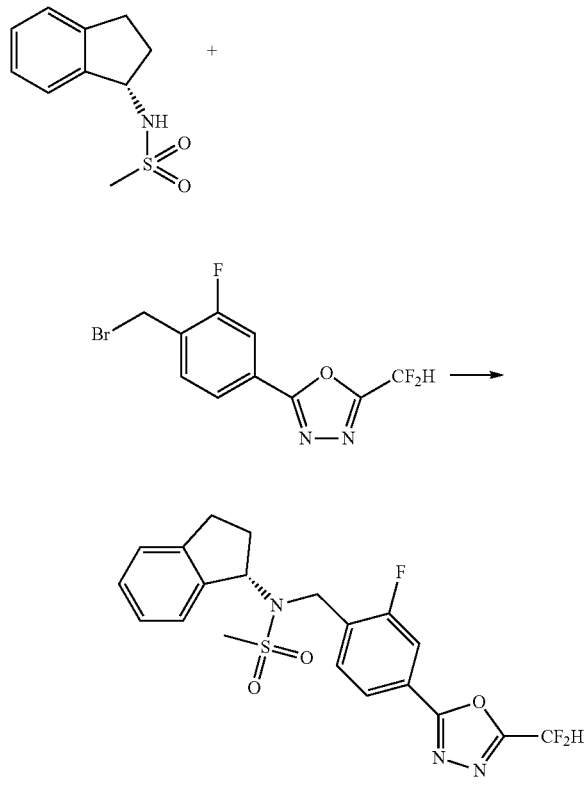

(S)—N-(2,3-dihydro-1H-inden-1-yl)methanesulfonamide (0.200 g, 0.947 mmol), 2-(4-(bromomethyl)-3-fluorophenyl)-5-(difluoromethyl)-1,3,4-oxadiazole (0.320 g, 1.041 mmol), potassium carbonate (0.262 g, 1.893 mmol) and potassium iodide (0.047 g, 0.284 mmol) were mixed at the room temperature in N,N-dimethylformide (10 mL) and then stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give (S)—N-(4-(5-(difluoromethyl)-1,3,4-oxadiazol-2-yl)-2-fluorobenzyl)-N-(2,3-dihydro-1H-inden-1-yl)methanesulfonamide as white solid (0.011 g, 2.7%).

$^1$H NMR (400 MHz, CDCl$_3$) δ 7.83-7.81 (m, 1H), 7.72-7.68 (m, 1H), 7.59-7.56 (m, 1H), 7.21-7.18 (m, 2H), 7.16-7.15 (m, 1H), 7.07-7.04 (m, 1H), 7.03 (s, 0.25H), 6.90 (s, 0.5H), 6.77 (s, 0.25H), 5.62-5.59 (m, 1H), 4.43-4.29 (m, 2H), 3.05 (s, 3H), 2.98-2.81 (m, 2H), 2.54-2.45 (m, 1H), 2.06-1.97 (m, 1H); LRMS (ES) m/z 438.2 (M$^+$+1).

EXAMPLE 255

Compound 11750, N-(4-(5-(difluoromethyl)-1,3,4-oxadiazol-2-yl)benzyl)-N-(5-methyl-4,5,6,7-tetrahydrothiazolo[5,4-c]pyridin-2-yl)methanesulfonamide

[Step 1] tert-butyl 2-((4-(methoxycarbonyl)benzyl)amino)-6,7-dihydrothiazolo[5,4-c]pyridine-5(4H)-carboxylate

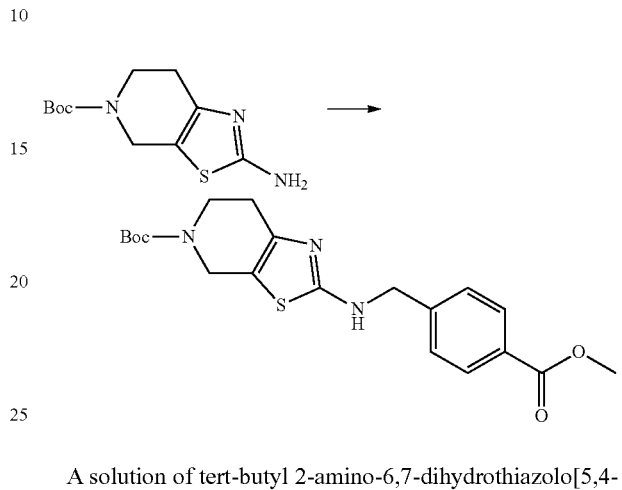

A solution of tert-butyl 2-amino-6,7-dihydrothiazolo[5,4-c]pyridine-5(4H)-carboxylate (0.500 g, 1.958 mmol), methyl 4-formylbenzoate (0.354 g, 2.154 mmol) and acetic acid (0.135 mL, 2.350 mmol) in dichloromethane (20 mL) was stirred at the room temperature for 30 min, and mixed with sodium triacetoxyborohydride (0.830 g, 3.916 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 12 g cartridge; ethyl acetate/hexane=0% to 40%) to give tert-butyl 2-((4-(methoxycarbonyl)benzyl)amino)-6,7-dihydrothiazolo[5,4-c]pyridine-5(4H)-carboxylate as white solid (0.350 g, 44.3%).

[Step 2] tert-butyl 2-(N-(4-(methoxycarbonyl)benzyl)methylsulfonamido)-6,7-dihydrothiazolo[5,4-c]pyridine-5(4H)-carboxylate

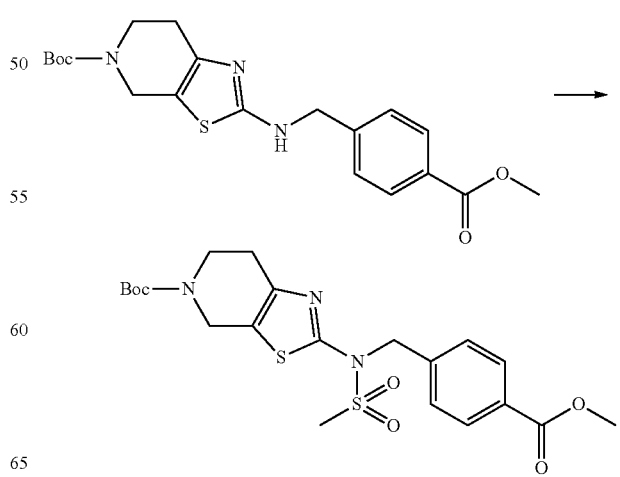

A solution of tert-butyl 2-((4-(methoxycarbonyl)benzyl)amino)-6,7-dihydrothiazolo[5,4-c]pyridine-5(4H)-carboxylate (0.170 g, 0.421 mmol), TEA (0.056 g, 0.548 mmol), N,N-dimethylpyridin-4-amine (0.005 g, 0.042 mmol) and methanesulfonyl chloride (0.039 mL, 0.506 mmol) in dichloromethane (10 mL) was stirred at 50° C. for 12 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 30%) to give tert-butyl 2-(N-(4-(methoxycarbonyl)benzyl)methylsulfonamido)-6,7-dihydrothiazolo[5,4-c]pyridine-5(4H)-carboxylate as white solid (0.110 g, 54.2%).

[Step 3] methyl 4-((N-(4,5,6,7-tetrahydrothiazolo[5,4-c]pyridin-2-yl)methylsulfonamido)methyl)benzoate hydrochloride

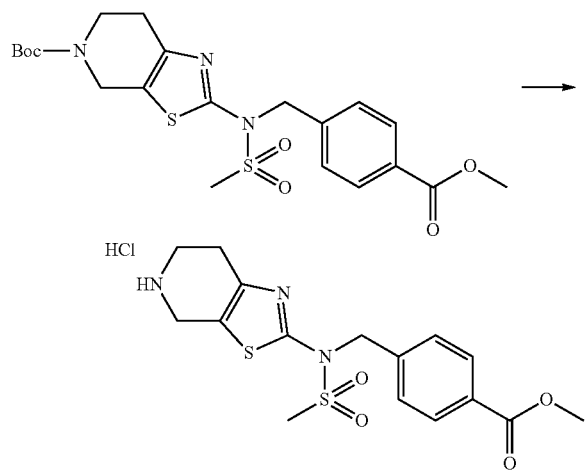

A solution of tert-butyl 2-(N-(4-(methoxycarbonyl)benzyl)methylsulfonamido)-6,7-dihydrothiazolo[5,4-c]pyridine-5(4H)-carboxylate (0.110 g, 0.228 mmol) and hydrogen chloride (4.00 M solution in 1,4-dioxane, 0.114 mL, 0.457 mmol) in dichloromethane (10 mL) was stirred at the room temperature for 5 hr, and concentrated under the reduced pressure to remove the solvent. The title compound was used without further purification (methyl 4-((N-(4,5,6,7-tetrahydrothiazolo[5,4-c]pyridin-2-yl)methylsulfonamido)methyl)benzoate hydrochloride, 0.089 g, 93.2%, white solid).

[Step 4] methyl 4-((N-(5-methyl-4,5,6,7-tetrahydrothiazolo[5,4-c]pyridin-2-yl)methylsulfonamido)methyl)benzoate

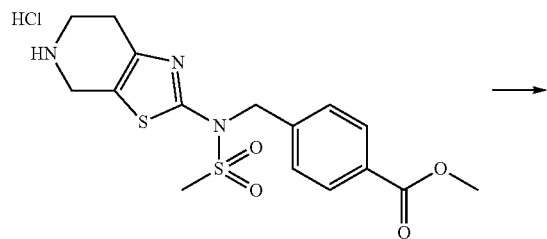

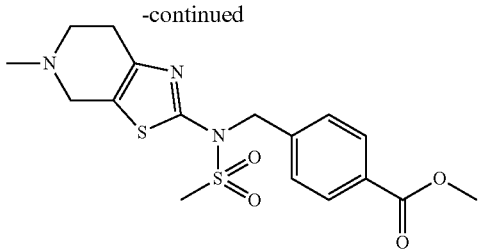

A solution of methyl 4-((N-(4,5,6,7-tetrahydrothiazolo[5,4-c]pyridin-2-yl)methylsulfonamido)methyl)benzoate hydrochloride (0.089 g, 0.213 mmol), paraformaldehyde (0.013 g, 0.426 mmol) and acetic acid (0.015 mL, 0.256 mmol) in (10 mL) was stirred at the room temperature for 30 min, and mixed with sodium triacetoxyborohydride (0.090 g, 0.426 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; methanol/dichloromethane=0% to 5%) to give methyl 4-((N-(5-methyl-4,5,6,7-tetrahydrothiazolo[5,4-c]pyridin-2-yl)methylsulfonamido)methyl)benzoate as yellow solid (0.073 g, 86.7%).

[Step 5] N-(4-(hydrazinecarbonyl)benzyl)-N-(5-methyl-4,5,6,7-tetrahydrothiazolo[5,4-c]pyridin-2-yl)methanesulfonamide

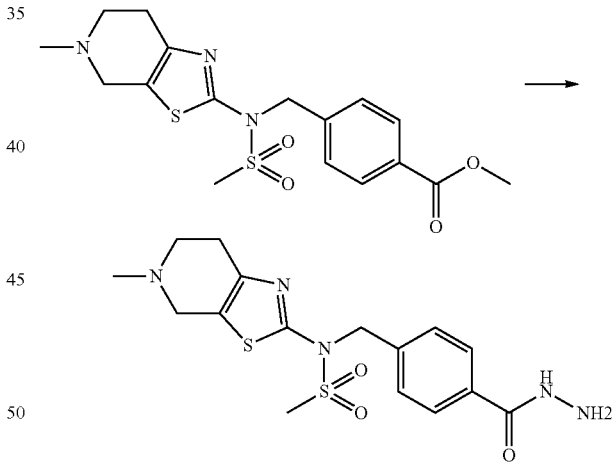

A solution of methyl 4-((N-(5-methyl-4,5,6,7-tetrahydrothiazolo[5,4-c]pyridin-2-yl)methylsulfonamido)methyl)benzoate (0.035 g, 0.088 mmol) and hydrazine monohydrate (0.043 mL, 0.885 mmol) in ethanol (10 mL) was stirred at 90° C. for 12 hr, cooled down to the room temperature to terminate the reaction and concentrated under the reduced pressure to remove the solvent. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The title compound was used without further purification (N-(4-(hydrazinecarbonyl)benzyl)-N-(5-methyl-4,5,6,7-tetrahydrothiazolo[5,4-c]pyridin-2-yl)methanesulfonamide, 0.021 g, 60.0%, white solid).

[Step 6] Compound 11750

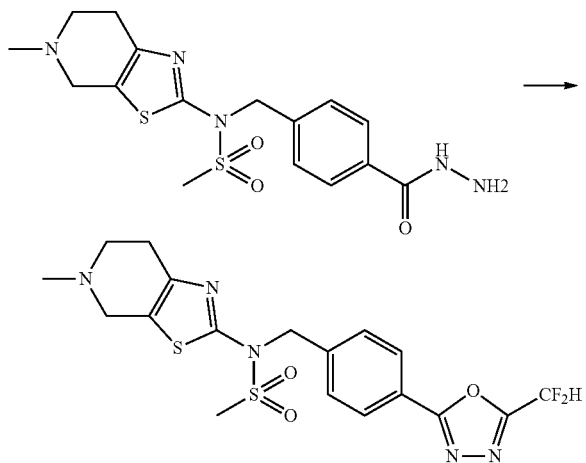

A solution of N-(4-(hydrazinecarbonyl)benzyl)-N-(5-methyl-4,5,6,7-tetrahydrothiazolo[5,4-c]pyridin-2-yl)methanesulfonamide (0.038 g, 0.096 mmol), TEA (0.049 g, 0.480 mmol) and 2,2-difluoroacetic anhydride (0.050 g, 0.288 mmol) in tetrahydrofuran (5 mL) was stirred at 70° C. for 12 hr and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 40%) to give N-(4-(5-(difluoromethyl)-1,3,4-oxadiazol-2-yl)benzyl)-N-(5-methyl-4,5,6,7-tetrahydrothiazolo[5,4-c]pyridin-2-yl)methanesulfonamide as white solid (0.010 g, 22.8%).

$^1$H NMR (400 MHz, CDCl$_3$) δ 8.09 (d, 2H, J=6.7 Hz), 7.63 (d, 2H, J=8.5 Hz), 7.05 (s, 0.2H), 6.92 (s, 0.5H), 6.80 (s, 0.3H), 5.19 (s, 2H), 3.54 (s, 2H), 3.09 (s, 3H), 2.84-2.78 (m, 4H), 2.49 (s, 3H); LRMS (ES) m/z 456.3 (M$^+$+1).

EXAMPLE 256

Compound 11751, N-(4-(5-(difluoromethyl)-1,3,4-oxadiazol-2-yl)benzyl)-2-(4-(2-morpholino-2-oxoethyl)piperazin-1-yl)-N-phenylethane-1-sulfonamide

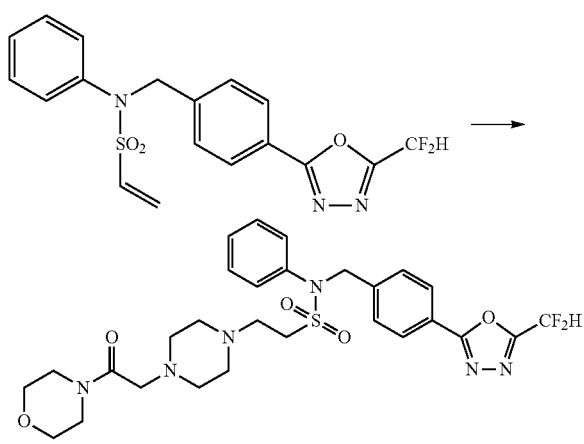

A solution of N-(4-(5-(difluoromethyl)-1,3,4-oxadiazol-2-yl)benzyl)-N-phenylethenesulfonamide (0.100 g, 0.255 mmol), 1-(morpholin-4-yl)-2-(piperazin-1-yl)ethan-1-one (0.109 g, 0.511 mmol) and N-,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-2-(4-(2-morpholino-2-oxoethyl)piperazin-1-yl)-N-phenylethane-1-sulfonamide as white solid (0.015 g, 9.7%).

$^1$H NMR (400 MHz, CDCl$_3$) δ 8.04-8.02 (m, 2H), 7.46 (d, 2H, J=8.3 Hz), 7.36-7.28 (m, 5H), 6.92 (t, 1H, J=51.7 Hz), 5.00 (s, 2H), 3.77-3.66 (m, 6H), 3.69-3.59 (m, 2H), 3.58-3.51 (m, 4H), 3.36-3.31 (m, 2H), 3.11-3.06 (m, 2H), 2.87-2.82 (m, 6H)); LRMS (ES) m/z 605.2 (M$^+$+1).

EXAMPLE 257

Compound 11752, N-(4-(5-(difluoromethyl)-1,3,4-oxadiazol-2-yl)benzyl)-2-(1,4-oxazepan-4-yl)-N-phenylethane-1-sulfonamide

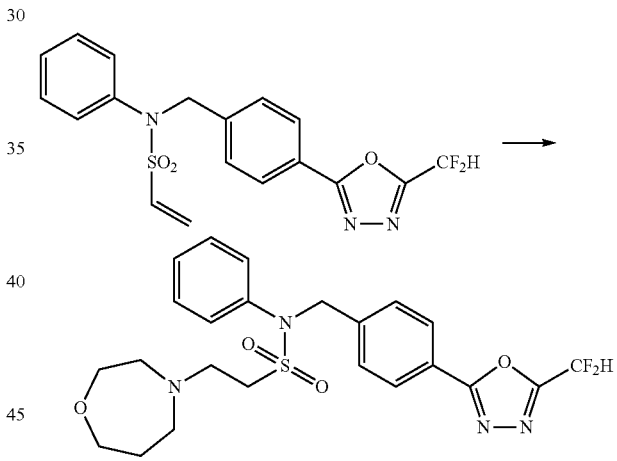

A solution of N-(4-(5-(difluoromethyl)-1,3,4-oxadiazol-2-yl)benzyl)-N-phenylethenesulfonamide (0.100 g, 0.255 mmol), Homomorpholine Hydrochloride (0.070 g, 0.511 mmol) and N-,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-2-(1,4-oxazepan-4-yl)-N-phenylethane-1-sulfonamide as white solid (0.017 g, 13.5%).

$^1$H NMR (400 MHz, CDCl$_3$) δ 8.04-8.02 (m, 2H), 7.47 (d, 2H, J=8.4 Hz), 7.38-7.27 (m, 5H), 6.91 (t, 1H, J J=51.7 Hz), 4.99 (s, 2H), 3.84-3.71 (m, 4H), 3.40-3.31 (m, 2H), 3.17-3.09 (m, 2H), 2.86-2.75 (m, 4H), 2.00-1.97 (m, 2H); LRMS (ES) m/z 493.1 (M$^+$+1).

EXAMPLE 258

Compound 11753, (R)—N-(4-(5-(difluoromethyl)-1,3,4-oxadiazol-2-yl)benzyl)-2-(3-fluoropyrrolidin-1-yl)-N-phenylethane-1-sulfonamide

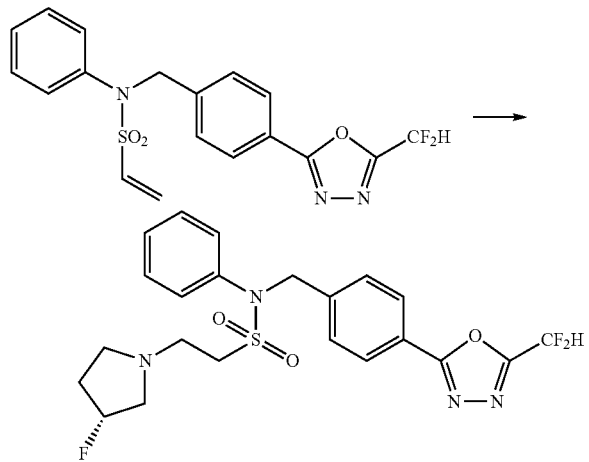

A solution of N-(4-(5-(difluoromethyl)-1,3,4-oxadiazol-2-yl)benzyl)-N-phenylethenesulfonamide (0.100 g, 0.255 mmol), (R)-(−)3-fluoropyrrolidin hydrochloride (0.064 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give (R)—N-(4-(5-(difluoromethyl)-1,3,4-oxadiazol-2-yl)benzyl)-2-(3-fluoropyrrolidin-1-yl)-N-phenylethane-1-sulfonamide as white solid (0.089 g, 72.5%).

$^1$H NMR (700 MHz, CDCl$_3$) δ 7.98-7.97 (m, 2H), 7.45 (d, 2H, J=8.5 Hz), 7.34-7.23 (m, 5H), 6.90 (t, 1H, J=51.7 Hz), 5.23 (m, 1H), 4.99 (s, 2H), 3.32-3.30 (m, 2H), 3.07-2.95 (m, 4H), 2.70-2.63 (m, 1H), 2.42-2.41 (m, 1H), 2.23-2.18 (m, 2H); LRMS (ES) m/z 481.3 (M$^+$+1).

EXAMPLE 259

Compound 11754, (R)—N-(4-(5-(difluoromethyl)-1,3,4-oxadiazol-2-yl)benzyl)-2-(3-(dimethylamino)pyrrolidin-1-yl)-N-phenylethane-1-sulfonamide

[Step 1] Compound 11754

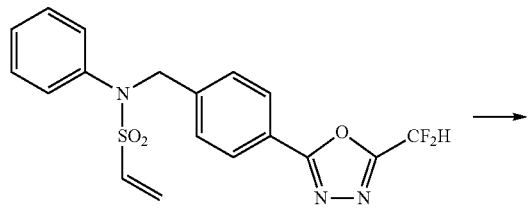

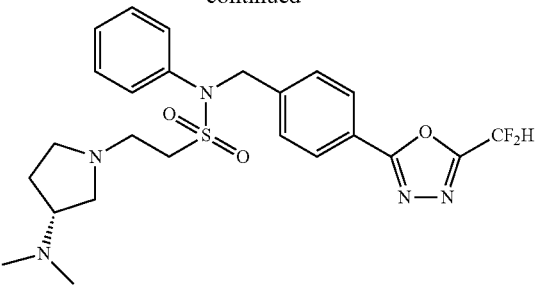

A solution of N-(4-(5-(difluoromethyl)-1,3,4-oxadiazol-2-yl)benzyl)-N-phenylethenesulfonamide (0.100 g, 0.255 mmol), (R)-(+)-3-(dimethylamino)pyrrolidine dihydrochloride (0.096 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give (R)—N-(4-(5-(difluoromethyl)-1,3,4-oxadiazol-2-yl)benzyl)-2-(3-(dimethylamino)pyrrolidin-1-yl)-N-phenylethane-1-sulfonamide as white solid (0.082 g, 63.5%).

$^1$H NMR (700 MHz, CDCl$_3$) δ 8.00 (d, 2H, J=8.5 Hz), 7.44 (d, 2H, J=8.5 Hz), 7.33-7.24 (m, 5H), 6.90 (t, 1H, J=51.7 Hz), 4.96 (s, 2H), 3.28 (t, 2H, J J=7.5 Hz), 3.05-2.98 (m, 2H), 2.97-2.90 (m, 2H), 2.78-2.59 (m, 2H), 2.47 (m, 1H), 2.27 (s, 6H), 2.06-1.98 (m, 1H), 1.79 (m, 1H); LRMS (ES) m/z 506.4 (M$^+$+1).

EXAMPLE 260

Compound 11755, (S)—N-(4-(5-(difluoromethyl)-1,3,4-oxadiazol-2-yl)benzyl)-2-(3-(dimethylamino)pyrrolidin-1-yl)-N-phenylethane-1-sulfonamide

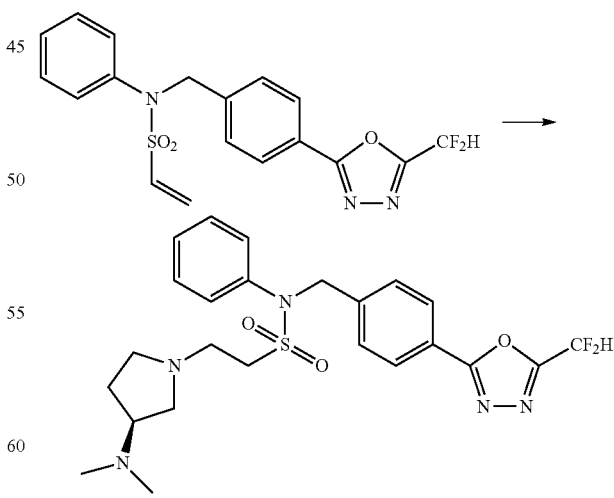

A solution of N-(4-(5-(difluoromethyl)-1,3,4-oxadiazol-2-yl)benzyl)-N-phenylethenesulfonamide (0.100 g, 0.255 mmol), (S)-(−)-3-dimethylaminopyrrolidine dihydrochloride (0.096 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give (S)—N-(4-(5-(difluoromethyl)-1,3,4-oxadiazol-2-yl)benzyl)-2-(3-(dimethylamino)pyrrolidin-1-yl)-N-phenylethane-1-sulfonamide as white solid (0.120 g, 92.9%).

$^1$H NMR (700 MHz, CDCl$_3$) δ 8.07-7.01 (m, 2H), 7.46-7.44 (m, 2H), 7.34-7.26 (m, 5H), 6.91 (t, 1H, J J=51.7 Hz), 4.97 (s, 2H), 3.28 (t, 2H, J=7.4 Hz), 3.05-3.00 (m, 2H), 2.98-2.84 (m, 1H), 2.84-2.79 (m, 1H), 2.74-2.68 (m, 1H), 2.65-2.59 (m, 1H), 2.55-2.50 (m, 1H), 2.29 (s, 6H), 2.08-1.99 (m, 1H), 1.85-1.77 (m, 1H); LRMS (ES) m/z 506.3 (M$^+$+1).

EXAMPLE 261

Compound 11756, N-(4-(5-(difluoromethyl)-1,3,4-oxadiazol-2-yl)benzyl)-2-(isoindolin-2-yl)-N-phenylethane-1-sulfonamide

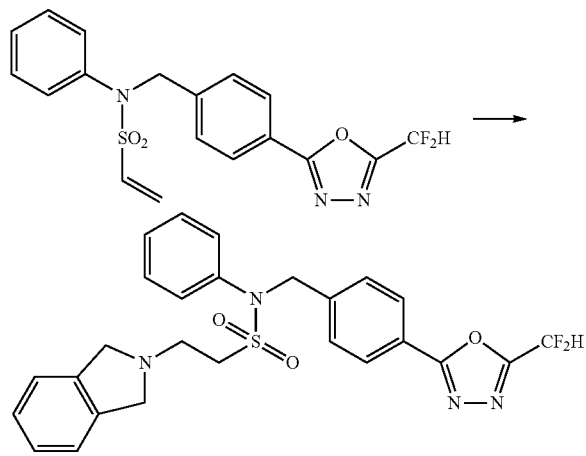

A solution of N-(4-(5-(difluoromethyl)-1,3,4-oxadiazol-2-yl)benzyl)-N-phenylethenesulfonamide (0.100 g, 0.255 mmol), isoindoline (0.061 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-2-(isoindolin-2-yl)-N-phenylethane-1-sulfonamide as white solid (0.032 g, 24.5%).

$^1$H NMR (700 MHz, CDCl$_3$) δ 8.02 (d, 2H, J=8.5 Hz), 7.46 (d, 2H, J=8.5 Hz), 7.35-7.24 (m, 5H),), 6.91 (t, 1H, J=51.7 Hz), 5.01 (s, 2H), 4.11 (s, 4H), 3.51-3.46 (dd, 1H, J=9.1, 5.7 Hz), 3.37-3.32 (m, 1H); LRMS (ES) m/z 511.3 (M$^+$+1).

EXAMPLE 262

Compound 11757, N-(4-(5-(difluoromethyl)-1,3,4-oxadiazol-2-yl)benzyl)-2-(4-ethylpiperazin-1-yl)-N-phenylethane-1-sulfonamide

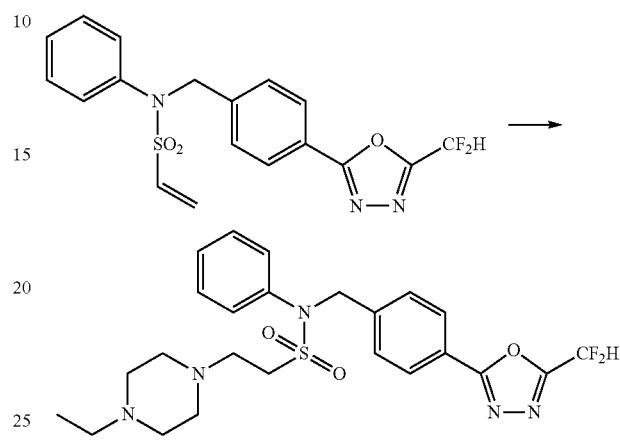

A solution of N-(4-(5-(difluoromethyl)-1,3,4-oxadiazol-2-yl)benzyl)-N-phenylethenesulfonamide (0.100 g, 0.255 mmol), 1-ethylpiperazine (0.061 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-2-(4-ethylpiperazin-1-yl)-N-phenylethane-1-sulfonamide as white solid (0.032 g, 24.5%).

$^1$H NMR (700 MHz, CDCl$_3$) δ 8.04-8.02 (m, 2H), 7.46 (d, 2H, J=8.5 Hz), 7.35-7.28 (m, 5H), 6.91 (t, 1H, J=51.7 Hz), 4.97 (s, 2H), 3.30-3.28 (m, 2H), 2.98-2.96 (m, 2H), 2.66-2.57 (m, 10H), 1.19 (t, 3H, J=7.2 Hz); LRMS (ES) m/z 506.1 (M$^+$+1).

EXAMPLE 263

Compound 11758, N-(4-(5-(difluoromethyl)-1,3,4-oxadiazol-2-yl)benzyl)-2-(4-(2-methoxyethyl)piperazin-1-yl)-N-phenylethane-1-sulfonamide

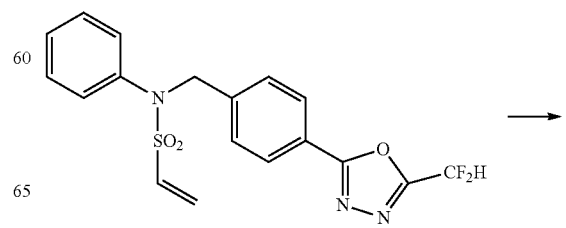

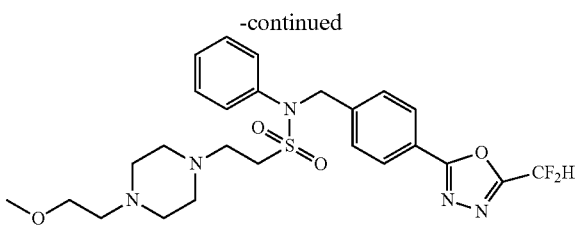

A solution of N-(4-(5-(difluoromethyl)-1,3,4-oxadiazol-2-yl)benzyl)-N-phenylethenesulfonamide (0.100 g, 0.255 mmol), 1-(2-methoxyethyl)piperazine (0.074 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-2-(4-(2-methoxyethyl)piperazin-1-yl)-N-phenylethane-1-sulfonamide as white solid (0.040 g, 29.2%).

$^1$H NMR (700 MHz, CDCl$_3$) δ 8.01-8.00 (m, 2H), 7.45 (d, 2H, J=8.5 Hz), 7.34-7.26 (m, 5H), 6.91 (t, 1H, J=51.7 Hz), 4.96 (s, 2H), 3.55 (t, 3H, J=5.5 Hz), 3.36 (s, 3H), 3.29-3.27 (m, 2H), 2.94-2.93 (m, 2H), 2.65-2.60 (m, 10H); LRMS (ES) m/z 536.4 (M$^+$+1).

EXAMPLE 264

Compound 11759, 2-(4-acetyl-1,4-diazepan-1-yl)-N-(4-(5-(difluoromethyl)-1,3,4-oxadiazol-2-yl)benzyl)-N-phenylethane-1-sulfonamide

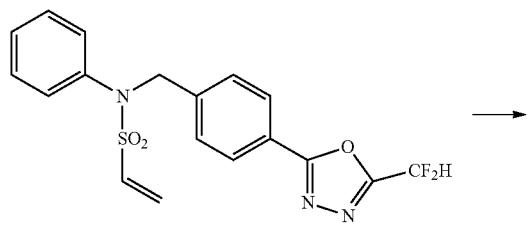

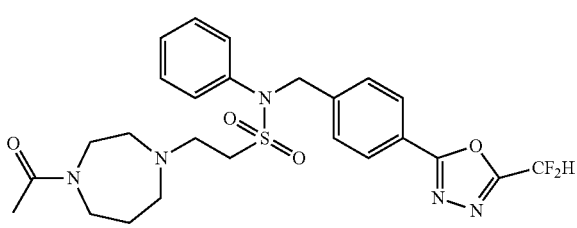

A solution of N-(4-(5-(difluoromethyl)-1,3,4-oxadiazol-2-yl)benzyl)-N-phenylethenesulfonamide (0.100 g, 0.255 mmol), N-acetylhomopiperazine (0.073 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(4-acetyl-1,4-diazepan-1-yl)-N-(4-(5-(difluoromethyl)-1,3,4-oxadiazol-2-yl)benzyl)-N-phenylethane-1-sulfonamide as white solid (0.032 g, 23.5%).

$^1$H NMR (700 MHz, CDCl$_3$) δ 8.04-8.00 (m, 2H), 7.45 (d, 2H, J=8.3 Hz), 7.36-7.27 (m, 5H), 6.91 (t, 1H, J=51.7 Hz), 4.96 (s, 2H), 3.68-3.66 (m, 1H), 3.64-3.59 (m, 1H), 3.56-3.51 (m, 2H), 3.36-3.33 (m, 1H), 3.32-3.27 (m, 1H), 3.13-3.07 (m, 2H), 2.79-2.66 (m, 4H), 2.11-2.09 (m, 3H), 1.97 (m, 1H), 1.88-1.87 (m, 1H); LRMS (ES) m/z 534.3 (M$^+$+1).

EXAMPLE 265

Compound 11760, 2-(4-benzyl-1,4-diazepan-1-yl)-N-(4-(5-(difluoromethyl)-1,3,4-oxadiazol-2-yl)benzyl)-N-phenylethane-1-sulfonamide

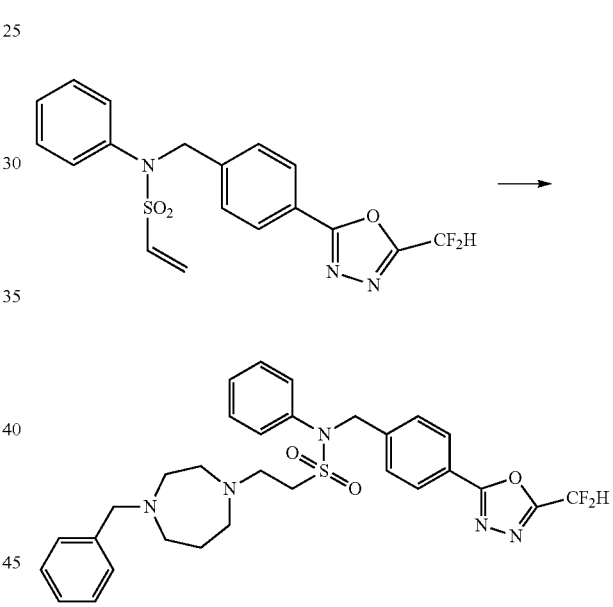

A solution of N-(4-(5-(difluoromethyl)-1,3,4-oxadiazol-2-yl)benzyl)-N-phenylethenesulfonamide (0.100 g, 0.255 mmol), 1-Benzylhomopiperazine (0.097 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(4-benzyl-1,4-diazepan-1-yl)-N-(4-(5-(difluoromethyl)-1,3,4-oxadiazol-2-yl)benzyl)-N-phenylethane-1-sulfonamide as white solid (0.032 g, 21.5%).

$^1$H NMR (700 MHz, CDCl$_3$) δ 8.03-7.98 (m, 2H), 7.47-7.44 (m, 2H), 7.38-7.28 (m, 10H),), 6.92 (t, 1H, J=51.7 Hz), 4.97 (s, 2H), 3.82 (s, 2H), 3.30-3.28 (m, 2H), 3.13-3.11 (m, 2H), 2.85-2.80 (m, 8H), 1.96 (m, 2H); LRMS (ES) m/z 582.4 (M$^+$+1).

EXAMPLE 266

Compound 11761, 2-(4-(cyclopropanecarbonyl)piperazin-1-yl)-N-(4-(5-(difluoromethyl)-1,3,4-oxadiazol-2-yl)benzyl)-N-phenylethane-1-sulfonamide

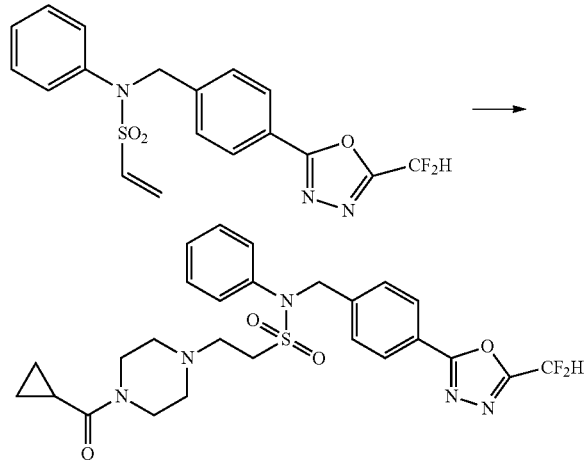

A solution of N-(4-(5-(difluoromethyl)-1,3,4-oxadiazol-2-yl)benzyl)-N-phenylethenesulfonamide (0.100 g, 0.255 mmol), 1-(cyclopropylcarbonyl)piperazine (0.079 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give 2-(4-(cyclopropanecarbonyl)piperazin-1-yl)-N-(4-(5-(difluoromethyl)-1,3,4-oxadiazol-2-yl)benzyl)-N-phenylethane-1-sulfonamide as white solid (0.034 g, 24.4%).

¹H NMR (700 MHz, CDCl₃) δ 8.03-8.02 (m, 2H), 7.47-7.45 (m, 2H), 7.36-7.30 (m, 2H), 7.33-7.275 (m, 3H), 6.91 (t, 1H, J=51.7 Hz), 4.98 (s, 2H), 3.77 (m, 2H), 3.73-3.71 (m, 2H), 3.40-3.35 (t, 2H, J=7.2 Hz), 3.01-2.99 (m, 2H), 2.63-2.55 (m, 4H), 1.75-1.71 (tt, 1H, J=8.0, 4.7 Hz), 1.01-0.99 (m, 2H), 0.81 (m, 2H); LRMS (ES) m/z 546.0 (M⁺+1).

EXAMPLE 267

Compound 11762, 2-(4-benzylpiperidin-1-yl)-N-(4-(5-(difluoromethyl)-1,3,4-oxadiazol-2-yl)benzyl)-N-phenylethane-1-sulfonamide

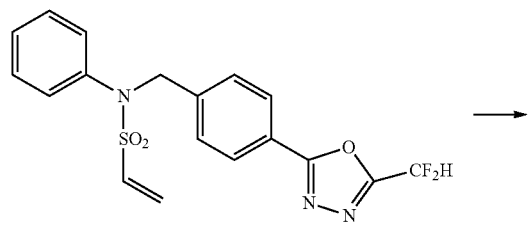

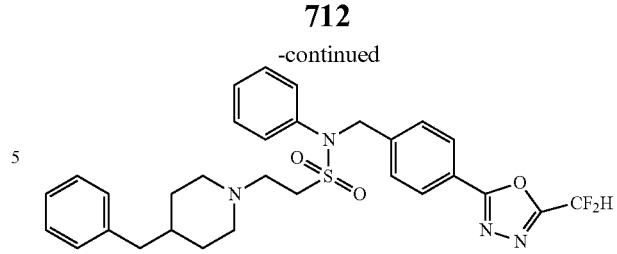

A solution of N-(4-(5-(difluoromethyl)-1,3,4-oxadiazol-2-yl)benzyl)-N-phenylethenesulfonamide (0.100 g, 0.255 mmol), 4-benzylpiperidine (0.090 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give 2-(4-benzylpiperidin-1-yl)-N-(4-(5-(difluoromethyl)-1,3,4-oxadiazol-2-yl)benzyl)-N-phenylethane-1-sulfonamide as white solid (0.042 g, 29.0%).

¹H NMR (700 MHz, CDCl₃) δ 8.06-8.02 (m, 2H), 7.46 (d, 2H, J=8.5 Hz), 7.36-7.14 (m, 10H), 6.91 (t, 1H, J=51.7 Hz), 4.97 (s, 2H), 3.30-3.28 (m, 2H), 2.90-2.88 (m, 4H), 2.58-2.57 (m, 2H), 2.04-2.01 (m, 2H), 1.71-1.69 (m, 2H), 1.57-1.5\6 (m, 1H), 1.34-1.32 (m, 2H); LRMS (ES) m/z 567.0 (M⁺+1).

EXAMPLE 268

Compound 11763, N-(4-(5-(difluoromethyl)-1,3,4-oxadiazol-2-yl)benzyl)-2-(4-morpholinopiperidin-1-yl)-N-phenylethane-1-sulfonamide

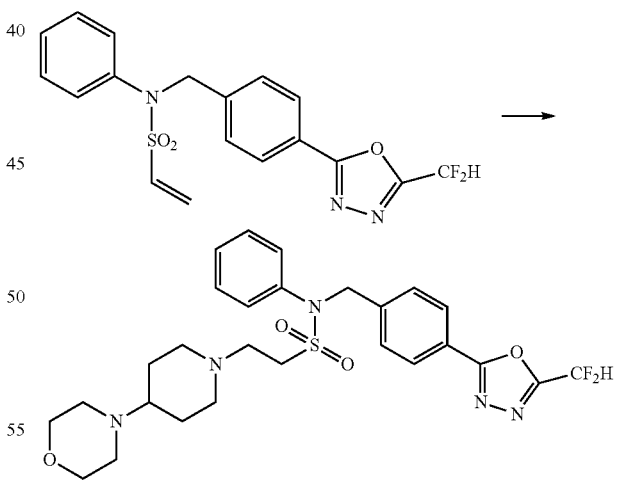

A solution of N-(4-(5-(difluoromethyl)-1,3,4-oxadiazol-2-yl)benzyl)-N-phenylethenesulfonamide (0.100 g, 0.255 mmol), 4-morpholinopiperidine (0.087 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give N-(4-(5-(difluoromethyl)-1,3,4-oxadiazol-2-yl)benzyl)-2-(4-morpholinopiperidin-1-yl)-N-phenylethane-1-sulfonamide as white solid (0.110 g, 76.7%).

¹H NMR (700 MHz, CDCl₃) δ 8.01-8.00 (m, 2H), 7.45 (d, 2H, J=8.5 Hz), 7.34-7.26 (m, 5H), 6.91 (t, 1H, J J=51.7 Hz), 4.96 (d, 2H), 3.75 (t, 4H, J=4.6 Hz), 3.29-3.27 (m, 2H), 2.97-2.95 (dt, 2H, J=11.3, 3.4 Hz), 2.90-2.88 (m, 2H), 2.58 (t, 4H, J=4.7 Hz), 2.23-2.22 (m, 1H), 2.10-2.07 (td, 1H, J=11.8, 2.3 Hz), 1.90-1.86 (dt, 1H, J J=12.8, 3.0 Hz), 1.61-1.55 (td, 1H, J=12.1, 3.7 Hz); LRMS (ES) m/z 562.1 (M⁺+1).

EXAMPLE 269

Compound 11764, N-(4-(5-(difluoromethyl)-1,3,4-oxadiazol-2-yl)benzyl)-2-(4-(3-methyl-1,2,4-oxadiazol-5-yl)piperidin-1-yl)-N-phenylethane-1-sulfonamide

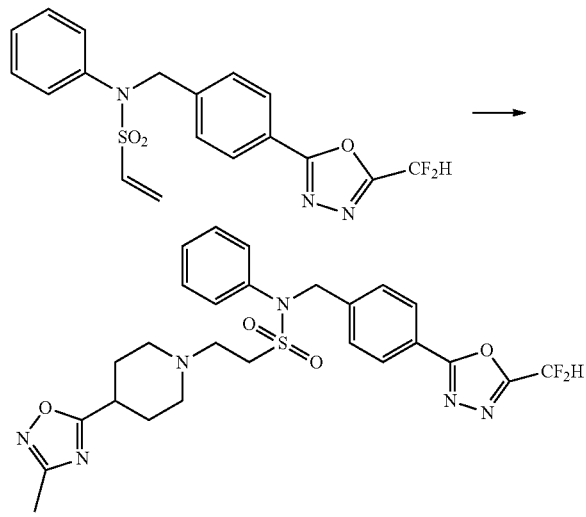

A solution of N-(4-(5-(difluoromethyl)-1,3,4-oxadiazol-2-yl)benzyl)-N-phenylethenesulfonamide (0.100 g, 0.255 mmol), 4-(3-methyl-1,2,4-oxadiazol-5-yl)piperidine (0.085 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give N-(4-(5-(difluoromethyl)-1,3,4-oxadiazol-2-yl)benzyl)-2-(4-(3-methyl-1,2,4-oxadiazol-5-yl)piperidin-1-yl)-N-phenylethane-1-sulfonamide as white solid (0.115 g, 80.6%).

¹H NMR (700 MHz, CDCl₃) δ 8.02-8.00 (m, 2H), 7.46-7.45 (m, 2H), 7.34-7.27 (m, 5H), 6.91 (t, 1H, J=51.7 Hz), 4.97 (s, 2H), 3.33-3.31 (m, 2H), 2.96-2.93 (m, 5H), 2.38 (s, 3H), 2.29-2.27 (m, 2H), 2.15-2.13 (m, 2H), 1.98-1.93 (m, 2H); LRMS (ES) m/z 559.3 (M⁺+1).

EXAMPLE 270

Compound 11765, 2-(benzyl(ethyl)amino)-N-(4-(5-(difluoromethyl)-1,3,4-oxadiazol-2-yl)benzyl)-N-phenylethane-1-sulfonamide

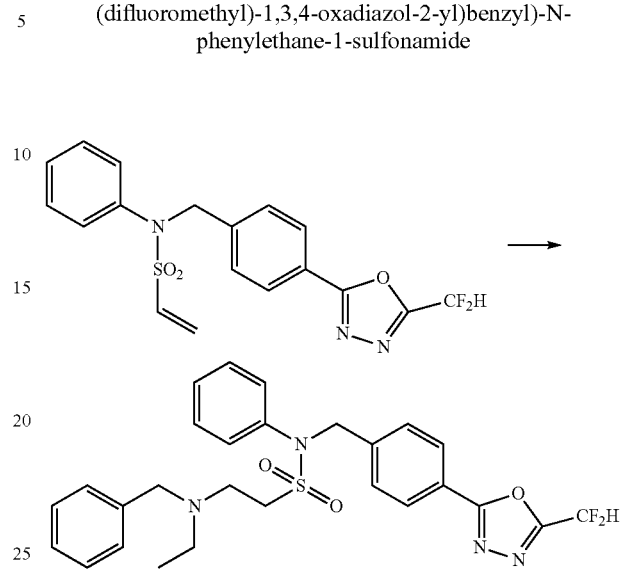

A solution of N-(4-(5-(difluoromethyl)-1,3,4-oxadiazol-2-yl)benzyl)-N-phenylethenesulfonamide (0.100 g, 0.255 mmol), N-ethylbenzylamine (0.069 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give 2-(benzyl(ethyl)amino)-N-(4-(5-(difluoromethyl)-1,3,4-oxadiazol-2-yl)benzyl)-N-phenylethane-1-sulfonamide as white solid (0.018 g, 13.4%).

¹H NMR (700 MHz, CDCl₃) δ 8.04-7.93 (m, 2H), 7.45-7.24 (m, 10H), 7.34-7.21 (m, 2H), 6.91 (t, 1H, J=51.7 Hz), 4.82 (s, 2H), 3.64 (s, 2H), 3.26 (m, 2H), 3.05-3.02 (m, 2H), 2.64-2.59 (m, 2H), 1.13 (t, 3H, J=7.1 Hz); LRMS (ES) m/z 527.4 (M⁺+1).

EXAMPLE 271

Compound 11766, N-(4-(5-(difluoromethyl)-1,3,4-oxadiazol-2-yl)benzyl)-N-phenyl-2-(4-phenylpiperazin-1-yl)ethane-1-sulfonamide

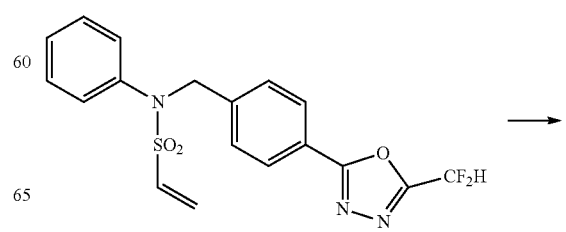

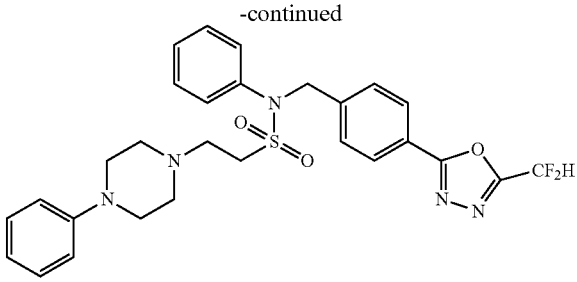

A solution of N-(4-(5-(difluoromethyl)-1,3,4-oxadiazol-2-yl)benzyl)-N-phenylethenesulfonamide (0.100 g, 0.255 mmol), 1-phenylpiperazine (0.083 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-N-phenyl-2-(4-phenylpiperazin-1-yl)ethane-1-sulfonamide as white solid (0.021 g, 14.8%).

$^1$H NMR (700 MHz, CDCl$_3$) δ 8.05-7.97 (m, 2H), 7.49-7.41 (m, 2H), 7.38-7.28 (m, 8H), 7.00-6.88 (m, 2H), 6.91 (t, 1H, J=51.7 Hz), 5.01 (s, 2H), 3.47 (m, 2H), 3.32-3.25 (m, 4H), 3.09-3.05 (m, 2H), 2.91-2.80 (m, 4H); LRMS (ES) m/z 555.1 (M$^+$+1).

EXAMPLE 272

Compound 11767, N-(4-(5-(difluoromethyl)-1,3,4-oxadiazol-2-yl)benzyl)-N-phenyl-2-(4-(pyridin-2-yl)piperazin-1-yl)ethane-1-sulfonamide

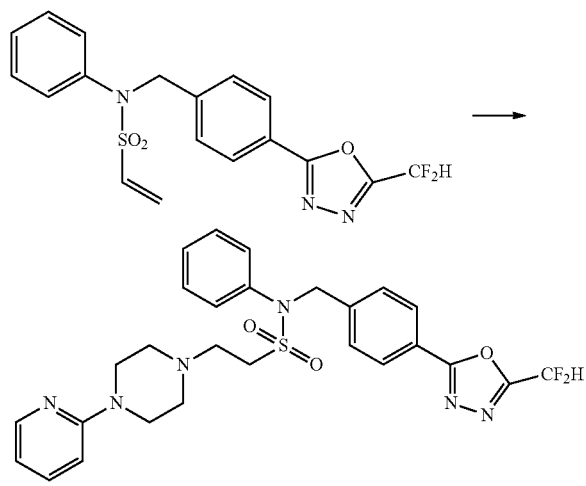

A solution of N-(4-(5-(difluoromethyl)-1,3,4-oxadiazol-2-yl)benzyl)-N-phenylethenesulfonamide (0.100 g, 0.255 mmol), 1-(2-pyridyl)piperazine (0.083 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-N-phenyl-2-(4-(pyridin-2-yl)piperazin-1-yl)ethane-1-sulfonamide as white solid (0.025 g, 17.6%).

$^1$H NMR (400 MHz, CDCl$_3$) δ 8.22-8.16 (m, 1H), 8.04-7.97 (m, 2H), 7.51 (m, 1H), 7.49-7.38 (m, 2H), 7.41-7.25 (m, 5H), 6.91 (t, 1H, J J=51.7 Hz), 6.70-6.68 (m, 2H), 5.01 (s, 2H), 3.67 (t, 4H, J=5.0 Hz), 3.44 (t, 2H, J=7.4 Hz), 3.04 (dd, 2H, J=8.8, 6.1 Hz), 2.27-2.67 (m, 4H); LRMS (ES) m/z 555.2 (M$^+$+1).

EXAMPLE 273

Compound 11768, N-(4-(5-(difluoromethyl)-1,3,4-oxadiazol-2-yl)benzyl)-N-phenyl-2-(4-(pyridin-4-yl)piperazin-1-yl)ethane-1-sulfonamide

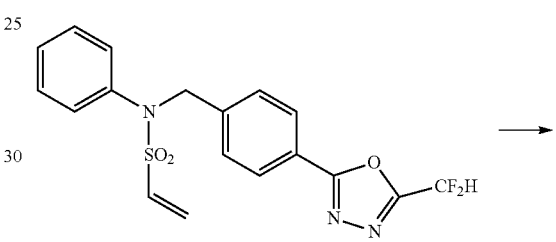

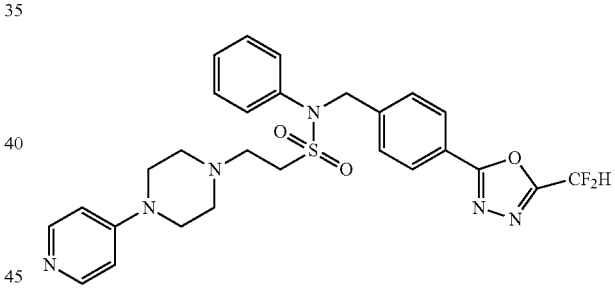

A solution of N-(4-(5-(difluoromethyl)-1,3,4-oxadiazol-2-yl)benzyl)-N-phenylethenesulfonamide (0.100 g, 0.255 mmol), 1-(4-pyridyl)piperazine (0.083 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-N-phenyl-2-(4-(pyridin-4-yl)piperazin-1-yl)ethane-1-sulfonamide as white solid (0.023 g, 16.2%).

$^1$H NMR (400 MHz, CDCl$_3$) δ 8.30-8.26 (m, 2H), 8.04-8.02 (m, 2H), 7.47-7.45 (m, 2H), 7.38-7.28 (m, 5H), 6.92 (t, 1H, J=51.7 Hz), 6.78-6.73 (m, 2H), 4.98 (s, 2H), 3.46 (t, 4H, J=5.1 Hz), 3.35-3.31 (m, 2H), 2.99-2.96 (m, 2H), 2.71-2.63 (m, 4H); LRMS (ES) m/z 555.2 (M$^+$+1).

EXAMPLE 274

Compound 11769, N-(4-(5-(difluoromethyl)-1,3,4-oxadiazol-2-yl)benzyl)-2-(4-(4-fluorophenyl)piperazin-1-yl)-N-phenylethane-1-sulfonamide

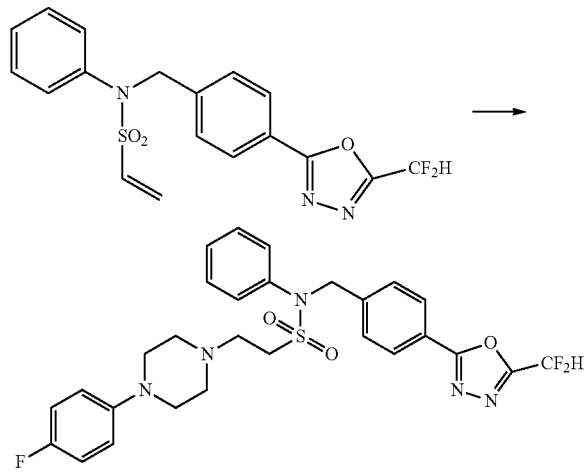

A solution of N-(4-(5-(difluoromethyl)-1,3,4-oxadiazol-2-yl)benzyl)-N-phenylethenesulfonamide (0.100 g, 0.255 mmol), 1-(4-fluorophenyl)piperazine Dihydrochloride (0.129 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-2-(4-(4-fluorophenyl)piperazin-1-yl)-N-phenylethane-1-sulfonamide as white solid (0.110 g, 75.3%).

$^1$H NMR (700 MHz, CDCl$_3$) δ8.02-7.97 (m, 2H), 7.46-7.42 (m, 2H), 7.36-7.23 (m, 5H), 6.98-6.93 (m, 2H), 6.91-6.85 (m, 3H), 5.00 (s, 2H), 3.36-3.34 (m, 2H), 3.16-3.15 (m, 4H), 3.01-2.99 (m, 2H), 2.69-2.68 (m, 4H); LRMS (ES) m/z 572.1 (M$^+$+1).

EXAMPLE 275

Compound 11770, 2-(4-(3,4-dichlorophenyl)piperazin-1-yl)-N-(4-(5-(difluoromethyl)-1,3,4-oxadiazol-2-yl)benzyl)-N-phenylethane-1-sulfonamide

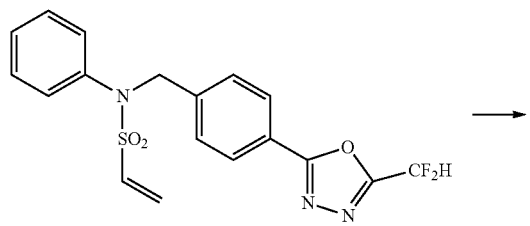

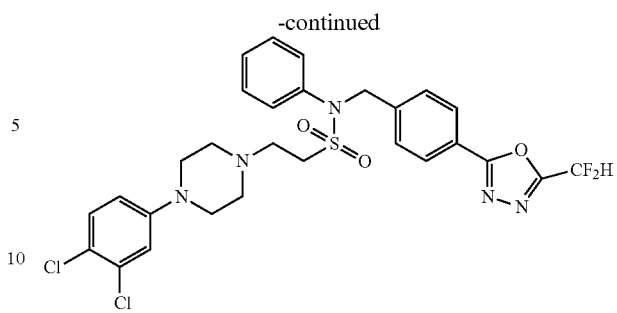

A solution of N-(4-(5-(difluoromethyl)-1,3,4-oxadiazol-2-yl)benzyl)-N-phenylethenesulfonamide (0.100 g, 0.255 mmol), 1-(3,4-dichlorophenyl)piperazine (0.118 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(4-(3,4-dichlorophenyl)piperazin-1-yl)-N-(4-(5-(difluoromethyl)-1,3,4-oxadiazol-2-yl)benzyl)-N-phenylethane-1-sulfonamide as white solid (0.087 g, 54.8%).

$^1$H NMR (700 MHz, CDCl$_3$) δ 8.02-7.98 (m, 2H), 7.47-7.43 (m, 2H), 7.36-7.25 (m, 6H), 6.99 (s, 1H), 6.92 (t, 1H, J=51.7 Hz), 6.75-6.74 (dd, 2H, J=8.9, 2.9 Hz), 4.99 (s, 2H), 3.39-3.37 (t, 2H, J=7.3 Hz), 3.23-3.22 (t, 4H, J=5.0 Hz), 3.02-3.00 (m, 2H), 2.69-2.65 (t, 2H, J=4.8 Hz); LRMS (ES) m/z 622.3 (M$^+$+1).

EXAMPLE 276

Compound 11771, N-(4-(5-(difluoromethyl)-1,3,4-oxadiazol-2-yl)benzyl)-2-(4-phenethylpiperazin-1-yl)-N-phenylethane-1-sulfonamide

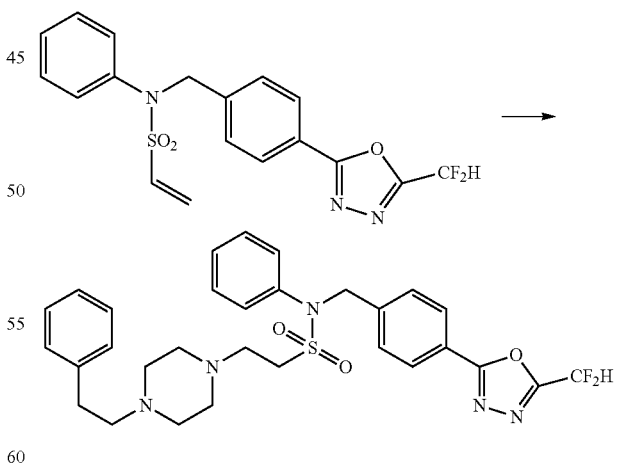

A solution of N-(4-(5-(difluoromethyl)-1,3,4-oxadiazol-2-yl)benzyl)-N-phenylethenesulfonamide (0.100 g, 0.255 mmol), 1-(2-phenylethyl)piperazine (0.097 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give N-(4-(5-(difluoromethyl)-1,3,4-oxadiazol-2-yl)benzyl)-2-(4-phenethylpiperazin-1-yl)-N-phenylethane-1-sulfonamide as white solid (0.100 g, 67.3%).

¹H NMR (700 MHz, CDCl₃) δ 8.01-7.98 (m, 2H), 7.47-7.43 (d, 2H, J J=8.4 Hz), 7.37-7.21 (m, 10H), 6.91 (t, 1H, J=51.7 Hz), 4.98 (s, 2H), 3.32-3.30 (m, 2H), 2.97-2.95 (m, 2H), 2.86-2.83 (m, 2H), 2.67-2.61 (m, 10H); LRMS (ES) m/z 582.4 (M⁺+1).

EXAMPLE 277

Compound 11772, N-(4-(5-(difluoromethyl)-1,3,4-oxadiazol-2-yl)benzyl)-N-phenyl-2-(4-(2-(pyridin-4-yl)ethyl)piperazin-1-yl)ethane-1-sulfonamide

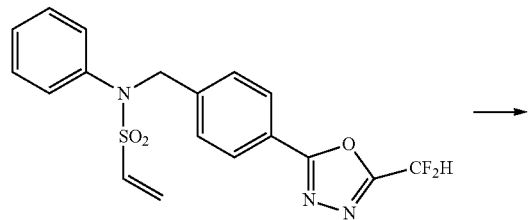

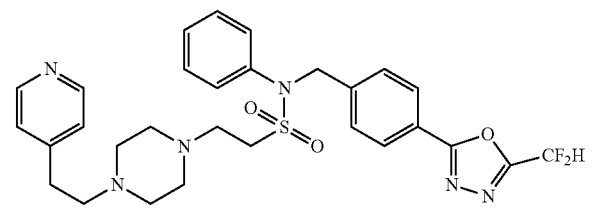

A solution of N-(4-(5-(difluoromethyl)-1,3,4-oxadiazol-2-yl)benzyl)-N-phenylethenesulfonamide (0.100 g, 0.255 mmol), 1-(2-pyridin-4-yl-ethyl)piperazine (0.098 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give N-(4-(5-(difluoromethyl)-1,3,4-oxadiazol-2-yl)benzyl)-N-phenyl-2-(4-(2-(pyridin-4-yl)ethyl)piperazin-1-yl)ethane-1-sulfonamide as white solid (0.110 g, 73.9%).

¹H NMR (700 MHz, CDCl₃) δ 8.49-8.45 (m, 2H), 8.01-7.99 (m, 2H), 7.44 (d, 2H, J=8.4 Hz), 7.33-7.26 (m, 5H), 7.15-7.14 (m, 2H), 6.91 (t, 1H, J=51.7 Hz), 4.96 (s, 2H), 3.30-3.28 (m, 2H), 2.94-2.92 (m, 2H), 2.83-2.81 (dd, 2H, J=9.5, 6.4 Hz), 2.67-2.58 (m, 10H); LRMS (ES) m/z 583.1 (M⁺+1).

EXAMPLE 278

Compound 11773, 2-(4-cinnamylpiperazin-1-yl)-N-(4-(5-(difluoromethyl)-1,3,4-oxadiazol-2-yl)benzyl)-N-phenylethane-1-sulfonamide

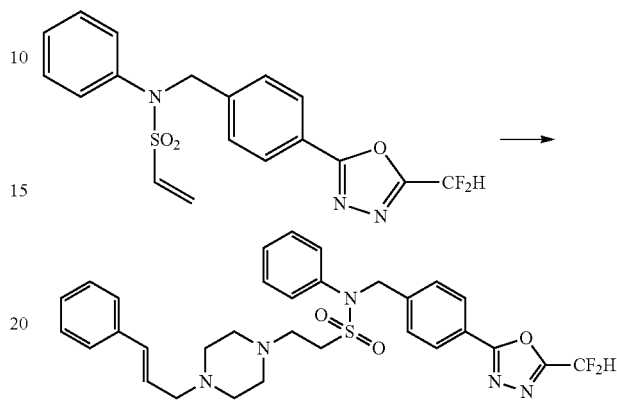

A solution of N-(4-(5-(difluoromethyl)-1,3,4-oxadiazol-2-yl)benzyl)-N-phenylethenesulfonamide (0.100 g, 0.255 mmol), Trans-1-cinnamyl piperazine (0.103 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=3% to 5%) to give 2-(4-cinnamylpiperazin-1-yl)-N-(4-(5-(difluoromethyl)-1,3,4-oxadiazol-2-yl)benzyl)-N-phenylethane-1-sulfonamide as white solid (0.120 g, 79.1%).

¹H NMR (700 MHz, CDCl₃) δ 8.02-7.97 (m, 2H), 7.47-7.42 (m, 2H), 7.40-7.36 (m, 2H), 7.33-7.30 (s, 3H), 7.36-7.21 (m, 5H), 6.91 (t, 1H, J=51.7 Hz), 6.57-6.52 (dd, 1H, J=15.9, 1.5 Hz), 6.31-6.24 (dt, 1H, J=15.9, 6.8 Hz), 4.97 (s, 2H), 3.31-3.29 (m, 2H), 3.20-3.19 (dd, 2H, J=6.9, 1.4 Hz), 2.95-2.93 (m, 2H), 2.58 (m, 8H); LRMS (ES) m/z 594.2 (M⁺+1).

EXAMPLE 279

Compound 11774, N-(benzo[d]oxazol-6-yl)-N-(4-(5-(difluoromethyl)-1,3,4-oxadiazol-2-yl)-2-fluorobenzyl)methanesulfonamide

[Step 1] N-(benzo[d]oxazol-6-yl)methanesulfonamide

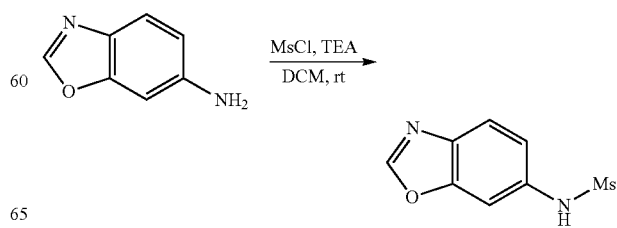

A solution of benzo[d]oxazol-6-amine (0.500 g, 3.727 mmol), methanesulfonyl chloride (0.317 mL, 4.100 mmol) and triethylamine (0.779 mL, 5.591 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give N-(benzo[d]oxazol-6-yl)methanesulfonamide as purple solid (0.351 g, 44.4%).

[Step 2] Compound 11774

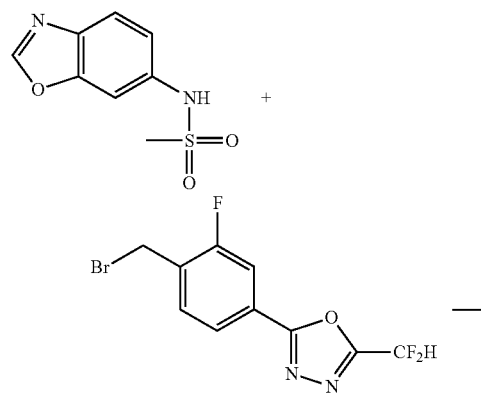

A solution of N-(benzo[d]oxazol-6-yl)methanesulfonamide (0.030 g, 0.141 mmol), 2-(4-(bromomethyl)-3-fluorophenyl)-5-(difluoromethyl)-1,3,4-oxadiazole (0.052 g, 0.170 mmol), potassium carbonate (0.039 g, 0.283 mmol) and potassium iodide (0.012 g, 0.071 mmol) in N,N-dimethylformide (2 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give N-(benzo[d]oxazol-6-yl)-N-(4-(5-(difluoromethyl)-1,3,4-oxadiazol-2-yl)-2-fluorobenzyl)methanesulfonamide as yellow oil (0.040 g, 64.5%).

¹H NMR (400 MHz, CD3OD) δ8.50 (s, 1H), 7.86~7.69 (m, 5H), 7.51 (dd, 1H, J=8.5, 1.9 Hz), 7.21 (t, 1H, J=51.6 Hz), 5.14 (s, 2H), 3.13 (s, 3H); LRMS (ES) m/z 439.2 (M⁺+1).

EXAMPLE 280

Compound 11775, N-(benzo[d]thiazol-6-yl)-N-(4-(5-(difluoromethyl)-1,3,4-oxadiazol-2-yl)-2-fluorobenzyl)methanesulfonamide

[Step 1] N-(benzo[d]thiazol-6-yl)methanesulfonamide

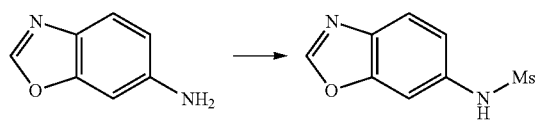 [SMILES: Nc1ccc2ncoc2c1 ; CS(=O)(=O)Nc1ccc2ncoc2c1]

A solution of benzo[d]thiazol-6-amine (0.500 g, 3.329 mmol), methanesulfonyl chloride (0.283 mL, 3.662 mmol) and triethylamine (0.696 mL, 4.993 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give N-(benzo[d]thiazol-6-yl)methanesulfonamide as light violet solid (0.320 g, 42.1%).

[Step 2] Compound 11775

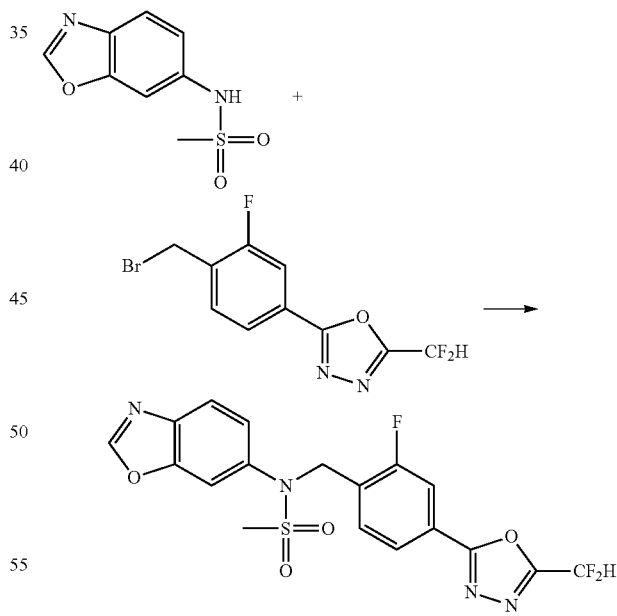

A solution of N-(benzo[d]thiazol-6-yl)methanesulfonamide (0.020 g, 0.088 mmol), 2-(4-(bromomethyl)-3-fluorophenyl)-5-(difluoromethyl)-1,3,4-oxadiazole (0.032 g, 0.105 mmol), potassium carbonate (0.024 g, 0.175 mmol) and potassium iodide (0.007 g, 0.044 mmol) in N,N-dimethylformide (2 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give N-(benzo[d]thiazol-6-yl)-N-(4-(5-(difluoromethyl)-1,3,4-oxadiazol-2-yl)-2-fluorobenzyl)methanesulfonamide as yellow oil (0.021 g, 52.7%).

¹H NMR (400 MHz, CD3OD) δ9.27 (s, 1H), 8.18 (d, 1H, J=1.9 Hz), 8.04 (d, 1H, J=8.7 Hz), 7.84 (dd, 1H, J=8.0, 1.1 Hz), 7.74~7.70 (m, 2H), 7.63 (dd, 1H, J=8.7, 2.0 Hz), 7.20 (t, 1H, J=51.6 Hz), 5.16 (s, 2H), 3.14 (s, 3H); LRMS (ES) m/z 445.2 (M⁺+1).

EXAMPLE 281

Compound 11776, N-(4-(5-(difluoromethyl)-1,3,4-oxadiazol-2-yl)-2-fluorobenzyl)-N-(1,3,4-thiadiazol-2-yl)methanesulfonamide

[Step 1] N-(1,3,4-thiadiazol-2-yl)methanesulfonamide

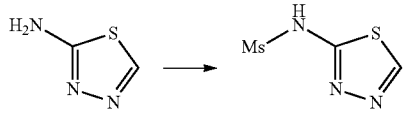 [SMILES: Nc1nncs1 ; CS(=O)(=O)Nc1nncs1]

A solution of 1,3,4-thiadiazol-2-amine (0.300 g, 2.966 mmol), methanesulfonyl chloride (0.253 mL, 3.263 mmol) and triethylamine (0.620 mL, 4.450 mmol) in dichloromethane (3 mL) was stirred at the room temperature for 3 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give N-(1,3,4-thiadiazol-2-yl)methanesulfonamide as white solid (0.382 g, 71.8%).

[Step 2] Compound 11776

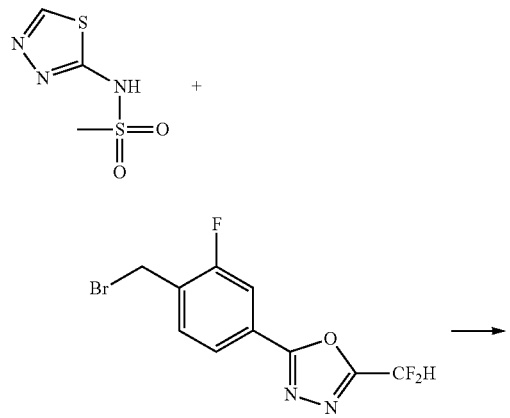

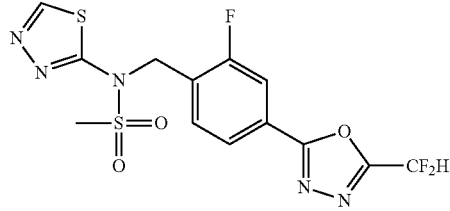

A solution of N-(1,3,4-thiadiazol-2-yl)methanesulfonamide (0.030 g, 0.167 mmol), 2-(4-(bromomethyl)-3-fluorophenyl)-5-(difluoromethyl)-1,3,4-oxadiazole (0.062 g, 0.201 mmol), potassium carbonate (0.046 g, 0.335 mmol) and potassium iodide (0.014 g, 0.084 mmol) in N,N-dimethylformide (2 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=0% to 50%) to give N-(4-(5-(difluoromethyl)-1,3,4-oxadiazol-2-yl)-2-fluorobenzyl)-N-(1,3,4-thiadiazol-2-yl)methanesulfonamide as yellow oil (0.027 g, 39.3%).

¹H NMR (400 MHz, CD3OD) δ8.64 (s, 1H), 8.00~7.99 (m, 2H), 7.62~7.57 (m, 1H), 7.24 (t, 1H, J=51.7 Hz), 5.55 (s, 2H), 3.02 (s, 3H); LRMS (ES) m/z 406.1 (M⁺+1).

EXAMPLE 282

Compound 11777, N-(3-chlorophenyl)-N-(4-(5-(difluoromethyl)-1,3,4-oxadiazol-2-yl)benzyl)-1-(1-ethylazetidin-3-yl)piperidine-4-sulfonamide

[Step 1] tert-butyl 3-(4-(N-(3-chlorophenyl)-N-(4-(5-(difluoromethyl)-1,3,4-oxadiazol-2-yl)benzyl)sulfamoyl)piperidin-1-yl)azetidine-1-carboxylate

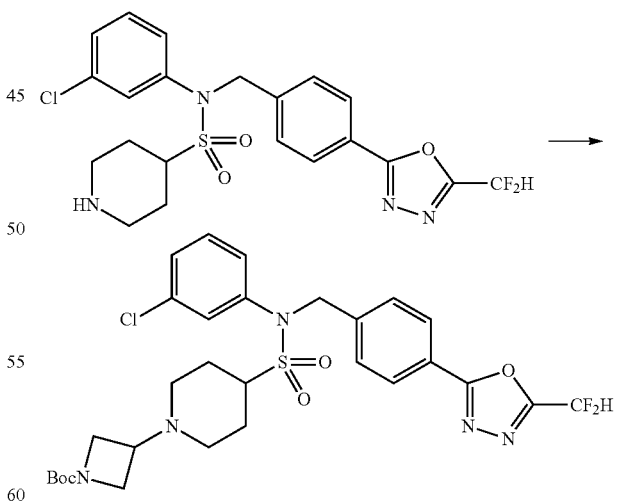

A mixture of N-(3-chlorophenyl)-N-(4-(5-(difluoromethyl)-1,3,4-oxadiazol-2-yl)benzyl)piperidine-4-sulfonamide hydrochloride (0.760 g, 1.463 mmol), tert-butyl 3-oxoazetidine-1-carboxylate (0.752 g, 4.390 mmol) and N,N-diisopropylethylamine (0.510 mL, 2.927 mmol) in dichloromethane (20 mL) was treated at the room temperature with sodium triacetoxyborohydride (0.620 g, 2.927 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=60% to 90%) to give tert-butyl 3-(4-(N-(3-chlorophenyl)-N-(4-(5-(difluoromethyl)-1,3,4-oxadiazol-2-yl)benzyl)sulfamoyl)piperidin-1-yl)azetidine-1-carboxylate as white solid (0.795 g, 85.1%).

[Step 2] 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride

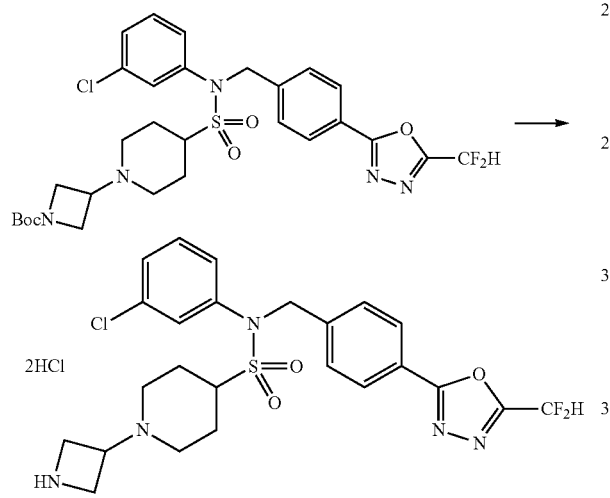

A solution of tert-butyl 3-(4-(N-(3-chlorophenyl)-N-(4-(5-(difluoromethyl)-1,3,4-oxadiazol-2-yl)benzyl)sulfamoyl)piperidin-1-yl)azetidine-1-carboxylate (0.795 g, 1.246 mmol) in 1,4-dioxane (6 mL) was mixed at the room temperature with hydrogen chloride (4.00 M solution in 1,4-dioxane, 3.115 mL, 12.458 mmol), and stirred at the same temperature for 1 hr. The reaction mixture was diluted with ethyl acetate (5 mL) and hexane (30 mL) and stirred. The resulting precipitates were collected by filtration, washed by hexane, and dried to give 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride as white solid (0.752 g, 98.8%).

[Step 3] Compound 11777

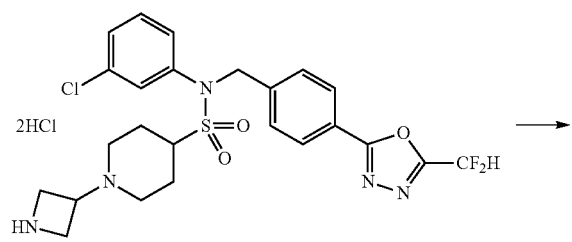

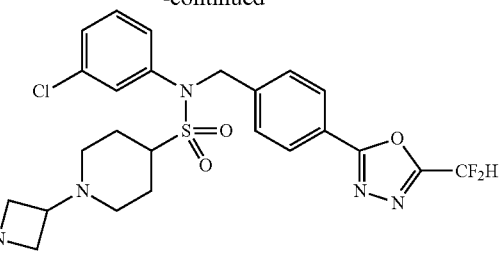

A mixture of 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride (0.050 g, 0.082 mmol), acetaldehyde (0.023 mL, 0.409 mmol) and N,N-diisopropylethylamine (0.043 mL, 0.246 mmol) in dichloromethane (5 mL) was treated at the room temperature with sodium triacetoxyborohydride (0.035 g, 0.164 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 10%) to give N-(3-chlorophenyl)-N-(4-(5-(difluoromethyl)-1,3,4-oxadiazol-2-yl)benzyl)-1-(1-ethylazetidin-3-yl)piperidine-4-sulfonamide as beige solid (0.021 g, 45.3%).

¹H NMR (400 MHz, DMSO-d6) δ 7.99 (d, 2H, J=8.4 Hz), 7.66 (s, 0.25H), 7.55 (t, 1H, J=2.0 Hz), 7.54 (s, 0.5H), 7.51 (d, 2H, J=8.4 Hz), 7.44 (m, 1H), 7.41 (s, 0.25H), 7.35 (t, 1H, J=8.0 Hz), 7.29 (m, 1H), 5.11 (s, 2H), 3.65-3.55 (m, 2H), 3.34 (m, 1H), 3.09 (s, 2H), 2.97 (q, 1H, J=6.6 Hz), 2.82 (d, 2H, J=11.0 Hz), 2.70-2.61 (m, 2H), 2.07 (d, 2H, J=12.2 Hz), 1.91-1.81 (m, 2H), 1.74-1.61 (m, 2H), 0.97-0.90 (t, 3H, J=7.1 Hz); LRMS (ES) m/z 566.1 (M⁺+1).

EXAMPLE 283

Compound 11778, N-(3-chlorophenyl)-N-(4-(5-(difluoromethyl)-1,3,4-oxadiazol-2-yl)benzyl)-1-(1-isopropylazetidin-3-yl)piperidine-4-sulfonamide

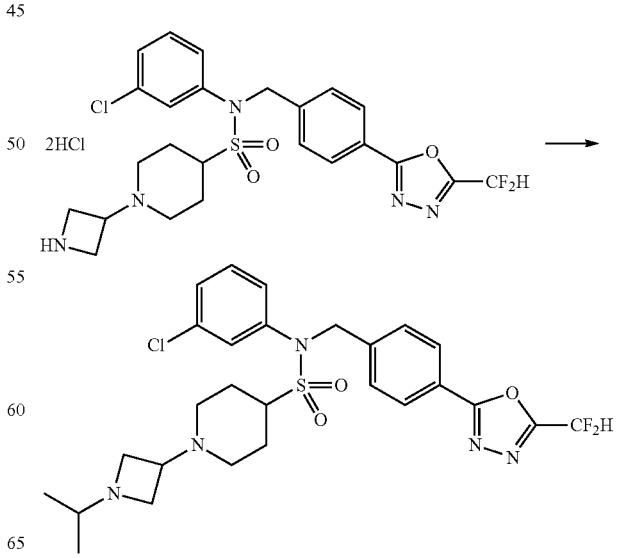

A mixture of 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride (0.050 g, 0.082 mmol), acetone (0.030 mL, 0.409 mmol) and N,N-diisopropylethylamine (0.043 mL, 0.246 mmol) in dichloromethane (5 mL) was treated at the room temperature with sodium triacetoxyborohydride (0.035 g, 0.164 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give N-(3-chlorophenyl)-N-(4-(5-(difluoromethyl)-1,3,4-oxadiazol-2-yl)benzyl)-1-(1-isopropylazetidin-3-yl)piperidine-4-sulfonamide as white solid (0.026 g, 54.8%).

$^1$H NMR (400 MHz, DMSO-d6) δ 7.99 (d, 2H, J=8.4 Hz), 7.66 (s, 0.25H), 7.55 (t, 1H, J=2.0 Hz), 7.53 (s, 0.5H), 7.51 (d, 2H, J=8.4 Hz), 7.44 (ddd, 1H, J=8.0, 2.2, 1.2 Hz), 7.41 (s, 0.25H), 7.35 (t, 1H, J=8.0 Hz), 7.29 (ddd, 1H, J=8.0, 2.1, 1.2 Hz), 5.11 (s, 2H), 3.43 (s, 2H), 3.10 (m, 1H), 2.93-2.73 (m, 5H), 2.34 (m, 1H), 2.11-2.03 (m, 2H), 1.89-1.78 (m, 2H), 1.67 (qd, 2H, J=11.9, 3.7 Hz), 0.86 (d, 6H, J=6.2 Hz); LRMS (ES) m/z 580.1 (M$^+$+1).

EXAMPLE 284

Compound 11779, 1-(1-acetylazetidin-3-yl)-N-(3-chlorophenyl)-N-(4-(5-(difluoromethyl)-1,3,4-oxadiazol-2-yl)benzyl)piperidine-4-sulfonamide

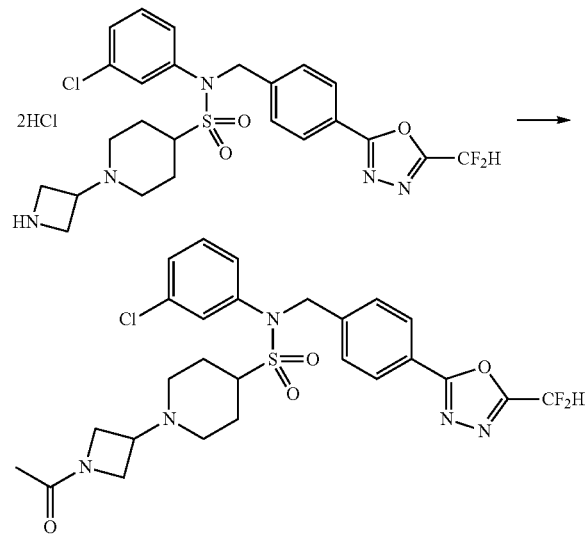

A mixture of 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride (0.050 g, 0.082 mmol) in dichloromethane (5 mL) was treated at the room temperature with acetyl chloride (0.017 mL, 0.246 mmol) and N,N-diisopropylethylamine (0.057 mL, 0.327 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give 1-(1-acetylazetidin-3-yl)-N-(3-chlorophenyl)-N-(4-(5-(difluoromethyl)-1,3,4-oxadiazol-2-yl)benzyl)piperidine-4-sulfonamide as white solid (0.030 g, 63.2%).

$^1$H NMR (400 MHz, DMSO-d6) δ 7.99 (d, 2H, J=8.4 Hz), 7.66 (s, 0.25H), 7.56 (t, 1H, J=2.1 Hz), 7.53 (s, 0.5H), 7.51 (d, 2H, J=8.4 Hz), 7.45 (ddd, 1H, J=8.0, 2.1, 1.2 Hz), 7.40 (s, 0.25H), 7.35 (t, 1H, J=8.0 Hz), 7.28 (ddd, 1H, J=8.0, 2.0, 1.1 Hz), 5.12 (s, 2H), 4.09 (m, 1H), 3.91 (m, 1H), 3.82 (m, 1H), 3.62 (dd, 1H, J=9.9, 5.1 Hz), 3.37 (m, 1H), 3.09 (m, 1H), 2.89 (t, 2H, J=12.8 Hz), 2.09 (d, 2H, J=11.9 Hz), 1.96-1.83 (m, 2H), 1.79-1.66 (m, 5H); LRMS (ES) m/z 580.3 (M$^+$+1).

EXAMPLE 285

Compound 11780, N-(3-chlorophenyl)-N-(4-(5-(difluoromethyl)-1,3,4-oxadiazol-2-yl)benzyl)-1-(1-propionylazetidin-3-yl)piperidine-4-sulfonamide

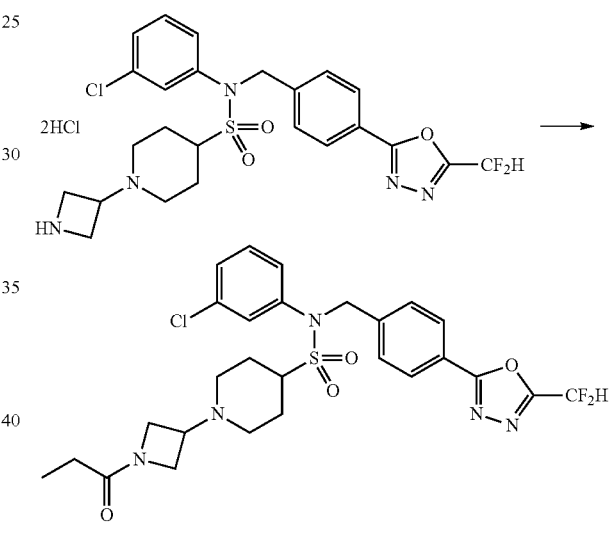

A mixture of 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride (0.050 g, 0.082 mmol) in dichloromethane (5 mL) was treated at the room temperature with propionyl chloride (0.021 mL, 0.246 mmol) and N,N-diisopropylethylamine (0.057 mL, 0.327 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(3-chlorophenyl)-N-(4-(5-(difluoromethyl)-1,3,4-oxadiazol-2-yl)benzyl)-1-(1-propionylazetidin-3-yl)piperidine-4-sulfonamide as white solid (0.029 g, 59.6%).

$^1$H NMR (400 MHz, DMSO-d6) δ 7.99 (d, 2H, J=8.4 Hz), 7.66 (s, 0.25H), 7.56 (t, 1H, J=2.0 Hz), 7.53 (s, 0.5H), 7.51 (d, 2H, J=8.4 Hz), 7.45 (ddd, 1H, J=8.1, 2.1, 1.2 Hz), 7.40 (s, 0.25H), 7.35 (t, 1H, J=8.0 Hz), 7.29 (ddd, 1H, J=8.0, 2.0, 1.1 Hz), 5.12 (s, 2H), 4.07 (t, 1H, J=9.7 Hz), 3.90 (m, 1H), 3.81 (m, 1H), 3.62 (dd, 1H, J=9.8, 5.1 Hz), 3.37 (m, 1H), 3.09 (m, 1H), 2.94-2.83 (m, 2H), 2.13-2.01 (m, 4H), 1.88 (q, 2H, J=10.9 Hz), 1.70 (q, 2H, J=12.1 Hz), 0.95 (t, 3H, J=7.5 Hz); LRMS (ES) m/z 594.3 (M$^+$+1).

EXAMPLE 286

Compound 11781, N-(3-chlorophenyl)-N-((5-(5-(difluoromethyl)-1,3,4-oxadiazol-2-yl)pyridin-2-yl)methyl)-1-(1-isopropylazetidin-3-yl)piperidine-4-sulfonamide

[Step 1] tert-butyl 3-(4-(N-(3-chlorophenyl)-N-((5-(5-(difluoromethyl)-1,3,4-oxadiazol-2-yl)pyridin-2-yl)methyl)sulfamoyl)piperidin-1-yl)azetidine-1-carboxylate

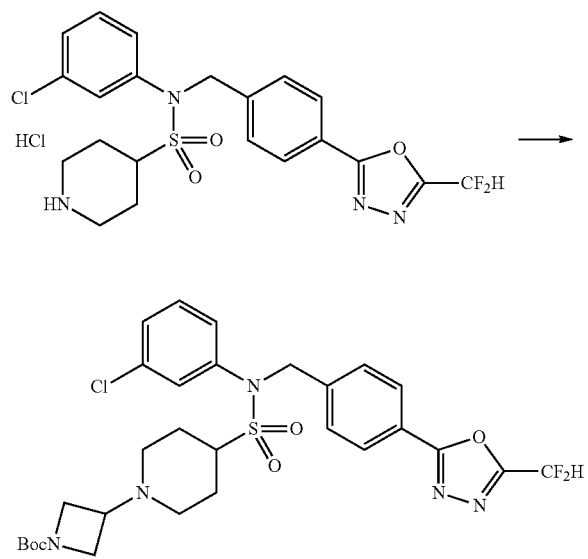 [SMILES: Cl ; O=S(=O)(C1CCNCC1)N(Cc1ccc(-c2nnc(C(F)F)o2)cc1)c1cccc(Cl)c1 ; CC(C)(C)OC(=O)N1CC(N2CCC(S(=O)(=O)N(Cc3ccc(-c4nnc(C(F)F)o4)cc3)c3cccc(Cl)c3)CC2)C1]

A mixture of N-(3-chlorophenyl)-N-((5-(5-(difluoromethyl)-1,3,4-oxadiazol-2-yl)pyridin-2-yl)methyl)piperidine-4-sulfonamide dihydrochloride (0.490 g, 0.880 mmol), tert-butyl 3-oxoazetidine-1-carboxylate (0.452 g, 2.640 mmol) and N,N-diisopropylethylamine (0.460 mL, 2.640 mmol) in dichloromethane (15 mL) was treated at the room temperature with sodium triacetoxyborohydride (0.373 g, 1.760 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=70% to 100%) to give tert-butyl 3-(4-(N-(3-chlorophenyl)-N-((5-(5-(difluoromethyl)-1,3,4-oxadiazol-2-yl)pyridin-2-yl)methyl)sulfamoyl)piperidin-1-yl)azetidine-1-carboxylate as white solid (0.386 g, 68.6%).

[Step 2] 1-(azetidin-3-yl)-N-(3-chlorophenyl)-N-((5-(5-(difluoromethyl)-1,3,4-oxadiazol-2-yl)pyridin-2-yl)methyl)piperidine-4-sulfonamide trihydrochloride

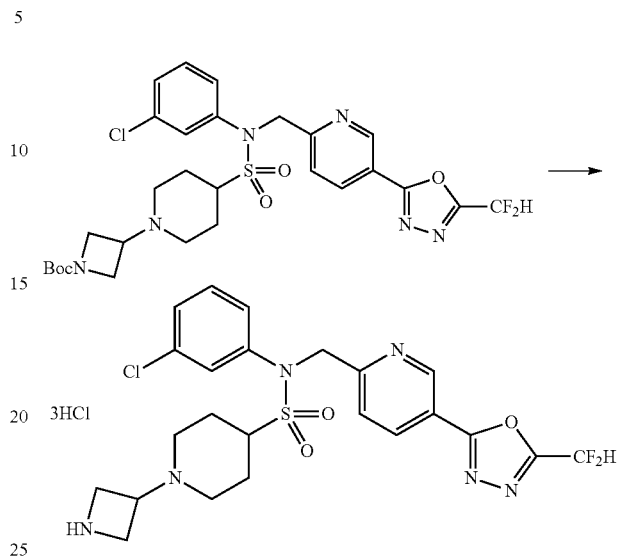

A solution of tert-butyl 3-(4-(N-(3-chlorophenyl)-N-((5-(5-(difluoromethyl)-1,3,4-oxadiazol-2-yl)pyridin-2-yl)methyl)sulfamoyl)piperidin-1-yl)azetidine-1-carboxylate (0.386 g, 0.604 mmol) in 1,4-dioxane (5 mL) was mixed at the room temperature with hydrogen chloride (4.00 M solution in 1,4-dioxane, 2.265 mL, 9.059 mmol), and stirred at the same temperature for 1 hr. The reaction mixture was diluted with ethyl acetate (5 mL) and hexane (30 mL) and stirred. The resulting precipitates were collected by filtration, washed by hexane, and dried to give 1-(azetidin-3-yl)-N-(3-chlorophenyl)-N-((5-(5-(difluoromethyl)-1,3,4-oxadiazol-2-yl)pyridin-2-yl)methyl)piperidine-4-sulfonamide trihydrochloride as white solid (0.372 g, 95.0%).

[Step 3] Compound 11781

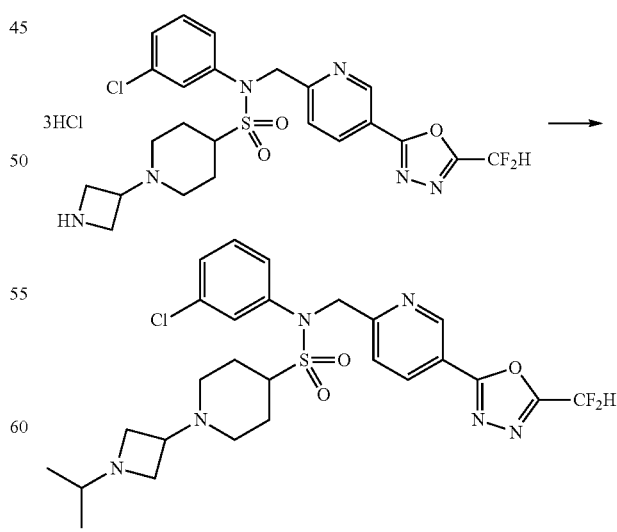

A mixture of 1-(azetidin-3-yl)-N-(3-chlorophenyl)-N-((5-(5-(difluoromethyl)-1,3,4-oxadiazol-2-yl)pyridin-2-yl)

methyl)piperidine-4-sulfonamide trihydrochloride (0.050 g, 0.077 mmol), acetone (0.028 mL, 0.386 mmol) and N,N-diisopropylethylamine (0.054 mL, 0.308 mmol) in dichloromethane (5 mL) was treated at the room temperature with sodium triacetoxyborohydride (0.033 g, 0.154 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give N-(3-chlorophenyl)-N-((5-(5-(difluoromethyl)-1,3,4-oxadiazol-2-yl)pyridin-2-yl)methyl)-1-(1-isopropylazetidin-3-yl)piperidine-4-sulfonamide as white solid (0.020 g, 44.6%).

$^1$H NMR (400 MHz, DMSO-d6) δ 9.11 (d, 1H, J=2.3 Hz), 8.42 (dd, 1H, J=8.3, 2.3 Hz), 7.73-7.63 (m, 2.25H), 7.57 (s, 0.5H), 7.51 (m, 1H), 7.44 (s, 0.25H), 7.38 (m, 1H), 7.32 (m, 1H), 5.21 (s, 2H), 4.10-4.02 (m, 2H), 3.85 (m, 1H), 3.61 (m, 1H), 3.45-3.42 (m, 2H), 3.16 (m, 1H), 3.02 (m, 1H), 2.84 (m, 1H), 2.18-2.12 (m, 2H), 2.00-1.89 (m, 2H), 1.72 (m, 2H), 1.19-1.08 (m, 6H); LRMS (ES) m/z 581.1 (M$^+$+1).

EXAMPLE 287

Compound 11782, N-(3-chlorophenyl)-N-((5-(5-(difluoromethyl)-1,3,4-oxadiazol-2-yl)pyridin-2-yl)methyl)-1-(1-propionylazetidin-3-yl)piperidine-4-sulfonamide

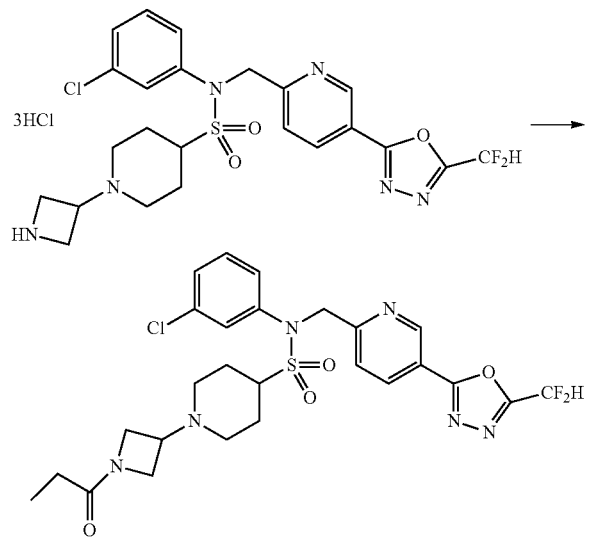

A mixture of 1-(azetidin-3-yl)-N-(3-chlorophenyl)-N-((5-(5-(difluoromethyl)-1,3,4-oxadiazol-2-yl)pyridin-2-yl)methyl)piperidine-4-sulfonamide trihydrochloride (0.050 g, 0.077 mmol) in dichloromethane (5 mL) was treated at the room temperature with propionyl chloride (0.020 mL, 0.231 mmol) and N,N-diisopropylethylamine (0.054 mL, 0.308 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(3-chlorophenyl)-N-((5-(5-(difluoromethyl)-1,3,4-oxadiazol-2-yl)pyridin-2-yl)methyl)-1-(1-propionylazetidin-3-yl)piperidine-4-sulfonamide as white solid (0.027 g, 58.8%).

$^1$H NMR (400 MHz, DMSO-d6) δ 9.10 (dd, 1H, J=2.3, 0.8 Hz), 8.41 (dd, 1H, J=8.2, 2.3 Hz), 7.72-7.67 (m, 1.25H), 7.64 (t, 1H, J=2.0 Hz), 7.56 (s, 0.5H), 7.51 (ddd, 1H, J=8.0, 2.2, 1.2 Hz), 7.44 (s, 0.25H), 7.37 (t, 1H, J=8.0 Hz), 7.31 (ddd, 1H, J=8.1, 2.0, 1.1 Hz), 5.21 (s, 2H), 4.07 (t, 1H, J=7.9 Hz), 3.91 (m, 1H), 3.81 (m, 1H), 3.63 (m, 1H), 3.40 (m, 1H), 3.09 (m, 1H), 2.88 (t, 2H, J=12.9 Hz), 2.11 (d, 2H, J=12.0 Hz), 2.07-1.99 (m, 2H), 1.95-1.83 (m, 2H), 1.69 (q, 2H, J=12.1 Hz), 0.95 (t, 3H, J=7.5 Hz); LRMS (ES) m/z 595.1 (M$^+$+1).

EXAMPLE 288

Compound 11783, N-(3-chlorophenyl)-1-(1-(cyclopropanecarbonyl)azetidin-3-yl)-N-(4-(5-(difluoromethyl)-1,3,4-oxadiazol-2-yl)benzyl)piperidine-4-sulfonamide

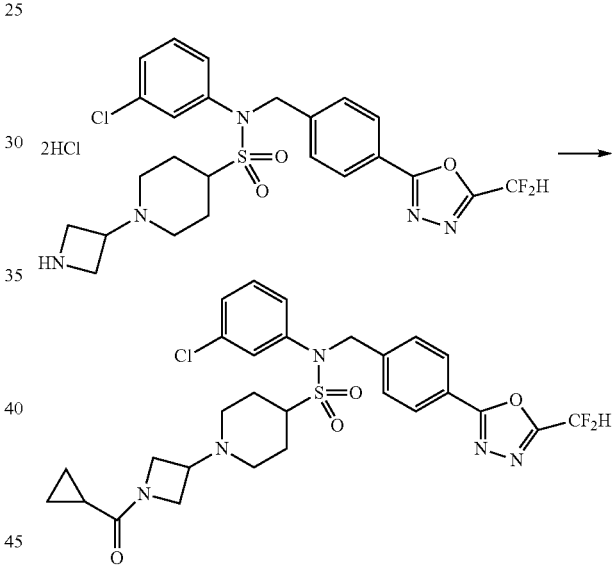

A mixture of 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride (0.050 g, 0.082 mmol) in dichloromethane (5 mL) was treated at the room temperature with cyclopropanecarbonyl chloride (0.026 g, 0.246 mmol) and N,N-diisopropylethylamine (0.057 mL, 0.327 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(3-chlorophenyl)-1-(1-(cyclopropanecarbonyl)azetidin-3-yl)-N-(4-(5-(difluoromethyl)-1,3,4-oxadiazol-2-yl)benzyl)piperidine-4-sulfonamide as beige solid (0.039 g, 78.6%).

$^1$H NMR (400 MHz, DMSO-d6) δ 7.99 (d, 2H, J=8.4 Hz), 7.66 (s, 0.25H), 7.56 (t, 1H, J=2.0 Hz), 7.53 (s, 0.5H), 7.51 (d, 2H, J=8.4 Hz), 7.45 (ddd, 1H, J=8.0, 2.1, 1.2 Hz), 7.40

(s, 0.25H), 7.35 (t, 1H, J=8.0 Hz), 7.29 (ddd, 1H, J=8.0, 2.0, 1.1 Hz), 5.12 (s, 2H), 4.24 (t, 1H, J=7.9 Hz), 4.03 (m, 1H), 3.83 (dd, 1H, J=9.8, 7.2 Hz), 3.65 (dd, 1H, J=9.8, 5.1 Hz), 3.38 (m, 1H), 3.14 (p, 1H, J=6.3 Hz), 2.90 (s, 2H), 2.09 (d, 2H, J=11.9 Hz), 1.94-1.85 (m, 2H), 1.72 (m, 2H), 1.50 (m, 1H), 0.71-0.65 (m, 4H); LRMS (ES) m/z 606.1 (M$^+$+1).

EXAMPLE 289

Compound 11784, N-(3-chlorophenyl)-1-(1-(cyclopropanecarbonyl)azetidin-3-yl)-N-((5-(5-(difluoromethyl)-1,3,4-oxadiazol-2-yl)pyridin-2-yl)methyl)piperidine-4-sulfonamide

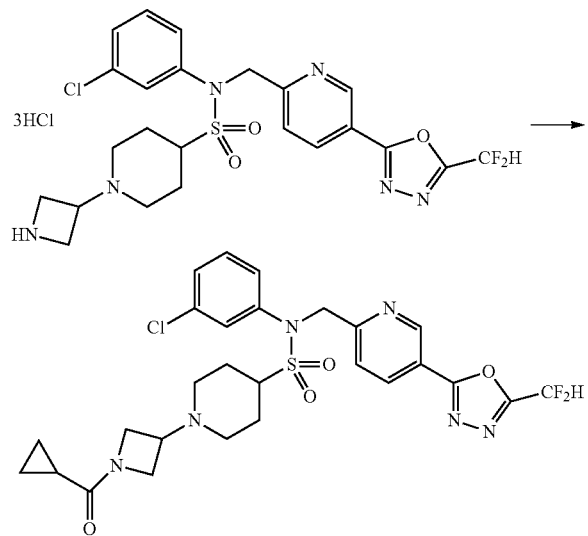

A mixture of 1-(azetidin-3-yl)-N-(3-chlorophenyl)-N-((5-(5-(difluoromethyl)-1,3,4-oxadiazol-2-yl)pyridin-2-yl)methyl)piperidine-4-sulfonamide trihydrochloride (0.050 g, 0.077 mmol) in dichloromethane (5 mL) was treated at the room temperature with cyclopropanecarbonyl chloride (0.024 g, 0.231 mmol) and N,N-diisopropylethylamine (0.054 mL, 0.308 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(3-chlorophenyl)-1-(1-(cyclopropanecarbonyl)azetidin-3-yl)-N-((5-(5-(difluoromethyl)-1,3,4-oxadiazol-2-yl)pyridin-2-yl)methyl)piperidine-4-sulfonamide as white solid (0.017 g, 36.3%).

$^1$H NMR (400 MHz, DMSO-d6) δ 9.10 (dd, 1H, J=2.3, 0.8 Hz), 8.41 (dd, 1H, J=8.3, 2.3 Hz), 7.72-7.67 (m, 1.25H), 7.65 (t, 1H, J=2.0 Hz), 7.56 (s, 0.5H), 7.51 (ddd, 1H, J=8.1, 2.2, 1.2 Hz), 7.44 (s, 0.25H), 7.37 (t, 1H, J=8.0 Hz), 7.31 (ddd, 1H, J=8.0, 2.0, 1.1 Hz), 5.22 (s, 2H), 4.24 (t, 1H, J=7.9 Hz), 4.03 (dd, 1H, J=8.6, 4.9 Hz), 3.84 (m, 1H), 3.65 (dd, 1H, J=9.7, 5.1 Hz), 3.41 (m, 1H), 3.14 (m, 1H), 2.90 (s, 2H), 2.13 (d, 2H, J=12.2 Hz), 1.90 (m, 2H), 1.72-1.68 (m, 2H), 1.50 (m, 1H), 0.71-0.66 (m, 4H); LRMS (ES) m/z 607.1 (M$^+$+1).

EXAMPLE 290

Compound 11785, N-(3-chlorophenyl)-N-(4-(5-(difluoromethyl)-1,3,4-oxadiazol-2-yl)benzyl)-1-(1-methylazetidin-3-yl)piperidine-4-sulfonamide

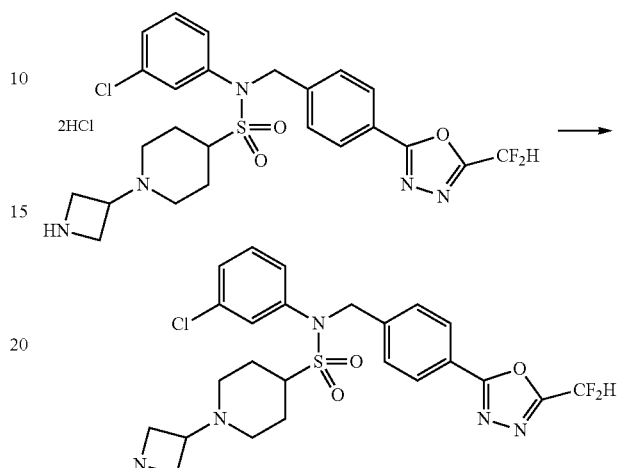

A mixture of 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride (0.050 g, 0.082 mmol), paraformaldehyde (0.012 g, 0.409 mmol) and N,N-diisopropylethylamine (0.043 mL, 0.246 mmol) in dichloromethane (5 mL) was treated at the room temperature with sodium triacetoxyborohydride (0.035 g, 0.164 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give N-(3-chlorophenyl)-N-(4-(5-(difluoromethyl)-1,3,4-oxadiazol-2-yl)benzyl)-1-(1-methylazetidin-3-yl)piperidine-4-sulfonamide as white solid (0.016 g, 35.4%).

$^1$H NMR (400 MHz, DMSO-d6) δ 7.99 (d, 2H, J=8.4 Hz), 7.66 (s, 0.25H), 7.58-7.48 (m, 3.5H), 7.44 (m, 1H), 7.41 (s, 0.25H), 7.35 (t, 1H, J=7.9 Hz), 7.29 (m, 1H), 5.11 (s, 2H), 3.49-3.44 (m, 2H), 3.21 (m, 1H), 2.90-2.74 (m, 4H), 2.31-2.15 (m, 4H), 2.06 (d, 2H, J=12.3 Hz), 1.83 (t, 2H, J=11.6 Hz), 1.73-1.63 (m, 2H); LRMS (ES) m/z 552.3 (M$^+$+1).

EXAMPLE 291

Compound 11786, N-(3-chloro-4-fluorophenyl)-N-((5-(5-(difluoromethyl)-1,3,4-oxadiazol-2-yl)pyridin-2-yl)methyl)-2-(4-fluoropiperidin-1-yl)ethane-1-sulfonamide

[Step 1] methyl 6-(((3-chloro-4-fluorophenyl)amino)methyl)nicotinate

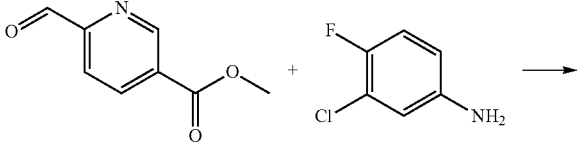

-continued

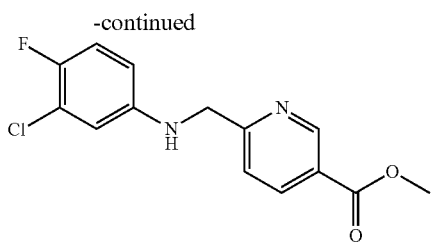

A mixture of methyl 6-formylnicotinate (1.000 g, 6.055 mmol) and 3-chloro-4-fluoroaniline (0.970 g, 6.661 mmol) in tetrahydrofuran (50 mL) was stirred at the room temperature for 30 min, and treated with sodium triacetoxyborohydride (1.925 g, 9.083 mmol). The reaction mixture was stirred at the same temperature for additional 18 hr. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/dichloromethane=0% to 5%) to give methyl 6-(((3-chloro-4-fluorophenyl)amino)methyl)nicotinate as brown solid (0.510 g, 28.6%).

[Step 2] methyl 6-((N-(3-chloro-4-fluorophenyl)vinylsulfonamido)methyl)nicotinate

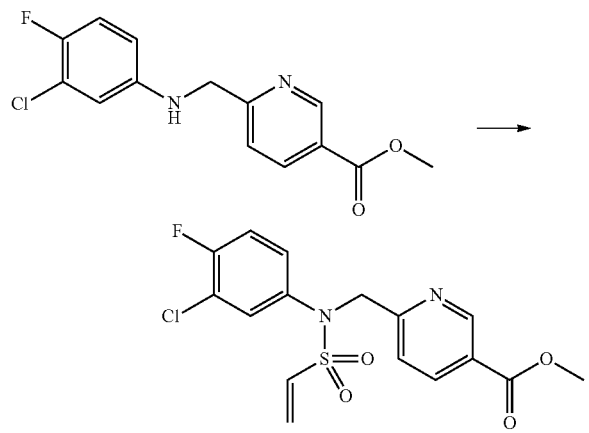

A solution of methyl 6-(((3-chloro-4-fluorophenyl)amino)methyl)nicotinate (0.510 g, 1.731 mmol) in dichloromethane (10 mL) was mixed at the room temperature with 2-chloroethane-1-sulfonyl chloride (0.310 g, 1.904 mmol) and triethylamine (0.289 mL, 2.077 mmol), and stirred at the same temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=20% to 50%) to give methyl 6-((N-(3-chloro-4-fluorophenyl)vinylsulfonamido)methyl)nicotinate as brown solid (0.247 g, 37.1%).

[Step 3] methyl 6-(((N-(3-chloro-4-fluorophenyl)-2-(4-fluoropiperidin-1-yl)ethyl)sulfonamido)methyl)nicotinate

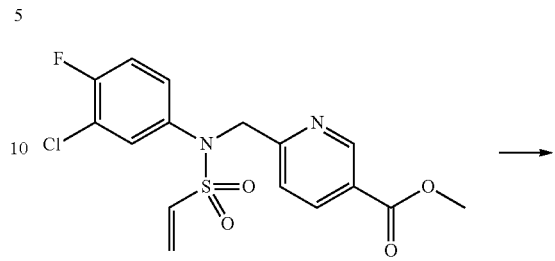

A mixture of methyl 6-((N-(3-chloro-4-fluorophenyl)vinylsulfonamido)methyl)nicotinate (0.247 g, 0.642 mmol) and 4-fluoropiperidine hydrochloride (0.179 g, 1.284 mmol) in dichloromethane (10 mL) was treated at the room temperature with triethylamine (0.268 mL, 1.926 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=60% to 90%) to give methyl 6-(((N-(3-chloro-4-fluorophenyl)-2-(4-fluoropiperidin-1-yl)ethyl)sulfonamido)methyl)nicotinate as light yellow solid (0.250 g, 79.8%).

[Step 4] N-(3-chloro-4-fluorophenyl)-2-(4-fluoropiperidin-1-yl)-N-((5-(hydrazinecarbonyl)pyridin-2-yl)methyl)ethane-1-sulfonamide

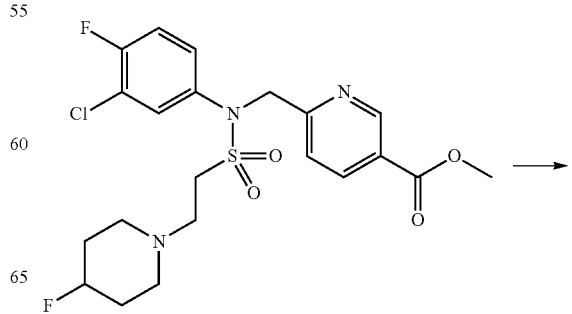

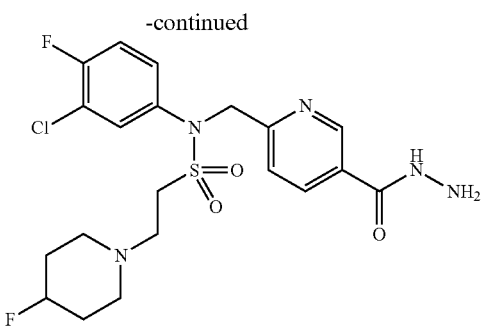

A solution of methyl 6-(((N-(3-chloro-4-fluorophenyl)-2-(4-fluoropiperidin-1-yl)ethyl)sulfonamido)methyl)nicotinate (0.250 g, 0.512 mmol) in tetrahydrofuran (7 mL)/ethanol (7 mL) was mixed at the room temperature with hydrazine monohydrate (0.498 mL, 10.247 mmol). The reaction mixture was heated at reflux for 18 hr, cooled down to the room temperature to terminate the reaction and concentrated under the reduced pressure to remove the solvent. The residue was diluted with water (30 mL) and stirred. The resulting precipitates were collected by filtration, washed by water, and dried to give N-(3-chloro-4-fluorophenyl)-2-(4-fluoropiperidin-1-yl)-N-((5-(hydrazinecarbonyl)pyridin-2-yl)methyl)ethane-1-sulfonamide as white solid (0.230 g, 92.0%).

[Step 5] Compound 11786

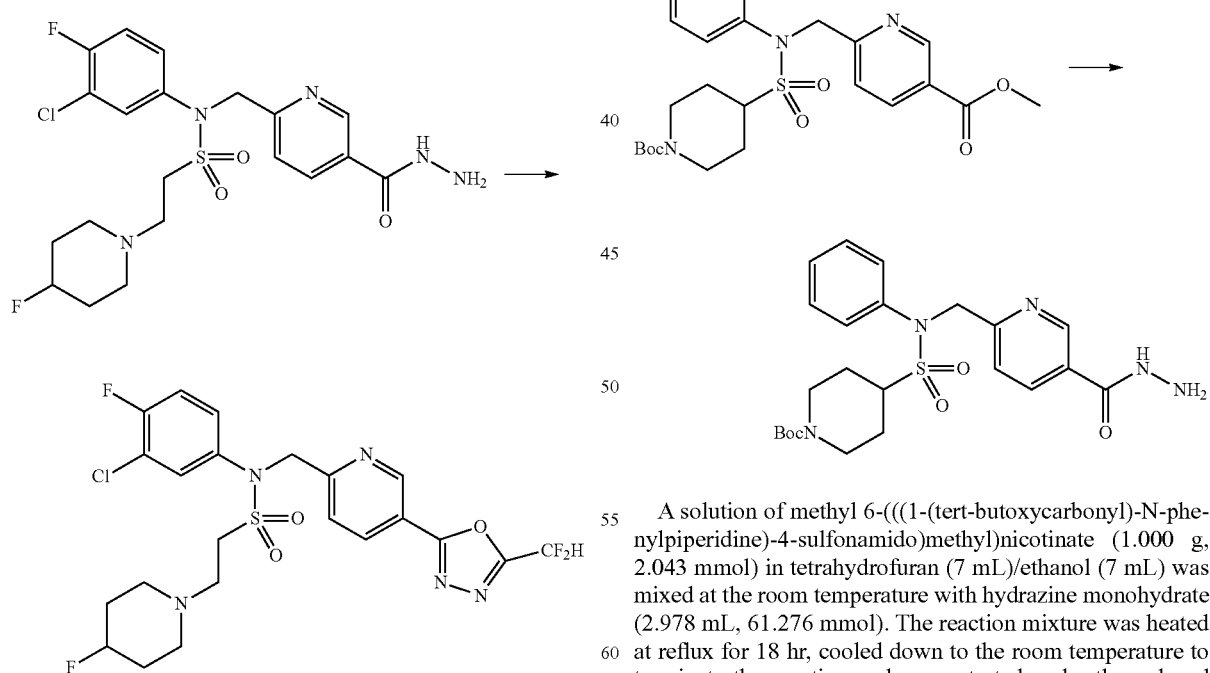

A solution of N-(3-chloro-4-fluorophenyl)-2-(4-fluoropiperidin-1-yl)-N-((5-(hydrazinecarbonyl)pyridin-2-yl)methyl)ethane-1-sulfonamide (0.230 g, 0.471 mmol) in tetrahydrofuran (10 mL) was mixed at 50° C. with 2,2-difluoroacetic anhydride (0.176 mL, 1.414 mmol) and triethylamine (0.263 mL, 1.885 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=60% to 90%) to give N-(3-chloro-4-fluorophenyl)-N-((5-(5-(difluoromethyl)-1,3,4-oxadiazol-2-yl)pyridin-2-yl)methyl)-2-(4-fluoropiperidin-1-yl)ethane-1-sulfonamide as light yellow solid (0.146 g, 56.5%).

$^1$H NMR (400 MHz, DMSO-d6) δ 9.11 (s, 1H), 8.41 (d, 1H, J=8.3 Hz), 7.83 (d, 1H, J=5.4 Hz), 7.74 (d, 1H, J=8.3 Hz), 7.70 (s, 0.25H), 7.57 (s, 0.5H), 7.53 (s, 1H), 7.43 (d, 1H, J=8.2 Hz), 7.40 (s, 0.25H), 5.15 (s, 2H), 4.70 (d, 1H, J=49.1 Hz), 3.54 (t, 2H, J=7.2 Hz), 2.80-2.73 (m, 2H), 2.59 (s, 2H), 2.38 (s, 2H), 1.94-1.80 (m, 2H), 1.80-1.66 (m, 2H); LRMS (ES) m/z 548.2 (M$^+$+1).

EXAMPLE 292

Compound 11790, N-((5-(5-(difluoromethyl)-1,3,4-oxadiazol-2-yl)pyridin-2-yl)methyl)-1-(1-methoxypropan-2-yl)-N-phenylpiperidine-4-sulfonamide

[Step 1] tert-butyl 4-(N-((5-(hydrazinecarbonyl)pyridin-2-yl)methyl)-N-phenylsulfamoyl)piperidine-1-carboxylate A solution of methyl 6-(((1-(tert-butoxycarbonyl)-N-phenylpiperidine)-4-sulfonamido)methyl)nicotinate (1.000 g, 2.043 mmol) in tetrahydrofuran (7 mL)/ethanol (7 mL) was mixed at the room temperature with hydrazine monohydrate (2.978 mL, 61.276 mmol). The reaction mixture was heated at reflux for 18 hr, cooled down to the room temperature to terminate the reaction and concentrated under the reduced pressure to remove the solvent. The residue was diluted with water (50 mL) and stirred. The resulting precipitates were collected by filtration, washed by water, and dried to give tert-butyl 4-(N-((5-(hydrazinecarbonyl)pyridin-2-yl)methyl)-N-phenylsulfamoyl)piperidine-1-carboxylate as white solid (0.899 g, 89.9%).

[Step 2] tert-butyl 4-(N-((5-(5-(difluoromethyl)-1,3,4-oxadiazol-2-yl)pyridin-2-yl)methyl)-N-phenylsulfamoyl)piperidine-1-carboxylate

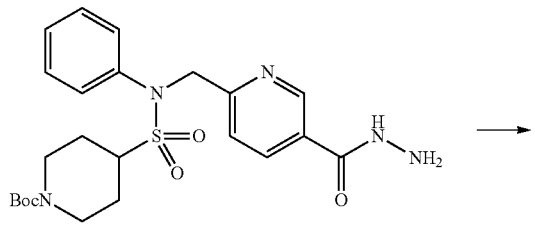

A mixture of tert-butyl 4-(N-((5-(hydrazinecarbonyl)pyridin-2-yl)methyl)-N-phenylsulfamoyl)piperidine-1-carboxylate (0.899 g, 1.836 mmol) and triethylamine (1.024 mL, 7.345 mmol) in tetrahydrofuran (20 mL) was treated at the room temperature with 2,2-difluoroacetic anhydride (0.685 mL, 5.509 mmol). The reaction mixture was heated at reflux for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=20% to 50%) to give tert-butyl 4-(N-((5-(5-(difluoromethyl)-1,3,4-oxadiazol-2-yl)pyridin-2-yl)methyl)-N-phenylsulfamoyl)piperidine-1-carboxylate as white solid (0.882 g, 87.4%).

[Step 3] N-((5-(5-(difluoromethyl)-1,3,4-oxadiazol-2-yl)pyridin-2-yl)methyl)-N-phenylpiperidine-4-sulfonamide dihydrochloride

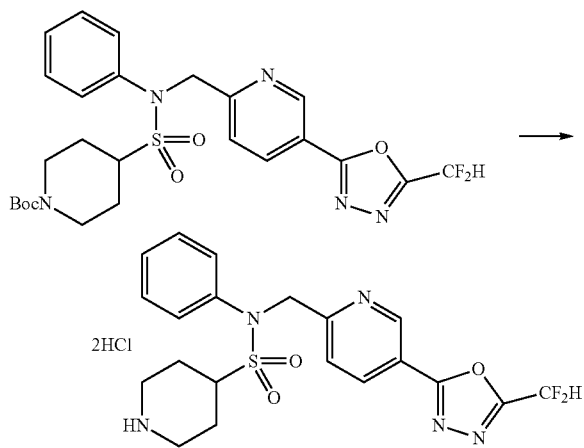

A solution of tert-butyl 4-(N-((5-(5-(difluoromethyl)-1,3,4-oxadiazol-2-yl)pyridin-2-yl)methyl)-N-phenylsulfamoyl)piperidine-1-carboxylate (0.882 g, 1.605 mmol) in 1,4-dioxane (5 mL) was mixed at the room temperature with hydrochloric acid (4.00 M solution in 1,4-dioxane, 6.018 mL, 24.072 mmol), and stirred at the same temperature for 1 hr. The reaction mixture was diluted with ethyl acetate (10 mL) and hexane (30 mL) and stirred. The resulting precipitates were collected by filtration, washed by hexane, and dried to give N-((5-(5-(difluoromethyl)-1,3,4-oxadiazol-2-yl)pyridin-2-yl)methyl)-N-phenylpiperidine-4-sulfonamide dihydrochloride as white solid (0.760 g, 90.7%).

[Step 4] Compound 11790

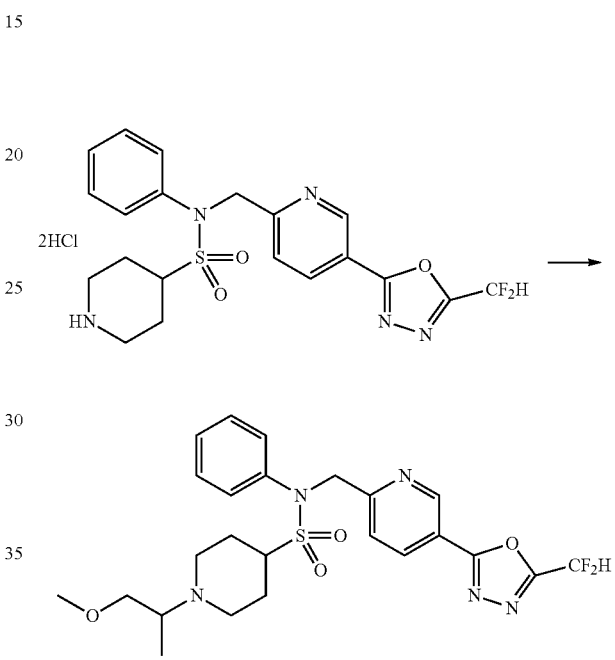

A mixture of N-((5-(5-(difluoromethyl)-1,3,4-oxadiazol-2-yl)pyridin-2-yl)methyl)-N-phenylpiperidine-4-sulfonamide dihydrochloride (0.050 g, 0.096 mmol), 1-methoxypropan-2-one (0.042 g, 0.479 mmol) and N,N-diisopropylethylamine (0.050 mL, 0.287 mmol) in dichloromethane (5 mL) was treated at the room temperature with sodium triacetoxyborohydride (0.041 g, 0.191 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 10%) to give N-((5-(5-(difluoromethyl)-1,3,4-oxadiazol-2-yl)pyridin-2-yl)methyl)-1-(1-methoxypropan-2-yl)-N-phenylpiperidine-4-sulfonamide as light yellow oil (0.009 g, 18.0%).

$^1$H NMR (400 MHz, DMSO-d6) δ 9.08 (d, 1H, J=2.2 Hz), 8.41 (dd, 1H, J J=8.2, 2.3 Hz), 7.74-7.67 (m, 1.25H), 7.56 (s, 0.5H), 7.50 (d, 2H, J=7.5 Hz), 7.43 (s, 0.25H), 7.39-7.30 (m, 2H), 7.24 (t, 1H, J=7.3 Hz), 5.17 (s, 2H), 3.39 (m, 1H), 3.27-3.18 (m, 5H), 2.93-2.85 (m, 2H), 2.77 (p, 1H, J=6.4 Hz), 2.36-2.23 (m, 2H), 2.07 (d, 2H, J=12.0 Hz), 1.71-1.58 (m, 2H), 0.93 (d, 3H, J=6.7 Hz); LRMS (ES) m/z 522.4 (M⁺+1).

EXAMPLE 293

Compound 11791, N-((5-(5-(difluoromethyl)-1,3,4-oxadiazol-2-yl)pyridin-2-yl)methyl)-1-(3-hydroxy-cyclobutyl)-N-phenylpiperidine-4-sulfonamide

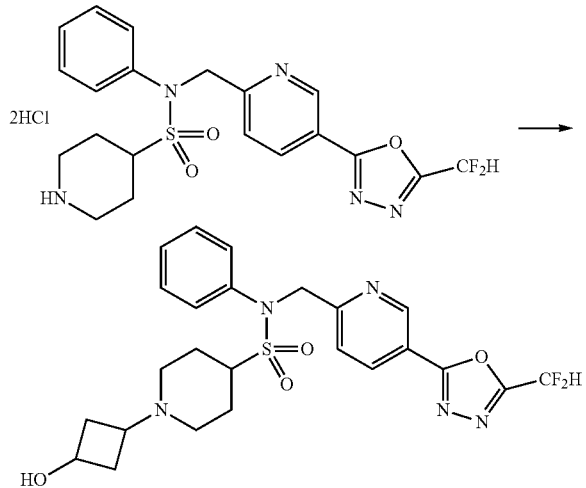

A mixture of N-((5-(5-(difluoromethyl)-1,3,4-oxadiazol-2-yl)pyridin-2-yl)methyl)-N-phenylpiperidine-4-sulfonamide dihydrochloride (0.090 g, 0.172 mmol), 3-hydroxycyclobutan-1-one (0.044 g, 0.517 mmol) and N,N-diisopropylethylamine (0.090 mL, 0.517 mmol) in dichloromethane (5 mL) was treated at the room temperature with sodium triacetoxyborohydride (0.073 g, 0.345 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-((5-(5-(difluoromethyl)-1,3,4-oxadiazol-2-yl)pyridin-2-yl)methyl)-1-(3-hydroxycyclobutyl)-N-phenylpiperidine-4-sulfonamide as pale orange solid (0.039 g, 43.6%).

$^1$H NMR (400 MHz, DMSO-d6) δ 9.09 (d, 1H, J=2.2 Hz), 8.41 (dd, 1H, J=8.2, 2.3 Hz), 7.72-7.68 (m, 1.25H), 7.56 (s, 0.5H), 7.49 (d, 2H, J=7.5 Hz), 7.43 (s, 0.25H), 7.38-7.31 (m, 2H), 7.25 (t, 1H, J=7.3 Hz), 5.17 (s, 2H), 4.93 (m, 1H), 4.18 (m, 0.5H), 3.78 (m, 0.5H), 3.00-2.80 (m, 2H), 2.34 (m, 1H), 2.15-2.03 (m, 4H), 2.00 (m, 1H), 1.90-1.54 (m, 6H); LRMS (ES) m/z 520.4 (M$^+$+1).

EXAMPLE 294

Compound 11792, N-(4-(5-(difluoromethyl)-1,3,4-oxadiazol-2-yl)benzyl)-1-(3-hydroxycyclobutyl)-N-(m-tolyl)piperidine-4-sulfonamide

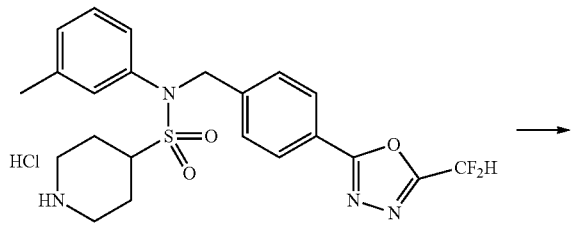

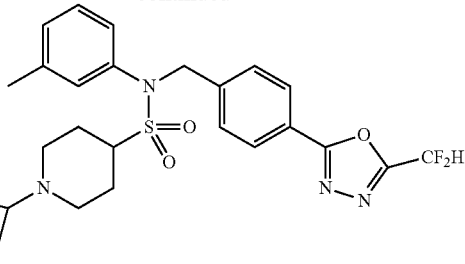

A mixture of N-(4-(5-(difluoromethyl)-1,3,4-oxadiazol-2-yl)benzyl)-N-(m-tolyl)piperidine-4-sulfonamide hydrochloride (0.090 g, 0.180 mmol), 3-hydroxycyclobutan-1-one (0.047 g, 0.541 mmol) and N,N-diisopropylethylamine (0.063 mL, 0.361 mmol) in dichloromethane (5 mL) was treated at the room temperature with sodium triacetoxyborohydride (0.076 g, 0.361 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)benzyl)-1-(3-hydroxycyclobutyl)-N-(m-tolyl)piperidine-4-sulfonamide as light yellow solid (0.031 g, 32.3%).

$^1$H NMR (400 MHz, DMSO-d6) δ 7.98 (d, 2H, J=6.6 Hz), 7.66 (s, 0.25H), 7.53 (s, 0.5H), 7.50 (d, 2H, J=8.3 Hz), 7.40 (s, 0.25H), 7.27-7.16 (m, 3H), 7.04 (m, 1H), 5.05 (s, 2H), 4.93 (m, 1H), 4.14 (m, 0.5H), 3.75 (m, 0.5H), 3.19 (m, 1H), 2.93 (m, 1H), 2.91-2.78 (m, 2H), 2.33 (m, 1H), 2.25 (s, 3H), 2.13-2.02 (m, 3H), 1.86 (m, 1H), 1.77-1.53 (m, 5H); LRMS (ES) m/z 533.4 (M$^+$+1).

EXAMPLE 295

Compound 11793, N-(3-chlorophenyl)-N-(4-(5-(difluoromethyl)-1,3,4-oxadiazol-2-yl)benzyl)-1-(3-hydroxycyclobutyl)piperidine-4-sulfonamide

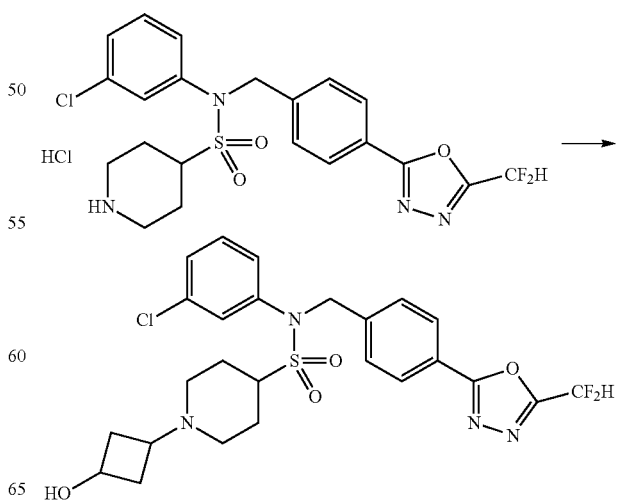

A mixture of N-(3-chlorophenyl)-N-(4-(5-(difluoromethyl)-1,3,4-oxadiazol-2-yl)benzyl)piperidine-4-sulfonamide hydrochloride (0.050 g, 0.096 mmol), 3-hydroxycyclobutan-1-one (0.025 g, 0.289 mmol) and N,N-diisopropylethylamine (0.034 mL, 0.193 mmol) in dichloromethane (5 mL) was treated at the room temperature with sodium triacetoxyborohydride (0.041 g, 0.193 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 5%) to give N-(3-chlorophenyl)-N-(4-(5-(difluoromethyl)-1,3,4-oxadiazol-2-yl)benzyl)-1-(3-hydroxycyclobutyl)piperidine-4-sulfonamide as orange solid (0.021 g, 39.4%).

$^1$H NMR (400 MHz, DMSO-d6) δ 8.04-7.95 (m, 2H), 7.65 (s, 0.25H), 7.56-7.42 (m, 3.5H), 7.41-7.38 (m, 1.25H), 7.37-7.27 (m, 2H), 5.11 (s, 2H), 4.93 (m, 1H), 4.20 (m, 1H), 3.03-2.88 (m, 2H), 2.34 (m, 1H), 2.16-2.05 (m, 4H), 2.04-1.97 (m, 2H), 1.92-1.85 (m, 2H), 1.79-1.58 (m, 3H); LRMS (ES) m/z 553.2 (M⁺+1).

EXAMPLE 296

Compound 11794, 1-cyclobutyl-N-((5-(5-(difluoromethyl)-1,3,4-oxadiazol-2-yl)pyridin-2-yl)methyl)-N-phenylpiperidine-4-sulfonamide

[Step 1] methyl 6-(((1-cyclobutyl-N-phenylpiperidine)-4-sulfonamido)methyl)nicotinate

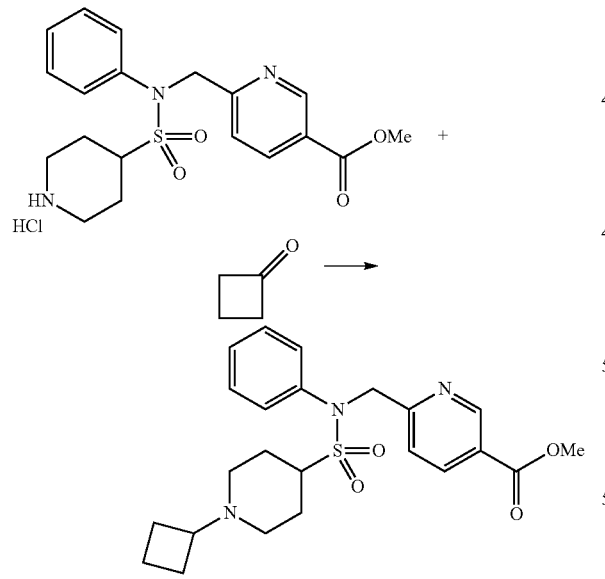

A solution of methyl 6-((N-phenylpiperidine-4-sulfonamido)methyl)nicotinate hydrochloride (0.202 g, 0.474 mmol) and cyclobutanone (0.053 mL, 0.711 mmol) in dichloromethane (20 mL) was stirred at the room temperature for 10 min, and mixed with sodium triacetoxyborohydride (0.302 g, 1.423 mmol). The reaction mixture was stirred at the same temperature for additional 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 30%) to give methyl 6-(((1-cyclobutyl-N-phenylpiperidine)-4-sulfonamido)methyl)nicotinate as white solid (0.100 g, 47.5%).

[Step 2] 1-cyclobutyl-N-((5-(hydrazinecarbonyl)pyridin-2-yl)methyl)-N-phenylpiperidine-4-sulfonamide

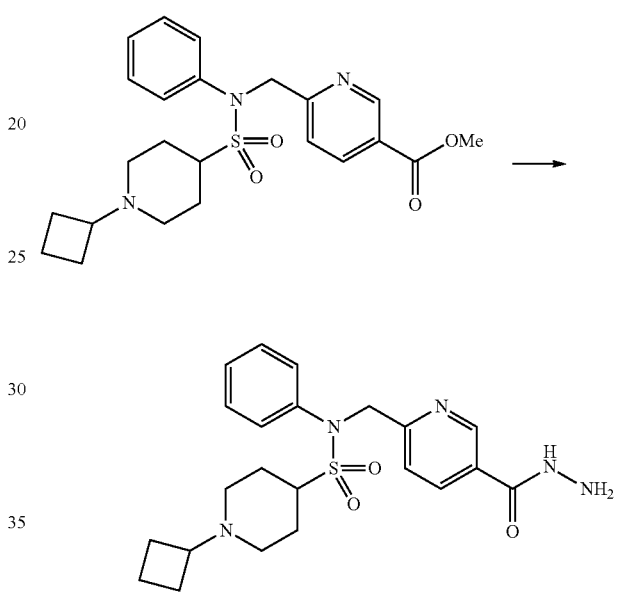

Methyl 6-(((1-cyclobutyl-N-phenylpiperidine)-4-sulfonamido)methyl)nicotinate (0.100 g, 0.225 mmol) and hydrazine monohydrate (0.329 mL, 6.763 mmol) were mixed at the room temperature in ethanol (8 mL), stirred at 80° C. for 18 hr, cooled down to the room temperature to terminate the reaction, and concentrated under the reduced pressure to remove the solvent. The title compound was used without further purification (1-cyclobutyl-N-((5-(hydrazinecarbonyl)pyridin-2-yl)methyl)-N-phenylpiperidine-4-sulfonamide, 0.078 g, 78.0%, white solid).

[Step 3] Compound 11794

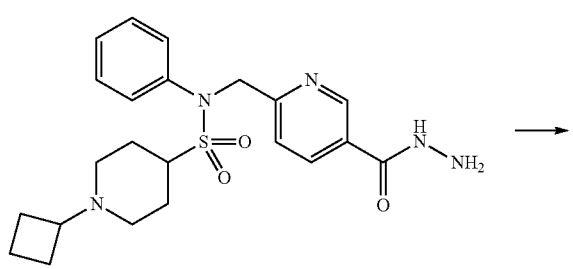

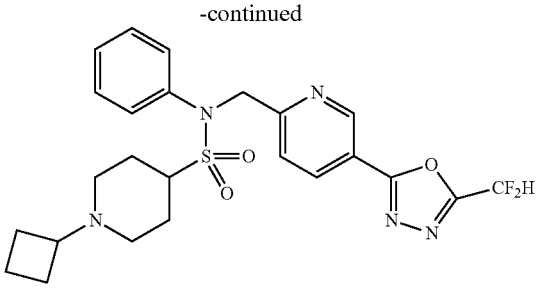

A solution of 1-cyclobutyl-N-((5-(hydrazinecarbonyl) pyridin-2-yl)methyl)-N-phenylpiperidine-4-sulfonamide (0.058 g, 0.131 mmol) and triethylamine (0.091 mL, 0.654 mmol) in tetrahydrofuran (10 mL) was mixed at the room temperature with 2,2-difluoroacetic anhydride (0.049 mL, 0.392 mmol), stirred at 80° C. for 1 hr and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give 1-cyclobutyl-N-((5-(5-(difluoromethyl)-1,3,4-oxadiazol-2-yl)pyridin-2-yl) methyl)-N-phenylpiperidine-4-sulfonamide as white solid (0.032 g, 48.6%).

$^1$H NMR (400 MHz, CDCl$_3$) δ 9.17 (s, 1H), 8.34 (dd, 1H, J=8.2, 2.2 Hz), 7.70-7.65 (m, 1H), 7.41-7.39 (m, 2H), 7.34-7.30 (m, 2H), 7.26-7.23 (m, 1H), 7.04 (s, 0.25H), 6.91 (s, 0.5H), 6.78 (s, 0.25H), 5.16 (s, 2H), 3.18-2.74 (m, 4H), 2.47-1.23 (m, 13H); LRMS (ES) m/z 504.1 (M$^+$+1).

EXAMPLE 297

Compound 11795, (S)—N-(4-(5-(difluoromethyl)-1, 3,4-oxadiazol-2-yl)benzyl)-2-(3-fluoropyrrolidin-1-yl)-N-phenylethane-1-sulfonamide

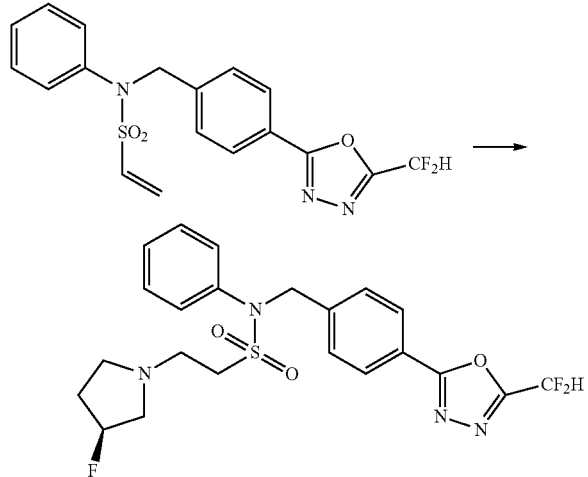

A solution of N-(4-(5-(difluoromethyl)-1,3,4-oxadiazol-2-yl)benzyl)-N-phenylethenesulfonamide (0.100 g, 0.255 mmol), (S)-(+)-3-fluoropyrrolidine, HCl (0.064 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give (S)—N-(4-(5-(difluoromethyl)-1,3,4-oxadiazol-2-yl)benzyl)-2-(3-fluoropyrrolidin-1-yl)-N-phenylethane-1-sulfonamide as white solid (0.015 g, 12.2%).

$^1$H NMR (400 MHz, CDCl$_3$) δ 8.03 (d, 2H, J=8.3 Hz), 7.47 (d, 2H, J=8.3 Hz), 7.36-7.26 (m, 5H), 6.91 (t, 1H, J=51.7 Hz), 5.32-5.19 (s, 1H), 5.01 (s, 2H), 3.42-3.41 (s, 2H), 3.18-3.11 (m, 2H), 3.08-2.97 (m, 3H), 2.68 (m, 1H), 2.31-2.15 (m, 2H); LRMS (ES) m/z 481.3 (M$^+$+1).

EXAMPLE 298

Compound 11796, 2-(dibenzylamino)-N-(4-(5-(difluoromethyl)-1,3,4-oxadiazol-2-yl)benzyl)-N-phenylethane-1-sulfonamide

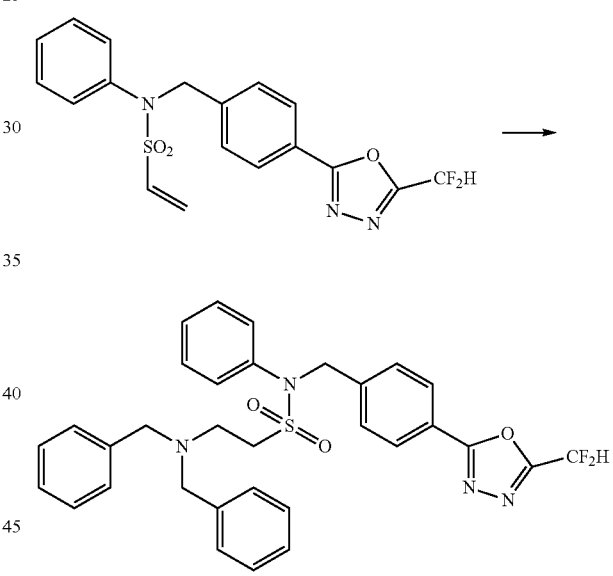

A solution of N-(4-(5-(difluoromethyl)-1,3,4-oxadiazol-2-yl)benzyl)-N-phenylethenesulfonamide (0.100 g, 0.255 mmol), dibenzylamine (0.101 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(dibenzylamino)-N-(4-(5-(difluoromethyl)-1,3,4-oxadiazol-2-yl)benzyl)-N-phenylethane-1-sulfonamide as white solid (0.054 g, 35.9%).

$^1$H NMR (400 MHz, CDCl$_3$) δ 8.00-7.98 (m, 2H), 7.41-7.24 (m, 15H), 6.95 (m, 2H), 6.91 (t, 1H, J=51.7 Hz), 4.71 (s, 2H), 3.66 (m, 4H), 3.23 (m, 2H), 3.06 (m, 2H); LRMS (ES) m/z 590.1 (M$^+$+1).

EXAMPLE 299

Compound 11797, N-(4-(5-(difluoromethyl)-1,3,4-oxadiazol-2-yl)benzyl)-2-(dimethylamino)-N-phenylethane-1-sulfonamide

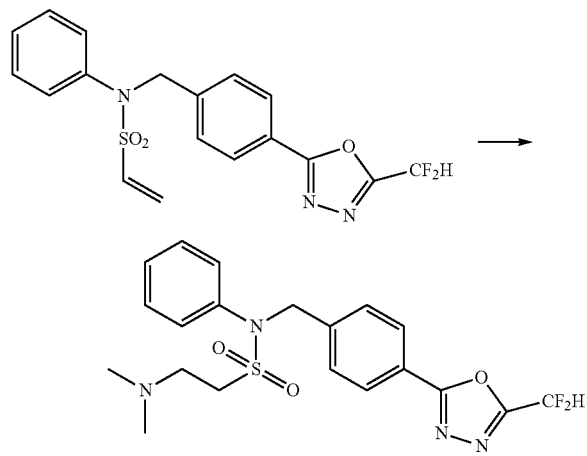

A solution of N-(4-(5-(difluoromethyl)-1,3,4-oxadiazol-2-yl)benzyl)-N-phenylethenesulfonamide (0.100 g, 0.255 mmol), dimethyl amine (2.00 M in THF solution, 0.255 mL, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give N-(4-(5-(difluoromethyl)-1,3,4-oxadiazol-2-yl)benzyl)-2-(dimethylamino)-N-phenylethane-1-sulfonamide as white solid (0.052 g, 46.6%).

$^1$H NMR (700 MHz, CDCl$_3$) δ 8.03-8.02 (m, 2H), 7.47-7.46 (m, 2H), 7.44-7.13 (m, 5H), 6.91 (t, 1H, J=51.7 Hz), 4.97 (s, 2H), 3.40-3.35 (m, 2H), 3.04-2.90 (m, 2H), 2.39 (s, 6H); LRMS (ES) m/z 437.3 (M$^+$+1).

EXAMPLE 300

Compound 11798, 2-(diethylamino)-N-(4-(5-(difluoromethyl)-1,3,4-oxadiazol-2-yl)benzyl)-N-phenylethane-1-sulfonamide

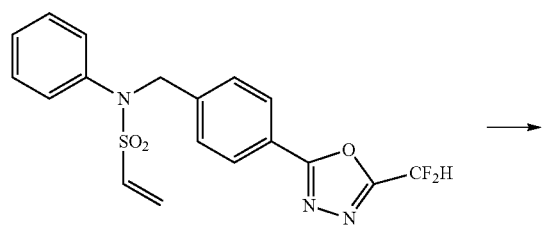

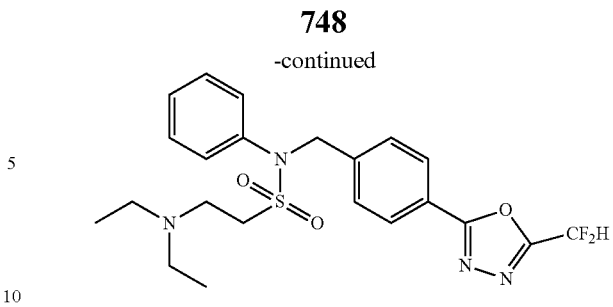

A solution of N-(4-(5-(difluoromethyl)-1,3,4-oxadiazol-2-yl)benzyl)-N-phenylethenesulfonamide (0.100 g, 0.255 mmol), diethyl amine (0.056 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(diethylamino)-N-(4-(5-(difluoromethyl)-1,3,4-oxadiazol-2-yl)benzyl)-N-phenylethane-1-sulfonamide as white solid (0.064 g, 53.9%).

$^1$H NMR (700 MHz, CDCl$_3$) δ 8.03-8.02 (m, 2H), 7.47-7.43 (m, 2H), 7.35-7.26 (m, 5H), 6.91 (t, 1H, J=51.7 Hz), 4.99 (s, 2H), 3.36-3.31 (m, 2H), 3.07-3.02 (m, 2H), 2.65-2.59 (m, 4H), 1.10 (t, 6H, J=7.2 Hz); LRMS (ES) m/z 465.0 (M$^+$+1).

EXAMPLE 301

Compound 11799, N-(4-(5-(difluoromethyl)-1,3,4-oxadiazol-2-yl)benzyl)-2-(3-hydroxyazetidine-1-yl)-N-phenylethane-1-sulfonamide

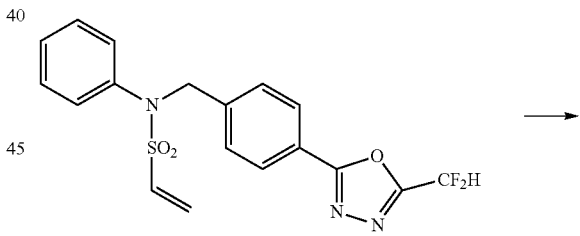

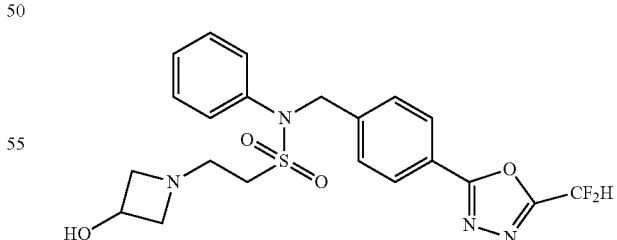

A solution of N-(4-(5-(difluoromethyl)-1,3,4-oxadiazol-2-yl)benzyl)-N-phenylethenesulfonamide (0.100 g, 0.255 mmol), 3-hydroxyazetidine HCl (0.056 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic

EXAMPLE 302

Compound 11800, (S)—N-(4-(5-(difluoromethyl)-1,3,4-oxadiazol-2-yl)benzyl)-2-(3-hydroxypyrrolidin-1-yl)-N-phenylethane-1-sulfonamide

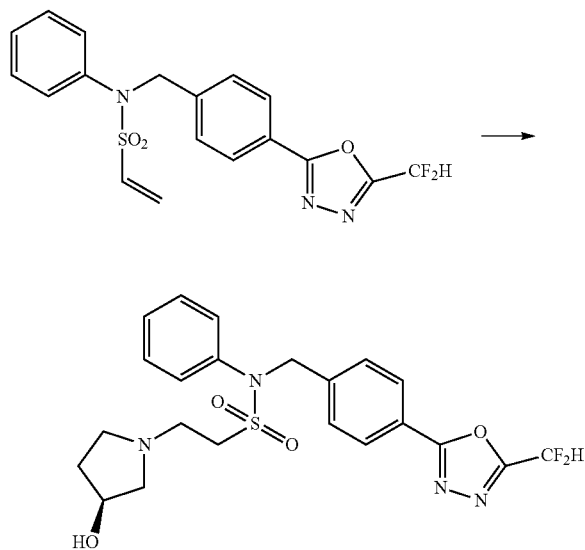 [SMILES: C=CS(=O)(=O)N(Cc1ccc(-c2nnc(C(F)F)o2)cc1)c1ccccc1 ; O=S(=O)(CCN1CC[C@H](O)C1)N(Cc1ccc(-c2nnc(C(F)F)o2)cc1)c1ccccc1]

A solution of N-(4-(5-(difluoromethyl)-1,3,4-oxadiazol-2-yl)benzyl)-N-phenylethenesulfonamide (0.100 g, 0.255 mmol), (s)-3-pyrrolidinol (0.045 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Waters, C18; acetonitrile/aqueous 0.1%-formic acid solution=10% to 90%) to give (S)—N-(4-(5-(difluoromethyl)-1,3,4-oxadiazol-2-yl)benzyl)-2-(3-hydroxypyrrolidin-1-yl)-N-phenylethane-1-sulfonamide as white solid (0.040 g, 32.7%).

¹H NMR (700 MHz, CD3OD) δ 7.98-7.97 (m, 2H), 7.45 (d, 2H, J=8.9 Hz), 7.32-7.25 (m, 5H), 6.97 (t, 1H, J=51.7 Hz), 4.97 (s, 2H), 4.42-4.38 (m, 1H), 3.48-3.46 (m, 2H), 3.23-3.21 (m, 2H), 3.09-3.05 (m, 1H), 3.02-3.00 (m, 1H), 2.87-2.84 (m, 2H), 2.17-2.14 (m, 1H), 1.87-1.85 (m, 1H); LRMS (ES) m/z 479.2 (M⁺+1).

EXAMPLE 303

Compound 11801, (R)—N-(4-(5-(difluoromethyl)-1,3,4-oxadiazol-2-yl)benzyl)-2-(3-hydroxypyrrolidin-1-yl)-N-phenylethane-1-sulfonamide

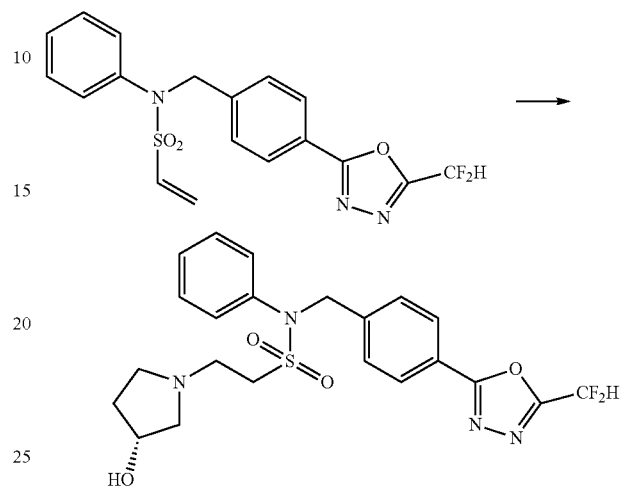

A solution of N-(4-(5-(difluoromethyl)-1,3,4-oxadiazol-2-yl)benzyl)-N-phenylethenesulfonamide (0.100 g, 0.255 mmol), (R)-3-pyrrolidinol (0.045 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Waters, C18; acetonitrile/aqueous 0.1%-formic acid solution=10% to 90%) to give (R)—N-(4-(5-(difluoromethyl)-1,3,4-oxadiazol-2-yl)benzyl)-2-(3-hydroxypyrrolidin-1-yl)-N-phenylethane-1-sulfonamide as white solid (0.036 g, 29.4%).

¹H NMR (700 MHz, CD3OD) δ 8.03-8.01 (m, 2H), 7.55 (d, 2H, J=8.5 Hz), 7.44-7.43 (m, 2H), 7.37-7.28 (m, 3H), 7.21 (t, 1H, J=51.7 Hz), 5.07 (s, 2H), 4.43-4.41 (m, 1H), 3.49-3.47 (m, 2H), 3.16-3.14 (m, 2H), 3.02-2.93 (m, 1H), 2.92-2.88 (dd, 1H, J=10.6, 5.5 Hz), 2.79-2.69 (m, 2H), 2.21-2.14 (ddt, 1H, J=13.7, 8.3, 6.9 Hz), 1.84 (ddddd, 1H, J=13.4, 8.0, 5.5, 2.8, 0.9 Hz); LRMS (ES) m/z 479.0 (M⁺+1).

EXAMPLE 304

Compound 11802, (S)—N-(4-(5-(difluoromethyl)-1,3,4-oxadiazol-2-yl)benzyl)-2-(2-(hydroxymethyl)pyrrolidin-1-yl)-N-phenylethane-1-sulfonamide

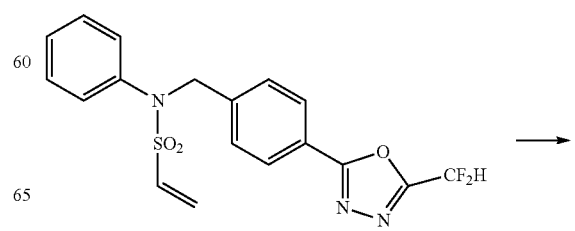

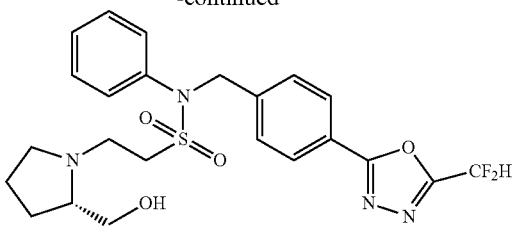

A solution of N-(4-(5-(difluoromethyl)-1,3,4-oxadiazol-2-yl)benzyl)-N-phenylethenesulfonamide (0.100 g, 0.255 mmol), L-prolinol (0.052 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give (S)—N-(4-(5-(difluoromethyl)-1,3,4-oxadiazol-2-yl)benzyl)-2-(2-(hydroxymethyl)pyrrolidin-1-yl)-N-phenylethane-1-sulfonamide as white solid (0.049 g, 38.9%).

$^1$H NMR (700 MHz, CD3OD) δ 8.02-8.01 (m, 2H),7.54 (d, 2H, J=8.5 Hz), 7.42-7.38 (m, 2H), 7.37-7.32 (dd, 2H, J=8.6, 7.1 Hz), 7.30-7.25 (m, 1H), 7.21 (t, 1H, J=51.7 Hz), 5.06 (s, 2H), 3.67-3.62 (dd, 1H, J=11.5, 4.6 Hz), 3.60-3.50 (m, 4H), 3.33 (m, 1H), 3.12-3.11 (ddd, 1H, J=11.5, 8.6, 4.8 Hz), 3.02-2.95 (m, 1H), 2.66-2.59 (td, 1H, J=9.5, 7.4 Hz), 2.06-2.03 (m, 1H), 1.91 (m, 2H), 1.73 (dddd, 1H, J=12.6, 9.1, 6.7, 5.0 Hz); LRMS (ES) m/z 493.0 (M$^+$+1).

EXAMPLE 305

Compound 11803, (R)—N-(4-(5-(difluoromethyl)-1,3,4-oxadiazol-2-yl)benzyl)-2-(2-(hydroxymethyl)pyrrolidin-1-yl)-N-phenylethane-1-sulfonamide

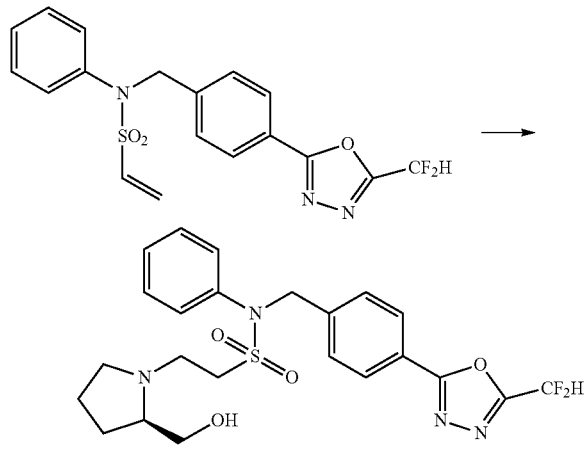

A solution of N-(4-(5-(difluoromethyl)-1,3,4-oxadiazol-2-yl)benzyl)-N-phenylethenesulfonamide (0.100 g, 0.255 mmol), (R)-(−)-prolinol (0.052 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give (R)—N-(4-(5-(difluoromethyl)-1,3,4-oxadiazol-2-yl)benzyl)-2-(2-(hydroxymethyl)pyrrolidin-1-yl)-N-phenylethane-1-sulfonamide as white solid (0.053 g, 42.1%).

$^1$H NMR (700 MHz, CD3OD) δ 8.02-8.01 (m, 2H), 7.54 (d, 2H, J=8.5 Hz), 7.43-7.41 (m, 2H), 7.38-7.35 (m, 2H), 7.31-7.29 (m, 1H), 7.21 (t, 1H, J=51.7 Hz), 5.06 (s, 2H), 3.68-3.66 (dd, 1H, J=11.6, 4.5 Hz), 3.62-3.56 (m, 4H), 3.34 (m, 1H), 3.14-3.13 (ddt, 1H, J=9.8, 7.1, 4.8 Hz), 3.04 (dtd, 1H, J=8.7, 6.3, 4.8 Hz), 2.68-2.66 (td, 1H, J=9.5, 7.4 Hz), 2.07-2.04 (m, 1H), 1.92-1.85 (m, 2H), 1.74 (m, 1H); LRMS (ES) m/z 493.0 (M$^+$+1).

EXAMPLE 306

Compound 11804, (S)—N-(4-(5-(difluoromethyl)-1,3,4-oxadiazol-2-yl)benzyl)-2-(3-(hydroxymethyl)pyrrolidin-1-yl)-N-phenylethane-1-sulfonamide

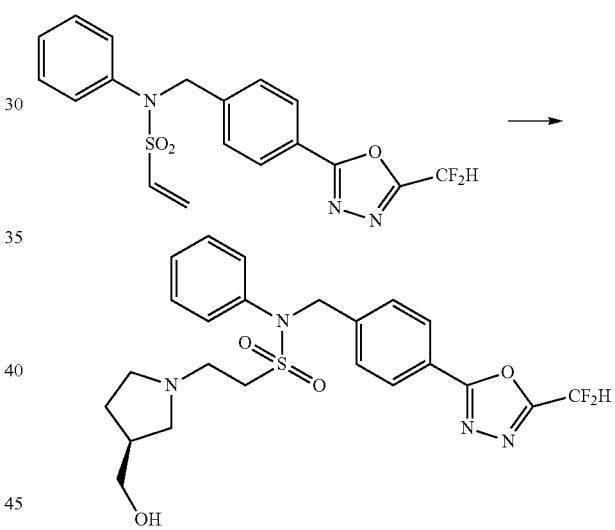

A solution of N-(4-(5-(difluoromethyl)-1,3,4-oxadiazol-2-yl)benzyl)-N-phenylethenesulfonamide (0.100 g, 0.255 mmol), (S)-pyrrolidin-3-ylmethanol (0.052 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give (S)—N-(4-(5-(difluoromethyl)-1,3,4-oxadiazol-2-yl)benzyl)-2-(3-(hydroxymethyl)pyrrolidin-1-yl)-N-phenylethane-1-sulfonamide as white solid (0.035 g, 27.8%).

$^1$H NMR (700 MHz, CD3OD) δ 8.02-8.01 (m, 2H),7.54 (d, 2H, J=8.4 Hz), 7.43-7.42 (m, 2H), 7.38-7.35 (m, 2H), 7.31-7.29 (m, 1H), 7.21 (t, 1H, J=51.7 Hz), 5.06 (s, 2H), 3.59-3.57 (ddd, 3H, J=10.7, 5.6, 2.2 Hz), 3.54-3.51 (dd, 1H, J=10.7, 6.8 Hz), 3.33-3.30 (m, 2H), 3.15-3.13 (dd, 1H, J=10.4, 8.1 Hz), 3.04-3.02 (m, 2H), 2.85-2.84 (dd, 1H, J=10.4, 6.5 Hz), 2.54-2.51 (tt, 1H, J=8.4, 6.3 Hz), 2.12-2.05 (m, 1H), 1.74-1.71 (dtd, 1H, J=13.6, 7.5, 6.2 Hz); LRMS (ES) m/z 493.0 (M$^+$+1).

EXAMPLE 307

Compound 11805, (R)—N-(4-(5-(difluoromethyl)-1,3,4-oxadiazol-2-yl)benzyl)-2-(3-(hydroxymethyl)pyrrolidin-1-yl)-N-phenylethane-1-sulfonamide

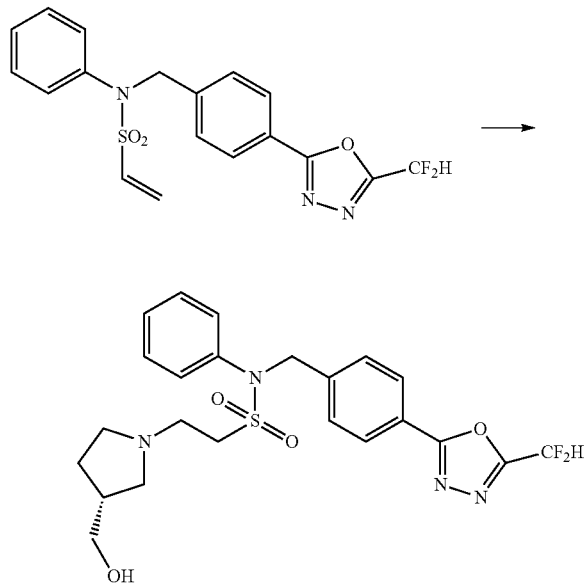 [SMILES: C=CS(=O)(=O)N(Cc1ccc(-c2nnc(C(F)F)o2)cc1)c1ccccc1 ; O=S(=O)(CCN1CC[C@@H](CO)C1)N(Cc1ccc(-c2nnc(C(F)F)o2)cc1)c1ccccc1]

A solution of N-(4-(5-(difluoromethyl)-1,3,4-oxadiazol-2-yl)benzyl)-N-phenylethenesulfonamide (0.100 g, 0.255 mmol), (R)-3-(hydroxymethyl)pyrrolidine (0.052 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give (R)—N-(4-(5-(difluoromethyl)-1,3,4-oxadiazol-2-yl)benzyl)-2-(3-(hydroxymethyl)pyrrolidin-1-yl)-N-phenylethane-1-sulfonamide as white solid (0.040 g, 31.8%).

$^1$H NMR (700 MHz, CD3OD) δ 8.04-8.03 (m, 2H),7.55 (d, 2H, J=8.5 Hz), 7.43-7.42 (m, 2H), 7.38-7.36 (m, 2H), 7.31-7.28 (m, 1H), 7.21 (t, 1H, J=51.7 Hz), 5.07 (s, 2H), 3.58-3.52 (dd, 1H, J=10.6, 5.9 Hz), 3.54-3.50 (m, 3H), 3.23-3.20 (m, 2H), 3.04-3.01 (dd, 1H, J=10.1, 8.0 Hz), 2.92-2.90 (t, 2H, J=7.2 Hz), 2.73-2.71 (dd, 1H, J=10.1, 6.3 Hz), 2.50-2.48 (tdd, 1H, J=8.9, 6.4, 4.0 Hz), 2.09-2.05 (m, 1H), 1.69-1.67 (dtd, 1H, J=13.4, 7.3, 6.0 Hz); LRMS (ES) m/z 493.0 (M$^+$+1).

EXAMPLE 308

Compound 11806, N-(4-(5-(difluoromethyl)-1,3,4-oxadiazol-2-yl)benzyl)-2-(2-methyl-1H-imidazol-1-yl)-N-phenylethane-1-sulfonamide

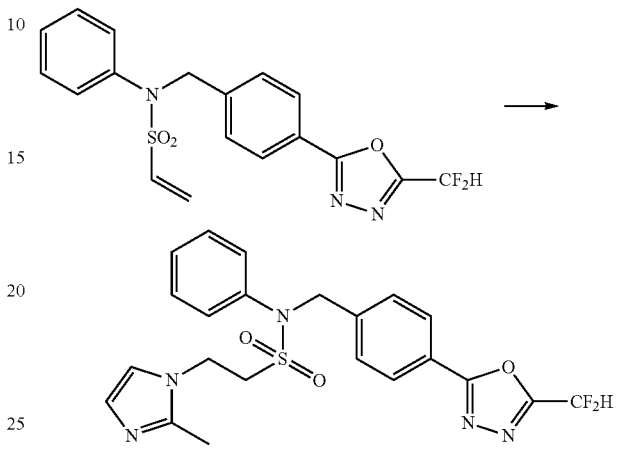

A solution of N-(4-(5-(difluoromethyl)-1,3,4-oxadiazol-2-yl)benzyl)-N-phenylethenesulfonamide (0.100 g, 0.255 mmol), 2-methylimidazole (0.042 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(2-methyl-1H-imidazol-1-yl)-N-phenylethane-1-sulfonamide as white solid (0.034 g, 28.1%).

$^1$H NMR (700 MHz, CD3OD) δ 8.02-8.01 (m, 2H),7.52 (d, 2H, J=8.5 Hz), 7.39-7.35 (m, 4H), 7.32-7.28 (m, 2H), 7.21 (t, 1H, J=51.7 Hz), 7.11 (m, 1H), 5.01 (s, 2H), 4.52 (t, 2H, J=6.5 Hz), 3.76 (t, 2H, J=6.5 Hz), 2.50 (s, 3H); LRMS (ES) m/z 474.3 (M$^+$+1).

EXAMPLE 309

Compound 11807, N-(4-(5-(difluoromethyl)-1,3,4-oxadiazol-2-yl)benzyl)-2-(5-methyl-1H-imidazol-1-yl)-N-phenylethane-1-sulfonamide

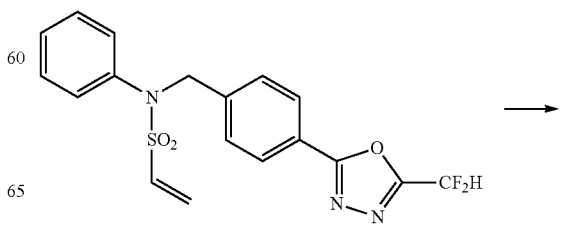

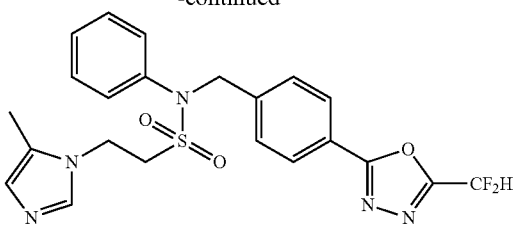

A solution of N-(4-(5-(difluoromethyl)-1,3,4-oxadiazol-2-yl)benzyl)-N-phenylethenesulfonamide (0.100 g, 0.255 mmol), 4-methylimidazole (0.042 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(5-methyl-1H-imidazol-1-yl)-N-phenylethane-1-sulfonamide as white solid (0.060 g, 49.6%).

¹H NMR (700 MHz, CD3OD) δ 8.01-7.94 (m, 2H), 7.52-7.51 (m, 2H), 7.39-7.34 (m, 5H), 7.29 (m, 1H), 7.28 (m, 1H), 7.21 (t, 1H, J=51.7 Hz), 5.02 (d, 2H, J=8.3 Hz), 4.54-4.51 (td, 2H, J=6.7, 2.3 Hz), 3.76-3.72 (dt, 2H, J=19.3, 6.7 Hz), 2.29-2.28 (m, 3H); LRMS (ES) m/z 474.1 (M⁺+1).

EXAMPLE 310

Compound 11808, N-(4-(5-(difluoromethyl)-1,3,4-oxadiazol-2-yl)benzyl)-2-(4-(hydroxymethyl)-1H-imidazol-1-yl)-N-phenylethane-1-sulfonamide

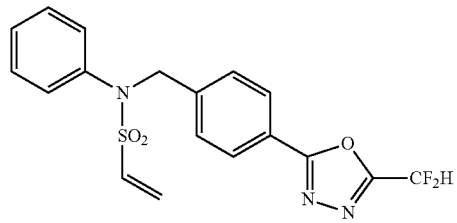

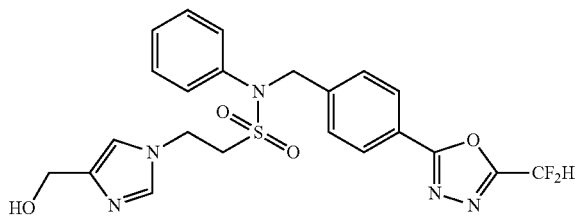

A solution of N-(4-(5-(difluoromethyl)-1,3,4-oxadiazol-2-yl)benzyl)-N-phenylethenesulfonamide (0.100 g, 0.255 mmol), (1H-imidazole-4-yl)methanol (0.05 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(4-(hydroxymethyl)-1H-imidazol-1-yl)-N-phenylethane-1-sulfonamide as white solid (0.043 g, 34.4%).

¹H NMR (400 MHz, CD3OD) δ 7.98 (d, 2H, J=8.3 Hz), 7.49 (dd, 2H, J=8.5, 2.3 Hz), 7.40-7.28 (m, 7H), 7.21 (t, 1H, J J=51.6 Hz), 5.01 (d, 2H, J=5.9 Hz), 4.66-4.55 (m, 4H), 3.88 (t, 1H, J=6.9 Hz), 3.76 (t, 1H, J=6.7 Hz); LRMS (ES) m/z 490.3 (M⁺+1).

EXAMPLE 311

Compound 11809, N-(4-(5-(difluoromethyl)-1,3,4-oxadiazol-2-yl)benzyl)-N-phenyl-2-(1H-1,2,4-triazol-1-yl)ethane-1-sulfonamide

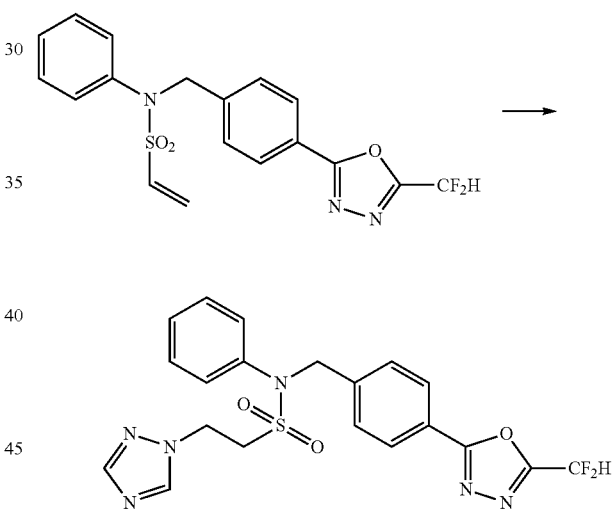

A solution of N-(4-(5-(difluoromethyl)-1,3,4-oxadiazol-2-yl)benzyl)-N-phenylethenesulfonamide (0.100 g, 0.255 mmol), 1,2,4-1H-triazole (0.035 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-N-phenyl-2-(1H-1,2,4-triazol-1-yl)ethane-1-sulfonamide as white solid (0.030 g, 25.5%).

¹H NMR (400 MHz, CDCl₃) δ 8.38 (s, 1H), 8.05-8.01 (m, 3H), 7.41 (d, 2H, J=8.4 Hz), 7.37-7.23 (m, 5H), 6.91 (t, 1H, J=51.7 Hz), 4.85 (s, 2H), 4.69 (t, 2H, J=6.8 Hz), 3.71 (t, 2H, J=6.8 Hz); LRMS (ES) m/z 461.0 (M⁺+1).

EXAMPLE 312

Compound 11810, N-(4-(5-(difluoromethyl)-1,3,4-oxadiazol-2-yl)benzyl)-2-(4-(hydroxymethyl)piperidin-1-yl)-N-phenylethane-1-sulfonamide

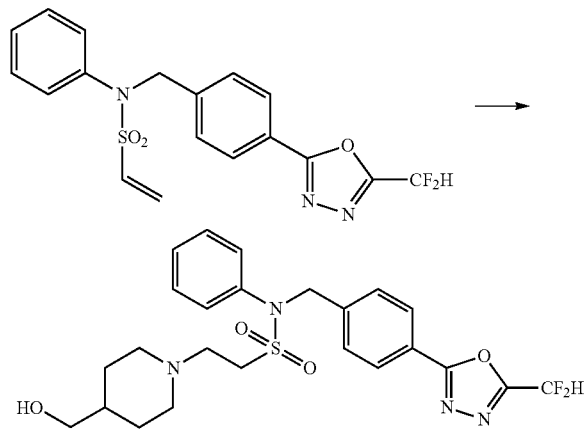

A solution of N-(4-(5-(difluoromethyl)-1,3,4-oxadiazol-2-yl)benzyl)-N-phenylethenesulfonamide (0.100 g, 0.255 mmol), piperidin-4-ylmethanol (0.059 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(4-(hydroxymethyl)piperidin-1-yl)-N-phenylethane-1-sulfonamide as white solid (0.100 g, 77.3%).

$^1$H NMR (400 MHz, CDCl$_3$) δ 8.00 (d, 2H, J=8.3 Hz), 7.45 (d, 2H, J=8.3 Hz), 7.35-7.24 (m, 5H), 6.91 (t, 1H, J=51.7 Hz), 4.97 (s, 2H), 3.51 (d, 2H, J J=6.4 Hz), 3.34-3.31 (m, 2H), 2.96-2.90 (m, 4H), 2.10 (td, 1H, J=11.7, 2.5 Hz), 1.97 (m, 1H), 1.81-1.78 (m, 2H), 1.56-1.49 (m, 1H), 1.37-1.33 (m, 2H); LRMS (ES) m/z 507.3 (M$^+$+1).

EXAMPLE 313

Compound 11811, N-(4-(5-(difluoromethyl)-1,3,4-oxadiazol-2-yl)benzyl)-2-(3-(hydroxymethyl)piperidin-1-yl)-N-phenylethane-1-sulfonamide

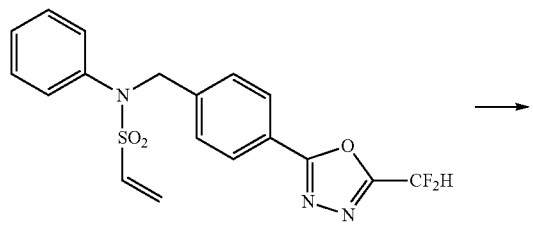

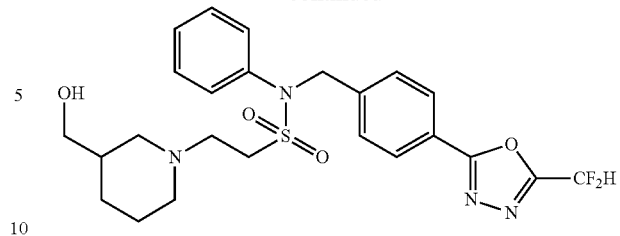

A solution of N-(4-(5-(difluoromethyl)-1,3,4-oxadiazol-2-yl)benzyl)-N-phenylethenesulfonamide (0.100 g, 0.255 mmol), 3-piperidinemethanol (0.059 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(3-(hydroxymethyl)piperidin-1-yl)-N-phenylethane-1-sulfonamide as white solid (0.090 g, 69.5%).

$^1$H NMR (400 MHz, CDCl$_3$) δ 8.01 (d, 2H, J=8.2 Hz), 7.45 (d, 2H, J=8.2 Hz), 7.35-7.24 (m, 5H), 6.91 (t, 1H, J=51.7 Hz), 4.97 (s, 2H), 3.62-3.47 (m, 2H) 3.34 (t, 2H, J=7.4 Hz), 2.92 (qt, 4H, J=7.4, 4.5 Hz), 2.75 (dd, 1H, J=10.2, 5.4 Hz), 2.17 (td, 1H, J=10.4, 2.6 Hz), 2.01 (t, 1H, J J=10.1 Hz), 1.87 (dd, 1H, J=11.7, 6.3 Hz), 1.76 (ddt, 1H, J=15.6, 8.6, 4.2 Hz), 1.74-1.55 (m, 1H), 1.08 (td, 1H, J=14.0, 12.7, 6.0 Hz)); LRMS (ES) m/z 507.4 (M$^+$+1).

EXAMPLE 314

Compound 11812, (S)-1-(2-(N-(4-(5-(difluoromethyl)-1,3,4-oxadiazol-2-yl)benzyl)-N-phenylsulfamoyl)ethyl)pyrrolidine-2-carboxamide

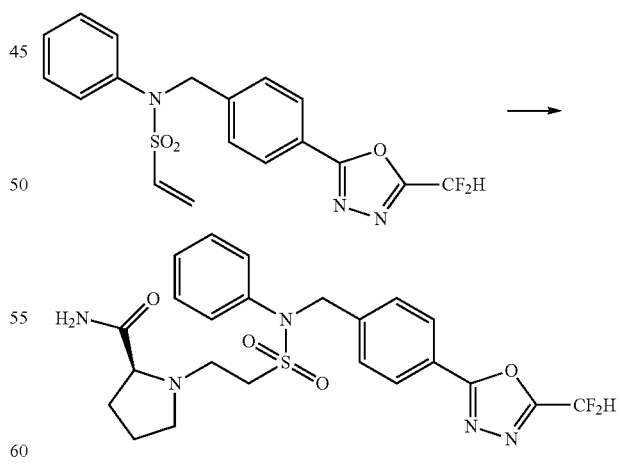

A solution of N-(4-(5-(difluoromethyl)-1,3,4-oxadiazol-2-yl)benzyl)-N-phenylethenesulfonamide (0.100 g, 0.255 mmol), L-prolinamide (0.058 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Waters, C18; acetonitrile/aqueous 0.1%-formic acid solution=10% to 90%) to give (S)-1-(2-(N-(4-(5-(difluoromethyl)-1,3,4-oxadiazol-2-yl)benzyl)-N-phenylsulfamoyl)ethyl)pyrrolidine-2-carboxamide as white solid (0.120 g, 92.9%).

¹H NMR (400 MHz, DMSO-d6) δ7.95 (d, 2H, J=8.0 Hz), 7.48 (d, 2H, J=8.1 Hz), 7.39-7.21 (m, 6H), 7.08 (br, 2H), 4.99 (s, 2H), 3.99 (q, 1H, J=5.3 Hz), 3.45 (m, 2H), 3.32-3.15 (m, 2H), 2.95-2.82 (m, 2H), 2.31 (m, 1H), 2.07 (m, 1H), 1.74-1.69 (m, 2H); LRMS (ES) m/z 506.3 (M⁺+1).

EXAMPLE 315

Compound 11813, (R)-1-(2-(N-(4-(5-(difluoromethyl)-1,3,4-oxadiazol-2-yl)benzyl)-N-phenylsulfamoyl)ethyl)pyrrolidine-2-carboxamide

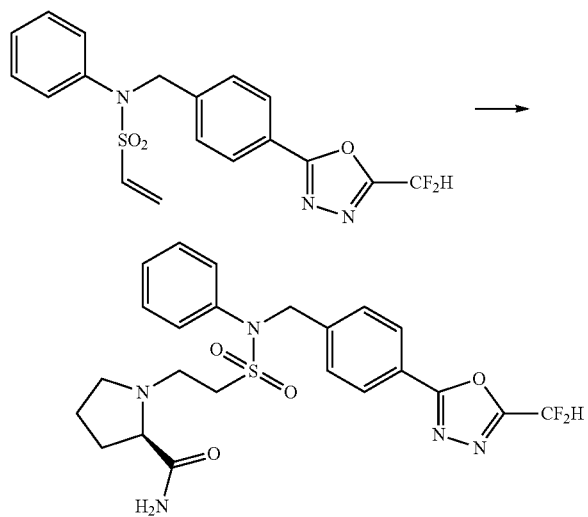

A solution of N-(4-(5-(difluoromethyl)-1,3,4-oxadiazol-2-yl)benzyl)-N-phenylethenesulfonamide (0.100 g, 0.255 mmol), D-(−)-prolinamide (0.058 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Waters, C18; acetonitrile/aqueous 0.1%-formic acid solution=10% to 90%) to give (R)-1-(2-(N-(4-(5-(difluoromethyl)-1,3,4-oxadiazol-2-yl)benzyl)-N-phenylsulfamoyl)ethyl)pyrrolidine-2-carboxamide as white solid (0.120 g, 92.9%).

¹H NMR (400 MHz, DMSO-d6) δ 7.96 (d, 2H, J=8.4 Hz), 7.50 (d, 2H, J=8.3 Hz), 7.43-7.22 (m, 6H), 7.11 (br, 2H), 5.00 (s, 2H), 4.02 (q, 1H, J=5.2 Hz), 3.47 (m, 2H), 3.32 (s, 1H), 3.15-3.13 (m, 1H), 2.94-2.81 (m, 2H), 2.34-2.30 (m, 1H), 2.06 (m, 1H), 1.74-1.69 (m, 2H); LRMS (ES) m/z 506.1 (M⁺+1).

EXAMPLE 316

Compound 11814, tert-butyl 7-(2-(N-(4-(5-(difluoromethyl)-1,3,4-oxadiazol-2-yl)benzyl)-N-phenylsulfamoyl)ethyl)-2,7-diazaspiro[3.5]nonane-2-carboxylate

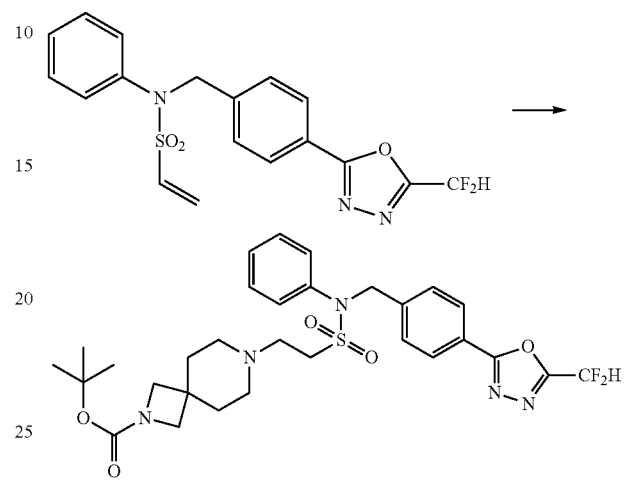

A solution of N-(4-(5-(difluoromethyl)-1,3,4-oxadiazol-2-yl)benzyl)-N-phenylethenesulfonamide (0.100 g, 0.255 mmol), 2,7-diazaspiro[3.5]nonane-2-carboxylic acid tert-butyl ester (0.116 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Waters, C18; acetonitrile/aqueous 0.1%-formic acid solution=10% to 90%) to give tert-butyl 7-(2-(N-(4-(5-(difluoromethyl)-1,3,4-oxadiazol-2-yl)benzyl)-N-phenylsulfamoyl)ethyl)-2,7-diazaspiro[3.5]nonane-2-carboxylate as white solid (0.040 g, 25.3%).

¹H NMR (700 MHz, CD3OD) δ 8.01 (d, 2H, J=8.4 Hz), 7.54 (d, 2H, J=8.4 Hz), 7.43-7.41 (m, 2H), 7.37-7.34 (m, 2H), 7.30-7.28 (m, 1H), 7.21 (t, 1H, J=51.7 Hz), 5.05 (s, 2H), 3.64-3.63 (s, 4H), 3.43-3.41 (m, 2H), 2.90-2.87 (m, 2H), 2.49 (s, 4H), 1.85 (m, 4H), 1.46 (s, 9H); LRMS (ES) m/z 618.4 (M⁺+1).

EXAMPLE 317

Compound 11815, N-(4-(5-(difluoromethyl)-1,3,4-oxadiazol-2-yl)benzyl)-2-(3,3-difluoropyrrolidin-1-yl)-N-phenylethane-1-sulfonamide

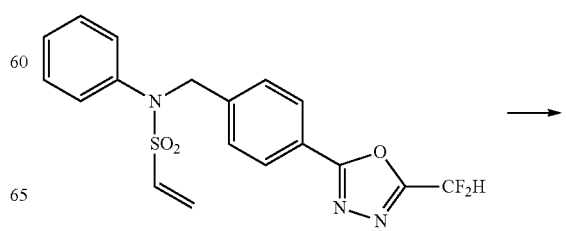

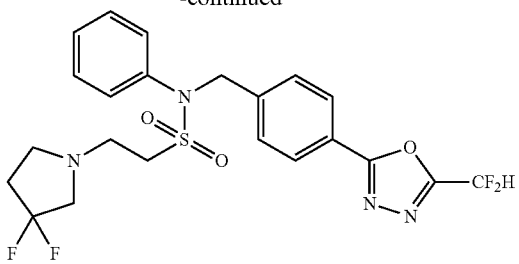

A solution of N-(4-(5-(difluoromethyl)-1,3,4-oxadiazol-2-yl)benzyl)-N-phenylethenesulfonamide (0.100 g, 0.255 mmol), 3,3-difluoropyrrolidine hydrochloride (0.073 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(3,3-difluoropyrrolidin-1-yl)-N-phenylethane-1-sulfonamide as white solid (0.035 g, 27.5%).

$^1$H NMR (700 MHz, CD3OD) δ 8.03-8.02 (m, 2H),7.55 (d, 2H, J=8.5 Hz), 7.43-7.42 (m, 2H), 7.37-7.35 (m, 2H), 7.30-7.28 (m, 1H), 7.21 (t, 1H, J=51.7 Hz), 5.06 (s, 2H), 3.43-3.40 (m, 2H), 3.02-2.98 (m, 4H), 2.85-2.83 (t, 2H, J=7.0 Hz), 2.31 (tt, 2H, J=14.6, 7.0 Hz); LRMS (ES) m/z 499.1 (M$^+$+1).

EXAMPLE 318

Compound 11816, N-(4-(5-(difluoromethyl)-1,3,4-oxadiazol-2-yl)benzyl)-2-(1H-imidazol-1-yl)-N-phenylethane-1-sulfonamide

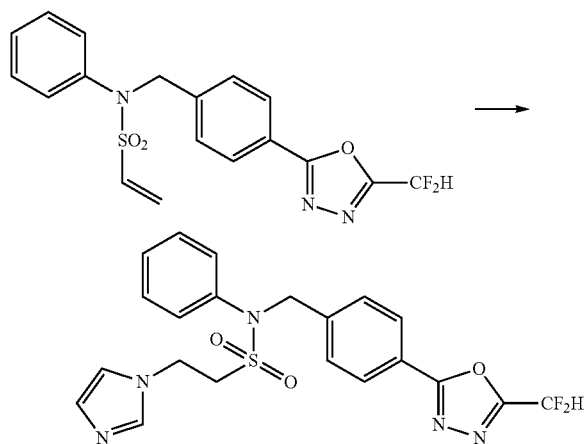

A solution of N-(4-(5-(difluoromethyl)-1,3,4-oxadiazol-2-yl)benzyl)-N-phenylethenesulfonamide (0.100 g, 0.255 mmol), imidazole (0.035 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(1H-imidazol-1-yl)-N-phenylethane-1-sulfonamide as white solid (0.042 g, 35.8%).

$^1$H NMR (700 MHz, CD3OD) δ 8.03-8.02 (m, 2H),7.86 (s, 1H),7.53 (d, 2H, J=8.5 Hz), 7.39-7.35 (m, 4H), 7.31-7.28 (m, 2H), 7.21 (t, 1H, J=51.7 Hz), 7.06 (s, 1H), 5.01 (s, 2H), 4.57 (t, 2H, J=6.8 Hz), 3.75 (t, 2H, J=6.8 Hz); LRMS (ES) m/z 460.0 (M$^+$+1).

EXAMPLE 319

Compound 11817, (S)—N-(4-(5-(difluoromethyl)-1,3,4-oxadiazol-2-yl)benzyl)-2-(3-hydroxypiperidin-1-yl)-N-phenylethane-1-sulfonamide

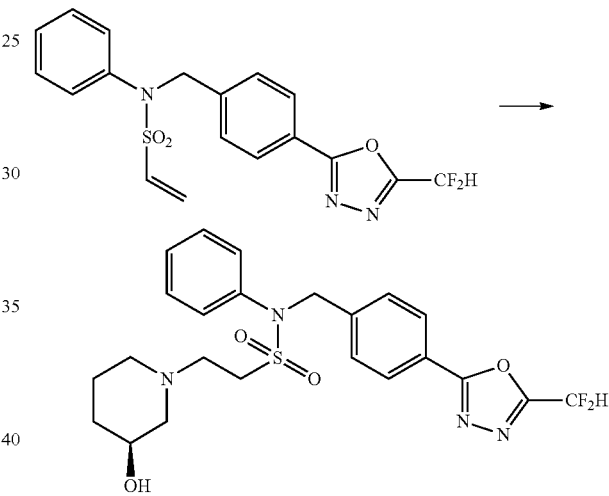

A solution of N-(4-(5-(difluoromethyl)-1,3,4-oxadiazol-2-yl)benzyl)-N-phenylethenesulfonamide (0.100 g, 0.255 mmol), (S)-3-hydroxypiperidine hydrochloride (0.070 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give (S)—N-(4-(5-(difluoromethyl)-1,3,4-oxadiazol-2-yl)benzyl)-2-(3-hydroxypiperidin-1-yl)-N-phenylethane-1-sulfonamide as white solid (0.051 g, 40.5%).

$^1$H NMR (700 MHz, CD3OD) δ 7.98 (d, 2H, J=8.3 Hz), 7.51 (d, 2H, J=8.3 Hz), 7.44-7.42 (m, 2H), 7.37-7.34 (m, 2H), 7.30-7.28 (m, 1H), 7.21 (t, 1H, J=51.6 Hz), 5.05 (s, 2H), 3.87 (tt, 1H, J=7.5, 3.4 Hz), 3.59 (td, 2H, J=6.9, 2.3 Hz), 3.21 (dd, 2H, J=8.3, 6.9 Hz), 3.07 (dd, 1H, J=11.4, 3.2 Hz), 2.92 (m, 1H), 2.66 (m, 1H), 2.58 (m, 1H), 1.92 (m, 2H), 1.74-1.59 (m, 1H), 1.47 (m, 1H); LRMS (ES) m/z 493.3 (M$^+$+1).

EXAMPLE 320

Compound 11818, 2-(4-cyanopiperidin-1-yl)-N-(4-(5-(difluoromethyl)-1,3,4-oxadiazol-2-yl)benzyl)-N-phenylethane-1-sulfonamide

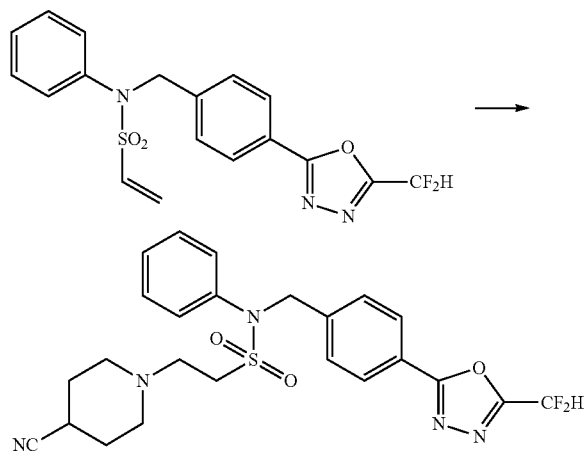

A solution of N-(4-(5-(difluoromethyl)-1,3,4-oxadiazol-2-yl)benzyl)-N-phenylethenesulfonamide (0.100 g, 0.255 mmol), 4-cyanopiperidine (0.056 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give 2-(4-cyanopiperidin-1-yl)-N-(4-(5-(difluoromethyl)-1,3,4-oxadiazol-2-yl)benzyl)-N-phenylethane-1-sulfonamide as white solid (0.080 g, 62.4%).

$^1$H NMR (700 MHz, CD3OD) δ 8.03 (d, 2H, J=8.3 Hz), 7.55 (d, 2H, J=8.3 Hz), 7.43-7.41 (m, 2H), 7.37-7.35 (m, 2H), 7.30-7.28 (m, 1H), 7.21 (t, 1H, J=51.7 Hz), 5.06 (s, 2H), 3.43-3.42 (m, 2H), 2.91-2.89 (m, 2H), 2.84-2.74 (m, 3H), 2.45 (m, 2H), 2.02-1.98 (m, 2H), 1.88-1.84 (m, 2H); LRMS (ES) m/z 502.3 (M$^+$+1).

EXAMPLE 321

Compound 11819, N-(4-(5-(difluoromethyl)-1,3,4-oxadiazol-2-yl)benzyl)-2-(4-(4-fluorophenyl)piperidin-1-yl)-N-phenylethane-1-sulfonamide

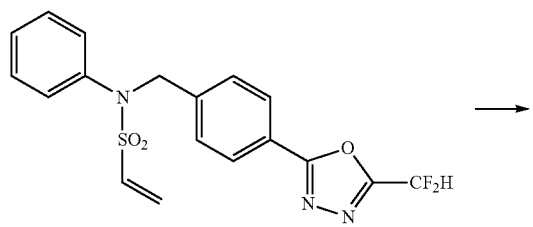

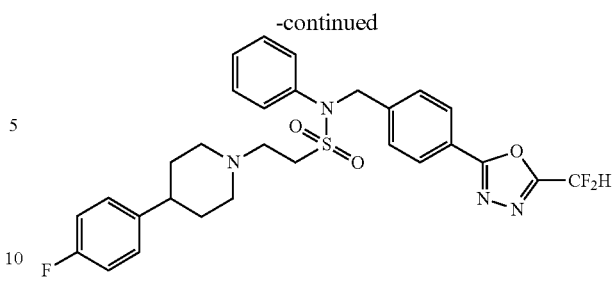

A solution of N-(4-(5-(difluoromethyl)-1,3,4-oxadiazol-2-yl)benzyl)-N-phenylethenesulfonamide (0.100 g, 0.255 mmol), 4-(4-fluoro-phenyl)-piperidine hydrochloride (0.110 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(4-(4-fluorophenyl)piperidin-1-yl)-N-phenylethane-1-sulfonamide as white solid (0.040 g, 27.4%).

$^1$H NMR (400 MHz, CDCl$_3$) δ 7.74 (d, 2H, J=8.3 Hz), 7.23-7.20 (m, 2H), 7.15-7.03 (m, 4H), 6.98-6.96 (m, 2H), 6.83-6.68 (m, 4H), 4.76 (s, 2H), 3.65-3.59 (m, 2H), 3.43-3.41 (m, 2H), 3.29-3.27 (m, 2H), 2.84-2.81 (m, 2H), 2.59-2.55 (m, 1H), 1.97-1.92 (m, 2H), 1.84-1.80 (m, 2H); LRMS (ES) m/z 571.2 (M$^+$+1).

EXAMPLE 322

Compound 11820, methyl 1-(2-(N-(4-(5-(difluoromethyl)-1,3,4-oxadiazol-2-yl)benzyl)-N-phenylsulfamoyl)ethyl)azetidine-3-carboxylate

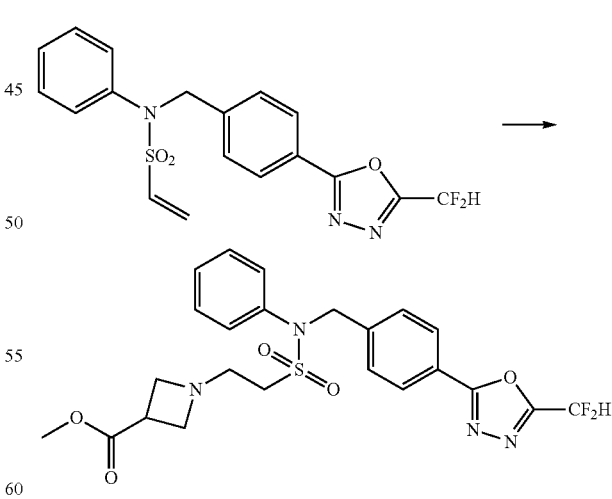

A solution of N-(4-(5-(difluoromethyl)-1,3,4-oxadiazol-2-yl)benzyl)-N-phenylethenesulfonamide (0.100 g, 0.255 mmol), methyl azetidine-3-carboxylate hydrochloride (0.077 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give methyl 1-(2-(N-(4-(5-(difluoromethyl)-1,3,4-oxadiazol-2-yl)benzyl)-N-phenylsulfamoyl)ethyl)azetidine-3-carboxylate as white solid (0.042 g, 32.5%).

$^1$H NMR (400 MHz, CD3OD) δ 8.04-8.02 (m, 2H),7.55 (d, 2H, J=8.5 Hz), 7.43-7.42 (m, 2H), 7.37-7.35 (m, 2H), 7.31-7.28 (m, 1H), 7.21 (t, 1H, J=51.7 Hz), 5.06 (s, 2H), 3.76-3.74 (m, 2H), 3.75 (s, 3H), 3.65-3.62 (m, 2H), 3.45-3.40 (m, 1H), 3.33-3.32 (m, 2H), 3.14-3.13 (t, 2H, J=7.1 Hz); LRMS (ES) m/z 507.3 (M$^+$+1).

EXAMPLE 323

Compound 11821, 2-(3,3-difluoroazetidin-1-yl)-N-(4-(5-(difluoromethyl)-1,3,4-oxadiazol-2-yl)benzyl)-N-phenylethane-1-sulfonamide

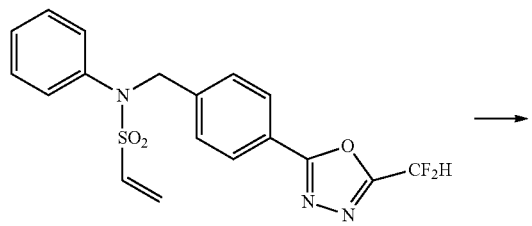

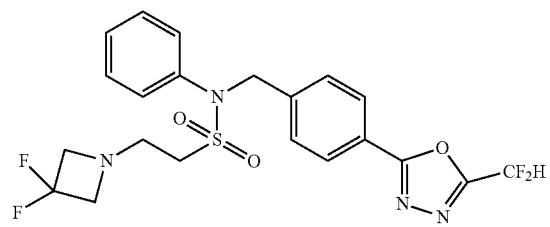

A solution of N-(4-(5-(difluoromethyl)-1,3,4-oxadiazol-2-yl)benzyl)-N-phenylethenesulfonamide (0.100 g, 0.255 mmol), 3,3-difluoroazetidine hydrochloride (0.066 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(3,3-difluoroazetidin-1-yl)-N-(4-(5-(difluoromethyl)-1,3,4-oxadiazol-2-yl)benzyl)-N-phenylethane-1-sulfonamide as white solid (0.065 g, 52.5%).

$^1$H NMR (400 MHz, CD3OD) δ 8.02-8.00 (m, 2H), 7.54 (d, 2H, J=8.5 Hz), 7.43-7.41 (m, 2H), 7.42-7.33 (m, 2H), 7.30-7.28 (m, 1H), 7.21 (t, 1H, J=51.6 Hz), 5.05 (s, 2H), 3.69 (t, 4H, J=12.1 Hz), 3.37-3.30 (m, 4H), 3.11-3.07 (m, 2H)); LRMS (ES) m/z 485.3 (M$^+$+1).

EXAMPLE 324

Compound 11822, N-(4-(5-(difluoromethyl)-1,3,4-oxadiazol-2-yl)benzyl)-2-(4-hydroxypiperidin-1-yl)-N-phenylethane-1-sulfonamide

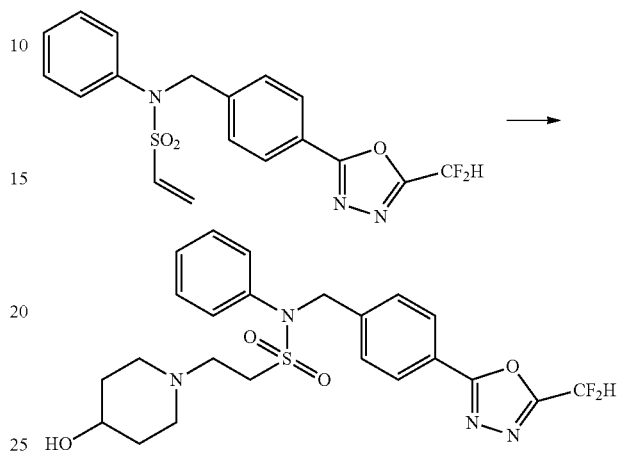

A solution of N-(4-(5-(difluoromethyl)-1,3,4-oxadiazol-2-yl)benzyl)-N-phenylethenesulfonamide (0.100 g, 0.255 mmol), 4-hydroxy piperidine (0.052 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Waters, C18; acetonitrile/aqueous 0.1%-formic acid solution=10% to 90%) to give N-(4-(5-(difluoromethyl)-1,3,4-oxadiazol-2-yl)benzyl)-2-(4-hydroxypiperidin-1-yl)-N-phenylethane-1-sulfonamide as white solid (0.046 g, 36.6%).

$^1$H NMR (400 MHz, CD3OD) δ 8.00 (d, 2H, J=8.4 Hz), 7.53 (d, 2H, J=8.4 Hz), 7.43-7.42 (m, 2H), 7.37-7.34 (m, 2H), 7.31-7.29 (m, 1H), 7.21 (t, 1H, J=51.6 Hz), 5.05 (s, 2H), 3.73 (m, 1H), 3.52-3.37 (m, 2H), 3.07-2.97 (m, 4H), 2.53-2.50 (m, 2H), 1.96-1.91 (m, 2H), 1.68-1.63 (m, 2H); LRMS (ES) m/z 493.0 (M$^+$+1).

EXAMPLE 325

Compound 11836, N-(3-chlorophenyl)-N-(4-(5-(difluoromethyl)-1,3,4-oxadiazol-2-yl)benzyl)-1-(1-(2-hydroxyacetyl)azetidin-3-yl)piperidine-4-sulfonamide

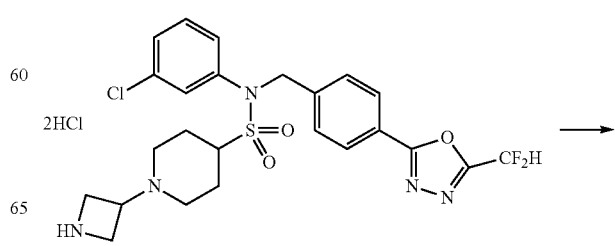

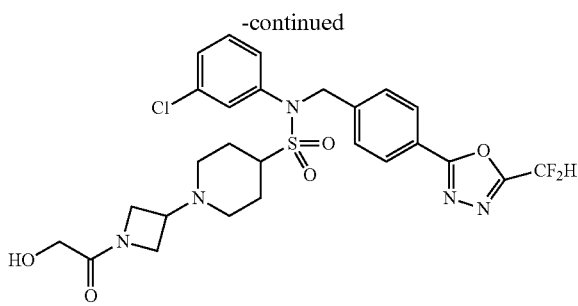

A mixture of 1-(azetidin-3-yl)-N-(3-chlorophenyl)-N-(4-(5-(difluoromethyl)-1,3,4-oxadiazol-2-yl)benzyl)piperidine-4-sulfonamide dihydrochloride (0.080 g, 0.131 mmol), 2-hydroxyacetic acid (0.030 g, 0.393 mmol), 1-ethyl-3-(3-dimethylaminopropyl)carbodiimide (EDC, 0.081 g, 0.524 mmol) and 1H-benzo[d][1,2,3]triazol-1-ol (HOBt, 0.071 g, 0.524 mmol) in dichloromethane (5 mL) was treated at the room temperature with N,N-diisopropylethylamine (0.182 mL, 1.048 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give the concentrate, and then the concentrate was dissolved in diethylether (5 mL) and hexane (30 mL) and stirred. The resulting precipitates were collected by filtration, washed by hexane, and dried to give N-(3-chlorophenyl)-N-(4-(5-(difluoromethyl)-1,3,4-oxadiazol-2-yl)benzyl)-1-(1-(2-hydroxyacetyl)azetidin-3-yl)piperidine-4-sulfonamide as white solid (0.059 g, 75.6%).

$^1$H NMR (400 MHz, DMSO-d6) δ 7.99 (d, 2H, J=8.4 Hz), 7.66 (s, 0.25H), 7.56 (t, 1H, J=2.0 Hz), 7.53 (s, 0.5H), 7.51 (d, 2H, J=8.4 Hz), 7.45 (m, 1H), 7.40 (s, 0.25H), 7.35 (t, 1H, J=8.0 Hz), 7.29 (m, 1H), 5.12 (s, 2H), 4.89 (m, 1H), 4.19-4.13 (m, 2H), 3.97 (m, 1H), 3.90-3.85 (m, 2H), 3.69 (m, 1H), 3.38 (m, 1H), 3.13 (m, 1H), 2.93-2.84 (m, 2H), 2.11-2.07 (m, 2H), 1.91-1.87 (m, 2H), 1.75-1.68 (m, 2H); LRMS (ES) m/z 596.3 (M$^+$+1).

EXAMPLE 326

Compound 11837, N-((5-(5-(difluoromethyl)-1,3,4-oxadiazol-2-yl)pyridin-2-yl)methyl)-1-(1-isopropylazetidin-3-yl)-N-(m-tolyl)piperidine-4-sulfonamide

[Step 1] methyl 6-((N-(m-tolyl)piperidine-4-sulfonamido)methyl)nicotinate dihydrochloride

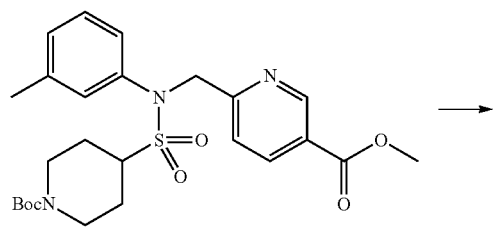

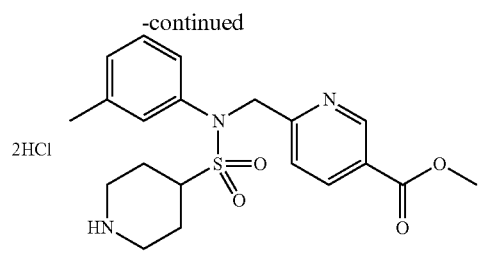

A solution of methyl 6-(((1-(tert-butoxycarbonyl)-N-(m-tolyl)piperidine)-4-sulfonamido)methyl)nicotinate (0.510 g, 1.013 mmol) in 1,4-dioxane (5 mL) was mixed at the room temperature with hydrochloric acid (4.00 M solution in 1,4-dioxane, 5.063 mL, 20.254 mmol), and stirred at the same temperature for 1 hr. The reaction mixture was diluted with ethyl acetate (5 mL) and hexane (30 mL) and stirred. The resulting precipitates were collected by filtration, washed by hexane, and dried to give methyl 6-((N-(m-tolyl)piperidine-4-sulfonamido)methyl)nicotinate dihydrochloride as white solid (0.460 g, 95.3%).

[Step 2] methyl 6-(((1-(1-(tert-butoxycarbonyl)azetidin-3-yl)-N-(m-tolyl)piperidine)-4-sulfonamido)methyl)nicotinate

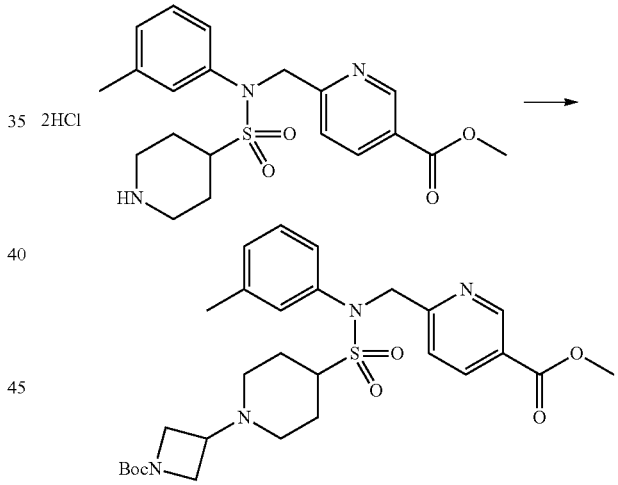

A mixture of methyl 6-((N-(m-tolyl)piperidine-4-sulfonamido)methyl)nicotinate dihydrochloride (0.460 g, 0.966 mmol), tert-butyl 3-oxoazetidine-1-carboxylate (0.331 g, 1.931 mmol) and N,N-diisopropylethylamine (0.505 mL, 2.897 mmol) in dichloromethane (20 mL) was treated at the room temperature with sodium triacetoxyborohydride (0.409 g, 1.931 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; methanol/dichloromethane=0% to 5%) to give methyl 6-(((1-(1-(tert-butoxycarbonyl)azetidin-3-yl)-N-(m-tolyl)piperidine)-4-sulfonamido)methyl)nicotinate as beige solid (0.520 g, 96.4%).

[Step 3] tert-butyl 3-(4-(N-((5-(hydrazinecarbonyl)pyridin-2-yl)methyl)-N-(m-tolyl)sulfamoyl)piperidin-1-yl)azetidine-1-carboxylate

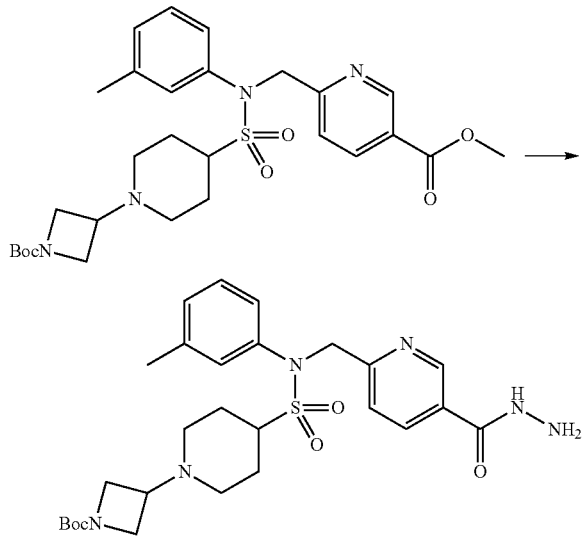

A solution of methyl 6-(((1-(1-(tert-butoxycarbonyl)azetidin-3-yl)-N-(m-tolyl)piperidine)-4-sulfonamido)methyl)nicotinate (0.520 g, 0.931 mmol) in tetrahydrofuran (5 mL)/ethanol (10 mL) was mixed at the room temperature with hydrazine monohydrate (0.905 mL, 18.615 mmol). The reaction mixture was heated at reflux for 18 hr, cooled down to the room temperature to terminate the reaction and concentrated under the reduced pressure to remove the solvent. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with ethyl acetate (10 mL) and hexane (30 mL) and stirred. The resulting precipitates were collected by filtration, washed by hexane, and dried to give tert-butyl 3-(4-(N-((5-(hydrazinecarbonyl)pyridin-2-yl)methyl)-N-(m-tolyl)sulfamoyl)piperidin-1-yl)azetidine-1-carboxylate as white solid (0.370 g, 71.2%).

[Step 4] tert-butyl 3-(4-(N-((5-(5-(difluoromethyl)-1,3,4-oxadiazol-2-yl)pyridin-2-yl)methyl)-N-(m-tolyl)sulfamoyl)piperidin-1-yl)azetidine-1-carboxylate

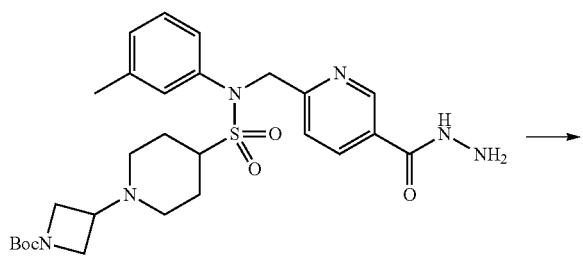

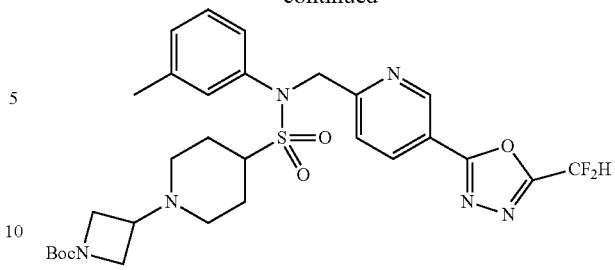

A mixture of tert-butyl 3-(4-(N-((5-(hydrazinecarbonyl)pyridin-2-yl)methyl)-N-(m-tolyl)sulfamoyl)piperidin-1-yl)azetidine-1-carboxylate (0.370 g, 0.662 mmol) and triethylamine (0.369 mL, 2.649 mmol) in tetrahydrofuran (10 mL) was treated at the room temperature with 2,2-difluoroacetic anhydride (0.247 mL, 1.987 mmol). The reaction mixture was heated at reflux for 1 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=70% to 100%) to give tert-butyl 3-(4-(N-((5-(5-(difluoromethyl)-1,3,4-oxadiazol-2-yl)pyridin-2-yl)methyl)-N-(m-tolyl)sulfamoyl)piperidin-1-yl)azetidine-1-carboxylate as white solid (0.350 g, 85.4%).

[Step 5] 1-(azetidin-3-yl)-N-((5-(5-(difluoromethyl)-1,3,4-oxadiazol-2-yl)pyridin-2-yl)methyl)-N-(m-tolyl)piperidine-4-sulfonamide trihydrochloride

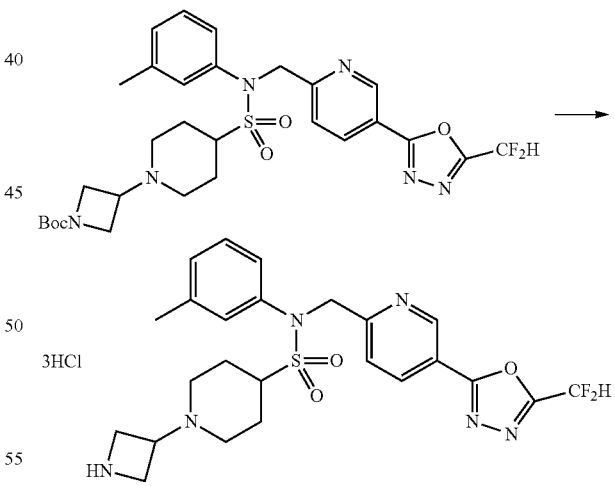

A solution of tert-butyl 3-(4-(N-((5-(5-(difluoromethyl)-1,3,4-oxadiazol-2-yl)pyridin-2-yl)methyl)-N-(m-tolyl)sulfamoyl)piperidin-1-yl)azetidine-1-carboxylate (0.350 g, 0.566 mmol) in 1,4-dioxane (5 mL) was mixed at the room temperature with hydrochloric acid (4.00 M solution in 1,4-dioxane, 2.829 mL, 11.314 mmol), and stirred at the same temperature for 1 hr. The reaction mixture was diluted with diethylether (20 mL) and hexane (30 mL) and stirred. The resulting precipitates were collected by filtration, washed by hexane, and dried to give 1-(azetidin-3-yl)-N-

((5-(5-(difluoromethyl)-1,3,4-oxadiazol-2-yl)pyridin-2-yl)methyl)-N-(m-tolyl)piperidine-4-sulfonamide trihydrochloride as light yellow solid (0.310 g, 87.3%).

[Step 6] Compound 11837

EXAMPLE 327

Compound 11838, 1-(1-acetylazetidin-3-yl)-N-((5-(5-(difluoromethyl)-1,3,4-oxadiazol-2-yl)pyridin-2-yl)methyl)-N-(m-tolyl)piperidine-4-sulfonamide

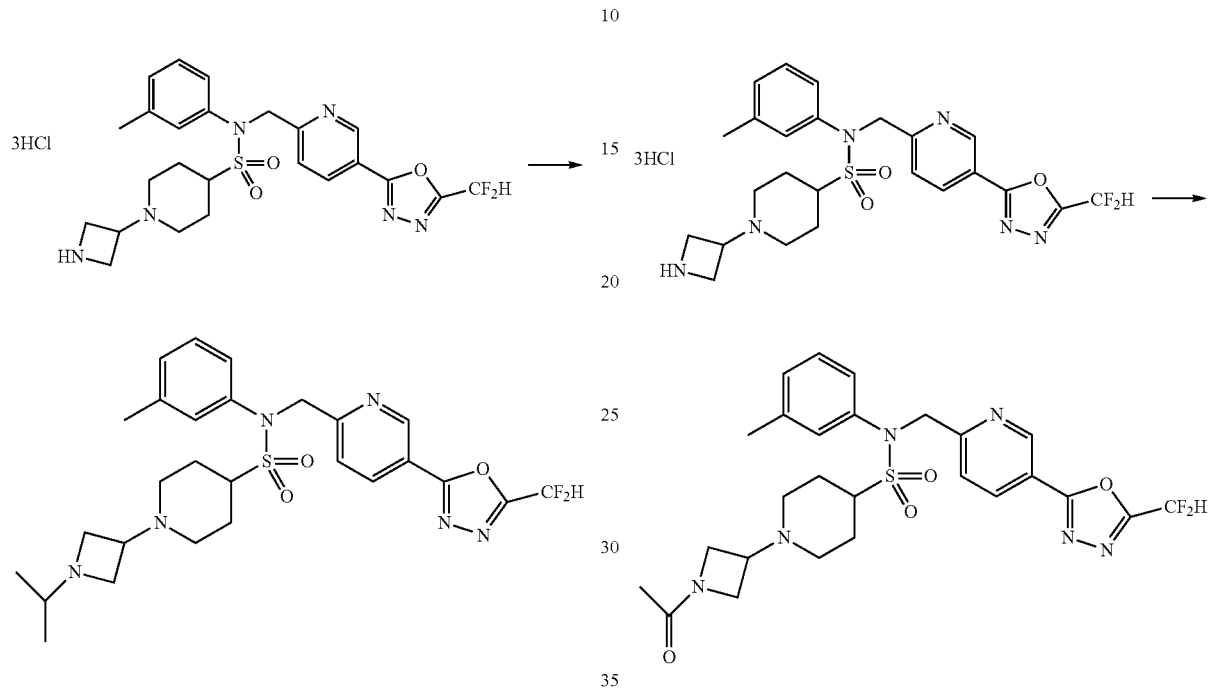

A mixture of 1-(azetidin-3-yl)-N-((5-(5-(difluoromethyl)-1,3,4-oxadiazol-2-yl)pyridin-2-yl)methyl)-N-(m-tolyl)piperidine-4-sulfonamide trihydrochloride (0.080 g, 0.127 mmol), acetone (0.047 mL, 0.637 mmol) and N,N-diisopropylethylamine (0.089 mL, 0.510 mmol) in dichloromethane (5 mL) was treated at the room temperature with sodium triacetoxyborohydride (0.054 g, 0.255 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=5% to 15%) to give the concentrate, and then the concentrate was dissolved in diethylether (5 mL) and hexane (30 mL) and stirred. The resulting precipitates were collected by filtration, washed by hexane, and dried to give N-((5-(5-(difluoromethyl)-1,3,4-oxadiazol-2-yl)pyridin-2-yl)methyl)-1-(1-isopropylazetidin-3-yl)-N-(m-tolyl)piperidine-4-sulfonamide as white solid (0.028 g, 39.2%).

$^1$H NMR (400 MHz, DMSO-d6) δ 9.09 (dd, 1H, J=2.1, 0.8 Hz), 8.41 (dd, 1H, J J=8.3, 2.3 Hz), 7.71 (d, 1H, J=8.6 Hz), 7.57 (t, 1H, J=51.3 Hz), 7.33 (s, 1H), 7.30 (d, 1H, J=8.0 Hz), 7.22 (t, 1H, J=7.7 Hz), 7.06 (d, 1H, J=7.5 Hz), 5.15 (s, 2H), 3.57-3.39 (m, 3H), 3.29-3.22 (m, 2H), 2.84-2.80 (m, 3H), 2.53 (m, 1H), 2.27 (s, 3H), 2.13-2.09 (m, 2H), 1.87-1.81 (m, 2H), 1.69-1.61 (m, 2H), 0.91 (d, 6H, J=4.2 Hz); LRMS (ES) m/z 561.1 (M$^+$+1).

A mixture of 1-(azetidin-3-yl)-N-((5-(5-(difluoromethyl)-1,3,4-oxadiazol-2-yl)pyridin-2-yl)methyl)-N-(m-tolyl)piperidine-4-sulfonamide trihydrochloride (0.080 g, 0.127 mmol) and N,N-diisopropylethylamine (0.089 mL, 0.510 mmol) in dichloromethane (5 mL) was treated at the room temperature with acetic anhydride (0.024 mL, 0.255 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give the concentrate, and then the concentrate was dissolved in diethylether (5 mL) and hexane (30 mL) and stirred. The resulting precipitates were collected by filtration, washed by hexane, and dried to give 1-(1-acetylazetidin-3-yl)-N-((5-(5-(difluoromethyl)-1,3,4-oxadiazol-2-yl)pyridin-2-yl)methyl)-N-(m-tolyl)piperidine-4-sulfonamide as white solid (0.036 g, 50.4%).

$^1$H NMR (400 MHz, DMSO-d6) δ 9.09 (dd, 1H, J J=2.1, 0.8 Hz), 8.41 (dd, 1H, J=8.3, 2.3 Hz), 7.71 (d, 1H, J=8.6 Hz), 7.56 (t, 1H, J=51.3 Hz), 7.34 (s, 1H), 7.30 (d, 1H, J=8.0 Hz), 7.22 (t, 1H, J=7.7 Hz), 7.06 (d, 1H, J J=7.5 Hz), 5.16 (s, 2H), 4.09 (m, 1H), 3.91 (m, 1H), 3.81 (m, 1H), 3.63 (m, 1H), 3.30 (m, 1H), 3.09 (m, 1H), 2.92-2.85 (m, 2H), 2.27 (s, 3H), 2.16-2.10 (m, 2H), 1.90-1.84 (m, 2H), 1.76-1.67 (m, 5H); LRMS (ES) m/z 561.2 (M$^+$+1).

EXAMPLE 328

Compound 11839, N-((5-(5-(difluoromethyl)-1,3,4-oxadiazol-2-yl)pyridin-2-yl)methyl)-1-(1-(2-hydroxyacetyl)azetidin-3-yl)-N-(m-tolyl)piperidine-4-sulfonamide

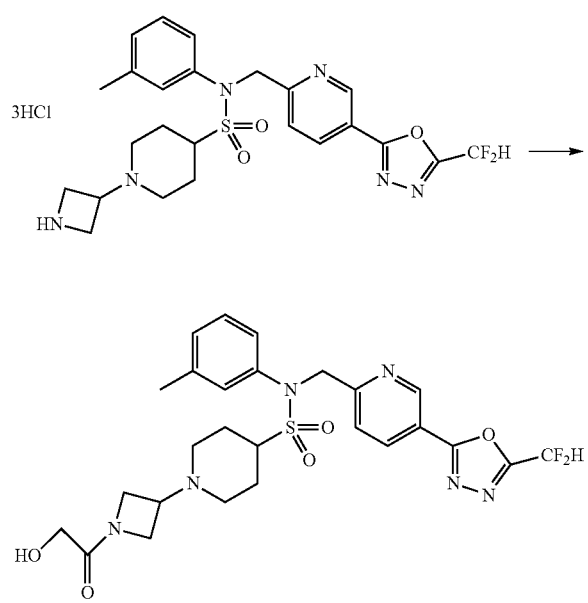

A mixture of 1-(azetidin-3-yl)-N-((5-(5-(difluoromethyl)-1,3,4-oxadiazol-2-yl)pyridin-2-yl)methyl)-N-(m-tolyl)piperidine-4-sulfonamide trihydrochloride (0.080 g, 0.127 mmol), 2-hydroxyacetic acid (0.029 g, 0.382 mmol), 1-Ethyl-3-(3-dimethylaminopropyl)carbodiimide (EDC, 0.079 g, 0.510 mmol) and 1H-benzo[d][1,2,3]triazol-1-ol (HOBt, 0.069 g, 0.510 mmol) in dichloromethane (5 mL) was treated at the room temperature with N,N-diisopropylethylamine (0.178 mL, 1.019 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 10%) to give the concentrate, and then the concentrate was dissolved in diethylether (5 mL) and hexane (30 mL) and stirred. The resulting precipitates were collected by filtration, washed by hexane, and dried to give N-((5-(5-(difluoromethyl)-1,3,4-oxadiazol-2-yl)pyridin-2-yl)methyl)-1-(1-(2-hydroxyacetyl)azetidin-3-yl)-N-(m-tolyl)piperidine-4-sulfonamide as white solid (0.031 g, 42.2%).

$^1$H NMR (400 MHz, DMSO-d6) δ 9.09 (dd, 1H, J=2.1, 0.8 Hz), 8.41 (dd, 1H, J=8.3, 2.3 Hz), 7.71 (d, 1H, J=8.6 Hz), 7.56 (t, 1H, J=51.3 Hz), 7.33 (s, 1H), 7.30 (d, 1H, J=8.0 Hz), 7.22 (t, 1H, J=7.7 Hz), 7.06 (d, 1H, J=7.5 Hz), 5.16 (s, 2H), 4.88 (m, 1H), 4.60 (m, 1H), 4.19-4.08 (m, 2H), 3.98 (m, 1H), 3.91-3.87 (m, 2H), 3.69 (m, 1H), 3.16 (m, 1H), 2.92-2.84 (m, 2H), 2.27 (s, 3H), 2.15-2.10 (m, 2H), 1.90-1.84 (m, 2H), 1.75-1.67 (m, 2H); LRMS (ES) m/z 577.3 (M⁺+1).

EXAMPLE 329

Compound 11840, N-(3-chlorophenyl)-N-(4-(5-(difluoromethyl)-1,3,4-oxadiazol-2-yl)benzyl)-1-(3-fluorocyclobutyl)piperidine-4-sulfonamide

[Step 1] methyl 4-((N-(3-chlorophenyl)piperidine-4-sulfonamido)methyl)benzoate hydrochloride

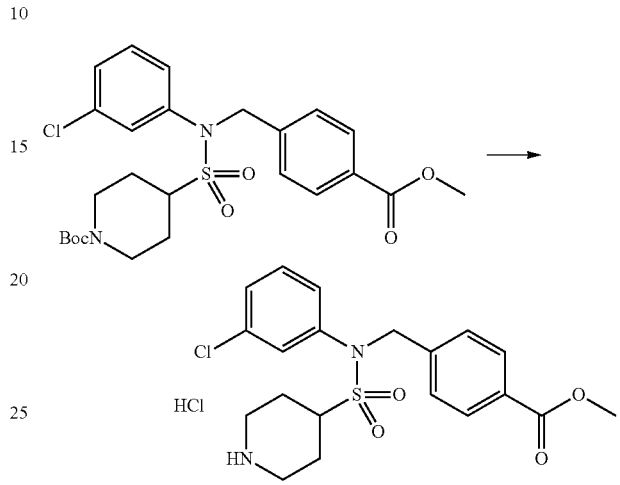

A solution of tert-butyl 4-(N-(3-chlorophenyl)-N-(4-(methoxycarbonyl)benzyl)sulfamoyl)piperidine-1-carboxylate (0.937 g, 1.791 mmol) in 1,4-dioxane (10 mL) was mixed at the room temperature with hydrogen chloride (4.00 M solution in 1,4-dioxane, 8.957 mL, 35.829 mmol), and stirred at the same temperature for 1 hr. The reaction mixture was diluted with ethyl acetate (20 mL) and hexane (40 mL) and stirred. The resulting precipitates were collected by filtration, washed by hexane, and dried to give methyl 4-((N-(3-chlorophenyl)piperidine-4-sulfonamido)methyl) benzoate hydrochloride as white solid (0.790 g, 96.0%).

[Step 2] methyl 4-(((N-(3-chlorophenyl)-1-(3-hydroxycyclobutyl)piperidine)-4-sulfonamido)methyl)benzoate

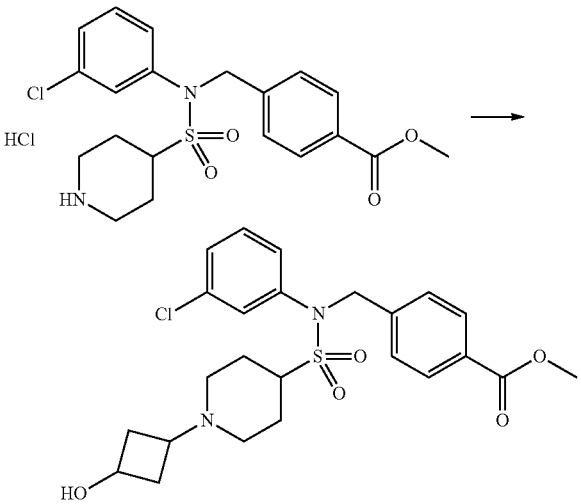

A mixture of methyl 4-((N-(3-chlorophenyl)piperidine-4-sulfonamido)methyl)benzoate hydrochloride (0.790 g, 1.720 mmol), 3-hydroxycyclobutan-1-one (0.296 g, 3.439 mmol) and N,N-diisopropylethylamine (0.599 mL, 3.439 mmol) in dichloromethane (20 mL) was treated at the room temperature with sodium triacetoxyborohydride (0.729 g, 3.439 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 40 g cartridge; methanol/dichloromethane=0% to 5%) to give methyl 4-(((N-(3-chlorophenyl)-1-(3-hydroxycyclobutyl)piperidine)-4-sulfonamido)methyl)benzoate as beige solid (0.830 g, 97.9%).

[Step 3] methyl 4-(((N-(3-chlorophenyl)-1-(3-fluorocyclobutyl)piperidine)-4-sulfonamido)methyl) benzoate

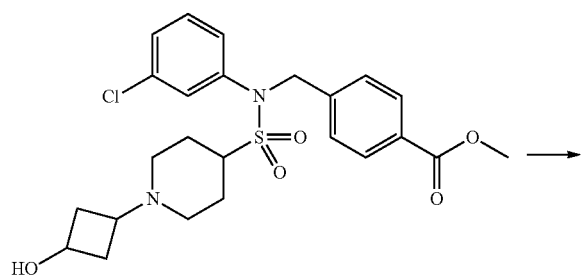

A solution of methyl 4-(((N-(3-chlorophenyl)-1-(3-hydroxycyclobutyl)piperidine)-4-sulfonamido)methyl)benzoate (0.650 g, 1.318 mmol) in dichloromethane (30 mL) was mixed at the room temperature with Bis(2-methoxyethyl) aminosulfur trifluoride (0.365 mL, 1.978 mmol). The reaction mixture was heated at reflux for 18 hr and cooled down to the room temperature to terminate the reaction. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 40 g cartridge; methanol/dichloromethane=0% to 5%) to give methyl 4-(((N-(3-chlorophenyl)-1-(3-fluorocyclobutyl)piperidine)-4-sulfonamido)methyl)benzoate as dark brown solid (0.530 g, 81.2%).

[Step 4] N-(3-chlorophenyl)-1-(3-fluorocyclobutyl)-N-(4-(hydrazinecarbonyl)benzyl)piperidine-4-sulfonamide

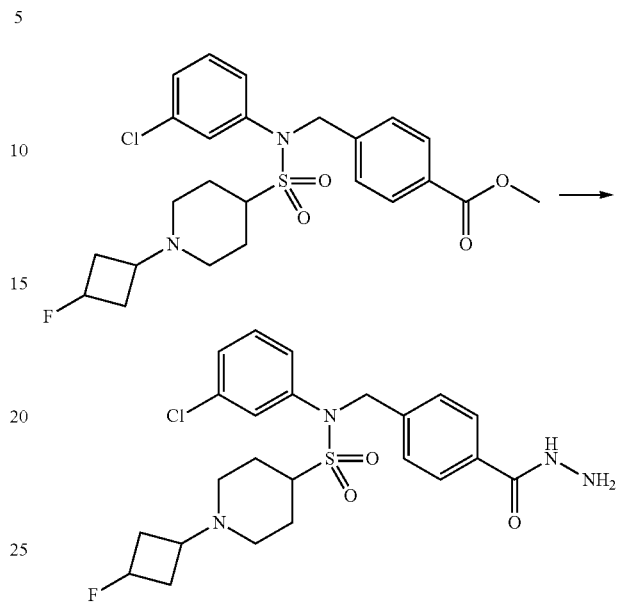

A solution of methyl 4-(((N-(3-chlorophenyl)-1-(3-fluorocyclobutyl)piperidine)-4-sulfonamido)methyl)benzoate (0.530 g, 1.071 mmol) in tetrahydrofuran (5 mL)/ethanol (10 mL) was mixed at the room temperature with hydrazine monohydrate (1.041 mL, 21.414 mmol). The reaction mixture was heated at reflux for 18 hr, cooled down to the room temperature to terminate the reaction and concentrated under the reduced pressure to remove the solvent. The title compound was used without further purification (N-(3-chlorophenyl)-1-(3-fluorocyclobutyl)-N-(4-(hydrazinecarbonyl)benzyl)piperidine-4-sulfonamide, 0.530 g, 100.0%, brown solid).

[Step 5] Compound 11840

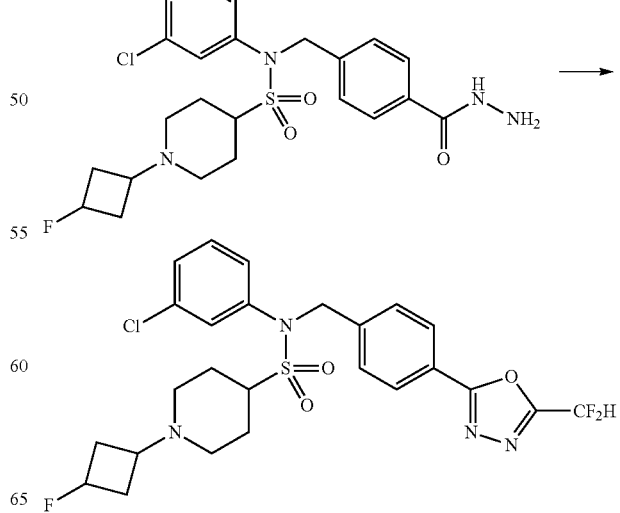

A mixture of N-(3-chlorophenyl)-1-(3-fluorocyclobutyl)-N-(4-(hydrazinecarbonyl)benzyl)piperidine-4-sulfonamide (0.530 g, 1.071 mmol) and triethylamine (0.597 mL, 4.283 mmol) in tetrahydrofuran (10 mL) was treated at the room temperature with 2,2-difluoroacetic anhydride (0.399 mL, 3.212 mmol). The reaction mixture was heated at reflux for 1 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 5%) to give the concentrate, and then the concentrate was dissolved in diethylether (5 mL) and hexane (30 mL) and stirred. The resulting precipitates were collected by filtration, washed by hexane, and dried to give N-(3-chlorophenyl)-N-(4-(5-(difluoromethyl)-1,3,4-oxadiazol-2-yl)benzyl)-1-(3-fluorocyclobutyl)piperidine-4-sulfonamide as beige solid (0.049 g, 8.2%).

$^1$H NMR (400 MHz, DMSO-d6) δ 7.99 (d, 2H, J=8.4 Hz), 7.66 (s, 0.25H), 7.55 (t, 1H, J=2.0 Hz), 7.54 (s, 0.5H), 7.51 (d, 2H, J=8.4 Hz), 7.44 (m, 1H), 7.40 (s, 0.25H), 7.35 (t, 1H, J=8.0 Hz), 7.29 (m, 1H), 5.18 (m, 0.5H), 5.11 (s, 2H), 5.04 (m, 0.5H), 3.29 (m, 1H), 2.99-2.85 (m, 3H), 2.43 (m, 1H), 2.26-2.16 (m, 3H), 2.09-2.04 (m, 2H), 1.83-1.75 (m, 2H), 1.72-1.66 (m, 2H); LRMS (ES) m/z 555.3 (M$^+$+1).

EXAMPLE 330

Compound 11841, N-(3-chlorophenyl)-N-((5-(5-(difluoromethyl)-1,3,4-oxadiazol-2-yl)pyridin-2-yl)methyl)-1-(3-fluorocyclobutyl)piperidine-4-sulfonamide

[Step 1] methyl 6-((N-(3-chlorophenyl)piperidine-4-sulfonamido)methyl)nicotinate dihydrochloride

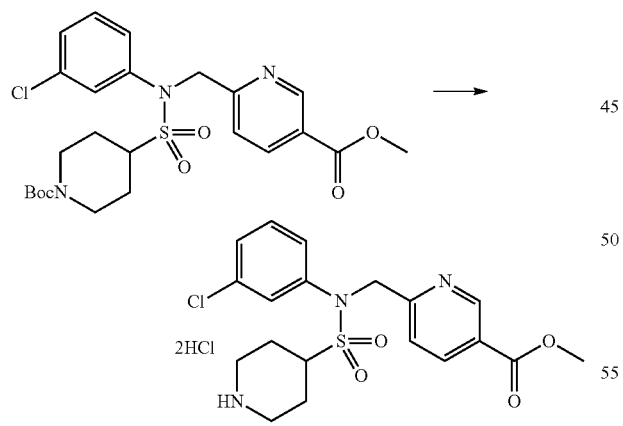

A solution of methyl 6-(((1-(tert-butoxycarbonyl)-N-(3-chlorophenyl)piperidine)-4-sulfonamido)methyl)nicotinate (0.845 g, 1.613 mmol) in 1,4-dioxane (10 mL) was mixed at the room temperature with hydrogen chloride (4.00 M solution in 1,4-dioxane, 6.047 mL, 24.188 mmol), and stirred at the same temperature for 1 hr. The reaction mixture was diluted with ethyl acetate (20 mL) and hexane (40 mL) and stirred. The resulting precipitates were collected by filtration, washed by hexane, and dried to give methyl 6-((N-(3-chlorophenyl)piperidine-4-sulfonamido)methyl)nicotinate dihydrochloride as beige solid (0.780 g, 97.4%).

[Step 2] methyl 6-(((N-(3-chlorophenyl)-1-(3-hydroxycyclobutyl)piperidine)-4-sulfonamido)methyl)nicotinate

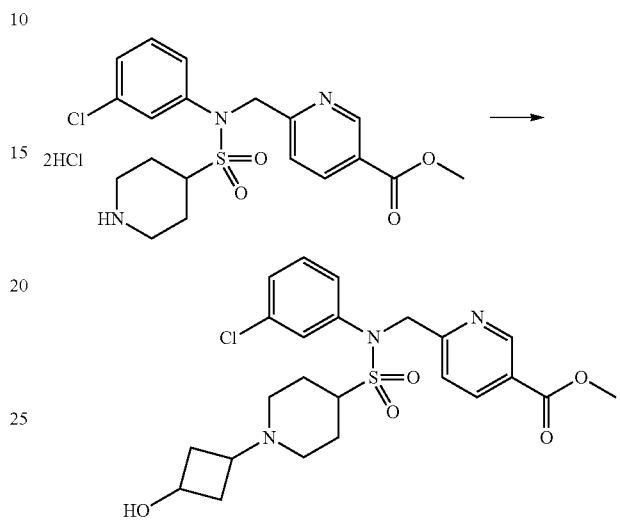

A mixture of methyl 6-((N-(3-chlorophenyl)piperidine-4-sulfonamido)methyl)nicotinate dihydrochloride (0.780 g, 1.570 mmol), 3-hydroxycyclobutan-1-one (0.270 g, 3.140 mmol) and N,N-diisopropylethylamine (0.820 mL, 4.710 mmol) in dichloromethane (20 mL) was treated at the room temperature with sodium triacetoxyborohydride (0.665 g, 3.140 mmol), and stirred at the same temperature for 18 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; methanol/dichloromethane=0% to 5%) to give methyl 6-(((N-(3-chlorophenyl)-1-(3-hydroxycyclobutyl)piperidine)-4-sulfonamido)methyl)nicotinate as beige solid (0.710 g, 91.5%).

[Step 3] methyl 6-(((N-(3-chlorophenyl)-1-(3-fluorocyclobutyl)piperidine)-4-sulfonamido)methyl)nicotinate

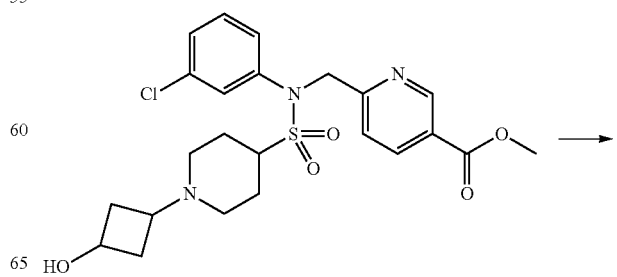

-continued

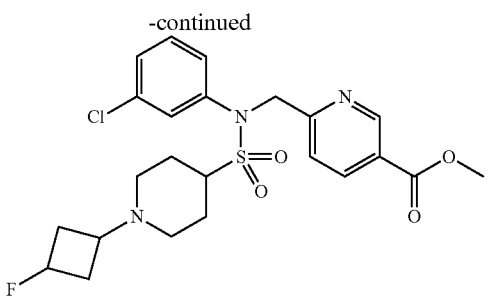

A solution of methyl 6-(((N-(3-chlorophenyl)-1-(3-hydroxycyclobutyl)piperidine)-4-sulfonamido)methyl)nicotinate (0.580 g, 1.174 mmol) in dichloromethane (30 mL) was mixed at the room temperature with Bis(2-methoxyethyl)aminosulfur trifluoride (0.325 mL, 1.761 mmol). The reaction mixture was heated at reflux for 18 hr and cooled down to the room temperature to terminate the reaction. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 40 g cartridge; methanol/dichloromethane=0% to 5%) to give methyl 6-(((N-(3-chlorophenyl)-1-(3-fluorocyclobutyl)piperidine)-4-sulfonamido)methyl)nicotinate as dark brown solid (0.420 g, 72.1%).

[Step 4] N-(3-chlorophenyl)-1-(3-fluorocyclobutyl)-N-((5-(hydrazinecarbonyl)pyridin-2-yl)methyl)piperidine-4-sulfonamide

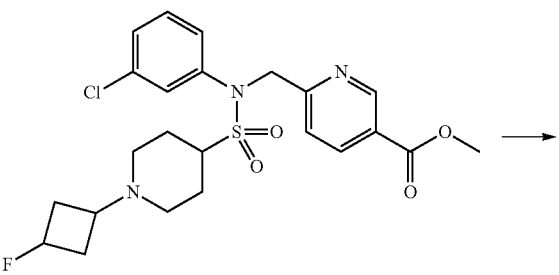

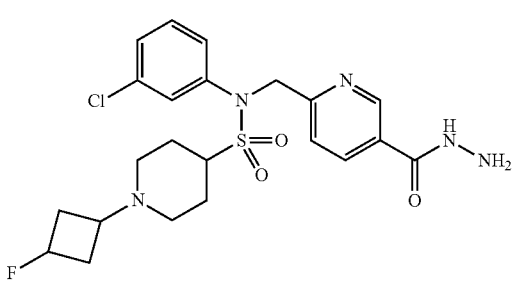

A solution of methyl 6-(((N-(3-chlorophenyl)-1-(3-fluorocyclobutyl)piperidine)-4-sulfonamido)methyl)nicotinate (0.420 g, 0.847 mmol) in tetrahydrofuran (5 mL)/ethanol (10 mL) was mixed at the room temperature with hydrazine monohydrate (0.823 mL, 16.936 mmol). The reaction mixture was heated at reflux for 18 hr, cooled down to the room temperature to terminate the reaction and concentrated under the reduced pressure to remove the solvent. The title compound was used without further purification (N-(3-chlorophenyl)-1-(3-fluorocyclobutyl)-N-((5-(hydrazinecarbonyl)pyridin-2-yl)methyl)piperidine-4-sulfonamide, 0.420 g, 100.0%, brown solid).

[Step 5] Compound 11841

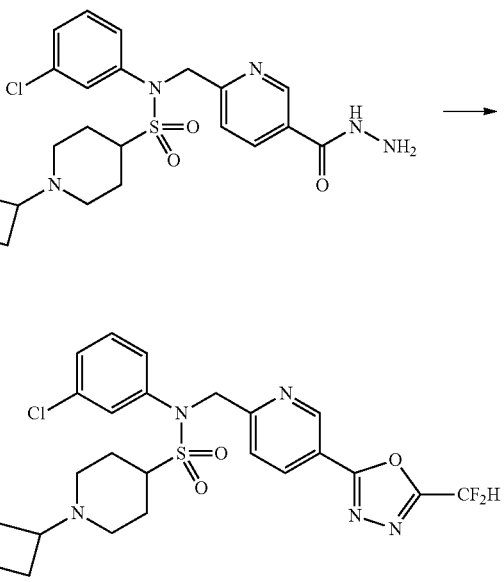

A mixture of N-(3-chlorophenyl)-1-(3-fluorocyclobutyl)-N-((5-(hydrazinecarbonyl)pyridin-2-yl)methyl)piperidine-4-sulfonamide (0.420 g, 0.847 mmol) and triethylamine (0.472 mL, 3.387 mmol) in tetrahydrofuran (10 mL) was treated at the room temperature with 2,2-difluoroacetic anhydride (0.316 mL, 2.540 mmol). The reaction mixture was heated at reflux for 1 hr and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 12 g cartridge; methanol/dichloromethane=0% to 5%) to give the concentrate, and then the concentrate was dissolved in diethylether (5 mL) and hexane (30 mL) and stirred. The resulting precipitates were collected by filtration, washed by hexane, and dried to give N-(3-chlorophenyl)-N-((5-(5-(difluoromethyl)-1,3,4-oxadiazol-2-yl)pyridin-2-yl)methyl)-1-(3-fluorocyclobutyl)piperidine-4-sulfonamide as beige solid (0.036 g, 7.6%).

$^1$H NMR (400 MHz, DMSO-d6) δ 9.10 (d, 1H, J=2.2 Hz), 8.41 (m, 1H), 7.72-7.67 (m, 1.25H), 7.63 (t, 1H, J=2.1 Hz), 7.56 (s, 0.5H), 7.51 (m, 1H), 7.43 (s, 0.25H), 7.37 (t, 1H, J=8.0 Hz), 7.31 (m, 1H), 5.21 (s, 2H), 5.11 (m, 1H), 3.40 (m, 1H), 2.97-2.86 (m, 3H), 2.55 (m, 1H), 2.28-2.17 (m, 3H), 2.12-2.08 (m, 2H), 1.78 (t, 2H, J=12.0 Hz), 1.71-1.64 (m, 2H); LRMS (ES) m/z 556.3 (M$^+$+1).

EXAMPLE 331

Compound 11842, 2-(4-(4-chlorophenyl)-3,6-dihydropyridin-1(2H)-yl)-N-(4-(5-(difluoromethyl)-1,3,4-oxadiazol-2-yl)benzyl)-N-phenylethane-1-sulfonamide

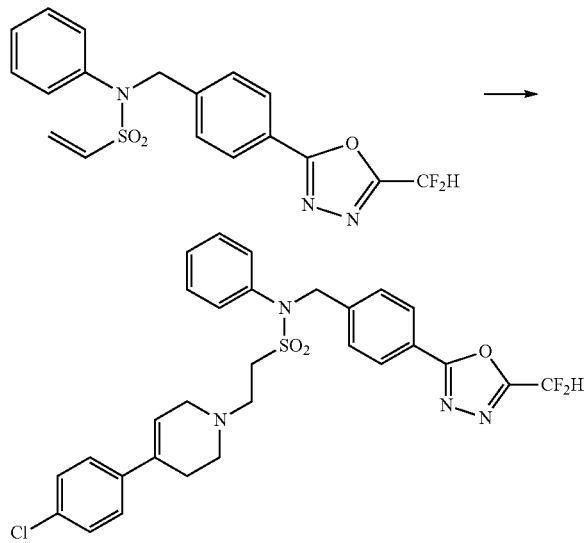

A solution of N-(4-(5-(difluoromethyl)-1,3,4-oxadiazol-2-yl)benzyl)-N-phenylethenesulfonamide (0.100 g, 0.255 mmol), 4-(4-chlorophenyl)-1,2,3,6-tetrahydropyridine monohydrochloride (0.118 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(4-(4-chlorophenyl)-3,6-dihydropyridin-1(2H)-yl)-N-(4-(5-(difluoromethyl)-1,3,4-oxadiazol-2-yl)benzyl)-N-phenylethane-1-sulfonamide as white solid (0.070 g, 46.8%).

$^1$H NMR (400 MHz, DMSO): δ 8.01-7.94 (m, 2H), 7.53 (d, 2H, J=8.1 Hz), 7.46 (dd, 4H, J=10.1, 8.0 Hz), 7.42-7.30 (m, 6H), 7.25 (t, 1H, J=7.3 Hz), 5.06 (s, 2H), 3.52 (t, 2H, J=7.3 Hz), 3.36 (d, 2H, J=9.4 Hz), 3.16 (q, 2H, J=3.0 Hz), 2.90 (t, 2H, J=7.3 Hz), 2.72 (t, 2H, J=5.6 Hz), 2.51-2.44 (m, 3H); LRMS (ES) m/z 586.3 (M$^+$+1).

EXAMPLE 332

Compound 11843, 2-(1H-benzo[de]isoquinolin-2(3H)-yl)-N-(4-(5-(difluoromethyl)-1,3,4-oxadiazol-2-yl)benzyl)-N-phenylethane-1-sulfonamide

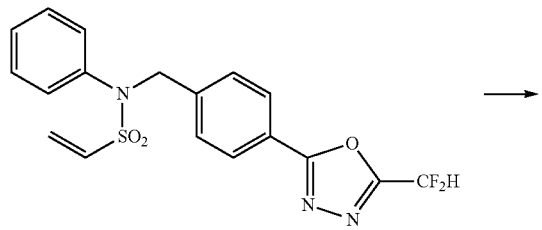

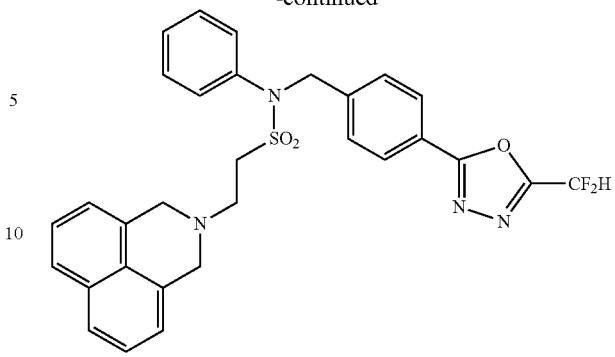

A solution of N-(4-(5-(difluoromethyl)-1,3,4-oxadiazol-2-yl)benzyl)-N-phenylethenesulfonamide (0.100 g, 0.255 mmol), 2,3-dihydro-1h-benz[De]Isoquinoline (0.086 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(1H-benzo[de]isoquinolin-2(3H)-yl)-N-(4-(5-(difluoromethyl)-1,3,4-oxadiazol-2-yl)benzyl)-N-phenylethane-1-sulfonamide as orange color solid (0.040 g, 27.9%).

$^1$H NMR (400 MHz, DMSO-d6): δ 7.94-7.87 (m, 2H), 7.78 (d, 2H, J=8.2 Hz), 7.53-7.17 (m, 12H), 4.98 (s, 2H), 4.05 (d, 4H, J=11.8 Hz), 3.62 (t, 2H, J=7.0 Hz), 3.16-3.04 (m, 2H); LRMS (ES) m/z 561.3 (M$^+$+1).

EXAMPLE 333

Compound 11844, 2-(4-(benzo[d]isoxazol-3-yl)piperazin-1-yl)-N-(4-(5-(difluoromethyl)-1,3,4-oxadiazol-2-yl)benzyl)-N-phenylethane-1-sulfonamide

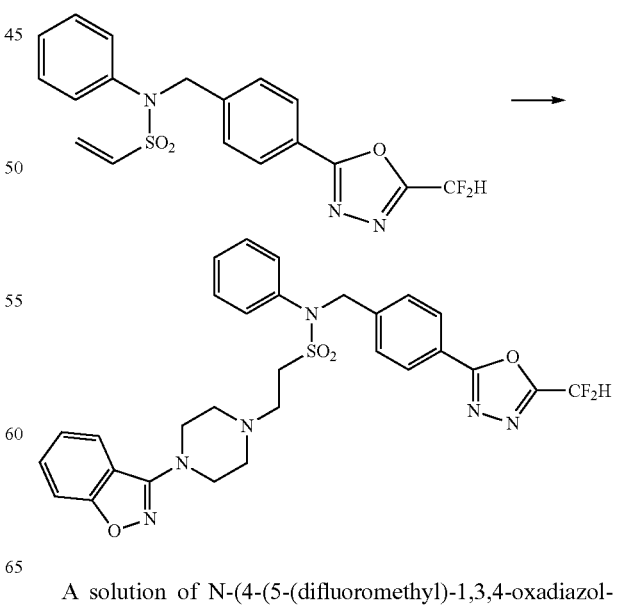

A solution of N-(4-(5-(difluoromethyl)-1,3,4-oxadiazol-2-yl)benzyl)-N-phenylethenesulfonamide (0.100 g, 0.255 mmol), 3-(1-piperazinyl)-1,2-benzisoxazole, 96% (0.104 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=3% to 5%) to give 2-(4-(benzo[d]isoxazol-3-yl)piperazin-1-yl)-N-(4-(5-(difluoromethyl)-1,3,4-oxadiazol-2-yl)benzyl)-N-phenylethane-1-sulfonamide as white solid (0.030 g, 19.7%).

$^1$H NMR (400 MHz, DMSO-d6): δ 7.98 (dd, 2H, J=8.6, 2.3 Hz), 7.63-7.48 (m, 5H), 7.46 (dd, 2H, J=7.6, 1.7 Hz), 7.35 (t, 2H, J=7.8 Hz), 7.35-7.21 (m, 2H), 5.07 (s, 2H), 3.52 (dd, 6H, J=6.1, 3.8 Hz), 2.87 (dd, 2H, J=8.4, 6.2 Hz), 2.67 (t, 4H, J=4.9 Hz); LRMS (ES) m/z 595.3 (M$^+$+1).

EXAMPLE 334

Compound 11845, N-(4-(5-(difluoromethyl)-1,3,4-oxadiazol-2-yl)benzyl)-2-(4-(2-methoxyphenyl)piperidin-1-yl)-N-phenylethane-1-sulfonamide

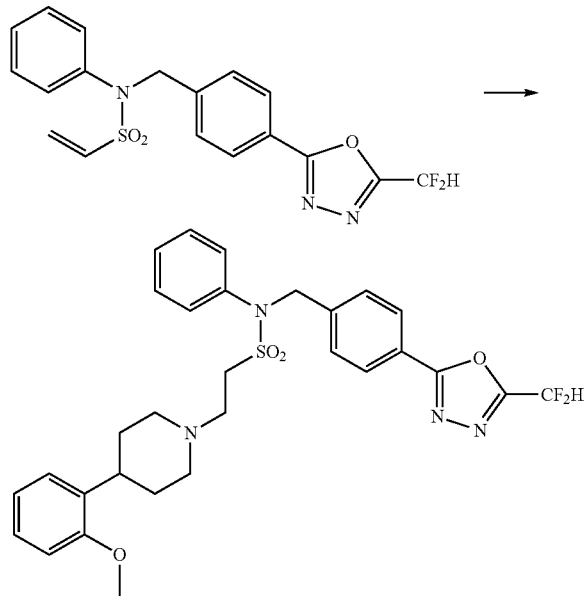

A solution of N-(4-(5-(difluoromethyl)-1,3,4-oxadiazol-2-yl)benzyl)-N-phenylethenesulfonamide (0.100 g, 0.255 mmol), 4-(2-methoxyphenyl)piperidine (0.098 g, 0.511 mmol) and N,N-diisopropylethylamine (0.176 mL, 1.022 mmol) in dichloromethane (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; acetonitrile/aqueous 0.1%-formic acid solution=10% to 90%) to give N-(4-(5-(difluoromethyl)-1,3,4-oxadiazol-2-yl)benzyl)-2-(4-(2-methoxyphenyl)piperidin-1-yl)-N-phenylethane-1-sulfonamide as white solid (0.070 g, 47.0%).

$^1$H NMR (400 MHz, CD3OD): δ 8.08-8.00 (m, 2H), 7.60-7.53 (m, 2H), 7.49-7.25 (m, 6H), 7.24-7.13 (m, 2H), 6.98-6.87 (m, 2H), 5.09 (s, 2H), 3.83 (s, 3H), 3.53-3.41 (m, 2H), 3.10 (d, 2H, J=11.3 Hz), 3.06-2.93 (m, 2H), 2.31 (td, 2H, J=11.3, 3.7 Hz), 1.86-1.72 (m, 5H); LRMS (ES) m/z 583.4 (M$^+$+1).

EXAMPLE 335

Compound 11847, (S)-1-(2-(N-((5-(5-(difluoromethyl)-1,3,4-oxadiazol-2-yl)pyridin-2-yl)methyl)-N-phenylsulfamoyl)ethyl)pyrrolidine-2-carboxamide

[Step 1] 2-(difluoromethyl)-5-(6-methylpyridin-3-yl)-1,3,4-oxadiazole

A solution of 6-methylnicotinohydrazide (5.000 g, 33.075 mmol), 2,2-difluoroacetic anhydride (12.336 mL, 99.226 mmol) and triethylamine (23.050 mL, 165.377 mmol) in tetrahydrofuran (40 mL) was stirred at the room temperature for 6 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; dichloromethane/methanol=0% to 5%) to give 2-(difluoromethyl)-5-(6-methylpyridin-3-yl)-1,3,4-oxadiazole as brown solid (6.200 g, 88.8%).

[Step 2] 2-(6-(bromomethyl)pyridin-3-yl)-5-(difluoromethyl)-1,3,4-oxadiazole

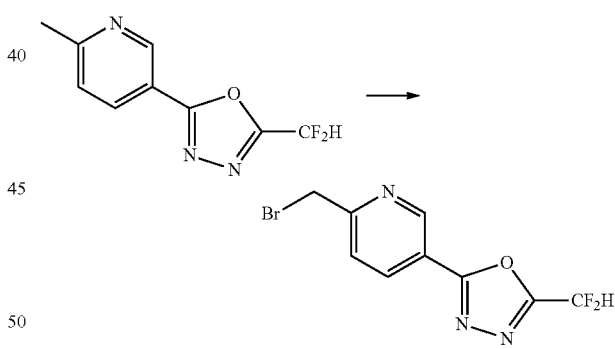

A mixture of 2-(difluoromethyl)-5-(6-methylpyridin-3-yl)-1,3,4-oxadiazole (6.200 g, 29.360 mmol), N-Bromosuccinimide (5.487 g, 30.828 mmol) and Azobisisobutyronitrile (0.482 g, 2.936 mmol) in chloroform (100 mL) was heated at reflux for 12 hr, and cooled down to the ambient temperature to terminate the reaction. Then, aqueous N-sodium thiosulfate (Na2S2O3) solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=10% to 20%) to give 2-(6-(bromomethyl)pyridin-3-yl)-5-(difluoromethyl)-1,3,4-oxadiazole as purple color solid (1.830 g, 21.5%).

785

[Step 3] N-((5-(5-(difluoromethyl)-1,3,4-oxadiazol-2-yl)pyridin-2-yl)methyl)-N-phenylethenesulfonamide

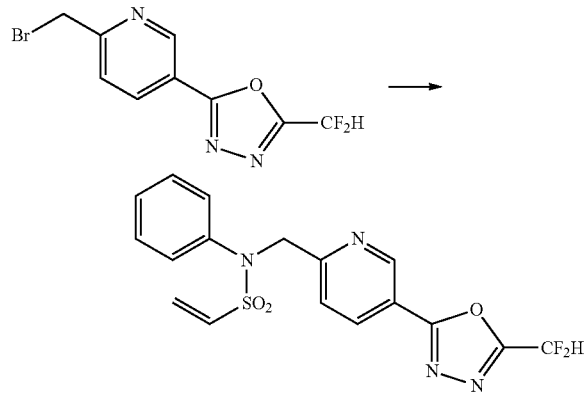

A solution of N-phenylethenesulfonamide (1.830 g, 9.987 mmol), 2-(6-(bromomethyl)pyridin-3-yl)-5-(difluoromethyl)-1,3,4-oxadiazole (2.897 g, 9.987 mmol), potassium carbonate (1.380 g, 9.987 mmol) and potassium iodide (0.166 g, 0.999 mmol) in N,N-dimethylformamide (5 mL) was stirred at the room temperature for 6 hr, and concentrated under the reduced pressure to remove the solvent. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=10% to 20%) to give N-((5-(5-(difluoromethyl)-1,3,4-oxadiazol-2-yl)pyridin-2-yl)methyl)-N-phenylethenesulfonamide as brown color solid (1.890 g, 48.2%).

[Step 4] Compound 11847

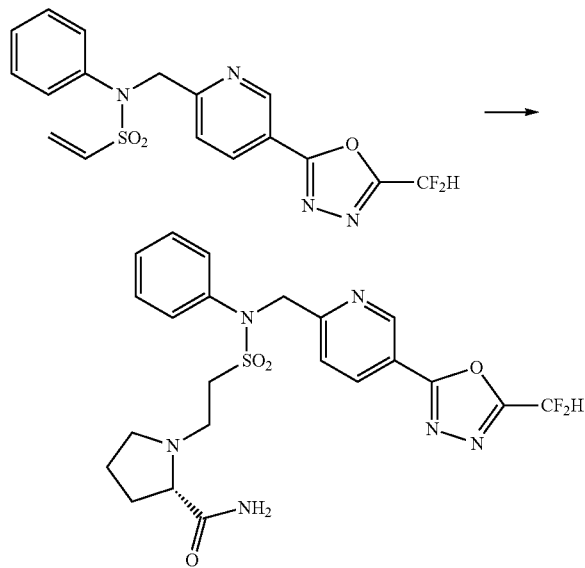

786

A solution of N-((5-(5-(difluoromethyl)-1,3,4-oxadiazol-2-yl)pyridin-2-yl)methyl)-N-phenylethenesulfonamide (0.100 g, 0.255 mmol), L-Prolinamide (0.058 g, 0.510 mmol) and N,N-diisopropylethylamine (0.176 mL, 1.019 mmol) in dichloromethane (5 mL) was stirred at the room temperature for 24 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=5% to 10%) to give (S)-1-(2-(N-((5-(5-(difluoromethyl)-1,3,4-oxadiazol-2-yl)pyridin-2-yl)methyl)-N-phenylsulfamoyl)ethyl)pyrrolidine-2-carboxamide as white solid (0.040 g, 31.0%).

$^1$H NMR (400 MHz, CD3OD): δ 9.17 (dd, 1H, J=2.2, 0.8 Hz), 8.44 (dd, 1H, J=8.2, 2.2 Hz), 7.76 (dd, 1H, J=8.3, 0.8 Hz), 7.52-7.45 (m, 2H), 7.45-7.29 (m, 3H), 7.34-7.20 (m, 2H), 5.17 (s, 1H), 3.55 (ddd, 2H, J=7.4, 6.2, 3.0 Hz), 3.33-3.22 (m, 2H), 3.26-3.11 (m, 1H), 3.14-2.99 (m, 1H), 2.99-2.80 (m, 1H), 2.40 (td, 1H, J=9.2, 6.7 Hz), 2.28-2.12 (m, 1H), 1.92-1.71 (m, 2H); LRMS (ES) m/z 507.1 (M⁺+1).

EXAMPLE 336

Compound 11848, (R)-1-(2-(N-((5-(5-(difluoromethyl)-1,3,4-oxadiazol-2-yl)pyridin-2-yl)methyl)-N-phenylsulfamoyl)ethyl)pyrrolidine-2-carboxamide

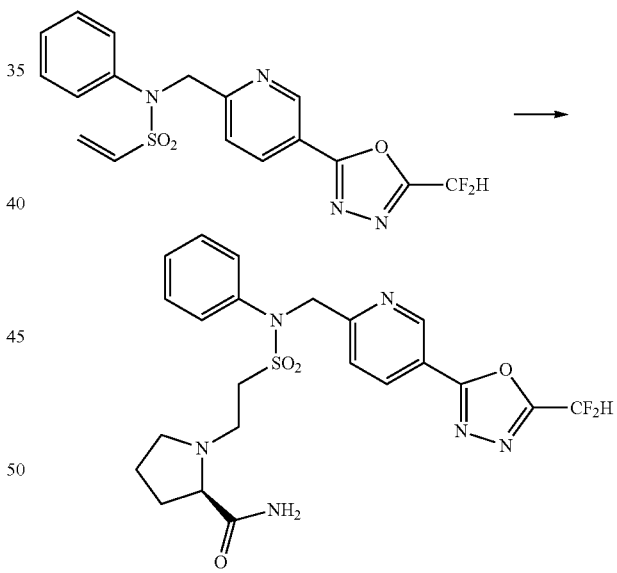

A solution of N-((5-(5-(difluoromethyl)-1,3,4-oxadiazol-2-yl)pyridin-2-yl)methyl)-N-phenylethenesulfonamide (0.100 g, 0.255 mmol), D-(−)-Prolinamide (0.058 g, 0.510 mmol) and Diisopropylethylamine (0.176 mL, 1.019 mmol) in dichloromethane (5 mL) was stirred at the room temperature for 24 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=5% to 10%) to give (R)-1-(2-(N-((5-(5-(difluoromethyl)-1,3,4-oxadiazol- 2-yl)pyridin-2-yl)methyl)-N-phenylsulfamoyl)ethyl)pyrrolidine-2-carboxamide as white solid (0.045 g, 34.9%).

$^1$H NMR (400 MHz, CD3OD): δ 9.17 (dd, 1H, J=2.2, 0.8 Hz), 8.43 (dd, 1H, J=8.3, 2.3 Hz), 7.76 (dd, 1H, J=8.2, 0.8 Hz), 7.55-7.44 (m, 2H), 7.46-7.35 (m, 1H), 7.40-7.19 (m, 3H), 5.17 (s, 2H), 3.63-3.46 (m, 2H), 3.32-2.76 (m, 3H), 2.65 (q, 1H, J=7.3 Hz), 2.45-2.28 (m, 1H), 2.30-2.12 (m, 1H), 1.92-1.71 (m, 3H); LRMS (ES) m/z 507.3 (M$^+$+1).

EXAMPLE 337

Compound 11849, (2S,4R)-1-(2-(N-((5-(5-(difluoromethyl)-1,3,4-oxadiazol-2-yl)pyridin-2-yl)methyl)-N-phenylsulfamoyl)ethyl)-4-hydroxypyrrolidine-2-carboxamide

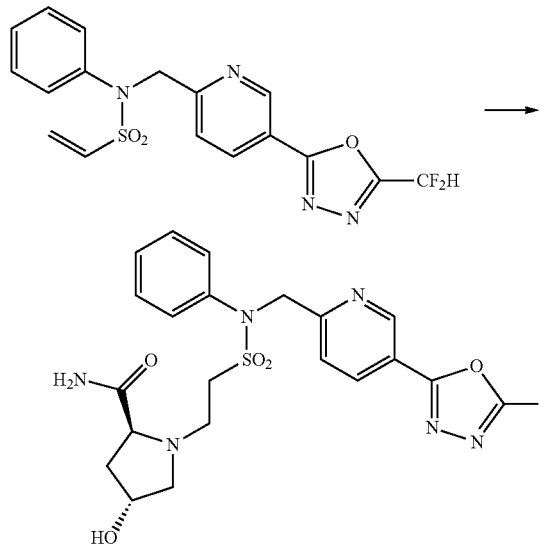

A solution of N-((5-(5-(difluoromethyl)-1,3,4-oxadiazol-2-yl)pyridin-2-yl)methyl)-N-phenylethenesulfonamide (0.100 g, 0.255 mmol), (2s,4r)-4-hydroxypyrrolidine-2-carboxamide; hydrochloride (0.085 g, 0.510 mmol) and Diisopropylethylamine (0.176 mL, 1.019 mmol) in dichloromethane (5 mL) was stirred at the room temperature for 24 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=5% to 10%) to give (2S,4R)-1-(2-(N-((5-(5-(difluoromethyl)-1,3,4-oxadiazol-2-yl)pyridin-2-yl)methyl)-N-phenylsulfamoyl)ethyl)-4-hydroxypyrrolidine-2-carboxamide as white solid (0.050 g, 37.5%).

$^1$H NMR (400 MHz, CD3OD): δ 9.17 (dd, 1H, J=2.2, 0.8 Hz), 8.43 (dd, 1H, J=8.3, 2.3 Hz), 7.76 (dd, 1H, J=8.2, 0.8 Hz), 7.55-7.44 (m, 2H), 7.46-7.35 (m, 1H), 7.40-7.19 (m, 3H), 5.17 (s, 2H), 3.63-3.46 (m, 2H), 3.32-2.76 (m, 3H), 2.65 (q, 1H, J=7.3 Hz), 2.45-2.28 (m, 1H), 2.30-2.12 (m, 1H), 1.92-1.71 (m, 3H); LRMS (ES) m/z 523.3 (M$^+$+1).

Measurement of Activity of the Compounds of the Present Invention and Analysis Protocol

EXPERIMENTAL EXAMPLE 1

HDAC Enzyme Activity Inhibition Assays (In Vitro)

In order to examine the HDAC6 selectivity of the compounds of formula I of the present invention by HDAC1 and HDAC6 enzymatic activity inhibition assays, an experiment was performed using a conventional substance as a control.

HDAC enzyme activity was measured using a HDAC Fluorimetric Drug Discovery Kit (BML-AK511, 516, Enzo Life Science). For the HDAC1 enzyme activity test, human recombinant HDAC1 (BML-SE456) was used as an enzyme source, and Fluor de Lys®-"SIRT1 (BNL-KI177) was used as a substrate. A 5-fold dilution of the compound was seeded into a 96-well plate, and then 0.3 μg of the enzyme and 10 μM of the substrate were added to each well of the plate and allowed to react at 30° C. for 60 minutes. Then, Fluor de Lys®-Developer II (BML-KI176) was added thereto and allowed to react for 30 minutes, after which the fluorescence value (Ex 360, Em 460) was measured using a multi-plate reader (Flexstation 3, Molecular Device). The HDAC6 enzyme was tested using human recombinant HDAC6 (382180) (Calbiochem) according to the same protocol as the HDAC1 enzyme activity test method. Based on the resulting values, each IC$_{50}$ value was calculated using GraphPad Prism4.0 program.

TABLE 2

Results of HDAC enzyme activity inhibition assays

| Ex. | Comp. | HDAC1 (nM) | HDAC6 (nM) | HDAC6 selectivity (fold) |
|---|---|---|---|---|
| 1 | 11044 | ND | 331 | 302 |
| 2 | 11045 | ND | 158 | 633 |
| 3 | 11078 | ND | 3467 | 29 |
| 4 | 11088 | 51360 | 127 | 404 |
| 5 | 11089 | 47853 | 50 | 957 |
| 6 | 11120 | ND | 38 | 2631 |
| 7 | 11121 | ND | 2536 | 39 |
| 8 | 11128 | ND | 520 | 192 |
| 9 | 11129 | ND | 2101 | 48 |
| 10 | 11133 | ND | 345 | 290 |
| 11 | 11151 | ND | 135 | 741 |
| 12 | 11152 | ND | 58 | 1724 |
| 13 | 11153 | ND | 126 | 793 |
| 14 | 11154 | ND | 19 | 5263 |
| 15 | 11155 | ND | 80 | 1250 |
| 16 | 11156 | ND | 29 | 3448 |
| 17 | 11167 | 34219 | 38 | 900 |
| 18 | 11168 | ND | 23 | 4348 |
| 19 | 11169 | 41062 | 38 | 1081 |
| 20 | 11170 | ND | 14 | 7143 |
| 21 | 11171 | 26607 | 21 | 1267 |
| 22 | 11172 | ND | 9 | 11111 |
| 23 | 11173 | 28620 | 661 | 43 |
| 24 | 11174 | ND | 1310 | 76 |
| 25 | 11175 | ND | 179 | 559 |
| 26 | 11176 | ND | 28 | 3571 |
| 27 | 11177 | 18908 | 57 | 332 |
| 28 | 11178 | ND | 20 | 5000 |
| 29 | 11179 | 7809 | 37 | 211 |
| 30 | 11180 | ND | 62 | 1613 |
| 31 | 11181 | ND | 33 | 3030 |
| 32 | 11182 | ND | 17 | 5882 |
| 33 | 11183 | ND | 235 | 426 |
| 34 | 11184 | 2274 | 36 | 63 |
| 35 | 11186 | ND | 231 | 433 |
| 36 | 11190 | 19512 | 129 | 151 |
| 37 | 11191 | ND | 20 | 5000 |
| 38 | 11192 | 7005 | 65 | 108 |
| 39 | 11193 | ND | 27 | 3704 |
| 40 | 11194 | ND | 65 | 1538 |

TABLE 2-continued

Results of HDAC enzyme activity inhibition assays

| Ex. | Comp. | HDAC1 (nM) | HDAC6 (nM) | HDAC6 selectivity (fold) |
|---|---|---|---|---|
| 41 | 11195 | ND | 64 | 1563 |
| 42 | 11196 | 28672 | 65 | 441 |
| 43 | 11197 | ND | 15 | 6667 |
| 44 | 11216 | 27965 | 76 | 368 |
| 45 | 11217 | ND | 13 | 7692 |
| 46 | 11218 | ND | 233 | 429 |
| 47 | 11219 | ND | 94 | 1064 |
| 48 | 11220 | 26204 | 31 | 845 |
| 49 | 11221 | ND | 101 | 990 |
| 50 | 11222 | ND | 412 | 243 |
| 51 | 11225 | ND | 24 | 4167 |
| 52 | 11226 | 11576 | 39 | 297 |
| 53 | 11227 | ND | 23 | 4348 |
| 54 | 11229 | ND | 85 | 1176 |
| 55 | 11230 | ND | 33 | 3030 |
| 56 | 11231 | ND | 22 | 4545 |
| 57 | 11248 | ND | 112 | 893 |
| 58 | 11249 | ND | 37 | 2703 |
| 59 | 11250 | ND | 100 | 1000 |
| 60 | 11251 | ND | 64 | 1563 |
| 61 | 11252 | ND | 39 | 2564 |
| 62 | 11253 | ND | 666 | 150 |
| 63 | 11254 | ND | 29 | 3448 |
| 64 | 11255 | ND | 47 | 2128 |
| 65 | 11256 | ND | 13 | 7692 |
| 66 | 11271 | ND | 129 | 775 |
| 67 | 11272 | ND | 51 | 1961 |
| 68 | 11273 | ND | 79 | 1266 |
| 69 | 11274 | ND | 41 | 2439 |
| 70 | 11275 | ND | 73 | 1370 |
| 71 | 11276 | ND | 25 | 4000 |
| 72 | 11277 | ND | 187 | 535 |
| 73 | 11278 | ND | 52 | 1923 |
| 74 | 11279 | ND | 111 | 901 |
| 75 | 11280 | ND | 79 | 1266 |
| 76 | 11281 | ND | 44 | 2273 |
| 77 | 11282 | ND | 128 | 781 |
| 78 | 11283 | ND | 54 | 1852 |
| 79 | 11284 | ND | 27 | 3704 |
| 80 | 11287 | ND | 29 | 3448 |
| 81 | 11288 | ND | 47 | 2128 |
| 82 | 11289 | ND | 28 | 3571 |
| 83 | 11290 | ND | 49 | 2041 |
| 84 | 11291 | ND | 31 | 3226 |
| 85 | 11292 | ND | 56 | 1786 |
| 86 | 11323 | ND | 110 | 909 |
| 87 | 11324 | ND | 21 | 4762 |
| 88 | 11338 | ND | 513 | 195 |
| 89 | 11345 | ND | 28 | 3571 |
| 90 | 11346 | ND | 23 | 4348 |
| 91 | 11347 | ND | 103 | 971 |
| 92 | 11348 | ND | 132 | 758 |
| 93 | 11350 | ND | 10 | 10000 |
| 94 | 11351 | ND | 69 | 1449 |
| 95 | 11352 | ND | 8 | 12500 |
| 96 | 11353 | ND | 26 | 3846 |
| 97 | 11354 | ND | 8 | 12500 |
| 98 | 11355 | ND | 16 | 6250 |
| 99 | 11366 | ND | 11 | 9091 |
| 100 | 11367 | ND | 16 | 6250 |
| 101 | 11368 | ND | 15 | 6667 |
| 102 | 11372 | ND | 9 | 11111 |
| 103 | 11373 | ND | 10 | 10000 |
| 104 | 11377 | ND | 22 | 4545 |
| 105 | 11386 | ND | 76 | 1316 |
| 106 | 11387 | ND | 92 | 1087 |
| 107 | 11388 | ND | 75 | 1333 |
| 108 | 11389 | ND | 960 | 104 |
| 109 | 11390 | ND | 13 | 7692 |
| 110 | 11392 | ND | 100 | 1000 |
| 111 | 11402 | ND | 76 | 1316 |
| 112 | 11403 | ND | 78 | 1282 |
| 113 | 11404 | ND | 105 | 952 |
| 114 | 11405 | ND | 67 | 1493 |
| 115 | 11406 | ND | 230 | 435 |
| 116 | 11411 | ND | 7 | 14286 |
| 117 | 11412 | ND | 12 | 8333 |
| 118 | 11426 | ND | 13 | 7692 |
| 119 | 11427 | ND | 284 | 352 |
| 120 | 11428 | ND | 15 | 6667 |
| 121 | 11429 | 18704 | 65 | 288 |
| 122 | 11430 | 22220 | 42 | 529 |
| 123 | 11431 | 28088 | 62 | 453 |
| 124 | 11432 | 16510 | 61 | 271 |
| 125 | 11433 | ND | 12 | 8333 |
| 126 | 11447 | ND | 18 | 5556 |
| 127 | 11448 | ND | 21 | 4762 |
| 128 | 11451 | 27165 | 9 | 3018 |
| 129 | 11452 | 27515 | 8 | 3439 |
| 130 | 11460 | 27271 | 10 | 2727 |
| 131 | 11461 | 27690 | 10 | 2769 |
| 132 | 11462 | 21083 | 8 | 2635 |
| 133 | 11463 | 22309 | 8 | 2789 |
| 134 | 11497 | 21816 | 8 | 2727 |
| 135 | 11501 | 56678 | 15 | 3779 |
| 136 | 11502 | 78107 | 14 | 5579 |
| 137 | 11503 | 71875 | 15 | 4792 |
| 138 | 11504 | 86221 | 18 | 4790 |
| 139 | 11505 | 60400 | 13 | 4646 |
| 140 | 11506 | 59719 | 12 | 4977 |
| 141 | 11507 | 51403 | 14 | 3672 |
| 142 | 11508 | 49567 | 23 | 2155 |
| 143 | 11514 | 40350 | 43 | 938 |
| 144 | 11518 | 39843 | 68 | 586 |
| 145 | 11520 | ND | 32 | 3125 |
| 146 | 11521 | 43329 | 18 | 2407 |
| 147 | 11522 | ND | 24 | 4167 |
| 148 | 11539 | ND | 23 | 4348 |
| 149 | 11540 | ND | 10 | 10000 |
| 150 | 11541 | ND | 16 | 6250 |
| 151 | 11552 | ND | 14 | 7143 |
| 152 | 11553 | ND | 17 | 5882 |
| 153 | 11554 | ND | 23 | 4348 |
| 154 | 11564 | ND | 21 | 4762 |
| 155 | 11565 | 46512 | 149 | 312 |
| 156 | 11566 | ND | 89 | 1124 |
| 157 | 11567 | 30926 | 4326 | 7 |
| 158 | 11573 | 2544 | 2290 | 1 |
| 159 | 11582 | ND | 23 | 4348 |
| 160 | 11583 | ND | 23 | 4348 |
| 161 | 11588 | ND | 44 | 2273 |
| 162 | 11589 | ND | 43 | 2326 |
| 163 | 11605 | ND | ND | ND |
| 164 | 11606 | ND | 1520 | 66 |
| 165 | 11625 | ND | 139 | 719 |
| 166 | 11628 | ND | 48 | 2083 |
| 167 | 11629 | ND | 96 | 1041 |
| 168 | 11630 | ND | 31 | 3225 |
| 169 | 11631 | ND | 229 | 436 |
| 170 | 11632 | ND | 63 | 1587 |
| 171 | 11633 | ND | 46 | 2173 |
| 172 | 11634 | ND | 48 | 2083 |
| 173 | 11636 | ND | 116 | 862 |
| 174 | 11637 | 66980 | 20 | 3349 |
| 175 | 11638 | 40912 | 23 | 1778 |
| 176 | 11639 | 77694 | 42 | 1849 |
| 177 | 11645 | 77906 | 61 | 1277 |
| 178 | 11646 | 108816 | 15 | 7254 |
| 179 | 11647 | 79792 | 22 | 3626 |
| 180 | 11648 | 498032 | 60 | 8300 |
| 181 | 11655 | ND | 58 | 1724 |
| 182 | 11656 | ND | 63 | 1587 |
| 183 | 11657 | ND | 82 | 1219 |
| 184 | 11658 | ND | 40 | 2500 |
| 185 | 11663 | ND | 173 | 578 |
| 186 | 11665 | ND | 19 | 5263 |
| 187 | 11668 | ND | 138 | 724 |
| 188 | 11669 | ND | 111 | 900 |
| 189 | 11675 | ND | 182 | 549 |
| 190 | 11676 | ND | 71 | 1408 |

TABLE 2-continued

Results of HDAC enzyme activity inhibition assays

| Ex. | Comp. | HDAC1 (nM) | HDAC6 (nM) | HDAC6 selectivity (fold) |
|---|---|---|---|---|
| 191 | 11677 | ND | 57 | 1754 |
| 192 | 11678 | 54610 | 56 | 975 |
| 193 | 11679 | 61331 | 23 | 2666 |
| 194 | 11680 | 76400 | 29 | 2634 |
| 195 | 11681 | ND | 15 | 6667 |
| 196 | 11682 | ND | 22 | 4545 |
| 197 | 11683 | ND | 7 | 14285 |
| 198 | 11684 | ND | 16 | 6250 |
| 199 | 11685 | ND | 17 | 5882 |
| 200 | 11686 | 60296 | 92.1 | 654 |
| 201 | 11687 | 79144 | 106.7 | 741 |
| 202 | 11688 | 20214 | 47.7 | 423 |
| 203 | 11689 | 20008 | 46.6 | 429 |
| 204 | 11690 | 54825 | 224.5 | 244 |
| 205 | 11691 | 34216 | 80.5 | 425 |
| 206 | 11692 | 71655 | 54.7 | 1309 |
| 207 | 11693 | ND | 504.2 | 198 |
| 208 | 11694 | ND | 464 | 215 |
| 209 | 11695 | 61397 | 200.5 | 306 |
| 210 | 11696 | 51448 | 177.7 | 289 |
| 211 | 11697 | ND | 988.4 | 101 |
| 212 | 11698 | ND | 661 | 151 |
| 213 | 11699 | ND | 128.8 | 776 |
| 214 | 11700 | ND | 127.8 | 782 |
| 215 | 11705 | ND | 156.9 | 637 |
| 216 | 11706 | ND | 662.4 | 150 |
| 217 | 11707 | 42459 | 71.1 | 597 |
| 218 | 11708 | 65126 | 77.8 | 837 |
| 219 | 11709 | 80425 | 75.5 | 1065 |
| 220 | 11710 | 29435 | 50.9 | 578 |
| 221 | 11711 | 61289 | 70.1 | 874 |
| 222 | 11712 | ND | 377.9 | 264 |
| 223 | 11717 | ND | 113.7 | 879 |
| 224 | 11718 | ND | 73.9 | 1353 |
| 225 | 11719 | ND | 84.9 | 1177 |
| 226 | 11721 | ND | 21.1 | 4739 |
| 227 | 11722 | 41031 | 32.4 | 1266 |
| 228 | 11723 | ND | 78.6 | 1272 |
| 229 | 11724 | ND | 134.9 | 741 |
| 230 | 11725 | ND | 242.6 | 412 |
| 231 | 11726 | ND | 127.8 | 782 |
| 232 | 11727 | 33464 | 56.3 | 594 |
| 233 | 11728 | 21592 | 47.6 | 453 |
| 234 | 11729 | ND | 1763 | 56 |
| 235 | 11730 | ND | 2531 | 39 |
| 236 | 11731 | ND | 1752 | 57 |
| 237 | 11732 | ND | 542.3 | 184 |
| 238 | 11733 | ND | 490.4 | 203 |
| 239 | 11734 | ND | 754.9 | 132 |
| 240 | 11735 | ND | 809 | 123 |
| 241 | 11736 | ND | 461.2 | 216 |
| 242 | 11737 | ND | 69.4 | 1440 |
| 243 | 11738 | ND | 68.2 | 1466 |
| 244 | 11739 | ND | 674.9 | 148 |
| 245 | 11740 | ND | 530.9 | 188 |
| 246 | 11741 | ND | 1742 | 57 |
| 247 | 11742 | ND | 239.1 | 418 |
| 248 | 11743 | ND | 68.2 | 1466 |
| 249 | 11744 | ND | 531 | 188 |
| 250 | 11745 | ND | 231.2 | 432 |
| 251 | 11746 | ND | 127.4 | 784 |
| 252 | 11747 | ND | 95.2 | 1050 |
| 253 | 11748 | ND | 433.3 | 230 |
| 254 | 11749 | ND | 390.7 | 255 |
| 255 | 11750 | ND | 1294 | 77 |
| 256 | 11751 | ND | 85.4 | 1170 |
| 257 | 11752 | ND | 115.1 | 868 |
| 258 | 11753 | ND | 104.9 | 953 |
| 259 | 11754 | ND | 70.4 | 1420 |
| 260 | 11755 | ND | 72.6 | 1377 |
| 261 | 11756 | ND | 377.5 | 264 |
| 262 | 11757 | ND | 69.1 | 1447 |
| 263 | 11758 | ND | 96.2 | 1039 |
| 264 | 11759 | ND | 101.6 | 984 |
| 265 | 11760 | ND | 196.7 | 508 |
| 266 | 11761 | ND | 102.4 | 976 |
| 267 | 11762 | ND | 999.6 | 100 |
| 268 | 11763 | ND | 105.4 | 948 |
| 269 | 11764 | ND | 136.7 | 731 |
| 270 | 11765 | ND | 189.8 | 526 |
| 271 | 11766 | ND | 312.7 | 319 |
| 272 | 11767 | ND | 118.4 | 844 |
| 273 | 11768 | ND | 38.3 | 2610 |
| 274 | 11769 | ND | 278.3 | 359 |
| 275 | 11770 | ND | 886.3 | 112 |
| 276 | 11771 | ND | 321.1 | 311 |
| 277 | 11772 | ND | 48.6 | 2057 |
| 278 | 11773 | ND | 269.7 | 370 |
| 279 | 11774 | ND | 66.5 | 1503 |
| 280 | 11775 | ND | 34.4 | 2906 |
| 281 | 11776 | ND | 881.8 | 113 |
| 282 | 11777 | ND | 28.8 | 3472 |
| 283 | 11778 | ND | 36.7 | 2724 |
| 284 | 11779 | ND | 40.1 | 2493 |
| 285 | 11780 | ND | 52.8 | 1893 |
| 286 | 11781 | ND | 18.8 | 5319 |
| 287 | 11782 | ND | 24.8 | 4032 |
| 288 | 11783 | ND | 69.4 | 1440 |
| 289 | 11784 | ND | 31.7 | 3154 |
| 290 | 11785 | ND | 47.8 | 2092 |
| 291 | 11786 | ND | 54.7 | 1828 |
| 292 | 11790 | ND | 44.6 | 2227 |
| 293 | 11791 | ND | 47.3 | 2114 |
| 294 | 11792 | ND | 82.1 | 1218 |
| 295 | 11793 | ND | 58.2 | 1718 |
| 296 | 11794 | ND | 45.6 | 2192 |
| 297 | 11795 | ND | 68.2 | 1466 |
| 298 | 11796 | ND | 1777 | 56 |
| 299 | 11797 | ND | 121.7 | 821 |
| 300 | 11798 | ND | 185.8 | 538 |
| 301 | 11799 | ND | 193.6 | 516 |
| 302 | 11800 | ND | 44.4 | 2252 |
| 303 | 11801 | ND | 34.0 | 2941 |
| 304 | 11802 | ND | 35.1 | 2849 |
| 305 | 11803 | ND | 21.8 | 4587 |
| 306 | 11804 | ND | 32.1 | 3115 |
| 307 | 11805 | ND | 33.1 | 3021 |
| 308 | 11806 | ND | 25.0 | 4000 |
| 309 | 11807 | ND | 63.1 | 1584 |
| 310 | 11808 | ND | 34.7 | 2881 |
| 311 | 11809 | ND | 30.1 | 3222 |
| 312 | 11810 | ND | 35.8 | 2793 |
| 313 | 11811 | ND | 42.4 | 2358 |
| 314 | 11812 | ND | 32.9 | 3039 |
| 315 | 11813 | ND | 34.1 | 2932 |
| 316 | 11814 | ND | 1134 | 88 |
| 317 | 11815 | ND | 75.4 | 1326 |
| 318 | 11816 | ND | 37.1 | 2695 |
| 319 | 11817 | ND | 58.2 | 1718 |
| 320 | 11818 | ND | 60.7 | 1647 |
| 321 | 11819 | ND | 351 | 284 |
| 322 | 11820 | ND | 60.5 | 1652 |
| 323 | 11821 | ND | 133.8 | 747 |
| 324 | 11822 | ND | 73.28 | 1365 |
| 325 | 11836 | ND | 31.78 | 3147 |
| 326 | 11837 | ND | 24 | 4167 |
| 327 | 11838 | ND | 44.63 | 2241 |
| 328 | 11839 | ND | 44.73 | 2236 |
| 329 | 11840 | ND | 192.2 | 520 |
| 330 | 11841 | ND | 35.84 | 2790 |
| 331 | 11842 | ND | 825.9 | 121 |
| 332 | 11843 | ND | 993.7 | 101 |
| 333 | 11844 | ND | 580.6 | 172 |
| 334 | 11845 | ND | 973.4 | 103 |
| 335 | 11847 | 24519 | 55.12 | 445 |
| 336 | 11848 | 38926 | 58.9 | 661 |
| 337 | 11849 | ND | 62.3 | 1605 |

As can be seen in Table 2 above, the 1,3,4-oxadiazole sulfonamide derivative compounds, stereoisomers thereof or pharmaceutically acceptable salts thereof according to the present invention showed superior selective HDAC6 inhibitory activities in the HDAC1 and HDAC6 activity inhibition assays.

EXPERIMENTAL EXAMPLE 2

Analysis of the Effect of HDAC6-Specific Inhibitors on Mitochondrial Axonal Transport (In Vitro)

The effect of HDAC6-specific inhibitors on mitochondrial axonal transport was analyzed. Specifically, in order to examine whether the compounds represented by formula I according to the present invention selectively inhibit HDAC6 activity to increase the acetylation of tubulin, which is a major substrate of HDAC6, thereby improving the mitochondrial axonal transport velocity reduced by amyloid-beta treatment in neuronal axons, a comparison experiment was performed using a compound that have already been developed as a control.

Hippocampal neurons from Sprague-Dawley (SD) rat embryos at embryonic day 17-18 (E17-18) were cultured in an extracellular matrix-coated dish for imaging for 7 days, and then treated with 1 M of an amyloid-beta peptides. After 24 hours, the neurons were treated with compounds for 3 hours on the 8th days in vitro and treated with MitoTracker Red CMXRos (Life Technologies, NY, USA) for the last 5 minutes to stain the mitochondria. Axonal transport of the stained mitochondria was imaged using a confocal microscope (Leica SP8; Leica Microsystems, UK) at 1-second intervals for 1 minute, and the transport velocity per second of each mitochondrion was determined using the IMARIS analysis software (BITPLANE, Zurich, Switzerland).

As a result, it was found that the 1,3,4-oxadiazole sulfonamide derivative compounds, stereoisomers thereof or pharmaceutically acceptable salts according to the present invention improved the velocity of mitochondrial axonal transport.

The invention claimed is:
1. An 1,3,4-oxadiazole sulfonamide derivative compound represented by formula I, a stereoisomer thereof or a pharmaceutically acceptable salt thereof:

[Formula I]

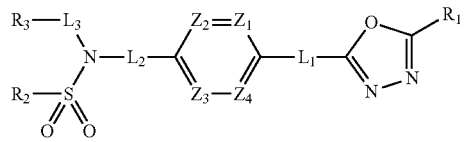

wherein $R_1$ is —$CX_2H$ or —$CX_3$;
$R_2$ is —($C_1$-$C_4$ alkyl), —($C_1$-$C_4$ alkyl)-O($C_1$-$C_4$ alkyl), —($C_1$-$C_4$)—C(=O)—O($C_1$-$C_4$ alkyl), —($C_1$-$C_4$ alkyl)-O—C(=O)—($C_1$-$C_4$ alkyl), —($C_1$-$C_4$ alkyl)-$NR^AR^B$, —($C_1$-$C_4$ alkyl)-aryl, —($C_1$-$C_4$ alkyl)-heteroaryl, -aryl, -heteroaryl,

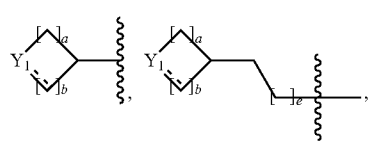

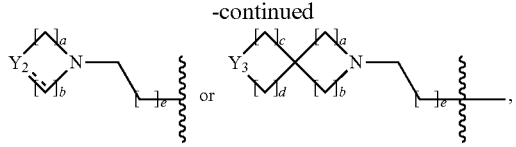

wherein at least one H of the —($C_1$-$C_4$ alkyl), —($C_1$-$C_4$ alkyl)-O($C_1$-$C_4$ alkyl), —($C_1$-$C_4$ alkyl)-C(=O)—O ($C_1$-$C_4$ alkyl), —($C_1$-$C_4$ alkyl)-O—C(=O)—($C_1$-$C_4$ alkyl) or —($C_1$-$C_4$ alkyl)-$NR^AR^B$ may be substituted with —X or —OH,
at least one H of the —($C_1$-$C_4$ alkyl)-aryl, —($C_1$-$C_4$ alkyl)heteroaryl, -aryl or heteroaryl may be substituted with —X, —OH, —O($C_1$-$C_4$ alkyl), —($C_1$-$C_4$ alkyl), —$CF_3$, —$CF_2H$, —($C_1$-$C_4$ alkyl)-OH, —C(=O)—($C_1$-$C_4$ alkyl), —C(=O)—O($C_1$-$C_4$ alkyl), —($C_1$-$C_4$ alkyl)-C(=O)—($C_1$-$C_4$ alkyl), —C(=O)—$CF_3$ or —C(=O)—$CF_2H$, and at least one H of

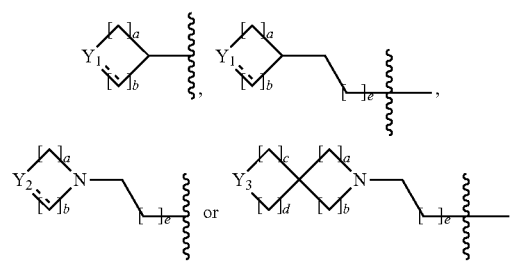

may be substituted with —X, —OH, —O($C_1$-$C_4$ alkyl), —$NR^AR^B$, —CN, —($C_1$-$C_4$ alkyl), —$CF_3$, —$CF_2H$, —($C_1$-$C_4$ alkyl)-OH, —($C_1$-$C_4$ alkyl)-$NR^AR^B$, —C(=O)—($C_1$-$C_4$ alkyl), —C(=O)—$CF_3$, —C(=O)—$CF_2H$, —C(=O)—$NR^AR^B$, —C(=O)—O($C_1$-$C_4$ alkyl), —($C_1$-$C_4$ alkyl)-C(=O)—($C_1$-$C_4$ alkyl), —($C_1$-$C_4$ alkyl)-OC(=O)—$CF_2H$, —($C_3$-$C_6$ heterocycloalkyl), —($C_1$-$C_4$ alkyl)-aryl, -aryl or -heteroaryl, wherein at least one H of the —($C_1$-$C_4$ alkyl)-aryl, -aryl or -heteroaryl may be substituted with —X, —OH, —O($C_1$-$C_4$ alkyl) or —($C_1$-$C_4$ alkyl);
$R_3$ is —H, —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), -aryl, -heteroaryl,

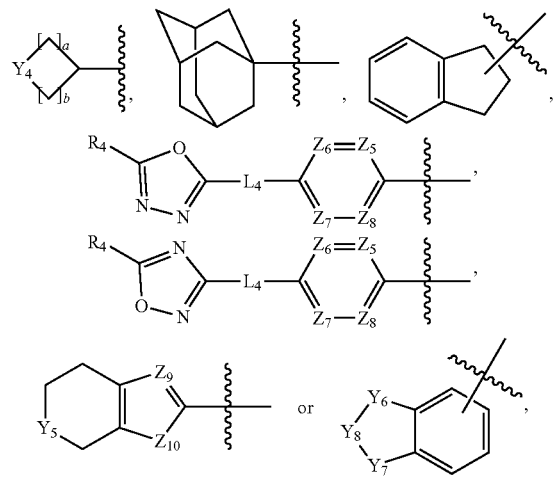

wherein at least one H of the —(C₁-C₄ alkyl), —(C₁-C₄ alkyl)-O(C₁-C₄ alkyl) or —(C₁-C₄ alkyl)-C(=O)—O(C₁-C₄ alkyl) may be substituted with —X or —OH, at least one H of the aryl or -heteroaryl may be substituted with —X, —OH, —O(C₁-C₄ alkyl), —(C₁-C₄ alkyl), —CF₃, —CF₂H, —(C₁-C₄ alkyl)-OH, —C(=O)—(C₁-C₄ alkyl), —C(=O)—O(C₁-C₄ alkyl), —(C₁-C₄ alkyl)-C(=O)—(C₁-C₄ alkyl), —C(=O)—CF₃, —C(=O)—CF₂H,

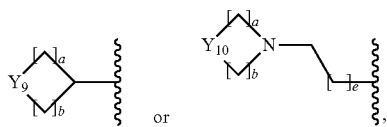

at least one H of

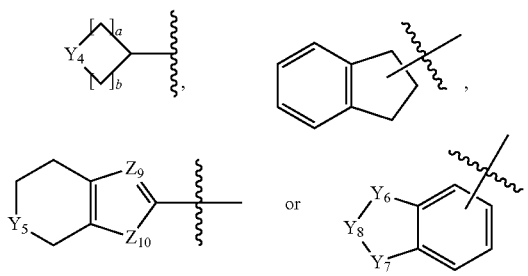

may be substituted with —X, —OH, —O(C₁-C₄ alkyl), —(C₁-C₄ alkyl), —C(=O)—(C₁-C₄ alkyl), —C(=O)—O(C₁-C₄ alkyl) or —(C₃-C₆ heterocycloalkyl);

R₄ is —CX₂H or —CX₃;

L₁ to L₄ are each independently a bond or —(C₁-C₂ alkylene)-;

Z₁ to Z₈ are each independently N or CR^Z, wherein at least three of Z₁ to Z₄ or Z₅ to Z₈ may not be simultaneously N, and R^Z is —H, —X or —O(C₁-C₄ alkyl);

Z₉ and Z₁₀ are each independently N or S;

Y₁ to Y₃ are each independently —CH₂—, —NR^C—, —O— or —S(=O)₂—;

Y₄ to Y₇ are each independently —CH₂—, —NR^D— or —O—;

Y₈ is —C(=O), —CH₂— or —NR^E—;

Y₉ and Y₁₀ are each independently —NR^F— or —S(=O)₂—;

R^A and R^B are each independently —H, —(C₁-C₄ alkyl), —(C₁-C₄ alkyl)-aryl, —C(=O)—CF₂H or —C(=O)—O(C₁-C₄ alkyl);

R^C to R^E are each independently —H, —(C₁-C₄ alkyl), —(C₁-C₄ alkyl)-OH, —(C₁-C₄ alkyl)-O—(C₁-C₄ alkyl), —C(=O)—(C₁-C₄ alkyl), —C(=O)—O(C₁-C₄ alkyl), —C(=O)—(C₃-C₇ cycloalkyl), —(C₁-C₄ alkyl)-C(=O)—(C₂-C₆ heterocycloalkyl), —S(=O)₂—(C₁-C₄ alkyl), —(C₁-C₄ alkyl)-aryl, —(C₂-C₄ alkenyl)-aryl, —(C₁-C₄ alkyl)-heteroaryl, -aryl, -heteroaryl,

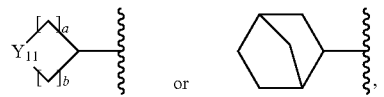

wherein at least one H of the —(C₁-C₄ alkyl)-aryl, —(C₂-C₄ alkenyl)-aryl, —(C₁-C₄ alkyl)-heteroaryl, -aryl, -heteroaryl,

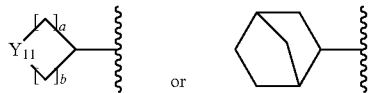

may be substituted with —X, —OH, —O(C₁-C₄ alkyl), —(C₁-C₄ alkyl) or —CF₃;

Y₁₁ is —CH₂—, —NR^F— or —O—;

R^F is —(C₁-C₄ alkyl), —C(=O)—(C₁-C₄ alkyl), —C(=O)—(C₁-C₄ alkyl)-OH, —C(=O)—(C₃-C₇ cycloalkyl) or —S(=O)₂—(C₁-C₄ alkyl);

═══ is a single bond or a double bond, provided that
═══ is a double bond, Y₁ or Y₂ is —CH—;

a to e are each independently an integer of 0, 1, 2 or 3, provided that a and b may not be simultaneously 0, and c and d may not be simultaneously 0; and X is F, Cl, Br or I.

2. The 1,3,4-oxadiazole sulfonamide derivative compound represented by formula I, stereoisomer thereof or pharmaceutically acceptable salt thereof according to claim 1, wherein R₁ is —CX₂H or —CX₃;

R₂ is —(C₁-C₄ alkyl), —(C₁-C₄ alkyl)-O(C₁-C₄ alkyl), —(C₁-C₄ alkyl)-C(=O)—O(C₁-C₄ alkyl), —(C₁-C₄ alkyl)-O—C(=O)—(C₁-C₄ alkyl), —(C₁-C₄ alkyl)-NR^AR^B, —(C₁-C₄ alkyl)-heteroaryl, -aryl, -heteroaryl,

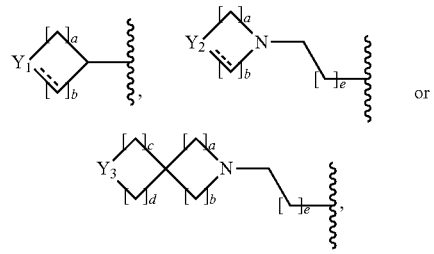

wherein at least one H of the —(C₁-C₄ alkyl), —(C₁-C₄ alkyl)-O(C₁-C₄ alkyl), —(C₁-C₄ alkyl)-C(=O)—O(C₁-C₄ alkyl), —(C₁-C₄ alkyl)-O—C(=O)—(C₁-C₄ alkyl) or —(C₁-C₄ alkyl)-NR^AR^B may be substituted with —X or —OH, at least one H of the —(C₁-C₄ alkyl)-heteroaryl, -aryl or -heteroaryl may be substituted with —O(C₁-C₄ alkyl), —(C₁-C₄ alkyl) or —(C₁-C₄ alkyl)-OH, and at least one H of

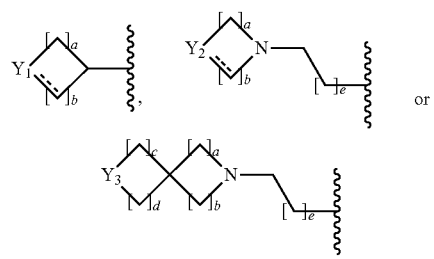

may be substituted with —X, —OH, —NR$^A$R$^B$, —CN, —(C$_1$-C$_4$ alkyl), —(C$_1$-C$_4$ alkyl)-OH, —(C$_1$-C$_4$ alkyl)-NR$^A$R$^B$, —C(=O)—NR$^A$R$^B$, —C(=O)—O(C$_1$-C$_4$ alkyl), —(C$_1$-C$_4$ alkyl)-C(=O)—(C$_1$-C$_4$ alkyl), —(C$_1$-C$_4$ alkyl)-OC(=O)—CF$_2$H, —(C$_3$-C$_6$ heterocycloalkyl), —(C$_1$-C$_4$ alkyl)-aryl, -aryl or -heteroaryl, wherein at least one H of the —(C$_1$-C$_4$ alkyl)-aryl, -aryl or -heteroaryl may be substituted with —X, —OH, —O(C$_1$-C$_4$ alkyl) or —(C$_1$-C$_4$ alkyl);

R$_3$ is —H, —(C$_1$-C$_4$ alkyl), -aryl, -heteroaryl,

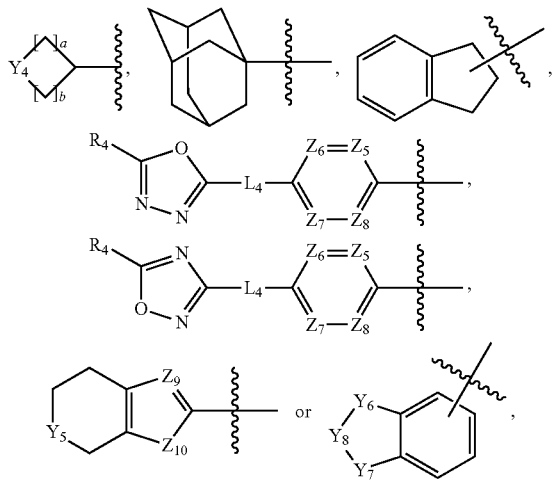

wherein at least one H of the —(C$_1$-C$_4$ alkyl) may be substituted with —X or —OH, at least one H of the -aryl or -heteroaryl may be substituted with —X, —O(C$_1$-C$_4$ alkyl), —(C$_1$-C$_4$ alkyl), —CF$_3$, —C(=O)—(C$_1$-C$_4$ alkyl),

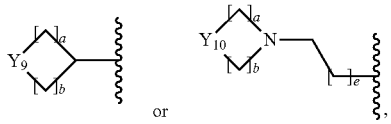

and
at least one H of

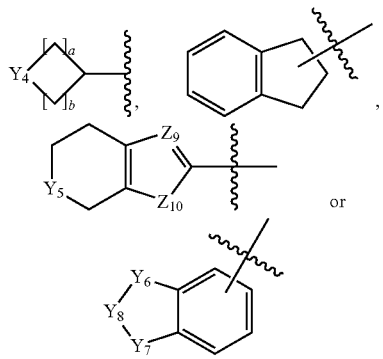

may be substituted with —(C$_1$-C$_4$ alkyl), —C(=O)—(C$_1$-C$_4$ alkyl), —C(=O)—O(C$_1$-C$_4$ alkyl) or —(C$_3$-C$_6$ heterocycloalkyl);

R$_4$ is —CX$_2$H or —CX$_3$;

L$_1$ to L$_4$ are each independently a bond or —(C$_1$-C$_2$ alkylene)-;

Z$_1$ to Z$_8$ are each independently N or CR$^Z$, wherein at least three of Z$_1$ to Z$_4$ or Z$_5$ to Z$_8$ may not be simultaneously N, and R$^Z$ is —H, —X or —O(C$_1$-C$_4$ alkyl);

Z$_9$ and Z$_{10}$ are each independently N or S;

Y$_1$ to Y$_3$ are each independently —CH$_2$—, —NR$^C$—, —O— or —S(=O)$_2$—;

Y$_4$ to Y$_7$ are each independently —CH$_2$—, —NR$^D$— or —O—;

Y$_8$ is —C(=O), —CH$_2$— or —NR$^E$—;

Y$_9$ and Y$_{10}$ are each independently —NR$^F$— or —S(=O)$_2$—;

R$^A$ and R$^B$ are each independently —H, —(C$_1$-C$_4$ alkyl), —(C$_1$-C$_4$ alkyl)-aryl, —C(=O)—CF$_2$H or —C(=O)—O(C$_1$-C$_4$ alkyl);

R$^C$ to R$^E$ are each independently —H, —(C$_1$-C$_4$ alkyl), —(C$_1$-C$_4$ alkyl)-OH, —(C$_1$-C$_4$ alkyl)-O—(C$_1$-C$_4$ alkyl), —C(=O)—(C$_1$-C$_4$ alkyl), —C(=O)—O(C$_1$-C$_4$ alkyl), —C(=O)—(C$_3$-C$_7$ cycloalkyl), —(C$_1$-C$_4$ alkyl)-C(=O)—(C$_2$-C$_6$ heterocycloalkyl), —S(=O)$_2$—(C$_1$-C$_4$ alkyl), —(C$_1$-C$_4$ alkyl)-aryl, —(C$_2$-C$_4$ alkenyl)-aryl, —(C$_1$-C$_4$ alkyl)-heteroaryl, -aryl, -heteroaryl,

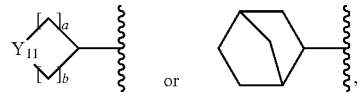

wherein at least one H of the —(C$_1$-C$_4$ alkyl)-aryl, —(C$_2$-C$_4$ alkenyl)-aryl, —(C$_1$-C$_4$ alkyl)-heteroaryl, -aryl, -heteroaryl,

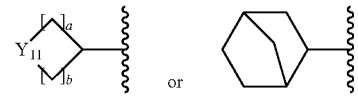

may be substituted with —X, —OH, —O(C$_1$-C$_4$ alkyl), —(C$_1$-C$_4$ alkyl) or —CF$_3$;

Y$_{11}$ is —CH$_2$—, —NR$^F$— or —O—;

R$^F$ is —(C$_1$-C$_4$ alkyl), —C(=O)—(C$_1$-C$_4$ alkyl), —C(=O)—(C$_1$-C$_4$ alkyl)-OH, —C(=O)—(C$_3$-C$_7$ cycloalkyl) or —S(=O)$_2$—(C$_1$-C$_4$ alkyl);

===== is a single bond or a double bond, provided that ===== is a double bond, Y$_1$ or Y$_2$ is —CH—;

a to e are each independently an integer of 0, 1, 2 or 3, provided that a and b may not be simultaneously 0, and c and d may not be simultaneously 0; and X is F, Cl, Br or I.

3. The 1,3,4-oxadiazole sulfonamide derivative compound represented by formula I, stereoisomer thereof or pharmaceutically acceptable salt thereof according to claim 2, wherein R$_1$ is —CX$_2$H;

R$_2$ is —(C$_1$-C$_4$ alkyl), —(C$_1$-C$_4$ alkyl)-C(=O)—O(C$_1$-C$_4$ alkyl), —(C$_1$-C$_4$ alkyl)-NR$^A$R$^B$, -heteroaryl,

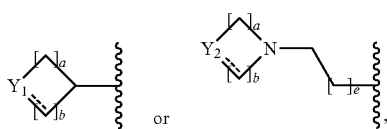 or 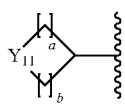, wherein at least one H of the —(C$_1$-C$_4$ alkyl), —(C$_1$-C$_4$ alkyl)-C(=O)—O(C$_1$-C$_4$ alkyl) or —(C$_1$-C$_4$ alkyl)-NR$^A$R$^B$ may be substituted with —X or —OH,
at least one H of the -heteroaryl may be substituted with —O(C$_1$-C$_4$ alkyl), —(C$_1$-C$_4$ alkyl) or —(C$_1$-C$_4$ alkyl)-OH, and
at least one H of

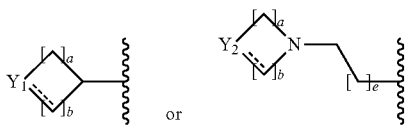

may be substituted with —(C$_1$-C$_4$ alkyl) or —(C$_1$-C$_4$ alkyl)-OH;
R$_3$ is -aryl, -heteroaryl or

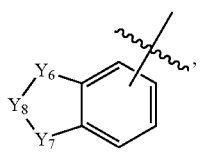, wherein at least one H of the -aryl or -heteroaryl may be substituted with —X, —O(C$_1$-C$_4$ alkyl), —(C$_1$-C$_4$ alkyl), —CF$_3$ or —C(=O)—(C$_1$-C$_4$ alkyl), and
at least one H of

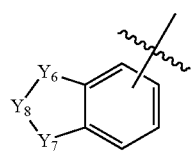

may be substituted with —(C$_1$-C$_4$ alkyl);
L$_1$ and L$_3$ are each independently a bond;
L$_2$ is —(C$_1$ alkylene)-;
Z$_1$ to Z$_4$ are each independently N or CR$^Z$, wherein at least two of Z$_1$ to Z$_4$ may not be simultaneously N, and R$^Z$ is —H or —X;
Y$_1$ is —NR$^C$—, —O— or —S(=O)$_2$—;
Y$_2$ is —CH$_2$— or —NR$^C$—;
Y$_6$ and Y$_7$ are each independently —O—;
Y$_8$ is —CH$_2$—;
R$^A$ and R$^B$ are each independently —(C$_1$-C$_4$ alkyl);
R$^C$ is —(C$_1$-C$_4$ alkyl), —(C$_1$-C$_4$ alkyl)-OH, —C(=O)—(C$_1$-C$_4$ alkyl), —S(=O)$_2$—(C$_1$-C$_4$ alkyl) or

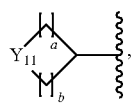, wherein at least one H of

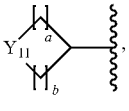

may be substituted with —(C$_1$-C$_4$ alkyl);
Y$_{11}$ is —NR$^F$— or —O—;
R$^F$ is —(C$_1$-C$_4$ alkyl), —C(=O)—(C$_1$-C$_4$ alkyl), —C(=O)—(C$_1$-C$_4$ alkyl)-OH or —S(=O)$_2$—(C$_1$-C$_4$ alkyl);
- - - - is a single bond;
a, b and e are each independently an integer of 0, 1 or 2, provided that a and b may not be simultaneously 0; and
X is F, Cl, Br or I.

4. The 1,3,4-oxadiazole sulfonamide derivative compound represented by formula I, stereoisomer thereof or pharmaceutically acceptable salt thereof according to claim 3,
wherein R$_1$ is —CF$_2$H;
R$_2$ is —(C$_1$-C$_4$ alkyl), —(C$_1$-C$_4$ alkyl)-NR$^A$R$^B$,

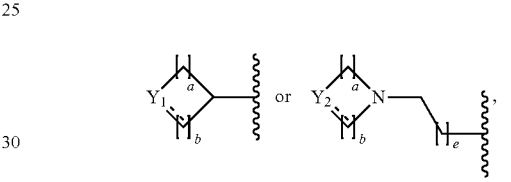

wherein at least one H of the —(C$_1$-C$_4$ alkyl) or —(C$_1$-C$_4$ alkyl)-NR$^A$R$^B$ may be substituted with —X or —OH, and
at least one H of

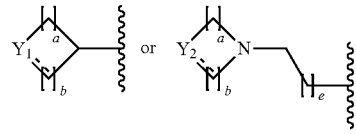

may be substituted with —(C$_1$-C$_4$ alkyl);
R$_3$ is -aryl or -heteroaryl,
wherein at least one H of the -aryl or -heteroaryl may be substituted with —X or —(C$_1$-C$_4$ alkyl);
L$_1$ and L$_3$ are each independently a bond;
L$_2$ is —(C$_1$ alkylene)-;
Z$_1$ to Z$_4$ are each independently N or CR$^Z$, wherein at least two of Z$_1$ to Z$_4$ may not be simultaneously N, and R$^Z$ is H or —X;
Y$_1$ is —NR$^C$—, —O— or —S(=O)$_2$—;
Y$_2$ is —NR$^C$—;
R$^A$ and R$^B$ are each independently —(C$_1$-C$_4$ alkyl);
R$^C$ is —(C$_1$-C$_4$ alkyl), —C(=O)—(C$_1$-C$_4$ alkyl), —S(=O)$_2$—(C$_1$-C$_4$ alkyl) or wherein at least one H of

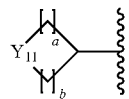

may be substituted with —(C$_1$-C$_4$ alkyl);
Y$_{11}$ is —NR$^F$— or —O—;
R$^F$ is —(C$_1$-C$_4$ alkyl), —C(=O)—(C$_1$-C$_4$ alkyl), —C(=O)—(C$_1$-C$_4$ alkyl)-OH or —S(=O)$_2$—(C$_1$-C$_4$ alkyl);

⸺ ⸺ is a single bond;

a, b and e are each independently an integer of 0, 1 or 2, provided that a and b may not be simultaneously 0; and X is F, Cl or Br.

5. The 1,3,4-oxadiazole sulfonamide derivative compound represented by formula I, stereoisomer thereof or pharmaceutically acceptable salt thereof according to claim 1, wherein the compound represented by formula I is selected from the group consisting of compounds described in the following table:

| Ex. | Comp. | Structure |
|---|---|---|
| 1 | 11044 | 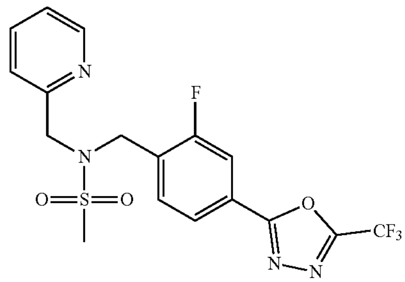 [SMILES: CS(=O)(=O)N(Cc1ccccn1)Cc1ccc(-c2nnc(C(F)(F)F)o2)cc1F] |
| 2 | 11045 | 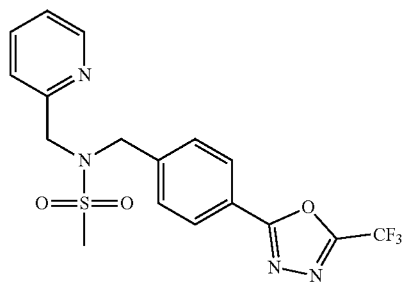 [SMILES: CS(=O)(=O)N(Cc1ccc(-c2nnc(C(F)(F)F)o2)cc1)Cc1ccccn1] |
| 3 | 11078 | 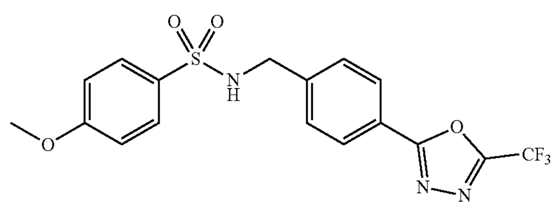 [SMILES: COc1ccc(S(=O)(=O)NCc2ccc(-c3nnc(C(F)(F)F)o3)cc2)cc1] |
| 4 | 11088 | 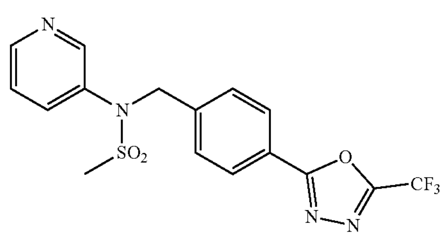 [SMILES: CS(=O)(=O)N(Cc1ccc(-c2nnc(C(F)(F)F)o2)cc1)c1cccnc1] |
| 5 | 11089 | 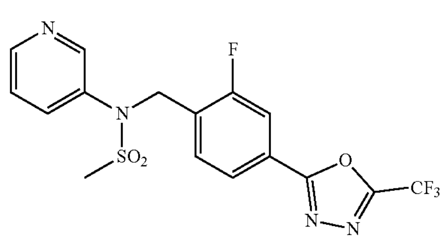 [SMILES: CS(=O)(=O)N(Cc1ccc(-c2nnc(C(F)(F)F)o2)cc1F)c1cccnc1] |

-continued

| Ex. | Comp. | Structure |
|---|---|---|
| 6 | 11120 | 3-pyridyl-N(SO2Me)-CH2-(2-fluoro-4-(5-(CF2H)-1,3,4-oxadiazol-2-yl)phenyl) |
| 7 | 11121 | MeSO2NH-CH2-(4-(5-(CF3)-1,3,4-oxadiazol-2-yl)phenyl) |
| 8 | 11128 | (2-pyridyl)CH2-N(SO2Me)-CH2-(5-(5-(CF3)-1,3,4-oxadiazol-2-yl)pyridin-2-yl) |
| 9 | 11129 | 3-pyridyl-N(SO2Me)-CH2-(2-methoxy-4-(5-(CF3)-1,3,4-oxadiazol-2-yl)phenyl) |
| 10 | 11133 | 3-pyridyl-N(SO2Me)-CH2-(3-fluoro-4-(5-(CF3)-1,3,4-oxadiazol-2-yl)phenyl) |
| 11 | 11151 | phenyl-N(SO2-3-pyridyl)-CH2-(4-(5-(CF3)-1,3,4-oxadiazol-2-yl)phenyl) |

-continued

| Ex. | Comp. | Structure |
|---|---|---|
| 12 | 11152 | 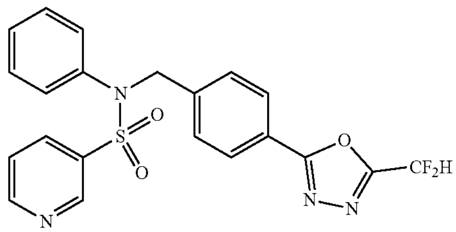 [SMILES: O=S(=O)(c1cccnc1)N(Cc1ccc(-c2nnc(C(F)F)o2)cc1)c1ccccc1] |
| 13 | 11153 | 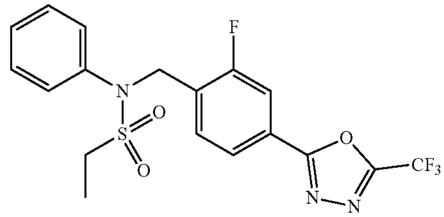 [SMILES: CCS(=O)(=O)N(Cc1ccc(-c2nnc(C(F)(F)F)o2)cc1F)c1ccccc1] |
| 14 | 11154 | 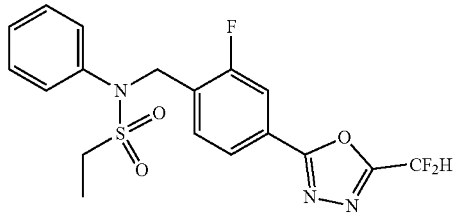 [SMILES: CCS(=O)(=O)N(Cc1ccc(-c2nnc(C(F)F)o2)cc1F)c1ccccc1] |
| 15 | 11155 | 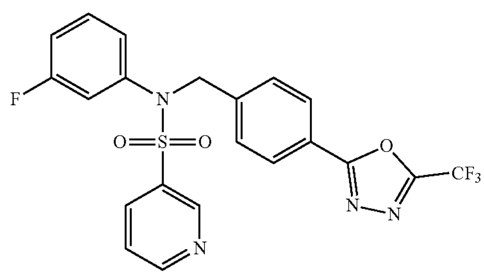 [SMILES: O=S(=O)(c1cccnc1)N(Cc1ccc(-c2nnc(C(F)(F)F)o2)cc1)c1cccc(F)c1] |
| 16 | 11156 | 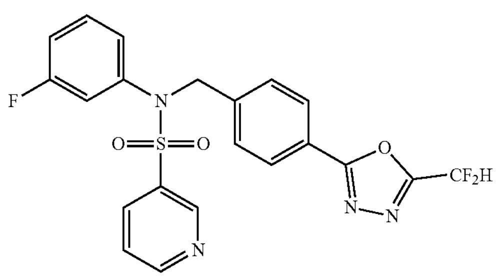 [SMILES: O=S(=O)(c1cccnc1)N(Cc1ccc(-c2nnc(C(F)F)o2)cc1)c1cccc(F)c1] |
| 17 | 11167 | 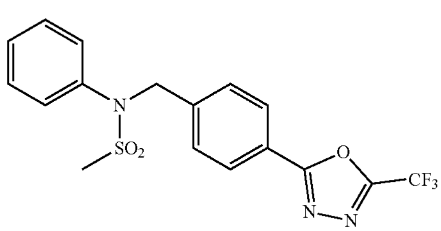 [SMILES: CS(=O)(=O)N(Cc1ccc(-c2nnc(C(F)(F)F)o2)cc1)c1ccccc1] |

-continued
| Ex. | Comp. | Structure |
|---|---|---|
| 18 | 11168 | 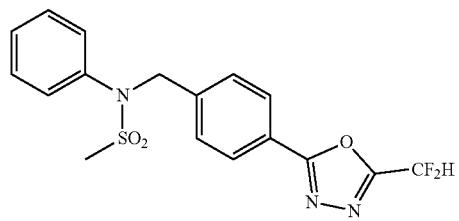 [SMILES: CS(=O)(=O)N(Cc1ccc(-c2nnc(C(F)F)o2)cc1)c1ccccc1] |
| 19 | 11169 | 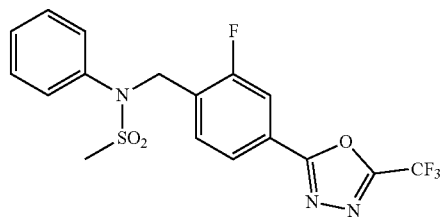 [SMILES: CS(=O)(=O)N(Cc1ccc(-c2nnc(C(F)(F)F)o2)cc1F)c1ccccc1] |
| 20 | 11170 | 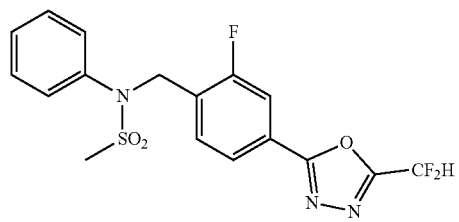 [SMILES: CS(=O)(=O)N(Cc1ccc(-c2nnc(C(F)F)o2)cc1F)c1ccccc1] |
| 21 | 11171 | 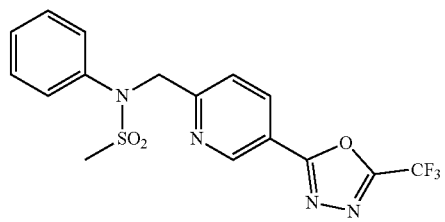 [SMILES: CS(=O)(=O)N(Cc1ccc(-c2nnc(C(F)(F)F)o2)cn1)c1ccccc1] |
| 22 | 11172 | 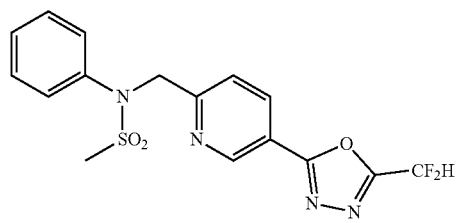 [SMILES: CS(=O)(=O)N(Cc1ccc(-c2nnc(C(F)F)o2)cn1)c1ccccc1] |
| 23 | 11173 | 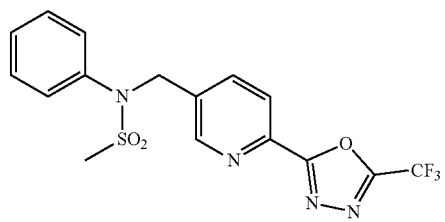 [SMILES: CS(=O)(=O)N(Cc1ccc(-c2nnc(C(F)(F)F)o2)nc1)c1ccccc1] |
| 24 | 11174 | 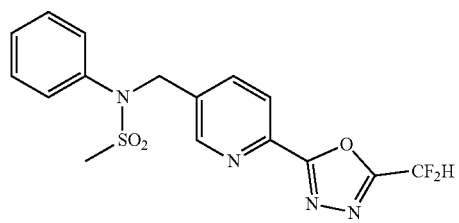 [SMILES: CS(=O)(=O)N(Cc1ccc(-c2nnc(C(F)F)o2)nc1)c1ccccc1] |

-continued
| Ex. | Comp. | Structure |
|---|---|---|
| 25 | 11175 | 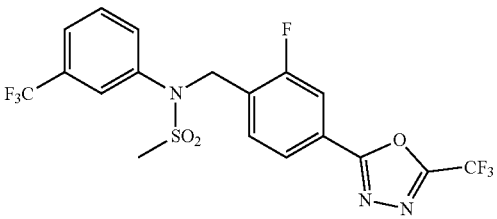 [SMILES: CS(=O)(=O)N(Cc1ccc(-c2nnc(C(F)(F)F)o2)cc1F)c1cccc(C(F)(F)F)c1] |
| 26 | 11176 | 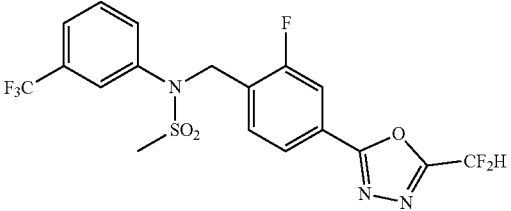 [SMILES: CS(=O)(=O)N(Cc1ccc(-c2nnc(C(F)F)o2)cc1F)c1cccc(C(F)(F)F)c1] |
| 27 | 11177 | 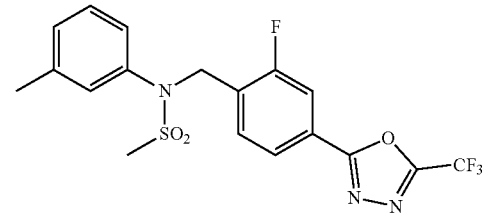 [SMILES: Cc1cccc(N(Cc2ccc(-c3nnc(C(F)(F)F)o3)cc2F)S(C)(=O)=O)c1] |
| 28 | 11178 | 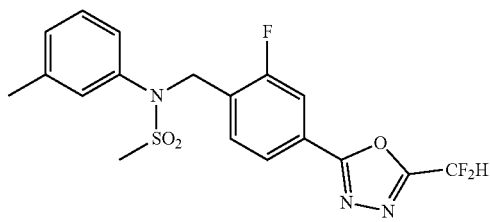 [SMILES: Cc1cccc(N(Cc2ccc(-c3nnc(C(F)F)o3)cc2F)S(C)(=O)=O)c1] |
| 29 | 11179 | 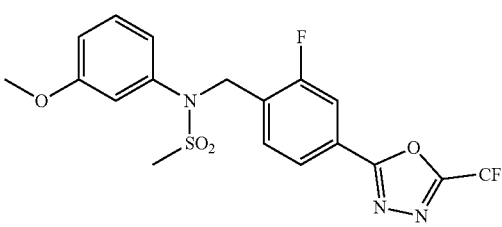 |
| 30 | 11180 | 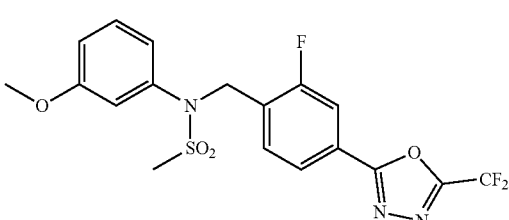 |
| 31 | 11181 | 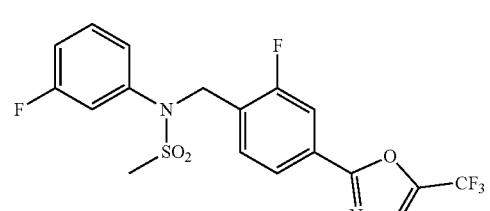 |

-continued

| Ex. | Comp. | Structure |
|---|---|---|
| 32 | 11182 | 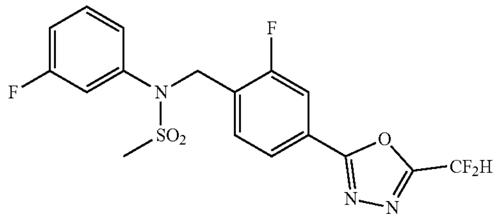 [SMILES: CS(=O)(=O)N(Cc1ccc(-c2nnc(C(F)F)o2)cc1F)c1cccc(F)c1] |
| 33 | 11183 | 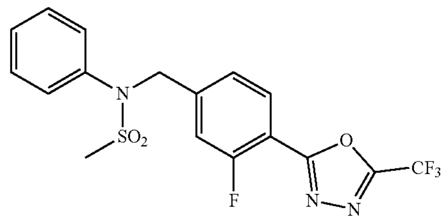 [SMILES: CS(=O)(=O)N(Cc1ccc(-c2nnc(C(F)(F)F)o2)c(F)c1)c1ccccc1] |
| 34 | 11184 | 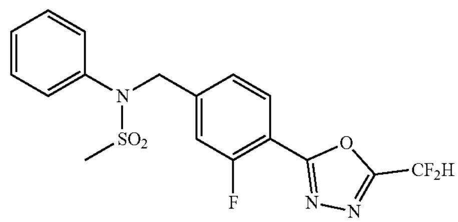 [SMILES: CS(=O)(=O)N(Cc1ccc(-c2nnc(C(F)F)o2)c(F)c1)c1ccccc1] |
| 35 | 11186 | 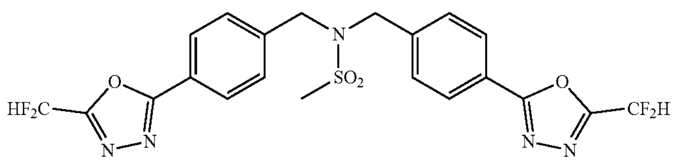 |
| 36 | 11190 | 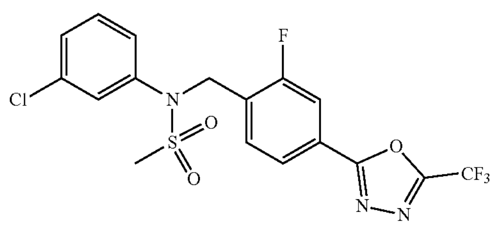 [SMILES: CS(=O)(=O)N(Cc1ccc(-c2nnc(C(F)(F)F)o2)cc1F)c1cccc(Cl)c1] |
| 37 | 11191 | 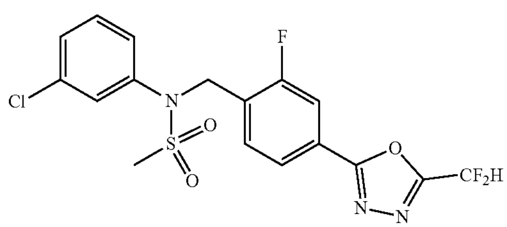 [SMILES: CS(=O)(=O)N(Cc1ccc(-c2nnc(C(F)F)o2)cc1F)c1cccc(Cl)c1] |
| 38 | 11192 | 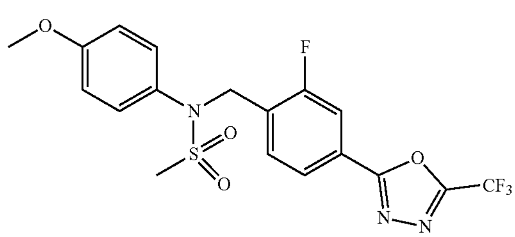 [SMILES: COc1ccc(N(Cc2ccc(-c3nnc(C(F)(F)F)o3)cc2F)S(C)(=O)=O)cc1] |

-continued

| Ex. | Comp. | Structure |
|---|---|---|
| 39 | 11193 | 4-methoxyphenyl-N(SO2Me)-CH2-(2-F-phenyl)-5-(CF2H)-1,3,4-oxadiazole |
| 40 | 11194 | pyrimidin-5-yl-N(SO2Me)-CH2-(2-F-phenyl)-5-(CF3)-1,3,4-oxadiazole |
| 41 | 11195 | pyrimidin-5-yl-N(SO2Me)-CH2-(2-F-phenyl)-5-(CF2H)-1,3,4-oxadiazole |
| 42 | 11196 | 3-bromophenyl-N(SO2Me)-CH2-(2-F-phenyl)-5-(CF3)-1,3,4-oxadiazole |
| 43 | 11197 | 3-bromophenyl-N(SO2Me)-CH2-(2-F-phenyl)-5-(CF2H)-1,3,4-oxadiazole |
| 44 | 11216 | 3-fluorophenyl-N(SO2Me)-CH2-(pyridin-2-yl)-5-(CF3)-1,3,4-oxadiazole |
| 45 | 11217 | 3-fluorophenyl-N(SO2Me)-CH2-(pyridin-2-yl)-5-(CF2H)-1,3,4-oxadiazole |

-continued
| Ex. | Comp. | Structure |
|---|---|---|
| 46 | 11218 | 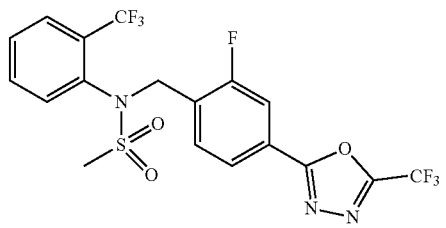 |
| 47 | 11219 | 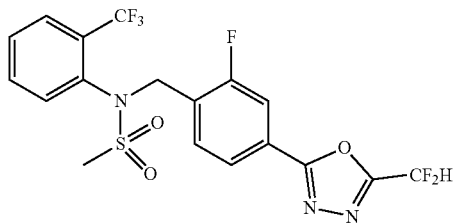 |
| 48 | 11220 | 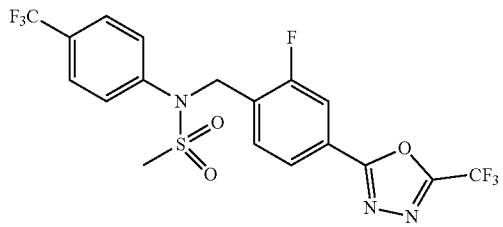 [SMILES: CS(=O)(=O)N(Cc1ccc(-c2nnc(C(F)(F)F)o2)cc1F)c1ccc(C(F)(F)F)cc1] |
| 49 | 11221 | 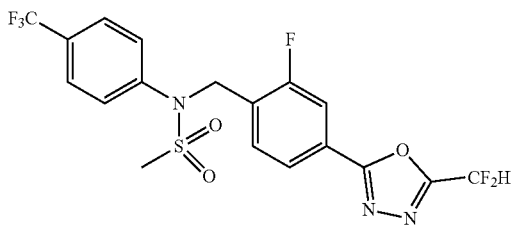 [SMILES: CS(=O)(=O)N(Cc1ccc(-c2nnc(C(F)F)o2)cc1F)c1ccc(C(F)(F)F)cc1] |
| 50 | 11222 | 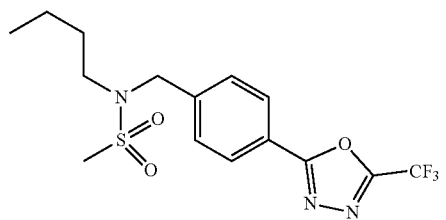 [SMILES: CCCCN(Cc1ccc(-c2nnc(C(F)(F)F)o2)cc1)S(C)(=O)=O] |
| 51 | 11225 | 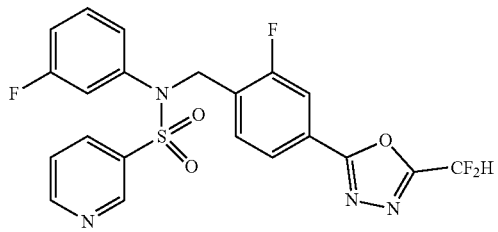 [SMILES: O=S(=O)(c1cccnc1)N(Cc1ccc(-c2nnc(C(F)F)o2)cc1F)c1cccc(F)c1] |

-continued
| Ex. | Comp. | Structure |
|---|---|---|
| 52 | 11226 | 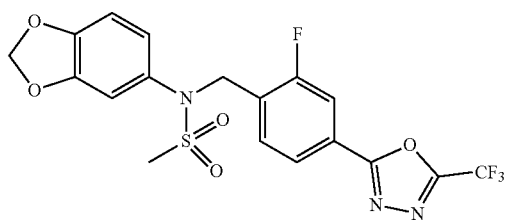 [SMILES: CS(=O)(=O)N(Cc1ccc(-c2nnc(C(F)(F)F)o2)cc1F)c1ccc2c(c1)OCO2] |
| 53 | 11227 | 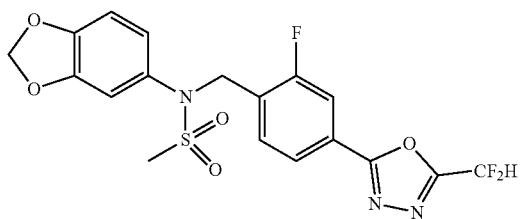 [SMILES: CS(=O)(=O)N(Cc1ccc(-c2nnc(C(F)F)o2)cc1F)c1ccc2c(c1)OCO2] |
| 54 | 11229 | 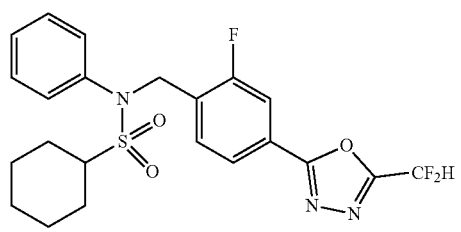 [SMILES: O=S(=O)(C1CCCCC1)N(Cc1ccc(-c2nnc(C(F)F)o2)cc1F)c1ccccc1] |
| 55 | 11230 | 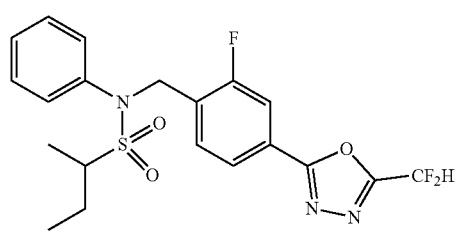 [SMILES: CCC(C)S(=O)(=O)N(Cc1ccc(-c2nnc(C(F)F)o2)cc1F)c1ccccc1] |
| 56 | 11231 | 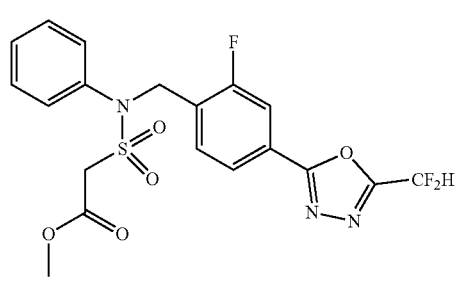 [SMILES: COC(=O)CS(=O)(=O)N(Cc1ccc(-c2nnc(C(F)F)o2)cc1F)c1ccccc1] |
| 57 | 11248 | 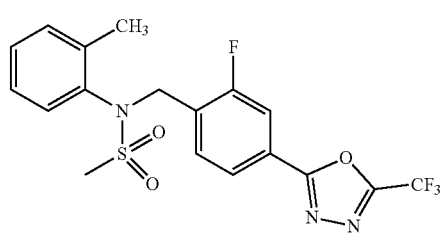 |

-continued
| Ex. | Comp. | Structure |
|---|---|---|
| 58 | 11249 | 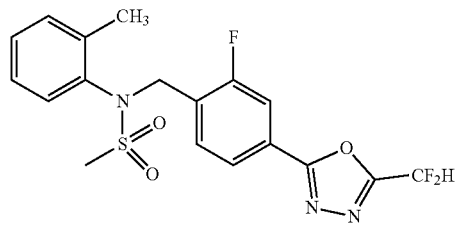 |
| 59 | 11250 | 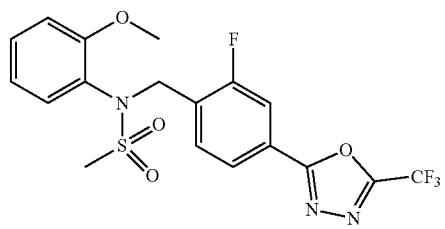 [SMILES: COc1ccccc1N(Cc1ccc(-c2nnc(C(F)(F)F)o2)cc1F)S(C)(=O)=O] |
| 60 | 11251 | 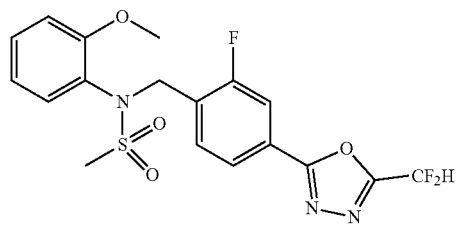 [SMILES: COc1ccccc1N(Cc1ccc(-c2nnc(C(F)F)o2)cc1F)S(C)(=O)=O] |
| 61 | 11252 | 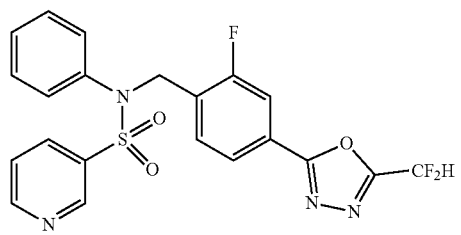 [SMILES: O=S(=O)(c1cccnc1)N(Cc1ccc(-c2nnc(C(F)F)o2)cc1F)c1ccccc1] |
| 62 | 11253 | 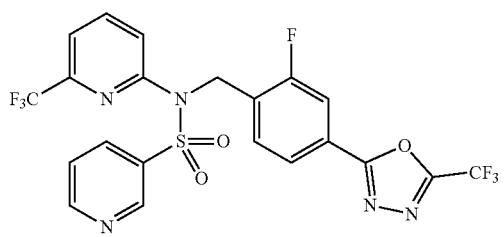 [SMILES: O=S(=O)(c1cccnc1)N(Cc1ccc(-c2nnc(C(F)(F)F)o2)cc1F)c1cccc(C(F)(F)F)n1] |
| 63 | 11254 | 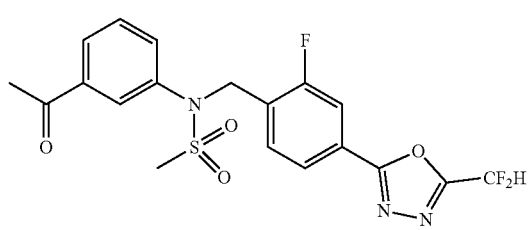 [SMILES: CC(=O)c1cccc(N(Cc2ccc(-c3nnc(C(F)F)o3)cc2F)S(C)(=O)=O)c1] |

US 10,538,498 B2
821                                                                 822
-continued
| Ex. | Comp. | Structure |
|---|---|---|
| 64 | 11255 | 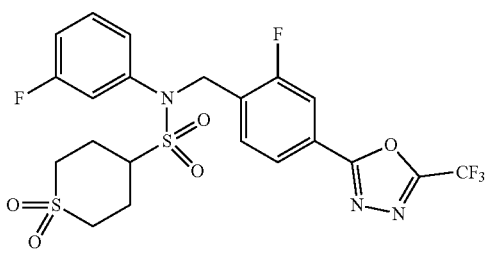 [SMILES: O=S1(=O)CCC(S(=O)(=O)N(Cc2ccc(-c3nnc(C(F)(F)F)o3)cc2F)c2cccc(F)c2)CC1] |
| 65 | 11256 | 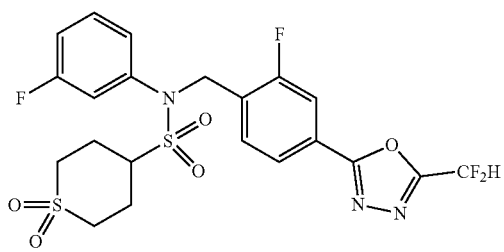 [SMILES: O=S1(=O)CCC(S(=O)(=O)N(Cc2ccc(-c3nnc(C(F)F)o3)cc2F)c2cccc(F)c2)CC1] |
| 66 | 11271 | 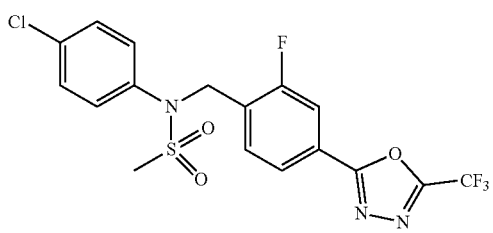 [SMILES: CS(=O)(=O)N(Cc1ccc(-c2nnc(C(F)(F)F)o2)cc1F)c1ccc(Cl)cc1] |
| 67 | 11272 | 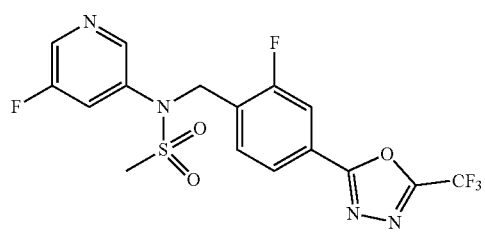 [SMILES: CS(=O)(=O)N(Cc1ccc(-c2nnc(C(F)(F)F)o2)cc1F)c1cncc(F)c1] |
| 68 | 11273 | 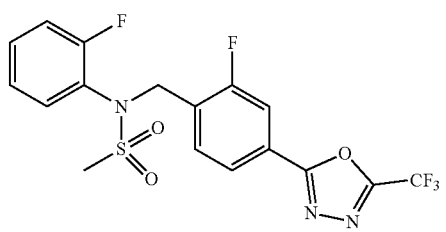 [SMILES: CS(=O)(=O)N(Cc1ccc(-c2nnc(C(F)(F)F)o2)cc1F)c1ccccc1F] |
| 69 | 11274 | 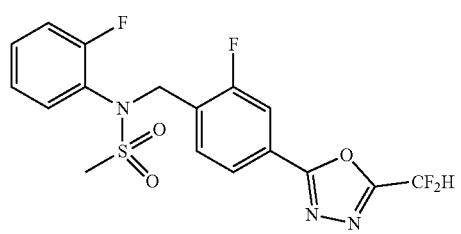 [SMILES: CS(=O)(=O)N(Cc1ccc(-c2nnc(C(F)F)o2)cc1F)c1ccccc1F] |

-continued

| Ex. | Comp. | Structure |
|---|---|---|
| 70 | 11275 | 4-F-C6H4-N(SO2Me)-CH2-(2-F-C6H3)-[1,3,4-oxadiazol-2-yl]-5-CF3 |
| 71 | 11276 | 4-F-C6H4-N(SO2Me)-CH2-(2-F-C6H3)-[1,3,4-oxadiazol-2-yl]-5-CF2H |
| 72 | 11277 | 4-Br-C6H4-N(SO2Me)-CH2-(2-F-C6H3)-[1,3,4-oxadiazol-2-yl]-5-CF3 |
| 73 | 11278 | 4-Br-C6H4-N(SO2Me)-CH2-(2-F-C6H3)-[1,3,4-oxadiazol-2-yl]-5-CF2H |
| 74 | 11279 | 2-Cl-C6H4-N(SO2Me)-CH2-(2-F-C6H3)-[1,3,4-oxadiazol-2-yl]-5-CF3 |
| 75 | 11280 | 2-Cl-C6H4-N(SO2Me)-CH2-(2-F-C6H3)-[1,3,4-oxadiazol-2-yl]-5-CF2H |

-continued
| Ex. | Comp. | Structure |
|---|---|---|
| 76 | 11281 | 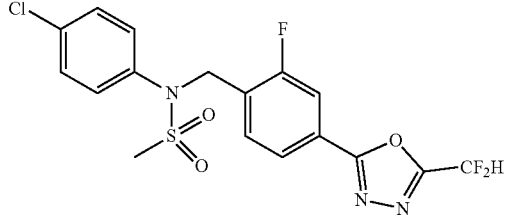 [SMILES: CS(=O)(=O)N(Cc1ccc(-c2nnc(C(F)F)o2)cc1F)c1ccc(Cl)cc1] |
| 77 | 11282 | 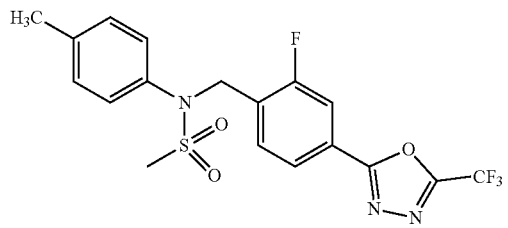 [SMILES: Cc1ccc(N(Cc2ccc(-c3nnc(C(F)(F)F)o3)cc2F)S(C)(=O)=O)cc1] |
| 78 | 11283 | 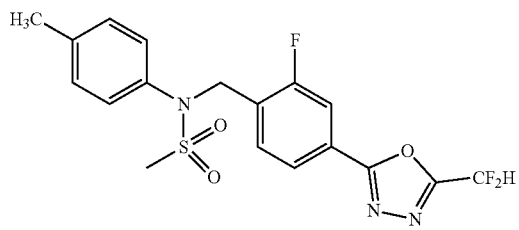 [SMILES: Cc1ccc(N(Cc2ccc(-c3nnc(C(F)F)o3)cc2F)S(C)(=O)=O)cc1] |
| 79 | 11284 | 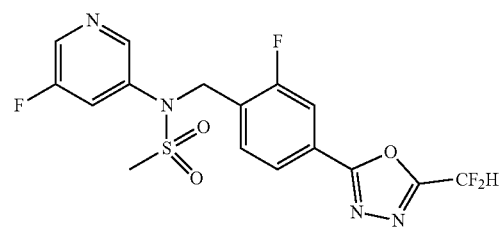 [SMILES: CS(=O)(=O)N(Cc1ccc(-c2nnc(C(F)F)o2)cc1F)c1cncc(F)c1] |
| 80 | 11287 | 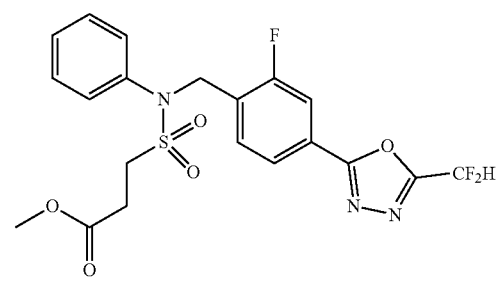 [SMILES: COC(=O)CCS(=O)(=O)N(Cc1ccc(-c2nnc(C(F)F)o2)cc1F)c1ccccc1] |
| 81 | 11288 | 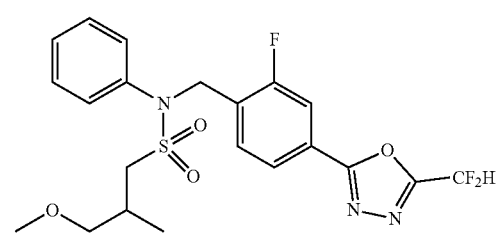 [SMILES: COCC(C)CS(=O)(=O)N(Cc1ccc(-c2nnc(C(F)F)o2)cc1F)c1ccccc1] |

-continued
| Ex. | Comp. | Structure |
|---|---|---|
| 82 | 11289 | 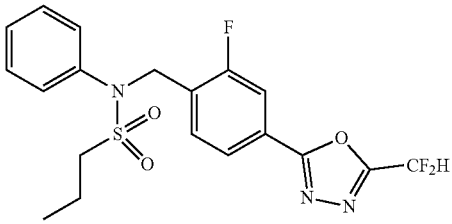 [SMILES: CCCS(=O)(=O)N(Cc1ccc(-c2nnc(C(F)F)o2)cc1F)c1ccccc1] |
| 83 | 11290 | 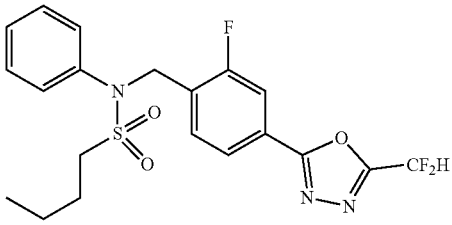 [SMILES: CCCCS(=O)(=O)N(Cc1ccc(-c2nnc(C(F)F)o2)cc1F)c1ccccc1] |
| 84 | 11291 | 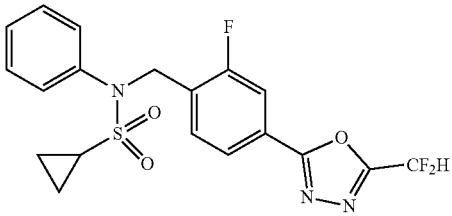 [SMILES: O=S(=O)(C1CC1)N(Cc1ccc(-c2nnc(C(F)F)o2)cc1F)c1ccccc1] |
| 85 | 11292 | 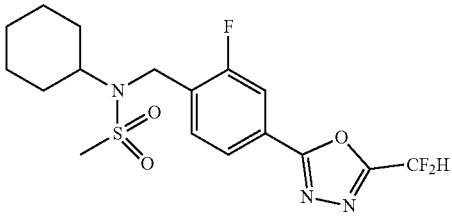 [SMILES: CS(=O)(=O)N(Cc1ccc(-c2nnc(C(F)F)o2)cc1F)C1CCCCC1] |
| 86 | 11323 | 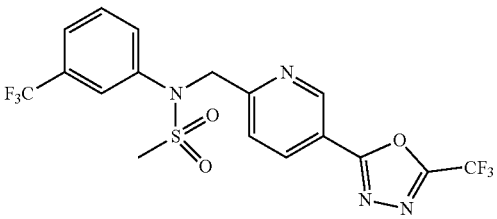 [SMILES: CS(=O)(=O)N(Cc1ccc(-c2nnc(C(F)(F)F)o2)cn1)c1cccc(C(F)(F)F)c1] |
| 87 | 11324 | 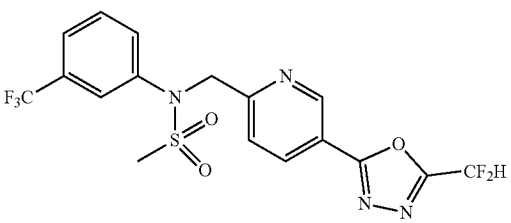 [SMILES: CS(=O)(=O)N(Cc1ccc(-c2nnc(C(F)F)o2)cn1)c1cccc(C(F)(F)F)c1] |
| 88 | 11338 | 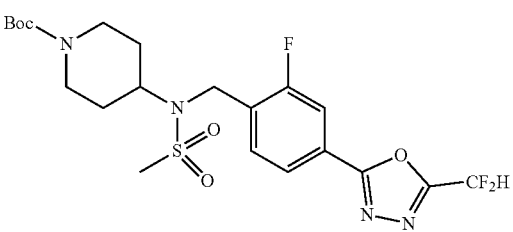 [SMILES: CC(C)(C)OC(=O)N1CCC(N(Cc2ccc(-c3nnc(C(F)F)o3)cc2F)S(C)(=O)=O)CC1] |

| Ex. | Comp. | Structure |
|---|---|---|
| 89 | 11345 | 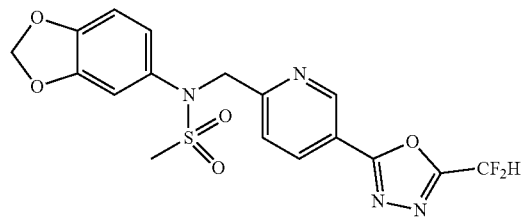 [SMILES: CS(=O)(=O)N(Cc1ccc(-c2nnc(C(F)F)o2)cn1)c1ccc2c(c1)OCO2] |
| 90 | 11346 | 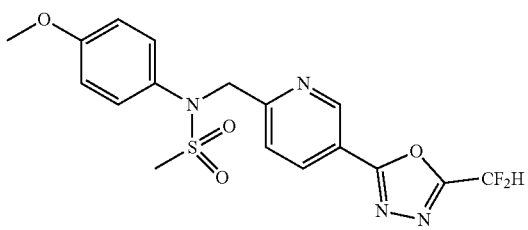 [SMILES: COc1ccc(N(Cc2ccc(-c3nnc(C(F)F)o3)cn2)S(C)(=O)=O)cc1] |
| 91 | 11347 | 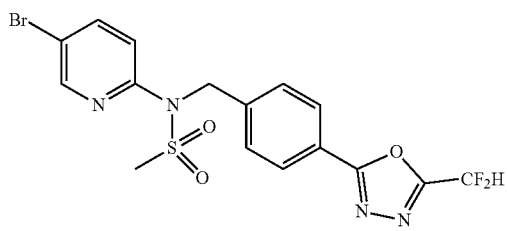 [SMILES: CS(=O)(=O)N(Cc1ccc(-c2nnc(C(F)F)o2)cc1)c1ccc(Cl)cn1] |
| 92 | 11348 | 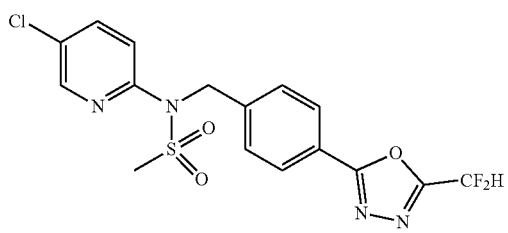 |
| 93 | 11350 | 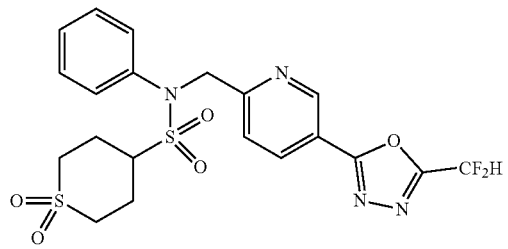 [SMILES: O=S1(=O)CCC(S(=O)(=O)N(Cc2ccc(-c3nnc(C(F)F)o3)cn2)c2ccccc2)CC1] |
| 94 | 11351 | 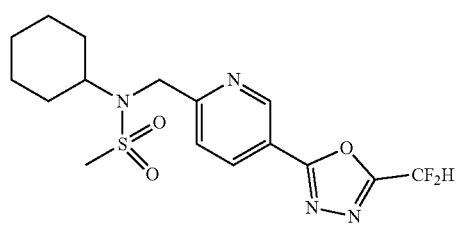 [SMILES: CS(=O)(=O)N(Cc1ccc(-c2nnc(C(F)F)o2)cn1)C1CCCCC1] |

-continued

| Ex. | Comp. | Structure |
|---|---|---|
| 95 | 11352 | 3-chlorophenyl-N-(methylsulfonyl)-N-((5-(5-(difluoromethyl)-1,3,4-oxadiazol-2-yl)pyridin-2-yl)methyl) |
| 96 | 11353 | pyridin-3-yl-N-(methylsulfonyl)-N-((5-(5-(difluoromethyl)-1,3,4-oxadiazol-2-yl)pyridin-2-yl)methyl) |
| 97 | 11354 | 3-bromophenyl-N-(methylsulfonyl)-N-((5-(5-(difluoromethyl)-1,3,4-oxadiazol-2-yl)pyridin-2-yl)methyl) |
| 98 | 11355 | 3-methylphenyl-N-(methylsulfonyl)-N-((5-(5-(difluoromethyl)-1,3,4-oxadiazol-2-yl)pyridin-2-yl)methyl) |
| 99 | 11366 | 3-bromophenyl-N-(ethylsulfonyl)-N-((5-(5-(difluoromethyl)-1,3,4-oxadiazol-2-yl)pyridin-2-yl)methyl) |
| 100 | 11367 | phenyl-N-((1-methylpiperidin-4-yl)sulfonyl)-N-((5-(5-(difluoromethyl)-1,3,4-oxadiazol-2-yl)pyridin-2-yl)methyl) |
| 101 | 11368 | phenyl-N-((1-ethylpiperidin-4-yl)sulfonyl)-N-((5-(5-(difluoromethyl)-1,3,4-oxadiazol-2-yl)pyridin-2-yl)methyl) |

-continued
| Ex. | Comp. | Structure |
|---|---|---|
| 102 | 11372 | 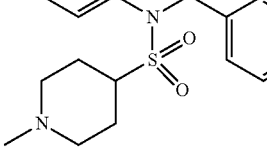 |
| 103 | 11373 | 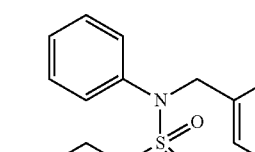 |
| 104 | 11377 | 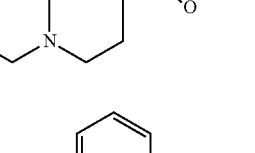 |
| 105 | 11386 | 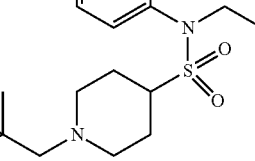 |
| 106 | 11387 | 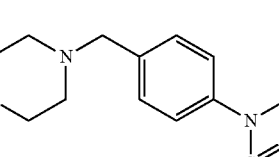 |
| 107 | 11388 | 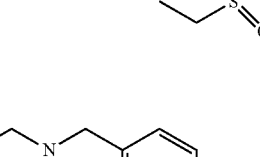 |

-continued
| Ex. | Comp. | Structure |
|---|---|---|
| 108 | 11389 | 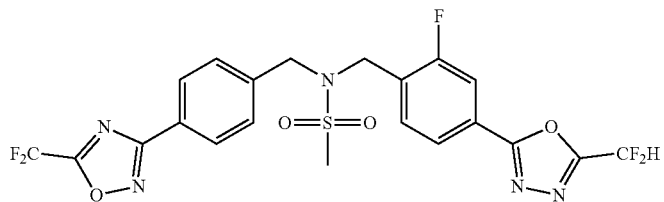 |
| 109 | 11390 | 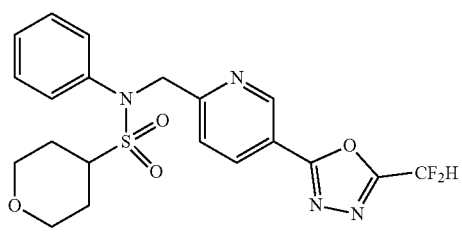 [SMILES: O=S(=O)(C1CCOCC1)N(Cc1ccc(-c2nnc(C(F)F)o2)cn1)c1ccccc1] |
| 110 | 11392 | 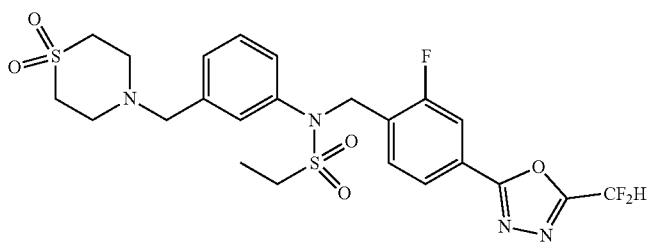 [SMILES: CCS(=O)(=O)N(Cc1ccc(-c2nnc(C(F)F)o2)cc1F)c1cccc(CN2CCS(=O)(=O)CC2)c1] |
| 111 | 11402 | 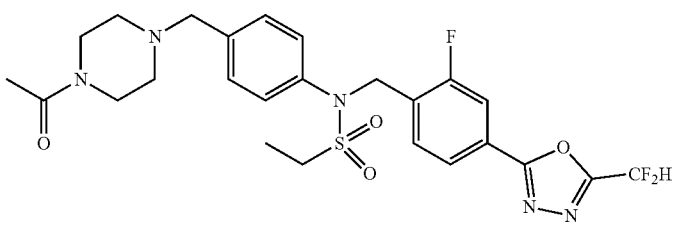 [SMILES: CCS(=O)(=O)N(Cc1ccc(-c2nnc(C(F)F)o2)cc1F)c1ccc(CN2CCN(C(C)=O)CC2)cc1] |
| 112 | 11403 | 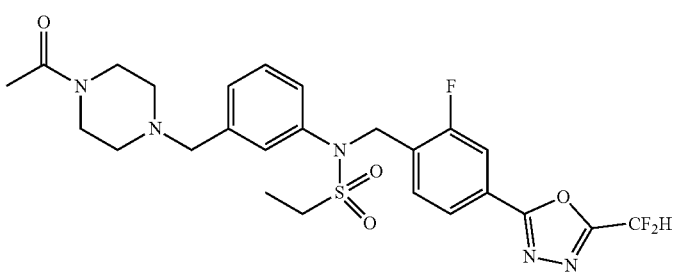 [SMILES: CCS(=O)(=O)N(Cc1ccc(-c2nnc(C(F)F)o2)cc1F)c1cccc(CN2CCN(C(C)=O)CC2)c1] |
| 113 | 11404 | 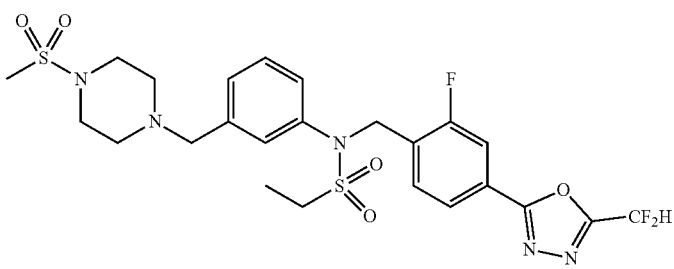 [SMILES: CCS(=O)(=O)N(Cc1ccc(-c2nnc(C(F)F)o2)cc1F)c1cccc(CN2CCN(S(C)(=O)=O)CC2)c1] |

-continued
| Ex. | Comp. | Structure |
|---|---|---|
| 114 | 11405 | 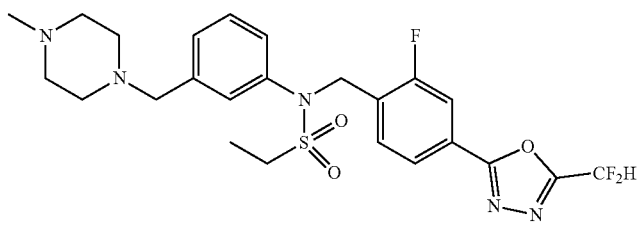 [SMILES: CCS(=O)(=O)N(Cc1ccc(-c2nnc(C(F)F)o2)cc1F)c1cccc(CN2CCN(C)CC2)c1] |
| 115 | 11406 | 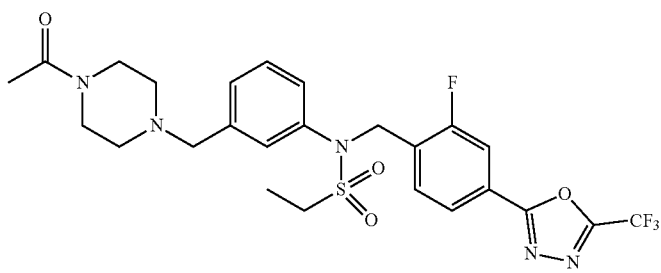 [SMILES: CCS(=O)(=O)N(Cc1ccc(-c2nnc(C(F)(F)F)o2)cc1F)c1cccc(CN2CCN(C(C)=O)CC2)c1] |
| 116 | 11411 | 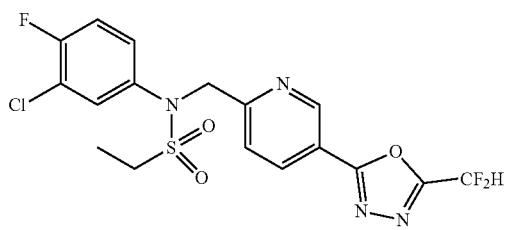 [SMILES: CCS(=O)(=O)N(Cc1ccc(-c2nnc(C(F)F)o2)cn1)c1ccc(F)c(Cl)c1] |
| 117 | 11412 | 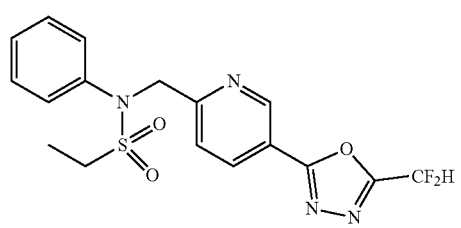 [SMILES: CCS(=O)(=O)N(Cc1ccc(-c2nnc(C(F)F)o2)cn1)c1ccccc1] |
| 118 | 11426 | 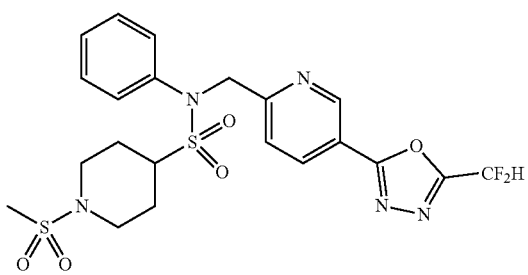 [SMILES: CS(=O)(=O)N1CCC(S(=O)(=O)N(Cc2ccc(-c3nnc(C(F)F)o3)cn2)c2ccccc2)CC1] |
| 119 | 11427 | 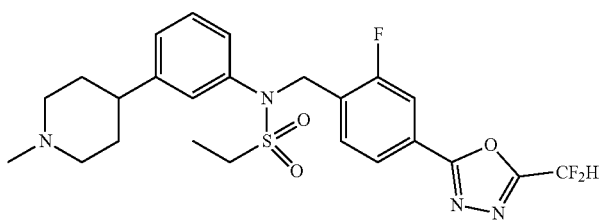 [SMILES: CCS(=O)(=O)N(Cc1ccc(-c2nnc(C(F)F)o2)cc1F)c1cccc(C2CCN(C)CC2)c1] |

| Ex. | Comp. | Structure |
|---|---|---|
| 120 | 11428 | 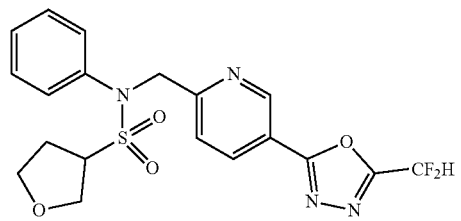 [SMILES: O=S(=O)(C1CCOC1)N(Cc1ccc(-c2nnc(C(F)F)o2)cn1)c1ccccc1] |
| 121 | 11429 | 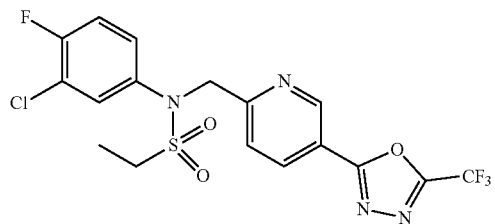 [SMILES: CCS(=O)(=O)N(Cc1ccc(-c2nnc(C(F)(F)F)o2)cn1)c1ccc(F)c(Cl)c1] |
| 122 | 11430 | 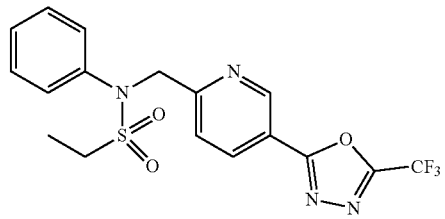 [SMILES: CCS(=O)(=O)N(Cc1ccc(-c2nnc(C(F)(F)F)o2)cn1)c1ccccc1] |
| 123 | 11431 | 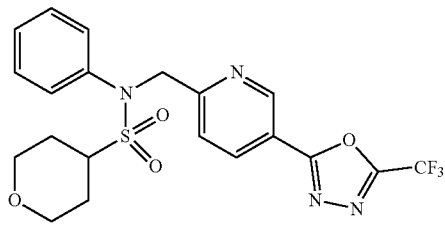 [SMILES: O=S(=O)(C1CCOCC1)N(Cc1ccc(-c2nnc(C(F)(F)F)o2)cn1)c1ccccc1] |
| 124 | 11432 | 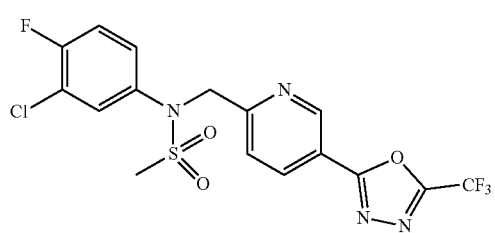 [SMILES: CS(=O)(=O)N(Cc1ccc(-c2nnc(C(F)(F)F)o2)cn1)c1ccc(F)c(Cl)c1] |
| 125 | 11433 | 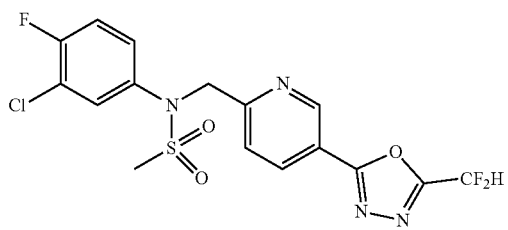 [SMILES: CS(=O)(=O)N(Cc1ccc(-c2nnc(C(F)F)o2)cn1)c1ccc(F)c(Cl)c1] |

| Ex. | Comp. | Structure |
|---|---|---|
| 126 | 11447 | 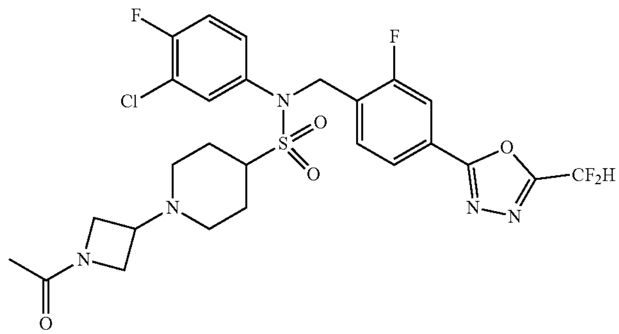 [SMILES: CC(=O)N1CC(N2CCC(S(=O)(=O)N(Cc3ccc(-c4nnc(C(F)F)o4)cc3F)c3ccc(F)c(Cl)c3)CC2)C1] |
| 127 | 11448 | 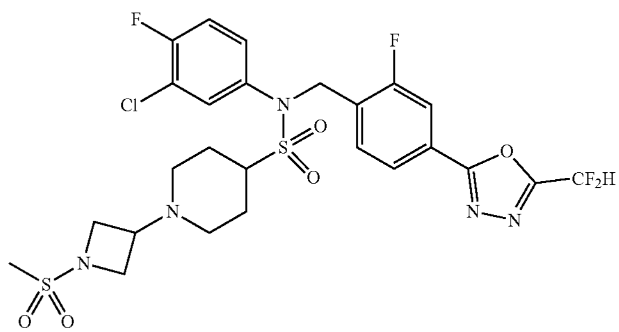 [SMILES: CS(=O)(=O)N1CC(N2CCC(S(=O)(=O)N(Cc3ccc(-c4nnc(C(F)F)o4)cc3F)c3ccc(F)c(Cl)c3)CC2)C1] |
| 128 | 11451 | 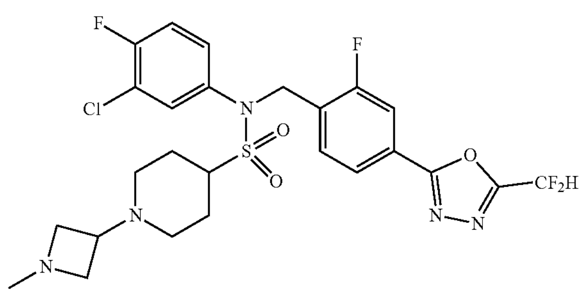 [SMILES: CN1CC(N2CCC(S(=O)(=O)N(Cc3ccc(-c4nnc(C(F)F)o4)cc3F)c3ccc(F)c(Cl)c3)CC2)C1] |
| 129 | 11452 | 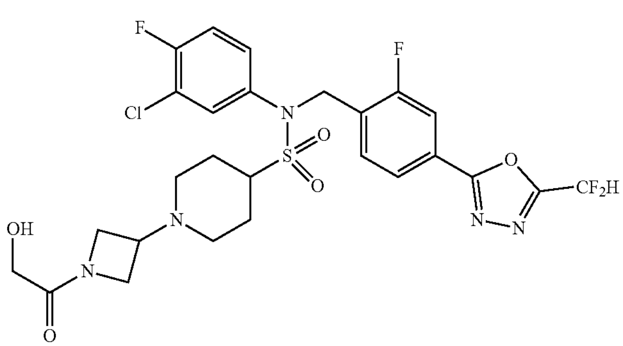 [SMILES: O=C(CO)N1CC(N2CCC(S(=O)(=O)N(Cc3ccc(-c4nnc(C(F)F)o4)cc3F)c3ccc(F)c(Cl)c3)CC2)C1] |
| 130 | 11460 | 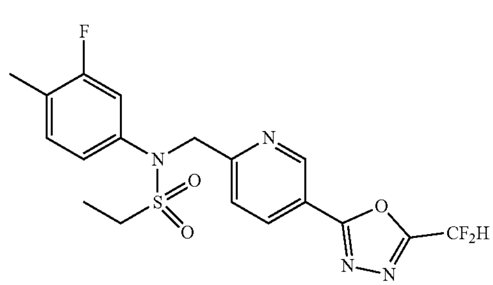 [SMILES: CCS(=O)(=O)N(Cc1ccc(-c2nnc(C(F)F)o2)cn1)c1ccc(C)c(F)c1] |

-continued
| Ex. | Comp. | Structure |
|---|---|---|
| 131 | 11461 | 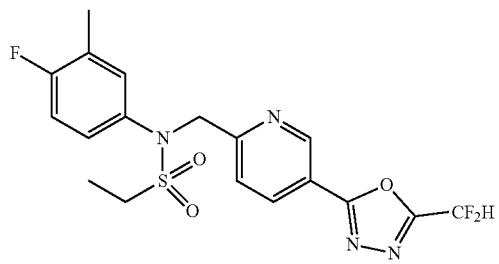 [SMILES: CCS(=O)(=O)N(Cc1ccc(-c2nnc(C(F)F)o2)cn1)c1ccc(F)c(C)c1] |
| 132 | 11462 | 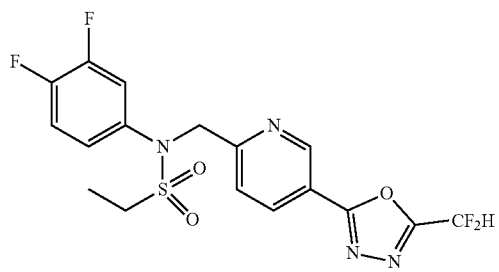 [SMILES: CCS(=O)(=O)N(Cc1ccc(-c2nnc(C(F)F)o2)cn1)c1ccc(F)c(F)c1] |
| 133 | 11463 | 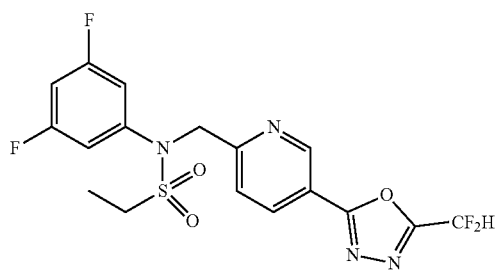 [SMILES: CCS(=O)(=O)N(Cc1ccc(-c2nnc(C(F)F)o2)cn1)c1cc(F)cc(F)c1] |
| 134 | 11497 | 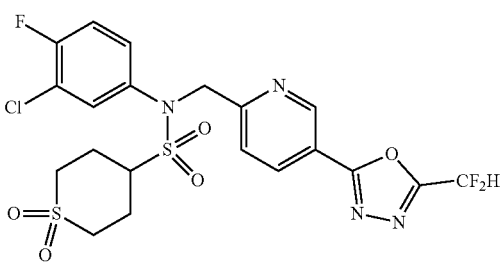 [SMILES: O=S1(=O)CCC(S(=O)(=O)N(Cc2ccc(-c3nnc(C(F)F)o3)cn2)c2ccc(F)c(Cl)c2)CC1] |
| 135 | 11501 | 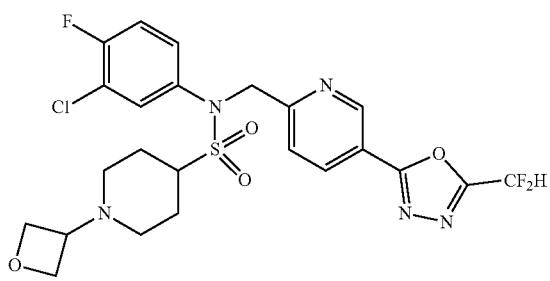 [SMILES: O=S(=O)(C1CCN(C2COC2)CC1)N(Cc1ccc(-c2nnc(C(F)F)o2)cn1)c1ccc(F)c(Cl)c1] |

-continued
| Ex. | Comp. | Structure |
|---|---|---|
| 136 | 11502 | 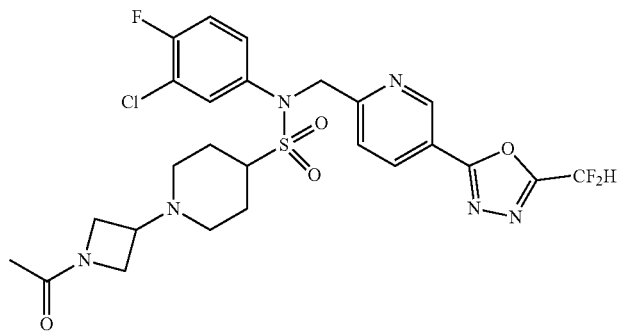 [SMILES: CC(=O)N1CC(N2CCC(S(=O)(=O)N(Cc3ccc(-c4nnc(C(F)F)o4)cn3)c3ccc(F)c(Cl)c3)CC2)C1] |
| 137 | 11503 | 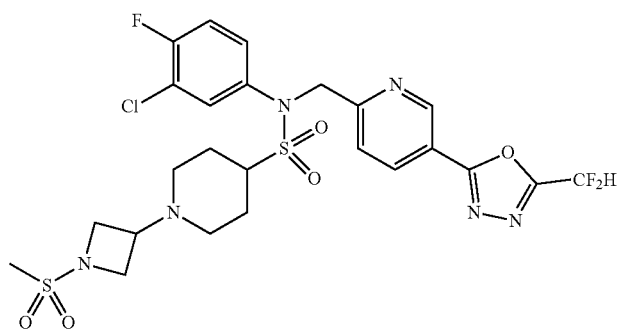 [SMILES: CS(=O)(=O)N1CC(N2CCC(S(=O)(=O)N(Cc3ccc(-c4nnc(C(F)F)o4)cn3)c3ccc(F)c(Cl)c3)CC2)C1] |
| 138 | 11504 | 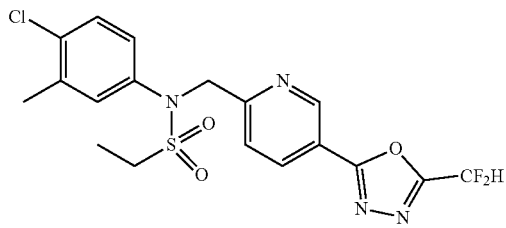 [SMILES: CCS(=O)(=O)N(Cc1ccc(-c2nnc(C(F)F)o2)cn1)c1ccc(Cl)c(C)c1] |
| 139 | 11505 | 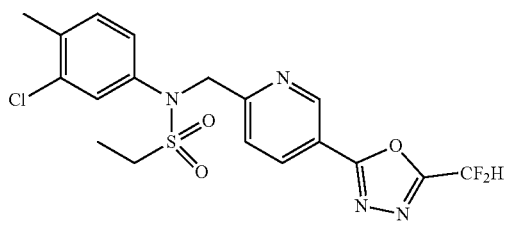 [SMILES: CCS(=O)(=O)N(Cc1ccc(-c2nnc(C(F)F)o2)cn1)c1ccc(C)c(Cl)c1] |
| 140 | 11506 | 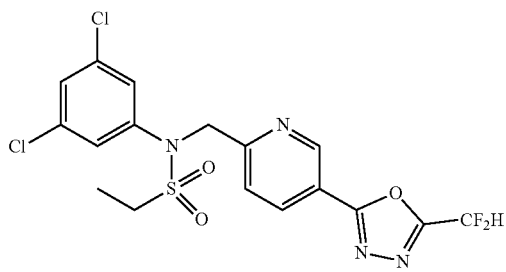 [SMILES: CCS(=O)(=O)N(Cc1ccc(-c2nnc(C(F)F)o2)cn1)c1cc(Cl)cc(Cl)c1] |

-continued
| Ex. | Comp. | Structure |
|---|---|---|
| 141 | 11507 | 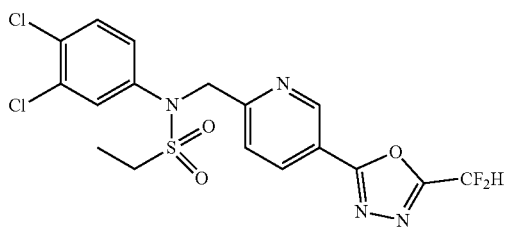 |
| 142 | 11508 | 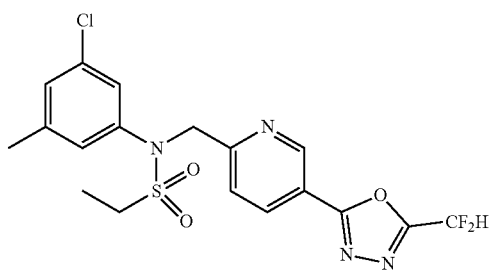 [SMILES: CCS(=O)(=O)N(Cc1ccc(-c2nnc(C(F)F)o2)cn1)c1cc(C)cc(Cl)c1] |
| 143 | 11514 | 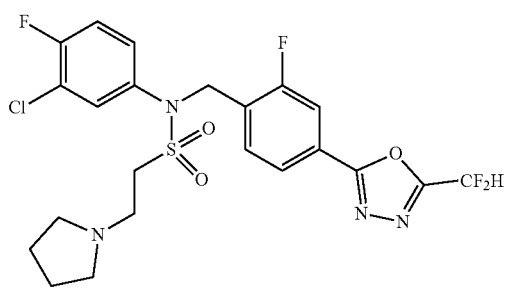 [SMILES: O=S(=O)(CCN1CCCC1)N(Cc1ccc(-c2nnc(C(F)F)o2)cc1F)c1ccc(F)c(Cl)c1] |
| 144 | 11518 | 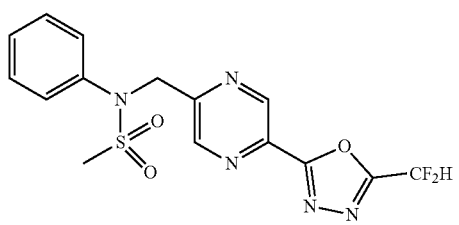 [SMILES: CS(=O)(=O)N(Cc1cnc(-c2nnc(C(F)F)o2)cn1)c1ccccc1] |
| 145 | 11520 | 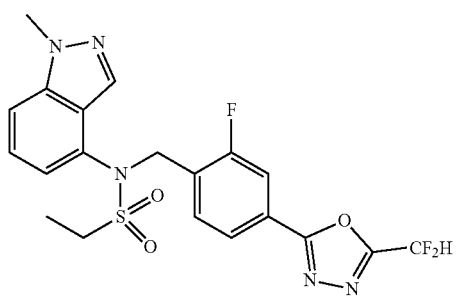 [SMILES: CCS(=O)(=O)N(Cc1ccc(-c2nnc(C(F)F)o2)cc1F)c1cccc2c1cnn2C] |
| 146 | 11521 | 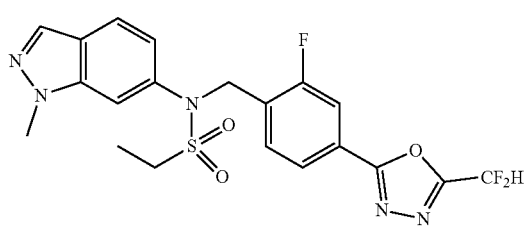 [SMILES: CCS(=O)(=O)N(Cc1ccc(-c2nnc(C(F)F)o2)cc1F)c1ccc2cnn(C)c2c1] |

-continued

| Ex. | Comp. | Structure |
|---|---|---|
| 147 | 11522 | 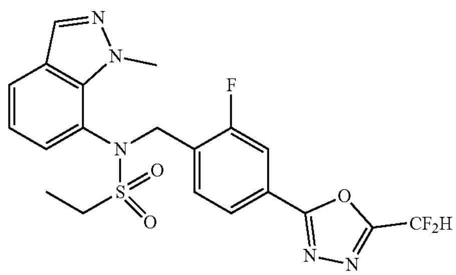 [SMILES: CCS(=O)(=O)N(Cc1ccc(-c2nnc(C(F)F)o2)cc1F)c1cccc2cnn(C)c12] |
| 148 | 11539 | 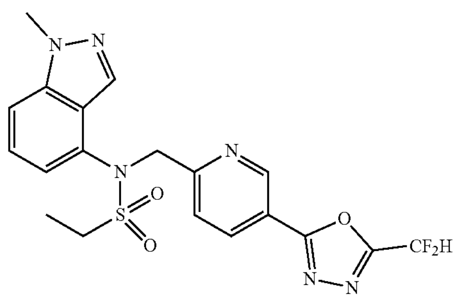 [SMILES: CCS(=O)(=O)N(Cc1ccc(-c2nnc(C(F)F)o2)cn1)c1cccc2c1cnn2C] |
| 149 | 11540 | 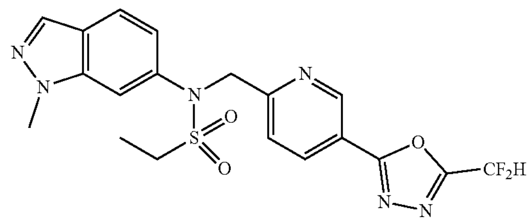 [SMILES: CCS(=O)(=O)N(Cc1ccc(-c2nnc(C(F)F)o2)cn1)c1ccc2cnn(C)c2c1] |
| 150 | 11541 | 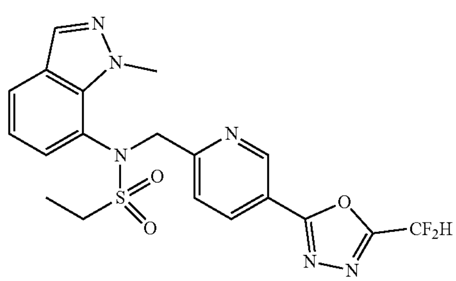 [SMILES: CCS(=O)(=O)N(Cc1ccc(-c2nnc(C(F)F)o2)cn1)c1cccc2cnn(C)c12] |
| 151 | 11552 | 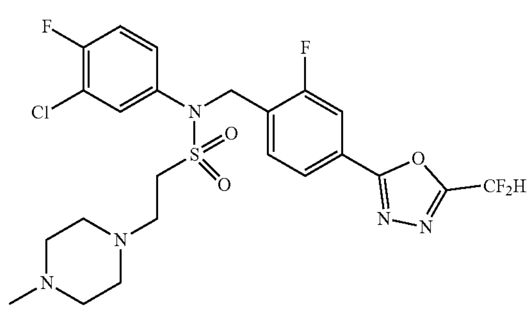 [SMILES: CN1CCN(CCS(=O)(=O)N(Cc2ccc(-c3nnc(C(F)F)o3)cc2F)c2ccc(F)c(Cl)c2)CC1] |

| Ex. | Comp. | Structure |
|---|---|---|
| 152 | 11553 | 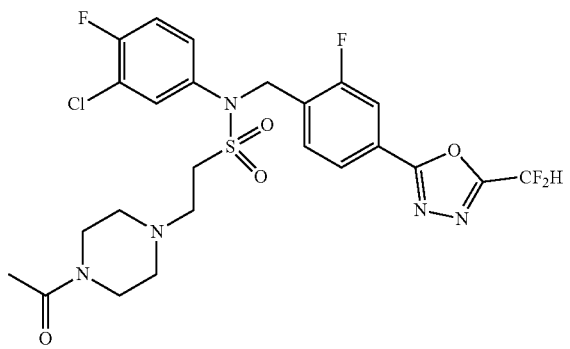 [SMILES: CC(=O)N1CCN(CCS(=O)(=O)N(Cc2ccc(-c3nnc(C(F)F)o3)cc2F)c2ccc(F)c(Cl)c2)CC1] |
| 153 | 11554 | 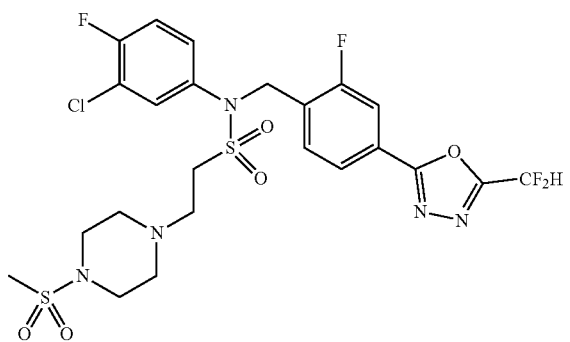 [SMILES: CS(=O)(=O)N1CCN(CCS(=O)(=O)N(Cc2ccc(-c3nnc(C(F)F)o3)cc2F)c2ccc(F)c(Cl)c2)CC1] |
| 154 | 11564 | 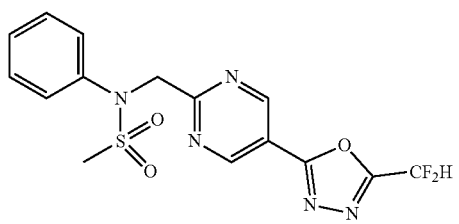 [SMILES: CS(=O)(=O)N(Cc1ncc(-c2nnc(C(F)F)o2)cn1)c1ccccc1] |
| 155 | 11565 | 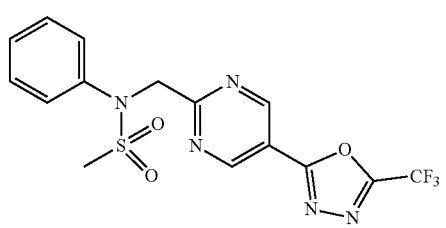 [SMILES: CS(=O)(=O)N(Cc1ncc(-c2nnc(C(F)(F)F)o2)cn1)c1ccccc1] |
| 156 | 11566 | 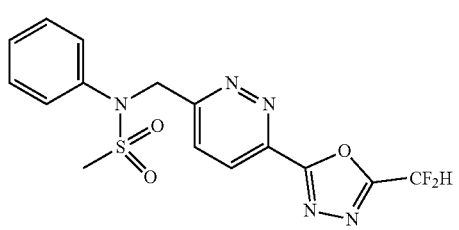 [SMILES: CS(=O)(=O)N(Cc1ccc(-c2nnc(C(F)F)o2)nn1)c1ccccc1] |
| 157 | 11567 | 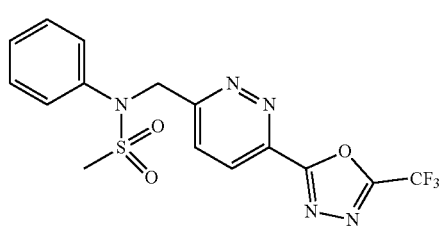 [SMILES: CS(=O)(=O)N(Cc1ccc(-c2nnc(C(F)(F)F)o2)nn1)c1ccccc1] |

| Ex. | Comp. | Structure |
|---|---|---|
| 158 | 11573 | 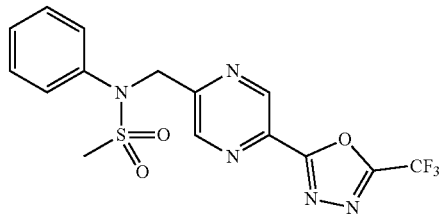 [SMILES: CS(=O)(=O)N(Cc1cnc(-c2nnc(C(F)(F)F)o2)cn1)c1ccccc1] |
| 159 | 11582 | 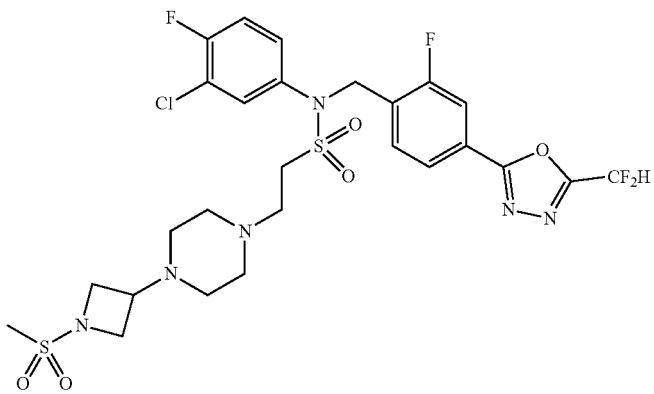 [SMILES: CS(=O)(=O)N1CC(N2CCN(CCS(=O)(=O)N(Cc3ccc(-c4nnc(C(F)F)o4)cc3F)c3ccc(F)c(Cl)c3)CC2)C1] |
| 160 | 11583 | 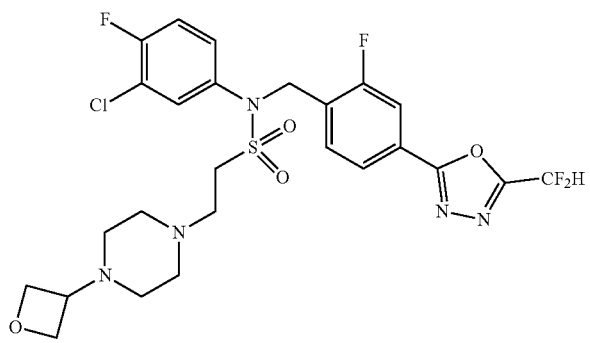 [SMILES: O=S(=O)(CCN1CCN(C2COC2)CC1)N(Cc1ccc(-c2nnc(C(F)F)o2)cc1F)c1ccc(F)c(Cl)c1] |
| 161 | 11588 | 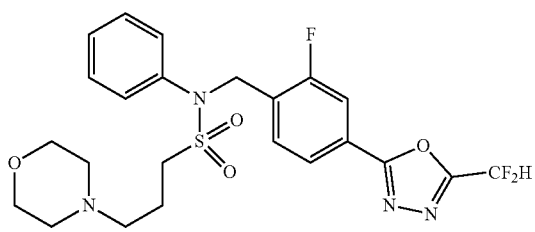 [SMILES: O=S(=O)(CCCN1CCOCC1)N(Cc1ccc(-c2nnc(C(F)F)o2)cc1F)c1ccccc1] |
| 162 | 11589 | 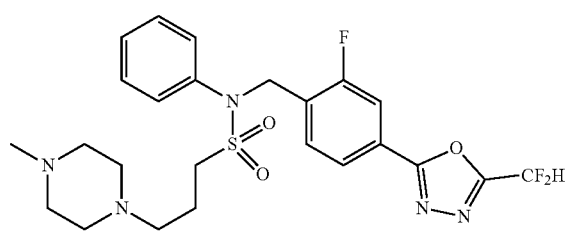 [SMILES: CN1CCN(CCCS(=O)(=O)N(Cc2ccc(-c3nnc(C(F)F)o3)cc2F)c2ccccc2)CC1] |

| Ex. | Comp. | Structure |
|---|---|---|
| 163 | 11605 | 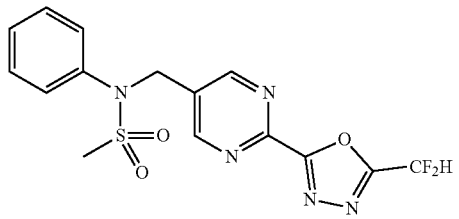 [SMILES: CS(=O)(=O)N(Cc1cnc(-c2nnc(C(F)F)o2)nc1)c1ccccc1] |
| 164 | 11606 | 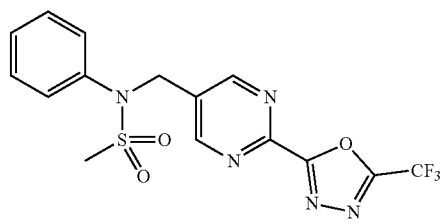 [SMILES: CS(=O)(=O)N(Cc1cnc(-c2nnc(C(F)(F)F)o2)nc1)c1ccccc1] |
| 165 | 11625 | 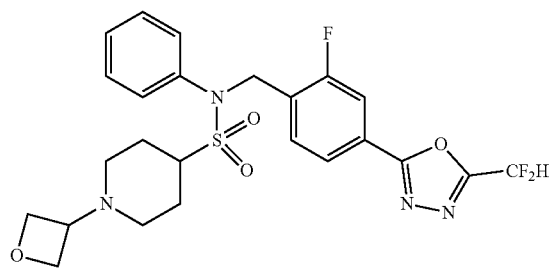 [SMILES: O=S(=O)(C1CCN(C2COC2)CC1)N(Cc1ccc(-c2nnc(C(F)F)o2)cc1F)c1ccccc1] |
| 166 | 11628 | 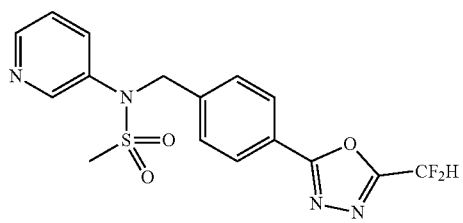 [SMILES: CS(=O)(=O)N(Cc1ccc(-c2nnc(C(F)F)o2)cc1)c1cccnc1] |
| 167 | 11629 | 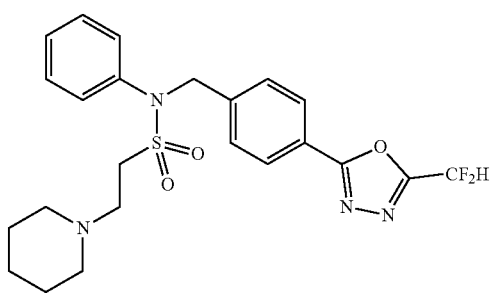 [SMILES: O=S(=O)(CCN1CCCCC1)N(Cc1ccc(-c2nnc(C(F)F)o2)cc1)c1ccccc1] |
| 168 | 11630 | 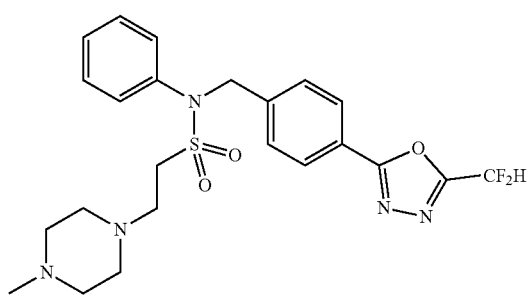 [SMILES: CN1CCN(CCS(=O)(=O)N(Cc2ccc(-c3nnc(C(F)F)o3)cc2)c2ccccc2)CC1] |

| Ex. | Comp. | Structure |
|---|---|---|
| 169 | 11631 | 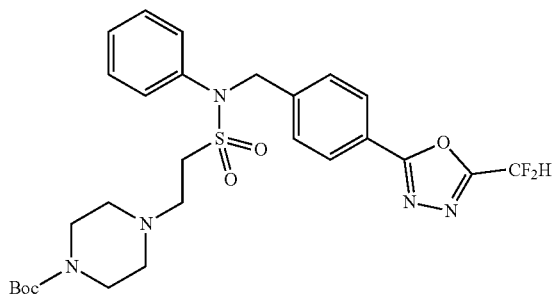 [SMILES: CC(C)(C)OC(=O)N1CCN(CCS(=O)(=O)N(Cc2ccc(-c3nnc(C(F)F)o3)cc2)c2ccccc2)CC1] |
| 170 | 11632 | 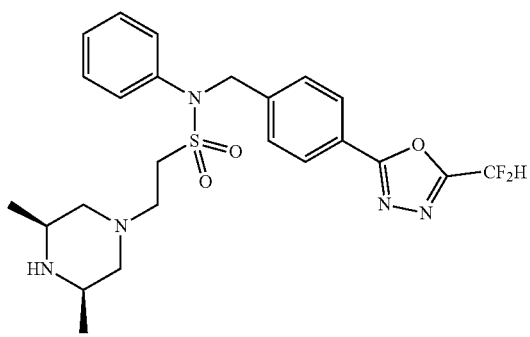 [SMILES: C[C@@H]1CN(CCS(=O)(=O)N(Cc2ccc(-c3nnc(C(F)F)o3)cc2)c2ccccc2)C[C@H](C)N1] |
| 171 | 11633 | 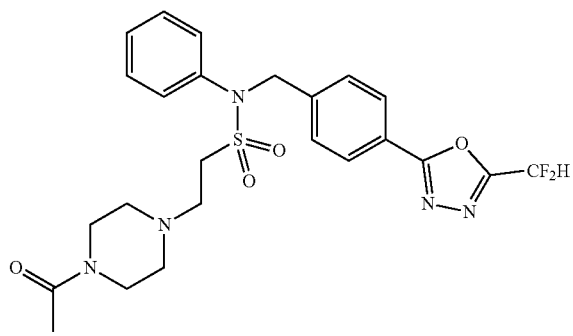 [SMILES: CC(=O)N1CCN(CCS(=O)(=O)N(Cc2ccc(-c3nnc(C(F)F)o3)cc2)c2ccccc2)CC1] |
| 172 | 11634 | 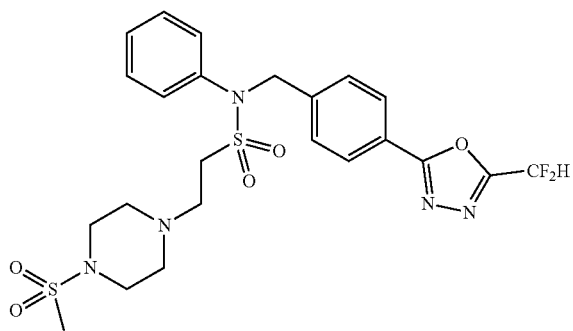 [SMILES: CS(=O)(=O)N1CCN(CCS(=O)(=O)N(Cc2ccc(-c3nnc(C(F)F)o3)cc2)c2ccccc2)CC1] |
| 173 | 11636 | 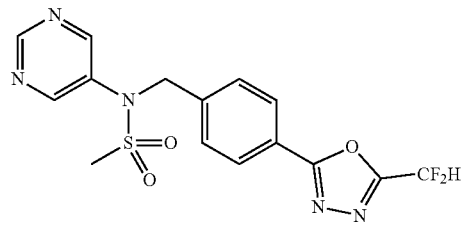 [SMILES: CS(=O)(=O)N(Cc1ccc(-c2nnc(C(F)F)o2)cc1)c1cncnc1] |

-continued
| Ex. | Comp. | Structure |
|---|---|---|
| 174 | 11637 | 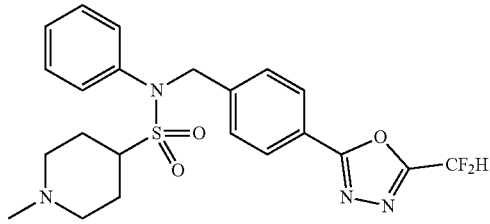 [SMILES: CN1CCC(S(=O)(=O)N(Cc2ccc(-c3nnc(C(F)F)o3)cc2)c2ccccc2)CC1] |
| 175 | 11638 | 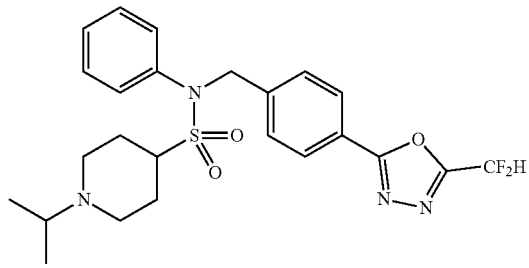 [SMILES: CC(C)N1CCC(S(=O)(=O)N(Cc2ccc(-c3nnc(C(F)F)o3)cc2)c2ccccc2)CC1] |
| 176 | 11639 | 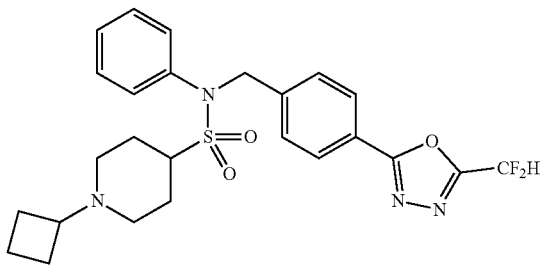 [SMILES: O=S(=O)(C1CCN(C2CCC2)CC1)N(Cc1ccc(-c2nnc(C(F)F)o2)cc1)c1ccccc1] |
| 177 | 11645 | 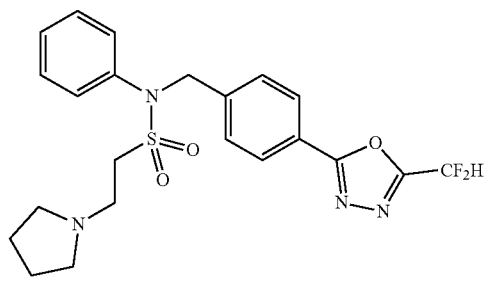 [SMILES: O=S(=O)(CCN1CCCC1)N(Cc1ccc(-c2nnc(C(F)F)o2)cc1)c1ccccc1] |
| 178 | 11646 | 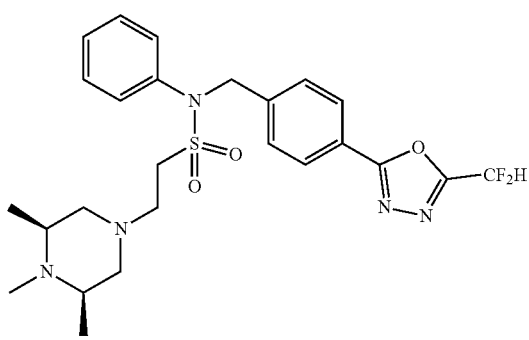 [SMILES: C[C@@H]1CN(CCS(=O)(=O)N(Cc2ccc(-c3nnc(C(F)F)o3)cc2)c2ccccc2)C[C@H](C)N1C] |

| Ex. | Comp. | Structure |
|---|---|---|
| 179 | 11647 | 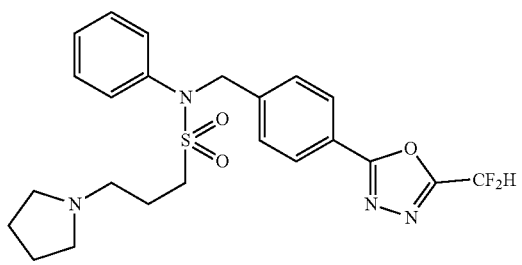 [SMILES: O=S(=O)(CCCN1CCCC1)N(Cc1ccc(-c2nnc(C(F)F)o2)cc1)c1ccccc1] |
| 180 | 11648 | 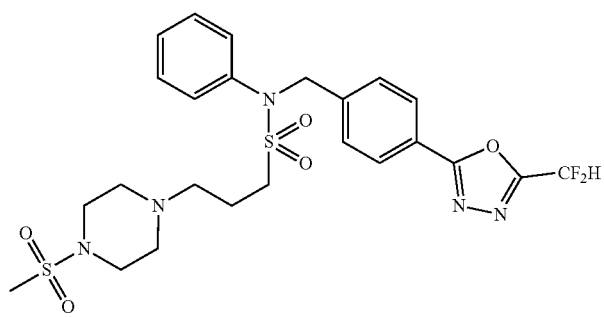 [SMILES: CS(=O)(=O)N1CCN(CCCS(=O)(=O)N(Cc2ccc(-c3nnc(C(F)F)o3)cc2)c2ccccc2)CC1] |
| 181 | 11655 | 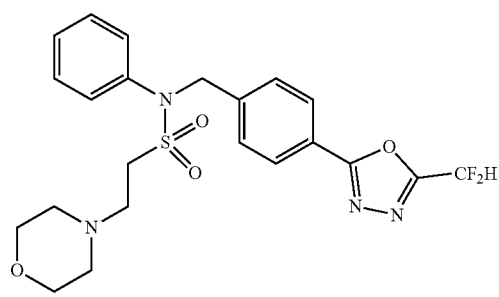 [SMILES: O=S(=O)(CCN1CCOCC1)N(Cc1ccc(-c2nnc(C(F)F)o2)cc1)c1ccccc1] |
| 182 | 11656 | 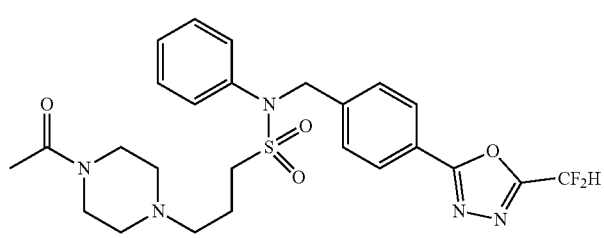 [SMILES: CC(=O)N1CCN(CCCS(=O)(=O)N(Cc2ccc(-c3nnc(C(F)F)o3)cc2)c2ccccc2)CC1] |
| 183 | 11657 | 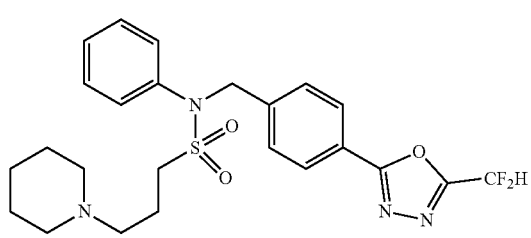 [SMILES: O=S(=O)(CCCN1CCCCC1)N(Cc1ccc(-c2nnc(C(F)F)o2)cc1)c1ccccc1] |
| 184 | 11658 | 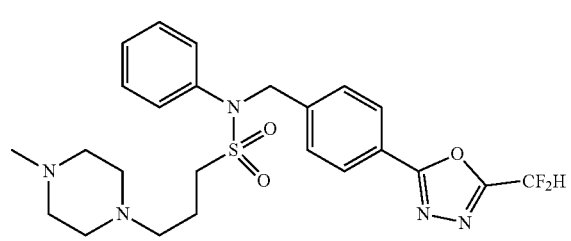 [SMILES: CN1CCN(CCCS(=O)(=O)N(Cc2ccc(-c3nnc(C(F)F)o3)cc2)c2ccccc2)CC1] |

| Ex. | Comp. | Structure |
|---|---|---|
| 185 | 11663 | 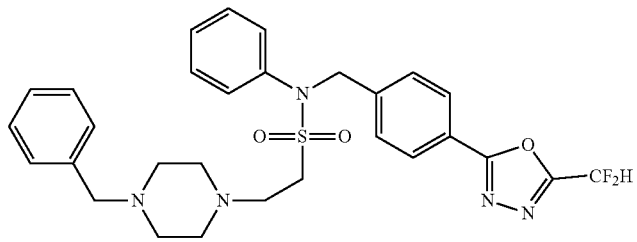 [SMILES: O=S(=O)(CCN1CCN(Cc2ccccc2)CC1)N(Cc1ccc(-c2nnc(C(F)F)o2)cc1)c1ccccc1] |
| 186 | 11665 | 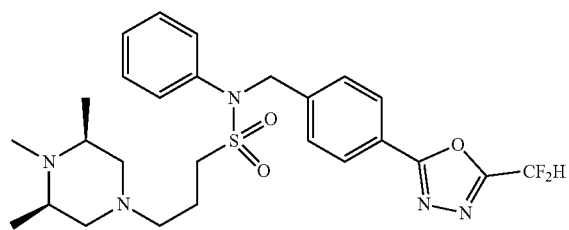 [SMILES: C[C@@H]1CN(CCCS(=O)(=O)N(Cc2ccc(-c3nnc(C(F)F)o3)cc2)c2ccccc2)C[C@H](C)N1C] |
| 187 | 11668 | 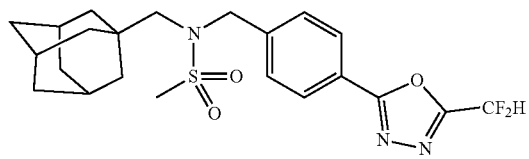 [SMILES: CS(=O)(=O)N(Cc1ccc(-c2nnc(C(F)F)o2)cc1)CC12CC3CC(CC(C3)C1)C2] |
| 188 | 11669 | 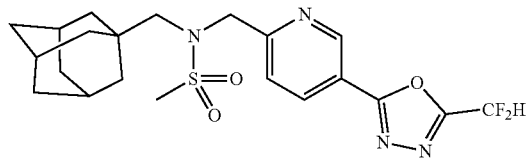 [SMILES: CS(=O)(=O)N(Cc1ccc(-c2nnc(C(F)F)o2)cn1)CC12CC3CC(CC(C3)C1)C2] |
| 189 | 11675 | 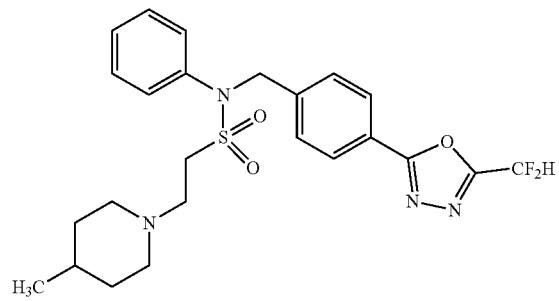 [SMILES: CC1CCN(CCS(=O)(=O)N(Cc2ccc(-c3nnc(C(F)F)o3)cc2)c2ccccc2)CC1] |
| 190 | 11676 | 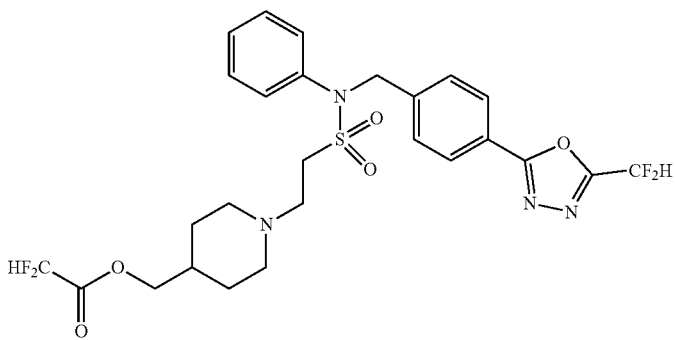 |

-continued
| Ex. | Comp. | Structure |
|---|---|---|
| 191 | 11677 | 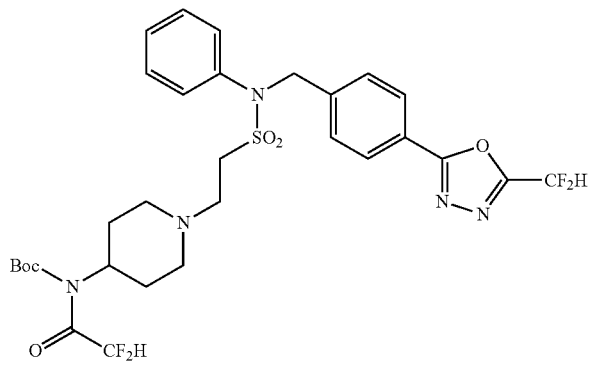 [SMILES: CC(C)(C)OC(=O)N(C(=O)C(F)F)C1CCN(CCS(=O)(=O)N(Cc2ccc(-c3nnc(C(F)F)o3)cc2)c2ccccc2)CC1] |
| 192 | 11678 | 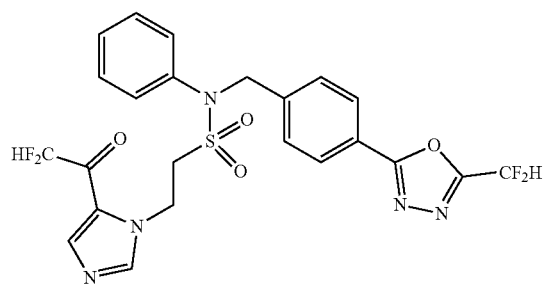 |
| 193 | 11679 | 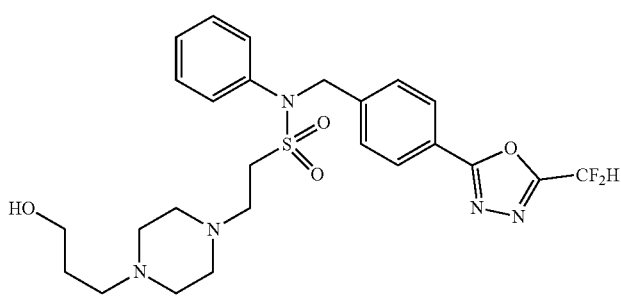 [SMILES: O=S(=O)(CCN1CCN(CCCO)CC1)N(Cc1ccc(-c2nnc(C(F)F)o2)cc1)c1ccccc1] |
| 194 | 11680 | 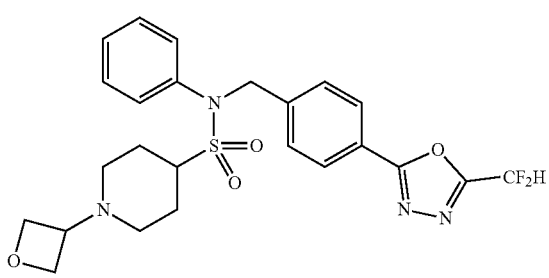 [SMILES: O=S(=O)(C1CCN(C2COC2)CC1)N(Cc1ccc(-c2nnc(C(F)F)o2)cc1)c1ccccc1] |
| 195 | 11681 | 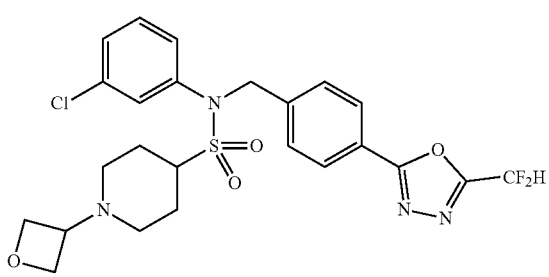 [SMILES: O=S(=O)(C1CCN(C2COC2)CC1)N(Cc1ccc(-c2nnc(C(F)F)o2)cc1)c1cccc(Cl)c1] |

-continued
| Ex. | Comp. | Structure |
|---|---|---|
| 196 | 11682 | 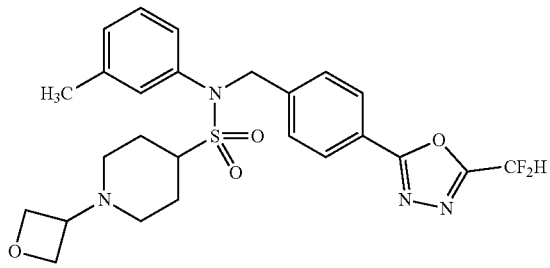 [SMILES: Cc1cccc(N(Cc2ccc(-c3nnc(C(F)F)o3)cc2)S(=O)(=O)C2CCN(C3COC3)CC2)c1] |
| 197 | 11683 | 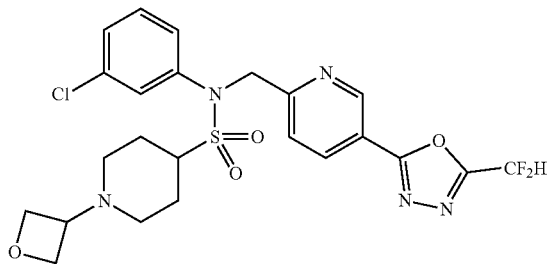 [SMILES: O=S(=O)(C1CCN(C2COC2)CC1)N(Cc1ccc(-c2nnc(C(F)F)o2)cn1)c1cccc(Cl)c1] |
| 198 | 11684 | 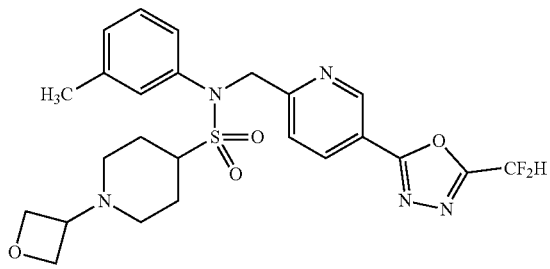 [SMILES: Cc1cccc(N(Cc2ccc(-c3nnc(C(F)F)o3)cn2)S(=O)(=O)C2CCN(C3COC3)CC2)c1] |
| 199 | 11685 | 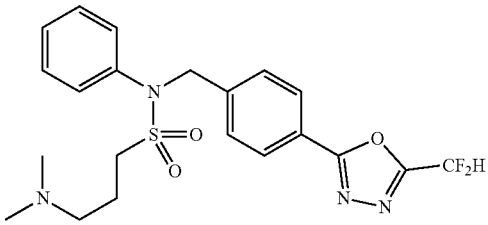 [SMILES: CN(C)CCCS(=O)(=O)N(Cc1ccc(-c2nnc(C(F)F)o2)cc1)c1ccccc1] |
| 200 | 11686 | 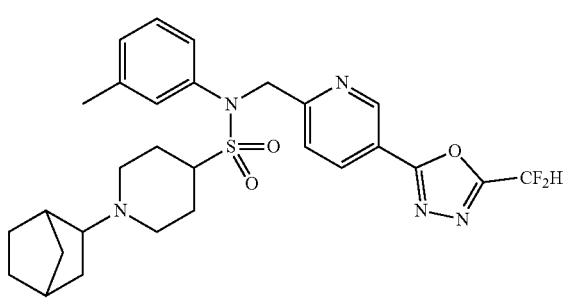 [SMILES: Cc1cccc(N(Cc2ccc(-c3nnc(C(F)F)o3)cn2)S(=O)(=O)C2CCN(C3CC4CCC3C4)CC2)c1] |

| Ex. | Comp. | Structure |
|---|---|---|
| 201 | 11687 | 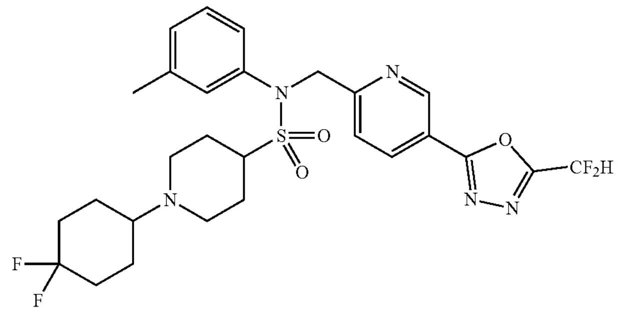 [SMILES: Cc1cccc(N(Cc2ccc(-c3nnc(C(F)F)o3)cn2)S(=O)(=O)C2CCN(C3CCC(F)(F)CC3)CC2)c1] |
| 202 | 11688 | 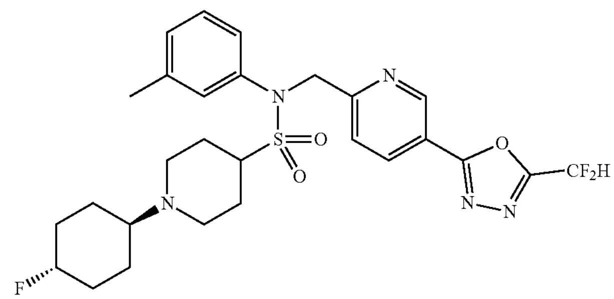 [SMILES: Cc1cccc(N(Cc2ccc(-c3nnc(C(F)F)o3)cn2)S(=O)(=O)C2CCN([C@H]3CC[C@H](F)CC3)CC2)c1] |
| 203 | 11689 | 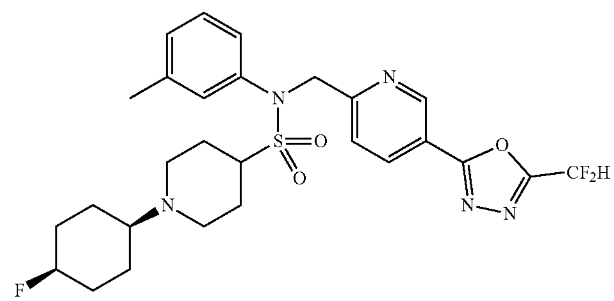 [SMILES: Cc1cccc(N(Cc2ccc(-c3nnc(C(F)F)o3)cn2)S(=O)(=O)C2CCN([C@H]3CC[C@@H](F)CC3)CC2)c1] |
| 204 | 11690 | 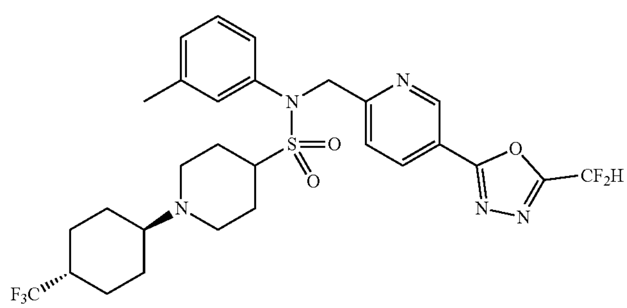 [SMILES: Cc1cccc(N(Cc2ccc(-c3nnc(C(F)F)o3)cn2)S(=O)(=O)C2CCN([C@H]3CC[C@H](C(F)(F)F)CC3)CC2)c1] |
| 205 | 11691 | 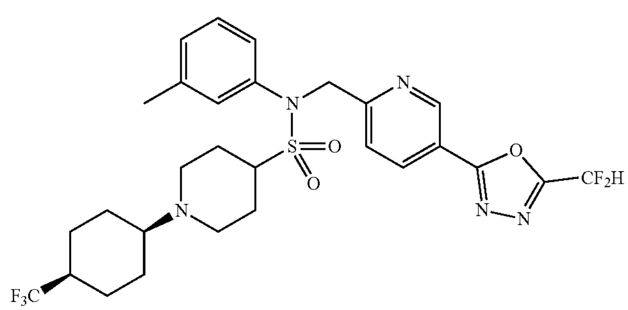 [SMILES: Cc1cccc(N(Cc2ccc(-c3nnc(C(F)F)o3)cn2)S(=O)(=O)C2CCN([C@H]3CC[C@@H](C(F)(F)F)CC3)CC2)c1] |

| Ex. | Comp. | Structure |
|---|---|---|
| 206 | 11692 | 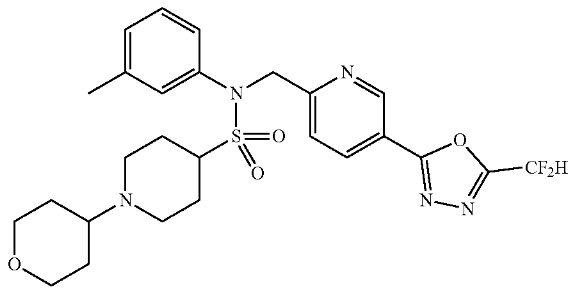 [SMILES: Cc1cccc(N(Cc2ccc(-c3nnc(C(F)F)o3)cn2)S(=O)(=O)C2CCN(C3CCOCC3)CC2)c1] |
| 207 | 11693 | 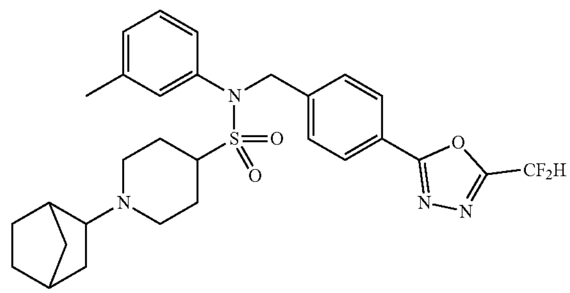 [SMILES: Cc1cccc(N(Cc2ccc(-c3nnc(C(F)F)o3)cc2)S(=O)(=O)C2CCN(C3CC4CCC3C4)CC2)c1] |
| 208 | 11694 | 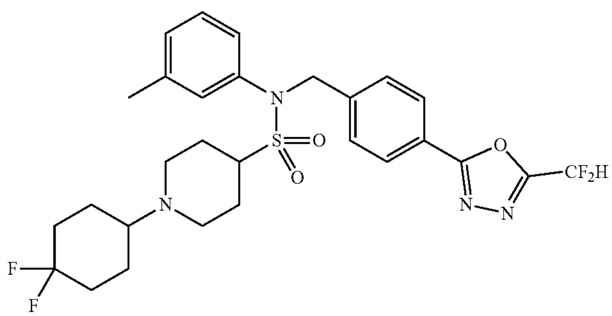 [SMILES: Cc1cccc(N(Cc2ccc(-c3nnc(C(F)F)o3)cc2)S(=O)(=O)C2CCN(C3CCC(F)(F)CC3)CC2)c1] |
| 209 | 11695 | 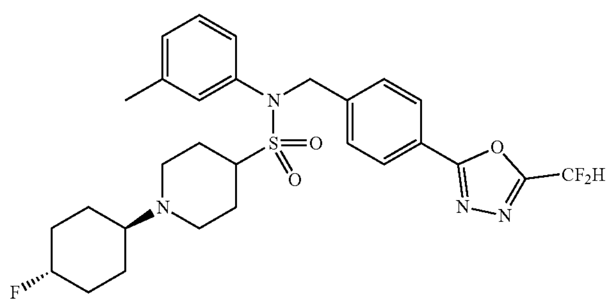 [SMILES: Cc1cccc(N(Cc2ccc(-c3nnc(C(F)F)o3)cc2)S(=O)(=O)C2CCN([C@H]3CC[C@H](F)CC3)CC2)c1] |
| 210 | 11696 | 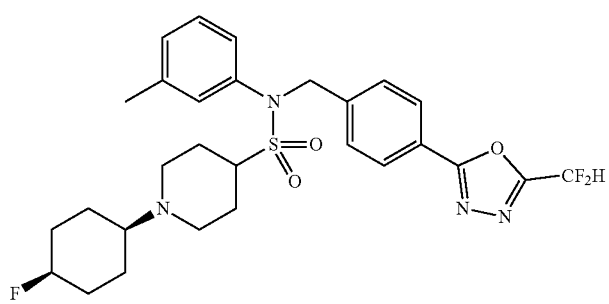 [SMILES: Cc1cccc(N(Cc2ccc(-c3nnc(C(F)F)o3)cc2)S(=O)(=O)C2CCN([C@H]3CC[C@@H](F)CC3)CC2)c1] |

| Ex. | Comp. | Structure |
|---|---|---|
| 211 | 11697 | 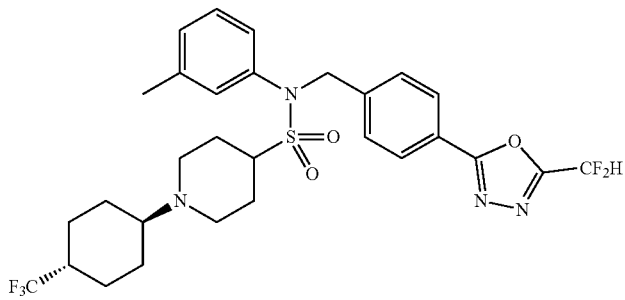 [SMILES: Cc1cccc(N(Cc2ccc(-c3nnc(C(F)F)o3)cc2)S(=O)(=O)C2CCN([C@H]3CC[C@H](C(F)(F)F)CC3)CC2)c1] |
| 212 | 11698 | 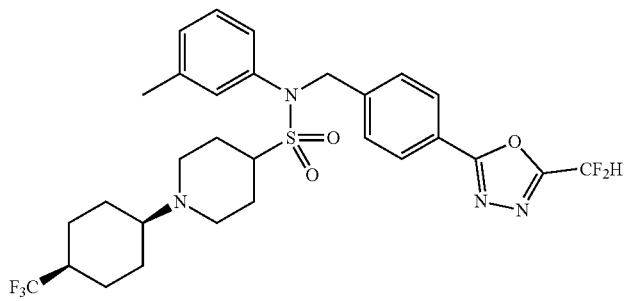 [SMILES: Cc1cccc(N(Cc2ccc(-c3nnc(C(F)F)o3)cc2)S(=O)(=O)C2CCN([C@H]3CC[C@@H](C(F)(F)F)CC3)CC2)c1] |
| 213 | 11699 | 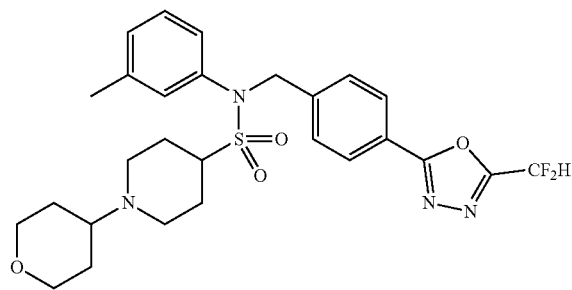 [SMILES: Cc1cccc(N(Cc2ccc(-c3nnc(C(F)F)o3)cc2)S(=O)(=O)C2CCN(C3CCOCC3)CC2)c1] |
| 214 | 11700 | 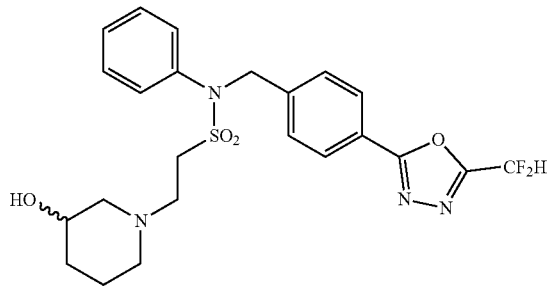 [SMILES: O=S(=O)(CCN1CCCC(O)C1)N(Cc1ccc(-c2nnc(C(F)F)o2)cc1)c1ccccc1] |
| 215 | 11705 | 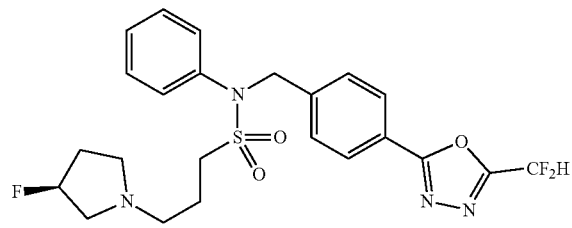 [SMILES: O=S(=O)(CCCN1CC[C@H](F)C1)N(Cc1ccc(-c2nnc(C(F)F)o2)cc1)c1ccccc1] |

| Ex. | Comp. | Structure |
|---|---|---|
| 216 | 11706 | 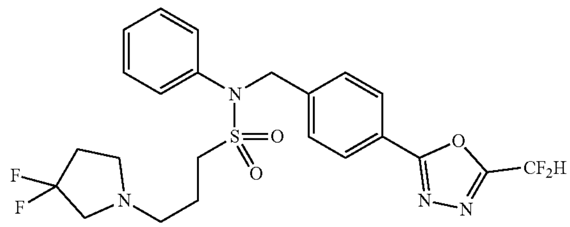 [SMILES: O=S(=O)(CCCN1CCC(F)(F)C1)N(Cc1ccc(-c2nnc(C(F)F)o2)cc1)c1ccccc1] |
| 217 | 11707 | 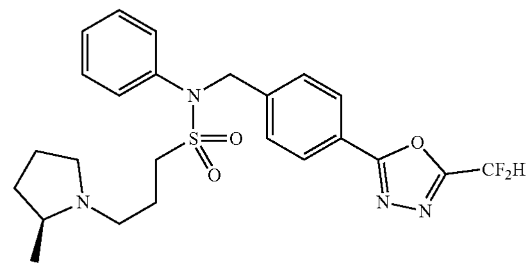 [SMILES: C[C@H]1CCCN1CCCS(=O)(=O)N(Cc1ccc(-c2nnc(C(F)F)o2)cc1)c1ccccc1] |
| 218 | 11708 | 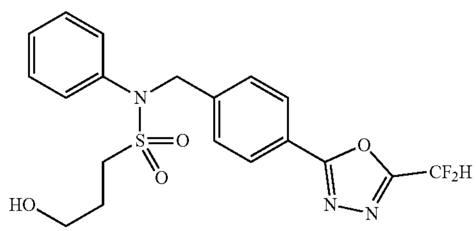 [SMILES: O=S(=O)(CCCO)N(Cc1ccc(-c2nnc(C(F)F)o2)cc1)c1ccccc1] |
| 219 | 11709 | 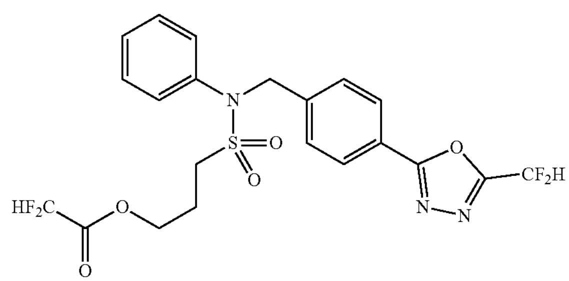 |
| 220 | 11710 | 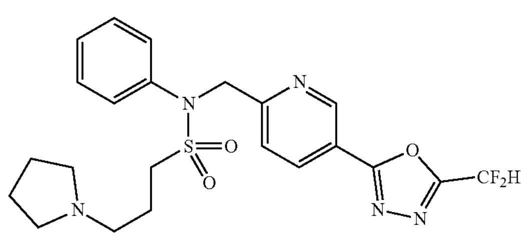 [SMILES: O=S(=O)(CCCN1CCCC1)N(Cc1ccc(-c2nnc(C(F)F)o2)cn1)c1ccccc1] |
| 221 | 11711 | 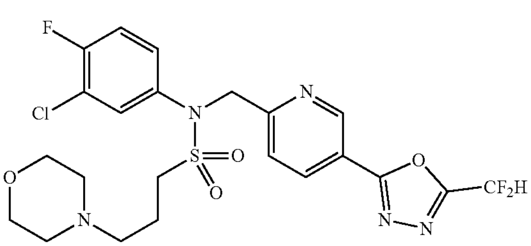 [SMILES: O=S(=O)(CCCN1CCOCC1)N(Cc1ccc(-c2nnc(C(F)F)o2)cn1)c1ccc(F)c(Cl)c1] |

-continued

| Ex. | Comp. | Structure |
|---|---|---|
| 222 | 11712 | 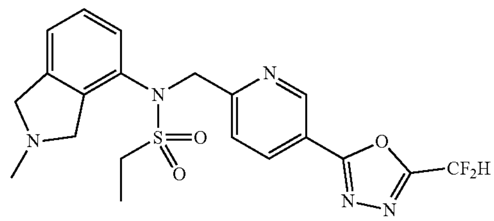 [SMILES: CCS(=O)(=O)N(Cc1ccc(-c2nnc(C(F)F)o2)cn1)c1cccc2c1CN(C)C2] |
| 223 | 11717 | 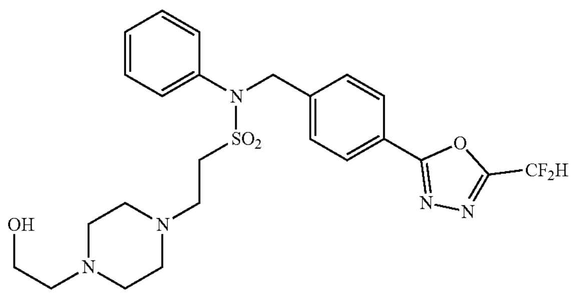 [SMILES: O=S(=O)(CCN1CCN(CCO)CC1)N(Cc1ccc(-c2nnc(C(F)F)o2)cc1)c1ccccc1] |
| 224 | 11718 | 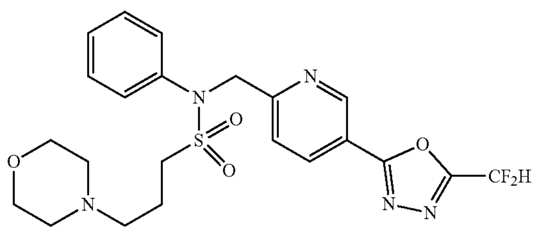 [SMILES: O=S(=O)(CCCN1CCOCC1)N(Cc1ccc(-c2nnc(C(F)F)o2)cn1)c1ccccc1] |
| 225 | 11719 | 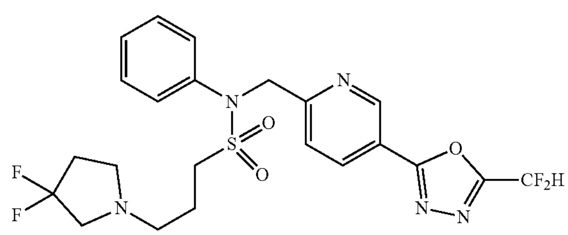 [SMILES: O=S(=O)(CCCN1CCC(F)(F)C1)N(Cc1ccc(-c2nnc(C(F)F)o2)cn1)c1ccccc1] |
| 226 | 11721 | 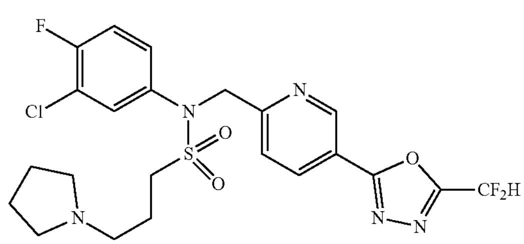 [SMILES: O=S(=O)(CCCN1CCCC1)N(Cc1ccc(-c2nnc(C(F)F)o2)cn1)c1ccc(F)c(Cl)c1] |
| 227 | 11722 | 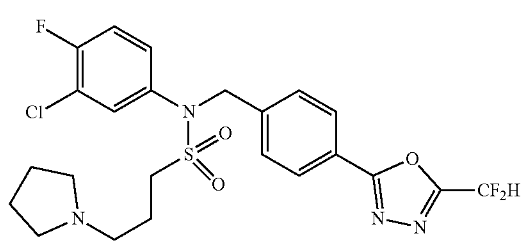 [SMILES: O=S(=O)(CCCN1CCCC1)N(Cc1ccc(-c2nnc(C(F)F)o2)cc1)c1ccc(F)c(Cl)c1] |

| Ex. | Comp. | Structure |
|---|---|---|
| 228 | 11723 | 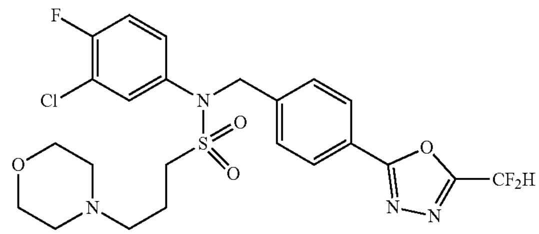 [SMILES: O=S(=O)(CCCN1CCOCC1)N(Cc1ccc(-c2nnc(C(F)F)o2)cc1)c1ccc(F)c(Cl)c1] |
| 229 | 11724 | 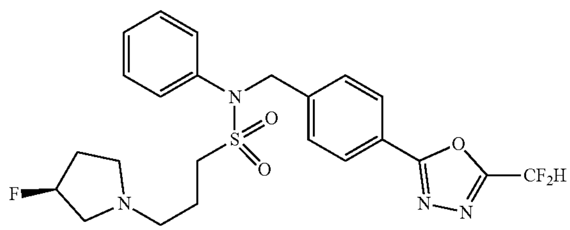 [SMILES: O=S(=O)(CCCN1CC[C@H](F)C1)N(Cc1ccc(-c2nnc(C(F)F)o2)cc1)c1ccccc1] |
| 230 | 11725 | 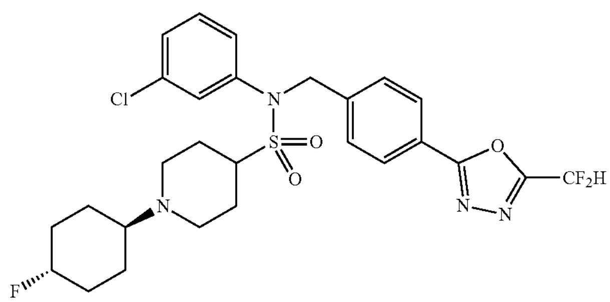 [SMILES: O=S(=O)(C1CCN([C@H]2CC[C@H](F)CC2)CC1)N(Cc1ccc(-c2nnc(C(F)F)o2)cc1)c1cccc(Cl)c1] |
| 231 | 11726 | 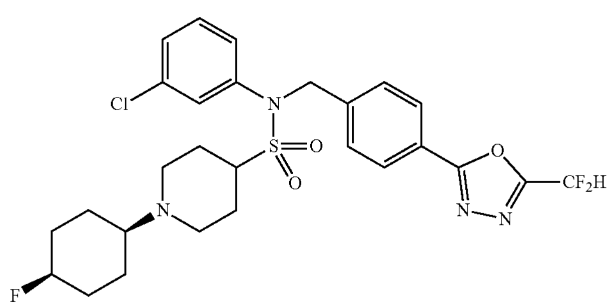 [SMILES: O=S(=O)(C1CCN([C@H]2CC[C@@H](F)CC2)CC1)N(Cc1ccc(-c2nnc(C(F)F)o2)cc1)c1cccc(Cl)c1] |
| 232 | 11727 | 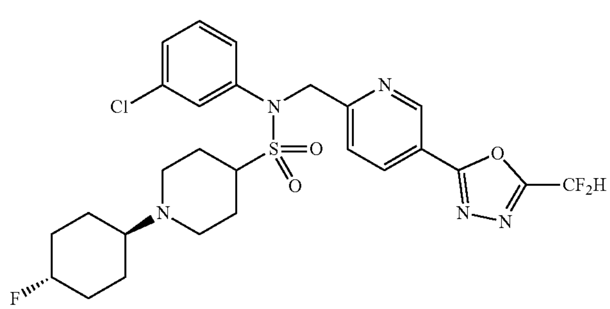 [SMILES: O=S(=O)(C1CCN([C@H]2CC[C@H](F)CC2)CC1)N(Cc1ccc(-c2nnc(C(F)F)o2)cn1)c1cccc(Cl)c1] |

-continued
| Ex. | Comp. | Structure |
|---|---|---|
| 233 | 11728 | 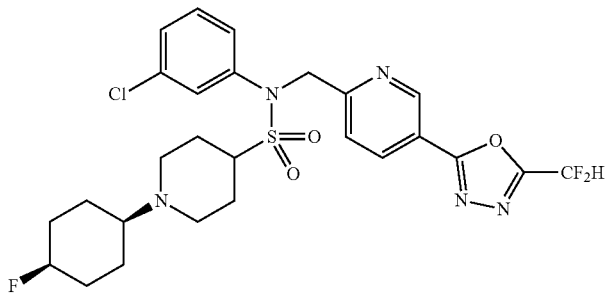 [SMILES: O=S(=O)(C1CCN([C@H]2CC[C@@H](F)CC2)CC1)N(Cc1ccc(-c2nnc(C(F)F)o2)cn1)c1cccc(Cl)c1] |
| 234 | 11729 | 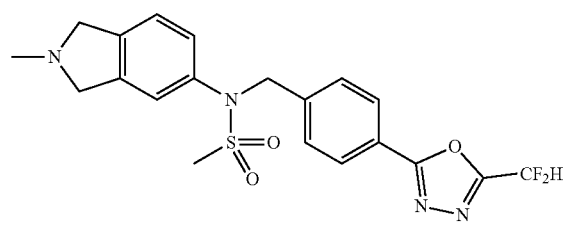 [SMILES: CN1Cc2ccc(N(Cc3ccc(-c4nnc(C(F)F)o4)cc3)S(C)(=O)=O)cc2C1] |
| 235 | 11730 | 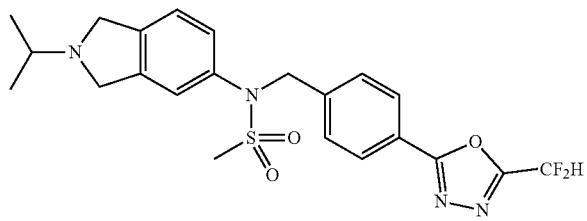 [SMILES: CC(C)N1Cc2ccc(N(Cc3ccc(-c4nnc(C(F)F)o4)cc3)S(C)(=O)=O)cc2C1] |
| 236 | 11731 | 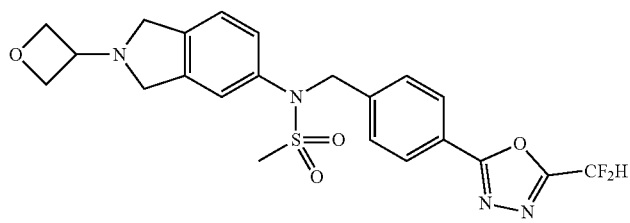 [SMILES: CS(=O)(=O)N(Cc1ccc(-c2nnc(C(F)F)o2)cc1)c1ccc2c(c1)CN(C1COC1)C2] |
| 237 | 11732 | 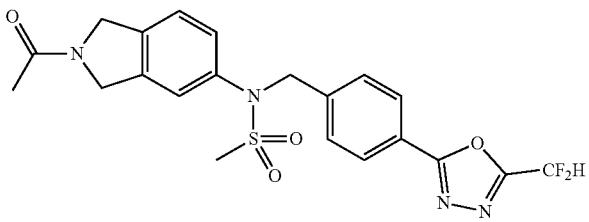 [SMILES: CC(=O)N1Cc2ccc(N(Cc3ccc(-c4nnc(C(F)F)o4)cc3)S(C)(=O)=O)cc2C1] |
| 238 | 11733 | 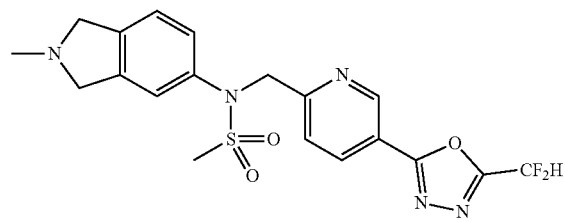 [SMILES: CN1Cc2ccc(N(Cc3ccc(-c4nnc(C(F)F)o4)cn3)S(C)(=O)=O)cc2C1] |

-continued

| Ex. | Comp. | Structure |
|---|---|---|
| 239 | 11734 | 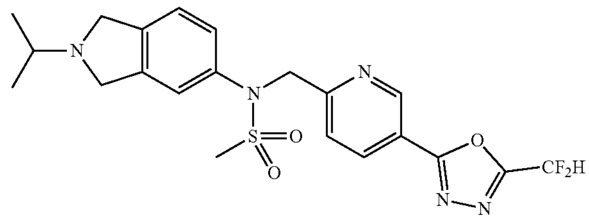 [SMILES: CC(C)N1Cc2ccc(N(Cc3ccc(-c4nnc(C(F)F)o4)cn3)S(C)(=O)=O)cc2C1] |
| 240 | 11735 | 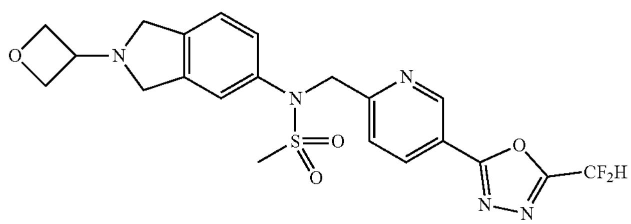 [SMILES: CS(=O)(=O)N(Cc1ccc(-c2nnc(C(F)F)o2)cn1)c1ccc2c(c1)CN(C1COC1)C2] |
| 241 | 11736 | 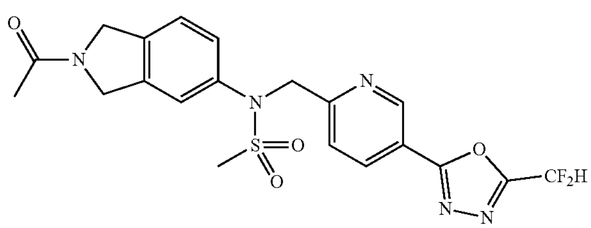 [SMILES: CC(=O)N1Cc2ccc(N(Cc3ccc(-c4nnc(C(F)F)o4)cn3)S(C)(=O)=O)cc2C1] |
| 242 | 11737 | 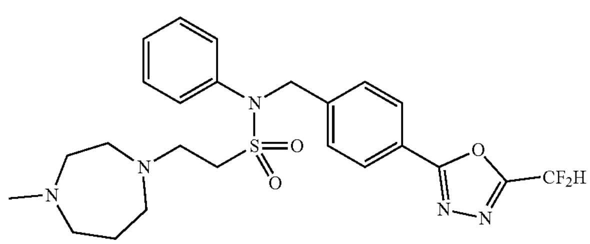 [SMILES: CN1CCCN(CCS(=O)(=O)N(Cc2ccc(-c3nnc(C(F)F)o3)cc2)c2ccccc2)CC1] |
| 243 | 11738 | 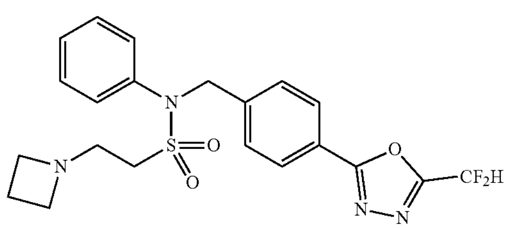 [SMILES: O=S(=O)(CCN1CCC1)N(Cc1ccc(-c2nnc(C(F)F)o2)cc1)c1ccccc1] |
| 244 | 11739 | 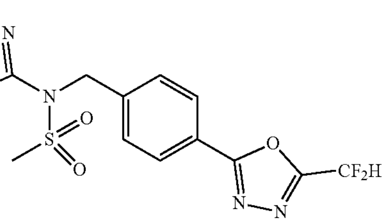 |

-continued
| Ex. | Comp. | Structure |
|---|---|---|
| 245 | 11740 | 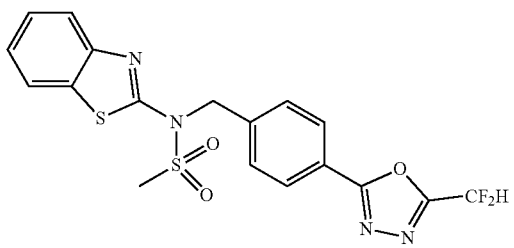 [SMILES: CS(=O)(=O)N(Cc1ccc(-c2nnc(C(F)F)o2)cc1)c1nc2ccccc2s1] |
| 246 | 11741 | 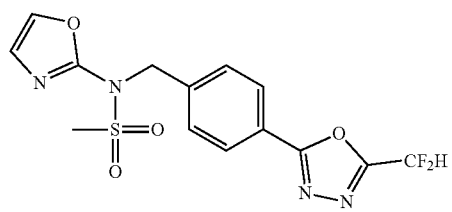 [SMILES: CS(=O)(=O)N(Cc1ccc(-c2nnc(C(F)F)o2)cc1)c1ncco1] |
| 247 | 11742 | 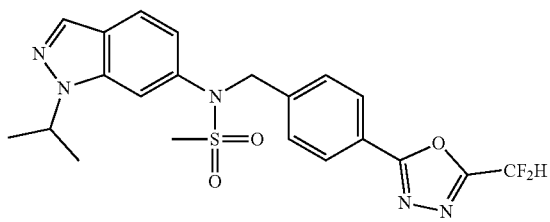 [SMILES: CC(C)n1ncc2ccc(N(Cc3ccc(-c4nnc(C(F)F)o4)cc3)S(C)(=O)=O)cc21] |
| 248 | 11743 | 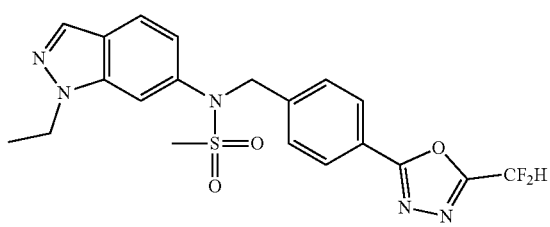 [SMILES: CCn1ncc2ccc(N(Cc3ccc(-c4nnc(C(F)F)o4)cc3)S(C)(=O)=O)cc21] |
| 249 | 11744 | 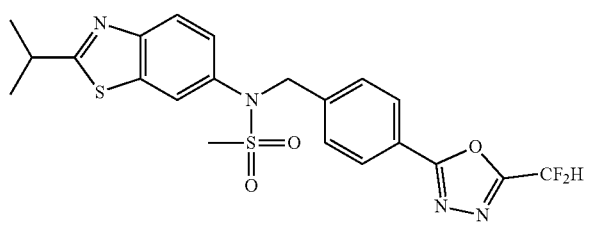 [SMILES: CC(C)c1nc2ccc(N(Cc3ccc(-c4nnc(C(F)F)o4)cc3)S(C)(=O)=O)cc2s1] |
| 250 | 11745 | 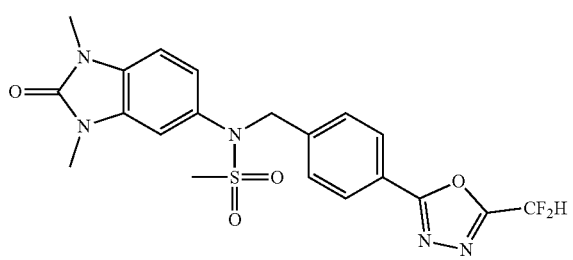 [SMILES: Cn1c(=O)n(C)c2cc(N(Cc3ccc(-c4nnc(C(F)F)o4)cc3)S(C)(=O)=O)ccc21] |

-continued

| Ex. | Comp. | Structure |
|---|---|---|
| 251 | 11746 | 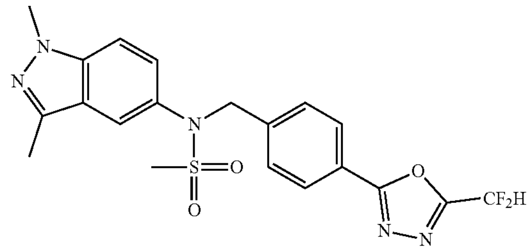 [SMILES: Cc1nn(C)c2ccc(N(Cc3ccc(-c4nnc(C(F)F)o4)cc3)S(C)(=O)=O)cc12] |
| 252 | 11747 | 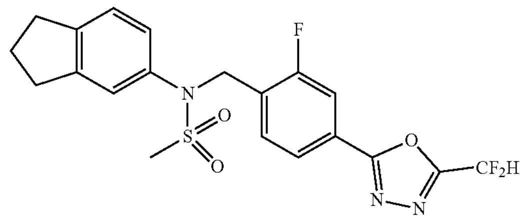 [SMILES: CS(=O)(=O)N(Cc1ccc(-c2nnc(C(F)F)o2)cc1F)c1ccc2c(c1)CCC2] |
| 253 | 11748 | 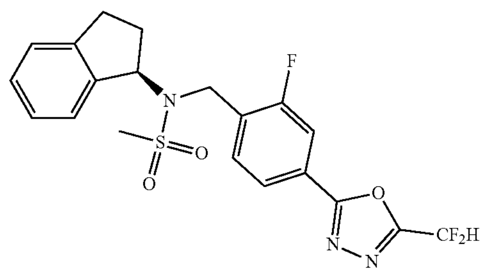 [SMILES: CS(=O)(=O)N(Cc1ccc(-c2nnc(C(F)F)o2)cc1F)[C@@H]1CCc2ccccc21] |
| 254 | 11749 | 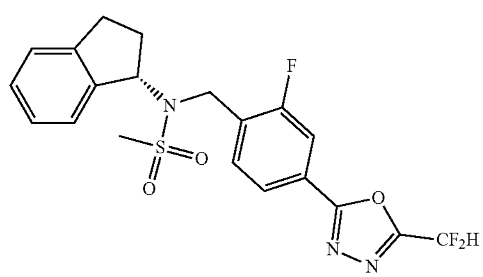 [SMILES: CS(=O)(=O)N(Cc1ccc(-c2nnc(C(F)F)o2)cc1F)[C@H]1CCc2ccccc21] |
| 255 | 11750 | 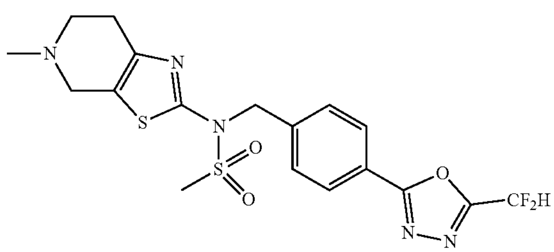 [SMILES: CN1CCc2nc(N(Cc3ccc(-c4nnc(C(F)F)o4)cc3)S(C)(=O)=O)sc2C1] |
| 256 | 11751 | 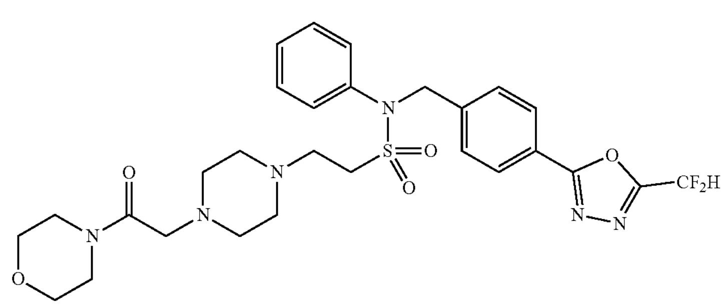 [SMILES: O=C(CN1CCN(CCS(=O)(=O)N(Cc2ccc(-c3nnc(C(F)F)o3)cc2)c2ccccc2)CC1)N1CCOCC1] |

-continued
| Ex. | Comp. | Structure |
|---|---|---|
| 257 | 11752 | 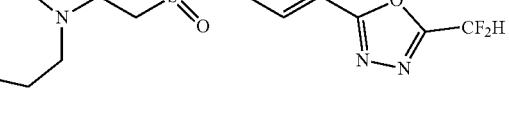 |
| 258 | 11753 | 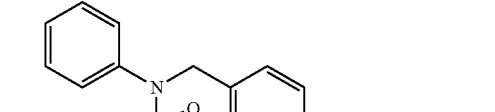 |
| 259 | 11754 | 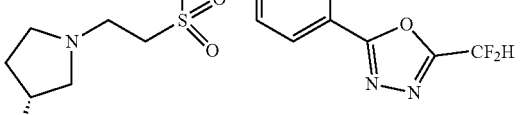 |
| 260 | 11755 | 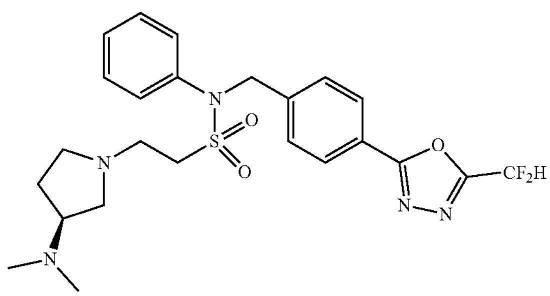 [SMILES: CN(C)[C@H]1CCN(CCS(=O)(=O)N(Cc2ccc(-c3nnc(C(F)F)o3)cc2)c2ccccc2)C1] |
| 261 | 11756 | 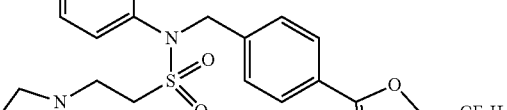 |
| 262 | 11757 | 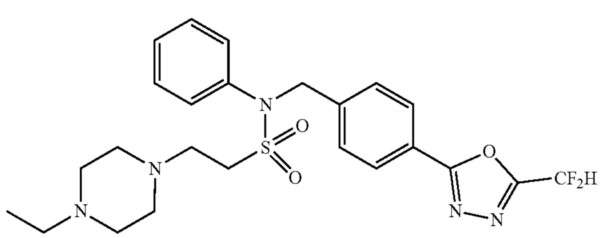 [SMILES: CCN1CCN(CCS(=O)(=O)N(Cc2ccc(-c3nnc(C(F)F)o3)cc2)c2ccccc2)CC1] |

-continued
| Ex. | Comp. | Structure |
|---|---|---|
| 263 | 11758 | 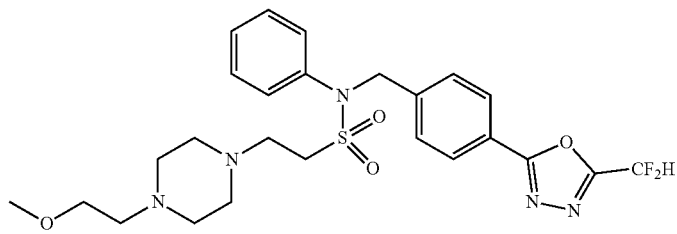 [SMILES: COCCN1CCN(CCS(=O)(=O)N(Cc2ccc(-c3nnc(C(F)F)o3)cc2)c2ccccc2)CC1] |
| 264 | 11759 | 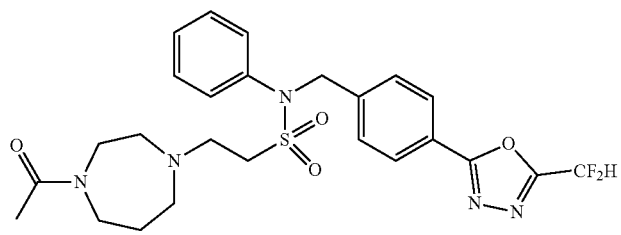 [SMILES: CC(=O)N1CCCN(CCS(=O)(=O)N(Cc2ccc(-c3nnc(C(F)F)o3)cc2)c2ccccc2)CC1] |
| 265 | 11760 | 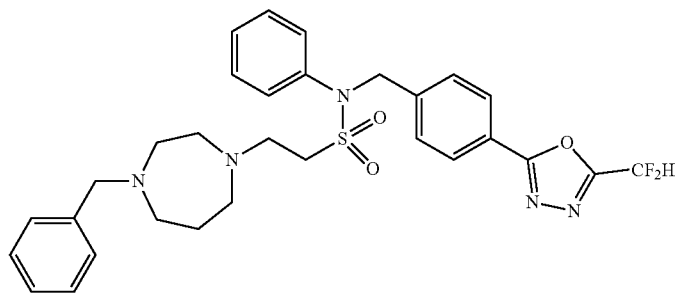 [SMILES: O=S(=O)(CCN1CCCN(Cc2ccccc2)CC1)N(Cc1ccc(-c2nnc(C(F)F)o2)cc1)c1ccccc1] |
| 266 | 11761 | 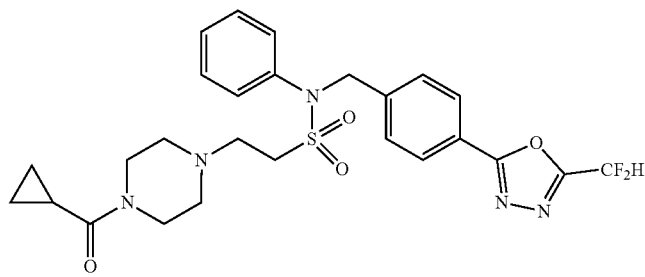 [SMILES: O=C(C1CC1)N1CCN(CCS(=O)(=O)N(Cc2ccc(-c3nnc(C(F)F)o3)cc2)c2ccccc2)CC1] |
| 267 | 11762 | 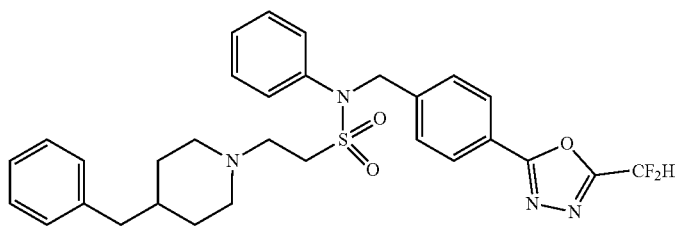 [SMILES: O=S(=O)(CCN1CCC(Cc2ccccc2)CC1)N(Cc1ccc(-c2nnc(C(F)F)o2)cc1)c1ccccc1] |

-continued
| Ex. | Comp. | Structure |
|---|---|---|
| 268 | 11763 | 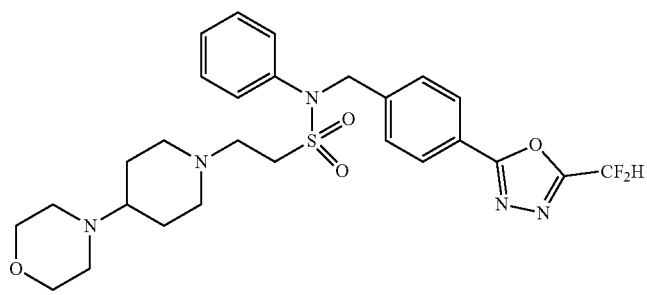 [SMILES: O=S(=O)(CCN1CCC(N2CCOCC2)CC1)N(Cc1ccc(-c2nnc(C(F)F)o2)cc1)c1ccccc1] |
| 269 | 11764 | 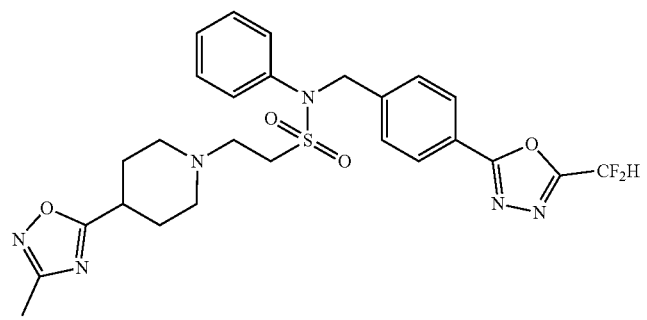 [SMILES: Cc1noc(C2CCN(CCS(=O)(=O)N(Cc3ccc(-c4nnc(C(F)F)o4)cc3)c3ccccc3)CC2)n1] |
| 270 | 11765 | 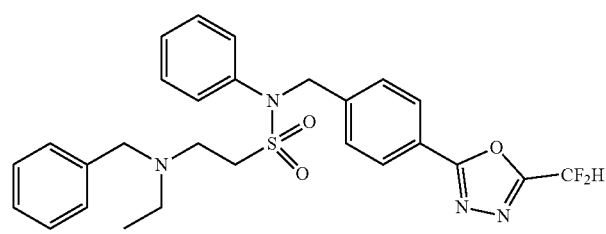 [SMILES: CCN(CCS(=O)(=O)N(Cc1ccc(-c2nnc(C(F)F)o2)cc1)c1ccccc1)Cc1ccccc1] |
| 271 | 11766 | 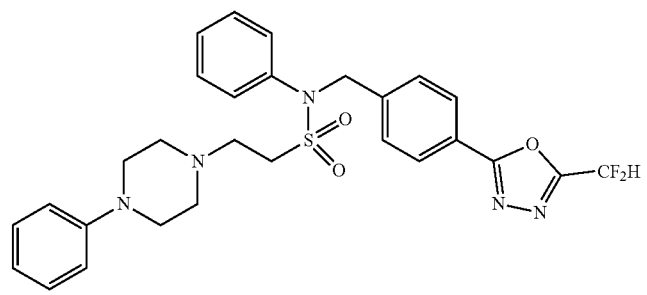 [SMILES: O=S(=O)(CCN1CCN(c2ccccc2)CC1)N(Cc1ccc(-c2nnc(C(F)F)o2)cc1)c1ccccc1] |
| 272 | 11767 | 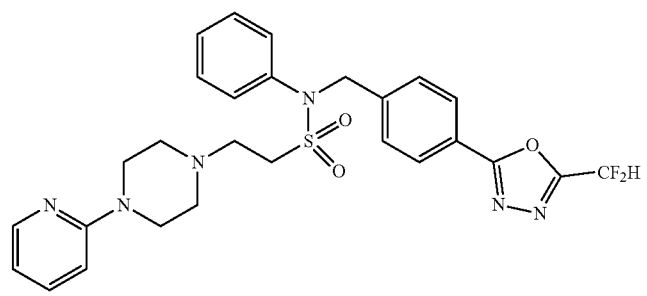 [SMILES: O=S(=O)(CCN1CCN(c2ccccn2)CC1)N(Cc1ccc(-c2nnc(C(F)F)o2)cc1)c1ccccc1] |

| Ex. | Comp. | Structure |
|---|---|---|
| 273 | 11768 | 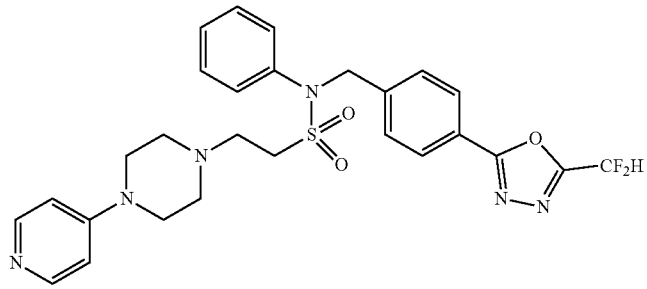 [SMILES: O=S(=O)(CCN1CCN(c2ccncc2)CC1)N(Cc1ccc(-c2nnc(C(F)F)o2)cc1)c1ccccc1] |
| 274 | 11769 | 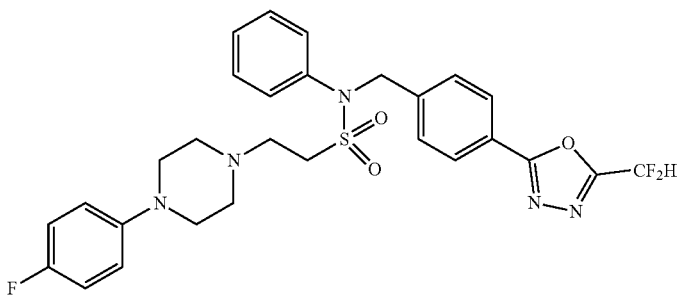 [SMILES: O=S(=O)(CCN1CCN(c2ccc(F)cc2)CC1)N(Cc1ccc(-c2nnc(C(F)F)o2)cc1)c1ccccc1] |
| 275 | 11770 | 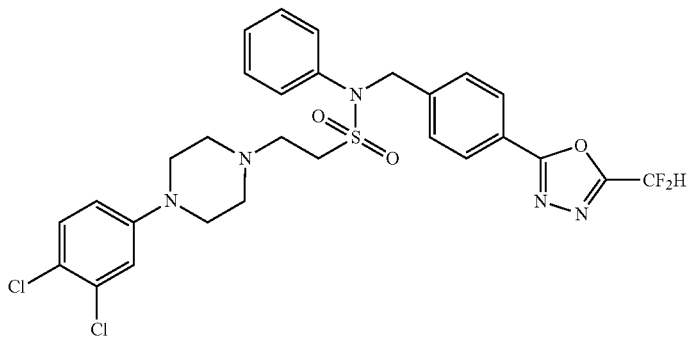 [SMILES: O=S(=O)(CCN1CCN(c2ccc(Cl)c(Cl)c2)CC1)N(Cc1ccc(-c2nnc(C(F)F)o2)cc1)c1ccccc1] |
| 276 | 11771 | 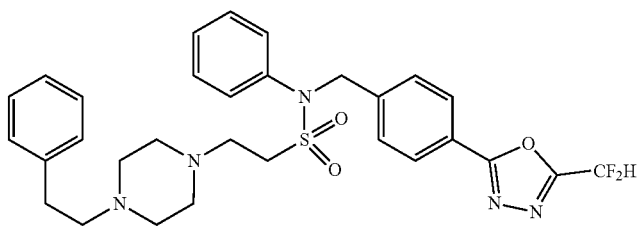 [SMILES: O=S(=O)(CCN1CCN(CCc2ccccc2)CC1)N(Cc1ccc(-c2nnc(C(F)F)o2)cc1)c1ccccc1] |
| 277 | 11772 | 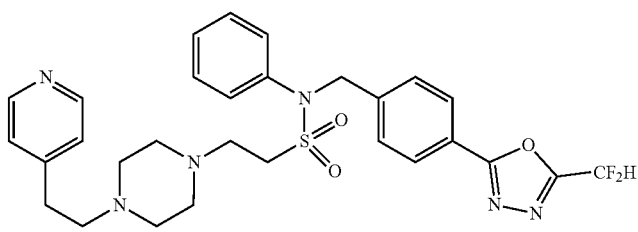 [SMILES: O=S(=O)(CCN1CCN(CCc2ccncc2)CC1)N(Cc1ccc(-c2nnc(C(F)F)o2)cc1)c1ccccc1] |

| Ex. | Comp. | Structure |
|---|---|---|
| 278 | 11773 | 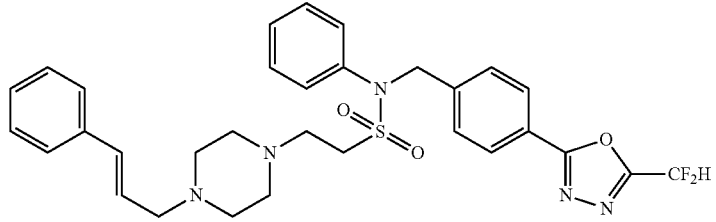 [SMILES: O=S(=O)(CCN1CCN(C/C=C/c2ccccc2)CC1)N(Cc1ccc(-c2nnc(C(F)F)o2)cc1)c1ccccc1] |
| 279 | 11774 | 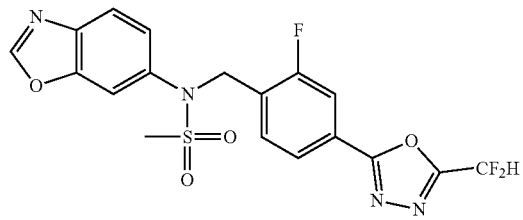 |
| 280 | 11775 | 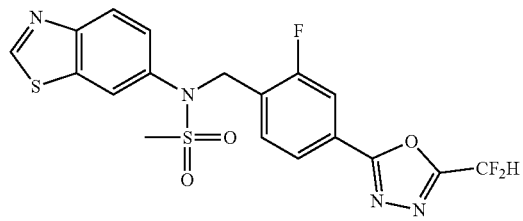 [SMILES: CS(=O)(=O)N(Cc1ccc(-c2nnc(C(F)F)o2)cc1F)c1ccc2ncsc2c1] |
| 281 | 11776 | 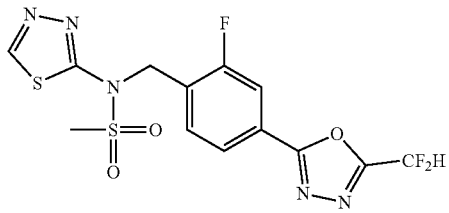 [SMILES: CS(=O)(=O)N(Cc1ccc(-c2nnc(C(F)F)o2)cc1F)c1nncs1] |
| 282 | 11777 | 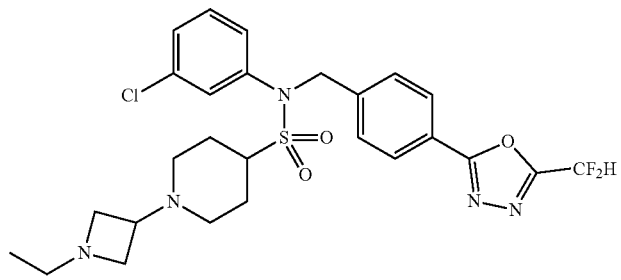 [SMILES: CCN1CC(N2CCC(S(=O)(=O)N(Cc3ccc(-c4nnc(C(F)F)o4)cc3)c3cccc(Cl)c3)CC2)C1] |
| 283 | 11778 | 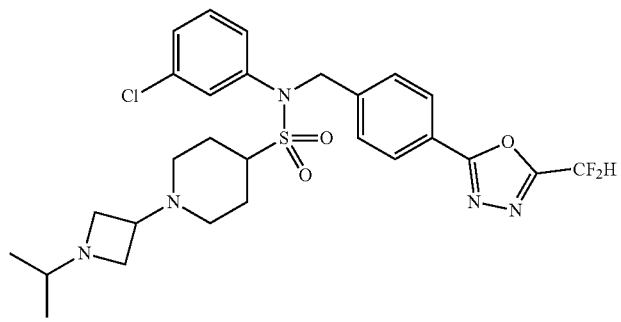 |

| Ex. | Comp. | Structure |
|---|---|---|
| 284 | 11779 | 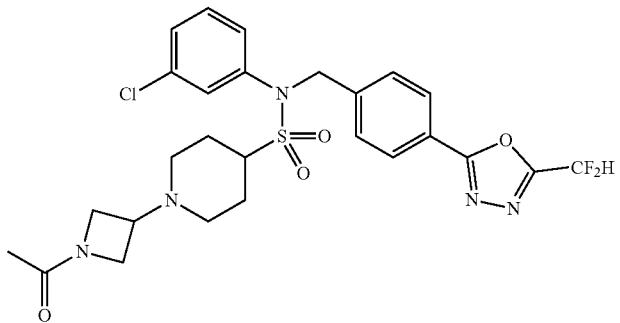 [SMILES: CC(=O)N1CC(N2CCC(S(=O)(=O)N(Cc3ccc(-c4nnc(C(F)F)o4)cc3)c3cccc(Cl)c3)CC2)C1] |
| 285 | 11780 | 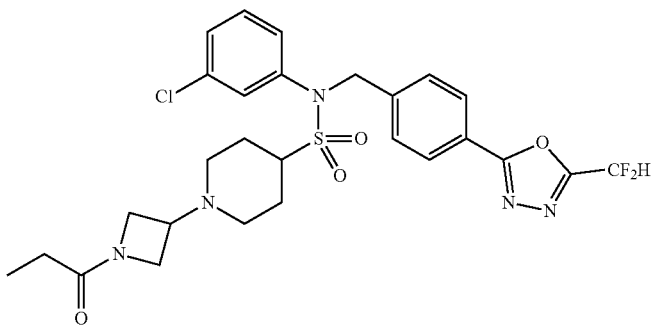 [SMILES: CCC(=O)N1CC(N2CCC(S(=O)(=O)N(Cc3ccc(-c4nnc(C(F)F)o4)cc3)c3cccc(Cl)c3)CC2)C1] |
| 286 | 11781 | 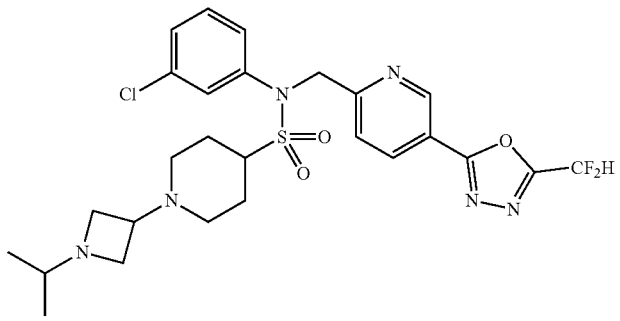 [SMILES: CC(C)N1CC(N2CCC(S(=O)(=O)N(Cc3ccc(-c4nnc(C(F)F)o4)cn3)c3cccc(Cl)c3)CC2)C1] |
| 287 | 11782 | 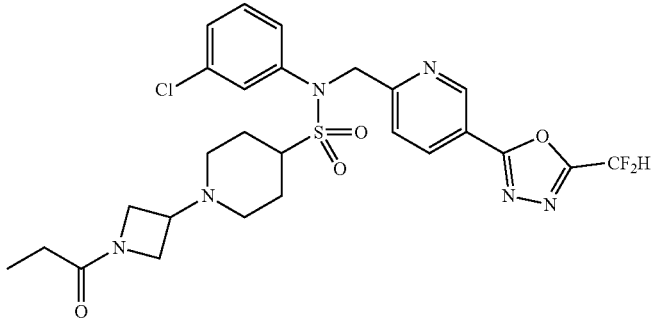 [SMILES: CCC(=O)N1CC(N2CCC(S(=O)(=O)N(Cc3ccc(-c4nnc(C(F)F)o4)cn3)c3cccc(Cl)c3)CC2)C1] |

-continued
| Ex. | Comp. | Structure |
|---|---|---|
| 288 | 11783 | 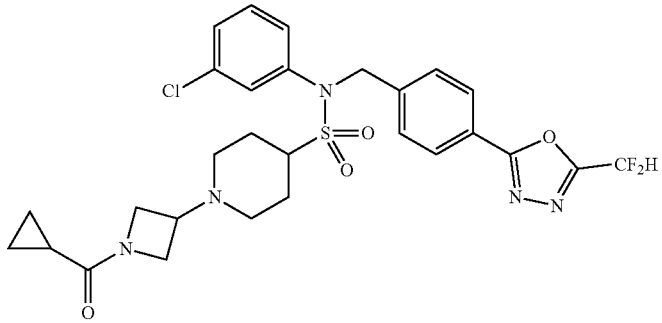 [SMILES: O=C(C1CC1)N1CC(N2CCC(S(=O)(=O)N(Cc3ccc(-c4nnc(C(F)F)o4)cc3)c3cccc(Cl)c3)CC2)C1] |
| 289 | 11784 | 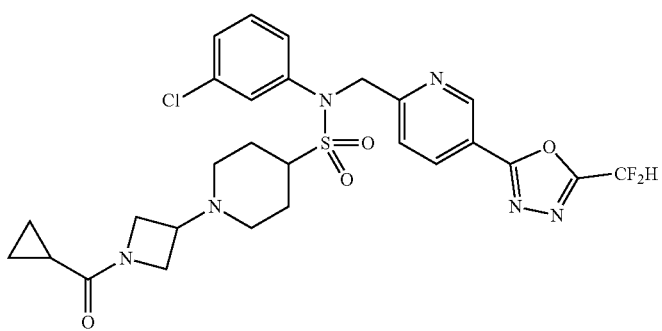 [SMILES: O=C(C1CC1)N1CC(N2CCC(S(=O)(=O)N(Cc3ccc(-c4nnc(C(F)F)o4)cn3)c3cccc(Cl)c3)CC2)C1] |
| 290 | 11785 | 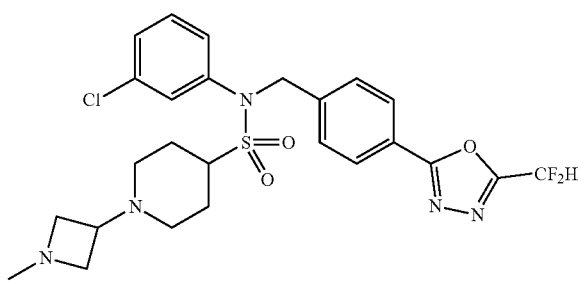 [SMILES: CN1CC(N2CCC(S(=O)(=O)N(Cc3ccc(-c4nnc(C(F)F)o4)cc3)c3cccc(Cl)c3)CC2)C1] |
| 291 | 11786 | 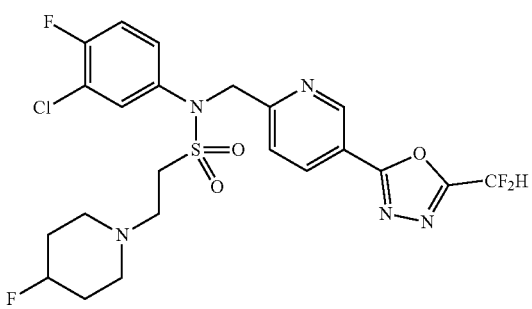 [SMILES: O=S(=O)(CCN1CCC(F)CC1)N(Cc1ccc(-c2nnc(C(F)F)o2)cn1)c1ccc(F)c(Cl)c1] |
| 292 | 11790 | 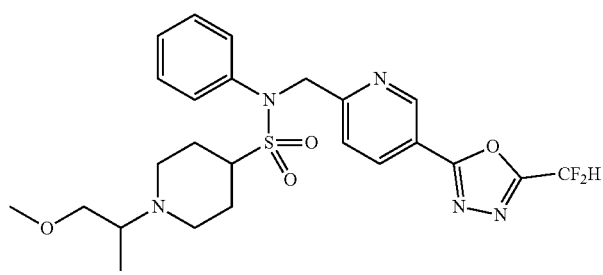 [SMILES: COCC(C)N1CCC(S(=O)(=O)N(Cc2ccc(-c3nnc(C(F)F)o3)cn2)c2ccccc2)CC1] |

| Ex. | Comp. | Structure |
|---|---|---|
| 293 | 11791 | 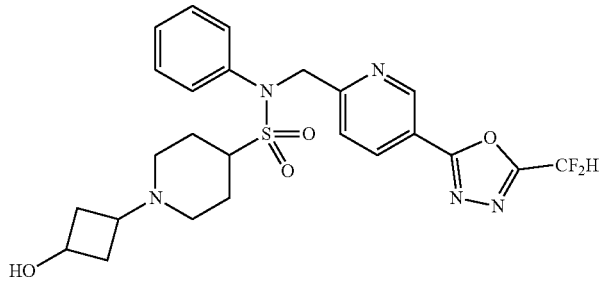 [SMILES: O=S(=O)(C1CCN(C2CC(O)C2)CC1)N(Cc1ccc(-c2nnc(C(F)F)o2)cn1)c1ccccc1] |
| 294 | 11792 | 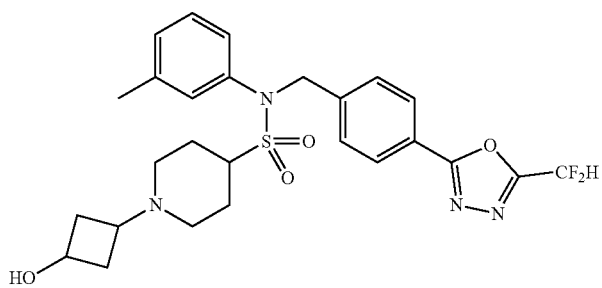 [SMILES: Cc1cccc(N(Cc2ccc(-c3nnc(C(F)F)o3)cc2)S(=O)(=O)C2CCN(C3CC(O)C3)CC2)c1] |
| 295 | 11793 | 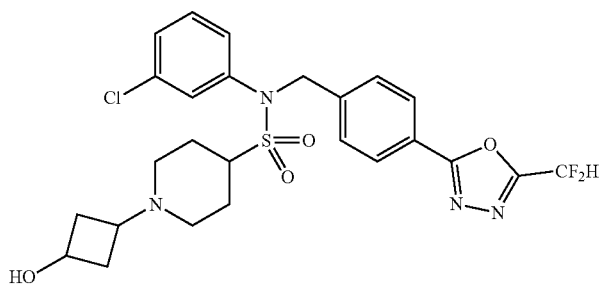 [SMILES: O=S(=O)(C1CCN(C2CC(O)C2)CC1)N(Cc1ccc(-c2nnc(C(F)F)o2)cc1)c1cccc(Cl)c1] |
| 296 | 11794 | 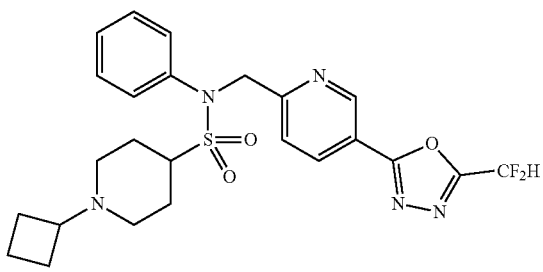 [SMILES: O=S(=O)(C1CCN(C2CCC2)CC1)N(Cc1ccc(-c2nnc(C(F)F)o2)cn1)c1ccccc1] |
| 297 | 11795 | 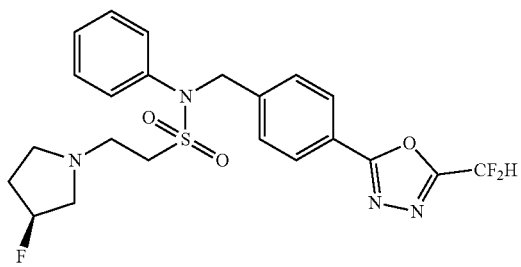 [SMILES: O=S(=O)(CCN1CC[C@H](F)C1)N(Cc1ccc(-c2nnc(C(F)F)o2)cc1)c1ccccc1] |

-continued

| Ex. | Comp. | Structure |
|---|---|---|
| 298 | 11796 | 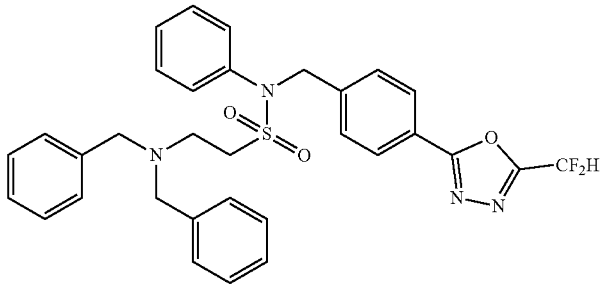 [SMILES: O=S(=O)(CCN(Cc1ccccc1)Cc1ccccc1)N(Cc1ccc(-c2nnc(C(F)F)o2)cc1)c1ccccc1] |
| 299 | 11797 | 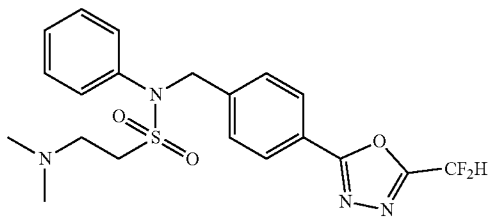 [SMILES: CN(C)CCS(=O)(=O)N(Cc1ccc(-c2nnc(C(F)F)o2)cc1)c1ccccc1] |
| 300 | 11798 | 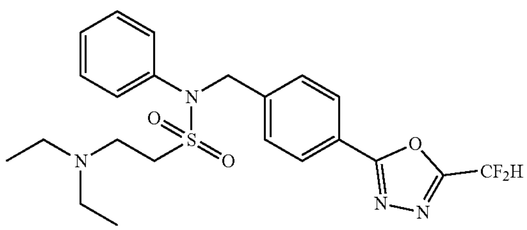 [SMILES: CCN(CC)CCS(=O)(=O)N(Cc1ccc(-c2nnc(C(F)F)o2)cc1)c1ccccc1] |
| 301 | 11799 | 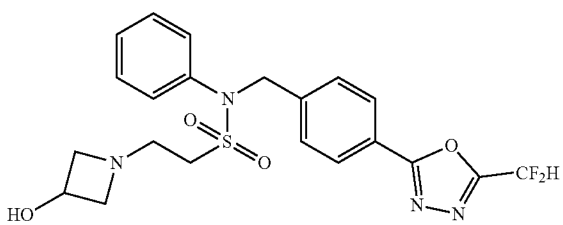 [SMILES: O=S(=O)(CCN1CC(O)C1)N(Cc1ccc(-c2nnc(C(F)F)o2)cc1)c1ccccc1] |
| 302 | 11800 | 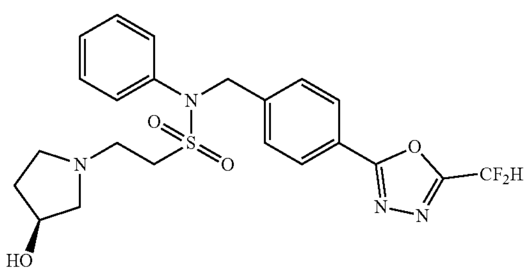 [SMILES: O=S(=O)(CCN1CC[C@H](O)C1)N(Cc1ccc(-c2nnc(C(F)F)o2)cc1)c1ccccc1] |
| 303 | 11801 | 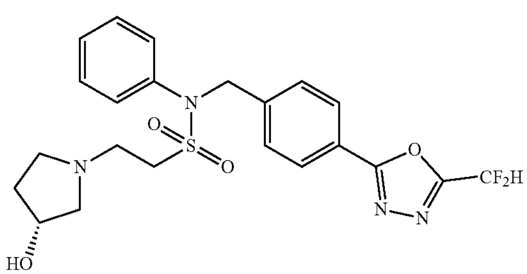 [SMILES: O=S(=O)(CCN1CC[C@@H](O)C1)N(Cc1ccc(-c2nnc(C(F)F)o2)cc1)c1ccccc1] |

-continued
| Ex. | Comp. | Structure |
|---|---|---|
| 304 | 11802 | 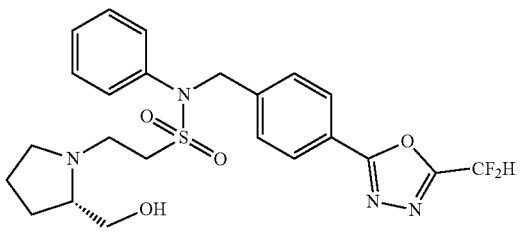 [SMILES: O=S(=O)(CCN1CCC[C@H]1CO)N(Cc1ccc(-c2nnc(C(F)F)o2)cc1)c1ccccc1] |
| 305 | 11803 | 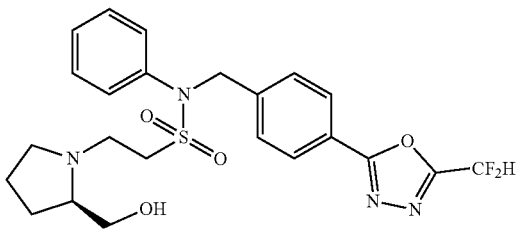 [SMILES: O=S(=O)(CCN1CCC[C@@H]1CO)N(Cc1ccc(-c2nnc(C(F)F)o2)cc1)c1ccccc1] |
| 306 | 11804 | 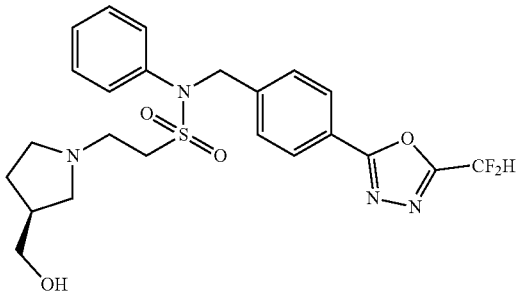 [SMILES: O=S(=O)(CCN1CC[C@H](CO)C1)N(Cc1ccc(-c2nnc(C(F)F)o2)cc1)c1ccccc1] |
| 307 | 11805 | 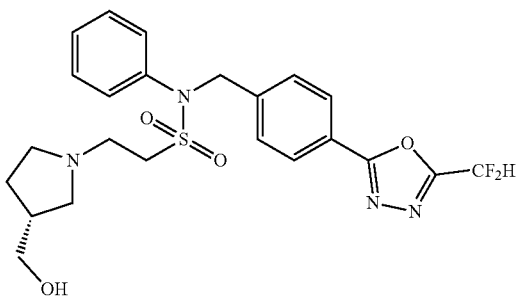 [SMILES: O=S(=O)(CCN1CC[C@@H](CO)C1)N(Cc1ccc(-c2nnc(C(F)F)o2)cc1)c1ccccc1] |
| 308 | 11806 | 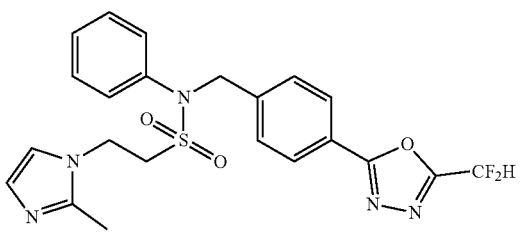 [SMILES: Cc1nccn1CCS(=O)(=O)N(Cc1ccc(-c2nnc(C(F)F)o2)cc1)c1ccccc1] |
| 309 | 11807 | 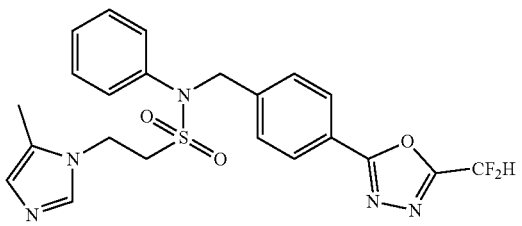 |

-continued
| Ex. | Comp. | Structure |
|---|---|---|
| 310 | 11808 | 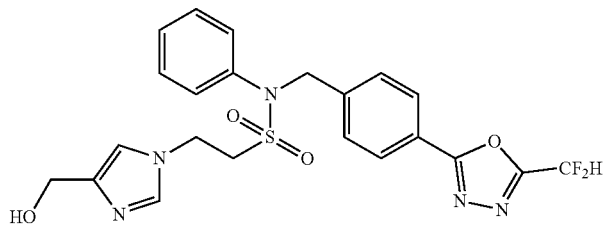 [SMILES: O=S(=O)(CCn1cnc(CO)c1)N(Cc1ccc(-c2nnc(C(F)F)o2)cc1)c1ccccc1] |
| 311 | 11809 | 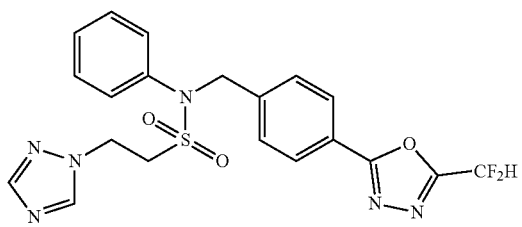 |
| 312 | 11810 | 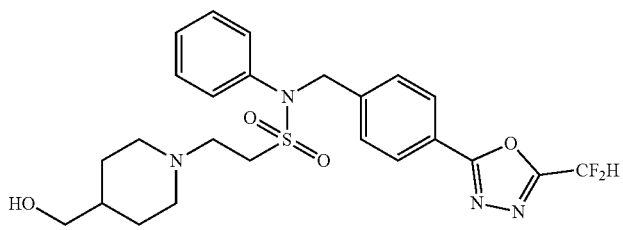 [SMILES: O=S(=O)(CCN1CCC(CO)CC1)N(Cc1ccc(-c2nnc(C(F)F)o2)cc1)c1ccccc1] |
| 313 | 11811 | 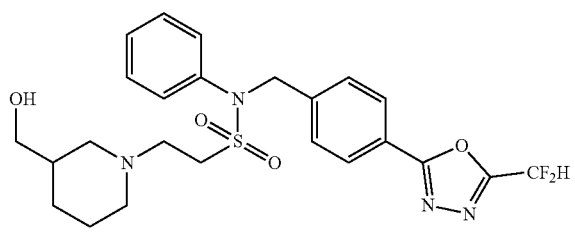 [SMILES: O=S(=O)(CCN1CCCC(CO)C1)N(Cc1ccc(-c2nnc(C(F)F)o2)cc1)c1ccccc1] |
| 314 | 11812 | 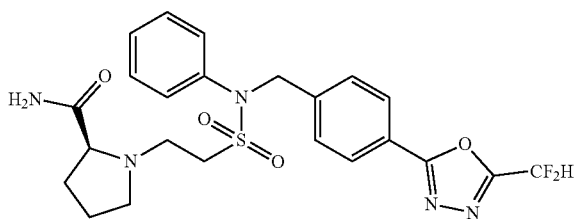 [SMILES: NC(=O)[C@@H]1CCCN1CCS(=O)(=O)N(Cc1ccc(-c2nnc(C(F)F)o2)cc1)c1ccccc1] |
| 315 | 11813 | 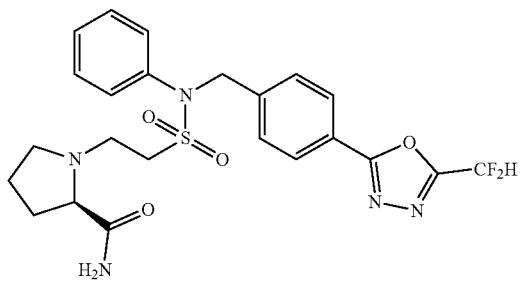 [SMILES: NC(=O)[C@H]1CCCN1CCS(=O)(=O)N(Cc1ccc(-c2nnc(C(F)F)o2)cc1)c1ccccc1] |

| Ex. | Comp. | Structure |
|---|---|---|
| 316 | 11814 | 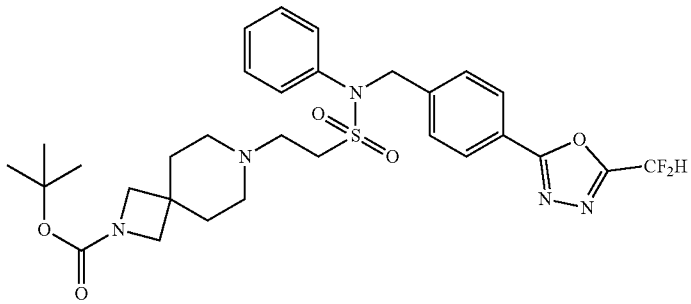 [SMILES: CC(C)(C)OC(=O)N1CC2(CCN(CCS(=O)(=O)N(Cc3ccc(-c4nnc(C(F)F)o4)cc3)c3ccccc3)CC2)C1] |
| 317 | 11815 | 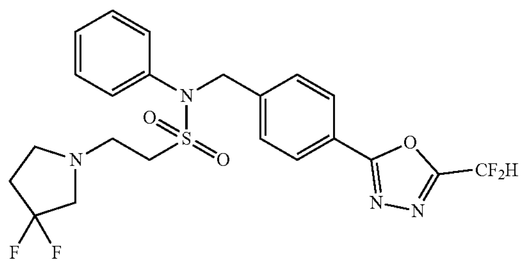 [SMILES: O=S(=O)(CCN1CCC(F)(F)C1)N(Cc1ccc(-c2nnc(C(F)F)o2)cc1)c1ccccc1] |
| 318 | 11816 | 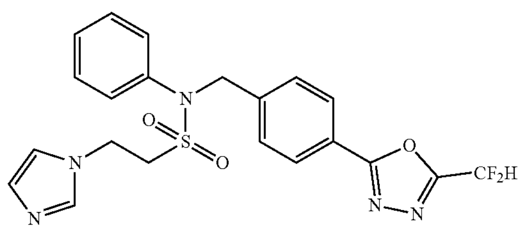 [SMILES: O=S(=O)(CCn1ccnc1)N(Cc1ccc(-c2nnc(C(F)F)o2)cc1)c1ccccc1] |
| 319 | 11817 | 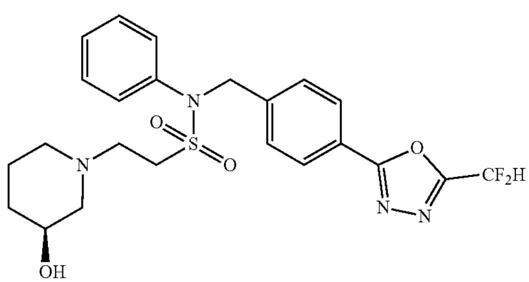 [SMILES: O=S(=O)(CCN1CCC[C@H](O)C1)N(Cc1ccc(-c2nnc(C(F)F)o2)cc1)c1ccccc1] |
| 320 | 11818 | 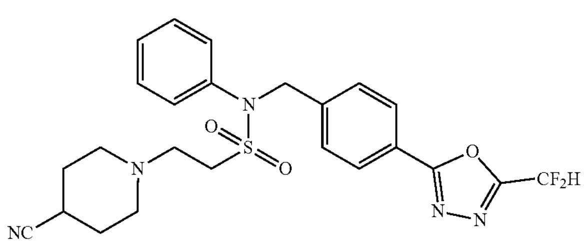 [SMILES: N#CC1CCN(CCS(=O)(=O)N(Cc2ccc(-c3nnc(C(F)F)o3)cc2)c2ccccc2)CC1] |

-continued
| Ex. | Comp. | Structure |
|---|---|---|
| 321 | 11819 | 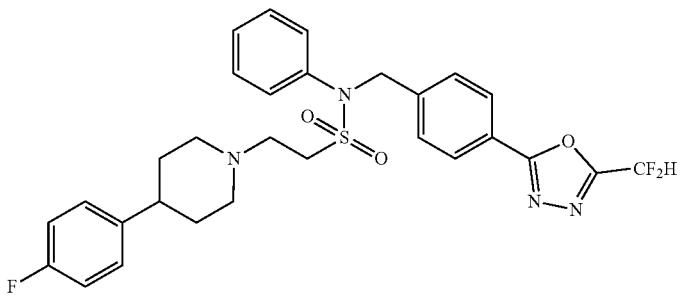 [SMILES: O=S(=O)(CCN1CCC(c2ccc(F)cc2)CC1)N(Cc1ccc(-c2nnc(C(F)F)o2)cc1)c1ccccc1] |
| 322 | 11820 | 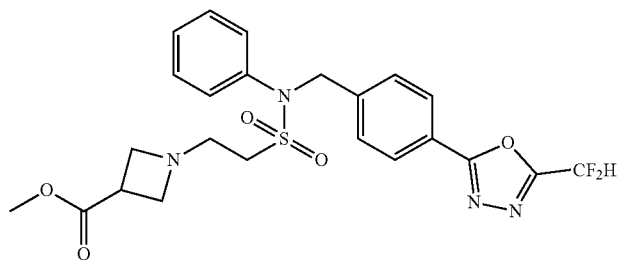 [SMILES: COC(=O)C1CN(CCS(=O)(=O)N(Cc2ccc(-c3nnc(C(F)F)o3)cc2)c2ccccc2)C1] |
| 323 | 11821 | 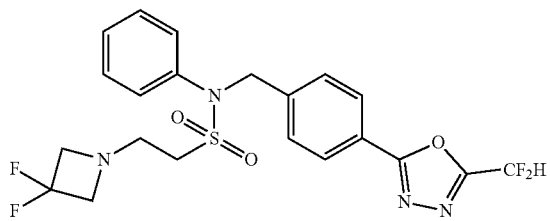 [SMILES: O=S(=O)(CCN1CC(F)(F)C1)N(Cc1ccc(-c2nnc(C(F)F)o2)cc1)c1ccccc1] |
| 324 | 11822 | 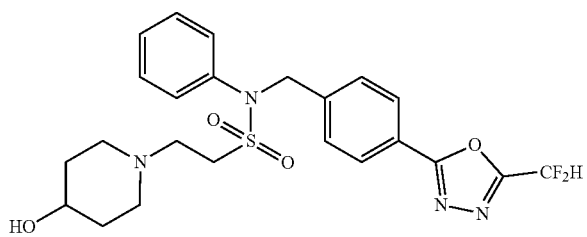 |
| 325 | 11836 | 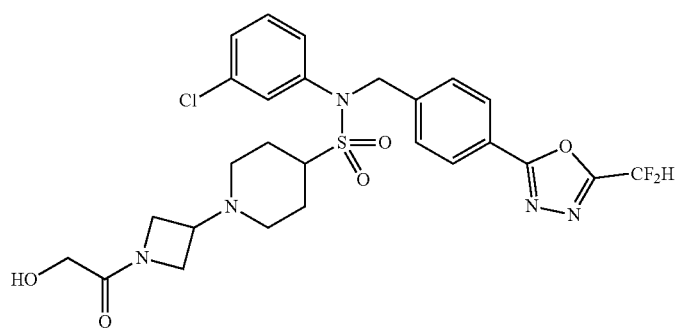 [SMILES: O=C(CO)N1CC(N2CCC(S(=O)(=O)N(Cc3ccc(-c4nnc(C(F)F)o4)cc3)c3cccc(Cl)c3)CC2)C1] |

-continued

| Ex. | Comp. | Structure |
|---|---|---|
| 326 | 11837 | 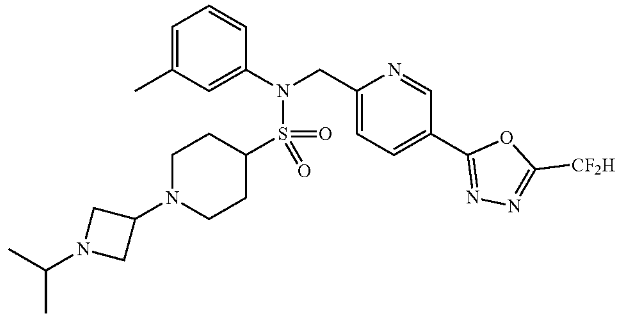 [SMILES: Cc1cccc(N(Cc2ccc(-c3nnc(C(F)F)o3)cn2)S(=O)(=O)C2CCN(C3CN(C(C)C)C3)CC2)c1] |
| 327 | 11838 | 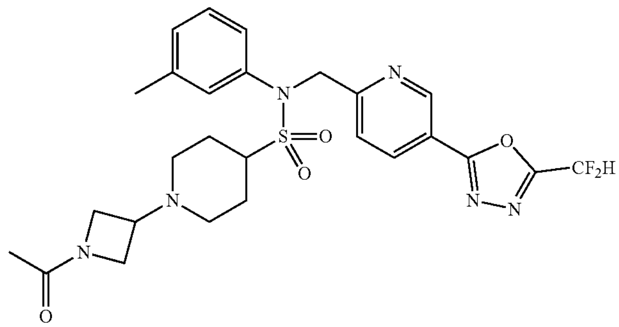 [SMILES: CC(=O)N1CC(N2CCC(S(=O)(=O)N(Cc3ccc(-c4nnc(C(F)F)o4)cn3)c3cccc(C)c3)CC2)C1] |
| 328 | 11839 | 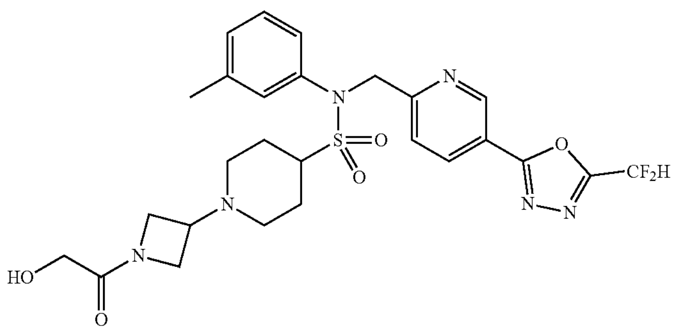 [SMILES: Cc1cccc(N(Cc2ccc(-c3nnc(C(F)F)o3)cn2)S(=O)(=O)C2CCN(C3CN(C(=O)CO)C3)CC2)c1] |
| 329 | 11840 | 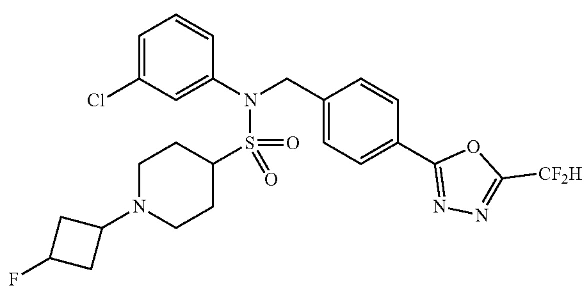 [SMILES: O=S(=O)(C1CCN(C2CC(F)C2)CC1)N(Cc1ccc(-c2nnc(C(F)F)o2)cc1)c1cccc(Cl)c1] |
| 330 | 11841 | 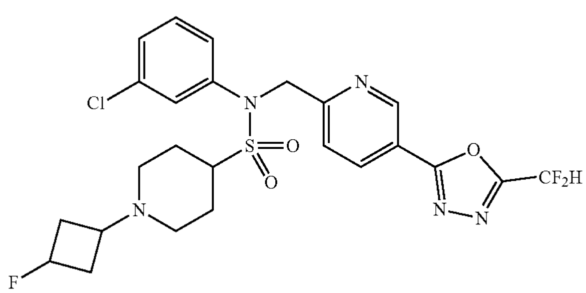 [SMILES: O=S(=O)(C1CCN(C2CC(F)C2)CC1)N(Cc1ccc(-c2nnc(C(F)F)o2)cn1)c1cccc(Cl)c1] |

| Ex. | Comp. | Structure |
|---|---|---|
| 331 | 11842 | 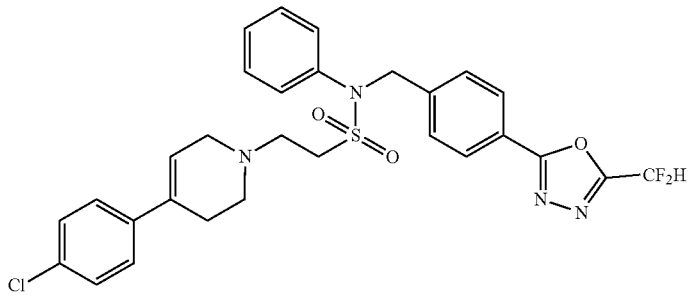 [SMILES: O=S(=O)(CCN1CC=C(c2ccc(Cl)cc2)CC1)N(Cc1ccc(-c2nnc(C(F)F)o2)cc1)c1ccccc1] |
| 332 | 11843 | 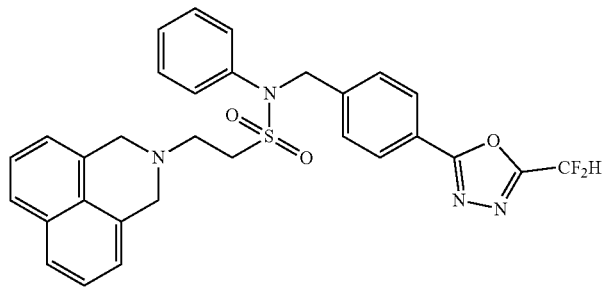 [SMILES: O=S(=O)(CCN1Cc2cccc3cccc(c23)C1)N(Cc1ccc(-c2nnc(C(F)F)o2)cc1)c1ccccc1] |
| 333 | 11844 | 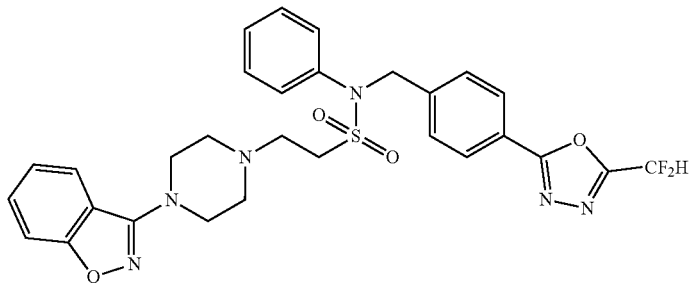 [SMILES: O=S(=O)(CCN1CCN(c2noc3ccccc23)CC1)N(Cc1ccc(-c2nnc(C(F)F)o2)cc1)c1ccccc1] |
| 334 | 11845 | 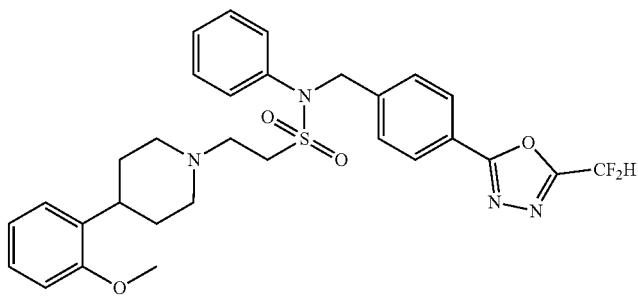 [SMILES: COc1ccccc1C1CCN(CCS(=O)(=O)N(Cc2ccc(-c3nnc(C(F)F)o3)cc2)c2ccccc2)CC1] |
| 335 | 11847 | 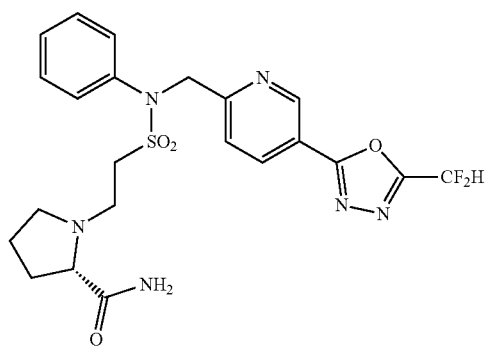 [SMILES: NC(=O)[C@@H]1CCCN1CCS(=O)(=O)N(Cc1ccc(-c2nnc(C(F)F)o2)cn1)c1ccccc1] |

| Ex. | Comp. | Structure |
|---|---|---|
| 336 | 11848 | 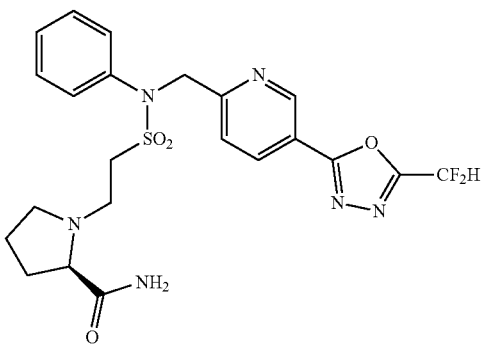 [SMILES: NC(=O)[C@H]1CCCN1CCS(=O)(=O)N(Cc1ccc(-c2nnc(C(F)F)o2)cn1)c1ccccc1] |
| 337 | 11849 | 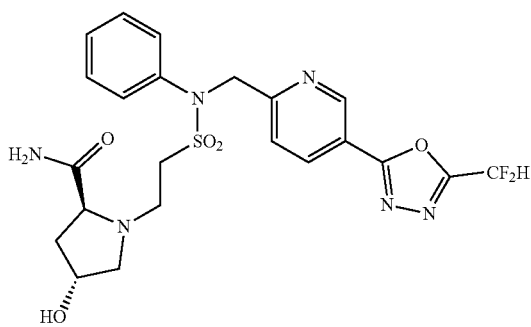 [SMILES: NC(=O)[C@@H]1C[C@@H](O)CN1CCS(=O)(=O)N(Cc1ccc(-c2nnc(C(F)F)o2)cn1)c1ccccc1] |
6. The 1,3,4-oxadiazole sulfonamide derivative compound represented by formula I, stereoisomer thereof or pharmaceutically acceptable salt thereof according to claim 5, wherein the compound represented by formula I is selected from the group consisting of compounds described in the following table:
| Ex. | Comp. | Structure |
|---|---|---|
| 14 | 11154 | 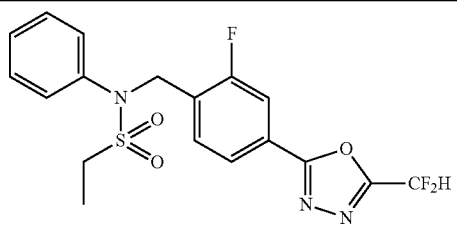 |
| 16 | 11156 | 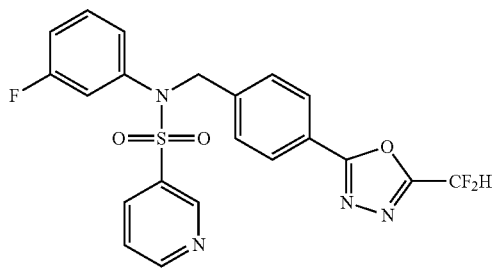 [SMILES: O=S(=O)(c1cccnc1)N(Cc1ccc(-c2nnc(C(F)F)o2)cc1)c1cccc(F)c1] |
| 18 | 11168 | 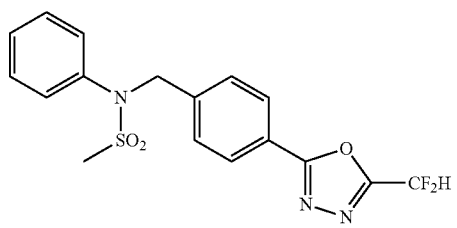 |

| Ex. | Comp. | Structure |
|---|---|---|
| 20 | 11170 | 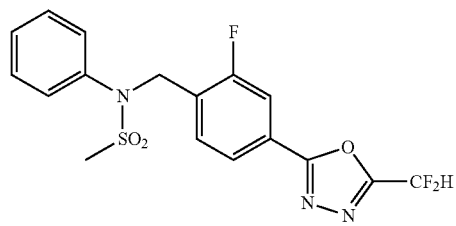 [SMILES: CS(=O)(=O)N(Cc1ccc(-c2nnc(C(F)F)o2)cc1F)c1ccccc1] |
| 21 | 11171 | 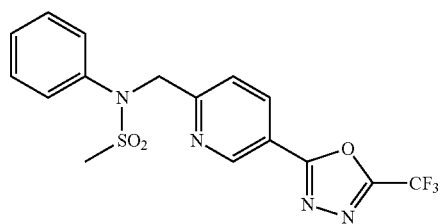 [SMILES: CS(=O)(=O)N(Cc1ccc(-c2nnc(C(F)(F)F)o2)cn1)c1ccccc1] |
| 22 | 11172 | 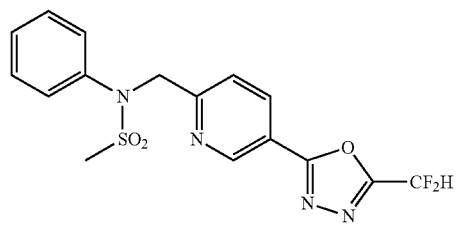 [SMILES: CS(=O)(=O)N(Cc1ccc(-c2nnc(C(F)F)o2)cn1)c1ccccc1] |
| 26 | 11176 | 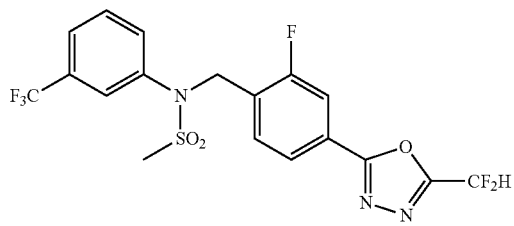 [SMILES: CS(=O)(=O)N(Cc1ccc(-c2nnc(C(F)F)o2)cc1F)c1cccc(C(F)(F)F)c1] |
| 28 | 11178 | 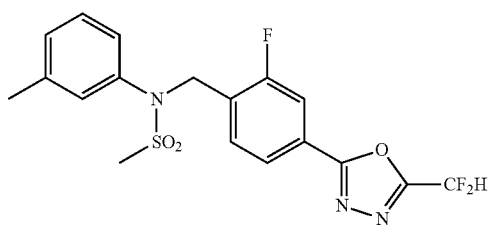 [SMILES: Cc1cccc(N(Cc2ccc(-c3nnc(C(F)F)o3)cc2F)S(C)(=O)=O)c1] |
| 32 | 11182 | 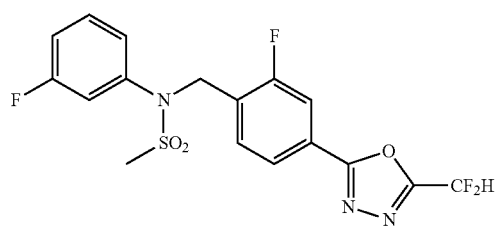 [SMILES: CS(=O)(=O)N(Cc1ccc(-c2nnc(C(F)F)o2)cc1F)c1cccc(F)c1] |

-continued
| Ex. | Comp. | Structure |
|---|---|---|
| 37 | 11191 | 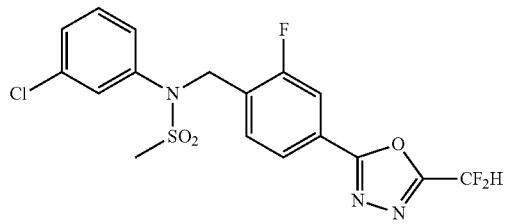 [SMILES: CS(=O)(=O)N(Cc1ccc(-c2nnc(C(F)F)o2)cc1F)c1cccc(Cl)c1] |
| 39 | 11193 | 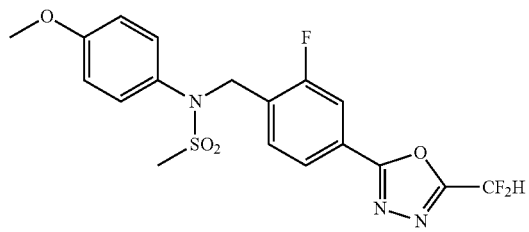 [SMILES: COc1ccc(N(Cc2ccc(-c3nnc(C(F)F)o3)cc2F)S(C)(=O)=O)cc1] |
| 43 | 11197 | 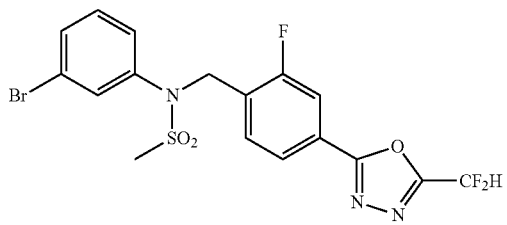 |
| 45 | 11217 | 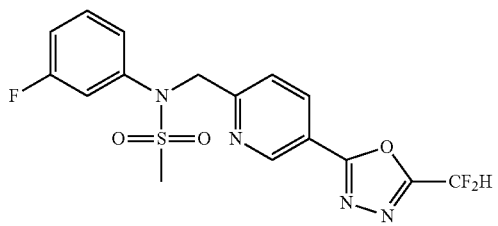 [SMILES: CS(=O)(=O)N(Cc1ccc(-c2nnc(C(F)F)o2)cn1)c1cccc(F)c1] |
| 51 | 11225 | 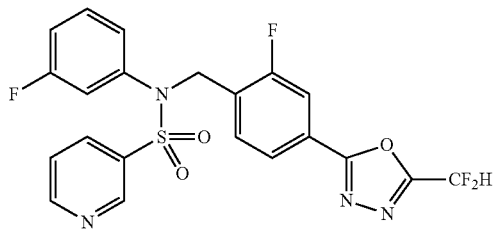 [SMILES: O=S(=O)(c1cccnc1)N(Cc1ccc(-c2nnc(C(F)F)o2)cc1F)c1cccc(F)c1] |
| 53 | 11227 | 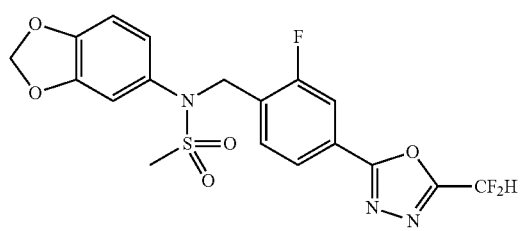 [SMILES: CS(=O)(=O)N(Cc1ccc(-c2nnc(C(F)F)o2)cc1F)c1ccc2c(c1)OCO2] |

-continued
| Ex. | Comp. | Structure |
|---|---|---|
| 56 | 11231 | 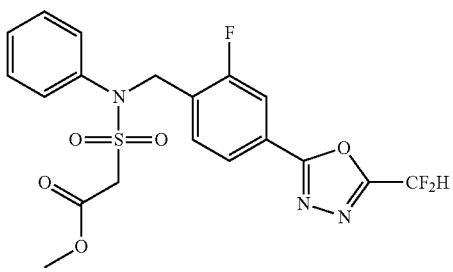 [SMILES: COC(=O)CS(=O)(=O)N(Cc1ccc(-c2nnc(C(F)F)o2)cc1F)c1ccccc1] |
| 63 | 11254 | 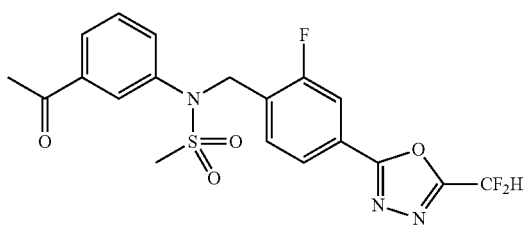 [SMILES: CC(=O)c1cccc(N(Cc2ccc(-c3nnc(C(F)F)o3)cc2F)S(C)(=O)=O)c1] |
| 65 | 11256 | 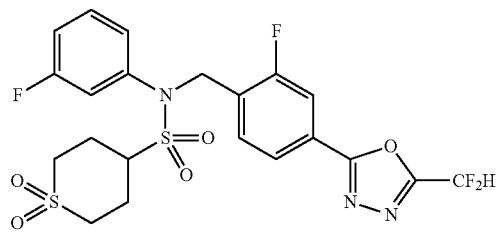 [SMILES: O=S1(=O)CCC(S(=O)(=O)N(Cc2ccc(-c3nnc(C(F)F)o3)cc2F)c2cccc(F)c2)CC1] |
| 71 | 11276 | 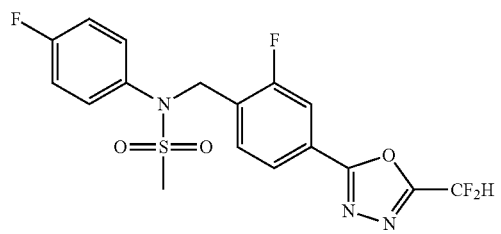 [SMILES: CS(=O)(=O)N(Cc1ccc(-c2nnc(C(F)F)o2)cc1F)c1ccc(F)cc1] |
| 79 | 11284 | 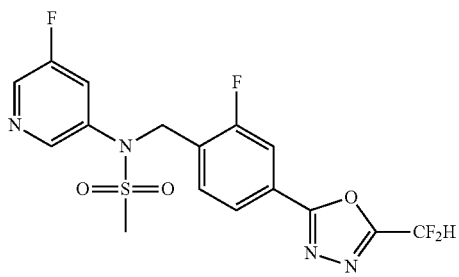 [SMILES: CS(=O)(=O)N(Cc1ccc(-c2nnc(C(F)F)o2)cc1F)c1cncc(F)c1] |
| 80 | 11287 | 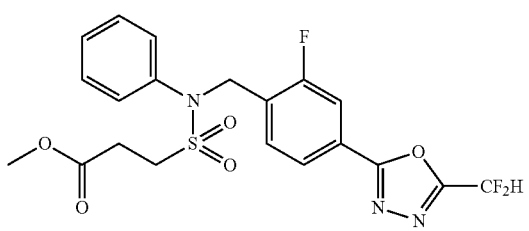 [SMILES: COC(=O)CCS(=O)(=O)N(Cc1ccc(-c2nnc(C(F)F)o2)cc1F)c1ccccc1] |

-continued
| Ex. | Comp. | Structure |
|---|---|---|
| 82 | 11289 | 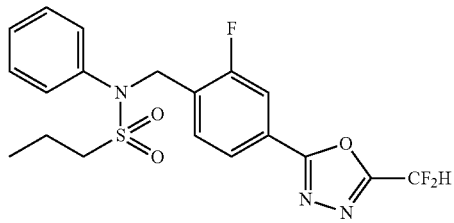 [SMILES: CCCS(=O)(=O)N(Cc1ccc(-c2nnc(C(F)F)o2)cc1F)c1ccccc1] |
| 87 | 11324 | 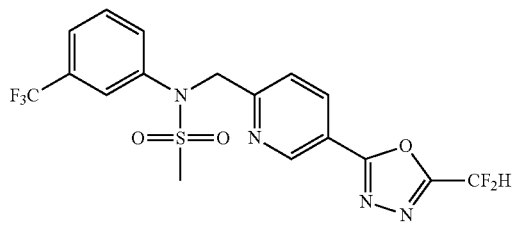 [SMILES: CS(=O)(=O)N(Cc1ccc(-c2nnc(C(F)F)o2)cn1)c1cccc(C(F)(F)F)c1] |
| 89 | 11345 | 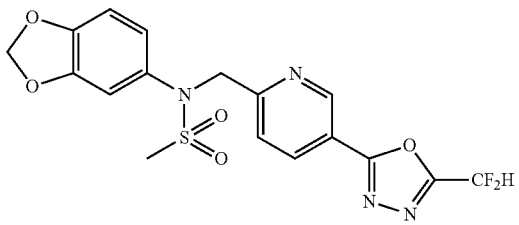 [SMILES: CS(=O)(=O)N(Cc1ccc(-c2nnc(C(F)F)o2)cn1)c1ccc2c(c1)OCO2] |
| 90 | 11346 | 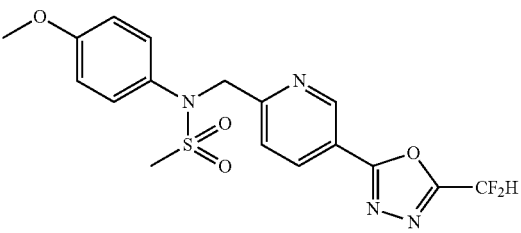 [SMILES: COc1ccc(N(Cc2ccc(-c3nnc(C(F)F)o3)cn2)S(C)(=O)=O)cc1] |
| 93 | 11350 | 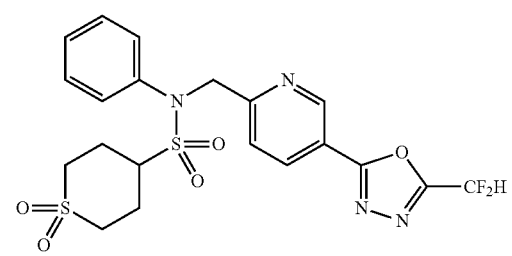 [SMILES: O=S1(=O)CCC(S(=O)(=O)N(Cc2ccc(-c3nnc(C(F)F)o3)cn2)c2ccccc2)CC1] |
| 95 | 11352 | 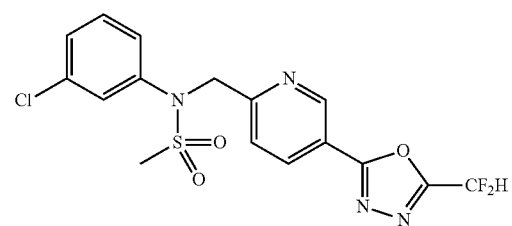 [SMILES: CS(=O)(=O)N(Cc1ccc(-c2nnc(C(F)F)o2)cn1)c1cccc(Cl)c1] |

-continued

| Ex. | Comp. | Structure |
|---|---|---|
| 96 | 11353 | 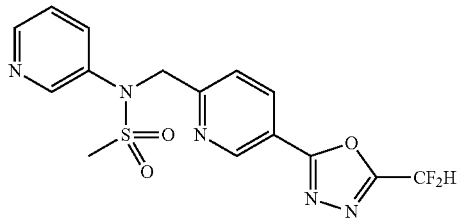 [SMILES: CS(=O)(=O)N(Cc1ccc(-c2nnc(C(F)F)o2)cn1)c1cccnc1] |
| 97 | 11354 | 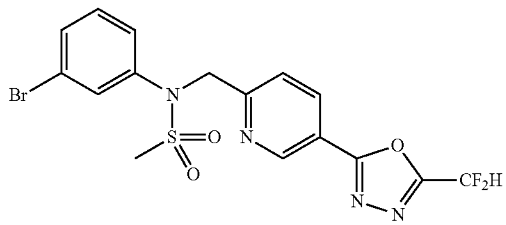 [SMILES: CS(=O)(=O)N(Cc1ccc(-c2nnc(C(F)F)o2)cn1)c1cccc(Br)c1] |
| 98 | 11355 | 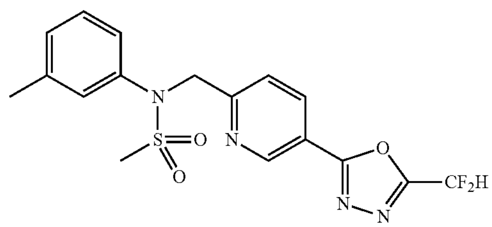 [SMILES: Cc1cccc(N(Cc2ccc(-c3nnc(C(F)F)o3)cn2)S(C)(=O)=O)c1] |
| 99 | 11366 | 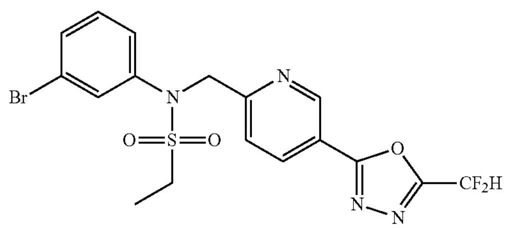 [SMILES: CCS(=O)(=O)N(Cc1ccc(-c2nnc(C(F)F)o2)cn1)c1cccc(Br)c1] |
| 100 | 11367 | 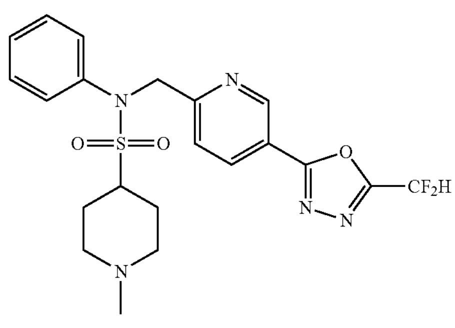 [SMILES: CN1CCC(S(=O)(=O)N(Cc2ccc(-c3nnc(C(F)F)o3)cn2)c2ccccc2)CC1] |
| 101 | 11368 | 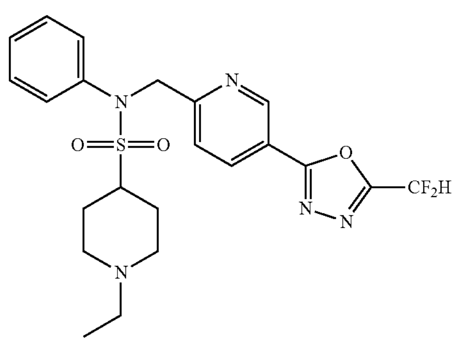 [SMILES: CCN1CCC(S(=O)(=O)N(Cc2ccc(-c3nnc(C(F)F)o3)cn2)c2ccccc2)CC1] |

-continued
| Ex. | Comp. | Structure |
|---|---|---|
| 102 | 11372 | 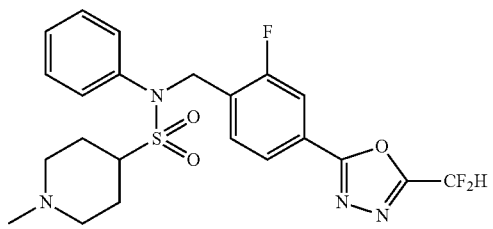 [SMILES: CN1CCC(S(=O)(=O)N(Cc2ccc(-c3nnc(C(F)F)o3)cc2F)c2ccccc2)CC1] |
| 103 | 11373 | 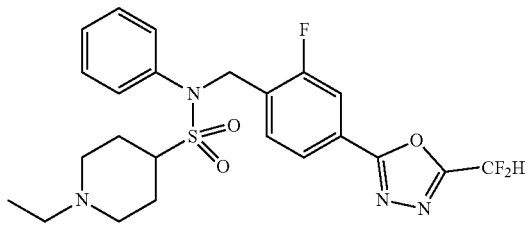 [SMILES: CCN1CCC(S(=O)(=O)N(Cc2ccc(-c3nnc(C(F)F)o3)cc2F)c2ccccc2)CC1] |
| 104 | 11377 | 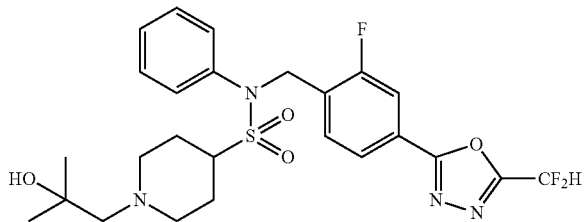 [SMILES: CC(C)(O)CN1CCC(S(=O)(=O)N(Cc2ccc(-c3nnc(C(F)F)o3)cc2F)c2ccccc2)CC1] |
| 109 | 11390 | 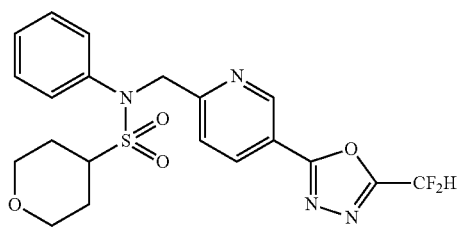 [SMILES: O=S(=O)(C1CCOCC1)N(Cc1ccc(-c2nnc(C(F)F)o2)cn1)c1ccccc1] |
| 116 | 11411 | 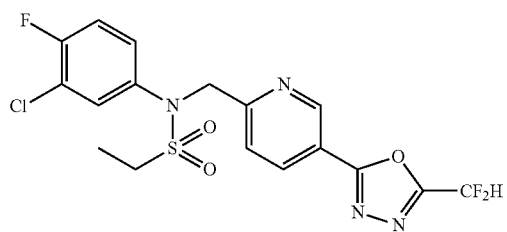 |
| 117 | 11412 | 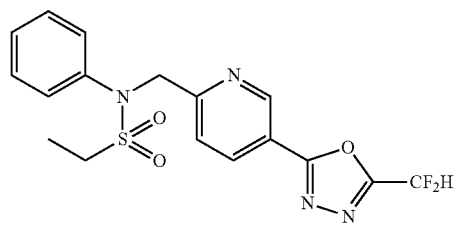 [SMILES: CCS(=O)(=O)N(Cc1ccc(-c2nnc(C(F)F)o2)cn1)c1ccccc1] |

-continued

| Ex. | Comp. | Structure |
|---|---|---|
| 118 | 11426 | 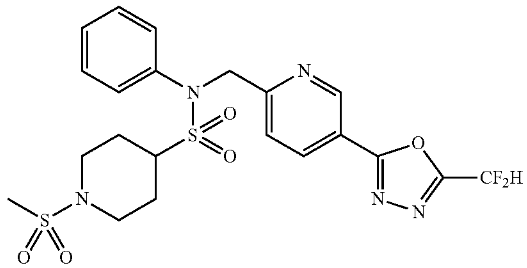 [SMILES: CS(=O)(=O)N1CCC(S(=O)(=O)N(Cc2ccc(-c3nnc(C(F)F)o3)cn2)c2ccccc2)CC1] |
| 120 | 11428 | 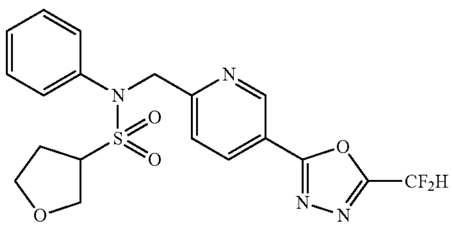 [SMILES: O=S(=O)(C1CCOC1)N(Cc1ccc(-c2nnc(C(F)F)o2)cn1)c1ccccc1] |
| 125 | 11433 | 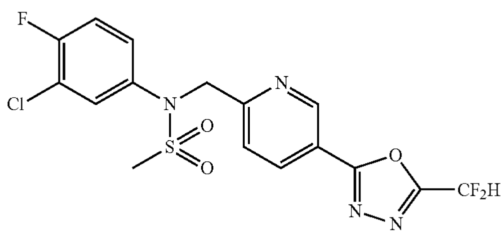 [SMILES: CS(=O)(=O)N(Cc1ccc(-c2nnc(C(F)F)o2)cn1)c1ccc(F)c(Cl)c1] |
| 126 | 11447 | 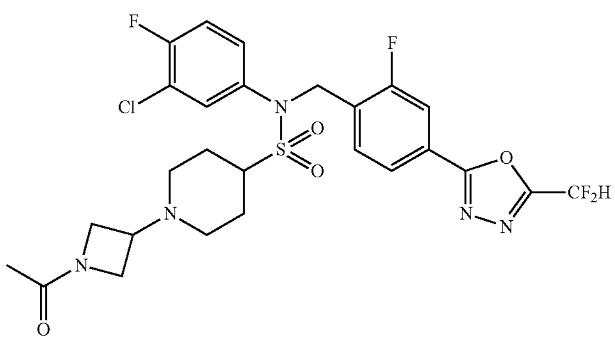 [SMILES: CC(=O)N1CC(N2CCC(S(=O)(=O)N(Cc3ccc(-c4nnc(C(F)F)o4)cc3F)c3ccc(F)c(Cl)c3)CC2)C1] |
| 127 | 11448 | 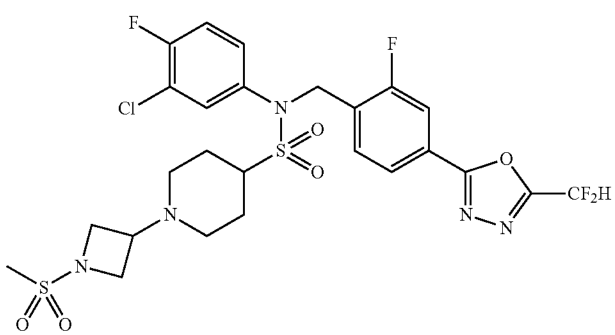 [SMILES: CS(=O)(=O)N1CC(N2CCC(S(=O)(=O)N(Cc3ccc(-c4nnc(C(F)F)o4)cc3F)c3ccc(F)c(Cl)c3)CC2)C1] |

-continued

| Ex. | Comp. | Structure |
|---|---|---|
| 128 | 11451 | 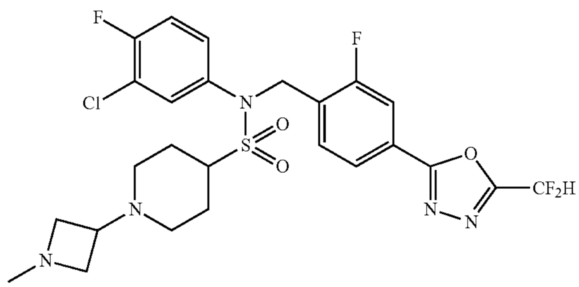 [SMILES: CN1CC(N2CCC(S(=O)(=O)N(Cc3ccc(-c4nnc(C(F)F)o4)cc3F)c3ccc(F)c(Cl)c3)CC2)C1] |
| 129 | 11452 | 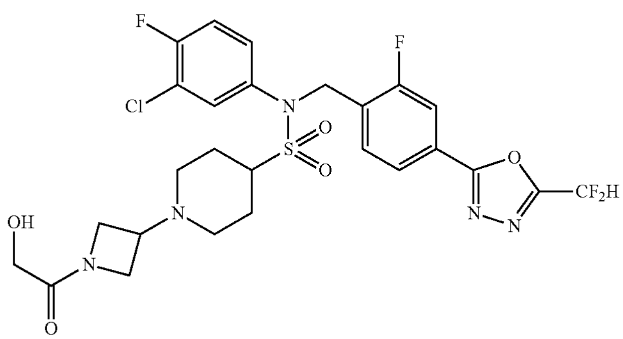 [SMILES: O=C(CO)N1CC(N2CCC(S(=O)(=O)N(Cc3ccc(-c4nnc(C(F)F)o4)cc3F)c3ccc(F)c(Cl)c3)CC2)C1] |
| 130 | 11460 | 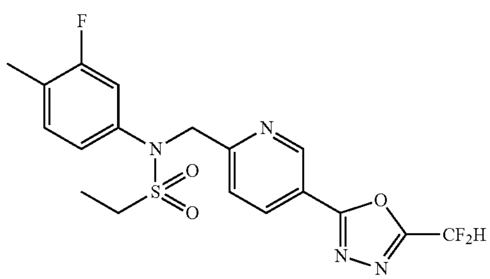 [SMILES: CCS(=O)(=O)N(Cc1ccc(-c2nnc(C(F)F)o2)cn1)c1ccc(C)c(F)c1] |
| 131 | 11461 | 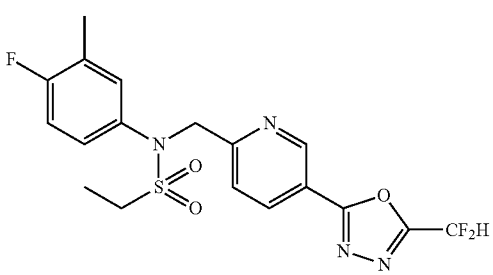 [SMILES: CCS(=O)(=O)N(Cc1ccc(-c2nnc(C(F)F)o2)cn1)c1ccc(F)c(C)c1] |
| 132 | 11462 | 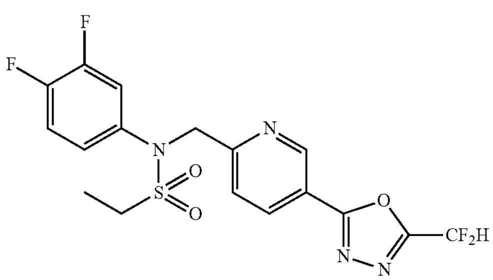 [SMILES: CCS(=O)(=O)N(Cc1ccc(-c2nnc(C(F)F)o2)cn1)c1ccc(F)c(F)c1] |

| Ex. | Comp. | Structure |
|---|---|---|
| 133 | 11463 | 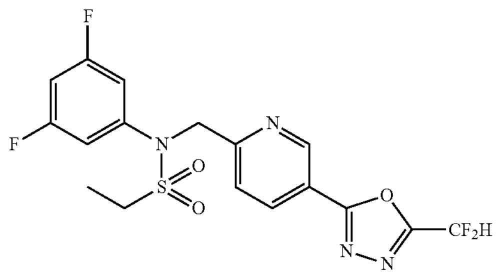 [SMILES: CCS(=O)(=O)N(Cc1ccc(-c2nnc(C(F)F)o2)cn1)c1cc(F)cc(F)c1] |
| 134 | 11497 | 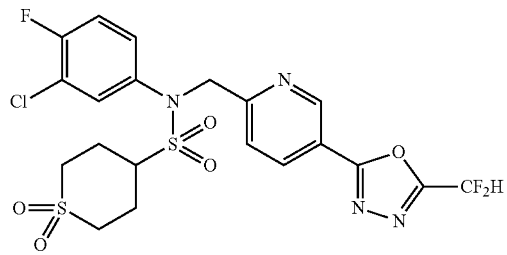 [SMILES: O=S1(=O)CCC(S(=O)(=O)N(Cc2ccc(-c3nnc(C(F)F)o3)cn2)c2ccc(F)c(Cl)c2)CC1] |
| 135 | 11501 | 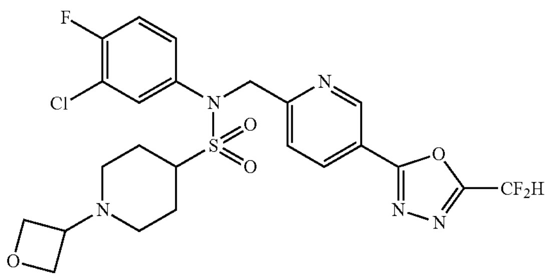 [SMILES: O=S(=O)(C1CCN(C2COC2)CC1)N(Cc1ccc(-c2nnc(C(F)F)o2)cn1)c1ccc(F)c(Cl)c1] |
| 136 | 11502 | 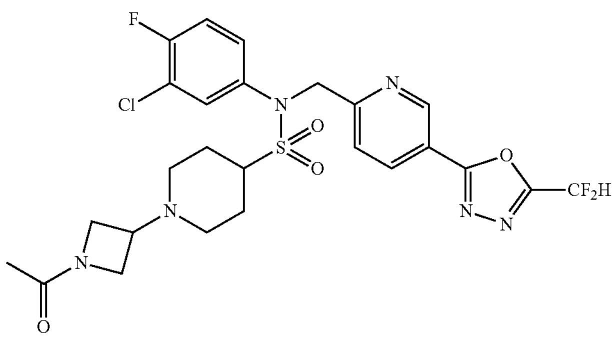 [SMILES: CC(=O)N1CC(N2CCC(S(=O)(=O)N(Cc3ccc(-c4nnc(C(F)F)o4)cn3)c3ccc(F)c(Cl)c3)CC2)C1] |
| 137 | 11503 | 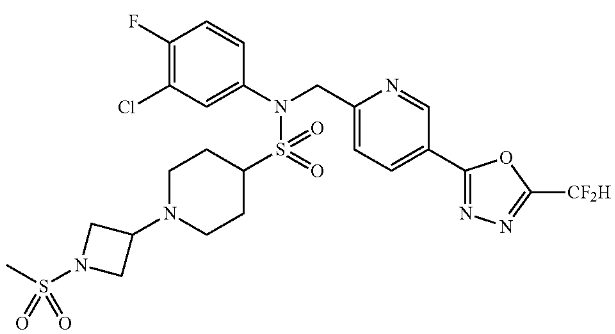 [SMILES: CS(=O)(=O)N1CC(N2CCC(S(=O)(=O)N(Cc3ccc(-c4nnc(C(F)F)o4)cn3)c3ccc(F)c(Cl)c3)CC2)C1] |

-continued

| Ex. | Comp. | Structure |
|---|---|---|
| 138 | 11504 | 4-chloro-3-methylphenyl-N-[(5-(5-(difluoromethyl)-1,3,4-oxadiazol-2-yl)pyridin-2-yl)methyl]ethanesulfonamide |
| 139 | 11505 | 3-chloro-4-methylphenyl-N-[(5-(5-(difluoromethyl)-1,3,4-oxadiazol-2-yl)pyridin-2-yl)methyl]ethanesulfonamide |
| 140 | 11506 | 3,5-dichlorophenyl-N-[(5-(5-(difluoromethyl)-1,3,4-oxadiazol-2-yl)pyridin-2-yl)methyl]ethanesulfonamide |
| 141 | 11507 | 3,4-dichlorophenyl-N-[(5-(5-(difluoromethyl)-1,3,4-oxadiazol-2-yl)pyridin-2-yl)methyl]ethanesulfonamide |
| 142 | 11508 | 3-chloro-5-methylphenyl-N-[(5-(5-(difluoromethyl)-1,3,4-oxadiazol-2-yl)pyridin-2-yl)methyl]ethanesulfonamide |
| 146 | 11521 | N-(1-methyl-1H-indazol-6-yl)-N-[(4-(5-(difluoromethyl)-1,3,4-oxadiazol-2-yl)-2-fluorophenyl)methyl]ethanesulfonamide |

| Ex. | Comp. | Structure |
|---|---|---|
| 147 | 11522 | (1-methyl-1H-indazol-7-yl)-N-(2-fluoro-4-(5-(difluoromethyl)-1,3,4-oxadiazol-2-yl)benzyl)ethanesulfonamide |
| 148 | 11539 | (1-methyl-1H-indazol-4-yl)-N-((5-(5-(difluoromethyl)-1,3,4-oxadiazol-2-yl)pyridin-2-yl)methyl)ethanesulfonamide |
| 149 | 11540 | (1-methyl-1H-indazol-6-yl)-N-((5-(5-(difluoromethyl)-1,3,4-oxadiazol-2-yl)pyridin-2-yl)methyl)ethanesulfonamide |
| 150 | 11541 | (1-methyl-1H-indazol-7-yl)-N-((5-(5-(difluoromethyl)-1,3,4-oxadiazol-2-yl)pyridin-2-yl)methyl)ethanesulfonamide |
| 151 | 11552 | N-(3-chloro-4-fluorophenyl)-N-(2-fluoro-4-(5-(difluoromethyl)-1,3,4-oxadiazol-2-yl)benzyl)-2-(4-methylpiperazin-1-yl)ethanesulfonamide |

| Ex. | Comp. | Structure |
|---|---|---|
| 152 | 11553 | 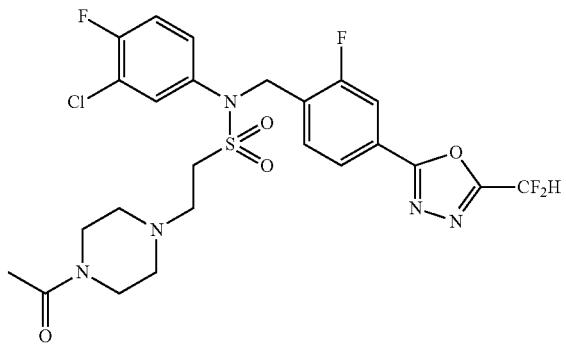 [SMILES: CC(=O)N1CCN(CCS(=O)(=O)N(Cc2ccc(-c3nnc(C(F)F)o3)cc2F)c2ccc(F)c(Cl)c2)CC1] |
| 153 | 11554 | 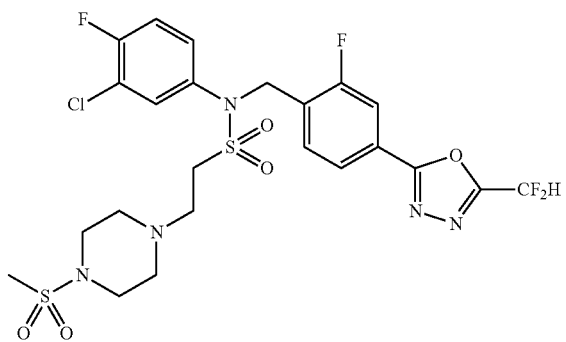 [SMILES: CS(=O)(=O)N1CCN(CCS(=O)(=O)N(Cc2ccc(-c3nnc(C(F)F)o3)cc2F)c2ccc(F)c(Cl)c2)CC1] |
| 154 | 11564 | 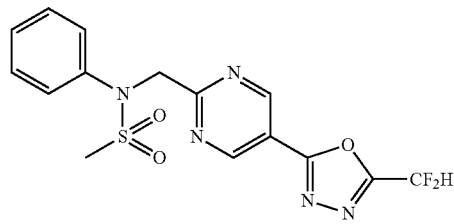 [SMILES: CS(=O)(=O)N(Cc1ncc(-c2nnc(C(F)F)o2)cn1)c1ccccc1] |
| 159 | 11582 | 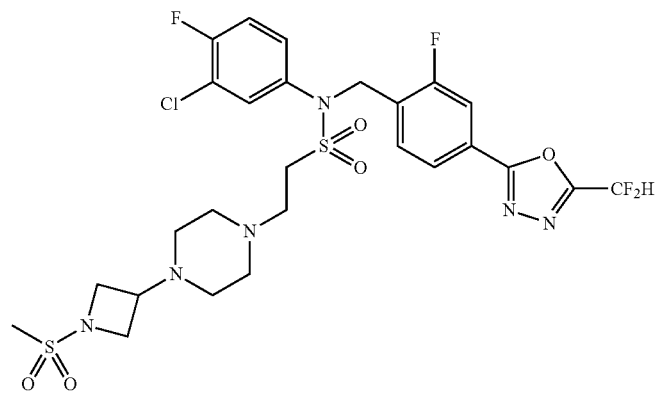 [SMILES: CS(=O)(=O)N1CC(N2CCN(CCS(=O)(=O)N(Cc3ccc(-c4nnc(C(F)F)o4)cc3F)c3ccc(F)c(Cl)c3)CC2)C1] |

| Ex. | Comp. | Structure |
|---|---|---|
| 160 | 11583 | 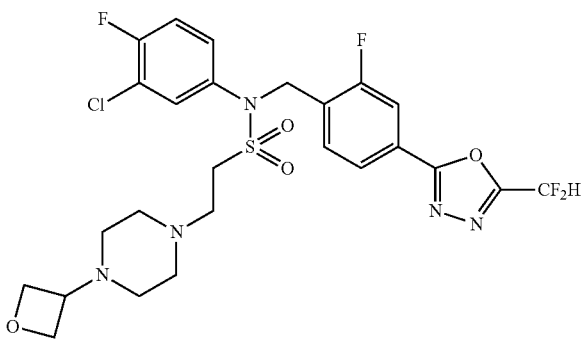 [SMILES: O=S(=O)(CCN1CCN(C2COC2)CC1)N(Cc1ccc(-c2nnc(C(F)F)o2)cc1F)c1ccc(F)c(Cl)c1] |
| 174 | 11637 | 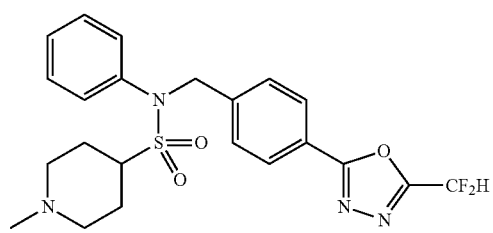 [SMILES: CN1CCC(S(=O)(=O)N(Cc2ccc(-c3nnc(C(F)F)o3)cc2)c2ccccc2)CC1] |
| 175 | 11638 | 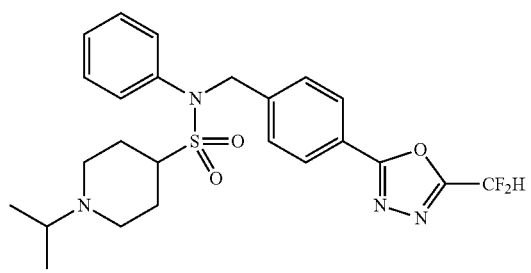 [SMILES: CC(C)N1CCC(S(=O)(=O)N(Cc2ccc(-c3nnc(C(F)F)o3)cc2)c2ccccc2)CC1] |
| 178 | 11646 | 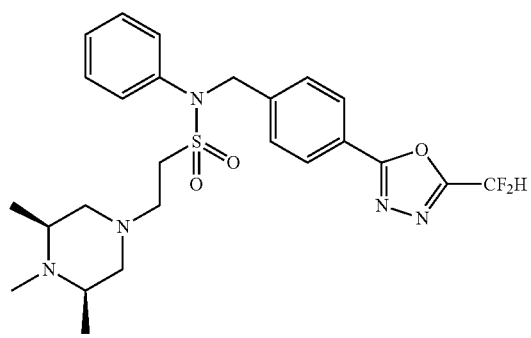 [SMILES: C[C@@H]1CN(CCS(=O)(=O)N(Cc2ccc(-c3nnc(C(F)F)o3)cc2)c2ccccc2)C[C@H](C)N1C] |
| 179 | 11647 | 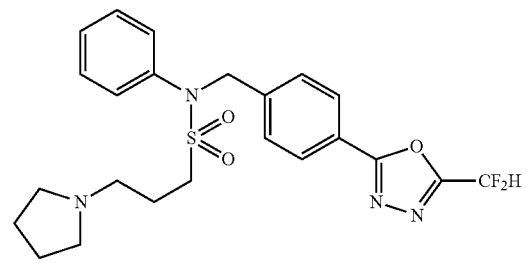 [SMILES: O=S(=O)(CCCN1CCCC1)N(Cc1ccc(-c2nnc(C(F)F)o2)cc1)c1ccccc1] |

| Ex. | Comp. | Structure |
|---|---|---|
| 186 | 11665 | 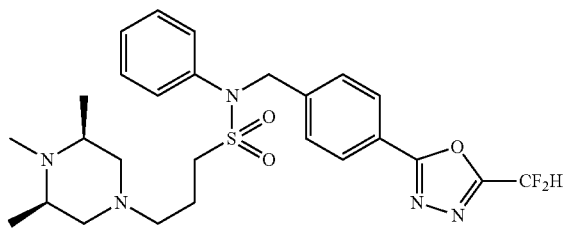 [SMILES: C[C@@H]1CN(CCCS(=O)(=O)N(Cc2ccc(-c3nnc(C(F)F)o3)cc2)c2ccccc2)C[C@H](C)N1C] |
| 193 | 11679 | 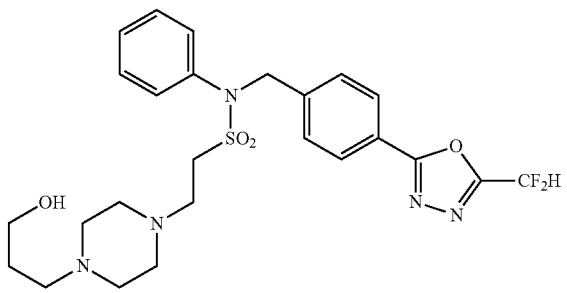 [SMILES: O=S(=O)(CCN1CCN(CCCO)CC1)N(Cc1ccc(-c2nnc(C(F)F)o2)cc1)c1ccccc1] |
| 194 | 11680 | 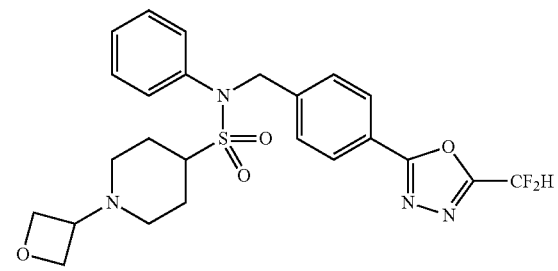 [SMILES: O=S(=O)(C1CCN(C2COC2)CC1)N(Cc1ccc(-c2nnc(C(F)F)o2)cc1)c1ccccc1] |
| 195 | 11681 | 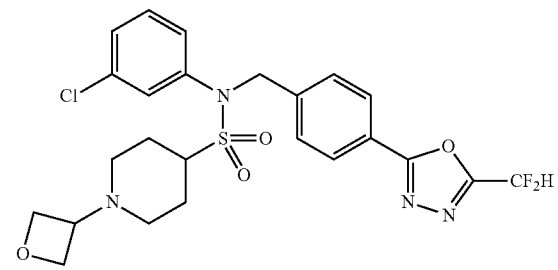 [SMILES: Cc1cccc(N(Cc2ccc(-c3nnc(C(F)F)o3)cc2)S(=O)(=O)C2CCN(C3COC3)CC2)c1] |
| 196 | 11682 | 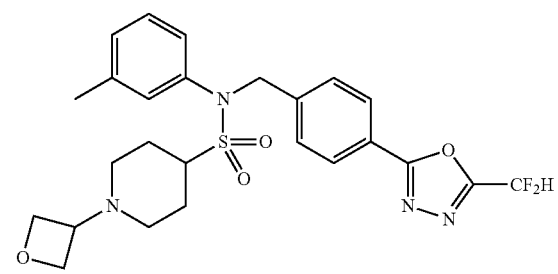 |

| Ex. | Comp. | Structure |
|---|---|---|
| 197 | 11683 | 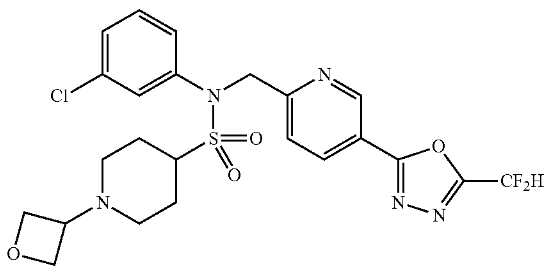 |
| 198 | 11684 | 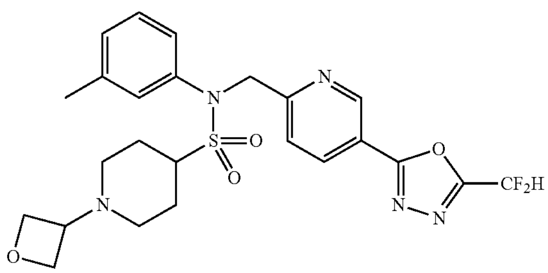 [SMILES: Cc1cccc(N(Cc2ccc(-c3nnc(C(F)F)o3)cn2)S(=O)(=O)C2CCN(C3COC3)CC2)c1] |
| 199 | 11685 | 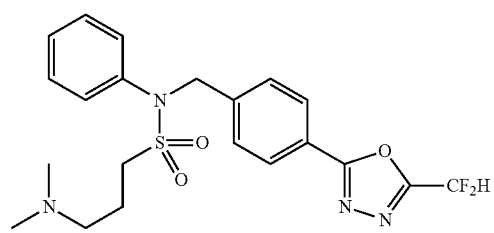 [SMILES: CN(C)CCCS(=O)(=O)N(Cc1ccc(-c2nnc(C(F)F)o2)cc1)c1ccccc1] |
| 226 | 11721 | 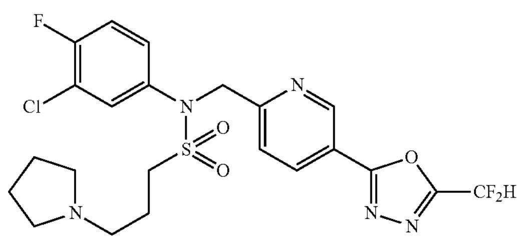 [SMILES: O=S(=O)(CCCN1CCCC1)N(Cc1ccc(-c2nnc(C(F)F)o2)cn1)c1ccc(F)c(Cl)c1] |
| 282 | 11777 | 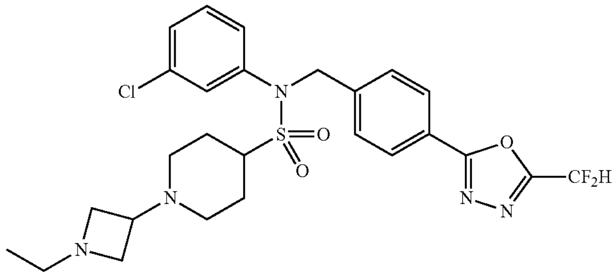 [SMILES: CCN1CC(N2CCC(S(=O)(=O)N(Cc3ccc(-c4nnc(C(F)F)o4)cc3)c3cccc(Cl)c3)CC2)C1] |

| Ex. | Comp. | Structure |
|---|---|---|
| 286 | 11781 | 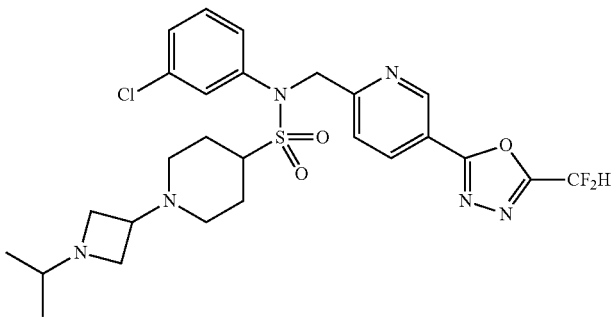 [SMILES: CC(C)N1CC(N2CCC(S(=O)(=O)N(Cc3ccc(-c4nnc(C(F)F)o4)cn3)c3cccc(Cl)c3)CC2)C1] |
| 287 | 11782 | 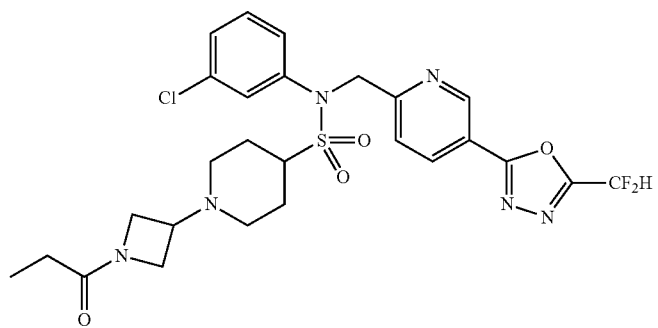 [SMILES: CCC(=O)N1CC(N2CCC(S(=O)(=O)N(Cc3ccc(-c4nnc(C(F)F)o4)cn3)c3cccc(Cl)c3)CC2)C1] |
| 304 | 11803 | 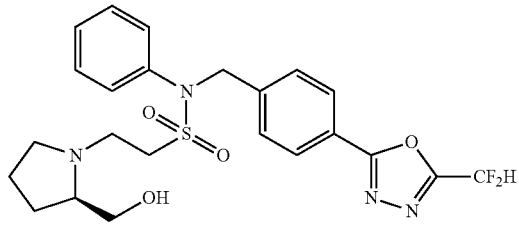 [SMILES: O=S(=O)(CCN1CCC[C@@H]1CO)N(Cc1ccc(-c2nnc(C(F)F)o2)cc1)c1ccccc1] |
| 307 | 11806 | 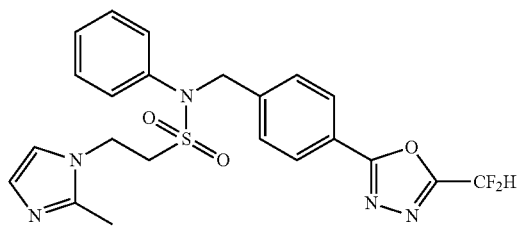 [SMILES: Cc1nccn1CCS(=O)(=O)N(Cc1ccc(-c2nnc(C(F)F)o2)cc1)c1ccccc1] |
| 310 | 11809 | 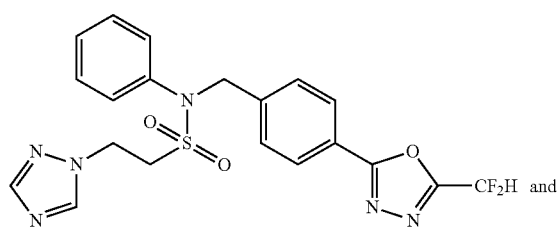 [SMILES: O=S(=O)(CCn1cncn1)N(Cc1ccc(-c2nnc(C(F)F)o2)cc1)c1ccccc1 ; "and"] and |

| Ex. | Comp. | Structure |
|---|---|---|
| 326 | 11837 | *(structure)* |

7. The 1,3,4-oxadiazole sulfonamide derivative compound represented by formula I, stereoisomer thereof or pharmaceutically acceptable salt thereof according to claim 6, wherein the compound represented by formula I is selected from the group consisting of compounds described in the following table:

| Ex. | Comp. | Structure |
|---|---|---|
| 14 | 11154 | *(structure)* |
| 20 | 11170 | *(structure)* |
| 22 | 11172 | *(structure)* |
| 28 | 11178 | *(structure)* |

-continued

| Ex. | Comp. | Structure |
|---|---|---|
| 32 | 11182 | 3-fluoro-N-(2-fluoro-4-(5-(difluoromethyl)-1,3,4-oxadiazol-2-yl)benzyl)-N-methanesulfonyl-aniline |
| 37 | 11191 | 3-chloro-N-(2-fluoro-4-(5-(difluoromethyl)-1,3,4-oxadiazol-2-yl)benzyl)-N-methanesulfonyl-aniline |
| 43 | 11197 | 3-bromo-N-(2-fluoro-4-(5-(difluoromethyl)-1,3,4-oxadiazol-2-yl)benzyl)-N-methanesulfonyl-aniline |
| 45 | 11217 | 3-fluoro-N-((5-(5-(difluoromethyl)-1,3,4-oxadiazol-2-yl)pyridin-2-yl)methyl)-N-methanesulfonyl-aniline |
| 65 | 11256 | N-(2-fluoro-4-(5-(difluoromethyl)-1,3,4-oxadiazol-2-yl)benzyl)-N-(3-fluorophenyl)-tetrahydro-2H-thiopyran-4-sulfonamide 1,1-dioxide |
| 93 | 11350 | N-((5-(5-(difluoromethyl)-1,3,4-oxadiazol-2-yl)pyridin-2-yl)methyl)-N-phenyl-tetrahydro-2H-thiopyran-4-sulfonamide 1,1-dioxide |

-continued

| Ex. | Comp. | Structure |
|---|---|---|
| 95 | 11352 | 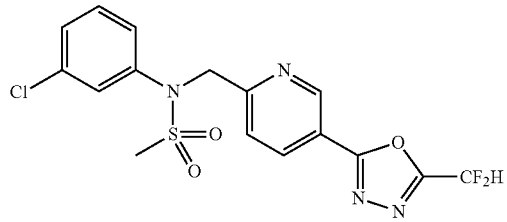 [SMILES: CS(=O)(=O)N(Cc1ccc(-c2nnc(C(F)F)o2)cn1)c1cccc(Cl)c1] |
| 97 | 11354 | 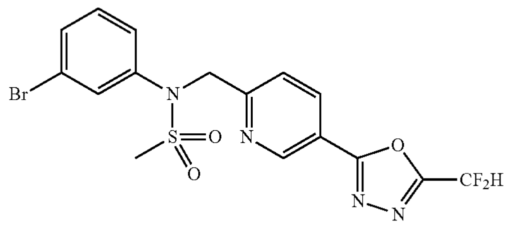 [SMILES: CS(=O)(=O)N(Cc1ccc(-c2nnc(C(F)F)o2)cn1)c1cccc(Br)c1] |
| 98 | 11355 | 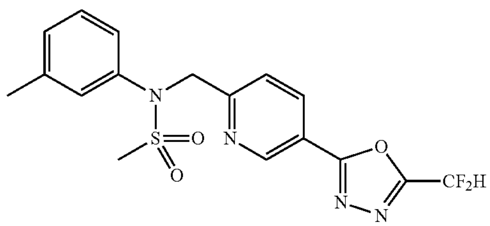 [SMILES: Cc1cccc(N(Cc2ccc(-c3nnc(C(F)F)o3)cn2)S(C)(=O)=O)c1] |
| 99 | 11366 | 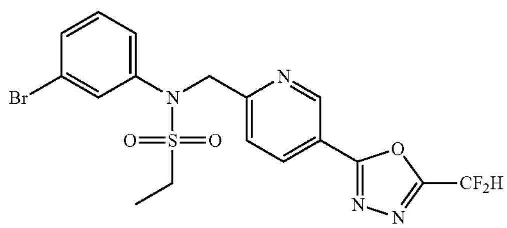 [SMILES: CCS(=O)(=O)N(Cc1ccc(-c2nnc(C(F)F)o2)cn1)c1cccc(Br)c1] |
| 100 | 11367 | 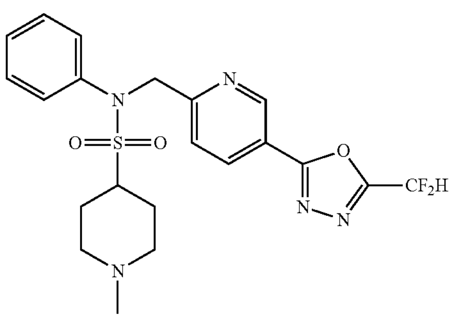 [SMILES: CN1CCC(S(=O)(=O)N(Cc2ccc(-c3nnc(C(F)F)o3)cn2)c2ccccc2)CC1] |
| 101 | 11368 | 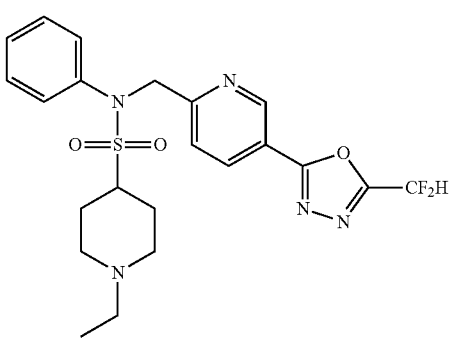 [SMILES: CCN1CCC(S(=O)(=O)N(Cc2ccc(-c3nnc(C(F)F)o3)cn2)c2ccccc2)CC1] |

-continued
| Ex. | Comp. | Structure |
|---|---|---|
| 102 | 11372 | 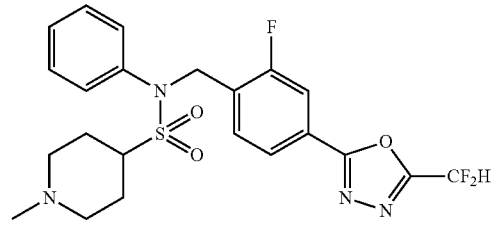 [SMILES: CN1CCC(S(=O)(=O)N(Cc2ccc(-c3nnc(C(F)F)o3)cc2F)c2ccccc2)CC1] |
| 103 | 11373 | 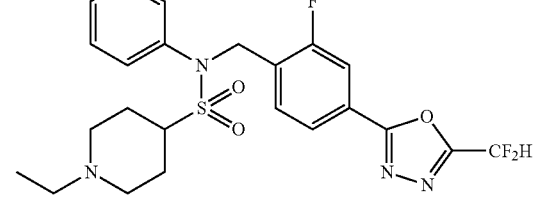 |
| 109 | 11390 | 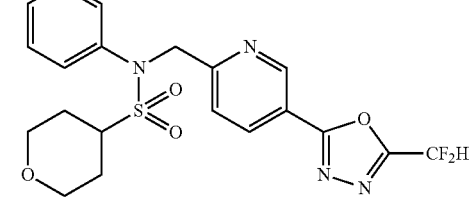 |
| 116 | 11411 | 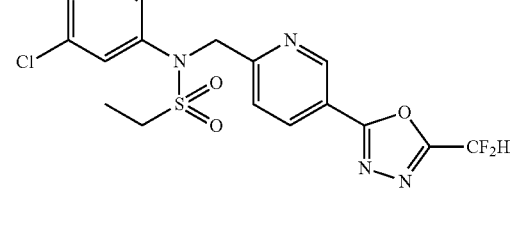 |
| 117 | 11412 | 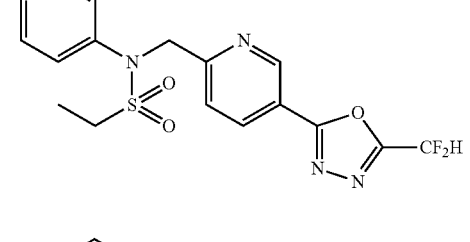 |
| 118 | 11426 | 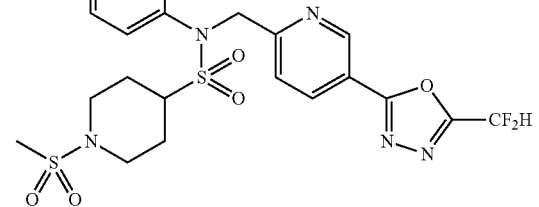 |

-continued

| Ex. | Comp. | Structure |
|---|---|---|
| 120 | 11428 | 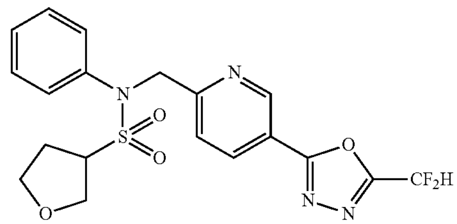 [SMILES: O=S(=O)(C1CCOC1)N(Cc1ccc(-c2nnc(C(F)F)o2)cn1)c1ccccc1] |
| 125 | 11433 | 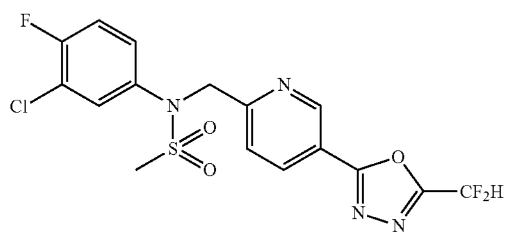 [SMILES: CS(=O)(=O)N(Cc1ccc(-c2nnc(C(F)F)o2)cn1)c1ccc(F)c(Cl)c1] |
| 126 | 11447 | 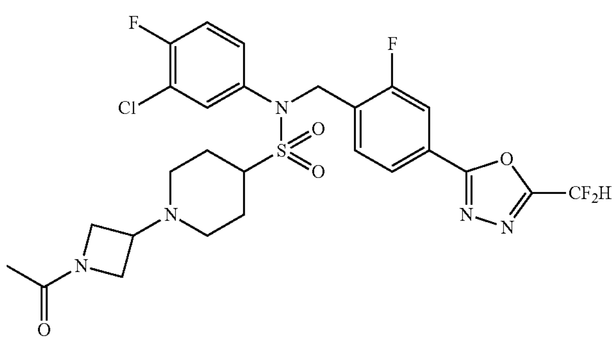 [SMILES: CC(=O)N1CC(N2CCC(S(=O)(=O)N(Cc3ccc(-c4nnc(C(F)F)o4)cc3F)c3ccc(F)c(Cl)c3)CC2)C1] |
| 128 | 11451 | 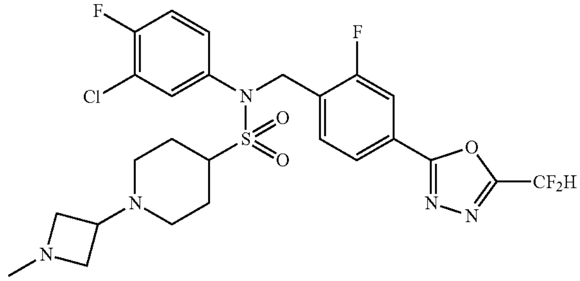 [SMILES: CN1CC(N2CCC(S(=O)(=O)N(Cc3ccc(-c4nnc(C(F)F)o4)cc3F)c3ccc(F)c(Cl)c3)CC2)C1] |
| 129 | 11452 | 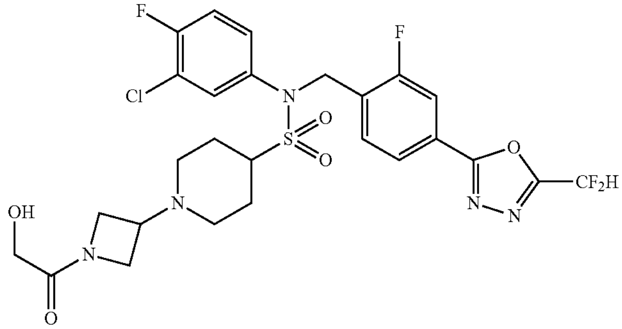 [SMILES: O=C(CO)N1CC(N2CCC(S(=O)(=O)N(Cc3ccc(-c4nnc(C(F)F)o4)cc3F)c3ccc(F)c(Cl)c3)CC2)C1] |

-continued

| Ex. | Comp. | Structure |
|---|---|---|
| 130 | 11460 | 3-fluoro-4-methylphenyl-N-(ethylsulfonyl)-N-((5-(5-(difluoromethyl)-1,3,4-oxadiazol-2-yl)pyridin-2-yl)methyl)amine |
| 131 | 11461 | 4-fluoro-3-methylphenyl-N-(ethylsulfonyl)-N-((5-(5-(difluoromethyl)-1,3,4-oxadiazol-2-yl)pyridin-2-yl)methyl)amine |
| 132 | 11462 | 3,4-difluorophenyl-N-(ethylsulfonyl)-N-((5-(5-(difluoromethyl)-1,3,4-oxadiazol-2-yl)pyridin-2-yl)methyl)amine |
| 133 | 11463 | 3,5-difluorophenyl-N-(ethylsulfonyl)-N-((5-(5-(difluoromethyl)-1,3,4-oxadiazol-2-yl)pyridin-2-yl)methyl)amine |
| 134 | 11497 | 3-chloro-4-fluorophenyl-N-((1,1-dioxidotetrahydro-2H-thiopyran-4-yl)sulfonyl)-N-((5-(5-(difluoromethyl)-1,3,4-oxadiazol-2-yl)pyridin-2-yl)methyl)amine |

-continued
| Ex. | Comp. | Structure |
|---|---|---|
| 135 | 11501 | 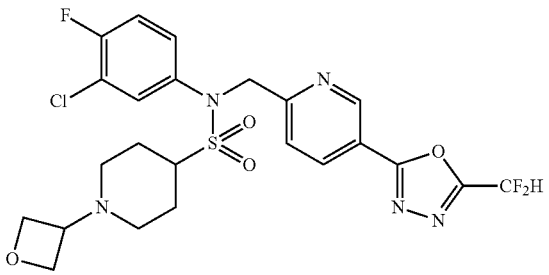 [SMILES: O=S(=O)(C1CCN(C2COC2)CC1)N(Cc1ccc(-c2nnc(C(F)F)o2)cn1)c1ccc(F)c(Cl)c1] |
| 136 | 11502 | 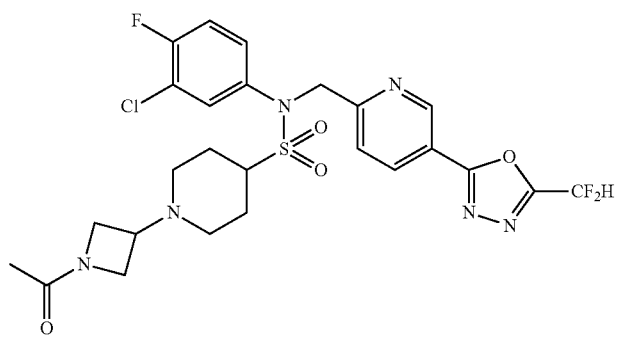 [SMILES: CC(=O)N1CC(N2CCC(S(=O)(=O)N(Cc3ccc(-c4nnc(C(F)F)o4)cn3)c3ccc(F)c(Cl)c3)CC2)C1] |
| 137 | 11503 | 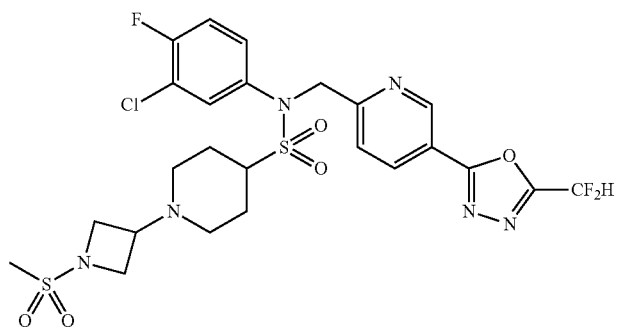 [SMILES: CS(=O)(=O)N1CC(N2CCC(S(=O)(=O)N(Cc3ccc(-c4nnc(C(F)F)o4)cn3)c3ccc(F)c(Cl)c3)CC2)C1] |
| 138 | 11504 | 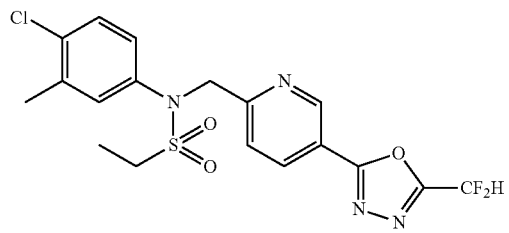 |
| 139 | 11505 | 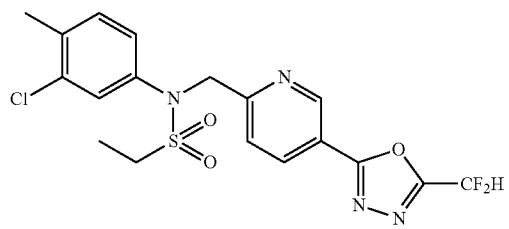 [SMILES: CCS(=O)(=O)N(Cc1ccc(-c2nnc(C(F)F)o2)cn1)c1ccc(C)c(Cl)c1] |

-continued

| Ex. | Comp. | Structure |
|---|---|---|
| 140 | 11506 | 3,5-dichlorophenyl-N-(ethylsulfonyl)-N-{[5-(5-(difluoromethyl)-1,3,4-oxadiazol-2-yl)pyridin-2-yl]methyl}aniline |
| 141 | 11507 | 3,4-dichlorophenyl-N-(ethylsulfonyl)-N-{[5-(5-(difluoromethyl)-1,3,4-oxadiazol-2-yl)pyridin-2-yl]methyl}aniline |
| 146 | 11521 | N-(1-methyl-1H-indazol-6-yl)-N-{[2-fluoro-4-(5-(difluoromethyl)-1,3,4-oxadiazol-2-yl)phenyl]methyl}ethanesulfonamide |
| 149 | 11540 | N-(1-methyl-1H-indazol-6-yl)-N-{[5-(5-(difluoromethyl)-1,3,4-oxadiazol-2-yl)pyridin-2-yl]methyl}ethanesulfonamide |
| 150 | 11541 | N-(1-methyl-1H-indazol-7-yl)-N-{[5-(5-(difluoromethyl)-1,3,4-oxadiazol-2-yl)pyridin-2-yl]methyl}ethanesulfonamide |
| 151 | 11552 | N-(3-chloro-4-fluorophenyl)-N-{[2-fluoro-4-(5-(difluoromethyl)-1,3,4-oxadiazol-2-yl)phenyl]methyl}-2-(4-methylpiperazin-1-yl)ethanesulfonamide |

| Ex. | Comp. | Structure |
|---|---|---|
| 152 | 11553 | 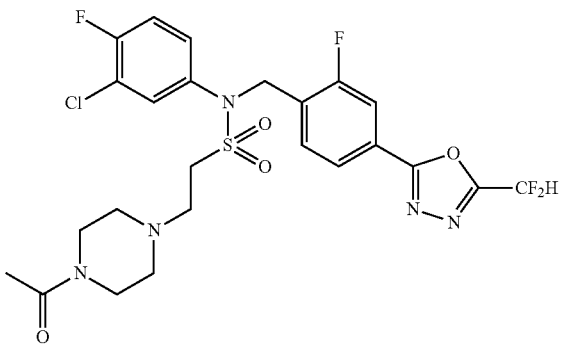 [SMILES: CC(=O)N1CCN(CCS(=O)(=O)N(Cc2ccc(-c3nnc(C(F)F)o3)cc2F)c2ccc(F)c(Cl)c2)CC1] |
| 174 | 11637 | 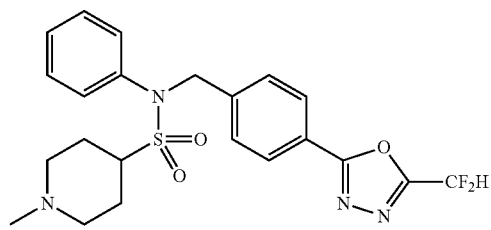 [SMILES: CN1CCC(S(=O)(=O)N(Cc2ccc(-c3nnc(C(F)F)o3)cc2)c2ccccc2)CC1] |
| 178 | 11646 | 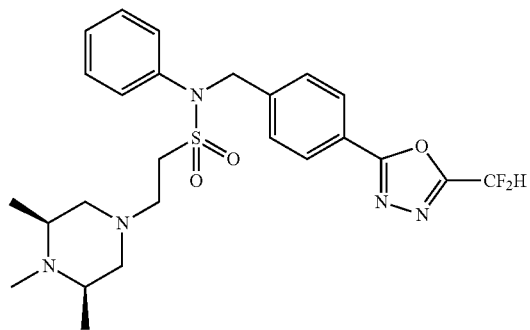 [SMILES: C[C@@H]1CN(CCS(=O)(=O)N(Cc2ccc(-c3nnc(C(F)F)o3)cc2)c2ccccc2)C[C@H](C)N1C] |
| 186 | 11665 | 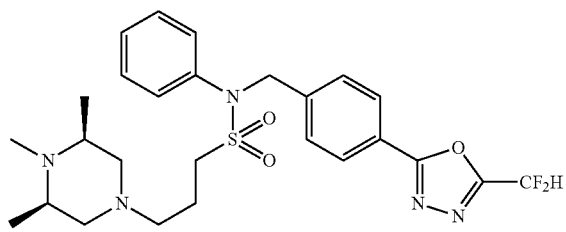 [SMILES: C[C@@H]1CN(CCCS(=O)(=O)N(Cc2ccc(-c3nnc(C(F)F)o3)cc2)c2ccccc2)C[C@H](C)N1C] |
| 195 | 11681 | 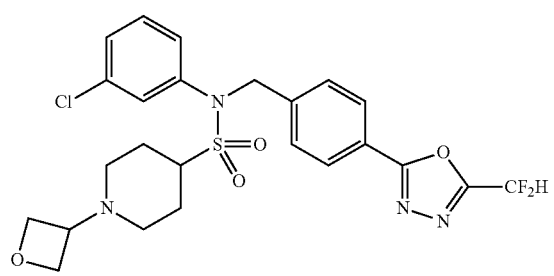 |

-continued

| Ex. | Comp. | Structure |
|---|---|---|
| 197 | 11683 | 3-chlorophenyl-N-((5-(5-(difluoromethyl)-1,3,4-oxadiazol-2-yl)pyridin-2-yl)methyl)-1-(oxetan-3-yl)piperidine-4-sulfonamide |
| 198 | 11684 | N-((5-(5-(difluoromethyl)-1,3,4-oxadiazol-2-yl)pyridin-2-yl)methyl)-3-methylphenyl-1-(oxetan-3-yl)piperidine-4-sulfonamide |
| 199 | 11685 | 3-(dimethylamino)-N-(4-(5-(difluoromethyl)-1,3,4-oxadiazol-2-yl)benzyl)-N-phenylpropane-1-sulfonamide and |
| 286 | 11781 | 3-chlorophenyl-N-((5-(5-(difluoromethyl)-1,3,4-oxadiazol-2-yl)pyridin-2-yl)methyl)-1-(1-isopropylazetidin-3-yl)piperidine-4-sulfonamide |

8. A pharmaceutical composition comprising, as an active ingredient, the compound represented by formula I, stereoisomer thereof or pharmaceutically acceptable salt thereof according to of claim 1.

* * * * *

UNITED STATES PATENT AND TRADEMARK OFFICE
CERTIFICATE OF CORRECTION

PATENT NO. : 10,538,498 B2
APPLICATION NO. : 15/747952
DATED : January 21, 2020
INVENTOR(S) : Jaekwang Lee et al.

It is certified that error appears in the above-identified patent and that said Letters Patent is hereby corrected as shown below:

In the Claims

Column 794, Line 14, in Claim 1:
Delete "heteroaryl" and insert -- -heteroaryl --, therefor.

Column 795, Line 4, in Claim 1:
Delete "aryl" and insert -- -aryl --, therefor.

Column 919-920, Line 2, in Claim 5:

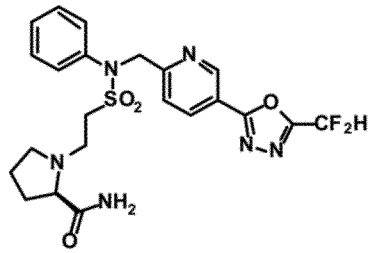

After " ", insert -- and --, therefor.

Signed and Sealed this
Ninth Day of June, 2020

Andrei Iancu
*Director of the United States Patent and Trademark Office*